US012662491B2

(12) United States Patent
Ericsson et al.

(10) Patent No.: US 12,662,491 B2
(45) Date of Patent: Jun. 23, 2026

(54) COMPOUNDS TARGETING RNA-BINDING PROTEINS OR RNA-MODIFYING PROTEINS

(71) Applicant: Redona Therapeutics, Inc., Watertown, MA (US)

(72) Inventors: Anna M. Ericsson, Shrewsbury, MA (US); Shomir Ghosh, Brookline, MA (US); Darren Martin Harvey, Acton, MA (US)

(73) Assignee: Redona Therapeutics, Inc., Watertown, MA (US)

(*) Notice: Subject to any disclaimer, the term of this patent is extended or adjusted under 35 U.S.C. 154(b) by 553 days.

(21) Appl. No.: 17/908,576

(22) PCT Filed: Mar. 2, 2021

(86) PCT No.: PCT/US2021/020494
§ 371 (c)(1),
(2) Date: Feb. 14, 2023

(87) PCT Pub. No.: WO2021/178420
PCT Pub. Date: Sep. 10, 2021

(65) Prior Publication Data

US 2024/0254136 A1 Aug. 1, 2024

Related U.S. Application Data

(60) Provisional application No. 62/984,677, filed on Mar. 3, 2020.

(51) Int. Cl.

| | |
|---|---|
| ***C07D 498/04*** | (2006.01) |
| ***A61K 31/4709*** | (2006.01) |
| ***A61K 31/497*** | (2006.01) |
| ***A61K 31/4985*** | (2006.01) |
| ***A61K 31/501*** | (2006.01) |
| ***A61K 31/506*** | (2006.01) |
| ***C07D 401/04*** | (2006.01) |
| ***C07D 401/14*** | (2006.01) |
| ***C07D 405/14*** | (2006.01) |
| ***C07D 471/04*** | (2006.01) |
| ***C07D 487/08*** | (2006.01) |

(52) U.S. Cl.
CPC ........ *C07D 498/04* (2013.01); *A61K 31/4709* (2013.01); *A61K 31/497* (2013.01); *A61K 31/4985* (2013.01); *A61K 31/501* (2013.01); *A61K 31/506* (2013.01); *C07D 401/04* (2013.01); *C07D 401/14* (2013.01); *C07D 405/14* (2013.01); *C07D 471/04* (2013.01); *C07D 487/08* (2013.01)

(58) Field of Classification Search
CPC .. C07D 498/04; C07D 401/14; C07D 405/14; C07D 471/04; C07D 487/08; A61K 31/4709; A61K 31/497; A61K 31/4985; A61K 31/501; A61K 31/506
See application file for complete search history.

(56) References Cited

U.S. PATENT DOCUMENTS

| | | | | |
|---|---|---|---|---|
| 5,073,556 | A | 12/1991 | Iwata et al. | |
| 6,329,391 | B1 | 12/2001 | Ledoussal et al. | |
| 2007/0238719 | A1 | 10/2007 | Hopkins et al. | |
| 2007/0238720 | A1 | 10/2007 | Hopkins et al. | |
| 2007/0249577 | A1 | 10/2007 | Hopkins et al. | |
| 2014/0328858 | A1* | 11/2014 | Gregory ............... | A61K 31/713 514/19.5 |

FOREIGN PATENT DOCUMENTS

| | | | |
|---|---|---|---|
| CN | 1278813 | A | 1/2001 |
| CN | 102101859 | A | 6/2011 |
| CN | 107949562 | A | 4/2018 |
| CN | 110520422 | A | 11/2019 |
| EP | 0304087 | A2 | 2/1989 |
| EP | 352123 | A2 | 1/1990 |
| GB | 2442951 | A | 4/2008 |
| JP | 3-209367 | A | 9/1991 |
| JP | 1-128288 | A | 4/1992 |
| JP | 6-230776 | A | 8/1994 |
| JP | H-11147883 | A | 6/1999 |
| JP | 6219583 | B2 | 10/2017 |
| RU | 2558835 | C2 | 8/2015 |
| WO | 1990/06307 | A2 | 6/1990 |
| WO | 1992/09579 | A1 | 6/1992 |
| WO | 1992/10191 | A1 | 6/1992 |

(Continued)

OTHER PUBLICATIONS

Current Results, https://www.currentresults.com/Environment-Facts/Plants-Animals/number-species.php; last visited May 2, 2022.*

(Continued)

*Primary Examiner* — Alicia L Otton

(74) *Attorney, Agent, or Firm* — McCarter & English, LLP; Steven G. Davis

(57) ABSTRACT

The invention relates to a compound represented by Formula (I): or a pharmaceutically acceptable salt thereof, compositions comprising the same and methods of preparing and using the same. The variables are described herein.

(I)

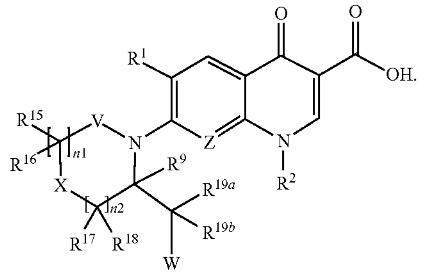

19 Claims, No Drawings

(56) References Cited

FOREIGN PATENT DOCUMENTS

| | | | |
|---|---|---|---|
| WO | 1992/21659 | A1 | 12/1992 |
| WO | 1996/23775 | A1 | 8/1996 |
| WO | 1999/14214 | A1 | 3/1999 |
| WO | 2005/026147 | A1 | 3/2005 |
| WO | 2008/085913 | A1 | 7/2008 |
| WO | 2009/137130 | A2 | 11/2009 |
| WO | 2011031740 | A1 | 3/2011 |

OTHER PUBLICATIONS

Piskounova et al., Lin28A and Lin28B Inhibit let-7 MicroRNA Biogenesis by Distinct Mechanisms, Cell 147: 1066-1079, 2011.*
Perrin, Make mouse studies work, Nature (507): 423-425, 2014.*
Hinman et al., Novel antibacterial class: a series of tetracyclic derivatives. J Med Chem. Aug. 10, 2006;49(16):4842-56.
Lin et al., Identification of small molecule inhibitors of Zcchc11 TUTase activity. RNA Biol. 2015;12(8):792-800.
International Search Report and Written Opinion for Application No. PCT/US2021/020494, dated Apr. 28, 2021, 8 bages.

* cited by examiner

COMPOUNDS TARGETING RNA-BINDING PROTEINS OR RNA-MODIFYING PROTEINS

RELATED APPLICATIONS

This application is a U.S. National Stage filing, under 35 U.S.C § 371(c), of International Application No. PCT/US2021/020494, filed on Mar. 2, 2021, which claims the benefit of U.S. Provisional Application Ser. No. 62/984,677, filed Mar. 3, 2020, the entire teachings of each of which are incorporated herein by reference.

BACKGROUND OF THE INVENTION

RNA-binding proteins and RNA-modifying proteins play important roles in post-transcriptional gene regulation processes, such as RNA splicing, transport, translation, and localization. Recent studies have demonstrated that dysregulated expression of some of these proteins can lead to disease occurrence, such as cancers.

Let 7 miRNA is known as a tumor suppressor of miRNA targeting oncogenes K-Ras, c-myc, and HMGA2. A number of human cancer cell lines and primary tumors express low levels of let-7 family miRNAs. It has been demonstrated that increased let-7 expression can effectively inhibit cancer growth in mouse models of lung and breast cancers. Lin28 proteins play important roles in regulating let-7 miRNA level in cells. Lin28B functions in the nucleus and inhibits the miRNA microprocessor by sequestering primary let-7 transcripts. In contrast, Lin28A-mediated inhibition of let-7 expression involves recruitment of a 3' terminal uridylyl transferase (TUTase) (e.g., Zcchc11/TUTase4/TUT4/Z11 or Zcchc6/TUTase7/TUT7/Z6) to let-7 precursor RNA to block processing by Dicer in the cell cytoplasm. TUTase activity is required for the Lin28-mediated inhibition of let-7 biogenesis. It has been found that Zcchc11 expression is up-regulated in primary human liver and colorectal tumors compared with normal tissues. In addition, Zcchc11 knockdown has been shown to inhibit tumorigenesis of human breast, ovarian, melanoma, prostate, and liver cancer cells in mouse xenograft models and lung metastasis of liver cancer cells.

As such, there is a need for targeted therapies that modulate the TUTase activities for treating diseases or disorders mediated by let 7 miRNA.

SUMMARY OF THE INVENTION

The present invention provides compounds that can modulate the activities TUTase Zcchc11 (or Z11). In certain embodiments, the compounds of the invention have inhibitory activities against Z11 TUTase. The compounds of the invention have quinolone cores similar to quinolone antibiotics. However, certain compounds of the invention exhibit reduced or minimal antibiotic activity.

In a first aspect, the present invention is directed to a compound represented by Formula (I):

(I)

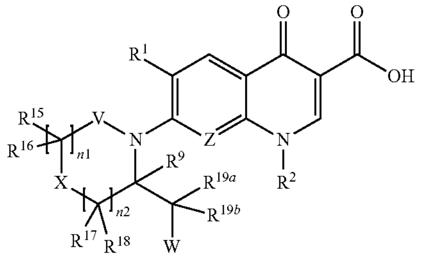

or a pharmaceutically acceptable salt thereof, wherein:

W is —$CH_2Y$—$R^3$, —$S(O)_2R^3$, —$SCH_2R^3$, Y—$R^3$, —OC(═O)$NR^{11}R^{12}$ or —N(C═O)$NR^{11}R^{12}$;

V is —C(═O)—, —S(═O)$_2$— or $CR^{13}R^{14}$;

X is $CR^4R^5$, $NR^6$ or O;

Y is $NR^7$ or O;

Z is $CR^8$ or N;

$R^1$ is halo, —CN, —$OR^{1a}$, —C≡CH, a $C_{3-6}$ carbocyclyl, or a $C_{1-6}$alkyl, wherein the $C_{1-6}$alkyl is optionally substituted with one or more $R^{10}$;

$R^{1a}$ is H or $C_{1-6}$ alkyl optionally substituted with one or more $R^{10}$;

$R^{10}$, for each occurrence, is independently selected from halo, —CN and —$OR^{10a}$;

$R^{10a}$, for each occurrence, is independently selected from H and $C_{1-6}$ alkyl;

$R^2$ is —CN, —$CHR^zCN$, —C(O)$NH_2$, —$CHR^zC(O)NH_2$, 3- to 12-membered carbocyclyl, —($CHR^z$)-(3- to 12-membered carbocyclyl), 3- to 12-membered heterocyclyl, or —($CHR^z$)-(3 to 12-membered heterocyclyl), wherein the 3 to 12-membered carbocyclyl and the 3 to 12-membered heterocyclyl represented by $R^2$ or in the group represented by $R^2$ are optionally substituted with one or more $R^{20}$, and $R^z$ is H or methyl;

$R^{20}$, for each occurrence, is independently selected from H, halo, CN, oxo, —C(O)$R^{20a}$, —C(O)$_2R^{20a}$, —C(O)$NR^{20a}$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —$OR^{20a}$, —OC(O)$R^{20a}$, —OC(O)N($R^{20a}$)$_2$, —$SR^{20a}$, —S(O)$_2R^{20a}$, —S(O)N($R^{20a}$)$_2$, —S(O)$_2$N($R^{20a}$)$_2$, $C_{1-6}$ alkyl, $C_{3-8}$cycloalkyl, and 4- to 7-membered monocyclic heterocyclyl, wherein the $C_{1-6}$ alkyl, $C_{3-8}$cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$alkyl, $C_{3-8}$cycloalkyl and 4- to 7-membered monocyclic heterocyclyl, wherein the $C_{1-6}$ alkyl, $C_{3-8}$cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —C═O, —C(O)O($C_1$-$C_6$ alkyl), 4- to 6-membered heterocyclyl optionally substituted with OH, —N($R^{25a}$)$_2$, —$OR^{25a}$, phenyl optionally substituted with $C_{1-6}$ alkyl, halo, —N($R^{25a}$)$_2$ or —$OR^{25a}$; and $R^{25a}$ is H, $C_{1-6}$alkyl; or two $R^{25a}$ together with the nitrogen atom from which they are attached form a 4- to 7-membered heterocyclyl, wherein the $C_{1-6}$alkyl is optionally substituted with $—OCH_3$;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, $—C(O)R^{30a}$, $—C(O)_2R^{30a}$, $—C(O)NR^{30a}$, $—N(R^{30a})_2$, $—N(R^{30a})C(O)R^{30a}$, $—N(R^{30a})C(O)_2R^{30a}$, $—N(R^{30a})C(O)N(R^{30a})_2$, $—N(R^{30a})S(O)_2R^{30a}$, $—OR^{30a}$, $—OC(O)R^{30a}$, $—OC(O)N(R^{30a})_2$, $—SR^{30a}$, $—S(O)_2R^{30a}$, $—S(O)N(R^{30a})_2$, $—S(O)_2N(R^{30a})_2$, $C_{1-6}$ alkyl, $C_{3-8}$cycloalkyl, and 4- to 7-membered monocyclic heterocyclyl, wherein the $C_{1-6}$ alkyl, $C_{3-8}$cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$cycloalkyl and 4- to 7-membered monocyclic heterocyclyl, wherein the $C_{1-6}$ alkyl, $C_{3-8}$cycloalkyl and 4- to 7-membered monocyclic heterocyclyl represented by $R^{30a}$ are each optionally substituted with one or more $R^{35}$;

$R^{35}$, for each occurrence, is independently H, $—NH_2$, $C_{1-6}$alkyl, halo and $—OR^{35a}$; and $R^{35a}$ is H or $C_{1-6}$ alkyl;

alternatively, when Y is $NR^7$, $R^7$ and $R^3$ together with the N atom from which $R^7$ is attached can form a 4 to 12-membered heterocyclyl optionally substituted with or more $R^{30}$;

$R^4$, $R^5$, $R^{15}$, $R^{16}$, $R^{17}$ and $R^{18}$ are each independently selected from H, $C_{1-6}$ alkyl, halo, $—NHC(O)CH_3$, 4- to 6-membered carbocyclyl, or 4- to 6-membered heterocyclyl, wherein the $C_{1-6}$ alkyl is optionally substituted with one or more substituents independently selected from halo, and wherein the heterocyclyl and carbocyclyl are optionally substituted with halo, —CN, $—OR^{4a}$, $C_1$-$C_6$ alkyl or =O (when the carbocyclyl or heterocyclyl are non-aromatic), or wherein $R^{15}$ and $R^{16}$ taken together or $R^{17}$ and $R^{18}$ taken together are =NOH or $=NHOCH_3$;

$R^{4a}$ is H or $C_{1-6}$ alkyl, optionally substitute with one or more halo;

$R^6$ is H or $C_{1-6}$alkyl optionally substituted with one or more substituents independently selected from halo, —CN and $—OR^{6a}$;

$R^{6a}$ is H or $C_{1-6}$ alkyl optionally substitute with one or more halo;

$R^7$ is H or $C_{1-6}$ alkyl optionally substituted with one or more halo;

$R^8$ is H, halo, —CN, $—OR^{8a}$ or $C_{1-6}$ alkyl optionally substituted with one or more halo;

$R^{8a}$ is H or $C_{1-6}$ alkyl optionally substituted with one or more halo;

$R^9$, $R^{13}$ and $R^{14}$ are each independently selected from H, $C_{1-6}$alkyl, and $C_{3-6}$ cycloalkyl, wherein the $C_{1-6}$ alkyl and the $C_{3-6}$ cycloalkyl are each optionally substituted with one or more substituents independently selected from halo, —CN, $—OR^{9a}$ and $C_{1-6}$ alkyl optionally substituted with one or more halo;

$R^{9a}$ is H or $C_{1-6}$ alkyl optionally substituted with one or more halo;

$R^{11}$ and $R^{12}$ are each independently H or $C_{1-6}$ alkyl, or $R^{11}$ and $R^{12}$ together with the nitrogen atom from which they are attached form a 4- to 7-membered monocyclic heterocyclyl optionally substituted with one or more substituents independently selected from $C_{1-6}$ alkyl, halo, —OH, and $C_{1-6}$ alkoxy;

or any two of $R^4$, $R^5$, $R^9$, $R^{13}$, $R^{14}$, $R^{15}$, $R^{16}$, $R^{17}$ and $R^{18}$ together form a $—C_{1-5}$ alkylene-, optionally substituted with one or more substituents independently selected from halo, $—OR^a$, $—N(R^a)_2$ and $C_{1-6}$ alkyl;

or $R^4$ and $R^{15}$ taken together with their intervening carbon atoms form phenyl or a 6 membered heteroaryl; and $R^a$, for each occurrence, is independently H or $C_{1-6}$ alkyl optionally substituted with one or more halo;

$R^{19a}$ and $R^{19b}$ are each independently H or $C_{1-6}$ alkyl optionally substituted with one or more halo, or $R^{19a}$ and $R^{19b}$ together with the carbon atom from which they are attached form —C(=O); or one $R^{21}$ group and one $R^{31}$ group taken together form $—O—CH_2CH_2—O—$ or $—O—CH_2CH_2—NH—$; and n1 is 0, 1 or 2; and n2 is 0, 1 or 2, provided when X is $NR^6$ or O, n1 and n2 cannot be 0.

In a second aspect, the present invention is directed to a compound represented by Formula (I'),

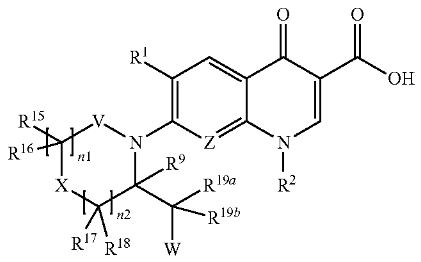

(I')

or a pharmaceutically acceptable salt thereof, wherein:

W is $Y—R^3$, $—OC(=O)NR^{11}R^{12}$ or $—N(C=O)NR^{11}R^{12}$;

V is —C(=O)—, $—S(=O)_2—$ or $CR^{13}R^{14}$;

X is $CR^4R^5$, $NR^6$ or O;

Y is $NR^7$ or O;

Z is $CR^8$ or N;

$R^1$ is halo, CN, $—OR^{1a}$, —C≡CH, or a $C_{1-6}$alkyl, wherein the $C_{1-6}$ alkyl is optionally substituted with one or more $R^{10}$;

$R^{1a}$ is H or $C_{1-6}$alkyl optionally substituted with one or more $R^{10}$;

$R^{10}$, for each occurrence, is independently selected from halo, CN and $OR^{10a}$;

$R^{10a}$, for each occurrence, is independently selected from H and $C_{1-6}$ alkyl;

$R^2$ is a 3 to 12-membered carbocyclyl or a 3 to 12-membered heterocyclyl, wherein the 3 to 12-membered carbocyclyl and the 3 to 12-membered heterocyclyl represented by $R^2$ are optionally substituted with one or more $R^{20}$;

$R^{20}$, for each occurrence, is independently selected from H, halo, CN, oxo, $—C(O)R^{20a}$, $—C(O)_2R^{20a}$, $—C(O)NR^{20a}$, $—N(R^{20a})_2$, $—N(R^{20a})C(O)R^{20a}$, $—N(R^{20a})C(O)_2R^{20a}$, $—N(R^{20a})C(O)N(R^{20a})_2$, $—N(R^{20a})S(O)_2R^{20a}$, $—OR^{20a}$, $—OC(O)R^{20a}$, $—OC(O)N(R^{20a})_2$, $—SR^{20a}$, $—S(O)_2R^{20a}$, $—S(O)N(R^{20a})_2$, $—S(O)_2N(R^{20a})_2$, $C_{1-6}$ alkyl, $C_{3-8}$cycloalkyl, and 4- to 7-membered monocyclic heterocyclyl, wherein the $C_{1-6}$ alkyl, $C_{3-8}$cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$ alkyl, $C_{3-8}$cycloalkyl and 4- to 7-membered monocyclic heterocyclyl, wherein the $C_{1-6}$ alkyl, $C_{3-8}$cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, $—N(R^{25a})_2$, $—OR^{25a}$, phenyl optionally substituted with $C_{1-6}$ alkyl, halo, $—N(R^{25a})_2$ or $—OR^{25a}$; and $R^{25a}$ is H or $C_{1-6}$alkyl;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, $—C(O)R^{30a}$, $—C(O)_2R^{30a}$, $—C(O)NR^{30a}$, $—N(R^{30a})_2$, $—N(R^{30a})C(O)R^{30a}$, $—N(R^{30a})C(O)_2R^{30a}$, $—N(R^{30a})C(O)N(R^{30a})_2$, $—N(R^{30a})S(O)_2R^{30a}$, $—OR^{30a}$, $—OC(O)R^{30a}$, $—OC(O)N(R^{30a})_2$, $—SR^{30a}$, $—S(O)_2R^{30a}$, $—S(O)N(R^{30a})_2$, $—S(O)_2N(R^{30a})_2$, $C_{1-6}$ alkyl, $C_{3-8}$cycloalkyl, and 4- to 7-membered monocyclic heterocyclyl, wherein the $C_{1-6}$ alkyl, $C_{3-8}$cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$cycloalkyl and 4- to 7-membered monocyclic heterocyclyl, wherein the $C_{1-6}$ alkyl, $C_{3-8}$cycloalkyl and 4- to 7-membered monocyclic heterocyclyl represented by $R^{30a}$ are each optionally substituted with one or more $R^{35}$;

$R^{35}$, for each occurrence, is independently H, $C_{1-6}$alkyl, halo and $—OR^{35a}$; and $R^{35a}$ is H or $C_{1-6}$alkyl;

alternatively, when Y is $NR^7$, $R^7$ and $R^3$ together with the N atom from which $R^7$ is attached can form a 4 to 12-membered heterocyclyl optionally substituted with or more $R^{30}$;

$R^4$, $R^5$, $R^{15}$, $R^{16}$, $R^{17}$ and $R^{18}$ are each independently selected from H, $C_{1-6}$ alkyl, halo, —CN and $—OR^{4a}$, wherein the $C_{1-6}$ alkyl is optionally substituted with one or more substituents independently selected from halo, CN and $—OR^{4a}$;

$R^{4a}$ is H or $C_{1-6}$ alkyl optionally substitute with one or more halo;

$R^6$ is H or $C_{1-6}$alkyl optionally substituted with one or more substituents independently selected from halo, CN and $—OR^{6a}$;

$R^{6a}$ is H or $C_{1-6}$ alkyl optionally substitute with one or more halo;

$R^7$ is H or $C_{1-6}$ alkyl optionally substituted with one or more halo;

$R^8$ is H, halo, CN, $—OR^{8a}$ or $C_{1-6}$ alkyl optionally substituted with one or more halo;

$R^{8a}$ is H or $C_{1-6}$ alkyl optionally substituted with one or more halo;

$R^9$, $R^{13}$ and $R^{14}$ are each independently selected from H, $C_{1-6}$alkyl and $C_{3-6}$ cycloalkyl, wherein the $C_{1-6}$ alkyl and the $C_{3-6}$ cycloalkyl are each optionally substituted with one or more substituents independently selected from halo, CN, $—OR^{9a}$ and $C_{1-6}$ alkyl optionally substituted with one or more halo;

$R^{9a}$ is H or $C_{1-6}$ alkyl optionally substituted with one or more halo;

$R^{11}$ and $R^{12}$ are each independently H or $C_{1-6}$ alkyl, or $R^{11}$ and $R^{12}$ together with the nitrogen atom from which they are attached form a 4- to 7-membered monocyclic heterocyclyl optionally substituted with one or more substituents independently selected from $C_{1-6}$ alkyl, halo, OH, and $C_{1-6}$ alkoxy;

or any two of $R^4$, $R^5$, $R^9$, $R^{13}$, $R^{14}$, $R^{15}$, $R^{16}$, $R^{17}$ and $R^{18}$ together form a $—C_{1-5}$ alkylene- optionally substituted with one or more substituents independently selected from halo, $—OR^a$, $—N(R^a)_2$ and $C_{1-6}$ alkyl;

$R^a$, for each occurrence, is independently H or $C_{1-6}$ alkyl optionally substituted with one or more halo;

$R^{19a}$ and $R^{19b}$ are each independently H or $C_{1-6}$ alkyl optionally substituted with one or more halo or $R^{9a}$ and $R^{9b}$ together with the carbon atom from which they are attached form —C(═O)—;

n1 is 0, 1 or 2; and n2 is 0, 1 or 2, provided when X is $NR^6$ or O, n1 and n2 cannot be 0.

In a third aspect, the present invention provides a composition (e.g., a pharmaceutical composition) comprising a compound disclosed herein, or a salt (e.g., a pharmaceutically acceptable salt) thereof. The composition may also include a carrier (e.g., a pharmaceutically acceptable carrier).

In a fourth aspect, the present invention also includes a method of treating a disease or disorder in a subject comprising administering to the subject in need thereof a therapeutically effective amount of a compound disclosed herein, or a salt (e.g., a pharmaceutically acceptable salt) thereof, wherein the disease or disorder is mediated by Z11 TUTase. Also included in the present invention is a compound disclosed herein, or a salt (e.g., a pharmaceutically acceptable salt) thereof for use in a method of treating a disease or disorder in a subject, wherein the disease or disorder is mediated by Z11 TUTase. The present invention also includes use of a compound disclosed herein, or a salt (e.g., a pharmaceutically acceptable salt) thereof for the manufacture of a medicament for treating a disease or disorder in a subject, wherein the disease or disorder is mediated by Z11 TUTase.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. In the event that one or more of the incorporated literature references, patents or similar materials differ from or contradict this application, including but not limited to defined terms, term usage, described techniques or the like, this application controls.

It should be understood that any of the embodiments described herein, including those described under different aspects of the invention (e.g., compounds, compositions, methods of making and using) and different parts of the specification can be combined with one or more other embodiments of the invention, unless explicitly disclaimed or improper. Combination of embodiments are not limited to those specific combinations claimed via the multiple dependent claims.

Definitions and General Terminology

As used herein, the term "alkyl" refers to a fully saturated branched or unbranched hydrocarbon moiety having 1 to 20 carbon atoms. Preferably the alkyl comprises 1 to 6 carbon atoms, or 1 to 4 carbon atoms. Representative examples of alkyl include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Alkylene" as used herein refers to a saturated linear or branched-chain divalent hydrocarbon radical of one to twenty carbon atoms ($C_{1-20}$), examples of which include, but are not limited to, those having the same core structures of the alkyl groups as exemplified above. "Divalent" means that the alkylene has two points of attachment to the remainder of the molecule. Preferably, the alkylene has one to sixteen carbon atoms ($C_{1-16}$) or one to ten carbon atoms ($C_{1-10}$). More preferably, the alkylene has one to seven carbon atoms ($C_{1-7}$), one to six carbon atoms ($C_{1-6}$), one to five carbon atoms ($C_{1-8}$), one to four carbon atoms ($C_{1-4}$) or one to three carbon atoms ($C_{1-3}$). In certain embodiments, alkylene is preferably $-(CH_2)-$, $-(CH_2)_2-$ or $-(CH_2)_3-$.

As used herein, the term "carbocyclyl" refers to a saturated or unsaturated monocyclic or bicyclic (e.g., fused, bridged, or spiro bicyclic) hydrocarbon ring having 3-12 ring carbon atoms. The term "carbocyclyl" encompasses cycloalkyl groups and aromatic groups (i.e., aryl). In certain embodiments, the carbocyclyl is a 3- to 7-membered monocyclic carbocyclyl. Exemplary 3- to 7-membered monocyclic carbocyclyls include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl.

The term "cycloalkyl" refers to completely saturated monocyclic or bicyclic (e.g., fused, bridged, or spiro bicyclic) hydrocarbon ring having 3-12 ring carbon atoms, 3-8 ring carbon atoms, 3-6 ring carbon atoms, or 5-7 ring carbon atoms. Exemplary bicyclic carbocyclyl groups include bicyclo[2.1.1]hexyl, bicyclo[2.2.1]heptyl, bicyclo[2.2.1]heptenyl, 6,6-dimethylbicyclo[3.1.1]heptyl, or 2,6,6-trimethylbicyclo[3.1.1]heptyl, spiro[2.2]pentanyl, and spiro[3.3]heptanyl. Examples of monocyclic cycloalkyl groups include, but are not limited to, cyclopropyl, cyclobutyl, cyclopentyl, cyclohexyl, cycloheptyl, cyclooctyl, cyclononyl, cyclodecyl, cycloundecyl, cyclododecyl, and the like. Preferably, the cycloalkyl is 3 to 8 membered monocyclic ring, 3 to 7 membered monocyclic ring or 3 to 6 membered monocyclic ring. Even more preferably, the cycloalkyl is cyclopropyl, cyclobutyl, cyclopentyl, or cyclohexyl.

The term "aryl" refers to an aromatic hydrocarbon ring system having six to fourteen carbon ring atoms. The term "aryl" may be used interchangeably with the terms "aryl ring" "aromatic ring," "aryl group" and "aromatic group." "Aryl group" also includes an aromatic hydrocarbon ring system fused to a non-aromatic carbocyclic ring system, such as a cycloalkyl group. Examples includes phenyl, naphthyl, anthracenyl, 1,2-dihydronaphthyl, 1,2,3,4-tetrahydronaphthyl, fluorenyl, indanyl, indenyl and the like. An aryl group is monovalent, i.e., has one point of attachment to the remainder of the molecule. A "substituted aryl group" is substituted at any one or more substitutable ring atom, which is a ring carbon atom bonded to a hydrogen. Preferably, the aryl is phenyl.

The term "alkoxy" as used herein refers to the group —OR, in which R is an alkyl as defined above. Preferably, the alkyl group has one to sixteen carbon atoms ($C_{1-16}$) or one to ten carbon atoms ($C_{1-10}$). More preferably, the alkyl group has one to eight carbon atoms ($C_{1-8}$), one to seven carbon atoms ($C_{1-7}$), one to six carbon atoms ($C_{1-6}$), one to four carbon atoms ($C_{1-4}$) or one to three carbon atoms ($C_{1-3}$). Non-limiting examples include: $-OCH_3$, $-OCH_2CH_3$, $-OCH_2CH_2CH_3$, $-OCH(CH_3)_2$, $-OCH(CH_2)_2$, —O-cyclopropyl, —O-cyclobutyl, —O-cyclopentyl and —O-cyclohexyl.

The terms "heterocycle," "heterocyclyl," "heterocyclic" and "heterocyclic ring" are used interchangeably herein and refer to a cyclic group which contains at least one heteroatom, e.g., N, O or S, and may be aromatic (heteroaryl) or non-aromatic. It can be monocyclic or bicyclic (e.g., fused, bridged or spiro bicyclic ring) having 3 to 12 ring members, preferably, 4 to 12 ring members, 3 to 7 ring members, 3 to 6 ring members, 4 to 7 ring members, 5 to 7 ring members, or 4 to 6 ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings.

In one embodiment, a heterocyclyl is a 3- to 7-membered monocyclic heterocyclyl (saturated or partially unsaturated (i.e., non-aromatic)) having 1-2 heteroatoms selected from O, S and N. Examples of 3- to 7-membered monocyclic heterocyclyl include, but are not limited to, aziridinyl, oxiranyl, thirranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl. In one embodiment, a heterocyclyl is a 4- to 7-membered monocyclic heterocyclyl (saturated or partially unsaturated (i.e., non-aromatic)). In one embodiment, a heterocyclyl is a 5-to 7-membered monocyclic heterocyclyl (saturated or partially unsaturated).

In one embodiment, a heterocyclyl is a 4- to 6-membered monocyclic heterocyclyl (saturated or partially unsaturated) having 1-2 heteroatoms selected from O, S and N. Examples of a 4- to 6-membered monocyclic heterocyclic include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a 4- to 6-membered saturated monocyclic heterocyclyl. In one embodiment, the 4- to 6-membered saturated monocyclic heterocyclyl contains 1-2 heteroatoms independently selected from O, S and N. Examples of saturated 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is azetidinyl, pyrrolidinyl, piperidinyl, oxetanyl, tetrahydrofuranyl, or tetrahydropyranyl.

In one embodiment, a heterocyclyl is a 7 to 10-membered saturated or partially saturated bicyclic (e.g., fused, bridged or spiro) heterocyclyl. In one embodiment, a 7 to 10-membered saturated or partially saturated bicyclic heterocyclyl is a fused bicyclic heterocyclyl having a monocyclic heterocycle fused to a carbocycle or a heterocycle, wherein at least one of the ring is non-aromatic. Examples of a 7 to 10-membered saturated or partially saturated fused bicyclic heterocyclyl include, but are not limited to, 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, 1,3-dihydroisobenzofuranyl, and isochromanyl. In one embodiment, a 7 to 10-membered saturated or partially saturated bicyclic heterocyclyl is a spiro bicyclic heterocyclyl, such as oxaspiro[2.4]heptanyl, 2,6-diazaspiro[3.3]heptanyl, oxa-6-azaspiro[3.3]heptanyl, 2,2,6-diazaspiro[3.3]heptanyl, 3-azaspiro[5.5]undecanyl, 3,9-diazaspiro[5.5]undecanyl, 7-azaspiro[3.5]nonanyl, 2,6-diazaspiro[3.4]octanyl, 8-azaspiro[4.5]decanyl, 1,6-diazaspiro[3.3]heptanyl, 5-azaspiro[2.5]octanyl, 4,7-diazaspiro[2.5]octanyl, 5-oxa-2-azaspiro[3.4]octanyl, 6-oxa-1-azaspiro[3.3]heptanyl, 3-azaspiro[5.5]undecanyl, 3,9-diazaspiro[5.5]undecanyl, and the like. In one embodiment, the 7 to 10-membered saturated or partially saturated bicyclic heterocyclyl is 2-azaspiro[3.3]heptan-6-yl.

As used herein, "heteroaryl" can be used interchangeably with "heteroaromatic," "heteroaryl ring," "heteroaryl group," "heteroaromatic ring," and "heteroaromatic group." It refers to aromatic ring systems having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings (e.g., bicyclic) in which a monocyclic heteroaromatic ring is fused to one or more other aromatic or heteroaromatic rings. Preferably, the heteroaryl is 5 to 10-membered.

In one embodiment, a heteroaryl is "5 or 6-membered monocyclic heteroaryl," which means a monocyclic aromatic ring system having five or six ring atoms selected from carbon and at least one (typically 1 to 3, more typically 1 or 2) heteroatoms (e.g., oxygen, nitrogen or sulfur). Examples of a 5 or 6-membered monocyclic heteroaryl include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridinyl (or pyridyl, e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), thienyl (e.g., 2-thienyl, 3-thienyl), pyranyl, thiopyranyl, pyrazinyl, oxazinyl, thiazinyl, dioxinyl, dithiinyl, oxathianyl, triazinyl and tetrazinyl. Preferably, the 5 or 6-membered monocyclic heteroaryl is pyridinyl, pyridazinyl, or pyrazinyl.

In one embodiment, a heteroaryl is "9 or 10-membered bicyclic heteroaryl," which refers to bicyclic aromatic ring system with 9 or 10 ring atoms selected from carbon and at least one (typically 1 to 3, more typically 1 or 2) heteroatoms (e.g., oxygen, nitrogen or sulfur), in which a monocyclic heteroaromatic ring fused to an aromatic or heteroaromatic ring. Examples of a 9 or 10-membered bicyclic heteroaryl include, but are not limited to, azaindolyl, benzimidazolyl, benzofuryl, benzoisoxazolyl, benzoisothiazolyl, benzothiadiazolyl, benzothiazolyl, benzothienyl, benzotriazolyl, benzoxadiazolyl, benzoxazolyl, furopyridinyl, imidazopyridyl, imidazopyrimidinyl, indazolyl, indolizinyl, indolyl, isoquinolinyl, oxazolopyridinyl, purinyl, pyrazolopyrimidinyl, pyrazolopyrazinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinoxalinyl, quinolinyl, isoquinolinyl, thiazolopyridinyl, thienopyridinyl, thienopyrimidinyl, thienopyrazinyl, napthyridyl, and the like. Preferably, the 9 or 10-membered bicyclic heteroaryl is indolyl, indazolyl, or benzimidazolyl.

The term "fused ring system", as used herein, is a ring system that has two rings each of which are independently selected from a carbocyclyl or a heterocyclyl, wherein the two ring structures share two adjacent ring atoms. In one embodiment, a fused ring system have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, and S. In one embodiment, a bridged ring system have from 6 to 12 ring members.

The term "spiro ring system," as used herein, is a ring system that has two rings each of which are independently selected from a carbocyclyl or a heterocyclyl, wherein the two ring structures having one ring atom in common. In one embodiment, spiro ring systems have from 5 to 12 ring members.

The heterocycle or heteroaryl groups may be carbon (carbon-linked) or nitrogen (nitrogen-linked) attached where such is possible. By way of example and not limitation, carbon bonded heterocycle or heteroaryl groups are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydro-pyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycle or heteroaryl heteroarylene groups are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole or isoindoline, or position 4 of a morpholine.

The heteroatoms present in heteroaryl or heterocyclyl can include the oxidized forms such as NO, SO, and $SO_2$.

The term "Halogen" or "halo" as used herein refers to F, Cl, Br or I. Preferably, halo is F, Cl, or Br.

If a group is described as being "optionally substituted," the group may be either (1) not substituted, or (2) substituted. If a carbon of a group is described as being optionally substituted with one or more of a list of substituents, one or more of the hydrogen atoms on the carbon (to the extent there are any) may separately and/or together be replaced with an independently selected optional substituent. If a group is substituted with one or more substituents, it can be substituted with 1, 2, 3, 4, 5, 6, or more independently selected substituents. In certain embodiments, it can be substituted with 1, 2, 3, 4, 5 or 6 independently selected substituents. In certain embodiments, it can be substituted with 1, 2 or 3 independently selected substituents.

Suitable substituents for an alkyl, alkenyl, alkynyl, cycloalkyl, carbocyclyl, aryl, heteroaryl, and heterocyclyl are those which do not significantly adversely affect the biological activity of the bifunctional compound. Unless otherwise specified, exemplary substituents for these groups include linear, branched or cyclic alkyl, alkenyl or alkynyl having from 1 to 10 carbon atoms, aryl, heteroaryl, heterocyclyl, halogen, guanidinium [$—NH(C{=}NH)NH_2$], $—OR^{100}$, $NR^{101}R^{102}$, $—NO_2$, $—NR^{101}COR^{102}$, $—SR^{100}$, a sulfoxide represented by $—SOR^{101}$, a sulfone represented by $—SO_2R_{101}$, a sulfonate $—SO_3M$, a sulfate $—OSO_3M$, a sulfonamide represented by $—SO_2NR^{101}R^{102}$, cyano, an azido, $—COR^{101}$, $—OCOR^{101}$, $—OCONR^{101}R^{102}$ and a polyethylene glycol unit $(—OCH_2CH_2)_nR^{101}$ wherein M is H or a cation (such as $Na^+$ or $K^+$); $R^{101}$, $R^{102}$ and $R^{103}$ are each independently selected from H, linear, branched or cyclic alkyl, alkenyl or alkynyl having from 1 to 10 carbon atoms, a polyethylene glycol unit $(—OCH_2CH_2)_n—R^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and $R^{104}$ is H or a linear or branched alkyl having 1 to 4 carbon atoms, wherein the alkyl, alkenyl, alkynyl, aryl, heteroaryl and heterocyclyl in the groups represented by $R^{100}$, $R^{101}$, $R^{102}$, $R^{103}$ and $R^{104}$ are optionally substituted with one or more (e.g., 2, 3, 4, 5, 6 or more) substituents independently selected from halogen, —OH, —CN, $—NO_2$, and unsubstituted linear or branched alkyl having 1 to 4 carbon atoms. Preferably, the substituent for the optionally substituted alkyl, alkylene, cycloalkylene, arylene, and heteroarylene described above is selected from the group consisting of halogen, —CN, $—NR^{101}R^{102}$, $—CF_3$, $—OR^{100}$, aryl, heteroaryl, heterocyclyl, $—SR^{101}$, $—SOR^{101}$, $—SO_2R^{101}$, and $—SO_3M$. Alternatively, the suitable substituent is selected from the group consisting of -halogen, —OH, $—NO_2$, —CN, $C_{1-4}$ alkyl, $—OR^{100}$, $NR^{101}R^{102}$, $—NR^{101}COR^{102}$, $—SR^{100}$, $—SO_2R^{101}$, $—SO_2NR^{101}R^{102}$, $—COR^{101}$, $—OCOR^{101}$, and $—OCONR^{101}R^{102}$, wherein $R^{100}$, $R^{101}$, and $R^{102}$ are each independently —H or $C_{1-4}$ alkyl.

As used herein, an integer "between" x and y includes integers x and y unless otherwise specified to the contrary. For example, "an integer between 1 and 5" can be 1, 2, 3, 4, or 5.

The term "salt" as used herein refers to organic or inorganic salts of a bifunctional compound of the invention. Preferably, a salt is a pharmaceutically acceptable salt. Other non-pharmaceutically acceptable salts are also included in the present invention. The salts include salts, formed by reacting a bifunctional compound of the invention, which comprises a basic group, with an inorganic acid or organic acid (such as a carboxylic acid), and salts, formed by reacting a bifunctional compound of the invention, which comprises an acidic group, with an inorganic base or organic base (such as an amine). Exemplary salts include those pharmaceutically acceptable salts described immediately below.

The term "pharmaceutically acceptable salt" as used herein refers to pharmaceutically acceptable organic or inorganic salts of a bifunctional compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention contains one or more basic moieties, desired salts (e.g., pharmaceutically acceptable salts) may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention contains one or more acidic moieties, desired salts (e.g., pharmaceutically acceptable salts) may be prepared by any suitable method, for example, treatment of the free acid with an inorganic, such as an alkali metal hydroxide or alkaline earth metal hydroxide, organic base, such as an amine (primary, secondary or tertiary), or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The term "treat", "treatment" or "treating" refers to reversing, alleviating, reducing the likelihood of developing, or inhibiting the progress of a disease or disorder, or one or more symptoms thereof. In some embodiments, treatment may be administered after one or more symptoms have developed, i.e., therapeutic treatment. In some embodiments, treatment may be administered in the absence of symptoms. For example, treatment may be administered to a susceptible subject prior to the onset of symptoms (e.g., in light of a history of symptoms and/or in light of genetic or other susceptibility factors), i.e., prophylactic treatment. Treatment may also be continued after symptoms have resolved, for example, to prevent or delay their recurrence.

The term "effective amount" refers to an amount of an active compound sufficient to carry out a specifically stated purpose, e.g., inhibiting the activity of Z11.

The term "therapeutically effective amount" means that an amount of an active compound that elicits the desired biological response in a subject, e.g., "treating" a disease or disorder in a subject. Such response includes alleviation of the symptoms of the disease or disorder being treated, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the therapeutically effective amount is well within the capability of those skilled in the art, especially in light of the detailed disclosure provided herein. Toxicity and therapeutic efficacy of a compound of the present invention can be determined by standard pharmaceutical procedures in cell cultures and in experimental animals. The therapeutically effective amount of a compound of the present invention or other therapeutic agent to be administered to a subject will depend on the stage, category and status of the disease and characteristics of the subject, such as general health, age, sex, body weight and drug tolerance. The therapeutically effective amount of the compound of the present invention or other therapeutic agent to be administered will also depend on administration route and dosage form. Dosage amount and interval can be adjusted individually to provide plasma levels of the active compound that are sufficient to maintain desired therapeutic effects.

Exemplary Compounds

In a first aspect, the present invention is directed to a compound represented by Formula (I) or (I'), or a pharmaceutically acceptable salt thereof, wherein the variables are described above for Formula (I) or (I').

In certain embodiments, for compounds of Formula (I) and (I') described above, any two of $R^4$, $R^5$, $R^9$, $R^{13}$, $R^{14}$, $R^{15}$, $R^{16}$, $R^{17}$ and $R^{18}$ together form a —$C_{1-5}$alkylene- optionally substituted with one or more substituents independently selected from halo and $C_{1-6}$alkyl. For example, $R^{13}$ and $R^{15}$ together with the carbon atoms to which they are attached can form a cycloalkyl that is fused with the ring containing variables V and X. In another example, $R^{13}$ and $R^9$ together with the carbon atoms to which they are attached and the ring containing variables V and X form a bridged bicyclic ring.

In a first embodiment, a compound of the present invention is represented by Formula (Ia) or (Ib):

(Ia)

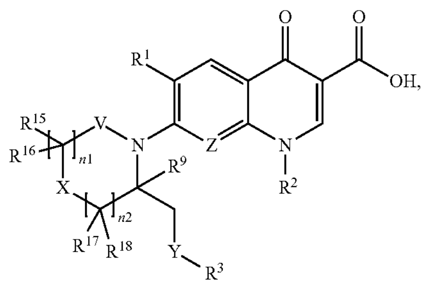

or (Ib)

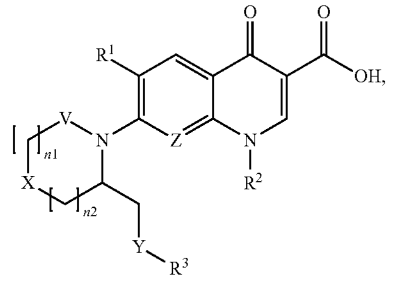

, or a pharmaceutically acceptable salt thereof, wherein:

X is $CR^4R^5$, $NR^6$ or O;

Y is $NR^7$ or O;

Z is $CR^8$ or N;

$R^1$ is halo, CN, —$OR^{1a}$, —C≡CH, or $C_{1-6}$ alkyl, wherein the $C_{1-6}$alkyl is optionally substituted with one or more $R^{10}$;

$R^{1a}$ is H or $C_{1-6}$alkyl optionally substituted with one or more $R^{10}$;

$R^{10}$, for each occurrence, is independently selected from halo, CN and $OR^{10a}$;

$R^{10a}$, for each occurrence, is independently selected from H and $C_{1-6}$ alkyl;

$R^2$ is a 3 to 12-membered carbocyclyl or a 3 to 12-membered heterocyclyl, wherein the 3 to 12-membered carbocyclyl and the 3 to 12-membered heterocyclyl represented by $R^2$ are optionally substituted with one or more $R^{20}$;

$R^{20}$, for each occurrence, is independently selected from H, halo, CN, oxo, —$C(O)R^{20a}$, —$C(O)_2R^{20a}$, —$C(O)NR^{20a}$, —$N(R^{20a})_2$, —$N(R^{20a})C(O)R^{20a}$, —$N(R^{20a})C(O)_2R^{20a}$, —$N(R^{20a})C(O)N(R^{20a})_2$, —$N(R^{20a})S(O)_2R^{20a}$, —$OR^{20a}$, —$OC(O)R^{20a}$, —$OC(O)N(R^{20a})_2$, —$SR^{20a}$, —$S(O)_2R^{20a}$, —$S(O)N(R^{20a})_2$, —$S(O)_2N(R^{20a})_2$, $C_{1-6}$ alkyl, $C_{3-8}$cycloalkyl, and 4- to 7-membered monocyclic heterocyclyl, wherein the $C_{1-6}$alkyl, $C_{3-8}$cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$ alkyl, $C_{3-8}$cycloalkyl and 4- to 7-membered monocyclic heterocyclyl, wherein the $C_{1-6}$alkyl, $C_{3-8}$cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —$N(R^{25a})_2$, —$OR^{25a}$, phenyl optionally substituted with $C_{1-6}$alkyl, halo, —$N(R^{25a})_2$ or —$OR^{25a}$; and $R^{25a}$ is H or $C_{1-6}$ alkyl;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, —$C(O)R^{30a}$, —$C(O)_2R^{30a}$, —$C(O)NR^{30a}$, —$N(R^{30a})_2$, —$N(R^{30a})C(O)R^{30a}$, —$N(R^{30a})C(O)_2R^{30a}$, —$N(R^{30a})C(O)N(R^{30a})_2$, —$N(R^{30a})S(O)_2R^{30a}$, —$OR^{30a}$, —$OC(O)R^{30a}$, —$OC(O)N(R^{30a})_2$, —$SR^{30a}$, —$S(O)_2R^{30a}$, —$S(O)N(R^{30a})_2$, —$S(O)_2N(R^{30a})_2$, $C_{1-6}$ alkyl, $C_{3-8}$cycloalkyl, and 4- to 7-membered monocyclic heterocyclyl, wherein the $C_{1-6}$alkyl, $C_{3-8}$cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$cycloalkyl and 4- to 7-membered monocyclic heterocyclyl, wherein the $C_{1-6}$ alkyl, $C_{3-8}$cycloalkyl and 4- to 7-membered monocyclic heterocyclyl represented by $R^{30a}$ are each optionally substituted with one or more $R^{35}$;

$R^{35}$, for each occurrence, is independently H, $C_{1-6}$ alkyl, halo and —$OR^{35a}$; and $R^{35a}$ is H or $C_{1-6}$ alkyl;

alternatively, when Y is $NR^7$, $R^7$ and $R^3$ together with the N atom from which $R^7$ is attached can form a 4 to 12-membered heterocyclyl optionally substituted with or more $R^{30}$.

$R^4$ and $R^5$ are each independently selected from H, $C_{1-6}$ alkyl, halo, —CN and —$OR^{4a}$, wherein the $C_{1-6}$ alkyl is optionally substituted with one or more substituents independently selected from halo, CN and —$OR^{4a}$;

$R^{4a}$ is H or $C_{1-6}$ alkyl optionally substitute with one or more halo;

$R^6$ is H or $C_{1-6}$ alkyl optionally substituted with one or more substituents independently selected from halo, CN and —$OR^{6a}$;

$R^{6a}$ is H or $C_{1-6}$alkyl optionally substitute with one or more halo;

$R^7$ is H or $C_{1-6}$ alkyl optionally substituted with one or more halo;

$R^8$ is H, halo, CN, —$OR^{8a}$ or $C_{1-6}$ alkyl optionally substituted with one or more halo;

$R^{8a}$ is H or $C_{1-6}$alkyl optionally substituted with one or more halo;

n1 is 0, 1 or 2; and n2 is 0, 1 or 2, or, for formula (I) or (Ia), any two of $R^4$, $R^5$, $R^9$, $R^{13}$, $R^{14}$, $R^{15}$, $R^{16}$, $R^{17}$ and $R^{18}$ together form a —$C_{1-5}$ alkylene- optionally substituted with one or more substituents independently selected from halo, —$OR^a$, —$N(R^a)_2$ and $C_{1-6}$ alkyl; wherein $R^a$, for each occurrence, is independently H or $C_{1-6}$ alkyl optionally substituted with one or more halo.

In a second embodiment, for compounds of Formula (I), (I'), (Ia), or (Ib), or a pharmaceutically acceptable salt thereof described in the first aspect or first embodiment, X is $CH_2$; and the remaining variables are as defined in the first aspect or the first embodiment.

In a third embodiment, for compounds of Formula (I), (I'), (Ia), or (Ib), or a pharmaceutically acceptable salt thereof described in the first aspect or the first or second embodiment, n1 and n2 are both 0; n1 and n2 are both 1; n1 is 0 and n2 is 1; or n1 is 1 and n2 is 0; and the remaining variables are as defined in the first aspect or in the first or second embodiment.

In a fourth embodiment, for compounds of Formula (I), (I'), (Ia), or (Ib), or a pharmaceutically acceptable salt thereof described in the first aspect or the first or second embodiment, X is O; and n1 and n2 are both 1; and the remaining variables are as defined in the first aspect or the first embodiments.

In a fifth embodiment, the invention provides a compound of Formula (IIa) or (IIb):

(IIa)

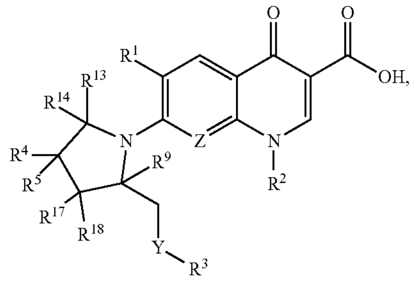

or (IIb)

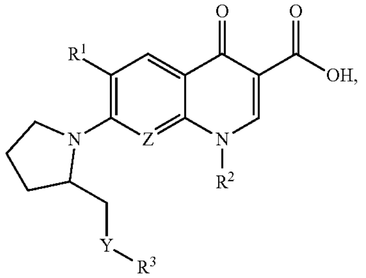

or a pharmaceutically acceptable salt thereof, wherein the variables are described for Formula (Ia) or (Ib) in the first embodiment.

In a sixth embodiment, the compound of Formula (IIa) or (IIb) or a pharmaceutically acceptable salt thereof is represented by Formula (II-1a) or (II-1b) respectively:

(II-1a)

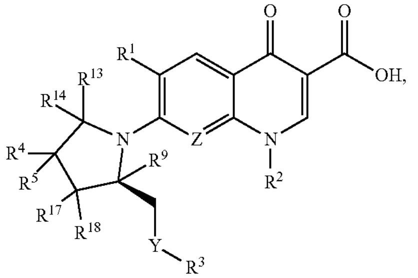

or

-continued (II-1b)

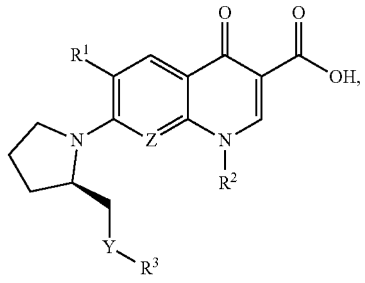

or a pharmaceutically acceptable salt thereof, wherein the variables are as defined for Formula (IIa) or (IIb) in the fifth embodiment.

In a specific embodiment, for compounds of Formula (IIa), (IIb), (II-1a) or (II-1b), or a pharmaceutically acceptable salt thereof described in the fifth or sixth embodiment, Y is NH or O; and the variables are as in the fifth or sixth embodiment.

In a seventh embodiment, the invention provides a compound of Formula (IIIa) or (IIIb):

(IIIa)

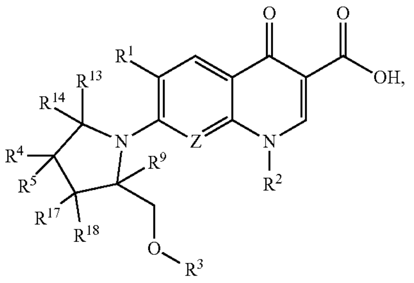

or (IIIb)

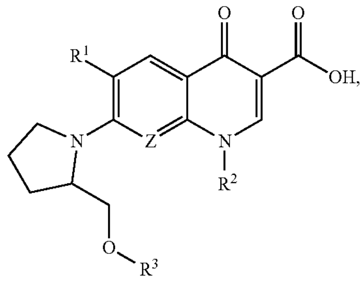

or a pharmaceutically acceptable salt thereof, wherein the variables are as defined for Formula (Ia) or (Ib) in the first embodiment.

In an eighth embodiment, a compound of Formula (IIIa) or (IIIb) or a pharmaceutically acceptable salt thereof is represented by Formula (IIIa-1a) or (III-1b) respectively:

(III-1a)

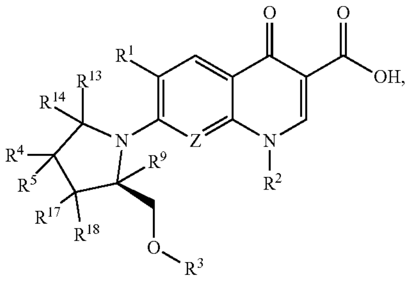

or (III-1b)

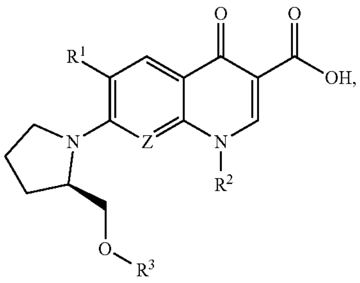

or a pharmaceutically acceptable salt thereof, wherein the variables are as defined in the seventh embodiment.

In a ninth embodiment, a compound of Formula (IIIa) or (IIIb), or a pharmaceutically acceptable salt thereof described in the seventh embodiment is represented by Formula (IVa) or (IVb):

(IVa)

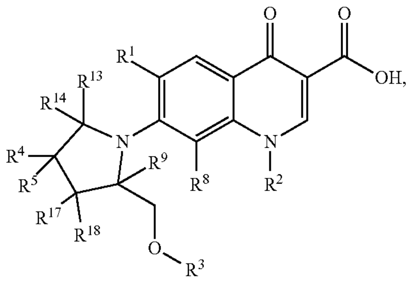

(IVb)

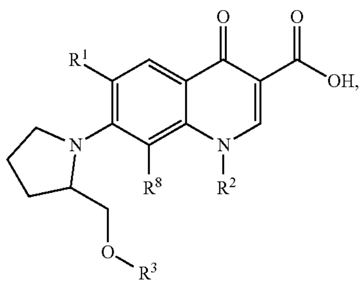

or a pharmaceutically acceptable salt thereof, wherein the variables are as defined for Formula (IIIa) or (IIIb) in the seventh embodiment.

In a tenth embodiment, a compound of Formula (IVa) or (IVb) or a pharmaceutically acceptable salt thereof described in the ninth embodiment is represented by Formula (IV-1a) or (IV-1b):

(IV-1a)

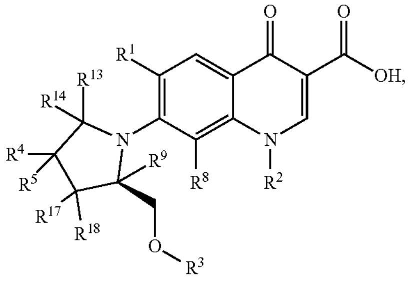

or (IV-1b)

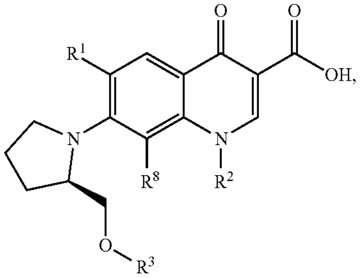

or a pharmaceutically acceptable salt thereof, wherein the variables are as defined for Formula (IVa) or (IVb) in the ninth embodiment.

In an eleventh embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a) and (IV-1b) or a pharmaceutically acceptable salt thereof), $R^8$ is H, halo, or $OR^{8a}$; and the remaining variables are as defined in the first aspect or in the first, second, third, fourth, fifth, sixth, seventh, eighth, ninth or tenth embodiment or any specific embodiments described therein.

In a twelfth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a) and (IV-1b) or a pharmaceutically acceptable salt thereof), $R^8$ is H, F, Cl or $—OCH_3$; and the remaining variables are as defined in the first aspect or in the first, second, third, fourth, fifth, sixth, seventh, eighth, ninth or tenth embodiment or any specific embodiments described therein. In a specific embodiment, $R^8$ is H.

In a thirteenth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a) and (IV-1b) or a pharmaceutically acceptable salt thereof), $R^1$ is F, Cl, Br, CN, $—OR^9$ or $C_{1-6}$alkyl; and the remaining variables are as defined in the first aspect or the first, second, third, fourth, fifth, sixth, seventh, eighth, ninth, tenth, eleventh or twelfth embodiments or any specific embodiments described therein. In a specific embodiment, $R^1$ is Cl, Br, CN, $—OR^9$ or $C_{1-6}$alkyl. In a more specific embodiment, $R^1$ is Cl, CN or $CH_3$.

In a fourteenth embodiment, the present invention provides a compound represented by the following formula:

(IVAa)

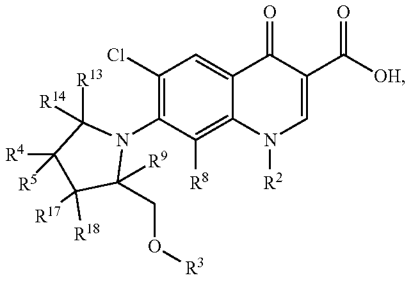

(IVBa)

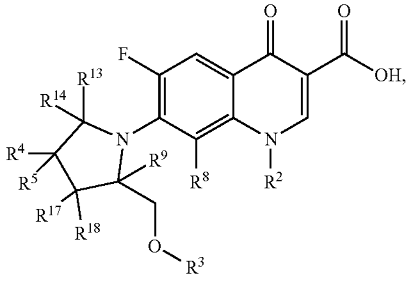

(IVCa)

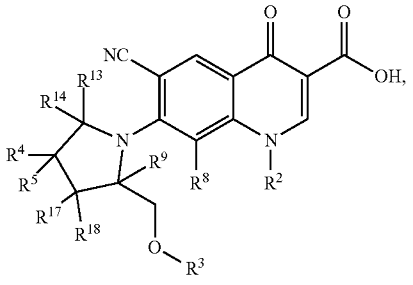

(IVDa)

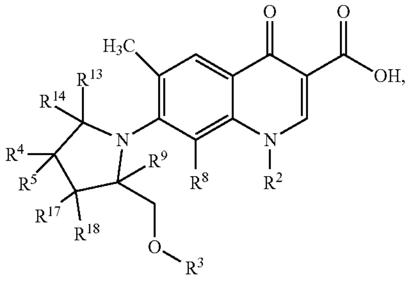

(IVAb)

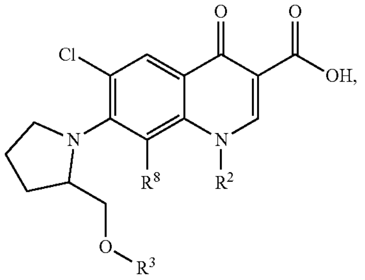

-continued
(IVBb)
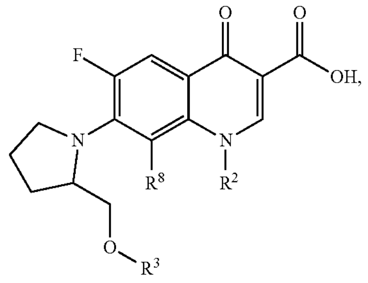
(IVCb)
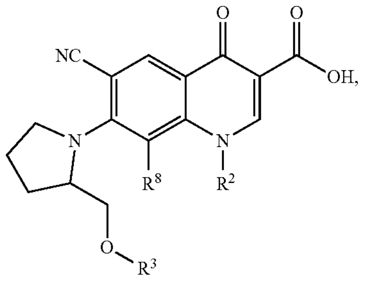
or
(IVDb)
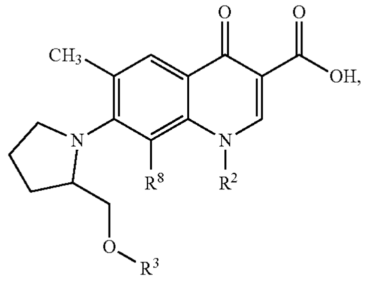
or a pharmaceutically acceptable salt thereof, wherein $R^8$ is H or F; and the remaining variables are as defined in the first embodiment.
In a fifteenth embodiment, the invention provides a compound represented by the following formula:
(IVA-1a)
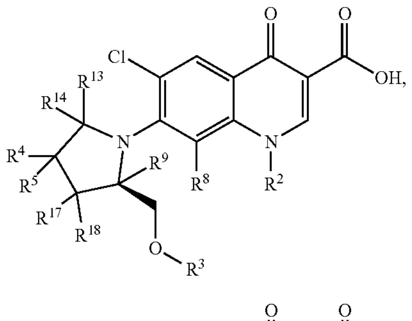
(IVB-1a)
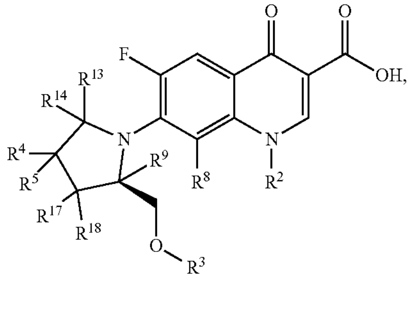
-continued
(IVC-1a)
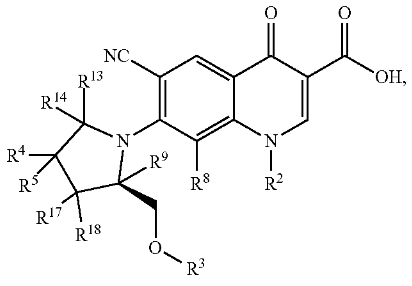
(IVD-1a)
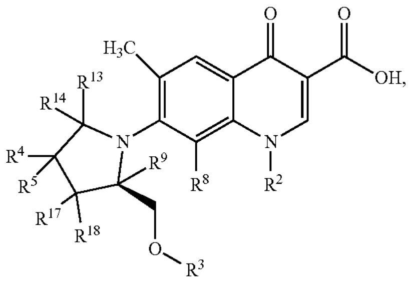
(IVA-1b)
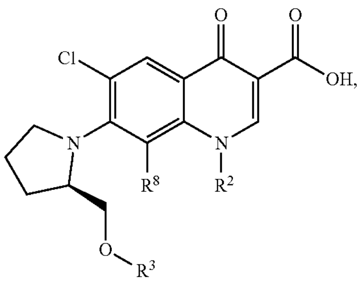
(IVB-1b)
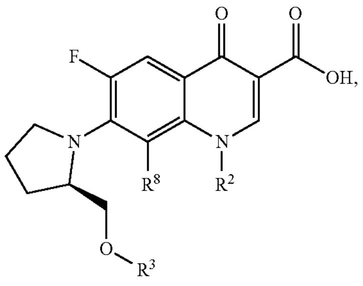
(IVC-1b)
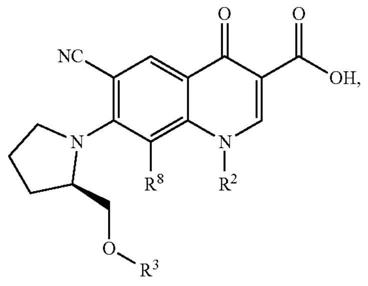
or -continued (IVD-1b)

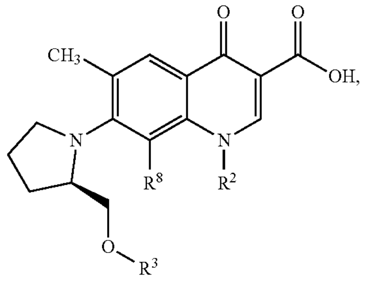

or a pharmaceutically acceptable salt thereof, wherein the variables are as defined in the fourteenth embodiment.

In a sixteenth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), or (IVD-1b) or a pharmaceutically acceptable salt thereof), $R^3$ is phenyl, a 5 or 6-membered monocyclic heteroaryl or a 9 or 10-membered bicyclic heteroaryl, wherein the phenyl, 5 or 6-membered monocyclic heteroaryl and 9 or 10-membered bicyclic heteroaryl represented by $R^3$ are each optionally substituted with one to three $R^{30}$; and the remaining variables are as defined in the first, second, third, fourth, fifth, sixth, seventh, eighth, ninth, tenth, eleventh, twelfth, thirteenth, fourteenth or fifteenth embodiment or any specific embodiments described therein.

In a seventeenth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), or (IVD-1b)) or a pharmaceutically acceptable salt thereof), $R^3$ is phenyl, pyridinyl, pyrimidinyl, pyrazinyl, pyridazinyl, 1H-pyrrolo[2,3-c]pyridinyl or 1H-imidazo[4,5-c]pyridinyl, each of which is optionally substituted with one to three $R^{30}$; and the remaining variables are as defined in the sixteenth embodiment.

In an eighteenth embodiment, for compounds or pharmaceutically acceptable salts thereof described in the sixteenth or seventeenth embodiment, $R^{30}$, for each occurrence, is H, halo, CN, $—C(O)NR^{30a}$, $—N(R^{30a})_2$, $—N(R^{30a})C(O)R^{30a}$, $—N(R^{30a})S(O)_2R^{30a}$, $—OR^{30a}$, and $C_{1-6}$alkyl, wherein the $C_{1-6}$alkyl is optionally substituted with one to three $R^{31}$;

$R^{30a}$, for each occurrence, is independently H or $C_{1-6}$alkyl optionally substituted with one to three $R^{35}$;

$R^{35}$, for each occurrence, is independently H, halo and $—OR^{35a}$; and $R^{35a}$ is H or $C_{1-3}$alkyl; and the remaining variables are as defined in the sixteenth or seventeenth embodiment.

In a specific embodiment, for compounds or a pharmaceutically acceptable salt thereof described in the eighteenth embodiment, $R^{30}$, for each occurrence, is H, halo, CN, $—OR^{30a}$ and $C_{1-6}$alkyl optionally substituted with one to three halo; $R^{30a}$ is H or $C_{1-6}$alkyl optionally substituted with one to three halo; and the remaining variables are as defined in the eighteenth embodiment.

In another specific embodiment, for compounds or a pharmaceutically acceptable salt thereof described in the eighteenth embodiment, $R^{30}$, for each occurrence, is H, F, Cl, Br, CN, $—OCH_3$, $—CH_3$, $—CH_2CH_3$ or $—CF_3$; and the remaining variables are as defined in the eighteenth embodiment.

In a nineteenth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), or (IVD-1b) or a pharmaceutically acceptable salt thereof), $R^3$ is selected from 3-chloropyridin-2-yl, 3-methylpyridin-2-yl, 3-bromopyridin-2-yl, 3-cyanopyridin-2-yl, 3-ethylpyridin-2-yl, 3-fluoropyridin-2-yl, 3-methoxypyridin-2-yl, 3-trifluoromethylpyridin-2-yl, pyridin-2-yl, 1H-pyrrolo[2,3-c]pyridin-5-yl, 1H-pyrrolo[2,3-c]pyridin-7-yl, 1H-pyrrolo[2,3-c]pyridin-6-yl, 1H-imidazo[4,5-c]pyridin-4-yl, 2,6-dimethylphenyl, phenyl, pyradzin-3-yl, pyrimidin-4-yl, 5-methylpyridin-2-yl, 4-methylpyridin-2-yl, pyrimidin-2-yl, pyrazin-2-yl, pyridazin-3-yl, and pyridin-3-yl, and the remaining variables are as defined in the first, second, third, fourth, fifth, sixth, seventh, eighth, ninth, tenth, eleventh, twelfth, thirteenth, fourteenth or fifteenth embodiment or any specific embodiments described therein.

In a twentieth embodiment, the invention provides a compound represented by Formula (Va) or (Vb):

(Va)

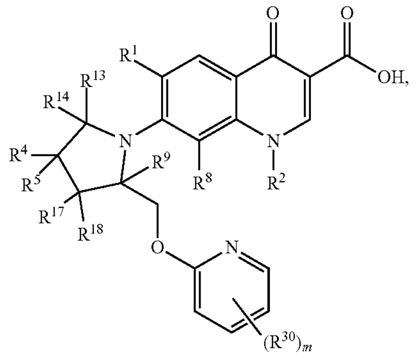

or (Vb)

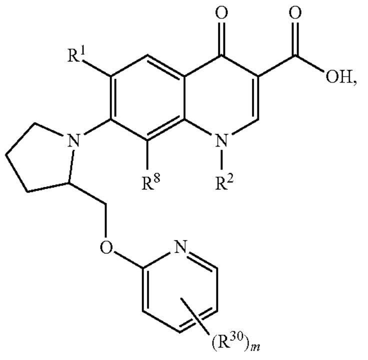

or a pharmaceutically acceptable salt thereof, wherein m is 0, 1 or 2; and the remaining variables are as defined in the first aspect or in the first, eleventh, twelfth or thirteen embodiments or any specific embodiments described therein.

In a twenty-first embodiment, a compound of Formula (Va) or (Vb) or a pharmaceutically acceptable salt thereof is represented by Formula (V-1a) or (V-1b):

(V-1a)
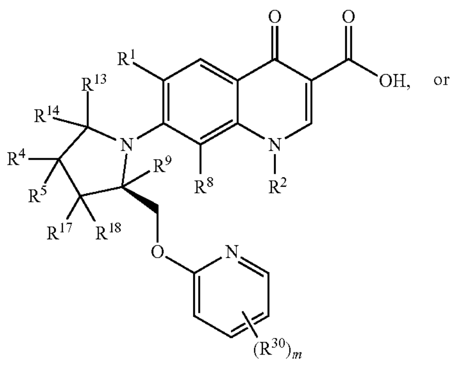
or
(V-1b)
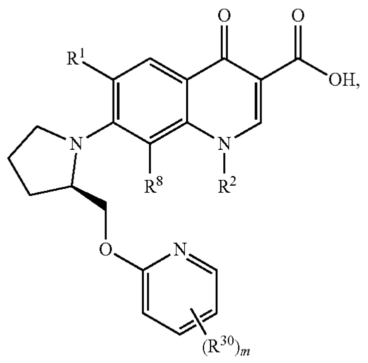
or a pharmaceutically acceptable salt thereof, wherein the variables are as defined in the twentieth embodiment.
In a twenty-second embodiment, a compound of Formula (Va) or (Vb) or a pharmaceutically acceptable salt thereof, is represented by Formula (VAa), (VBa), (VCa), (VDa), (VAb), (VBb), (VCb) or (VDb):
(VAa)
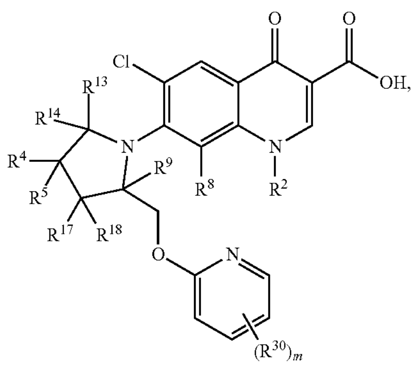
-continued
(VBa)
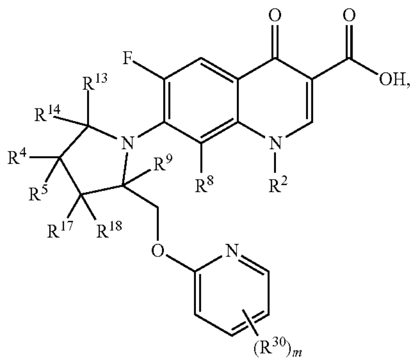
(VCa)
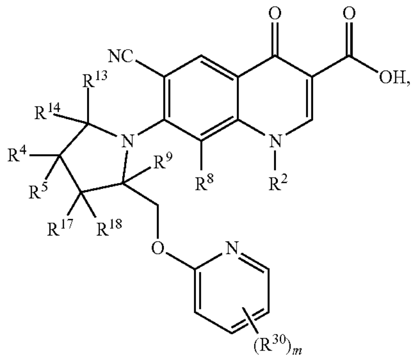
(VDa)
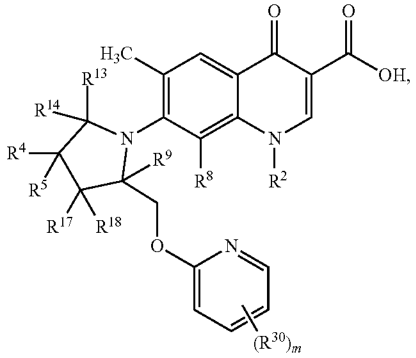
(VAb)
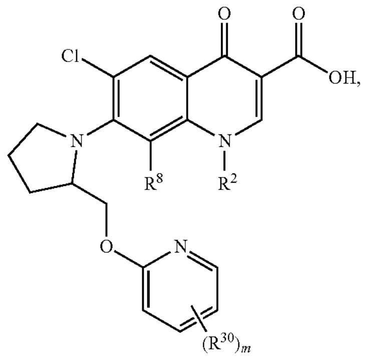

-continued
(VBb)
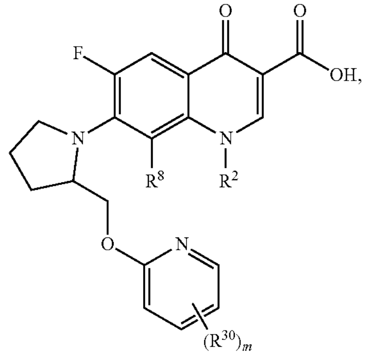
(VCb)
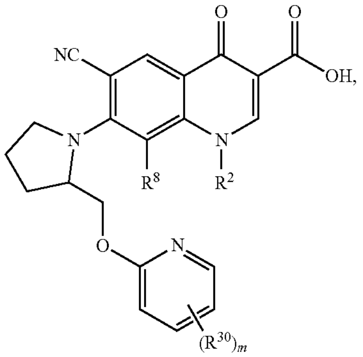
or
(VDb)
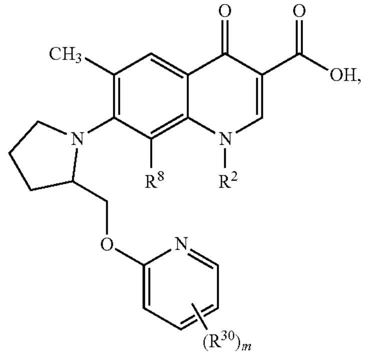
or a pharmaceutically acceptable salt thereof, wherein the variables are as defined in the twentieth embodiment.
In a twenty-third embodiment, a compound of Formula (Va) or (Vb) or a pharmaceutically acceptable salt thereof is represented by Formula (VA-1a), (VB-1a), (VC-1a), (VD-1a), (VA-1b), (VB-1b), (VC-1b) or (VD-1b):
(VA-1a)
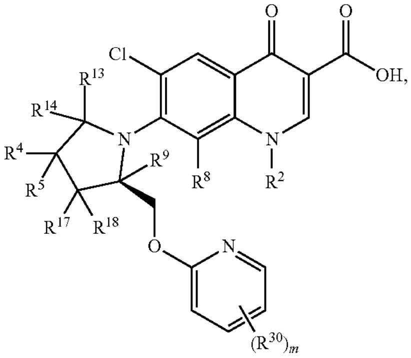
(VB-1a)
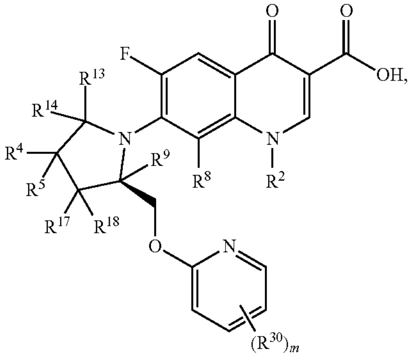
(VC-1a)
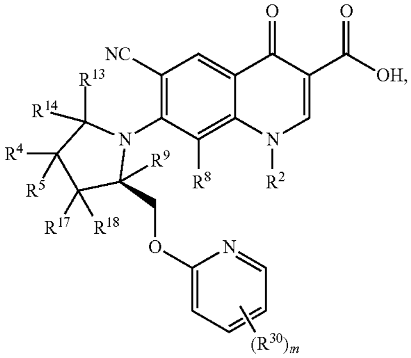
(VD-1a)
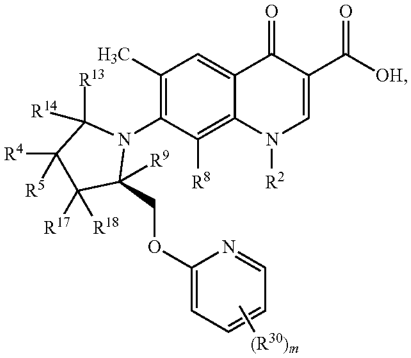

-continued (VA-1b)

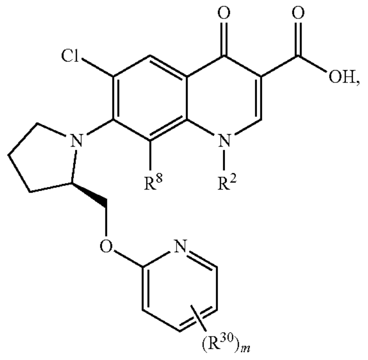

(VB-1b)

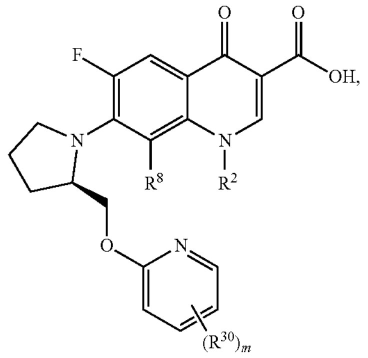

(VC-1b)

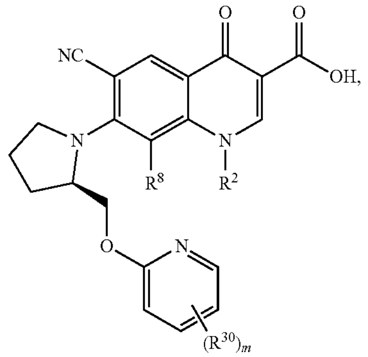

or (VD-1d)

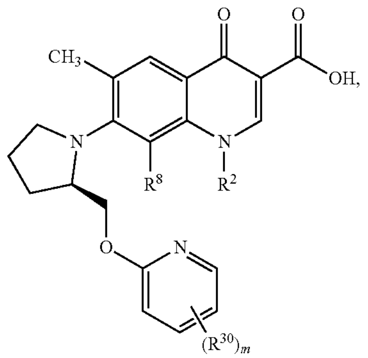

or a pharmaceutically acceptable salt thereof, wherein $R^8$ is H or F; and the remaining variables are as defined in the twentieth embodiment.

In a twenty-fourth embodiment, the present invention provides a compound of Formula (VIa) or (VIb):

(VIa)

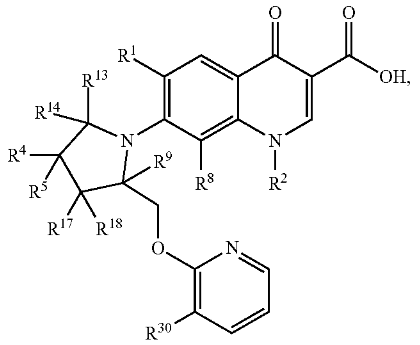

or (VIb)

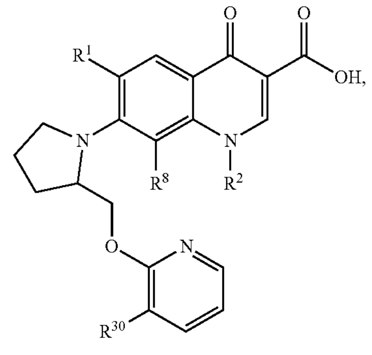

or a pharmaceutically acceptable salt thereof, wherein $R^{30}$ is H, halo, CN, —$OR^{30a}$, and $C_{1-6}$alkyl optionally substituted with one to three halo; and $R^{30a}$ is H or $C_{1-6}$alkyl optionally substituted with one to three halo; and the remaining variables are as defined in the twentieth embodiment In a twenty-fifth embodiment, a compound of Formula (VIa) or (VIb) or a pharmaceutically acceptable salt thereof is represented by Formula (VI-1a) or (VI-1b):

(VI-1a)

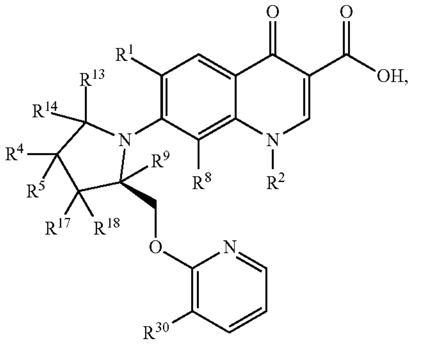

or

-continued
(VI-1b)
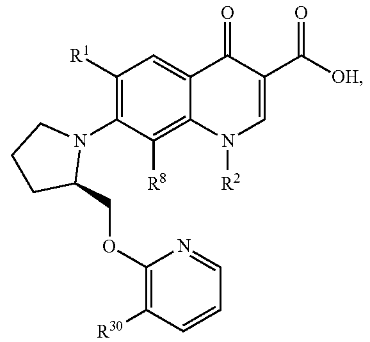
or a pharmaceutically acceptable salt thereof, wherein the variables are as defined in the twenty-fourth embodiment.
In a twenty-sixth embodiment, a compound of Formula (VIa) or (VIb) or a pharmaceutically acceptable salt thereof is represented by Formula (VIAa), (VIBa), (VICa), (VIDa), (VIAb), (VIBb), (VICb) or (VIDb):
(VIAa)
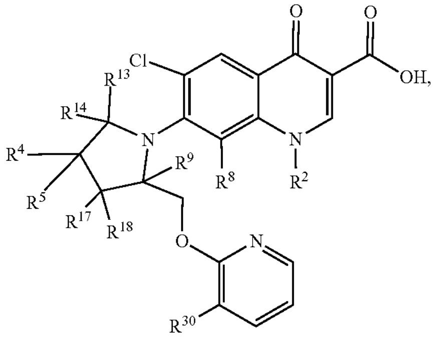
(VIBa)
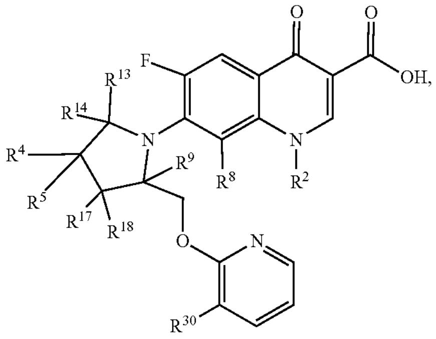
(VICa)
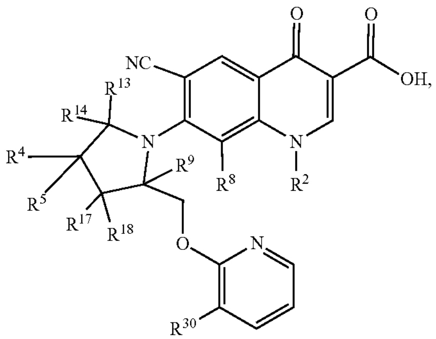
-continued
(VIDa)
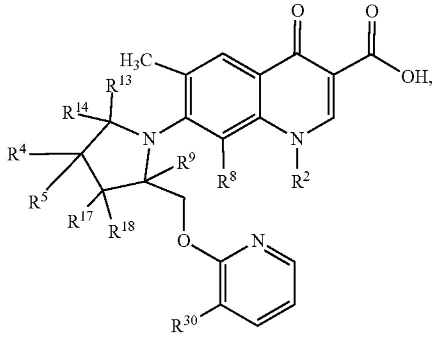
(VIAb)
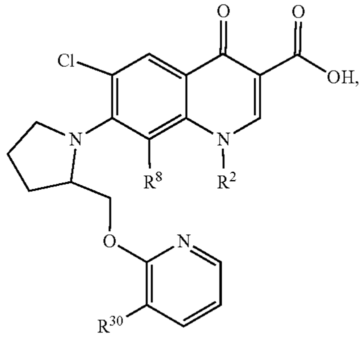
(VIBb)
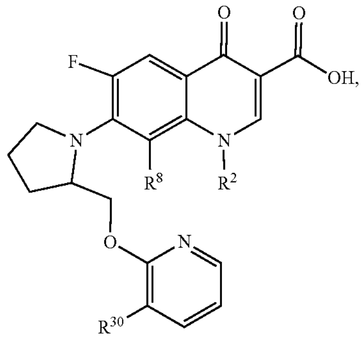
(VICb)
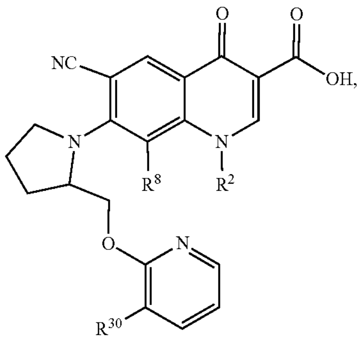
or -continued
(VIDb)
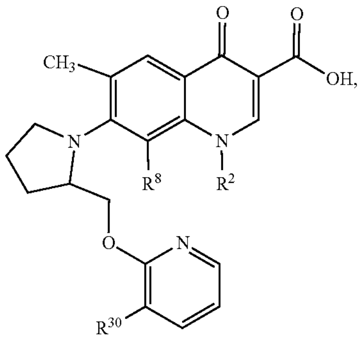
or a pharmaceutically acceptable salt thereof, wherein the variables are as defined in the twenty-fourth embodiment.
In a twenty-seventh embodiment, a compound of Formula (VIa) or (VIb) or a pharmaceutically acceptable salt thereof is represented by Formula (VIA-1a), (VIB-1a), (VIC-1a), (VID-1a), (VIA-1b), (VIB-1b), (VIC-1b) or (VID-1b):
(VIA-1a)
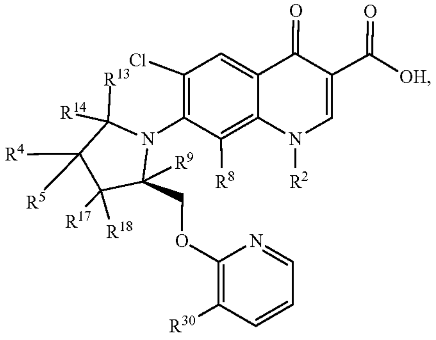
(VIB-1a)
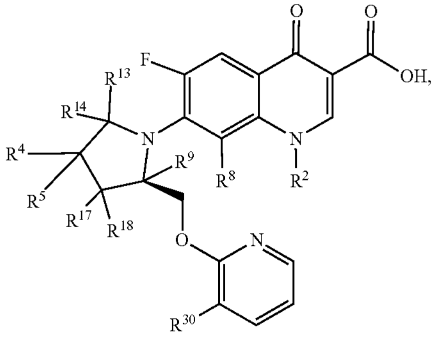
(VIC-1a)
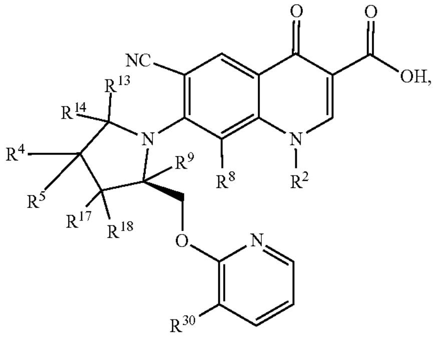
-continued
(VID-1a)
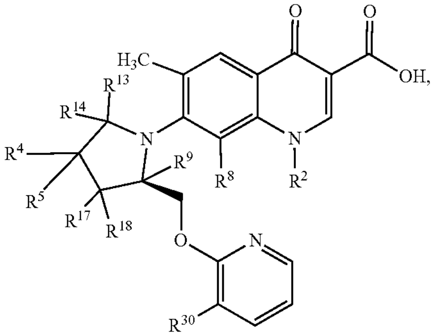
(VIA-1b)
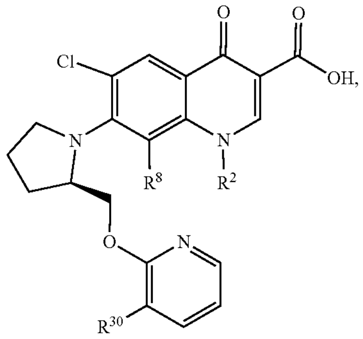
(VIB-1b)
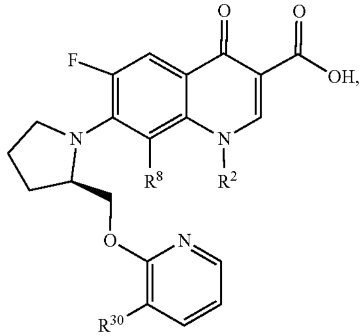
(VIC-1b)
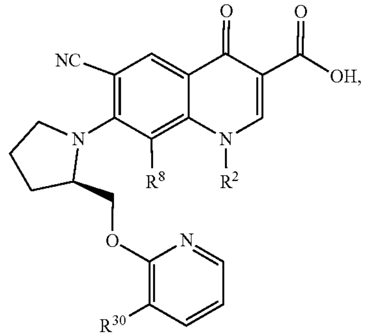
or -continued (VID-1b)

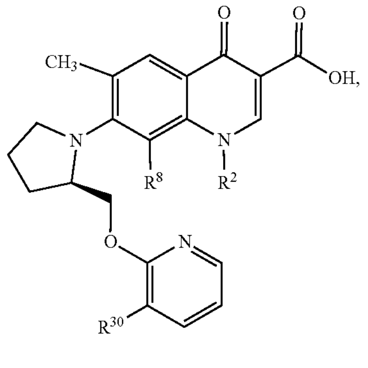

or a pharmaceutically acceptable salt thereof, wherein the variables are as defined in the twenty-fourth embodiment.

In a twenty-eighth embodiment, for compounds of Formula (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b) or a pharmaceutically acceptable salt thereof, $R^{30}$, for each occurrence, is independently H, F, Cl, Br, CN, —$CH_3$, —$CH_2CH_3$, —$OCH_3$, or —$CF_3$; and the remaining variables are as defined in the twentieth, twenty-first, twenty-second, twenty-third, twenty-fourth, twenty-fifth, twenty-sixth or twenty-seventh embodiment or any specific embodiments described therein.

In a twenty-ninth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof):

$R^2$ is $C_{3-8}$cycloalkyl, phenyl, a 4 to 6-membered saturated monocyclic heterocyclyl, a 7 to 10-membered saturated or partially saturated bicyclic heterocyclyl, a 5 or 6-membered monocyclic heteroaryl or a 9 to 10-membered bicyclic heteroaryl, each of which is optionally substituted with one to three $R^{20}$;

$R^{20}$, for each occurrence, is independently selected from H, halo, —CN, oxo, —C(O)$R^{20a}$, —C(O)$NR^{20a}$, —N($R^{20a}$)$_2$, —N($R^{20a}$)C(O)$R^{20a}$, —N($R^{20a}$)S(O)$_2$ $R^{20a}$, —$OR^{20a}$, $C_{1-6}$alkyl, $C_{3-8}$cycloalkyl, and 4- to 7-membered saturated monocyclic heterocyclyl, wherein the $C_{1-6}$alkyl, $C_{3-8}$cycloalkyl, and 4- to 7-membered saturated monocyclic heterocyclyl represented by $R^{20}$ are each optionally substituted with one or two $R^{25}$;

$R^{20a}$, for each occurrence, is independently selected from H and $C_{1-6}$alkyl, wherein the $C_{1-6}$alkyl represented by $R^{20a}$ is optionally substituted with one or more $R^{25}$ $R^{25}$, for each occurrence, is independently H, $C_{1-6}$alkyl, halo, —N($R^{25a}$)$_2$, —$OR^{25}$a, phenyl optionally substituted with $C_{1-6}$alkyl, halo, —N($R^{25a}$)$_2$ or —$OR^{25a}$; and $R^{25a}$ is H or $C_{1-6}$alkyl; and the remaining variables as defined above in the first aspect or the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, or twenty-eighth embodiment or any specific embodiments described therein.

In a thirtieth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof), $R^2$ is phenyl or a 6-membered monocyclic heteroaryl containing 1 to 3 nitrogen atoms, wherein the phenyl and the 6-membered monocyclic heteroaryl are each optionally substituted with one to three $R^{20}$; and the remaining variables are as defined in the twenty-ninth embodiment.

In a thirty-first embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof), $R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{21}$; and the remaining variables are as defined in the twenty-ninth embodiment.

In a thirty-second embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof), $R^2$ is selected from phenyl, pyridinyl, and pyrazinyl, each of which is optionally substituted with one or two $R^{20}$; and the remaining variables are as defined in the twenty-ninth embodiment.

In a thirty-third embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof), $R^2$ is represented by the following formula:

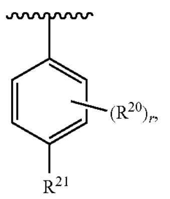

wherein $R^{21}$ is H, halo, —CN, —C(O)$R^{20a}$, —C(O)N$R^{20a}$, —N($R^{20a}$)$_2$, —N($R^{20a}$)C(O)$R^{20a}$, —N($R^{20a}$)S(O)$_2R^{20a}$, —O$R^{21a}$, $C_{1-6}$alkyl, $C_{3-8}$cycloalkyl, and 4- to 7-membered saturated monocyclic heterocyclyl, wherein the $C_{1-6}$alkyl, $C_{3-8}$cycloalkyl, and 4- to 7-membered saturated monocyclic heterocyclyl represented by $R^{21}$ are each optionally substituted with one or two $R^{25}$;

$R^{21a}$ is H or $C_{1-6}$alkyl, wherein the $C_{1-6}$alkyl represented by $R^{21a}$ is optionally substituted with one or more $R^{25}$ $R^{25}$, for each occurrence, is independently $C_{1-6}$alkyl, halo, —N($R^{25a}$)$_2$, —O$R^{25a}$, phenyl optionally substituted with $C_{1-6}$ alkyl, halo, —N($R^{25a}$)$_2$ or —O$R^{25a}$;

$R^{25a}$ is H or $C_{1-6}$ alkyl; and r is 0, 1 or 2; and the remaining variables are as defined in the twenty-ninth embodiment.

In one embodiment, for compounds or pharmaceutically acceptable salts described in the thirty-third embodiment, $R^{21a}$ is $C_{1-6}$alkyl optionally substituted with one or more $R^{25}$; and the remaining variables are as defined in the thirty-third embodiment.

In another embodiment, or compounds or pharmaceutically acceptable salts described in the thirty-third embodiment, $R^{21}$ is H, —F, —Cl, —$CH_3$, —$CH_2OH$, —$OCH_3$, —OH, —$OCH_2CH_2OCH_3$, —$OCH_2CH_2OH$, —$OCH_2CH_2N(CH_3)_2$, (4-methoxybenzyl)oxy, —$NHCH_2CH_2OMe$, —$NHSO_2CH_3$, or —NHC(O)$CH_3$; and the remaining variables are as defined in the thirty-third embodiment.

In a thirty-fourth embodiment, for compounds or pharmaceutically acceptable salts described herein (e.g., compounds of Formula (I), (I'), (Ia), (Ib), (IIa), (IIb), (II-1a), (II-1b), (IIIa), (IIIb), (III-1a), (III-1b), (IVa), (IVb), (IV-1a), (IV-1b), (IVAa), (IVBa), (IVCa), (IVDa), (IVAb), (IVBb), (IVCb), (IVDb), (IVA-1a), (IVB-1a), (IVC-1a), (IVD-1a), (IVA-1b), (IVB-1b), (IVC-1b), (IVD-1b), (Va), (Vb), (V-1a), (V-1b), (VAa), (VAb), (VBa), (VBb), (VCa), (VCb), (VDa), (VDb), (VA-1a), (VA-1b), (VB-1a), (VB-1b), (VC-1a), (VC-1b), (VID-1a), (VID-1b), (VIa), (VIb), (VI-1a), (VI-1b), (VIAa), (VIAb), (VIBa), (VIBb), (VICa), (VICb), (VIDa), (VIDb), (VIA-1a), (VIA-1b), (VIB-1a), (VIB-1b), (VIC-1a), (VIC-1b), (VID-1a) or (VID-1b), or a pharmaceutically acceptable salt thereof), $R^{20}$, for each occurrence, is independently selected from —F, —OH, —Cl, —$CH_3$, —$CH_2CH_3$, —$CH_2OH$, —$CH_2OCH_3$, —$CH_2CH_2OCH_3$, —$CH_2CH_2OH$, —$CH_2CH_2N(CH_3)_2$, —$CF_3$, —$OCH_3$, —$OCH_2CH_2OCH_3$, —$OCH_2CH_2OH$, —$OCH_2CH_2N(CH_3)_2$, (4-methoxybenzyl)oxy, oxo, —C(O)$CH_3$, —$NH_2$, —$NHCH_3$, —$N(CH_3)_2$, —$N(CH_3)(CH_2CH_2OCH_3)$, —$NHCH_2CH_2OMe$, —$NHCH_2CH_2NHCH_3$, —$NHCH_2CH_2N(CH_3)_2$, —$NHSO_2CH_3$, —$NHSO_2CH_2CH_3$, —NHC(O)$CH_3$, azetidin-yl, 3-aminoazeitidin-1-yl, piperidin-1-yl, morpholinyl, and pyrrolidin-1-yl; and the remaining variables are as defined in the twenty-ninth, thirtieth, thirty-first, thirty-second or thirty-third embodiment.

In a thirty-fifth embodiment, the present invention provides a compound represented by Formula (VIIA-1a), (VIIB-1a), (VIIC-1a), (VIID-1a), (VIIA-1b), (VIIB-1b), (VIIC-1b), (VIID-1b):

(VIIA-1a)

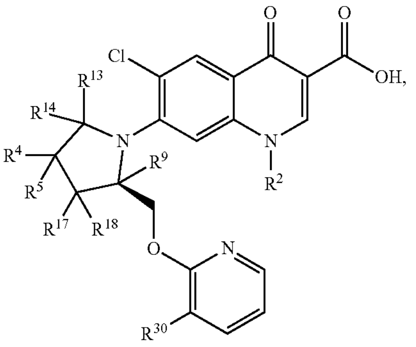

(VIIB-1a)

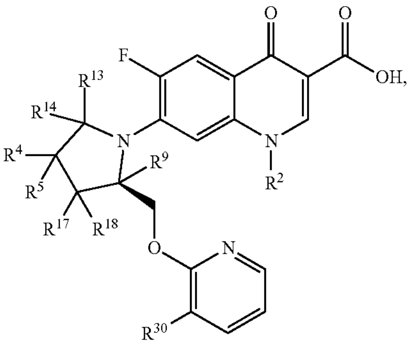

(VIIC-1a)

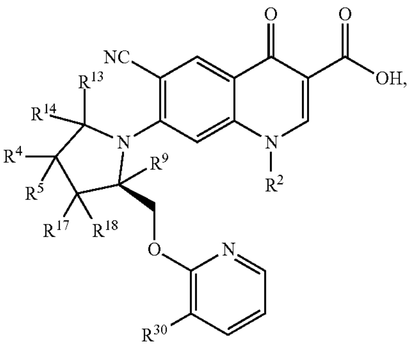

-continued (VIID-1a)

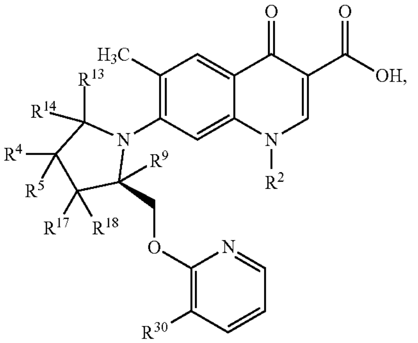

(VIIA-1b)

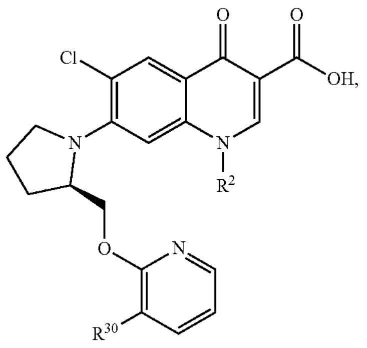

(VIIC-1b)

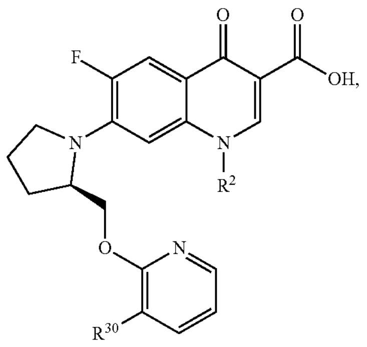

(VIIC-1b)

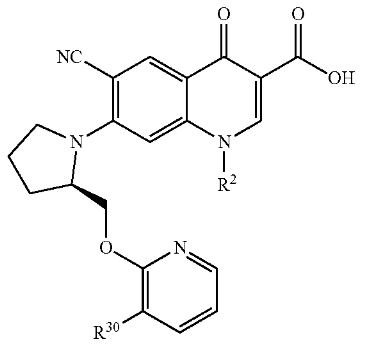

or

-continued (VIID-1b)

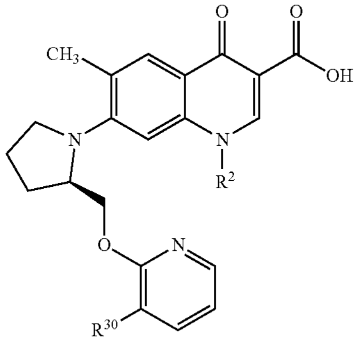

or a pharmaceutically acceptable salt thereof, wherein:

$R^{30}$ is H, halo, CN, —$OR^{30a}$, and $C_{1-6}$alkyl optionally substituted with one to three halo; and $R^{30a}$ is H or $C_{1-6}$alkyl optionally substituted with one to three halo;

$R^2$ is phenyl or a 6-membered monocyclic heteroaryl containing 1 to 3 nitrogen atoms, wherein the phenyl and the 6-membered monocyclic heteroaryl are each optionally substituted with one to three $R^{20}$;

$R^{20}$, for each occurrence, is independently selected from halo, and —$N(R^{20a})_2$; and $R^{20a}$, for each occurrence, is independently selected from H and $C_{1-3}$alkyl, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —$N(R^{25a})_2$, or —$OR^{25a}$; and $R^{25a}$ is H or $C_{1-6}$ alkyl.

In a thirty-sixth embodiment, for compounds of Formula (VIIA-1a), (VIIB-1a), (VIIC-1a), (VIID-1a), (VIIA-1b), (VIIB-1b), (VIIC-1b), (VIID-1b) or a pharmaceutically acceptable salt thereof, $R^{30}$ is halo or $C_{1-3}$alkyl; $R^2$ is phenyl, pyridinyl or pyrazinyl, each of which is optionally substituted with —$N(R^{20a})_2$; $R^{20a}$, for each occurrence, is H or methyl, or two $R^{20a}$ together with the nitrogen atom from which they are attached form a 4- to 6-membered heterocyclyl optionally substituted with one $R^{25}$; $R^{25}$ is —$N(R^{25a})_2$; and $R^{25a}$ is H or Me; and the remaining variables are as defined in the thirty-fifth embodiments. In a specific embodiment, $R^{30}$ is Cl or methyl; and $R^2$ is phenyl, pyridin-3-yl, or pyrazin-2-yl, each of which is optionally substituted with —$NH_2$, azetidin-1-yl, 3-aminoazetidin-1-yl or 3-(dimethylamino)azetidin-1-yl.

In a thirty-seventh embodiment, for compounds of Formula (I), (I'), (IIa), (II-1a), (IIIa), (III-1a), (IVa), (IV-1a), (IVAa), (IVBa), (IVCa), (IVDa), (IVA-1a), (IVB-1a), (IVC-1a), (IVD-1a), (Va), (V-1a), (VAa), (VBa), (VCa), (VDa), (VA-1a), (VB-1a), (VC-1a), (VD-1a), (VIa), (VI-1a), (VIAa), (VIBa), (VICa), (VIDa), (VIA-1a), (VIB-1a), (VIC-1a), (VID-1a), (VIIA-1a), (VIIB-1a), (VIIC-1a), or (VIID-1a) or a pharmaceutically acceptable salt thereof described in any one of the fifth to thirty-sixth embodiments, $R^4$, $R^5$, $R^{13}$, $R^{14}$, $R^{17}$ and $R^{18}$ are all H, and $R^9$ is $C_{1-6}$alkyl or $C_{3-6}$ cycloalkyl, wherein the $C_{1-6}$ alkyl and the $C_{3-6}$ cycloalkyl are each optionally substituted with one or more substituents independently selected from halo, CN, —$OR^{9a}$ and $C_{1-6}$ alkyl optionally substituted with one or more halo; wherein $R^{9a}$ is H or $C_{1-6}$ alkyl optionally substituted with one or more halo; and the remaining variables are as defined in the fifth to thirty-sixth embodiments. In a specific embodiment, $R^9$ is $C_{1-6}$alkyl optionally substituted with one to three halo. In a more specific embodiment, $R^9$ is —$CH_3$.

In a thirty-eighth embodiment, for compounds of Formula (I), (I'), (Ia), (IIa), (II-1a), (IIIa), (III-1a), (IVa), (IV-1a), (IVAa), (IVBa), (IVCa), (IVDa), (IVA-1a), (IVB-1a), (IVC-1a), (IVD-1a), (Va), (V-1a), (VAa), (VBa), (VCa), (VDa), (VA-1a), (VB-1a), (VC-1a), (VD-1a), (VIa), (VI-1a), (VIAa), (VIBa), (VICa), (VIDa), (VIA-1a), (VIB-1a), (VIC-1a), (VID-1a), (VIIA-1a), (VIIB-1a), (VIIC-1a), or (VIID-1a) or a pharmaceutically acceptable salt thereof described in any one of the fifth to thirty-sixth embodiments, $R^5$, $R^9$, $R^{13}$, $R^{14}$, $R^{17}$ and $R^{18}$ are all H, and $R^4$ is $C_{1-6}$ alkyl, halo, —CN or —$OR^{4a}$, wherein the $C_{1-6}$ alkyl is optionally substituted with one or more substituents independently selected from halo, CN and —$OR^{4a}$; and $R^{4a}$ is H or $C_{1-6}$ alkyl optionally substitute with one or more halo; and the remaining variables are as defined in the fifth to thirty-sixth embodiments. In a specific embodiment, $R^4$ is halo. In a more specific embodiment, $R^4$ is F.

In a thirty-ninth embodiment, for compounds of Formula (I), (I'), (Ia), (IIa), (II-1a), (IIIa), (III-1a), (IVa), (IV-1a), (IVAa), (IVBa), (IVCa), (IVDa), (IVA-1a), (IVB-1a), (IVC-1a), (IVD-1a), (Va), (V-1a), (VAa), (VBa), (VCa), (VDa), (VA-1a), (VB-1a), (VC-1a), (VD-1a), (VIa), (VI-1a), (VIAa), (VIBa), (VICa), (VIDa), (VIA-1a), (VIB-1a), (VIC-1a), (VID-1a), (VIIA-1a), (VIIB-1a), (VIIC-1a), or (VIID-1a) or a pharmaceutically acceptable salt thereof described in any one of the fifth to thirty-sixth embodiments, $R^4$, $R^5$, $R^{14}$, $R^{17}$ and $R^{18}$ are all H, and $R^{13}$ and $R^9$ together form a —$C_{1-3}$ alkylene- optionally substituted with one or more substituents independently selected from halo, —$OR^a$, —$N(R^a)_2$ and $C_{1-6}$ alkyl; wherein $R^a$, for each occurrence, is independently H or $C_{1-6}$ alkyl optionally substituted with one or more halo; and the remaining variables are as defined in the fifth to thirty-sixth embodiments. In a specific embodiment, $R^{13}$ and $R^9$ together form a —$CH_2CH_2$—, optionally substituted with one or two substituents independently selected from halo, —$OR^a$, —$N(R^a)_2$ and $C_{1-3}$ alkyl; wherein $R^a$, for each occurrence, is independently H or $C_{1-3}$ alkyl optionally substituted with one or more halo. In a more specific embodiment, $R^{13}$ and $R^9$ together form a —$CH_2CH_2$—.

In a fortieth embodiment, the compound is represented by Formula (IV-1a):

(IV-1a)

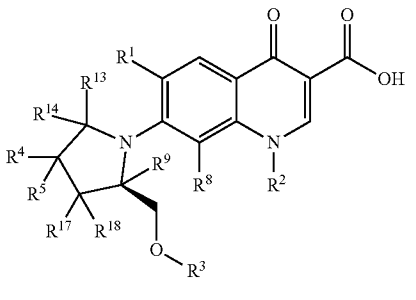

or a pharmaceutically acceptable salt thereof, wherein:

$R^1$ is F, Cl, CN or $CH_3$;

$R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyrimidinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{20}$;

$R^{20}$, for each occurrence, is independently selected from H, halo, —CN, oxo, —$C(O)R^{20a}$, —$C(O)NR^{20a}$, —$N(R^{20a})_2$, —$N(R^{20a})C(O)R^{20a}$, —$N(R^{20a})S(O)_2R^{20a}$, —$OR^{20a}$, $C_{1-6}$ alkyl, $C_{3-8}$cycloalkyl, and 4- to 7-membered saturated monocyclic heterocyclyl, wherein the $C_{1-6}$ alkyl, $C_{3-8}$ cycloalkyl, and 4- to 7-membered saturated monocyclic heterocyclyl represented by $R^{20}$ are each optionally substituted with one or two $R^{25}$;

$R^{20a}$, for each occurrence, is independently selected from H and $C_{1-6}$ alkyl, wherein the $C_{1-6}$ alkyl represented by $R^{20a}$ is optionally substituted with one or more $R^{25}$ $R^{25}$, for each occurrence, is independently H, $C_{1-6}$ alkyl, halo, —$N(R^{25a})_2$, —$OR^{25a}$, phenyl optionally substituted with $C_{1-6}$ alkyl, halo, —$N(R^{25a})_2$ or —$OR^{25a}$; and $R^{25a}$ is H, $C_{1-6}$ alkyl, or $C_{1-6}$ alkyl substituted with —$OCH_3$;

$R^3$ is phenyl, pyridinyl, pyrimidinyl, pyrazinyl, pyridazinyl, 1H-pyrrolo[2,3-c]pyridinyl, 1H-imidazo[4,5-c]pyridinyl, 1H-pyrrolo[2,3-b]pyridinyl, 1H-imidazo[4,5-b]pyridinyl, 1H-pyrrolo[3,2-b]pyridinyl, 3H-imidazo[4,5-b]pyridinyl, or 1H-imidazo[4,5-c]pyridinyl, each of which is optionally substituted with one to three $R^{30}$;

$R^{30}$, for each occurrence, is H, halo, CN, —$C(O)NR^{30a}$, —$N(R^{30a})_2$, —$N(R^{30a})C(O)R^{30a}$, —$N(R^{30a})S(O)_2R^{30a}$, —$OR^{30a}$, and $C_{1-6}$ alkyl, wherein the $C_{1-6}$ alkyl is optionally substituted with one to three $R^{35}$;

$R^{30a}$, for each occurrence, is independently H, $C_{1-6}$ alkyl optionally substituted with one to three $R^{35}$ or $C_{3-6}$ cycloalkyl;

$R^{35}$, for each occurrence, is independently H, halo and —$OR^{35a}$; and $R^{35a}$ is H or $C_{1-3}$ alkyl;

$R^4$ is H, halo, CN, —$OR^{4a}$, $C_{1-6}$ alkyl, pyridinyl, or pyrazolyl, wherein the $C_{1-6}$ alkyl is optionally substituted with one or more substituents independently selected from halo, CN and —$OR^{4a}$; wherein the pyridinyl, or pyrazolyl is optionally substituted with —OH, —$C_1$-$C_6$ alkyl or —O—$C_1$-$C_6$ alkyl; and $R^{4a}$ is H, $C_{1-6}$ alkyl optionally substituted with one or more halo, or $C_3$-$C_6$ cycloalkyl;

$R^5$ is H or halo, or $R^4$ and $R^5$ taken together are =NOH, or =$NHOCH_3$, or $R^4$ and $R^5$ taken together with the carbon to which they are connected form a $C_3$-$C_6$ cycloalkyl, or $R^5$ and $R^{13}$ taken together with their intervening atoms form a cyclopropyl; and;

$R^8$, $R^{13}$ and $R^{14}$ are each H;

$R^9$ is H, $C_1$-$C_6$ alkoxy or $C_1$-$C_6$ alkyl, or $R^9$ and $R^{13}$ together form a $C_{1-3}$ alkylene- optionally substituted with one or more substituents independently selected from halo, $OR^a$, $N(R^a)_2$ and $C_{1-6}$ alkyl; wherein $R^a$, for each occurrence, is independently H or $C_{1-6}$ alkyl optionally substituted with one or more halo;

$R^{17}$ is H, halo or $C_{1-6}$ alkyl; and $R^{18}$ is H, —OH, —$O(C_1$-$C_6$ alkyl) or $C_{1-6}$ alkyl, or $R^{17}$ and $R^{18}$ taken together are =NOH or =$NHOCH_3$).

In a forty-first embodiment, the compound is represented by Formula (IV-1a):

(IV-1a)

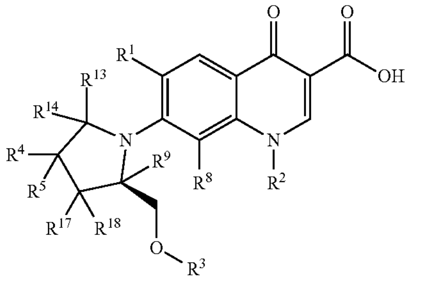

or a pharmaceutically acceptable salt thereof, wherein:

$R^1$ is F, Cl, CN or $CH_3$;

$R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyrimidinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{20}$;

$R^{20}$, for each occurrence, is independently selected from —F, —OH, —Cl, $—CH_3$, $—CH_2CH_3$, $—CH_2OH$, $—CH_2OCH_3$, $—CH_2CH_2OCH_3$, $—CH_2CH_2OH$, $—CH_2CH_2N(CH_3)_2$, $—CF_3$, $—OCH_3$, $—OCH_2CH_2OCH_3$, $—OCH_2CH_2OH$, $—OCH_2CH_2N(CH_3)_2$, (4-methoxybenzyl)oxy, oxo, $—C(O)CH_3$, $—NH_2$, $—NHCH_3$, $—N(CH_3)_2$, $—N(CH_3)(CH_2CH_2OCH_3)$, $—NHCH_2CH_2OMe$, $—NHCH_2CH_2NHCH_3$, $—NHCH_2CH_2N(CH_3)_2$, $—NHSO_2CH_3$, $—NHSO_2CH_2CH_3$, $—NHC(O)CH_3$, azetidin-yl, 3-aminoazeitidin-1-yl, piperidin-1-yl, morpholinyl, pyrrolidin-1-yl; and 3-(dimethylamino)azetidin-1-yl or

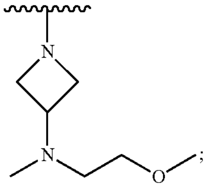

$R^3$ is phenyl, pyridinyl, pyrimidinyl, pyrazinyl, pyridazinyl, 1H-pyrrolo[2,3-c]pyridinyl, 1H-pyrrolo[3,2-c]pyridinyl, or 1H-imidazo[4,5-c]pyridinyl, 1H-imidazo[4,5-c]pyridinyl, 1H-pyrrolo[2,3-b]pyridinyl, 1H-imidazo[4,5-b]pyridinyl; 1H-pyrrolo[3,2-b]pyridinyl, or 3H-imidazo[4,5-b]pyridinyl each of which is optionally substituted with one to three $R^{31}$;

$R^{30}$, for each occurrence, is H, F, Cl, Br, CN, $—OCH_3$, —O(cyclopropyl), $—NH_2$, $—NH(CH_3)_2$, $—CH_3$, $—CH_2CH_3$ or $—CF_3$;

$R^4$ is H, halo, —CN, $OR^{4a}$, $C_{1-6}$ alkyl, pyridinyl, or pyrazolyl, wherein the $C_{1-6}$ alkyl is optionally substituted with one or more substituents independently selected from halo, CN and $—OR^{4a}$; wherein the pyridinyl, or pyrazolyl is optionally substituted with —OH, $—CH_3$ or $—OCH_3$; and $R^{4a}$ is H, $—CH_3$, cyclopropyl or $—CH_2CH_3$ optionally substituted with one or more halo, or cyclopropyl;

$R^5$ is H or F, or $R^4$ and $R^5$ taken together are $=NHOCH_3$, or $R^4$ and $R^5$ taken together with the carbon to which they are connected form cyclopropyl, or $R^5$ and $R^{13}$ taken together with their intervening atoms form a cyclopropyl; and $R^8$, $R^{13}$ and $R^{14}$ are each H;

$R^9$ is H or $—CH_3$, or $R^9$ and $R^{13}$ together form a $—C_2$ alkylene-;

$R^{17}$ is H, F or $—CH_3$; and $R^{18}$ is H, —OH, $—OCH_3$ or $—CH_3$, or $R^{17}$ and $R^{18}$ taken together are $=NHOCH_3$.

In a forty-second embodiment, the compound is represented by Formula (IV-1a):

(IV-1a)

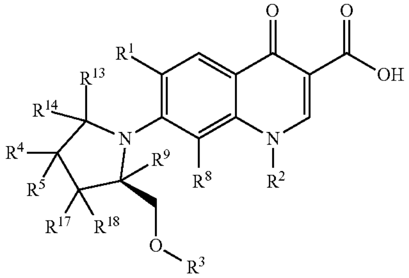

or a pharmaceutically acceptable salt thereof, wherein:

$R^1$ is F or Cl;

$R^2$ is selected from pyridinyl, pyriminidinyl and pyridazinyl, each of which is substituted with $R^{20}$;

$R^{20}$, for each occurrence, is independently selected from $—NH_2$, $—NHCH_3$, $N(CH_3)_2$, and 4- to 7-membered saturated monocyclic heterocyclyl, wherein the 4- to 7-membered saturated monocyclic heterocyclyl represented by $R^{20}$ substituted with $—N(R^{25a})_2$;

$R^{25a}$ is H, $C_{1-6}$ alkyl, or $C_{1-6}$ alkyl substituted with $—OCH_3$;

$R^3$ is pyridinyl, 1H-imidazo[4,5-c]pyridinyl, 1H-pyrrolo[2,3-b]pyridinyl, 1H-pyrrolo[3,2-b]pyridinyl, 3H-imidazo[4,5-b]pyridinyl, each of which is optionally substituted with one to three $R^{30}$;

$R^{30}$, for each occurrence, is H, halo, $C_1$-$C_6$alkyl, $—N(R^{30a})_2$ or $—OR^{30a}$;

$R^{30a}$, for each occurrence, is independently H, $C_{1-6}$ alkyl or $C_{3-6}$ cycloalkyl;

$R^4$ is H, halo, $—OR^{4a}$, $C_{1-6}$ alkyl, pyridinyl, or pyrazolyl, wherein the pyridinyl, or pyrazolyl is optionally substituted with —OH, $—C_1$-$C_6$alkyl or $—O—(C_1$-$C_6$ alkyl);

$R^{4a}$ is H, $C_{1-6}$ alkyl or $C_3$-$C_6$ cycloalkyl;

$R^5$ is H or halo, or $R^4$ and $R^5$ taken together are =NOH or $=NHOCH_3$, or $R^4$ and $R^5$ taken together with the carbon to which they are connected form a $C_3$-$C_6$ cycloalkyl, or $R^5$ and $R^{13}$ taken together with their intervening atoms form a cyclopropyl; and;

$R^8$, $R^{13}$ and $R^{14}$ are each H;

$R^9$ is H or $C_1$-$C_6$ alkyl;

$R^{17}$ is H, halo, $C_1$-$C_6$ alkoxy or $C_{1-6}$ alkyl;

$R^{18}$ is H, or $C_{1-6}$ alkyl

In a forty-third embodiment, the compound is represented by Formula (IV-1a):

(IV-1a)

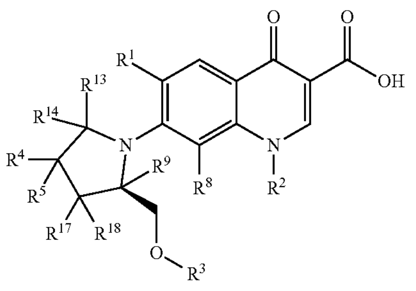

or a pharmaceutically acceptable salt thereof, wherein:

$R^1$ is F or Cl;

$R^2$ is selected from pyridinyl, pyrimidinyl and pyridazinyl, each of which is substituted with $R^{20}$;

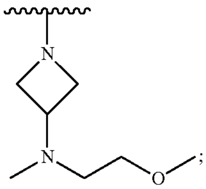

;

$R^{20}$ is —$NH_2$, —$NHCH_3$, $N(CH_3)_2$, 3-(dimethylamino)azetidin-1-yl or $R^3$ is pyridinyl, 1H-imidazo[4,5-c]pyridinyl, 1H-pyrrolo[2,3-b]pyridinyl, 1H-pyrrolo[3,2-b]pyridinyl, or 3H-imidazo[4,5-b]pyridinyl each of which is optionally substituted with one to three $R^{30}$;

$R^{30}$, for each occurrence, is H, Cl, $CH_3$, —$OCH_3$, —O(cyclopropyl), —$NH_2$, —$NHCH_3$ or —$N(CH_3)_2$;

$R^4$ is H, F, OH, —$OCH_3$, —O-(cyclopropyl), —$C_1$-$C_3$ alkyl, pyridinyl, or pyrazolyl, wherein the pyridinyl or pyrazolyl is optionally substituted with —OH, —$CH_3$, —$OCH_3$ or —O(Cyclopropyl);

$R^5$ is H or F, or $R^4$ and $R^5$ taken together are =$NHOCH_3$, or $R^4$ and $R^5$ taken together with the carbon to which they are connected form cyclopropyl, or $R^5$ and $R^{13}$ taken together with their intervening atoms form a cyclopropyl; and $R^8$, $R^{13}$ and $R^{14}$ are each H;

$R^9$ is H or —$CH_3$;

$R^{17}$ is H, F, —$OCH_3$ or —$CH_3$; and $R^{18}$ is H or —$CH_3$.

In one embodiment, the invention provides a compound selected from those described in Example section, e.g., Examples 1-1 to 1-43, Examples 2-1 to 2-89, and Examples 3-1 to 3-116, including pharmaceutically acceptable salts thereof and the neutral form.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereoisomeric purity of the compounds is at least 20%, 30%, 40%, 50%, 60%, 70%, 80%, 90%, 95%, 97%, 99%, 99.5% or 99.9%. "Stereoisomeric purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity is the weight percent of the desired stereoisomers encompassed by the name or structure relative to the combined weight of all of the stereoisomers.

When a disclosed compound is named or depicted by structure without indicating the stereochemistry, and the compound has one or more chiral centers, it is to be understood that the name or structure encompasses one enantiomer of compound in pure or substantially pure form, as well as mixtures thereof (such as a racemic mixture of the compound, mixtures enriched in one enantiomer relative to its corresponding optical isomer, mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

Pharmaceutical Compositions and Methods of Administration

In the second aspect, the compounds herein disclosed, and their pharmaceutically acceptable salts thereof may be formulated as pharmaceutical compositions or "formulations."

A typical formulation is prepared by mixing a compound described herein, or a pharmaceutically acceptable salt thereof, and a carrier, diluent or excipient. Suitable carriers, diluents and excipients are well known to those skilled in the art. The particular carrier, diluent or excipient used will depend upon the means and purpose for which a compound described herein is being formulated.

The formulations may be prepared using conventional dissolution and mixing procedures.

The terms "administer", "administering" or "administration" in reference to a compound, composition or dosage form of the invention means introducing the compound into the system of the subject or patient in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g. orally (including, but not limited to solid dosage forms including hard or soft capsules (e.g. gelatin capsules), tablets, pills, powders, sublingual tablets, troches, lozenges, and granules; and liquid dosage forms including, but are not limited to, pharmaceutically acceptable emulsions, microemulsions, aqueous or oil solutions, suspensions, syrups and elixirs, by inhalation (e.g. with an aerosol, gas, inhaler, nebulizer or the like), to the ear (e.g. using ear drops), topically (e.g. using creams, gels, inhalants, liniments, lotions, ointments, patches, pastes, powders, solutions, sprays, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via ear drops, via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

In another aspect, a compound described herein or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In the third aspect, the invention also provides a method of treating a disease or disorder in a subject, wherein the disease or disorder is mediated by Z11 TUTase. The method comprises administering to the subject a therapeutically effective amount of the compound or the composition described herein, solvates thereof, and salts thereof.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition, or affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term "tumor" or "tumor cell" are used interchangeably herein, refers to the tissue mass or tissue type of cell that is undergoing abnormal proliferation.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo. See also Freshney, Culture Animal Cells: A Man. Basic Tech. (3rd ed., 1994).

The term "biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. As used herein, the term "biological sample" also refers to a cell or population of cells or a quantity of tissue or fluid from a subject. "Biological sample" can also refer to cells or tissue analyzed in vivo, i.e., without removal from the subject. The term "tissue" is intended to include intact cells, blood, blood preparations such as plasma and serum, bones, joints, muscles, smooth muscles, and organs.

The terms "patient", "subject" and "individual" are used interchangeably herein, and refer to an animal, particularly a human, to whom treatment is provided. The term "subject" as used herein refers to human and non-human animals, such as apes, monkeys, horses, cattle, sheep, goats, dogs, cats, rabbits, guinea pigs, rats, and mice. In one embodiment, the subject is human.

As used herein, a "reference level" refers to the protein (e.g., Z11, Lin28A, Lin28B) level or RNA level (e.g., let 7 miRNA) in a biological sample free of disease or disorder described herein (e.g., cancer). In certain embodiments, the biological sample is obtained from a healthy subject (e.g., healthy human) who is free of cancer. In certain embodiments, the biological sample is obtained from the same subject (e.g., patient to be treated) from an earlier time when the subject is free of cancer. Alternatively, the biological sample is non-cancerous tissue obtained from the same subject (e.g., patient to be treated), preferably of the same tissue type as the cancerous tissue.

In certain embodiments, the disease or disorder is characterized by an increase in Lin28A or Lin28B level as compared to a reference level. In certain embodiments, the disease or disorder is characterized by a decrease in let 7 miRNA level as compared to the reference level. In yet another embodiment, the decrease in let 7 miRNA level is mediated by Z11 TUTase.

In certain embodiments, the compounds or compositions of the present invention can be used in a method of increasing let 7 miRNA level in a cancer cell.

In certain embodiments, the compounds or compositions of the present invention can be used for the treatment of adult and/or pediatric oncology including in solid phase tumors/malignancies, locally advanced tumors, human soft tissue sarcomas, metastatic cancer, including lymphatic metastases, blood cell malignancies including multiple myeloma, acute and chronic leukemias, lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

In certain embodiments, the compounds or compositions described herein can be used for treating a cancer. Cancers include, but are not limited to, biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms's tumor. In certain embodiments, the cancer is breast cancer, prostate cancer, lung cancer, ovarian cancer, colorectal cancer or brain cancer. In some embodiments, the cancer cells are metastatic. In some embodiments, the cancer does not express LIN28A/B.

In certain embodiments, the compounds or compositions of the present invention can be used for treating breast cancer. In certain embodiments, the compounds or compositions of the present invention can be used for treating a lung cancer, a hepatic cancer or leukemia, for example but not limited to lung carcinoma, chronic myelogenous leukemia (CML) and HCC (hepatic cell carcinoma).

In certain embodiments, the compounds or compositions described herein are useful to be administered to a subject who has cancer regression. In certain embodiments, the compounds or compositions described herein are useful to be administered to a subject who has a therapy-resistant cancer, for example a chemotherapy resistant cancer. In some embodiments, the compounds or compositions described herein are useful to be administered to a subject who has cancer and has been exposed to adjuvant cancer therapies.

In some embodiments, the compounds or compositions described herein are useful to be administered to a subject with a malignant cancer. In some embodiments, the compounds or compositions described herein are also useful to be administered to and for the treatment of a subject with a cancer or tumor comprising a cancer stem cell.

In some embodiments, the compounds or compositions described herein are also useful in the treatment of other disease or disorders associated with abnormal cellular proliferation or differentiation of stem cells. Thus, treatment can be directed to a subject who is affected but asymptomatic with cancer, for example, a disease of an organ or tissue in a subject characterized by poorly controlled or uncontrolled multiplication of normal or abnormal cells in that tissue and its effect on the body as a whole. Cancer diseases which can be treated by the compounds or compositions described herein include, for example but are not limited to, benign neoplasms, dysplasias, hyperplasias as well as neoplasms showing metastatic growth or any other transformations, e.g., leukoplakias which often precede a breakout of cancer.

In some embodiments, the compounds or compositions described herein can be used for treating inflammatory disorders, such as asthma (Kumar, M., Ahmad, T., Sharma, A. et al. Let-7 microRNA-mediated regulation of IL-13 and allergic airway inflammation. *J. Allergy Clin. Immunol.* 128(5), 1077-1085 (2011)), chronic obstructive pulmonary disease (COPD) (Van Pottelberge, G. R., Mestdagh, P., Bracke, K. R. et al. MicroRNA Expression in Induced Sputum of Smokers and Patients with Chronic Obstructive Pulmonary Disease. *Am. J. Respir. Crit. Care Med.* 183, 898-906, (2010); Conickx, G., Cogos, F. A., van den Berge, M. et al. *Sci Rep* 7, 12871 (2017)), endometriosis (Sahin, C., Mamillapalli, R., Yi, K. W., and Taylor, H. S. microRNA Let-7b: A Novel treatment for endometriosis. *J Cell Mol Med.* 22, 5346-5353 (2018)), and the like.

In some embodiments, the compounds or compositions described herein can be used for treating atherosclerosis, such as diabetes-associated atherosclerosis (Brennan, E., Wang, Bo., McClelland, A. et al. Protective Effect of let-7 miRNA Family in Regulating Inflammation in Diabetes-Associated Atherosclerosis. *Diabetes* 66, 2266-2277 (2017)).

In some embodiments, the compounds or compositions described herein can be used for treating liver diseases (McDaniel, K., Hall, C., Sato, K. et al. Lin28 and let-7: roles and regulation in liver diseases. *Am J Physiol Gastrointes Liver Physiol.* 310(10), G757 (2016)). Examples of liver diseases include, but are not limited to, liver fibrosis (Matsuura K., De Giorgi, V., Schechterly, C. et al. Circulating let-7 levels in plasma and extracellular vesicles correlate with hepatic fibrosis progression in chronic hepatitis C. *Hepatology* 64(3), 732-745 (2016); Matsuura K., Aizawa, N., Enomoto, H., et al. Circulating let-7 Levels in Serum Correlate With the Severity of Hepatic Fibrosis in Chronic Heptatis C. *Open Forum Infectious Diseases* 5, 11 (2018); Zhang, Y., Guo, J., Li, Y. et al. let-7a suppresses liver fibrosis via TGFβ/SMAD signaling transduction pathway. *Experimental and Therapeutic Medicine* 17, 3935-3942 (2019)), hepatitis, alcoholic liver disease (ALD) (McDanile K., Huang L., Sato, K. et al. The let-7/Lin28 axis regulates activation of hepatic stellate cells in alcoholic liver injury. *J. Biol. Chem.* 292(27), 11336-11347 (2017)), nonalcoholic fatty liver disease (NAFLD), hepatocellular carcinoma (HCC), biliary diseases (e.g., primary biliary cirrhosis (PBC) and primary sclerosing cholangitis (PSC)), polycystic liver diseases (PCLD), and the like.

In some embodiments, the compounds or compositions described herein can be used for treating kidney diseases, such as renal fibrosis (Wang, B., Ja, J. C., Hagiwara, S. et al. Transforming growth factor-β1-mediated renal fibrosis is dependent on the regulation of transforming growth factor receptor 1 expression by let-7b. *Kidney International,* 85, 352-361 (2014); Nagai, T., Kanasaki, M., Srivastava, S. P. et al. N-acetyl-seryl-aspartyl-lysyl-proline Inhibits Diabetes-Associated Kidney Fibrosis and Endothelial-Mesenchymal Transition. *BioMed Research International,* 2014, 696475 (2014); Brenna, E. P., Nolan, K. A., Borgeson, E. et al. Lipoxins Attenuate Renal Fibrosis by Inducing let-7c and Suppressing TGFβR1. *J Am Soc Nephrol* 24, 627-637 (2013)), diabetic nephropathy (Bhatt, K., Kato, Mi., and Natarajan, R. Mini-review: emerging roles of microRNAs in the pathophysiology of renal diseases. *Am J Physiol Renal Physiol* 310, F109-F118 (2016); Park, J. T., Kato, M., Lating, L. et al. Repression of let-7 by transforming growth factor-$\beta_1$-induced Lin28 upregulates collagen expression in glomerular mesangial cells under diabetic conditions. *Am J Physiol Renal Physiol,* 307, F1390-F1403 (2014)), chronic kidney disease (CKD) (Lv, W., Fan, F., Wang, Y. et al. Therapeutic potential of microRNAs for the treatment of renal fibrosis and CKD. *Physiol Genomics.* 50(1), 20-34 (2018)), diabetic kidney disease (DKD) (Kato, M. Noncoding RNAs as therapeutic targets in early stage diabetic kidney disease. *Kidney Res Clin Pract* 37, 197-200 (2018)).

In some embodiments, the compounds or compositions described herein can be used for treating systemic scleroderma (SSc) (see, for example, Makino, K., Jinnin, M., Hirano, A. et al. The Downregulation of microRNA let-7a Contributes to the Excessive Expression of Type I Collagen in Systemic and Localized Scleroderma. *J Immunol* 190, 3905-3915 (2013)). In some embodiments, the compounds or compositions described herein can be used for treating pulmonary hypertension in patients with systemic scleroderma (SSc) (Izumiya, Y., Jinnn, M., Kimura, Y. et al. Expression of Let-7 family microRNAs in skin correlates negatively with severity of pulmonary hypertension in patients with systemic scleroderma. *IJC Heart & Vasculature* 8, 98-102 (2015)).

In some embodiments, the compounds or compositions described herein can be used for treating lung fibrosis (Huleihel, L., Ben-Yehudah, A., Milosevic, J. et al. Let-7d microRNA affects mesenchymal phenotypic properties of lung fibroblasts. *Am J Physiol Lung Cell Mol Physiol* 306, L534-542 (2014)), such as idiopathic pulmonary fibrosis (IPF) (Liang, H., Liu, S., Chen, Y. et al. miR-26a suppresses EMT by disrupting the Lin28B/let-7d axis: potential cross-talks among miRNAs in IPF. *J. Mol. Med.* 94, 655-665 (2016); Pandit, K. V., Corcoran, D., Yousef, H. et al. Inhibition and Role of Let-7d in Idiopathic Pulmonary Fibrosis. *Am J respire Crit Care Med* 182, 220-229 (2010)).

In some embodiments, the compounds or compositions described herein can be used for treating multiple sclerosis (Angelou, C. C., Wells, A. C., Vijayaraghavan, J. et al. Differentiation of Pathogenic Th17 Cells Is Negative Regulated by Let-7 MicroRNAs in a Mouse Model of Multiple Sclerosis. *Front. Immunol.* 10, 3125 (2019); Kimura, K., Hohjoh, H., Fukuoka, M. et al. Circulating exosomes suppress the induction of regulatory T cells via let-7i in multiple sclerosis. *Nature Communications* 9, 17 (2018)).

In some embodiments, the compounds or compositions described herein can be used in preventing bone loss and/or stimulating bone healing in a subject in need thereof. In certain embodiments, the compounds or compositions described herein can be used in accelerating fracture healing, including bone regeneration in large bony defects, prevention and/or treatment of osteoarthritis and other osteopathy-related conditions (e.g., inflammation-induced bone loss associated with aging and rheumatoid arthritis), prevention and/or treatment of osteogenesis imperfect and osteomalacia, spinal fusion, and craniofacial re-construction of the mandible, maxilla, and cranial bones (Ansari, M. Y., Khan, N. M., Ahmad, N. et al. Genetic Inactivation of ZCCHC6 Suppresses Interleukin-6 Expression and Reduces the Severity of Experimental Osteoarthritis in Mice. *Arthritis & Rheumatology* 71 (4), pp583-593 (2019); US2019/0101533; US2019/0101533; WO 2017/156557; and WO 2018/005608).

In some embodiments, the compounds or compositions described herein can be used in treating IL-6 mediated diseases, for example, those described in US756011, US2012/0253016 and WO 92/19759, all of which are incorporated by reference herein. Examples of IL-6 mediated diseases include, but are not limited to, rheumatoid arthritis, juvenile idiopathic arthritis, systemic juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer neuroinvasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, and post-operative inflammation.

In some embodiments, the IL-6 mediated diseases is an IL-6 mediated immune related disease selected from rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, osteolysis, aseptic loosening of orthopedic implants, inflammatory bowel disease, ulcerative colitis, systemic lupus erythematosus, cutaneous lupus erythematosus, lupus nephritis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity and preeclampsia.

In some embodiments, the IL-mediated disease is a cardiovascular disease, such as cardiac stun syndrome, myocardial infarction, congestive heart failure, stroke, ischemic stroke, hemorrhage, acute coronary syndrome, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like.

In some embodiments, the IL-mediated disease is an infectious disease, such as, acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *E. coli* O157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *Mycobacterium tuberculosis, Mycobacterium avium intracellulare, Pneumocystis carinii* pneumonia, pelvic inflammatory disease, orchitis/epidydimitis, *Legionella*, lyme disease, influenza a, epstein-barr virus, viral-associated hemaphagocytic syndrome, viral encephalitis/aseptic meningitis, and the like.

In some embodiments, the IL-mediated disease is a malignant disease, such as, leukemia, acute leukemia, acute lymphoblastic leukemia (ALL), acute lymphocytic leukemia, B-cell, T-cell or FAB ALL, acute myeloid leukemia (AML), acute myelogenous leukemia, chromic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkett's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

In some embodiments, the IL-mediated disease is a neurologic disease, such as, neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; Dementia pugilistica; neurotraumatic injury (e.g., spinal cord injury, brain injury, concussion, repetitive concussion); pain; inflammatory pain; autism; depression; stroke; cognitive disorders; epilepsy; and the like.

In some embodiments, the IL-mediated disease includes, for example, bodily injury or a trauma associated with oral surgery including periodontal surgery, tooth extraction(s), endodontic treatment, insertion of tooth implants, application and use of tooth prosthesis; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is an aphthous wound, a traumatic wound or a herpes associated wound.

The dose for the treatment methods described herein above ranges from 1 μg to 1000 mg of compound or pharmaceutically acceptable salt thereof per kg of subject body mass.

EXEMPLIFICATION

Abbreviations d doublet
dd doublet of doublet
m multiplet
s singlet
t triplet
q quartet
brs/bs broad singlet
dd doublet of doublet
td triplet of doublet
dt doublet of triplet
DEAD diethyl azadicarboxylate
DCM dichloromethane
DIPEA N,N-diisopropylethylamine
DMF N, N-dimethyl formamide
DMSO dimethyl sulfoxide
eq equivalent (s)
g gram (s)
h hour (s)
NaH sodium hydride
THF tetrahydrofuran
$BBr_3$ boron tribromide
CDI carbonyl diimidazole
EtOAc ethyl acetate
ACN acetonitrile
TLC thin layer chromatography
RT room temperature
° C. degree Celsius
mmol millimoles
μmol micromoles
ESI electrospray ionization
EtOAc ethyl acetate
HCl hydrochloric acid
IPA isopropyl alcohol
$K_2CO_3$ potassium carbonate
LiOH lithium hydroxide
MeOH methanol
MS mass spectrometry
RBF round bottomed flask
TEA triethyl amine General Analytical Methods LC-MS Conditions

| S. NO | Conditions |
|---|---|
| 1 | Column: Luna omega polar c18 (2.1*50 mm*1.8μ) • Mobile phase-A: 0.05% Formic acid in Aqueous, Mobile phase-B: 0.05% Formic acid in Acetonitrile:Methanol (1:1), Wavelength PDA, Sample concentration: 0.5 mg/mL • Gradient (T/% B): 0/2, 2/50, 2.8/80, 4/80, 4.2/2, Run time: 5.3 minutes, Diluent: A:B (9:1) |
| 2 | Column: Waters BEH C18(50*2.1 mm*1.7μ) • Mobile phase-A: 0.01% Formic acid in Aqueous, Mobile phase-B: Acetonitrile, Wavelength: PDA, Sample concentration: 0.5 mg/mL • Gradient (T/% B): 0/10, 3.0/90, 4.5/90, 4.6/10 • Run time: 5.6 minutes. Diluent: A:B (7:3) |
| 3 | Column: Luna C8(50*4.6 mm*3.0μ) • Mobile phase-A: 0.01% TFA in Aqueous, Mobile phase-B: Acetonitrile, Wavelength: PDA, Sample concentration: 0.5 mg/mL, Gradient (T/% B): 0/50, 1.8/95, 8.0/95, 8.1/50 • Run time: 9.5 minutes. Diluent: A:B (1:1) |

Prep. HPLC Conditions

| S. NO | Conditions |
|---|---|
| 1 | Column: X bridge Amide (250*19.0 mm*5.0μ) • Mobile phase A: 5 mM Ammonium bicarbonate in Aqueous • Mobile phase-B: Acetonitrile:Methanol (1:1) • Wavelength: PDA • Gradient (T/% B): 0/10, 10/50, 15/80, 20/95 • Flow: 16.0 mL/min • Run time: 20 minutes |
| 2 | Column: Luna C18 (250*21.2 mm*5.0 u), Mobile phase-A: 0.05% TFA in Aqueous, Mobile phase-B: Acetonitrile, Wavelength: PDA, Gradient (T/% B): 0/30, 12/50, 15/95, 20/95, 20.1/30, Run time: 25 minutes, Flow: 16.0 mL/min. |
| 3 | Column: X bridge-C8 (250*19.0 mm*3μ), Mobile phase-A: 0.01% Formic acid in Aqueous, Mobile phase-B: Acetonitrile, Wavelength: PDA, Sample concentration: 30 mg/mL, Gradient (T/% B): 0/50, 10/95, 25/95, Run time: 25 mins, Flow: 20.0 mL/min |

HPLC Conditions

| S. NO | Conditions |
|---|---|
| 1 | Column: X bridge Amide (250*4.6 mm*3.5μ), Mobile phase-A: 5 mM Ammonium bicarbonate in Aqueous, Mobile phase-B: Acetonitrile:Methanol (1:1), Wavelength: PDA, Sample concentration: 0.5 mg/mL, Gradient (T/% B): 0/10, 8/50, 12/95, 15/95, 15.1/10, Run time: 15 mins, Diluent: A:B (9:1) |
| 2 | Column: Luna C18(250*4.6 mm*3.5 u) • Mobile phase-A: 0.05% TFA in AQ, Mobile phase-B: Acetonitrile, Wavelength: PDA, Sample concentration: 0.5 mg/mL, Gradient (T/% B): 0/30, 10/50, 12/95, 20/95, 20.1/30, Run time: 20 mins, Diluent: A:B (7:3) |

-continued

| S. NO | Conditions |
|---|---|
| 3 | Column: X bridge C8(150*4.6 mm*3μ), Mobile phase-A: 0.01% Formic acid in Aqueous, Mobile phase-B: Acetonitrile, Wavelength: PDA, Sample concentration: 0.5 mg/mL, Gradient (T/% B): 0/50, 10/95, 25/95, 25.1/50, Run time: 25 mins, Diluent: A:B (1:1) |

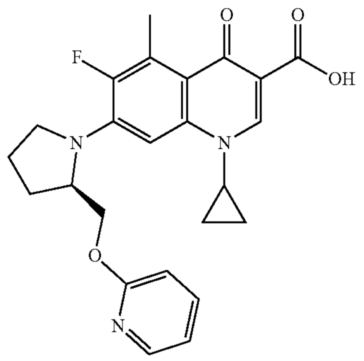 [SMILES: Cc1c(F)c(N2CCC[C@@H]2COc2ccccn2)cc2c1c(=O)c(C(=O)O)cn2C1CC1]

Example 1: Synthesis of (R)-1-cyclopropyl-6-fluoro-5-methyl-4-oxo-7-(2-((pyridin-2-yloxy)methyl)pyrrolidin-1-yl)-1,4-dihydroquinoline-3-carboxylic acid

Step 1. Synthesis of 3,4,6-trifluoro-2-methylbenzoyl chloride

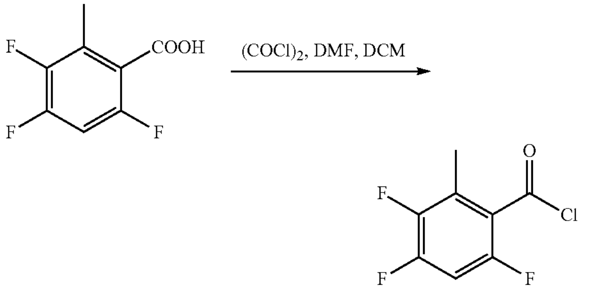

Step 2. Synthesis of ethyl 3-oxo-3-(3,4,6-trifluoro-2-methylphenyl)propanoate

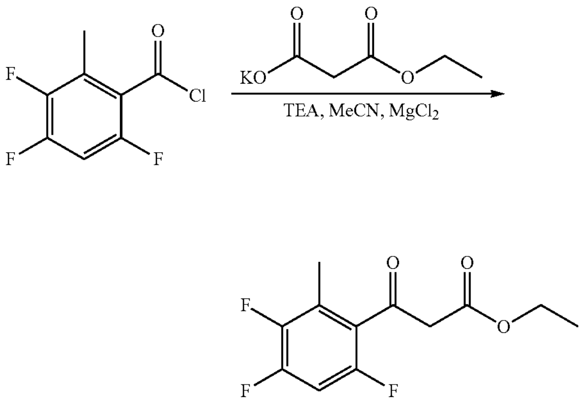

To a mixture of 3,4,6-trifluoro-2-methylbenzoyl chloride (100 mg, 0.48 mmol, 1.0 equiv) and 1-ethyl 3-potassium propanedioate (163 mg, 0.96 mmol, 2.0 equiv) in MeCN (5 mL) was added TEA (97 mg, 0.96 mmol, 2.0 equiv) and $MgCl_2$ (91 mg, 0.96 mmol, 2.00 equiv). The resulting mixture was stirred for 4 h at 25° C. The resulting mixture was concentrated under vacuum. The resulting mixture was concentrated under reduced pressure. The mixture was acidified to pH 4 with HCl (aq.). The aqueous layer was extracted with methylbenzene (10 mL×3). The organic solution was concentrated under vacuum. This resulted in ethyl 3-oxo-3-(3,4,6-trifluoro-2-methylphenyl)propanoate (100 mg, 80.15%) as a yellow oil.

Step 3. Synthesis of Ethyl 1-cyclopropyl-6,7-difluoro-5-methyl-4-oxoquinoline-3-carboxylate

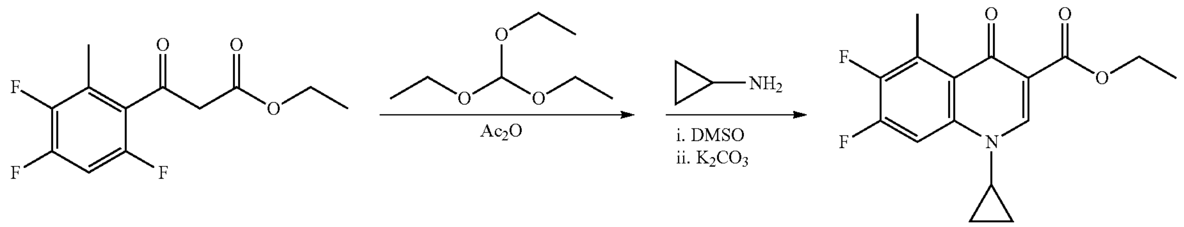

To a mixture of 3,4,6-trifluoro-2-methylbenzoic acid (100 mg, 0.52 mmol, 1.0 equiv) and $(COCl)_2$ (133 mg, 1.05 mmol, 2.0 equiv) in DCM (2 mL) was added DMF (0.1 mL) at 0° C. The resulting mixture was stirred overnight at 25° C. The resulting mixture was concentrated under vacuum. The residue was used for next step directly.

To a mixture of ethyl 3-oxo-3-(3,4,6-trifluoro-2-methylphenyl)propanoate (100 mg, 0.38 mmol, 1.0 equiv) in acetic anhydride (117 mg, 1.15 mmol, 3.0 equiv) was added triethyl orthoformate (85 mg, 0.57 mmol, 1.5 equiv). The resulting mixture was stirred for 2 h at 100° C. The resulting mixture was concentrated under vacuum. Then the resulting mixture in DMSO (3 mL) was added aminocyclopropane (22 mg, 0.38 mmol, 1.0 equiv). The resulting mixture was stirred for 2 h at 25° C. Then, the resulting mixture was added $K_2CO_3$ (26 mg, 0.19 mmol, 0.5 equiv). The resulting mixture was stirred for 1 h at 100° C. The reaction was quenched by the addition of 20 mL water. The precipitated solids were collected by filtration. This resulted in ethyl 1-cyclopropyl-6,7-difluoro-5-methyl-4-oxoquinoline-3-carboxylate (100 mg, 84.68%) as a yellow solid.

Step 4. Synthesis of 1-cyclopropyl-6,7-difluoro-5-methyl-4-oxoquinoline-3-carboxylic acid

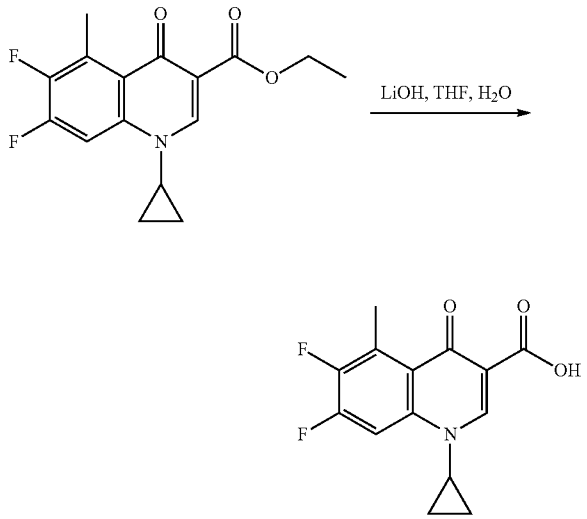

To a mixture of ethyl 1-cyclopropyl-6,7-difluoro-5-methyl-4-oxoquinoline-3-carboxylate (100 mg, 0.325 mmol, 1.0 equiv) in THF (2 mL) and $H_2O$ (0.5 mL) was added LiOH (39 mg, 1.62 mmol, 5.0 equiv). The resulting mixture was stirred overnight at 25° C. The resulting mixture was concentrated under reduced pressure. The mixture was acidified to pH 4 with HCl (aq.). The precipitated solids were collected by filtration and washed with water (10 mL×3). This resulted in 1-cyclopropyl-6,7-difluoro-5-methyl-4-oxoquinoline-3-carboxylic acid (90 mg, 99.0%) as a yellow solid.

Step 5. Synthesis of 1-cyclopropyl-6-fluoro-5-methyl-4-oxo-7-[(2R)-2-[(pyridin-2-yloxy)methyl]pyrrolidin-1-yl]quinoline-3-carboxylic acid

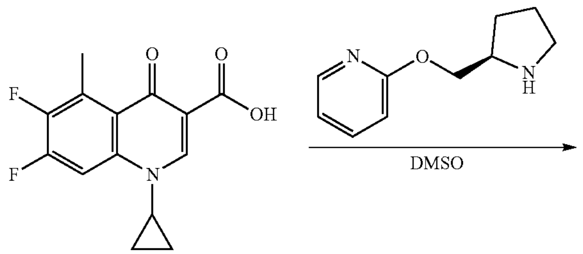

-continued

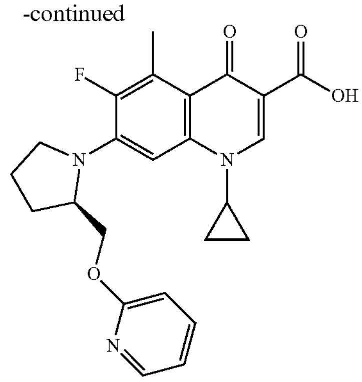

To a mixture of 1-cyclopropyl-6,7-difluoro-5-methyl-4-oxoquinoline-3-carboxylic acid (40 mg, 0.14 mmol, 1.0 equiv) in DMSO (2 mL) was added 2-[(2R)-pyrrolidin-2-ylmethoxy]pyridine (25 mg, 0.14 mmol, 1.0 equiv). The resulting mixture was stirred for 1 h at 100° C. The mixture was purified by Prep-HPLC with the following conditions (Column: XSelect CSH Prep C18 OBD Column, 5 um, 19*150 mm; Mobile Phase A:Water (0.05% FA), Mobile Phase B:ACN; Flow rate:25 mL/min; Gradient:48 B to 67 B in 8 min; 254 nm; RT1:7.02; RT2; Injection Volumn: ml; Number Of Runs;) to afford 1-cyclopropyl-6-fluoro-5-methyl-4-oxo-7-[(2R)-2-[(pyridin-2-yloxy)methyl]pyrrolidin-1-yl]quinoline-3-carboxylic acid (11.6 mg) as a yellow solid. LCMS (ESI) $[M+H]^+$: 438.1 $^1H$ NMR (300 MHz, DMSO-$d_6$) δ 15.99 (s, 1H), 8.56 (s, 1H), 8.14-7.99 (m, 1H), 7.75-7.63 (m, 1H), 7.19 (d, J=8.1 Hz, 1H), 6.99-6.89 (m, 1H), 6.77-6.70 (m, 1H), 4.65 (s, 1H), 4.51-4.40 (m, 1H), 4.38-4.20 (m, 1H), 3.71 (d, J=25.2 Hz, 2H), 3.53 (d, J=8.7 Hz, 1H), 2.74 (d, J=3.5 Hz, 3H), 2.20-1.88 (m, 4H), 1.24 (d, J=6.3 Hz, 2H), 1.18-0.91 (m, 2H).

Potency Lin28a-dep Z1 $IC_{50}$ (μM)+

Example 2: Synthesis of (R)-6-chloro-4-oxo-7-(2-((pyridin-2-yloxy)methyl)pyrrolidin-1-yl)-1-(pyrimidin-2-yl)-1,4-dihydroquinoline-3-carboxylic acid

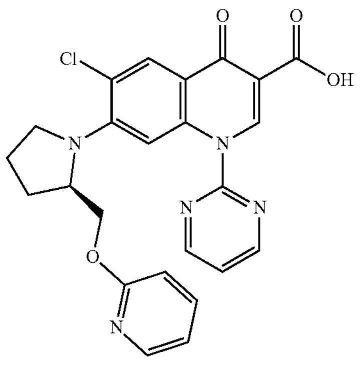 [SMILES: O=C(O)c1cn(-c2ncccn2)c2cc(N3CCC[C@@H]3COc3ccccn3)c(Cl)cc2c1=O]

Step 1. Synthesis of 5-chloro-2,4-difluorobenzoyl chloride

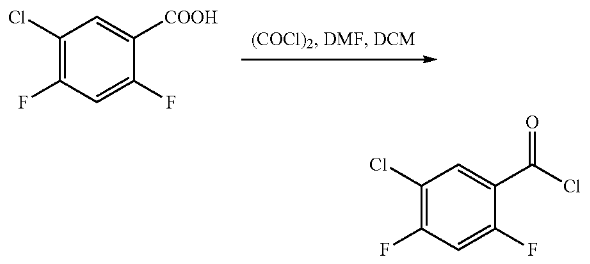

To a stirred mixture of 5-chloro-2,4-difluorobenzoic acid (5.0 g, 26.0 mmol, 1.0 equiv) and $(COCl)_2$ (19.8 g, 155.80 mmol, 6.0 equiv) in DCM (50 mL) was added DMF (1 mL) dropwise at 0° C. under air atmosphere. The resulting mixture was stirred overnight at room temperature under nitrogen atmosphere. The resulting mixture was concentrated under reduced pressure. The crude product was used in the next step directly without further purification.

Step 2. Synthesis of ethyl 3-(5-chloro-2,4-difluorophenyl)-3-oxopropanoate

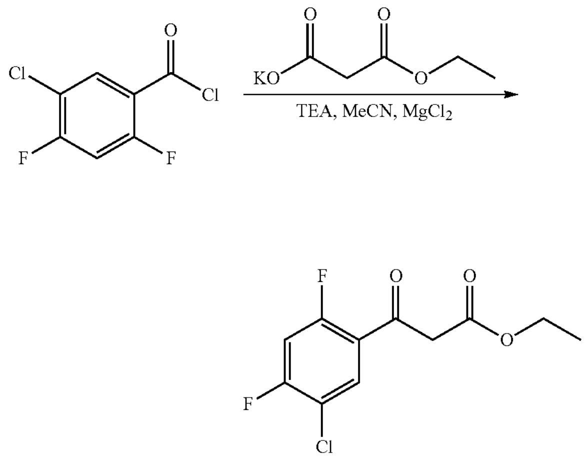

To a stirred mixture of 1-ethyl 3-potassium propanedioate (8.07 g, 47.41 mmol, 2.00 equiv) and $MgCl_2$ (5.64 g, 49.25 mmol, 2.5 equiv) in MeCN (100 mL) was added TEA (4.80 g, 47.41 mmol, 2.0 equiv) dropwise at 0° C. under air atmosphere. The resulting mixture was stirred overnight at room temperature under nitrogen atmosphere. To the above mixture was added 5-chloro-2,4-difluorobenzoyl chloride (5.0 g, 23.70 mmol, 1.00 equiv) in portions at 0° C. The resulting mixture was stirred for additional 2.5 h at room temperature. The mixture was acidified to pH 5 with conc. HCl. The resulting mixture was extracted with toluene (40 mL×3). The combined organic layers were washed with water (20 mL×2), dried over anhydrous $Na_2SO_4$. After filtration, the filtrate was concentrated under reduced pressure. The residue was purified by silica gel column chromatography, eluted with hexane/EtOAc (6:1) to afford ethyl 3-(5-chloro-2,4-difluorophenyl)-3-oxopropanoate (3.1 g, 48%) as a white solid. LCMS (ESI) $[M+H]^+$: 263.1.

Step 3. Synthesis of ethyl 6-chloro-7-fluoro-4-oxo-1-(pyrimidin-2-yl)quinoline-3-carboxylate

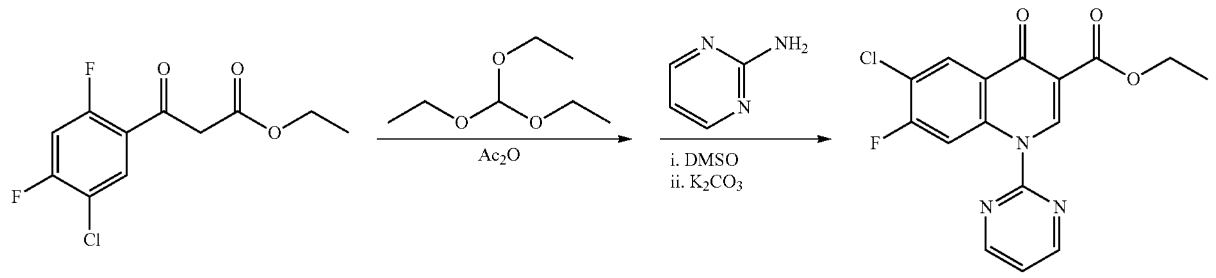

A solution of ethyl 3-(5-chloro-2,4-difluorophenyl)-3-oxopropanoate (2.0 g, 7.62 mmol, 1.0 equiv) and triethyl orthoformate (1.7 g, 11.40 mmol, 1.5 equiv) in $Ac_2O$ (2.3 g, 22.85 mmol, 3.0 equiv) was stirred for 1.5 h at 100° C. under nitrogen atmosphere. The resulting mixture was concentrated under reduced pressure. The residue was dissolved in DMSO (20 mL). To the above mixture was added 2-aminopyrimidine (720 mg, 7.62 mmol, 1.0 equiv) in portions over 2 min at room temperature. The resulting mixture was stirred overnight at room temperature. To the above mixture was added $K_2CO_3$ (530 mg, 3.81 mmol, 0.5 equiv) in portions at room temperature. The resulting mixture was stirred for additional 2 h at 40° C. The mixture was allowed to cool down to room temperature. The resulting mixture was extracted with EtOAc (20 mL×3). The combined organic layers were washed with water (15 mL×2), dried over anhydrous $Na_2SO_4$. After filtration, the filtrate was concentrated under reduced pressure. The residue was purified by silica gel column chromatography, eluted with $CH_2Cl_2$/MeOH (10:1) to afford ethyl 6-chloro-7-fluoro-4-oxo-1-(pyrimidin-2-yl)quinoline-3-carboxylate (500 mg, 19%) as a red solid. LCMS (ESI) $[M+H]^+$: 348.1.

Step 4. Synthesis of 6-chloro-7-fluoro-4-oxo-1-(pyrimidin-2-yl)quinoline-3-carboxylic acid

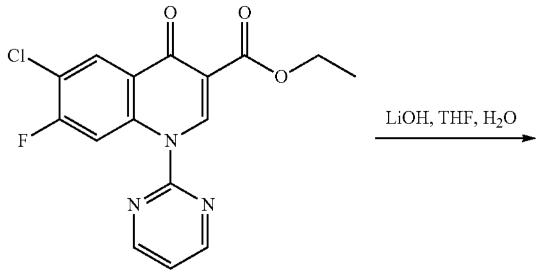

-continued

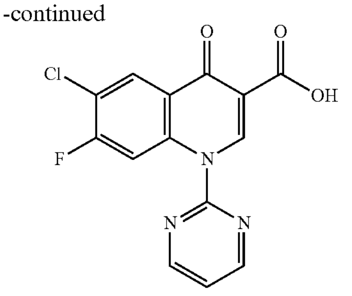

A mixture of ethyl 6-chloro-7-fluoro-4-oxo-1-(pyrimidin-2-yl)quinoline-3-carboxylate (300 mg, 0.86 mmol, 1.0 equiv) and LiOH (83 mg, 3.45 mmol, 4.0 equiv) in THF (4.0 mL) and $H_2O$ (1.0 mL) was stirred for 5 h at room temperature under nitrogen atmosphere. The mixture was acidified to pH 6 with conc. HCl. The resulting mixture was extracted with EtOAc (10 mL×3). The combined organic layers were washed with water (5 mL×2), dried over anhydrous $Na_2SO_4$. After filtration, the filtrate was concentrated under reduced pressure. The resulting mixture was washed with (5 mL×3) of hexane/EtOAc (5:1), to afford 6-chloro-7-fluoro-4-oxo-1-(pyrimidin-2-yl)quinoline-3-carboxylic acid (160 mg, 58%) as a red solid. LCMS (ESI) $[M+H]^+$: 320.2.

Step 5. Synthesis of 6-chloro-4-oxo-7-[(2R)-2-[(pyridin-2-yloxy)methyl]pyrrolidin-1-yl]-1-(pyrimidin-2-yl)quinoline-3-carboxylic acid

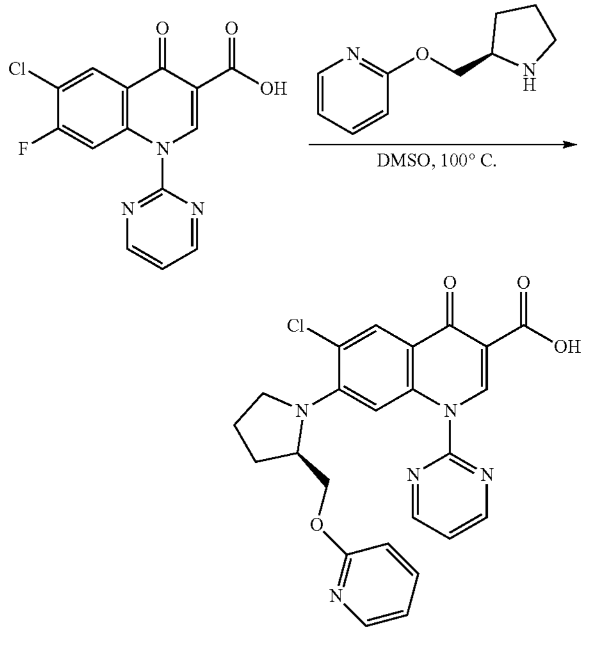

A solution of 6-chloro-7-fluoro-4-oxo-1-(pyrimidin-2-yl) quinoline-3-carboxylic acid (80 mg, 0.25 mmol, 1.0 equiv) and 2-[(2R)-pyrrolidin-2-ylmethoxy]pyridine (357 mg, 2.00 mmol, 8.0 equiv) in DMSO (4.0 mL) was stirred overnight at 100° C. under nitrogen atmosphere. The mixture was allowed to cool down to room temperature. The crude product (100 mg) was purified by Prep-HPLC with the following conditions (Column: XSelect CSH Prep C18 OBD Column, 5 um, 19*150 mm; Mobile Phase A:Water (0.05% FA), Mobile Phase B:ACN; Flow rate:25 mL/min; Gradient:42 B to 73 B in 8 min; 254 nm; RT1:7.67) to afford 6-chloro-4-oxo-7-[(2R)-2-[(pyridin-2-yloxy)methyl]pyrrolidin-1-yl]-1-(pyrimidin-2-yl)quinoline-3-carboxylic acid (25.7 mg, 21.5%) as a yellow solid. LCMS (ESI) $[M+H]^+$: 478.1. $^1H$ NMR (300 MHz, DMSO-$d_6$) δ 14.73 (s, 1H), 9.18 (s, 1H), 8.98 (s, 2H), 8.14 (s, 1H), 8.00-7.85 (m, 1H), 7.74 (s, 1H), 7.67-7.53 (m, 1H), 7.47 (s, 1H), 6.87 (t, J=5.7 Hz, 1H), 6.61 (d, J=7.9 Hz, 1H), 4.58 (s, 1H), 4.40-4.11 (m, 2H), 3.74 (s, 1H), 3.33-3.30 (m, 1H), 2.23 (s, 1H), 2.10-1.65 (m, 3H).

Potency Lin28a-dep Z11 $IC_{50}$ (μM)+++

Example 3: Synthesis of (R)-1-cyclopropyl-6-fluoro-8-methoxy-4-oxo-7-(2-((pyridin-2-yloxy)methyl)pyrrolidin-1-yl)-1,4-dihydroquinoline-3-carboxylic acid

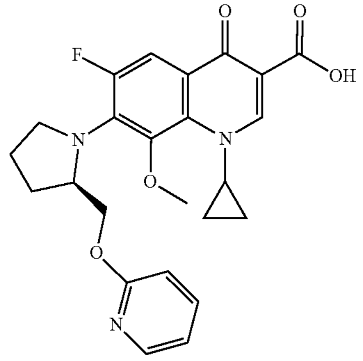 [SMILES: COc1c(N2CCC[C@@H]2COc2ccccn2)c(F)cc2c(=O)c(C(=O)O)cn(C3CC3)c12]

Step 1. Synthesis of 2,4,5-trifluoro-3-methoxybenzoyl chloride

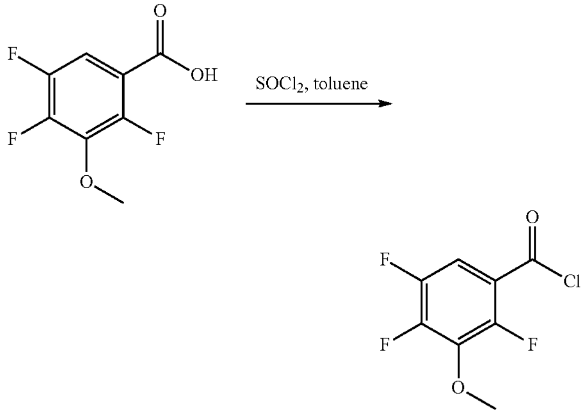

To a solution of 2,4,5-trifluoro-3-methoxybenzoic acid (500 mg, 2.43 mmol, 1.0 equiv) in toluene (8.0 mL) at 0° C. was added $SOCl_2$ (866 mg, 7.28 mmol, 3.0 equiv). The resulting mixture was stirred overnight at 25° C. The resulting mixture was concentrated under vacuum. This resulted in 2,4,5-trifluoro-3-methoxybenzoyl chloride (500 mg, crude) as a yellow semi-solid.

Step 2. Synthesis of ethyl 3-oxo-3-(2,4,5-trifluoro-3-methoxyphenyl)propanoate

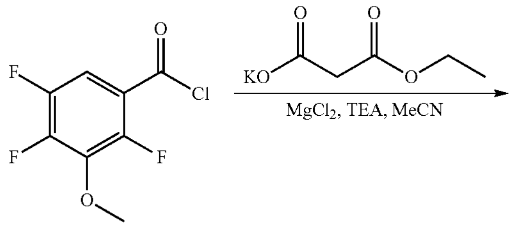

-continued

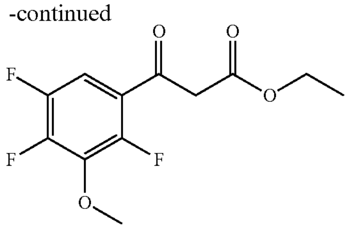

A stirred solution of 1-ethyl 3-potassium propanedioate (758 mg, 4.45 mmol, 2.0 equiv) in anhydrous acetonitrile (10 mL) under nitrogen was cooled to 10-15° C. To this mixture was added TEA (451 mg, 4.45 mmol, 2.0 equiv) followed by $MgCl_2$ (530 mg, 5.57 mmol, 2.5 equiv), and stirring continued at 20-25° C. for 2.5 h. The resultant slurry was re-cooled to 0° C. and 2,4,5-trifluoro-3-methoxybenzoyl chloride (500 mg, 2.23 mmol, 1.0 equiv) added dropwise over 15 min followed by the addition of TEA (23 mg, 0.22 mmol, 0.1 equiv). The mixture was stirred at room temperature for 18 h and then concentrated under reduced pressure to remove acetonitrile. Toluene (8 mL) was added and the mixture concentrated under reduced pressure. More toluene (8 mL) was added and the mixture stirred and cooled to 10-15° C. Aqueous HCl (13%, 10 mL) was added while the temperature was kept below 25° C. The aqueous layer was separated and the organic layer washed with aqueous HCl (12%, 10 mL) followed by water (8 mL) and then concentrated under reduced pressure to give ethyl 3-oxo-3-(2,4,5-trifluoro-3-methoxyphenyl)propanoate (1.0 g, crude) as a yellow oil. LCMS (ESI) $[M+H]^+$: 276.

Step 3. Synthesis of ethyl 1-cyclopropyl-6,7-difluoro-8-methoxy-4-oxoquinoline-3-carboxylate

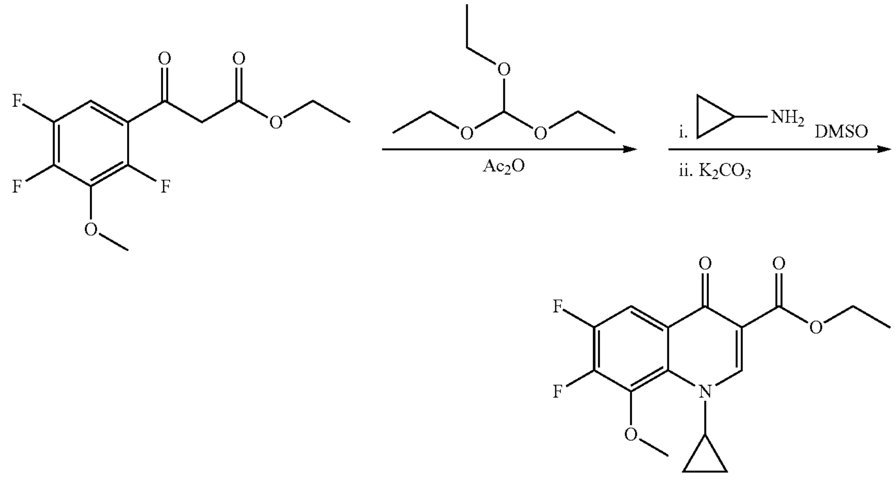

To a mixture of ethyl 3-oxo-3-(2,4,5-trifluoro-3-methoxyphenyl)propanoate (1.0 g, 3.62 mmol, 1.0 equiv) in acetic anhydride (1.1 g, 10.86 mmol, 3.0 equiv) was added triethyl orthoformate (0.8 g, 5.43 mmol, 1.5 equiv). The resulting mixture was stirred at 100° C. for 2 h. The resulting mixture was concentrated under vacuum. To the resulting mixture in DMSO (12 mL) was added aminocyclopropane (0.2 g, 3.62 mmol, 1.0 equiv). The resulting mixture was stirred at 25° C. for 2 h. To the resulting mixture was added $K_2CO_3$ (0.3 g, 1.81 mmol, 0.5 equiv). The resulting mixture was stirred at 100° C. for 1 h. The reaction was quenched by the addition of 15 mL water. The precipitated solids were collected by filtration. This resulted in ethyl 1-cyclopropyl-6,7-difluoro-8-methoxy-4-oxoquinoline-3-carboxylate (300 mg, 26%) as a yellow solid. LCMS (ESI) $[M+H]^+$: 324.

Step 4. Synthesis of 1-cyclopropyl-6,7-difluoro-8-methoxy-4-oxoquinoline-3-carboxylic acid

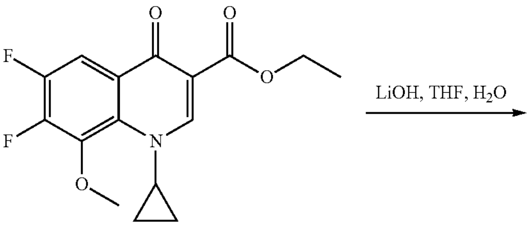

-continued

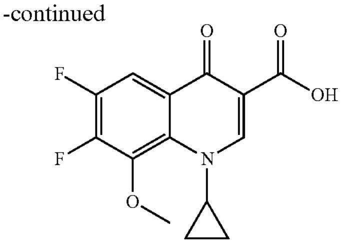

To a mixture of ethyl 1-cyclopropyl-6,7-difluoro-8-methoxy-4-oxoquinoline-3-carboxylate (300 mg, 0.93 mmol, 1.0 equiv) in THF (5.0 mL) was added LiOH (89 mg, 3.71 mmol, 4.0 equiv) and $H_2O$ (1.0 mL). The resulting mixture was stirred for 3 h at room temperature. The mixture was neutralized to pH 6 with HCl (aq.). The resulting mixture was filtered. This resulted in 1-cyclopropyl-6,7-difluoro-8-methoxy-4-oxoquinoline-3-carboxylic acid (250 mg, 91%) as a white solid. LCMS (ESI) $[M+H]^+$: 296.

Step 5. Synthesis of 1-cyclopropyl-6-fluoro-8-methoxy-4-oxo-7-[(2R)-2-[(pyridine-2-yloxy)methyl]pyrrolidin-1-yl]quinoline-3-carboxylic acid

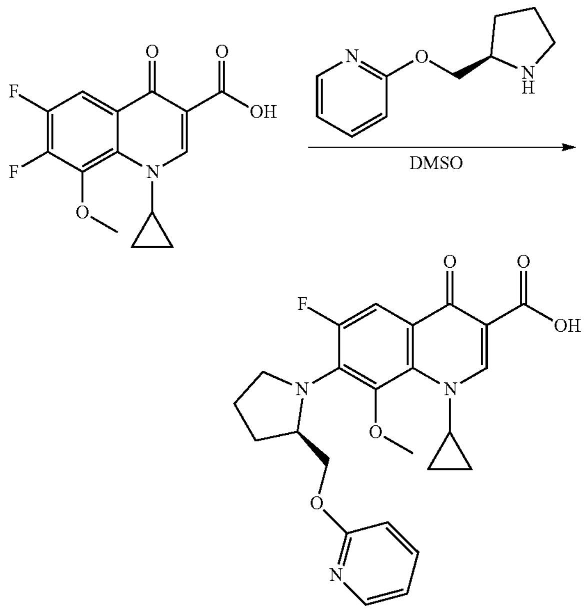

To a mixture of 1-cyclopropyl-6,7-difluoro-8-methoxy-4-oxoquinoline-3-carboxylic acid (220 mg, 0.75 mmol, 1.0 equiv) in DMSO (8.0 mL) was added 2-[(2R)-pyrrolidin-2-ylmethoxy]pyridine (199 mg, 1.12 mmol, 1.5 equiv). The resulting mixture was stirred for 48 h at 80° C. The mixture was allowed to cool down to room temperature. The resulting mixture was concentrated under vacuum. The crude product was purified by Prep-HPLC with the following conditions (Column: XBridge Shield RP18 OBD Column, 5 um, 19*150 mm; Mobile Phase A:Water(0.1% FA), Mobile Phase B: ACN; Flow rate: 25 mL/min; Gradient: 60% B to 90% B in 8 min; 254/220 nm; Rt: 7.31 min) to afford 1-cyclopropyl-6-fluoro-8-methoxy-4-oxo-7-[(2R)-2-[(pyridin-2-yloxy)methyl]pyrrolidin-1-yl]quinoline-3-carboxylic acid (56.9 mg, 16.84%) as a light yellow solid. LCMS (ESI) $[M+H]^+$: 454.35. $^1H$ NMR (400 MHz, DMSO-$d_6$) δ 8.66 (s, 1H), 8.04-7.95 (m, 1H), 7.68-7.53 (m, 2H), 6.88 (d, J=7.1, 5.0, 1.0 Hz, 1H), 6.55 (s, 1H), 4.62-4.53 (m, 1H), 4.36-4.21 (m, 2H), 4.14 (d, J=7.4, 4.0 Hz, 1H), 3.92-3.83 (m, 1H), 3.59 (s, 3H), 3.37 (s, 1H), 2.37-2.21 (m, 1H), 2.06 (d, J=12.5 Hz, 1H), 2.01-1.72 (m, 2H), 1.29-1.06 (m, 2H), 0.99-0.67 (m, 2H).

Potency Lin28a-dep Z11 $IC_{50}$ (μM)+

Example 4: Synthesis of (R)-6-fluoro-4-oxo-7-(2-(phenoxymethyl)pyrrolidin-1-yl)-1-phenyl-1,4-dihydroquinoline-3-carboxylic acid

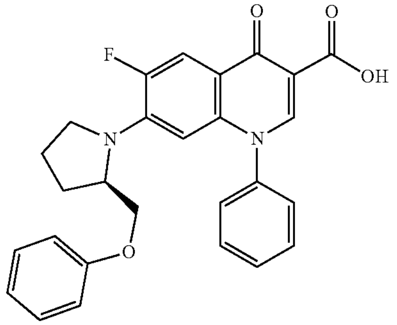 [SMILES: O=C(O)c1cn(-c2ccccc2)c2cc(N3CCC[C@@H]3COc3ccccc3)c(F)cc2c1=O]

Step 1. Synthesis of tert-butyl (2R)-2-(2-chlorophenoxymethyl)pyrrolidine-1-carboxylate

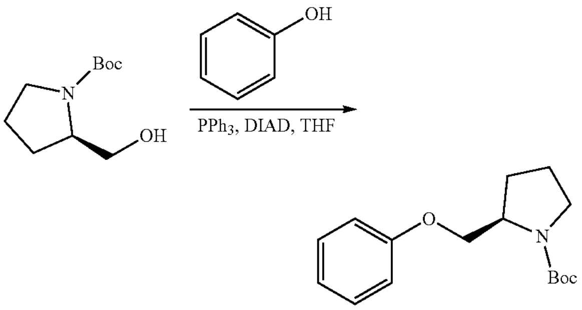

To a mixture of phenol (3.0 g, 31.87 mmol, 1.0 equiv), tert-butyl (2R)-2-(hydroxymethyl)pyrrolidine-1-carboxylate (6.4 g, 31.87 mmol, 1.0 equiv) and $PPh_3$ (16.7 g, 63.75 mmol, 2.0 equiv) in THF (50 mL) was added DIAD (8.2 g, 63.75 mmol, 2.0 equiv). The resulting solution was stirred overnight at 25° C. The resulting mixture was concentrated under vacuum. The residue was purified by reverse phase flash chromatography eluting with 5-60% acetonitrile in water to afford tert-butyl (2R)-2-(phenoxymethyl)pyrrolidine (1.1 g, 20%) as colorless oil. LCMS (ESI) $[M+H]^+$: 278.1

Step 2. Synthesis of (2R)-2-(phenoxymethyl)pyrrolidine

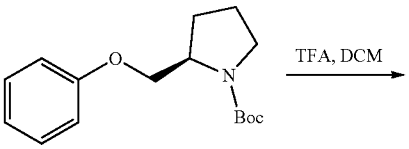

-continued

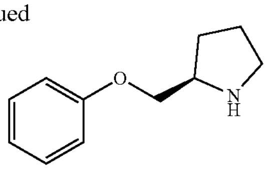

To a mixture of tert-butyl (2R)-2-(phenoxymethyl)pyrrolidine (500 mg, 1.60 mmol, 1.0 equiv) in DCM (10 mL) was added TFA (2 mL). The resulting solution was stirred for 1 h at 25° C. The resulting mixture was concentrated. This resulted in (2R)-2-(phenoxymethyl)pyrrolidine (840 mg, crude) as yellow oil. LCMS (ESI) $[M+H]^+$:178.1.

Step 3. Synthesis of 6-fluoro-4-oxo-7-[(2R)-2-(phenoxymethyl)pyrrolidin-1-yl]-1-phenylquinoline-3-carboxylic acid

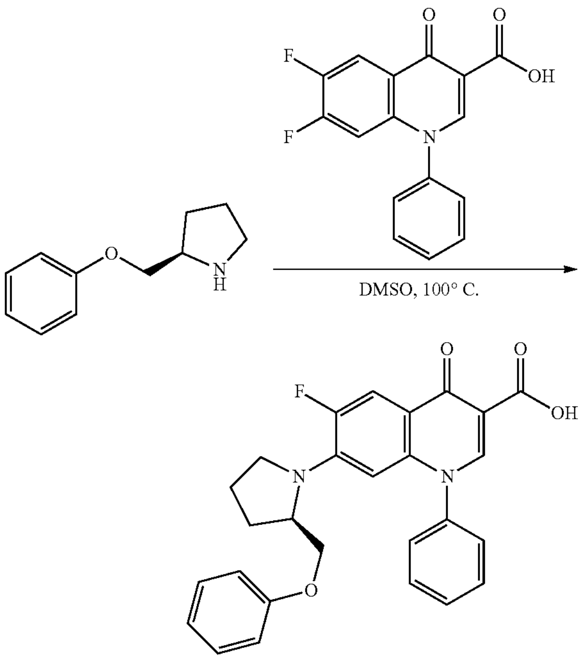

To a mixture of 6,7-difluoro-4-oxo-1-phenylquinoline-3-carboxylic acid (100 mg, 0.33 mmol, 1.0 equiv) in DMSO (2 mL) was added (2R)-2-(phenoxymethyl)pyrrolidine (58 mg, 0.33 mmol, 1.0 equiv). The resulting solution was stirred for 1 h at 80° C. The precipitated solids were collected and purified by Prep.-HPLC with the following conditions (Column: XSelect CSH Prep C18 OBD Column, 5 um, 19*150 mm; Mobile Phase A:Water (0.05% FA), Mobile Phase B:ACN; Flow rate:25 mL/min; Gradient:50 B to 75 B in 8 min; 254 nm; RT1:6.86). This resulted in 6-fluoro-4-oxo-7-[(2R)-2-(phenoxymethyl)pyrrolidin-1-yl]-1-phenylquinoline-3-carboxylic acid (59.4 mg 39.0%) as a yellow solid. LCMS (ESI) $[M+H]^+$: 459.1. $^1H$ NMR (300 MHz, DMSO-$d_6$) δ 15.41 (s, 1H), 8.53 (s, 1H), 7.92 (d, J=14.5 Hz, 1H), 7.66 (m, 4H), 7.41 (t, J=7.7 Hz, 1H), 7.26 (t, J=7.7 Hz, 2H), 6.94 (t, J=7.4 Hz, 1H), 6.82 (d, J=8.0 Hz, 2H), 6.09 (d, J=7.5 Hz, 1H), 4.34-4.24 (m, 1H), 3.90 (q, J=3.7 Hz, 1H), 3.82 (t, J=8.4 Hz, 1H), 3.38-3.36 (m, 1H), 3.27-3.14 (m, 1H), 2.20-1.76 (m, 4H).

Potency Lin28a-dep Z11 $IC_{50}$ (μM)+

Example 5: Synthesis of (R)-6-fluoro-7-(2-(((3-methylpyridin-2-yl)oxy)methyl)pyrrolidin-1-yl)-4-oxo-1-phenyl-1,4-dihydroquinoline-3-carboxylic acid

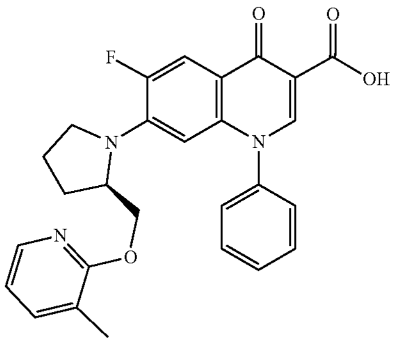 [SMILES: Cc1cccnc1OC[C@H]1CCCN1c1cc2c(cc1F)c(=O)c(C(=O)O)cn2-c1ccccc1]

Step 1. Synthesis of ethyl 6,7-difluoro-4-oxo-1-phenyl-1,4-dihydroquinoline-3-carboxylate

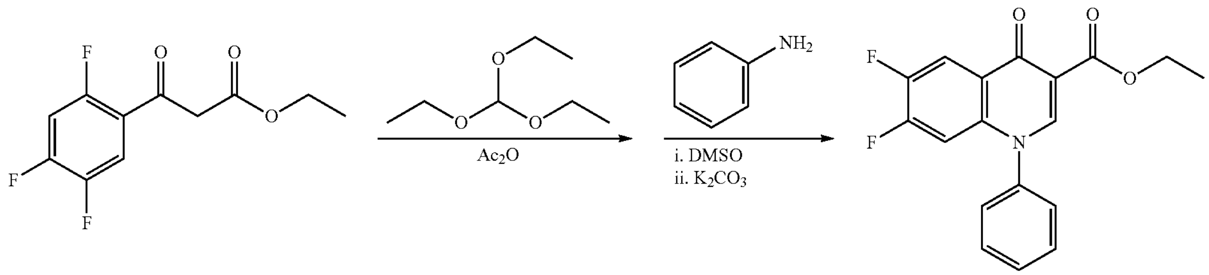

To a mixture of ethyl 3-oxo-3-(2,4,5-trifluorophenyl)propanoate (5.0 g, 20.31 mmol, 1.0 equiv), in acetic anhydride (6.2 g, 60.93 mmol, 3.0 equiv) was added triethyl orthoformate (4.5 g, 30.46 mmol, 1.5 equiv). The resulting mixture was stirred at 100° C. for 2 h. The resulting mixture was concentrated under vacuum. To the resulting mixture in DMSO (50 mL) was added aniline (2.2 g, 24.37 mmol, 1.2 equiv), The resulting mixture was stirred at 25° C. for 2 h. To the resulting mixture was added $K_2CO_3$ (2.8 g, 20.31 mmol, 1.0 equiv). The resulting mixture was stirred at 100° C. for 1 h. The reaction was quenched by the addition of 500 mL water. The precipitated solids were collected by filtration. This resulted in ethyl 6,7-difluoro-4-oxo-1-phenyl-1,4-dihydroquinoline-3-carboxylate (4.7 g 70.2%) as a yellow solid. LCMS (ESI) $[M+H]^+$: 330.1.

Step 2. Synthesis of 6,7-difluoro-4-oxo-1-phenyl-1,4-dihydroquinoline-3-carboxylic acid

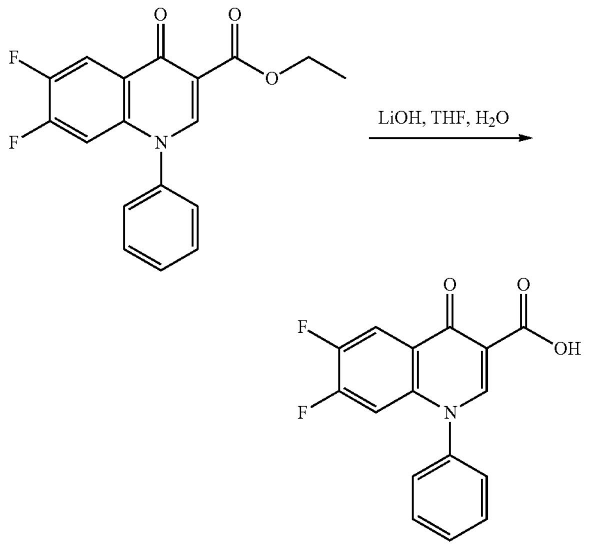

To a mixture of ethyl 6,7-difluoro-4-oxo-1-phenyl-1,4-dihydroquinoline-3-carboxylate (2.0 g, 6.07 mmol, 1.0 equiv) in THF (100 mL) and $H_2O$ (10 mL) was added LiOH (1.1 g, 48.58 mmol, 8.0 equiv). The resulting mixture was stirred at 25° C. overnight. The resulting mixture was concentrated under reduced pressure. The mixture was acidified to pH 4 with HCl (aq.). The precipitated solids were collected by filtration and washed with water (50 mL×3). This resulted in 6,7-difluoro-4-oxo-1-phenyl-1,4-dihydroquinoline-3-carboxylic acid (1.6 g 89.6%) as a yellow solid. LCMS (ESI) $[M+H]^+$: 302.1

Step 3. Synthesis of (R)-6-fluoro-7-(2-(((3-methylpyridin-2-yl)oxy)methyl)pyrrolidin-1-yl)-4-oxo-1-phenyl-1,4-dihydroquinoline-3-carboxylic acid

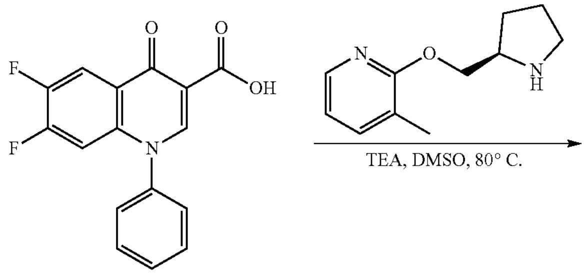

-continued

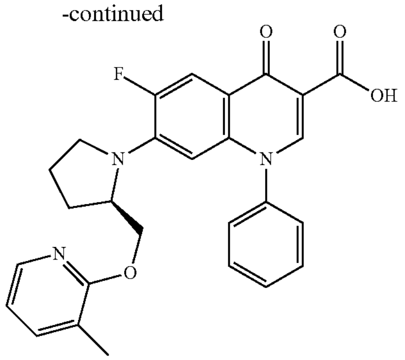

To a solution of 6,7-difluoro-4-oxo-1-phenyl-1,4-dihydroquinoline-3-carboxylic acid (100 mg, 0.33 mmol, 1.0 equiv) in DMSO (10 mL) was added (R)-3-methyl-2-(pyrrolidin-2-ylmethoxy)pyridine (63 mg, 0.33 mmol, 1.0 equiv). The resulting solution was stirred for 1 h at 100° C. The mixture was purified by Prep.-HPLC (Column: SunFire Prep C18 OBD Column, 19×150 mm 5 um 10 nm; Mobile Phase A:Water (0.05% FA), Mobile Phase B:ACN; Flow rate:25 mL/min; Gradient:52 B to 82 B in 8 min; 254/220 nm; RT1:7.77; RT2; Injection Volumn: ml; Number Of Runs;). This resulted in (R)-6-fluoro-7-(2-(((3-methylpyridin-2-yl)oxy)methyl)pyrrolidin-1-yl)-4-oxo-1-phenyl-1,4-dihydroquinoline-3-carboxylic acid (42.6 mg, 27%) as a yellow solid. LCMS (ESI) $[M+H]^+$: 474.1. $^1H$ NMR (300 MHz, DMSO-$d_6$) δ 15.51-15.37 (m, 1H), 8.54-8.50 (m, 1H), 7.95-7.82 (m, 2H), 7.73-7.55 (m, 4H), 7.54-7.41 (m, 2H), 6.93-6.82 (m, 1H), 6.09-5.99 (m, 1H), 4.47-4.34 (m, 1H), 4.30-4.16 (m, 2H), 3.36-3.35 (m, 1H), 3.24-3.11 (m, 1H), 2.15-1.84 (m, 7H).

Potency Lin28a-dep Z11 $IC_{50}$ (μM)++++

Example 6: Synthesis of (R)-7-(2-(((3-ethylpyridin-2-yl)oxy)methyl)pyrrolidin-1-yl)-6-fluoro-4-oxo-1-phenyl-1,4-dihydroquinoline-3-carboxylic acid

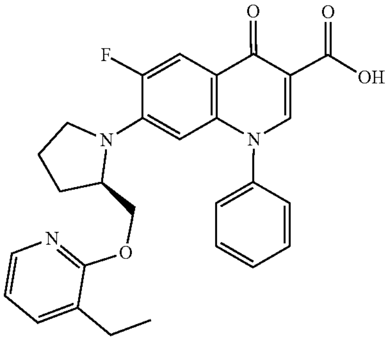 [SMILES: CCc1cccnc1OC[C@H]1CCCN1c1cc2c(cc1F)c(=O)c(C(=O)O)cn2-c1ccccc1]

Step 1. Synthesis of tert-butyl (2R)-2-[[(3-iodopyridin-2-yl)oxy]methyl]pyrroledine-1-carboxylate

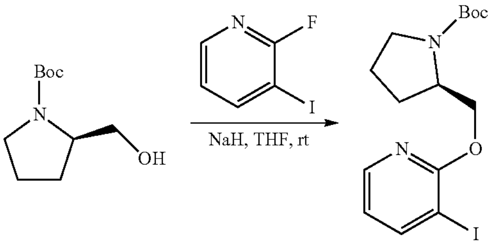

To a mixture of 2-fluoro-3-iodopyridine (5.0 g, 22.42 mmol, 1.0 equiv) in THF (50 mL) was added NaH (1.6 g, 67.26 mmol, 3.0 equiv) and tert-butyl (2R)-2-(hydroxymethyl)pyrrolidine-1-carboxylate (22.56 g, 112.11 mmol, 1.0 equiv). The resulting mixture was stirred overnight at 70° C. The reaction was quenched with water. The resulting mixture was extracted with EtOAc (3×50 mL). The combined organic layers were collected and dried with anhydrous $Na_2SO_4$. The resulting mixture was concentrated under vacuum. The residue was purified by silica gel column chromatography eluting with Petroleum ether/EtOAc (1:1). This resulted in tert-butyl (2R)-2-[[(3-iodopyridin-2-yl)oxy]methyl]pyrrolidine-1-carboxylate (5.2 g, 11%) as a colorless oil. LCMS (ESI) $[M+H]^+$: 405.0

Step 2. Synthesis of tert-butyl (R)-2-(((3-vinylpyridin-2-yl)oxy)methyl)pyrrolidine-1-carboxylate

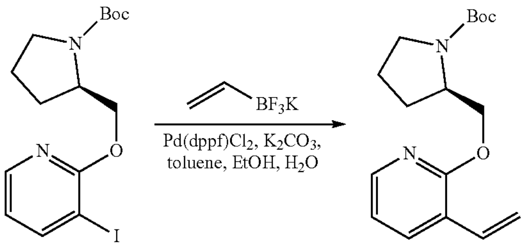

To a mixture of tert-butyl (2R)-2-[[(3-iodopyridin-2-yl)oxy]methyl]pyrrolidine-1-carboxylate (2.0 g, 4.94 mmol, 1.0 equiv) in toluene (7 mL), EtOH (2 mL), $H_2O$ (1 mL) was added $K_2CO_3$ (2.0 g, 14.84 mmol, 3.0 equiv), $Pd(dppf)Cl_2$ (360 mg, 0.49 mmol, 0.1 equiv) and ethenyltrifluorolambda4-borane potassium (990 mg, 7.42 mmol, 1.5 equiv). The resulting mixture was stirred for additional 1 h at 80° C. under nitrogen atmosphere. The resulting mixture was concentrated under vacuum. The residue was purified by silica gel column chromatography eluting with Petroleum ether/EtOAc (1:1). This resulted in tert-butyl (R)-2-(((3-vinylpyridin-2-yl)oxy)methyl)pyrrolidine-1-carboxylate (1.0 g, 69%) as a colorless oil. LCMS (ESI) $[M+H]^+$: 307.1

Step 3. Synthesis of tert-butyl (R)-2-(((3-ethylpyridin-2-yl)oxy)methyl)pyrrolidine-1-carboxylate

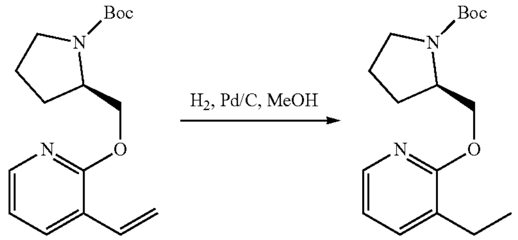 [SMILES: C=Cc1cccnc1OC[C@H]1CCCN1C(=O)OC(C)(C)C ; "H2, Pd/C, MeOH" ; CCc1cccnc1OC[C@H]1CCCN1C(=O)OC(C)(C)C]

To a mixture of tert-butyl (R)-2-(((3-vinylpyridin-2-yl)oxy)methyl)pyrrolidine-1-carboxylate (1.0 g, 3.28 mmol, 1.0 equiv) in MeOH (100 mL), Pd/C (349 mg, 0.328 mmol, 0.1 equiv, 10%), The resulting mixture was stirred for 0.5 h at room temperature under a hydrogen atmosphere. The resulting mixture was filtered; the filter cake was washed with DCM (100 mL). The filtrate was concentrated under reduced pressure. The residue was purified by silica gel column chromatography, eluted with Petroleum ether/EtOAc (1:1). This resulted in tert-butyl (R)-2-(((3-ethylpyridin-2-yl)oxy)methyl)pyrrolidine-1-carboxylate (507 mg, 50%) as a colorless oil. LCMS (ESI) $[M+H]^+$: 307.1

Step 4. Synthesis of (R)-3-ethyl-2-(pyrrolidin-2-ylmethoxy)pyridine

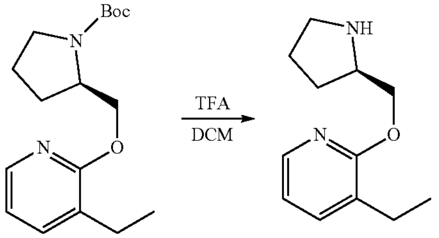

To a solution of tert-butyl (R)-2-(((3-ethylpyridin-2-yl)oxy)methyl)pyrrolidine-1-carboxylate (200 mg, 0.65 mmol, 1.0 equiv) in DCM (5 mL) was added TFA (2 mL) dropwise. The resulting mixture was stirred for 0.5 h at room temperature. The resulting mixture was concentrated. This resulted in (R)-3-ethyl-2-(pyrrolidin-2-ylmethoxy)pyridine (206 mg, crude) as a colorless oil. LCMS (ESI) $[M+H]^+$: 207.1

Step 5. Synthesis of 7-[(2R)-2-[[(3-ethylpyridin-2-yl)oxy]methyl]pyrrolidin-1-yl]-6-fluoro-4-oxo-1-phenylquinoline-3-carboxylic acid

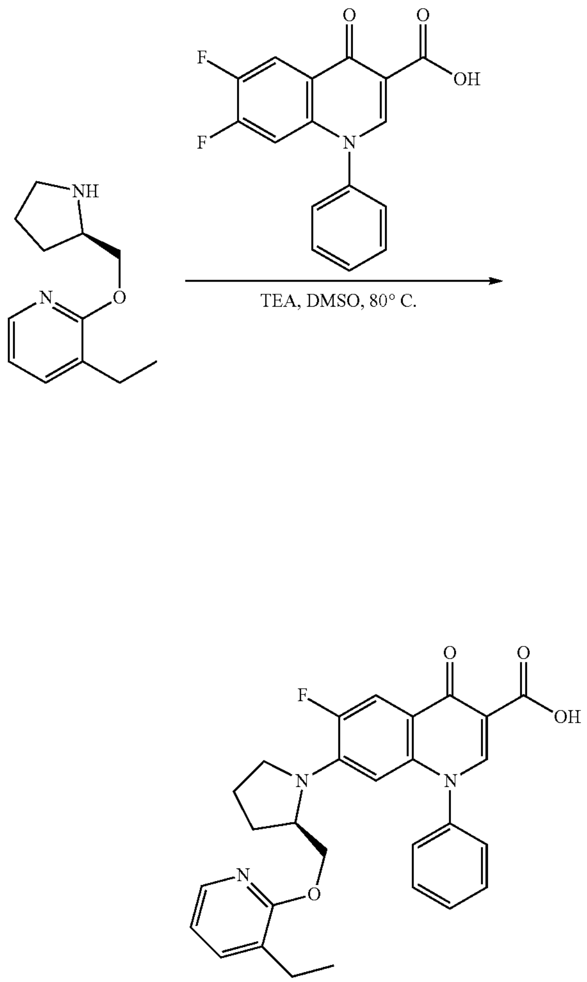

To a mixture of 3-ethyl-2-[(2R)-pyrrolidin-2-ylmethoxy] pyridine (68 mg, 0.33 mmol, 1.0 equiv) in DMSO (5 mL) was added TEA (100 mg, 0.98 mmol, 3 equiv) and 6,7-difluoro-4-oxo-1-phenylquinoline-3-carboxylic acid (99 mg, 0.33 mmol, 1.0 equiv). The resulting mixture was stirred for additional 1 h at 80° C. The precipitated solids were collected and crude product was purified by Prep.-HPLC with the following conditions (Column: SunFire Prep C18 OBD Column, 19×150 mm 5 um 10 nm; Mobile Phase A:Water(0.1% FA), Mobile Phase B:ACN; Flow rate:25 m/min; Gradient:62 B to 70 B in 10 min; 254 nm; RT1:9.48). This resulted in 7-[(2R)-2-[[(3-ethylpyridin-2-yl)oxy] methyl]pyrrolidin-1-yl]-6-fluoro-4-oxo-1-phenylquinoline-3-carboxylic acid (25.1 mg, 15.3%) as a yellow solid. LCMS (ESI) $[M+H]^+$: 488.1 $^1H$ NMR (300 MHz, DMSO-$d_6$) δ 15.42 (s, 1H), 8.52 (s, 1H), 7.99-7.81 (m, 2H), 7.76-7.55 (m, 4H), 7.49 (d, J=7.3 Hz, 2H), 6.90 (dd, J=7.2, 4.9 Hz, 1H), 6.05 (d, J=7.4 Hz, 1H), 4.50-4.33 (m, 1H), 4.17 (qd, J=10.9, 9.9, 3.4 Hz, 2H), 3.24-3.14 (m, 2H), 2.37 (q, J=7.6 Hz, 2H), 2.14-1.84 (m, 4H), 1.01 (t, J=7.5 Hz, 3H)

Potency Lin28a-dep Z11 $IC_{50}$ (μM)+

Example 7: Synthesis of 6-fluoro-1-(4-hydroxyphenyl)-7-((2R)-4-methyl-2-(((3-methylpyridin-2-yl)oxy)methyl)pyrrolidin-1-yl)-4-oxo-1,4-dihydroquinoline-3-carboxylic acid

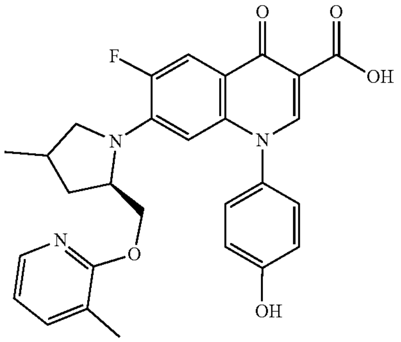 [SMILES: Cc1cccnc1OC[C@H]1CC(C)CN1c1cc2c(cc1F)c(=O)c(C(=O)O)cn2-c1ccc(O)cc1]

Step 1. Synthesis of 1-tert-butyl 2-methyl (2R)-4-(oxan-2-yloxy)pyrrolidine-1,2-dicarboxylate

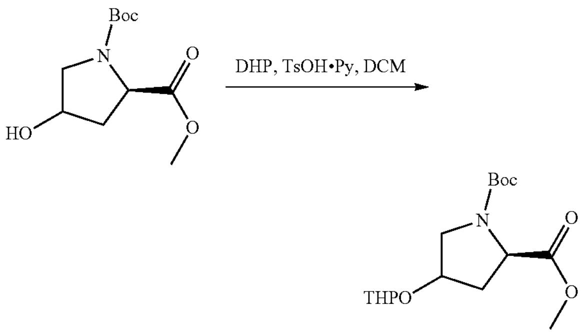

To a mixture of 1-tert-butyl 2-methyl (2R)-4-hydroxypyrrolidine-1,2-dicarboxylate (10 g, 40.77 mmol) in DCM (100.00 mL) was added DHP (5.14 g, 61.10 mmol) and TsOH-Py (1.02 g, 4.05 mmol). The resulting mixture was stirred for 4 h at room temperature. The reaction mixture was diluted with 500 ml $H_2O$. The resulting solution was extracted with DCM (300 mL×3) and the organic layers were combined. The organic layer was washed with brine (200 mL×2). The organic layer was dried over anhydrous sodium sulfate and concentrated under vacuum. The residue was purified by flash chromatography on silica gel eluting with EtOAc/Petroleum ether (0-50%) to afford 1-tert-butyl 2-methyl (2R)-4-(oxan-2-yloxy)pyrrolidine-1,2-dicarboxylate (13 g, 89.0% yield) as a yellow oil. LCMS (ESI) $[M+H]^+$: 330.20.

Step 2. Synthesis of tert-butyl (2R)-2-(hydroxymethyl)-4-(oxan-2-yloxy)pyrroledine-1-carboxylate

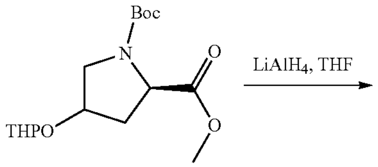

-continued

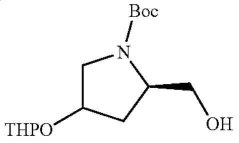

To a mixture of 1-tert-butyl 2-methyl (2R)-4-(oxan-2-yloxy)pyrrolidine-1,2-dicarboxylate (6 g, 18.21 mmol) in THF (50.00 mL) were added $LiAlH_4$ (0.83 g, 21.85 mmol) at 0° C., The mixture was stirred at room temperature for 0.5 h. The reaction was quenched with $Na_2SO_4 \cdot 10H_2O$ at 0° C. The mixture was filtered and the filter cake was washed with EtOAc. The filtrate was dried over anhydrous sodium sulfate and concentrated under vacuum. The residue was purified by flash chromatography on silica gel eluting with EtOAc/Petroleum ether (40%-50%) to afford tert-butyl (2R)-2-(hydroxymethyl)-4-(oxan-2-yloxy)pyrrolidine-1-carboxylate (2.5 g, 41.0% yield) as a yellow oil. LCMS (ESI) $[M+H]^+$: 302.21.

Step 3. Synthesis of tert-butyl (2R)-2-[(benzyloxy)methyl]-4-(oxan-2-yloxy)pyrrolidine-1-carboxylate

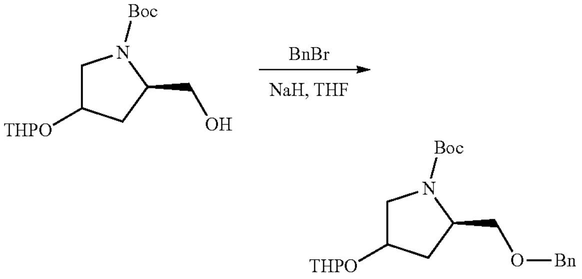

To a mixture of tert-butyl (2R)-2-(hydroxymethyl)-4-(oxan-2-yloxy)pyrrolidine-1-carboxylate (2.50 g, 8.29 mmol) in THF (30.00 mL) was added NaH (0.80 g, 33.33 mmol) at 0° C. The mixture was stirred at room temperature for 0.5 h. The benzyl bromide (1.70 g, 9.93 mmol) was added and the mixture was stirred at room temperature for 2 h. The reaction was quenched with $H_2O$ at 0° C. Then the reaction mixture was diluted with 200 mL $H_2O$. The resulting solution was extracted with EtOAc (200 mL×3) and the organic layers were combined. The organic layer was washed with brine, dried over anhydrous sodium sulfate and concentrated under vacuum. The residue was purified by Prep.-HPLC to afford tert-butyl (2R)-2-[(benzyloxy)methyl]-4-(oxan-2-yloxy)pyrrolidine-1-carboxylate (1.3 g, 41.0% yield) as a yellow oil. LCMS (ESI) $[M+H]^+$: 392.25.

Step 4. Synthesis of tert-butyl (2R)-2-[(benzyloxy)methyl]-4-hydroxypyrrolidine-1-carboxylate

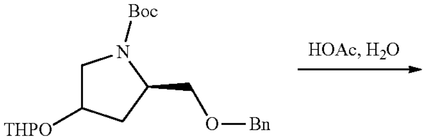

-continued

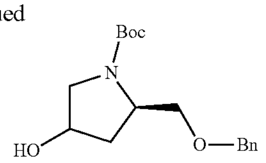

To a mixture of tert-butyl (2R)-2-[(benzyloxy)methyl]-4-(oxan-2-yloxy)pyrrolidine-1-carboxylate (1.3 g, 3.32 mmol) in THF (4.00 mL) were added AcOH (4 mL) and $H_2O$ (4.00 mL). The mixture was stirred at room temperature for 2 h. The reaction mixture was diluted with 50 ml $H_2O$. The resulting solution was extracted with EtOAc (300 mL×3) and the organic layers were combined. The organic layer was washed with brine (200 mL×2). The organic layer was dried over anhydrous sodium sulfate and concentrated under vacuum. The residue was purified by flash chromatography on silica gel eluting with EtOAc/Petroleum ether (40-60%) to afford tert-butyl (2R)-2-[(benzyloxy)methyl]-4-hydroxypyrrolidine-1-carboxylate (800 mg, 70% yield) as a yellow oil. LCMS (ESI) $[M+H]^+$: 308.15.

Step 5. Synthesis of tert-butyl (2R)-2-[(benzyloxy)methyl]-4-oxopyrrolidine-1-carboxylate

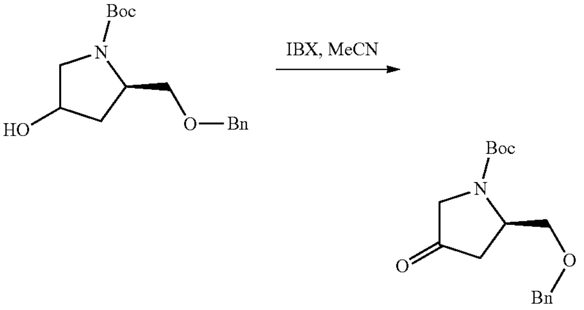

To a mixture of tert-butyl (2R)-2-[(benzyloxy)methyl]-4-hydroxypyrrolidine-1-carboxylate (800 mg, 2.60 mmol) in ACN (10.00 mL) was added IBX (1.09 g, 3.90 mmol). The mixture was stirred at 80° C. for 2 h. The residue was purified by reverse phase flash chromatography to afford tert-butyl (2R)-2-[(benzyloxy)methyl]-4-oxopyrrolidine-1-carboxylate (500 mg, 59% yield) as a yellow oil. LCMS (ESI) $[M+H]^+$: 306.15.

Step 6. Synthesis of tert-butyl (2R)-2-[(benzyloxy)methyl]-4-methylidenepyrrolidine-1-carboxylate

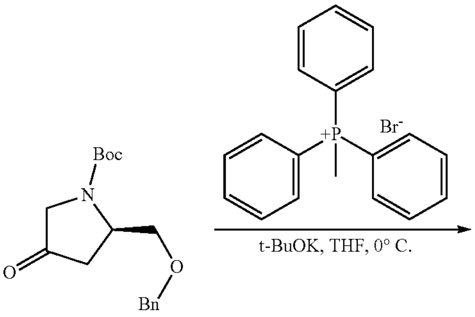

-continued

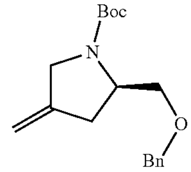

To a mixture of methyltriphenylphosphonium bromide (874 mg, 2.45 mmol) in THF (3.00 mL) were added t-BuOK (551 mg, 4.91 mmol) at 0° C. The mixture was stirred at room temperature for 1 h. Then tert-butyl (2R)-2-[(benzyloxy)methyl]-4-oxopyrrolidine-1-carboxylate (500 mg, 1.63 mmol) was added and the mixture was stirred for 3 h at room temperature. The residue was purified by reverse phase flash chromatography to afford tert-butyl (2R)-2-[(benzyloxy)methyl]-4-methylidenepyrrolidine-1-carboxylate (450 mg, 90% yield) as a colorless oil. LCMS (ESI) $[M+H]^+$: 304.18.

Step 7. Synthesis of tert-butyl (2R)-2-(hydroxymethyl)-4-methylpyrrolidine-1-carboxylate

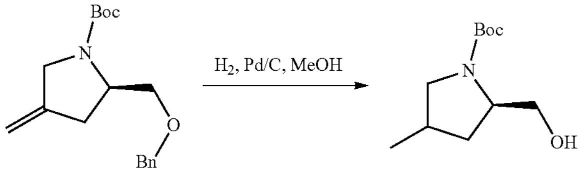 [SMILES: C=C1C[C@H](COCc2ccccc2)N(C(=O)OC(C)(C)C)C1 ; CC1C[C@H](CO)N(C(=O)OC(C)(C)C)C1]

Under hydrogen, to a mixture of tert-butyl (2R)-2-[(benzyloxy)methyl]-4-methylidenepyrrolidine-1-carboxylate (450 mg, 1.48 mmol) in MeOH (10 mL) was added Pd/C (60 mg, 0.56 mmol). The resulting mixture was stirred for 1 h at room temperature. After filtration, the filtrate was concentrated to afford tert-butyl (2R)-2-(hydroxymethyl)-4-methylpyrrolidine-1-carboxylate (300 mg, 93%) as a colorless oil. LCMS (ESI) $[M+H]^+$: 216.19

Step 8. Synthesis of 3-methyl-2-(((2R)-4-methylpyrrolidin-2-yl)methoxy)pyridine

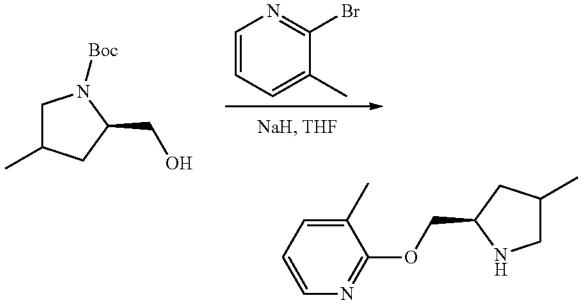

To a mixture of tert-butyl (2R)-2-(hydroxymethyl)-4-methylpyrrolidine-1-carboxylate (300 mg, 1.39 mmol) in THF (10 mL) was added NaH (133 mg, 5.54 mmol) at 0° C. The resulting mixture was stirred at room temperature for 0.5 h. Then 2-bromo-3-methylpyridine was added and stirred at 70° C. overnight. The reaction was quenched with 20 mL water at 0° C. The resulting mixture was extracted with EtOAc (200 mL×3). The combined organic layers were dried over anhydrous sodium sulfate and concentrated under vacuum. The residue was purified by reverse phase flash chromatography eluting with ACN/$H_2O$ (0.1% FA) (80%-90%) to afford 3-methyl-2-(((2R)-4-methylpyrrolidin-2-yl)methoxy)pyridine (200 mg, 69%) as a dark yellow oil. LCMS (ESI) $[M+H]^+$: 307.21

Step 9. Synthesis of 6-fluoro-1-(4-hydroxyphenyl)-7-[(2R)-4-methyl-2-[[(3-methylpyridin-2-yl)oxy]methyl]pyrrolidin-1-yl]-4-oxoquinoline-3-carboxylic acid

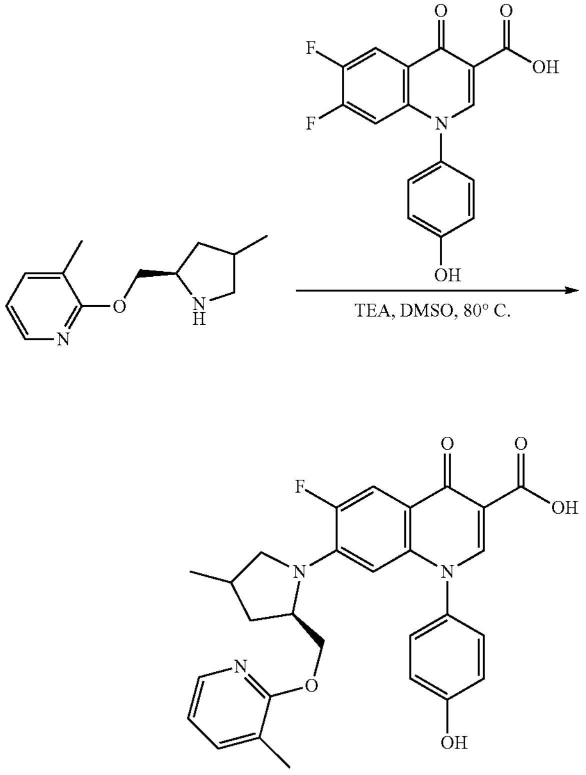

To a mixture of 6,7-difluoro-1-(4-hydroxyphenyl)-4-oxoquinoline-3-carboxylic acid (150 mg, 0.47 mmol) in DMSO (3 mL) was added 3-methyl-2-[[(2R)-4-methylpyrrolidin-2-yl]methoxy]pyridine (117 mg, 0.56 mmol) and TEA (287 mg, 2.83 mmol). The resulting mixture was stirred for 16 h at room temperature. The residue was purified by Prep.-HPLC (Column: SunFire Prep C18 OBD Column, 19×150 mm 5 um 10 nm; Mobile Phase A:Water(0.1% FA), Mobile Phase B:ACN; Flow rate:25 mL/min; Gradient:50 B to 70 B in 8 min; 254/220 nm; RT1:7.73/8.22) to afford 6-fluoro-1-(4-hydroxyphenyl)-7-[(2R)-4-methyl-2-[[(3-methylpyridin-2-yl)oxy]methyl]pyrrolidin-1-yl]-4-oxoquinoline-3-carboxylic acid (8.2 mg, 3.4% yield) as a yellow solid. LCMS (ESI) $[M+H]^+$: 504.2. $^1H$ NMR (300 MHz, DMSO-$d_6$) δ 15.41 (s, 1H), 8.51 (s, 1H), 7.98-7.82 (m, 2H), 7.76-7.54 (m, 4H), 7.49 (d, J=7.3 Hz, 2H), 7.02-6.81 (m, 1H), 6.04 (d, J=7.4 Hz, 1H), 4.39 (m, 1H), 4.29-4.04 (m, 2H), 3.23-3.12 (m, 2H), 2.36 (q, J=7.6 Hz, 2H), 2.14-1.85 (m, 4H), 1.00 (t, J=7.5 Hz, 3H).

Potency Lin28a-dep Z11 $IC_{50}$ (μM)++++

Example 8: Synthesis of (R)-6-chloro-7-(2-(1-((3-chloropyridin-2-yl)oxy) ethyl)pyrrolidin-1-yl)-4-oxo-1-phenyl-1,4-dihydroquinoline-3-carboxylic acid

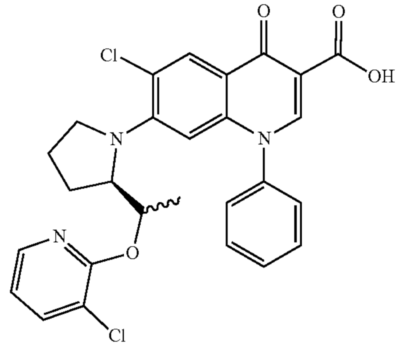 [SMILES: CC(Oc1ncccc1Cl)[C@H]1CCCN1c1cc2c(cc1Cl)c(=O)c(C(=O)O)cn2-c1ccccc1]

Step 1. Synthesis of tert-butyl (2R)-2-[methoxy (methyl)carbamoyl]pyrrolidine-1-carboxylate

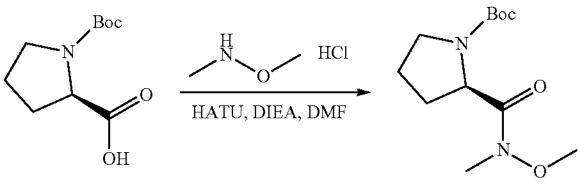

To a mixture of (2R)-1-(tert-butoxycarbonyl)pyrrolidine-2-carboxylic acid (1.0 g, 4.65 mmol, 1.0 equiv) in DMF (12 mL) was added N,O-dimethylhydroxylamine (0.3 g, 5.58 mmol, 1.2 equiv), DIEA (2.4 g, 18.58 mmol, 4.0 equiv) and HATU (2.7 g, 6.97 mmol, 1.5 equiv). The resulting mixture was stirred for 3 h at room temperature under nitrogen atmosphere. The reaction was quenched by the addition of water (10 mL). The resulting mixture was concentrated under vacuum. The residue was purified by reverse phase flash chromatography with the following conditions: column, C18 silica gel; mobile phase, MeCN in water, 5% to 100% gradient in 30 min; detector, UV 254 nm and UV 220 nm. This resulted in tert-butyl (2R)-2-[methoxy(methyl) carbamoyl]pyrrolidine-1-carboxylate (1.0 g, 83.3%) as a colorless oil. LCMS (ESI) $[M+H]^+$: 259.

Step 2. Synthesis of tert-butyl (2R)-2-acetylpyrrolidine-1-carboxylate

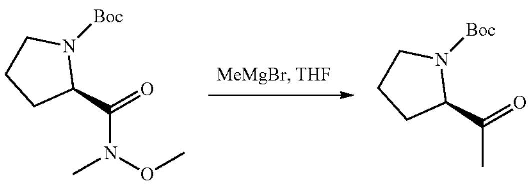 [SMILES: CON(C)C(=O)[C@H]1CCCN1C(=O)OC(C)(C)C ; CC(=O)[C@H]1CCCN1C(=O)OC(C)(C)C]

To a mixture of tert-butyl (2R)-2-[methoxy(methyl)carbamoyl]pyrrolidine-1-carboxylate (900 mg, 3.48 mmol, 1.0 equiv) in THF (9 mL) at −78° C. was added MeMgBr (1.2 g, 10.45 mmol, 3.0 equiv). The resulting mixture was stirred for 2 h at room temperature under nitrogen atmosphere. The reaction was quenched by the addition of water (8 mL). The resulting mixture was extracted with EtOAc (3×10 mL). The combined organic layers were dried over anhydrous $Na_2SO_4$. After concentration, the residue was purified by silica gel column chromatography eluting with Petroleum ether/EtOAc (3:1) to afford tert-butyl (2R)-2-acetylpyrrolidine-1-carboxylate (700 mg, 94.2%) as a light yellow oil.

Step 3. Synthesis of tert-butyl (2R)-2-(1-hydroxyethyl) pyrrolidine-1-carboxylate

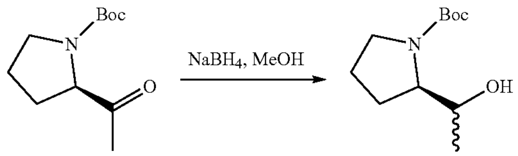

To a mixture of tert-butyl (2R)-2-acetylpyrrolidine-1-carboxylate (700 mg, 3.28 mmol, 1.0 equiv) in MeOH (7 mL) was added $NaBH_4$ (248 mg, 6.56 mmol, 2.0 equiv) at 0° C. The resulting mixture was stirred for 2 h at room temperature. The reaction was quenched by the addition of water (6 mL). The resulting mixture was extracted with EtOAc (3×8 mL). The combined organic layers were dried over anhydrous $Na_2SO_4$. The residue was purified by silica gel column chromatography eluting with Petroleum ether/EtOAc (1:1) to afford tert-butyl (2R)-2-(1-hydroxyethyl) pyrrolidine-1-carboxylate (600 mg, 84.9%) as a colorless oil. LCMS (ESI) $[M+H]^+$: 216.

Step 4. Synthesis of tert-butyl (2R)-2-[1-[(3-chloro-pyridin-2-yl) oxy] ethyl] pyrrolidine-1-carboxylate

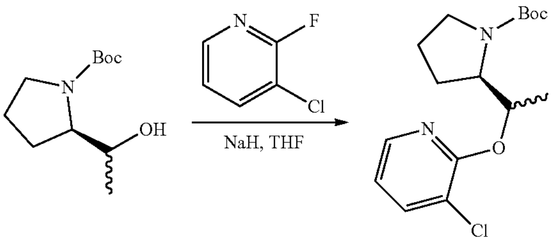

To a mixture of tert-butyl (2R)-2-(1-hydroxyethyl)pyrrolidine-1-carboxylate (500 mg, 2.32 mmol, 1.0 equiv) in THF (6 mL) was added NaH (167 mg, 6.97 mmol, 3.0 equiv) at 0° C. under nitrogen atmosphere. The resulting mixture was stirred for 30 min at room temperature under nitrogen atmosphere. To the above mixture was added 3-chloro-2-fluoropyridine (367 mg, 2.79 mmol, 1.2 equiv). The resulting mixture was stirred for additional 2.5 h at 70° C. The mixture was allowed to cool down to room temperature. The reaction was quenched by the addition of water (6 mL) at 0° C. The resulting mixture was concentrated under vacuum. The residue was purified by reverse phase flash chromatography with the following conditions: column, C18 silica gel;

mobile phase, MeCN in water, 5% to 100% gradient in 30 min; detector, UV 254 nm UV 220 nm. This resulted in tert-butyl (2R)-2-[1-[(3-chloropyridin-2-yl) oxy] ethyl] pyrrolidine-1-carboxylate (126 mg, 29.6%) as a light yellow oil. LCMS (ESI) $[M+H]^+$: 327.

Step 5. Synthesis of 3-chloro-2-[1-[(2R)-pyrrolidin-2-yl]ethoxy]pyridine

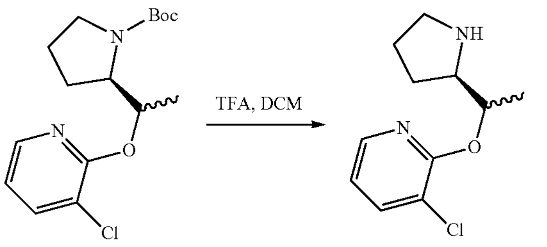

To a mixture of tert-butyl (2R)-2-[1-[(3-chloropyridin-2-yl) oxy] ethyl] pyrrolidine-1-carboxylate (126 mg, 0.39 mmol, 1.0 equiv) in DCM (3 mL) was added TFA (0.6 mL). The resulting mixture was stirred for 1.5 h at room temperature. The resulting mixture was concentrated under vacuum. This resulted in 3-chloro-2-[1-[(2R)-pyrrolidin-2-yl]ethoxy]pyridine (100 mg, crude) as a light yellow oil. LCMS (ESI) $[M+H]^+$: 227.

Step 6. Synthesis of 6-chloro-7-[(2R)-2-[1-[(3-chloropyridin-2-yl)oxy]ethyl]pyrrolidin-1-yl]-4-oxo-1-phenylquinoline-3-carboxylic acid

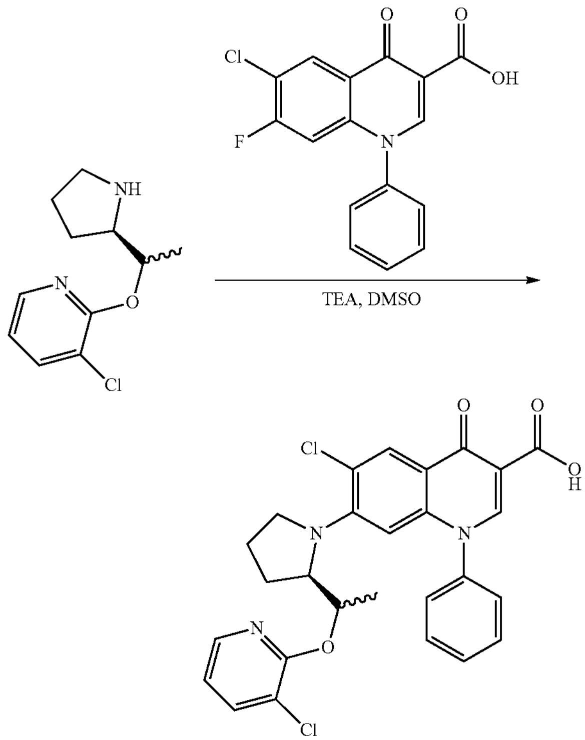

To a mixture of 6-chloro-7-fluoro-4-oxo-1-phenylquinoline-3-carboxylic acid (80 mg, 0.25 mmol, 1.0 equiv) in DMSO (3.5 mL) was added TEA (127 mg, 1.26 mmol, 5.0 equiv) and 3-chloro-2-[1-[(2R)-pyrrolidin-2-yl]ethoxy]pyridine (86 mg, 0.38 mmol, 1.5 equiv). The resulting mixture was stirred for 2 h at 80° C. The mixture was allowed to cool down to room temperature. The resulting mixture was concentrated under vacuum. The crude product was purified by Prep.-HPLC with the following conditions (Column: XBridge Shield RP18 OBD Column, 5 um, 19*150 mm; Mobile Phase A:Water(0.1% FA), Mobile Phase B: ACN; Flow rate: 25 mL/min; Gradient: 60% B to 90% B in 8 min; 254/220 nm; Rt: 7.31 min) to afford 6-chloro-7-[(2R)-2-[1-[(3-chloropyridin-2-yl)oxy]ethyl]pyrrolidin-1-yl]-4-oxo-1-phenylquinoline-3-carboxylic acid (14.4 mg, 10.91%) as a light yellow solid. LCMS (ESI) $[M+H]^+$: 524.0. $^1H$ NMR (300 MHz, DMSO-$d_6$) δ 15.07 (s, 1H), 8.53 (s, 1H), 8.12 (s, 1H), 7.82 (dd, J=7.7, 1.7 Hz, 1H), 7.78-7.53 (m, 5H), 7.34 (d, J=7.2 Hz, 1H), 6.78 (dd, J=7.7, 4.9 Hz, 1H), 6.06 (s, 1H), 5.44-5.31 (m, 1H), 4.50-4.37 (m, 1H), 3.28-3.15 (m, 1H), 3.03 (t, J=7.8 Hz, 1H), 2.25-2.07 (m, 2H), 2.01 (dd, J=9.9, 4.1 Hz, 1H), 1.81-1.66 (m, 1H), 1.17 (d, J=6.5 Hz, 3H). Potency Lin28a-dep Z11 $IC_{50}$ (μM)+++

Example 9: Synthesis of (R)-6-chloro-7-(2-(((3-chloropyridin-2-yl)oxy)methyl)pyrrolidin-1-yl)-8-fluoro-1-(1-methylcyclopropyl)-4-oxo-1,4-dihydroquinoline-3-carboxylic acid

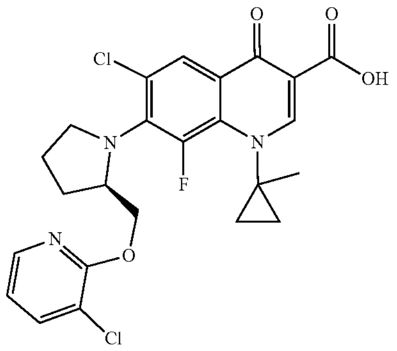 [SMILES: CC1(n2cc(C(=O)O)c(=O)c3cc(Cl)c(N4CCC[C@@H]4COc4ncccc4Cl)c(F)c32)CC1]

Step 1. Synthesis of methyl 2,3,4-trifluoro-5-nitrobenzoate

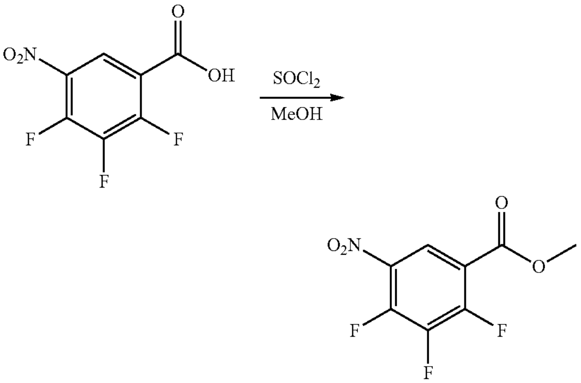

A solution of 2,3,4-trifluoro-5-nitrobenzoic acid (5.00 g, 22.62 mmol) in methanol (30.0 mL) was added thionyl chloride (8.07 g, 67.84 mmol) and stirred at 60° C. for 4 hours. The solvent was concentrated under vacuum. The residue was dissolved in DCM and washed with sodium bicarbonate solution. The organic layer was dried over anhydrous sodium sulfate and concentrated under vacuum to afford methyl 2,3,4-trifluoro-5-nitrobenzoate (5.1 g, 95.9%) as a light yellow oil.

Step 2. Synthesis of methyl 5-amino-2,3,4-trifluorobenzoate

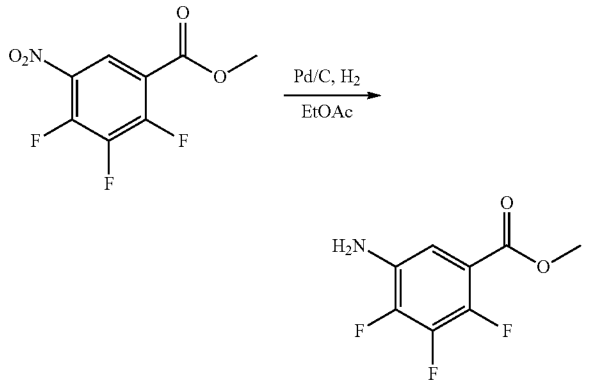

Under hydrogen, a solution of methyl 2,3,4-trifluoro-5-nitrobenzoate (5.80 g, 24.67 mmol) in ethyl acetate (100.0 mL) was added Pd/C (1.00 g, 9.39 mmol) at room temperature. The resulting solution was stirred at room temperature for 3 hours. The solid was filtered out. The organic layer was concentrated under vacuum. The residue was purified by flash chromatography on silica gel eluting with EtOAc/Petroleum ether (0%-20%) to afford methyl 5-amino-2,3,4-trifluorobenzoate (4.5 g, 88.9%) as a white solid. LCMS: m/z=206 $[M+H]^+$ Step 3. Synthesis of methyl 5-chloro-2,3,4-trifluorobenzoate

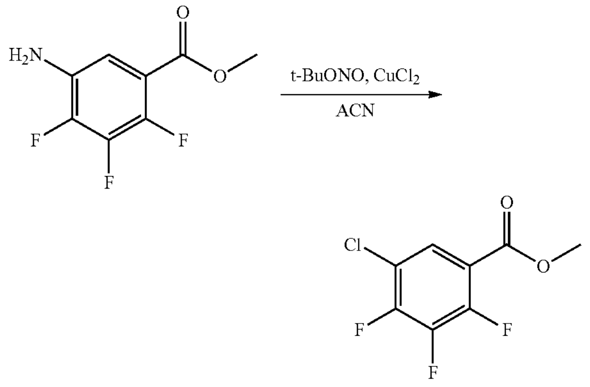

Under nitrogen, a solution of methyl 5-amino-2,3,4-trifluorobenzoate (5.00 g, 24.37 mmol) and $CuCl_2$ (6.55 g, 48.75 mmol) in ACN (100.0 mL) was added t-BuONO (5.03 g, 48.78 mmol) at 70° C. The resulting solution was stirred at 70° C. for 1 hour. The solvent was cooled and added hydrochloric acid (3 M) to adjust the pH to 3. The mixture was quenched with water, extracted with DCM and washed with brine. The organic layer was dried over anhydrous sodium sulfate and concentrated under vacuum. The residue was purified by flash chromatography on silica gel eluting with EtOAc/Petroleum ether (0%-10%) to afford methyl 5-chloro-2,3,4-trifluorobenzoate (3.5 g, 63.9%) as a white solid.

Step 4. Synthesis of 5-chloro-2,3,4-trifluorobenzoic acid

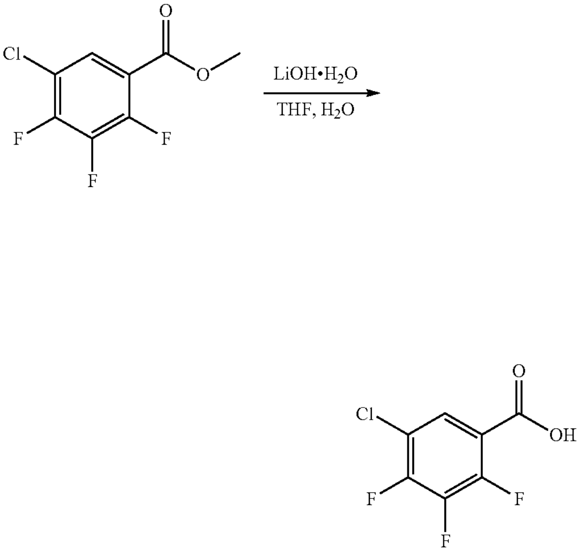

A solution of methyl 5-chloro-2,3,4-trifluorobenzoate (5.00 g, 22.26 mmol) in THF (50.0 mL) was added lithium hydroxide hydrate (3.74 g, 89.13 mmol) in $H_2O$ (25.0 mL) and stirred at room temperature for 2 hours. The solvent was concentrated under vacuum. The residue was dissolved in water. The pH was adjusted to 3 with hydrochloric acid (3 M). The solid was filtered, washed with water and concentrated under vacuum to afford 5-chloro-2,3,4-trifluorobenzoic acid (3.7 g, 78.9%) as a white solid.

Step 5. Synthesis of 5-chloro-2,3,4-trifluorobenzoyl chloride

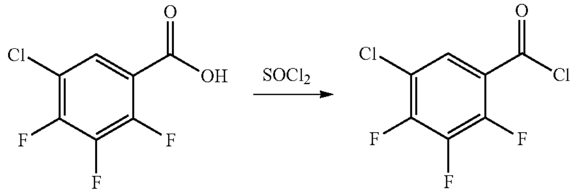

A solution of 5-chloro-2,3,4-trifluorobenzoic acid (600.0 mg, 2.85 mmol) in thionyl chloride (10.0 mL) was stirred at 80° C. for 3 hours. The solvent was concentrated under vacuum to afford 5-chloro-2,3,4-trifluorobenzoyl chloride (630 mg, 96.5%) as a light yellow oil.

Step 6. Synthesis of ethyl 3-(5-chloro-2,3,4-trifluorophenyl)-3-oxopropanoate

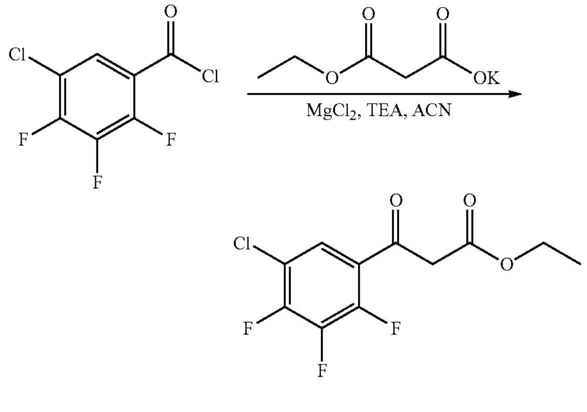

Under nitrogen, a solution of 1-ethyl 3-potassium propanedioate (936.58 mg, 5.50 mmol) and $MgCl_2$ (654.9 mg, 6.88 mmol) in ACN (50.0 mL) was added TEA (835.2 mg, 8.25 mmol) at 5° C. and stirred at room temperature for 2 hours. Then 5-chloro-2,3,4-trifluorobenzoyl chloride (630.0 mg, 2.75 mmol) in ACN was added dropwise at 5° C. and stirred at room temperature for 16 hours. The reaction mixture was quenched with hydrochloric acid (3 M) to adjust the pH to 3. The reaction mixture was extracted with DCM and washed with brine. The organic layer was dried over anhydrous sodium sulfate and concentrated under vacuum. The residue was purified by flash chromatography on silica gel eluting with EtOAc/petroleum ether (0%-30%) to afford ethyl 3-(5-chloro-2,3,4-trifluorophenyl)-3-oxopropanoate (450 mg, 58.2%) as a white solid.

Step 7. Synthesis of ethyl (Z)-2-(5-chloro-2,3,4-trifluorobenzoyl)-3-ethoxyacrylate

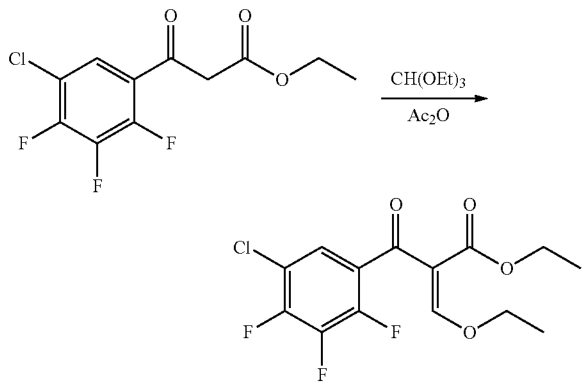

A solution of ethyl 3-(5-chloro-2,3,4-trifluorophenyl)-3-oxopropanoate (450.0 mg, 1.60 mmol) and triethyl orthoformate (356.4 mg, 2.41 mmol) in acetic anhydride (982.2 mg, 9.62 mmol) was stirred at 100° C. for 2 hours. The solvent was concentrated under vacuum to afford ethyl (2Z)-2-[(Z)-5-chloro-2,3,4-trifluorobenzoyl]-3-ethoxyprop-2-enoate (500 mg, 92.6%) as a yellow oil. LCMS: m/z=337 $[M+H]^+$ Step 8. Synthesis of ethyl 6-chloro-7,8-difluoro-1-(1-methylcyclopropyl)-4-oxo-1,4-dihydroquinoline-3-carboxylate

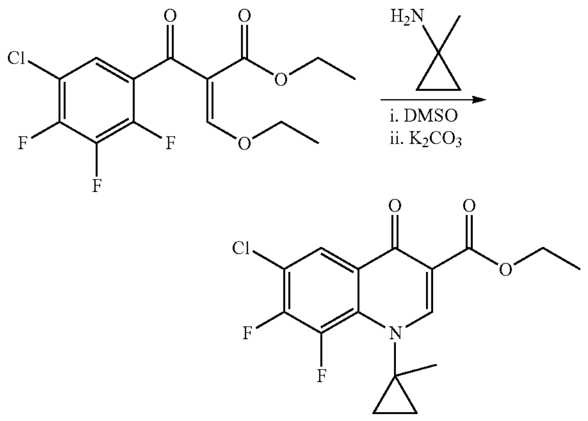

A solution of ethyl (2Z)-2-[(Z)-5-chloro-2,3,4-trifluorobenzoyl]-3-ethoxyprop-2-enoate (500.0 mg, 1.49 mmol) and 1-methylcyclopropan-1-amine (105.6 mg, 1.49 mmol) in DMSO (8.0 mL) was stirred at room temperature for 2 hours. Then $K_2CO_3$ (205.2 mg, 1.49 mmol) was added and stirred at room temperature for 2 hours. The reaction mixture was quenched with water, extracted with EtOAc and washed with brine. The organic layer was dried over anhydrous sodium sulfate and concentrated under vacuum. The residue was purified by flash chromatography on silica gel eluting with EtOAc/petroleum ether (0%-60%) to afford ethyl 6-chloro-7,8-difluoro-1-(1-methylcyclopropyl)-4-oxoquinoline-3-carboxylate (200 mg, 39.4%) as a white solid. LCMS: m/z=342 $[M+H]^+$ Step 9. Synthesis of 6-chloro-7,8-difluoro-1-(1-methylcyclopropyl)-4-oxo-1,4-dihydroquinoline-3-carboxylic acid

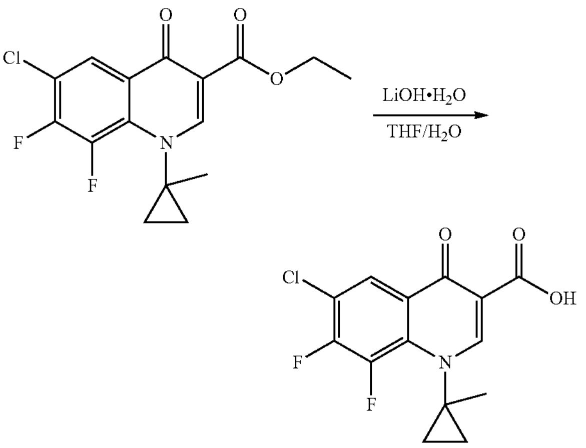

Into a 10-mL sealed tube, was placed ethyl 6-chloro-7,8-difluoro-1-(1-methylcyclopropyl)-4-oxoquinoline-3-carboxylate (100.0 mg, 0.29 mmol), THF (2.0 mL), $H_2O$ (1.0 mL), lithium hydroxide hydrate (61.4 mg, 1.46 mmol). The resulting solution was stirred for 2 hours at room temperature. The solids were collected by filtration. This resulted in 90 mg (98.05%) of 6-chloro-7,8-difluoro-1-(1-methylcyclopropyl)-4-oxoquinoline-3-carboxylic acid as a white solid. LCMS: m/z=314 [M+H]$^+$ Step 10. Synthesis of (R)-6-chloro-7-(2-(((3-chloropyridin-2-yl)oxy)methyl)pyrolidin-1-yl)-8-fluoro-1-(1-methylcyclopropyl)-4-oxo-1,4-dihydroquinoline-3-carboxylic acid

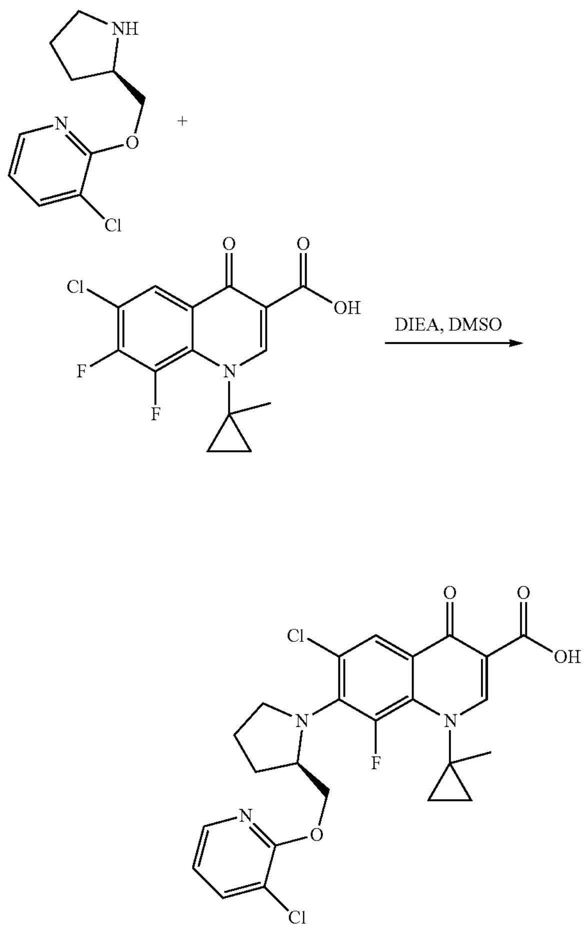

Into a 10-mL sealed tube, was placed 6-chloro-7,8-difluoro-1-(1-methylcyclopropyl)-4-oxoquinoline-3-carboxylic acid (80.0 mg, 0.26 mmol), DMSO (2.0 mL), 3-chloro-2-[(2R)-pyrrolidin-2-ylmethoxy]pyridine (65.1 mg, 0.31 mmol), N,N-diisopropylethylamine (98.9 mg, 0.77 mmol). The resulting solution was stirred for 5 hours at 60° C. The residue was purified by reverse phase flash chromatography eluting with ACN/water (0%-40%, basic system). This resulted in 30 mg (20.65%) of 6-chloro-7-[(2R)-2-[[(3-chloropyridin-2-yl)oxy]methyl]pyrrolidin-1-yl]-8-fluoro-1-(1-methylcyclopropyl)-4-oxoquinoline-3-carboxylic acid as a white solid. LCMS: m/z=506 [M+H]$^+$. $^1$H NMR (300 MHz, DMSO-$d_6$) δ 14.63 (s, 1H), 8.86 (d, J=1.7 Hz, 1H), 8.19-7.91 (m, 2H), 7.71 (m, 1H), 6.92 (m, 1H), 4.65 (s, 1H), 4.42-4.11 (m, 2H), 3.91-3.72 (m, 1H), 3.23 (s, 1H), 2.27 (m, 1H), 2.08 (s, 1H), 2.00-1.75 (m, 2H), 1.61 (s, 3H), 1.28 (d, J=16.3 Hz, 2H), 1.11 (m, 2H).

Potency Lin28a-dep Z11 $IC_{50}$ (μM)+++

Example 10: Synthesis of (R)-7-(2-(((3-chloropyridin-2-yl)(methyl)amino)methyl)pyrrolidin-1-yl)-6-fluoro-1-(4-hydroxyphenyl)-4-oxo-1,4-dihydroquinoline-3-carboxylic acid

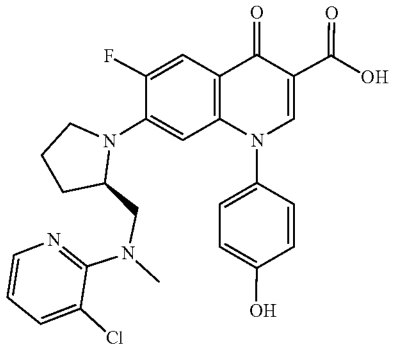 [SMILES: CN(C[C@H]1CCCN1c1cc2c(cc1F)c(=O)c(C(=O)O)cn2-c1ccc(O)cc1)c1ncccc1Cl]

Step 1. Synthesis of tert-butyl (2R)-2-[[(3-chloropyridin-2-yl)(methyl)amino]methyl]pyrroledine-1-carboxylate

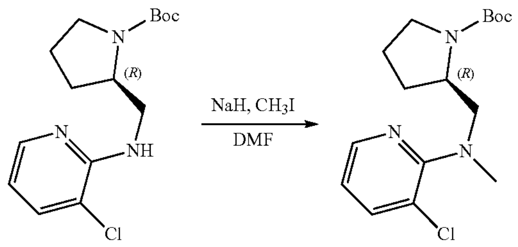

To a solution of tert-butyl (2R)-2-[[(3-chloropyridin-2-yl) amino] methyl] pyrrolidine-1-carboxylate (1.0 g, 3.21 mmol, 1.0 equiv) in DMF (10 mL) was added NaH (120 mg, 4.81 mmol, 1.5 equiv) and $CH_3I$ (910 mg, 6.41 mmol, 2.0 equiv). The reaction was stirred at 0° C. for 2 h. The reaction was then quenched by the addition of water. The resulting solution was extracted with 30 mL×3 of ethyl acetate. The combined organic layers were dried over anhydrous sodium sulfate and concentrated under vacuum. The residue was applied onto a silica gel column chromatography eluting with ethyl acetate/Petroleum ether (1/3). This resulted in tert-butyl (2R)-2-[[(3-chloropyridin-2-yl)(methyl)amino] methyl]pyrrolidine-1-carboxylate (850 mg, 81.3%) as yellow oil. LCMS (ESI) [M+H]$^+$: 326.

Step 2. Synthesis of 3-chloro-N-methyl-N-[(2R)-pyrrolidin-2-ylmethyl]pyridin-2-amine

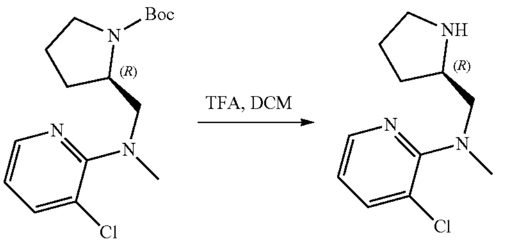

To a solution of tert-butyl (2R)-2-[[(3-chloropyridin-2-yl)(methyl)amino]methyl]pyrrolidine-1-carboxylate (800 mg, 2.46 mmol, 1.0 equiv) in DCM (5 mL) was added TFA (1 mL). The resulting solution was stirred at room temperature for 2 h. The pH value of the solution was adjusted to 10. The resulting mixture was concentrated under vacuum. This resulted in 3-chloro-N-[(2R)-pyrrolidin-2-ylmethyl] pyridin-2-amine (500 mg, crude) as yellow oil. LCMS (ESI) $[M+H]^+$: 226.

Step 3. Synthesis of 7-[(2R)-2-[[(3-chloropyridin-2-yl)(methyl)amino]methyl]pyrrolidin-1-yl]-6-fluoro-1-(4-hydroxyphenyl)-4-oxoquinoline-3-carboxylic acid

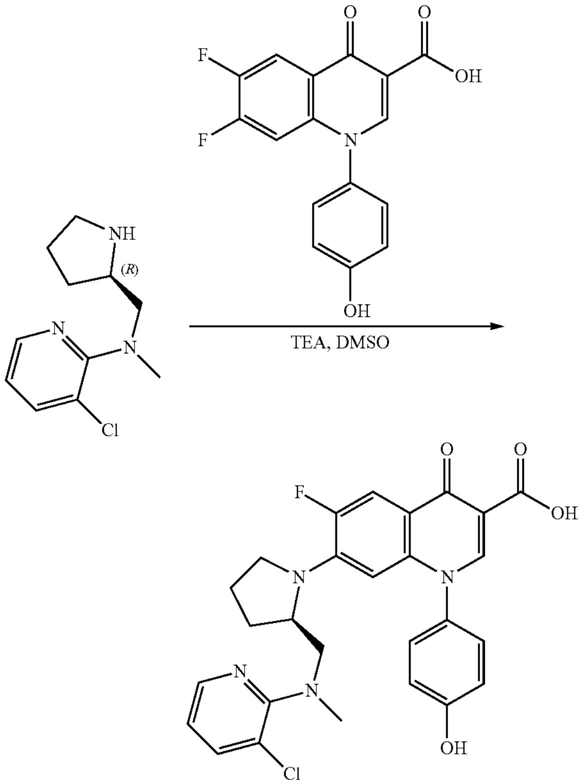

To a solution of 6,7-difluoro-1-(4-hydroxyphenyl)-4-oxoquinoline-3-carboxylic acid (100 mg, 0.32 mmol, 1.0 equiv), in DMSO (2 mL) was added TEA (96 mg, 0.95 mmol, 3.0 equiv) and 3-chloro-N-methyl-N-[(2R)-pyrrolidin-2-ylmethyl]pyridin-2-amine (85 mg, 0.38 mmol, 1.2 equiv). The reaction was stirred at 80° C. for 2 h. The mixture was purified by Prep.-HPLC with the following conditions: Column: X Bridge Shield RP18 OBD Column, 5 um, 19*150 mm; Mobile Phase A: Water(0.1% FA), Mobile Phase B: acetonitrile; Flow rate: 25 mL/min; Gradient: 25 B to 45 B in 15 min; 254 nm. This resulted in 7-[(2R)-2-[[(3-chloropyridin-2-yl) amino] methyl] pyrrolidin-1-yl]-6-fluoro-1-(4-hydroxyphenyl)-4-oxoquinoline-3-carboxylic acid (60.8 mg, 36.88%) as a yellow solid. LCMS (ESI): $[M+H]^+$: 523.1. $^1H$ NMR (300 MHz, DMSO-d6) δ 15.53 (s, 1H), 10.15 (s, 1H), 8.42 (s, 1H), 7.84-7.72 (m, 2H), 7.49-7.35 (m, 3H), 7.01 (d, J=7.9 Hz, 1H), 6.96-6.86 (m, 1H), 6.53-6.44 (m, 1H), 6.43-6.35 (m, 1H), 6.02 (d, J=7.4 Hz, 1H), 4.45 (s, 1H), 3.59-3.49 (m, 1H), 3.32-3.29 (m, 1H), 3.28-3.22 (m, 1H), 3.13-3.04 (m, 1H), 2.06-1.79 (m, 4H).

Potency Lin28a-dep Z11 $IC_{50}$ (μM)+++

Example 11: Synthesis of (R)-7-(2-((1H-pyrrolo[3,2-b]pyridin-1-yl)methyl)pyrroledin-1-yl)-6-fluoro-1-(4-hydroxyphenyl)-4-oxo-1,4-dihydroquinoline-3-carboxylic acid

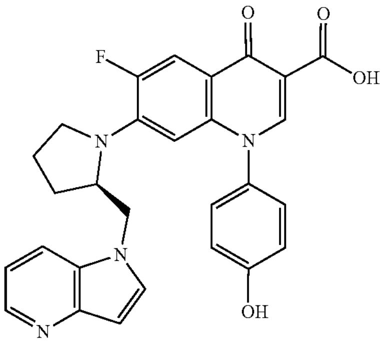 [SMILES: O=C(O)c1cn(-c2ccc(O)cc2)c2cc(N3CCC[C@@H]3Cn3ccc4ncccc43)c(F)cc2c1=O]

Step 1. Synthesis of tert-butyl (2R)-2-[[(4-methylpyridin-2-yl)oxy]methyl]pyrrolidine-1-carboxylate

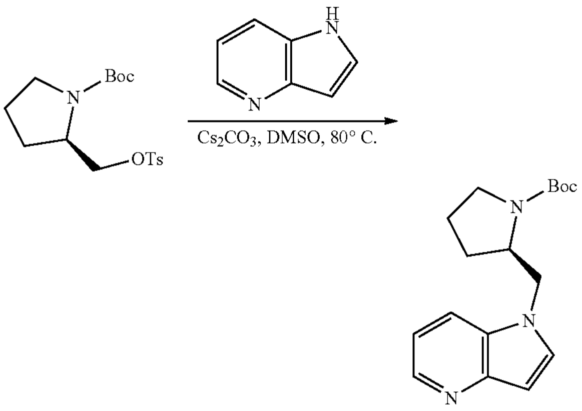

To a mixture of tert-butyl (2R)-2-[[(4-methylbenzenesulfonyl)oxy]methyl]pyrrolidine-1-carboxylate (200 mg, 0.56 mmol, 1.0 equiv) and 4-azaindole (133 mg, 1.13 mmol, 2.0 equiv) in DMSO (2.0 mL) was added $Cs_2CO_3$ (550 mg, 1.69 mmol, 3.0 equiv) at room temperature under nitrogen atmosphere. The resulting mixture was stirred at 80° C. overnight under nitrogen atmosphere. The reaction was quenched by the addition of water (1 mL) at 0° C. The resulting mixture was concentrated under vacuum. The residue was purified by reverse phase flash chromatography with the following conditions: column, C18 silica gel; mobile phase, ACN in w ater, 5% to 95% gradient in 30 min; detector, UV 254 nm and UV 220 nm. This resulted in tert-butyl (2R)-2-[[(4-methylpyridin-2-yl)oxy]methyl]pyrrolidine-1-carboxylate (100 mg, 59% yield). LCMS (ESI) $[M+H]^+$: 302.1

Step 2. Synthesis of (2R)-2-[pyrrolo[3,2-b]pyridin-1-ylmethyl]pyrrolidine

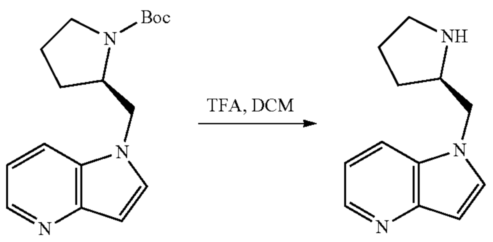

To a mixture of tert-butyl (2R)-2-[pyrrolo[3,2-b]pyridin-1-ylmethyl]pyrrolidine-1-carboxylate (100 mg, 0.33 mmol, 1.0 equiv) in DCM (5 mL) was added TFA (2 mL) at 0° C. under nitrogen atmosphere. The resulting mixture was stirred for 1.5 h at room temperature under nitrogen atmosphere. The resulting mixture was concentrated under vacuum. The crude product (2R)-2-[pyrrolo[3,2-b]pyridin-1-ylmethyl]pyrrolidine (160 mg, crude) was used in the next step directly without further purification. LCMS (ESI) $[M+H]^+$: 202.12.

Step 3. Synthesis of 6-fluoro-1-(4-hydroxyphenyl)-4-oxo-7-[(2R)-2-[pyrrolo[3,2-b]pyridin-1-ylmethyl]pyrrolidin-1-yl]quinoline-3-carboxylic acid

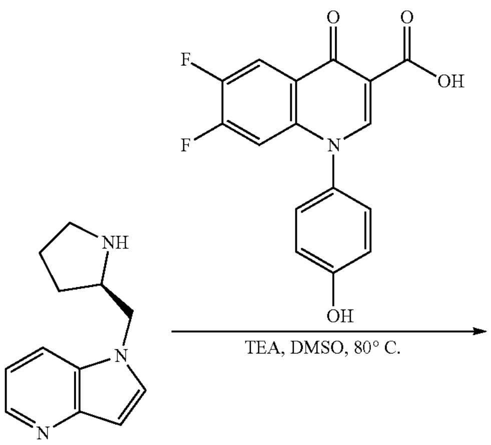

-continued

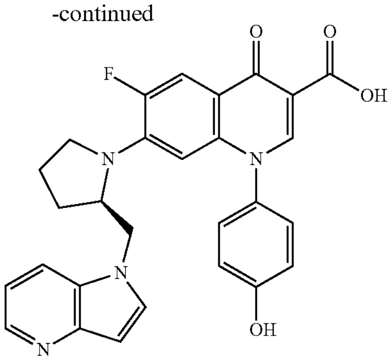

To a mixture of (2R)-2-[pyrrolo[3,2-b]pyridin-1-ylmethyl]pyrrolidine (60 mg, 0.30 mmol, 1.0 equiv) and 6,7-difluoro-1-(4-hydroxyphenyl)-4-oxoquinoline-3-carboxylic acid (32 mg, 0.10 mmol, 0.3 equiv) in DMSO (1.0 mL) was added TEA (181 mg, 1.79 mmol, 6.0 equiv) at room temperature under nitrogen atmosphere. The resulting mixture was stirred overnight at 80° C. under nitrogen atmosphere. The crude product (80 mg) was purified by Prep-HPLC with the following conditions (Column: XSelect CSH Prep C18 OBD Column, 5 um, 19*150 mm; Mobile Phase A:Water (0.05% FA), Mobile Phase B:ACN; Flow rate:25 mL/min; Gradient:9 B to 30 B in 8 min; 254 nm; RT1:7.9) to afford 6-fluoro-1-(4-hydroxyphenyl)-4-oxo-7-[(2R)-2-[pyrrolo[3,2-b]pyridin-1-ylmethyl]pyrrolidin-1-yl]quinoline-3-carboxylic acid (46.9 mg, 31.3%) as a white solid. LCMS (ESI) $[M+H]^+$: 499.20. $^1H$ NMR (400 MHz, DMSO-$d_6$) δ 10.24 (s, 1H), 8.48 (s, 1H), 8.35 (d, J=4.8 Hz, 1H), 7.90-7.76 (m, 2H), 7.52-7.43 (m, 3H), 7.21 (s, 1H), 7.09-6.99 (m, 2H), 6.59 (d, J=3.2 Hz, 1H), 6.12 (d, J=7.5 Hz, 1H), 4.47 (d, J=6.7 Hz, 1H), 4.27 (d, J=6.0 Hz, 2H), 3.15 (d, J=8.7 Hz, 2H), 1.94-1.72 (m, 3H), 1.71-1.60 (m, 1H).

Potency Lin28a-dep Z11 $IC_{50}$ (μM)++++

Example 12: Synthesis of (R)-7-(2-(((1H-pyrrolo[3,2-c]pyridine-6-yl)oxy)methyl)pyrrolidin-1-yl)-6-fluoro-1-(4-hydroxyphenyl)-4-oxo-1,4-dihydroquinoline-3-carboxylic acid

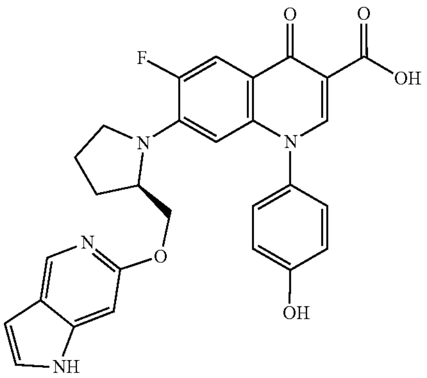 [SMILES: O=C(O)c1cn(-c2ccc(O)cc2)c2cc(N3CCC[C@@H]3COc3cc4[nH]ccc4cn3)c(F)cc2c1=O]

Step 1. Synthesis of 6-chloro-1-[[2-(trimethylsilyl)ethoxy]methyl]pyrrolo[3,2-c]pyridine

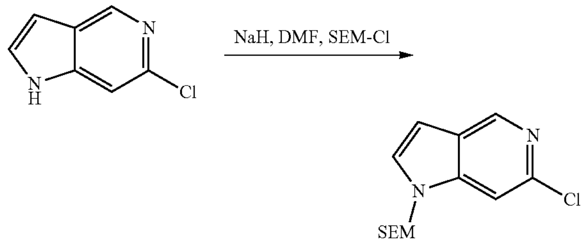

To a mixture of 6-chloro-1H-pyrrolo[3,2-c]pyridine (2.0 g, 13.11 mmol, 1.0 equiv) in DMF (15 mL) was added NaH (0.4 g, 15.73 mmol, 1.2 equiv) at 0° C. under nitrogen atmosphere. The resulting mixture was stirred for 15 min at room temperature under nitrogen atmosphere. To the above mixture was added SEM-Cl (2.6 g, 15.73 mmol, 1.2 equiv) at 0° C. The resulting mixture was stirred for additional 1.5 h at room temperature. The reaction was quenched by the addition of water (15 mL) at 0° C. The resulting mixture was extracted with EtOAc (3×15 mL). The combined organic layers were washed with brine (5×10 mL), dried over anhydrous $Na_2SO_4$. The resulting mixture was concentrated under reduced pressure. The residue was purified by silica gel column chromatography eluting with Petroleum ether/EtOAc (4:1) to afford 6-chloro-1-[[2-(trimethylsilyl)ethoxy]methyl]pyrrolo[3,2-c]pyridine (2.7 g, 72.8%) as a yellow oil. LCMS (ESI) $[M+H]^+$: 283.

Step 2. Synthesis of tert-butyl (2R)-2-[[(1-[[2-(trimethylsilyl)ethoxy]methyl]pyrrolo[3,2-c]pyridin-6-yl)oxy]methyl]pyrrolidine-1-carboxylate

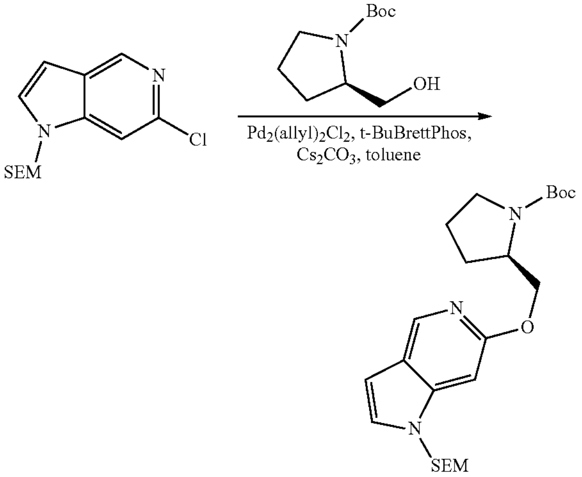

To a mixture of 6-chloro-1-[[2-(trimethylsilyl)ethoxy]methyl]pyrrolo[3,2-c]pyridine (1.0 g, 3.54 mmol, 1.0 equiv) in toluene (12 mL) was added tert-butyl (2R)-2-(hydroxymethyl)pyrrolidine-1-carboxylate (4.3 g, 21.21 mmol, 6.0 equiv), $Cs_2CO_3$ (3.5 g, 10.61 mmol, 3.0 equiv), $Pd_2(allyl)_2Cl_2$ (0.1 g, 0.35 mmol, 0.1 equiv) and t-BuBrettPhos (0.2 g, 0.35 mmol, 0.1 equiv). The resulting mixture was stirred for 3.5 h at 80° C. under nitrogen atmosphere. The mixture was allowed to cool down to room temperature. The resulting mixture was filtered, the filter cake was washed with MeOH (3×8 mL). The filtrate was concentrated under reduced pressure. The residue was purified by silica gel column chromatography eluting with Petroleum ether/EtOAc (2:1) to afford tert-butyl (2R)-2-[[(1-[[2-(trimethylsilyl)ethoxy]methyl]pyrrolo[3,2-c]pyridin-6-yl)oxy]methyl]pyrrolidine-1-carboxylate (590 mg, 37.3%) as a light yellow oil. LCMS (ESI) $[M+H]^+$: 448.

Step 3. Synthesis of (2R)-2-([1H-pyrrolo[3,2-c]pyridin-6-yloxy]methyl)pyrrolidine

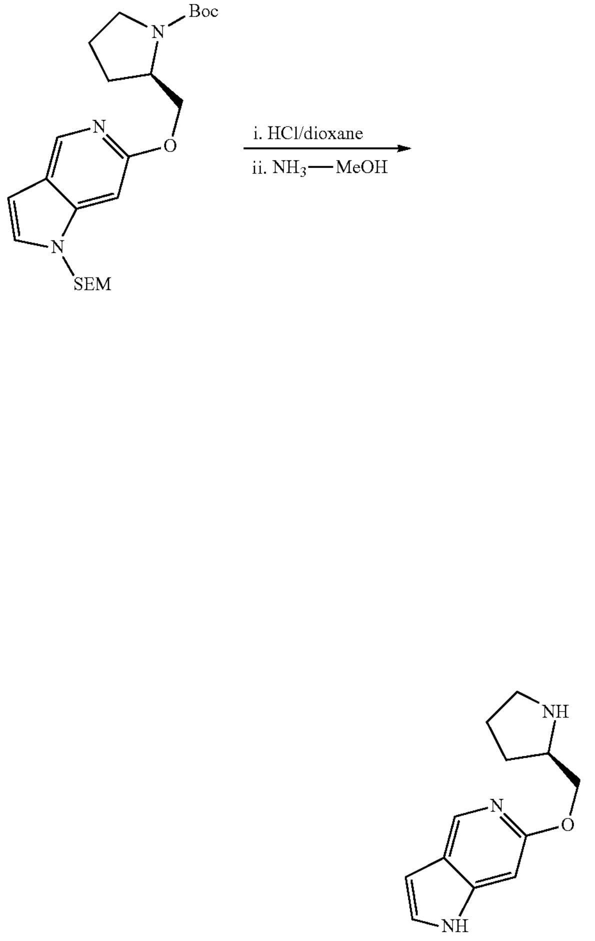

To a mixture of tert-butyl (2R)-2-[[(1-[[2-(trimethylsilyl)ethoxy]methyl]pyrrolo[3,2-c]pyridin-6-yl)oxy]methyl]pyrrolidine-1-carboxylate (590 mg, 1.32 mmol, 1.0 equiv) in HCl (gas) in 1,4-dioxane (6 mL) at 0° C. The resulting mixture was stirred for 2 h at room temperature. The resulting mixture was concentrated under reduced pressure. To the above mixture was added the solution of ammonia (5 mL, 7M in MeOH) at 0° C. The resulting mixture was stirred for additional 3.5 h at room temperature. The resulting mixture was concentrated under vacuum. This resulted in (2R)-2-([1H-pyrrolo[3,2-c]pyridin-6-yloxy]methyl)pyrrolidine (300 mg, crude) as a light yellow oil. LCMS (ESI) $[M+H]^+$: 218.

Step 4. Synthesis of 6-fluoro-1-(4-hydroxyphenyl)-4-oxo-7-[(2R)-2-([1H-pyrrolo[3,2-c]pyridin-6-yloxy]methyl)pyrrolidin-1-yl]quinoline-3-carboxylic acid

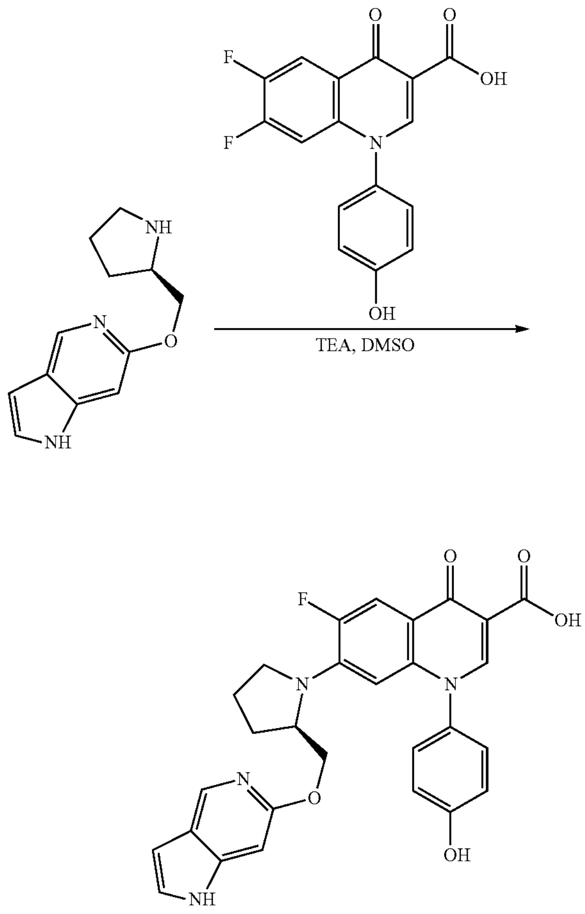

To a mixture of 6,7-difluoro-1-(4-hydroxyphenyl)-4-oxo-quinoline-3-carboxylic acid (300 mg, 0.95 mmol, 1.0 equiv) in DMSO (6 mL) was added TEA (287 mg, 2.84 mmol, 3.0 equiv) and (2R)-2-([1H-pyrrolo[3,2-c]pyridin-6-yloxy]methyl)pyrrolidine (411 mg, 1.89 mmol, 2.0 equiv). The resulting mixture was stirred for 2 h at 80° C. The mixture was allowed to cool down to room temperature. The resulting mixture was concentrated under vacuum. The crude product was purified by Prep.-HPLC with the following conditions (Column: XBridge Shield RP18 OBD Column, 5 um, 19*150 mm; Mobile Phase A: Water(0.05% FA), Mobile Phase B: ACN; Flow rate: 25 mL/min; Gradient: 60% B to 90% B in 8 min; 254/220 nm; Rt: 7.31 min) to afford 6-fluoro-1-(4-hydroxyphenyl)-4-oxo-7-[(2R)-2-([1H-pyrrolo[3,2-c]pyridin-6-yloxy]methyl)pyrrolidin-1-yl]quinoline-3-carboxylic acid (25.0 mg, 5.14%) as a yellow solid. LCMS (ESI) $[M+H]^+$: 515.25. $^1H$ NMR (300 MHz, DMSO-$d_6$) δ 15.49 (s, 1H), 11.12 (s, 1H), 10.16 (s, 1H), 8.43 (s, 1H), 8.22 (d, J=19.7 Hz, 1H), 7.88 (d, J=14.5 Hz, 1H), 7.40 (d, J=8.5, 2.7 Hz, 1H), 7.31-7.19 (m, 2H), 6.96 (s, 1H), 6.90-6.78 (m, 1H), 6.52-6.38 (m, 2H), 6.07 (d, J=7.5 Hz, 1H), 4.45 (s, 1H), 4.25 (d, J=5.3 Hz, 2H), 3.13 (d, J=7.0 Hz, 2H), 2.13-1.87 (m, 4H).

Potency Lin28a-dep Z11 $IC_{50}$ (μM)++++

Example 13: Synthesis of (R)-1-(6-aminopyridin-3-yl)-6-fluoro-7-(2-(((3-methylpyridin-2-yl)oxy)methyl)pyrrolidin-1-yl)-4-oxo-1,4-dihydroquinoline-3-carboxylic acid

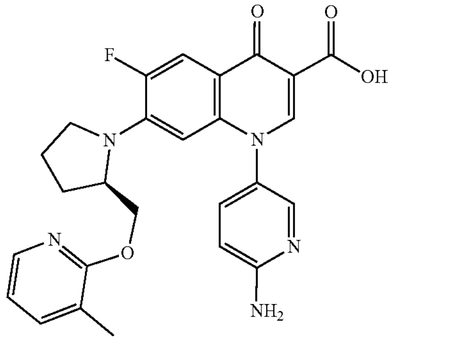 [SMILES: Cc1cccnc1OC[C@H]1CCCN1c1cc2c(cc1F)c(=O)c(C(=O)O)cn2-c1ccc(N)nc1]

Step 1. Synthesis of ethyl (R)-1-(6-acetamidopyridin-3-yl)-6-fluoro-7-(2-(((3-methylpyridin-2-yl)oxy)methyl)pyrrolidin-1-yl)-4-oxo-1,4-dihydroquinoline-3-carboxylate

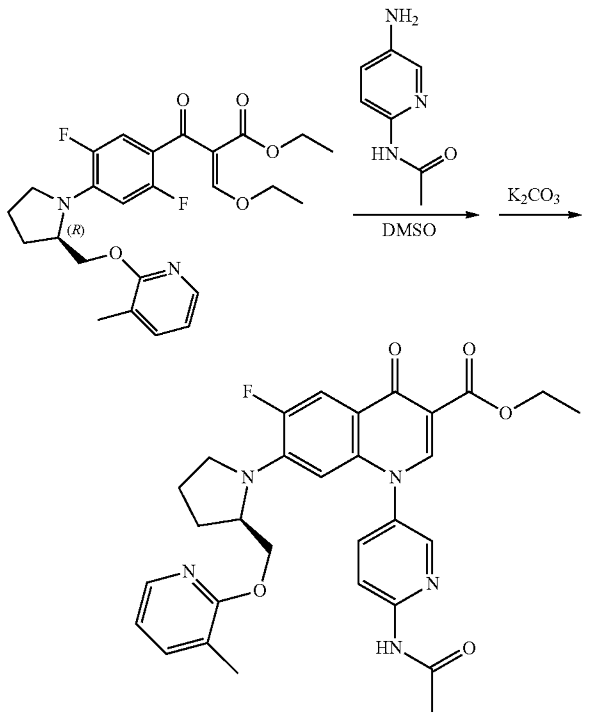

To a mixture of ethyl (R,Z)-2-(2,5-difluoro-4-(2-(((3-methylpyridin-2-yl)oxy)methyl)pyrrolidin-1-yl)benzoyl)-3-ethoxyacrylate (350 mg, 0.63 mmol) in DMSO (5 mL) was added N-(5-aminopyridin-2-yl)acetamide (114 mg, 0.75 mmol). The resulting mixture was stirred for 1 h at room temperature. Then $K_2CO_3$ (87 mg, 0.62 mmol) was added and stirred at 100° C. for 1 h. The reaction was quenched with water at room temperature. The solid was collected by filtration, washed by water and dried to afford ethyl (R)-1-(6-acetamidopyridin-3-yl)-6-fluoro-7-(2-(((3-methylpyridin-2-yl)oxy)methyl)pyrrolidin-1-yl)-4-oxo-1,4-dihydroquinoline-3-carboxylate (200 mg, crude) as a yellow solid. LCMS (ESI) $[M+H]^+$: 560.3.

Step 2. Synthesis of (R)-1-(6-aminopyridin-3-yl)-6-fluoro-7-(2-(((3-methylpyridin-2-yl)oxy)methyl)pyrrolidin-1-yl)-4-oxo-1,4-dihydroquinoline-3-carboxylic acid

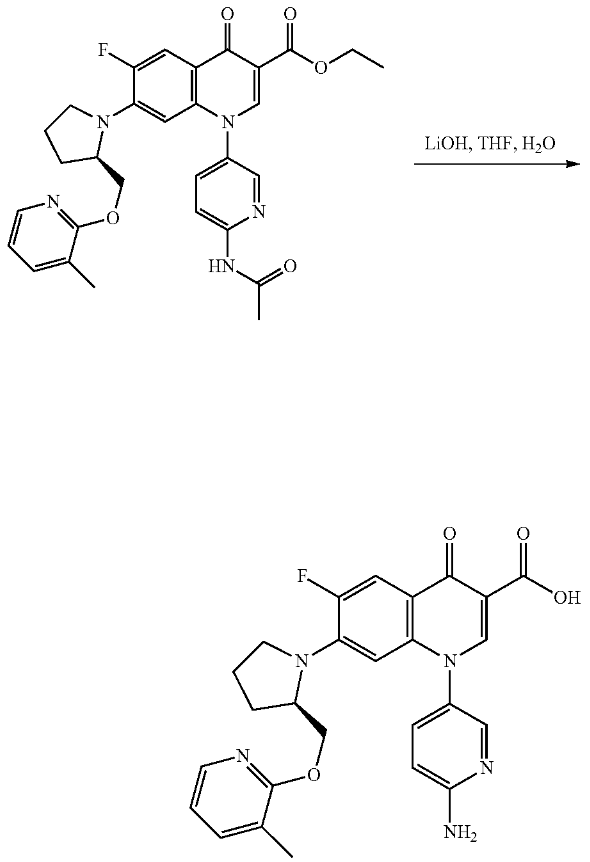

To a mixture of ethyl (R)-1-(6-acetamidopyridin-3-yl)-6-fluoro-7-(2-(((3-methylpyridin-2-yl)oxy)methyl)pyrrolidin-1-yl)-4-oxo-1,4-dihydroquinoline-3-carboxylate (200 mg, 0.12 mmol) in THF (3 mL) were added $LiOH \cdot H_2O$ (131 mg, 3.12 mmol) in $H_2O$ (1 mL) under nitrogen. The mixture was stirred at 100° C. for 2 h. The residue was purified by Prep.-HPLC (Column: Gemini-NX C18 AXAI Packed, 21.2*150 mm 5 um; Mobile Phase A:Water(0.1% FA), Mobile Phase B:ACN; Flow rate:25 mL/min; Gradient:51 B to 71 B in 15 min; 254 nm; RT1:17.1; RT2; Injection Volumn: ml; Number Of Runs;) to afford (R)-1-(6-aminopyridin-3-yl)-6-fluoro-7-(2-(((3-methylpyridin-2-yl)oxy)methyl)pyrrolidin-1-yl)-4-oxo-1,4-dihydroquinoline-3-carboxylic acid (79.2 mg, 29.5% yield) as a yellow solid. LCMS (ESI) $[M+H]^+$: 490.15. $^1H$ NMR (300 MHz, DMSO-$d_6$) δ 15.41 (s, 1H), 8.48 (s, 1H), 8.11 (d, J=2.8 Hz, 1H), 7.94-7.81 (m, 2H), 7.57 (t, J=7.4 Hz, 1H), 7.47 (d, J=7.2 Hz, 1H), 6.93-6.79 (m, 1H), 6.71-6.36 (m, 3H), 6.16 (d, J=7.4 Hz, 1H), 4.66-4.45 (m, 1H), 4.34-4.16 (m, 2H), 3.31-3.15 (m, 2H), 2.19-1.84 (m, 7H).

Potency Lin28a-dep Z11 $IC_{50}$ (μM)++++

Example 14: Synthesis of 6-fluoro-7-[(2R)-2-[[(3-methylpyridin-2-yl)oxy]methyl]pyrrolidin-1-yl]-1-(oxan-4-yl)-4-oxoquinoline-3-carboxylic acid

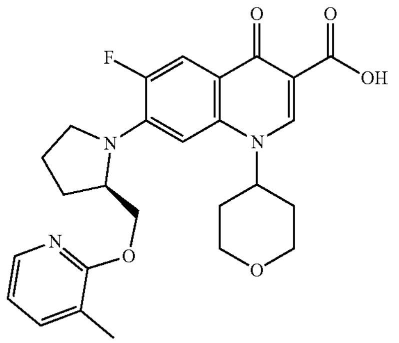 [SMILES: Cc1cccnc1OC[C@H]1CCCN1c1cc2c(cc1F)c(=O)c(C(=O)O)cn2C1CCOCC1]

Step 1. Synthesis of 3-methyl-2-[(2R)-pyrrolidin-2-ylmethoxy]pyridine

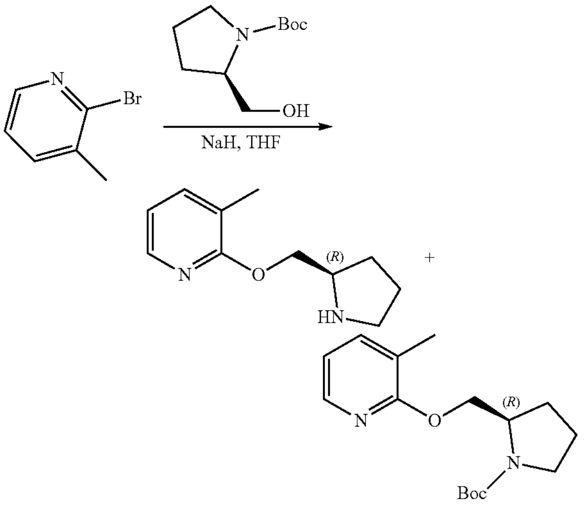

To a mixture of tert-butyl (2R)-2-(hydroxymethyl)pyrrolidine-1-carboxylate (10.0 g, 49.71 mmol, 1 equiv) in THF (20 mL) was added NaH (7.9 g, 199.22 mmol, 4.0 equiv) at 0° C. The resulting mixture was stirred at room temperature for 0.5 h. Then 2-bromo-3-methylpyridine was added and stirred at 70° C. overnight. The reaction was quenched with 20 mL water at 0° C. The resulting mixture was extracted with EtOAc (200 mL×3) and the organic layers were combined. The organic layer was dried over anhydrous sodium sulfate and concentrated under vacuum. The residue was purified by reverse phase flash chromatography eluting with $ACN/H_2O$(0.1% FA) (80%-90%) to afford 3-methyl-2-[(2R)-pyrrolidin-2-ylmethoxy]pyridine (7.50 g, 78%) as a dark yellow oil. LCMS (ESI) $[M+H]^+$:193.1 and tert-butyl (2R)-2-[[(3-methylpyridin-2-yl)oxy]methyl]pyrrolidine-1-carboxylate (1.6 g) as a light yellow oil. LCMS (ESI) $[M+H]^+$:293.1.

Step 2. Synthesis of 3-[2,5-difluoro-4-[(2R)-2-[[(3-methylpyridin-2-yl)oxy]methyl]pyrolidin-1-yl]phenyl]-3-oxopropanoate

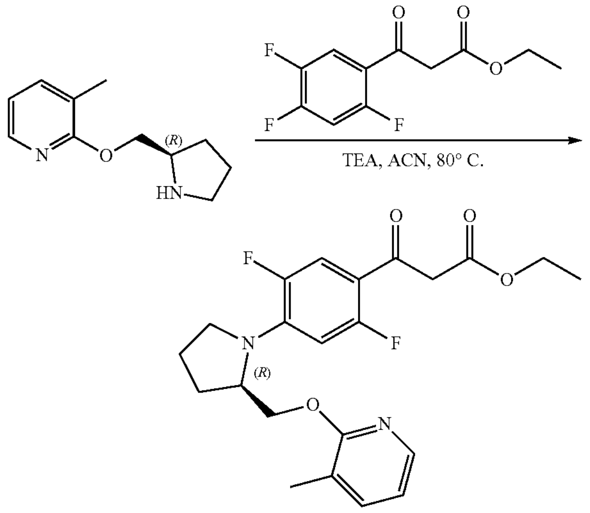

To a mixture of methyl 3-methyl-2-[(2R)-pyrrolidin-2-ylmethoxy]pyridine (1.00 g, 5.20 mmol, 1.0 equiv) in ACN (10 mL) was added ethyl 3-oxo-3-(2,4,5-trifluorophenyl) propanoate (1.28 g, 5.20 mmol, 1.0 equiv) and TEA (1.58 g, 15.60 mmol, 3.0 equiv). The resulting mixture was stirred for 2 h at 80° C. The residue was purified by reverse phase flash chromatography eluting with ACN/$H_2O$ (0.05% $NH_4HCO_3$) (60%-80%) to afford ethyl 3-[2,5-difluoro-4-[(2R)-2-[[(3-methylpyridin-2-yl)oxy]methyl]pyrrolidin-1-yl]phenyl]-3-oxopropanoate (600 mg, 25.4% yield) as a yellow oil. LCMS (ESI) $[M+H]^+$: 419.17.

Step 3. Synthesis of ethyl (2Z)-2-[(Z)-2,5-difluoro-4-[(2R)-2-[[(3-methylpyridin-2-yl)oxy]methyl]pyrrolidin-1-yl]benzoyl]-3-ethoxyprop-2-enoate

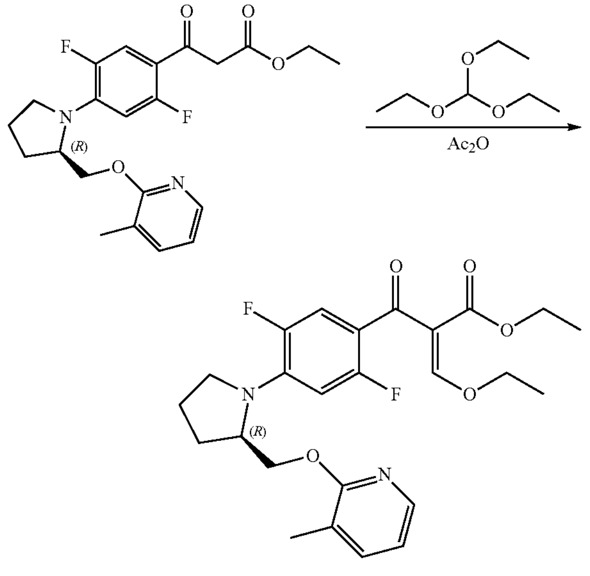

To a mixture of ethyl 3-[2,5-difluoro-4-[(2R)-2-[[(3-methylpyridin-2-yl)oxy]methyl]pyrrolidin-1-yl]phenyl]-3-oxopropanoate (200 mg, 0.47 mmol, 1.0 equiv) in acetic anhydride (146 mg, 1.43 mmol, 2.99 equiv) were added triethyl orthoformate (106 mg, 0.71 mmol, 1.5 equiv). The resulting mixture was stirred for 8 h at 80° C. The solvent was concentrated under vacuum to afford ethyl (2Z)-2-[(Z)-2,5-difluoro-4-[(2R)-2-[[(3-methylpyridin-2-yl)oxy] methyl]pyrrolidin-1-yl]benzoyl]-3-ethoxyprop-2-enoate (250 mg, crude) as a yellow oil. LCMS (ESI) $[M+H]^+$: 475.20.

Step 4. Synthesis of ethyl 6-fluoro-7-[(2R)-2-[[(3-methylpyridin-2-yl)oxy]methyl]pyrrolidin-1-yl]-1-(oxan-4-yl)-4-oxoquinoline-3-carboxylate

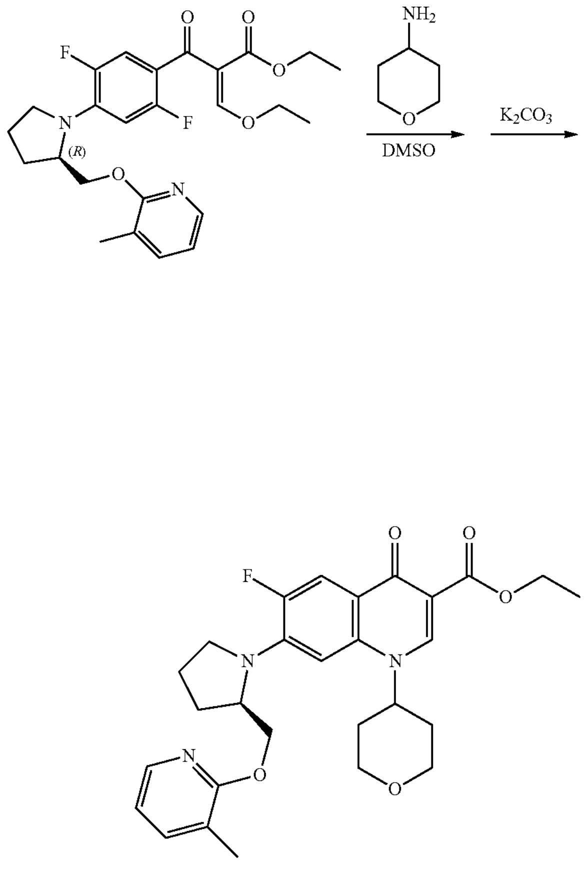

To a mixture of ethyl (2Z)-2-[(Z)-2,5-difluoro-4-[(2R)-2-[[(3-methylpyridin-2-yl)oxy]methyl]pyrrolidin-1-yl]benzoyl]-3-ethoxyprop-2-enoate (250 mg, 0.52 mmol, 1.0 equiv) in DMSO (5.00 mL) was added oxan-4-amine (64 mg, 0.63 mmol, 1.20 equiv). The resulting mixture was stirred for 1 h at room temperature. Then $K_2CO_3$ (73 mg, 0.52 mmol, 1.00 equiv) was added and stirred at 100° C. for 1 h. The reaction was quenched with water at room temperature. The solid was collected by filtration, washed by water and dried to afford ethyl 6-fluoro-7-[(2R)-2-[[(3-methylpyridin-2-yl)oxy]methyl]pyrrolidin-1-yl]-1-(oxan-4-yl)-4-oxoquinoline-3-carboxylate (200 mg, crude) as a yellow solid. LCMS (ESI) $[M+H]^+$: 510.23.

Step 5. Synthesis of 6-fluoro-7-[(2R)-2-[[(3-methylpyridin-2-yl)oxy]methyl]pyrolidin-1-yl]-1-(oxan-4-yl)-4-oxoquinoline-3-carboxylic acid

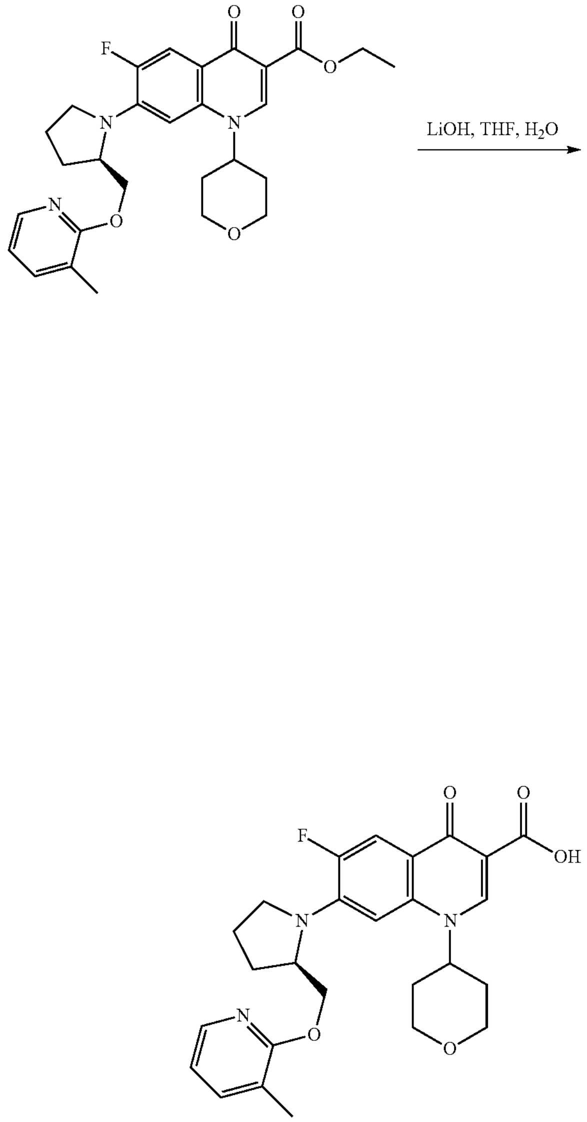

To a mixture of ethyl 6-fluoro-7-[(2R)-2-[[(3-methylpyridin-2-yl)oxy]methyl]pyrrolidin-1-yl]-1-(oxan-4-yl)-4-oxoquinoline-3-carboxylate (200 mg, 0.39 mmol, 1.0 equiv) in THF (3.00 mL) was added $LiOH{\cdot}H_2O$ (131.0 mg, 3.12 mmol, 8.0 equiv) and $H_2O$ (1.00 mL). The mixture was stirred at room temperature for 2 h. The residue was purified by Prep.-HPLC to afford 6-fluoro-7-[(2R)-2-[[(3-methylpyridin-2-yl)oxy]methyl]pyrrolidin-1-yl]-1-(oxan-4-yl)-4-oxoquinoline-3-carboxylic acid (34.4 mg, 18%) as a yellow solid. LCMS (ESI) $[M+H]^+$: 482.20. $^1H$ NMR (300 MHz, DMSO-d6) δ 15.52 (s, 1H), 8.65 (s, 1H), 7.92-7.81 (m, 2H), 7.48 (d, J=7.1 Hz, 1H), 6.96 (d, J=7.2 Hz, 1H), 6.86-6.82 (m, 1H), 5.01 (s, 1H), 4.79 (s, 1H), 4.39-4.28 (m, 2H), 4.02 (d, J=11.2 Hz, 1H), 3.91 (d, J=11.3 Hz, 1H), 3.79 (s, 1H), 3.65-3.48 (m, 3H), 2.19 (s, 2H), 2.03 (d, J=10.4 Hz, 9H).

Potency Lin28a-dep Z11 $IC_{50}$ (μM)++++

Example 15: Synthesis of (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylic acid

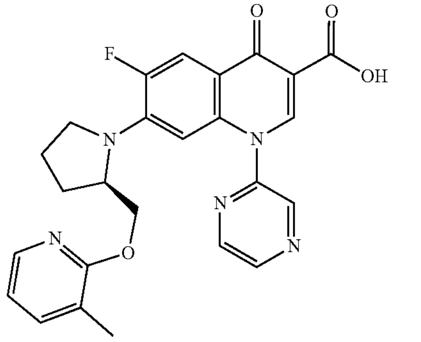 [SMILES: Cc1cccnc1OC[C@H]1CCCN1c1cc2c(cc1F)c(=O)c(C(=O)O)cn2-c1cnccn1]

Step 1. Synthesis of ethyl (R,Z)-2-(2,5-difluoro-4-(2-(((3-methylpyridin-2-yl)oxy)methyl)pyrrolidin-1-yl)benzoyl)-3-ethoxyacrylate

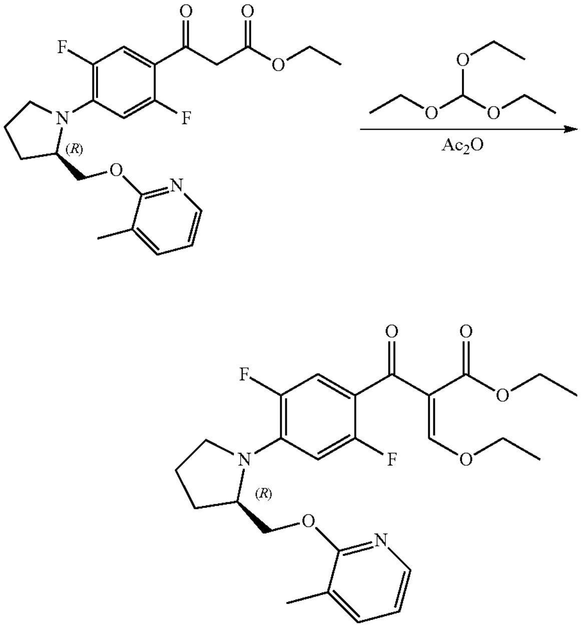

To a mixture of ethyl (R)-3-(2,5-difluoro-4-(2-(((3-methylpyridin-2-yl)oxy)methyl)pyrrolidin-1-yl)phenyl)-3-oxopropanoate (300 mg, 0.69 mmol, 1.0 equiv) in acetic anhydride (220 mg, 2.65 mmol, 2.99 equiv) were added triethyl orthoformate (159 mg, 106 mmol, 1.5 equiv). The resulting mixture was stirred for 8 h at 80° C. The solvent was concentrated under vacuum to afford ethyl (R,Z)-2-(2,5-difluoro-4-(2-(((3-methylpyridin-2-yl)oxy)methyl)pyrrolidin-1-yl)benzoyl)-3-ethoxyacrylate (350 mg, crude) as a yellow oil. LCMS (ESI) $[M+H]^+$: 475.20.

Step 2. Synthesis of ethyl (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylate

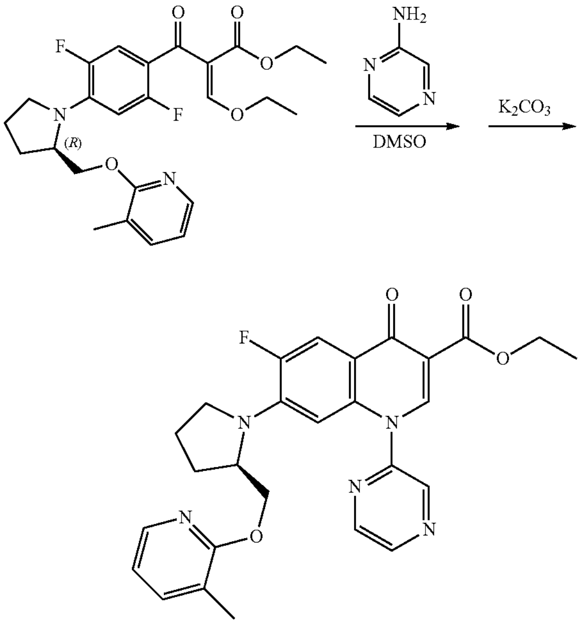

To a mixture of ethyl (R,Z)-2-(2,5-difluoro-4-(2-(((3-methylpyridin-2-yl)oxy)methyl)pyrrolidin-1-yl)benzoyl)-3-ethoxyacrylate (350 mg, 0.73 mmol, 1.0 equiv) in DMSO (5.00 mL) was added 2-aminopyrazine (84 mg, 0.88 mmol, 1.20 equiv). The resulting mixture was stirred for 1 h at room temperature. Then $K_2CO_3$ (101 mg, 0.73 mmol, 1.00 equiv) was added and stirred at 100° C. for 1 h. The reaction was quenched with water at room temperature. The solid was collected by filtration, washed by water and dried to afford ethyl (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylate (350 mg, crude) as a yellow solid. LCMS (ESI) $[M+H]^+$: 504.20.

Step 3. Synthesis of (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylic acid

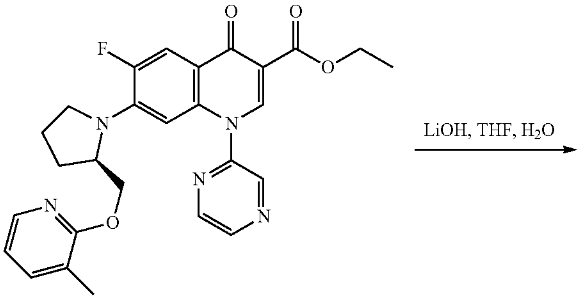

-continued

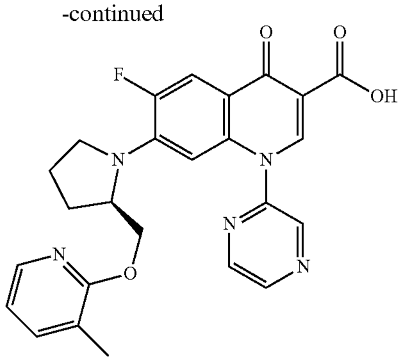

To a mixture of ethyl (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylate (350 mg, 0.69 mmol, 1.0 equiv) in THF (5.00 mL) was added $LiOH \cdot H_2O$ (233 mg, 5.55 mmol, 7.99 equiv) and $H_2O$ (1.70 mL). The mixture was stirred at room temperature for 2 h. The mixture was concentrated to give the residue which was purified by Prep.-HPLC to afford (R)-6-fluoro-7-(2-(((3-methylpyridin-2-yl)oxy)methyl)pyrrolidin-1-yl)-4-oxo-1-(pyrazin-2-yl)-1,4-dihydroquinoline-3-carboxylic acid (69.7 mg, 23%) as a yellow solid. LCMS (ESI) $[M+H]^+$: 476.10. $^1H$ NMR (300 MHz, DMSO-$d_6$) δ 15.18 (s, 1H), 9.15 (s, 1H), 8.92 (d, J=2.4 Hz, 1H), 8.91 (s, 1H), 8.75 (s, 1H), 7.90 (d, J=14.5 Hz, 1H), 7.85 (dd, J=5.1, 1.8 Hz, 1H), 7.49 (d, J=7.1 Hz, 1H), 6.85 (dd, J=7.1, 5.0 Hz, 1H), 6.29 (d, J=7.3 Hz, 1H), 4.62-4.48 (m, 1H), 4.32-4.12 (m, 2H), 3.52-3.40 (m, 1H), 3.30-3.21 (m, 1H), 2.17-1.82 (m, 7H).

Potency Lin28a-dep Z11 $IC_{50}$ (μM)++++

Example 16: Synthesis of (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylic acid

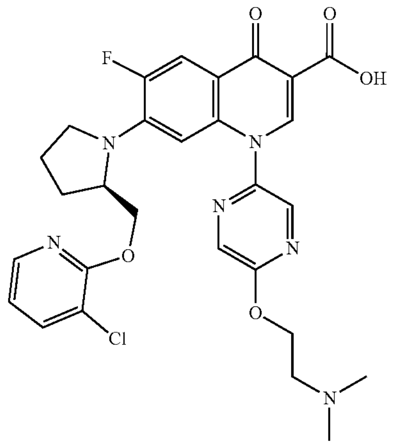 [SMILES: CN(C)CCOc1cnc(-n2cc(C(=O)O)c(=O)c3cc(F)c(N4CCC[C@@H]4COc4ncccc4Cl)cc32)cn1]

Step 1. Synthesis of tert-butyl N-(5-chloropyrazin-2-yl)carbamate

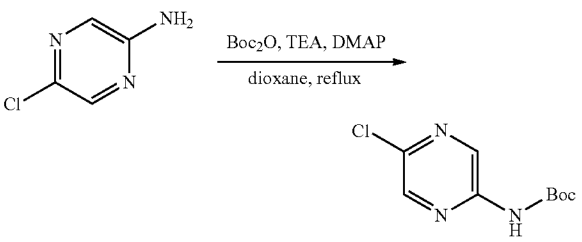

To a mixture of 5-chloro-pyrazinamine (5 g, 38.59 mmol) in dioxane (50 mL) was added $Boc_2O$ (12 g, 54.98 mmol), DMAP (9 g, 73.66 mmol) and TEA (3.51 g, 10.78 mmol). The resulting mixture was stirred for 1 h at 100° C. The reaction mixture was diluted with 500 ml $H_2O$. The resulting solution was extracted with EtOAc (300 mL×3) and the organic layers were combined. The organic layer was dried over anhydrous sodium sulfate and concentrated under vacuum. The residue was purified by reverse phase flash chromatography eluting with ACN/$H_2O$ (0.05% $NH_4HCO_3$) (80%-100%) to afford tert-butyl N-(5-chloropyrazin-2-yl) carbamate (8 g, 90% yield) as a yellow solid. LCMS (ESI) $[M+H]^+$: 230.27.

Step 2. Synthesis of tert-butyl N-[5-[2-(dimethylamino)ethoxy]pyrazin-2-yl]carbamate

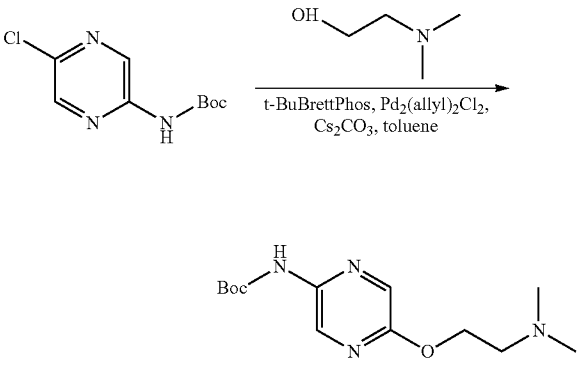

To a mixture of tert-butyl N-(5-chloropyrazin-2-yl)carbamate (1 g, 4.35 mmol) in Toluene (10 mL) was added dimethylaminoethanol (1.55 g, 17.41 mmol), t-BuBrettPhos (211 mg, 0.43 mmol), $Pd_2(allyl)_2Cl_2$ (159 mg, 0.43 mmol) and $Cs_2CO_3$ (4.26 g, 13.06 mmol). The resulting mixture was stirred for 2 h at 80° C. The reaction mixture was diluted with 200 mL $H_2O$. The resulting solution was extracted with EtOAc (100 mL×3) and the organic layers were combined. The organic layer was dried over anhydrous sodium sulfate and concentrated under vacuum. The residue was purified by reverse phase flash chromatography eluting with ACN/$H_2O$ (0.05% $NH_4HCO_3$) (80%-100%) to afford tert-butyl N-[5-[2-(dimethylamino)ethoxy]pyrazin-2-yl]carbamate (300 mg, 22% yield) as a yellow oil. LCMS (ESI) $[M+H]^+$: 601.24.

Step 3. Synthesis of 5-[2-(dimethylamino)ethoxy]pyrazin-2-amine

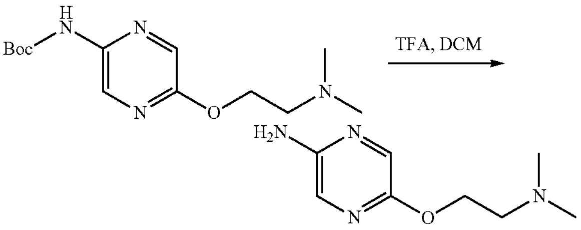

To a mixture of tert-butyl N-[5-[2-(dimethylamino)ethoxy]pyrazin-2-yl]carbamate (180 mg, 0.63 mmol) in DCM (2 mL) was added TFA (2 mL). The resulting mixture was stirred for 1 h at room temperature. The filtrate was collected by filtration and concentrated to afford 5-[2-(dimethylamino)ethoxy]pyrazin-2-amine (200 mg, crude) as a yellow oil. LCMS (ESI) $[M+H]^+$: 183.24.

Step 4. Synthesis of ethyl (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylate

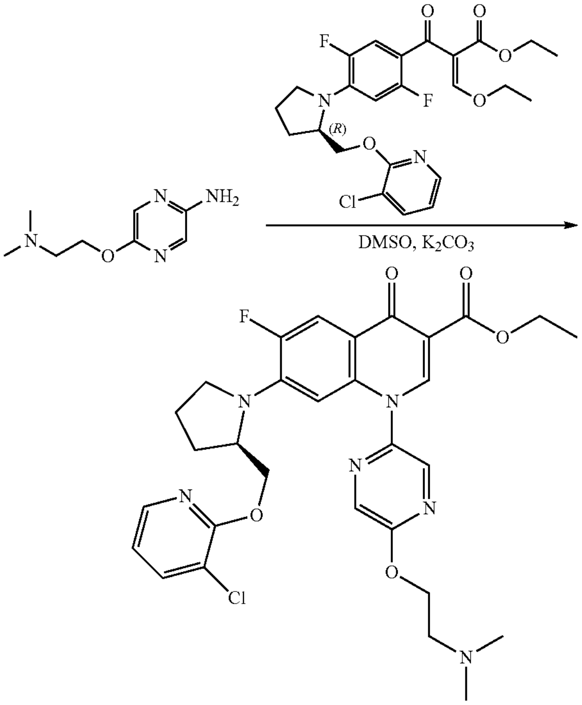

To a mixture of ethyl (R,Z)-2-(4-(2-(((3-chloropyridin-2-yl)oxy)methyl)pyrrolidin-1-yl)-2,5-difluorobenzoyl)-3-ethoxyacrylate (200 mg, 0.42 mmol) in DMSO (5.00 mL) was added 5-[2-(dimethylamino)ethoxy]pyrazin-2-amine (92 mg, 0.50 mmol). The resulting mixture was stirred for 1 h at room temperature. Then $K_2CO_3$ (58 mg, 0.42 mmol) was added and stirred at 100° C. for 1 h. The reaction was quenched with water at room temperature. The solid was collected by filtration, washed by water and dried to afford ethyl (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylate (100 mg, crude) as a yellow solid. LCMS (ESI) $[M+H]^+$: 589.24.

Step 5. Synthesis of (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylic acid

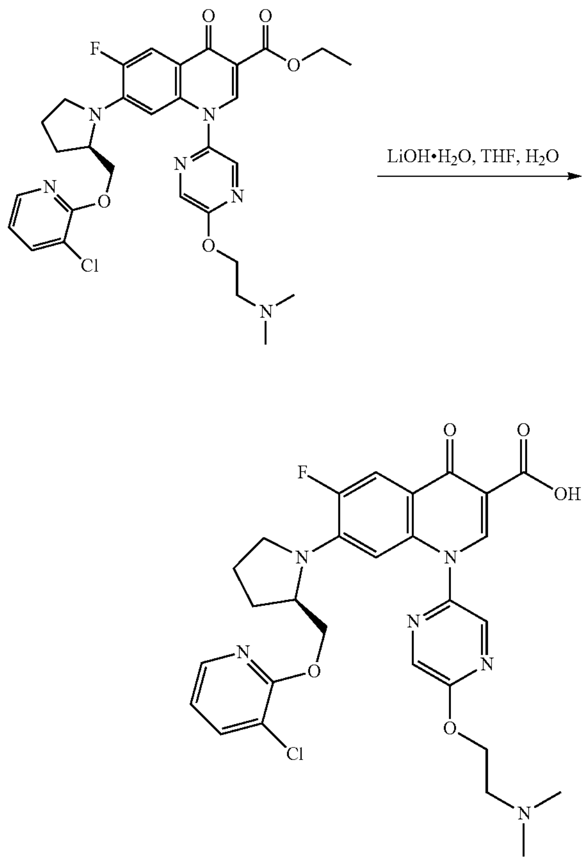

To a mixture of ethyl (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylate (100 mg, 0.17 mmol) in THF (3 mL) was added $LiOH{\cdot}H_2O$ (35 mg, 0.83 mmol,) and $H_2O$ (1.00 mL). The mixture was stirred at room temperature for 2 h. The residue was purified by Prep.-HPLC (Column: YMC-Actus Triart C18, 20*250 mm, 5 um, 12 nm; Mobile Phase A:Water(10 mmol/L $NH_4HCO_3$), Mobile Phase B:ACN; Flow rate:25 mL/min; Gradient:5 B to 61 B in 2 min; 254 nm; RT1:8.72) to afford (R)-7-(2-(((3-chloropyridin-2-yl)oxy)methyl)pyrrolidin-1-yl)-1-(5-(2-(dimethylamino)ethoxy)pyrazin-2-yl)-6-fluoro-4-oxo-1,4-dihydroquinoline-3-carboxylic acid (6.0 mg, 6%) as a yellow solid. LCMS (ESI) $[M+H]^+$:583.25. $^1H$ NMR (400 MHz, DMSO-$d_6$) δ 8.89-8.48 (m, 2H), 8.30 (s, 1H), 8.14-7.53 (m, 3H), 6.99 (s, 1H), 6.28-6.17 (m, 1H), 4.65-4.40 (m, 3H), 4.35-4.15 (m, 2H), 3.35 (s, 1H), 3.21 (s, 1H), 2.68 (s, 2H), 2.27-2.22 (m, 6H), 2.08 (s, 2H), 1.99-1.81 (m, 2H).

Potency Lin28a-dep Z11 $IC_{50}$ (μM)++++

Example 17: Synthesis of (R)-1-(4-(2-(dimethylamino)ethoxy)phenyl)-6-fluoro-7-(2-(((3-methylpyridin-2-yl)oxy)methyl)pyrrolidin-1-yl)-4-oxo-1,4-dihydroquinoline-3-carboxylic acid

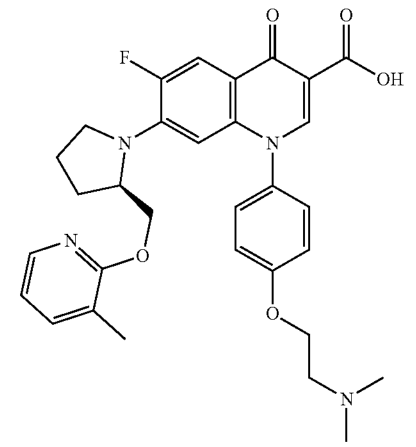 [SMILES: Cc1cccnc1OC[C@H]1CCCN1c1cc2c(cc1F)c(=O)c(C(=O)O)cn2-c1ccc(OCCN(C)C)cc1]

Step 1. Synthesis of dimethyl[2-(4-nitrophenoxy)ethyl]amine

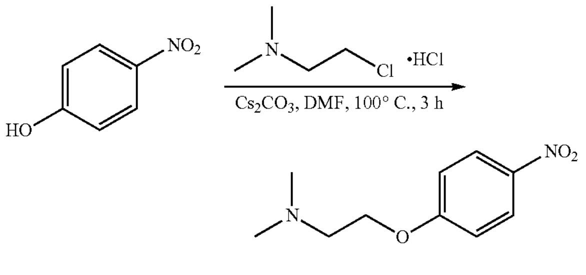

To a mixture of 4-nitrophenol (500 mg, 3.59 mmol) in DMF (10 mL) was added dimethylaminoethyl chloride hydrochloride (776 mg, 5.38 mmol) and $Cs_2CO_3$ (3.51 g, 10.78 mmol). The resulting mixture was stirred for 1 h at 100° C. The reaction mixture was diluted with 50 ml $H_2O$. The resulting solution was extracted with EtOAc (100 mL×3) and the organic layers were combined. The organic layer was dried over anhydrous sodium sulfate and concentrated under vacuum. The residue was purified by reverse phase flash chromatography eluting with ACN/$H_2O$ (0.05% $NH_4HCO_3$)(80%-100%) to afford dimethyl[2-(4-nitrophenoxy)ethyl]amine (400 mg, 47% yield) as a white solid. LCMS (ESI) $[M+H]^+$: 211.24.

Step 2. Synthesis of 4-[2-(dimethylamino)ethoxy]aniline

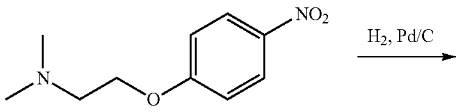

-continued

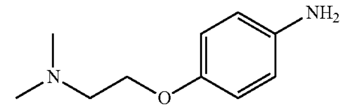

Under nitrogen, to a mixture of dimethyl[2-(4-nitrophenoxy)ethyl]amine (400 mg, 1.90 mmol) in MeOH (10 mL) was added Pd/C (99 mg, 0.93 mmol). Then the nitrogen atmosphere was replaced by hydrogen atmosphere. The resulting mixture was stirred for 1 h at room temperature. The filtrate was collected by filtration and concentrated to afford 4-[2-(dimethylamino)ethoxy]aniline (250 mg, crude) as a yellow oil. LCMS (ESI) $[M+H]^+$: 181.24.

Step 3. Synthesis of ethyl 1-[4-[2-(dimethylamino)ethoxy]phenyl]-6-fluoro-7-[(2R)-2-[[(3-methylpyridin-2-yl)oxy]methyl]pyrrolidin-1-yl]-4-oxoquinoline-3-carboxylate

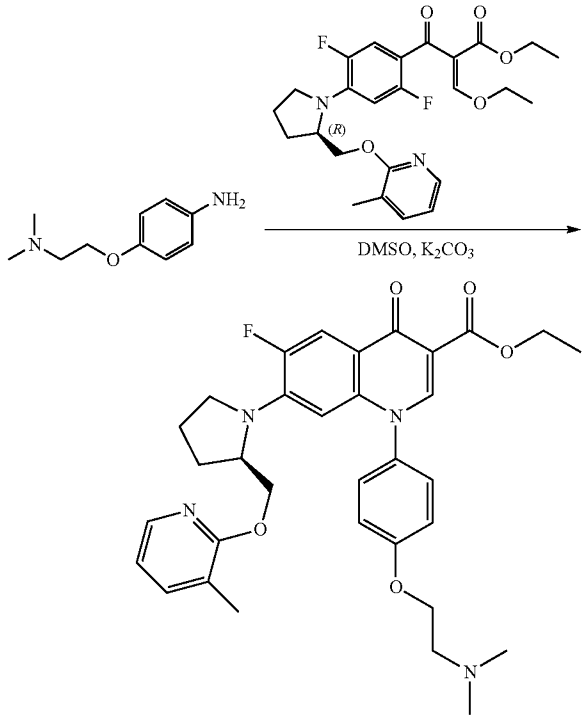

To a mixture of ethyl (2Z)-2-[(Z)-2,5-difluoro-4-[(2R)-2-[[(3-methylpyridin-2-yl)oxy]methyl]pyrrolidin-1-yl]benzoyl]-3-ethoxyprop-2-enoate (200 mg, 0.42 mmol) in DMSO (5.00 mL) was added 4-[2-(dimethylamino)ethoxy]aniline (91 mg, 0.50 mmol). The resulting mixture was stirred for 1 h at room temperature. Then $K_2CO_3$ (58 mg, 0.42 mmol) was added and stirred at 100° C. for 1 h. The reaction was quenched with water at room temperature. The solid was collected by filtration, washed by water and dried to afford ethyl 1-[4-[2-(dimethylamino)ethoxy]phenyl]-6-fluoro-7-[(2R)-2-[[(3-methylpyridin-2-yl)oxy]methyl]pyrrolidin-1-yl]-4-oxoquinoline-3-carboxylate (250 mg, crude) as a yellow solid. LCMS (ESI) $[M+H]^+$: 589.24.

Step 4. Synthesis of (R)-1-(4-(2-(dimethylamino)ethoxy)phenyl)-6-fluoro-7-(2-(((3-methylpyridin-2-yl)oxy)methyl)pyrrolidin-1-yl)-4-oxo-1,4-dihydroquinoline-3-carboxylic acid

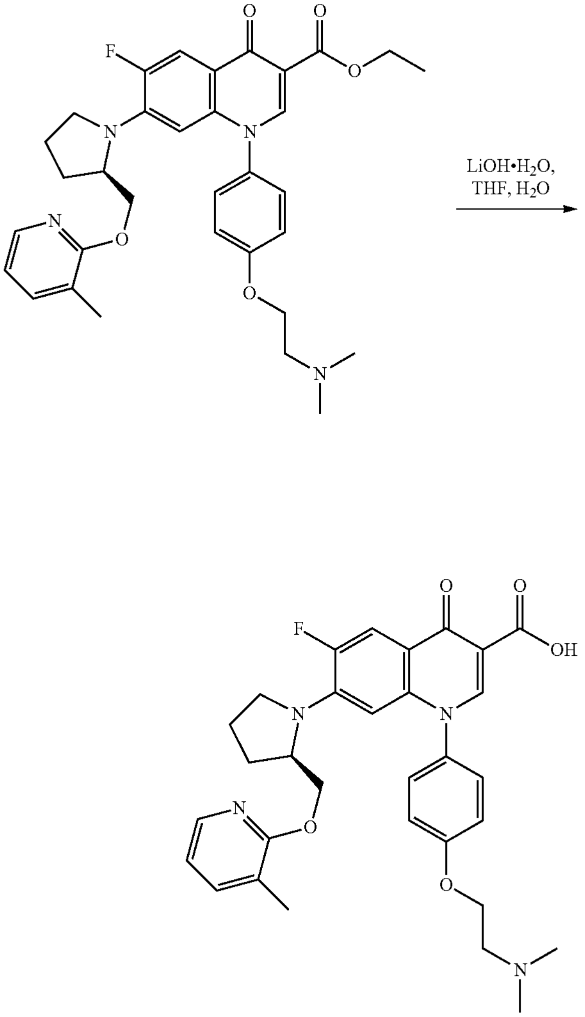

To a mixture of ethyl 1-[4-[2-(dimethylamino)ethoxy]phenyl]-6-fluoro-7-[(2R)-2-[[(3-methylpyridin-2-yl)oxy]methyl]pyrrolidin-1-yl]-4-oxoquinoline-3-carboxylate (250 mg, 0.42 mmol) in THF (3 mL) was added $LiOH{\cdot}H_2O$ (142 mg, 3.38 mmol) and $H_2O$ (1.00 mL). The mixture was stirred at room temperature for 2 h. The residue was purified by Prep.-HPLC (Column: Gemini-NX C18 AXAI Packed, 21.2*150 mm 5 um; Mobile Phase A:Water(0.1% FA), Mobile Phase B:ACN; Flow rate:25 mL/min; Gradient:23 B to 30 B in 9 min; 254 nm; RT1:6.67) to afford (R)-1-(4-(2-(dimethylamino)ethoxy)phenyl)-6-fluoro-7-(2-(((3-methylpyridin-2-yl)oxy)methyl)pyrrolidin-1-yl)-4-oxo-1,4-dihydroquinoline-3-carboxylic acid (46.2 mg, 19%) as a yellow solid. LCMS (ESI) $[M+H]^+$: 561.25. $^1H$ NMR (300 MHz, DMSO-$d_6$) δ 8.47 (s, 1H), 8.19 (s, 1H), 7.94-7.83 (m, 2H), 7.57-7.45 (m, 3H), 7.21 (s, 1H), 6.98 (s, 1H), 6.92-6.82 (m, 1H), 6.10 (m, 1H), 4.43 (s, 1H), 4.23 (m, 1H), 4.13 (m, 3H), 3.37 (s, 1H), 3.21 (s, 1H), 2.69 (m, 2H), 2.06 (s, 6H), 2.04 (s, 2H), 1.99-1.85 (s, 5H).

Potency Lin28a-dep Z11 $IC_{50}$ (μM)++++

Example 18: Synthesis of (R)-6-chloro-7-(2-(((3-chloropyridin-2-yl)oxy)methyl)pyrrolidin-1-yl)-1-(1,3-dihydroisobenzofuran-5-yl)-4-oxo-1,4-dihydroquinoline-3-carboxylic acid

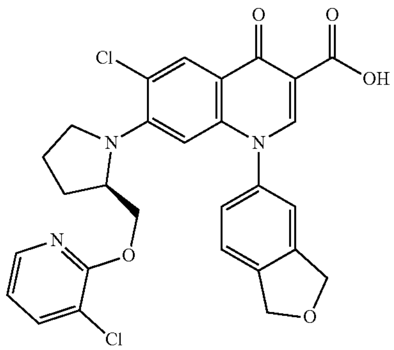 [SMILES: O=C(O)c1cn(-c2ccc3c(c2)COC3)c2cc(N3CCC[C@@H]3COc3ncccc3Cl)c(Cl)cc2c1=O]

Step 1. Synthesis of ethyl (R)-3-(5-chloro-4-(2-(((3-chloropyridin-2-yl)oxy)methyl)pyrrolidin-1-yl)-2-fluorophenyl)-3-oxopropanoat

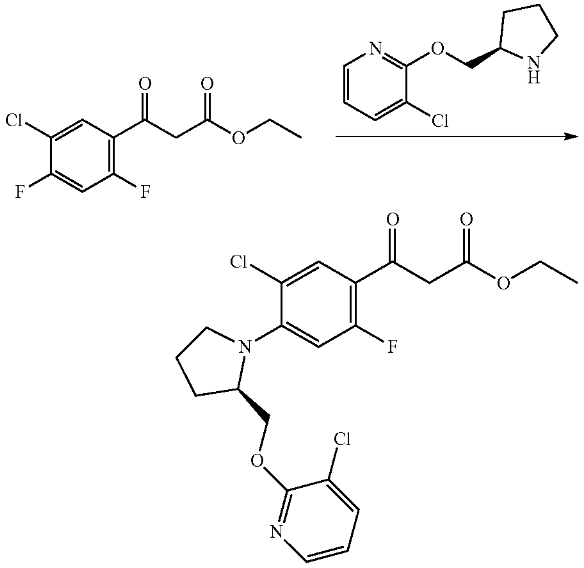

To a mixture of ethyl 3-(5-chloro-2,4-difluorophenyl)-3-oxopropanoate (500 mg, 1.90 mmol) in ACN (5 mL) was added 3-chloro-2-[(2R)-pyrrolidin-2-ylmethoxy]pyridine (485 mg, 2.28 mmol) and TEA (1.16 g, 11.42 mmol). The resulting mixture was stirred for 2 h at 80° C. The residue was purified by reverse phase flash chromatography eluting with ACN/$H_2O$ (0.05% $NH_4HCO_3$) (60%-80%) to afford ethyl (R)-3-(5-chloro-4-(2-(((3-chloropyridin-2-yl)oxy)methyl)pyrrolidin-1-yl)-2-fluorophenyl)-3-oxopropanoate (300 mg, 33% yield) as a yellow oil. LCMS (ESI) $[M+H]^+$: 455.24.

Step 2. Synthesis of ethyl (R,Z)-2-(5-chloro-4-(2-(((3-chloropyridin-2-yl)oxy)methyl)pyrrolidin-1-yl)-2-fluorobenzoyl)-3-ethoxyacrylate

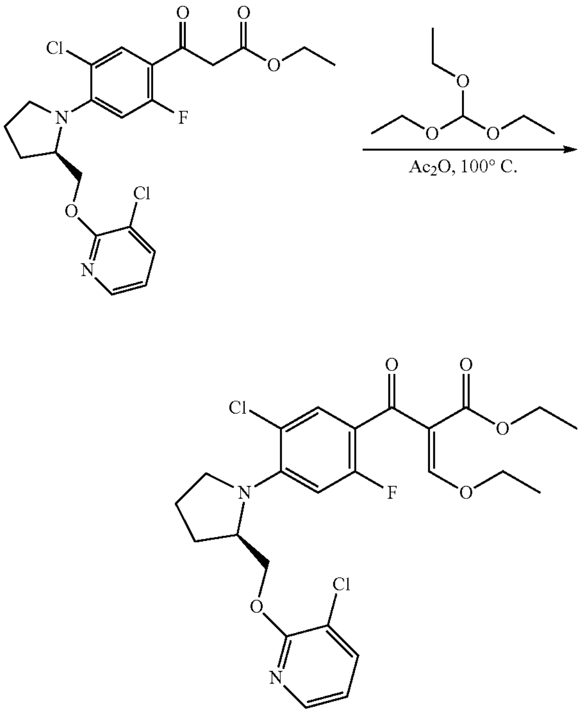

To a mixture of ethyl (R)-3-(5-chloro-4-(2-(((3-chloropyridin-2-yl)oxy)methyl)pyrrolidin-1-yl)-2-fluorophenyl)-3-oxopropanoate (300 mg, 0.65 mmol) in acetic anhydride (146 mg, 1.43 mmol) were added triethyl orthoformate (106 mg, 0.71 mmol). The resulting mixture was stirred for 8 h at 80° C. The solvent was concentrated under vacuum to afford ethyl (R,Z)-2-(5-chloro-4-(2-(((3-chloropyridin-2-yl)oxy)methyl)pyrrolidin-1-yl)-2-fluorobenzoyl)-3-ethoxyacrylate (360 mg, crude) as a yellow oil. LCMS (ESI) $[M+H]^+$: 511.24.

Step 3. Synthesis of ethyl (R)-6-chloro-7-(2-(((3-chloropyridin-2-yl)oxy)methyl)pyrolidin-1-yl)-1-(1,3-dihydroisobenzofuran-5-yl)-4-oxo-1,4-dihydroquinoline-3-carboxylate

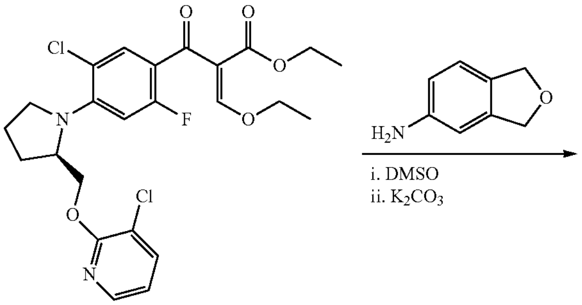

-continued

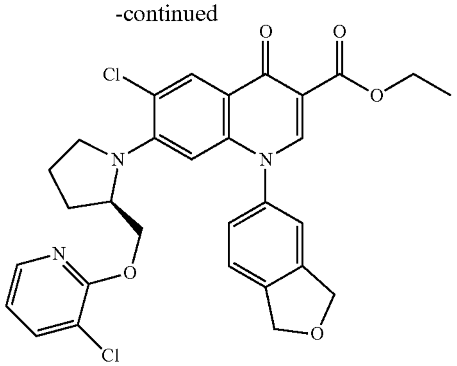

To a mixture of ethyl (R,Z)-2-(5-chloro-4-(2-(((3-chloropyridin-2-yl)oxy)methyl)pyrrolidin-1-yl)-2-fluorobenzoyl)-3-ethoxyacrylate (360 mg, 0.70 mmol) in DMSO (5.00 mL) was added 1,3-dihydro-2-benzofuran-5-amine (114 mg, 0.84 mmol). The resulting mixture was stirred for 1 h at 100° C. Then $K_2CO_3$ (97 mg, 0.70 mmol) was added and stirred at 100° C. for 1 h. The reaction was quenched with water at room temperature. The solid was collected by filtration, washed by water and dried to afford ethyl (R)-6-chloro-7-(2-(((3-chloropyridin-2-yl)oxy)methyl)pyrrolidin-1-yl)-1-(1,3-dihydroisobenzofuran-5-yl)-4-oxo-1,4-dihydroquinoline-3-carboxylate (350 mg, crude) as a yellow solid. LCMS (ESI) $[M+H]^+$: 580.20.

Step 4. Synthesis of (R)-6-chloro-7-(2-(((3-chloropyridin-2-yl)oxy)methyl)pyrolidin-1-yl)-1-(1,3-dihydroisobenzofuran-5-yl)-4-oxo-1,4-dihydroquinoline-3-carboxylic acid

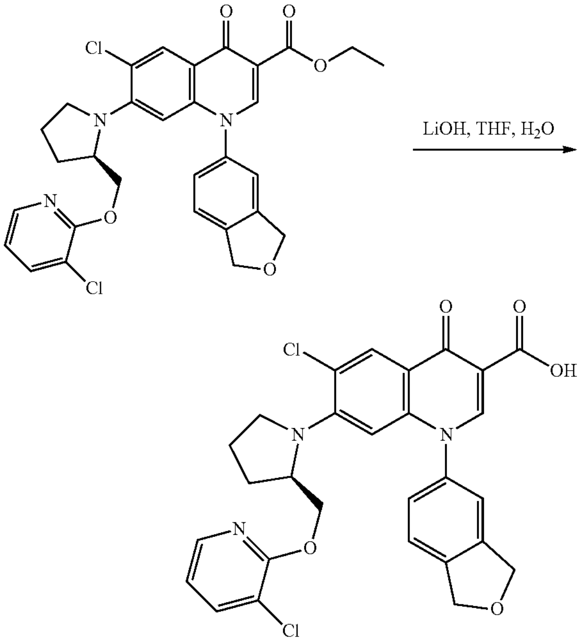

To a mixture of ethyl (R)-6-chloro-7-(2-(((3-chloropyridin-2-yl)oxy)methyl)pyrrolidin-1-yl)-1-(1,3-dihydroisobenzofuran-5-yl)-4-oxo-1,4-dihydroquinoline-3-carboxylate (350 mg, 0.60 mmol) in THF (3 mL) was added $LiOH \cdot H_2O$ (57 mg, 2.38 mmol) and $H_2O$ (1.00 mL). The mixture was stirred at room temperature for 2 h. The residue was purified by Prep.-HPLC(Column: XSelect CSH Prep C18 OBD Column, 5 um, 19*150 mm; Mobile Phase A:Water(0.1% FA), Mobile Phase B:ACN; Flow rate:25 mL/min; Gradient: 53 B to 77 B in 8 min; 254 nm; RT1:7.2) to afford (R)-6-chloro-7-(2-(((3-chloropyridin-2-yl)oxy)methyl)pyrrolidin-1-yl)-1-(1,3-dihydroisobenzofuran-5-yl)-4-oxo-1,4-dihydroquinoline-3-carboxylic acid (70 mg, 21%) as a yellow solid. LCMS (ESI) $[M+H]^+$: 552.0. $^1H$ NMR (300 MHz, DMSO-$d_6$) δ 15.08 (s, 1H), 8.55 (s, 1H), 8.17 (s, 1H), 7.89 (d, J=4.8 Hz, 1H), 7.83 (dd, J=7.7, 1.6 Hz, 1H), 7.74-7.27 (m, 3H), 7.03-6.87 (m, 1H), 6.37 (d, J=4.3 Hz, 1H), 5.11 (s, 3H), 5.04-4.84 (m, 1H), 4.71-4.55 (m, 1H), 4.36-4.19 (m, 2H), 3.58-3.40 (m, 1H), 3.26-3.09 (m, 1H), 2.26 (d, J=15.5 Hz, 1H), 2.05-1.65 (m, 3H).

Potency Lin28a-dep Z11 $IC_{50}$ (μM)++++

Example 19: Synthesis of (R)-6-chloro-7-(2-(((3-chloropyridin-2-yl)oxy)methyl)pyrrolidin-1-yl)-4-oxo-1-(pyrazin-2-yl)-1,4-dihydro-1,8-naphthyridine-3-carboxylic acid

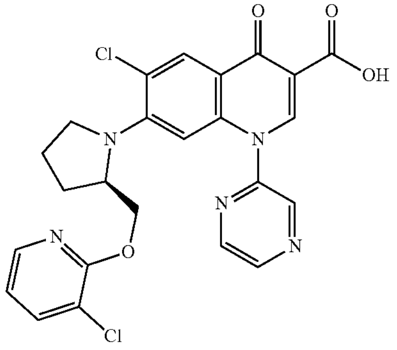 [SMILES: O=C(O)c1cn(-c2cnccn2)c2cc(N3CCC[C@@H]3COc3ncccc3Cl)c(Cl)cc2c1=O]

Step 1. Synthesis of ethyl 3-oxo-3-(2,5,6-trichloropyridin-3-yl)propanoate

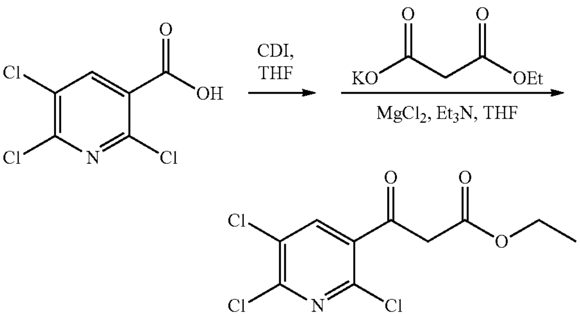

Under a nitrogen atmosphere, a mixture of 2,5,6-trichloropyridine-3-carboxylic acid (1.8 g, 7.95 mmol) and CDI (1.6 g, 9.54 mmol) in THF (40 mL) was stirred for 3 h at 60° C. Then the mixture was added to a suspension of 1-ethyl 3-potassium propanedioate (1.4 g, 7.93 mmol), $Et_3N$ (116 mg, 1.15 mmol), $MgCl_2$ (1.1 g, 12.00 mmol) in THF (40 mL) and the mixture was stirred overnight at room temperature. Then the reaction was adjusted pH to 3-4 with 1N HCl (aq.). The mixture was diluted with EtOAc (200 mL), washed with water (80 mL), brine (80 mL), dried over $Na_2SO_4$, filtrated, concentrated and purified by flash chromatography on silica gel eluting with EtOAc/Petroleum ether (0-100%) to afford ethyl 3-oxo-3-(2,5,6-trichloropyridin-3-yl)propanoate (300 mg, 12.73%) as a light yellow oil. LCMS (ESI) $[M+H]^+$: 296.

Step 2. Synthesis of ethyl 6,7-dichloro-4-oxo-1-(pyrazin-2-yl)-1,8-naphthyridine-3-carboxylate

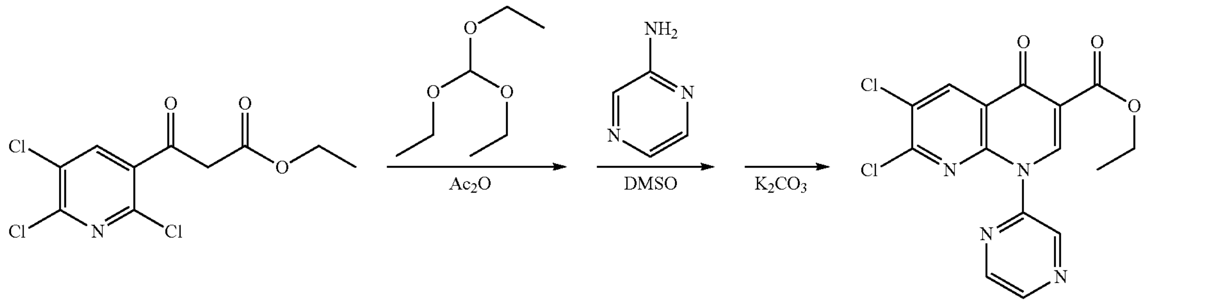

Under a nitrogen atmosphere, a mixture of ethyl 3-oxo-3-(2,5,6-trichloropyridin-3-yl)propanoate (300 mg, 1.01 mmol) and triethyl orthoformate (225 mg, 1.52 mmol) in $Ac_2O$ (620 mg, 6.07 mmol) was stirred for 1 h at 100° C. Then the mixture was evaporated to give the residue. The residue was dissolved in DMSO (5 mL) and 2-aminopyrazine (96 mg, 1.01 mmol) was added and the mixture was stirred for 1 h. Then $K_2CO_3$ (140 mg, 1.01 mmol) was added into the mixture and stirred for additional 1 h at room temperature. Then the reaction was adjusted pH to 3-4 with 1N HCl (aq.). The mixture was diluted with EtOAc (200 mL), washed with water (80 mL), brine (80 mL), dried over $Na_2SO_4$, filtrated, concentrated and purified by flash chromatography on silica gel eluting with EtOAc/Petroleum ether (0-100%) to afford ethyl 6,7-dichloro-4-oxo-1-(pyrazin-2-yl)-1,8-naphthyridine-3-carboxylate (240 mg, 64.96%) as a red solid. LCMS (ESI) $[M+H]^+$: 365.

Step 3. Synthesis of ethyl (R)-6-chloro-7-(2-(((3-chloropyridin-2-yl)oxy)methyl)pyrrolidin-1-yl)-4-oxo-1-(pyrazin-2-yl)-1,4-dihydro-1,8-naphthyridine-3-carboxylate

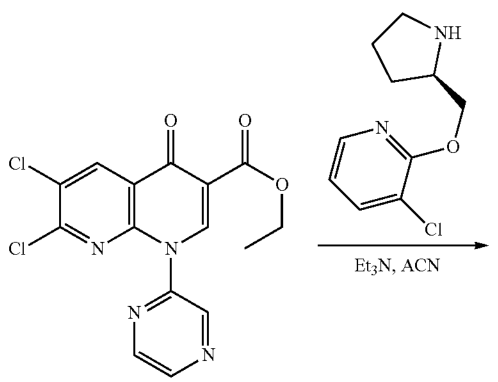

-continued

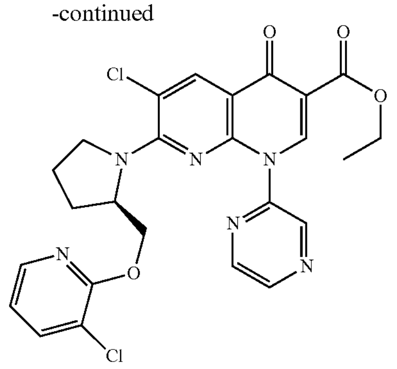

Under a nitrogen atmosphere, a mixture of ethyl 6,7-dichloro-4-oxo-1-(pyrazin-2-yl)-1,8-naphthyridine-3-carboxylate (70 mg, 0.19 mmol), 3-chloro-2-[(2R)-pyrrolidin-2-ylmethoxy]pyridine (61 mg, 0.29 mmol), $Et_3N$ (116 mg, 1.15 mmol) and ACN (3 mL) was stirred overnight at 80° C. The reaction was cooled to room temperature and used directly without further purification. LCMS (ESI) $[M+H]^+$: 541.

Step 4. Synthesis of 6-chloro-7-[(2R)-2-[[(3-chloropyridin-2-yl)oxy]methyl]pyrrolidin-1-yl]-4-oxo-1-(pyrazin-2-yl)-1,8-naphthyridine-3-carboxylic acid

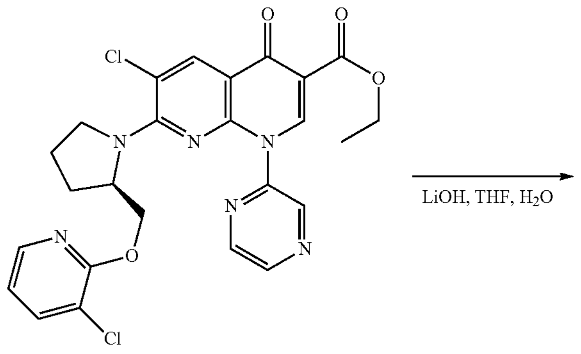

-continued

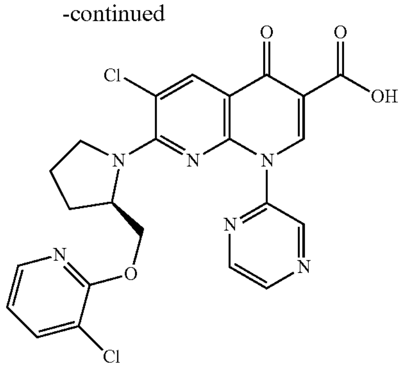

LiOH·$H_2O$ (1N, 0.38 mL, 0.38 mmol) in water was added into the mixture from the previous step and the mixture was stirred for 2 h. Then the reaction was adjusted pH to 3-4. The mixture was filtrated, washed with water and ACN. The filtrate was evaporated under reduced pressure to afford 6-chloro-7-[(2R)-2-[[(3-chloropyridin-2-yl)oxy]methyl] pyrrolidin-1-yl]-4-oxo-1-(pyrazin-2-yl)-1,8-naphthyridine-3-carboxylic acid (23.4 mg, 22.59%) as a light yellow solid. LCMS (ESI) $[M+H]^+$: 513.1. $^1$H NMR (300 MHz, Chloroform-d) δ 14.60 (s, 1H), 9.09 (d, J=1.4 Hz, 1H), 9.02 (s, 1H), 8.61 (d, J=2.5 Hz, 1H), 8.53 (dd, J=2.5, 1.5 Hz, 1H), 8.48 (s, 1H), 7.91 (dd, J=4.9, 1.7 Hz, 1H), 7.63 (dd, J=7.6, 1.7 Hz, 1H), 6.85 (dd, J=7.6, 4.9 Hz, 1H), 4.86 (m, 1H), 4.34-4.19 (m, 2H), 4.15-3.97 (m, 1H), 3.95-3.78 (m, 1H), 2.28-2.03 (m, 3H), 2.02-1.84 (m, J=7.2 Hz, 1H).

Potency Lin28a-dep Z11 $IC_{50}$ (μM)++++

Example 20: Synthesis of (R)-6,8-difluoro-1-(2-fluoro-4-hydroxyphenyl)-7-(2-(((3-methylpyridin-2-yl)oxy)methyl)pyrrolidin-1-yl)-4-oxo-1,4-dihydroquinoline-3-carboxylic acid

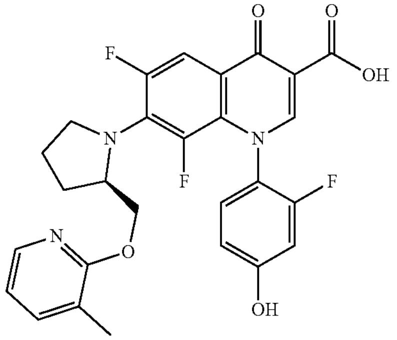 [SMILES: Cc1cccnc1OC[C@H]1CCCN1c1c(F)cc2c(=O)c(C(=O)O)cn(-c3ccc(O)cc3F)c2c1F]

Step 1. Synthesis of ethyl 6,7,8-trifluoro-1-(2-fluoro-4-hydroxyphenyl)-4-oxoquinoline-3-carboxylate

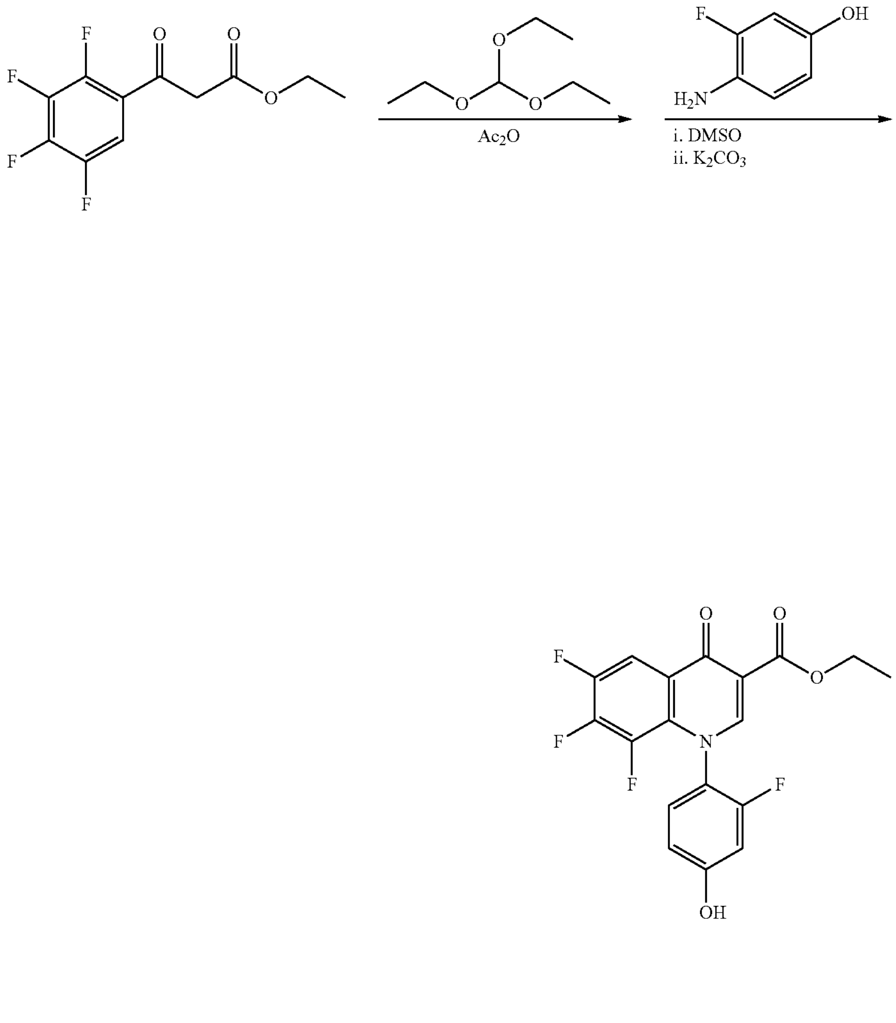

A mixture of ethyl 3-oxo-3-(2,3,4,5-tetrafluorophenyl) propanoate (300 mg, 1.13 mmol), triethyl orthoformate (252 mg, 1.70 mmol) and acetic anhydride (347 mg, 3.40 mmol) at 100° C. The mixture was allowed to cool down to room temperature. The resulting mixture was concentrated under vacuum. The crude product was used in the next step directly without further purification. To the residue in DMSO (5 mL) was added 4-amino-3-fluorophenol (129 mg, 1.02 mmol) and the mixture was stirred for 12 h at room temperature. Then $K_2CO_3$ (156 mg, 1.13 mmol) was added and the resulting mixture was stirred for 2 h at room temperature. Then the reaction was quenched with water (5 mL). The precipitated solids were collected by filtration and washed with water (2×10 mL). This resulted in ethyl 6,7,8-trifluoro-1-(2-fluoro-4-hydroxyphenyl)-4-oxoquinoline-3-carboxylate (140 mg, 32.4%) as a yellow solid. LCMS (ESI) $[M+H]^+$: 382.

Step 2. Synthesis of ethyl 6,8-difluoro-1-(2-fluoro-4-hydroxyphenyl)-7-[(2R)-2-[[(3-methylpyridin-2-yl)oxy]methyl]pyrrolidin-1-yl]-4-oxoquinoline-3-carboxylate

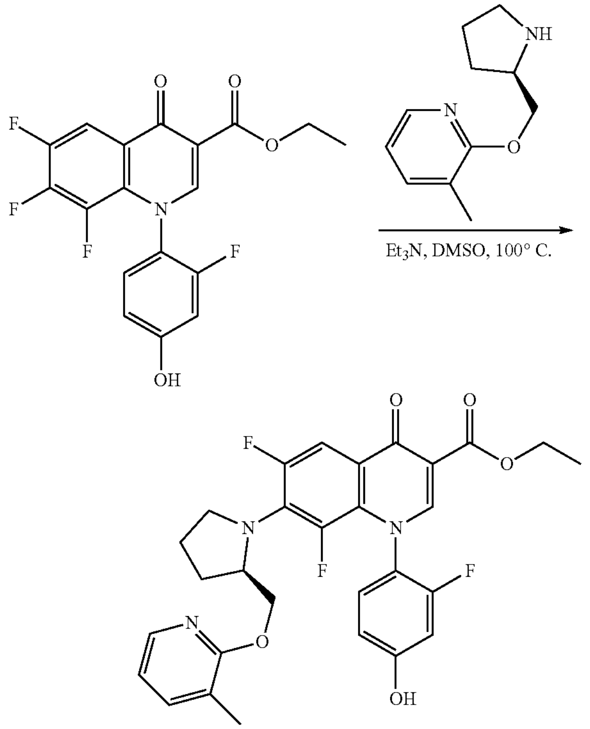

A mixture of 3-methyl-2-[(2R)-pyrrolidin-2-ylmethoxy] pyridine (212 mg, 1.10 mmol), $Et_3N$ (223 mg, 2.20 mmol), DMSO (2 mL) and ethyl 6,7,8-trifluoro-1-(2-fluoro-4-hydroxyphenyl)-4-oxoquinoline-3-carboxylate (210 mg, 0.55 mmol) was stirred for 12 h at 100° C. under nitrogen atmosphere. Desired product could be detected by LCMS. The mixture was allowed to cool down to room temperature. The aqueous layer was extracted with EtOAc (3×10 mL). The resulting mixture was concentrated under vacuum. The residue was purified by reverse phase flash chromatography eluting with $ACN/H_2O$ (0-95%) to afford ethyl 6,8-difluoro-1-(2-fluoro-4-hydroxyphenyl)-7-[(2R)-2-[[(3-methylpyridin-2-yl)oxy]methyl]pyrrolidin-1-yl]-4-oxoquinoline-3-carboxylate (60 mg, 19.7%) as a light yellow solid. LCMS (ESI) $[M+H]^+$: 554.

Step 3. Synthesis of 6,8-difluoro-1-(2-fluoro-4-hydroxyphenyl)-7-[(2R)-2-[[(3-methylpyridin-2-yl)oxy]methyl]pyrrolidin-1-yl]-4-oxoquinoline-3-carboxylic acid

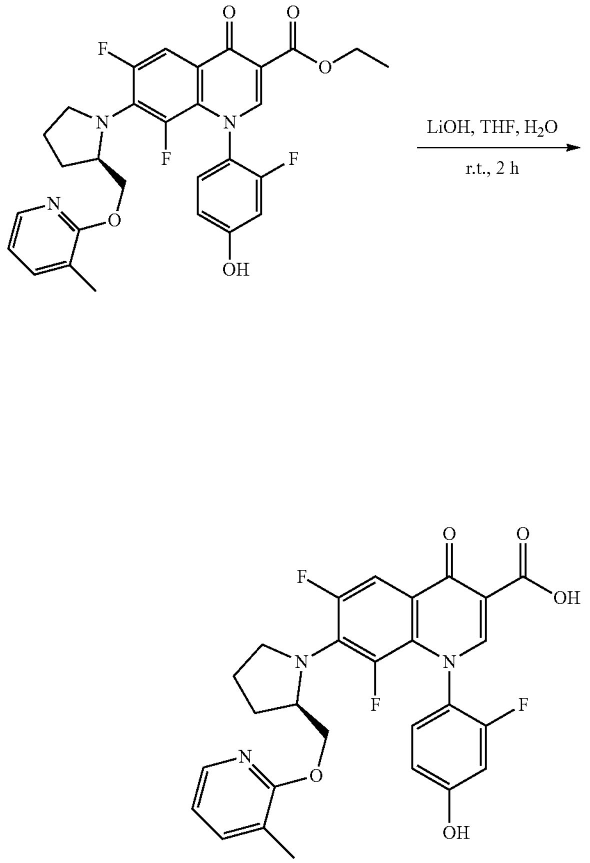

To a stirred solution of ethyl 6,8-difluoro-1-(2-fluoro-4-hydroxyphenyl)-7-[(2R)-2-[[(3-methylpyridin-2-yl)oxy]methyl]pyrrolidin-1-yl]-4-oxoquinoline-3-carboxylate (60.0 mg, 0.10 mmol) in THF (2 mL) was added $LiOH \cdot H_2O$ (23 mg, 0.54 mmol) and $H_2O$ (0.5 mL) and the mixture was stirred for 2 h at room temperature. The resulting mixture was purified by Prep.-HPLC with the following conditions (Column: Gemini-NX C18 AXAI Packed, 21.2*150 mm 5 um; Mobile Phase A:Water(0.1% FA), Mobile Phase B:ACN; Flow rate:25 mL/min; Gradient:60 B to 65 B in 8 min; 254 nm) to afford 6,8-difluoro-1-(2-fluoro-4-hydroxyphenyl)-7-[(2R)-2-[[(3-methylpyridin-2-yl)oxy]methyl]pyrrolidin-1-yl]-4-oxoquinoline-3-carboxylic acid (10.4 mg, 18.26%) as a light yellow solid. LCMS (ESI) $[M+H]^+$: 526.2. $^1H$ NMR (300 MHz, DMSO-$d_6$) δ 14.75 (s, 1H), 10.51 (s, 1H), 8.47 (s, 1H), 7.90-7.71 (m, 2H), 7.62-7.47 (m, 1H), 7.43 (d, J=7.3 Hz, 1H), 6.91-6.64 (m, 3H), 4.61-4.42 (m, 1H), 4.33-4.12 (m, 2H), 3.77-3.61 (m, 1H), 3.41-3.36 (m, 1H), 2.25-2.13 (m, 1H), 2.03-1.90 (m, 1H), 1.86-1.71 (m, 5H).

Potency Lin28a-dep Z11 $IC_{50}$ (μM)++++

Example 21: Synthesis of (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylic acid

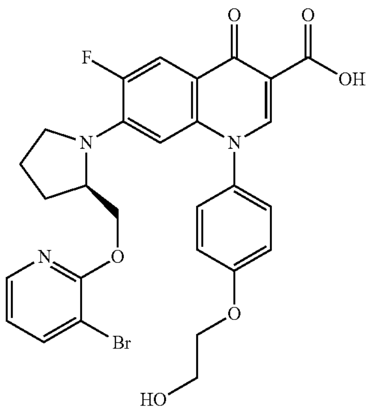 [SMILES: O=C(O)c1cn(-c2ccc(OCCO)cc2)c2cc(N3CCC[C@@H]3COc3ncccc3Br)c(F)cc2c1=O]

Step 1. Synthesis of 2-(4-nitrophenoxy)ethan-1-ol

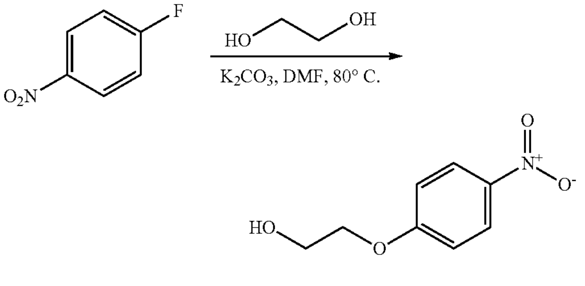

To a mixture of 1-fluoro-4-nitrobenzene (3.0 g, 21.27 mmol) and ethane-1,2-diol (2.6 g, 42.55 mmol) in DMF (40 mL) was added $K_2CO_3$ (8.8 g, 63.81 mmol). The mixture was stirred at room temperature for 16 h. The mixture was poured into ice water. The mixture was filtered. The filtrate was extracted with EtOAc (50 mL×3). The combined organic phase was dried over $Na_2SO_4$ and concentrated to afford 2-(4-nitrophenoxy)ethan-1-ol (1.0 g, 26%) as yellow solid. $^1$H NMR (300 MHz, DMSO-$d_6$) δ 8.26-8.16 (m, 2H), 7.21-7.12 (m, 2H), 4.97 (t, J=5.5 Hz, 1H), 4.19-4.10 (m, 2H), 3.75 (q, J=5.1 Hz, 2H).

Step 2. Synthesis of 2-(4-aminophenoxy)ethan-1-ol

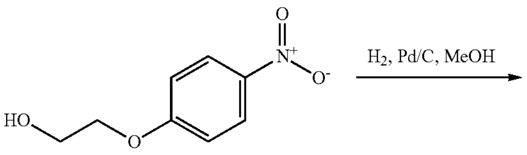

-continued

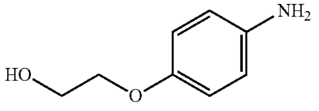

To a solution of 2-(4-nitrophenoxy)ethan-1-ol (1.0 g, 5.46 mmol) in MeOH (15 mL) was added Pd/C (200 mg). The mixture was degassed and stirred at room temperature under $H_2$ for 1.5 h. The mixture was filtered. The filtrate was concentrated to afford 2-(4-aminophenoxy)ethan-1-ol (700 mg, 84%) as yellow oil. LCMS (ESI) $[M+H]^+$: 154.

Step 3. Synthesis of ethyl 6,7-difluoro-1-(4-(2-hydroxyethoxy)phenyl)-4-oxo-1,4-dihydroquinoline-3-carboxylate

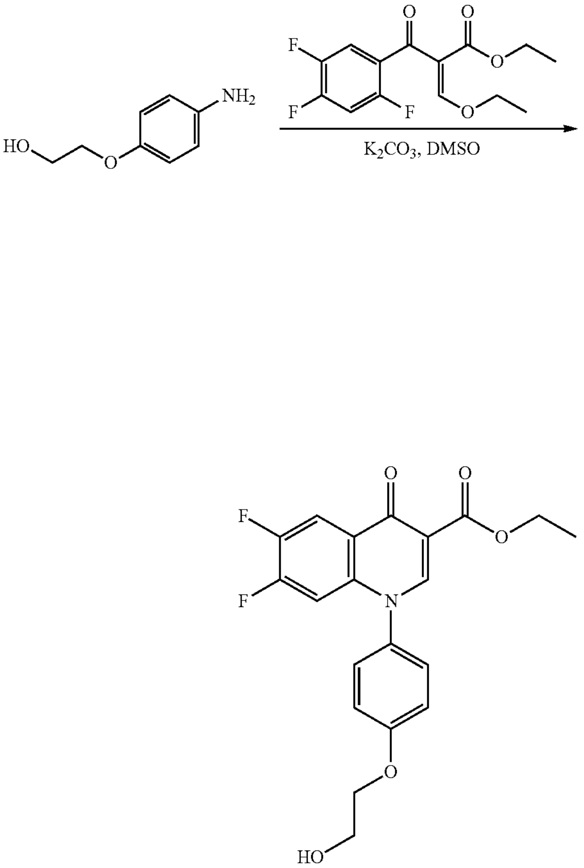

To a solution of ethyl (Z)-3-ethoxy-2-(2,4,5-trifluorobenzoyl)acrylate (1.2 g, 4.07 mmol) in DMSO (25 mL) was added 2-(4-aminophenoxy)ethan-1-ol (622 mg, 4.07 mmol). The solution was stirred at room temperature for 1 h. $K_2CO_3$ (673 mg, 4.88 mmol) was then added. The mixture was stirred at room temperature for another 1 h. The reaction mixture was poured into water. The solid was collected by filtration and dried to afford ethyl 6,7-difluoro-1-(4-(2-hydroxyethoxy)phenyl)-4-oxo-1,4-dihydroquinoline-3-carboxylate (1.4 g, 88%) as light yellow solid. LCMS (ESI) $[M+H]^+$: 390.

Step 4. Synthesis of ethyl (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylate

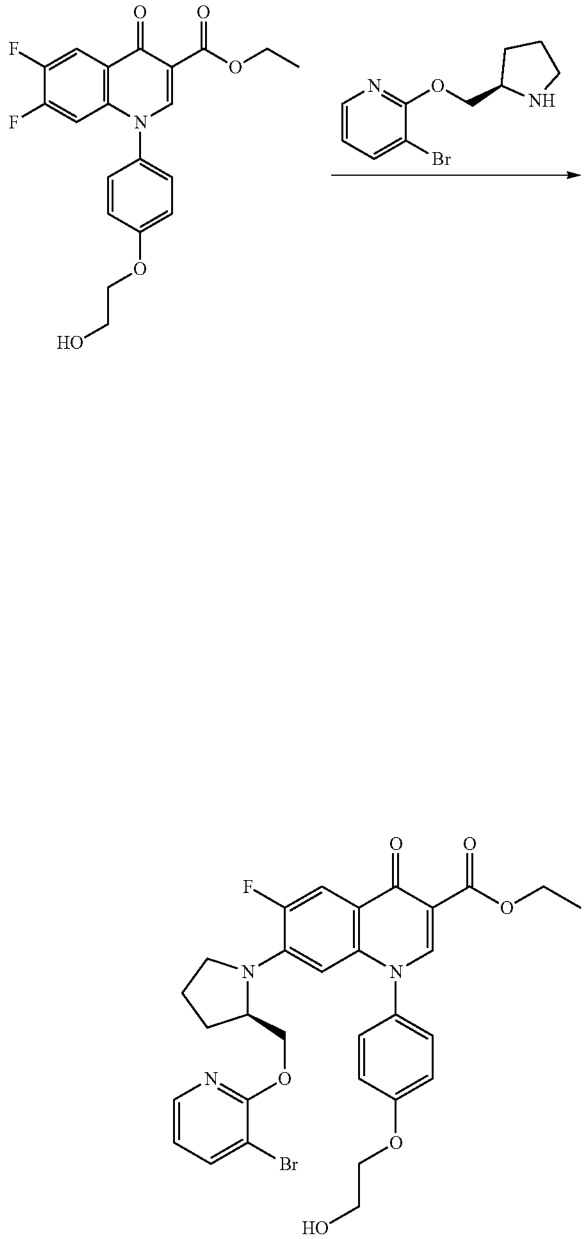

To a solution of ethyl 6,7-difluoro-1-(4-(2-hydroxyethoxy)phenyl)-4-oxo-1,4-dihydroquinoline-3-carboxylate (500 mg, 1.28 mmol) and TEA (648 mg, 6.40 mmol) in DMSO (10 mL) was added (R)-3-bromo-2-(pyrrolidin-2-ylmethoxy)pyridine (987 mg, 3.85 mmol). The mixture was stirred at 100° C. for 3 h. The reaction solution was purified by reverse phase flash column with 40-80% acetonitrile in water to afford ethyl (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylate (670 mg, 84%) as light yellow solid. LCMS (ESI) $[M+H]^+$: 626.

Step 5. Synthesis of (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylic acid

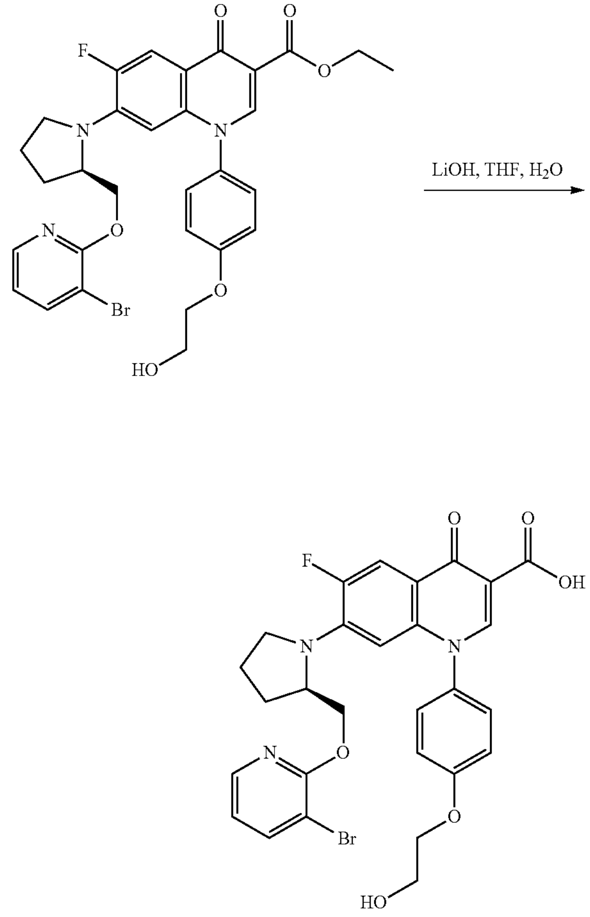

To a stirred solution of ethyl (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylate (60 mg, 0.10 mmol) in THF (1 mL) at room temperature under nitrogen was added $LiOH \cdot H_2O$ (16 mg, 0.38 mmol) in water (1 mL). The mixture was stirred at room temperature for 1 h. The reaction was quenched by the addition of HOAc to adjust pH 5. The mixture was purified by prep-HPLC (Column: XSelect CSH Prep C18 OBD Column, 5 um, 19*150 mm; Mobile Phase A:Water(0.1% FA), Mobile Phase B:ACN; Flow rate:25 mL/min; Gradient:38 B to 68 B in 8 min; 254 nm; RT1:7.65) to afford (R)-7-(2-(((3-bromopyridin-2-yl)oxy)methyl)pyrrolidin-1-yl)-6-fluoro-1-(4-(2-hydroxyethoxy)phenyl)-4-oxo-1,4-dihydroquinoline-3-carboxylic acid (32.3 mg, 54%) as off-white solid. LCMS (ESI) $[M+H]^+$: 600.10. $^1H$ NMR (300 MHz, DMSO-$d_6$) δ 15.43 (s, 1H), 8.47 (s, 1H), 8.06-7.95 (m, 2H), 7.88 (d, J=14.4 Hz, 1H), 7.58-7.49 (m, 2H), 7.24-7.14 (m, 1H), 7.09-6.99 (m, 1H), 6.98-6.88 (m, 1H), 6.08 (d, J=7.5 Hz, 1H), 4.97 (t, J=5.4 Hz, 1H), 4.50-4.44 (m, 1H), 4.35-4.29 (m, 2H), 4.11-4.02 (m, 2H), 3.83-3.72 (m, 2H), 3.33-3.25 (m, 1H), 3.21-3.13 (m, 1H), 2.14-2.02 (m, 2H), 2.04-1.81 (m, 2H).

Potency Lin28a-dep Z11 $IC_{50}$ (μM)++++

Example 22: Synthesis of (R)-6-fluoro-1-(2-fluoro-4-hydroxyphenyl)-4-oxo-7-(2-((pyrimidin-2-yloxy)methyl)pyrrolidin-1-yl)-1,4-dihydroquinoline-3-carboxylic acid

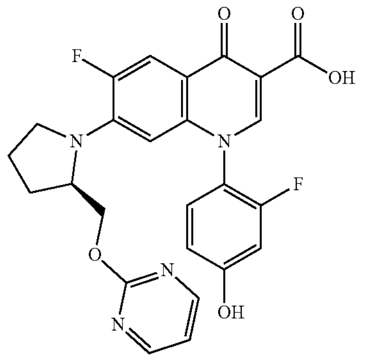 [SMILES: O=C(O)c1cn(-c2ccc(O)cc2F)c2cc(N3CCC[C@@H]3COc3ncccn3)c(F)cc2c1=O]

Step 1. Synthesis of ethyl 6,7-difluoro-1-[2-fluoro-4-[(4-methoxyphenyl)methoxy]phenyl]-4-oxoquinoline-3-carboxylate

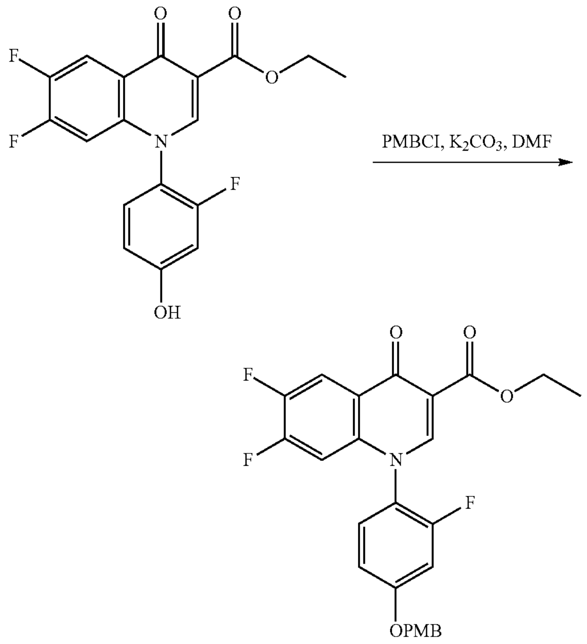

To a solution of ethyl 6,7-difluoro-1-(2-fluoro-4-hydroxyphenyl)-4-oxoquinoline-3-carboxylate (10.0 g, 27.53 mmol, 1.0 equiv) in DMF (100 mL) was added $K_2CO_3$ (11.4 g, 82.58 mmol, 3.0 equiv) and 4-methoxybenzyl chloride (6.5 g, 41.29 mmol, 1.5 equiv). The reaction was stirred at 70° C. for 2 h. The reaction was then quenched by water. The resulting solution was extracted with 150×3 mL of ethyl acetate. The organic layers combined and dried over anhydrous sodium sulfate, concentrated under vacuum. The residue was applied onto a silica gel column with dichloromethane/ethyl acetate (1/2). This resulted in ethyl 6,7-difluoro-1-[2-fluoro-4-[(4-methoxyphenyl)methoxy]phenyl]-4-oxoquinoline-3-carboxylate (4.2 g, 31.6%) as yellow oil. LCMS (ESI) $[M+H]^+$: 484.

Step 2. Synthesis of ethyl 6-fluoro-7-[(2R)-2-(hydroxymethyl)pyrrolidin-1-yl]-1-[4-[(4-methoxyphenyl)methoxy]phenyl]-4-oxoquinoline-3-carboxylate

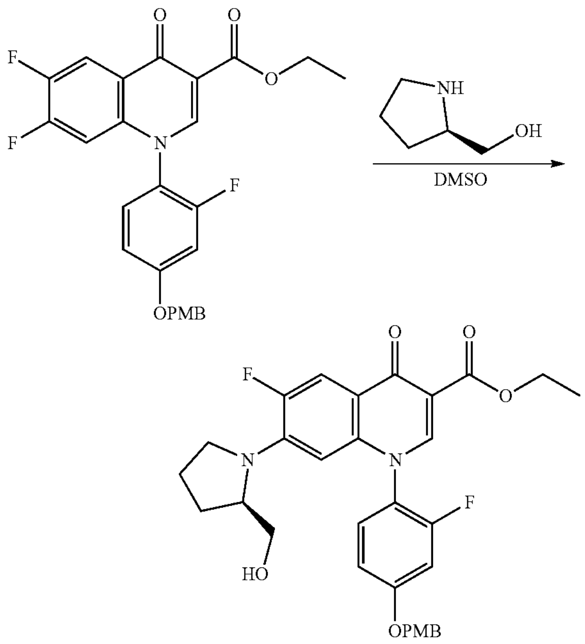

To a solution of ethyl 6,7-difluoro-1-[4-[(4-methoxyphenyl)methoxy]phenyl]-4-oxoquinoline-3-carboxylate (2.0 g, 4.30 mmol, 1.0 equiv) in DMSO (25 mL) was added $K_2CO_3$ (1.8 g, 12.89 mmol, 3.0 equiv) and (R)-pyrrolidin-2-ylmethanol (650 mg, 6.45 mmol, 1.5 equiv). The reaction was stirred at 100° C. for 2 h under $N_2$ atmosphere. The crude product was purified by Flash-Prep-HPLC with the $NH_4HCO_3$/acetonitrile=40% increasing to 50% within 15 min; Detector, 254/220 nm. This resulted in ethyl 6-fluoro-7-[(2R)-2-(hydroxymethyl)pyrrolidin-1-yl]-1-[4-[(4-methoxyphenyl)methoxy]phenyl]-4-oxoquinoline-3-carboxylate (1.5 g, 63.9%) as yellow oil. LCMS (ESI) $[M+H]^+$: 547.

Step 3. Synthesis of (R)-6-fluoro-1-(2-fluoro-4-((4-methoxybenzyl)oxy)phenyl)-4-oxo-7-(2-((pyrimidin-2-yloxy)methyl)pyrrolidin-1-yl)-1,4-dihydroquinoline-3-carboxylic acid

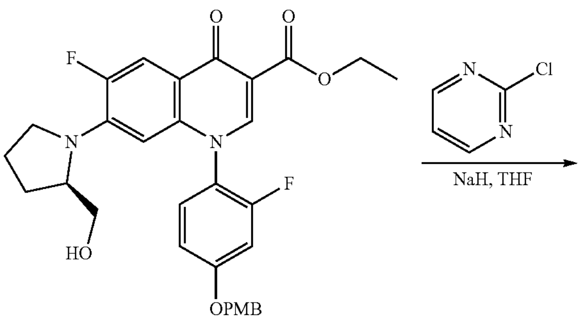

-continued

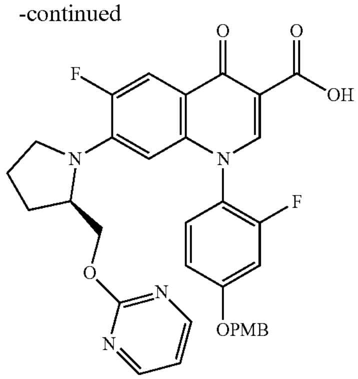

-continued

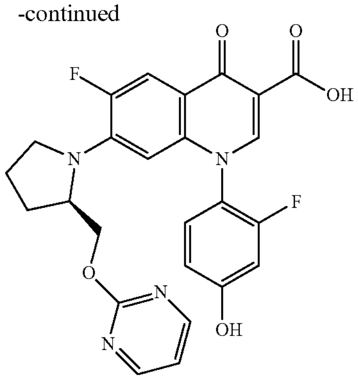

To a solution of ethyl 6-fluoro-1-[2-fluoro-4-[(4-methoxyphenyl) methoxy] phenyl]-7-[(2R)-2-(hydroxymethyl) pyrrolidin-1-yl]-4-oxoquinoline-3-carboxylate (150 mg, 0.27 mmol, 1.0 equiv) in THF (5 mL) was added NaH (10 mg, 0.40 mmol, 1.5 equiv). The reaction was stirred at room temperature for 0.5 h. Then, 2-chloropyrimidine (37 mg, 0.32 mmol, 1.2 equiv) was added into the solution. The reaction was stirred at room temperature for 2 h. The reaction was then quenched by the addition of water. The residue was purified by reverse phase flash chromatography to afford (R)-6-fluoro-1-(2-fluoro-4-((4-methoxybenzyl) oxy)phenyl)-4-oxo-7-(2-((pyrimidin-2-yloxy)methyl)pyrrolidin-1-yl)-1,4-dihydroquinoline-3-carboxylic acid (12.3 mg, 7.53%) as a light yellow solid. LCMS (ESI): $[M+H]^+$: 615.15. $^1H$ NMR (400 MHz, DMSO-$d_6$) δ 8.52 (d, J=4.7 Hz, 2H), 8.38 (s, 1H), 7.82 (d, J=14.8 Hz, 1H), 7.69-7.57 (m, 1H), 7.44 (d, J=8.5 Hz, 2H), 7.34-7.26 (m, 0.5H), 7.16-7.03 (m, 2H), 7.03-6.96 (m, 2H), 6.92-6.86 (m, 0.5H), 6.00-5.91 (m, 1H), 5.19-5.04 (m, 2H), 4.37-4.17 (m, 3H), 3.79 (s, 3H), 3.31-3.29 (m, 1H), 3.21-3.13 (m, 1H), 2.14-1.85 (m, 4H).

Step 4. Synthesis of (R)-6-fluoro-1-(2-fluoro-4-hydroxyphenyl)-4-oxo-7-(2-((pyrimidin-2-yloxy) methyl)pyrrolidin-1-yl)-1,4-dihydroquinoline-3-carboxylic acid

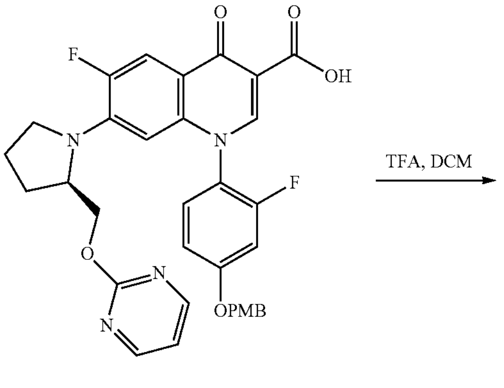

To a solution of (R)-6-fluoro-1-(2-fluoro-4-((4-methoxybenzyl)oxy)phenyl)-4-oxo-7-(2-((pyrimidin-2-yloxy) methyl)pyrrolidin-1-yl)-1,4-dihydroquinoline-3-carboxylic acid (30 mg, 0.05 mmol, 1.0 equiv) in DCM (2 mL) was added TFA (0.5 mL). The reaction was stirred at room temperature for 2 h. The solution concentrated under vacuum. The residue was purified by the prep-HPLC with the following conditions: Column: X Select CSH Prep C18 OBD Column, 5 um, 19*150 mm; Mobile Phase A: Water (0.05% FA), Mobile Phase B: acetonitrile; Flow rate: 25 mL/min; Gradient: 30 B to 55 B in 8 min; 254 nm. This resulted in (R)-6-fluoro-1-(2-fluoro-4-hydroxyphenyl)-4-oxo-7-(2-((pyrimidin-2-yloxy)methyl)pyrrolidin-1-yl)-1,4-dihydroquinoline-3-carboxylic acid (10.3 mg, 42.68%) as a yellow solid. LCMS (ESI) $[M+H]^+$: 495.30. $^1H$ NMR (400 MHz, DMSO-$d_6$) δ 15.29 (s, 1H), 10.62 (s, 1H), 8.60 (d, J=2.8 Hz, 1H), 8.52 (dd, J=4.8, 1.8 Hz, 2H), 7.88 (dd, J=14.5, 2.2 Hz, 1H), 7.60-7.50 (m, 1H), 7.17-7.08 (m, 4.8 Hz, 1H), 6.94-6.81 (m, 1H), 6.73-6.65 (m, 1H), 6.08-6.00 (m, 1H), 4.44 (s, 1H), 4.35-4.22 (m, 2H), 3.32-3.30 (m, 1H), 3.26-3.17 (m, 1H), 2.17-1.88 (m, 4H).

Potency Lin28a-dep Z11 $IC_{50}$ (μM)+++

Example 23: Synthesis of (R)-6-fluoro-1-(4-hydroxyphenyl)-7-(2-((5-methyl-6-oxopyridazin-1 (6H)-yl)methyl)pyrrolidin-1-yl)-4-oxo-1,4-dihydroquinoline-3-carboxylic acid

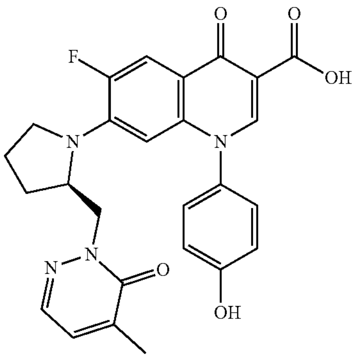 [SMILES: Cc1ccnn(C[C@H]2CCCN2c2cc3c(cc2F)c(=O)c(C(=O)O)cn3-c2ccc(O)cc2)c1=O]

Step 1. Synthesis of ethyl (R)-6-fluoro-7-(2-(hydroxymethyl)pyrrolidin-1-yl)-1-(4-((4-methoxybenzyl)oxy)phenyl)-4-oxo-1,4-dihydroquinoline-3-carboxylate

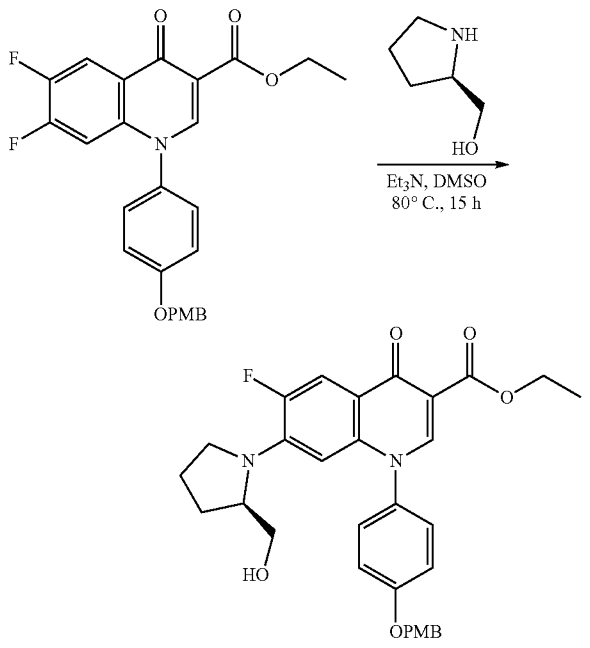

Into a 10-mL sealed tube, was placed ethyl 6,7-difluoro-1-(4-((4-methoxybenzyl)oxy)phenyl)-4-oxo-1,4-dihydroquinoline-3-carboxylate (820.0 mg, 1.762 mmol), DMSO (5.0 mL), $Et_3N$ (1782.7 mg, 17.617 mmol), (R)-pyrrolidin-2-ylmethanol (213.8 mg, 2.114 mmol). The resulting solution was stirred for 15 hour at 80° C. The residue was purified by reverse phase flash chromatography eluting with ACN/water (0%-70%, basic system). This resulted in 780 mg (81.00%) of ethyl (R)-6-fluoro-7-(2-(hydroxymethyl) pyrrolidin-1-yl)-1-(4-((4-methoxybenzyl)oxy)phenyl)-4-oxo-1,4-dihydroquinoline-3-carboxylate as a yellow solid. LCMS (ESI) $[M+H]^+$: 547.

Step 2. Synthesis of ethyl (R)-7-(2-(bromomethyl) pyrrolidin-1-yl)-6-fluoro-1-(4-((4-methoxybenzyl) oxy)phenyl)-4-oxo-1,4-dihydroquinoline-3-carboxylate

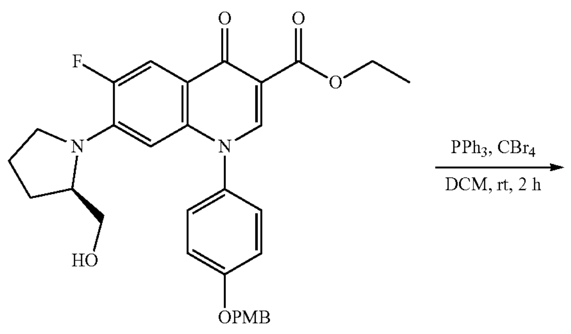

-continued

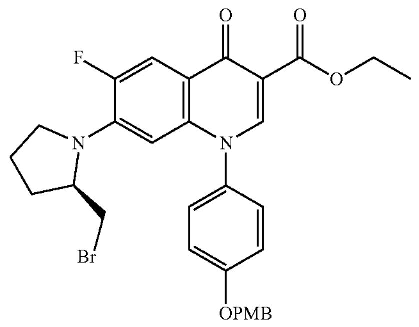

Into a 40-mL sealed tube, was placed ethyl (R)-6-fluoro-7-(2-(hydroxymethyl)pyrrolidin-1-yl)-1-(4-((4-methoxybenzyl)oxy)phenyl)-4-oxo-1,4-dihydroquinoline-3-carboxylate (500.0 mg, 0.915 mmol), DCM (10.0 mL), $PPh_3$ (719.8 mg, 2.744 mmol), $CBr_4$ (910.1 mg, 2.744 mmol). The resulting solution was stirred for 2 hours at 0° C. The resulting solution was extracted with 3×50 mL of dichloromethane. The organic phase was combined and concentrated under reduced pressure. The residue was applied onto a silica gel column eluting with ethyl acetate/petroleum ether (1:2). This resulted in 400 mg (71.74%, crude) of ethyl (R)-7-(2-(bromomethyl)pyrrolidin-1-yl)-6-fluoro-1-(4-((4-methoxybenzyl)oxy)phenyl)-4-oxo-1,4-dihydroquinoline-3-carboxylate as a brown solid. LCMS (ESI) $[M+H]^+$: 569.

Step 3. Synthesis of ethyl (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylate

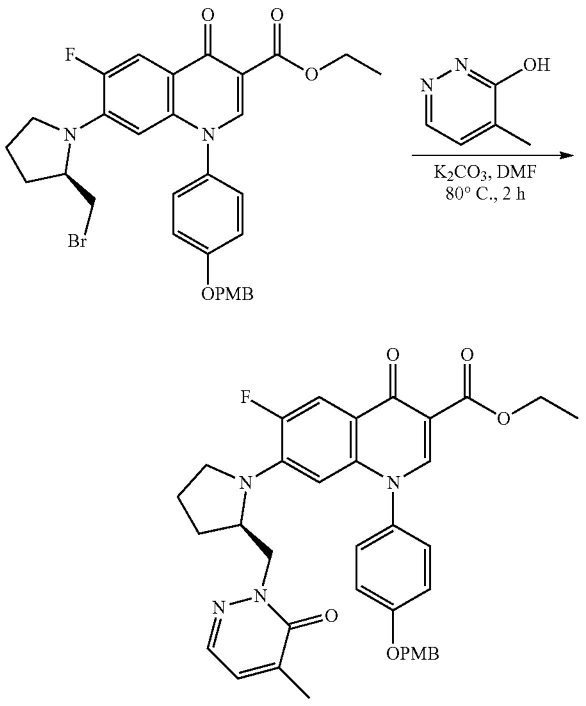

Into a 40-mL sealed tube, was placed ethyl (R)-7-(2-(bromomethyl)pyrrolidin-1-yl)-6-fluoro-1-(4-((4-methoxybenzyl)oxy)phenyl)-4-oxo-1,4-dihydroquinoline-3-carboxylate (300.0 mg, 0.492 mmol), DMF (10.0 mL), $K_2CO_3$ (204.1 mg, 1.477 mmol), 4-methylpyridazin-3-ol (54.2 mg, 0.492 mmol). The resulting solution was stirred for 2 hour at 80° C. The residue was purified by reverse phase flash chromatography eluting with ACN/water (0%-50%, basic system). This resulted in 200 mg (63.62%, crude) of ethyl (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylate as a yellow solid. LCMS (ESI) $[M+H]^+$: 639.

Step 4. Synthesis of (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylic acid

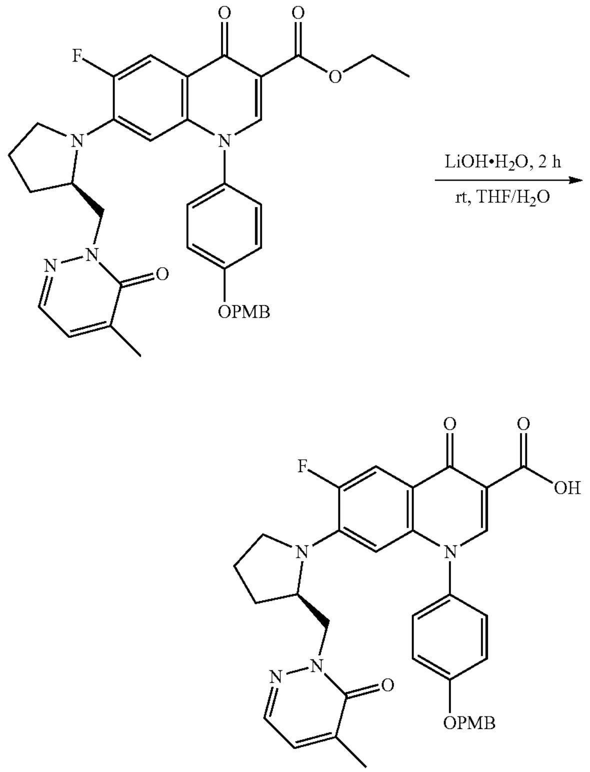

Into a 10-mL sealed tube, was placed ethyl (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylate (200.0 mg, 0.313 mmol), $LiOH{\cdot}H_2O$ (65.7 mg, 1.566 mmol), THF (4.0 mL), $H_2O$ (2.0 mL). The resulting solution was stirred for 2 hours at room temperature. The pH value of the solution was adjusted to 4-5 with AcOH. The solids were collected by filtration. This resulted in 160 mg (83.68%) of (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylic acid as a yellow solid. LCMS (ESI) $[M+H]^+$: 611.

Step 5. Synthesis of (R)-6-fluoro-1-(4-hydroxyphenyl)-7-(2-((5-methyl-6-oxopyridazin-1(6H)-yl)methyl)pyrrolidin-1-yl)-4-oxo-1,4-dihydroquinoline-3-carboxylic acid

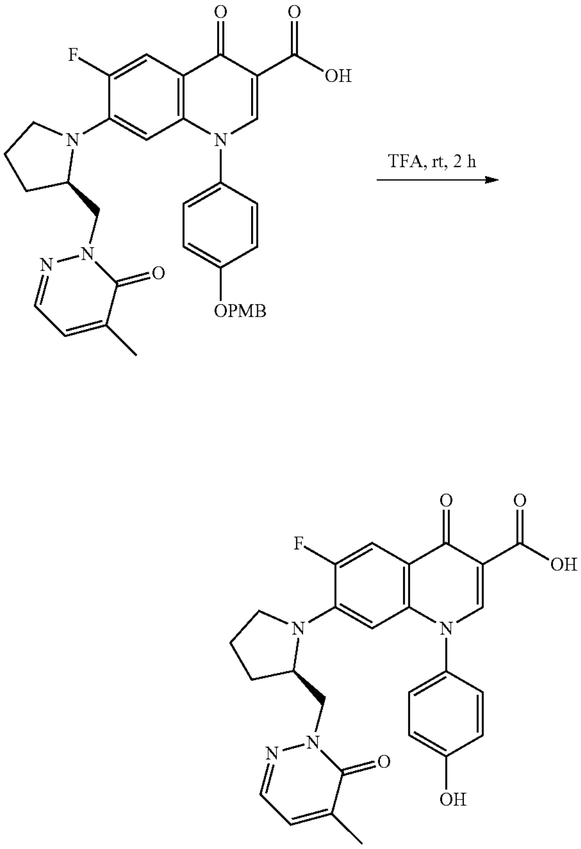

Into a 10-mL sealed tube, was placed (R)-6-fluoro-1-(4-((4-methoxybenzyl)oxy)phenyl)-7-(2-((5-methyl-6-oxopyridazin-1(6H)-yl)methyl)pyrrolidin-1-yl)-4-oxo-1,4-dihydroquinoline-3-carboxylic acid (80.0 mg, 0.131 mmol) and TFA (2.0 mL). The resulting solution was stirred for 2 hours at room temperature. The residue was purified by reverse phase flash chromatography eluting with ACN/water (0%-40%, basic system). This resulted in 20 mg (31.12%) of (R)-6-fluoro-1-(4-hydroxyphenyl)-7-(2-((5-methyl-6-oxopyridazin-1(6H)-yl)methyl)pyrrolidin-1-yl)-4-oxo-1,4-dihydroquinoline-3-carboxylic acid as a solid. LCMS (ESI) $[M+H]^+$: 491. $^1H$ NMR (300 MHz, DMSO-$d_6$) δ 15.42 (s, 1H), 10.17 (s, 1H), 8.45 (s, 1H), 7.80 (d, J=14.4 Hz, 1H), 7.66 (d, J=3.9 Hz, 1H), 7.45 (s, 2H), 7.20 (d, J=3.7 Hz, 1H), 7.00 (m, 2H), 6.31 (d, J=7.4 Hz, 1H), 4.38 (s, 1H), 4.27-4.07 (m, 1H), 3.96-3.72 (m, 1H), 3.52 (s, 1H), 3.28 (s, 1H), 2.00 (s, 3H), 1.92 (s, 3H), 1.76 (s, 1H).

Potency Lin28a-dep Z11 $IC_{50}$ (μM)++++

Example 24: Synthesis of (R)-6-chloro-1-(1-methylcyclopropyl)-4-oxo-7-(2-oxo-5-((pyridin-2-yloxy)methyl)pyrrolidin-1-yl)-1,4-dihydroquinoline-3-carboxylic acid

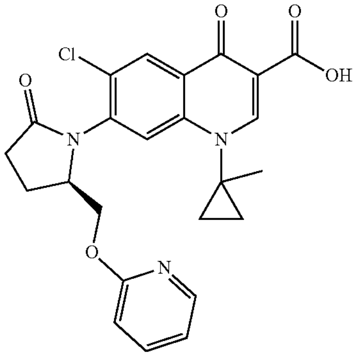 [SMILES: CC1(n2cc(C(=O)O)c(=O)c3cc(Cl)c(N4C(=O)CC[C@@H]4COc4ccccn4)cc32)CC1]

Step 1. Synthesis of (R)-5-((pyridin-2-yloxy)methyl)pyrrolidin-2-one

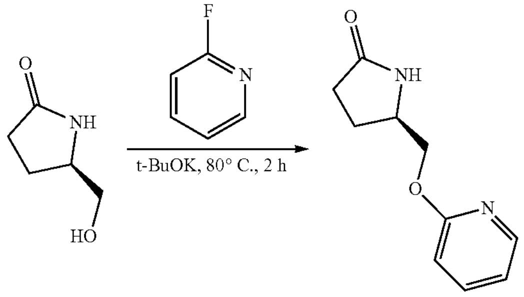

Under nitrogen, into a 40-mL sealed tube, was placed (R)-5-(hydroxymethyl)pyrrolidin-2-one (500.0 mg, 4.343 mmol), DMF (10.0 mL), 2-fluoropyridine (506.0 mg, 5.211 mmol), tert-butoxypotassium (1462.0 mg, 13.029 mmol). The resulting solution was stirred for 5 hour at 80° C. The residue was purified by reverse phase flash chromatography eluting with ACN/water (0%-40%, basic system). This resulted in 600 mg (71.9%) of (R)-5-((pyridin-2-yloxy)methyl)pyrrolidin-2-one as an off-white solid. LCMS (ESI) $[M+H]^+$: 193.

Step 2. Synthesis of (R)-6-chloro-1-(1-methylcyclopropyl)-4-oxo-7-(2-oxo-5-((pyridin-2-yloxy)methyl)pyrrolidin-1-yl)-1,4-dihydroquinoline-3-carboxylic acid

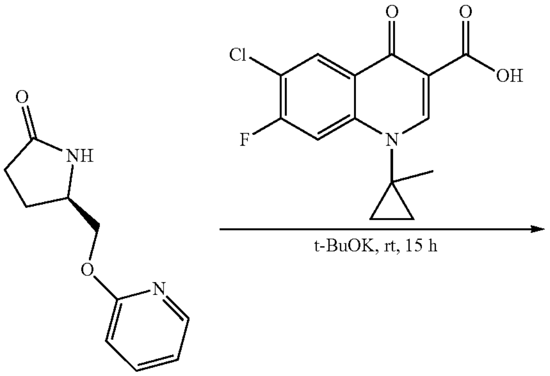

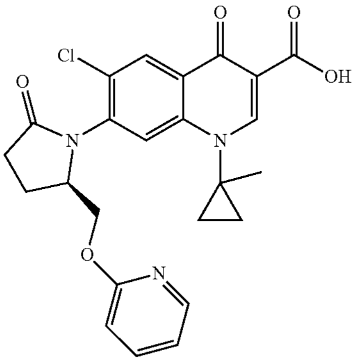

Under nitrogen, into a 10-mL sealed tube was placed 6-chloro-7-fluoro-1-(1-methylcyclopropyl)-4-oxo-1,4-dihydroquinoline-3-carboxylic acid (100.0 mg, 0.338 mmol), DMSO (3.0 mL), (R)-5-((pyridin-2-yloxy)methyl)pyrrolidin-2-one (78.0 mg, 0.406 mmol), tert-butoxypotassium (113.9 mg, 1.015 mmol). The resulting solution was stirred for 15 hour at room temperature. The residue was purified by reverse phase flash chromatography eluting with ACN/water (0%-50%, basic system). This resulted in 36.8 mg (23.26%) of (R)-6-chloro-1-(1-methylcyclopropyl)-4-oxo-7-(2-oxo-5-((pyridin-2-yloxy)methyl)pyrrolidin-1-yl)-1,4-dihydroquinoline-3-carboxylic acid as a white solid. LCMS (ESI) $[M+H]^+$: 468.2. $^1H$ NMR (300 MHz, DMSO-$d_6$) δ 14.66 (s, 1H), 8.86 (d, J=1.8 Hz, 1H), 8.40 (d, J=2.5 Hz, 1H), 8.29-8.05 (m, 2H), 7.56 (d, J=9.0 Hz, 1H), 6.92 (m, 1H), 6.46 (d, J=8.0 Hz, 1H), 4.71 (s, 1H), 4.54-4.19 (m, 2H), 2.82-2.55 (m, 3H), 2.12 (m, 1H), 1.42 (m, 4H), 1.22-0.90 (m, 3H).

Potency Lin28a-dep Z11 $IC_{50}$ (μM)+

Example 25: 6-fluoro-1-[3-(methoxymethyl) cyclobutyl]-4-oxo-7-[(2R)-2-[(pyridin-2-yloxy) methyl] pyrrolidin-1-yl]-1,4-dihydroquinoline-3-carboxylic acid

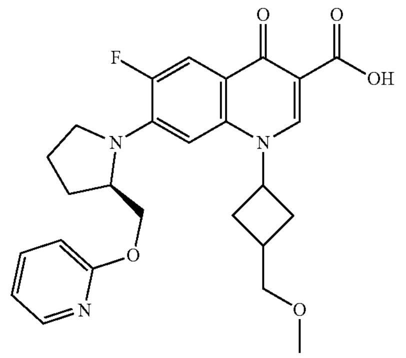 [SMILES: COCC1CC(n2cc(C(=O)O)c(=O)c3cc(F)c(N4CCC[C@@H]4COc4ccccn4)cc32)C1]

Step 1: Synthesis of N, N-dibenzyl-3-(methoxymethyl) cyclobutan-1-amine

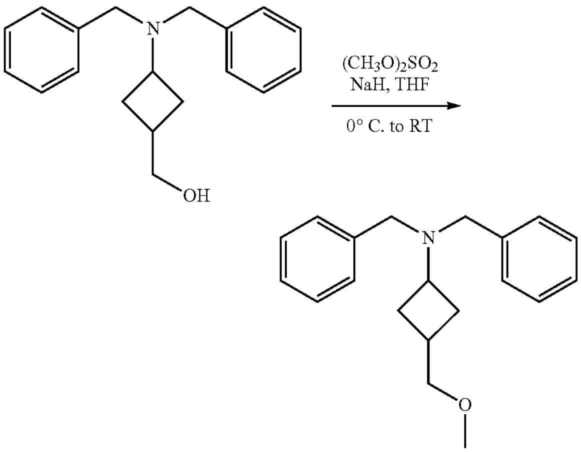

To a stirred suspension of sodium hydride (63.5 mg, 2.65 mmol) in THF (10 mL), was added [3-(dibenzylamino) cyclobutyl] methanol (500 mg, 1.77 mmol) at 0° C. and stirred for 30 min at same temperature before the addition of dimethyl sulfate (200 μL, 2.12 mmol). The reaction mixture was slowly warmed to room temperature and stirred for 2 h. The reaction mixture was quenched with ice cold saturated ammonium chloride solution and the product was extracted with EtOAc. The combined organic layer was dried over anhydrous sodium sulphate and evaporated under reduced pressure. The obtained crude material was purified by silica gel column chromatography using 10% EtOAc/hexane. The relevant fractions containing the product were combined and distilled under vaccum to N, N-dibenzyl-3-(methoxymethyl) cyclobutan-1-amine (300 mg, 56%) as a colorless liquid. MS (ESI) m/z: 296.5 $[M+H]^+$.

Step 2: Synthesis of 3-(methoxymethyl)cyclobutan-1-amine hydrochloride

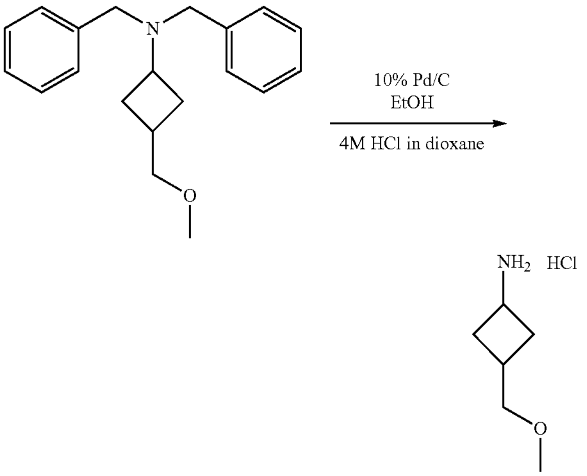

To a stirred solution of N, N-dibenzyl-3-(methoxymethyl) cyclobutan-1-amine (2.4 g, 8.12 mmol) in EtOH (30 mL), was added acetic acid (1 mL) followed by 10% Pd/C (864 mg, 8.12 mmol) under nitrogen atmosphere. The reaction mixture was hydrogenated under balloon pressure at room temperature for 16 h. The reaction mixture was filtered through celite pad and the filtrate was evaporated to afford crude. The crude was dissolved in dioxane and added 4M HCl in dioxane, stirred for 10 min. The volatiles were evaporated and the crude residue was triturated with diethyl ether, dried under vacuum to afford 3-(methoxymethyl) cyclobutan-1-amine hydrochloride (800 mg, 65%) as a colorless sticky gum which was taken forward for the next step without any purification.

Step 3: Synthesis of ethyl 6-fluoro-1-[3-(methoxymethyl)cyclobutyl]-4-oxo-7-[(2R)-2-[(pyridin-2-yloxy)methyl]pyrrolidin-1-yl]-1,4-dihydroquinoline-3-carboxylate

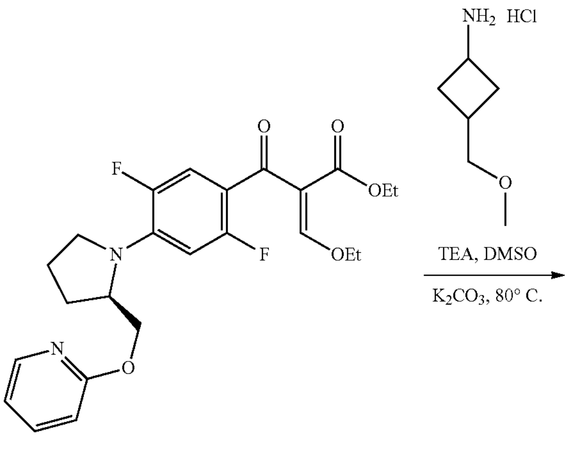

-continued

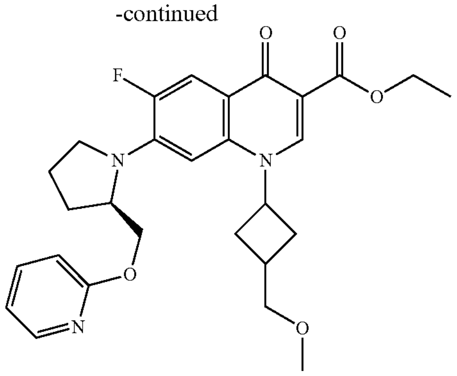

To a stirred solution of ethyl (R,Z)-2-(2,5-difluoro-4-(2-((pyridin-2-yloxy) methyl) pyrrolidin-1-yl) benzoyl)-3-ethoxyacrylate (300 mg, 0.652 mmol) in DMSO (3 mL), were added 3-(methoxymethyl) cyclobutan-1-amine hydrochloride (134 mg, 889 μmol), triethyl amine (0.18 ml, 1.78 mmol) then stirred for 1 h. Potassium carbonate (153 mg, 1.11 mmol) was added, the reaction mixture was heated to 80° C. and stirred for 2 h. After completion of reaction, the reaction mixture was cooled to room temperature and diluted with ice cold water. The precipitated solid was collected by filtration washed with water and dried under vacuum to afford ethyl 6-fluoro-1-[3-(methoxymethyl)cyclobutyl]-4-oxo-7-[(2R)-2-[(pyridin-2-yloxy) methyl]pyrrolidin-1-yl]-1,4-dihydroquinoline-3-carboxylate (77.7 mg, 20.6%) as an off white solid. MS (ESI) m/z: 510.2 $[M+H]^+$ Step 4: Synthesis of 6-fluoro-1-[3-(methoxymethyl) cyclobutyl]-4-oxo-7-[(2R)-2-[(pyridin-2-yloxy) methyl]pyrrolidin-1-yl]-1,4-dihydroquinoline-3-carboxylic acid

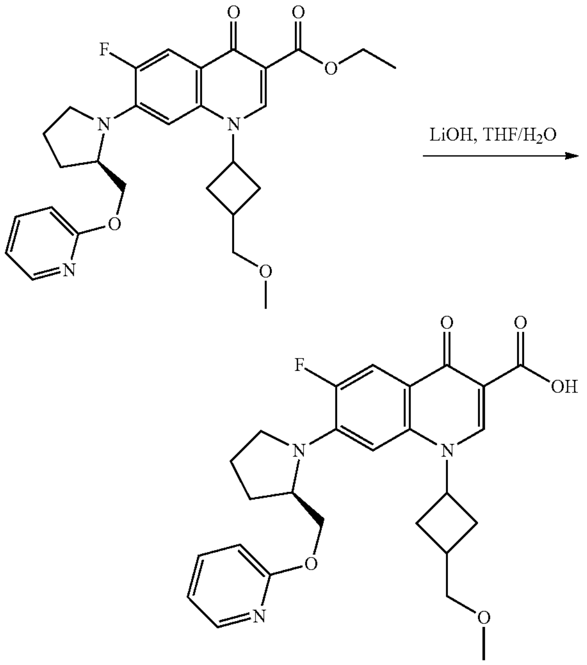

Experimental procedure as described above to obtain 6-fluoro-1-[3-(methoxymethyl) cyclobutyl]-4-oxo-7-[(2R)-2-[(pyridin-2-yloxy) methyl] pyrrolidin-1-yl]-1,4-dihydroquinoline-3-carboxylic acid (17.4 mg, 23%) as a pale brown solid.

$^1H$ NMR (400 MHz, DMSO-$d_6$) 15.55 (s, 1H), 8.53 (s, 1H), 8.08-8.05 (m, 1H), 7.84 (d, J=14.8 Hz, 1H), 7.69-7.65 (m, 1H), 6.96-6.93 (m, 1H), 6.81 (d, J=7.2 Hz, 1H), 6.72 (d, J=7.2 Hz, 1H), 5.00-4.92 (m, 1H), 4.72-4.64 (m, 1H), 4.45-4.38 (m, 1H), 4.31-4.22 (m, 1H), 3.80-3.70 (m, 1H), 3.54-3.46 (m, 1H), 3.34-3.28 (m, 2H), 3.24 (s, 3H), 2.77-2.67 (m, 2H), 2.43-2.30 (m, 1H), 2.25-1.95 (m, 6H), MS (ESI) m/z: 482.4 $[M+H]^+$.

Potency Lin28a-dep Z11 $IC_{50}$ (μM)++

Example 26: 6-chloro-7-[(2R)-2-{[(3-chloropyridin-2-yl) oxy] methyl} pyrrolidin-1-yl]-1-(6-methanesulfonamidopyridin-3-yl)-4-oxo-1,4-dihydroquinoline-3-carboxylic acid

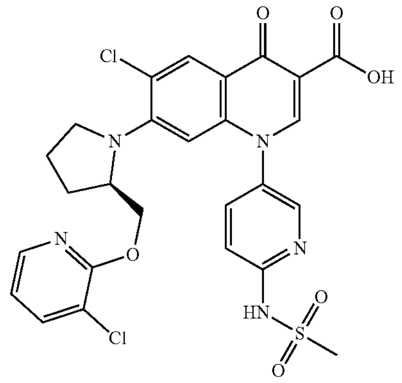 [SMILES: CS(=O)(=O)Nc1ccc(-n2cc(C(=O)O)c(=O)c3cc(Cl)c(N4CCC[C@@H]4COc4ncccc4Cl)cc32)cn1]

Step 1: Synthesis of ethyl 6-chloro-7-[(2R)-2-{[(3-chloropyridin-2-yl)oxy]methyl}pyrrolidin-1-yl]-1-[6-(N-methanesulfonylmethanesulfonamido)pyridin-3-yl]-4-oxo-1,4-dihydroquinoline-3-carboxylate

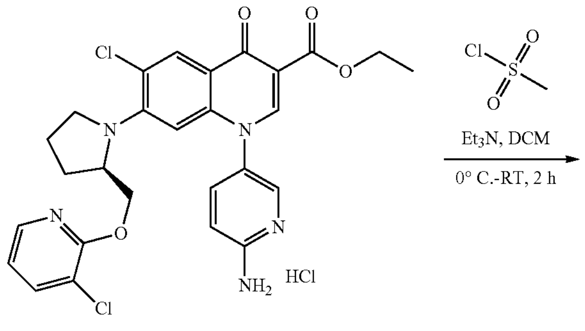

-continued

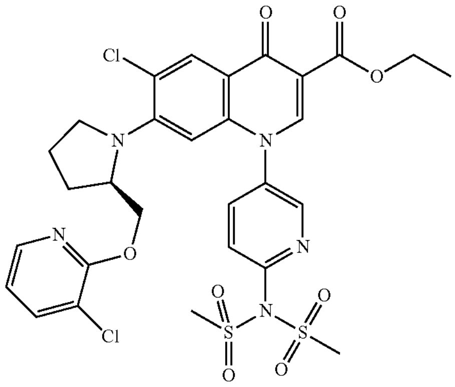

To a stirred solution of ethyl 1-(6-aminopyridin-3-yl)-6-chloro-7-[(2R)-2-{[(3-chloropyridin-2-yl) oxy] methyl} pyrrolidin-1-yl]-4-oxo-1,4-dihydroquinoline-3-carboxylate hydrochloride (180 mg, 0.304 mmol) in DCM (5 mL), was added triethylamine (0.13 mL, 0.914 mmol) and cooled to 0° C. before the addition of methane sulfonyl chloride (0.03 mL, 0.365 mmol). The reaction mixture was slowly warmed to room temperature and stirred for 2 h at room temperature. The reaction mixture was quenched with water and the product was extracted with DCM (2×10 mL). The combined organic layers were dried over anhydrous sodium sulphate and evaporated to afford ethyl 6-chloro-7-[(2R)-2-{[(3-chloropyridin-2-yl) oxy] methyl} pyrrolidin-1-yl]-1-[6-(N-methanesulfonylmethanesulfonamido) pyridin-3-yl]-4-oxo-1,4-dihydroquinoline-3-carboxylate (200 mg, crude) as a pale brown solid. MS (ESI) m/z: 710.2 $[M+H]^+$.

Step 2. Synthesis of 6-chloro-7-[(2R)-2-{[(3-chloropyridin-2-yl)oxy]methyl}pyrrolidin-1-yl]-1-(6-methanesulfonamidopyridin-3-yl)-4-oxo-1,4-dihydroquinoline-3-carboxylic acid

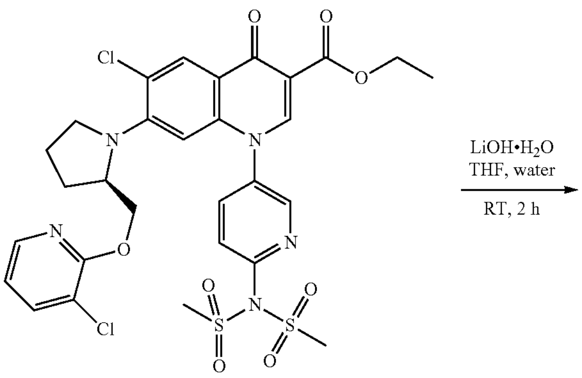

-continued

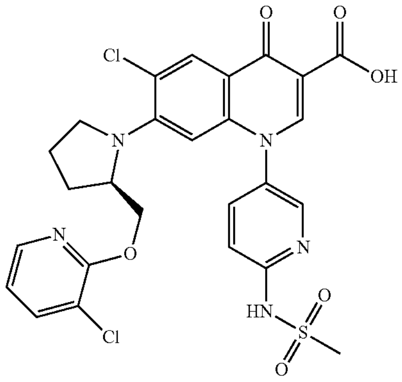

Experimental procedure as described above to obtain 6-chloro-7-[(2R)-2-{[(3-chloropyridin-2-yl) oxy] methyl}-pyrrolidin-1-yl]-1-(6-methanesulfonamidopyridin-3-yl)-4-oxo-1,4-dihydroquinoline-3-carboxylic acid (20 mg, 12%) as an off white solid. $^1$H NMR (400 MHz, DMSO-$d_6$) 15.03 (brs, 1H), 11.15 (s, 1H), 8.64 (d, J=8.4 Hz, 1H), 8.54 (t, J=6.4 Hz, 1H), 8.17 (s, 1H), 8.02-7.95 (m, 1H), 7.90-7.89 (dd, J=5.2, 1.6 Hz, 1H), 7.79 (d, J=5.6 Hz, 1H), 7.19-7.03 (m, 1H), 6.94 (dd, J=7.6, 5.2 Hz, 1H), 6.37 (s, 1H), 4.78 (s, 1H), 4.34-4.25 (m, 2H), 3.51-3.47 (m, 1H), 3.40 (s, 3H), 3.19-3.18 (m, 1H), 2.34-2.24 (m, 1H), 1.99-1.91 (m, 2H), 1.85-1.78 (m, 1H), MS (ESI) m/z: 604.2 $[M+H]^+$.

Potency Lin28a-dep Z11 $IC_{50}$ (μM)++++

Example 27: Synthesis of (R)-6-fluoro-1-(6-hydroxypyrazin-2-yl)-4-oxo-7-(2-((pyridin-2-yloxy) methyl) pyrrolidin-1-yl)-1,4-dihydroquinoline-3-carboxylic acid

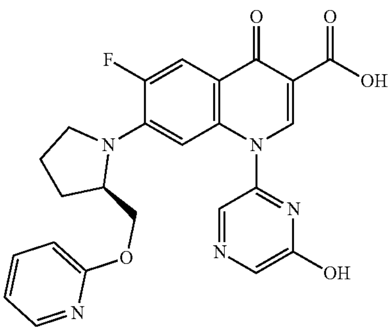 [SMILES: O=C(O)c1cn(-c2cncc(O)n2)c2cc(N3CCC[C@@H]3COc3ccccn3)c(F)cc2c1=O]

Step 1: Synthesis of ethyl 6-fluoro-1-(6-hydroxypyrazin-2-yl)-4-oxo-7-[(2R)-2-[(pyridin-2-yloxy) methyl] pyrrolidin-1-yl]-1,4-dihydroquinoline-3-carboxylate

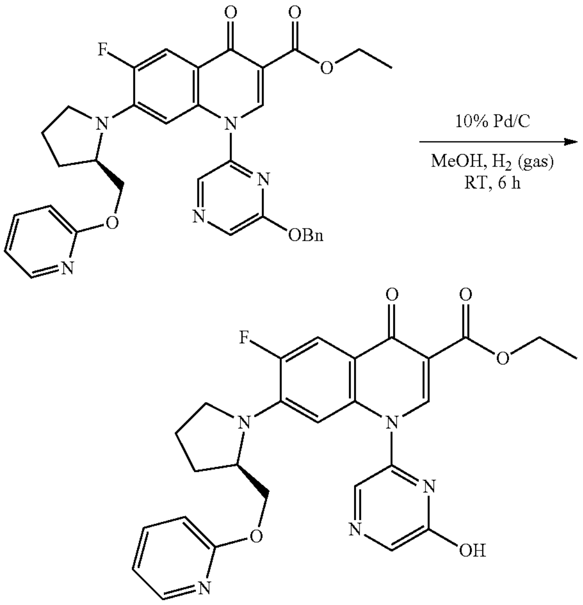

To a stirred solution of ethyl 1-[6-(benzyloxy) pyrazin-2-yl]-6-fluoro-4-oxo-7-[(2R)-2-[(pyridin-2-yloxy) methyl] pyrrolidin-1-yl]-1,4-dihydroquinoline-3-carboxylate (300 mg, 503 μmol) in MeOH (10 mL), was added 10% Pd/C (106 mg, 1.00 mmol) under nitrogen atmosphere. The reaction mixture was subjected to hydrogenation (under hydrogen, balloon pressure) at room temperature for 6 h. The reaction mixture was filtered through a pad of celite, washed the celite pad with 10% MeOH in DCM (100 mL). The combined filtrate was concentrated under reduced pressure to afford ethyl 6-fluoro-1-(6-hydroxypyrazin-2-yl)-4-oxo-7-[(2R)-2-[(pyridin-2-yloxy) methyl] pyrrolidin-1-yl]-1,4-dihydroquinoline-3-carboxylate (140 mg, 55.1%) as an off white solid. MS (ESI) m/z: 506.1 [M+H]$^+$ Step 2: Synthesis of 6-fluoro-1-(6-hydroxypyrazin-2-yl)-4-oxo-7-[(2R)-2-[(pyridin-2-yloxy) methyl] pyrrolidin-1-yl]-1,4-dihydroquinoline-3-carboxylic acid

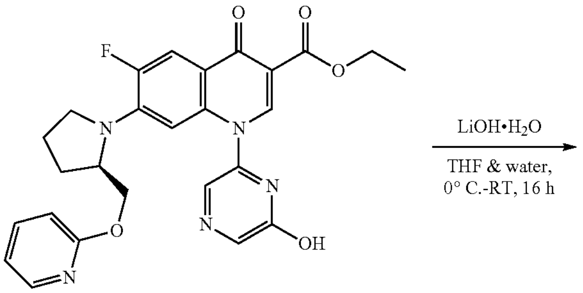

-continued

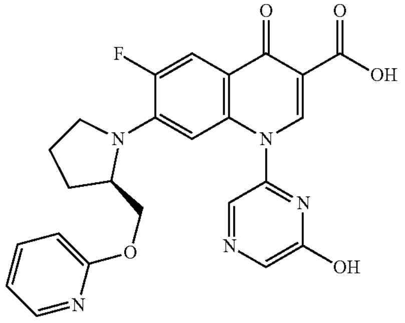

To a stirred solution of ethyl 6-fluoro-1-(6-hydroxypyrazin-2-yl)-4-oxo-7-[(2R)-2-[(pyridin-2-yloxy) methyl] pyrrolidin-1-yl]-1,4-dihydroquinoline-3-carboxylate (150 mg, 296 μmol) in THF (5 mL) and water (1 mL) was cooled to 0° C., was added LiOH·$H_2$O (62.1 mg, 1.48 mmol) and the reaction mixture was slowly warmed to room temperature and stirred for 16 h. The excess solvents were distilled under reduced pressure. The obtained residue was diluted with water and acidified with 1N HCl to pH 3-4 and the product was extracted with 10% MeOH in DCM. The combined organic layer was dried over anhydrous Na2SO4, filtered and evaporated under reduced pressure. The crude material obtained was triturated with IPA and ether (1:1 ratio, 50 mL) and dried under vacuum to afford 6-fluoro-1-(6-hydroxypyrazin-2-yl)-4-oxo-7-[(2R)-2-[(pyridin-2-yloxy) methyl] pyrrolidin-1-yl]-1,4-dihydroquinoline-3-carboxylic acid (58.1 mg, 41.2%) as pale green solid. $^1$H NMR (400 MHz, DMSO-$d_6$): δ 15.20 (s, 1H), 12.80 (brs, 1H), 8.81 (s, 1H), 8.41 (brs, 1H), 8.25 (brs, 1H), 8.01-7.99 (m, 1H), 7.88 (d, J=14.8 Hz, 1H), 7.67-7.63 (m, 1H), 6.94-6.91 (m, 1H), 6.66 (d, J=8.0 Hz, 1H), 6.48 (d, J=7.6 Hz, 1H), 4.52-4.48 (m, 1H), 4.27-4.19 (m, 2H), 3.47-3.42 (m, 1H), 3.16 (brs, 1H), 2.09-1.89 (m, 4H), MS: 478.3 [M+H]$^+$ Potency Lin28a-dep Z11 $IC_{50}$ (μM)+++

Example 28: Synthesis of (R)-1-(6-(3-aminoazetidin-1-yl) pyridin-3-yl)-6-chloro-7-(2-(((3-chloropyridin-2-yl) oxy) methyl) pyrrolidin-1-yl)-4-oxo-1,4-dihydroquinoline-3-carboxylic acid

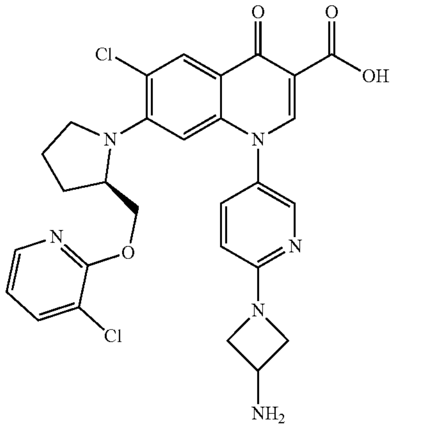 [SMILES: NC1CN(c2ccc(-n3cc(C(=O)O)c(=O)c4cc(Cl)c(N5CCC[C@@H]5COc5ncccc5Cl)cc43)cn2)C1]

Step 1: Synthesis of tert-butyl (1-(5-nitropyridin-2-yl) azetidin-3-yl) carbamate

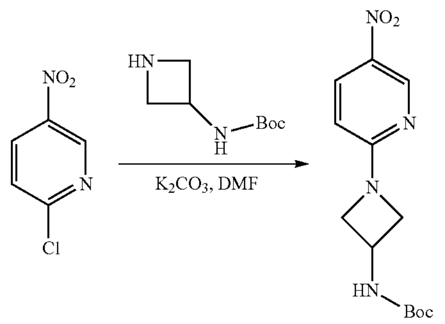 [SMILES: O=[N+]([O-])c1ccc(Cl)nc1 ; CC(C)(C)OC(=O)NC1CNC1 ; CC(C)(C)OC(=O)NC1CN(c2ccc([N+](=O)[O-])cn2)C1]

To a stirred solution of 2-chloro-5-nitropyridine (1 g, 6.30 mmol) in ACN (10 mL) at 0° C., were added tert-butyl N-(azetidin-3-yl)carbamate (1.30 g, 7.56 mmol) and potassium carbonate (1.74 g, 12.6 mmol). The reaction mixture was heated to 80° C. and stirred for 16 h. The reaction mixture was cooled to room temperature, ice-cold water was added and the product was extracted with ethyl acetate. The combined organic layers were dried over $Na_2SO_4$ and concentrated under reduced pressure. The resulting crude material was purified by column chromatography (eluted in 20-25% EtOAc in Hexane). The relevant fractions containing the product were combined and evaporated to dryness under reduced pressure to afford tert-butyl (1-(5-nitropyridin-2-yl) azetidin-3-yl) carbamate (800 mg, 44%) as a yellow solid, MS (ESI) m/z: 294.9 $[M+H]^+$ Step 2: Synthesis of (tert-butyl (1-(5-aminopyridin-2-yl)azetidin-3-yl)carbamate)

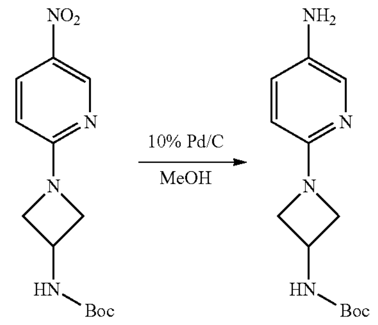 [SMILES: "MeOH" ; CC(C)(C)OC(=O)NC1CN(c2ccc([N+](=O)[O-])cn2)C1 ; CC(C)(C)OC(=O)NC1CN(c2ccc(N)cn2)C1]

To a stirred solution of tert-butyl N-[1-(5-nitropyridin-2-yl) azetidin-3-yl] carbamate (800 mg, 2.71 mmol) in MeOH (20 mL), was added Pd/C (433 mg, 2.71 mmol) at room temperature under nitrogen atmosphere. The reaction mixture was hydrogenated using $H_2$ balloon for a period of 6 h. After completion of reaction, the reaction mixture was filtered through a celite pad, the celite pad was further washed with MeOH and the filtrate was concentrated under reduced pressure to afford tert-butyl N-[1-(5-aminopyridin-2-yl) azetidin-3-yl] carbamate (600 mg, 85%) as a brown liquid and taken forward without purification.

Step 3: Synthesis of ethyl (R)-1-(6-(3-((tert-butoxycarbonyl)amino)azetidin-1-yl)pyridin-3-yl)-6-chloro-7-(2-(((3-chloropyridin-2-yl)oxy)methyl)pyrrolidin-1-yl)-4-oxo-1,4-dihydroquinoline-3-carboxylate

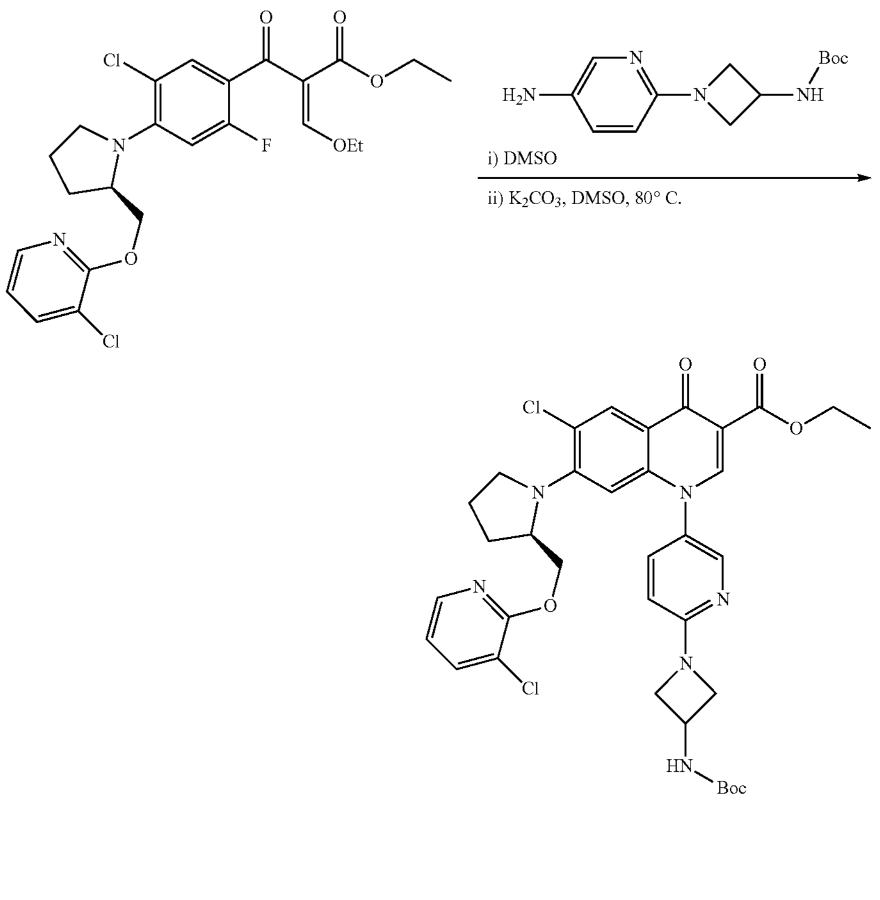

To a stirred solution of ethyl (2Z)-2-[(Z)-5-chloro-4-[(2R)-2-{[(3-chloropyridin-2-yl) oxy] methyl}pyrrolidin-1-yl]-2-fluorobenzoyl]-3-ethoxyprop-2-enoate (400 mg, 782 μmol) in DMSO (3 mL), was added tert-butyl N-[1-(5-aminopyridin-2-yl) azetidin-3-yl] carbamate (399 mg, 1.51 mmol) at room temperature and stirred at room temperature for 2 h. Then, potassium carbonate (161 mg, 1.25 mmol) was added to reaction mixture at same temperature, the mixture was heated to 80° C. and stirred for 6 h. The reaction mixture was cooled to room temperature and ice-cold water was added, the precipitated solid was collected by filtration, washed with water and dried. The resulting material was treated with charcoal in ethyl acetate and stirred for 10 mins, filtered through celite pad and washed the celite pad with EtOAc. The combined filtrate was concentrated under reduced pressure to afford ethyl 1-[16-(3-{[(tert-butoxy) carbonyl]amino}azetidin-1-yl)pyridin-3-yl]-6-chloro-7-[(2R)-2-{[(3-chloropyridin-2-yl)oxy]methyl}pyrrolidin-1-yl]-4-oxo-1,4-dihydroquinoline-3-carboxylate as a brown solid (280 mg, 50%), MS (ESI) m/z: 709.3 [M+H]$^+$ Step 4: Synthesis of (R)-1-(6-(3-((tert-butoxycarbonyl)amino)azetidin-1-yl)pyridin-3-yl)-6-chloro-7-(2-(((3-chloropyridin-2-yl)oxy)methyl)pyrrolidin-1-yl)-4-oxo-1,4-dihydroquinoline-3-carboxylic acid

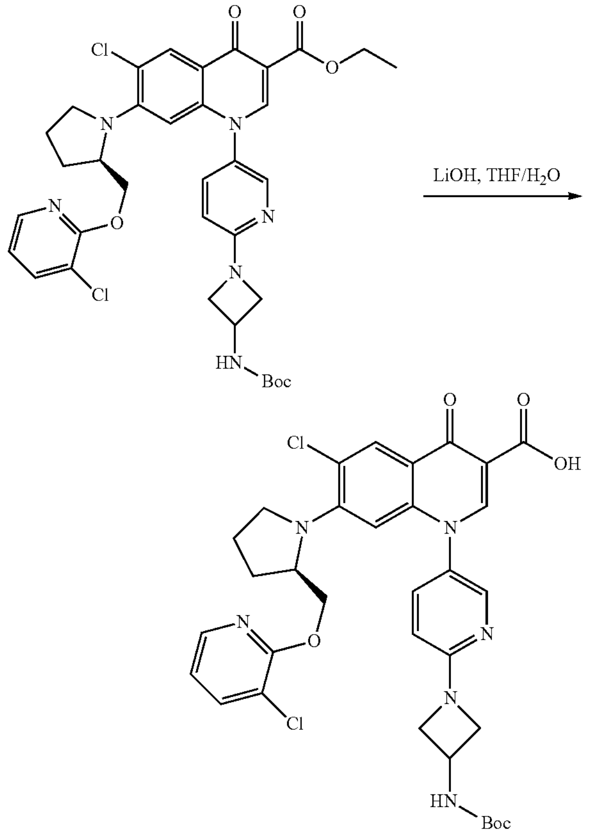

To a stirred solution of ethyl 1-[6-(3-{[(tert-butoxy) carbonyl] amino} azetidin-1-yl) pyridin-3-yl]-6-chloro-7-[(2R)-2-{[3-chloropyridin-2-yl) oxy] methyl} pyrrolidin-1-yl]-4-oxo-1,4-dihydroquinoline-3-carboxylate (250 mg, 352 μmol) in THF (2 mL) and water (2 mL), was added LiOH·H$_2$O (41.9 mg, 1.75 mmol) at 0° C. The reaction mixture was slowly warmed to room temperature and stirred for 4 h. The excess solvents were removed under reduced pressure, the resulting crude material was diluted with water (5 mL) and acidified with 1N HCl. The precipitated solid was collected by filtration, washed with water and dried under vacuum to afford 1-[6-(3-{[(tert-butoxy)carbonyl] amino}azetidin-1-yl)pyridin-3-yl]-6-chloro-7-[(2R)-2-{[(3-chloropyridin-2-yl)oxy]methyl}pyrrolidin-1-yl]-4-oxo-1,4-dihydroquinoline-3-carboxylic acid (200 mg, 74%) as brown solid, MS m/z: 681.2 [M+H]$^+$ Step 5: Synthesis of (R)-1-(6-(3-aminoazetidin-1-yl) pyridin-3-yl)-6-chloro-7-(2-(((3-chloropyridin-2-yl) oxy)methyl)pyrrolidin-1-yl)-4-oxo-1,4-dihydroquinoline-3-carboxylic acid

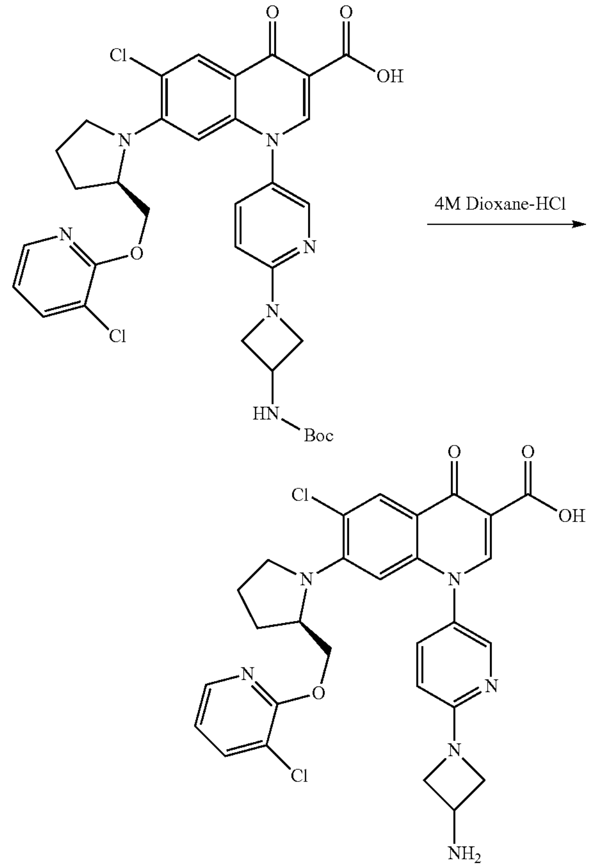

4M HCl in Dioxane (2 mL) was added to a stirred solution of 1-[6-(3-{[(tert-butoxy) carbonyl]amino} azetidin-1-yl) pyridin-3-yl]-6-chloro-7-[(2R)-2-{[(3-chloropyridin-2yl) oxy] methyl}pyrrolidin-1-yl]-4-oxo-1,4-dihydroquinoline-3-carboxylic acid (200 mg, 366 μmol) at 0° C. The reaction mixture was slowly warmed to room temperature and stirred for 6 h. The solvents were removed under reduced pressure and purified the crude material by prep-HPLC. The fractions were lyophilized to afford 1-[6-(3-aminoazetidin-1-yl) pyridin-3-yl]-6-chloro-7-[(2R)-2-{[(3-chloropyridin-2-yl) oxy] methyl} pyrrolidin-1-yl]-4-oxo-1,4-dihydroquinoline-3-carboxylic acid. (50.0 mg, 29%) as an off white solid.

$^1$H-NMR (400 MHz, DMSO-d$_6$): δ 8.48 (d, J=8.0 Hz, 1H), 8.24 (d, J=2.4 Hz, 1H), 8.15 (s, 1H), 7.89-7.90 (m, 1H), 7.81 (dd, J=8.0, 1.60 Hz, 1H), 7.71-7.64 (m, 1H), 6.96-6.91

(m, 1H), 6.58-6.33 (m, 2H), 4.76-4.66 (m, 1H), 4.36-4.19 (m, 4H), 3.99-3.93 (m, 1H), 3.76-3.72 (m, 2H), 3.57-3.47 (m, 1H), 3.21-3.17 (m, 1H), 2.26-2.24 (m, 1H), 1.98-1.90 (m, 2H), 1.81-1.78 (m, 1H). (COOH & NH2 Protons not observed) MS m/z: 581.3 $[M+H]^+$.

Potency Lin28a-dep Z11 $IC_{50}$ (μM)++++

Example 29: Synthesis of (R)-1-cyclopropyl-6,8-difluoro-4-oxo-7-(2-((pyridazin-3-yloxy)methyl) pyrrolidin-1-yl)-1,4-dihydroquinoline-3-carboxylic acid

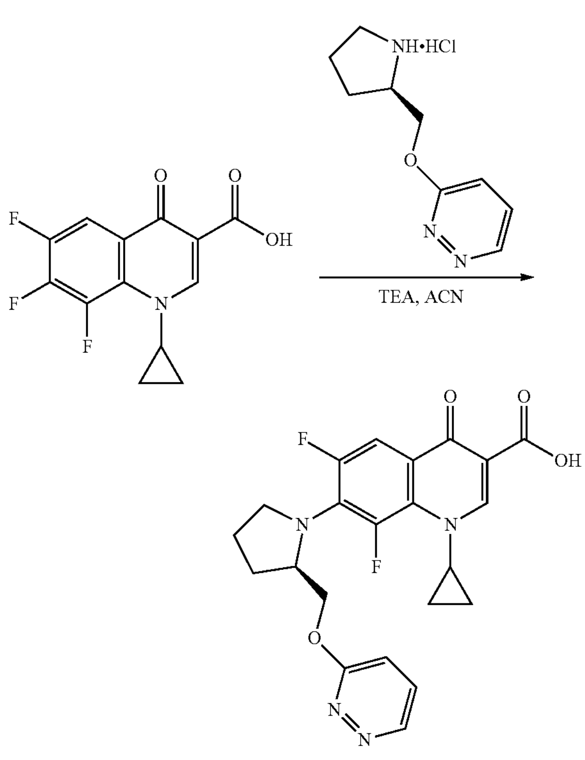

To a stirred solution of 3-{[(2R)-pyrrolidin-2-yl] methoxy} pyridazine hydrochloride (200 mg, 927 μmol) in DMSO (4 mL), were added triethylamine (233 mg, 2.31 mmol) followed by 1-cyclopropyl-6,7,8-trifluoro-4-oxo-1,4-dihydroquinoline-3-carboxylic acid (131 mg, 463 μmol) at room temperature. The reaction mixture was stirred at 100° C. for 16 h. Then, was cooled to room temperature, water (10 ml) was added and the product was extracted with EtOAc (2×20 mL). The combined organic layers were washed with $H_2O$ (15 mL), followed by brine solution (15 mL), dried over anhydrous sodium sulfate and concentrated under reduced pressure. The crude product was subjected to silica gel chromatography (100-200 mesh) and eluted the column by using 5-10% MeOH/DCM. The relevant fractions containing the product were combined and evaporated to dryness to afford 1-cyclopropyl-6,8-difluoro-4-oxo-7-[(2R)-2-[(pyridazin-3-yloxy) methyl] pyrrolidin-1-yl]-1,4-dihydroquinoline-3-carboxylic acid (7.71 mg, 2%) as pale-yellow solid. $^1H$ NMR (400 MHz, DMSO-$d_6$): δ 14.89 (s, 1H), 8.80 (dd, J=4.4, 1.2 Hz, 1H), 8.63 (s, 1H), 7.71 (dd, J=12.8, 1.2 Hz, 1H), 7.49 (dd, J=8.8, 1.2 Hz, 1H), 6.90 (dd, J=8.8, 1.2 Hz, 1H), 4.67 (brs, 1H), 4.56-4.54 (m, 1H), 4.49-4.47 (m, 1H), 4.10-4.02 (m, 1H), 3.90-3.82 (m, 1H), 3.50-3.40 (m, 1H), 2.38-2.28 (m, 1H), 2.10-2.00 (m, 1H), 1.92-1.82 (m, 2H), 1.18-1.11 (m, 4H), MS (ESI) m/z: 443.3 $[M+H]^+$ Potency Lin28a-dep Z11 $IC_{50}$ (μM)+++

Example 30: Synthesis of 3 (R)-6-fluoro-1-(3-methoxycyclobutyl)-7-(2-(((3-methylpyridin-2-yl) oxy)methyl)pyrrolidin-1-yl)-4-oxo-1,4-dihydroquinoline-3-carboxylic acid

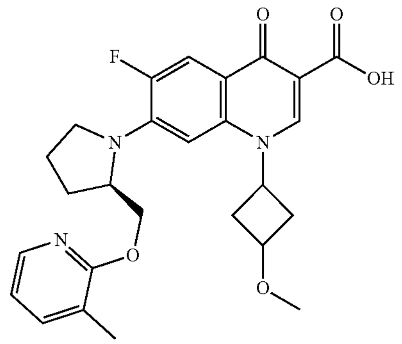 [SMILES: COC1CC(n2cc(C(=O)O)c(=O)c3cc(F)c(N4CCC[C@@H]4COc4ncccc4C)cc32)C1]

Step 1: Synthesis of ethyl (2Z)-2-[(Z)-2,5-difluoro-4-[(2R)-2-{[(3-methylpyridin-2-yl) oxy]methyl} pyrrolidin-1-yl] benzoyl]-3-(dimethylamino) prop-2-enoate

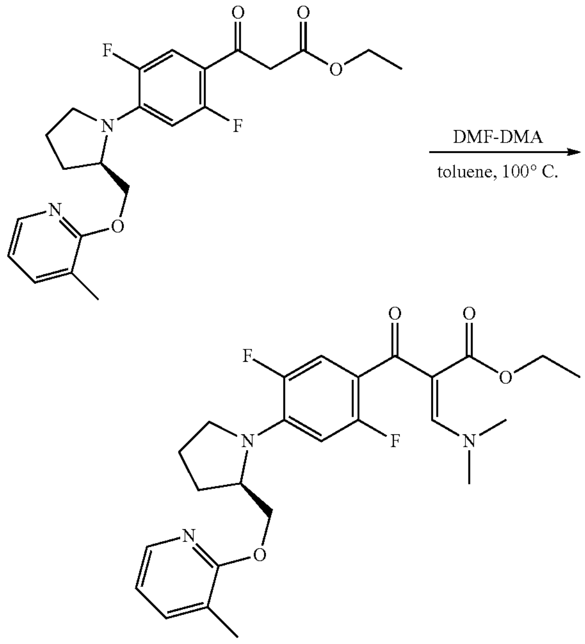

To a stirred solution of ethyl 3-{2,5-difluoro-4-[(2R)-2-{[(3-methylpyridin-2-yl) oxy] methyl}pyrrolidin-1-yl] phenyl}-3-oxopropanoate (300 mg, 716 μmol) in toluene (5 mL), was added (dimethoxy methyl) dimethylamine (85.3 mg, 716 μmol), the reaction mixture heated to 80° C. and stirred for 6 h. The reaction mixture was cooled to RT, solvents were evaporated and the obtained residue was azeotroped with toluene (10 mL) to afford ethyl (2Z)-2-[(Z)-2,5-difluoro-4-[(2R)-2-{[(3-methylpyridin-2-yl) oxy] methyl} pyrrolidin-1-yl] benzoyl]-3-(dimethylamino) prop-2-enoate (248 mg, crude) as brown liquid. The material was used for next step without further purification. MS (ESI) 474.1 $[M+H]^+$.

Step 2: Synthesis of (R)-ethyl 6-fluoro-1-(3-methoxycyclobutyl)-7-(2-(((3-methylpyridin-2-yl) oxy)methyl)pyrrolidin-1-yl)-4-oxo-1,4-dihydroquinoline-3-carboxylate

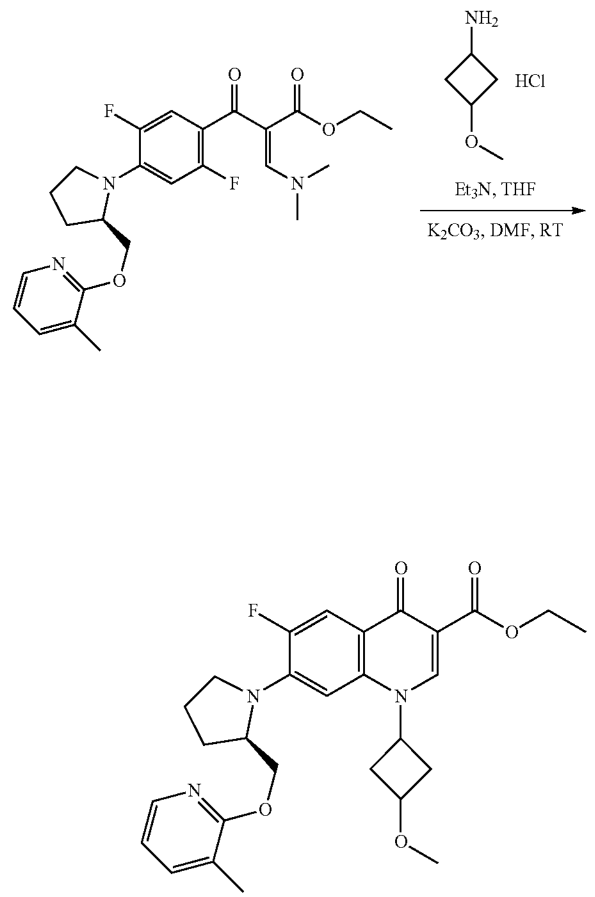

To a stirred solution of ethyl (2Z)-2-[(Z)-2,5-difluoro-4-[(2R)-2-{[(3-methylpyridin-2-yl) oxy]methyl} pyrrolidin-1-yl] benzoyl]-3-(dimethylamino) prop-2-enoate (250 mg, 527 μmol) in THF (5 mL), was added 3-methoxycyclobutan-1-amine hydrochloride (86.9 mg, 632 μmol) and triethylamine (95.5 μL, 685 μmol). The reaction mixture was stirred at room temperature for 6 h. After completion of reaction, solvents were removed under reduced pressure. The obtained crude material was dissolved in DMF (5 mL), potassium carbonate (72.8 mg, 527 μmol) was added and the reaction mixture was heated to 85° C., stirred for 2 h. The reaction mixture was cooled, ice-cold water (10 mL) was added and the product was extracted with Ethyl acetate (2×30 mL). The combined organic layers were washed with brine solution (15 mL), dried over sodium sulfate and evaporated to afford crude product. The crude product was purified by silica gel column chromatography (100-200 mesh) using 45-50% EtOAc/Hexanes. The relevant fractions containing the product were combined and distilled under reduced pressure to afford ethyl 6-fluoro-1-(3-methoxycyclobutyl)-7-[(2R)-2-{[(3-methylpyridin-2-yl) oxy] methyl} pyrrolidin-1-yl]-4-oxo-1,4-dihydroquinoline-3-carboxylate (163 mg, 61%) as brown solid. MS (ESI) 510.2 $[M+H]^+$.

Step 3: Synthesis of (R)-6-fluoro-1-(3-methoxycyclobutyl)-7-(2-(((3-methylpyridin-2-yl)oxy)methyl) pyrrolidin-1-yl)-4-oxo-1,4-dihydroquinoline-3-carboxylic acid

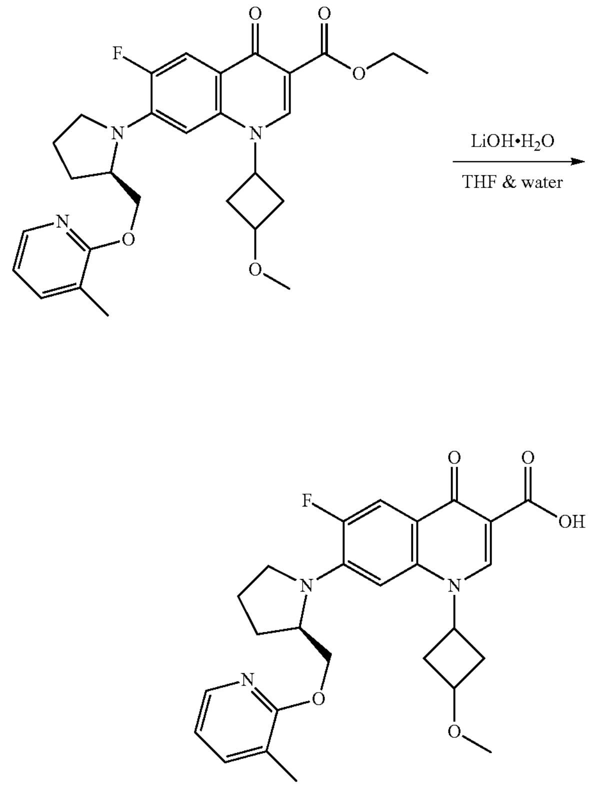

To a stirred solution of ethyl 6-fluoro-1-(3-methoxycyclobutyl)-7-[(2R)-2-{[(3-methylpyridin-2-yl) oxy] methyl} pyrrolidin-1-yl]-4-oxo-1,4-dihydroquinoline-3-carboxylate (115 mg, 225 μmol) in THF:Water (1:1, 6 mL), was added $LiOH \cdot H_2O$ (28.3 mg, 675 μmol) at 0° C. and the reaction mixture was stirred at room temperature for 6 h. The reaction mixture was re-cooled to 0° C. and pH was adjusted to 2-3 by using 1N HCl, the precipitated solid was filtered, washed with 10% IPA in diethyl ether and dried under vacuum. Further the solid material was lyophilized using ACN/water to afford 6-fluoro-1-(3-methoxycyclobutyl)-7-[(2R)-2-{[(3-methylpyridin-2-yl)oxy]methyl}pyrrolidin-1-yl]-4-oxo-1,4-dihydroquinoline-3-carboxylic acid (50.8 mg 47%) as pale brown solid. $^1H$ NMR (400 MHz, DMSO-$d_6$): δ 15.52 (s, 1H), 8.52 (s, 1H), 7.89 (d, J=4.0 Hz, 1H), 7.83 (d, J=14.8 Hz, 1H), 7.48 (d, J=6.4 Hz, 1H), 6.86-6.83 (m, 1H), 6.78 (d, J=7.2 Hz, 1H), 4.73-4.68 (m, 2H), 4.40-4.37 (m, 1H), 4.32-4.28 (m, 1H), 3.83-3.76 (m, 2H), 3.59-3.50 (m, 1H), 3.18 (s, 3H), 3.12-3.03 (m, 2H), 2.32-2.12 (m, 4H), 2.10-2.03 (m, 2H), 2.01 (s, 3H). MS (ESI) m/z: 482.4 $[M+H]^+$.

Potency Lin28a-dep Z11 $IC_{50}$ (μM)++++

Example 31: (R)-6-chloro-7-(2-(((3-chloropyridin-2-yl) oxy)methyl)pyrrolidin-1-yl)-1-(4-(ethylsulfonamido)phenyl)-4-oxo-1,4-dihydroquinoline-3-carboxylic acid

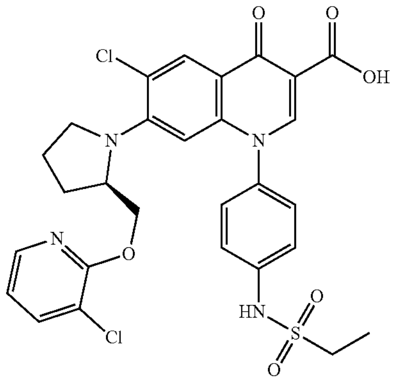 [SMILES: CCS(=O)(=O)Nc1ccc(-n2cc(C(=O)O)c(=O)c3cc(Cl)c(N4CCC[C@@H]4COc4ncccc4Cl)cc32)cc1]

Step 1: Synthesis of (R)-ethyl 6-chloro-7-(2-(((3-chloropyridin-2-yl)oxy)methyl)pyrrolidin-1-yl)-1-(4-(ethylsulfonamido)phenyl)-4-oxo-1,4-dihydroquinoline-3-carboxylate

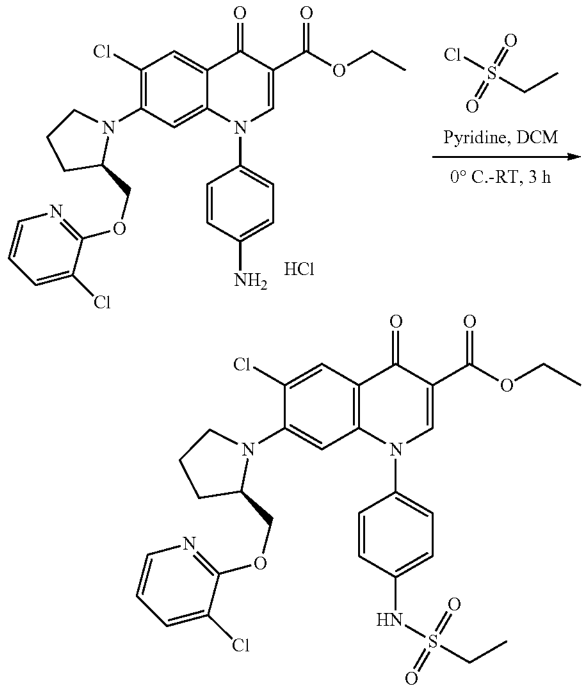

To a stirred solution of ethyl 1-(4-aminophenyl)-6-chloro-4-oxo-7-[(2R)-2-[(pyridin-2-yloxy) methyl]pyrrolidin-1-yl]-1,4-dihydroquinoline-3-carboxylate hydrochloride (100 mg, 169 μmol) in DCM (5 mL) at 0° C., was added pyridine (41.2 μL, 507 μmol) followed by ethane sulfonyl chloride (32.2 μL, 338 μmol). The reaction mixture was slowly warmed to room temperature and stirred for 3 h. After completion of reaction, ice cold water (15 mL) was added and the product was extracted with DCM (2×15 mL). The combined organic layers were washed with brine (15 mL) and dried over sodium sulphate and evaporated to dryness. The resulting crude material was triturated with diethyl ether & pentane to afford ethyl (R)-6-chloro-7-(2-(((3-chloropyridin-2-yl)oxy)methyl)pyrrolidin-1-yl)-1-(4-(ethylsulfonamido)phenyl)-4-oxo-1,4-dihydroquinoline-3-carboxylate (73.3 mg, 71.1%) as pale-yellow solid. MS (ESI) m/z: 645.2 $[M+H]^+$.

Step 2: Synthesis of (R)-6-chloro-7-(2-(((3-chloropyridin-2-yl)oxy)methyl)pyrrolidin-1-yl)-1-(4-(ethylsulfonamido)phenyl)-4-oxo-1,4-dihydroquinoline-3-carboxylic acid

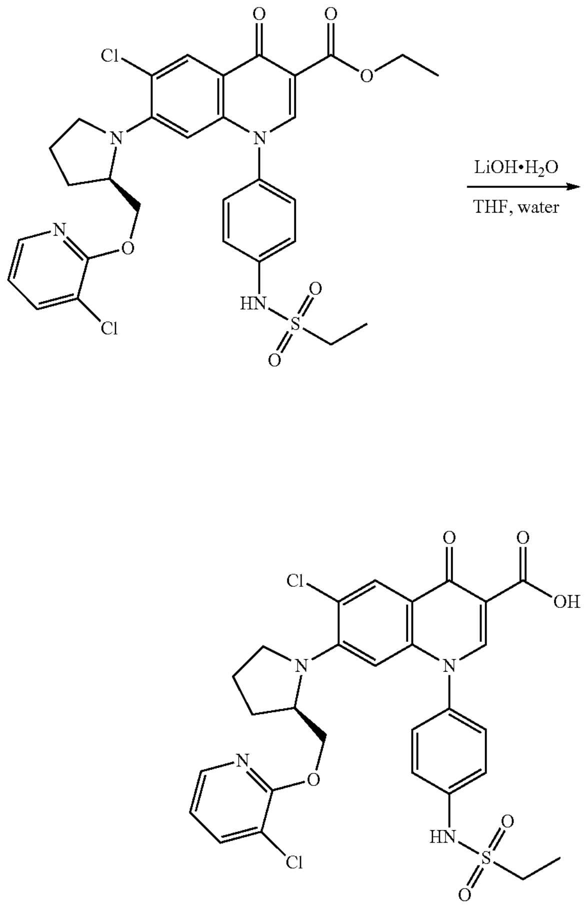

Experimental procedure described above to obtain (R)-6-chloro-7-(2-(((3-chloropyridin-2-yl) oxy) methyl) pyrrolidin-1-yl)-1-(4-(ethylsulfonamido) phenyl)-4-oxo-1,4-dihydroquinoline-3-carboxylic acid (42.7 mg, 61.2%) as pale-yellow solid. $^1$H-NMR (400 MHz, DMSO-$d_6$): δ 15.07 (s, 1H), 10.26 (bs, 1H), 8.55 (s, 1H), 8.16 (s, 1H), 7.87-7.88 (m, 1H), 7.81-7.79 (m, 1H), 7.58-7.46 (m, 3H), 7.35 (d, J=8.0 Hz, 1H), 6.94-6.91 (m, 1H), 6.34 (s, 1H), 4.74 (bs, 1H), 4.29-4.25 (m, 2H), 3.42-3.38 (m, 1H), 3.22 (q, J=7.2 Hz, 2H), 3.14 (t, J=8.0 Hz, 1H), 2.33-2.21 (m, 1H), 2.02-1.88 (m, 2H), 1.82-1.75 (m, 1H), 1.23 (t, J=7.6 Hz, 3H), MS (ESI) m/z: 617.2 $[M+H]^+$.

Potency Lin28a-dep Z11 $IC_{50}$ (μM)++++

Example 32: (R)-6-fluoro-1-(4-fluoroindolin-5-yl)-4-oxo-7-(2-((pyridin-2-yloxy) methyl) pyrrolidin-1-yl)-1,4-dihydroquinoline-3-carboxylic acid

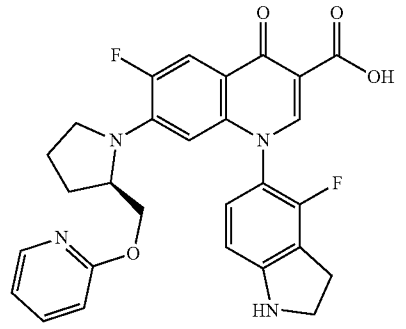 [SMILES: O=C(O)c1cn(-c2ccc3c(c2F)CCN3)c2cc(N3CCC[C@@H]3COc3ccccn3)c(F)cc2c1=O]

Step 1: Synthesis of 4-fluoroindolin-5-amine

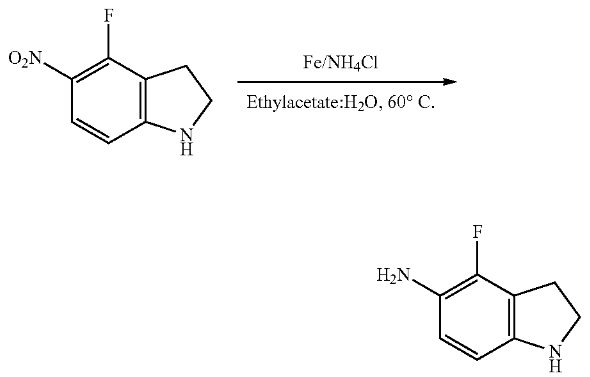

To a stirred solution of 4-fluoro-5-nitro-2,3-dihydro-1H-indole (550 mg, 3.01 mmol, Ref: WO2017/153952) in ethyl acetate (5 mL) and water (5 mL), was added iron (670 mg, 12.0 mmol) and ammonium chloride (1.28 g, 24.0 mmol) at RT and the reaction mixture was stirred at 60° C. for 12 h. The reaction mixture was cooled to RT and filtered through celite bed, washed the celite pad with EtOAc (50 mL). The organic layer was washed with brine, dried over sodium sulphate and evaporated to dryness. The crude product was purified by silica gel column chromatography (100-200 mesh) by using 10-15% EtOAc/Hexanes as an eluent. The relevant fractions containing the product were combined and evaporated to dryness to afford 4-fluoro-2,3-dihydro-1H-indol-5-amine (280 mg, 61%) as brown solid. MS (ESI) m/z:153.5

Step 2: Synthesis of ethyl (R)-6-fluoro-1-(4-fluoroindolin-5-yl)-4-oxo-7-(2-((pyridin-2-yloxy) methyl) pyrrolidin-1-yl)-1,4-dihydroquinoline-3-carboxylate

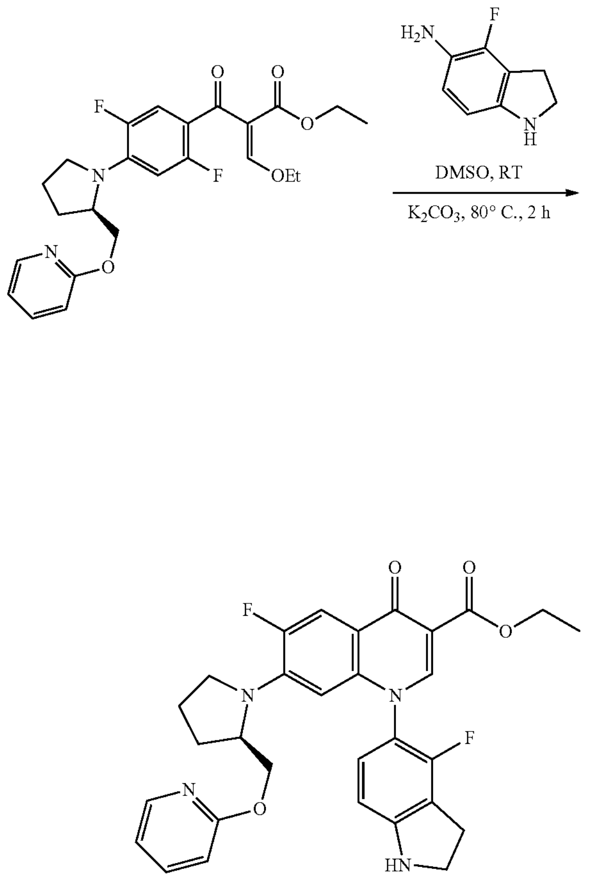

Experimental procedure as described above to obtain ethyl (R)-6-fluoro-1-(4-fluoroindolin-5-yl)-4-oxo-7-(2-((pyridin-2-yloxy) methyl) pyrrolidin-1-yl)-1,4-dihydroquinoline-3-carboxylate (200 mg, 56.17%) as a brown solid. MS (ESI) m/z: 547.3 $[M+H]^+$.

Step 3: Synthesis of (R)-6-fluoro-1-(4-fluoroindolin-5-yl)-4-oxo-7-(2-((pyridin-2-yloxy) methyl) pyrrolidin-1-yl)-1,4-dihydroquinoline-3-carboxylic acid

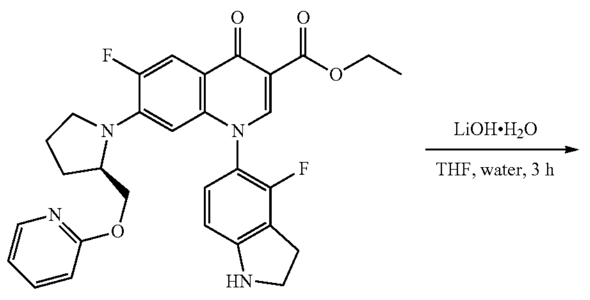

-continued

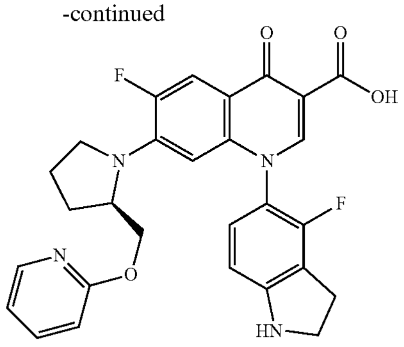

Experimental procedure as described above to obtain (R)-6-fluoro-1-(4-fluoroindolin-5-yl)-4-oxo-7-(2-((pyridin-2-yloxy) methyl) pyrrolidin-1-yl)-1,4-dihydroquinoline-3-carboxylic acid (45 mg, 23.8%) as a pale brown solid. $^{1}$H-NMR (400 MHz, DMSO-$d_6$): δ 15.32 (bs, 1H), 8.52 (bs, 1H), 8.04 (bs, 1H), 7.88 (d, J=13.6 Hz, 1H), 7.68-7.66 (m, 1H), 7.24-7.18 (m, 1H), 6.96 (s, 1H), 6.72-6.67 (m, 1H), 6.45 (d, J=8.0 Hz, 0.5H), 6.34 (bs, 1H), 6.26 (d, J=8.0 Hz, 0.5H), 6.19-6.16 (m, 1H), 4.41-4.33 (m, 1H), 4.23-4.16 (m, 2H), 3.64-3.51 (m, 2H), 3.42 (s, 1H), 3.10-5.08 (m, 1H), 2.93-2.90 (m, 1H), 2.68-2.50 (m, 1H), 2.06-1.93 (m, 4H), MS (ESI) m/z: 519.3 $[M+H]^+$.

Potency Lin28a-dep Z11 $IC_{50}$ (μM)++++

Example 33: 6-chloro-1-(5-hydroxypyrazin-2-yl)-4-oxo-7-[(2R)-2-[(pyridin-2-yloxy)methyl]pyrrolidin-1-yl]-1,4-dihydroquinoline-3-carboxylic acid

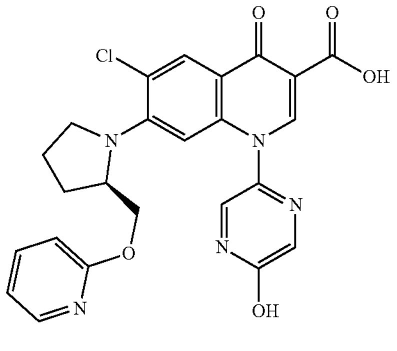

Step 1: Synthesis of ethyl 1-[5-(benzyloxy)pyrazin-2-yl]-6-chloro-4-oxo-7-[(2R)-2-[(pyridin-2-yloxy)methyl]pyrrolidin-1-yl]-1,4-dihydroquinoline-3-carboxylate

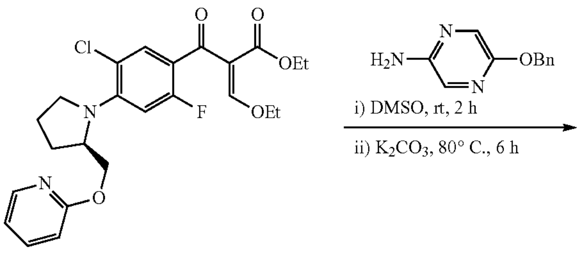

-continued

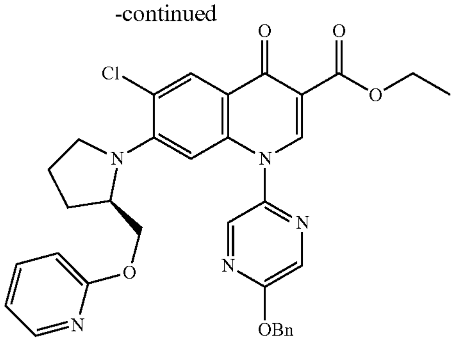

To a stirred solution of ethyl (R,Z)-2-(5-chloro-2-fluoro-4-(2-((pyridin-2-yloxy)methyl)pyrrolidin-1-yl)benzoyl)-3-ethoxyacrylate (450 mg, 1.06 mmol) in DMSO (7 mL) was added 5-(benzyloxy)pyrazin-2-amine (213 mg, 1.06 mmol) and stirred the reaction mixture at room temperature for 2 h. After completion of starting material (monitored by TLC), added potassium carbonate (146 mg, 1.06 mmol) and stirred the reaction mixture at 80° C. for 2 h. The reaction mixture was cooled to room temperature, poured into ice-cold water (15 mL) which resulted in precipitation. The precipitated solid was collected by filtration and washed with water (50 mL) & hexane (10 mL) to afford ethyl 1-[5-(benzyloxy)pyrazin-2-yl]-6-chloro-4-oxo-7-[(2R)-2-[(pyridin-2-yloxy)methyl]pyrrolidin-1-yl]-1,4-dihydroquinoline-3-carboxylate (260 mg, 424 μmol, 40%) as pale brown solid. MS (ESI) m/z: 612.3 $[M+H]^+$.

Step 2: Synthesis of [6-chloro-1-(5-hydroxypyrazin-2-yl)-4-oxo-7-[(2R)-2-[(pyridin-2-yloxy)methyl]pyrrolidin-1-yl]-1,4-dihydroquinoline-3-carboxylic acid]

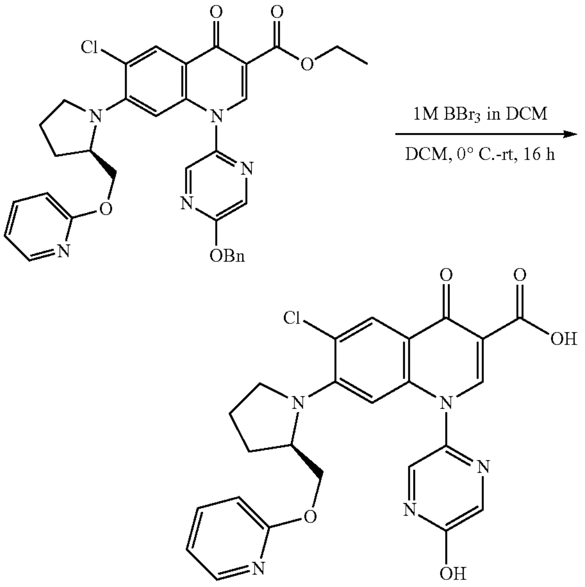

To a stirred solution of ethyl 1-[5-(benzyloxy)pyrazin-2-yl]-6-chloro-4-oxo-7-[(2R)-2-[(pyridin-2-yloxy)methyl]pyrrolidin-1-yl]-1,4-dihydroquinoline-3-carboxylate (500 mg, 816 μmol) in DCM (30 mL), was added boron tribromide solution 1.0 M in DCM (20.7 mL, 122 mmol) at 0° C.

under $N_2$ atmosphere. The resulting mixture was stirred at room temperature for 16 h. After completion of the reaction (monitored by TLC), the reaction mixture was quenched with ice cold water (20 mL) and extracted with EtOAc (3×25 mL). The combined organic layer was treated with charcoal (200 mg) then filtered through celite pad and concentrated under reduced pressure to get the crude compound, which was purified by Prep HPLC purification to afford 6-chloro-1-(5-hydroxypyrazin-2-yl)-4-oxo-7-[(2R)-2-[(pyridin-2-yloxy)methy-1]pyrrolidine-1-yl]-1,4-dihydro quinoline-3-carboxylic acid (27.3 mg, 7%) as an off white solid. $^1H$ NMR (400 MHz, DMSO-$d_6$): δ 15.05 (brs, 1H), 8.79 (s, 1H), 8.16 (s, 1H), 8.08 (brs, 1H), 8.00-7.97 (m, 1H), 7.75 (brs, 1H), 7.65-7.59 (m, 1H), 6.92-6.88 (m, 1H), 6.67 (s, 1H), 6.60 (d, J=8.0 Hz, 1H), 4.70-4.60 (m, 1H), 4.25-4.13 (m, 2H), 3.71-3.67 (m, 1H), 3.53-3.43 (m, 1H), 2.24-2.21 (m, 1H), 1.92-1.89 (m, 1H), 1.88-1.77 (m, 2H); MS (ESI) m/z: 494.3 $[M+H]^+$.

Potency Lin28a-dep Z11 $IC_{50}$ (μM)++++

Example 34: 6-Chloro-7-[(2R)-2-{[(3-chloropyridin-2-yl)oxy]methyl}pyrrolidin-1-yl]-1-[1-(2-hydroxyethyl)azetidin-3-yl]-4-oxo-1,4-dihydroquinoline-3-carboxylic acid

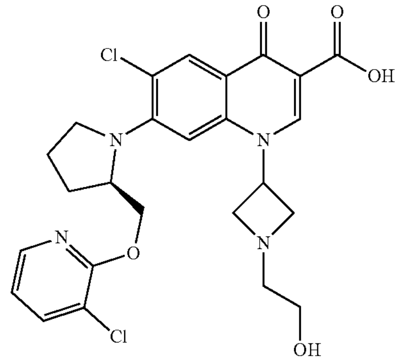 [SMILES: O=C(O)c1cn(C2CN(CCO)C2)c2cc(N3CCC[C@@H]3COc3ncccc3Cl)c(Cl)cc2c1=O]

Step 1: Synthesis of ethyl 1-{1-[(tert-butoxy) carbonyl] azetidin-3-yl}-6-chloro-7-[(2R)-2-{[(3-chloropyridin-2-yl) oxy] methyl} pyrrolidin-1-yl]-4-oxo-1,4-dihydroquinoline-3-carboxylate

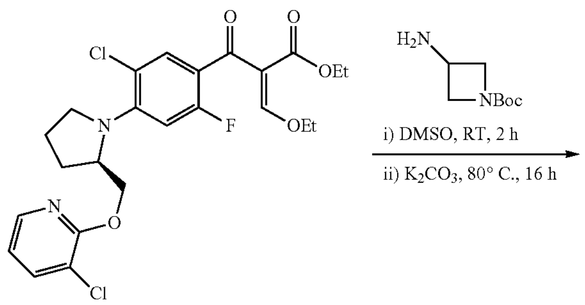

-continued

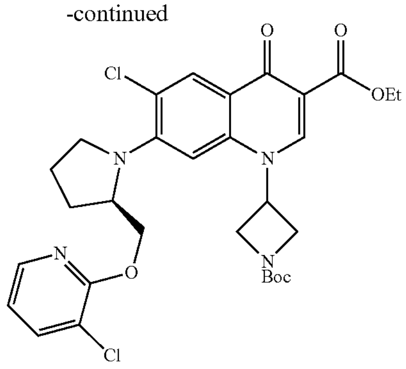

To a stirred solution of ethyl (2Z)-2-[(Z)-5-chloro-4-[(2R)-2-{[(3-chloropyridin-2-yl)oxy]methyl}pyrrolidin-1-yl]-2-fluorobenzoyl]-3-ethoxyprop-2-enoate (800 mg, 1.56 mmol) in DMSO (8 mL) was added tert-butyl 3-aminoazetidine-1-carboxylate (322 mg, 1.87 mmol) at room temperature. The reaction mixture was stirred at room temperature for 2 h. After completion of starting material (monitored by TLC), potassium carbonate (538 mg, 3.90 mmol) was added and stirred at 80° C. for 16 h. After completion of reaction (monitored by LCMS), the reaction mixture was gradually cooled, quenched with ice-cold water and precipitated solid was filtered and washed with water (20 ml). The obtained solid product was dissolved in EtOAc (25 ml) and treated with charcoal and filtered through celite bed. The filtrate was concentrated under vacuum and triturated with 10% EtOAc in pentane (20 ml) to afford ethyl 1-{1-[(tertbutoxy)carbonyl]azetidin-3-yl}-6-chloro-7-[(2R)-2-{[(3-chloropyridin-2-yl)oxy]methyl}pyrrolidin-1-yl]-4-oxo-1,4-dihydroquinoline-3-carboxylate (398 mg, 41%) as a brown solid. MS (ESI) m/z 617.3 $[M+H]^+$ Step 2: Synthesis of ethyl 1-(azetidin-3-yl)-6-chloro-7-[(2R)-2-{[(3-chloropyridin-2-yl)oxy]methyl}pyrrolidin-1-yl]-4-oxo-1,4-dihydroquinoline-3-carboxylate

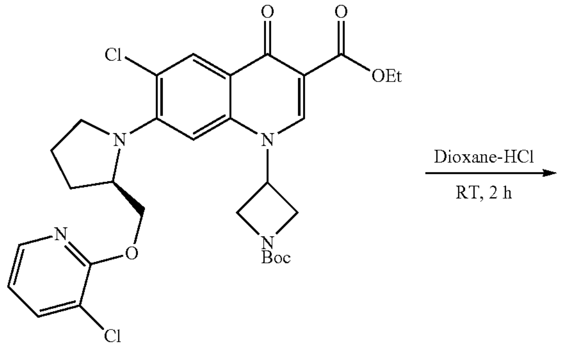

-continued

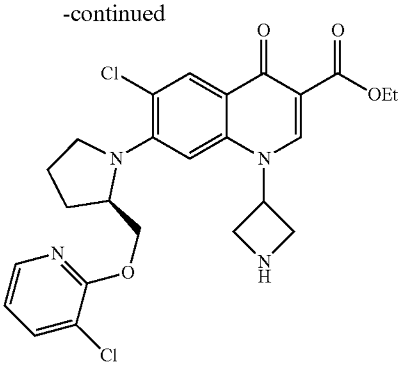

To a stirred solution of ethyl 1-{1-[(tert-butoxy) carbonyl] azetidin-3-yl}-6-chloro-7-[(2R)-2-{[(3-chloropyridin-2-yl) oxy] methyl} pyrrolidin-1-yl]-4-oxo-1,4-dihydroquinoline-3-carboxylate (500 mg, 809 µmol) in dioxane (5 mL) was cooled with ice bath and added 4.0 M HCl in Dioxane (5 mL). The reaction mixture was stirred at room temperature for 2 h. The excess of solvent was removed under vacuum and triturated with diethyl ether (2×20 ml) to afford ethyl 1-(azetidin-3-yl)-6-chloro-7-[(2R)-2-{[(3-chloropyridin-2-yl)oxy]methyl}pyrrolidin-1-yl]-4-oxo-1,4-dihydroquinoline-3-carboxylate (328 mg, 78%) as a yellow solid. MS (ESI) m/z 517.2 $[M+H]^+$ Step 3: Synthesis of ethyl 1-(1-{2-[(tert-butyldimethylsilyl)oxy] ethyl}azetidin-3-yl)-6-chloro-7-[(2R)-2-{[(3-chloropyridin-2-yl)oxy] methyl}pyrrolidin-1-yl]-4-oxo-1,4-dihydroquinoline-3-carboxylate

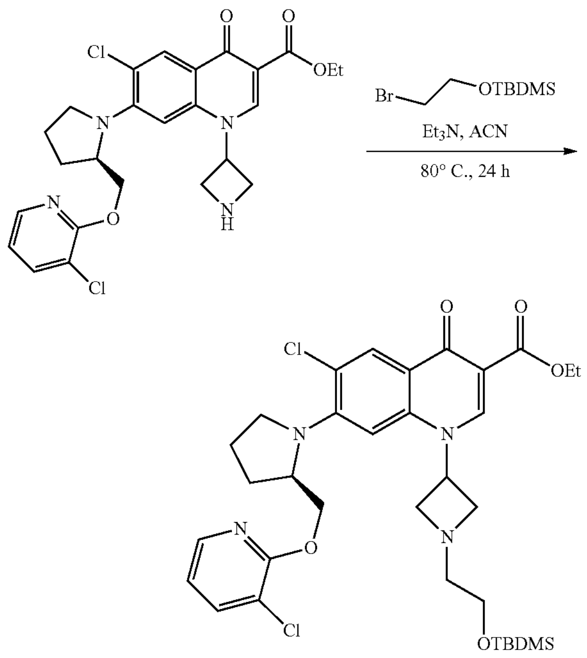

To a stirred solution of ethyl 1-(azetidin-3-yl)-6-chloro-7-[(2R)-2-{[(3-chloropyridin-2-yl)oxy]methyl}pyrrolidin-1-yl]-4-oxo-1,4-dihydroquinoline-3-carboxylate (150 mg, 289 µmol) in ACN (5 mL), was added triethylamine (200 µL, 1.44 mmol) and stirred at room temperature for 15 minutes and added (2-bromoethoxy)(tert-butyl)dimethylsilane (82.7 mg, 346 µmol) at room temperature. The reaction mixture was stirred at 80° C. for 24 h. After completion of reaction (monitored by TLC), the excess of solvent was removed under vacuum and diluted with EtOAc (20 ml) and washed with water (20 ml) and brine (20 ml). The organic layer was dried over anhydrous sodium sulfate and treated with charcoal and filtered through celite bed and concentrated under vacuum to afford ethyl 1-(1-{2-[(tert-butyldimethylsilyl) oxy]ethyl}azetidin-3-yl)-6-chloro-7-[(2R)-2-{[(3-chloropyridin-2-yl)oxy]methyl}pyrrolidin-1-yl]-4-oxo-1,4-dihydroquinoline-3-carboxylate (100 mg, 46%) as a yellow oil. MS (ESI) m/z 675.4 $[M+H]^+$.

Step 4: Synthesis of 6-chloro-7-[(2R)-2-{[(3-chloropyridin-2-yl)oxy]methyl} pyrrolidin-1-yl]-1-[1-(2-hydroxyethyl)azetidin-3-yl]-4-oxo-1,4-dihydroquinoline-3-carboxylic acid

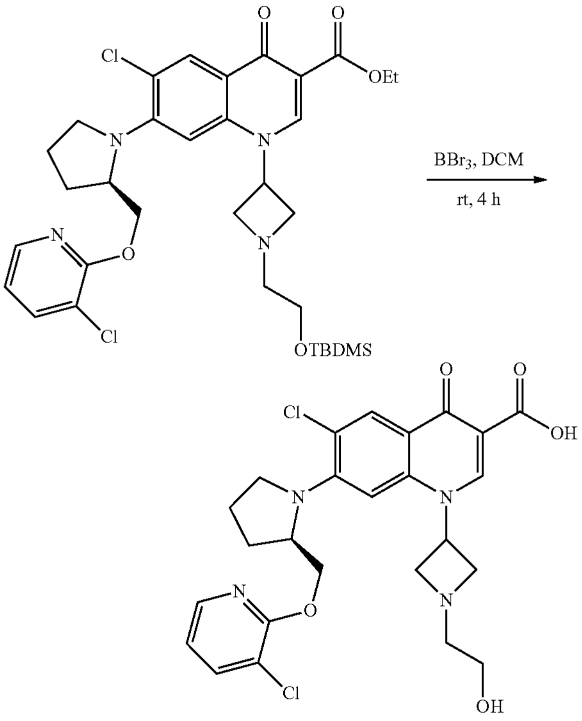

To a stirred solution of ethyl 1-(1-{2-[(tert-butyldimethylsilyl)oxy]ethyl}azetidin-3-yl)-6-chloro-7-[(2R)-2-{[(3-chloropyridin-2-yl)oxy]methyl}pyrrolidin-1-yl]-4-oxo-1,4-dihydroquinoline-3-carboxylate (100 mg, 132 µmol) in DCM (10 mL), was added $BBr_3$ 1.0 M in DCM (1 mL) drop wise at 10-15° C. The reaction mixture was stirred at room temperature for 4 h. After completion of reaction (monitored by TLC), the excess of solvent was removed under vacuum and diluted with EtOAc (30 ml) and washed with water (2×20 mL). The organic layer was dried over anhydrous sodium sulfate and concentrated under vacuum to afford crude compound. The crude product was purified by Prep HPLC and collected pure fractions were lyophilized to afford 6-chloro-7-[(2R)-2-{[(3-chloropyridin-2-yl)oxy] methyl}pyrrolidin-1-yl]-1-[1-(2-hydroxyethyl)azetidin-3-yl]-4-oxo-1,4-dihydroquinoline-3-carboxylic acid (10.6 mg, 15%) as an off-white solid. $^1$H NMR (400 MHz, DMSO-$d_6$) 15.25 (brs, 1H), 8.66 (s, 1H), 8.13 (s, 1H), 7.97 (dd, J=4.8, 1.6 Hz, 1H), 7.79 (dd, J=7.9, 1.6 Hz, 1H), 6.98 (brs, 1H), 6.92 (dd, J=7.6, 4.8 Hz, 1H), 5.26-5.15, (m, 1H), 4.97-4.92 (m, 1H), 4.48 (t, J=5.6 Hz, 1H), 4.42-4.36 (m, 2H), 3.95 (t, J=6.8 Hz, 1H), 3.88-3.19 (m, 2H), 3.43-3.28 (m, 5H), 2.68-2.49 (m, 2H), 2.34-2.29 (m, 1H), 2.09-1.85 (m, 3H). MS (ESI) m/z 533.3 [M+H]$^+$ Potency Lin28a-dep Z11 $IC_{50}$ (μM)+++

Example 35: 6-Cyano-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylic acid

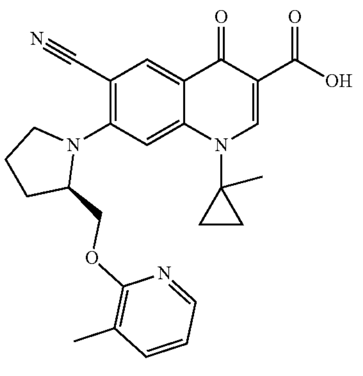 [SMILES: Cc1cccnc1OC[C@H]1CCCN1c1cc2c(cc1C#N)c(=O)c(C(=O)O)cn2C1(C)CC1]

Step 1: Synthesis of ethyl 3-(5-bromo-2,4-difluorophenyl)-3-oxopropanoate

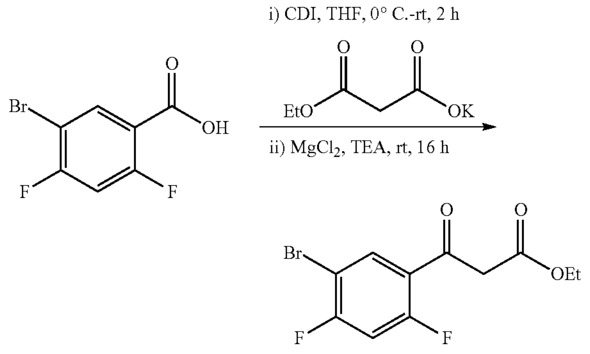

To a stirred solution of 5-bromo-2,4-difluorobenzoic acid (2.5 g, 10.5 mmol) in THF (50 mL) was added carbonyldiimidazole (3.40 g, 21.0 mmol) at 0° C. and stirred at rt for 2 h. Then, triethylamine (4.38 mL, 31.5 mmol), 1-ethyl 3-potassium propanedioate (2.67 g, 15.7 mmol) and magnesium chloride (799 mg, 8.40 mmol) were added to the reaction mixture and stirred at rt for 16 h. After completion of reaction, the reaction mixture was quenched with ice-cold water (50 mL) and extracted with EtOAc (2×50 mL). The combined organic layer was washed with brine (20 mL), dried over anhydrous sodium sulfate, concentrated under vaccum to afford the crude compound. The crude compound was purified by column chromatography with 10% EtOAC in hexane as eluent to afford ethyl 3-(5-bromo-2,4-difluorophenyl)-3-oxopropanoate (2.00 g, 62%) as pale yellow solid. $^1$H NMR (400 MHz, $CDCl_3$): δ 8.20 (t, J=7.6 Hz, 1H), 7.00-6.93 (m, 1H), 4.23-4.18 (m, 2H), 3.94 (d, J=3.6 Hz, 2H), 1.28 (t, J=3.2 Hz, 3H)

Step 2: Synthesis of ethyl 6-bromo-7-fluoro-1-(1-methylcyclopropyl)-4-oxo-1,4-dihydroquinoline-3-carboxylate

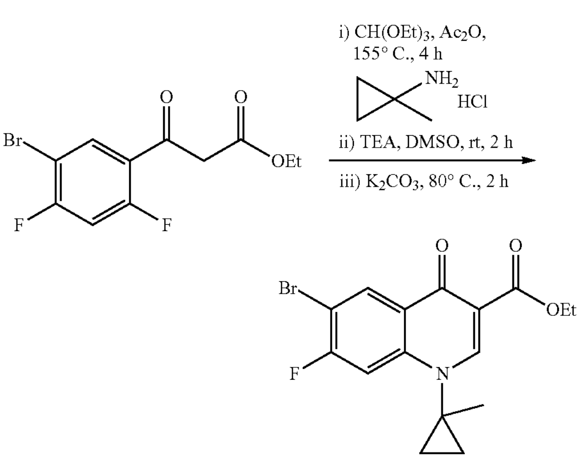

To a stirred solution of ethyl 3-(5-bromo-2,4-difluorophenyl)-3-oxopropanoate (1.5 g, 4.88 mmol) in triethyl orthoformate (1.21 mL, 7.32 mmol) was added acetic anhydride (691 μL, 7.32 mmol) at room temperature. The reaction was then heated to 155° C. and stirred for 4 h. After completion of starting material (monitored by TLC), reaction mixture was concentrated under reduced pressure and codistilled with toluene (2×5 mL) to afford the crude compound. The crude compound was dissolved in DMSO (15 mL), were added 1-methylcyclopropan-1-amine. HCl (347 mg, 4.88 mmol) and triethylamine (882 μL, 6.34 mmol) at room temperature and stirred for 2 h. Then, potassium carbonate (674 mg, 4.88 mmol) was added to the reaction mixture at RT. The mixture was stirred at 80° C. for 2 h. After completion of reaction, the reaction mixture was cooled to RT, quenched with ice-cold water (50 mL), which resulted in precipitation. The precipitated solid was filtered, washed with water & diethyl ether, dried under reduced pressure to afford ethyl 6-bromo-7-fluoro-1-(1-methylcyclopropyl)-4-oxo-1,4-dihydroquinoline-3-carboxylate (1.47 g, 82%) as brown solid. MS (ESI) m/z: 367.9 [M+H]$^+$ Step 3: Synthesis of ethyl 6-bromo-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylate

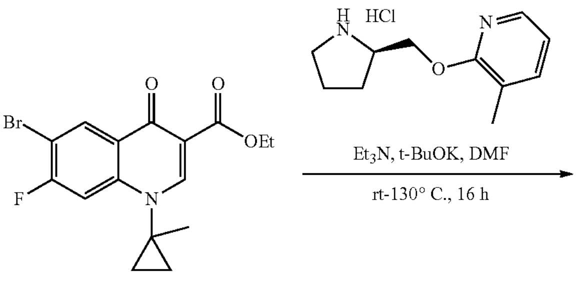

-continued

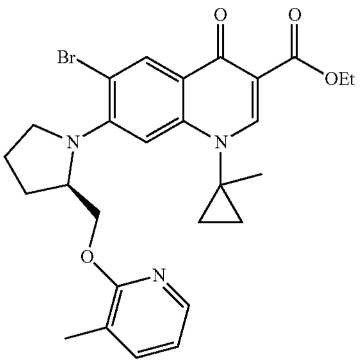

To a stirred solution of 3-methyl-2-{[(2S)-pyrrolidin-2-yl] methoxy} pyridine hydrochloride (651 mg, 2.85 mmol) in DMF (14 mL), were added triethylamine (264 μL, 1.90 mmol) and potassium tert-butoxide (639 mg, 5.70 mmol) at room temperature and stirred for 10 min. Then, ethyl 6-bromo-7-fluoro-1-(1-methylcyclopropyl)-4-oxo-1,4-dihydroquinoline-3-carboxylate (700 mg, 1.90 mmol) was added to the reaction mixture at RT and the reaction was stirred at 130° C. for 16 h. After completion of reaction, the reaction mixture was cooled to 0° C., quenched with ice-cold water (5 mL), which resulted in precipitation. The precipitated solid was filtered, washed with water & diethyl ether, dried over under reduced pressure to afford ethyl 6-bromo-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylate (108 mg, 10%) as brown solid. MS (ESI) m/z: 540.2 $[M+H]^+$

Step 4: Synthesis of ethyl 6-cyano-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylate

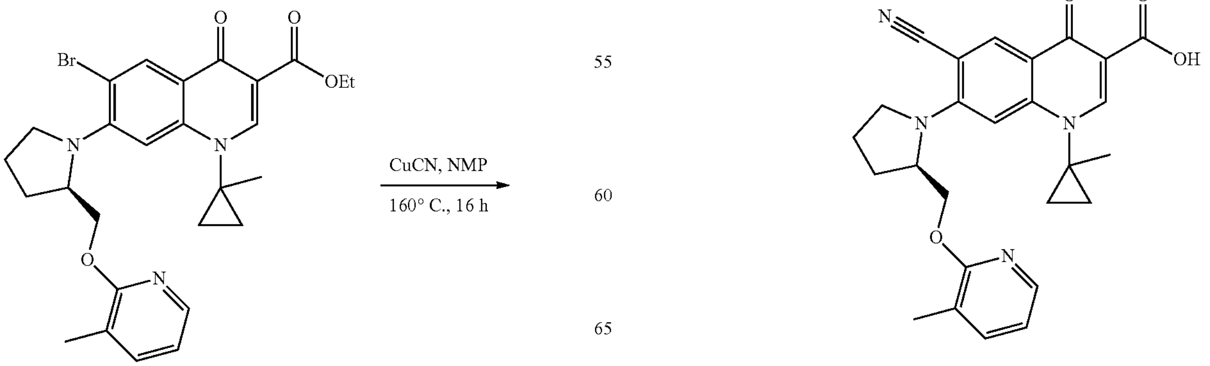

To a stirred solution of ethyl 6-bromo-1-(1-methylcyclopropyl)-7-[(2R)-2-{[(3-methylpyridin-2-yl)oxy]methyl} pyrrolidin-1-yl]-4-oxo-1,4-dihydroquinoline-3-carboxylate (108 mg, 199 μmol) in NMP (3 mL), was added copper(I) cyanide (35.6 mg, 398 μmol) at room temperature and degassed with argon for 10 min in a sealed tube. The reaction was stirred at 160° C. for 16 h. After completion of reaction, the reaction mixture was cooled to RT, diluted with ice-cold water (10 mL) and extracted with 10% MeOH in DCM (2×10 mL). The combined organic layer was washed with brine (15 mL), dried over anhydrous sodium sulfate, concentrated under reduced pressure to afford ethyl 6-cyano-1-(1-methylcyclopropyl)-7-[(2R)-2-{[(3-methylpyridin-2-yl)oxy]methyl} pyrrolidin-1-yl]-4-oxo-1,4-dihydroquinoline-3-carboxylate (72.0 mg, 74%) as brown solid. MS (ESI) m/z: 487.4 $[M+H]^+$

Step 5: Synthesis of 6-cyano-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylic acid

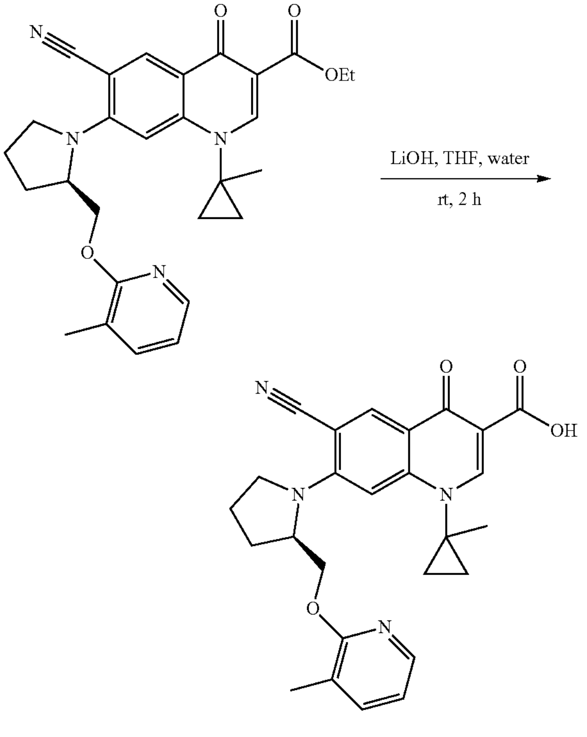

To a stirred solution of ethyl 6-cyano-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylate (72 mg, 147 μmol) in a mixture of THF (0.72 mL), EtOH (0.72 mL) & water (0.72 mL), was $LiOH \cdot H_2O$ (30.8 mg, 735 μmol). The reaction mixture was stirred at room temperature for 2 h. After completion of starting material, the reaction mixture was concentrated under reduced pressure and the crude compound was quenched with ice-cold water and acidified with 1N HCl (pH-3) which resulted in precipitation. The precipitated solid was filtered, dried and purified by prep HPLC and the fractions were lyophilized to afford 6-cyano-1-(1-methylcyclopropyl)-7-[(2R)-2-{[(3-methylpyridin-2-yl)oxy]methyl}pyrrolidin-1-yl]-4-oxo-1,4-dihydroquinoline-3-carboxylic acid (44.5 mg, 66%) as an off white solid. $^1$H NMR (400 MHz, DMSO-$d_6$, VT): δ 14.78 (s, 1H), 8.71 (s, 1H), 8.40 (s, 1H), 7.84-7.82 (m, 1H), 7.46-7.43 (m, 1H), 7.14 (s, 1H), 6.80 (dd, J=6.8, 4.8 Hz 1H), 4.93-4.90 (m, 1H), 4.50 (d, J=5.2 Hz, 2H), 3.94-3.91 (m, 1H), 3.73-3.69 (m, 1H), 2.35-2.06 (m, 4H), 2.07 (s, 3H), 1.57 (s, 3H), 1.41-1.16 (m, 4H). MS (ESI) m/z: 459.4 $[M+H]^+$ Potency Lin28a-dep Z11 $IC_{50}$ (μM)++++

Example 36: 1-(1-Acetylazetidin-3-yl)-6-chloro-7-[(2R)-2-{[(3-methylpyridin-2-yl)oxy]methyl}pyrrolidin-1-yl]-4-oxo-1,4-dihydroquinoline-3-carboxylic acid

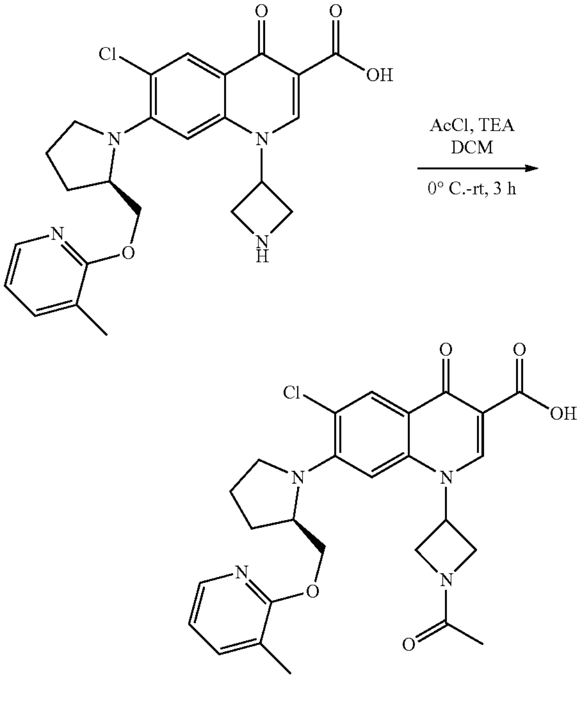

To a stirred solution of 1-(azetidin-3-yl)-6-chloro-7-[(2R)-2-{[(3-methylpyridin-2-yl)oxy]methyl}pyrrolidin-1-yl]-4-oxo-1,4-dihydroquinoline-3-carboxylic acid (100 mg, 196 μmol) in DCM (6 mL), was added triethylamine (81.9 μL, 588 μmol) followed by acetyl chloride (13.9 μL, 196 μmol) at 0° C., then the reaction mixture was stirred at room temperature for 3 h. After completion of the starting material, the reaction mixture was quenched with ice cold water and extracted with DCM (2×50 mL). The combined organic layer was washed with water (10 mL) and brine (10 mL) solution, dried over anhydrous sodium sulfate and concentrated under reduced pressure to get crude compound. The crude compound was purified by prep HPLC to afford desired 1-(1-acetylazetidin-3-yl)-6-chloro-7-[(2R)-2-{[(3-methylpyridin-2-yl)oxy]methyl}pyrrolidin-1-yl]-4-oxo-1,4-dihydroquinoline-3-carboxylic acid (19.6 mg, 20%) as pinkish brown solid. $^1$H NMR (400 MHz, DMSO-$d_6$, VT) δ 14.90 (s, 1H), 8.73 (s, 1H), 8.16 (s, 1H), 7.81 (dd, J=3.6, 1.2 Hz, 1H), 7.39 (dd, J=7.2, 0.8 Hz, 1H), 6.91 (s, 1H), 6.76 (dd, J=7.2, 4.8 Hz, 1H), 5.59-5.09 (m, 1H), 4.98-4.91 (m, 1H), 4.69-4.49 (m, 3H), 4.39 (dd, J=11.2, 4.8 Hz, 1H), 4.29 (dd, J=11.2, 5.2 Hz, 1H), 3.91-3.82 (m, 1H), 3.46-3.39 (m, 1H), 2.32-2.28 (m, 1H), 2.08-1.92 (m, 4H), 1.98 (s, 3H), 1.80 (s, 3H), MS (ESI) m/z: 511.3 $[M+H]^+$.

Potency Lin28a-dep Z11 $IC_{50}$ (μM)+++

Example 37: 6-Chloro-7-[(2R)-2-{[(3-chloropyridin-2-yl)oxy]methyl}pyrrolidin-1-yl]-1-[1-(2-methoxyethyl)-3-methylazetidin-3-yl]-4-oxo-1,4-dihydroquinoline-3-carboxylic acid

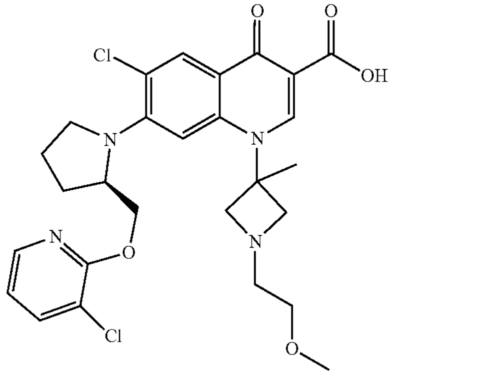 [SMILES: COCCN1CC(C)(n2cc(C(=O)O)c(=O)c3cc(Cl)c(N4CCC[C@@H]4COc4ncccc4Cl)cc32)C1]

Step 1: Synthesis of ethyl 1-{1-[(tert-butoxy)carbonyl]-3-methylazetidin-3-yl}-6-chloro-7-[(2R)-2-{[(3-chloropyridin-2-yl)oxy]methyl}pyrrolidin-1-yl]-4-oxo-1,4-dihydro quinoline-3-carboxylate

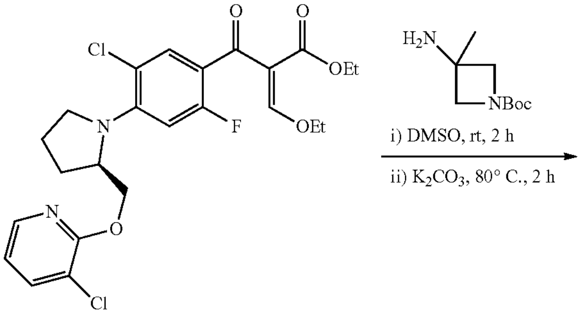

-continued

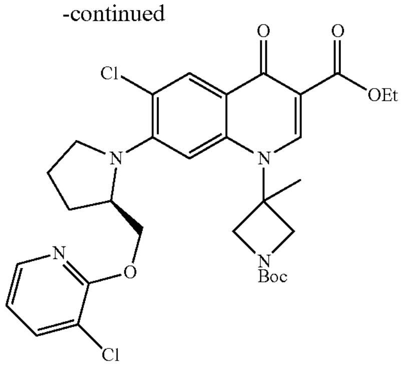

To the stirred solution of ethyl (2Z)-2-[(Z)-5-chloro-4-[(2R)-2-{[(3-chloropyridin-2-yl)oxy]methyl}pyrrolidin-1-yl]-2-fluorobenzoyl]-3-ethoxyprop-2-enoate (300 mg, 586 μmol) in DMSO (6 mL) was added tert-butyl 3-amino-3-methylazetidine-1-carboxylate (109 mg, 586 μmol) and stirred at room temperature for 2 h under $N_2$ atmosphere. After completion of starting material, potassium carbonate (80.9 mg, 586 μmol) was added and the resulting mixture was stirred at 80° C. for 2 h. After completion of reaction, the reaction mixture was quenched with ice-cold water (10 mL) and extracted with EtOAc (3×20 mL). The combined organic layer was washed with ice-cold water (2×10 mL), brine (10 mL), dried over anhydrous sodium sulfate, concentrated under reduced pressure to afford the ethyl 1-{1-[(tert-butoxy)carbonyl]-3-methylazetidin-3-yl}-6-chloro-7-[(2R)-2-{[(3-chloropyridin-2-yl)oxy]methyl}pyrrolidin-1-yl]-4-oxo-1,4-dihydroquinoline-3-carboxylate (210 mg, 57%) as pale brown solid. MS (ESI) m/z: 631.3 $[M+H]^+$.

Step 2: Synthesis of ethyl 6-chloro-7-[(2R)-2-{[(3-chloropyridin-2-yl)oxy]methyl}pyrrolidin-1-yl]-1-(3-methylazetidin-3-yl)-4-oxo-1,4-dihydroquinoline-3-carboxylate HCl

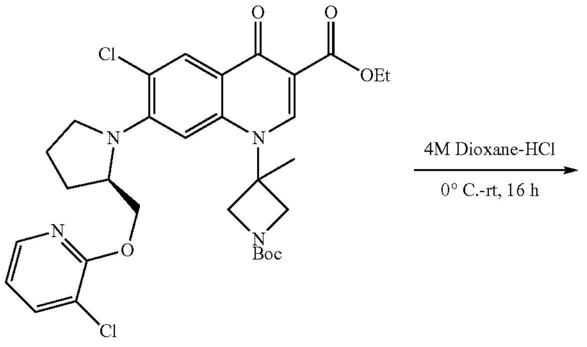

-continued

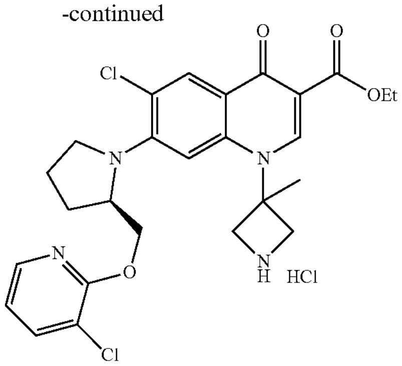

4N HCl in dioxane was added to ethyl 1-{1-[(tert-butoxy)carbonyl]-3-methylazetidin-3-yl}-6-chloro-7-[(2R)-2-{[(3-chloropyridin-2-yl)oxy]methyl}pyrrolidin-1-yl]-4-oxo-1,4-dihydro quinoline-3-carboxylate (300 mg, 332 μmol) at 0° C. The reaction mixture was stirred at rt for 16 h. After completion of reaction, reaction mixture was concentrated under reduced pressure to get crude residue which was washed with diethyl ether to afford ethyl 6-chloro-7-[(2R)-2-{[(3-chloropyridin-2-yl)oxy]methyl}pyrrolidin-1-yl]-1-(3-methylazetidin-3-yl)-4-oxo-1,4-dihydro quinoline-3-carboxylate. HCl (180 mg, 96%) as off-white solid. MS (ESI) m/z: 531.2 $[M+H]^+$.

Step 3: Synthesis of ethyl 6-chloro-7-[(2R)-2-{[(3-chloropyridin-2-yl)oxy]methyl}pyrrolidin-1-yl]-1-[1-(2-methoxyethyl)-3-methylazetidin-3-yl]-4-oxo-1,4-dihydroquinoline-3-carboxylate

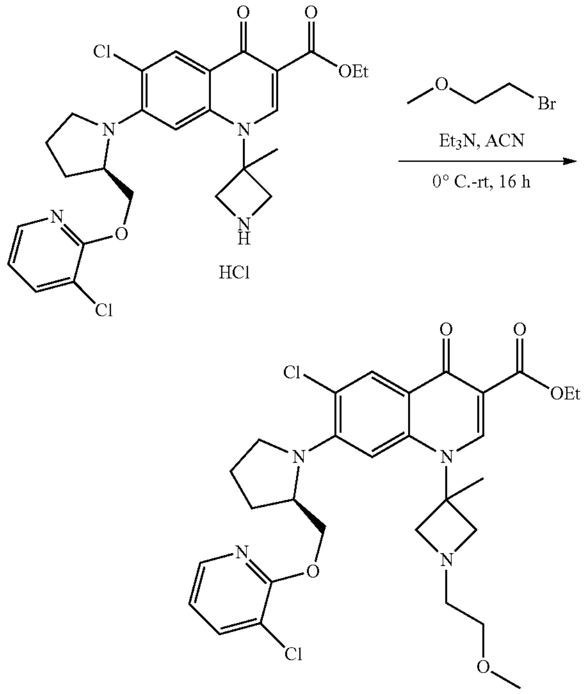

To a stirred solution of ethyl 6-chloro-7-[(2R)-2-{[(3-chloropyridin-2-yl)oxy]methyl}pyrrolidin-1-yl]-1-(3-methylazetidin-3-yl)-4-oxo-1,4-dihydroquinoline-3-carboxylate (250 mg, 338 μmol) in acetonitrile (5 mL) were added triethylamine (47.1 μL, 338 μmol) and 1-bromo-2-methoxyethane (31.7 μL, 338 μmol) at 0° C. The reaction mixture was warmed to room temperature and stirred for 16 h. After completion of reaction, reaction mixture was quenched with ice cold water (5 mL) and extracted with ethyl acetate (2×25 mL). The combined organic layer was washed with water (10 mL) and brine solution (10 mL), filtered and concentrated under reduced pressure to get crude compound. The crude compound was purified by column chromatography over silica gel (60-120 mesh) eluted with 30% ethyl acetate to afford ethyl 6-chloro-7-[(2R)-2-{[(3-chloropyridin-2-yl)oxy]methyl}pyrrolidin-1-yl]-1-[1-(2-methoxyethyl)-3-methylazetidin-3-yl]-4-oxo-1,4-dihydro quinoline-3-carboxylate (250 mg, 93%) as yellow solid. MS (ESI) m/z: 589.2 $[M+H]^+$.

Step 4: Synthesis of 6-chloro-7-[(2R)-2-{[(3-chloropyridin-2-yl)oxy]methyl} pyrrolidin-1-yl]-1-[1-(2-methoxyethyl)-3-methylazetidin-3-yl]-4-oxo-1,4-dihydroquinoline-3-carboxylic acid

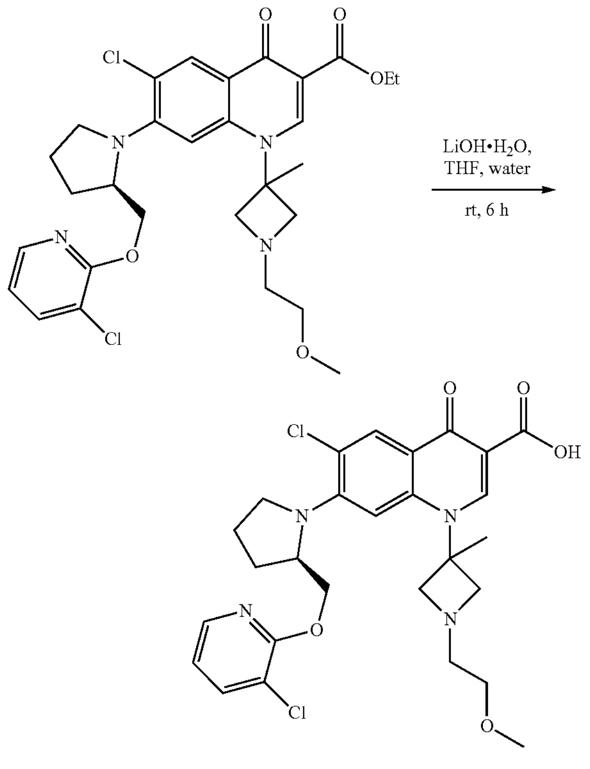

To a stirred solution of ethyl 6-chloro-7-[(2R)-2-{[(3-chloropyridin-2-yl)oxy]methyl}pyrrolidin-1-yl]-1-[1-(2-methoxyethyl)-3-methylazetidin-3-yl]-4-oxo-1,4-dihydro quinoline-3-carboxylate (250 mg, 317 μmol) in THF (2.5 mL) was added a solution of $LiOH \cdot H_2O$ (66.2 mg, 1.58 mmol) in water (2.5 mL). The resulting mixture was stirred at room temperature for 6 h. After completion of the reaction, concentrated under reduced pressure until to remove THF, then aqueous layer was acidified with 1N HCl (pH>2), which resulted in precipitation. The precipitated solid was filtered and washed with water followed by hexane to get the crude compound. The crude compound triturated with mixture of isopropyl alcohol, diethyl ether and n-pentane to afford 6-chloro-7-[(2R)-2-{[(3-chloropyridin-2-yl)oxy]methyl} pyrrolidin-1-yl]-1-[1-(2-methoxyethyl)-3-methylazetidin-3-yl]-4-oxo-1,4-dihydroquinoline-3-carboxylic acid (27 mg, 15%) as an off white solid. $^1H$ NMR (400 MHz, DMSO-$d_6$): δ 15.16 (s, 1H), 8.34 (s, 1H), 8.16 (s, 1H), 7.92 (d, J=4.0 Hz, 1H), 7.80 (dd, J=8.0, 1.6 Hz, 1H), 6.94-6.91 (m, 1H), 6.47 (s, 1H), 4.92-4.87 (m, 1H), 4.38-4.34 (m, 2H), 3.93-3.79 (m, 3H), 3.52-3.38 (m, 5H), 3.21 (s, 3H), 2.67-2.54 (m, 2H), 2.36-2.29 (m, 1H), 2.10-2.01 (m, 2H), 1.99-1.92 (m, 1H), 1.88 (s, 3H). MS (ESI) m/z: 561.3 $[M+H]^+$ Potency Lin28a-dep Z11 $IC_{50}$ (μM)+++

Example 38: 6-Chloro-7-[(2R)-2-{[(3-chloropyridin-2-yl)oxy]methyl}-pyrrolidin-1-yl]-1-[1-(2-methoxyethyl)pyrrolidin-3-yl]-4-oxo-1,4-dihydroquinoline-3-carboxylic acid

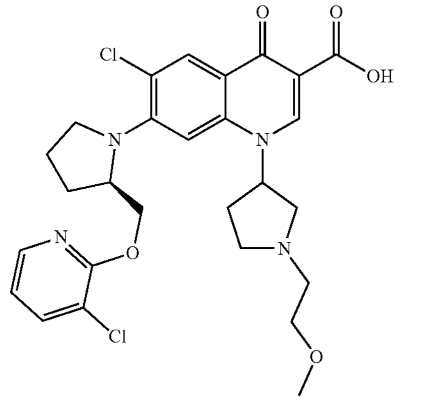 [SMILES: COCCN1CCC(n2cc(C(=O)O)c(=O)c3cc(Cl)c(N4CCC[C@@H]4COc4ncccc4Cl)cc32)C1]

Step 1: Synthesis of tert-butyl N-[1-(2-methoxyethyl) pyrrolidin-3-yl] carbamate

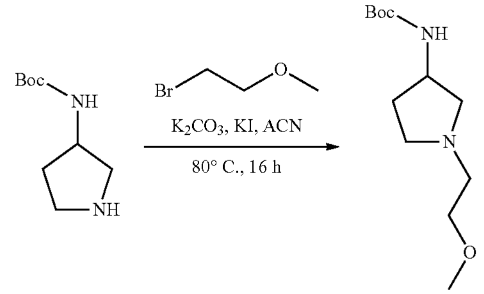

To a solution of tert-butyl N-(pyrrolidin-3-yl)carbamate (200 mg, 1.07 mmol) in MeCN (5 mL) were added potassium carbonate (147 mg, 1.07 mmol), potassium iodide (177 mg, 1.07 mmol) and 1-bromo-2-methoxyethane (162 mg, 1.17 mmol) at room temperature under $N_2$ atmosphere. Then resulting solution was stirred at 80° C. for 16 h. Excess solvent was concentrated under reduced pressure and quenched with ice cold water. The aqueous layer was extracted with EtOAc (3×10 mL). The combined organic layers were dried over sodium sulfate and concentrated under reduced pressure to afford tert-butyl N-[1-(2-methoxyethyl)pyrrolidin-3-yl]carbamate (240 mg crude) as yellow liquid. The product was proceeded to next step without purification. MS (ESI) m/z: 245.5 $[M+H]^+$.

Step 2: Synthesis of 1-(2-methoxyethyl)pyrrolidin-3-amine hydrochloride

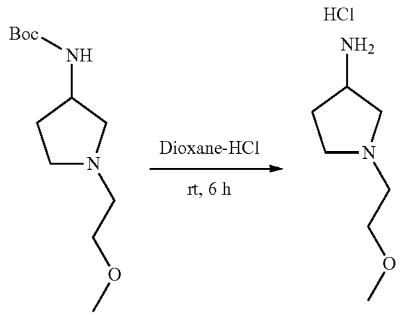

To a stirred solution of tert-butyl N-[1-(2-methoxyethyl) pyrrolidin-3-yl]carbamate (250 mg, 1.02 mmol) in dioxane (3 mL), was added 4M HCl in 1,4-dioxane (354 μL, 10.2 mmol) at 0° C. under $N_2$ atmosphere. The resulting mixture was slowly warmed to room temperature and stirred for 6 h. After completion of the reaction, the reaction mixture was concentrated under reduced pressure. The crude solid was triturated with diethyl ether (3×10 mL) to afford 1-(2-methoxyethyl)pyrrolidin-3-amine hydrochloride (150 mg, 81%) as pale yellow solid. MS (ESI) m/z: 145.5 $[M+H]^+$.

Step 3: Synthesis of ethyl 6-chloro-7-[(2R)-2-{[(3-chloropyridin-2-yl)oxy]methyl}pyrrolidin-1-yl]-1-[1-(2-methoxyethyl)pyrrolidin-3-yl]-4-oxo-1,4-dihydroquinoline-3-carboxylate

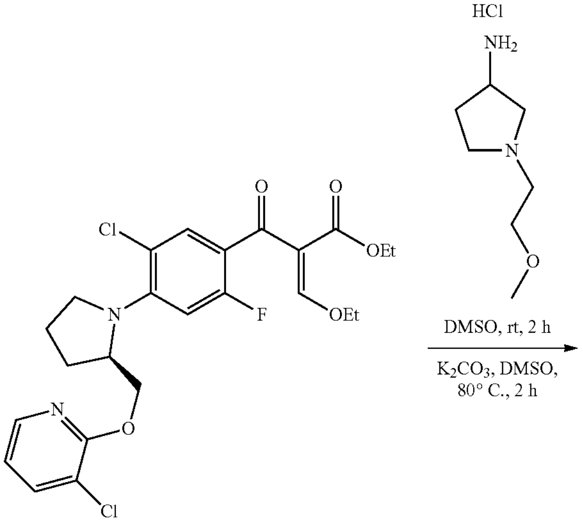

-continued

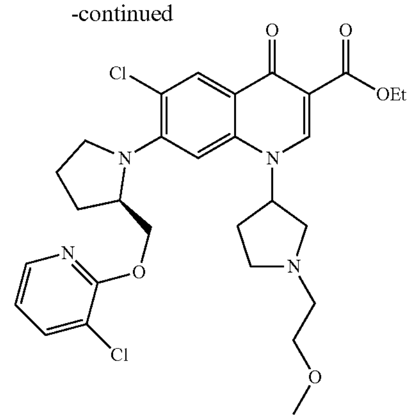

To a stirred solution of ethyl (2Z)-2-[(Z)-5-chloro-4-[(2R)-2-{[(3-chloropyridin-2-yl)oxy]-methyl}pyrrolidin-1-yl]-2-fluorobenzoyl]-3-ethoxyprop-2-enoate (300 mg, 586 μmol) in DMSO (4 mL) was added 1-(2-methoxyethyl) pyrrolidin-3-amine hydrochloride (105 mg, 586 μmol), followed by triethylamine (59.2 mg, 586 μmol) and stirred the reaction mixture at rt for 2 h under $N_2$ atmosphere. Then, potassium carbonate (80.9 mg, 586 μmol) was added. The resulting mixture was stirred at 80° C. for 2 h. After completion of reaction (monitored by TLC), the reaction mixture was quenched with ice-cold water (5 mL), which resulted in precipitation. Precipitated solid was collected by filtration and washed with water followed by hexane, then dried under vacuum filtration to get solid. The solid was dissolved in EtOH, treated with charcoal and filtered through celite pad. The filtrate was concentrated under reduced pressure to afford ethyl 6-chloro-7-[(2R)-2-{[(3-chloropyridin-2-yl)oxy]methyl}pyrrolidin-1-yl]-1-[1-(2-methoxyethyl)pyrrolidin-3-yl]-4-oxo-1,4-dihydroquinoline-3-carboxylate (114 mg, 33%) as pale brown solid. MS (ESI) m/z: 589.2 $[M+H]^+$.

Step 4: Synthesis of 6-chloro-7-[(2R)-2-{[(3-chloropyridin-2-yl)oxy]methyl}-pyrrolidin-1-yl]-1-[1-(2-methoxyethyl)pyrrolidin-3-yl]-4-oxo-1,4-dihydroquinoline-3-carboxylic acid

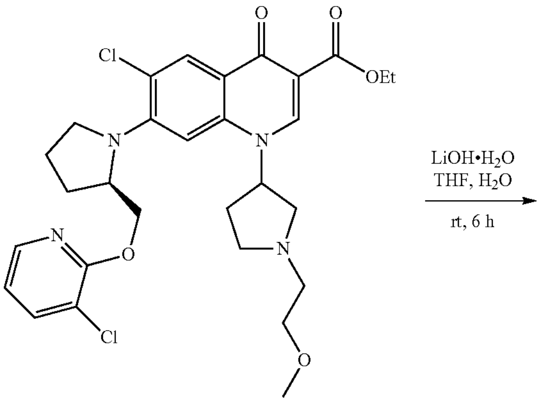

-continued

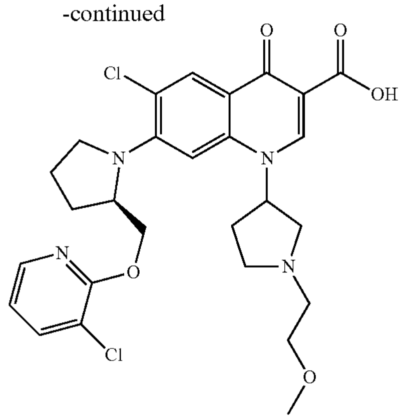

To a stirred solution of ethyl 6-chloro-7-[(2R)-2-{[(3-chloropyridin-2-yl)oxy]methyl}-pyrrolidin-1-yl]-1-[1-(2-methoxyethyl)pyrrolidin-3-yl]-4-oxo-1,4-dihydroquinoline-3-carboxylate (125 mg, 212 μmol) in THF (3 mL) was added a solution of $LiOH \cdot H_2O$ (44.0 mg, 1.05 mmol) in water (2 mL). The resulting mixture was stirred at room temperature for 6 h. After completion of the reaction (monitored by LCMS), reaction mixture was concentrated under reduced pressure, then aqueous layer was acidified with 1N HCl (pH ~3), which resulted in precipitation. The precipitated solid was collected by filtration and washed with water followed by hexane to get the crude compound. It was triturated with mixture of isopropyl alcohol, diethyl ether and n-pentane to afford desired to 6-chloro-7-[(2R)-2-{[(3-chloropyridin-2-yl)oxy]methyl}-pyrrolidin-1-yl]-1-[1-(2-methoxyethyl)pyrrolidin-3-yl]-4-oxo-1,4-dihydro quinoline-3-carboxylic acid (24.0 mg, 20%) as off white solid. $^1H$ NMR (400 MHz, DMSO-$d_6$, VT) δ 8.93 (brs, 1H), 8.15 (s, 1H), 7.92-7.88 (m, 1H), 7.70 (d, J=8.0 Hz, 1H), 7.26 (brs, 1H), 6.90-6.86 (m, 1H), 5.50 (brs, 1H), 5.04 (brs, 1H), 4.47-4.39 (m, 2H), 3.95-3.90 (m, 1H), 3.75-3.50 (m, 5H), 3.49-3.40 (m, 5H), 3.34-3.20 (m, 2H), 2.65-2.55 (m, 1H), 2.55-2.50 (m, 1H), 2.38-2.30 (m, 1H), 2.17-1.85 (m, 3H). MS (ESI) m/z: 561.3 $[M+H]^+$.

Potency Lin28a-dep Z11 $IC_{50}$ (μM)+++

Example 39: 6-chloro-7-[(2R)-2-{[(3-chloropyridin-2-yl)oxy]methyl}pyrrolidin-1-yl]-1-{1-[2-(dimethylamino)ethyl]pyrrolidin-3-yl}-4-oxo-1,4-dihydroquinoline-3-carboxylic acid

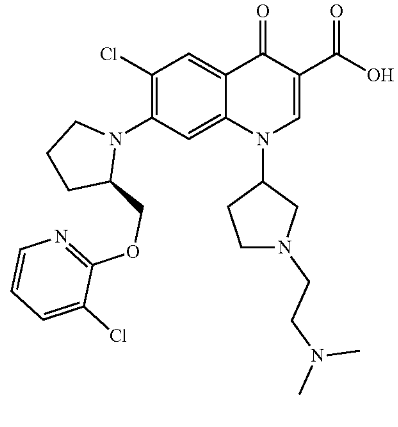 [SMILES: CN(C)CCN1CCC(n2cc(C(=O)O)c(=O)c3cc(Cl)c(N4CCC[C@@H]4COc4ncccc4Cl)cc32)C1]

Step 1: Synthesis of tert-butyl N-{1-[2-(dimethylamino)ethyl]pyrrolidin-3-yl}carbamate

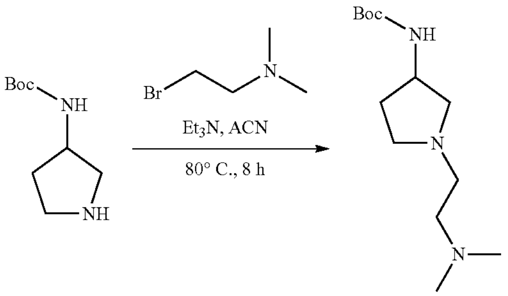

To a solution of tert-butyl N-(pyrrolidin-3-yl)carbamate (500 mg, 2.68 mmol) in acetonitrile (20 mL) were added triethylamine (1.11 mL, 8.04 mmol), and 1-(2-bromoethyl) dimethylamine (407 mg, 2.68 mmol) at room temperature under $N_2$ atmosphere. The resulting reaction mixture was stirred at 80° C. for 8 h under $N_2$ atmosphere. After completion of the reaction (monitored by TLC), the reaction mixture was concentrated under reduced pressure and quenched with ice cold water. The aqueous layer was extracted with EtOAc (2×100 mL). The combined organic layers was dried over sodium sulfate and concentrated under reduced pressure to afford tert-butyl N-{1-[2-(dimethylamino)ethyl]pyrrolidin-3-yl}carbamate (550 mg, crude) as yellow liquid. The product was proceeded to next step without purification. $^1H$ NMR (400 MHz, DMSO-$d_6$) δ 6.91 (s, 1H), 3.93-3.82 (m, 1H), 2.72-2.66 (m, 1H), 2.56-2.40 (m, 4H), 2.30-2.19 (m, 3H), 2.12 (s, 6H), 2.02-1.94 (m, 1H), 1.55-1.48 (m, 1H), 1.37 (s, 9H).

Step 2: Synthesis of 1-[2-(dimethylamino)ethyl] pyrrolidin-3-amine hydrochloride

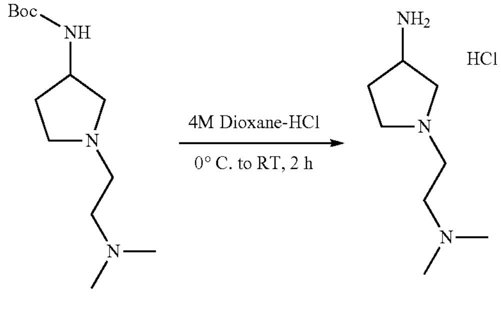 [SMILES: CN(C)CCN1CCC(NC(=O)OC(C)(C)C)C1 ; CN(C)CCN1CCC(N)C1 ; Cl]

4N HCl in dioxane (5 mL) was added to tert-butyl N-{1-[2-(dimethylamino)ethyl]pyrrolidin-3-yl}carbamate (500 mg, 1.94 mmol) at 0° C. under $N_2$ atmosphere and stirred at room temperature for 2 h. After completion of the reaction (monitored by TLC), the reaction mixture was concentrated under reduced pressure to remove volatile solvent. The crude solid was washed with diethyl ether (3×50 mL) and n-pentane to get 1-[2-(dimethylamino)ethyl] pyrrolidin-3-amine hydrochloride (250 mg, 67%) as brown solid. $^1H$ NMR (400 MHz, DMSO-$d_6$) δ 8.50 (brs, 2H), 3.93-3.87 (m, 1H), 3.56-3.39 (m, 4H), 3.29-3.21 (m, 4H), 2.81 (s, 6H), 2.33-2.16 (m, 1H), 2.08-1.98 (m, 1H).

Step 3: Synthesis of ethyl 6-chloro-7-[(2R)-2-{[(3-chloropyridin-2-yl)oxy]methyl}pyrrolidin-1-yl]-1-{1-[2-(dimethylamino)ethyl]pyrrolidin-3-yl}-4-oxo-1,4-di-hydroquinoline-3-carboxylate Step 4: Synthesis of 6-chloro-7-[(2R)-2-{[(3-chloropyridin-2-yl)oxy]methyl}pyrrolidin-1-yl]-1-{1-[2-(dimethylamino)ethyl]pyrrolidin-3-yl}-4-oxo-1,4-dihydroquinoline-3-carboxylic acid

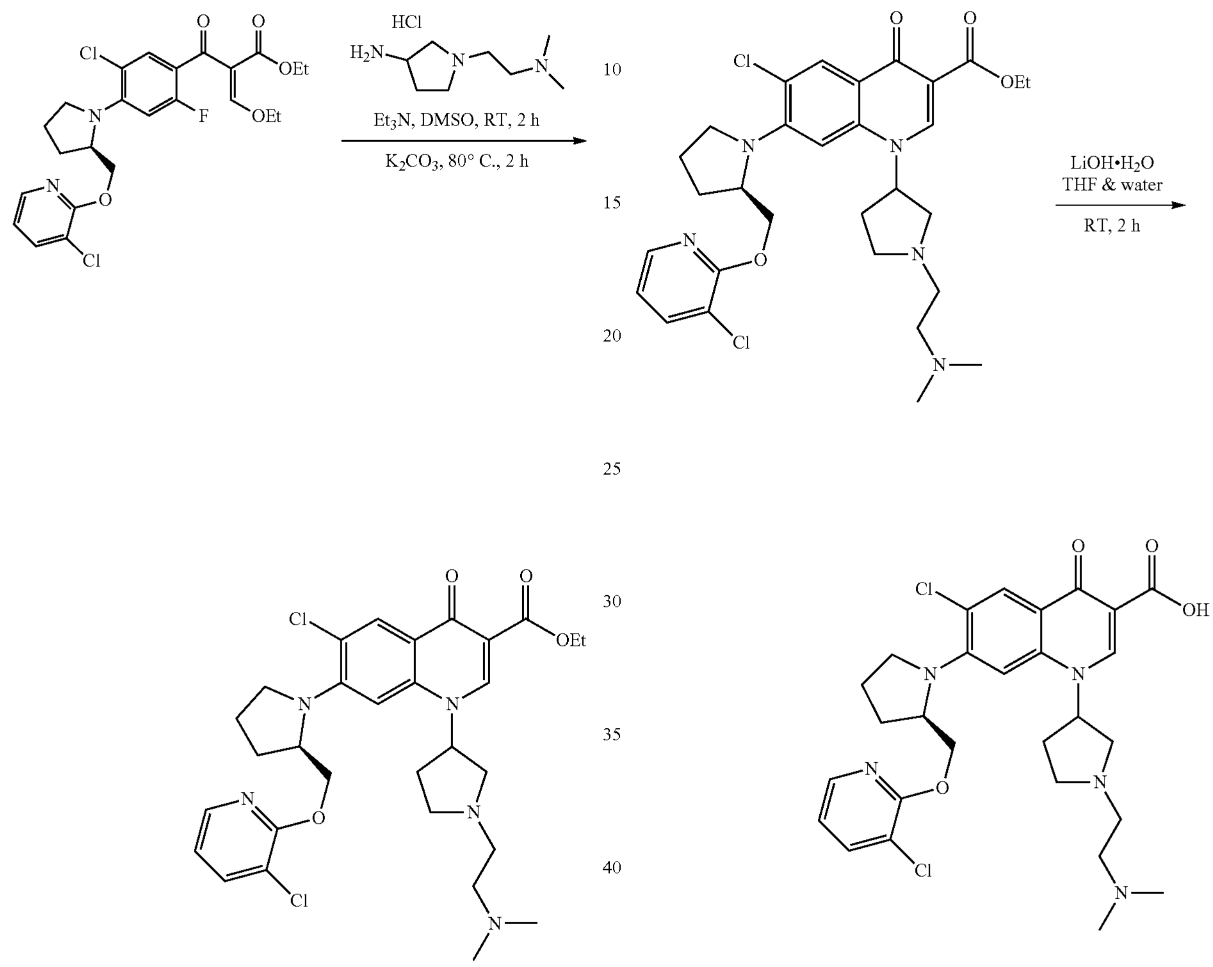

To a stirred solution of ethyl (2Z)-2-[(Z)-5-chloro-4-[(2R)-2-{[(3-chloropyridin-2-yl)oxy]methyl}pyrrolidin-1-yl]-2-fluorobenzoyl]-3-ethoxyprop-2-enoate (300 mg, 586 μmol) in DMSO (3 mL) was added 1-[2-(dimethylamino)ethyl]pyrrolidin-3-amine hydrochloride (138 mg, 878 μmol), followed by triethylamine (162 μL, 1.17 mmol) and stirred the reaction mixture at room temperature for 2 h under $N_2$ atmosphere. After completion of starting material, potassium carbonate (241 mg, 1.75 mmol) was added and the mixture was stirred at 80° C. for 2 h. Then, the reaction mixture was cooled and quenched with ice-cold water (5 mL), which resulted in precipitation. The precipitated solid was collected by filtration and washed with water followed by hexane, then dried under vacuum filtration to get solid. The solid was dissolved in EtOH, treated with charcoal and filtered through celite pad. The filtrate was concentrated under reduced pressure to afford ethyl 6-chloro-7-[(2R)-2-{[(3-chloropyridin-2-yl)oxy]methyl}pyrrolidin-1-yl]-1-{1-[2-(dimethylamino)ethyl]pyrrolidin-3-yl}-4-oxo-1,4-dihydroquinoline-3-carboxylate (124 mg, 35%) as pale brown solid. MS (ESI) m/z: 602.3 $[M+H]^+$.

To a stirred solution of ethyl 6-chloro-7-[(2R)-2-{[(3-chloropyridin-2-yl)oxy]methyl}pyrrolidin-1-yl]-1-{1-[2-(dimethylamino)ethyl]pyrrolidin-3-yl}-4-oxo-1,4-dihydroquinoline-3-carboxylate (100 mg, 165 μmol) in mixture of THF (3 mL):water (3 mL), was added $LiOH·H_2O$ (34.6 mg, 825 μmol). The resulting reaction mixture was stirred at room temperature for 2 h. After completion of the reaction (monitored by TLC), the reaction mixture was concentrated under reduced pressure, then aqueous layer was acidified with 1N HCl (pH-3), which resulted in precipitation. The precipitated solid was collected by filtration and was purified by prep HPLC to afford 6-chloro-7-[(2R)-2-{[(3-chloropyridin-2-yl)oxy]methyl}pyrrolidin-1-yl]-1-{1-[2-(dimethylamino) ethyl]pyrrolidin-3-yl}-4-oxo-1,4-dihydroquinoline-3-carboxylic acid (14.2 mg, 15%) as yellow solid. $^1H$ NMR (400 MHz, DMSO-$d_6$, VT) δ 15.31 (brs, 1H), 9.04 (s, 1H), 8.14 (s, 1H), 7.90-7.88 (m, 1H), 7.73-7.70 (m, 1H), 7.52-7.41 (m, 1H), 6.90-6.86 (m, 1H), 5.41 (brs, 1H), 4.95 (brs, 1H), 4.44-4.41 (m, 2H), 3.92-3.89 (m, 1H), 3.37-3.32 (m, 2H), 3.19-3.15 (m, 1H), 2.68-2.54 (m, 4H), 2.49-2.42 (m, 2H), 2.32-2.27 (m, 3H), 2.19 (s, 6H), 2.07-2.01 (m, 1H), 1.92-1.85 (m, 2H), MS (ESI) m/z: 574.3 $[M+H]^+$ Potency Lin28a-dep Z11 $IC_{50}$ (μM)++

Example 40: (R)-1-(6-aminopyridin-3-yl)-6-chloro-7-(2-(((3-chloropyridin-2-yl)oxy)methyl)pyrrolidin-1-yl)-4-oxo-1,4-dihydroquinoline-3-carboxylic acid

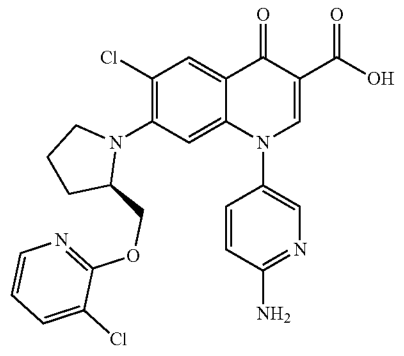

Step 1: Synthesis of ethyl 3-(5-chloro-2,4-difluorophenyl)-3-oxopropanoate

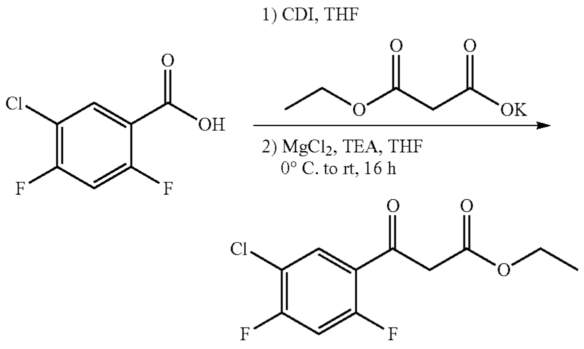

To a stirred solution of 5-chloro-2,4-difluorobenzoic acid (100 g, 519 mmol) in THF (1000 mL), was added CDI (168 g, 1.03 mol) in THF (1000 mL) drop wise at 0° C. The reaction mixture was slowly warmed to room temperature and stirred at same temperature for 1 h. After completion of reaction by TLC, potassium mono ethyl malonate (132.6 g, 775 mmol), magnesium chloride (39.4 g, 413 mmol) followed by triethylamine (220 mL, 1.57 mmol) were added at room temperature and continued the stirring for a period of 16 h. After completion of the reaction by TLC, the reaction mixture was evaporated under reduced pressure. The resulting residue was diluted with water (4000 mL) and extracted with EtOAc (3×3000 mL). The combined organic layers were washed with brine solution (2000 mL), dried over anhydrous sodium sulphate and evaporated to dryness afforded a sticky mass. Further it was triturated with methanol (400 mL), the precipitated solid was collected by filtration and dried under vacuum to afford ethyl 3-(5-chloro-2,4-difluorophenyl)-3-oxopropanoate (85.8 g, 63%) as an off white solid. $^{1}H$ NMR (400 MHz, DMSO-$d_6$) δ 7.86 (dd, J=8.8, 1.2 Hz, 1H), 7.47 (t, J=10.4 Hz, 1H), 5.12 (s, 1H), 4.01 (q, J=7.2 Hz, 2H), 1.16 (t, J=7.2 Hz, 3H).

Step 2: Synthesis of (R)-tert-butyl 2-(((3-chloropyridin-2-yl) oxy) methyl)pyrrolidine-1-carboxylate

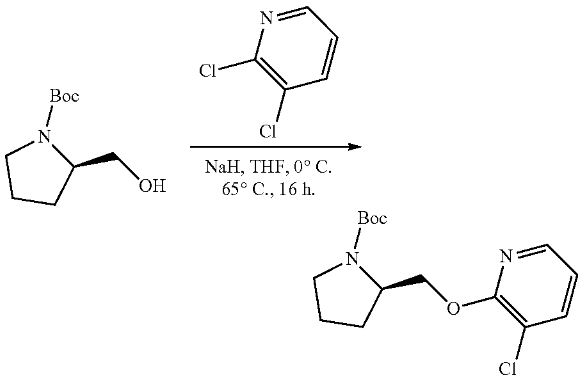

tert-butyl (R)-2-(hydroxymethyl) pyrrolidine-1-carboxylate (80 g, 397 mmol) in THF (500 mL) was added to a stirred suspension of sodium hydride (15 g, 357 mmol) in THF (150 mL) at 0° C. and continued the stirring at same temperature for 1 h before the addition of 2,3-dichloro pyridine (64.6 g, 437 mmol) in THF (30 mL). The reaction mixture was stirred at 65° C. for a period of 16 h. After completion of reaction, the reaction mixture was slowly poured in to ice water (500 mL) and the product was extracted with ethyl acetate (2×500 mL), the combined organic layers were successively washed with brine (250 mL), dried over sodium sulfate and evaporated under reduced pressure afforded crude material. The crude compound was subjected to silica gel column chromatography (100-200 mesh) and eluted with 5-10% EtOAc-Hexane. The relevant fractions containing the product were combined and evaporated to dryness afforded tert-butyl (R)-2-(((3-chloropyridin-2-yl) oxy) methyl) pyrrolidine-1-carboxylate (61 g, 50%) as pale-yellow liquid. MS (ESI) m/z: 313.0 $[M+H]^+$ relevant fractions were combined and concentrated under reduced pressure to afford tert-butyl (2R)-2-[(pyridin-3-yloxy) methyl] pyrrolidine-1-carboxylate (2.75 g, 99%) as an off white solid, MS (ESI) m/z: 279.4 $[M+H]^+$.

Step 3: Synthesis of (R)-3-chloro-2-(pyrrolidin-2-ylmethoxy) pyridine. HCl

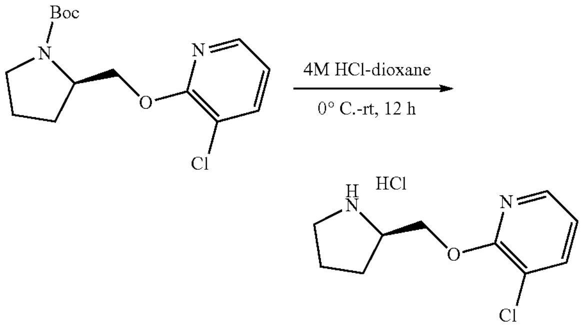

To a stirred solution of tert-butyl (R)2-{[(3-chloropyridin-2-yl) oxy] methyl} pyrrolidine-1-carboxylate (61.0 g, 195.01 mmol) in 4M 1,4 Dioxane-HCl (30 mL) at 0° C. The reaction mixture was slowly warmed to room temperature and stirred at RT for a period of 12 h. The excess solvent was removed under reduced pressure afforded a crude material. Further the crude material was triturated with diethyl ether (2×150 ml) and pentane (2×150 ml), finally dried under vacuum afforded (R)-3-chloro-2-[(pyrrolidin-2-yl) methoxy] pyridine. HCl (49 g, quantitative) as a white solid. MS (ESI) m/z: 213.1 [M+H]$^+$ (for Free base).

Step 4: Synthesis of ethyl (R)-3-(5-chloro-4-(2-(((3-chloropyridin-2-yl) oxy) methyl) pyrrolidin-1-yl)-2-fluorophenyl)-3-oxopropanoate

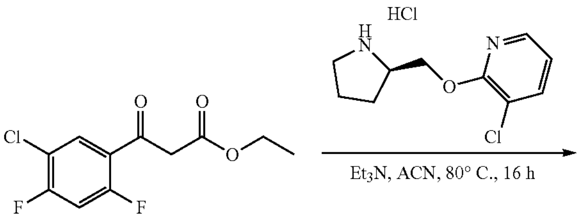

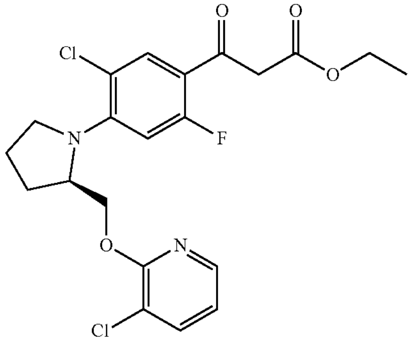

Triethyl amine (28.7 mL, 206.1 mmol) was added to the stirred solution of ethyl 3-(5-chloro-2,4-difluorophenyl)-3-oxopropanoate (36 g, 138.679 mmol) and (R)-3-chloro-2-(pyrrolidin-2-ylmethoxy) pyridine (49 g, 231.132 mmol) in ACN (200 mL), then the reaction mixture was stirred at 80° C. for a period of 16 h. Then, the reaction mixture was cooled to room temperature, the excess solvent was removed under reduced pressure, the residue was diluted with water (300 ml) and the product was extracted with DCM (2×500 ml). The combined organic layers were washed with brine (500 mL), dried over $Na_2SO_4$ and evaporated. The obtained crude material was subjected to silica gel column chromatography (100-200 mesh) and eluted the column with 10% EtOAc/Hexane. The relevant fractions containing the product were combined and evaporated to dryness afforded ethyl 3-{5-chloro-4-[(2R)-2-{[(3-chloropyridin-2-yl) oxy] methyl} pyrrolidin-1-yl]-2-fluorophenyl}-3-oxopropanoate (30 g, 77%) as green liquid, MS (ESI) m/z: 455.0 [M+H]$^+$ Step 5: Synthesis of ethyl (R,Z)-2-(5-chloro-4-(2-(((3-chloropyridin-2-yl)oxy)methyl)pyrrolidin-1-yl)-2-fluorobenzoyl)-3-ethoxyacrylate

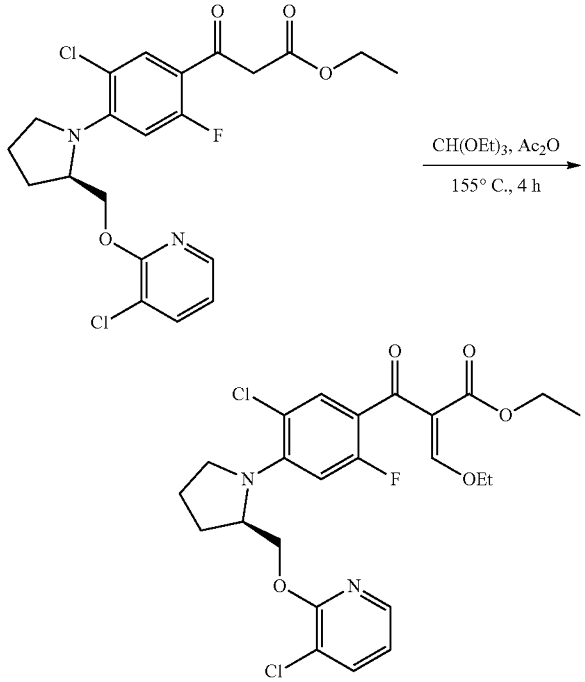

To a stirred solution of ethyl 3-{5-chloro-4-[(2R)-2-{[(3-chloropyridin-2-yl) oxy] methyl} pyrrolidin-1-yl]-2-fluorophenyl}-3-oxopropanoate (900 mg, 1.97 mmol) in acetic anhydride (117 μL, 2.07 mmol) at room temperature was added triethyl orthoformate (184 μL, 1.11 mmol) and stirred the reaction mixture at 155° C. for 4 h. After completion of reaction, the reaction mixture was cooled to room temperature, solvents were removed and the residue was azeotrope with toluene (2×10 mL) to afford ethyl (R,Z)-2-(5-chloro-4-(2-(((3-chloropyridin-2-yl) oxy) methyl) pyrrolidin-1-yl)-2-fluorobenzoyl)-3-ethoxyacrylate (747 mg, 74%) as brown liquid. The crude compound was used for the next step without further purification.

Step 6: Synthesis of (R)-ethyl 1-(6-acetamidopyridin-3-yl)-6-chloro-7-(2-(((3-chloropyridin-2-yl)oxy) methyl)pyrrolidin-1-yl)-4-oxo-1,4-dihydroquinoline-3-carboxylate

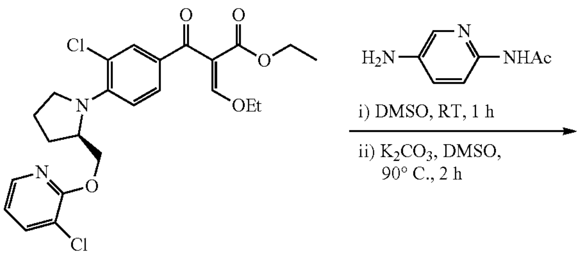

-continued

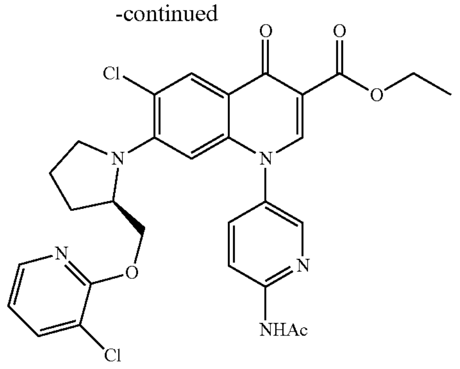

To a stirred solution of ethyl (2Z)-2-[(Z)-5-chloro-4-[(2R)-2-{[(3-chloropyridin-2-yl) oxy] methyl}pyrrolidin-1-yl]-2-fluorobenzoyl]-3-ethoxyprop-2-enoate (5 g, 9.77 mmol) in DMSO (40 mL) was added N-(5-aminopyridin-2-yl) acetamide (1.76 g, 11.7 mmol) and stirred at 27° C. for 1 h. Potassium carbonate (1.35 g, 9.77 mmol) was added to the above reaction mixture and heated the reaction mixture to 90° C. and stirred for 2 h. After completion of the reaction, the reaction mixture was cooled to room temperature, diluted the reaction mixture with ice-cold water and the product was extracted with Ethyl acetate (2×150 mL). The combined organic layers were washed with brine solution (70 mL), dried over sodium sulphate and evaporated to afford crude product. The crude product was purified by silica gel column chromatography (100-200 mesh) and eluted the column by using 60-70% EtOAc/Hexanes. The relevant fractions containing the required product were combined and distilled under reduced pressure to afford ethyl 6-chloro-7-[(2R)-2-{[(3-chloropyridin-2-yl) oxy] methyl} pyrrolidin-1-yl]-1-(6-acetamidopyridin-3-yl)-4-oxo-1,4-dihydroquinoline-3-carboxylate (1.71 g, 29%) as brown solid. MS (ESI) m/z: 596.5 $[M+H]^+$ Step 7: Synthesis of (R)-1-(6-aminopyridin-3-yl)-6-chloro-7-(2-(((3-chloropyridin-2-yl)oxy)methyl) pyrrolidin-1-yl)-4-oxo-1,4-dihydroquinoline-3-carboxylic acid

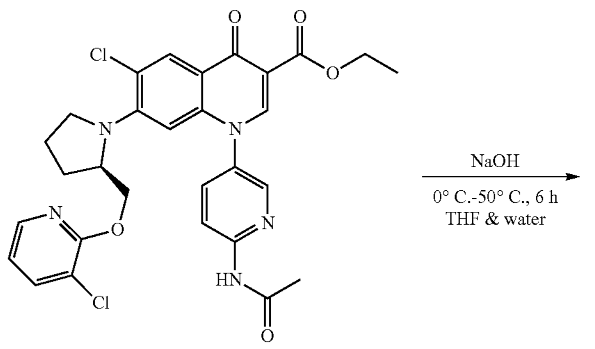

-continued

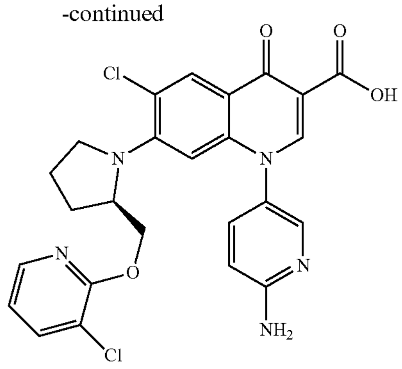

To a stirred solution of ethyl 6-chloro-7-[(2R)-2-{[(3-chloropyridin-2-yl) oxy] methyl} pyrrolidin-1-yl]-1-(6-acetamidopyridin-3-yl)-4-oxo-1,4-dihydroquinoline-3-carboxylate (2.4 g, 4.02 mmol) in THF and water (1:1, 50 mL) was added sodium hydroxide (479 mg, 12.0 mmol) at 0° C. The reaction mixture was heated to 50° C. for a period of 6 h. The reaction mixture was cooled to rt, the excess solvents were removed under reduced pressure, was diluted with water (20 ml) and acidified the aq. layer with 1N HCl at 0° C. The precipitated solid was collected by filtration, washed with water and dried under vacuum. The resulting material was triturated with washed with 10% IPA in diethyl ether (50 ml) and acetone (2×50 mL) and dried under vacuum and finally lyophilized to afford 1-(6-aminopyridin-3-yl)-6-chloro-7-[(2R)-2-{[(3-chloropyridin-2-yl)oxy]methyl}pyrrolidin-1-yl]-4-oxo-1,4-dihydroquinoline-3-carboxylic acid_(1.23 g, 58%) as an off-white solid. $^1H$ NMR (400 MHz, DMSO-$d_6$): δ 8.69 (d, J=16.4 Hz, 1H), 8.35 (s, 1H), 8.15 (d, J=2.8 Hz, 1H), 7.95-7.82 (m, 2H), 7.81-7.78 (m, 1H), 7.01-6.89 (m, 2H), 6.45 (d, J=8.4 Hz, 1H), 4.84-4.80 (m, 1H), 4.30 (s, 2H), 3.66-3.52 (m, 1H), 3.25-3.16 (m, 1H), 2.28-2.22 (m, 1H), 2.00-1.91 (m, 2H), 1.89-1.83 (m, 1H) ($-CO_2H$ & $-NH_2$ protons were not observed); MS (ESI) m/z: 526.2 $[M+H]^+$.

Potency Lin28a-dep Z11 $IC_{50}$ (μM)++++

Example 41: 6-chloro-7-[(2R,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid

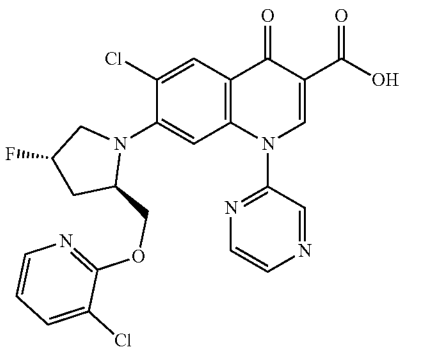 [SMILES: O=C(O)c1cn(-c2cnccn2)c2cc(N3C[C@@H](F)C[C@@H]3COc3ncccc3Cl)c(Cl)cc2c1=O]

Step 1: Synthesis of 1-tert-butyl 2-methyl (2R,4S)-4-fluoropyrrolidine-1,2-dicarboxylate

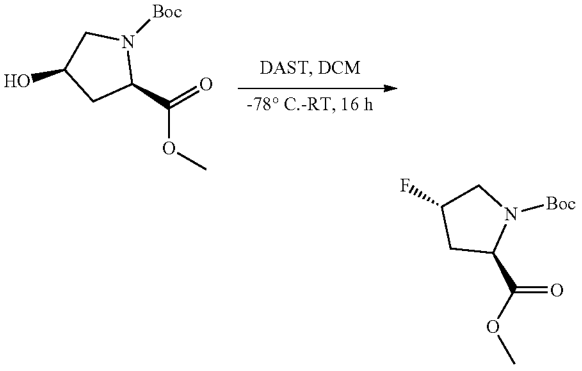

To a solution of 1-tert-butyl 2-methyl (2R,4R)-4-hydroxy-pyrrolidine-1,2-dicarboxylate (3 g, 12.2 mmol) in methylene chloride (30 mL) at −78° C., was added diethyl amino sulfur trifluoride (2.40 mL, 18.2 mmol) drop wise. The mixture was stirred at −78° C. for 2 h and then at RT for another 16 h. After completion of the reaction, the reaction was quenched with $NH_4Cl$ aqueous solution (5 mL) and was extracted with DCM (25 mL×3). The combined organic layers were dried over anhydrous $Na_2SO_4$ and concentrated in vacuo. The residue was purified by a nutral alumina column chromatography (PE/EtOAc (v/v)=20/1) to afford 1-tert-butyl 2-methyl (2R,4S)-4-fluoropyrrolidine-1,2-dicarboxylate (1.89 g, 7.64 mmol, 63% yield) as a colour less liquid. TLC System: 10% EtOAc/Hexanes, $R_f$: 0.5. $^1$H NMR (400 MHz, $CDCl_3$): δ 5.28-5.13 (m, 1H), 4.49-4.38 (m, 1H), 3.95-3.86 (m, 1H), 3.74 (s, 3H), 3.69-3.55 (dd, J=12.8, 3.2 Hz, 1H), 2.62-2.54 (m, 1H), 2.19-2.02 (m, 1H), 1.42 (s, 9H).

Step 2: Synthesis of tert-butyl (2R,4S)-4-fluoro-2-(hydroxymethyl)pyrrolidine-1-carboxylate

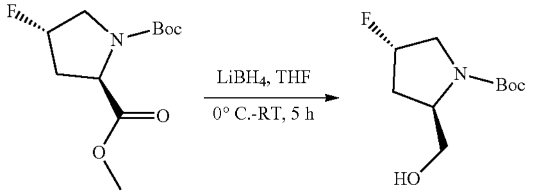 [SMILES: COC(=O)[C@H]1C[C@H](F)CN1C(=O)OC(C)(C)C ; "0° C.-RT, 5 h" ; CC(C)(C)OC(=O)N1C[C@@H](F)C[C@@H]1CO]

To a stirred solution of 1-tert-butyl 2-methyl (2R,4S)-4-fluoropyrrolidine-1,2-dicarboxylate (2.1 g, 7.64 mmol) in THF (50 mL), was added lithium borohydride (10.9 mL, 21.8 mmol) at 0° C. After 10 min, reaction mixture was allowed to room temperature and stirred for 5 h. After completion of reaction, reaction mixture quenched with acetic acid (1 mL) and water (3 mL) extract with ethyl acetate. The combined organic layer was washed with water, saturated $NaHCO_3$ solution and brine solution, dried over sodium sulfate filtered and concentrated to get tert-butyl (2R,4S)-4-fluoro-2-(hydroxymethyl)pyrrolidine-1-carboxylate (1.62 g, 7.38 mmol, 97% yield) as a colourless liquid. Which was used in next step with out any further purifications.

TLC System: 20% EtOAc/Hexanes, $R_f$: 0.3.

$^1$H NMR (400 MHz, $CDCl_3$): δ 5.16-5.03 (d, J=52.8 Hz, 1H), 4.84 (d, J=4.0 Hz, 1H), 4.16-4.14 (m, 1H), 3.89-3.74 (m, 2H), 3.60-3.55 (m, 2H), 2.36-2.29 (m, 1H), 1.81-1.70 (m, 1H), 1.48 (s, 9H).

Step 3: Synthesis of (2R,4S)-4-fluoropyrrolidin-2-yl]methanol hydrochloride

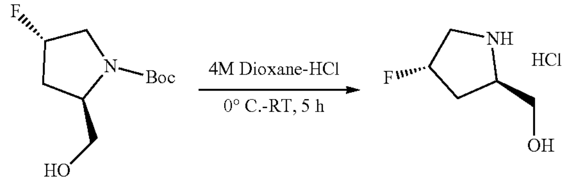 [SMILES: CC(C)(C)OC(=O)N1C[C@@H](F)C[C@@H]1CO ; "0° C.-RT, 5 h" ; OC[C@H]1C[C@H](F)CN1 ; Cl]

To a stirred solution of tert-butyl (2R,4S)-4-fluoro-2-(hydroxymethyl)pyrrolidine-1-carboxylate (1.8 g, 7.38 mmol) in 1,4-Dioxane (15 mL) was added Hydrochloric acid (3.67 mL, 14.7 mmol) at 0° C. The reaction was allowed to room temperature and stirred for 5 h. After completion of reaction, all volatiles were removed under vacuum, obtained solid was washed with diethylether (2×15 mL) to afford [(2R,4S)-4-fluoropyrrolidin-2-yl]methanol hydrochloride (888 mg, 5.70 mmol, 78%) as a off-white solid.

TLC System: 5% MeOH in DCM, $R_f$: 0.2.

$^1$H NMR (400 MHz, DMSO-$d_6$): δ 9.96 (bs, 1H), 9.33 (bs, 1H), 5.51-5.36 (d, J=57.2 Hz, 1H), 3.78-3.72 (m, 2H), 3.62-3.53 (m, 1H), 3.51-3.40 (m, 2H), 2.29-2.19 (m, 1H), 2.06-1.88 (m, 1H).

Step 4: Synthesis of ethyl 6-chloro-7-fluoro-4-oxo-1-(pyrazin-2-yl)-1,4-dihydroquinoline-3-carboxylate

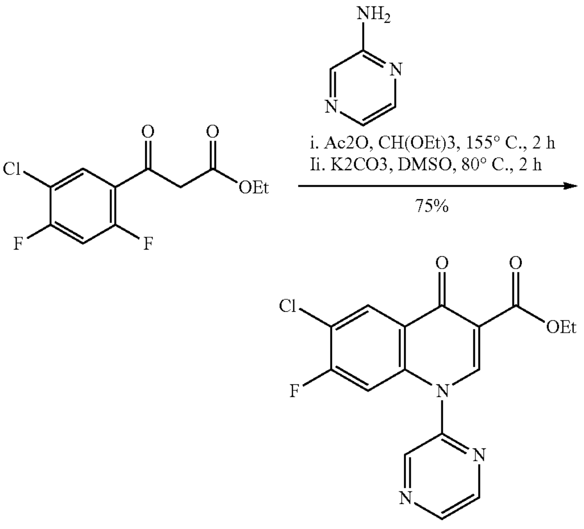

To a stirred solution of ethyl 3-(5-chloro-2,4-difluorophenyl)-3-oxopropanoate (2.0 g, 7.61 mmol) in triethyl orthoformate (1.88 mL, 11.4 mmol) was added acetic anhydride (1.07 mL, 11.4 mmol) and the resulting mixture was stirred at 155° C. for 2 h. After completion of reaction, concentrated under reduced pressure and azeotrope with toluene (2×25 ml) to get crude compound as brown liquid.

To a stirred solution of above crude compound in DMSO (20 mL) was added pyrazin-2-amine (868 mg, 9.13 mmol) at room temperature and stirred for 1 h. After completion of SM (monitored by TLC) was added potassium carbonate (1.05 g, 7.61 mmol) to the reaction mixture at RT. The reaction mixture was heated to 80° C. and stirred for 2 h. After completion of reaction, the reaction mixture was quenched with ice-cold water (50 mL), which resulted in precipitation. The precipitated solid was filtered and washed with water followed by diethyl ether and dried under vaccuo to afford ethyl 6-chloro-7-fluoro-4-oxo-1-(pyrazin-2-yl)-1,4-dihydroquinoline-3-carboxylate (1.98 g, 5.69 mmol, 75%) as pale yellow solid.

TLC system: 70% EtOAc in Hexane; Rf: 0.3.

MS (ESI) calcd for $C_{16}H_{11}ClFN_3O_3$: 347.05; found: 347.9 $[M+H]^+$ (rt: 2.74 min).

Step 5: Synthesis of ethyl 6-chloro-7-[(2R,4S)-4-fluoro-2-(hydroxymethyl)pyrrolidin-1-yl]-4-oxo-1-(pyrazin-2-yl)-1,4-dihydroquinoline-3-carboxylate

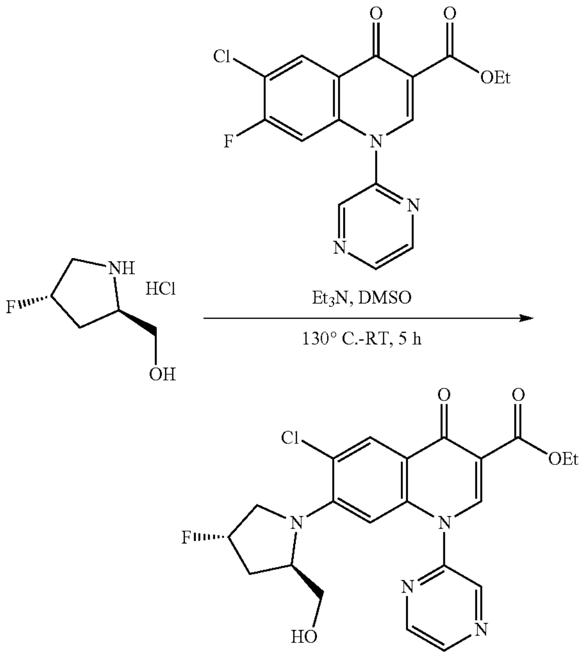

To a stirred solution of [(2R,4S)-4-fluoropyrrolidin-2-yl] methanol hydrochloride (1.11 g, 5.70 mmol) in dimethyl sulfoxide (15 mL), was added triethylamine (1.88 mL, 14.3 mmol) and stirred for 5 min. After 5 min, was added ethyl 6-chloro-7-fluoro-4-oxo-1-(pyrazin-2-yl)-1,4-dihydroquinoline-3-carboxylate (1 g, 2.87 mmol) and stirred at 130° C. for 16 h in sealed tube. After completion of reaction, reaction mixture was quenched with water and extracted with EtOAc (3×25 mL). The combined organic layer was washed with cold water, brine solution, dried over anhydrous Na2SO4 filtered and concentrated to get crude compound. The obtained crude compound was purified by column chromatography (eluted with 5% MeOH in DCM) to afford ethyl 6-chloro-7-[(2R,4S)-4-fluoro-2-(hydroxymethyl)pyrrolidin-1-yl]-4-oxo-1-(pyrazin-2-yl)-1,4-dihydroquinoline-3-carboxylate (445 mg, 995 μmol, 35%) as yellowish gummy material.

TLC System: 5% MeOH/DCM, $R_f$: 0.5

MS (ESI) calcd for $C_{21}H_{20}ClFN_4O_4$: 446.1; found: 447.0 $[M+H]^+$ (rt: 2.50 min).

Step 6: Synthesis of ethyl 6-chloro-7-((2R,4S)-2-(((3-chloropyridin-2-yl)oxy)methyl)-4-fluoropyrrolidin-1-yl)-4-oxo-1-(pyrazin-2-yl)-1,4-dihydroquinoline-3-carboxylate

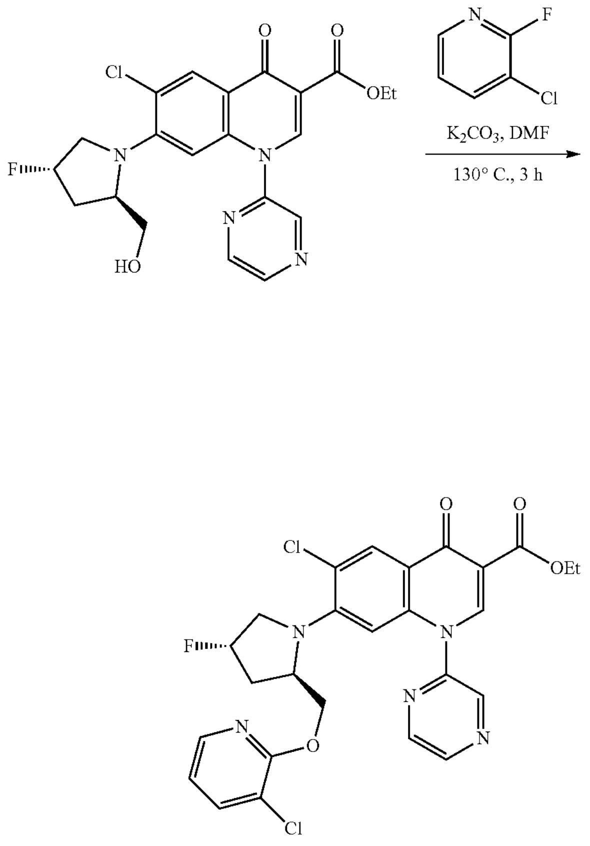

To a stirred solution of ethyl 6-chloro-7-[(2R,4S)-4-fluoro-2-(hydroxymethyl)pyrrolidin-1-yl]-4-oxo-1-(pyrazin-2-yl)-1,4-dihydroquinoline-3-carboxylate (500 mg, 995 μmol) in DMSO (10 mL) were added 3-chloro-2-fluoropyridine (653 mg, 4.97 mmol) and potassium carbonate (686 mg, 4.97 mmol) at room temperature. The reaction mixture was stirred at 130° C. for 3 h. After completion of reaction, reaction mixture was quenched with water and extracted with EtOAc (3×20 mL). The combined organic layer was washed with cold water, brine solution, dried over anhydrous $Na_2SO_4$ filtered and concentrated to get crude compound. The obtained crude compound was purified by column chromatography to afford ethyl 6-chloro-7-[(2R,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylate (105 mg, 188 μmol, 19%) as pale yellow gummy material.

TLC System: 100% EtOAc, $R_f$: 0.5

MS (ESI) calcd for $C_{26}H_{22}Cl_2FN_5O_4$: 557.10; found: 558.1 $[M+H]^+$ (rt: 3.21 min).

Step 7: Synthesis of 6-chloro-7-[(2R,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid

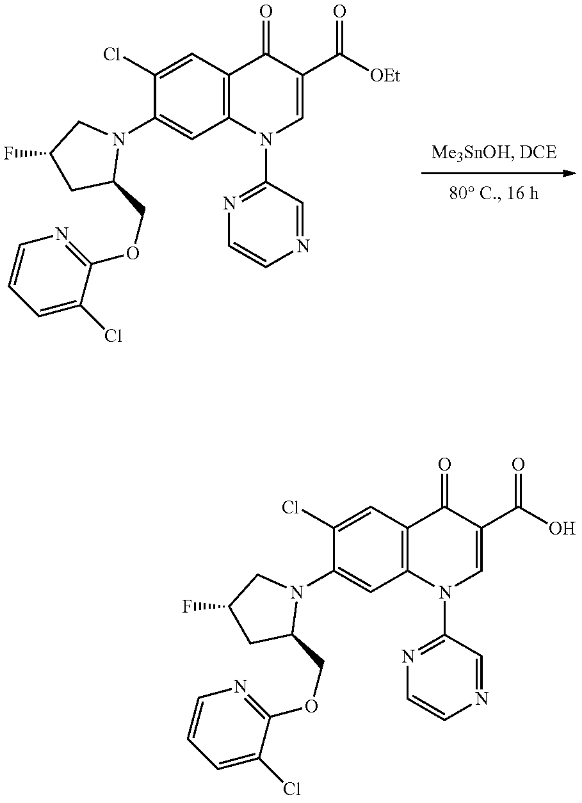

To a stirred solution of ethyl 6-chloro-7-[(2R,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylate (300 mg, 188 μmol) in ethylene dichloride (10 mL) was added trimethyl tin hydroxide (136 mg, 752 μmol) at room temperature. The reaction mixture was heated to 80° C. and stirred for 16 h. After completion of reaction, reaction mixture was diluted with DCM (20 mL) and organic layer was washed with water, brine solution, dried over anhydrous $Na_2SO_4$ filtered and concentrated to get crude. The obtained crude compound was purified by reverse phase prep HPLC and pure fractions were dried under lypholization to afford 6-chloro-7-[(2R,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid (25.4 mg, 48.0 μmol, 25% yield) as an off-white solid.

TLC System: 10% MeOH/DCM, $R_f$: 0.5

MS (ESI): calcd for $C_{24}H_{18}Cl_2FN_5O_4$: 529.07; found: 530.3 $[M+H]^+$ (rt: 5.977 min).

$^1H$ NMR (400 MHz, DMSO-$d_6$): δ 14.8 (bs, 1H), 9.13 (s, 1H), 8.95 (d, J=3.2 Hz, 2H), 8.79 (d, J=1.2 Hz, 2H), 8.21 (s, 1H), 7.86-7.85 (dd, J=4.8, 1.6 Hz, 1H), 7.80-7.77 (dd, J=4.0, 1.4 Hz, 1H), 6.94-6.91 (q, J=5.2 Hz, 1H), 6.67 (s, 1H), 5.46-5.33 (d, J=53.2 Hz, 1H), 4.85-4.83 (m, 1H), 4.43-4.39 (dd, J=12.0, 3.8 Hz, 1H), 4.29-4.26 (dd, J=11.8, 3.4 Hz, 1H), 3.91-3.75 (m, 1H), 2.42-2.40 (m, 1H), 2.24-2.20 (m, 1H).

Potency Lin28a-dep Z11 $IC_{50}$ (μM)++++

Example 42: Synthesis of 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylic acid

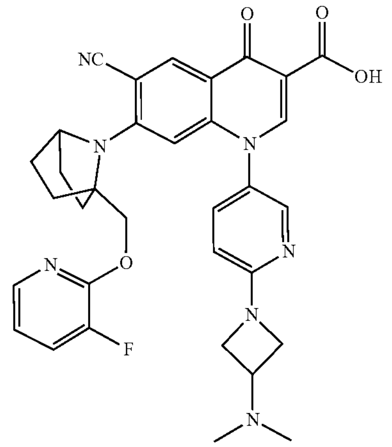 [SMILES: CN(C)C1CN(c2ccc(-n3cc(C(=O)O)c(=O)c4cc(C#N)c(N5C6CCC5(COc5ncccc5F)CC6)cc43)cn2)C1]

Step 1: Synthesis of (trans)-4-((tert-butoxycarbonyl)amino)cyclohexyl methanesulfonate

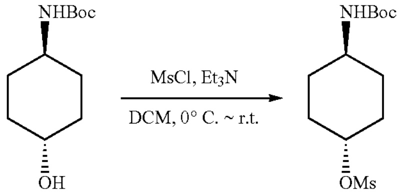 [SMILES: CC(C)(C)OC(=O)N[C@H]1CC[C@H](O)CC1 ; CC(C)(C)OC(=O)N[C@H]1CC[C@H](OS(C)(=O)=O)CC1]

To a stirred solution of tert-butyl ((trans)-4-hydroxycyclohexyl)carbamate (4.0 g, 18.59 mmol) and TEA (5.6 g, 55.77 mmol) in DCM (50 mL) at 0° C. was added MsCl (3.2 g, 27.89 mmol). The mixture was stirred at room temperature for 3 h. The reaction was quenched by the addition of 100 mL water.

The aqueous solution was extracted with DCM (50 mL×3). The combined organic phase was dried over $Na_2SO_4$ and concentrated to give the residue which was purified by flash column with 0-50% EtOAc in Petroleum ether to afford (trans)-4-((tert-butoxycarbonyl)amino)cyclohexyl methanesulfonate (3.3 g, 61%) as white solid. LCMS (ESI) $[M+H]^+$: 294.

Step 2: Synthesis of tert-butyl 7-azabicyclo[2.2.1]heptane-7-carboxylate

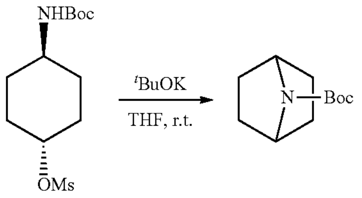 [SMILES: "tBuOK" ; CC(C)(C)OC(=O)N[C@H]1CC[C@H](OS(C)(=O)=O)CC1 ; CC(C)(C)OC(=O)N1C2CCC1CC2]

To a stirred solution of (trans)-4-((tert-butoxycarbonyl)amino)cyclohexyl methanesulfonate (4.0 g, 13.65 mmol) in anhydrous THF (100 mL) was added t-BuOK (4.6 g, 40.94 mmol) under $N_2$. The mixture was stirred at room temperature for 3 h. The mixture was concentrated under reduced pressure to give the residue which was purified by flash chromatography eluting with 0-50% EtOAc in Petroleum ether to afford tert-butyl 7-azabicyclo[2.2.1]heptane-7-carboxylate (1.5 g, 56%) as colorless oil. LCMS (ESI) $[M+H]^+$: 198.

Step 3: Synthesis of tert-butyl 1-formyl-7-azabicyclo[2.2.1]heptane-7-carboxylate

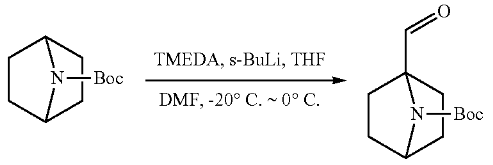 [SMILES: CC(C)(C)OC(=O)N1C2CCC1CC2 ; CC(C)(C)OC(=O)N1C2CCC1(C=O)CC2]

To a stirred solution of tert-butyl 7-azabicyclo[2.2.1]heptane-7-carboxylate (1.4 g, 7.10 mmol) and TMEDA (989 mg, 8.52 mmol) in anhydrous THF (20 mL) at −78° C. was added s-BuLi (4.3 mL, 10.65 mmol) under $N_2$. The mixture was stirred at this temperature for 1 h. DMF (622 mg, 8.52 mmol) was then added. The resultant was stirred for 1 h. The reaction was quenched by the addition of 40 mL water. The aqueous solution was extracted with EtOAc (50 mL×3). The combined organic phase was dried over $Na_2SO_4$ and concentrated under reduced pressure to give the residue which was purified by flash chromatography eluting with 0-50% EtOAc in Petroleum ether to afford tert-butyl 1-formyl-7-azabicyclo[2.2.1]heptane-7-carboxylate (700 mg, 44%) as colorless oil. LCMS (ESI) $[M+H]^+$:226.

Step 4: Synthesis of tert-butyl 1-(hydroxymethyl)-7-azabicyclo[2.2.1]heptane-7-carboxylate

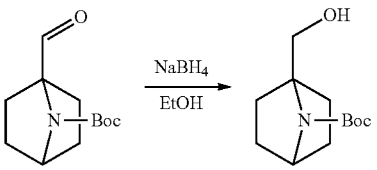 [SMILES: "EtOH" ; CC(C)(C)OC(=O)N1C2CCC1(C=O)CC2 ; "NaBH4" ; CC(C)(C)OC(=O)N1C2CCC1(CO)CC2]

To a stirred solution of tert-butyl 1-formyl-7-azabicyclo[2.2.1]heptane-7-carboxylate (700 mg, 3.10 mmol) in EtOH (10 mL) at 0° C. was added $NaBH_4$ (236 mg, 6.20 mmol). The mixture was stirred at room temperature for 1 h. The reaction was quenched by the addition of 20 mL water. The aqueous solution was extracted with EtOAc (20 mL×3). The combined organic solution was dried over $Na_2SO_4$ and concentrated under reduced pressure to give the residue which was purified by flash chromatography eluting with 0-50% EtOAc in Petroleum ether to afford tert-butyl 1-(hydroxymethyl)-7-azabicyclo[2.2.1]heptane-7-carboxylate (500 mg, 71%) as colorless oil. LCMS (ESI) $[M+H]^+$:228.

Step 5: Synthesis of tert-butyl 1-(((3-fluoropyridin-2-yl)oxy)methyl)-7-azabicyclo[2.2.1]heptane-7-carboxylate

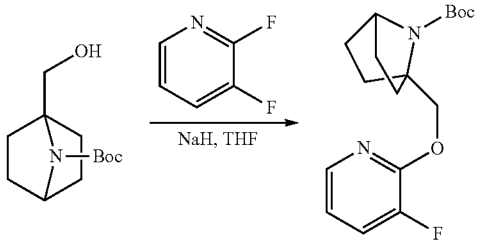

To a solution of tert-butyl 1-(hydroxymethyl)-7-azabicyclo[2.2.1]heptane-7-carboxylate (500 mg, 2.20 mmol) in anhydrous THF (10 mL) was added NaH (264 mg, 6.60 mmol) and 2,3-difluoropyridine (380 mg, 3.30 mmol) under $N_2$. The mixture was stirred at room temperature for 16 h. The reaction was quenched by the addition of 20 mL water. The aqueous solution was extracted with EtOAc (20 mL×3). The combined organic phase was dried over $Na_2SO_4$ and concentrated under reduced pressure to give the residue which was purified by flash chromatography eluting with 0-50% EtOAc in Petroleum ether to afford tert-butyl 1-(((3-fluoropyridin-2-yl)oxy)methyl)-7-azabicyclo[2.2.1]heptane-7-carboxylate (520 mg, 73%) as light yellow oil. LCMS (ESI) $[M+H]^+$: 323.

Step 6: Synthesis of 1-(((3-fluoropyridin-2-yl)oxy)methyl)-7-azabicyclo[2.2.1]heptane

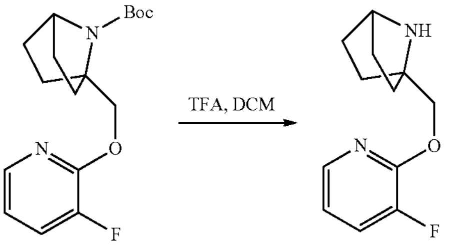

To a solution of tert-butyl 1-(((3-fluoropyridin-2-yl)oxy)methyl)-7-azabicyclo[2.2.1]heptane-7-carboxylate (520 mg, 1.61 mmol) in DCM (10 mL) was added TFA (5 mL). The solution was stirred at room temperature for 2 h. The reaction solution was concentrated under reduced pressure to give the residue which was dissolved in MeOH. $NH_3 \cdot H_2O$ was added to adjust pH 9. The mixture was concentrated under reduced pressure to give the residue which was purified by flash chromatography eluting with 0-10% MeOH in DCM to afford 1-(((3-fluoropyridin-2-yl)oxy)methyl)-7-azabicyclo[2.2.1]heptane (400 mg, crude) as light yellow oil. LCMS (ESI) $[M+H]^+$: 223.

Step 7: Synthesis of ethyl 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylate

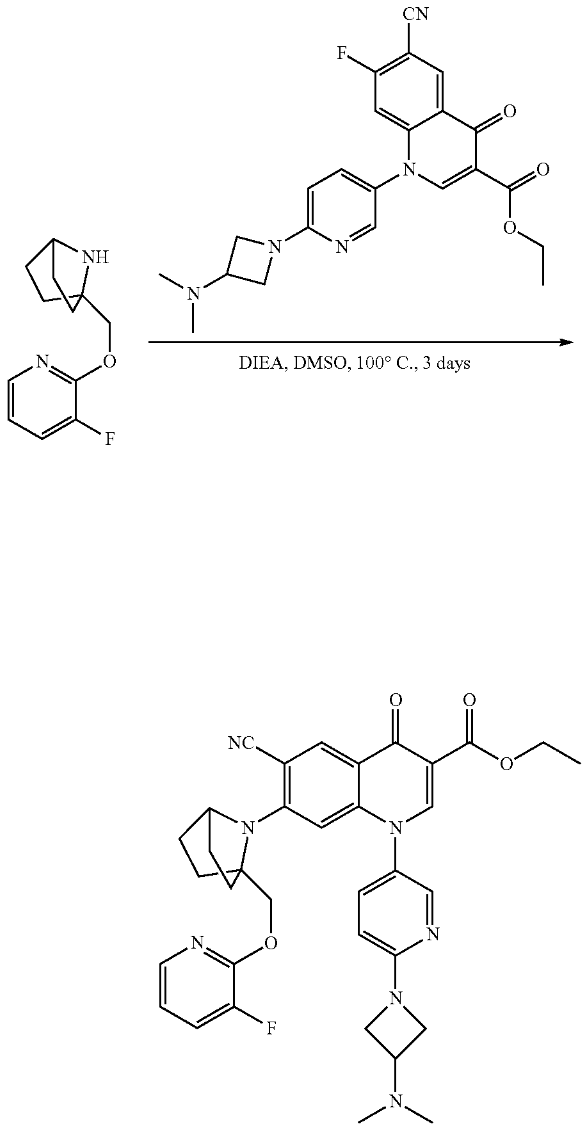

To a 8-mL sealed tube was added ethyl 6-cyano-1-(6-(3-(dimethylamino)azetidin-1-yl)pyridin-3-yl)-7-fluoro-4-oxo-1,4-dihydroquinoline-3-carboxylate (200 mg, 0.46 mmol), 1-(((3-fluoropyridin-2-yl)oxy)methyl)-7-azabicyclo[2.2.1]heptane (204 mg, 0.92 mmol) and DMSO (0.2 mL). The resulting mixture was heated at about 50° C. under vacuum for 1 h. Then DIEA (119 mg, 0.92 mmol, 2 equiv) was added into the mixture. The resulting mixture was stirred at 100° C. for 3 days under $N_2$. The mixture was purified by reverse phase flash chromatography eluting with 20-80% acetonitrile in water to afford ethyl 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylate (55 mg, 19%) as yellow solid. LCMS (ESI) $[M+H]^+$: 638.

Step 8: Synthesis of 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylic acid

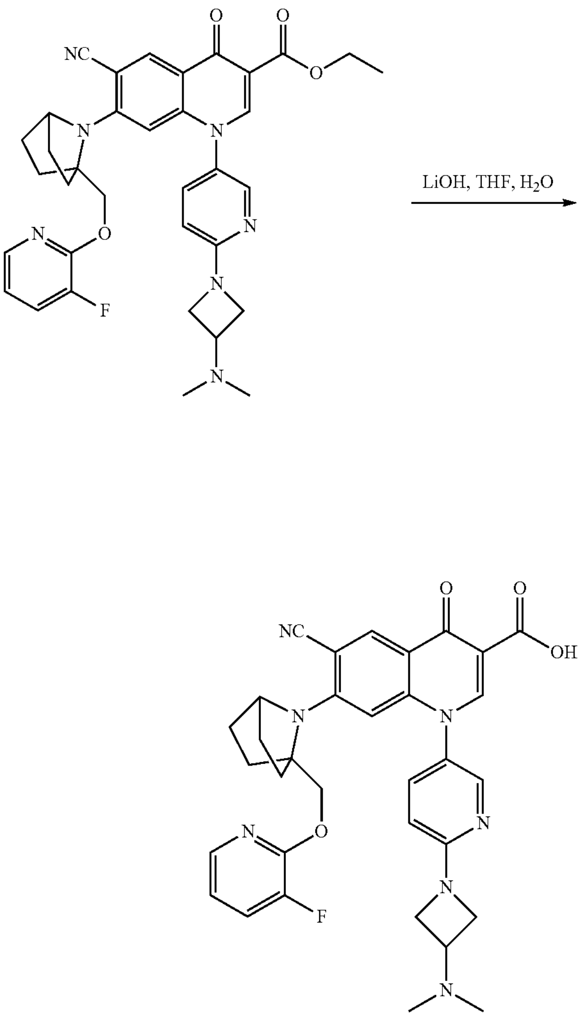

To a stirred solution of ethyl 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylate (85 mg, 0.13 mmol) in THF (2 mL) was added a solution of $LiOH \cdot H_2O$ (56 mg, 1.33 mmol) in $H_2O$ (2 mL) at room temperature under $N_2$. The resulting mixture was stirred at room temperature overnight. The mixture was acidified by AcOH. The mixture was purified by Prep.-HPLC to afford 6-cyano-1-(6-(3-(dimethylamino)azetidin-1-yl)pyridin-3-yl)-7-(1-(((3-fluoropyridin-2-yl)oxy)methyl)-7-azabicyclo[2.2.1]heptan-7-yl)-4-oxo-1,4-dihydroquinoline-3-carboxylic acid (45.5 mg, 57%) as yellow solid. LCMS (ESI) $[M+H]^+$:610.35. $^1H$ NMR (300 MHz, DMSO-d6) δ 8.59 (d, J=14.4 Hz, 2H), 8.24 (m, 1H), 7.89 (d, J=4.7 Hz, 1H), 7.78-7.52 (m, 2H), 7.10-6.96 (m, 1H), 6.74 (s, 1H), 6.42 (d, J=8.9 Hz, 1H), 4.62 (s, 2H), 4.31 (s, 1H), 3.98 (t, J=7.8 Hz, 2H), 3.81-3.68 (m, 2H), 3.26-3.11 (m, 1H), 2.12 (s, 6H), 1.73 (dd, J=24.4, 14.4 Hz, 6H), 1.54 (d, J=9.2 Hz, 2H).

Potency Lin28a-dep Z11 $IC_{50}$ (μM)++++

Example 43: Synthesis of (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid

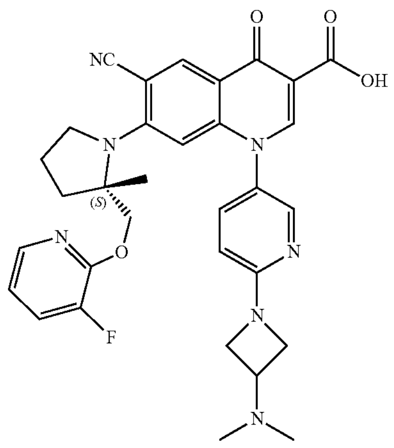

Step 1: Synthesis of (S)-1-(tert-butoxycarbonyl)-2-methylpyrrolidine-2-carboxylic acid

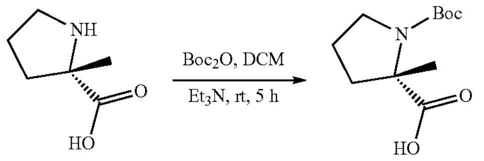

To a stirred solution of (S)-2-methylpyrrolidine-2-carboxylic acid (3.6 g, 27.87 mmol) in DCM (100 mL) was added $(Boc)_2O$ (18.25 g, 83.61 mmol, 3 equiv) and $Et_3N$ (8.46 g, 83.61 mmol, 3 equiv). The resulting mixture was stirred at room temperature for 5 h. Then the reaction was quenched by the addition of brine (200 mL). The mixture was extracted with DCM (100 mL×3). The combined organic phase was dried over $MgSO_4$. After filtration, the filtrate was concentrated under reduced pressure. This resulted in the crude product (S)-1-(tert-butoxycarbonyl)-2-methylpyrrolidine-2-carboxylic acid (6.38 g, 27.8 mmol) as colorless crystal. LCMS (ESI) $[M+H]^+$:230.

Step 2: Synthesis of tert-butyl (S)-2-(hydroxymethyl)-2-methylpyrrolidine-1-carboxylate

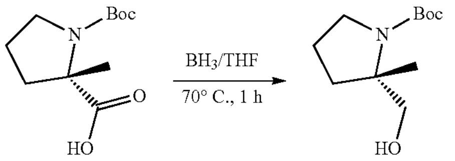 [SMILES: CC(C)(C)OC(=O)N1CCC[C@@]1(C)C(=O)O ; "70° C., 1 h" ; CC(C)(C)OC(=O)N1CCC[C@@]1(C)CO]

To a solution of (S)-1-(tert-butoxycarbonyl)-2-methylpyrrolidine-2-carboxylic acid (6.38 g, 27.8 mmol) in anhydrous THF (100 mL) was added $BH_3 \cdot Me_2S$ (10.56 g, 139 mmol, 5 equiv) at room temperature under $N_2$. Then the resulting mixture was stirred at 70° C. for 1 h. After cooling down to room temperature. The mixture was concentrated under reduced pressure. The residue was purified by silica gel column chromatography eluting with Petroleum ether/EtOAc=1:1 to afford tert-butyl (S)-2-(hydroxymethyl)-2-methylpyrrolidine-1-carboxylate (4.1 g, 19.04 mmol) as colorless oil. LCMS (ESI) $[M+H]^+$:216.

Step 3: Synthesis of tert-butyl (S)-2-(((3-fluoropyridin-2-yl)oxy)methyl)-2-methylpyrrolidine-1-carboxylate

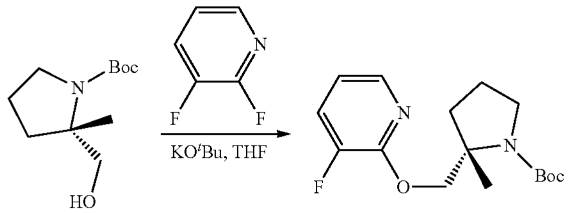

To a stirred solution of tert-butyl (S)-2-(hydroxymethyl)-2-methylpyrrolidine-1-carboxylate (4.1 g, 19.04 mmol) in anhydrous THF (100 mL) was added KO$^t$Bu (6.41 g, 57.12 mmol, 3 equiv) at 0° C. under $N_2$. After 10 min, 2,3-difluoropyridine (2.63 g, 22.85 mmol, 1.2 equiv) was added into the mixture and the resulting mixture was stirred at 0° C. for half an hour and followed by room temperature for 4 h. Then the reaction was quenched by the addition of brine (200 mL). The mixture was extracted with EtOAc (100 mL×3). The combined organic phase was dried over $MgSO_4$. After filtration, the filtrate was concentrated under reduced pressure. The residue was purified by silica gel column chromatography eluting with Petroleum ether/EtOAc=2:1 to afford tert-butyl (S)-2-(((3-fluoropyridin-2-yl)oxy)methyl)-2-methylpyrrolidine-1-carboxylate (4.3 g, 13.85 mmol) as colorless oil. LCMS (ESI) $[M+H]^+$:311.

Step 4: Synthesis of (S)-3-fluoro-2-((2-methylpyrrolidin-2-yl)methoxy)pyridine

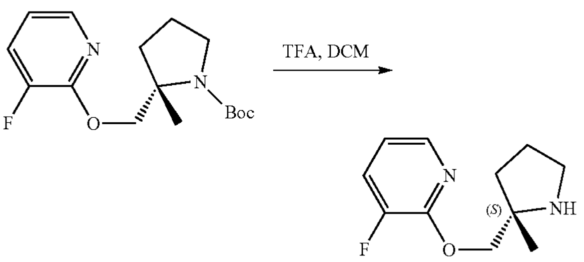

To a stirred solution of tert-butyl (S)-2-(((3-fluoropyridin-2-yl)oxy)methyl)-2-methylpyrrolidine-1-carboxylate (4.3 g, 13.85 mmol) in DCM (10 mL) was added TFA (15 mL). The mixture was stirred at room temperature for 4 h. The mixture was concentrated under reduced pressure. The residue was dissolved in sat. $NaHCO_3$ (200 mL) and extracted with EtOAc (100 mL×3). The combined organic phase was dried over $MgSO_4$. After filtration, the filtrate was concentrated under reduced pressure. This resulted in the (S)-3-fluoro-2-

((2-methylpyrrolidin-2-yl)methoxy)pyridine (2.6 g, 12.36 mmol) as colorless oil. LCMS (ESI) $[M+H]^+$:211.

Step 5: Synthesis of ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate

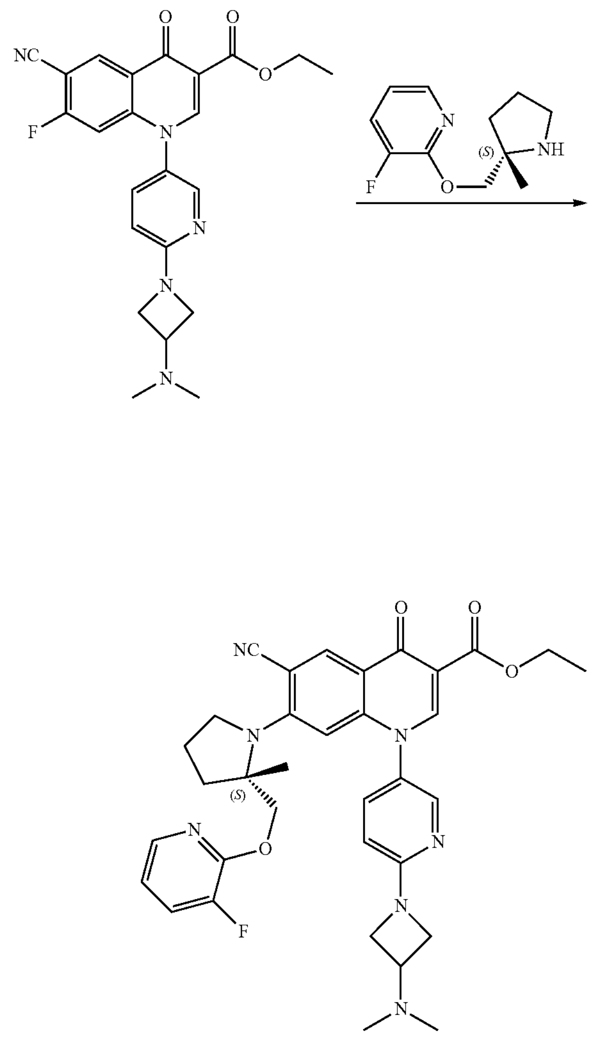

To a 8-mL sealed tube was added ethyl 6-cyano-1-(6-(3-(dimethylamino)azetidin-1-yl)pyridin-3-yl)-7-fluoro-4-oxo-1,4-dihydroquinoline-3-carboxylate (500 mg, 1.148 mmol), (S)-3-fluoro-2-((2-methylpyrrolidin-2-yl)methoxy)pyridine (724 mg, 3.445 mmol, 3 equiv) and DMSO (1 mL). The resulting mixture was heated at about 50° C. under vacuum for 1 h. Then DIEA (297 mg, 2.296 mmol, 2 equiv) was added into the mixture. The resulting mixture was stirred at 100° C. for 48 h under $N_2$. The mixture was purified by reverse phase chromatography eluting with Acetonitrile/water=7:3 to afford ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate (150 mg, 0.2397 mmol) as yellow solid. LCMS (ESI) $[M+H]^+$:626.

Step 6: Synthesis of (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid

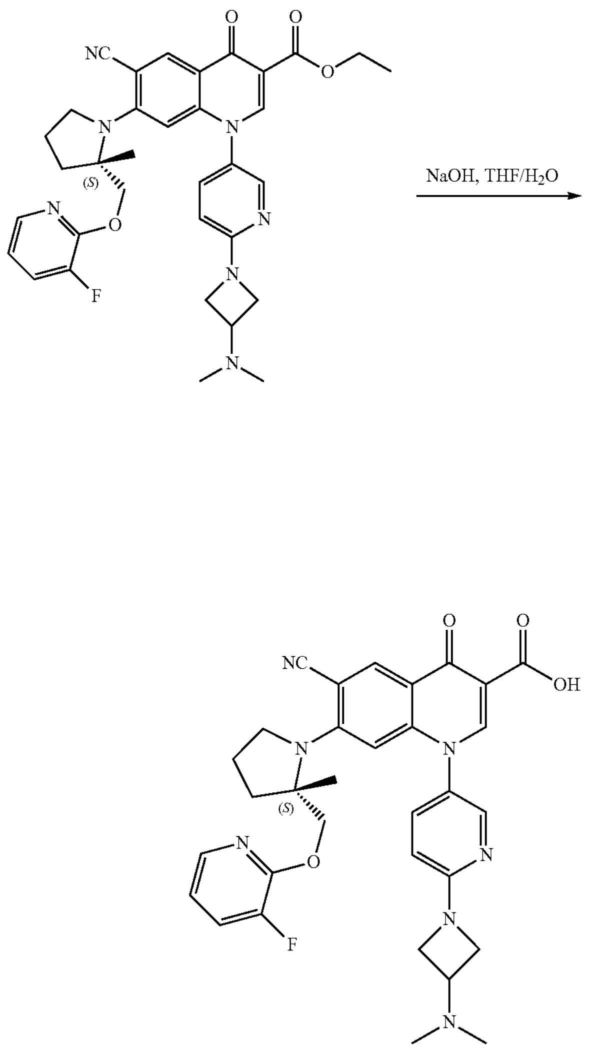

To a stirred solution of ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate (150 mg, 0.2397 mmol) in THF (4 mL) was added a solution of NaOH (19 mg, 0.4794 mmol, 2 equiv) in $H_2O$ (2 mL) at room temperature under $N_2$. The resulting mixture was stirred at room temperature overnight. The mixture was acidified by AcOH. The mixture was purified by Prep.-HPLC to afford (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid (32.8 mg) as yellow solid. LCMS (ESI) $[M+H]^+$:598.25. $^1H$ NMR (300 MHz, DMSO-d6) δ 14.69 (s, 1H), 8.63-8.07 (m, 3H), 7.91-7.51 (m, 3H), 7.01 (m, 1H), 6.60-6.25 (m, 2H), 4.34 (m, 2H), 4.08-3.83 (m, 4H), 3.81-3.59 (m, 2H), 3.21 (d, J=4.7 Hz, 1H), 2.28-2.19 (m, 1H), 2.13 (s, 6H), 1.97 (dd, J=19.6, 9.9 Hz, 3H), 1.22 (d, J=11.5 Hz, 3H).

Potency Lin28a-dep Z11 $IC_{50}$ (μM)++++

Example 44: Synthesis of rac-6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylic acid

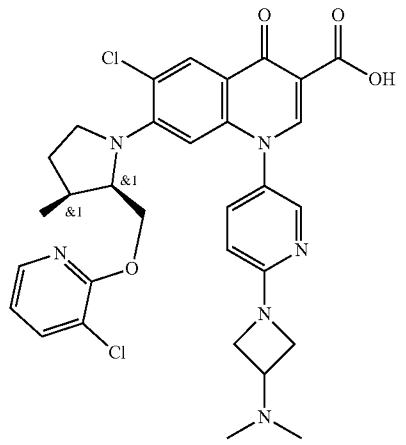 [SMILES: C[C@H]1CCN(c2cc3c(cc2Cl)c(=O)c(C(=O)O)cn3-c2ccc(N3CC(N(C)C)C3)nc2)[C@H]1COc1ncccc1Cl]

Step 1: Synthesis of 1-tert-butyl 2-methyl 3-bromopyrrole-1,2-dicarboxylate

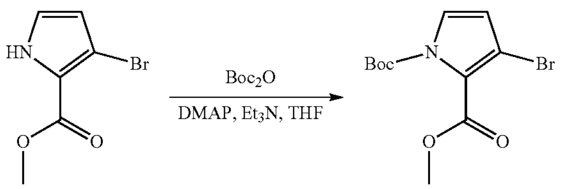

A mixture of methyl 3-bromo-1H-pyrrole-2-carboxylate (5.0 g, 24.51 mmol, 1.0 equiv), di-tert-butyl dicarbonate (8.0 g, 36.76 mmol, 1.5 equiv), DMAP (299 mg, 2.45 mmol, 0.1 equiv) and $Et_3N$ (7.4 g, 73.52 mmol, 3 equiv) in DCM (45 mL) was stirred for 1 h at room temperature under nitrogen atmosphere. The resulting mixture was concentrated under vacuum. The residue was purified by silica gel column chromatography, eluted with P E/EtOAc (5:1) to afford 1-tert-butyl 2-methyl 3-bromopyrrole-1,2-dicarboxylate (6.5 g, 87.21%) as a yellow oil.

Step 2: Synthesis of 1-tert-butyl 2-methyl 3-methylpyrrole-1,2-dicarboxylate

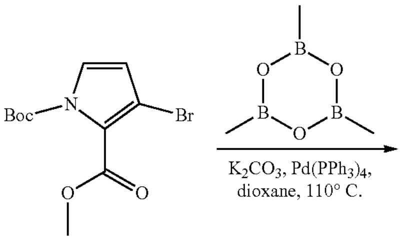

-continued

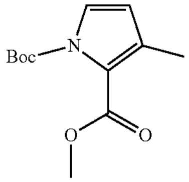

A mixture of 1-tert-butyl 2-methyl 3-bromopyrrole-1,2-dicarboxylate (6.50 g, 21.372 mmol, 1.00 equiv) and trimethyl-1,3,5,2,4,6-trioxatriborinane (26827.94 g, 213.717 mmol, 10 equiv) and $K_2CO_3$ (8861.07 g, 64.115 mmol, 3 equiv) and $Pd(PPh_3)_4$ (2469.63 g, 2.137 mmol, 0.1 equiv) in dioxane (50.00 mL, 590.204 mmol, 27.62 equiv) and $H_2O$ (10.00 mL, 555.084 mmol, 25.97 equiv) was stirred for 1 h at 100 degrees C. under nitrogen atmosphere. The resulting mixture was concentrated under vacuum. The residue was purified by silica gel column chromatography, eluted with PE/EtOAc (5:1) to afford 1-tert-butyl 2-methyl 3-methylpyrrole-1,2-dicarboxylate (2 g, 39.11%) as a yellow oil.

Step 3: Synthesis of rac-1-(tert-butyl) 2-methyl (2R,3S)-3-methylpyrrolidine-1,2-dicarboxylate

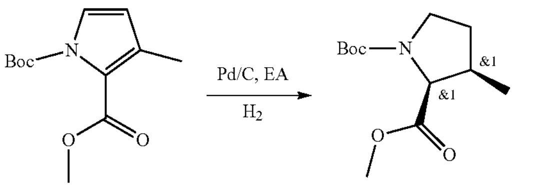 [SMILES: COC(=O)c1c(C)ccn1C(=O)OC(C)(C)C ; "H2" ; COC(=O)[C@@H]1[C@H](C)CCN1C(=O)OC(C)(C)C]

A mixture of ethyl 6,7-dichloro-1-(1-methylpyrazol-4-yl)-4-oxo-1,8-naphthyridine-3-carboxylate (400.00 mg, 1.089 mmol, 1.00 equiv) and 3-chloro-2-[(2R)-pyrrolidin-2-ylmethoxy]pyridine (347.53 mg, 1.634 mmol, 1.5 equiv) and K2CO3 (451.66 mg, 3.268 mmol, 3 equiv) in DMSO (3.50 mL, 49.275 mmol, 45.23 equiv) was stirred for 2 h at 50 degrees C. under nitrogen atmosphere. The residue was purified by reverse flash chromatography with the following conditions: column, C18 silica gel; mobile phase, MeOH in water, 10% to 50% gradient in 10 min; detector, UV 254 nm afford rac-1-(tert-butyl) 2-methyl (2R,3S)-3-methylpyrrolidine-1,2-dicarboxylate (300 mg, 50.68%) as yellow oil.

Step 4: Synthesis of rac-tert-butyl (2R,3S)-2-(hydroxymethyl)-3-methylpyrrolidine-1-carboxylate

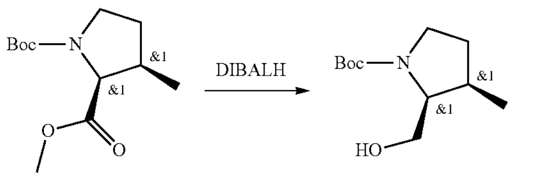 [SMILES: COC(=O)[C@@H]1[C@H](C)CCN1C(=O)OC(C)(C)C ; C[C@@H]1CCN(C(=O)OC(C)(C)C)[C@@H]1CO]

A mixture of rac-1-(tert-butyl) 2-methyl (2R,3S)-3-methylpyrrolidine-1,2-dicarboxylate (150.00 mg, 0.276 mmol, 1.00 equiv) and $Zn(CN)_2$ (162.09 mg, 1.380 mmol, 5 equiv) and Pd(PPh3)4 (31.90 mg, 0.028 mmol, 0.1 equiv) in DMSO (2.00 mL, 28.157 mmol, 102.01 equiv) was stirred for 2 h at 100 degrees C. under nitrogen atmosphere. The residue was purified by reverse flash chromatography with the following conditions: column, C18 silica gel; mobile phase, MeOH in water, 10% to 80% gradient in 20 min; detector, UV 254 nm afford rac-tert-butyl (2R,3S)-2-(hydroxymethyl)-3-methylpyrrolidine-1-carboxylate (70 mg, 47.49%) as yellow solid.

Step 5: Synthesis of rac-tert-butyl (2R,3S)-2-(((3-chloropyridin-2-yl)oxy)methyl)-3-methylpyrrolidine-1-carboxylate

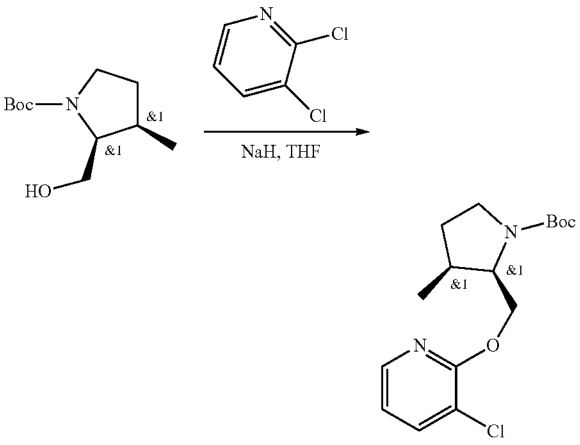

A mixture of rac-tert-butyl (2R,3S)-2-(hydroxymethyl)-3-methylpyrrolidine-1-carboxylate (1.00 g, 4.645 mmol, 1.00 equiv) and 3-chloro-2-fluoropyridine (1221.87 g, 9.290 mmol, 2 equiv) and NaH (334.40 mg, 13.934 mmol, 3 equiv) in THF (30.00 mL, 370.290 mmol, 79.72 equiv) was stirred for overnight at room temperature under nitrogen atmosphere. The reaction was then quenched by the addition of 30 mL of MeOH.

The resulting mixture was concentrated under reduced pressure. The residue was purified by reverse flash chromatography with the following conditions: column, C18 silica gel; mobile phase, MeOH in water, 10% to 80% gradient in 20 min; detector, UV 254 nm, afford rac-tert-butyl (2R,3S)-2-(((3-chloropyridin-2-yl)oxy)methyl)-3-methylpyrrolidine-1-carboxylate (600 mg, 39.53%) as yellow oil.

Step 6: Synthesis of rac-3-chloro-2-(((2R,3S)-3-methylpyrrolidin-2-yl)methoxy)pyridine

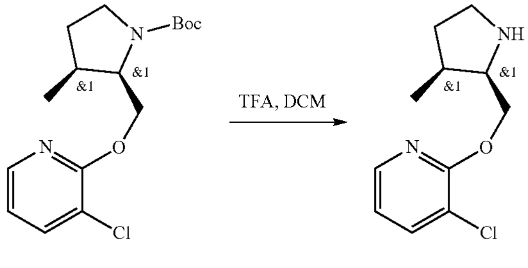 [SMILES: C[C@H]1CCN(C(=O)OC(C)(C)C)[C@H]1COc1ncccc1Cl ; C[C@H]1CCN[C@H]1COc1ncccc1Cl]

A mixture of rac-tert-butyl (2R,3S)-2-(((3-chloropyridin-2-yl)oxy)methyl)-3-methylpyrrolidine-1-carboxylate (600.00 mg, 1.836 mmol, 1.00 equiv) and TFA (0.50 mL, 6.732 mmol, 3.67 equiv) in DC M (2.00 mL, 31.460 mmol, 17.14 equiv) was stirred for 1 h at room temperature. The aqueous layer was extracted with EtOAc (3×5 mL) afford rac-3-chloro-2-(((2R,3S)-3-methylpyrrolidin-2-yl)methoxy)pyridine (300 mg, 72.08%) as yellow oil.

Step 7: Synthesis of rac-ethyl 6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylate

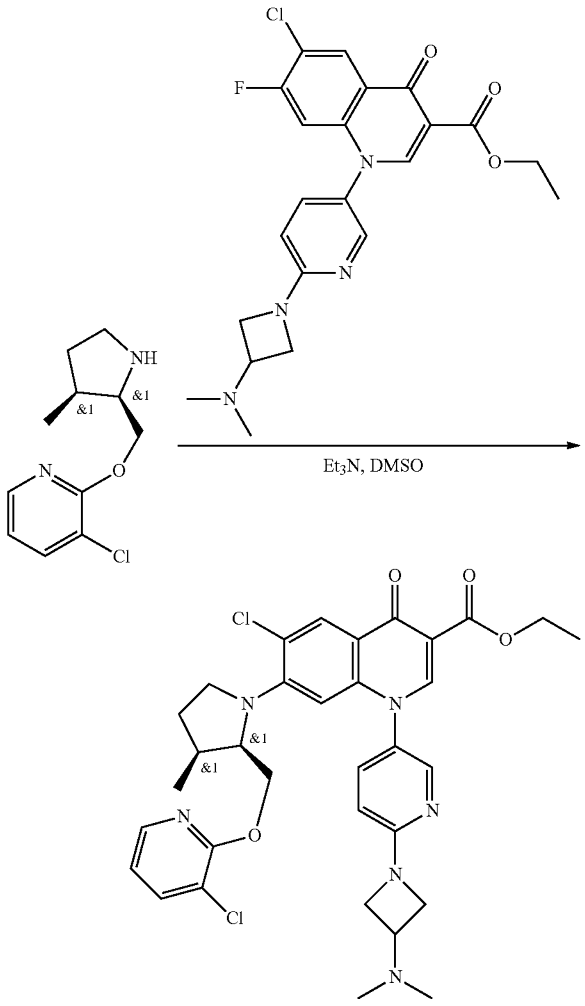

A mixture of rac-3-chloro-2-(((2R,3S)-3-methylpyrrolidin-2-yl)methoxy)pyridine (70 mg, 1.5 equiv) and ethyl 6-chloro-1-[16-[3-(dimethylamino)azetidin-1-yl]pyridin-3-yl]-7-fluoro-4-oxoquinoline-3-carboxylate (110 mg, 1.00 equiv) and DIEA (290 mg, 3 equiv) in DMSO (2.5 mL) was stirred for 1 h at 80 degrees C. under nitrogen atmosphere. The residue was purified by reverse flash chromatography with the following conditions: column, C18 silica gel; mobile phase, MeOH in water, 10% to 50% gradient in 10 min; detector, UV 254 nm afford rac-ethyl 6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylate (70 mg, 43.45%) as yellow solid.

Step 8: Synthesis of rac-6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylic acid

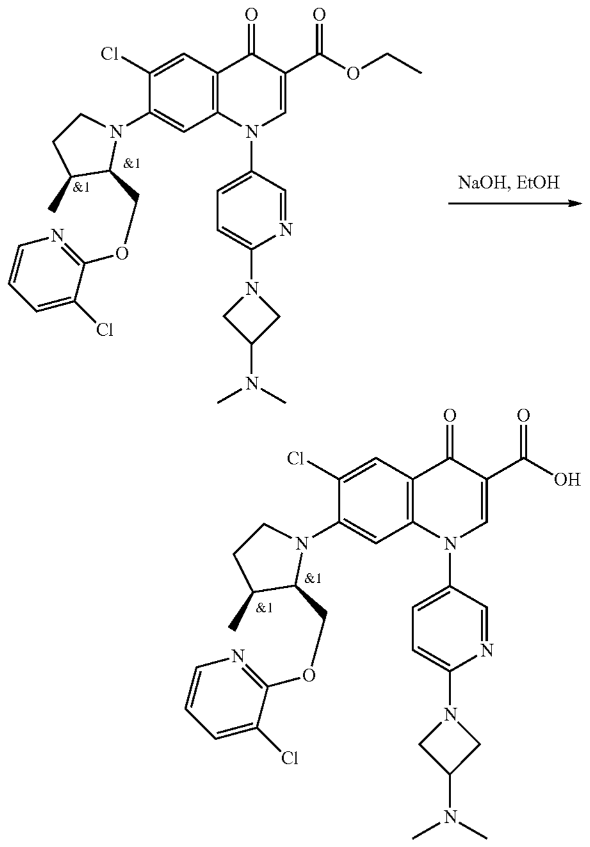

A mixture of rac-ethyl 6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylate (70.00 mg, 0.107 mmol, 1.00 equiv) and NaOH (12.89 mg, 0.322 mmol, 3 equiv) in EtOH (2.00 mL, 34.427 mmol, 320.46 equiv) was stirred for 1 h at room temperature under nitrogen atmosphere. The residue was purified by Prep-TLC (Column: XBridge Prep C18 OBD Column, 5 um, 19*150 mm; Mobile Phase A:Water(10 MMOL/L NH4HCO3), Mobile Phase B:ACN; Flow rate:25 m/min; Gradient:48 B to 62 B in 8 min; 254 nm; RT1:7.83; RT2; Injection Volumn: ml; Number Of Runs;) to afford rac-6-chloro-7-((2R,3S)-2-(((3-chloropyridin-2-yl)oxy)methyl)-3-methylpyrrolidin-1-yl)-1-(6-(3-(dimethylamino)azetidin-1-yl)pyridin-3-yl)-4-oxo-1,4-dihydroquinoline-3-carboxylic acid (23.8 mg, 35.53%) as a yellow solid. LCMS (ESI) $[M+H]^+$: 623.2. $^1H$ NMR (300 MHz, DMSO-$d_6$) δ 8.43 (s, 2H), 8.11 (s, 1H), 8.06-7.91 (m, 4H), 7.79 (s, 2H), 7.55 (s, 2H), 6.98 (s, 2H), 6.52 (s, 1H), 6.31 (d, J=9.0 Hz, 2H), 6.15 (s, 1H), 4.67 (s, 1H), 4.54 (s, 1H), 4.37 (s, 2H), 4.17 (s, 3H), 4.07-3.96 (m, 4H), 3.78 (s, 5H), 3.23 (s, 1H), 3.08 (s, 2H), 2.15 (s, 12H), 2.04 (s, 2H), 1.73 (s, 2H), 1.24 (s, OH), 1.07 (d, J=6.6 Hz, 6H).

Potency Lin28a-dep Z11 $IC_{50}$ (μM)++++

Example 45: 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylic acid

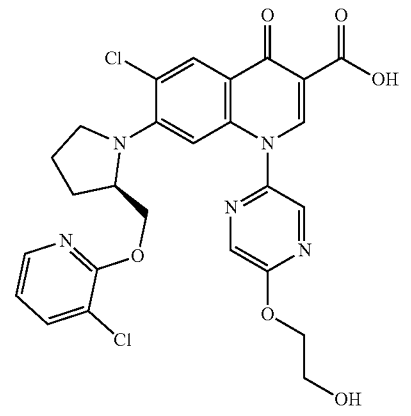 [SMILES: O=C(O)c1cn(-c2cnc(OCCO)cn2)c2cc(N3CCC[C@@H]3COc3ncccc3Cl)c(Cl)cc2c1=O]

Step 1: Synthesis of 2-[(5-aminopyrazin-2-yl)oxy]ethanol

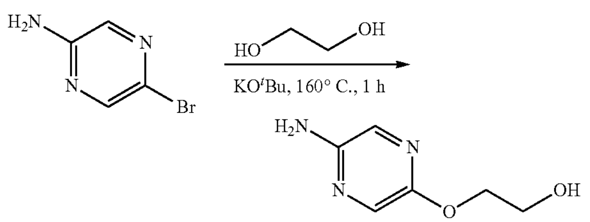

A mixture of 5-bromopyrazin-2-amine (500 mg, 2.87 mmol, 1 equiv), ethylene glycol (267 mg, 4.31 mmol, 1.5 equiv) and tert-butoxypotassium (967 mg, 8.62 mmol, 3 equiv) was stirred for 1 h at 160° C. The resulting mixture was concentrated under reduced pressure. The residue was purified by climbing board to afford 2-[(5-aminopyrazin-2-yl)oxy]ethanol (100 mg, 22.43%) as a yellow solid. LCMS (ESI) $[M+H]^+$: 156.07.

Step 2: Synthesis of ethyl (2Z)-2-[(Z)-5-chloro-2,4-difluorobenzoyl]-3-ethoxyprop-2-enoate

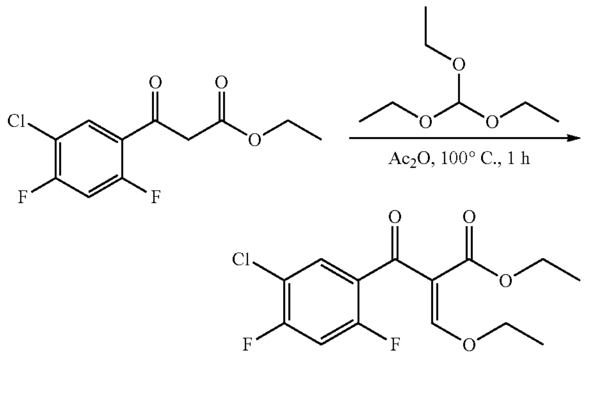

A mixture of ethyl 3-(5-chloro-2,4-difluorophenyl)-3-oxopropanoate (200 mg, 0.76 mmol, 1 equiv), $Ac_2O$(233 mg, 2.28 mmol, 3 equiv) and triethyl orthoformate (169 mg, 1.14 mmol, 1.5 equiv) was stirred for 1 h at 100° C. The resulting mixture was concentrated by vacuum to afford ethyl (2Z)-2-[(Z)-5-chloro-2,4-difluorobenzoyl]-3-ethoxy-prop-2-enoate (150 mg, crude) as a yellow oil. LCMS (ESI) $[M+H]^+$: 319.05.

Step 3: Synthesis of ethyl 6-chloro-7-fluoro-1-[5-(2-hydroxyethoxy)pyrazin-2-yl]-4-oxoquinoline-3-carboxylate

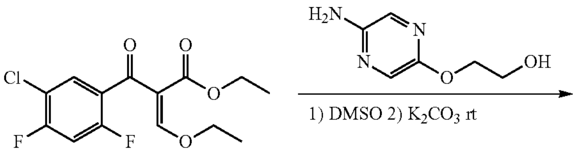

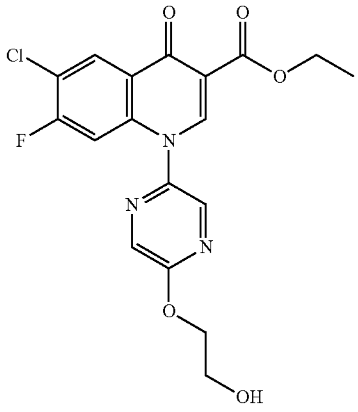

A mixture of ethyl (2Z)-2-[(Z)-5-chloro-2,4-difluorobenzoyl]-3-ethoxyprop-2-enoate (150 mg, 0.47 mmol, 1 equiv) and 2-[(5-aminopyrazin-2-yl)oxy]ethanol (109 mg, 0.70 mmol, 1.5 equiv) in DMSO (3 mL) was stirred for 1 h at room temperature. Subsequently, additional $K_2CO_3$ (65 mg, 0.47 mmol, 1 equiv) was supplied and keeping 1 h and continued reaction 1 h. The resulting mixture was purified by RP-flash chromatography eluting with $ACN/H_2O$(0.1% FA) (70%-80%) to afford ethyl 6-chloro-7-fluoro-1-[5-(2-hydroxyethoxy)pyrazin-2-yl]-4-oxoquinoline-3-carboxylate (50 mg, 26.05%) as a yellow solid. LCMS (ESI) $[M+H]^+$: 408.07.

Step 4: Synthesis of ethyl 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylate

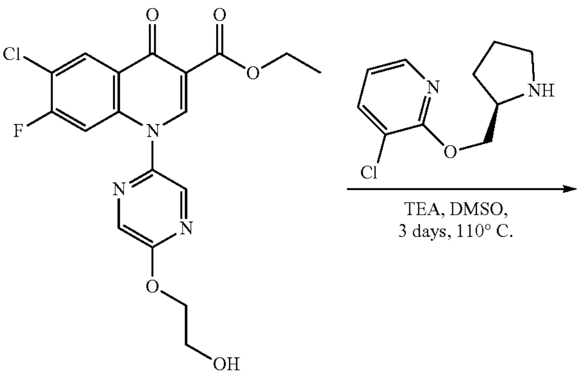

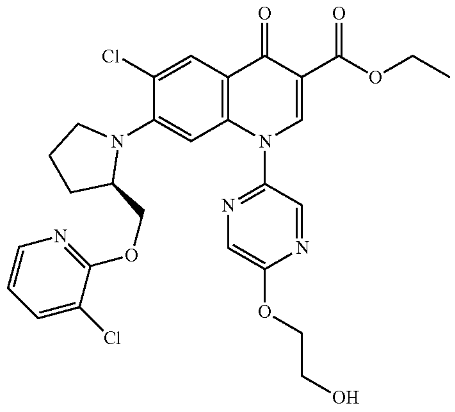

A mixture of ethyl 6-chloro-7-fluoro-1-[5-(2-hydroxyethoxy)pyrazin-2-yl]-4-oxoquinoline-3-carboxylate (50 mg, 0.12 mmol, 1 equiv), 3-chloro-2-[(2R)-pyrrolidin-2-ylmethoxy]pyridine (130 mg, 0.61 mmol, 5 equiv) and TEA (37 mg, 0.36 mmol, 3 equiv) in DMSO (1 mL) was stirred for 3 days at 110° C. The mixture was allowed to cool down to room temperature and quenched with water. The resulting mixture was purified by RP-flash chromatography eluting with $ACN/H_2O$(0.1% FA) (40%-50%) to afford ethyl 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylate (30 mg, 40.75%) as a yellow solid. LCMS (ESI) $[M+H]^+$: 600.13.

Step 5: Synthesis of 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylic acid

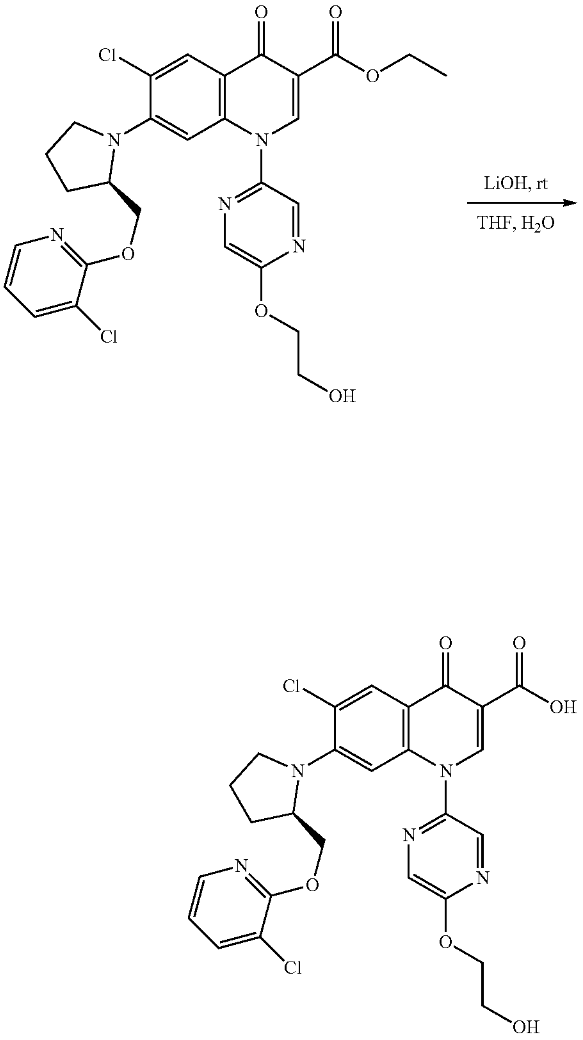

To a stirred mixture of ethyl 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylate (50 mg, 0.08 mmol, 1 equiv) in $H_2O$ (0.3 mL) and THF (0.9 mL) was added $LiOH{\cdot}H_2O$ (13 mg, 0.33 mmol, 4 equiv). The mixture was stirred for 1 h at room temperature. The resulting mixture was concentrated under reduced pressure and washed by water. The product was obtained by trituration to afford 6-chloro-7-[(2R)-2-[[(3-chloropyridin-2-yl)oxy]methyl]pyrrolidin-1-yl]-1-[5-(2-hydroxyethoxy)pyrazin-2-yl]-4-oxoquinoline-3-carboxylic acid (9.1 mg, 19.09%) as a yellow solid. LCMS (ESI) $[M+H]^+$: 572.10. $^1H$ NMR (300 MHz, DMSO-d6) δ 8.59 (d, J=15.8 Hz, 2H), 8.33 (s, 1H), 8.12 (s, 1H), 7.92-7.84 (m, 1H), 7.83-7.74 (m, 1H), 6.97-6.87 (m, 1H), 6.54 (s, 1H), 5.02 (t, J=5.5 Hz, 1H), 4.63 (s, 1H), 4.42 (t, J=5.0 Hz, 2H), 4.26 (t, J=3.9 Hz, 2H), 3.86-3.75 (m, 2H), 3.59 (d, J=8.4 Hz, 1H), 3.17 (d, J=5.6 Hz, 1H), 2.30-2.19 (m, 1H), 1.98-1.74 (m, 3H).

Potency Lin28a-dep Z11 $IC_{50}$ (μM)++++

Example 46: Synthesis of 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylic acid

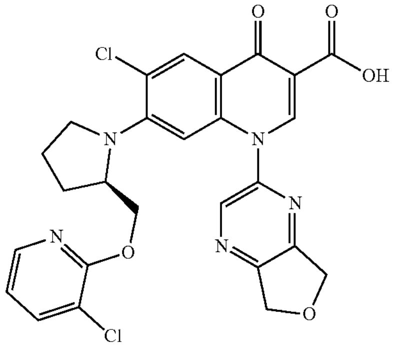

Step 1: Synthesis of iodo(iodomethoxy)methane

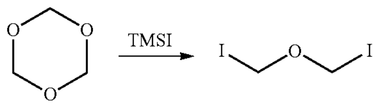 [SMILES: "TMSI" ; C1OCOCO1 ; ICOCI]

A mixture of trioxane (15.0 g, 166.52 mmol) and TMSI (100.0 g, 499.76 mmol) was stirred overnight at room temperature. The mixture was concentrated and purified by column chromatography on silica gel eluting with Petroleum ether to afford iodo(iodomethoxy)methane (15 g, 30.24%) as a yellow oil.

Step 2: Synthesis of tributyl([[(tributylstannyl)methoxy]methyl])stannane

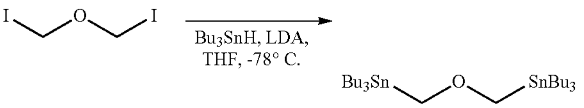

Under $N_2$, to a solution of tributyltin (25.8 g, 88.64 mmol) in THF (120.0 mL) was added LDA (44.3 mL, 88.63 mmol) and the mixture was stirred for 30 min at −78° C. Then iodo(iodomethoxy)methane (12.0 g, 40.28 mmol) was added at −78° C. and the mixture was stirred for 2 h at room temperature. The reaction was quenched with $NH_4Cl$ (240 mL) and extracted with EtOAc (3*200 mL). The combined organic layers was washed with water (200 mL), brine (200 mL), concentrated and purified by flash chromatography on silica gel eluting with Petroleum ether to afford tributyl([[(tributylstannyl)methoxy]methyl])stannane (5.0 g, 19.88%) as a colorless oil.

Step 3: Synthesis of 5H,7H-furo[3,4-b]pyrazin-2-amine

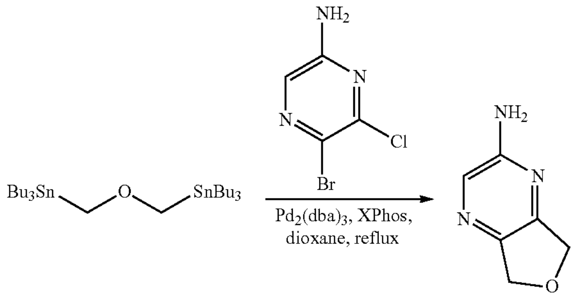

Under a nitrogen atmosphere, a mixture of 5-bromo-6-chloropyrazin-2-amine (1.6 g, 8.01 mmol), tributyl([[(tributylstannyl)methoxy]methyl])stannane (5.0 g, 8.01 mmol), $Pd_2(dba)_3 \cdot CHCl_3$ (82 mg, 0.08 mmol), XPhos (76 mg, 0.16 mmol) and dioxane (50.0 mL) was stirred overnight at 100° C. The reaction was diluted with EtOAc (300 mL), washed with water (50 mL), brine (50 mL), concentrated and purified by flash chromatography on silica gel eluting with EtOAc/Petroleum ether (0-100%) to afford 5H,7H-furo[3,4-b]pyrazin-2-amine (170 mg, 15.66%) as a white solid. LCMS (ESI) $[M+H]^+$: 138.

Step 4: Synthesis of ethyl 6-chloro-7-fluoro-1-[5H,7H-furo[3,4-b]pyrazin-2-yl]-4-oxoquinoline-3-carboxylate

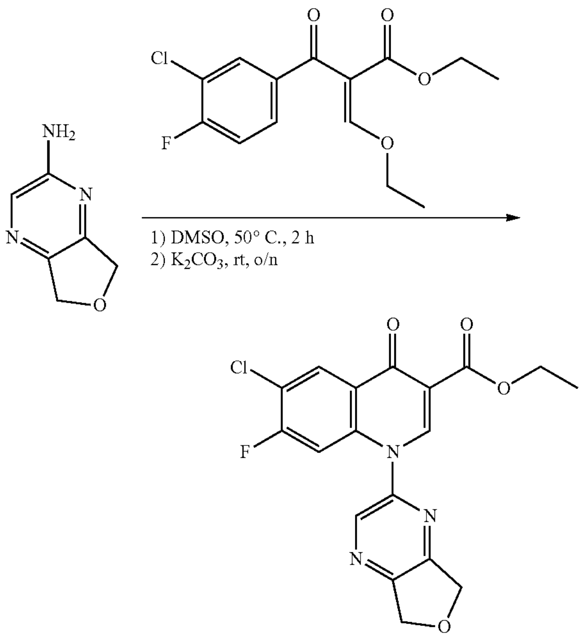

A mixture of ethyl (2Z)-2-[(Z)-5-chloro-2,4-difluorobenzoyl]-3-ethoxyprop-2-enoate (181 mg, 0.56 mmol), 5H,7H-furo[3,4-b]pyrazin-2-amine (77 mg, 0.56 mmol), DMSO (5.0 mL) was stirred overnight at room temperature. Then $K_2CO_3$ (78 mg, 0.56 mmol) was added and the mixture was stirred overnight at 50° C. The mixture was purified by RPFC to afford ethyl 6-chloro-7-fluoro-1-[5H,7H-furo[3,4-b]pyrazin-2-yl]-4-oxoquinoline-3-carboxylate (160 mg, 72.50%) as a red solid. LCMS (ESI) $[M+H]^+$: 390.

Step 5: Synthesis of ethyl 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylate

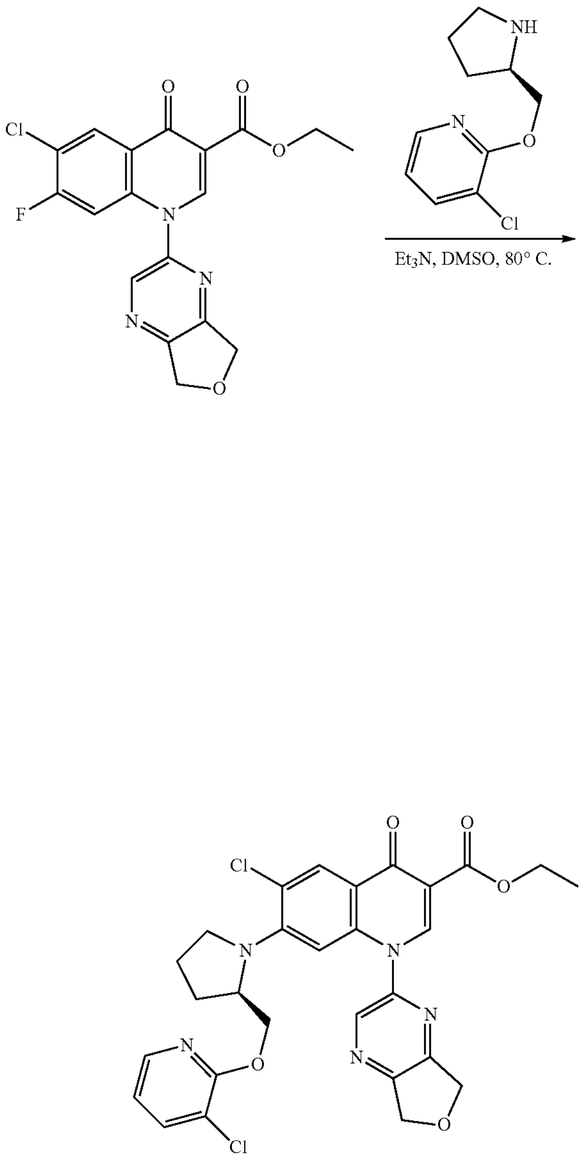

A mixture of ethyl 6-chloro-7-fluoro-1-[5H,7H-furo[3,4-b]pyrazin-2-yl]-4-oxoquinoline-3-carboxylate (100 mg, 0.25 mmol), 3-chloro-2-[(2R)-pyrrolidin-2-ylmethoxy]pyridine (109 mg, 0.51 mmol), $Et_3N$ (103 mg, 1.02 mmol) and DMSO (4.0 mL) was stirred overnight at 80° C. The mixture was cooled and purified by RPFC to afford ethyl 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylate (113 mg, 75.62%) as a light yellow solid. LCMS (ESI) $[M+H]^+$: 582.

Step 6: Synthesis of 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylic acid

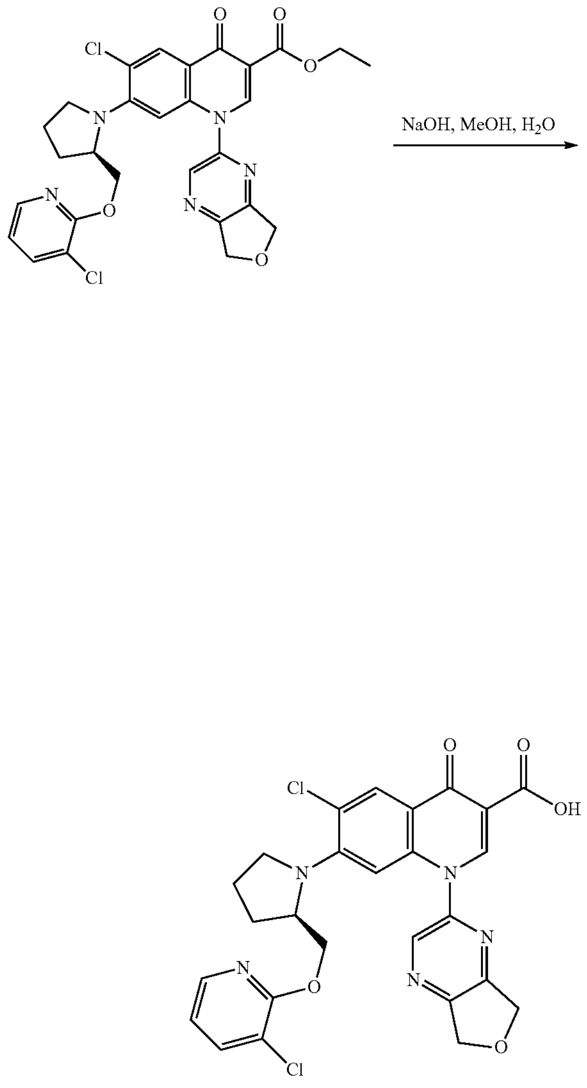

To a mixture of ethyl 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylate (108 mg, 0.18 mmol) in MeOH (2.0 mL) was added NaOH (0.93 mL, 0.93 mmol) and the mixture was stirred overnight at room temperature. The reaction was adjusted pH to 3-4 with 1N HCl. Then the mixture was concentrated and purified by prep-HPLC to afford 6-chloro-7-[(2R)-2-[[(3-chloropyridin-2-yl)oxy]methyl]pyrrolidin-1-yl]-1-[5H,7H-furo[3,4-b]pyrazin-2-yl]-4-oxoquinoline-3-carboxylic acid (29.4 mg, 28.29%) as a white solid. LCMS (ESI) $[M+H]^+$: 554.20. $^1H$ NMR (300 MHz, DMSO-$d_6$) δ 14.83 (s, 1H), 8.95 (s, 1H), 8.88 (s, 1H), 8.18 (s, 1H), 7.88 (dd, J=4.9, 1.7 Hz, 1H), 7.79 (dd, J=7.7, 1.7 Hz, 1H), 6.93 (dd, J=7.7, 4.9 Hz, 1H), 6.66 (s, 1H), 5.20 (d, J=1.7 Hz, 2H), 5.12 (d, J=4.2 Hz, 2H), 4.75 (s, 1H), 4.31 (qd, J=11.4, 4.3 Hz, 2H), 3.70-3.57 (m, 1H), 3.31-3.15 (m, 1H), 2.31-2.17 (m, 1H), 2.08-1.69 (m, 3H).

Potency Lin28a-dep Z11 $IC_{50}$ (μM)++++

Example 47: Synthesis of 6-chloro-7-(3-(((3-chloropyridin-2-yl)oxy)methyl)-1,1-dioxidoisothiazolidin-2-yl)-1-(6-(3-(dimethylamino)azetidin-1-yl)pyridin-3-yl)-4-oxo-1,4-dihydroquinoline-3-carboxylic acid

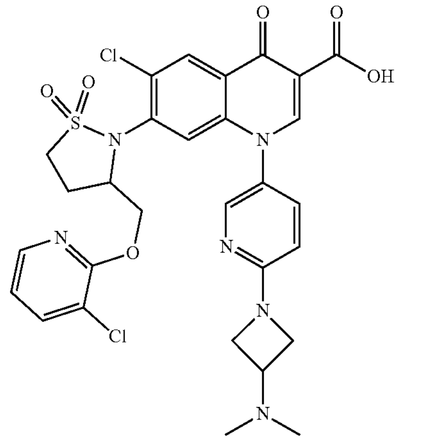 [SMILES: CN(C)C1CN(c2ccc(-n3cc(C(=O)O)c(=O)c4cc(Cl)c(N5C(COc6ncccc6Cl)CCS5(=O)=O)cc43)cn2)C1]

Step 1: Synthesis of 3-(hydroxymethyl)isothiazolidine 1,1-dioxide

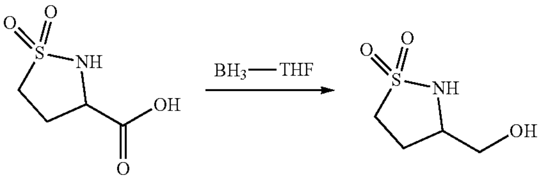

To a stirred solution of isothiazolidine-3-carboxylic acid 1,1-dioxide (600 mg, 3.64 mmol) in THF (15 mL) was added $BH_3$-THF (14.5 mL, 14.5 mmol) dropwise. The solution was stirred at room temperature for 2 h. The reaction was quenched by the addition of MeOH. The solution was concentrated to give the residue which was purified by flash column with 0-10% MeOH in DCM to afford 3-(hydroxymethyl)isothiazolidine 1,1-dioxide (510 mg, 93%) as colorless oil. LCMS (ESI) $[M+H]^+$: 152.

Step 2: Synthesis of 3-(((3-chloropyridin-2-yl)oxy)methyl)isothiazolidine 1,1-dioxide

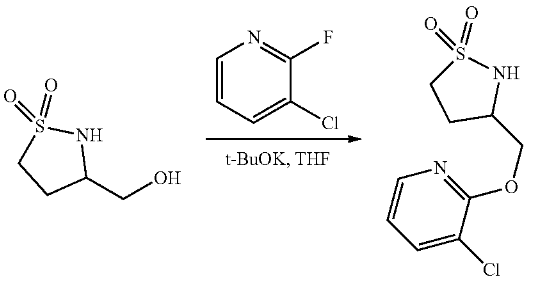 [SMILES: O=S1(=O)CCC(CO)N1 ; Fc1ncccc1Cl ; O=S1(=O)CCC(COc2ncccc2Cl)N1]

To a stirred mixture of 3-(hydroxymethyl)isothiazolidine 1,1-dioxide (510 mg, 3.38 mmol) and 3-chloro-2-fluoropyridine (663 mg, 5.07 mmol) in DMSO (10 mL) was added t-BuOK (1.14 g, 10.14 mmol). The mixture was stirred at room temperature for 1 h. The mixture was purified by reverse phase flash column with 20-80% acetonitrile in water to afford 3-(((3-chloropyridin-2-yl)oxy)methyl)isothiazolidine 1,1-dioxide (280 mg, 32%) as light yellow solid. LCMS (ESI) [M+H]$^+$: 263.

Step 3: Synthesis of ethyl 6-chloro-7-(3-(((3-chloropyridin-2-yl)oxy)methyl)-1,1-dioxidoisothiazolidin-2-yl)-1-(6-(3-(dimethylamino)azetidin-1-yl)pyridin-3-yl)-4-oxo-1,4-dihydroquinoline-3-carboxylate

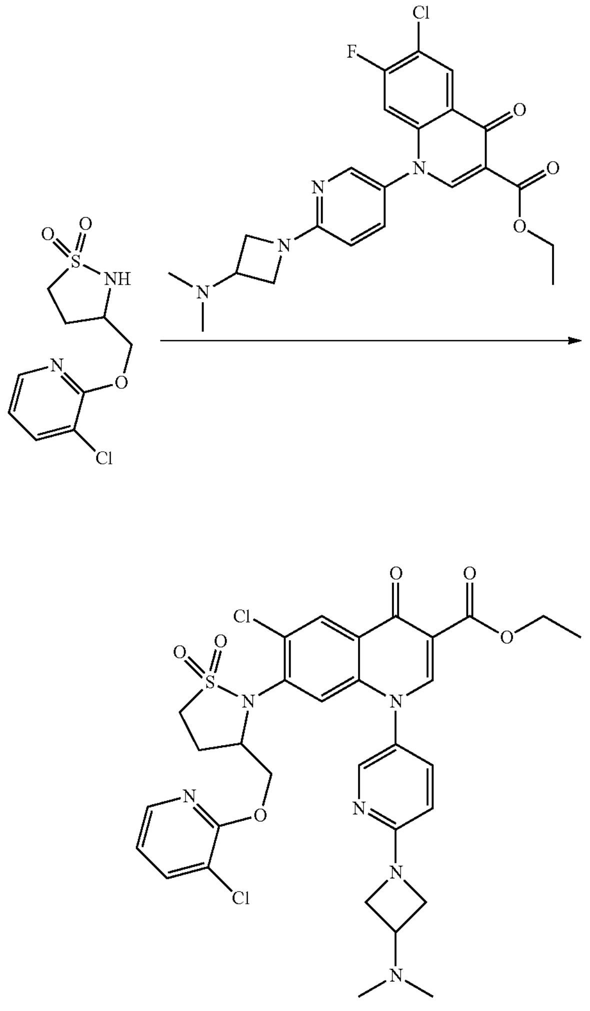

To a mixture of ethyl 6-chloro-1-(6-(3-(dimethylamino) azetidin-1-yl)pyridin-3-yl)-7-fluoro-4-oxo-1,4-dihydroquinoline-3-carboxylate (100 mg, 0.23 mmol) and 3-(((3-chloropyridin-2-yl)oxy)methyl)isothiazolidine 1,1-dioxide (118 mg, 0.45 mmol) in DMSO (3 mL) was added t-BuOK (76 mg, 0.68 mmol). The mixture was stirred at 80° C. for 2 h. The mixture was purified by reverse phase flash column with 5-30% acetonitrile in water to afford ethyl 6-chloro-7-(3-(((3-chloropyridin-2-yl)oxy)methyl)-1,1-dioxidoisothiazolidin-2-yl)-1-(6-(3-(dimethylamino)azetidin-1-yl)pyridin-3-yl)-4-oxo-1,4-dihydroquinoline-3-carboxylate (100 mg, 63%) as yellow solid. LCMS (ESI) [M+H]$^+$: 687.

Step 4: Synthesis of 6-chloro-7-(3-(((3-chloropyridin-2-yl)oxy)methyl)-1,1-dioxidoisothiazolidin-2-yl)-1-(6-(3-(dimethylamino)azetidin-1-yl)pyridin-3-yl)-4-oxo-1,4-dihydroquinoline-3-carboxylic acid

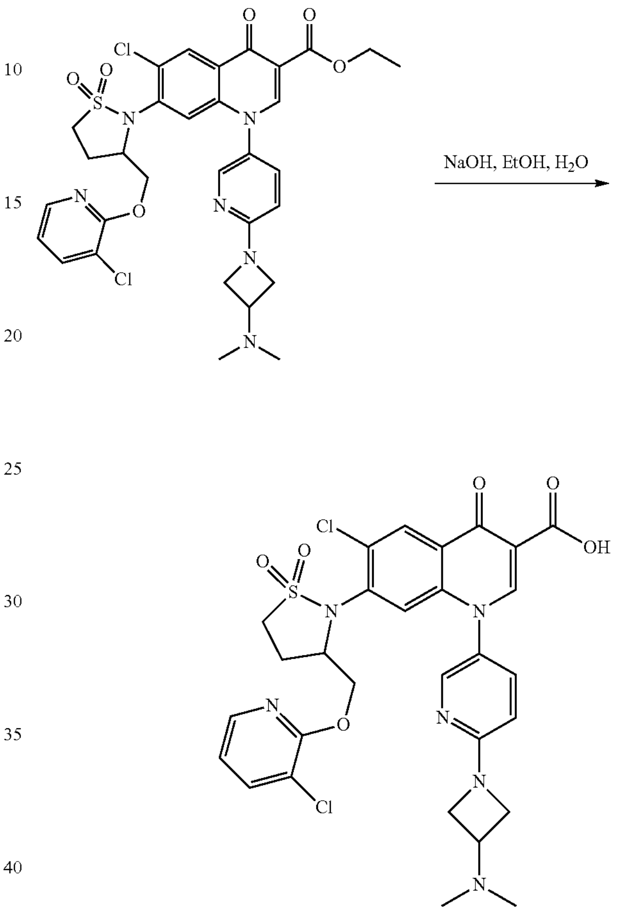

To a stirred mixture of ethyl 6-chloro-7-(3-(((3-chloropyridin-2-yl)oxy)methyl)-1,1-dioxidoisothiazolidin-2-yl)-1-(6-(3-(dimethylamino)azetidin-1-yl)pyridin-3-yl)-4-oxo-1,4-dihydroquinoline-3-carboxylate (60 mg, 0.09 mmol) in EtOH (1 mL) under nitrogen was added a solution of NaOH (14 mg, 0.35 mmol) in $H_2O$ (1 mL). The mixture was stirred at room temperature for 2 h. HOAc was added to adjust pH 5. The mixture was dissolved in DMSO and purified by prep-HPLC (Column: XSelect CSH Prep C18 OBD Column, 19*150 mm, 5 µm; Mobile Phase A: Water(0.1% FA), Mobile Phase B: ACN; Flow rate: 25 mL/min; Gradient: 15% B to 32% B in 8 min, 32% B; Wave Length: 254 nm; RT1 (min): 6.70; Number Of Runs: 0) to afford 6-chloro-7-(3-(((3-chloropyridin-2-yl)oxy)methyl)-1,1-dioxidoisothiazolidin-2-yl)-1-(6-(3-(dimethylamino)azetidin-1-yl) pyridin-3-yl)-4-oxo-1,4-dihydroquinoline-3-carboxylic acid (14.6 mg, 25%) as yellow solid. LCMS (ESI): [M+H]$^+$: 659.0. $^1$H NMR (300 MHz, DMSO-d6) δ 14.54 (s, 1H), 8.66 (s, 1H), 8.41 (s, 1H), 8.25-8.07 (m, 1H), 8.05-7.94 (m, 1H), 7.83-7.72 (m, 1H), 7.61-7.40 (m, 1H), 7.33 (d, J=6.1 Hz, 1H), 7.04-6.96 (m, 1H), 6.58-6.37 (m, 1H), 4.65-4.59 (m, 1H), 4.46-4.25 (m, 2H), 4.11 (t, J=8.0 Hz, 2H), 3.91-3.81 (m, 2H), 3.68-3.45 (m, 2H), 3.29-3.23 (m, 1H), 2.82-2.63 (m, 0H), 2.34-2.25 (m, 1H), 2.19 (s, 6H).

Potency Lin28a-dep Z11 $IC_{50}$ (μM)++++

Example 48: Synthesis of 6-chloro-7-(1-[[(3-chloropyridin-2-yl)oxy]methyl]-2-azabicyclo[3.1.0]hexan-2-yl)-1-[6-[3-(dimethylamino)azetidin-1-yl]pyridin-3-yl]-4-oxoquinoline-3-carboxylic acid

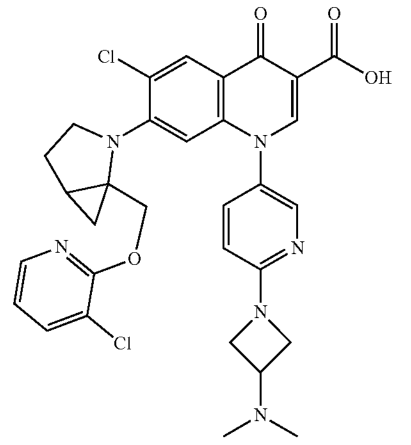 [SMILES: CN(C)C1CN(c2ccc(-n3cc(C(=O)O)c(=O)c4cc(Cl)c(N5CCC6CC65COc5ncccc5Cl)cc43)cn2)C1]

Step 1: Synthesis of Tert-butyl 2-azabicyclo[3.1.0]hexane-2-carboxylate

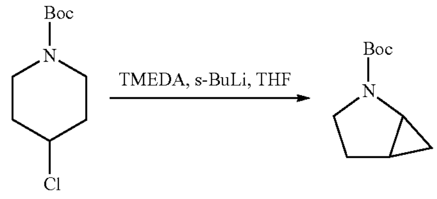 [SMILES: CC(C)(C)OC(=O)N1CCC(Cl)CC1 ; "TMEDA, s-BuLi, THF" ; CC(C)(C)OC(=O)N1CCC2CC21]

To a solution of placed tert-butyl 4-chloropiperidine-1-carboxylate (9.0 g, 40.96 mmol, 1.0 equiv) in THF (100 mL) was added TMEDA (5.71 g, 49.16 mmol, 1.2 equiv), s-BuLi (37.8 mL, 1.3 M, 49.16 mmol, 1.2 equiv) at −78° C. The resulting mixture was stirred at −78° C. for 6 h under $N_2$ atmosphere. LCMS (ESI) $[M+H]^+$: 184.

Step 2: Synthesis of Tert-butyl 1-formyl-2-azabicyclo[3.1.0]hexane-2-carboxylate

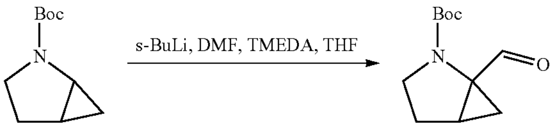 [SMILES: CC(C)(C)OC(=O)N1CCC2CC21 ; "s-BuLi, DMF, TMEDA, THF" ; CC(C)(C)OC(=O)N1CCC2CC21C=O]

To a solution of placed tert-butyl 2-azabicyclo[3.1.0]hexane-2-carboxylate (crude) in THF (50.00 mL) was added TMEDA (11.9 g, 102.32 mmol, 2.5 equiv) and s-BuLi (78.5 mL, 1.3 M, 102.319 mmol, 2.50 equiv) at −78° C. The resulting mixture was stirred at −78° C. for 2 h under $N_2$ atmosphere. Then, DMF (3.59 g, 49.115 mmol, 1.20 equiv) was added into the solution and stirred at −78° C. for 15 min under $N_2$ atmosphere. LCMS (ESI) $[M+H]^+$: 212.

Step 3: Synthesis of Tert-butyl 1-(hydroxymethyl)-2-azabicyclo[3.1.0]hexane-2-carboxylate

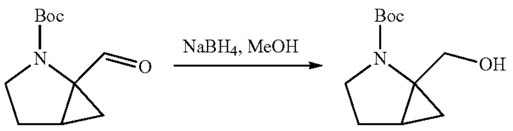

To a solution of placed tert-butyl 1-formyl-2-azabicyclo[3.1.0]hexane-2-carboxylate (crude) in MeOH (100 mL) was added $NaBH_4$ (6.2 g, 162.82 mmol, 4.0 equiv). The resulting mixture was stirred at room temperature for 2 h. The reaction was quenched by water. The resulting mixture was extracted with ethyl acetate dried (50 mL×3), dried over anhydrous sodium sulfate and concentrated under vacuum. The residue was applied onto a silica gel column with ethyl acetate/petroleum ether (1/3). This resulted in tert-butyl 1-formyl-2-azabicyclo[3.1.0]hexane-2-carboxylate (260 mg, 3.0%) as a yellow oil. LCMS (ESI) $[M+H]^+$: 214.

Step 4: Synthesis of Tert-butyl 1-[[(3-chloropyridin-2-yl)oxy]methyl]-2-azabicyclo[3.1.0]hexane-2-carboxylate

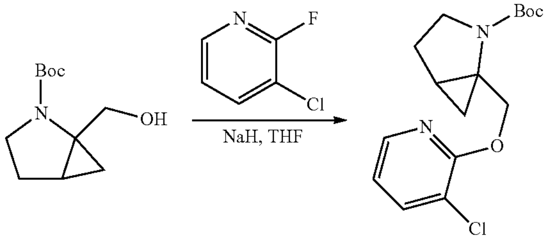

To a solution of placed tert-butyl 1-(hydroxymethyl)-2-azabicyclo[3.1.0]hexane-2-carboxylate (260 mg, 1.22 mmol, 1.0 equiv) in THF (2 mL) was added NaH (87.76 mg, 3.657 mmol, 3.00 equiv). The resulting mixture was stirred at room temperature for 0.5 h. Then, 3-chloro-2-fluoropyridine (240.52 mg, 1.829 mmol, 1.50 equiv) was added into the solution and stirred at room temperature for 1 h. The reaction was quenched by water. The resulting solution was concentrated under vacuum. The crude product was purified by reverse phase with Water (10 mmol/L $NH_4HCO_3$)/acetonitrile=80%—90 in 5 min; 220 nm. This resulted in tert-butyl 1-[[(3-chloropyridin-2-yl)oxy]methyl]-2-azabicyclo[3.1.0]hexane-2-carboxylate (100 mg, 25.3%) as a yellow oil. LCMS (ESI) $[M+H]^+$: 326.

Step 5: Synthesis of 1-[[(3-chloropyridin-2-yl)oxy]methyl]-2-azabicyclo[3.1.0]hexane

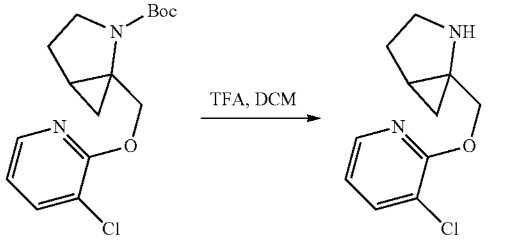

To a solution of placed tert-butyl 1-[[(3-chloropyridin-2-yl)oxy]methyl]-2-azabicyclo[3.1.0]hexane-2-carboxylate (100 mg, 0.31 mmol, 1.0 equiv) in DCM (2 mL) was added TFA (0.4 mL). The resulting solution was concentrated under vacuum. The crude product was purified by reverse phase with Water (10 mmol/L $NH_4HCO_3$)/acetonitrile=40%—50 in 5 min; 220 nm. This resulted in 1-[[(3-chloropyridin-2-yl)oxy]methyl]-2-azabicyclo[3.1.0]hexane (40 mg, 57.8%) as a yellow oil. LCMS (ESI) $[M+H]^+$: 226.

Step 6: Synthesis of 6-chloro-7-(1-[[(3-chloropyridin-2-yl)oxy]methyl]-2-azabicyclo[3.1.0]hexan-2-yl)-1-[6-[3-(dimethylamino)azetidin-1-yl]pyridin-3-yl]-4-oxoquinoline-3-carboxylic acid

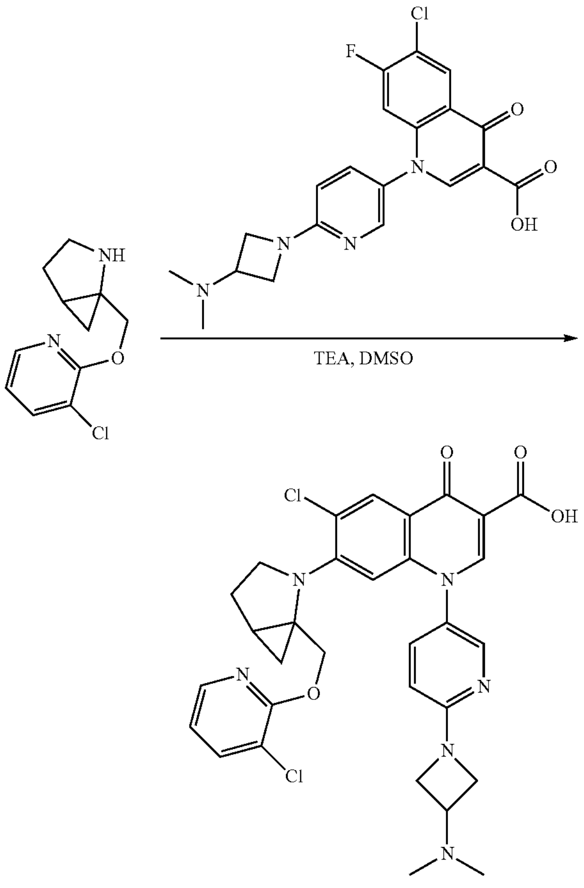

To a solution of placed 6-chloro-1-[6-[3-(dimethylamino)azetidin-1-yl]pyridin-3-yl]-7-fluoro-4-oxoquinoline-3-carboxylic acid (75 mg, 0.18 mmol, 1.0 equiv) in DMSO (2 mL) was added TEA (55 mg, 0.54 mmol, 3.0 equiv) and 1-[[(3-chloropyridin-2-yl)oxy]methyl]-2-azabicyclo[3.1.0]hexane (40 mg, 0.18 mmol, 1.0 equiv). The resulting mixture was stirred at 80° C. for 5 h. The crude product was purified by Flash-Prep-HPLC with the following conditions (IntelFlash-1): Column: Gemini-NX C18 AXAI Packed, 21.2*150 mm 5 um; Mobile Phase A: Water(0.1% FA), Mobile Phase B: acetonitrile; Flow rate: 25 mL/min; Gradient: 10 B to 10 B in 2 min; 254 nm. This resulted in 2 6-chloro-7-(1-[[(3-chloropyridin-2-yl)oxy]methyl]-2-azabicyclo[3.1.0]hexan-2-yl)-1-[6-[3-(dimethylamino)azetidin-1-yl]pyridin-3-yl]-4-oxoquinoline-3-carboxylic acid (16.8 mg, 11.27%) as a light yellow solid. LCMS (ESI) $[M+H]^+$: 621.10. $^1H$ NMR (400 MHz, DMSO-d6) δ 15.03 (s, 1H), 8.64 (d, J=3.4 Hz, 1H), 8.30 (t, J=3.3 Hz, 1H), 8.21 (s, 1H), 7.93-7.72 (m, 3H), 7.00-6.82 (m, 2H), 6.47 (dd, J=89.5, 8.8 Hz, 1H), 4.69 (dd, J=18.5, 12.0 Hz, 1H), 4.26-3.99 (m, 4H), 3.91-3.74 (m, 2H), 2.83 (p, J=7.7 Hz, 1H), 2.22 (s, 1H), 2.14 (s, 7H), 1.92-1.72 (m, 2H), 1.08-0.90 (m, 2H).

Potency Lin28a-dep Z11 $IC_{50}$ (μM)++++

Example 49: Synthesis of 6-chloro-1-[6-[3-(dimethylamino)azetidin-1-yl]pyridin-3-yl]-7-[(2R)-2-[[(dimethylcarbamoyl)oxy]methyl]pyrrolidin-1-yl]-4-oxoquinoline-3-carboxylic acid

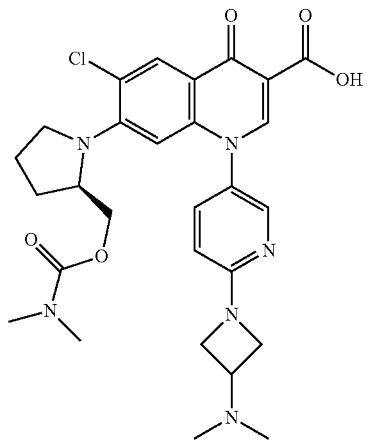 [SMILES: CN(C)C(=O)OC[C@H]1CCCN1c1cc2c(cc1Cl)c(=O)c(C(=O)O)cn2-c1ccc(N2CC(N(C)C)C2)nc1]

Step 1: Synthesis of ethyl 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylate

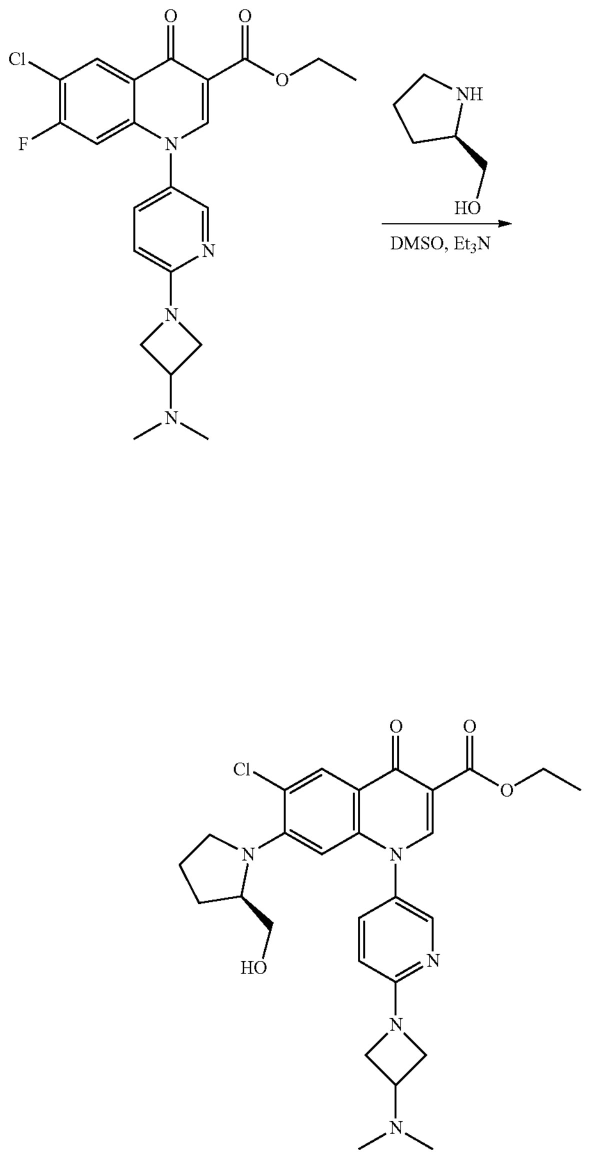

To a stirred solution of ethyl 6-chloro-1-[6-[3-(dimethylamino)azetidin-1-yl]pyridin-3-yl]-7-fluoro-4-oxoquinoline-3-carboxylate (200.00 mg, 0.450 mmol, 1.00 equiv) and $Et_3N$ (136.47 mg, 1.349 mmol, 3.00 equiv) in DMSO was added (R)-pyrrolidin-2-ylmethanol (136.41 mg, 1.349 mmol, 3.00 equiv) in portions at 80° C. under nitrogen atmosphere. The mixture was allowed to cool down to room temperature. The residue was purified by reverse phase flash chromatography with the following conditions: column, C18 silica gel; mobile phase, MeOH in water, 10% to 50% gradient in 10 min; detector, UV 254 nm to afford ethyl 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylate (160 mg, 67.66%).

Step 2: Synthesis of 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylic acid

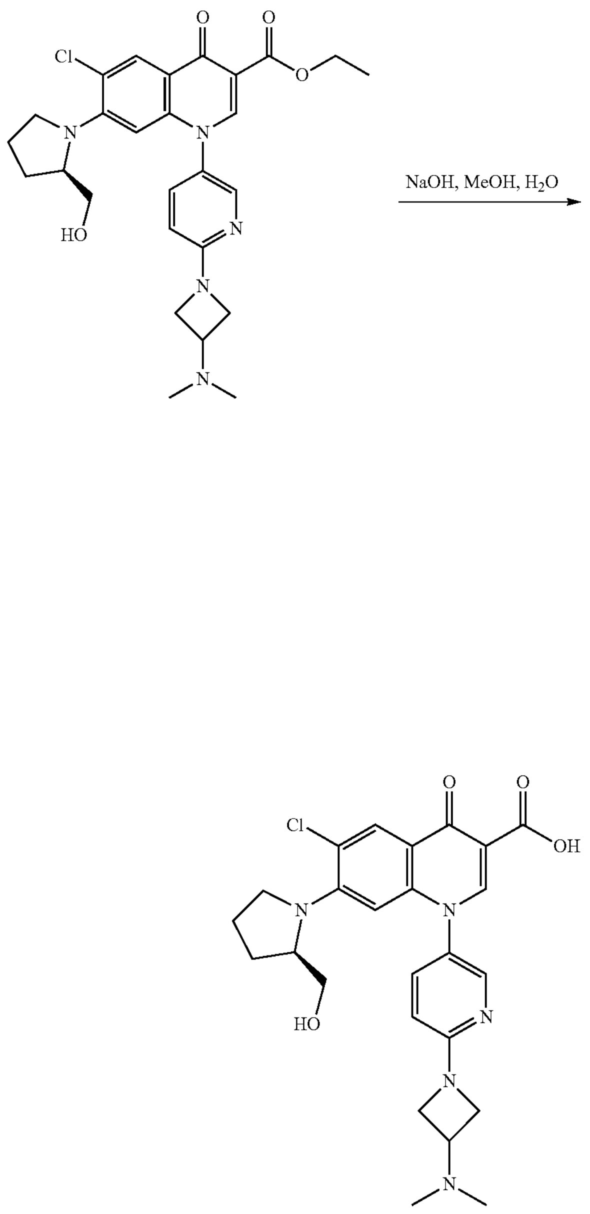

A solution of ethyl 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylate (110.00 mg, 0.209 mmol, 1.00 equiv) and NaOH (25.09 mg, 0.627 mmol, 3.00 equiv) in MeOH (1.50 mL), $H_2O$ (0.05 mL) was stirred for 1 h. The residue was purified by reverse phase flash chromatography with the following conditions: column, C18 silica gel; mobile phase, MeOH in water, 10% to 50% gradient in 10 min; detector, UV 254 nm. This resulted in 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylic acid (80 mg, 76.82%) as a yellow solid.

Step 3: Synthesis of 6-chloro-1-[6-[3-(dimethylamino)azetidin-1-yl]pyridin-3-yl]-7-[(2R)-2-[[(dimethylcarbamoyl)oxy]methyl]pyrrolidin-1-yl]-4-oxoquinoline-3-carboxylic acid

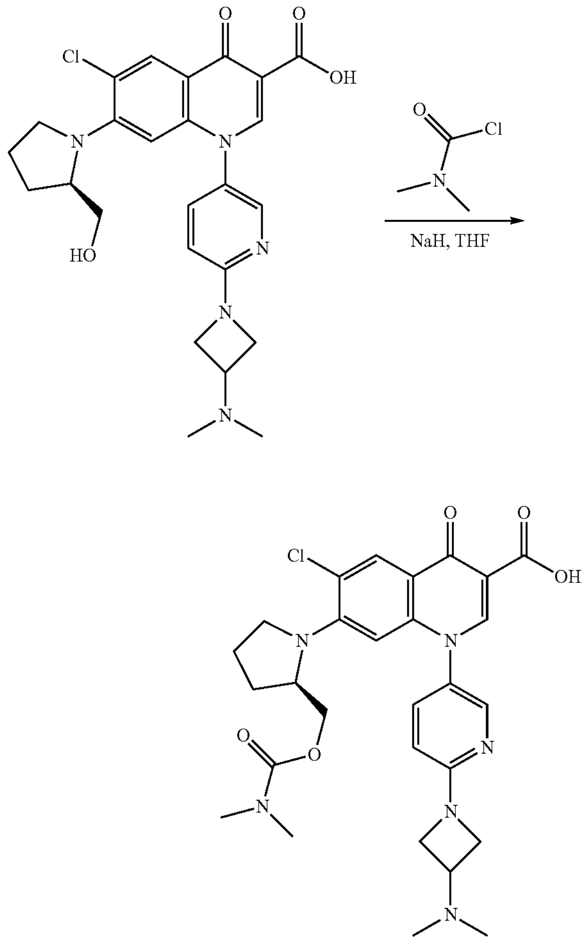

To a stirred solution of 6-chloro-1-[6-[3-(dimethylamino)azetidin-1-yl]pyridin-3-yl]-7-[(2R)-2-(hydroxymethyl)pyrrolidin-1-yl]-4-oxoquinoline-3-carboxylic acid (60.00 mg, 0.120 mmol, 1.00 equiv) and dimethylcarbamyl chloride (38.87 mg, 0.361 mmol, 3.00 equiv) in THF was added NaH (14.46 mg, 0.361 mmol, 3.00 equiv, 60%) in portions at room temperature under nitrogen atmosphere. The crude product (60 mg) was purified by Prep-HPLC with the following conditions (Column: Gemini-NX C18 AXAI Packed, 21.2*150 mm 5 um; Mobile Phase A:Water(0.1% FA), Mobile Phase B:ACN; Flow rate:25 mL/min; Gradient: 11 B to 30 B in 9 min; 254 nm; RT1:8.4;) to afford 6-chloro-1-[6-[3-(dimethylamino)azetidin-1-yl]pyridin-3-yl]-7-[(2R)-2-[[(dimethylcarbamoyl)oxy]methyl]pyrrolidin-1-yl]-4-oxoquinoline-3-carboxylic acid (15.9 mg) as a yellow solid. LCMS (ESI) $[M+H]^+$: 569.35. $^1H$ NMR (300 MHz, DMSO-$d_6$) δ 15.10 (s, 1H), 8.56 (d, J=6.2 Hz, 1H), 8.30 (d, J=2.3 Hz, 1H), 8.21 (s, 1H), 8.15 (s, 1H), 7.84-7.71 (m, 1H), 4.46 (d, J=18.4 Hz, 1H), 4.09 (d, J=8.0 Hz, 2H), 4.02-3.90 (m, 1H), 3.90-3.70 (m, 3H), 3.47 (s, 1H), 3.26-3.19 (m, 2H), 2.69 (d, J=5.8 Hz, 3H), 2.61 (s, 3H), 2.15 (s, 7H), 1.94 (s, 1H), 1.83-1.55 (m, 2H).

Potency Lin28a-dep Z11 $IC_{50}$ (μM)++++

Example 50: Synthesis of (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylic acid

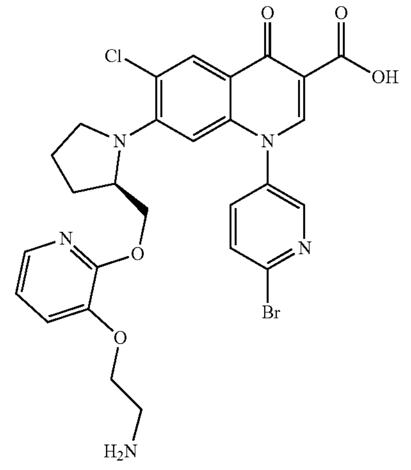 [SMILES: NCCOc1cccnc1OC[C@H]1CCCN1c1cc2c(cc1Cl)c(=O)c(C(=O)O)cn2-c1ccc(Br)nc1]

Step 1: Synthesis of 2-((4-methoxybenzyl)amino)ethan-1-ol

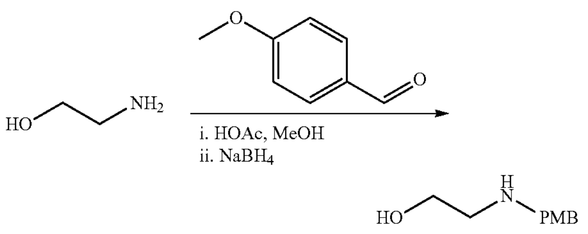

To a solution of 2-aminoethan-1-ol (3.0 g, 49.4 mmol) in MeOH (60 mL) was added 4-methoxybenzaldehyde (10.0 g, 73.71 mmol). The mixture was stirred at room temperature overnight. $NaBH_4$ (2.8 g, 73.71 mmol) was added to the mixture in portions. The mixture was stirred for another 1 h. The reaction was quenched by the addition of water. The mixture was concentrated to give the residue which was purified by reverse phase flash column with 5-50% acetonitrile in water to afford 2-((4-methoxybenzyl)amino)ethan-1-ol (4.5 g, 56%) as yellow oil. LCMS (ESI) $[M+H]^+$: 182.

Step 2: Synthesis of tert-butyl (2-hydroxyethyl)(4-methoxybenzyl)carbamate

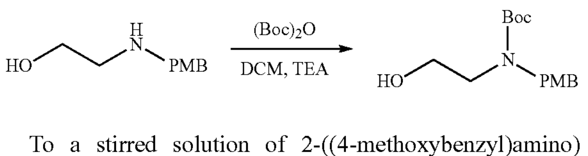

To a stirred solution of 2-((4-methoxybenzyl)amino)ethan-1-ol (1.0 g, 5.52 mmol) in $CHCl_3$ (10 mL) was added $Boc_2O$(1.32 g, 6.07 mmol). The solution was stirred at room temperature for 4 h. The solution was concentrated to give the residue which was purified by flash column with 0-40% EtOAc in petroleum ether to afford tert-butyl (2-hydroxyethyl)(4-methoxybenzyl)carbamate (1.4 g, 90%) as colorless oil. LCMS (ESI) $[M+H]^+$: 282.

Step 3: Synthesis of tert-butyl (2-((2-fluoropyridin-3-yl)oxy)ethyl)(4-methoxybenzyl)carbamate

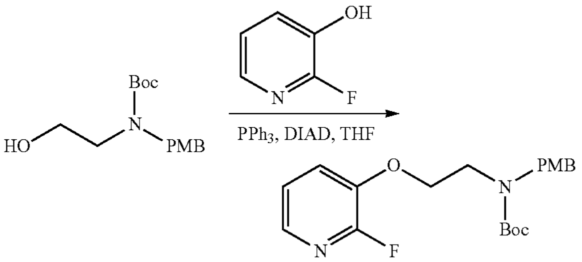

To a stirred mixture of 2-fluoropyridin-3-ol (3.0 g, 26.54 mmol), tert-butyl (2-hydroxyethyl)(4-methoxybenzyl)carbamate (11.2 g, 39.81 mmol) and $PPh_3$ (13.9 g, 53.08 mmol) in THF (50 mL) at 0° C. was added DIAD (10.7 g, 53.08 mmol). The mixture was stirred for 2 h. The reaction was quenched by the addition of 100 mL water. The aqueous solution was extracted with EtOAc (40 mL×3). The combined organic solution was dried over $Na_2SO_4$ and concentrated to give the residue which was purified by reverse flash column with 5-75% acetonitrile in water to afford tert-butyl (2-((2-fluoropyridin-3-yl)oxy)ethyl)(4-methoxybenzyl)carbamate (4.5 g, 45%) as yellow oil. LCMS (ESI) $[M+H]^+$: 377.

Step 4: Synthesis of tert-butyl (R)-(2-((2-((1-acetylpyrrolidin-2-yl)methoxy)pyridin-3-yl)oxy)ethyl)(4-methoxybenzyl)carbamate

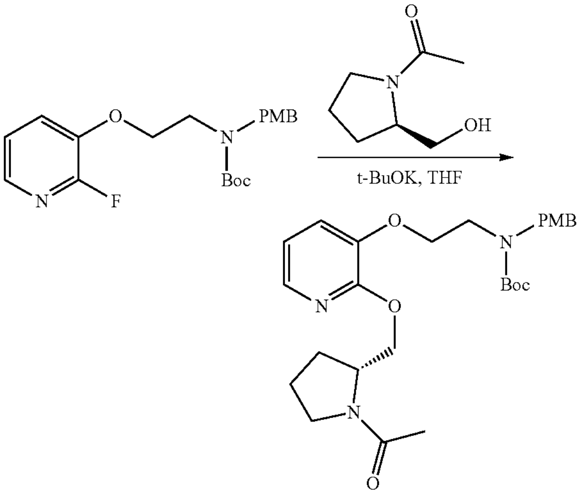

To a mixture of tert-butyl (2-((2-fluoropyridin-3-yl)oxy)ethyl)(4-methoxybenzyl)carbamate (2.0 g, 5.32 mmol) and (R)-1-(2-(hydroxymethyl)pyrrolidin-1-yl)ethan-1-one (1.1 g, 7.97 mmol) in THF (40 mL) was added t-BuOK (1.8 g, 15.96 mmol). The mixture was stirred at room temperature for 2 h. The reaction was quenched by the addition of 100 mL water. The aqueous solution was extracted with EtOAc (40 mL×3). The combined organic solution was dried over $Na_2SO_4$ and concentrated to give the residue which was purified by flash column with 0-8% MeOH in DCM to afford tert-butyl (R)-(2-((2-((1-acetylpyrrolidin-2-yl)methoxy)pyridin-3-yl)oxy)ethyl)(4-methoxybenzyl)carbamate (2.4 g, 90%) as colorless oil. LCMS (ESI) $[M+H]^+$: 500.

Step 5: Synthesis of tert-butyl (R)-(4-methoxybenzyl)(2-((2-(pyrrolidin-2-ylmethoxy)pyridin-3-yl)oxy)ethyl)carbamate

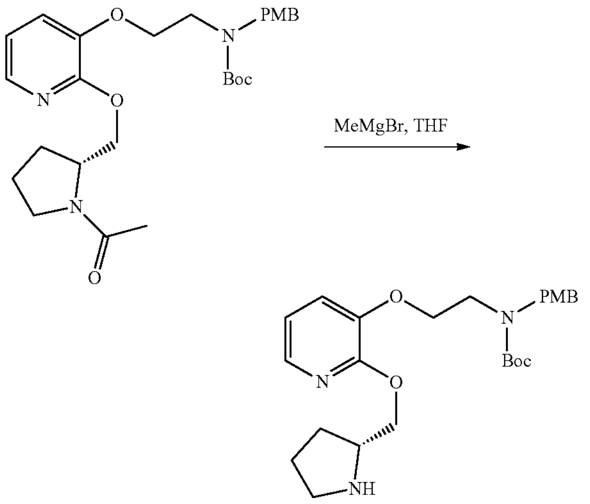

To a stirred solution of tert-butyl (R)-(2-((2-((1-acetylpyrrolidin-2-yl)methoxy)pyridin-3-yl)oxy)ethyl)(4-methoxybenzyl)carbamate (2.3 g, 4.61 mmol) in THF (20 mL) at −78° C. was added MeMgBr (23 mL, 23 mmol) dropwise. The solution was stirred at −78° C. to room temperature overnight. The reaction was quenched by the addition of 50 mL water. The aqueous solution was extracted with EtOAc (40 mL×3). The combined organic solution was dried over $Na_2SO_4$ and concentrated to give the residue which was purified by prep-HPLC to afford tert-butyl (R)-(4-methoxybenzyl)(2-((2-(pyrrolidin-2-ylmethoxy)pyridin-3-yl)oxy)ethyl)carbamate (560 mg, 27%) as yellow oil. LCMS (ESI) $[M+H]^+$: 458.

Step 6: Synthesis of ethyl (R)-1-(6-bromopyridin-3-yl)-7-(2-(((3-(2-((tert-butoxycarbonyl)(4-methoxybenzyl)amino)ethoxy)pyridin-2-yl)oxy)methyl)pyrrolidin-1-yl)-6-chloro-4-oxo-1,4-dihydroquinoline-3-carboxylate

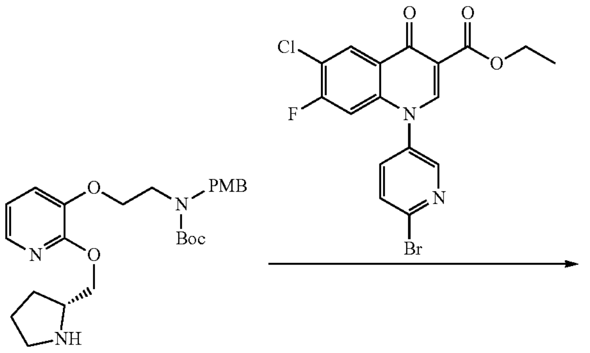

-continued

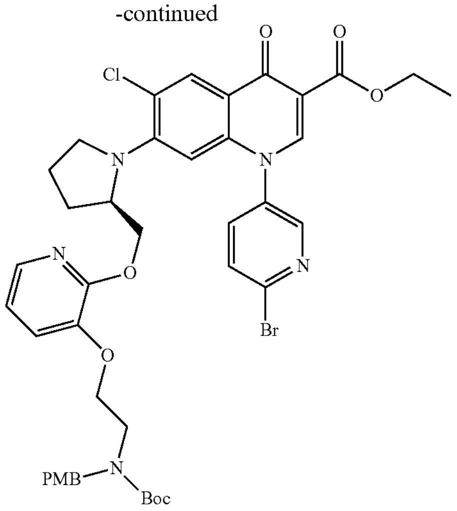

To a mixture of ethyl 1-(6-bromopyridin-3-yl)-6-chloro-7-fluoro-4-oxo-1,4-dihydroquinoline-3-carboxylate (200 mg, 0.47 mmol) and tert-butyl (R)-(4-methoxybenzyl)(2-((2-(pyrrolidin-2-ylmethoxy)pyridin-3-yl)oxy)ethyl)carbamate (431 mg, 0.94 mmol) in DMSO (5 mL) was added TEA (239 mg, 2.36 mmol). The mixture was stirred at 90° C. for 20 h. The solution was purified by reverse phase flash column with 20-90% acetonitrile in water to afford ethyl (R)-1-(6-bromopyridin-3-yl)-7-(2-(((3-(2-((tert-butoxycarbonyl)(4-methoxybenzyl)amino)ethoxy)pyridin-2-yl)oxy)methyl)pyrrolidin-1-yl)-6-chloro-4-oxo-1,4-dihydroquinoline-3-carboxylate (120 mg, 30%) as yellow solid. LCMS (ESI) [M+H]$^+$: 862.

Step 7: Synthesis of ethyl (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylate -continued

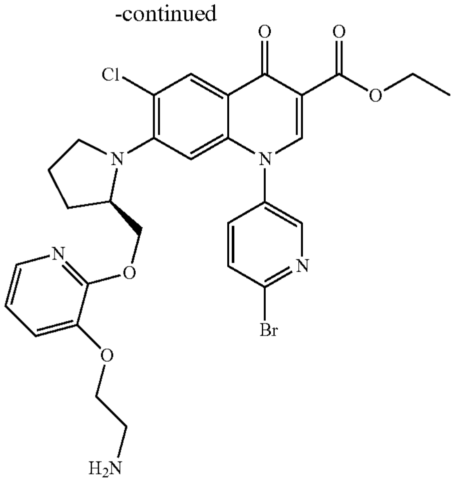

PH-TES-P2-562-7

A mixture solution of TfOH (2 mL) and TFA (2 mL) was added to ethyl (R)-1-(6-bromopyridin-3-yl)-7-(2-(((3-(2-((tert-butoxycarbonyl)(4-methoxybenzyl)amino)ethoxy)pyridin-2-yl)oxy)methyl)pyrrolidin-1-yl)-6-chloro-4-oxo-1,4-dihydroquinoline-3-carboxylate (120 mg, 0.14 mmol). The mixture was stirred at room temperature for 2 h. The solution was diluted with MeOH (5 mL) and purified by prep-HPLC (Column: YMC-Actus Triart C18, 20*250 mm, 5 m, 12 nm; Mobile Phase A: Water(0.1% FA), Mobile Phase B: ACN; Flow rate: 25 mL/min; Gradient: 25% B to 50% B in 8 min, 50% B; Wave Length: 254 nm; RT1 (min): 5.65; Number Of Runs: 0) to afford ethyl (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylate (59 mg, 66%) as yellow oil. LCMS (ESI) [M+H]$^+$: 642.

Step 8: Synthesis of (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylic acid

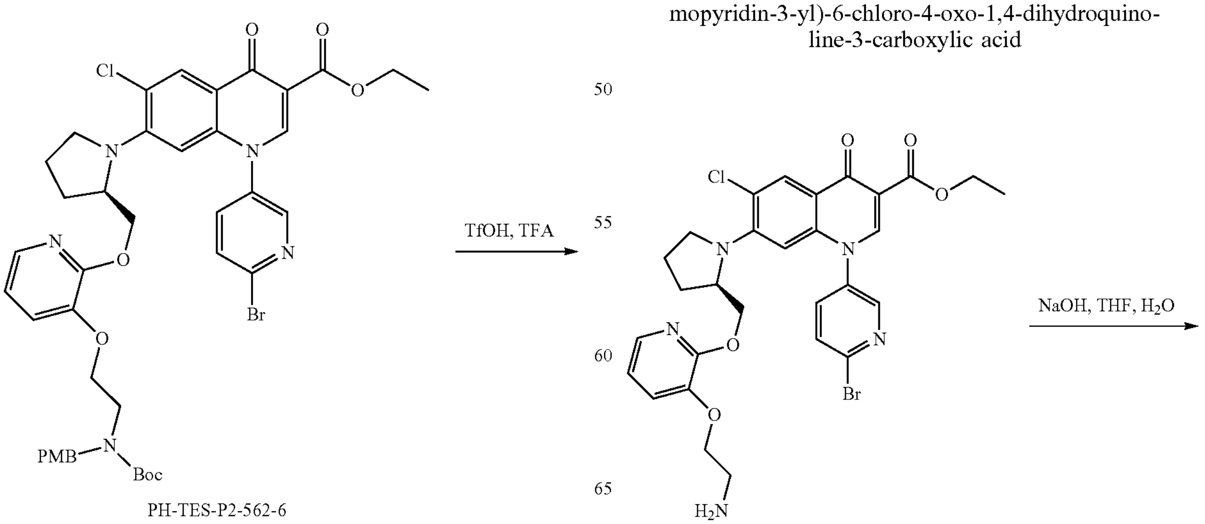

PH-TES-P2-562-6

-continued

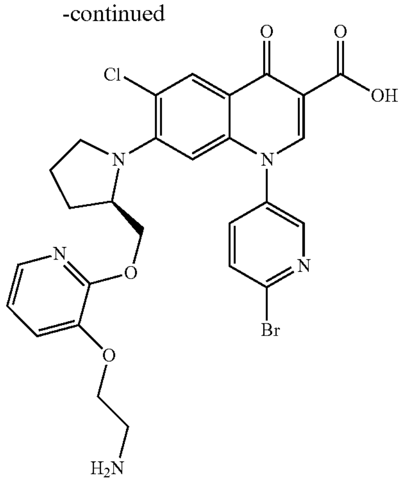

To a stirred solution of ethyl (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylate (59 mg, 0.09 mmol) in MeOH (4 mL) under nitrogen was added a solution of NaOH (37 mg, 0.92 mmol) in water (2 mL). The solution was stirred at room temperature for 4 h. 1M HCl was added to adjust pH 3. The mixture was purified by prep-HPLC (Column: XSelect CSH Prep C18 OBD Column, 19*150 mm, 5 μm; Mobile Phase A: Water(0.1% FA), Mobile Phase B: ACN; Flow rate: 25 mL/min; Gradient: 22% B to 28% B in 8 min, 28% B; Wave Length: 254/220 nm; RT1(min): 6.83; Number Of Runs: 0) to afford (R)-7-(2-(((3-(2-aminoethoxy)pyridin-2-yl)oxy)methyl)pyrrolidin-1-yl)-1-(6-bromopyridin-3-yl)-6-chloro-4-oxo-1,4-dihydroquinoline-3-carboxylic acid (18.7 mg, 33%) as yellow solid. LCMS (ESI): $[M+H+2]^+$: 616.15. $^1H$ NMR (300 MHz, DMSO-d6) δ 8.93-8.65 (m, 2H), 8.26 (s, 1H), 8.21-7.97 (m, 2H), 7.84-7.52 (m, 1H), 7.45-7.29 (m, 1H), 6.97 (s, 1H), 6.31 (s, 1H), 4.89-4.61 (m, 1H), 4.49-4.32 (m, 1H), 4.23-3.99 (m, 3H), 3.74-3.53 (m, 2H), 3.26-3.01 (m, 2H), 2.34-2.18 (m, 1H), 2.15-1.75 (m, 3H).

Potency Lin28a-dep Z11 $IC_{50}$ (μM)++++

Example 51: Synthesis of (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid

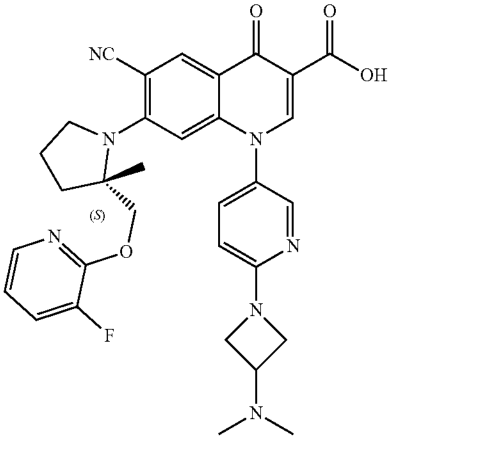

Step 1: Synthesis of (S)-1-(tert-butoxycarbonyl)-2-methylpyrrolidine-2-carboxylic acid

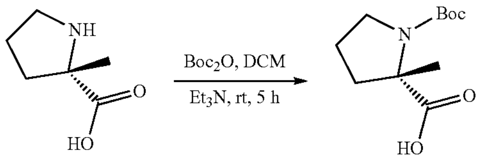

To a stirred solution of (S)-2-methylpyrrolidine-2-carboxylic acid (3.6 g, 27.87 mmol) in DCM (100 mL) was added $(Boc)_2O$ (18.25 g, 83.61 mmol, 3 equiv) and $Et_3N$ (8.46 g, 83.61 mmol, 3 equiv). The resulting mixture was stirred at room temperature for 5 h. Then the reaction was quenched by the addition of brine (200 mL). The mixture was extracted with DCM (100 mL×3). The combined organic phase was dried over $MgSO_4$. After filtration, the filtrate was concentrated under reduced pressure. This resulted in the crude product (S)-1-(tert-butoxycarbonyl)-2-methylpyrrolidine-2-carboxylic acid (6.38 g, 27.8 mmol) as colorless crystal. LCMS (ESI) $[M+H]^+$:230.

Step 2: Synthesis of tert-butyl (S)-2-(hydroxymethyl)-2-methylpyrrolidine-1-carboxylate

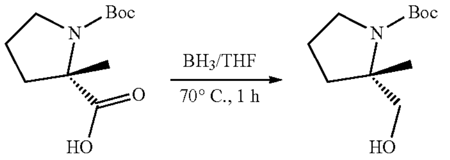 [SMILES: CC(C)(C)OC(=O)N1CCC[C@@]1(C)C(=O)O ; "70° C., 1 h" ; "BH3/THF" ; CC(C)(C)OC(=O)N1CCC[C@@]1(C)CO]

To a solution of (S)-1-(tert-butoxycarbonyl)-2-methylpyrrolidine-2-carboxylic acid (6.38 g, 27.8 mmol) in anhydrous THF (100 mL) was added $BH_3 \cdot Me_2S$ (10.56 g, 139 mmol, 5 equiv) at room temperature under $N_2$. Then the resulting mixture was stirred at 70° C. for 1 h. After cooling down to room temperature. The mixture was concentrated under reduced pressure. The residue was purified by silica gel column chromatography eluting with Petroleum ether/EtOAc=1:1 to afford tert-butyl (S)-2-(hydroxymethyl)-2-methylpyrrolidine-1-carboxylate (4.1 g, 19.04 mmol) as colorless oil. LCMS (ESI) $[M+H]^+$:216.

Step 3: Synthesis of tert-butyl (S)-2-(((3-fluoropyridin-2-yl)oxy)methyl)-2-methylpyrrolidine-1-carboxylate

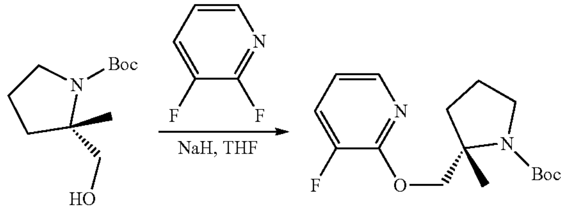

To a stirred solution of tert-butyl (S)-2-(hydroxymethyl)-2-methylpyrrolidine-1-carboxylate (4.1 g, 19.04 mmol) in anhydrous THF (100 mL) was added KO$^t$Bu (6.41 g, 57.12 mmol, 3 equiv) at 0° C. under $N_2$. After 10 min, 2,3-difluoropyridine (2.63 g, 22.85 mmol, 1.2 equiv) was added into the mixture and the resulting mixture was stirred at 0° C. for half an hour and followed by room temperature for 4 h. Then the reaction was quenched by the addition of brine (200 mL). The mixture was extracted with EtOAc (100 mL×3). The combined organic phase was dried over $MgSO_4$. After filtration, the filtrate was concentrated under reduced pressure. The residue was purified by silica gel column chromatography eluting with Petroleum ether/EtOAc=2:1 to afford tert-butyl (S)-2-(((3-fluoropyridin-2-yl)oxy)methyl)-2-methylpyrrolidine-1-carboxylate (4.3 g, 13.85 mmol) as colorless oil. LCMS (ESI) $[M+H]^+$:311.

Step 4: Synthesis of (S)-3-fluoro-2-((2-methylpyrrolidin-2-yl)methoxy)pyridine

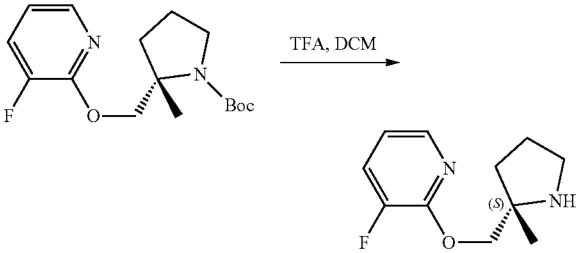

To a stirred solution of tert-butyl (S)-2-(((3-fluoropyridin-2-yl)oxy)methyl)-2-methylpyrrolidine-1-carboxylate (4.3 g, 13.85 mmol) in DCM (10 mL) was added TFA (15 mL). The mixture was stirred at room temperature for 4 h. The mixture was concentrated under reduced pressure. The residue was dissolved in sat. $NaHCO_3$ (200 mL) and extracted with EtOAc (100 mL×3). The combined organic phase was dried over $MgSO_4$. After filtration, the filtrate was concentrated under reduced pressure. This resulted in the (S)-3-fluoro-2-((2-methylpyrrolidin-2-yl)methoxy)pyridine (2.6 g, 12.36 mmol) as colorless oil. LCMS (ESI) $[M+H]^+$:211.

Step 5: Synthesis of ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate -continued

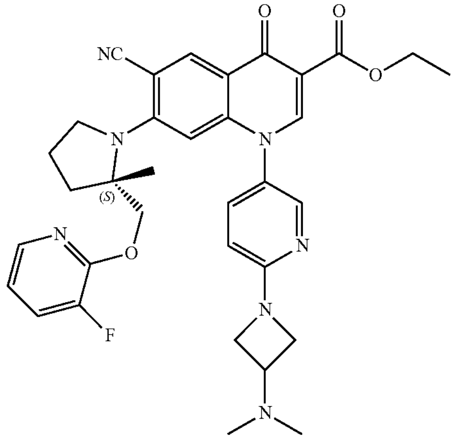

To a 8-mL sealed tube was added ethyl 6-cyano-1-(6-(3-(dimethylamino)azetidin-1-yl)pyridin-3-yl)-7-fluoro-4-oxo-1,4-dihydroquinoline-3-carboxylate (500 mg, 1.148 mmol), (S)-3-fluoro-2-((2-methylpyrrolidin-2-yl)methoxy)pyridine (724 mg, 3.445 mmol, 3 equiv) and DMSO (1 mL). The resulting mixture was heated at about 50° C. under vacuum for 1 h. Then DIEA (297 mg, 2.296 mmol, 2 equiv) was added into the mixture. The resulting mixture was stirred at 100° C. for 48 h under $N_2$. The mixture was purified by reverse phase chromatography eluting with Acetonitrile/water=7:3 to afford ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate (150 mg, 0.2397 mmol) as yellow solid. LCMS (ESI) $[M+H]^+$:626.

Step 6: Synthesis of (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid

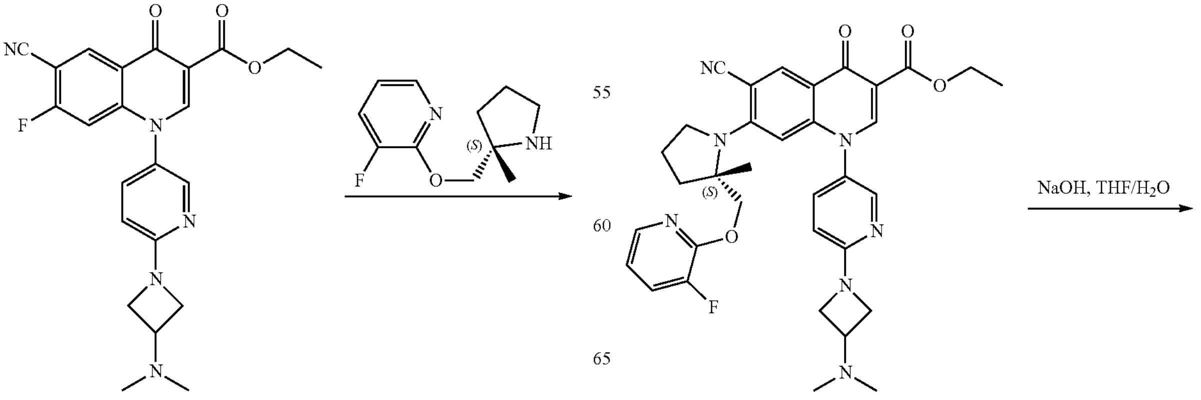

-continued

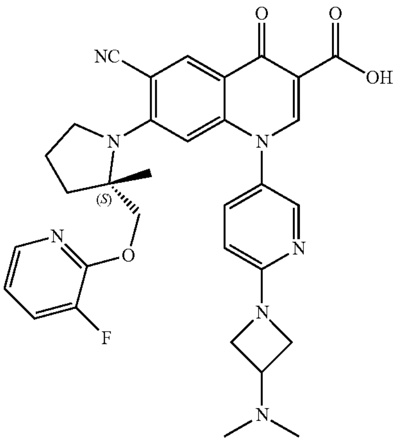

To a stirred solution of ethyl (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylate (150 mg, 0.2397 mmol) in THF (4 mL) was added a solution of NaOH (19 mg, 0.4794 mmol, 2 equiv) in $H_2O$ (2 mL) at room temperature under $N_2$. The resulting mixture was stirred at room temperature overnight. The mixture was acidified by AcOH. The mixture was purified by Prep.-HPLC to afford (S)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid (32.8 mg) as yellow solid. LCMS (ESI): $[M+H]^+$: 598.25. $^1H$ NMR (300 MHz, DMSO-d6) δ 14.69 (s, 1H), 8.69-8.08 (m, 3H), 7.94-7.51 (m, 3H), 7.07-6.91 (m, 1H), 6.61-6.27 (m, 2H), 4.46-4.22 (m, 2H), 4.06-3.87 (m, 3H), 3.80-3.61 (m, 2H), 3.26-3.12 (m, 1H), 2.35-2.22 (m, 1H), 2.13 (d, J=1.5 Hz, 6H), 2.08-1.80 (m, 3H), 1.29-1.15 (m, 3H).

Potency Lin28a-dep Z11 $IC_{50}$ (μM)++++

Example 52: Synthesis of 1-(6-(3-(dimethylamino)azetidin-1-yl)pyridin-3-yl)-6-methyl-4-oxo-7-(2-oxo-4-((pyridin-2-yloxy) methyl)azetidin-1-yl)-1,4-dihydroquinoline-3-carboxylic acid

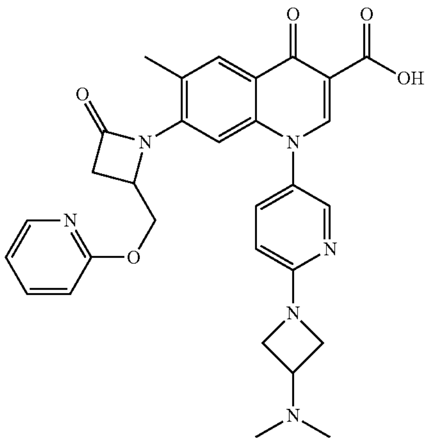 [SMILES: Cc1cc2c(=O)c(C(=O)O)cn(-c3ccc(N4CC(N(C)C)C4)nc3)c2cc1N1C(=O)CC1COc1ccccn1]

Step 1: Synthesis of 4-bromo-2-fluoro-5-methylbenzoyl chloride

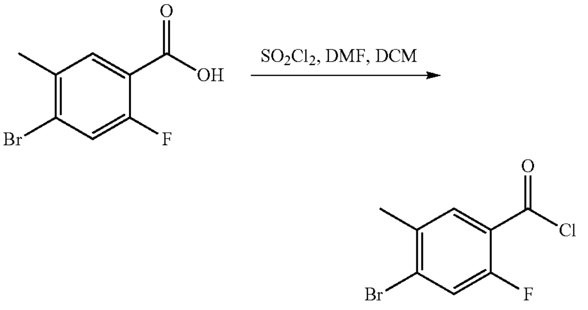

To a stirred solution of 4-bromo-2-fluoro-5-methylbenzoic acid (5 g, 21.4 mmol, 1 equiv) and thionyl chloride (15.31 g, 128.7 mmol, 6 equiv) in DCM was added DMF (20 mg, 0.2 mmol, 0.01 equiv) dropwise in portions at 50 degrees C. under nitrogen atmosphere. The resulting mixture was concentrated under vacuum. This resulted in 4-bromo-2-fluoro-5-methylbenzoyl chloride (5 g, 92.67%) as a yellow solid.

Step 2: Synthesis of ethyl 3-(4-bromo-2-fluoro-5-methylphenyl)-3-oxopropanoate

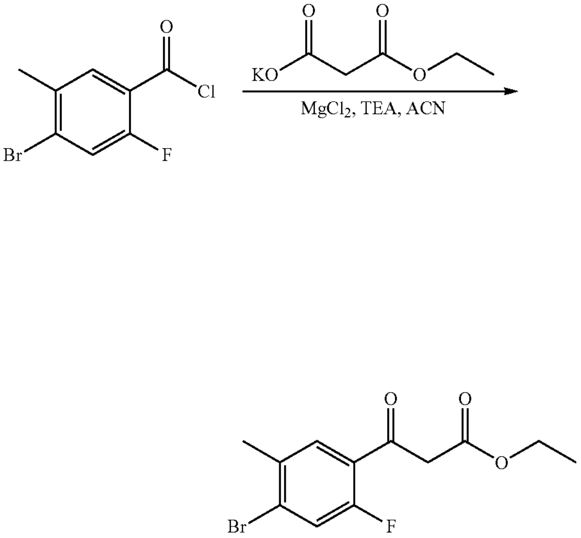

To a stirred solution of 1-ethyl 3-potassium propanedioate (6.77 g, 39.7 mmol, 2 equiv) and TEA (4.02 g, 39.7 mmol, 2 equiv) in acetonitrile was added 4-bromo-2-fluoro-5-methylbenzoyl chloride (5 g, 19.8 mmol, 1 equiv) dropwise in portions at room temperature under nitrogen atmosphere. The mixture was acidified/basified/neutralized to pH 5 with conc. HCl. The aqueous layer was extracted with EtOAc (3×100 mL). The residue was purified by silica gel column chromatography, eluted with PE/EA (10:1) to afford ethyl 3-(4-bromo-2-fluoro-5-methylphenyl)-3-oxopropanoate (5 g, 82.96%) as a yellow solid. LCMS (ESI) $[M+H]^+$: 303.

Step 3: Synthesis of ethyl (Z)-2-(4-bromo-2-fluoro-5-methylbenzoyl)-3-ethoxyacrylate

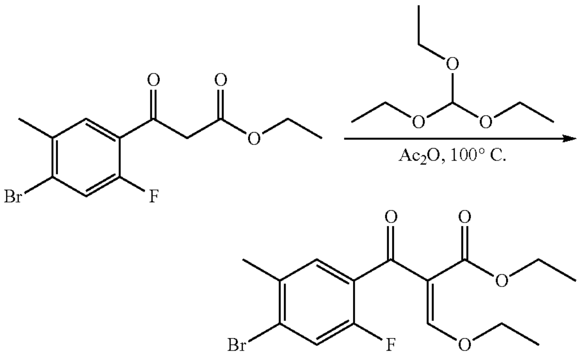

A solution of ethyl 3-(4-bromo-2-fluoro-5-methylphenyl)-3-oxopropanoate (3 g, 9.8 mmol, 1.00 equiv) and (diethoxymethoxy)ethane (1.4 g, 9.8 mmol, 1 equiv) in acetic anhydride (1 g, 9.8 mmol, 1 equiv) was stirred for 1 h at 100 degrees C. under nitrogen atmosphere. The resulting mixture was concentrated under vacuum. This resulted in ethyl (2Z)-2-[(Z)-4-bromo-2-fluoro-5-methylbenzoyl]-3-ethoxyprop-2-enoate (3 g, 84.39%) as a yellow oil. LCMS (ESI) $[M+H]^+$: 359.

Step 4: Synthesis of ethyl 7-bromo-1-(6-(3-(dimethylamino)azetidin-1-yl)pyridin-3-yl)-6-methyl-4-oxo-1,4-dihydroquinoline-3-carboxylate

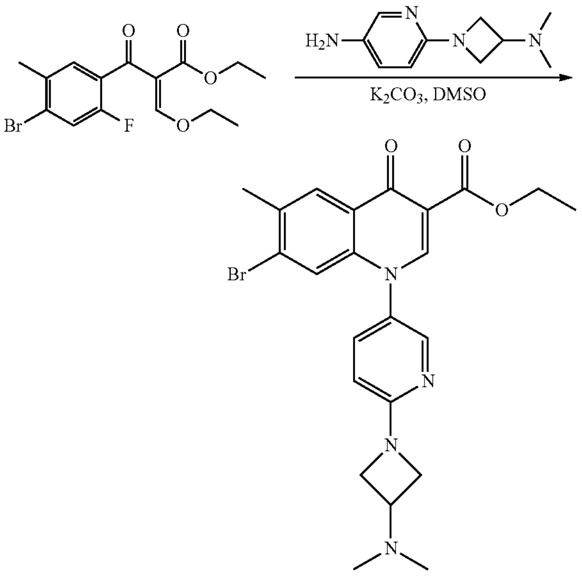

A solution of ethyl (2Z)-2-[(Z)-4-bromo-2-fluoro-5-methylbenzoyl]-3-ethoxyprop-2-enoate (3 g, 8.352 mmol, 1.00 equiv) and 6-[3-(dimethylamino) azetidin-1-yl]pyridin-3-amine (1.6 g, 8.3 mmol, 1 equiv) in DMSO was stirred for 1 h at room temperature under nitrogen atmosphere. Then the solution was add $K_2CO_3$ (1.1 g, 8.3 mmol, 1 equiv) at room temperature 1 h. The resulting mixture was diluted with water (20 mL). The precipitated solids were collected by filtration and washed with water (3×10 mL). This resulted in ethyl 7-bromo-1-(6-(3-(dimethylamino)azetidin-1-yl)pyridin-3-yl)-6-methyl-4-oxo-1,4-dihydroquinoline-3-carboxylate (3 g, 86.69%) as a yellow solid. LCMS (ESI) $[M+H]^+$: 485.

Step 5: Synthesis of 7-bromo-1-(6-(3-(dimethylamino)azetidin-1-yl)pyridin-3-yl)-6-methyl-4-oxo-1,4-dihydroquinoline-3-carboxylic acid

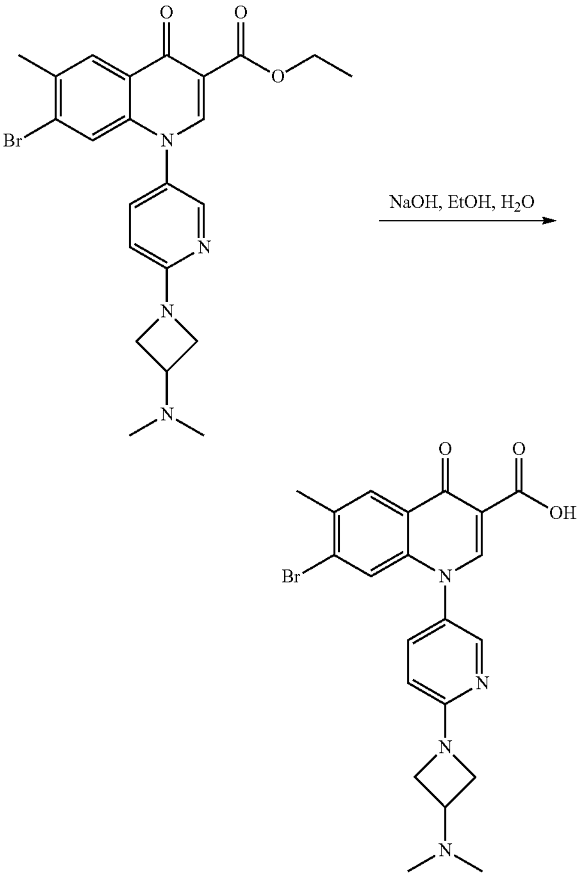

A solution of ethyl ethyl 7-bromo-1-(6-(3-(dimethylamino) azetidin-1-yl)pyridin-3-yl)-6-methyl-4-oxo-1,4-dihydroquinoline-3-carboxylate (200 mg, 0.148 mmol, 1 equiv) and NaOH (23 mg, 0.6 mmol, 2 equiv) in ethanol and $H_2O$ was stirred for 1 h at room temperature under nitrogen atmosphere. The mixture was acidified/basified/neutralized to pH 7 with conc. HCl. The residue was purified by reverse flash chromatography with the following conditions: column, silica gel; mobile phase, MeCN in water, 10% to 50% gradient in 10 min; detector, UV 254 nm. This resulted in 7-bromo-1-(6-(3-(dimethylamino)azetidin-1-yl)pyridin-3-yl)-6-methyl-4-oxo-1,4-dihydroquinoline-3-carboxylic acid (150 mg, 76.6%) as a yellow solid. MS (ESI): m/z 457 $[M+H]^+$ Step 6: Synthesis of 4-((pyridin-2-yloxy)methyl)azetidin-2-one

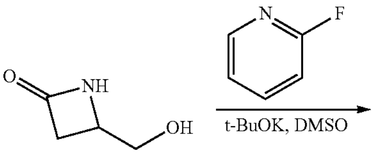

-continued

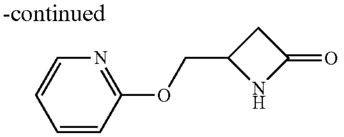

A solution of 4-(hydroxymethyl) azetidin-2-one (1 g, 10 mmol, 1 equiv) and 2-fluoropyridine (1.16 g, 12 mmol, 1.2 equiv), t-BuOK (3.36 g, 30 mmol, 3 equiv) in DMSO (5 mL) was stirred for 1 h at room temperature under nitrogen atmosphere. The residue was purified by reverse flash chromatography with the following conditions: column, silica gel; mobile phase, MeCN in water, 10% to 50% gradient in 10 min; detector, UV 254 nm. This resulted in 4-((pyridin-2-yloxy)methyl)azetidin-2-one (200 mg, 16.5%) as a yellow oil. MS (ESI): m/z 179 $[M+H]^+$ Step 7: Synthesis of 1-(6-(3-(dimethylamino)azetidin-1-yl)pyridin-3-yl)-6-methyl-4-oxo-7-(2-oxo-4-((pyridin-2-yloxy) methyl)azetidin-1-yl)-1,4-dihydroquinoline-3-carboxylic acid

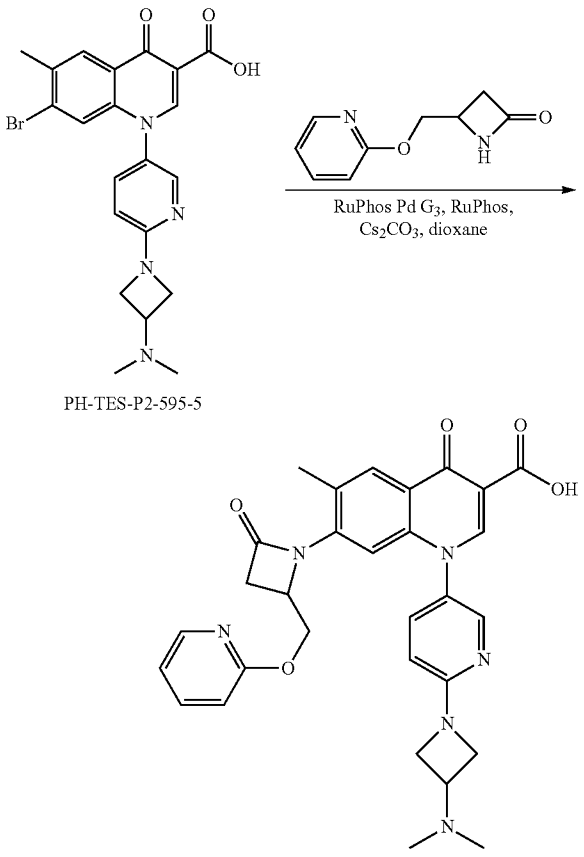

PH-TES-P2-595-5

PH-TES-P2-595

A solution of 7-bromo-1-[6-[3-(dimethylamino)azetidin-1-yl]pyridin-3-yl]-6-methyl-4-oxoquinoline-3-carboxylic acid (30 mg, 0.066 mmol, 1 equiv) and 4-[(pyridin-2-yloxy) methyl]azetidin-2-one (17.53 mg, 0.099 mmol, 1.5 equiv), 3rd Generation RuPhos precatalyst (5 mg, 0.007 mmol, 0.1 equiv), $Cs_2CO_3$ (64.12 mg, 0.198 mmol, 3 equiv) in dioxane was stirred for 1 h at 80 degrees C. under nitrogen atmosphere. The crude product (30 mg) was purified by Prep-HPLC with the following conditions (Column: Welch XB-C18, 21.2*250 mm, 5 μm; Mobile Phase A: Water(0.1% FA), Mobile Phase B: ACN; Flow rate: 25 mL/min; Gradient: 5% B to 5% B in 2 min, 5% B to 15% B in 2.5 min, 15% B to 40% B in 10.5 min, 40% B; Wave Length: 254 nm; RT1(min): 8.2; Number Of Runs: 0) to afford 1-[6-[3-(dimethylamino)azetidin-1-yl]pyridin-3-yl]-6-methyl-4-oxo-7-[2-oxo-4-[(pyridin-2-yloxy)methyl]azetidin-1-yl]quinoline-3-carboxylic acid (27.8 mg, 76.41%) as a yellow solid. $^1H$ NMR (300 MHz, DMSO-$d_6$) δ 15.08 (s, 1H), 8.62 (s, 1H), 8.36-8.15 (m, 2H), 8.04-7.90 (m, 1H), 7.73-7.59 (m, 2H), 7.14 (s, 1H), 7.03-6.86 (m, 1H), 6.63-6.44 (m, 2H), 4.72-4.65 (m, 1H), 4.54-4.41 (m, 2H), 4.19-4.05 (m, 2H), 3.89-3.77 (m, 2H), 3.24-3.17 (m, 2H), 3.08-2.94 (m, 1H), 2.47 (s, 3H), 2.16 (s, 6H). MS (ESI): m/z555.0 $[M+H]^+$ Potency Lin28a-dep Z11 $IC_{50}$ (μM)++

Example 53: Synthesis of 7-[(2R)-2-([[3-(2-Aminoethoxy)pyridin-2-yl]oxy]methyl)pyrrolidin-1-yl]-6-chloro-1-[6-(dimethylamino)pyridin-3-yl]-4-oxoquinoline-3-carboxylic acid

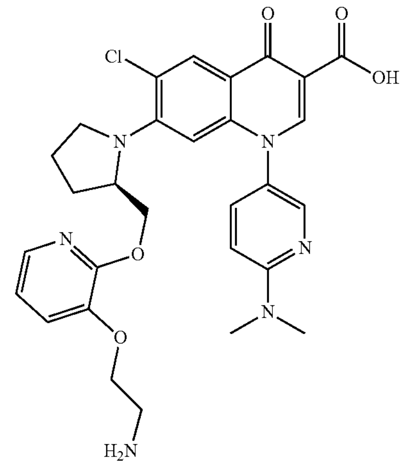 [SMILES: CN(C)c1ccc(-n2cc(C(=O)O)c(=O)c3cc(Cl)c(N4CCC[C@@H]4COc4ncccc4OCCN)cc32)cn1]

Step 1: Synthesis of N,N-Dimethyl-5-nitropyridin-2-amine

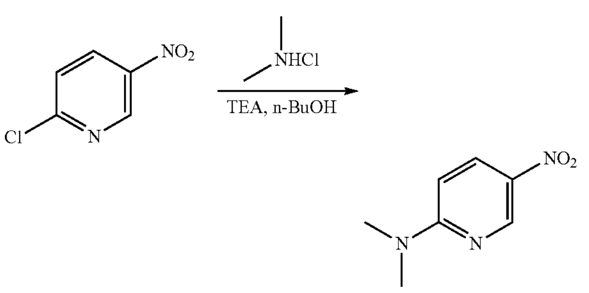

To a mixture of pyridine, 2-chloro-5-nitro-(2.0 g, 12.62 mmol, 1.0 equiv) in n-BuOH (65 mL) were added chlorodimethylamine (1.1 g, 13.88 mmol, 1.1 equiv) and TEA (3.8 g, 37.85 mmol, 3.0 equiv). The resulting mixture was stirred for 1.5 h at 100° C. under nitrogen atmosphere. The mixture was allowed to cool down to room temperature. The resulting mixture was concentrated under vacuum. The residue was purified by silica gel column chromatography, eluted with $CH_2Cl_2$/MeOH (10:1). This resulted in N,N-dimethyl-5-nitropyridin-2-amine (2.5 g, crude) as a red solid. LCMS (ESI) $[M+H]^+$: 168.1.

Step 2: Synthesis of N2,N2-Dimethylpyridine-2,5-diamine

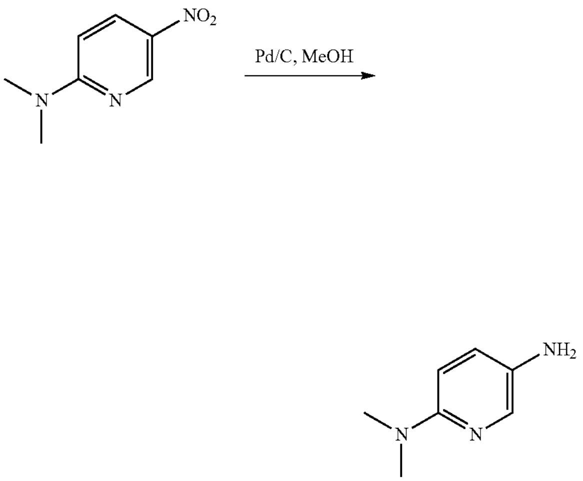

To a mixture of N,N-dimethyl-5-nitropyridin-2-amine (2.5 g, 14.96 mmol, 1.0 equiv) in MeOH (50 mL) were added Pd/C (1.6 g, 14.96 mmol, 1.0 equiv). The resulting mixture was stirred for 1.5 h at room temperature under hydrogen atmosphere. The resulting mixture was filtered, the filter cake was washed with MeOH (3×30 mL). The filtrate was concentrated under reduced pressure. This resulted in $N_2$,$N_2$-dimethylpyridine-2,5-diamine (850 mg, 41%) as a red solid. LCMS (ESI) $[M+H]^+$: 138.1.

Step 3: Synthesis of Ethyl 6-chloro-1-[6-(dimethylamino)pyridin-3-yl]-7-fluoro-4-oxoquinoline-3-carboxylate

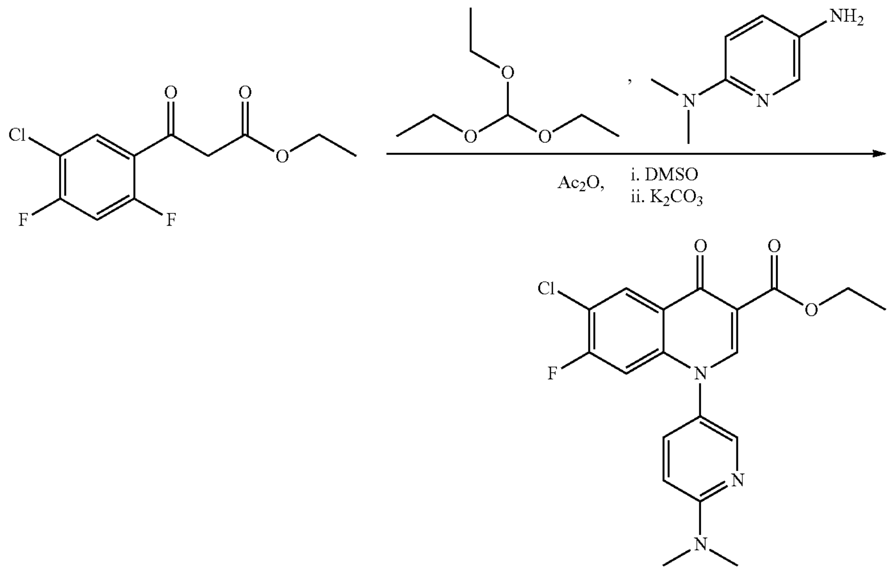

To a mixture of ethyl 3-(5-chloro-2,4-difluorophenyl)-3-oxopropanoate (1.0 g, 3.81 mmol, 1.0 equiv) in $Ac_2O$(1.2 g, 11.42 mmol, 3.0 equiv) was added triethyl orthoformate (0.9 g, 5.71 mmol, 1.5 equiv). The resulting mixture was stirred at 100° C. for 2 h. The resulting mixture was concentrated under vacuum. To the resulting mixture in DMSO (60 mL) was added $N_2$,$N_2$-dimethylpyridine-2,5-diamine (0.5 g, 3.81 mmol, 1.0 equiv). The resulting mixture was stirred at 25° C. for 2 h. To the resulting mixture was added $K_2CO_3$ (0.3 g, 1.90 mmol, 0.5 equiv). The resulting mixture was stirred at 100° C. for 1 h. The reaction was quenched by the addition of 65 mL water. The precipitated solids were collected by filtration. This resulted in ethyl 6-chloro-1-[6-(dimethylamino)pyridin-3-yl]-7-fluoro-4-oxoquinoline-3-carboxylate (800 mg, 54%) as a yellow solid. LCMS (ESI) $[M+H]^+$: 390.1.

Step 4: Synthesis of Ethyl 7-[(2R)-2-{[(3-{2-[(tert-butoxycarbonyl)[(4-methoxyphenyl)methyl]amino]ethoxy}pyridin-2-yl)oxy]methyl}pyrrolidin-1-yl]-6-chloro-1-[6-(dimethylamino)pyridin-3-yl]-4-oxoquinoline-3-carboxylate

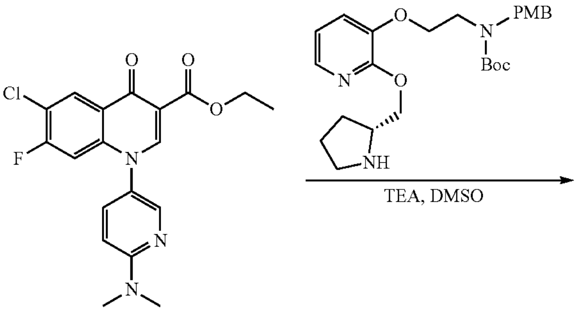

-continued

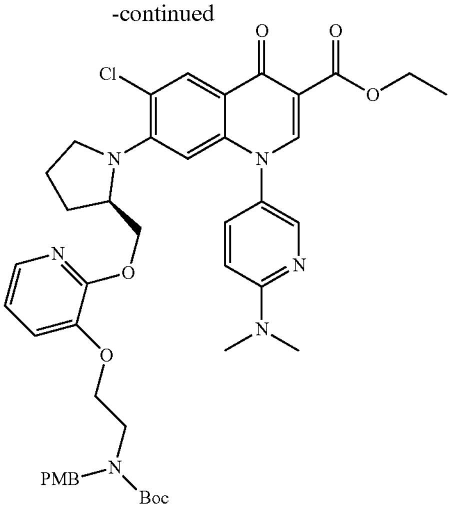

To a mixture of ethyl 6-chloro-1-[6-(dimethylamino)pyridin-3-yl]-7-fluoro-4-oxoquinoline-3-carboxylate (500 mg, 1.28 mmol, 1.0 equiv) in DMSO (15 mL) was added tert-butyl N-[(4-methoxyphenyl)methyl]-N-[2-({2-[(2R)-pyrrolidin-2-ylmethoxy]pyridin-3-yl}oxy)ethyl]carbamate (704 mg, 1.54 mmol, 1.2 equiv) and TEA (389 mg, 3.85 mmol, 3.0 equiv). The resulting mixture was stirred for 2 h at 100° C. under nitrogen atmosphere. The mixture was allowed to cool down to room temperature. The residue was purified by reverse flash chromatography with the following conditions: column, C18 silica gel; mobile phase, MeCN in water, 5% to 100% gradient in 30 min; detector, UV 254 nm and UV 220 nm. This resulted in ethyl 7-[(2R)-2-{[(3-{2-[(tert-butoxycarbonyl)[(4-methoxyphenyl)methyl]amino]ethoxy}pyridin-2-yl)oxy]methyl}pyrrolidin-1-yl]-6-chloro-1-[6-(dimethylamino)pyridin-3-yl]-4-oxoquinoline-3-carboxylate (400 mg, 38%) as a yellow solid. LCMS (ESI) $[M+H]^+$: 827.4.

Step 5: Synthesis of Ethyl 7-[(2R)-2-({[3-(2-aminoethoxy)pyridin-2-yl]oxy}methyl)pyrrolidin-1-yl]-6-chloro-1-[6-(dimethylamino)pyridin-3-yl]-4-oxoquinoline-3-carboxylate

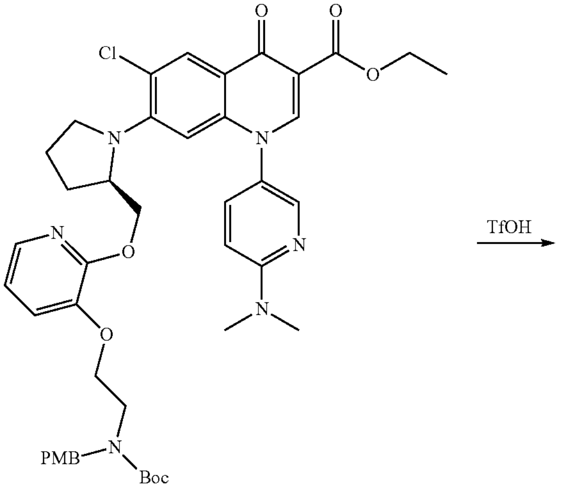

-continued

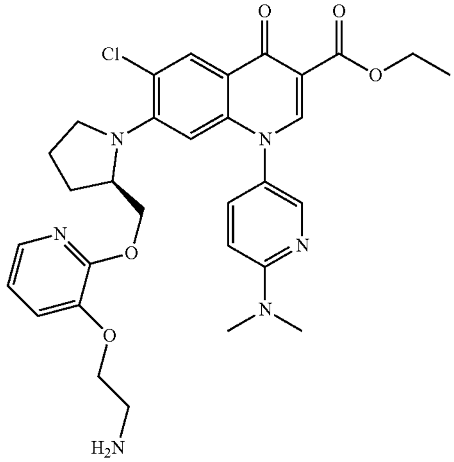

To a mixture of ethyl 7-[(2R)-2-{[(3-{2-[(tert-butoxycarbonyl)[(4-methoxyphenyl)methyl]amino]ethoxy}pyridin-2-yl)oxy]methyl}pyrrolidin-1-yl]-6-chloro-1-[6-(dimethylamino)pyridin-3-yl]-4-oxoquinoline-3-carboxylate (360 mg, 0.44 mmol, 1.0 equiv) in trifluoromethanesulfonic acid (2.5 mL). The resulting mixture was stirred for 2 h at room temperature. The resulting mixture was concentrated under vacuum. The residue was purified by reverse flash chromatography with the following conditions: column, C18 silica gel; mobile phase, MeCN in water, 5% to 100% gradient in 30 min; detector, UV 254 nm and UV 220 nm. This resulted in ethyl 7-[(2R)-2-({[3-(2-aminoethoxy)pyridin-2-yl]oxy}methyl)pyrrolidin-1-yl]-6-chloro-1-[6-(dimethylamino)pyridin-3-yl]-4-oxoquinoline-3-carboxylate (50 mg, 19%) as a yellow solid. LCMS (ESI) $[M+H]^+$: 607.2.

Step 6: Synthesis of 7-[(2R)-2-([[3-(2-Aminoethoxy)pyridin-2-yl]oxy]methyl)pyrrolidin-1-yl]-6-chloro-1-[6-(dimethylamino)pyridin-3-yl]-4-oxoquinoline-3-carboxylic acid

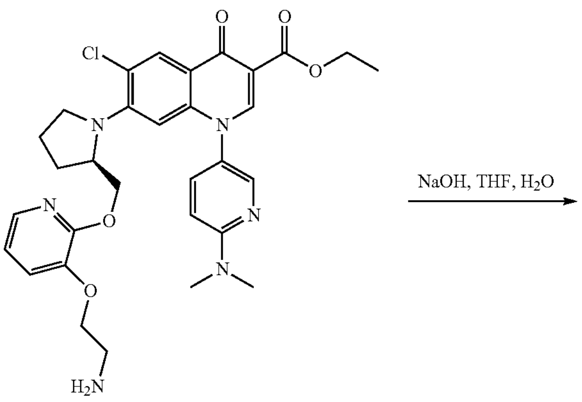

-continued

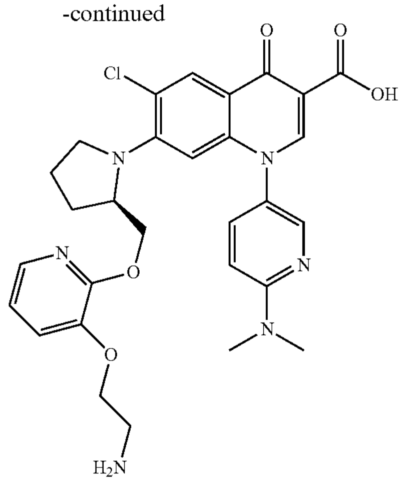

To a mixture of ethyl 7-[(2R)-2-([[3-(2-aminoethoxy)pyridin-2-yl]oxy]methyl)pyrrolidin-1-yl]-6-chloro-1-[6-(dimethylamino)pyridin-3-yl]-4-oxoquinoline-3-carboxylate (40 mg, 0.07 mmol, 1.0 equiv) in THF (1 mL) was added NaOH (26 mg, 0.66 mmol, 10.0 equiv) and $H_2O$ (1 mL). The resulting mixture was stirred for 1 h at room temperature under nitrogen atmosphere. The mixture was neutralized to pH 5 with HCl (aq.). The resulting mixture was concentrated under vacuum. The crude product was purified by Prep-HPLC with the following conditions (Column: XBridge Shield RP18 OBD Column, 5 um, 19*150 mm; Mobile Phase A:Water(0.1% FA), Mobile Phase B: ACN; Flow rate: 25 mL/min; Gradient: 60% B to 90% B in 8 min; 254/220 nm; Rt: 7.31 min). This resulted in 7-[(2R)-2-([[3-(2-aminoethoxy)pyridin-2-yl]oxy]methyl)pyrrolidin-1-yl]-6-chloro-1-[6-(dimethylamino)pyridin-3-yl]-4-oxoquinoline-3-carboxylic acid (5.7 mg, 14.94%) as a light yellow solid. LCMS (ESI) $[M+H]^+$: 579.25. $^1$H NMR (300 MHz, DMSO-d6) δ 8.59 (d, J=6.1 Hz, 1H), 8.34 (d, J=9.1 Hz, 1H), 8.24 (s, 1H), 7.75 (d, J=9.9 Hz, 1H), 7.64 (d, J=5.3 Hz, 1H), 7.37 (d, J=7.2 Hz, 1H), 7.04-6.85 (m, 1H), 6.60 (d, J=9.0 Hz, 1H), 6.46 (d, J=5.2 Hz, 1H), 4.76 (d, J=27.5 Hz, 1H), 4.45 (s, 1H), 4.21-4.03 (m, 3H), 3.74-3.53 (m, 1H), 3.17 (d, J=3.8 Hz, 7H), 2.38-2.23 (m, 1H), 2.12-1.75 (m, 3H).

Potency Lin28a-dep Z11 $IC_{50}$ (μM)++++

Example 54: Synthesis of (R)-7-(2-(((3-chloropyridin-2-yl)oxy)methyl)-5-oxopyrrolidin-1-yl)-6-cyano-1-(6-(3-(dimethylamino)azetidin-1-yl)pyridin-3-yl)-4-oxo-1,4-dihydroquinoline-3-carboxylic acid

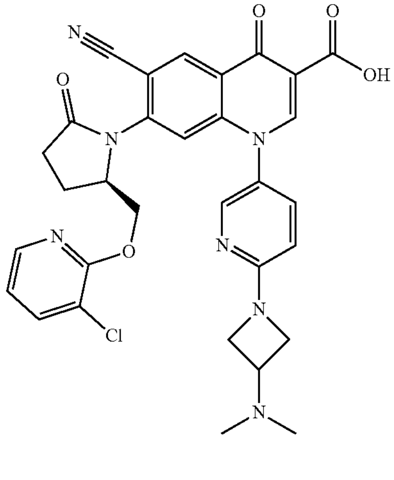 [SMILES: CN(C)C1CN(c2ccc(-n3cc(C(=O)O)c(=O)c4cc(C#N)c(N5C(=O)CC[C@@H]5COc5ncccc5Cl)cc43)cn2)C1]

Step 1: Synthesis of (R)-5-(((3-chloropyridin-2-yl)oxy)methyl)pyrrolidin-2-one

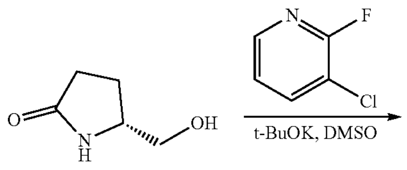

To a mixture of (5R)-5-(hydroxymethyl)pyrrolidin-2-one (6.0 g, 52.11 mmol, 1.0 equiv) and t-BuOK (17.5 g, 156.34 mmol, 3.0 equiv) in DMSO (15 ml) was added 3-chloro-2-fluoropyridine (8.2 g, 62.54 mmol, 1.2 equiv) at 0° C. The resulting mixture was stirred for 1 h at room temperature under nitrogen atmosphere. The residue was purified by reverse flash chromatography with the following conditions: column, silica gel; mobile phase, MeCN in water, 50% to 70% gradient in 20 min; detector, UV 254 nm. This resulted in ((R)-5-(((3-chloropyridin-2-yl)oxy)methyl)pyrrolidin-2-one (6 g, 50.80%) as a yellow solid. LCMS (ESI) $[M+H]^+$: 227.1.

Step 2: Synthesis of (R)-7-(2-(((3-chloropyridin-2-yl)oxy)methyl)-5-oxopyrrolidin-1-yl)-6-cyano-1-(6-(3-(dimethylamino)azetidin-1-yl)pyridin-3-yl)-4-oxo-1,4-dihydroquinoline-3-carboxylic acid

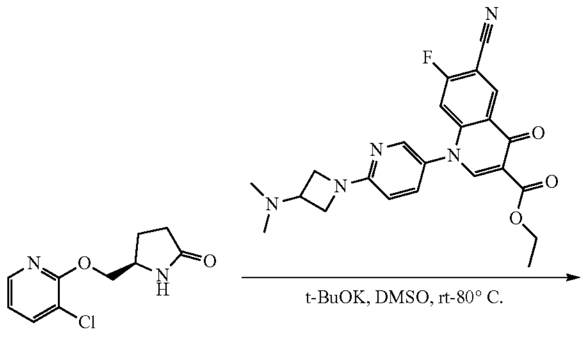

-continued

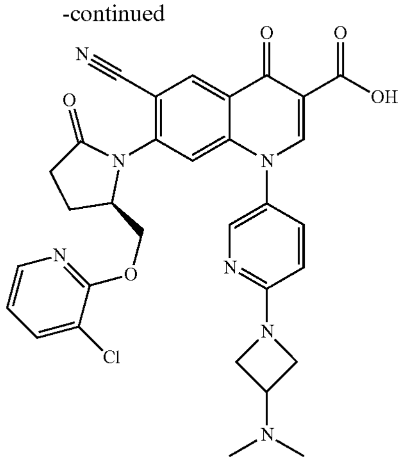

To a mixture of (5R)-5-[[(3-chloropyridin-2-yl)oxy]methyl]pyrrolidin-2-one (80 mg, 0.35 mmol, 1.0 equiv) and t-BuOK (119 mg, 1.06 mmol, 3.0 equiv) in DMSO (1 mL) after 30 min was added ethyl 6-cyano-1-[6-[3-(dimethylamino)azetidin-1-yl]pyridin-3-yl]-7-fluoro-4-oxoquinoline-3-carboxylate (184 mg, 0.42 mmol, 1.20 equiv) in portions at room temperature under nitrogen atmosphere. The resulting mixture was stirred for 1 h at 80° C. under nitrogen atmosphere. The mixture was acidified to pH 6 with acetic acid. The crude product (80 mg) was purified by Prep-HPLC with the following conditions (Column: Gemini-NX C18 AXAI Packed, 21.2*150 mm 5 um; Mobile Phase A:Water (0.1% FA), Mobile Phase B:ACN; Flow rate:25 mL/min; Gradient:13 B to 35 B in 8 min; 254 nm; RT1:5.0; RT2; Injection Volumn: ml; Number Of Runs;) to afford 7-[(2R)-2-[[(3-chloropyridin-2-yl)oxy]methyl]-5-oxopyrrolidin-1-yl]-6-cyano-1-[6-[3-(dimethylamino)azetidin-1-yl]pyridin-3-yl]-4-oxoquinoline-3-carboxylic acid (9.7 mg, 4.48%) as a yellow solid. LCMS (ESI) $[M+H]^+$: 614.0. $^1H$ NMR (300 MHz, DMSO-d6) δ 9.99 (s, 1H), 8.27 (d, J=7.1 Hz, 1H), 8.08-7.97 (m, 1H), 7.88-7.76 (m, 1H), 7.67 (d, J=2.4 Hz, 2H), 7.30-6.92 (m, 2H), 6.62-6.15 (m, 2H), 4.46 (d, J=4.0 Hz, 1H), 4.39-3.93 (m, 7H), 2.73 (s, 6H), 2.54 (s, 1H), 2.45-2.41 (m, 1H), 2.41-2.25 (m, 2H), 1.97 (s, 1H).

Potency Lin28a-dep Z11 $IC_{50}$ (μM)++

Example 55: Synthesis of (R)-26,63-dichloro-24-oxo-21,24-dihydro-5,7-dioxa-11-aza-2(1,7)-quinolina-1(5,2),6(2,6)-dipyridina-3(1,2)-pyrrolidinacycloundecaphane-23-carboxylic acid

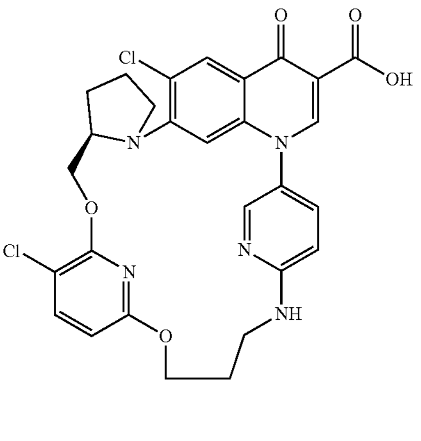 [SMILES: O=C(O)c1cn2c3cc(c(Cl)cc3c1=O)N1CCC[C@@H]1COc1nc(ccc1Cl)OCCCNc1ccc-2cn1]

Step 1: Synthesis of tert-butyl (R)-2-(((6-chloro-3-nitropyridin-2-yl)oxy)methyl)pyrrolidine-1-carboxylate

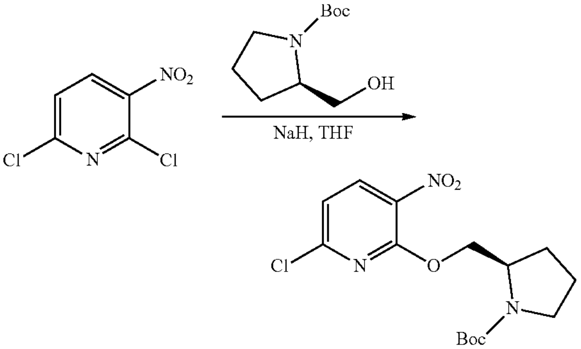

To a stirred solution of tert-butyl (2R)-2-(hydroxymethyl)pyrrolidine-1-carboxylate (12. g, 62.183 mmol, 1.2 equiv) and NaH (2.4 g, 103.6 mmol, 2 equiv) in THF was added 2,6-dichloro-3-nitropyridine (10 g, 51.8 mmol, 1 equiv) dropwise in portions at 0 degrees C. under nitrogen atmosphere 1 h. The reaction was quenched with Water at room temperature. The aqueous layer was extracted with EtOAc (3×100 mL). The resulting mixture was concentrated under reduced pressure. The residue was purified by silica gel column chromatography, eluted with PE/EA (5:1) to afford tert-butyl (2R)-2-[[(6-chloro-3-nitropyridin-2-yl)oxy]methyl]pyrrolidine-1-carboxylate (13 g, 70.12%) as a yellow solid. LCMS (ESI) $[M+H]^+$: 358.

Step 2: Synthesis of tert-butyl (R)-2-(((3-amino-6-chloropyridin-2-yl)oxy)methyl)pyrrolidine-1-carboxylate

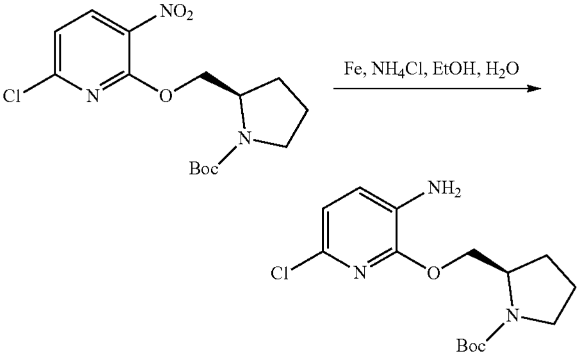

A solution of tert-butyl (2R)-2-[[(6-chloro-3-nitropyridin-2-yl)oxy]methyl]pyrrolidine-1-carboxylate (13 g, 36 mmol, 1 equiv) and Fe (10 g, 181 mmol, 5 equiv), $NH_4Cl$ (5.5 g, 109 mmol, 3 equiv) in ethanol and $H_2O$ was stirred for 1 h at 80 degrees C. under nitrogen atmosphere. The resulting mixture was filtered, the filter cake was washed with ethanol (3×100 mL). The filtrate was concentrated under reduced pressure. The residue was purified by silica gel column chromatography, eluted with PE/EA (3:1) to afford tert-butyl (2R)-2-[[(3-amino-6-chloropyridin-2-yl)oxy]methyl]pyrrolidine-1-carboxylate (6.6 g, 55.41%) as a yellow solid. LCMS (ESI) $[M+H]^+$: 328.

Step 3: Synthesis of tert-butyl (R)-2-(((3,6-dichloropyridin-2-yl)oxy)methyl)pyrrolidine-1-carboxylate

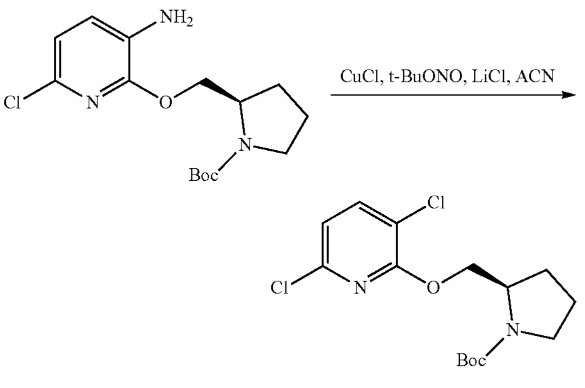

To a stirred mixture of CuCl (2391.85 mg, 24.161 mmol, 1.2 equiv) and LiCl (2560.63 mg, 60.402 mmol, 3 equiv) in acetonitrile was added t-$BuNO_2$ (3.6 g, 35.6 mmol, 1.7 equiv) and tert-butyl (2R)-2-[[(3-amino-6-chloropyridin-2-yl)oxy]methyl]pyrrolidine-1-carboxylate (6.6 g, 20.1 mmol, 1 equiv) in portions at 60 degrees C. under nitrogen atmosphere. The reaction was quenched with HCL(aq.) at 0 degrees C. The aqueous layer was extracted with EtOAc (3×100 mL). The residue was purified by silica gel column chromatography, eluted with PE/EA (5:1) to afford tert-butyl (2R)-2-[[(3,6-dichloropyridin-2-yl)oxy]methyl]pyrrolidine-1-carboxylate (3.5 g, 50.06%) as a yellow solid. LCMS (ESI) $[M+H]^+$: 347

Step 4: Synthesis of (R)-3,6-dichloro-2-(pyrrolidin-2-ylmethoxy)pyridine

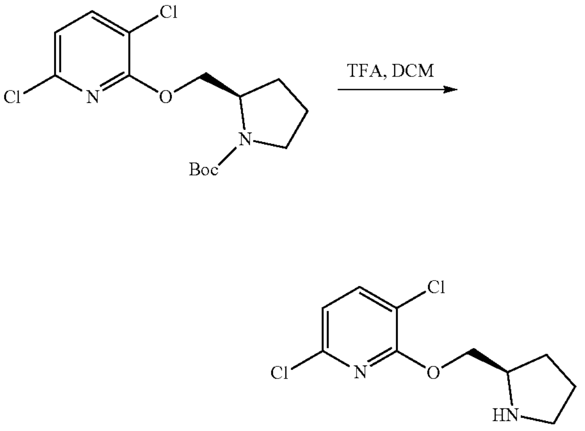

A solution of tert-butyl (2R)-2-[[(3,6-dichloropyridin-2-yl)oxy]methyl]pyrrolidine-1-carboxylate (3.5 g, 10 mmol, 1 equiv) and TFA (11.49 g, 100.7 mmol, 10 equiv) in DCM was stirred for 1 h at room temperature under nitrogen atmosphere. The resulting mixture was concentrated under vacuum. This resulted in 3,6-dichloro-2-[(2R)-pyrrolidin-2-ylmethoxy]pyridine (2 g, 80.29%) as a yellow oil. LCMS (ESI) $[M+H]^+$: 247.

Step 5: Synthesis of 3-((5-nitropyridin-2-yl)amino)propan-1-ol

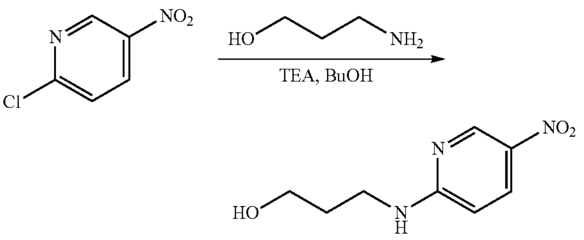

A solution of pyridine, 2-chloro-5-nitro-(10 g, 63.0 mmol, 1 equiv) and propanolamine (5 g, 75.6 mmol, 1.2 equiv), TEA (19 g, 189.2 mmol, 3 equiv) in BuOH was stirred for 1 h at 100 degrees C. under nitrogen atmosphere. The resulting mixture was concentrated under vacuum. The residue was purified by silica gel column chromatography, eluted with PE/EA (5:1) to afford 3-[(5-nitropyridin-2-yl)amino]propan-1-ol (11 g, 88.44%) as a yellow solid. LCMS (ESI) $[M+H]^+$: 198.

Step 6: Synthesis of 3-((5-aminopyridin-2-yl)amino)propan-1-ol

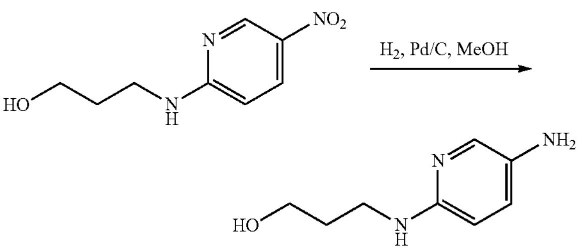

A solution of 3-[(5-nitropyridin-2-yl)amino]propan-1-ol (4.5 g, 22.820 mmol, 1 equiv) and Pd/C (242 mg, 2.28 mmol, 0.1 equiv) in MeOH was stirred for 1 h at room temperature under hydrogen atmosphere. The resulting mixture was filtered, the filter cake was washed with MeOH (3×100 mL). The filtrate was concentrated under reduced pressure. The resulting mixture was concentrated under vacuum. This resulted in 3-[(5-aminopyridin-2-yl)amino]propan-1-ol (3.8 g, 99.59%) as a yellow solid. LCMS (ESI) $[M+H]^+$: 168.

Step 7: Synthesis of ethyl (Z)-2-(5-chloro-2,4-difluorobenzoyl)-3-ethoxyacrylate

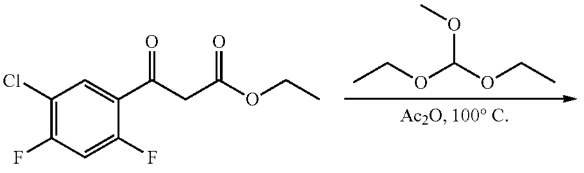

-continued

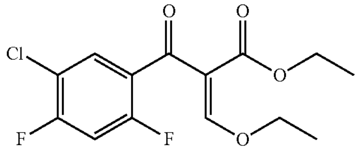

A solution of ethyl 3-(5-chloro-2,4-difluorophenyl)-3-oxopropanoate (5 g, 19.03 mmol, 1.00 equiv) and triethyl orthoformate (4.2 g, 28.555 mmol, 1.5 equiv) in $Ac_2O$(5.8 g, 57.111 mmol, 3 equiv) was stirred for 1 h at 100 degrees C. under nitrogen atmosphere. The resulting mixture was concentrated under vacuum. This resulted in ethyl (2Z)-2-[(Z)-5-chloro-2,4-difluorobenzoyl]-3-ethoxyprop-2-enoate (5.5 g, 90.65%) as a yellow oil.

Step 8: Synthesis of ethyl 6-chloro-7-fluoro-1-(6-((3-hydroxypropyl)amino)pyridin-3-yl)-4-oxo-1,4-dihydroquinoline-3-carboxylate

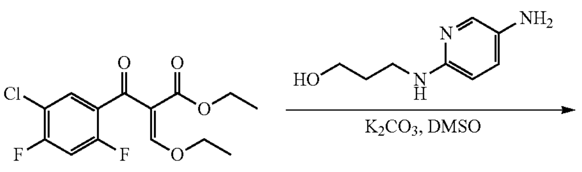

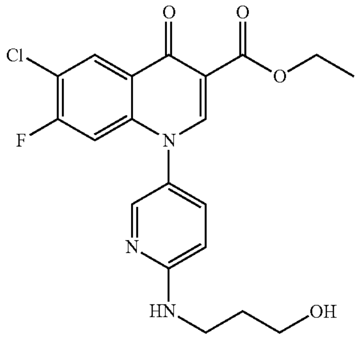

A solution of ethyl (2Z)-2-[(Z)-5-chloro-2,4-difluorobenzoyl]-3-ethoxyprop-2-enoate (5.5 g, 17.258 mmol, 1 equiv) and 3-[(5-aminopyridin-2-yl)amino]propan-1-ol (2.8 g, 17.25 mmol, 1 equiv) in DMSO was stirred for 1 h at room temperature under nitrogen atmosphere. Then The solution was add $K_2CO_3$ (2.3 g, 17.25 mmol, 1 equiv) at room temperature 1 h. The resulting mixture was diluted with water (20 mL). The precipitated solids were collected by filtration and washed with water (3x10 mL). This resulted in ethyl 6-chloro-7-fluoro-1-[6-[(3-hydroxypropyl)amino]pyridin-3-yl]-4-oxoquinoline-3-carboxylate (5 g, 69.01%) as a yellow solid. LCMS (ESI) $[M+H]^+$: 420

Step 9: Synthesis of ethyl (R)-6-chloro-7-(2-(((3,6-dichloropyridin-2-yl)oxy)methyl)pyrrolidin-1-yl)-1-(6-((3-hydroxypropyl)amino)pyridin-3-yl)-4-oxo-1,4-dihydroquinoline-3-carboxylate

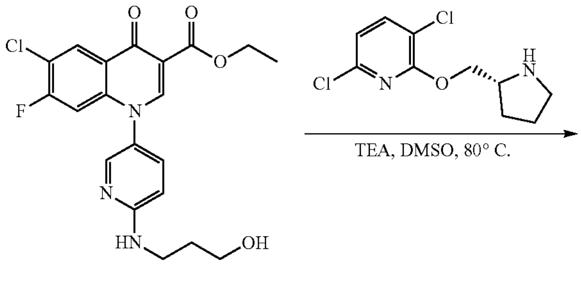

PH-TES-P2-619-8

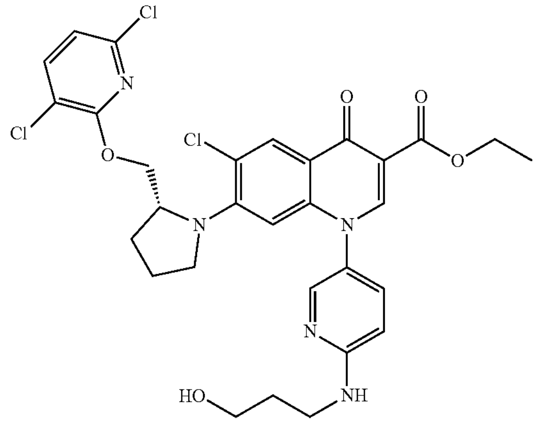

PH-TES-P2-619-9

A solution of ethyl 6-chloro-7-fluoro-1-[6-[(3-hydroxypropyl)amino]pyridin-3-yl]-4-oxoquinoline-3-carboxylate (1 g, 2.38 mmol, 1 equiv) and 3,6-dichloro-2-[(2R)-pyrrolidin-2-ylmethoxy]pyridine (1.7 g, 7.14 mmol, 3 equiv), TEA (0.72 g, 7.14 mmol, 3 equiv) in DMSO was stirred for 1 h at 100 degrees C. under nitrogen atmosphere. The residue was purified by reverse flash chromatography with the following conditions: column, silica gel; mobile phase, MeCN in water, 10% to 50% gradient in 10 min; detector, UV 254 nm. This resulted in ethyl 6-chloro-7-[(2R)-2-[[(3,6-dichloropyridin-2-yl)oxy]methyl]pyrrolidin-1-yl]-1-[6-[(3-hydroxypropyl)amino]pyridin-3-yl]-4-oxoquinoline-3-carboxylate (200 mg, 12.98%) as a yellow solid. LCMS (ESI) $[M+H]^+$: 646

Step 10: Synthesis of (R)-26,63-dichloro-24-oxo-21,24-dihydro-5,7-dioxa-11-aza-2(1,7)-quinolina-1(5,2),6(2,6)-dipyridina-3(1,2)-pyrrolidinacycloundecaphane-23-carboxylic acid

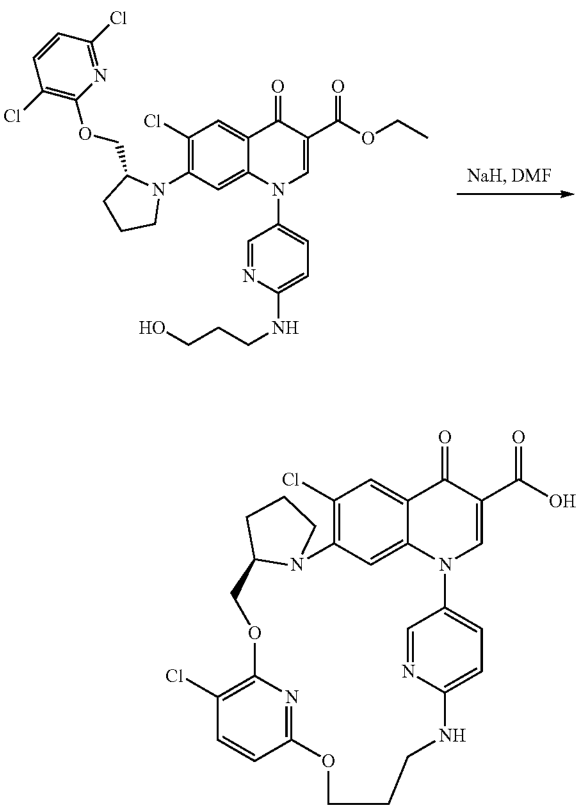

A solution of ethyl 6-chloro-7-[(2R)-2-[[(3,6-dichloropyridin-2-yl)oxy]methyl]pyrrolidin-1-yl]-1-[6-[(3-hydroxypropyl)amino]pyridin-3-yl]-4-oxoquinoline-3-carboxylate (200 mg, 0.31 mmol, 1.00 equiv) and NaH (29 mg, 1.23 mmol, 4 equiv) in DMF was stirred for 1 h at 50 degrees C. under nitrogen atmosphere. The resulting mixture was concentrated under reduced pressure. The crude product (200 mg) was purified by Prep-HPLC with the following conditions (Column: Gemini-NX C18 AXAI Packed, 21.2*150 mm 5 um; Mobile Phase A: Water(0.1% FA), Mobile Phase B: ACN; Flow rate: 25 mL/min; Gradient: 23% B to 31% B in 8 min, 31% B; Wave Length: 254 nm; RT1(min): 9.23; Number Of Runs: 0) to afford (R)-26,63-dichloro-24-oxo-21,24-dihydro-5,7-dioxa-11-aza-2(1,7)-quinolina-1(5,2),6(2,6)-dipyridina-3(1,2)-pyrrolidinacycloundecaphane-23-carboxylic acid (8.5 mg, 4.72%) as a yellow solid. $^1$H NMR (300 MHz, Methanol-$d_4$) δ 9.99 (s, 1H), 8.03 (s, 1H), 7.64-7.35 (m, 1H), 7.27-6.93 (m, 2H), 6.63 (d, J=8.6 Hz, 1H), 6.50-6.37 (m, 1H), 6.06-5.87 (m, 1H), 4.71-4.58 (m, 1H), 4.38-4.04 (m, 4H), 3.99-3.78 (m, 1H), 3.68-3.49 (m, 1H), 3.47-3.41 (m, 1H), 3.20-3.06 (m, 1H), 2.17-1.97 (m, 3H), 1.89-1.76 (m, 3H), 1.31 (s, 2H). MS (ESI): m/z 581.95 $[M+H]^+$ Potency Lin28a-dep Z11 $IC_{50}$ (μM)++

Example 56: Synthesis of 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylic acid

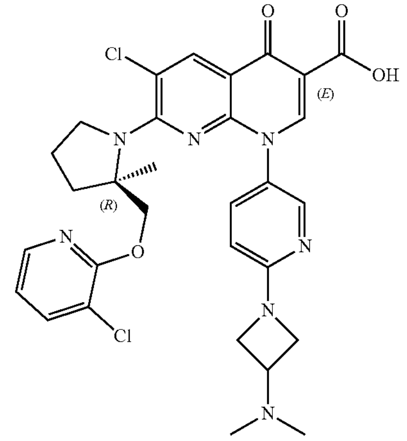

Step 1: Synthesis of ethyl 6,7-dichloro-1-[6-[3-(dimethylamino)azetidin-1-yl]pyridin-3-yl]-4-oxo-1,8-naphthyridine-3-carboxylate

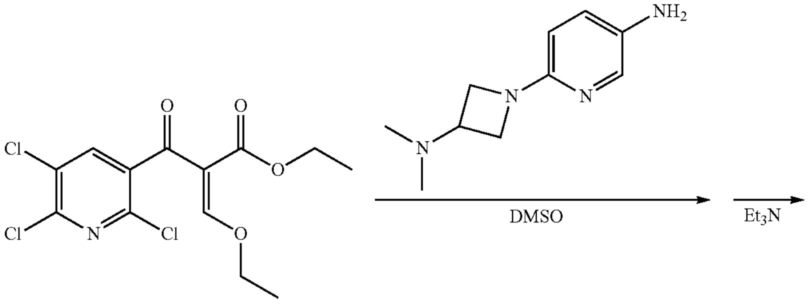

-continued

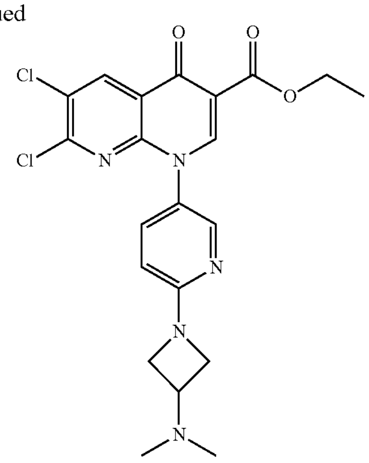

A mixture of ethyl (2Z)-3-ethoxy-2-[(Z)-2,5,6-trichloropyridine-3-carbonyl]prop-2-enoate (1.0 g, 2.83 mmol), 6-[3-(dimethylamino)azetidin-1-yl]pyridin-3-amine (0.5 g, 2.86 mmol) and DMSO (15.0 mL) was stirred overnight at room temperature. Then $Et_3N$ (0.8 g, 8.40 mmol) was added and the mixture was stirred overnight at room temperature. The resulting mixture was purified by RPFC to afford ethyl 6,7-dichloro-1-[6-[3-(dimethylamino)azetidin-1-yl]pyridin-3-yl]-4-oxo-1,8-naphthyridine-3-carboxylate (600 mg, 46.24%) as a yellow solid. LCMS (ESI) $[M+H]^+$: 462.

Step 2: Synthesis of ethyl 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylate

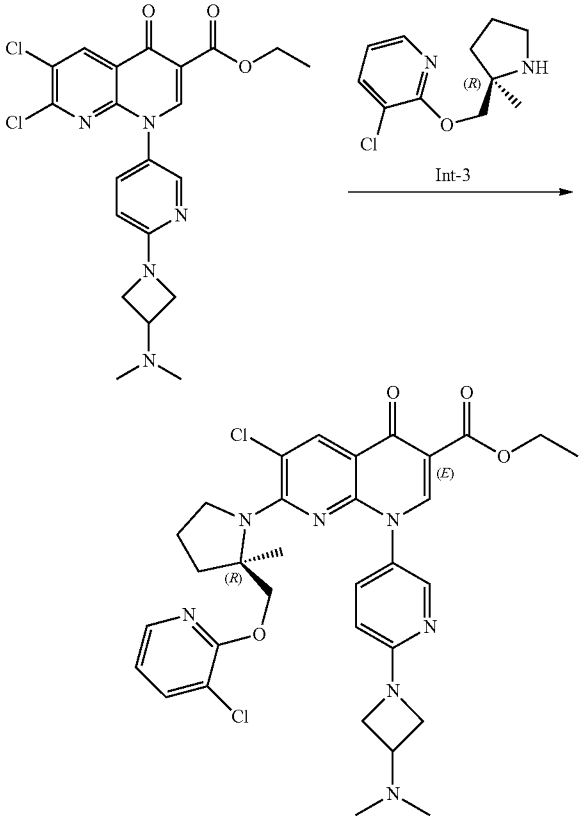

A mixture of ethyl 6,7-dichloro-1-[6-[3-(dimethylamino)azetidin-1-yl]pyridin-3-yl]-4-oxo-1,8-naphthyridine-3-carboxylate (200 mg, 0.43 mmol) and 3-chloro-2-[[(2R)-2-methylpyrrolidin-2-yl]methoxy]pyridine (392 mg, 1.73 mmol) was stirred for 2 h at 120° C.

The resulting mixture was purified by RPFC to afford ethyl 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylate (60 mg, 21.25%) as a yellow solid. LCMS (ESI) $[M+H]^+$: 652.

Step 3: Synthesis of 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylic acid

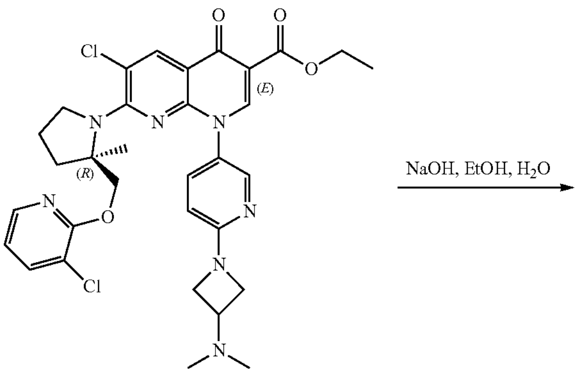

-continued

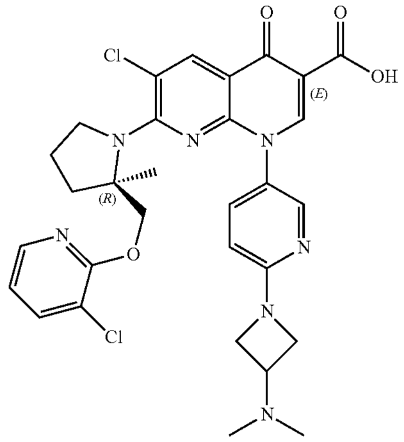

To a solution of ethyl 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylate (60 mg, 0.09 mmol) in EtOH (1.0 mL) was added NaOH (0.46 mL, 0.46 mmol) and the mixture was stirred for 2 h at room temperature. The reaction was quenched with 1 mL 1N HCl and the mixture was concentrated and purified by prep-HPLC to afford 6-chloro-7-[(2R)-2-[[(3-chloropyridin-2-yl)oxy]methyl]-2-methylpyrrolidin-1-yl]-1-[6-[3-(dimethylamino)azetidin-1-yl]pyridin-3-yl]-4-oxo-1,8-naphthyridine-3-carboxylic acid (29.5 mg, 50.66%) as a white solid. LCMS (ESI) $[M+H]^+$: 624.25. $^1H$ NMR (300 MHz, DMSO-$d_6$) δ 15.04 (s, 1H), 8.57 (s, 1H), 8.25 (s, 1H), 8.20 (d, J=2.5 Hz, 1H), 8.00 (s, 1H), 7.86 (d, J=7.6 Hz, 1H), 7.65 (s, 1H), 6.98 (s, 1H), 6.66-5.97 (m, 1H), 4.51 (s, 1H), 4.21-3.81 (m, 5H), 3.68 (q, J=6.5 Hz, 2H), 3.18 (s, 1H), 2.23-2.07 (m, 7H), 2.06-1.65 (m, 3H), 1.15 (s, 3H).

Potency Lin28a-dep Z11 $IC_{50}$ (μM)++++

Example 57: Synthesis of 6-Chloro-7-(7-(((3-chloropyridin-2-yl)oxy)methyl)-6-azaspiro[3.4]octan-6-yl)-1-(6-(3-(dimethylamino)azetidin-1-yl)pyridin-3-yl)-4-oxo-1,4-dihydroquinoline-3-carboxylic acid

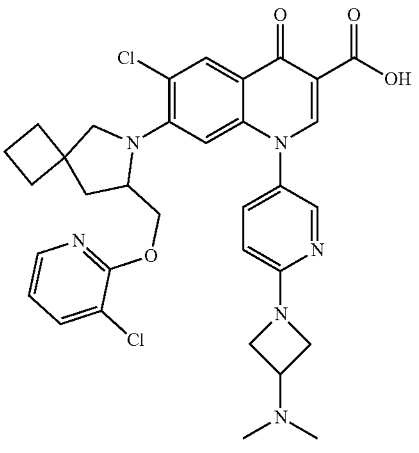 [SMILES: CN(C)C1CN(c2ccc(-n3cc(C(=O)O)c(=O)c4cc(Cl)c(N5CC6(CCC6)CC5COc5ncccc5Cl)cc43)cn2)C1]

Step 1: Synthesis of 1-allylcyclobutane-1-carbonitrile

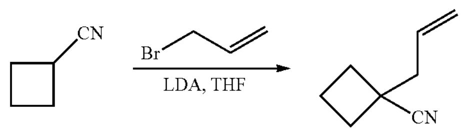

To a mixture of cyclobutanecarbonitrile (3 g, 36.98 mmol, 1.0 equiv) and allyl bromide (5.37 g, 44.38 mmol, 1.2 equiv) in THF(20 ml) was added LDA (7.92 g, 73.97 mmol, 2 equiv) at 0° C. under nitrogen atmosphere. The resulting mixture was stirred for 1 h at room temperature under nitrogen atmosphere. The residue was purified by silica gel column chromatography, eluted with PE/EA (1:1) to afford 1-allylcyclobutane-1-carbonitrile (1.4 g, 31.24%) as a yellow oil. LCMS (ESI) $[M+H]^+$: 122.1.

Step 2: Synthesis of (1-Allylcyclobutyl)methanamine

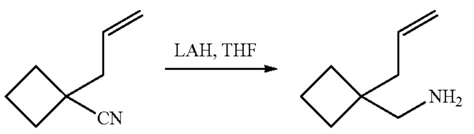

To a stirred mixture of 1-allylcyclobutane-1-carbonitrile (900 mg, 7.43 mmol, 1.0 equiv) in THF (5 ml) was added LAH (564 mg, 14.85 mmol, 2.0 equiv) at 0° C. under nitrogen atmosphere. The resulting mixture was stirred for 1 h at 0° C. under nitrogen atmosphere. The reaction was quenched by the addition of $NaSO_4 \cdot 10H_2O$ at 0° C. The resulting mixture was dried by $MgSO_4$. And it was concentrated under vacuum. The crude product was used in the next step directly without further purification. LCMS (ESI) $[M+H]^+$: 126.1.

Step 3: Synthesis of Tert-butyl ((1-allylcyclobutyl)methyl)carbamate

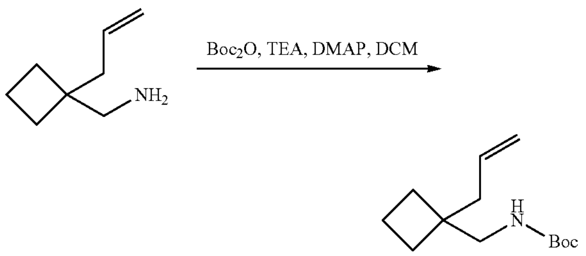

To a mixture of 1-[1-(prop-2-en-1-yl)cyclobutyl]methanamine (900 mg, 7.19 mmol, 1.0 equiv) and $Boc_2O$(3.14 g, 14.38 mmol, 2.0 equiv) in DCM (5 ml) was added TEA (3.64 g, 35.94 mmol, 5.0 equiv) and DMAP (88 mg, 0.72 mmol, 0.1 equiv) in portions at 0° C. under nitrogen atmosphere. The resulting mixture was stirred for 2 h at room temperature under nitrogen atmosphere. The resulting mixture was concentrated under vacuum. The residue was purified by silica gel column chromatography, eluted with PE/EA (1:1) to afford tert-butyl N-{[1-(prop-2-en-1-yl)cyclobutyl]methyl}carbamate (800 mg, 49.39%) as a light yellow oil. LCMS (ESI) $[M+H]^+$: 226.2.

Step 4: Synthesis of (6-Azaspiro[3.4]octan-7-yl)methanol

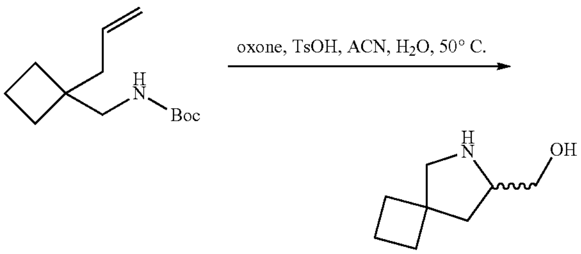

To a mixture of tert-butyl N-{[1-(prop-2-en-1-yl)cyclobutyl]methyl}carbamate (800 mg, 3.55 mmol, 1.0 equiv) and TsOH (1.22 g, 7.10 mmol, 2.0 equiv) in MeCN (5 ml) was added oxone (1.79 g, 10.65 mmol, 3.0 equiv) at 0° C. under nitrogen atmosphere. The resulting mixture was stirred for 2 h at 50° C. under nitrogen atmosphere. The resulting mixture was concentrated under vacuum. The crude product was used in the next step directly without further purification. LCMS (ESI) $[M+H]^+$: 142.1.

Step 5: Synthesis of Tert-butyl 7-(hydroxymethyl)-6-azaspiro[3.4]octane-6-carboxylate

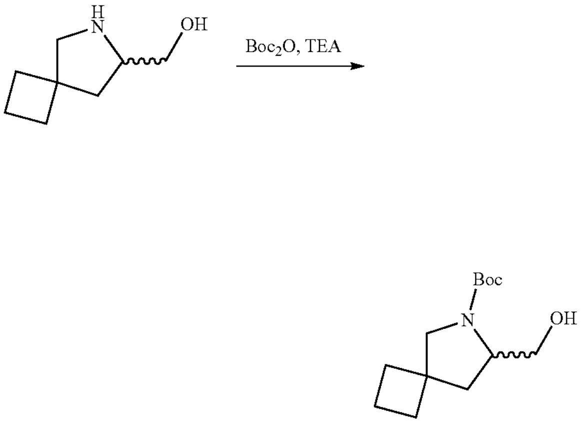 [SMILES: OCC1CC2(CCC2)CN1 ; "Boc2O, TEA" ; CC(C)(C)OC(=O)N1CC2(CCC2)CC1CO]

To a mixture of 6-azaspiro[3.4]octan-7-ylmethanol (600 mg, 4.25 mmol, 1.0 equiv) and $Boc_2O$(1.85 g, 8.50 mmol, 2.0 equiv) in DCM (5 ml) was added TEA (2.15 g, 21.25 mmol, 5.0 equiv) at 0° C. under nitrogen atmosphere. The resulting mixture was stirred for overnight at room temperature under nitrogen atmosphere. The resulting mixture was concentrated under vacuum. The residue was purified by silica gel column chromatography, eluted with $CH_2Cl_2$/MeOH (10:1) to afford tert-butyl 7-(hydroxymethyl)-6-azaspiro[3.4]octane-6-carboxylate (240 mg, 23.41%) as a light yellow solid. LCMS (ESI) $[M+H]^+$: 242.2.

Step 6: Synthesis of Tert-butyl 7-(((3-chloropyridin-2-yl)oxy)methyl)-6-azaspiro[3.4]octane-6-carboxylate

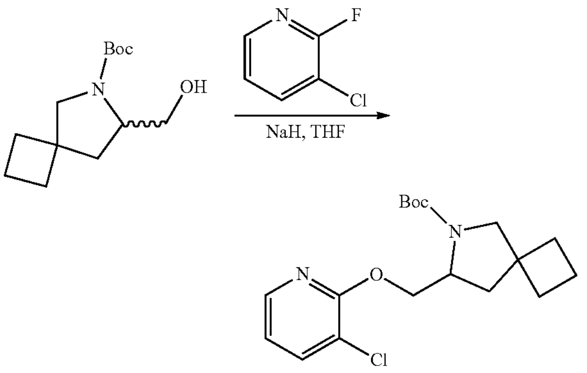

To a mixture of tert-butyl 7-(hydroxymethyl)-6-azaspiro[3.4]octane-6-carboxylate (230 mg, 0.95 mmol, 1.0 equiv) in THF (5 ml) was added NaH (69 mg, 2.86 mmol, 3.0 equiv) and 3-chloro-2-fluoropyridine (150 mg, 1.14 mmol, 1.2 equiv) at 0° C. under nitrogen atmosphere. The resulting mixture was stirred for 1 h at room temperature under nitrogen atmosphere. The reaction was quenched with MeOH at 0° C. The residue was purified by reverse flash chromatography with the following conditions: column, silica gel; mobile phase, MeCN in water, 50% to 60% gradient in 10 min; detector, UV 254 nm. This resulted in tert-butyl 7-{[(3-chloropyridin-2-yl)oxy]methyl}-6-azaspiro[3.4]octane-6-carboxylate (140 mg, 41.63%) as a light yellow oil. LCMS (ESI) $[M+H]^+$: 353.2.

Step 7: Synthesis of 7-(((3-Chloropyridin-2-yl)oxy)methyl)-6-azaspiro[3.4]octane

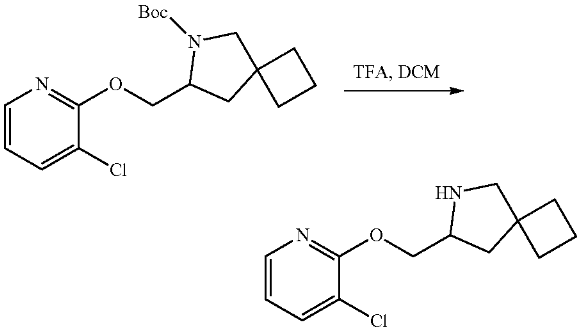

To a mixture of t tert-butyl 7-{[(3-chloropyridin-2-yl)oxy]methyl}-6-azaspiro[3.4]octane-6-carboxylate (140 mg, 0.40 mmol, 1.0 equiv) in DCM (3 ml) was added TFA (2 mL) at 0° C. under nitrogen atmosphere. The resulting mixture was stirred for 1 h at room temperature. The resulting mixture was concentrated under vacuum. This resulted in 7-(((3-chloropyridin-2-yl)oxy)methyl)-6-azaspiro[3.4]octane (180 mg, 180%) as a yellow solid. The crude product was used in the next step directly without further purification. LCMS (ESI) $[M+H]^+$: 253.1.

Step 8: Synthesis of 6-Chloro-7-(7-(((3-chloropyridin-2-yl)oxy)methyl)-6-azaspiro[3.4]octan-6-yl)-1-(6-(3-(dimethylamino)azetidin-1-yl)pyridin-3-yl)-4-oxo-1,4-dihydroquinoline-3-carboxylic acid

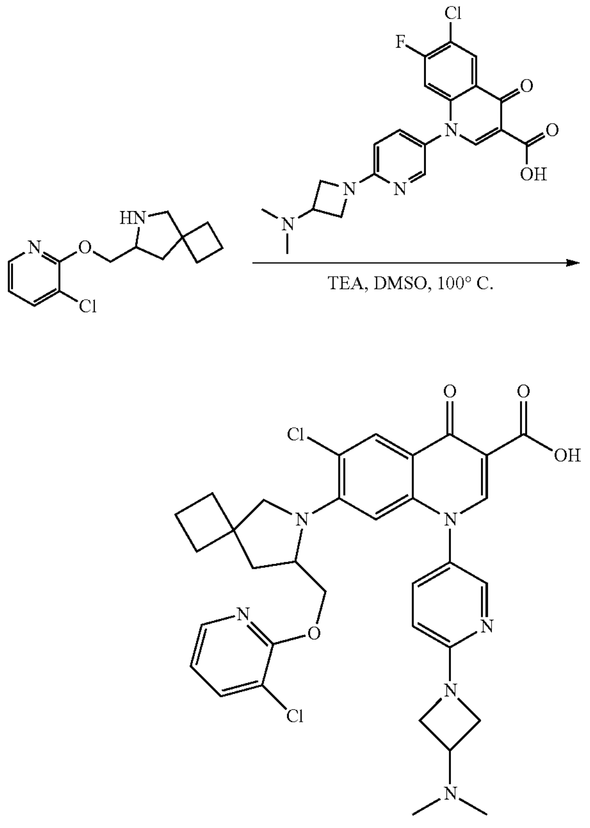 [SMILES: Clc1cccnc1OCC1CC2(CCC2)CN1 ; CN(C)C1CN(c2ccc(-n3cc(C(=O)O)c(=O)c4cc(Cl)c(F)cc43)cn2)C1 ; CN(C)C1CN(c2ccc(-n3cc(C(=O)O)c(=O)c4cc(Cl)c(N5CC6(CCC6)CC5COc5ncccc5Cl)cc43)cn2)C1]

To a mixture of 1-[[(3-chloropyridin-2-yl)oxy]methyl]-2-azabicyclo[2.1.1]hexane (150 mg, 0.5 mmol, 1.0 equiv) and 6-chloro-1-[6-[3-(dimethylamino)azetidin-1-yl]pyridin-3-yl]-7-fluoro-4-oxoquinoline-3-carboxylic acid (280 mg, 0.6 mmol, 1.2 equiv) in DMSO (1 mL) was added TEA (151 mg, 1.5 mmol, 3.0 equiv) under nitrogen atmosphere. The resulting mixture was stirred for overnight at 100° C. under nitrogen atmosphere. The crude product (100 mg) was purified by Prep-HPLC with the following conditions (Column: Gemini-NX C18 AXAI Packed, 21.2*150 mm 5 um; Mobile Phase A: Water(10 MMOL/L NH4HCO3), Mobile Phase B: ACN; Flow rate: 25 mL/min; Gradient: 10% B to 10% B in 2 min, 10% B to 48% B in 2.5 min, 48% B to 88% B in 12 min, 88% B; Wave Length: 254 nm; RT1(min): 10.98; Number Of Runs: 0) to afford 6 6-chloro-7-(7-(((3-chloropyridin-2-yl)oxy)methyl)-6-azaspiro[3.4]octan-6-yl)-1-(6-(3-(dimethylamino)azetidin-1-yl)pyridin-3-yl)-4-oxo-1,4-dihydroquinoline-3-carboxylic acid (59.5 mg, 18.36%) as a yellow solid. LCMS (ESI) $[M+H]^+$: 649.15. $^1H$ NMR (400 MHz, DMSO-$d_6$) δ 15.08 (s, 1H), 8.51 (d, J=9.5 Hz, 1H), 8.25 (d, J=2.6 Hz, 1H), 8.20 (s, 1H), 8.17 (s, 2H), 7.92-7.79 (m, 2H), 7.73-7.64 (m, 1H), 7.00-6.89 (m, 1H), 6.57 (d, J=8.9 Hz, 2H), 6.42 (d, J=13.5 Hz, 2H), 4.56 (s, 1H), 4.45 (s, 2H), 4.37-4.22 (m, 2H), 4.14-4.01 (m, 2H), 3.88-3.77 (m, 2H), 3.52 (d, J=9.2 Hz, 1H), 3.25 (d, J=8.3 Hz, 2H), 2.15 (s, 13H).

Potency Lin28a-dep Z11 $IC_{50}$ (μM)++++

Example 58: Synthesis of 6-chloro-7-[(2R)-2-[[(3-chloropyridin-2-yl)oxy]methyl]-4,4-dimethylpyrrolidin-1-yl]-1-[6-[3-(dimethylamino)azetidin-1-yl]pyridin-3-yl]-4-oxoquinoline-3-carboxylic acid

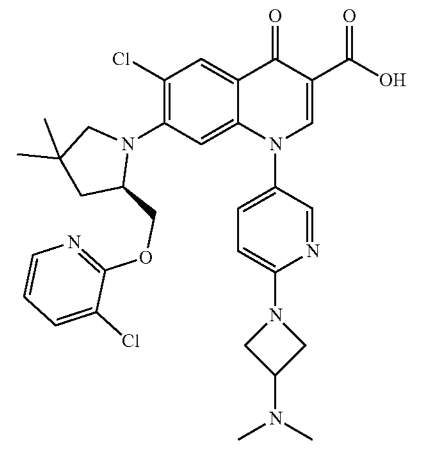 [SMILES: CN(C)C1CN(c2ccc(-n3cc(C(=O)O)c(=O)c4cc(Cl)c(N5CC(C)(C)C[C@@H]5COc5ncccc5Cl)cc43)cn2)C1]

Step 1: Synthesis of (5R)-5-[[(3-chloropyridin-2-yl)oxy]methyl]pyrrolidin-2-one

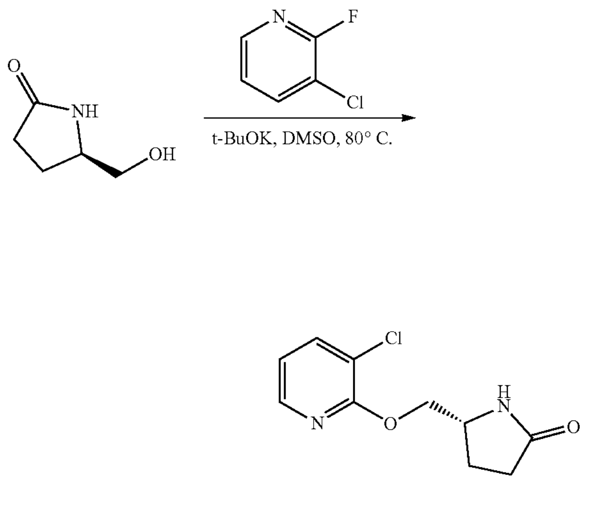

A mixture of (5R)-5-(hydroxymethyl)pyrrolidin-2-one (10 g, 86.85 mmol, 1 equiv), 3-chloro-2-fluoropyridine (17.14 g, 130.31 mmol, 1.5 equiv) and t-BuOK (29.24 g, 260.57 mmol, 3 equiv) in DMSO(50 mL) was stirred at 80° C. overnight. The resulting mixture extracted with ethyl acetate (3×100 mL). The combined organic layers were washed with brine (50 mL), dried over anhydrous $Na_2SO_4$ and concentrated under reduced pressure. The residue was purified by silica gel column chromatography, eluted with DCM/MeOH(20:1) to afford (5R)-5-[[(3-chloropyridin-2-yl)oxy]methyl]pyrrolidin-2-one (6.8 g, 34.54%) as a yellow oil. LCMS (ESI) $[M+H]^+$: 227.05.

Step 2: Synthesis of tert-butyl (2R)-2-[[(3-chloropyridin-2-yl)oxy]methyl]-5-oxopyrrolidine-1-carboxylate

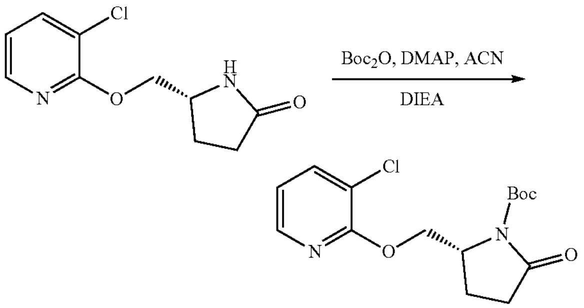

A mixture of (5R)-5-[[(3-chloropyridin-2-yl)oxy]methyl] pyrrolidin-2-one (6.7 g, 29.56 mmol, 1 equiv), $Boc_2O$(12.9 g, 59.1 mmol, 2 equiv), DMAP (0.72 g, 5.91 mmol, 0.2 equiv) and DIEA (7.64 g, 59.12 mmol, 2 equiv) in ACN (50 mL) was stirred for 2.5 h at room temperature. The resulting mixture was concentrated under reduced pressure. The residue was purified by silica gel column chromatography, eluted with 5% MeOH in DCM to afford tert-butyl (2R)-2-[[(3-chloropyridin-2-yl)oxy]methyl]-5-oxopyrrolidine-1-carboxylate (6 g, 62.11%) as a yellow solid. LCMS (ESI) $[M+H]^+$: 327.10.

Step 3: Synthesis of tert-butyl (5R)-5-[[(3-chloropyridin-2-yl)oxy]methyl]-3,3-dimethyl-2-oxopyrrolidine-1-carboxylate

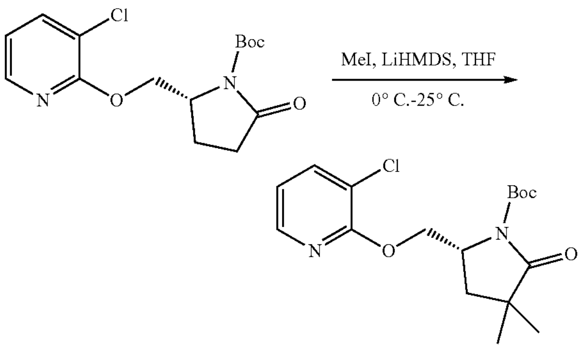

To a solution of tert-butyl (2R)-2-[[(3-chloropyridin-2-yl) oxy]methyl]-5-oxopyrrolidine-1-carboxylate (2 g, 6.12 mmol, 1 equiv) in THF (10 mL) was added LiHMDS (12 mL, 12 mmol, 2 equiv) at 0° C. dropwise. The mixture was stirred for 30 minutes. Subsequently, MeI (1.91 g, 13.46 mmol, 2.2 equiv) was supplied and the mixture was stirred for 2 h at 25° C. The resulting mixture was quenched with water and extracted with ethyl acetate (3×100 mL). The combined organic layers were washed with water (3×150 mL), dried over anhydrous $Na_2SO_4$ and concentrated under reduced pressure. The residue was purified by silica gel column chromatography, eluted with 30% ethyl acetate in hexane to afford tert-butyl (5R)-5-[[(3-chloropyridin-2-yl) oxy]methyl]-3,3-dimethyl-2-oxopyrrolidine-1-carboxylate (590 mg, 27.17%) as a grey solid. LCMS (ESI) $[M+H]^+$: 355.13.

Step 4: Synthesis of tert-butyl (2R)-2-[[(3-chloropyridin-2-yl)oxy]methyl]-4,4-dimethylpyrrolidine-1-carboxylate

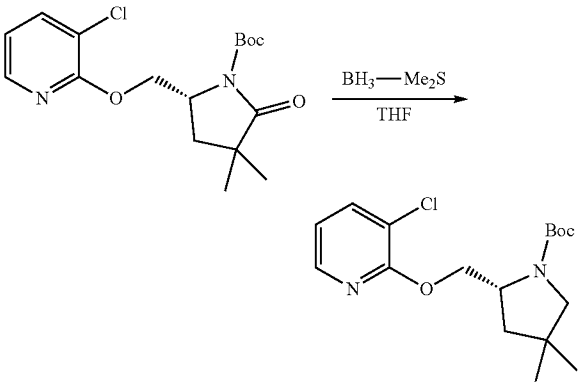

To a stirred solution of tert-butyl (5R)-5-[[(3-chloropyridin-2-yl)oxy]methyl]-3,3-dimethyl-2-oxopyrrolidine-1-carboxylate (530 mg, 1.49 mmol, 1 equiv) in THF (5 mL) was added $BH_3$-$Me_2S$ (0.99 mL, 13.05 mmol, 7 equiv) dropwise at room temperature. The mixture was stirred for 18 h. The resulting mixture was quenched dropwise with MeOH (5 mL) at 0° C. and concentrated under reduced pressure. The resulting mixture was purified by silica gel column chromatography, eluted with 40% ethyl acetate in hexane to afford tert-butyl (2R)-2-[[(3-chloropyridin-2-yl)oxy]methyl]-4,4-dimethylpyrrolidine-1-carboxylate (280 mg, 55%) as a yellow oil. LCMS (ESI) $[M+H]^+$: 341.16.

Step 5: Synthesis of 3-chloro-2-[[(2R)-4,4-dimethylpyrrolidin-2-yl]methoxy]pyridine

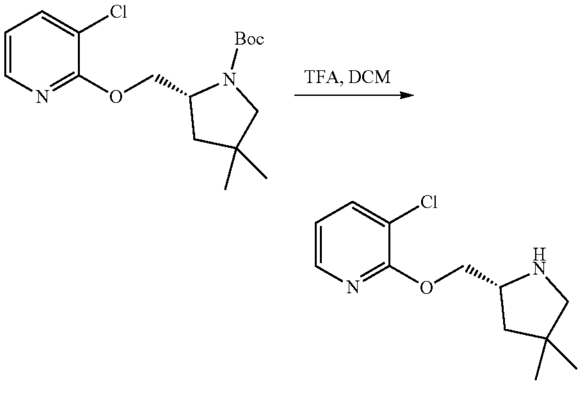

A mixture of tert-butyl (2R)-2-[[(3-chloropyridin-2-yl) oxy]methyl]-4,4-dimethylpyrrolidine-1-carboxylate (280 mg, 0.82 mmol, 1 equiv) in DCM (6 mL) and TFA (2 mL) was stirred at room temperature overnight. The resulting mixture was concentrated under reduced pressure. The residue was purified by RP-flash chromatography eluting with ACN/$H_2O$(0.1% FA) (10%-15%) to afford 3-chloro-2-[[(2R)-4,4-dimethylpyrrolidin-2-yl]methoxy]pyridine (130 mg, 65.74%) as a yellow oil. LCMS (ESI) $[M+H]^+$: 241.10.

Step 6: Synthesis of 6-chloro-7-[(2R)-2-[[(3-chloropyridin-2-yl)oxy]methyl]-4,4-dimethylpyrrolidin-1-yl]-1-[6-[3-(dimethylamino)azetidin-1-yl]pyridin-3-yl]-4-oxoquinoline-3-carboxylic acid

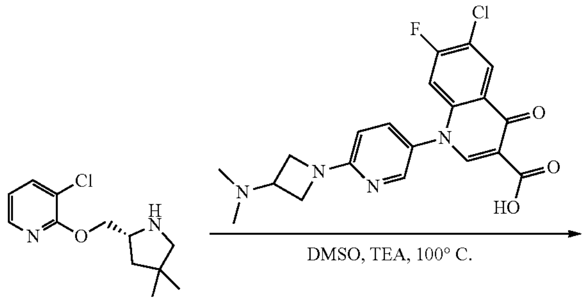

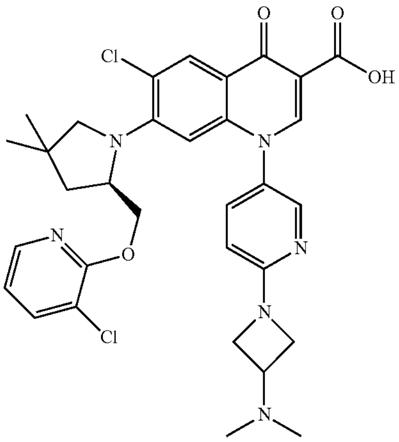

A stirred mixture of 3-chloro-2-[[(2R)-4,4-dimethylpyrrolidin-2-yl]methoxy]pyridine (80 mg, 0.33 mmol, 1 equiv), 6-chloro-1-[6-[3-(dimethylamino)azetidin-1-yl]pyridin-3-yl]-7-fluoro-4-oxoquinoline-3-carboxylic acid (69 mg, 0.16 mmol, 0.5 equiv) and TEA (50 mg, 0.49 mmol, 1.5 equiv) in DMSO (1 mL) was stirred for 10 h at 100° C. The resulting mixture was purified by Prep-HPLC with the following conditions (Column: SunFire Prep C18 OBD Column, 19×150 mm 5 um 10 nm; Mobile Phase A:Water (0.1% FA), Mobile Phase B:ACN; Flow rate:25 mL/min; Gradient:25 B to 45 B in 8 min; 254 nm; RT1:6.68; RT2; Injection Volumn: ml; Number Of Runs;) to afford 6-chloro-7-[(2R)-2-[[(3-chloropyridin-2-yl)oxy]methyl]-4,4-dimethylpyrrolidin-1-yl]-1-[6-[3-(dimethylamino)azetidin-1-yl]pyridin-3-yl]-4-oxoquinoline-3-carboxylic acid (6.6 mg, 2.82%) as a yellow solid. LCMS (ESI) $[M+H]^+$: 637.20. $^1H$ NMR (300 MHz, DMSO-d6) δ 15.07 (s, 1H), 8.51 (d, J=6.8 Hz, 1H), 8.25 (d, J=2.6 Hz, 1H), 8.17 (s, 1H), 7.91-7.80 (m, 2H), 7.69 (t, J=9.0 Hz, 1H), 7.00-6.89 (m, 1H), 6.58 (d, J=8.5 Hz, 0.5H), 6.41 (d, J=5.8 Hz, 1H), 6.34 (d, J=9.1 Hz, 0.5H), 4.67 (d, J=23.1 Hz, 1H), 4.30 (s, 2H), 4.07 (t, J=8.2 Hz, 2H), 3.91-3.74 (m, 2H), 3.43 (d, J=11.0 Hz, 1H), 3.25 (t, J=6.2 Hz, 1H), 2.92 (d, J=9.3 Hz, 1H), 2.15 (s, 6H), 2.03 (d, J=15.7 Hz, 1H), 1.82 (s, 1H), 1.13 (s, 3H), 1.01 (s, 3H).

Potency Lin28a-dep Z11 $IC_{50}$ (μM)++++

Example 59: Synthesis of 6-chloro-7-(2-{[(3-chloropyridin-2-yl)oxy]methyl}-3,3-dimethylpyrrolidin-1-yl)-1-{6-[3-(dimethylamino)azetidin-1-yl]pyridin-3-yl}-4-oxoquinoline-3-carboxylic acid

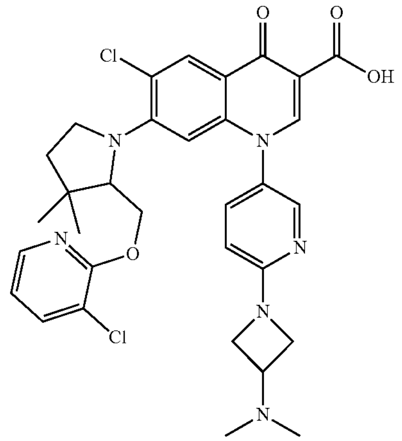 [SMILES: CN(C)C1CN(c2ccc(-n3cc(C(=O)O)c(=O)c4cc(Cl)c(N5CCC(C)(C)C5COc5ncccc5Cl)cc43)cn2)C1]

Step 1: Synthesis of 1,3-diethyl 2-[[(benzyloxy)carbonyl]amino]propanedioate

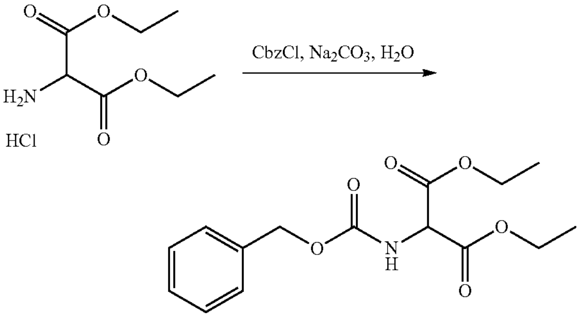

To a mixture of 1,3-diethyl 2-aminopropanedioate (30 g, 171.24 mmol, 1 equiv) and $Na_2CO_3$ (21.78 g, 205 mmol, 1.2 equiv) in $H_2O$ (150 mL) was added CbzCl (43.82 g, 256.87 mmol, 1.5 equiv) dropwise. The mixture was stirred for 2 h at 0° C. and then room temperature overnight. The resulting mixture was acid to pH 3 with HCl(aq.) and extracted with EtOAc(200 mL×3). The combine organic layers was washed with brine and dried with $Na_2SO_4$. The crude product was purified with the following conditions (PE:EA/3:1) to afford 1,3-diethyl 2-[[(benzyloxy)carbonyl]amino]propanedioate (30 g, 56.64%) as a colorless oil. LCMS (ESI) $[M+H]^+$: 310.12.

Step 2: Synthesis of 1-benzyl 2,2-diethyl 3,3-dimethylpyrrole-1,2,2-tricarboxylate

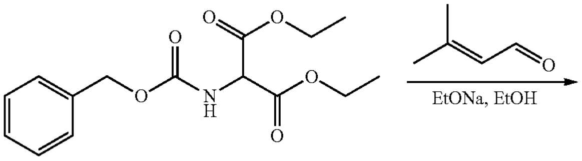

-continued

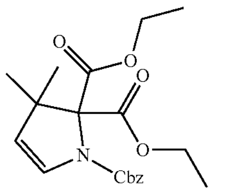

To a solution of 1,3-diethyl 2-{[(benzyloxy)carbonyl]amino}propanedioate (35 g, 113.15 mmol, 1.00 equiv) in EtOH (200 mL) was added a solution of EtONa (9.24 g, 135.78 mmol, 1.2 equiv) in EtOH (50 mL). The mixture was stirred for 15 min. Subsequently, a solution of prenal (10.47 g, 124.46 mmol, 1.1 equiv) in EtOH (100 mL) was supplied. The reaction was stirred for 24 h at 25° C. The resulting mixture was quenched with $H_2O$ and concentrated under reduced pressure. The residue was purified by silica gel column chromatography, eluted with 30% EtOAc in petroleum ether, to afford 1-benzyl 2,2-diethyl 3,3-dimethylpyrrole-1,2,2-tricarboxylate (11.2 g, 26.37%) as a yellow oil. LCMS (ESI) $[M+H]^+$: 376.17.

Step 3: Synthesis of 2,2-diethyl 3,3-dimethylpyrrolidine-2,2-dicarboxylate

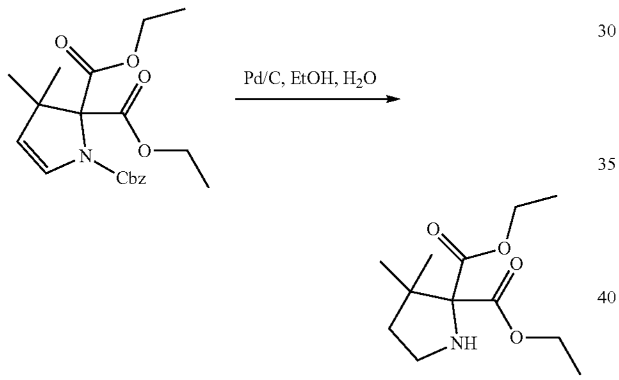

A mixture of 1-benzyl 2,2-diethyl 3,3-dimethylpyrrole-1,2,2-tricarboxylate (11.2 g, 29.83 mmol, 1 equiv) and Pd/C (11.2 g) in MeOH (150 mL) was stirred for 1 h at room temperature under hydrogen atmosphere. The resulting mixture was filtered and filtrate was concentrated under reduced pressure. The crude product of 2,2-diethyl 3,3-dimethylpyrrolidine-2,2-dicarboxylate (7.2 g, 99.19%) was used in the next step directly without further purification. LCMS (ESI) $[M+H]^+$: 244.15.

Step 4: Synthesis of ethyl 3,3-dimethylpyrrolidine-2-carboxylate

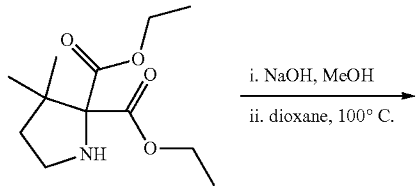

-continued

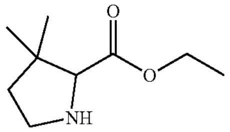

To a mixture of 2,2-diethyl 3,3-dimethylpyrrolidine-2,2-dicarboxylate (7.2 g, 29.59 mmol, 1 equiv) in MeOH (7 mL) and $H_2O$ (7 mL) was added NaOH (11.84 g, 295.93 mmol, 10 equiv). The mixture was stirred at room temperature overnight. The intermediate product was purified by reverse flash chromatography with the following conditions: column, C18 silica gel; mobile phase, ACN in water, 2% to 3% gradient in 10 min. Subsequently, intermediate product dispersed in dioxane was stirred for 3 h at 100° C. The resulting mixture was concentrated under reduced pressure to afford ethyl 3,3-dimethylpyrrolidine-2-carboxylate (4.8 g, 94.72%) as a colorless oil. LCMS (ESI) $[M+H]^+$: 172.13.

Step 5: Synthesis of 1-tert-butyl 2-ethyl 3,3-dimethylpyrrolidine-1,2-dicarboxylate

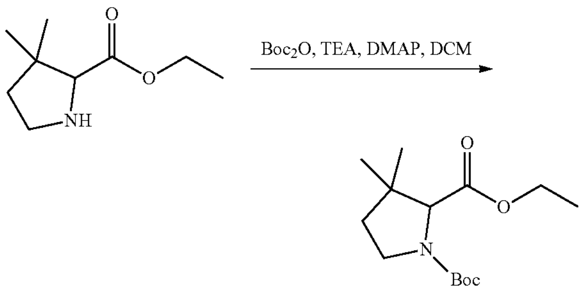

A mixture of ethyl 3,3-dimethylpyrrolidine-2-carboxylate (900 mg, 5.25 mmol, 1 equiv), $Boc_2O$(1.72 g, 7.88 mmol, 1.5 equiv), DMAP (0.13 g, 1.05 mmol, 0.2 equiv) and TEA (1.6 g, 15.76 mmol, 3 equiv) in DCM (10 mL) was stirred for 3 h at room temperature. The resulting mixture was concentrated under reduced pressure. The residue was purified by silica gel column chromatography, eluted with 15% EtOAc in petroleum ether to afford 1-tert-butyl 2-ethyl 3,3-dimethylpyrrolidine-1,2-dicarboxylate (350 mg, 24.54%) as a yellow oil. LCMS (ESI) $[M+H]^+$: 272.18.

Step 6: Synthesis of 4-[(1E)-3-(4-fluorophenyl)prop-1-en-1-yl]benzonitrile

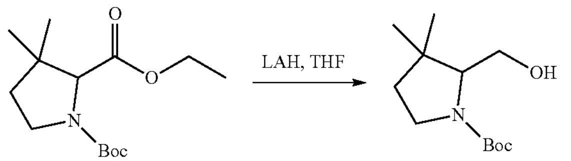 [SMILES: CCOC(=O)C1N(C(=O)OC(C)(C)C)CCC1(C)C ; CC(C)(C)OC(=O)N1CCC(C)(C)C1CO]

To a solution of 1-tert-butyl 2-ethyl 3,3-dimethylpyrrolidine-1,2-dicarboxylate (350 mg, 1.29 mmol, 1 equiv) in THF (5 mL) was added LAH (1.93 mL, 1.93 mmol, 1.5 equiv) dropwise at 0° C. The mixture was stirred for 0.5 h and quenched by $Na_2SO_4 \cdot 10H_2O$. The resulting mixture deals with filtration and filtrate was concentrated under reduced pressure. The residue was purified by RPFC, eluting with MeOH in water (15%-20%) to afford tert-butyl 2-(hydroxymethyl)-3,3-dimethylpyrrolidine-1-carboxylate (250 mg, 84.52%) as a yellow oil. LCMS (ESI) $[M+H]^+$: 230.17.

Step 7: Synthesis of tert-butyl 2-{[(3-chloropyridin-2-yl)oxy]methyl}-3,3-dimethylpyrrolidine-1-carboxylate

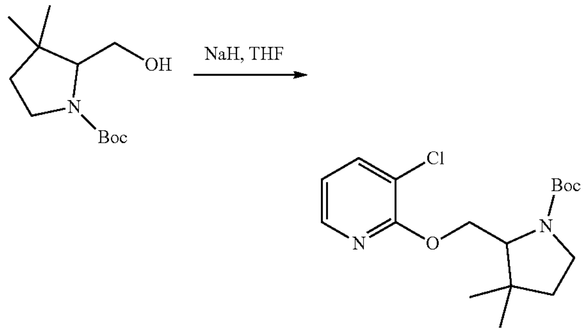

To a solution of tert-butyl 2-(hydroxymethyl)-3,3-dimethylpyrrolidine-1-carboxylate (200 mg, 0.87 mmol, 1 equiv) in THF (5 mL) was added NaH (62 mg, 2.61 mmol, 3 equiv) at 0° C. The reaction was stirred for 1 h and quenched with water. The resulting mixture was purified by RPFC, eluting with ACN in water (30%-35%) to afford tert-butyl 2-{[(3-chloropyridin-2-yl)oxy]methyl}-3,3-dimethylpyrrolidine-1-carboxylate (55 mg, 18.50%) as a colorless oil. LCMS (ESI) $[M+H]^+$: 341.16.

Step 8: Synthesis of 3-chloro-2-[(3,3-dimethylpyrrolidin-2-yl)methoxy]pyridine

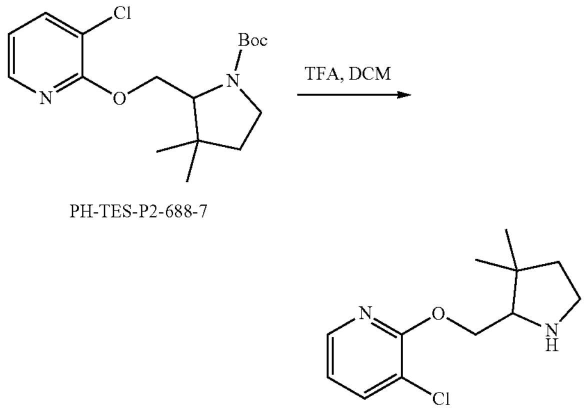

PH-TES-P2-688-7

PH-TES-P2-688-8

A mixture of tert-butyl 2-{[(3-chloropyridin-2-yl)oxy]methyl}-3,3-dimethylpyrrolidine-1-carboxylate (55 mg, 0.16 mmol, 1 equiv) in DCM (3 mL) and TFA (1 mL) was stirred for 5 h. The resulting mixture was concentrated under reduced pressure. The residue was purified by RP-flash chromatography eluting with $ACN/H_2O$(0.1% FA) (5%-10%) to afford 3-chloro-2-[(3,3-dimethylpyrrolidin-2-yl)methoxy]pyridine (40 mg, crude) as a yellow oil. LCMS (ESI) $[M+H]^+$: 241.10.

Step 9: Synthesis of 6-chloro-7-(2-{[(3-chloropyridin-2-yl)oxy]methyl}-3,3-dimethylpyrrolidin-1-yl)-1-{6-[3-(dimethylamino)azetidin-1-yl]pyridin-3-yl}-4-oxoquinoline-3-carboxylic acid

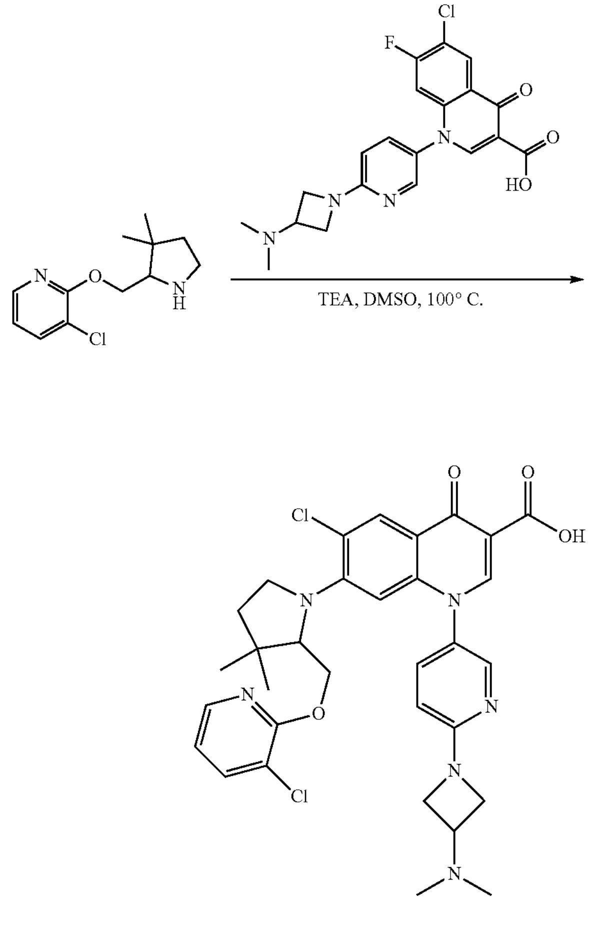

A mixture of 6-chloro-1-{6-[3-(dimethylamino)azetidin-1-yl]pyridin-3-yl}-7-fluoro-4-oxoquinoline-3-carboxylic acid (40 mg, 0.09 mmol, 1 equiv), 3-chloro-2-[(3,3-dimethylpyrrolidin-2-yl)methoxy]-6-methoxypyridine (36 mg, 0.13 mmol, 1.4 equiv) and TEA (29 mg, 0.28 mmol, 3 equiv) in DMSO (1 mL) was stirred for 2 h at 100° C. The resulting mixture was purified by Prep-HPLC with the following conditions (Column: XBridge Prep C18 OBD Column, 19*150 mm, 5 μm; Mobile Phase A: Water(10 MMOL/L NH4HCO3), Mobile Phase B: ACN; Flow rate: 25 mL/min; Gradient: 10% B to 10% B in 2 min, 10% B to 36% B in 2.5 min, 36% B to 65% B in 10.5 min, 65% B; Wave Length: 220 nm; RT1 (min): 11.2; Number Of Runs: 0) to afford 6-chloro-7-(2-{[(3-chloropyridin-2-yl)oxy]methyl}-3,3-dimethylpyrrolidin-1-yl)-1-{6-[3-(dimethylamino)azetidin-1-yl]pyridin-3-yl}-4-oxoquinoline-3-carboxylic acid (1.8 mg, 2.85%) as a yellow solid. LCMS (ESI) $[M+H]^+$: 637.20. $^1H$ NMR (300 MHz, DMSO-d6) δ 8.46 (s, 1H), 8.32-7.70 (m, 4H), 7.68-7.15 (m, 1H), 6.99 (s, 1H), 6.66-5.83 (m, 2H), 4.40 (d, J=10.5 Hz, 1H), 4.28-3.90 (m, 3H), 3.77 (s, 3H), 3.29-2.97 (m, 3H), 2.14 (s, 6H), 1.76 (d, J=36.7 Hz, 2H), 1.25-1.15 (m, 3H), 1.10 (s, 3H), 0.95 (s, 1H), 0.90-0.72 (m, 1H).

Potency Lin28a-dep Z11 $IC_{50}$ (μM)++++

Example 60: 6-chloro-7-[(2R)-2-[[(3-chloropyridin-2-yl)oxy]methyl]-4,4-difluoropyrrolidin-1-yl]-1-[6-[3-(dimethylamino)azetidin-1-yl]pyridin-3-yl]-4-oxo-1,8-naphthyridine-3-carboxylic acid

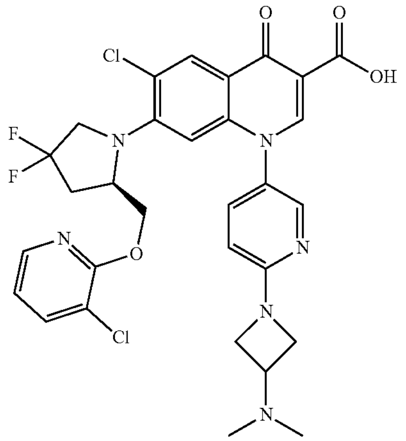 [SMILES: CN(C)C1CN(c2ccc(-n3cc(C(=O)O)c(=O)c4cc(Cl)c(N5CC(F)(F)C[C@@H]5COc5ncccc5Cl)cc43)cn2)C1]

Step 1: Synthesis of 1-(tert-butyl) 2-methyl (R)-4,4-difluoropyrrolidine-1,2-dicarboxylate

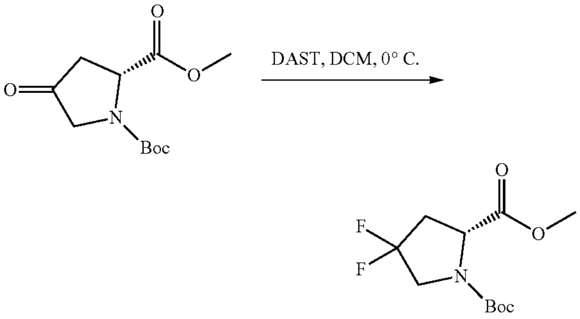

To a stirred solution of 1-(tert-butyl) 2-methyl (R)-4-oxopyrrolidine-1,2-dicarboxylate (3 g, 12.3 mmol, 1 equiv) in DCM was added DAST (18 g, 111.1 mmol, 9 equiv) in portions at 0 degrees C. under nitrogen atmosphere 1 h. The reaction was quenched with Water at 0 degrees C. The aqueous layer was extracted with DCM (3x10 mL). The residue was purified by silica gel column chromatography, eluted with PE/EA (1:1) to afford tert-butyl (2R)-4,4-difluoro-2-(hydroxymethyl)pyrrolidine-1-carboxylate (2.3 g, 85.72%) as a yellow solid. LCMS (ESI) $[M+H]^+$: 266.

Step 2: Synthesis of tert-butyl (R)-4,4-difluoro-2-(hydroxymethyl)pyrrolidine-1-carboxylate

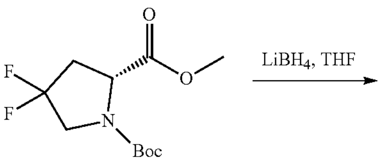

-continued

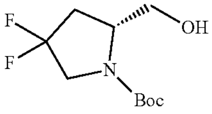

To a stirred solution of 1-tert-butyl 2-methyl (2R)-4,4-difluoropyrrolidine-1,2-dicarboxylate (3 g, 11.3 mmol, 1 equiv) in THF was added LiBH4 (492 mg, 22.6 mmol, 2 equiv) in portions at 0 degrees C. under nitrogen atmosphere 1 h. The reaction was quenched with Water at 0 degrees C. The aqueous layer was extracted with EtOAc (3x10 mL). The residue was purified by silica gel column chromatography, eluted with PE/EA (1:1) to afford tert-butyl (2R)-4,4-difluoro-2-(hydroxymethyl)pyrrolidine-1-carboxylate (2.3 g, 85.72%) as a yellow solid. LCMS (ESI) $[M+H]^+$: 238.

Step 3: Synthesis of tert-butyl (2R)-2-(((3-chloro-1,2-dihydropyridin-2-yl)oxy)methyl)-4,4-difluoropyrrolidine-1-carboxylat

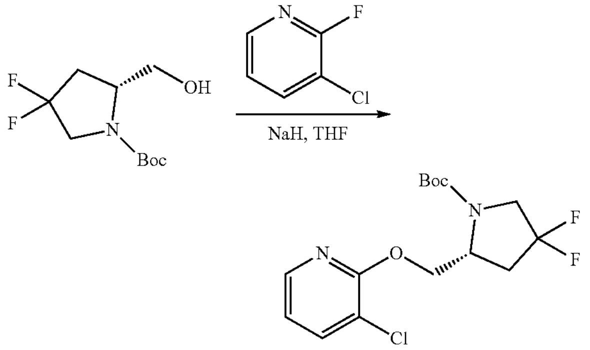

To a stirred solution of tert-butyl (2R)-4,4-difluoro-2-(hydroxymethyl)pyrrolidine-1-carboxylate (2.3 g, 9.6 mmol, 1 equiv) and NaH (465 mg, 19.3 mmol, 2 equiv) in THF was added 3-chloro-2-fluoropyridine (1.5 g, 11.6 mmol, 1.2 equiv) dropwise in portions at 0 degrees C. under nitrogen atmosphere 1 h. The reaction was quenched with Water at 0 degrees C. The aqueous layer was extracted with EtOAc (3x10 mL). The residue was purified by silica gel column chromatography, eluted with PE/EA (3:1) to afford tert-butyl (2R)-2-[[(3-chloro-1,2-dihydropyridin-2-yl)oxy]methyl]-4,4-difluoropyrrolidine-1-carboxylate (2.3 g, 67.63%) as a yellow solid. LCMS (ESI) $[M+H]^+$: 351.

Step 4: Synthesis of (R)-3-chloro-2-((4,4-difluoropyrrolidin-2-yl)methoxy)pyridine

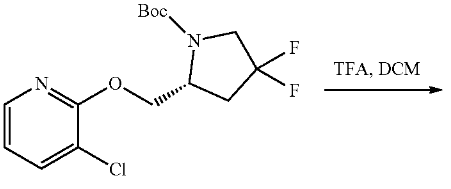

-continued

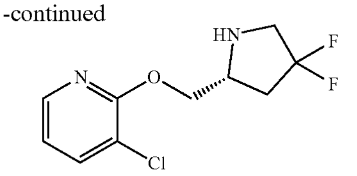

A solution of tert-butyl (2R)-2-[[(3-chloro-1,2-dihydropyridin-2-yl)oxy]methyl]-4,4-difluoropyrrolidine-1-carboxylate (1.1 g, 3.1 mmol, 1 equiv) and TFA (3575.52 mg, 31.3 mmol, 10 equiv) in DCM was stirred for 1 h at room temperature under nitrogen atmosphere. The resulting mixture was concentrated under vacuum. This resulted in 3-chloro-2-[[(2R)-4,4-difluoropyrrolidin-2-yl]methoxy]pyridine (700 mg, 89.77%) as a yellow oil. LCMS (ESI) $[M+H]^+$: 249.

Step 5: Synthesis of ethyl (R)-6-chloro-7-(2-(((3-chloropyridin-2-yl)oxy)methyl)-4,4-difluoropyrrolidin-1-yl)-1-(6-(3-(dimethylamino)azetidin-1-yl)pyridin-3-yl)-4-oxo-1,4-dihydro-1,8-naphthyridine-3-carboxylate

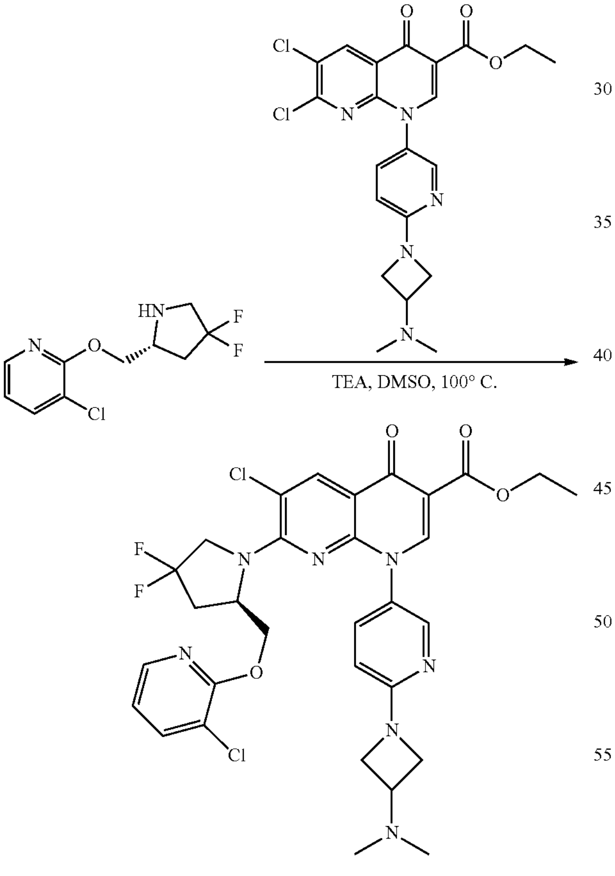

A solution of ethyl 6,7-dichloro-1-[6-[3-(dimethylamino)azetidin-1-yl]pyridin-3-yl]-4-oxo-1,8-naphthyridine-3-carboxylate (200 mg, 0.433 mmol, 1.00 equiv) and 3-chloro-2-[[(2R)-4,4-difluoropyrrolidin-2-yl]methoxy]pyridine (129.08 mg, 0.520 mmol, 1.2 equiv), TEA (131.32 mg, 1.299 mmol, 3 equiv) in DMSO was stirred for 1 h at 100 degrees C. under nitrogen atmosphere. The residue was purified by reverse flash chromatography with the following conditions: column, silica gel; mobile phase, MeCN in water, 10% to 50% gradient in 10 min; detector, UV 254 nm. This resulted in ethyl 6-chloro-7-[(2R)-2-[[(3-chloropyridin-2-yl)oxy]methyl]-4,4-difluoropyrrolidin-1-yl]-1-[6-[3-(dimethylamino)azetidin-1-yl]pyridin-3-yl]-4-oxo-1,8-naphthyridine-3-carboxylate (100 mg, 34.27%) as a yellow solid. LCMS (ESI) $[M+H]^+$: 674.

Step 6: Synthesis of 6-chloro-7-[(2R)-2-[[(3-chloropyridin-2-yl)oxy]methyl]-4,4-difluoropyrrolidin-1-yl]-1-[6-[3-(dimethylamino)azetidin-1-yl]pyridin-3-yl]-4-oxo-1,8-naphthyridine-3-carboxylic acid

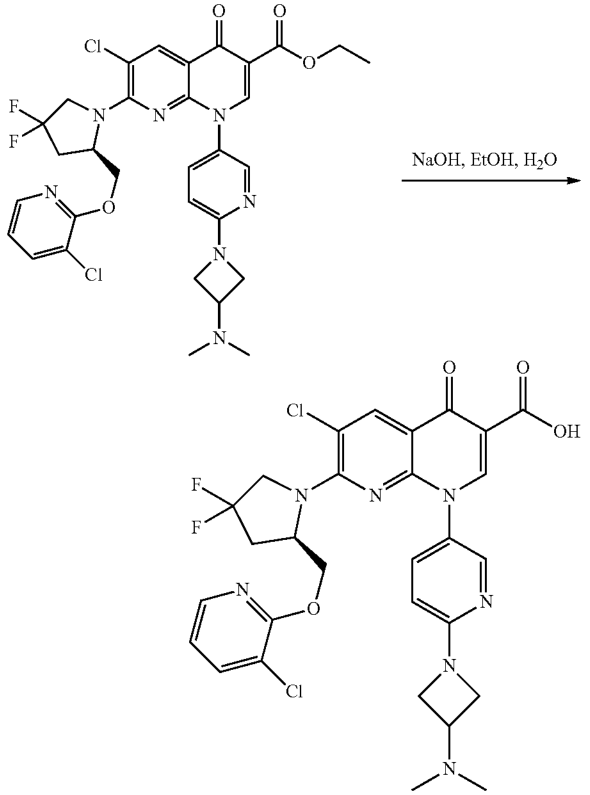

A solution of ethyl 6-chloro-7-[(2R)-2-[[(3-chloropyridin-2-yl)oxy]methyl]-4,4-difluoropyrrolidin-1-yl]-1-[6-[3-(dimethylamino)azetidin-1-yl]pyridin-3-yl]-4-oxo-1,8-naphthyridine-3-carboxylate (100 mg, 0.148 mmol, 1 equiv) and NaOH (11 mg, 0.3 mmol, 2 equiv) in ethanol and $H_2O$ was stirred for 1 h at room temperature under nitrogen atmosphere. The mixture was acidified/basified/neutralized to pH 7 with conc. HCl. The crude product (100 mg) was purified by Prep-HPLC with the following conditions (Column: Gemini-NX C18 AXAI Packed, 21.2*150 mm 5 um; Mobile Phase A: Water(0.1% FA), Mobile Phase B: ACN; Flow rate: 25 mL/min; Gradient: 24% B to 37% B in 10 min, 37% B; Wave Length: 254 nm; RT1(min): 8.97; Number Of Runs: 0) to afford 6-chloro-7-[(2R)-2-[[(3-chloropyridin-2-yl)oxy]methyl]-4,4-difluoropyrrolidin-1-yl]-1-[6-[3-(dimethylamino)azetidin-1-yl]pyridin-3-yl]-4-oxo-1,8-naphthyridine-3-carboxylic acid (38.3. mg, 39.96%) as a yellow solid. $^1H$ NMR (300 MHz, DMSO-$d_6$) δ 14.62 (s, 1H), 8.68 (s, 1H), 8.43 (s, 1H), 8.20 (s, 1H), 8.03-7.89 (m, 2H), 7.78-7.65 (m, 1H), 7.02 (s, 1H), 6.30-6.06 (m, 1H), 4.75 (s, 1H), 4.41-4.12 (m, 4H), 4.03-3.76 (m, 2H), 3.76-3.59 (m, 2H), 3.22-3.09 (m, 1H), 2.78-2.68 (m, 1H), 2.61-2.57 (m, 1H), 2.13 (s, 6H). MS (ESI): m/z 646.20 $[M+H]^+$ Potency Lin28a-dep Z11 $IC_{50}$ (μM)++++

Example 61: Synthesis of 7-[(2R)-2-[[(3-Chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid

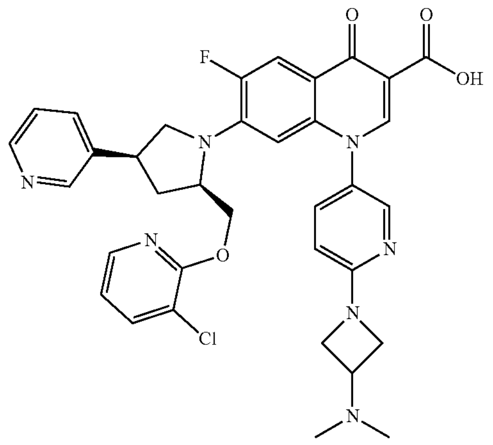 [SMILES: CN(C)C1CN(c2ccc(-n3cc(C(=O)O)c(=O)c4cc(F)c(N5C[C@H](c6cccnc6)C[C@@H]5COc5ncccc5Cl)cc43)cn2)C1]

Step 1: Synthesis of 1-Tert-butyl 2-methyl (2R)-4-(trifluoromethanesulfonyloxy)-2,3-dihydropyrrole-1,2-dicarboxylate

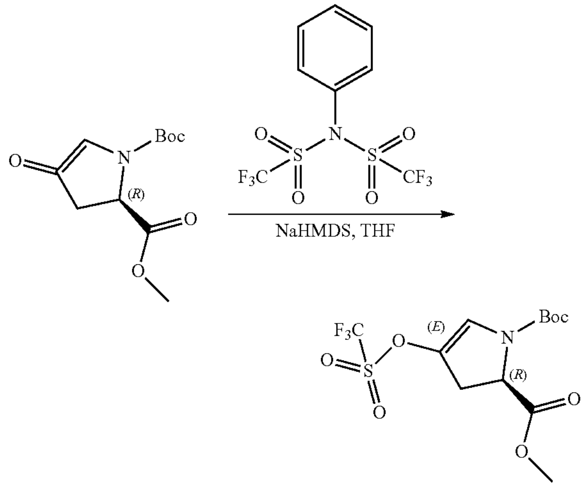

To a mixture of 1-tert-butyl 2-methyl (2R)-4-oxopyrrolidine-1,2-dicarboxylate (10.0 g, 41.11 mmol, 1.0 equiv) in THF (60 mL) were added 1,1,1-trifluoro-N-phenyl-N-trifluoromethanesulfonylmethanesulfonamide (17.6 g, 49.33 mmol, 1.2 equiv) and NaHMDS (13.8 g, 82.22 mmol, 2.0 equiv). The resulting mixture was stirred for 15 min at 0° C. under nitrogen atmosphere. The reaction was quenched by the addition of water (30 mL) at 0° C. The resulting mixture was extracted with EtOAc (3×50 mL). The combined organic layers dried over anhydrous $Na_2SO_4$. The resulting mixture was concentrated under vacuum. The residue was purified by silica gel column chromatography, eluted with PE/EA (3:1). This resulted in 1-tert-butyl 2-methyl (2R)-4-(trifluoromethanesulfonyloxy)-2,3-dihydropyrrole-1,2-dicarboxylate (5.5 g, 36%) as a yellow oil. LCMS (ESI) $[M+H]^+$: 376.1.

Step 2: Synthesis of 1-Tert-butyl 2-methyl (2R)-4-(pyridin-3-yl)-2,3-dihydropyrrole-1,2-dicarboxylate

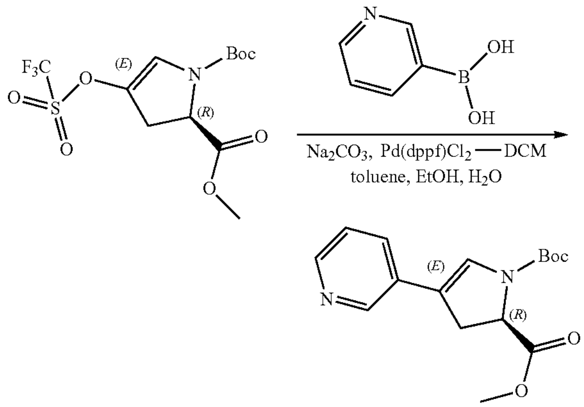

To a mixture of 1-tert-butyl 2-methyl (2R)-4-(trifluoromethanesulfonyloxy)-2,3-dihydropyrrole-1,2-dicarboxylate (5.5 g, 14.65 mmol, 1.0 equiv) in toluene (140 mL) were added EtOH (40 mL), $H_2O$ (20 mL), pyridin-3-ylboronic acid (1.8 g, 14.65 mmol, 1.0 equiv), $Na_2CO_3$ (4.7 g, 43.96 mmol, 3.0 equiv) and $Pd(dppf)Cl_2$ $CH_2Cl_2$ (6.0 g, 7.33 mmol, 0.5 equiv). The resulting mixture was stirred for 1.5 h at 60° C. under nitrogen atmosphere. The mixture was allowed to cool down to room temperature. The resulting mixture was concentrated under vacuum. The residue was purified by silica gel column chromatography, eluted with PE/EA (1:1). This resulted in 1-tert-butyl 2-methyl (2R)-4-(pyridin-3-yl)-2,3-dihydropyrrole-1,2-dicarboxylate (1.7 g, 38%) as a yellow oil. LCMS (ESI) $[M+H]^+$: 305.1.

Step 3: Synthesis of 1-Tert-butyl 2-methyl (2R)-4-(pyridin-3-yl)pyrrolidine-1,2-dicarboxylate

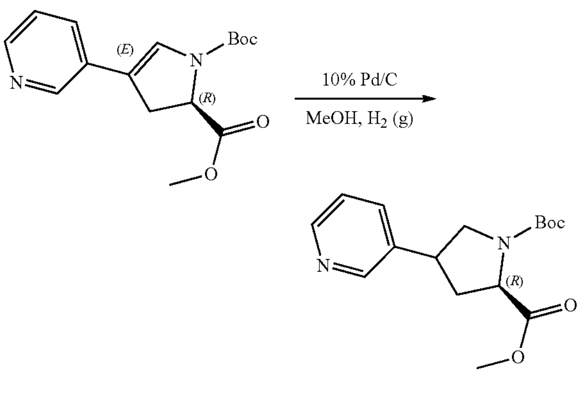

To a mixture of 1-tert-butyl 2-methyl (2R)-4-(pyridin-3-yl)-2,3-dihydropyrrole-1,2-dicarboxylate (1.7 g, 5.59 mmol, 1.0 equiv) in MeOH (25 mL) was added Pd/C (0.6 g, 5.59 mmol, 1.0 equiv). The resulting mixture was stirred for 1 h at room temperature under hydrogen atmosphere. The resulting mixture was filtered, the filter cake was washed with MeOH (3×10 mL). The filtrate was concentrated under reduced pressure. This resulted in 1-tert-butyl 2-methyl (2R)-4-(pyridin-3-yl)pyrrolidine-1,2-dicarboxylate (1.5 g, 88%) as a yellow crude oil. LCMS (ESI) $[M+H]^+$: 307.2.

Step 4: Synthesis of Tert-butyl (2R)-2-(hydroxymethyl)-4-(pyridin-3-yl)pyrrolidine-1-carboxylate

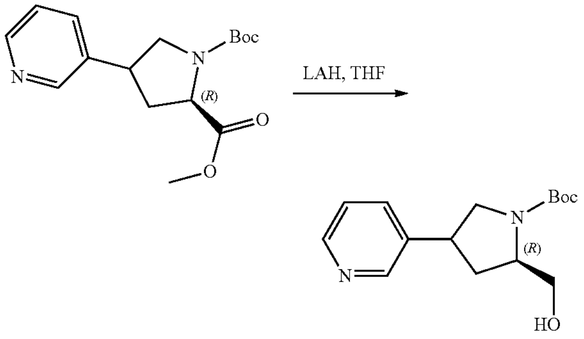

To a mixture of 1-tert-butyl 2-methyl (2R)-4-(pyridin-3-yl)pyrrolidine-1,2-dicarboxylate (1.5 g, 4.90 mmol, 1.0 equiv) in THF (20 mL) was added LAH (0.3 g, 7.34 mmol, 1.5 equiv) at 0° C. The resulting mixture was stirred for 15 min at 0° C. under nitrogen atmosphere. The reaction was quenched by sodium sulfate decahydrate at 0° C. The resulting mixture was dried over anhydrous $MgSO_4$. The resulting mixture was filtered, the filter cake was washed with EtOAc (3×10 mL). The filtrate was concentrated under reduced pressure. The residue was purified by silica gel column chromatography, eluted with PE/EtOAc (1:9). This resulted in tert-butyl (2R)-2-(hydroxymethyl)-4-(pyridin-3-yl)pyrrolidine-1-carboxylate (1.0 g, 73%) as a light yellow oil. LCMS (ESI) $[M+H]^+$: 279.2.

Step 5: Synthesis of Tert-butyl (2R)-2-[[(3-chloropyridin-2-yl)oxy]methyl]-4-(pyridin-3-yl)pyrrolidine-1-carboxylate

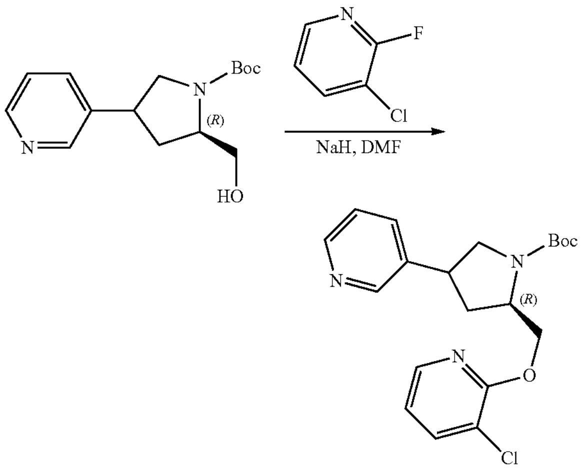

To a mixture of tert-butyl (2R)-2-(hydroxymethyl)-4-(pyridin-3-yl)pyrrolidine-1-carboxylate (1.0 g, 3.59 mmol, 1.0 equiv) in DMF (12 mL) was added NaH (0.3 g, 10.78 mmol, 3.0 equiv) at 0° C. The resulting mixture was stirred for 30 min at room temperature under nitrogen atmosphere. To the above mixture was added 3-chloro-2-fluoropyridine (0.7 g, 5.39 mmol, 1.5 equiv). The resulting mixture was stirred for additional 1.5 h at room temperature. The reaction was quenched by the addition of water (10 mL) at 0° C. The resulting mixture was extracted with EtOAc (3×10 mL). The combined organic layers were dried over anhydrous $Na_2SO_4$. The resulting mixture was concentrated under vacuum. The residue was purified by silica gel column chromatography, eluted with PE/EtOAc (5:1). This resulted in tert-butyl (2R)-2-[[(3-chloropyridin-2-yl)oxy]methyl]-4-(pyridin-3-yl)pyrrolidine-1-carboxylate (700 mg, 50%) as a light yellow oil. LCMS (ESI) $[M+H]^+$: 390.2.

Step 6: Synthesis of 3-Chloro-2-[[(2R)-4-(pyridin-3-yl)pyrrolidin-2-yl]methoxy]pyridine

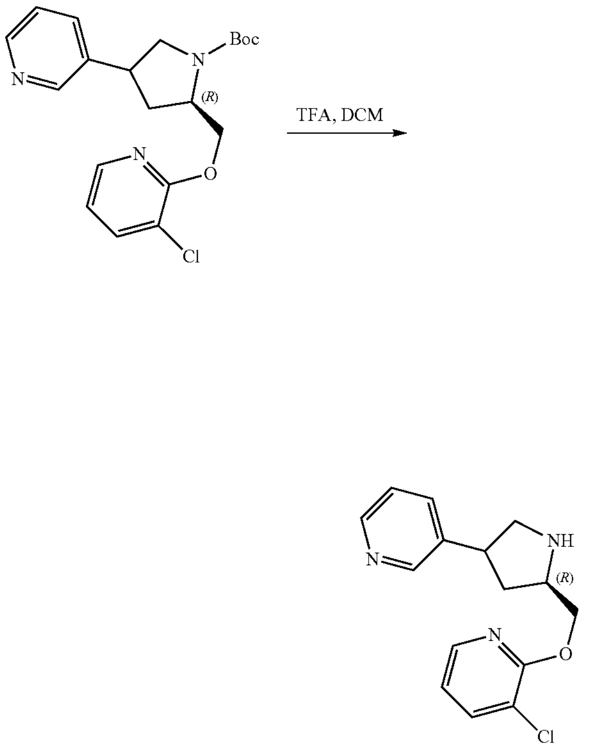

To a mixture of tert-butyl (2R)-2-[[(3-chloropyridin-2-yl)oxy]methyl]-4-(pyridin-3-yl)pyrrolidine-1-carboxylate (700 mg, 1.80 mmol, 1.0 equiv) in DCM (8 mL) was added TFA (4 mL). The resulting mixture was stirred for 1 h at room temperature under nitrogen atmosphere. The resulting mixture was concentrated under vacuum. The residue was purified by reverse flash chromatography with the following conditions: column, C18 silica gel; mobile phase, MeCN in water, 5% to 100% gradient in 30 min; detector, UV 254 nm and UV 220 nm. This resulted in 3-chloro-2-[[(2R)-4-(pyridin-3-yl)pyrrolidin-2-yl]methoxy]pyridine (350 mg, 67%) as a light yellow oil. LCMS (ESI) $[M+H]^+$: 290.1.

Step 7: Synthesis of 3-chloro-2-(((2R,4S)-4-(pyridin-3-yl)pyrrolidin-2-yl)methoxy)pyridine and 3-chloro-2-(((2R,4R)-4-(pyridin-3-yl)pyrrolidin-2-yl)methoxy)pyridine

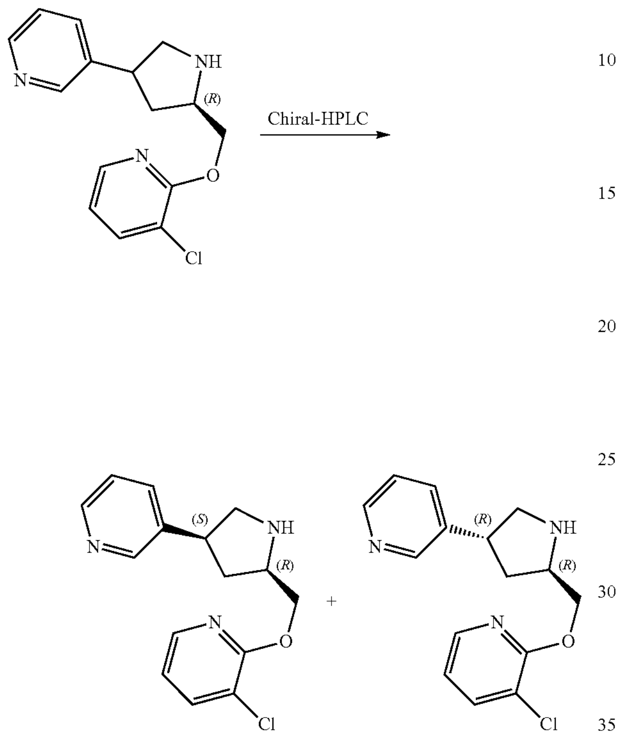

3-chloro-2-(((2R)-4-(pyridin-3-yl)pyrrolidin-2-yl)methoxy)pyridine (100 mg) was separated by Chiral-HPLC to afford 3-chloro-2-(((2R,4S)-4-(pyridin-3-yl)pyrrolidin-2-yl)methoxy)pyridine (70 mg) and 3-chloro-2-(((2R,4R)-4-(pyridin-3-yl)pyrrolidin-2-yl)methoxy)pyridine (10 mg).

Step 8: Synthesis of 7-[(2R)-2-[[(3-Chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid

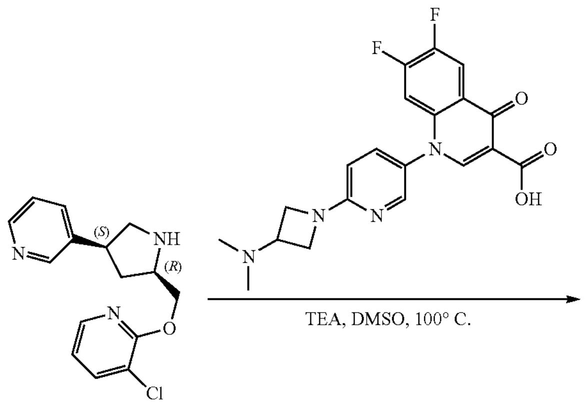

-continued

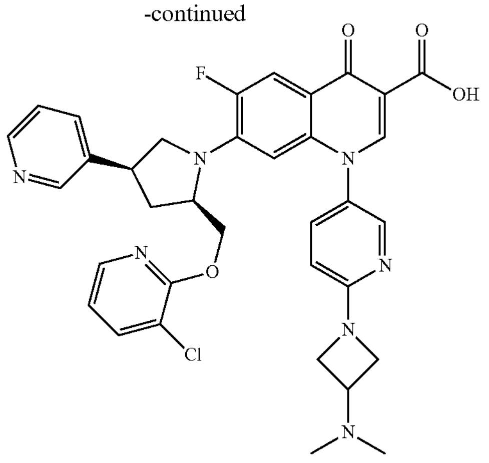

To a mixture of 1-[6-[3-(dimethylamino)azetidin-1-yl]pyridin-3-yl]-6,7-difluoro-4-oxoquinoline-3-carboxylic acid (65 mg, 0.16 mmol, 1.0 equiv) in DMSO (3.5 mL) was added TEA (49 mg, 0.49 mmol, 3.0 equiv) and 3-chloro-2-[[(2R,4S)-4-(pyridin-3-yl)pyrrolidin-2-yl]methoxy]pyridine (56 mg, 0.19 mmol, 1.2 equiv). The resulting mixture was stirred for 1 h at 100° C. under nitrogen atmosphere. The mixture was allowed to cool down to room temperature. The resulting mixture was concentrated under vacuum. The crude product was purified by Prep-HPLC with the following conditions (Column: XBridge Shield RP18 OBD Column, 5 um, 19*150 mm; Mobile Phase A:Water(0.1% FA), Mobile Phase B: ACN; Flow rate: 25 mL/min; Gradient: 60% B to 90% B in 8 min; 254/220 nm; Rt: 7.31 min). This resulted in 7-[(2R)-2-[[(3-chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid (29.7 mg, 27.30%) as a light yellow solid. LCMS (ESI) $[M+H]^+$: 670.25. $^1H$ NMR (400 MHz, DMSO-d6) δ 15.32 (s, 1H), 8.56 (d, J=2.5 Hz, 1H), 8.53-8.44 (m, 2H), 8.30-8.19 (m, 1H), 7.99-7.86 (m, 3H), 7.85-7.65 (m, 2H), 7.45-7.35 (m, 1H), 6.99 (d, J=4.9 Hz, 1H), 6.65-6.50 (m, 1H), 6.36-6.20 (m, 2H), 4.46 (d, J=9.7 Hz, 3H), 4.18-3.94 (m, 2H), 3.88-3.67 (m, 3H), 3.58-3.44 (m, 2H), 3.21 (s, 1H), 2.67 (m, J=11.4, 6.7 Hz, 1H), 2.12 (s, 7H).

Potency Lin28a-dep Z11 $IC_{50}$ (μM)++++

Example 62: Synthesis of 7-[(2R,4R)-2-[[(3-chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid

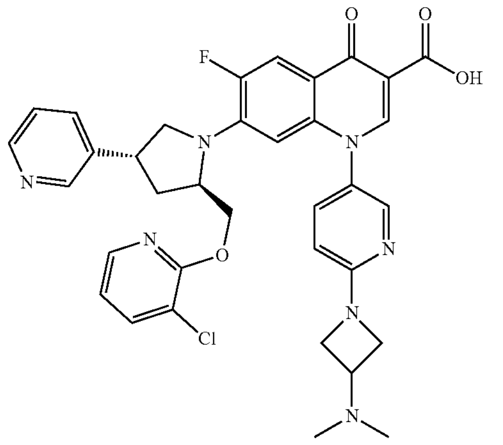

Step 1: Synthesis of 7-[(2R,4R)-2-[[(3-chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid

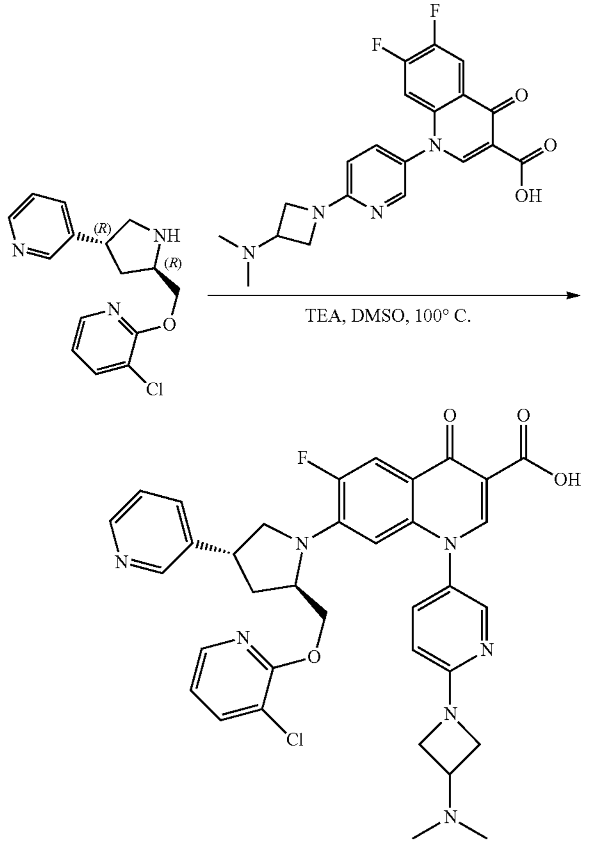

To a mixture of 1-[6-[3-(dimethylamino)azetidin-1-yl]pyridin-3-yl]-6,7-difluoro-4-oxoquinoline-3-carboxylic acid (8 mg, 0.02 mmol, 1.0 equiv) in DMSO (2 mL) was added TEA (6 mg, 0.06 mmol, 3.0 equiv) and 3-chloro-2-[[(2R,4R)-4-(pyridin-3-yl)pyrrolidin-2-yl]methoxy]pyridine (7 mg, 0.02 mmol, 1.2 equiv). The resulting mixture was stirred for 1 h at 100° C. under nitrogen atmosphere. The mixture was allowed to cool down to room temperature. The resulting mixture was concentrated under vacuum. The crude product was purified by Prep-HPLC with the following conditions (Column: XBridge Shield RP18 OBD Column, 5 um, 19*150 mm; Mobile Phase A:Water(0.1% FA), Mobile Phase B: ACN; Flow rate: 25 mL/min; Gradient: 60% B to 90% B in 8 min; 254/220 nm; Rt: 7.31 min) to afford 7-[(2R,4R)-2-[[(3-chloropyridin-2-yl)oxy]methyl]-4-(pyridin-3-yl)pyrrolidin-1-yl]-1-[6-[3-(dimethylamino)azetidin-1-yl]pyridin-3-yl]-6-fluoro-4-oxoquinoline-3-carboxylic acid (10.9 mg, 81.40%) as a light yellow solid. LCMS (ESI) $[M+H]^+$: 670.20. 1H NMR (300 MHz, DMSO-d6) δ 15.30 (s, 1H), 8.57 (s, 1H), 8.54-8.45 (m, 2H), 8.25 (d, J=2.8 Hz, 1H), 8.01-7.86 (m, 3H), 7.85-7.64 (m, 2H), 7.39 (d, J=7.9, 4.7 Hz, 1H), 7.07-6.92 (m, 1H), 6.59-6.19 (m, 2H), 4.47 (s, 3H), 4.02 (d, J=6.6 Hz, 2H), 3.88-3.66 (m, 3H), 3.49 (s, 2H), 3.22 (d, J=5.6 Hz, 1H), 2.79-2.62 (m, 1H), 2.23 (s, 1H), 2.12 (s, 6H).

Potency Lin28a-dep Z11 $IC_{50}$ (μM)++++

Example 63: Synthesis of 6-chloro-7-((2R)-2-(((3-chloropyridin-2-yl)oxy)methyl)-4-cyclobutylpyrrolidin-1-yl)-1-(6-(3-(dimethylamino)azetidin-1-yl)pyridin-3-yl)-4-oxo-1,4-dihydroquinoline-3-carboxylic acid

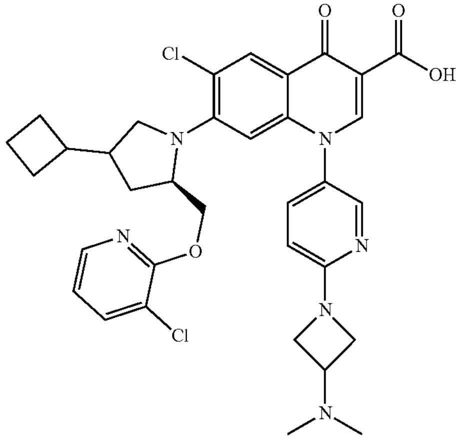 [SMILES: CN(C)C1CN(c2ccc(-n3cc(C(=O)O)c(=O)c4cc(Cl)c(N5CC(C6CCC6)C[C@@H]5COc5ncccc5Cl)cc43)cn2)C1]

Step 1: Synthesis of 1-(tert-butyl) 2-methyl (2R)-4-hydroxypyrrolidine-1,2-dicarboxylate

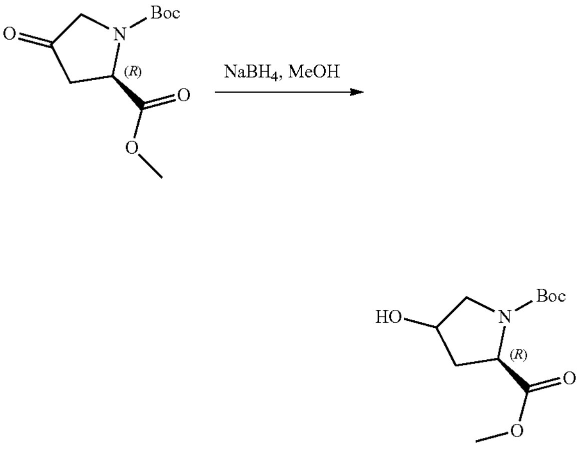

To a mixture of 1-(tert-butyl) 2-methyl (R)-4-oxopyrrolidine-1,2-dicarboxylate (5.0 g, 20.56 mmol, 1.0 equiv), in MeOH (50 mL) was added $NaBH_4$ (1.5 g, 41.13 mmol, 2.0 equiv). The resulting mixture was stirred at 0° C. for 1 h. The reaction was quenched with water. The resulting mixture was extracted with EtOAc(3*50 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in 1-(tert-butyl) 2-methyl (2R)-4-hydroxypyrrolidine-1,2-dicarboxylate (2.5 g, 49.7%) as a yellow solid. LCMS (ESI) $[M+H]^+$: 246.1.

Step 2: Synthesis of 1-(tert-butyl) 2-methyl (2R)-4-iodopyrrolidine-1,2-dicarboxylate

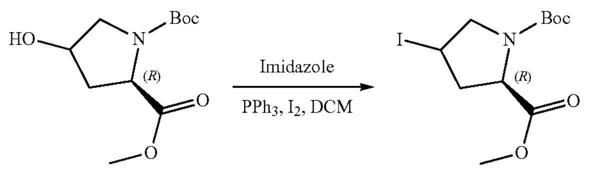

To a mixture of 1-(tert-butyl) 2-methyl (2R)-4-hydroxy-pyrrolidine-1,2-dicarboxylate (2.5 g, 10.20 mmol, 1.0 equiv) in DCM (20 mL) was added Imidazole (693.8 mg, 30.6 mmol, 3.0 equiv), triphenylphosphane (6.3 g, 30.6 mmol, 3.0 equiv) and diiodine (5.9 g, 30.6 mmol, 3.0 equiv). The resulting mixture was stirred at 0° C. overnight. The reaction was quenched with water. The resulting mixture was extracted with EtOAc (3*50 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in 1-(tert-butyl) 2-methyl (2R)-4-iodopyrrolidine-1,2-dicarboxylate (2.3 g, 63.8%) as a yellow solid. LCMS (ESI) $[M+H]^+$: 356.1

Step 3: Synthesis of 1-(tert-butyl) 2-methyl (2R)-4-cyclobutylpyrrolidine-1,2-dicarboxylate

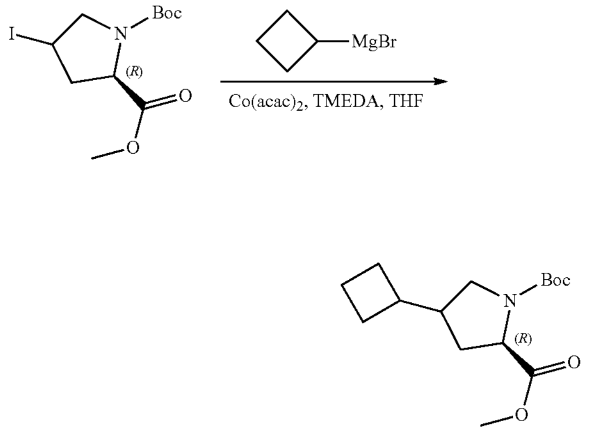

To a solution of 1-(tert-butyl) 2-methyl (2R)-4-iodopyrrolidine-1,2-dicarboxylate (2.3 g, 6.47 mmol, 1.0 equiv) in THF (30 mL) was added $Co(acac)_2$ (137.5 mg, 0.38 mmol, 0.6 equiv), Tetramethylethylenediamine (1.50 g, 12.9 mmol, 2.0 equiv) and cyclobutylmagnesium bromide (2.4 g, 15.5 mmol, 2.4 equiv). The resulting mixture was stirred at 0° C. overnight. The reaction was quenched with water. The resulting mixture was extracted with EtOAc(3*50 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in 1-(tert-butyl) 2-methyl (2R)-4-cyclobutylpyrrolidine-1,2-dicarboxylate (979.8 mg, 53.5%) of as a yellow solid. LCMS (ESI) $[M+H]^+$: 284.1.

Step 4: Synthesis of tert-butyl (2R)-4-cyclobutyl-2-(hydroxymethyl)pyrrolidine-1-carboxylate

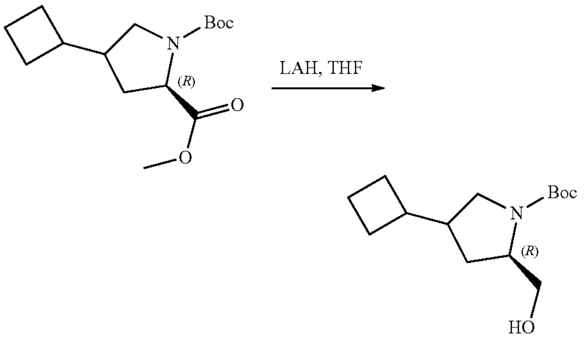

To a solution of 1-(tert-butyl) 2-methyl (2R)-4-cyclobutylpyrrolidine-1,2-dicarboxylate (900 mg, 3.18 mmol, 1.0 equiv) in THF (10 mL) was added Lithium aluminium hydride (1 mol/L, 5 mL, 4.77 mmol, 2.0 equiv). The resulting solution was stirred for 1 hr at 0° C. The reaction was quenched with $Na_2SO_4 \cdot 10H_2O$. The resulting mixture was filtered, the filter cake was washed with EA (100 mL), The filtrate was concentrated under reduced pressure. This resulted in tert-butyl (2R)-4-cyclobutyl-2-(hydroxymethyl) pyrrolidine-1-carboxylate (429.7 mg, 53.2%) of as a yellow solid. LCMS (ESI) $[M+H]^+$: 256.1.

Step 5: Synthesis of tert-butyl (2R)-2-(((3-chloropyridin-2-yl)oxy)methyl)-4-cyclobutylpyrrolidine-1-carboxylate

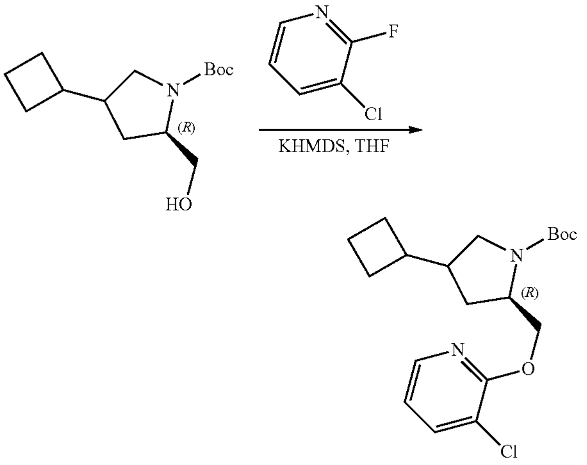

To a solution of tert-butyl (2R)-4-cyclobutyl-2-(hydroxymethyl)pyrrolidine-1-carboxylate (350 mg, 1.37 mmol, 1.0 equiv) in THF (5 mL) was added 3-chloro-2-fluoropyridine (215.3 mg, 1.64 mmol, 1.2 equiv) and Potassium bis(trimethylsilyl)amide (3 mL, 2.74 mmol, 2.0 equiv). The resulting solution was stirred for 1 hr at 0° C. The reaction was quenched with water. The resulting mixture was extracted with EtOAc(3*20 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in tert-butyl (2R)-2-(((3-chloropyridin-2-yl)oxy)methyl)-4-cyclobutylpyrrolidine-1-carboxylate (260.5 mg, 52.1%) of as a yellow solid. LCMS (ESI) $[M+H]^+$: 367.1.

Step 6: Synthesis of 3-chloro-2-(((2R)-4-cyclobutylpyrrolidin-2-yl)methoxy)pyridine

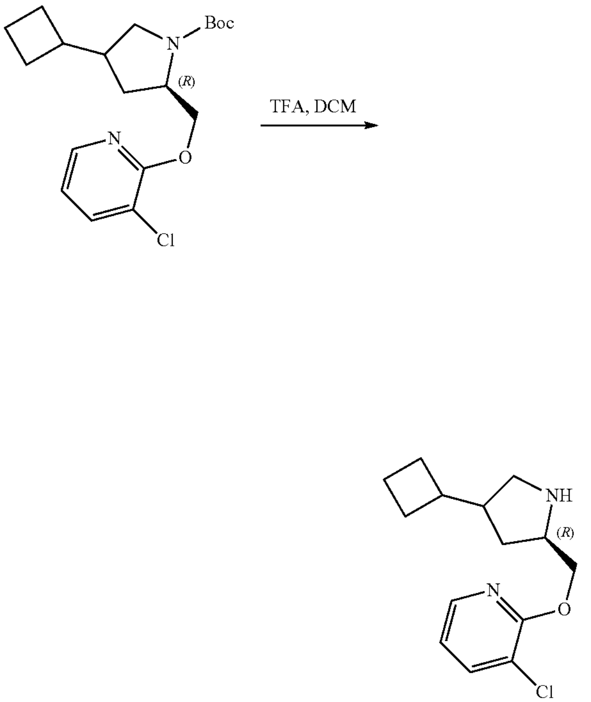

To a solution of tert-butyl (2R)-2-(((3-chloropyridin-2-yl)oxy)methyl)-4-cyclobutylpyrrolidine-1-carboxylate (150 mg, 0.40 mmol, 1.0 equiv) in DCM (3.0 mL) was added TFA (2.0 mL). The resulting solution was stirred for 1 hr at room temperature. The resulting mixture was concentrated under vacuum. This resulted in 3-chloro-2-(((2R)-4-cyclobutylpyrrolidin-2-yl)methoxy)pyridine (200 mg, crude) of as a yellow solid. LCMS (ESI) [M+H]$^+$: 267.1.

Step 7: Synthesis of 6-chloro-7-((2R)-2-(((3-chloropyridin-2-yl)oxy)methyl)-4-cyclobutylpyrrolidin-1-yl)-1-(6-(3-(dimethylamino)azetidin-1-yl)pyridin-3-yl)-4-oxo-1,4-dihydroquinoline-3-carboxylic acid

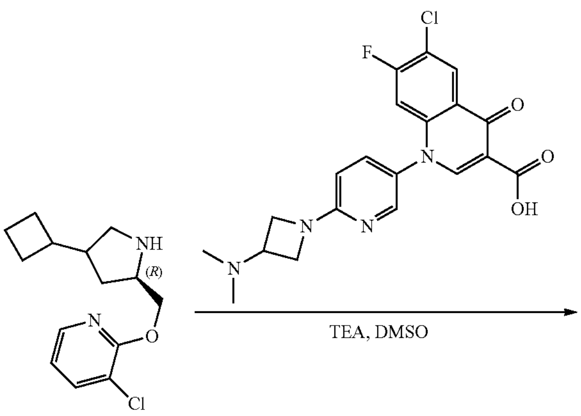

-continued

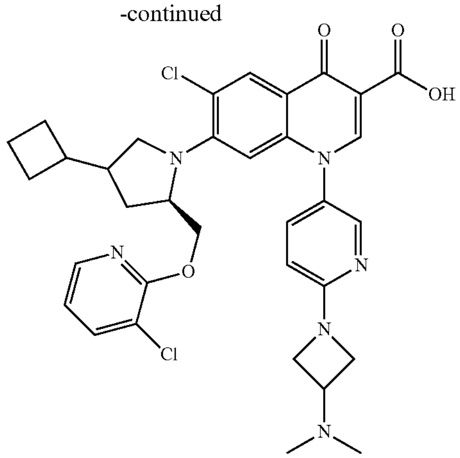

To a solution of 3-chloro-2-(((2R)-4-cyclobutylpyrrolidin-2-yl)methoxy)pyridine (100 mg, 0.37 mmol, 1.0 equiv) in DMSO (2 mL) was added 6-chloro-1-(6-(3-(dimethylamino)azetidin-1-yl)pyridin-3-yl)-7-fluoro-4-oxo-1,4-dihydroquinoline-3-carboxylic acid (231.4 mg, 0.55 mmol, 1.5 equiv) and TEA (112.1 mg, 1.11 mmol, 3.0 equiv). The resulting solution was stirred for 1 hr at 100° C. The mixture was purified by Prep-HPLC (Column: XSelect CSH Prep C18 OBD Column, 19*250 mm, 5 m; Mobile Phase A: Water(0.05% FA), Mobile Phase B: ACN; Flow rate: 25 mL/min; Gradient: 25% B to 55% B in 7 min, 55% B; Wave Length: 254/220 nm; RT1(min): 6.05; Number Of Runs: 0). This resulted in 6-chloro-7-((2R)-2-(((3-chloropyridin-2-yl)oxy)methyl)-4-cyclobutylpyrrolidin-1-yl)-1-(6-(3-(dimethylamino)azetidin-1-yl)pyridin-3-yl)-4-oxo-1,4-dihydroquinoline-3-carboxylic acid (4.5 mg, 0.02%) of as a yellow solid. LCMS (ESI) [M+H]$^+$: 663.2. $^1$H NMR (300 MHz, DMSO-d6) δ 15.15 (s, 1H), 8.59 (m, 1H), 8.41-8.18 (m, 2H), 8.03-7.85 (m, 2H), 7.80-7.62 (m, 1H), 7.02 (m, 1H), 6.70-6.33 (m, 2H), 4.77 (m, 1H), 4.45-4.22 (m, 2H), 4.13 (m, 2H), 3.88 (m, 2H), 3.28 (m, 2H), 2.91 (s, 1H), 2.39 (s, 2H), 2.22 (s, 6H), 2.05-1.77 (m, 4H), 1.68 (m, 2H), 1.35 (s, 1H). 1.31 (s, 1H).

Potency Lin28a-dep Z11 $IC_{50}$ (μM)++++

Example 64: Synthesis of 6-chloro-7-(3-(((3-chloro-6-methoxypyridin-2-yl)oxy)methyl)-2-azabicyclo[2.1.1]hexan-2-yl)-1-(6-(3-(dimethylamino)azetidin-1-yl)pyridin-3-yl)-4-oxo-1,4-dihydroquinoline-3-carboxylic acid

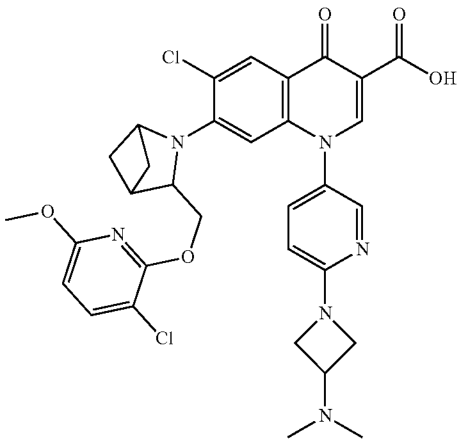 [SMILES: COc1ccc(Cl)c(OCC2C3CC(C3)N2c2cc3c(cc2Cl)c(=O)c(C(=O)O)cn3-c2ccc(N3CC(N(C)C)C3)nc2)n1]

Step 1: Synthesis of 2-(tert-butoxycarbonyl)-2-azabicyclo[2.1.1]hexane-3-carboxylic acid

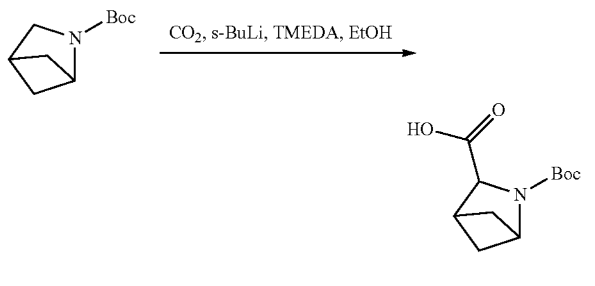

To a mixture of tert-butyl 2-azabicyclo[2.1.1]hexane-2-carboxylate (600 mg, 3.27 mmol, 1.0 equiv) in Diethyl ether (5 mL), $CO_2$ gas shielded to join s-BuLi (9.8 mL, 1 mol/L, 9.81 mmol, 3.0 equiv) and Tetramethylethylenediamine (1.13 g, 9.81 mmol, 3.0 equiv). The resulting mixture was stirred for 1 h at room temperature. The reaction was quenched with MeOH. The resulting mixture was concentrated under vacuum. This resulted in 2-(tert-butoxycarbonyl)-2-azabicyclo[2.1.1]hexane-3-carboxylic acid (400 mg, 47.1%) as a yellow solid. LCMS (ESI) $[M+H]^+$: 228.1.

Step 2: Synthesis of 2-(tert-butyl) 3-methyl 2-azabicyclo[2.1.1]hexane-2,3-dicarboxylate

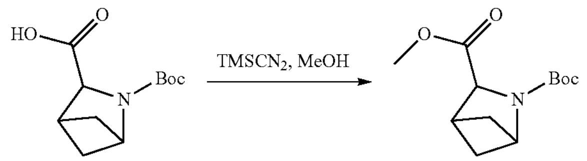 [SMILES: CC(C)(C)OC(=O)N1C2CC(C2)C1C(=O)O ; COC(=O)C1C2CC(C2)N1C(=O)OC(C)(C)C]

To a mixture of 2-(tert-butoxycarbonyl)-2-azabicyclo[2.1.1]hexane-3-carboxylic acid (400 mg, 1.76 mmol, 1.0 equiv) in MeOH (5 mL) was added A name could not be generated for this structure (298.6 mg, 2.64 mmol, 1.5 equiv). The resulting mixture was stirred for 16 h at room temperature. The resulting mixture was concentrated under vacuum. The precipitated solids were collected and crude product was purified by Prep-HPLC with the following conditions (Column: XBridge Shield RP18 OBD Column, 5 um, 19*150 mm; Mobile Phase A:Water(10 MMOL/L NH4HCO3), Mobile Phase B:ACN; Flow rate:25 mL/min; Gradient:25 B to 48 B in 7 min; 254/220 nm; RT1:5.90; RT2; Injection Volumn: ml; Number Of Runs;). This resulted in 2-(tert-butyl) 3-methyl 2-azabicyclo[2.1.1]hexane-2,3-dicarboxylate (200 mg, 47.1%) as a yellow solid. LCMS (ESI) $[M+H]^+$: 242.1.

Step 3: Synthesis of tert-butyl 3-(hydroxymethyl)-2-azabicyclo[2.1.1]hexane-2-carboxylate

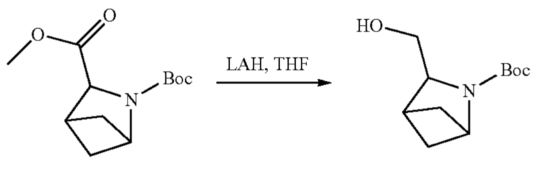 [SMILES: COC(=O)C1C2CC(C2)N1C(=O)OC(C)(C)C ; "LAH, THF" ; CC(C)(C)OC(=O)N1C2CC(C2)C1CO]

To a mixture of 2-(tert-butyl) 3-methyl 2-azabicyclo[2.1.1]hexane-2,3-dicarboxylate (200 mg, 0.82 mmol, 1.0 equiv), in THF (2 mL) was added Lithium aluminium hydride (1 mol/L, 1.23 mL, 1.23 mmol, 1.5 equiv). The resulting solution was stirred for 1 hr at 0° C. The reaction was quenched with $Na_2SO_4 \cdot 10H_2O$. The reaction was quenched with water. The resulting mixture was extracted with EtOAc(3*20 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in tert-butyl 3-(hydroxymethyl)-2-azabicyclo[2.1.1]hexane-2-carboxylate (100 mg, 57.4%) as a yellow solid. LCMS (ESI) $[M+H]^+$: 214.1.

Step 4: Synthesis of 1-(tert-butyl) 2-methyl (2R)-4-iodopyrrolidine-1,2-dicarboxylate

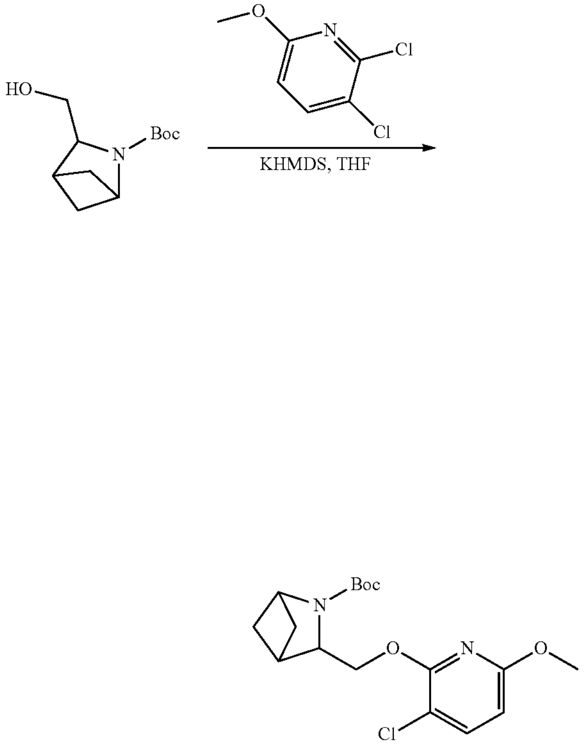

To a mixture of tert-butyl 3-(hydroxymethyl)-2-azabicyclo[2.1.1]hexane-2-carboxylate (100 mg, 0.46 mmol, 1.0 equiv) in THF (3 mL) was added 2,3-dichloro-6-methoxypyridine (122.1 mg, 0.69 mmol, 1.5 equiv) and Potassium bis(trimethylsilyl)amide (0.1 mL, 0.92 mmol, 2.0 equiv). The resulting solution was stirred for 1 hr at 0° C. The reaction was quenched with water. The resulting mixture was extracted with EtOAc(3*10 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in tert-butyl 3-(((3-chloro-6-methoxypyridin-2-yl)oxy)methyl)-2-azabicyclo[2.1.1]hexane-2-carboxylate (90 mg, 55.5%) as a yellow solid. LCMS (ESI) $[M+H]^+$: 355.1

Step 5: Synthesis of 3-(((3-chloro-6-methoxypyridin-2-yl)oxy)methyl)-2-azabicyclo[2.1.1]hexane

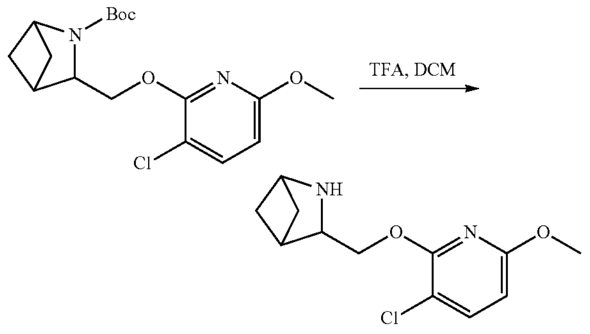

To a solution of tert-butyl 3-(((3-chloro-6-methoxypyridin-2-yl)oxy)methyl)-2-azabicyclo[2.1.1]hexane-2-carboxylate (90 mg, 0.25 mmol, 1.0 equiv) in DCM (2 mL) was added TFA (2.0 mL). The resulting solution was stirred for 1 hr at room temperature. The resulting mixture was concentrated under vacuum. This resulted in 3-(((3-chloro-6-methoxypyridin-2-yl)oxy)methyl)-2-azabicyclo[2.1.1]hexane (100 mg, crude) of as a yellow solid. LCMS (ESI) $[M+H]^+$: 255.0.

Step 6: Synthesis of 6-chloro-7-(3-(((3-chloro-6-methoxypyridin-2-yl)oxy)methyl)-2-azabicyclo[2.1.1]hexan-2-yl)-1-(6-(3-(dimethylamino)azetidin-1-yl)pyridin-3-yl)-4-oxo-1,4-dihydroquinoline-3-carboxylic acid

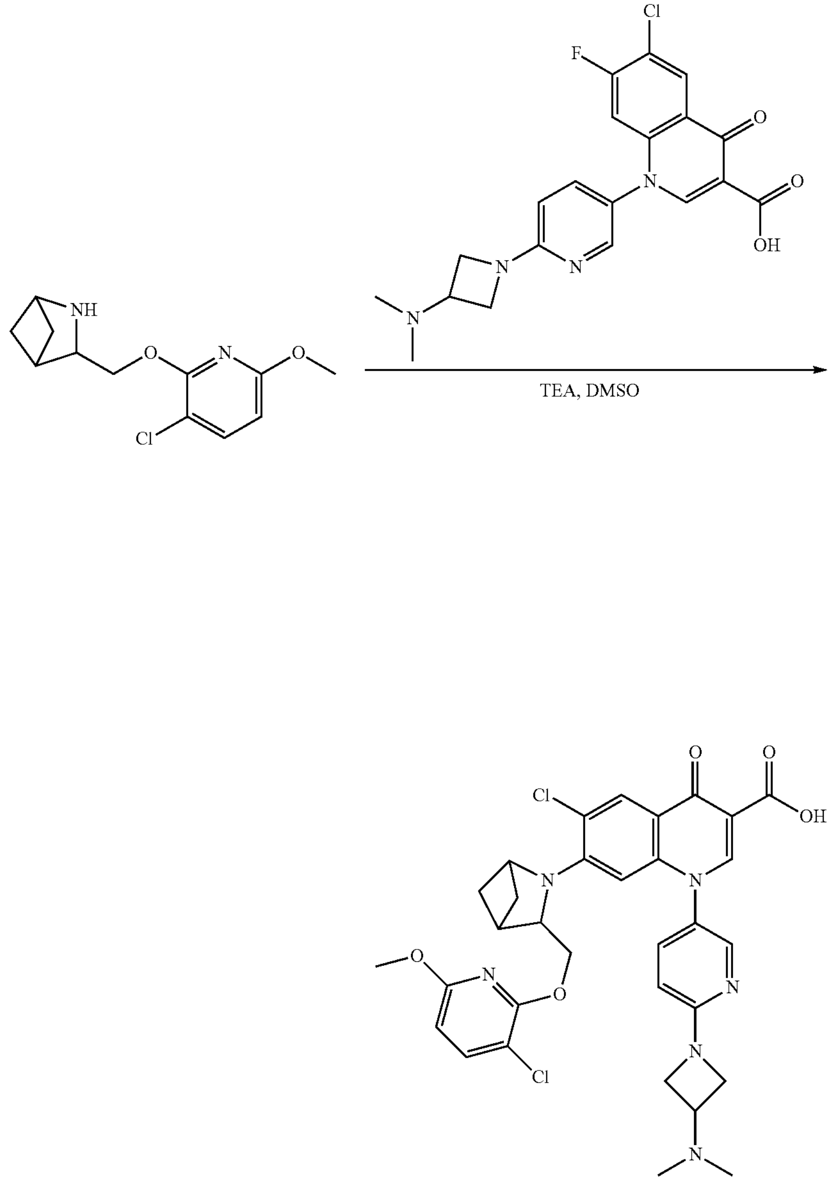

To a solution of 3-(((3-chloro-6-methoxypyridin-2-yl)oxy)methyl)-2-azabicyclo[2.1.1]hexane (100 mg, 0.39 mmol, 1.0 equiv) in DMSO (2 mL) was added was added 6-chloro-1-(6-(3-(dimethylamino)azetidin-1-yl)pyridin-3-yl)-7-fluoro-4-oxo-1,4-dihydroquinoline-3-carboxylic acid (231.4 mg, 0.55 mmol, 1.5 equiv) and TEA (112.1 mg, 1.11 mmol, 3.0 equiv). The resulting solution was stirred for 1 hr at 100° C. The mixture was purified by Prep-HPLC (Column: XSelect CSH Prep C18 OBD Column, 19*250 mm, 5 μm; Mobile Phase A: Water(0.05% FA), Mobile Phase B: ACN; Flow rate: 25 mL/min; Gradient: 25% B to 55% B in 7 min, 55% B; Wave Length: 254/220 nm; RT1 (min): 6.05; Number Of Runs: 0). This resulted in 6-chloro-7-(3-(((3-chloro-6-methoxypyridin-2-yl)oxy)methyl)-2-azabicyclo[2.1.1]hexan-2-yl)-1-(6-(3-(dimethylamino)azetidin-1-yl)pyridin-3-yl)-4-oxo-1,4-dihydroquinoline-3-carboxylic acid (3.3 mg, 0.01%) of as a yellow solid. LCMS (ESI) $[M+H]^+$: 651.1. $^1H$ NMR (300 MHz, Methanol-d4) δ 8.64 (s, 1H), 8.25 (m, 2H), 7.62 (m, 2H), 6.74-6.18 (m, 3H), 4.55 (m, 4H), 4.19 (m, 2H), 4.05 (s, 1H), 3.95 (m, 2H), 3.80 (s, 3H), 3.37 (s, 1H), 2.95 (s, 1H), 2.30 (s, 6H), 1.97 (d, J=8.9 Hz, 3H), 1.47 (s, 1H).

Potency Lin28a-dep Z11 $IC_{50}$ (μM)++++

Example 65: Synthesis of 1-(2-aminopyridin-4-yl)-6-chloro-7-[(2R)-2-({[3-chloro-6-(dimethylamino)pyridin-2-yl]oxy}methyl)-3-methylpyrrolidin-1-yl]-4-oxoquinoline-3-carboxylic acid

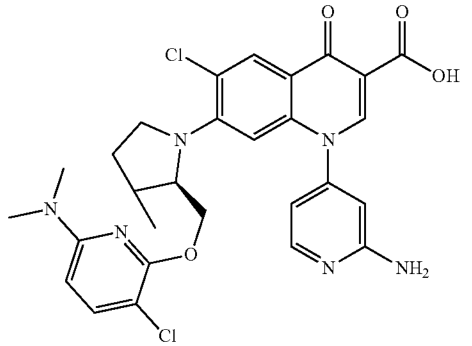 [SMILES: CC1CCN(c2cc3c(cc2Cl)c(=O)c(C(=O)O)cn3-c2ccnc(N)c2)[C@H]1COc1nc(N(C)C)ccc1Cl]

Step 1: Synthesis of Ethyl 1-{2-[(tert-butoxycarbonyl)amino]pyridin-4-yl}-6-chloro-7-fluoro-4-oxoquinoline-3-carboxylate

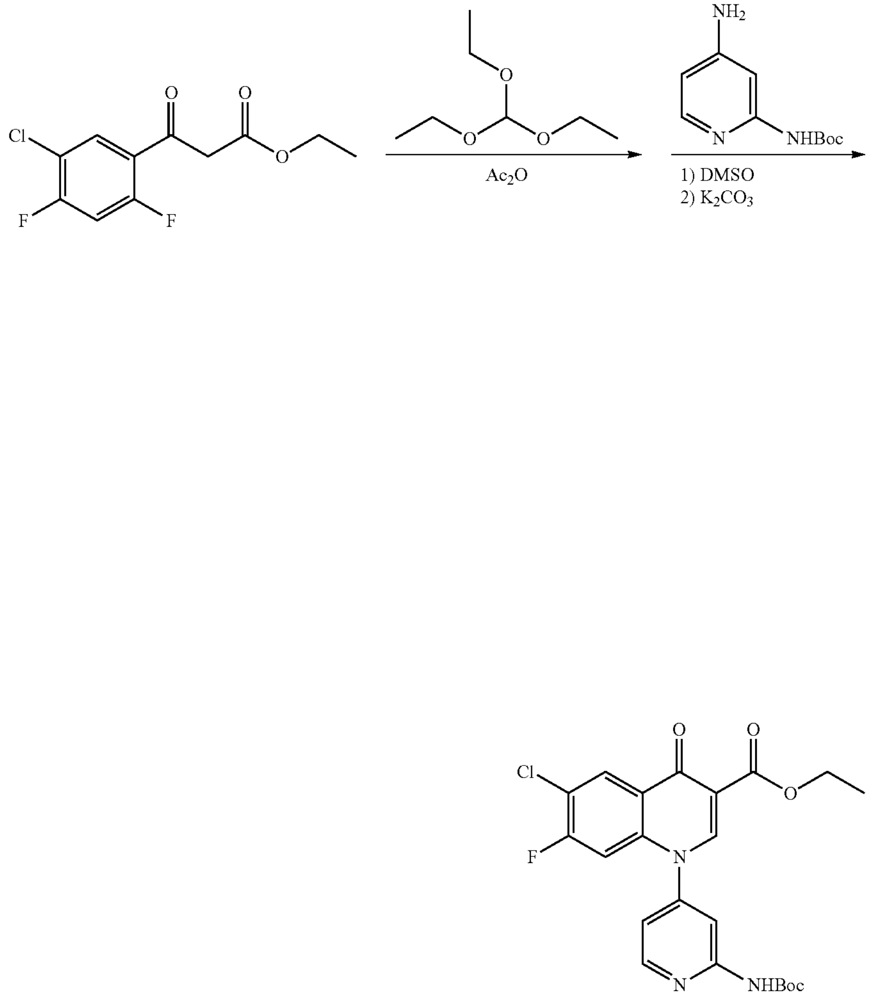

To a mixture of ethyl 3-(5-chloro-2,4-difluorophenyl)-3-oxopropanoate (1.0 g, 3.81 mmol, 1.0 equiv) in acetic anhydride (1.2 g, 11.42 mmol, 3.0 equiv) was added triethyl orthoformate (0.9 g, 5.71 mmol, 1.5 equiv). The resulting mixture was stirred at 100° C. for 2 h. The resulting mixture was concentrated under vacuum. To the resulting mixture in DMSO (70 mL) was added tert-butyl N-(4-aminopyridin-2-yl)carbamate (0.8 g, 3.81 mmol, 1.0 equiv). The resulting mixture was stirred at 25° C. for 2 h. To the resulting mixture was added $K_2CO_3$ (1.1 g, 7.61 mmol, 2.0 equiv). The resulting mixture was stirred at 100° C. for 1 h. The reaction was quenched by the addition of 80 mL water. The precipitated solids were collected by filtration. This resulted in ethyl 1-{2-[(tert-butoxycarbonyl)amino]pyridin-4-yl}-6-chloro-7-fluoro-4-oxoquinoline-3-carboxylate (1.8 g, crude) as a yellow solid. LCMS (ESI) $[M+H]^+$: 462.1.

Step 2: Synthesis of 1-(2-Aminopyridin-4-yl)-6-chloro-7-fluoro-4-oxoquinoline-3-carboxylic acid

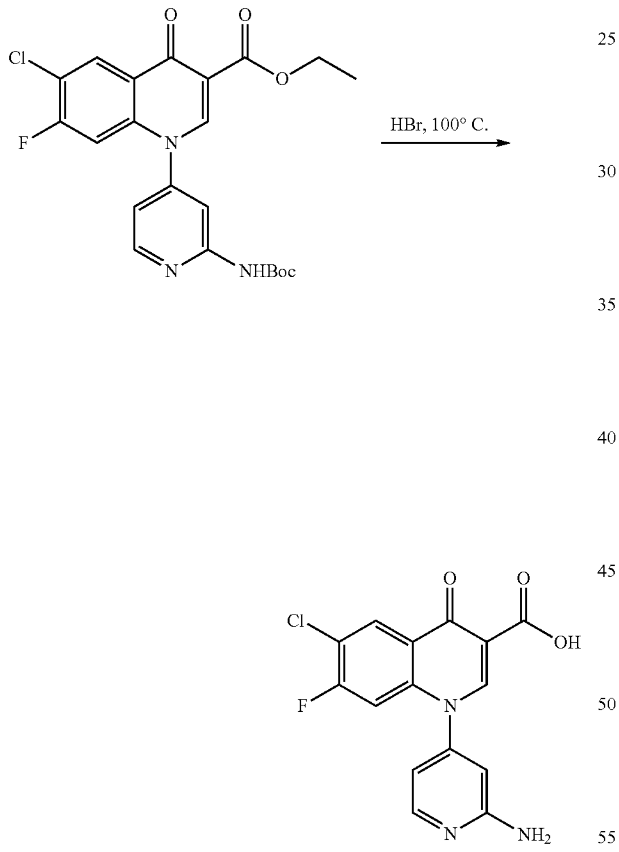

To a mixture of ethyl 1-{2-[(tert-butoxycarbonyl)amino]pyridin-4-yl}-6-chloro-7-fluoro-4-oxoquinoline-3-carboxylate (900 mg, 1.95 mmol, 1.0 equiv) in hydrogen bromide (10 mL). The resulting mixture was stirred for 1.5 h at 100° C. The mixture was allowed to cool down to room temperature. The precipitated solids were collected by filtration and washed with water (3×2 mL). This resulted in 1-(2-aminopyridin-4-yl)-6-chloro-7-fluoro-4-oxoquinoline-3-carboxylic acid (300 mg, 46%) as a white solid. LCMS (ESI) $[M+H]^+$: 334.0.

Step 3: Synthesis of 1-(2-aminopyridin-4-yl)-6-chloro-7-[(2R)-2-({[3-chloro-6-(dimethylamino)pyridin-2-yl]oxy}methyl)-3-methylpyrrolidin-1-yl]-4-oxoquinoline-3-carboxylic acid

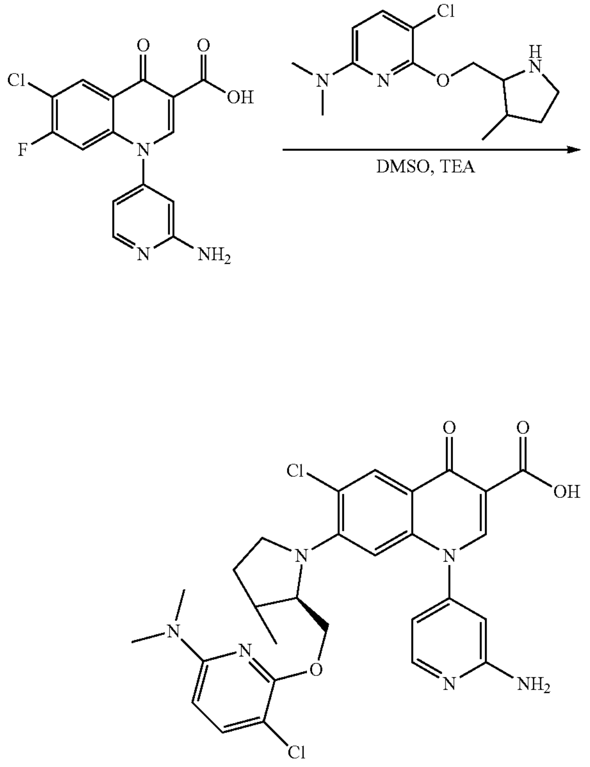

To a mixture of 1-(2-aminopyridin-4-yl)-6-chloro-7-fluoro-4-oxoquinoline-3-carboxylic acid (100 mg, 0.17 mmol, 1.0 equiv) in DMSO (6 mL) was added TEA (104 mg, 1.03 mmol, 6.0 equiv) and 5-chloro-N,N-dimethyl-6-[(3-methylpyrrolidin-2-yl)methoxy]pyridin-2-amine (55 mg, 0.21 mmol, 1.2 equiv). The resulting mixture was stirred for 2 h at 100° C. under nitrogen atmosphere. The mixture was allowed to cool down to room temperature. The crude product was purified by Prep-HPLC. This resulted in 1-(2-aminopyridin-4-yl)-6-chloro-7-[(2R)-2-({[3-chloro-6-(dimethylamino)pyridin-2-yl]oxy}methyl)-3-methylpyrrolidin-1-yl]-4-oxoquinoline-3-carboxylic acid (96.3 mg) as a light yellow solid. LCMS (ESI) $[M+H]^+$: 583.15. $^1H$ NMR (300 MHz, DMSO-d6) δ 15.05 (s, 1H), 8.55 (d, J=7.9 Hz, 1H), 8.29-7.93 (m, 2H), 7.42 (s, 1H), 6.78-6.46 (m, 4H), 6.36 (d, J=12.2 Hz, 1H), 6.14-5.71 (m, 1H), 5.01-4.77 (m, 1H), 4.72-3.91 (m, 2H), 3.47 (d, J=29.4 Hz, 1H), 3.27-3.02 (m, 1H), 2.78 (d, J=25.1 Hz, 6H), 2.60 (s, 1H), 2.19-2.02 (m, 1H), 1.52 (s, 1H), 1.27-1.08 (m, 3H).

Potency Lin28a-dep Z11 $IC_{50}$ (μM)++++

Example 66: Synthesis of 1-(2-Aminopyridin-4-yl)-7-((3R)-3-(((3-chloro-6-methoxypyridin-2-yl)oxy)methyl)-2-azabicyclo[3.1.0]hexan-2-yl)-6-fluoro-4-oxo-1,4-dihydroquinoline-3-carboxylic acid

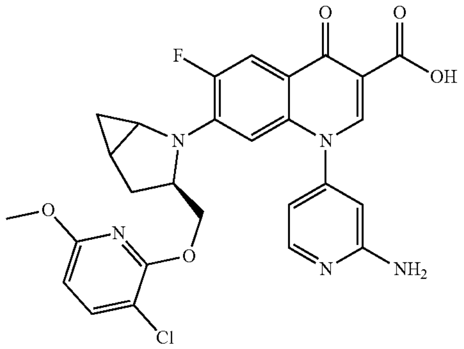 [SMILES: COc1ccc(Cl)c(OC[C@H]2CC3CC3N2c2cc3c(cc2F)c(=O)c(C(=O)O)cn3-c2ccnc(N)c2)n1]

Step 1: Synthesis of Tert-butyl N-(4-aminopyridin-2-yl)carbamate

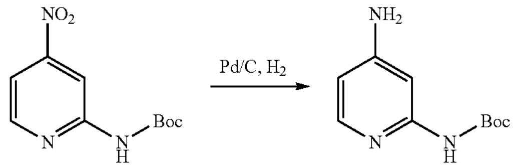 [SMILES: CC(C)(C)OC(=O)Nc1cc([N+](=O)[O-])ccn1 ; "Pd/C, H2" ; CC(C)(C)OC(=O)Nc1cc(N)ccn1]

To a mixture of tert-butyl N-(4-nitropyridin-2-yl)carbamate (2.7 g, 11.29 mmol, 1.0 equiv) in MeOH (20 ml) was added Pd/C (200 mg). The resulting mixture was stirred for 1 h at room temperature under hydrogen atmosphere. The resulting mixture was filtered, the filter cake was washed with MeOH (3x20 mL). The filtrate was concentrated under reduced pressure. The crude product was used in the next step directly without further purification.

Step 2: Synthesis of Ethyl 1-{2-[(tert-butoxycarbonyl)amino]pyridin-4-yl}-6,7-difluoro-4-oxoquinoline-3-carboxylate

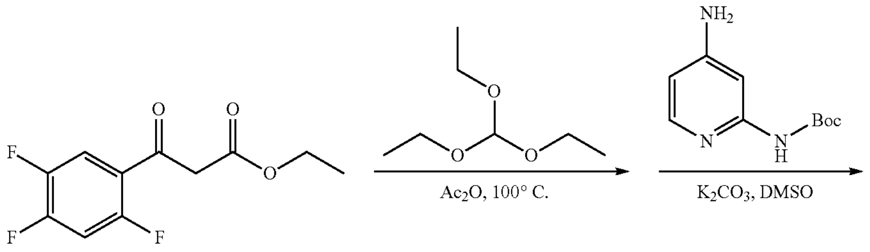

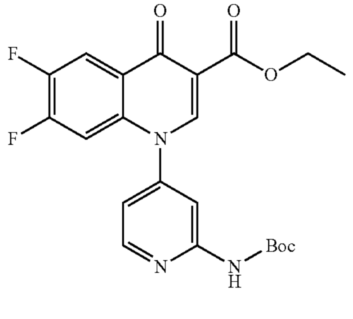

To a mixture of 1-ethoxy-3-(2,4,5-trifluorophenyl)propane-1,3-diol (85.0 g, 0.34 mol, 1.0 equiv) and triethyl orthoformate (2.71 g, 18.279 mmol, 1.5 equiv) was added $Ac_2O$(3.73 g, 36.56 mmol, 3.0 equiv). The resulting mixture was stirred for 2 h at 100° C. under nitrogen atmosphere. The resulting mixture was concentrated under vacuum. To the above mixture was added tert-butyl N-(4-aminopyridin-2-yl)carbamate (3.82 g, 18.28 mmol, 1.5 equiv) in DMSO (10 ml). The resulting mixture was stirred for 2 h at room temperature under nitrogen atmosphere. To the above mixture was added $K_2CO_3$ (228.6 g, 1.66 mol, 5.0 equiv). The resulting mixture was stirred overnight. The reaction was quenched with water at room temperature. The precipitated solids were collected by filtration and washed with water. The residue was purified by silica gel column chromatography, eluted with Petroleum ether/EtOAc (5:1) to afford ethyl 1-{2-[(tert-butoxycarbonyl)amino]pyridin-4-yl}-6,7-difluoro-4-oxoquinoline-3-carboxylate (1.32 g, 24.32%) as a yellow solid. LCMS (ESI) $[M+H]^+$: 446.1.

Step 3: Synthesis of 1-(2-Aminopyridin-4-yl)-6,7-difluoro-4-oxoquinoline-3-carboxylic acid

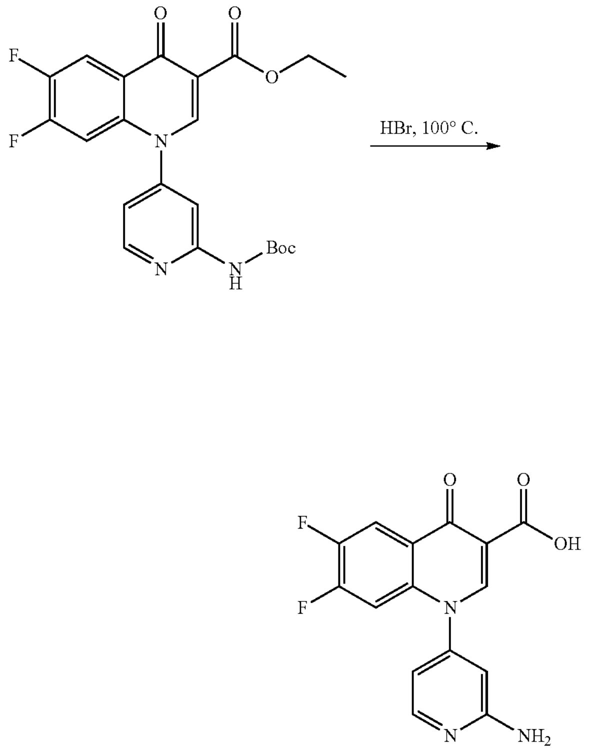

To a mixture of ethyl 1-{2-[(tert-butoxycarbonyl)amino]pyridin-4-yl}-6,7-difluoro-4-oxoquinoline-3-carboxylate (1.32 g, 2.96 mmol, 1.0 equiv) in HBr (5 mL) at 0° C. under nitrogen atmosphere. The final reaction mixture was irradiated with microwave radiation for 1 h at 100° C. The precipitated solids were collected by filtration and washed with water (3×10 mL). This resulted in 1-(2-aminopyridin-4-yl)-6,7-difluoro-4-oxoquinoline-3-carboxylic acid (630 mg, 67.01%) as a light yellow solid. LCMS (ESI) $[M+H]^+$: 318.1.

Step 4: Synthesis of 1-(2-Aminopyridin-4-yl)-7-((3R)-3-(((3-chloro-6-methoxypyridin-2-yl)oxy)methyl)-2-azabicyclo[3.1.0]hexan-2-yl)-6-fluoro-4-oxo-1,4-dihydroquinoline-3-carboxylic acid

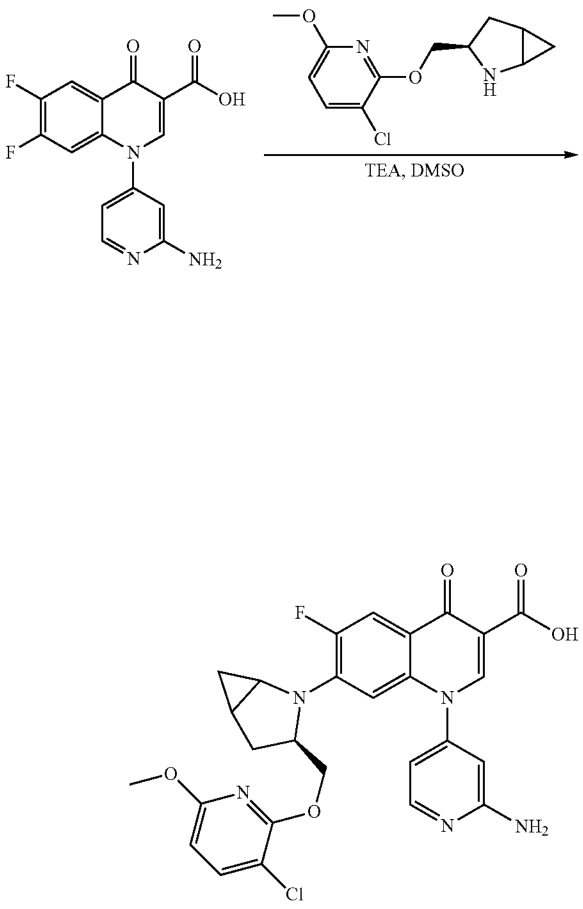

To a mixture of 1-(2-aminopyridin-4-yl)-6,7-difluoro-4-oxo-1,4-dihydroquinoline-3-carboxylic acid (40 mg, 0.13 mmol, 1.0 equiv) and (3R)-3-(((3-chloro-6-methoxypyridin-2-yl)oxy)methyl)-2-azabicyclo[3.1.0]hexane (38 mg, 0.15 mmol, 1.2 equiv) in DMSO (1 mL) was added TEA (40 mg, 0.39 mmol, 3.0 equiv) under nitrogen atmosphere. The resulting mixture was stirred for overnight at 80° C. under nitrogen atmosphere. The crude product (80 mg) was purified by Prep-HPLC with the following conditions (Column: XSelect CSH Prep C18 OBD Column, 19*250 mm, 5 μm; Mobile Phase A: Water(0.1% FA), Mobile Phase B: ACN; Flow rate: 25 mL/min; Gradient: 35% B to 61% B in 7 min, 61% B; Wave Length: 254/220 nm; RT1 (min): 6.97; Number Of Runs: 0) to afford 1-(2-aminopyridin-4-yl)-7-((3R)-3-(((3-chloro-6-methoxypyridin-2-yl)oxy)methyl)-2-azabicyclo[3.1.0]hexan-2-yl)-6-fluoro-4-oxo-1,4-dihydroquinoline-3-carboxylic acid (12.4 mg, 17.34%) as a yellow solid. LCMS (ESI) $[M+H]^+$: 552.15. $^1H$ NMR (300 MHz, DMSO-$d_6$) δ 15.28 (s, 1H), 8.55 (s, 1H), 8.09 (s, 1H), 7.89 (d, J=14.2 Hz, 1H), 7.74 (d, J=8.4 Hz, 1H), 6.73 (d, J=7.8 Hz, 2H), 6.64 (s, 1H), 6.52 (s, 2H), 6.42 (d, J=8.4 Hz, 1H), 4.46 (d, J=12.4 Hz, 3H), 3.77 (s, 3H), 3.09 (s, 1H), 2.33-2.20 (m, 1H), 2.05 (s, 1H), 1.79 (s, 1H), 0.90-0.81 (m, 1H), 0.39 (s, 1H).

Potency Lin28a-dep Z11 $IC_{50}$ (μM)++++

Example 67: 1-(5-Aminopyridazin-3-yl)-6-chloro-7-(2-(((3-chloro-6-methoxypyridin-2-yl)oxy)methyl)-3,3-dimethylpyrrolidin-1-yl)-4-oxo-1,4-dihydroquinoline-3-carboxylic acid

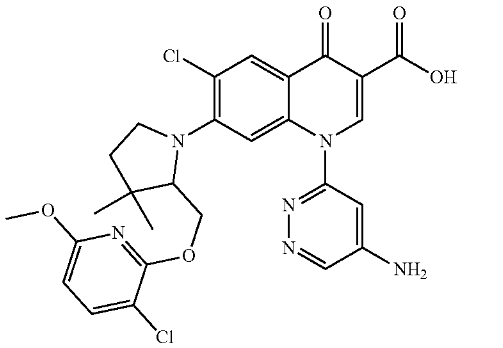 [SMILES: COc1ccc(Cl)c(OCC2N(c3cc4c(cc3Cl)c(=O)c(C(=O)O)cn4-c3cc(N)cnn3)CCC2(C)C)n1]

Step 1: Synthesis of 1-(5-Aminopyridazin-3-yl)-6-chloro-7-fluoro-4-oxo-1,4-dihydroquinoline-3-carboxylic acid

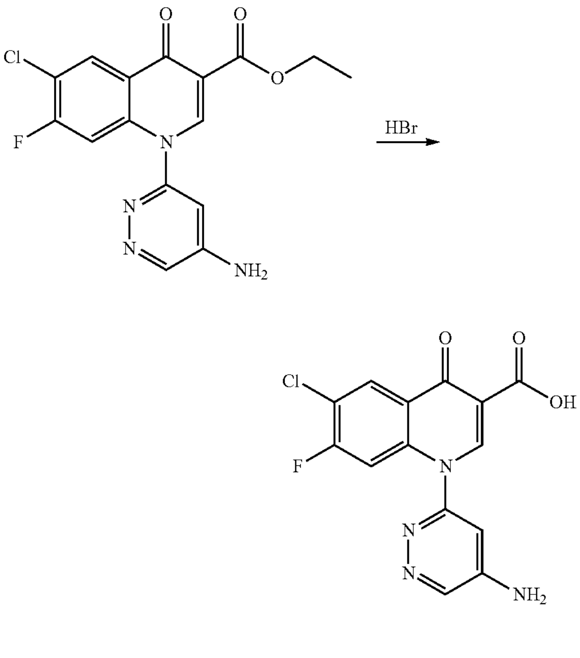

To a mixture of ethyl 1-(5-aminopyridazin-3-yl)-6-chloro-7-fluoro-4-oxo-1,4-dihydroquinoline-3-carboxylate (120 mg, 0.33 mmol, 1.0 equiv) in HBr (0.5 mL) at 0° C. under nitrogen atmosphere. The final reaction mixture was irradiated with microwave radiation for 1 h at 100° C. The precipitated solids were collected by filtration and washed with water (3×10 mL). This resulted in 1-(5-amino-pyridazin-3-yl)-6-chloro-7-fluoro-4-oxo-1,4-dihydroquinoline-3-carboxylic acid (68 mg, 60.9%). LCMS (ESI) $[M+H]^+$: 335.0.

Step 2: Synthesis of 1-(5-Aminopyridazin-3-yl)-6-chloro-7-(2-(((3-chloro-6-methoxypyridin-2-yl)oxy)methyl)-3,3-dimethylpyrrolidin-1-yl)-4-oxo-1,4-dihydroquinoline-3-carboxylic acid

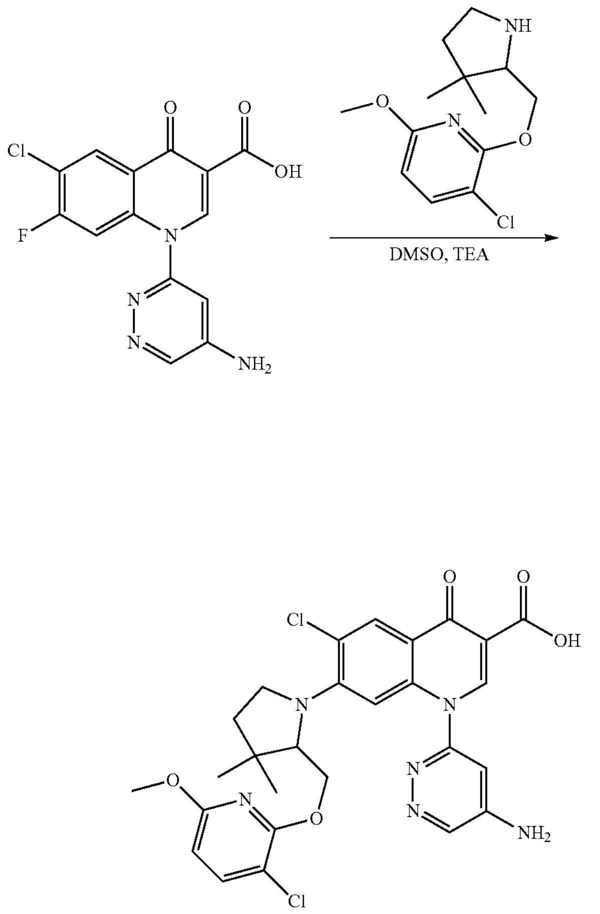

To a mixture of 1-(5-aminopyridazin-3-yl)-6-chloro-7-fluoro-4-oxo-1,4-dihydroquinoline-3-carboxylic acid (60 mg, 0.17 mmol, 1.0 equiv) and 3-chloro-2-((3,3-dimethylpyrrolidin-2-yl)methoxy)-6-methoxypyridine (58 mg, 0.21 mmol, 1.2 equiv) in DMSO (1 mL) was added TEA (52 mg, 0.51 mmol, 3.0 equiv) under nitrogen atmosphere. The resulting mixture was stirred for overnight at 80° C. under nitrogen atmosphere. The crude product (80 mg) was purified by Prep-HPLC with the following conditions (Column: XSelect CSH Prep C18 OBD Column, 19*250 mm, 5 μm; Mobile Phase A: Water(0.1% FA), Mobile Phase B: ACN; Flow rate: 25 mL/min; Gradient: 35% B to 61% B in 7 min, 61% B; Wave Length: 254/220 nm; RT1(min): 6.97; Number Of Runs: 0) to afford 1-(5-aminopyridazin-3-yl)-6-chloro-7-(2-(((3-chloro-6-methoxypyridin-2-yl)oxy)methyl)-3,3-dimethylpyrrolidin-1-yl)-4-oxo-1,4-dihydroquinoline-3-carboxylic acid (30.4 mg, 30.71%) as a yellow solid. LCMS (ESI) $[M+H]^+$: 585.15. $^1H$ NMR (300 MHz, DMSO-d6) δ 14.95 (s, 1H), 8.74-8.61 (m, 2H), 8.12 (s, 1H), 7.60 (d, J=8.4 Hz, 1H), 7.04 (s, 2H), 6.33 (d, J=8.4 Hz, 2H), 4.61 (s, 1H), 4.46 (d, J=4.5 Hz, 2H), 3.69 (s, 4H), 3.22 (d, J=7.5 Hz, 1H), 1.97 (s, 1H), 1.82-1.67 (m, 1H), 1.18 (d, J=12.4 Hz, 6H).

Potency Lin28a-dep Z11 $IC_{50}$ (μM)++++

Example 68: Synthesis of 7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydroquinoline-3-carboxylic acid

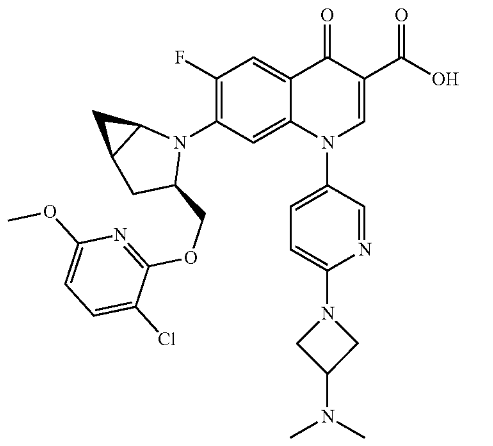 [SMILES: COc1ccc(Cl)c(OC[C@H]2C[C@H]3C[C@H]3N2c2cc3c(cc2F)c(=O)c(C(=O)O)cn3-c2ccc(N3CC(N(C)C)C3)nc2)n1]

Step 1: Synthesis of 3-chloro-6-methoxypyridin-2-amine

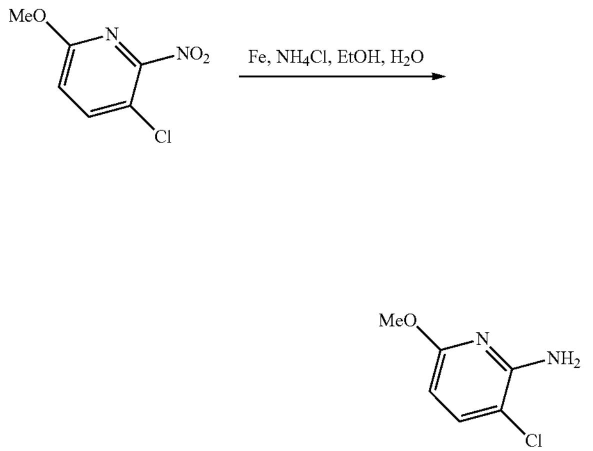

Into a 500 mL 3-necked round bottom flask, was placed 3-chloro-6-methoxy-2-nitropyridine (20.0 g, 106.06 mmol) in ethanol (200 mL) and $H_2O$ (20 mL) was added Fe (29.62 g, 530.32 mmol) and $NH_4Cl$ (34.04 g, 636.38 mmol), the reaction mixture was stirred for 5 hours at 80° C. The resulting mixture was filtered, the filtrate was evaporated under reduced pressure and the residue was applied onto a silica gel column eluting with ethyl acetate/petroleum ether (1:2). This resulted in 13.75 g (81.75%) of 3-chloro-6-methoxypyridin-2-amine as brown solid. $^1H$ NMR (400 MHz, DMSO-d6) δ 7.22 (d, J=8.5 Hz, 1H), 6.64 (d, J=8.5 Hz, 1H), 4.97 (s, 2H), 3.73 (s, 3H).

Step 2: Synthesis of 2,3-dichloro-6-methoxypyridine

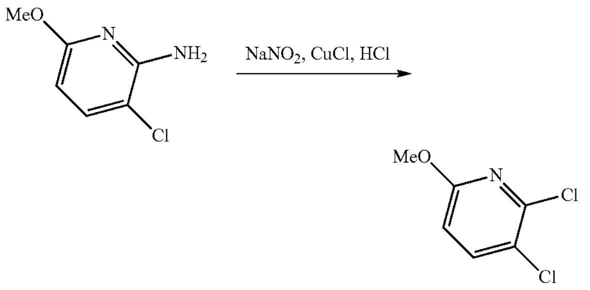

A solution of 3-chloro-6-methoxypyridin-2-amine (10.0 g, 63.06 mmol) in concentrated hydrochloric acid (160 mL) was cooled down to −5° C. At this temperature a solution of $NaNO_2$ (17.40 g, 252.23 mmol) in water (80 mL) was added within 30 min. After stirring for 30 min, CuCl (49.94 g, 504.46 mmol) was added slowly within 30 min. Stirring was continued at room temperature for 16 h and ammonia (25% aqueous solution, 300 mL) was slowly added at 10° C. The reaction mixture was extracted with EtOAc. Then the mixture solvent was evaporated under reduced pressure and the residue was applied onto a silica gel column with petroleum ether. This resulted in 5.2 g (46.33%) of 2,3-dichloro-6-methoxypyridine as white solid. $^1H$ NMR (300 MHz, DMSO-d6) δ 8.00 (dd, J=8.6, 2.5 Hz, 1H), 6.93 (dd, J=8.5, 2.3 Hz, 1H), 3.87 (s, 3H).

Step 3: Synthesis of 1-(tert-butyl) 2-methyl (R)-2,3-dihydro-1H-pyrrole-1,2-dicarboxylate

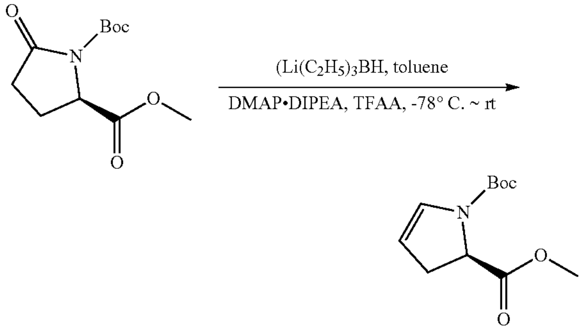

To a stirred solution of 1-(tert-butyl) 2-methyl (R)-5-oxopyrrolidine-1,2-dicarboxylate (550 g, 2.26 mol) in toluene (1 L) was added tri-ethyl lithium borane (1 M in THF) (2.5 L, 2.5 mol) at −78° C. and the mixture was stirred at room temperature for 1 h. Then, the mixture was re-cooled to −78° C., were added 4-dimethylaminopyridine (5.5 g, 45.05 mmol), N,N-diisopropylethylamine (2.25 L, 13.60 mol) followed by trifluoroacetic anhydride (380 mL, 5.65 mol) and the mixture was stirred at −78° C.-15° C. for 16 h. The resulting mixture was quenched with water and extracted with ethyl acetate. The combined organic layers were dried over $Na_2SO_4$, filtered and concentrated under reduced pressure. The residue was purified by silica gel column chromatography, eluting with 5% EtOAc in Hexanes to afford 1-(tert-butyl) 2-methyl (R)-2,3-dihydro- 1H-pyrrole-1,2-dicarboxylate (270 g, 53%) as a yellow oil. $^1$H NMR (300 MHz, DMSO-d6) δ 6.64-6.45 (m, 1H), 5.09-4.91 (m, 1H), 4.60 (dd, J=12.0, 5.2 Hz, 1H), 3.68 (d, J=7.7 Hz, 3H), 3.14-2.95 (m, 1H), 2.65-2.53 (m, 1H), 1.39 (d, J=19.1 Hz, 9H).

Step 4: Synthesis of 2-(tert-butyl) 3-methyl (1R,3R,5R)-2-azabicyclo[3.1.0]hexane-2,3-dicarboxylate

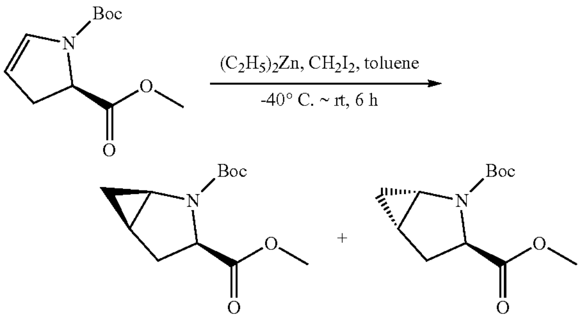

Into a 3000 mL 3-necked round-bottom flask, was placed 1-(tert-butyl) 2-methyl (R)-2,3-dihydro-1H-pyrrole-1,2-dicarboxylate (50.0 g, 220.01 mmol) in dichloromethane (1000 mL) was added a solution of diethylzinc (1M in heptane, 484.04 mL, 484.04 mmol) at 0° C., followed by diiodomethane (235.7 g, 880.05 mmol) over a period of 30 minutes and stirred for 30 minutes. The reaction mixture was gradually warmed to room temperature and stirred for 16 hours. The resulting mixture was concentrated under reduced pressure. To the above mixture was added 1000 mL dichloromethane, $Boc_2O$(72.03 g, 330.03 mmol) and $Et_3N$ (66.79 g, 660.06 mmol). The resulting mixture was stirred for additional 2 h at room temperature. Then the mixture solvent was evaporated under reduced pressure and the residue was applied onto a silica gel column eluting with ethyl acetate/petroleum ether (1:5). This resulted in 2-(tert-butyl) 3-methyl (1R,3R,5R)-2-azabicyclo[3.1.0]hexane-2,3-dicarboxylate (13.5 g, 25.43%, higher spot on TLC) as yellow oil and the byproduct 2-(tert-butyl) 3-methyl (1S,3R,5S)-2-azabicyclo[3.1.0]hexane-2,3-dicarboxylate (5.3 g, 9.98%, lower spot on TLC) as yellow oil. $^1$H NMR (400 MHz, DMSO-d6) δ 4.55-4.44 (m, 1H), 3.62 (d, J=9.7 Hz, 3H), 3.43-3.33 (m, 1H), 2.68-2.52 (m, 1H), 1.94-1.83 (m, 1H), 1.60-1.45 (m, 1H), 1.37 (d, J=39.6 Hz, 9H), 0.75-0.62 (m, 2H).

Step 5: Synthesis of tert-butyl (1R,3R,5R)-3-(hydroxymethyl)-2-azabicyclo[3.1.0]hexane-2-carboxylate

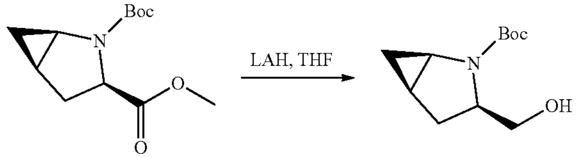 [SMILES: COC(=O)[C@H]1C[C@H]2C[C@H]2N1C(=O)OC(C)(C)C ; "LAH, THF" ; CC(C)(C)OC(=O)N1[C@@H](CO)C[C@H]2C[C@H]21]

Under nitrogen, into a 500 mL 3-necked round-bottom flask, was placed 2-(tert-butyl) 3-methyl (1R,3R,5R)-2-azabicyclo[3.1.0]hexane-2,3-dicarboxylate (9.7 g, 40.20 mmol) in dry THF (100 mL) was added a solution of $LiAlH_4$ (1M in THF, 48.24 mL, 48.24 mmol) at 0° C., The reaction mixture was stirred for 15 min. Then the reaction was quenched with $Na_2SO_4 \cdot 10H_2O$ at 0° C. The resulting mixture was filtered, the filtrate was evaporated under reduced pressure and the residue was applied onto a silica gel column eluting with ethyl acetate/petroleum ether (1:2). This resulted in 7.3 g (85.14%) of tert-butyl (1R,3R,5R)-3-(hydroxymethyl)-2-azabicyclo[3.1.0]hexane-2-carboxylate as yellow oil. $^1$H NMR (300 MHz, DMSO-d6) δ 4.78-4.68 (m, 1H), 4.03-3.88 (m, 1H), 3.48-3.34 (m, 2H), 3.22-3.10 (m, 1H), 2.31-2.14 (m, 1H), 1.97-1.82 (m, 1H), 1.52-1.29 (m, 10H), 0.69-0.57 (m, 2H).

Step 6: Synthesis of tert-butyl (1R,3R,5R)-3-(((3-chloro-6-methoxypyridin-2-yl)oxy)methyl)-2-azabicyclo[3.1.0]hexane-2-carboxylate

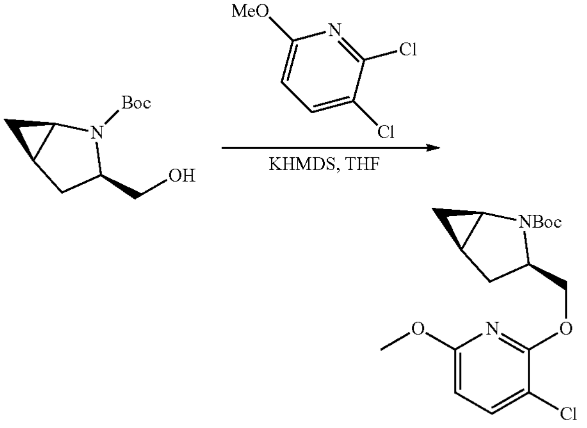

Under nitrogen, into a 500 mL 3-necked round-bottom flask, was placed tert-butyl (1R,3R,5R)-3-(hydroxymethyl)-2-azabicyclo[3.1.0]hexane-2-carboxylate (7.3 g, 34.23 mmol) in dry THF (100 mL) was added 2,3-dichloro-6-methoxypyridine (6.07 g, 37.65 mmol) at 0° C., followed by KHMDS (1M in THF, 68 mL, 68.00 mmol) was add and stirred for 20 minutes. The resulting mixture was extracted with EtOAc. The organic layer was applied onto a silica gel column eluting with ethyl acetate/petroleum ether (1:4). This resulted in 8.2 g (67.52%) of tert-butyl (1R,3R,5R)-3-(((3-chloro-6-methoxypyridin-2-yl)oxy)methyl)-2-azabicyclo[3.1.0]hexane-2-carboxylate as yellow oil. $^1$H NMR (300 MHz, DMSO-d6) δ 7.76 (dd, J=8.5, 2.7 Hz, 1H), 6.42 (dd, J=8.6, 2.7 Hz, 1H), 4.48-4.20 (m, 3H), 3.84 (s, 3H), 3.53-3.40 (m, 1H), 2.49-2.32 (m, 1H), 1.99-1.86 (m, 1H), 1.56-1.46 (m, 1H), 1.38 (d, J=24.1 Hz, 9H), 0.94-0.84 (m, 1H), 0.79-0.66 (m, 1H).

Step 7: Synthesis of (1R,3R,5R)-3-(((3-chloro-6-methoxypyridin-2-yl)oxy)methyl)-2-azabicyclo[3.1.0]hexane hydrochloride

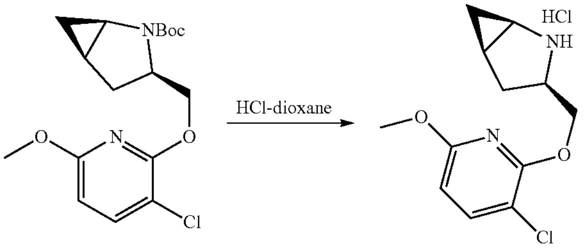 [SMILES: COc1ccc(Cl)c(OC[C@H]2C[C@H]3C[C@H]3N2C(=O)OC(C)(C)C)n1 ; "HCl-dioxane" ; COc1ccc(Cl)c(OC[C@H]2C[C@H]3C[C@H]3N2)n1 ; Cl]

Into a 500 mL 3-necked round-bottom flask, was placed tert-butyl (1R,3R,5R)-3-(((3-chloro-6-methoxypyridin-2-yl)oxy)methyl)-2-azabicyclo[3.1.0]hexane-2-carboxylate (8.2 g, 23.16 mmol) in dioxane (100 mL) was added a solution of HCl (4M in dioxane, 150 mL) at 0° C., The reaction mixture was gradually warmed to room temperature and stirred for 1 hour. The resulting mixture was concentrated under reduced pressure. The above mixture was washed with $Et_2O$. Then the resulting mixture was filtered, this resulted in 6.5 g (96.06%) of (1R,3R,5R)-3-(((3-chloro-6-methoxy-pyridin-2-yl)oxy)methyl)-2-azabicyclo[3.1.0]hexane hydrochloride as white solid. $^1H$ NMR (300 MHz, DMSO-d6) δ 10.50 (s, 1H), 9.25 (s, 1H), 7.81 (d, J=8.4 Hz, 1H), 6.49 (d, J=8.4 Hz, 1H), 4.56-4.29 (m, 3H), 3.86 (s, 3H), 3.34-3.23 (m, 1H), 2.60-2.52 (m, 1H), 1.95-1.77 (m, 2H), 1.14-0.99 (m, 2H).

Step 8: Synthesis of 7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydroquinoline-3-carboxylic acid

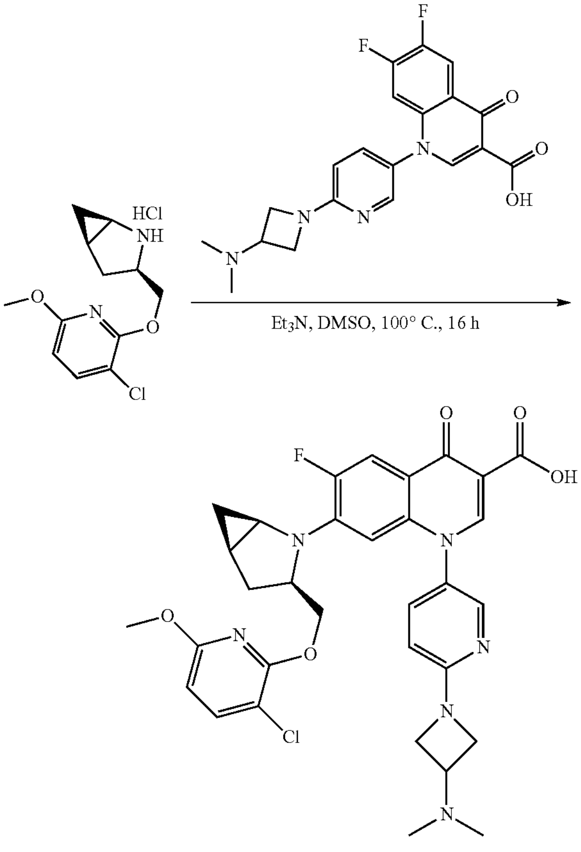 [SMILES: COc1ccc(Cl)c(OC[C@H]2C[C@H]3C[C@H]3N2)n1 ; Cl ; CN(C)C1CN(c2ccc(-n3cc(C(=O)O)c(=O)c4cc(F)c(F)cc43)cn2)C1 ; COc1ccc(Cl)c(OC[C@H]2C[C@H]3C[C@H]3N2c2cc3c(cc2F)c(=O)c(C(=O)O)cn3-c2ccc(N3CC(N(C)C)C3)nc2)n1]

To a mixture of 1-(6-(3-(dimethylamino)azetidin-1-yl)pyridin-3-yl)-6,7-difluoro-4-oxo-1,4-dihydroquinoline-3-carboxylic acid (4.0 g, 10.00 mmol, 1.0 equiv) in DMSO (60 mL) was added (1R,3R,5R)-3-(((3-chloro-6-methoxypyridin-2-yl)oxy)methyl)-2-azabicyclo[3.1.0]hexane hydrochloride (3.2 g, 11.00 mmol, 1.1 equiv) and $Et_3N$ (7.1 g, 70.00 mmol, 7.0 equiv). The mixture was stirred at 110° C. for 3 h. The solution was purified by reverse phase flash chromatography eluting with 20%-80% acetonitrile in water ($NH_4HCO_3$) to afford 7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydroquinoline-3-carboxylic acid (1.0838 g, 17%) as light yellow solid. LCMS (ESI) $[M+H]^+$: 635.20. $^1H$ NMR (300 MHz, DMSO-d6) δ 15.34 (s, 1H), 8.52 (d, J=3.4 Hz, 1H), 8.32-8.23 (m, 1H), 7.88 (d, J=13.3 Hz, 1H), 7.82-7.63 (m, 2H), 6.62-6.33 (m, 3H), 4.79-4.73 (m, 1H), 4.31-4.14 (m, 2H), 4.11-4.00 (m, 2H), 3.87-3.75 (m, 2H), 3.73 (d, J=2.1 Hz, 3H), 3.28-3.13 (m, 2H), 2.70-2.59 (m, 1H), 2.14 (s, 6H), 2.10-1.99 (m, 1H), 1.65-1.59 (m, 1H), 1.03-0.91 (m, 1H), 0.77-0.69 (m, 1H).

Potency Lin28a-dep Z11 $IC_{50}$ (μM)++++

Example 69: Synthesis of 6-chloro-7-[(2R,4Z)-2-[[(3-chloro-6-methoxypyridin-2-yl)oxy]methyl]-4-(methoxyimino)pyrrolidin-1-yl]-1-[6-[3-(dimethylamino)azetidin-1-yl]pyridin-3-yl]-4-oxoquinoline-3-carboxylic acid

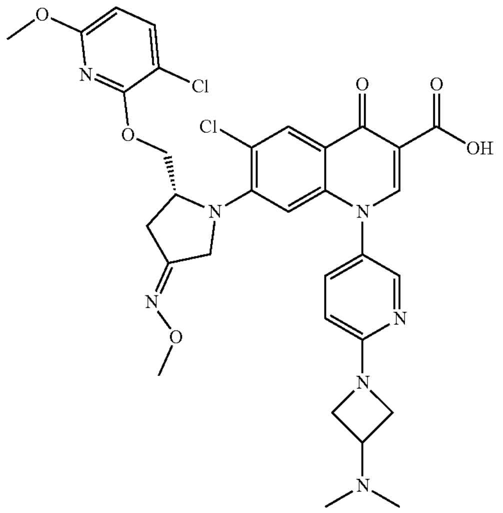 [SMILES: CO/N=C1/C[C@H](COc2nc(OC)ccc2Cl)N(c2cc3c(cc2Cl)c(=O)c(C(=O)O)cn3-c2ccc(N3CC(N(C)C)C3)nc2)C1]

Step 1: Synthesis of 1-tert-butyl 2-methyl (2R)-4,4-dimethoxypyrrolidine-1,2-dicarboxylate

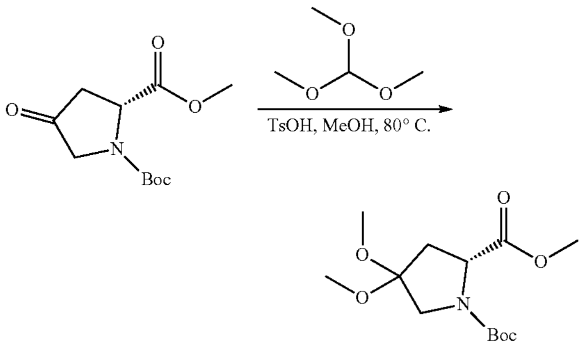

To a solution of 1-tert-butyl 2-methyl (2R)-4-oxopyrrolidine-1,2-dicarboxylate (1.0 g, 4.11 mmol, 1.0 equiv) in MeOH (5 mL) was added TsOH (35.3 mg, 0.20 mmol, 0.05 equiv) and trimethoxymethane (510.1 mg, 4.93 mmol, 1.20 equiv) The resulting mixture was stirred for additional 1 h at 80° C. The resulting mixture was concentrated under vacuum. The residue was purified by silica gel column chromatography, eluted with PE/EtOAc (1:1). This resulted in 1-tert-butyl 2-methyl (2R)-4,4-dimethoxypyrrolidine-1,2-dicarboxylate (780.2 mg, 65.58%) of as yellow oil. LCMS (ESI) $[M+H]^+$: 290.1.

Step 2: Synthesis of tert-butyl (2R)-2-(hydroxymethyl)-4,4-dimethoxypyrrolidine-1-carboxylate

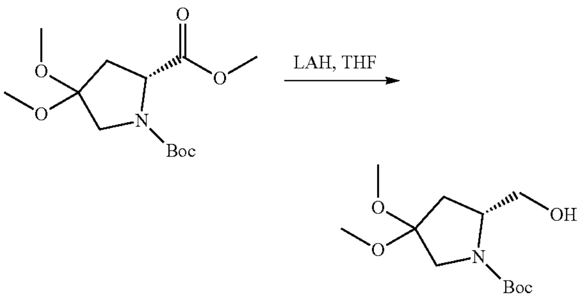

To a stirred solution of 1-tert-butyl 2-methyl (2R)-4,4-dimethoxypyrrolidine-1,2-dicarboxylate (770.0 mg, 2.661 mmol, 1.0 equiv) in THF (5 mL) was added LAH (121.2 mg, 3.19 mmol, 1.2 equiv). The resulting mixture was stirred for additional 1 h at 0° C. The reaction was quenched with water. The resulting mixture was extracted with EtOAc (3*50 mL). The combined organic layers were collected and dried with anhydrous $Na_2SO_4$. After filtration, the filtrate was concentrated under vacuum. The residue was purified by silica gel column chromatography, eluted with Petroleum ether/EtOAc (1:1). This resulted in tert-butyl (2R)-2-(hydroxymethyl)-4,4-dimethoxypyrrolidine-1-carboxylate (500 mg, 71.9%) of as yellow oil. LCMS (ESI) $[M+H]^+$: 262.1.

Step 3: Synthesis of tert-butyl (2R)-2-[[(3-chloro-6-methoxypyridin-2-yl)oxy]methyl]-4,4-dimethoxypyrrolidine-1-carboxylate

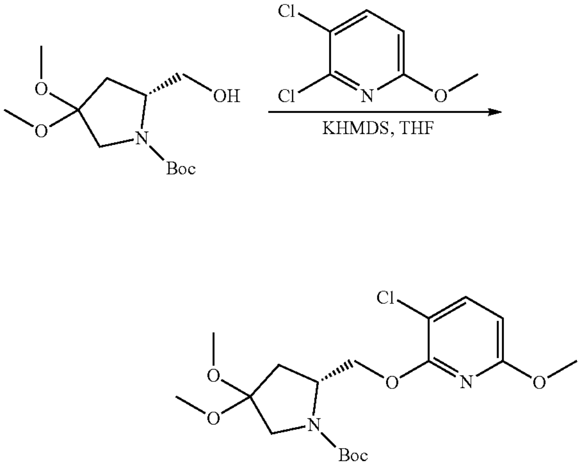

To a stirred solution of tert-butyl (2R)-2-(hydroxymethyl)-4,4-dimethoxypyrrolidine-1-carboxylate (500.0 mg, 1.91 mmol, 1.0 equiv) in THF (5 mL) was added 2,3-dichloro-6-methoxypyridine (408.7 mg, 2.29 mmol, 1.2 equiv) and KHMDS (763.3 mg, 3.82 mmol, 2.0 equiv). The resulting mixture was stirred for additional 1 h at 0° C. The reaction was quenched with water. The resulting mixture was extracted with EtOAc(3*10 mL) The combined organic layers was collected and dried with anhydrous Na2SO4. The resulting mixture was concentrated under vacuum. The residue was purified by silica gel column chromatography, eluted with PE/EtOAc (1:1). This resulted in tert-butyl (2R)-2-[[(3-chloro-6-methoxypyridin-2-yl)oxy]methyl]-4,4-dimethoxypyrrolidine-1-carboxylate (300 mg, 38.9%) of as yellow oil. LCMS (ESI) $[M+H]^+$: 403.1.

Step 4: Synthesis of 3-chloro-2-[[(2R)-4,4-dimethoxypyrrolidin-2-yl]methoxy]-6-methoxypyridine

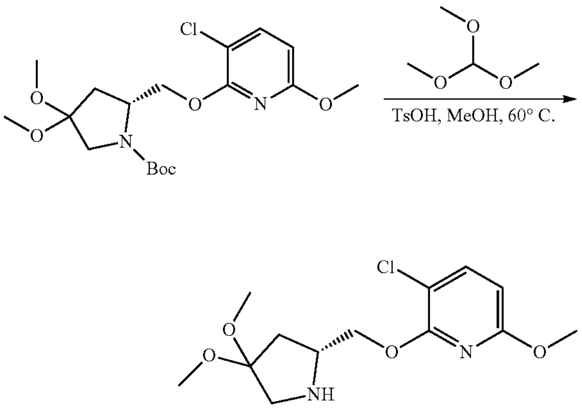

To a mixture of tert-butyl (2R)-2-[[(3-chloro-6-methoxypyridin-2-yl)oxy]methyl]-4,4-dimethoxypyrrolidine-1-carboxylate (300.0 mg, 0.74 mmol, 1.0 equiv) in MeOH (2 mL) was added TsOH (128.2 mg, 0.74 mmol, 1.0 equiv) and trimethyl orthoformate (39.5 mg, 0.37 mmol, 0.5 equiv). The resulting mixture was stirred for additional 2 h at 60° C. The reaction was quenched with water. The resulting mixture was extracted with EtOAc(3*10 mL) The combined organic layers was collected and dried with anhydrous $Na_2SO_4$. The resulting mixture was concentrated under vacuum. The residue was purified by silica gel column chromatography, eluted with PE/EtOAc (1:1). This resulted in 3-chloro-2-[[(2R)-4,4-dimethoxypyrrolidin-2-yl]methoxy]-6-methoxypyridine (282 mg, 98.2%) of as yellow oil. LCMS (ESI) $[M+H]^+$: 303.1.

Step 5: Synthesis of 6-chloro-7-[(2R)-2-[[(3-chloro-6-methoxypyridin-2-yl)oxy]methyl]-4,4-dimethoxy-pyrrolidin-1-yl]-1-[6-[3-(dimethylamino)azetidin-1-yl]pyridin-3-yl]-4-oxoquinoline-3-carboxylic acid
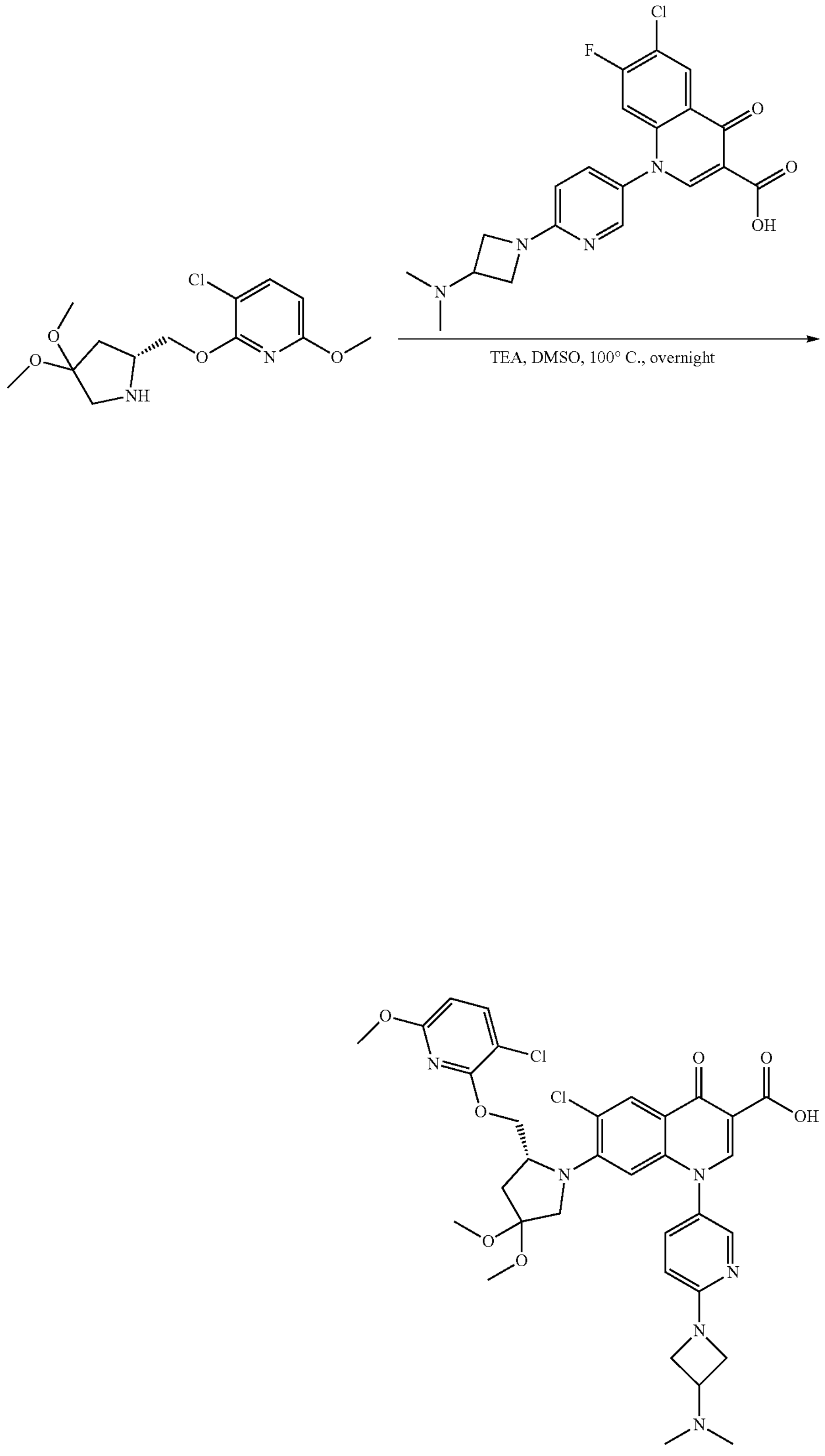

To a mixture of 3-chloro-2-[[(2R)-4,4-dimethoxypyrrolidin-2-yl]methoxy]-6-methoxypyridine (120.0 mg, 0.39 mmol, 1.0 equiv) in DMSO (2 mL) was added TEA (120.3 mg, 1.18 mmol, 3.0 equiv) and 6-chloro-1-[6-[3-(dimethylamino)azetidin-1-yl]pyridin-3-yl]-7-fluoro-4-oxoquinoline-3-carboxylic acid (165.2 mg, 0.39 mmol, 1.0 equiv). The resulting mixture was stirred for additional 1 h at 100° C. The resulting mixture was concentrated under vacuum. The residue was purified by reaverse phase flash column with 5-60% acetonitrile in water. This resulted in 6-chloro-7-[(2R)-2-[[(3-chloro-6-methoxypyridin-2-yl)oxy]methyl]-4,4-dimethoxypyrrolidin-1-yl]-1-[6-[3-(dimethylamino)azetidin-1-yl]pyridin-3-yl]-4-oxoquinoline-3-carboxylic acid (130 mg, 46.8%) of as a yellow solid. LCMS (ESI) [M+H]+: 699.2.

Step 6: Synthesis of 6-chloro-7-[(2R)-2-[[(3-chloro-6-methoxypyridin-2-yl)oxy]methyl]-4-oxopyrrolidin-1-yl]-1-[6-[3-(dimethylamino)azetidin-1-yl]pyridin-3-yl]-4-oxoquinoline-3-carboxylic acid

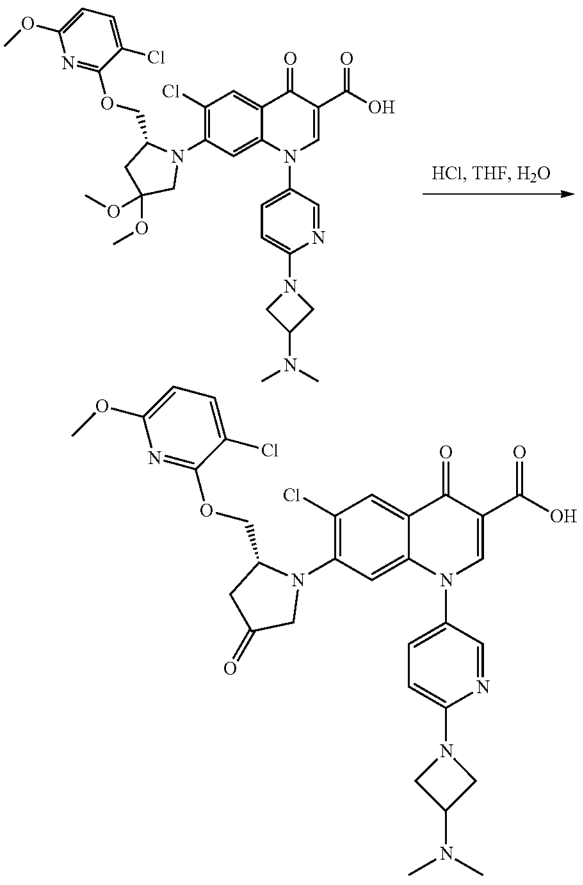

To a mixture of 6-chloro-7-[(2R)-2-[[(3-chloro-6-methoxypyridin-2-yl)oxy]methyl]-4,4-dimethoxypyrrolidin-1-yl]-1-[6-[3-(dimethylamino)azetidin-1-yl]pyridin-3-yl]-4-oxoquinoline-3-carboxylic acid (120.0 mg, 0.17 mmol, 1.0 equiv) in THF (5 mL) was added $H_2O$ (2 mL) and HCl (5 mL). The resulting solution was stirred for 1 h at 25° C. The resulting mixture was concentrated under vacuum. The residue was purified by reaverse phase flash column with 5-60% acetonitrile in water. This resulted in 6-chloro-7-[(2R)-2-[[(3-chloro-6-methoxypyridin-2-yl)oxy]methyl]-4-oxopyrrolidin-1-yl]-1-[6-[3-(dimethylamino)azetidin-1-yl]pyridin-3-yl]-4-oxoquinoline-3-carboxylic acid (38 mg, 33.90%) of as a yellow solid. LCMS (ESI) [M+H]+: 653.1.

Step 7: Synthesis of 6-chloro-7-[(2R,4Z)-2-[[(3-chloro-6-methoxypyridin-2-yl)oxy]methyl]-4-(methoxyimino)pyrrolidin-1-yl]-1-[6-[3-(dimethylamino)azetidin-1-yl]pyridin-3-yl]-4-oxoquinoline-3-carboxylic acid

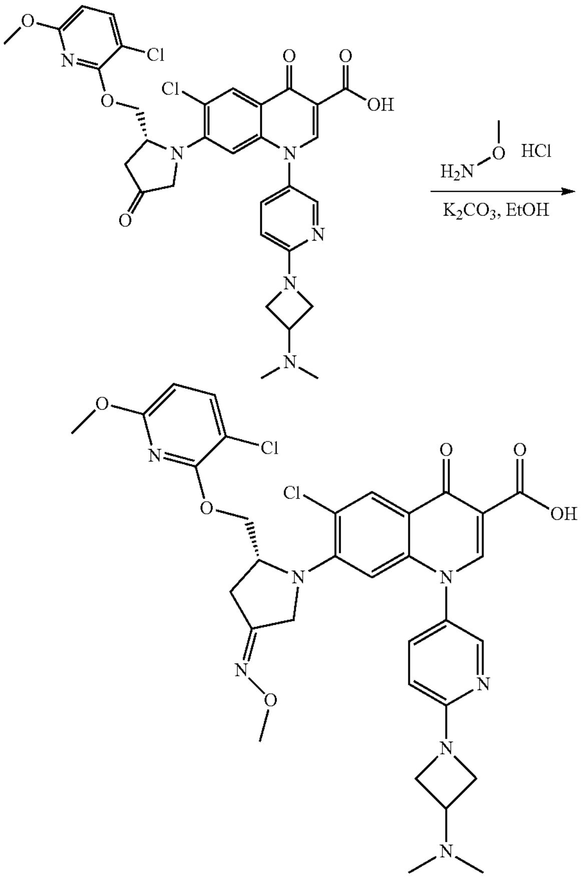

To a mixture of 6-chloro-7-[(2R)-2-[[(3-chloro-6-methoxypyridin-2-yl)oxy]methyl]-4-oxopyrrolidin-1-yl]-1-[6-[3-(dimethylamino)azetidin-1-yl]pyridin-3-yl]-4-oxoquinoline-3-carboxylic acid (38.0 mg, 0.05 mmol, 1.0 equiv) in EtOH (2 mL) was added $K_2CO_3$ (16.0 mg, 0.11 mmol, 2.0 equiv) and O— methylhydroxylamine hydrochloride (19.4 mg, 0.23 mmol, 4.0 equiv). The resulting mixture was stirred for 1 h at room temperature. The resulting mixture was concentrated. This resulted in 6-chloro-7-[(2R,4Z)-2-[[(3-chloro-6-methoxypyridin-2-yl)oxy]methyl]-4-(methoxyimino)pyrrolidin-1-yl]-1-[6-[3-(dimethylamino)azetidin-1-yl]pyridin-3-yl]-4-oxoquinoline-3-carboxylic acid (3.2 mg, 8.0%) of as a white solid. LCMS (ESI) $[M+H]^+$: 682.1. $^1H$ NMR (300 MHz, DMSO-d6) δ 8.57 (m, 1H), 8.30-8.14 (m, 2H), 7.79-7.54 (m, 2H), 6.50 (m, 2H), 6.37 (m, 1H), 5.16 (m, 1H), 4.45 (m, 1H), 4.37-4.18 (m, 2H), 4.11 (m, 2H), 3.94-3.74 (m, 6H), 3.67 (s, 4H), 3.27-3.20 (m, 1H), 3.06 (s, 1H), 2.68 (s, 1H), 2.16 (s, 6H).

Potency Lin28a-dep Z11 $IC_{50}$ (μM)++++

Example 70: Synthesis of 7-[(3R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid

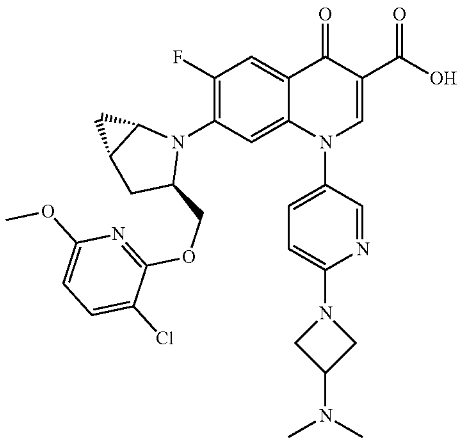 [SMILES: COc1ccc(Cl)c(OC[C@H]2C[C@@H]3C[C@@H]3N2c2cc3c(cc2F)c(=O)c(C(=O)O)cn3-c2ccc(N3CC(N(C)C)C3)nc2)n1]

Step 1: Synthesis of (5R)-5-[[(tert-butyldiphenylsilyl)oxy]methyl]pyrrolidin-2-one

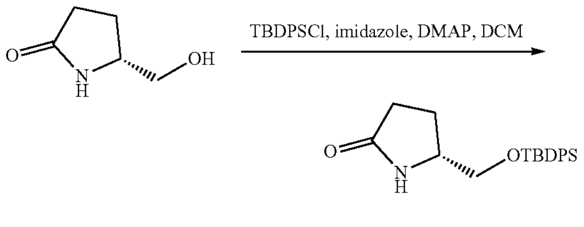

To a solution of 5-Hydroxymethylpyrrolidin-2-one (30.0 g, 260.57 mmol, 1.0 equiv) in dichloromethane (100 mL) was added imidazole (19.5 g, 286.62 mmol, 1.10 equiv), 4-dimethylaminopyridine (3.1 g, 26.05 mmol, 0.10 equiv) followed by tert-butyldiphenylsilyl chloride (157.5 g, 573.25 mmol, 2.20 equiv) at 0° C. The reaction mixture was gradually warmed to room temperature and upon completion of 2 h, diluted with dichloromethane, washed with water, brine and dried over anhydrous sodium sulfate. This resulted in (5R)-5-[[(tert-butyldiphenylsilyl)oxy]methyl]pyrrolidin-2-one (92.1 g, 99.98%) as yellow oil, LCMS (ESI) $[M+H]^+$: 354.1. $^1H$ NMR (300 MHz, Chloroform-d) δ 7.73-7.60 (m, 4H), 7.48-7.34 (m, 6H), 5.65-5.32 (m, 1H), 4.10-3.49 (m, 3H), 1.52 (m, 2H), 1.35-1.23 (m, 2H), 1.13-1.01 (m, 9H).

Step 2: Synthesis of tert-butyl (2R)-2-[[(tert-butyldiphenylsilyl)oxy]methyl]-5-oxopyrrolidine-1-carboxylate

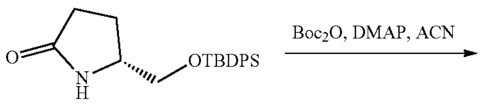

-continued

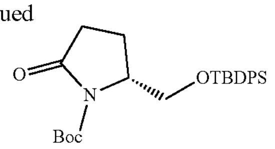

To a stirred solution of the above obtained compound (92.1 g, 260.51 mmol, 1.0 equiv) in acetonitrile (200 mL) was added 4-dimethylaminopyridine (35.0 g, 286.56 mmol, 1.1 equiv) and tert-butyldicarbonate (62.5 g, 286.56 mmol, 1.1 equiv). The resulting mixture was stirred overnight at room temperature. The reaction was quenched with water. The resulting mixture was extracted with EtOAc (3*300 mL). The combined organic layers were collected and dried with anhydrous $Na_2SO_4$. After filtration, the filtrate was concentrated under vacuum. The residue was purified by silica gel column chromatography, eluted with Petroleum ether/EtOAc (1:1). This resulted in tert-butyl (2R)-2-[[(tert-butyldiphenylsilyl)oxy]methyl]-5-oxopyrrolidine-1-carboxylate (79.8 g, 67.5%) as yellow solid. LCMS (ESI) $[M+H]^+$: 454.2. $^1H$ NMR (300 MHz, Chloroform-d) δ 7.70-7.59 (m, 4H), 7.50-7.35 (m, 6H), 4.28-4.18 (m, 1H), 3.91 (dd, J=10.4, 4.2 Hz, 1H), 3.72 (dd, J=10.4, 2.5 Hz, 1H), 2.81 (dt, J=17.6, 10.4 Hz, 1H), 2.53-2.38 (m, 1H), 2.25-2.04 (m, 2H), 1.45 (s, 9H), 1.07 (s, 9H).

Step 3: Synthesis of tert-butyl (2R)-2-[[(tert-butyldiphenylsilyl)oxy]methyl]-2,3-dihydropyrrole-1-carboxylate

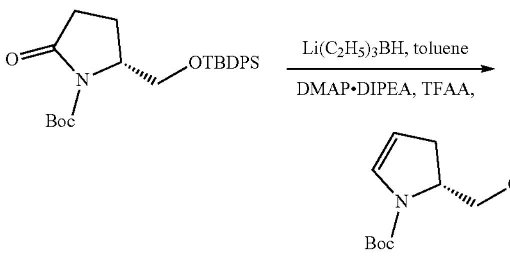

Lithium triethylborohydride (11 mL of 1.0 M/THF, 11.40 mmol, 1.0 equiv) was added dropwise to a mixture of tert-butyl (2R)-2-[[(tert-butyldiphenylsilyl)oxy]methyl]-5-oxopyrrolidine-1-carboxylate (5.0 g, 11.02 mmol, 1.0 equiv) in toluene (20 mL) at −50° C. under nitrogen atmosphere over 30 min and the mixture stirred for another 35 min while maintaining the internal temperature between −50° C. and −45° C. Hunig's base (3.7 g, 28.6 mmol, 2.0 equiv) was added dropwise over 10 min. Then, DMAP (20.0 mg, 0.14 mmol, 0.01 equiv) was added in one batch, followed by the addition of trifluoroacetic anhydride (2.6 g, 12.7 mmol, 1.1 equiv) over 15 min, while maintaining the internal temperature between −50° C. and −45° C. The cold bath was removed 10 min later, and the reaction mixture was stirred for 14 h while allowing it to rise to ambient temperature. It was diluted with toluene (20 mL), cooled with an ice-water bath, and treated slowly with water (40 mL) over 5 min. The phases were separated, and the organic layer was washed with water (100 mL, 2×) and concentrated in vacuo. The crude material was purified by flash chromatography (silica gel; 5 percent EtOAc in hexane). This resulted in tert-butyl (2R)-2-[[(tert-butyldiphenylsilyl)oxy]methyl]-2,3-dihydropyrrole-1-carboxylate (2.5 g, 52.0%) as yellow oil. LCMS (ESI) [M+H]+: 438.2. $^1$H NMR (300 MHz, DMSO-$d_6$) δ 7.60 m, 4H), 7.44 (m, 6H), 6.48 (s, 1H), 5.05 (m, 1H), 4.12 (m, 1H), 3.69 (s, 2H), 2.74 (m, 2H), 1.32 (m, 9H), 0.99 (m, 9H).

Step 4: Synthesis of tert-butyl (3R)-3-[[(tert-butyldiphenylsilyl)oxy]methyl]-2-azabicyclo[3.1.0]hexane-2-carboxylate

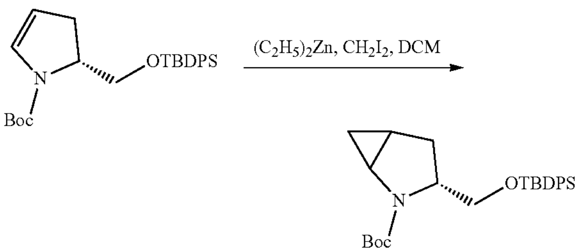

To a mixture of tert-butyl (2R)-2-[[(tert-butyldiphenylsilyl)oxy]methyl]-2,3-dihydropyrrole-1-carboxylate (2.5 g, 5.68 mmol, 1.0 equiv) in dichloromethane (20 mL) was added a solution of diethylzinc (1M in hexane, 6.2 mL, 1.4 equiv) followed by diiodomethane (0.68 mL, 8.55 mmol, 1.5 equiv) over a period of 15 minutes and stirred for 30 minutes. The reaction mixture was gradually warmed to room temperature and stirred for 3 hours. The pH of the reaction mixture was adjusted to 8 by addition of saturated sodium bicarbonate solution. The reaction was quenched with water. The resulting mixture was extracted with EtOAc (3*200 mL). The combined organic layers were collected and dried with anhydrous $Na_2SO_4$. The resulting mixture was concentrated under vacuum. The residue was purified by silica gel column chromatography, eluted with Petroleum ether/EtOAc (1:1). This resulted in (1.7 g, 65.8%) of tert-butyl (3R)-3-[[(tert-butyldiphenylsilyl)oxy]methyl]-2-azabicyclo[3.1.0]hexane-2-carboxylate as yellow oil. LCMS (ESI) [M+H]+: 452.2. $^1$H NMR (400 MHz, Chloroform-d) δ 7.69-7.62 (m, 4H), 7.39 (m, 6H), 3.92-3.61 (m, 3H), 3.18 (s, 1H), 2.33 (s, 1H), 2.04 (m, 1H), 1.51 (m, 1H), 1.48-1.22 (m, 9H), 1.05 (s, 9H), 0.87 (m, 1H), 0.34 (s, 1H).

Step 5: Synthesis of tert-butyl (3R)-3-(hydroxymethyl)-2-azabicyclo[3.1.0]hexane-2-carboxylate

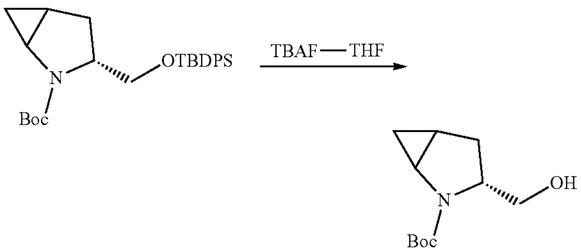

To a mixture of tert-butyl (3R)-3-(((tert-butyldiphenylsilyl)oxy)methyl)-2-azabicyclo[3.1.0]hexane-2-carboxylate (1.5 g, 3.32 mmol, 1.00 equiv) in dry tetrahydrofuran (20 mL) was added tetrabutylammonium fluoride (1M, in tetrahydrofuran 3.3 mL, 1.00 equiv) over a period of 10 minutes. The reaction mixture was gradually warmed to room temperature and stirred for 30 min. The reaction was quenched with water. The resulting mixture was extracted with EtOAc (3*50 mL). The combined organic layers were collected and dried with anhydrous $Na_2SO_4$. The resulting mixture was concentrated under vacuum. The residue was purified by silica gel column chromatography, eluted with Petroleum ether/EtOAc (1:1). This resulted in tert-butyl (3R)-3-(hydroxymethyl)-2-azabicyclo[3.1.0]hexane-2-carboxylate (618 mg, 90.50%) as yellow oil. LCMS (ESI) [M+H]+: 214.1. $^1$H NMR (300 MHz, DMSO-$d_6$) δ 4.86-4.60 (m, 1H), 3.71-3.53 (m, 1H), 3.52-3.42 (m, 1H), 3.30-3.18 (m, 1H), 3.06 (s, 1H), 2.08 (s, 1H), 2.00-1.78 (m, 1H), 1.55-1.46 (m, 1H), 1.40 (d, J=2.1 Hz, 9H), 0.84-0.68 (m, 1H), 0.37-0.07 (m, 1H).

Step 6: Synthesis of tert-butyl (3R)-3-(((3-chloro-6-methoxypyridin-2-yl)oxy)methyl)-2-azabicyclo[3.1.0]hexane-2-carboxylate

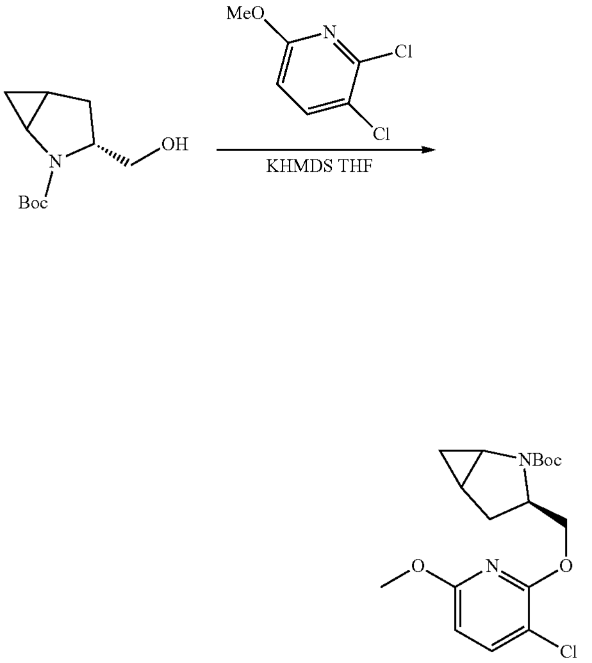

To a mixture of tert-butyl (3R)-3-(hydroxymethyl)-2-azabicyclo[3.1.0]hexane-2-carboxylate (500.0 mg, 2.34 mmol, 1.0 equiv) in THF (5 mL) was added 2,3-dichloro-6-methoxypyridine (623.2 mg, 3.52 mmol, 1.5 equiv). The resulting solution was stirred for 1 h at 0° C. The reaction was quenched with water. The resulting mixture was extracted with EtOAc (3*10 mL). The combined organic layers were collected and dried with anhydrous $Na_2SO_4$. The resulting mixture was concentrated under vacuum. The residue was purified by silica gel column chromatography, eluted with Petroleum ether/EtOAc (1:1). This resulted in tert-butyl (3R)-3-(((3-chloro-6-methoxypyridin-2-yl)oxy)methyl)-2-azabicyclo[3.1.0]hexane-2-carboxylate (432.2 mg, 51.7%) as yellow oil. LCMS (ESI) [M+H]+: 355.1. $^1$H NMR (300 MHz, DMSO-$d_6$) δ 6.97 m, 1H), 6.17 (m, 1H), 4.36-4.26 (m, 2H), 4.11-3.94 (m, 2H), 3.72 (s, 3H), 3.17-3.04 (m, 1H), 2.21-1.99 (m, 2H), 1.49-1.26 (m, 9H), 0.90-0.75 (m, 1H), 0.42-0.24 (m, 1H).

Step 7: Synthesis of (3R)-3-{[(3-chloro-6-methoxy-pyridin-2-yl)oxy]methyl}-2-azabicyclo[3.1.0]hexane

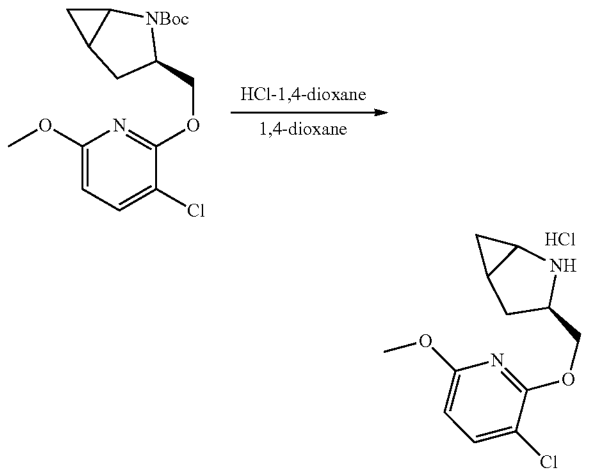

To a mixture of tert-butyl (3R)-3-{[(3-chloro-6-methoxy-pyridin-2-yl)oxy]methyl}-2-azabicyclo[3.1.0]hexane-2-carboxylate (200 mg, 0.56 mmol, 1.0 equiv) in 1,4-dioxane (3 mL) was added 4 M HCl in 1,4-dioxane (1 mL) at 0° C. and the mixture was stirred for 2 h at room temperature. The reaction was quenched with water. The resulting mixture was extracted with EtOAc (3*10 mL). The combined organic layers were collected and dried with anhydrous $Na_2SO_4$. The resulting mixture was concentrated under vacuum. The residue was purified by silica gel column chromatography, eluted with Petroleum ether/EtOAc (1:1). This resulted in (3R)-3-{[(3-chloro-6-methoxypyridin-2-yl)oxy]methyl}-2-azabicyclo [3.1.0]hexane (121.6 mg, 84.5%) as an white solid. LCMS (ESI) $[M+H]^+$: 255.1.

Step 8: Synthesis of 7-[(3R)-3-{[(3-chloro-6-methoxypyridin-2-yl)oxy]methyl}-2-azabicyclo [3.1.0]hexan-2-yl]-1-{6-[3-(dimethylamino)azetidin-1-yl]pyridin-3-yl}-6-fluoro-4-oxo-1,4-dihydroquinoline-3-carboxylic acid

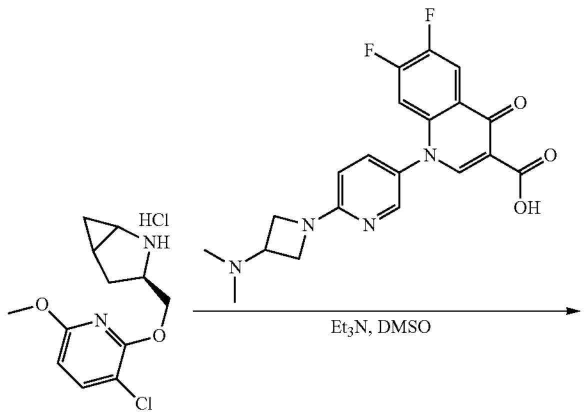

-continued

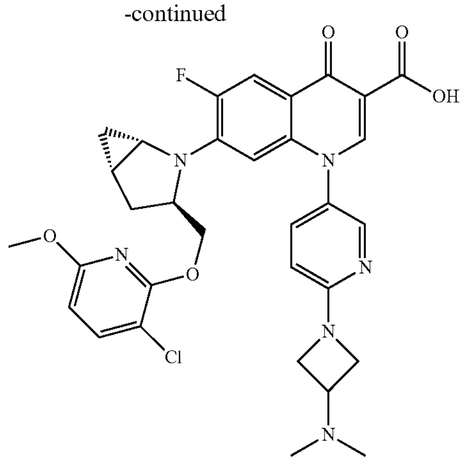

To a stirred mixture of (3R)-3-{[(3-chloro-6-methoxy-pyridin-2-yl)oxy]methyl}-2-azabicyclo[3.1.0]hexane (100 mg, 0.39 mmol, 1.0 equiv) in DMSO (2 mL) was added triethylamine (118.8 mg, 1.17 mmol, 3.0 equiv) and 1-{6-[3-(dimethylamino)azetidin-1-yl]pyridin-3-yl}-6,7-difluoro-4-oxo-1,4-dihydroquinoline-3-carboxylic acid (172 mg, 0.43 mmol, 1.1 equiv) and stirred at 100° C. for 16 h. The precipitated solids were collected and crude product was purified by Prep-HPLC with the following conditions (Column: XBridge Shield RP18 OBD Column, 5 um, 19*150 mm; Mobile Phase A:Water(10 MMOL/L $NH_4HCO_3$), Mobile Phase B:ACN; Flow rate:25 mL/min; Gradient:25 B to 48 B in 7 min; 254/220 nm; RT1:5.90; RT2; Injection Volumn: ml; Number Of Runs;). This resulted in 7-[(3R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid (9.3 mg, 3.7%) as a yellow solid. LCMS (ESI) $[M+H]^+$: 635.2 $^1H$ NMR (300 MHz, DMSO-$d_6$) δ 8.68-7.92 (m, 2H), 8.56-7.52 (m, 3H), 6.85-6.25 (m, 3H), 4.65-4.23 (m, 3H), 4.15-3.87 (m, 2H), 3.79-3.65 (m, 5H), 3.30-3.11 (m, 2H), 2.31-1.92 (m, 8H), 1.82-1.62 (m, 1H), 0.62-0.95 (m, 1H), 0.36-0.28 (m, 1H).

Potency Lin28a-dep Z11 $IC_{50}$ (μM)++++

Example 71: Synthesis of 7-[(2R)-2-[[(3-chloro-6-methoxypyridin-2-yl)oxy]methyl]-4-(1H-pyrazol-4-yl)pyrrolidin-1-yl]-1-[6-[3-(dimethylamino)azetidin-1-yl]pyridin-3-yl]-6-fluoro-4-oxoquinoline-3-carboxylic acid

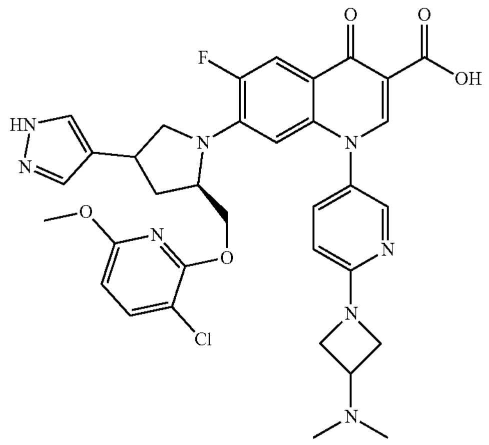 [SMILES: COc1ccc(Cl)c(OC[C@H]2CC(c3cn[nH]c3)CN2c2cc3c(cc2F)c(=O)c(C(=O)O)cn3-c2ccc(N3CC(N(C)C)C3)nc2)n1]

Step 1: Synthesis of 1-tert-butyl 2-methyl (2R)-4-[1-(oxan-2-yl)pyrazol-4-yl]-2,3-dihydropyrrole-1,2-dicarboxylate

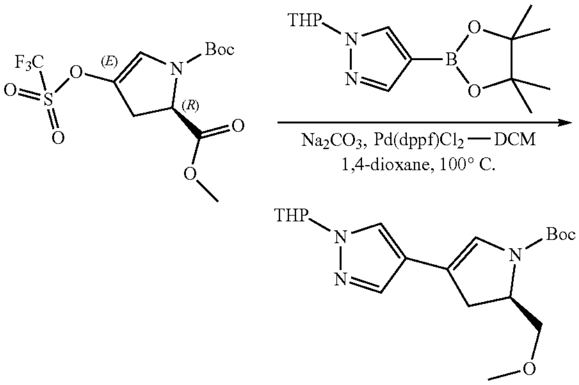

A mixture of 1-tert-butyl 2-methyl (2R)-4-(trifluoromethanesulfonyloxy)-2,3-dihydropyrrole-1,2-dicarboxylate (3 g, 7.993 mmol, 1.00 equiv) and 1-(oxan-2-yl)-4-(4,4,5,5-tetramethyl-1,3,2-dioxaborolan-2-yl)pyrazole (2.22 g, 7.993 mmol, 1 equiv), $Na_2CO_3$ (2.54 g, 23.979 mmol, 3 equiv), $Pd(dppf)Cl_2$ $CH_2Cl_2$ (651 mg, 0.8 mmol, 0.1 equiv) in 1,4-dioxane was stirred for 1 h at 100 degrees C. under nitrogen atmosphere. The resulting mixture was filtered, the filter cake was washed with ethanol (3×10 mL). The filtrate was concentrated under reduced pressure. The residue was purified by silica gel column chromatography, eluted with PE/EA (5:1) to afford 1-tert-butyl 2-methyl (2R)-4-[1-(oxan-2-yl)pyrazol-4-yl]-2,3-dihydropyrrole-1,2-dicarboxylate (3 g, 99.44%) as a yellow solid. LCMS (ESI) $[M+H]^+$: 378.

Step 2: Synthesis of 1-tert-butyl 2-methyl (2R)-4-[1-(oxan-2-yl)pyrazol-4-yl]pyrrolidine-1,2-dicarboxylate

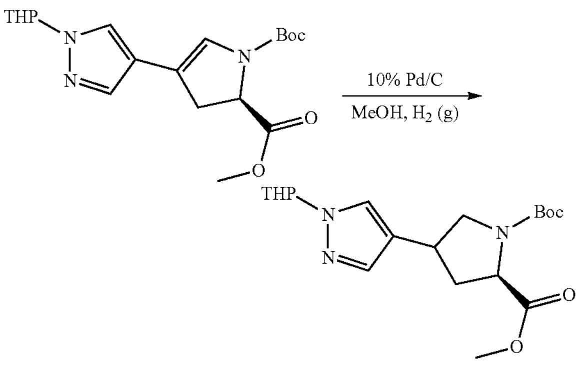

A solution of 1-tert-butyl 2-methyl (2R)-4-[1-(oxan-2-yl)pyrazol-4-yl]-2,3-dihydropyrrole-1,2-dicarboxylate (3 g, 7.9 mmol, 1 equiv) in MeOH was stirred for 1 h at room temperature under hydrogen atmosphere. The resulting mixture was filtered, the filter cake was washed with MeOH (3×10 mL). The filtrate was concentrated under reduced pressure. This resulted in 1-tert-butyl 2-methyl (2R)-4-[1-(oxan-2-yl)pyrazol-4-yl]pyrrolidine-1,2-dicarboxylate (2.8 g, 92.84%) as a yellow solid. LCMS (ESI) $[M+H]^+$: 380.

Step 3: Synthesis of tert-butyl (2R)-2-(hydroxymethyl)-4-[1-(oxan-2-yl)pyrazol-4-yl]pyrrolidine-1-carboxylate

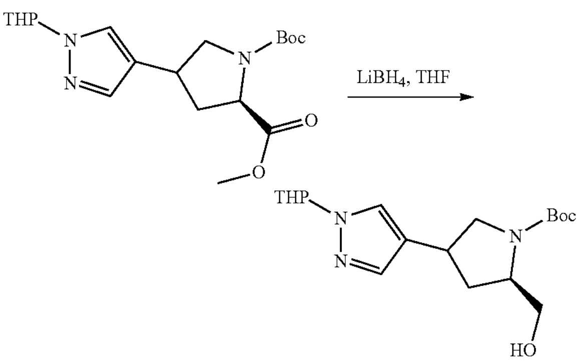

To a stirred solution of 1-tert-butyl 2-methyl (2R)-4-[1-(oxan-2-yl)pyrazol-4-yl]pyrrolidine-1,2-dicarboxylate (2.8 g, 7.3 mmol, 1 equiv) in THF was added $LiBH_4$ (241 mg, 11 mmol, 1.5 equiv) dropwise in portions at 0 degrees C. under nitrogen atmosphere. The reaction was quenched with Water at room temperature. The aqueous layer was extracted with EtOAc (3×100 mL). The resulting mixture was concentrated under reduced pressure. The residue was purified by silica gel column chromatography, eluted with PE/EA (1:1) to afford tert-butyl (2R)-2-(hydroxymethyl)-4-[1-(oxan-2-yl)pyrazol-4-yl]pyrrolidine-1-carboxylate (1.5 g, 57.84%) as a yellow solid. LCMS (ESI) $[M+H]^+$: 352.

Step 4: Synthesis of tert-butyl (2R)-2-[[(3-chloro-6-methoxypyridin-2-yl)oxy]methyl]-4-[1-(oxan-2-yl)pyrazol-4-yl]pyrrolidine-1-carboxylate

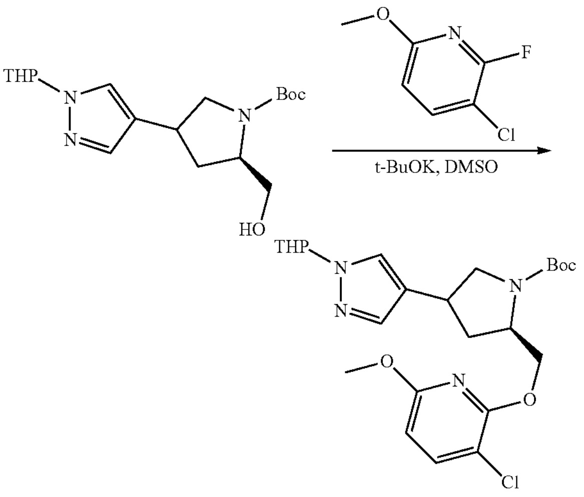

To a stirred solution of tert-butyl (2R)-2-(hydroxymethyl)-4-[1-(oxan-2-yl)pyrazol-4-yl]pyrrolidine-1-carboxylate (400 mg, 1.1 mmol, 1 equiv) and 3-chloro-2-fluoro-6-methoxypyridine (220 mg, 1.3 mmol, 1.2 equiv) in DMSO was added t-BuOK (383 mg, 3.4 mmol, 3 equiv) dropwise in portions at 80 degrees C. under nitrogen atmosphere. The residue was purified by reverse flash chromatography with the following conditions: column, silica gel; mobile phase, MeCN in water, 10% to 50% gradient in 10 min; detector, UV 254 nm. This resulted in tert-butyl (2R)-2-[[(3-chloro-6-methoxypyridin-2-yl)oxy]methyl]-4-[1-(oxan-2-yl)pyrazol-4-yl]pyrrolidine-1-carboxylate (130 mg, 23.17%) as a yellow solid. LCMS (ESI) $[M+H]^+$: 493.

Step 5: Synthesis of 3-chloro-6-methoxy-2-[[(2R)-4-(1H-pyrazol-4-yl)pyrrolidin-2-yl]methoxy]pyridine

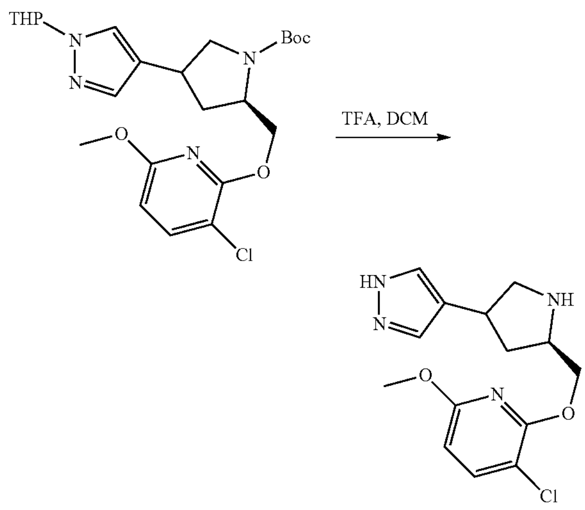

A solution of tert-butyl (2R)-2-[[(3-chloro-6-methoxypyridin-2-yl)oxy]methyl]-4-[1-(oxan-2-yl)pyrazol-4-yl]pyrrolidine-1-carboxylate (60 mg, 0.1 mmol, 1 equiv) and TFA (1 mL) in DCM was stirred for 1 h at room temperature under nitrogen atmosphere. The resulting mixture was concentrated under vacuum. This resulted in 3-chloro-6-methoxy-2-[[(2R)-4-(1H-pyrazol-4-yl)pyrrolidin-2-yl]methoxy]pyridine (30 mg, 79.83%) as a yellow solid. LCMS (ESI) $[M+H]^+$: 393.

Step 6: Synthesis of 7-[(2R)-2-[[(3-chloro-6-methoxypyridin-2-yl)oxy]methyl]-4-(1H-pyrazol-4-yl)pyrrolidin-1-yl]-1-[6-[3-(dimethylamino)azetidin-1-yl]pyridin-3-yl]-6-fluoro-4-oxoquinoline-3-carboxylic acid

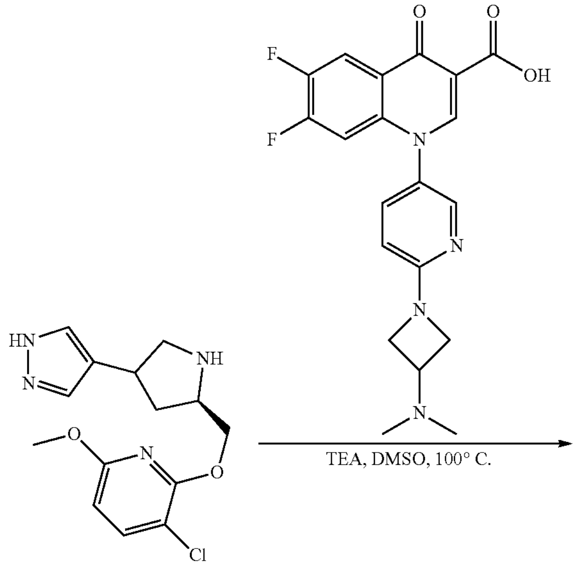

-continued

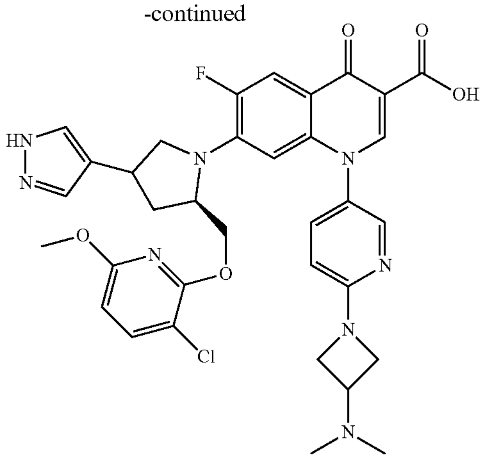

A solution of 3-chloro-6-methoxy-2-[[(2R)-4-(1H-pyrazol-4-yl)pyrrolidin-2-yl]methoxy]pyridine (55.53 mg, 0.180 mmol, 1.2 equiv) and 1-[6-[3-(dimethylamino)azetidin-1-yl]pyridin-3-yl]-6,7-difluoro-4-oxoquinoline-3-carboxylic acid (60 mg, 0.15 mmol, 1 equiv), TEA (45 mg, 0.45 mmol, 3 equiv) in DMSO was stirred for 1 h at 100 degrees C. under nitrogen atmosphere. The crude product (mg) was purified by Prep-HPLC with the following conditions (Column: Gemini-NX C18 AXAI Packed, 21.2*150 mm 5 um; Mobile Phase A: Water(0.1% FA), Mobile Phase B: ACN; Flow rate: 25 m/min; Gradient: 24% B to 44% B in 12 min, 44% B; Wave Length: 220 nm; RT1(min): 11.68; Number Of Runs: 0) to afford 7-[(2R)-2-[[(3-chloro-6-methoxypyridin-2-yl)oxy]methyl]-4-(1H-pyrazol-4-yl)pyrrolidin-1-yl]-1-[6-[3-(dimethylamino)azetidin-1-yl]pyridin-3-yl]-6-fluoro-4-oxoquinoline-3-carboxylic acid (31.2 mg, 30.21%) as a yellow solid. $^1H$ NMR (300 MHz, DMSO-$d_6$) δ 12.53 (s, 1H) 8.58-8.35 (m, 1H), 8.34-8.07 (m, 1H), 7.76-7.29 (m, 5H), 6.67-6.28 (m, 2H), 6.17-5.99 (m, 1H), 4.66-4.26 (m, 3H), 4.08-3.94 (m, 2H), 3.90-3.75 (m, 2H), 3.66-3.47 (m, 5H), 3.28-3.10 (m, 2H), 2.72-2.54 (m, 1H), 2.13 (s, 7H). MS (ESI): m/z 689.25 $[M+H]^+$ Potency Lin28a-dep Z11 $IC_{50}$ (μM)++++

Example 72: Synthesis of 7-[(3R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid

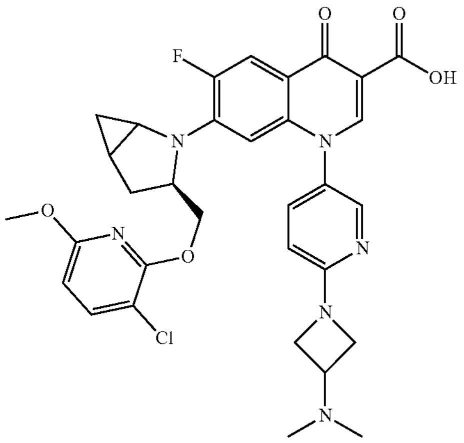 [SMILES: COc1ccc(Cl)c(OC[C@H]2CC3CC3N2c2cc3c(cc2F)c(=O)c(C(=O)O)cn3-c2ccc(N3CC(N(C)C)C3)nc2)n1]

Step 1: Synthesis of 1-tert-butyl 2-ethyl (2R)-2,3-dihydro-1H-pyrrole-1,2-dicarboxylate

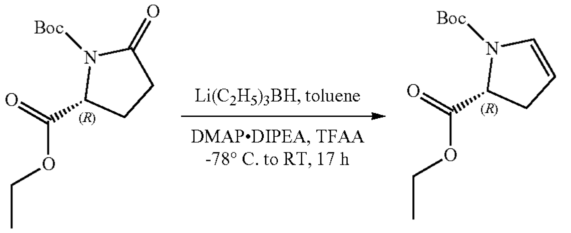

To a stirred solution of 1-tert-butyl 2-ethyl (2R)-5-oxopyrrolidine-1,2-dicarboxylate (6 g, 23.3 mmol) in toluene (10 mL) was added tri ethyl lithium borane (1 M in THF) (25.6 mL, 25.6 mmol) at −78° C. and the mixture was stirred at room temperature for 1 h. Then, the mixture was re-cooled to −78° C., were added 4-dimethylaminopyridine (56.9 mg, 466 µmol), N,N-diisopropylethylamine (25.5 mL, 139 mmol) followed by trifluoroacetic anhydride (3.92 mL, 27.9 mmol) and the mixture was allowed to room temperature and stirred for 16 h. After completion of reaction, reaction mixture was quenched with water (50 mL) (Slowly added at 0° C.), and extracted with ethyl acetate (2×100 mL). The combined organic layers were dried over Na2SO4, filtered and concentrated to get crude compound. The crude product was purified by 100-200 mesh silica gel column chromatography using 5% EtOAc/Hexanes as an eluent to afford 1-tert-butyl 2-ethyl (2R)-2,3-dihydro-1H-pyrrole-1,2-dicarboxylate (4.05 g, 72%) as color less liquid.

$^1$H NMR (400 MHz, $CDCl_3$) δ 6.66-6.51 (m, 1H), 4.96-4.90 (m, 1H), 4.70-4.54 (m, 1H), 4.28-4.15 (m, 2H), 3.12-3.00 (m, 1H), 2.69-2.60 (m, 1H), 1.48-1.44 (m, 9H), 1.31-1.24 (m, 3H).

Step 2: Synthesis of 2-tert-butyl 3-ethyl (3R)-2-azabicyclo[3.1.0]hexane-2,3-dicarboxylate

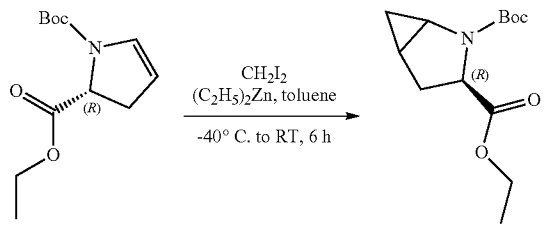

A stirred mixture of diiodomethane (8.86 g, 33.1 mmol) in Toluene (30 mL) was cooled to −40° C., diethylzinc (1 M in hexane) (18.2 mL, 18.2 mmol) was added slowly and stirred for 60 min. Then added 1-tert-butyl 2-ethyl (2R)-2,3-dihydro-1H-pyrrole-1,2-dicarboxylate (2 g, 8.28 mmol) and the mixture was allowed to room temperature for 6 h. The reaction mass was quenched with saturated ammonium bicarbonate (20 mL), filtered through celite pad and filtrate extracted with ethyl acetate (2×35 mL) The combined organic layer was washed with brine (30 mL) dried over sodium sulphate, concentrated under reduced pressure to get crude. The crude product was purified by 100-200 mesh silica gel column chromatography using 7% EtOAc/Hexanes as an eluent to afford 2-tert-butyl 3-ethyl (3R)-2-azabicyclo[3.1.0]hexane-2,3-dicarboxylate (510 mg, 24%) as yellow liquid (mixture of isomers).

1H NMR (400 MHz, CDCl3) δ 4.61-4.51 (m, 1H), 4.25-4.09 (m, 2H), 3.56-3.52 (m, 1H), 2.65-2.58 (m, 1H), 2.04-2.00 (m, 1H), 1.46-1.40 (m, 10H), 1.31-1.24 (m, 3H) 0.92-0.88 (m, 1H), 0.75-0.73 (m, 1H).

Step 3: Synthesis of tert-butyl (3R)-3-(hydroxymethyl)-2-azabicyclo[3.1.0]hexane-2-carboxylate

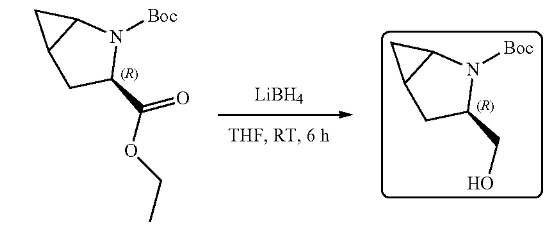

To a stirred solution of 2-tert-butyl 3-ethyl (3R)-2-azabicyclo[3.1.0]hexane-2,3-dicarboxylate (550 mg, 2.15 mmol) in THF (10 mL), was added lithium borohydride (1 M in THF) (3.22 mL, 3.22 mmol) at 0° C. The reaction was maintained at room temperature for 6 h. After completion of reaction, reaction mixture was quenched with saturated ammonium chloride (10 mL) (slowly added at 0° C.) and extracted with ethyl acetate (2×40 mL). The combined organic layers were dried over Na2SO4, filtered and concentrated to afford tert-butyl (3R)-3-(hydroxymethyl)-2-azabicyclo[3.1.0]hexane-2-carboxylate (410 mg) as a yellow liquid which is sufficiently pure to take for next step. 1H NMR (400 MHz, CDCl3) δ 4.86-4.85 (m, 1H), 4.40-4.34 (m, 1H), 3.62-3.61 (m, 1H), 3.50-3.47 (m, 2H), 2.47-2.41 (m, 1H), 1.78-1.71 (m, 1H), 1.47-1.43 (m, 10H), 0.89-0.85 (m, 1H), 0.40-0.39 (m, 1H).

Step 4: Synthesis of tert-butyl (3R)-3-{[(6-methoxy-3-nitropyridin-2-yl)oxy]methyl}-2-azabicyclo[3.1.0]hexane-2-carboxylate

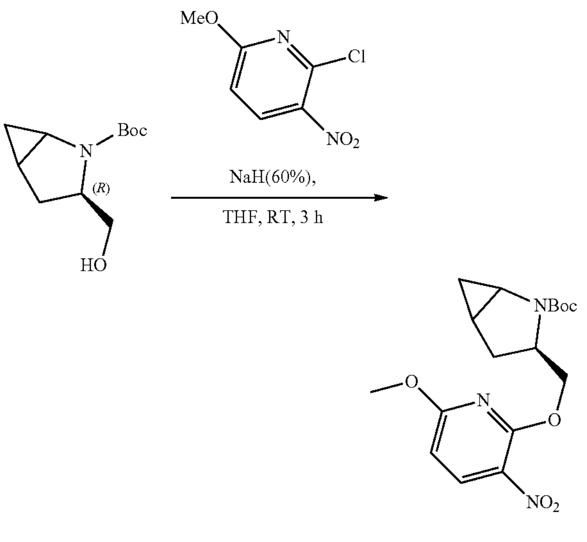

To a stirred mixture of tert-butyl (3R)-3-(hydroxymethyl)-2-azabicyclo[3.1.0]hexane-2-carboxylate (800 mg, 3.75 mmol) in THF (15 mL) was cooled to 0° C., sodium hydride (223 mg, 5.62 mmol) was added slowly and stirred for 5 min. Then, was added 2-chloro-6-methoxy-3-nitropyridine (848 mg, 4.50 mmol) and the mixture was stirred at RT for 3 h. Reaction mass was quenched with sat. ammonium chloride (5 mL) and extracted with ethyl acetate (2×40 mL). the combined organic layer was washed with brine (40 mL) dried over sodium sulphate. Concentrated under reduced pressure to get crude. The crude product was purified by 100-200 mesh silica gel column chromatography using 7% EtOAc/Hexanes as an eluent to afford tert-butyl (3R)-3-{[(6-methoxy-3-nitropyridin-2-yl)oxy]methyl}-2-azabicyclo[3.1.0]hexane-2-carboxylate (720 mg, 52%) as yellow liquid.

MS (ESI): m/z 366.0 $[M+H]^+$

Step 5: Synthesis of tert-butyl (3R)-3-{[(3-amino-6-methoxypyridin-2-yl)oxy]methyl}-2-azabicyclo[3.1.0]hexane-2-carboxylate

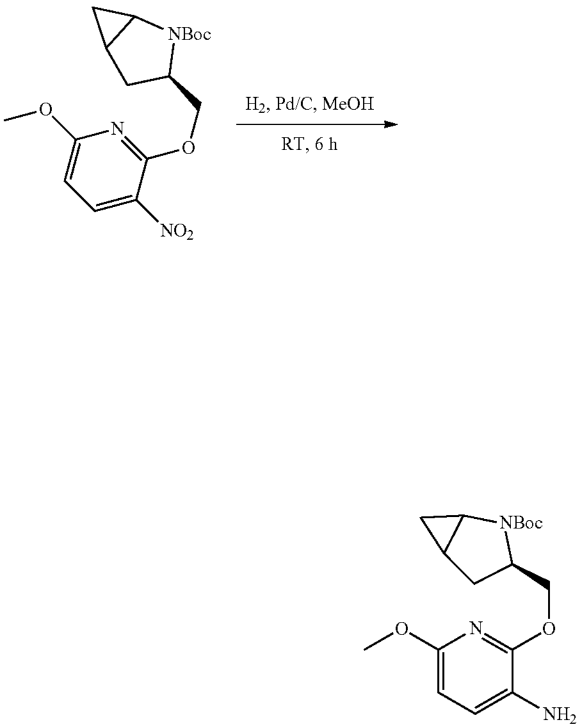

To a stirred solution of tert-butyl (3R)-3-{[(6-methoxy-3-nitropyridin-2-yl)oxy]methyl}-2-azabicyclo[3.1.0]hexane-2-carboxylate (600 mg, 1.64 mmol), was added 10% palladium on carbon (174 mg, 1.64 mmol) and the mixture was stirred under hydrogen atmosphere (balloon pressure) for 6 h. The reaction mixture was filtered through a pad of celite, the celite pad was washed several times with EtOAc:MeOH (1:1, 40 mL) and the combined filtrate was concentrated under reduced pressure to afford tert-butyl (3R)-3-{[(3-amino-6-methoxypyridin-2-yl)oxy]methyl}-2-azabicyclo[3.1.0]hexane-2-carboxylate (342 mg, 62%) as brown liquid.

MS (ESI) 336.0 m/z [M+H]+

Step 6: Synthesis of tert-butyl (3R)-3-{[(3-chloro-6-methoxypyridin-2-yl)oxy]methyl}-2-azabicyclo[3.1.0]hexane-2-carboxylate

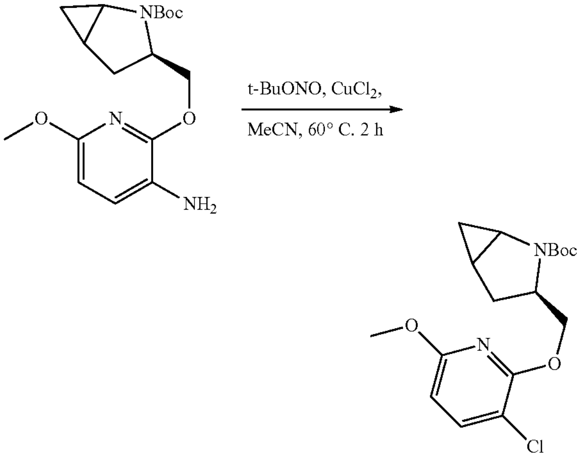

To a stirred solution of tert-butyl (3R)-3-{[(3-amino-6-methoxypyridin-2-yl)oxy]methyl}-2-azabicyclo[3.1.0]hexane-2-carboxylate (500 mg, 1.49 mmol) in ACN (5 mL), was cooled to 0-5° C., 2-methyl-2-propylnitrit (263 μL, 2.23 mmol) was added and stirred for 10 min., to this reaction mixture, copper(II) chloride (299 mg, 2.23 mmol) was added and stirred the mixture at 25-30° C. for 10 min., then, at 50-55° C. for 30 min. Lithium chloride (126 mg, 2.98 mmol) was added and continued heating for 30 min. reaction mixture was cooled to room temperature, concentrated under reduced pressure, purified using silica gel (100-200 mesh) column chromatography, eluted with 5% ethyl acetate in hexane to afford tert-butyl (3R)-3-{[(3-chloro-6-methoxypyridin-2-yl)oxy]methyl}-2-azabicyclo[3.1.0]hexane-2-carboxylate (138 mg, 26%) as pale yellow gum.

MS (ESI): m/z 355.0 [M+H]+

Step 7: Synthesis of (3R)-3-{[(3-chloro-6-methoxypyridin-2-yl)oxy]methyl}-2-azabicyclo[3.1.0]hexane

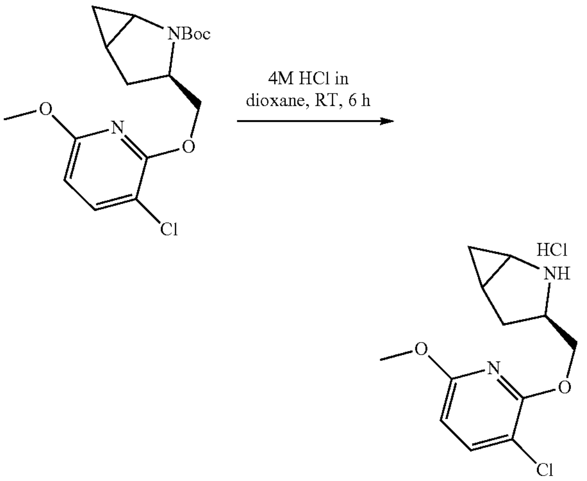

To a stirred solution of tert-butyl (3R)-3-{[(3-chloro-6-methoxypyridin-2-yl)oxy]methyl}-2-azabicyclo[3.1.0]hexane-2-carboxylate (150 mg, 422 μmol) in 1,4-dioxane (1 mL), was added 4 M HCl in 1,4-dioxane (0.5 mL) at 0° C. and the mixture was stirred for 6 h at room temperature. The volatiles were evaporated under reduced pressure, the crude compound was triturated with diethyl ether (20 mL) to afford (3R)-3-{[(3-chloro-6-methoxypyridin-2-yl)oxy]methyl}-2-azabicyclo[3.1.0]hexane (102 mg, 95%) as an off-white solid.

MS (ESI): m/z 255.0 $[M+H]^+$

Step 8: Synthesis of 7-[(3R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid

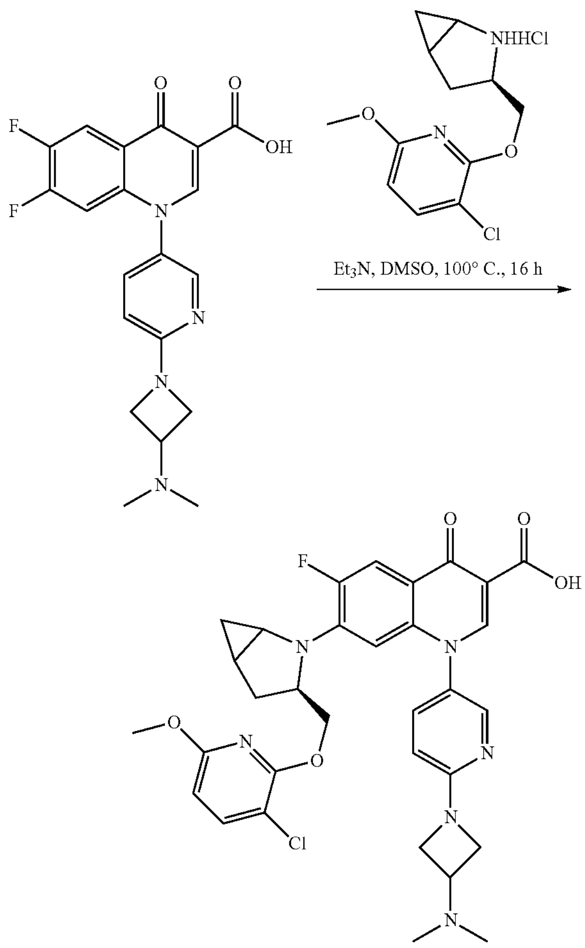

To a stirred mixture of (3R)-3-{[(3-chloro-6-methoxypyridin-2-yl)oxy]methyl}-2-azabicyclo[3.1.0]hexane (83.5 mg, 328 μmol) in DMSO (0.5 mL) was cooled to 0° C., triethylamine (195 μL, 1.36 mmol) was added slowly and stirred for 5 min. Then added 1-{6-[3-(dimethylamino)azetidin-1-yl]pyridin-3-yl}-6,7-difluoro-4-oxo-1,4-dihydroquinoline-3-carboxylic acid (110 mg, 274 μmol) and stirred at 130° C. for 16 h. The reaction mixture was quenched with ice-cold water (10 mL) and extracted with ethyl acetate (2×25 mL). the combined organic layer was washed with brine (10 mL) dried over sodium sulphate. Concentrated under reduced pressure to get crude. The crude product was triturated with diethyl ether and dried under vacuum. The obtained solid was purified by preparative RP HPLC. The relevant fractions containing product were lyophilized to afford 7-[(3R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid (34.3 mg, 20%) as pale yellow solid. 1H NMR (400 MHz, DMSO-d6) δ 15.40 (br s, 1H), 8.51 (d, J=4.8 Hz, 1H), 8.28-8.26 (m, 1H), 7.87 (d, J=13.2 Hz, 1H), 7.78-7.73 (m, 1H), 7.71-7.66 (m, 1H), 6.58-6.47 (m, 2H), 6.37-6.34 (m, 1H), 4.78-4.71 (m, 1H), 4.26-4.12 (m, 2H), 4.09-4.03 (m, 2H), 3.84-3.77 (m, 2H), 3.72 (d, J=3.2 Hz, 3H), 3.22-3.13 (m, 2H), 2.61-2.58 (m, 1H), 2.13 (s, 6H), 2.08-2.02 (m, 1H), 1.63-1.60 (m, 1H), 0.97-0.94 (m, 1H), 0.74-0.70 (m, 1H); MS (ESI): m/z 635.4 $[M+H]^+$ Potency Lin28a-dep Z11 $IC_{50}$ (μM)++++

Example 73: Synthesis of 7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydroquinoline-3-carboxylic acid

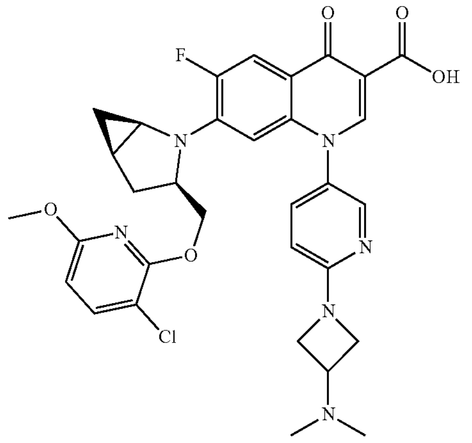 [SMILES: COc1ccc(Cl)c(OC[C@H]2C[C@H]3C[C@H]3N2c2cc3c(cc2F)c(=O)c(C(=O)O)cn3-c2ccc(N3CC(N(C)C)C3)nc2)n1]

Step 1: Synthesis of 3-chloro-6-methoxypyridin-2-amine

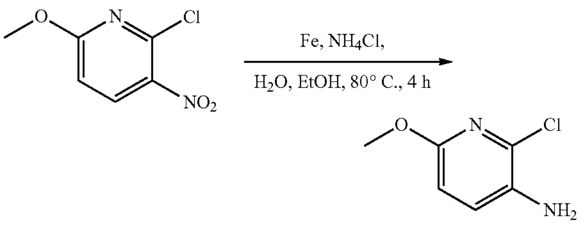

To a stirred solution of 2-chloro-6-methoxy-3-nitropyridine (15 g, 79.5 mmol) in$H_2O$ (75 mL) and EtOH (75 mL) was added ammonium chloride (21.2 g, 397 mmol) and cooled to 0° C. Then iron (22.1 g, 397 mmol) powder was added portion wise and heated to stir at 80° C. for 6 h. The reaction mixture was filtered through celite pad and the filtrate was evaporated. The crude residue was dissolved in DCM (500 mL) and washed with water (2×100 mL). The organic layer was dried over anhydrous sodium sulphate and evaporated to dryness to afford crude. The crude compound was purified by 100-200 mesh silica gel column chromatography using 5% EtOAc/Hexanes as an eluent. Collected pure fractions were evaporated to dryness to afford 2-chloro-6-methoxypyridin-3-amine (12.0 g, 95%) as a yellow solid $^1H$ NMR (400 MHz, $CDCl_3$) δ 7.08 (d, J=8.4 Hz, 1H), 6.57 (d, J=8.4 Hz, 1H), 3.88 (s, 3H), 3.88 (brs, 2H).

Step 2: Synthesis of 2,3-dichloro-6-methoxypyridine

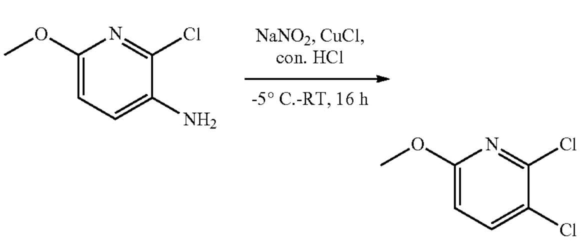

To a stirred solution of 2-chloro-6-methoxypyridin-3-amine (8 g, 50.4 mmol) in ACN (50 mL) was cooled to 0-5° C., 2-methyl-2-propylnitrit (8.95 mL, 75.6 mmol) added and stirred for 10 min. Simultaneously mixture of copper(II) chloride (10.1 g, 75.6 mmol) and lithium chloride (4.23 g, 100 mmol) in ACN(30 mL), and heated to 55-60° C. for 20 min, were added to above resulting solution and maintained same temperature further 30 min. RM was monitored by TLC. RM was concentrated under reduced pressure, purified using silica gel (100-200 mesh) column chromatography, eluted with 5% ethyl acetate in hexane. Concentrated respective fractions to afford 2,3-dichloro-6-methoxypyridine (2.80 g, 31%) as an off-white solid. 1H NMR (400 MHz, CDCl3) δ 7.59 (d, J=8.4 Hz, 1H), 6.64 (d, J=8.4 Hz, 1H), 3.93 (s, 3H).

Step 3: Synthesis of 1-(tert-butyl) 2-methyl (R)-2,3-dihydro-1H-pyrrole-1,2-dicarboxylate

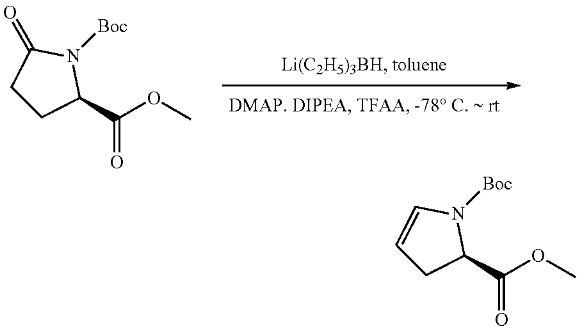

To a stirred solution of 1-tert-butyl 2-ethyl (2R)-5-oxopyrrolidine-1,2-dicarboxylate (50 g, 194 mmol) in TOLUENE (400 mL) was added lithium triethylborohydride (213 mL, 213 mmol) (1 M in THF) at −78° C. reaction was maintained room temperature for 1 h. After added 4-dimethylaminopyridine (709 mg, 5.81 mmol), N,N-diisopropylethylamine (212 mL, 1.16 mol), followed by trifluoroacetic anhydride (32.6 mL, 232 mmol) at −78° C. and slowly allowed to room temperature and stirred for 16 h. After completion of reaction, reaction mixture was quenched with water (150 mL) (Slowly added at 0° C.), and extracted with ethyl acetate (2×200 mL), combined organic layers were dried over Na2SO4, filtered and concentrated to get crude compound. The crude product was purified by 100-200 mesh silica gel Column chromatography using 5% EtOAc/Hexanes as an eluent to afford 1-tert-butyl 2-ethyl (2R)-2,3-dihydro-1H-pyrrole-1,2-dicarboxylate (27.0 g, 58%) as color less liquid. $^1$H NMR (400 MHz, DMSO-d$_6$) δ 6.65-6.51 (m, 1H), 4.95-4.90 (m, 1H), 4.66-4.54 (m, 1H), 4.28-4.15 (m, 2H), 3.12-3.00 (m, 1H), 2.69-2.60 (m, 1H), 1.48-1.44 (m, 9H), 1.31-1.24 (m, 3H).

Step 4: Synthesis of 2-(tert-butyl) 3-methyl (1R,3R,5R)-2-azabicyclo[3.1.0]hexane-2,3-dicarboxylate

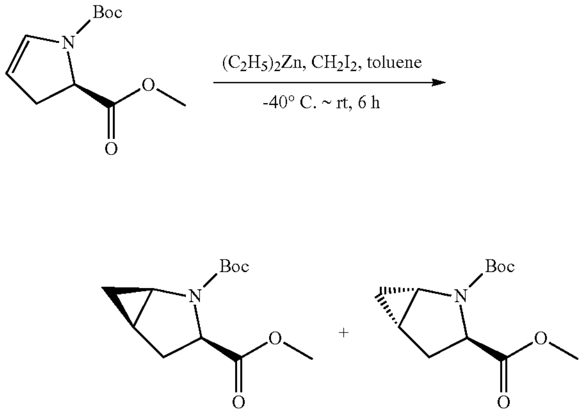

To a stirred mixture of 1-tert-butyl 2-ethyl (2R)-2,3-dihydro-1H-pyrrole-1,2-dicarboxylate (20 g, 82.8 mmol) in Toluene (300 mL) was cooled to −40° C., diethylzinc (1 M in hexane) (182 mL, 182 mmol) was added slowly and stirred for 60 min. Then added diiodomethane (26.6 mL, 331 mmol) in Toluene (100 mL) (white suspension was formed) and stirred at −40° C. to room temperature (while allowed to RT, reaction was mild exothermic in nature) for 6 hrs. Reaction was monitored by TLC. Reaction mass was quenched with sat. NaHCO$_3$ (200 mL) and filtered through the celite pad and filtrate was extracted with ethyl acetate (2×250 mL). The combined organic layer was washed with brine (100 mL), dried over sodium sulphate and concentrated under reduced pressure to get crude. The crude product was purified by 230-400 mesh silica gel Column chromatography using 2-3% EtOAc/Hexanes as an eluent to afford 2-tertbutyl 3-ethyl (1R,3R,5R)-2-azabicyclo[3.1.0]hexane-2,3-dicarboxylate (6.30 g, 24.6 mmol, top spot) and 2-tert-butyl 3-ethyl (1S,3R,5S)-2-azabicyclo[3.1.0]hexane2,3-dicarboxylate (3.00 g, 11.7 mmol, bottom spot) as yellow liquids. $^1$H NMR for major isomer: (400 MHz, VT at 90° C., DMSO-d$_6$) δ 4.45 (dd, J=3.2, 11.6 Hz, 1H), 4.10 (q, J=6.8 Hz, 2H), 3.42-3.37 (m, 1H), 2.56-2.46 (m, 1H), 1.92-1.86 (m, 1H), 1.58-1.50 (m, 1H), 1.37 (s, 9H), 1.18 (t, J=6.8 Hz, 3H), 0.75-0.70 (m, 1H), 0.69-0.62 (m, 1H).

Step 5: Synthesis of tert-butyl (1R,3R,5R)-3-(hydroxymethyl)-2-azabicyclo[3.1.0]hexane-2-carboxylate

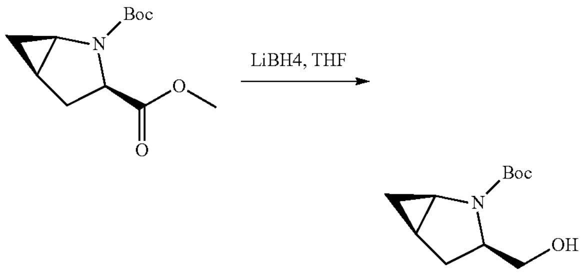

To a stirred solution of 2-tert-butyl 3-ethyl (1R,3R,5R)-2-azabicyclo[3.1.0]hexane-2,3dicarboxylate (3.3 g, 12.9 mmol) in THF (25 mL) was added lithium borohydride (9.65 mL, 19.3 mmol) (2 m in THF) at 0° C. reaction was maintained room temperature for 6 h. after completion of reaction, reaction mixture was quenched with saturated ammonium chloride (20 mL) (Slowly added at 0° C.), and extracted with ethyl acetate (2×50 mL), combined organic layers were dried over Na2SO4, filtered and concentrated to afford crude tert-butyl (1R,3R,5R) 3-(hydroxymethyl)-2-azabicyclo[3.1.0]hexane-2-carboxylate (2.70 g)) as a yellow liquid. $^1$H NMR (400 MHz, $CDCl_3$-d) δ 4.87-4.85 (m, 1H), 4.36-4.32 (m, 1H), 3.53-3.42 (m, 4H), 2.49-2.42 (m, 1H), 1.50-1.49 (m, 10H), 0.82-0.77 (m, 1H), 0.41-0.40 (m, 1H)

Step 6: Synthesis of tert-butyl (1R,3R,5R)-3-(((3-chloro-6-methoxypyridin-2-yl)oxy)methyl)-2-azabicyclo[3.1.0]hexane-2-carboxylate

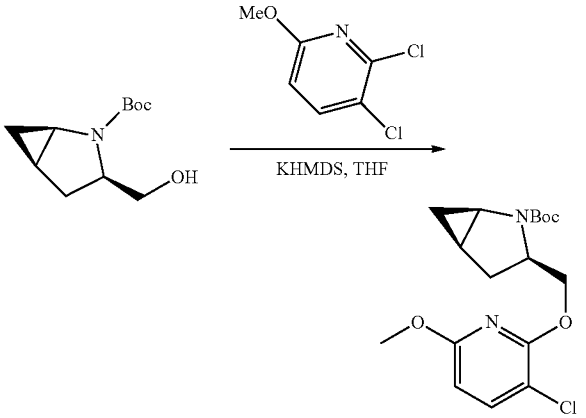

To a stirred solution of tert-butyl (1R,3R,5R)-3-(hydroxymethyl)-2-azabicyclo[3.1.0]hexane-2-carboxylate (8 g, 37.5 mmol) in THF (80 mL) were added 2,3-dichloro-6-methoxypyridine (8.01 g, 45.0 mmol) and potassium bis (trimethylsilyl)azanide (75.0 mL, 75.0 mmol) at 0° C. Reaction was allowed to room temperature for 1 h. Reaction was monitored by TLC. Reaction mass was quenched with water (50 mL) and extracted with ethyl acetate (2×70 mL), Organic layer washed with brine (50 mL) dried over sodium sulfate. Concentrated under reduced pressure to get crude. The crude product was purified by 100-200 mesh silica gel Column chromatography using 7% EtOAc/Hexanes as an eluent to afford tert-butyl (1R,3R,5R)-3-{[(3-chloro-6-methoxypyridin-2-yl)oxy]methyl}-2-azabicyclo[3.1.0]hexane-2-carboxylate (6.40 g, 48%) as yellow liquid. MS (ESI): m/z 355.0 $[M+H]^+$ Step 7: Synthesis of (1R,3R,5R)-3-(((3-chloro-6-methoxypyridin-2-yl)oxy)methyl)-2-azabicyclo[3.1.0]hexane hydrochloride

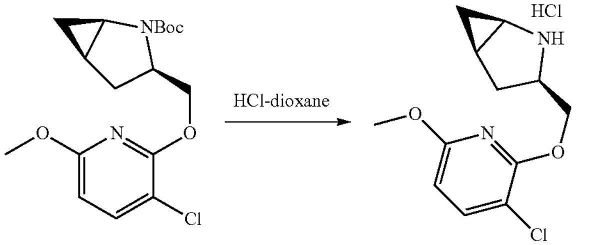 [SMILES: Cl ; COc1ccc(Cl)c(OC[C@H]2C[C@H]3C[C@H]3N2C(=O)OC(C)(C)C)n1 ; COc1ccc(Cl)c(OC[C@H]2C[C@H]3C[C@H]3N2)n1]

To a stirred solution of tert-butyl (1R,3R,5R)-3-{[(3-chloro-6-methoxypyridin-2-yl)oxy]methyl}-2-azabicyclo[3.1.0]hexane-2-carboxylate (10 g, 28.1 mmol) in 1,4-dioxane (30 mL), was added 4 M HCl in 1,4-dioxa (40 mL) at 0° C. and the mixture was stirred for 6 h at room temperature. The volatiles were evaporated under reduced pressure, the crude compound was triturated with diethyl ether (100 mL) to afford (1R,3R,5R)-3-{[(3-chloro-6-methoxypyridin-2-yl)oxy]methyl}-2-azabicyclo[3.1.0]hexane hydrochloride (7.51 g, 92%) as an off-white solid. MS (ESI): m/z 255.0 $[M+H]^+$ (for free base).

Step 8: Synthesis of 7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydroquinoline-3-carboxylic acid

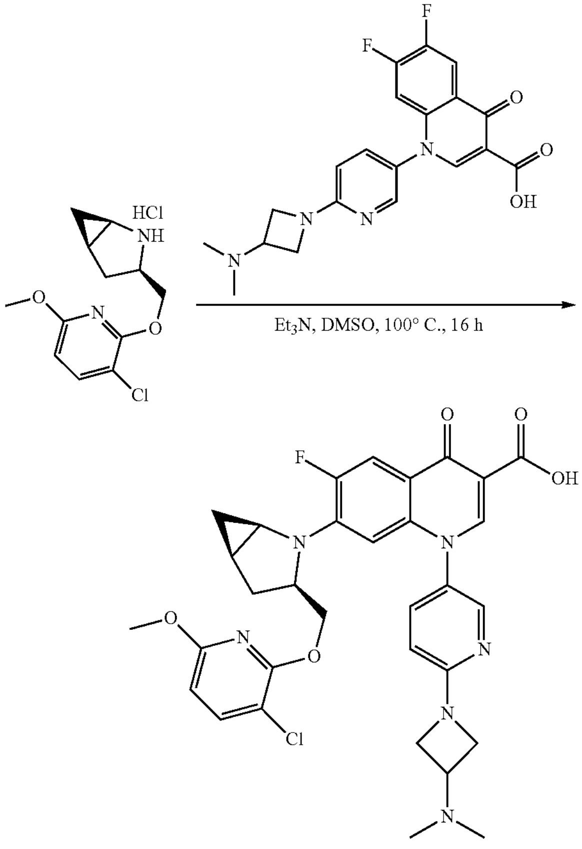

To a stirred mixture of (1R,3R,5R)-3-{[(3-chloro-6-methoxypyridin-2-yl)oxy]methyl}-2-azabicyclo[3.1.0]hexane (6.52 g, 22.5 mmol) in DMSO (100 mL) was cooled to 0° C., triethylamine (15.65 mL, 112.5 mmol) was added slowly and stirred for 5 min. Then added 1-{6-[3-(dimethylamino)azetidin-1-yl]pyridin-3-yl}-6,7-difluoro-4-oxo-1,4-dihydroquinoline-3-carboxylic acid (9 g, 22.5 mmol) and stirred at 100° C. for 16 hrs. Reaction was monitored by TLC. Reaction mass was quenched with ice cold water (20 mL) and extracted with ethyl acetate (2×50 mL), Organic layer washed with brine (20 mL) dried over sodium sulfate. Concentrated under reduced pressure to get crude. The crude product was washed with diethyl ether and dried under vacuum then, further purified by prep HPLC and the fraction was lyophilized to afford 7-[(1R,3R,5R)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid (5.65 g, 39.6%) as a pale brown solid. $^1$H NMR (400 MHz, DMSO-$d_6$) δ 15.40 (br s, 1H), 8.51 (d, J=4.8 Hz, 1H), 8.27-8.26 (m, 1H), 7.87 (d, J=13.2 Hz, 1H), 7.73-7.71 (m, 1H), 7.69-7.65 (m, 1H), 6.58-6.52 (m, 1H), 6.49-6.33 (m, 2H), 4.78-4.71 (m, 1H), 4.24-4.14 (m, 2H), 4.07-4.03 (m, 2H), 3.81-3.78 (m, 2H), 3.72 (d, J=3.2 Hz, 3H), 3.22-3.13

(m, 2H), 2.61-2.58 (m, 1H), 2.13 (s, 6H), 2.08-2.02 (m, 1H), 1.63-1.60 (m, 1H), 0.97-0.94 (m, 1H), 0.74-0.70 (m, 1H); MS (ESI): m/z 635.1. $[M+H]^+$. Prep-HPLC condition: Kinetex, C-18 column, 250×21.2×5 μm, A: 0.1% FA buffer, B: ACN, 0/10, 10/30, 20/40; diluent: Water/Acetonitrile.

Potency Lin28a-dep Z11 $IC_{50}$ (μM)++++

Example 74: Synthesis of 7-[(1S,3R,5S)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid

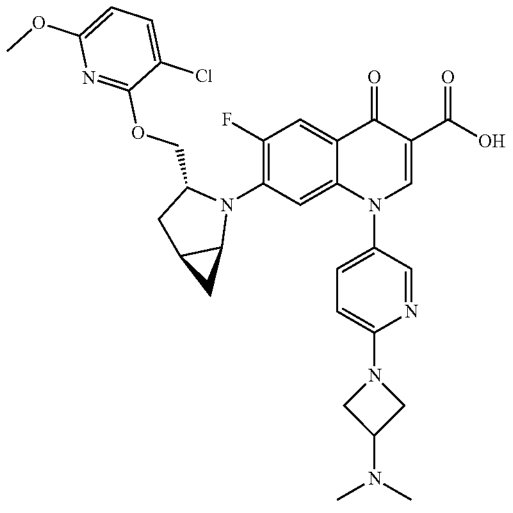 [SMILES: COc1ccc(Cl)c(OC[C@H]2C[C@@H]3C[C@@H]3N2c2cc3c(cc2F)c(=O)c(C(=O)O)cn3-c2ccc(N3CC(N(C)C)C3)nc2)n1]

Step 1: Synthesis of (5R)-5-{[(tert-butyldiphenylsilyl)oxy]methyl}pyrrolidin-2-one

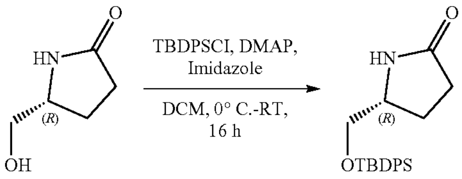

To a stirred solution of (5R)-5-(hydroxymethyl)pyrrolidin-2-one (5 g, 43.4 mmol) in DCM (150 mL) was added imidazole (6.5 g, 95.4 mmol) followed by 4-dimethylaminopyridine (530 mg, 4.33 mmol) and cooled to 0° C. Then added tert-butyl(chloro)diphenyl silane (11.8 mL, 45.4 mmol) drop wise and slowly allowed to stir at rt for 16 h. The reaction mixture was diluted with water and extracted with DCM. The organic layer was washed with brine solution and dried over anhydrous sodium sulphate, evaporated to dryness to afford crude (5R)-5-{[(tert-butyldiphenylsilyl)oxy]methyl}pyrrolidin-2-one (18.0 g) as a gummy liquid, which was carried out into next step without further purification. 1H NMR (400 MHz, CDCl3) δ 7.78-7.72 (m, 1H), 7.68-7.60 (m, 3H), 7.48-7.34 (m, 6H), 5.78 (s, 1H), 3.64-3.61 (m, 1H), 3.52-3.51 (m, 1H), 3.50-3.48 (m, 1H), 2.36-2.31 (m, 2H), 2.16-2.01 (m, 1H), 1.73-1.61 (m, 1H), 1.05 (s, 9H).

Step 2: Synthesis of tert-butyl (2R)-2-{[(tert-butyldiphenylsilyl)oxy]methyl}-5-oxopyrrolidine-1-carboxylate

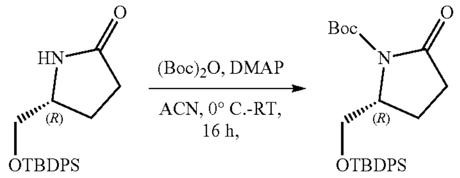

To a stirred solution of (5R)-5-{[(tert-butyldiphenylsilyl)oxy]methyl}pyrrolidin-2-one (18 g, 50.9 mmol) in ACN (180 mL) was added 4-dimethylaminopyridine (7.45 g, 61.0 mmol) and cooled to 0° C. Then added di-tert-butyl di carbonate (12.8 mL, 55.9 mmol) drop wise and allowed to stir at room temperature for 16 h. The reaction mixture was diluted with EtOAc and washed with water followed by brine solution. The organic layer was dried over anhydrous sodium sulphate and evaporated to afford crude. The crude compound was purified by 100-200 mesh silica gel column chromatography using 2-5% EtOAc/hexanes as an eluent. Collected pure fractions were evaporated to dryness to afford tert-butyl (2R)-2-{[(tert-butyldiphenylsilyl)oxy]methyl}-5-oxopyrrolidine-1-carboxylate (16.0 g, 69%) as a white crystalline solid. 1H NMR (400 MHz, CDCl3) δ 7.65-7.59 (m, 4H), 7.44-7.26 (m, 6H), 4.22-4.19 (m, 1H), 3.91-3.87 (m, 1H), 3.72-3.68 (m, 1H), 2.81-2.77 (m, 1H), 2.44-2.38 (m, 1H), 2.15-2.10 (m, 2H), 1.43 (s, 9H), 1.04 (s, 9H).

Step 3: Synthesis of tert-butyl (2R)-2-{[(tert-butyldiphenylsilyl)oxy]methyl}-5-hydroxypyrrolidine-1-carboxylate

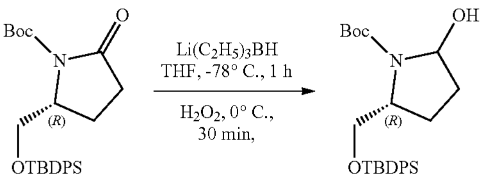

To a stirred solution of tert-butyl (2R)-2-{[(tert-butyldiphenylsilyl)oxy]methyl}-5-oxopyrrolidine-1-carboxylate (16 g, 35.2 mmol) in THF (160 mL) was added lithium triethylborohydride (38.7 mL, 38.7 mmol) drop wise at −78° C. and stirred at same temperature for 1 h. The reaction mixture was quenched with saturated $NaHCO_3$ solution (60 mL) and slowly allowed to stir at 0° C., then hydrogen peroxide (1.14 mL, 48.9 mmol) was added. The reaction mixture was stirred for another 30 min at the same temperature and diluted with DCM. The organic layer was washed with water followed by brine solution and dried over anhydrous sodium sulphate, evaporated to dryness to afford crude tert-butyl (2R)-2-{[(tert-butyldiphenylsilyl)oxy]methyl}-5-hydroxypyrrolidine-1-carboxylate (14.0 g, 88%) as a pale yellow gum. 1H NMR (400 MHz, CDCl3) δ 7.68-7.66 (m, 4H), 7.45-7.26 (m, 6H), 5.56-5.42 (m, 1H), 4.05-3.96 (m, 1H), 3.90-3.82 (m, 1H), 3.76-3.52 (m, 2H), 2.25-2.12 (m, 1H), 2.10-1.92 (m, 1H), 1.88-1.82 (m, 2H), 1.52 (s, 3H), 1.34 (s, 6H), 1.06 (s, 9H).

Step 4: Synthesis of tert-butyl (2R)-2-{[(tert-butyl-diphenylsilyl)oxy]methyl}-2,3-dihydro-1H-pyrrole-1-carboxylate

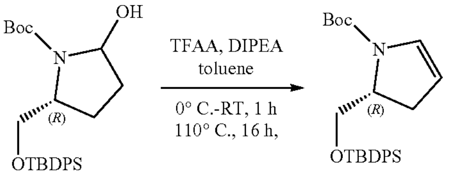

To a stirred solution of tert-butyl (2R)-2-{[(tert-butyldiphenylsilyl)oxy]methyl}-5-hydroxypyrrolidine-1-carboxylate (14 g, 30.7 mmol) in Toluene (100 mL) was added N,N-diisopropylethylamine (53.3 mL, 307 mmol) and cooled to 0° C. Trifluoroacetic anhydride (6.48 mL, 46.0 mmol) was added drop wise slowly and stirred for 1 h at rt then heated 110° C. for 16 h. The reaction mixture was cooled to rt and diluted with EtOAc. The organic layer was washed with water followed by brine solution and dried over anhydrous sodium sulphate, evaporated to afford crude. The crude compound was purified by 100-200 mesh silica gel column chromatography using 2% EtOAc/hexanes as an eluent. Collected pure fractions were evaporated to dryness to afford tert-butyl (2R)-2-{[(tert-butyldiphenylsilyl)oxy]methyl}-2,3-dihydro-1H-pyrrole-1-carboxylate (10.0 g, 75%) as a pale brown liquid. MS (ESI): m/z 438 $[(M+H]^+$ Step 5: Synthesis of tert-butyl (1S,3R,5S)-3-{[(tert-butyldiphenylsilyl)oxy]methyl}-2-azabicyclo[3.1.0]hexane-2-carboxylate

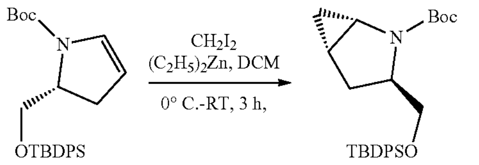

To a stirred solution of diiodomethane (5.0 mL, 59.2 mmol) in DCM (20 mL) was added bis(ethyl) zinc (1M in hexane, 27.3 mL, 27.3 mmol) drop wise at 0° C. and stirred for 30 min. Then added a solution of tert-butyl (2R)-2-{[(tert-butyldiphenylsilyl)oxy]methyl}-2,3-dihydro-1H-pyrrole-1-carboxylate (10 g, 22.8 mmol) in DCM (80 mL) drop wise at the same temperature and slowly allowed to stir at rt for 3 h. The reaction mixture was cooled to 0° C. and slowly quenched with saturated $NaHCO_3$ solution, then diluted with DCM. The organic layer was separated and washed with brine solution, dried over anhydrous sodium sulphate, evaporated to afford crude. The crude compound was purified by 100-200 mesh silica gel column chromatography using 2% EtOAc/hexanes as an eluent. Collected pure fractions were evaporated to dryness to afford tert-butyl (1S,3R,5S)-3-{[(tert-butyldiphenylsilyl)oxy]methyl}-2-azabicyclo[3.1.0]hexane-2-carboxylate (6.5 g, 63%) as a pale-yellow gum. 1HNMR (400 MHz, CDCl3) δ 7.68-7.62 (m, 4H), 7.44-7.34 (m, 6H), 3.92-3.80 (m, 1H), 3.74-3.68 (m, 2H), 3.22-3.13 (m, 1H), 2.40-2.27 (m, 1H), 2.10-1.96 (m, 1H), 1.54-1.48 (m, 1H), 1.40 (s, 9H), 1.05 (s, 9H), 0.90-0.78 (m, 1H), 0.38-0.30 (m, 1H); MS (ESI): m/z 452 [M+H]+.

Step 6: Synthesis of tert-butyl (1S,3R,5S)-3-(hydroxymethyl)-2-azabicyclo[3.1.0]hexane-2-carboxylate

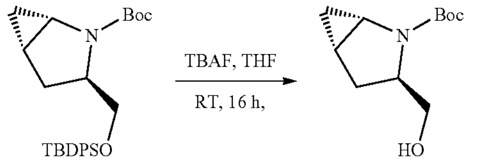

To a stirred solution of tert-butyl (3R)-3-{[(tert-butyldiphenylsilyl)oxy]methyl}-2-azabicyclo[3.1.0]hexane-2-carboxylate (6.5 g, 14.3 mmol) in THF (40 mL) was added 1M tetra-n-butylammonium fluoride (54.3 mL, 54.3 mmol) in THF at rt and stirred for 16 h. The reaction mixture was evaporated under reduced pressure and the crude material was subjected to 100-200 mesh silica gel column chromatography using 15% EtOAc/hexanes as an eluent. Collected pure fractions were evaporated to afford tert-butyl (1S,3R,5S)-3-(hydroxymethyl)-2-azabicyclo[3.1.0]hexane-2-carboxylate (2.80 g, 92%) as a brown liquid. 1H NMR (400 MHz, CDCl3) δ 4.85 (bs, 1H), 3.72-3.68 (m, 1H), 3.64-3.58 (m, 2H), 3.28-3.21 (m, 1H), 2.18-2.12 (m, 1H), 1.80-1.72 (m, 1H), 1.58-1.42 (m, 10H), 0.78-0.64 (m, 1H), 0.42-0.38 (m, 1H).

Step 7: Synthesis of T-902-int-01B [tert-butyl [(1S,3R,5S)-3-{[(6-methoxy-3-nitropyridin-2-yl)oxy]methyl}-2-azabicyclo[3.1.0]hexane-2-carboxylate]

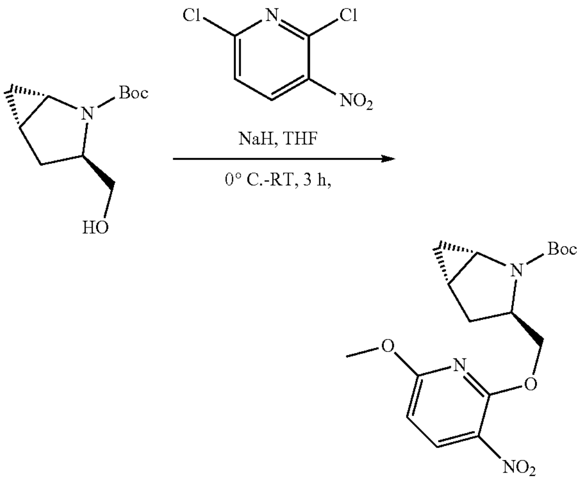

To a stirred mixture of tert-butyl (1S,3R,5S)-3-(hydroxymethyl)-2-azabicyclo[3.1.0]hexane-2-carboxylate (2.8 g, 13.1 mmol) in THF (30 mL) was added sodium hydride (626 mg, 15.7 mmol) at 0° C., then added 2-chloro-6-methoxy-3-nitropyridine (2.47 g, 13.1 mmol) and allowed to stir at RT for 3 hrs. Reaction was monitored by TLC. The reaction mixture was quenched with ice cold water and extracted with ethyl acetate (2×10 mL). Combined organic layers were washed with brine, dried over anhydrous sodium sulphate and concentrated under reduced pressure to get crude. The crude product was purified by 100-200 mesh silica gel Column chromatography using 10% EtOAc/

Hexanes as an eluent to afford tert-butyl (1S,3R,5S)-3-{[(6-methoxy-3-nitropyridin-2-yl)oxy]methyl}-2-azabicyclo[3.1.0]hexane-2-carboxylate (3.50 g, 73%) as a yellow liquid. MS (ESI): m/z 266 [(M-Boc)+H]+.

Step 8: Synthesis of tert-butyl (1S,3R,5S)-3-{[(3-amino-6-methoxypyridin-2-yl)oxy]methyl}-2-azabicyclo[3.1.0]hexane-2-carboxylate

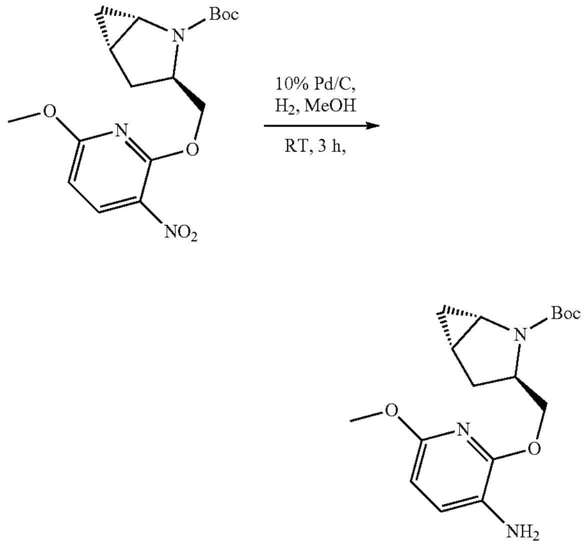

To a stirred solution of tert-butyl (1S,3R,5S)-3-{[(6-methoxy-3-nitropyridin-2-yl)oxy]methyl}-2-azabicyclo[3.1.0]hexane-2-carboxylate (1.1 g, 3.01 mmol) in Methanol (20 mL) was added 10% palladium on carbon (500 mg, 469 μmol) and hydrogenated under H2 balloon pressure at RT for 3 h. The reaction mixture was filtered through celite bed, washed with EtOAc and the filtrate was evaporated to afford crude. The crude compound was purified by 100-200 mesh silica gel column chromatography using 50% EtOAc/Hexanes as an eluent. Collected pure fractions were evaported to dryness to afford tert-butyl (1S,3R,5S)-3-{[(3-amino-6-methoxypyridin-2-yl)oxy]methyl}-2-azabicyclo[3.1.0]hexane-2-carboxylate (587 mg, 59%) as a brown gum. MS (ESI): m/z 336.1 [M+H]+.

Step 9: Synthesis of tert-butyl (1S,3R,5S)-3-{[(3-chloro-6-methoxypyridin-2-yl)oxy]methyl}-2-azabicyclo[3.1.0]hexane-2-carboxylate

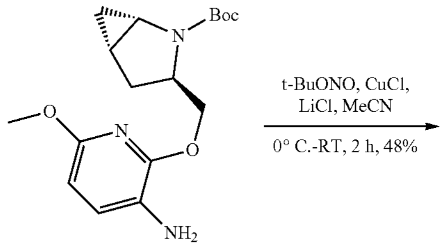

-continued

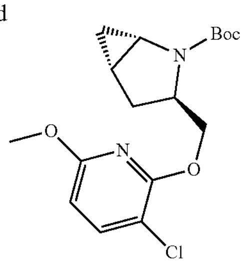

To a stirred solution of tert-butyl (1S,3R,5S)-3-{[(3-amino-6-methoxypyridin-2-yl)oxy]methyl}-2-azabicyclo[3.1.0]hexane-2-carboxylate (1.1 g, 3.27 mmol) in ACN (6 mL) was added 2-methyl-2-propylnitrit (582 μL, 4.90 mmol) drop wise at 0° C. and stirred at the same temperature for 15 min. A suspension of copper (II) chloride (658 mg, 4.90 mmol) and lithium chloride (415 mg, 9.80 mmol) in ACN (4 mL) was heated at 60° C. for 5 min then cooled to room temperature. The solution was added drop wise to the above reaction mixture at 0° C. and allowed to stir at RT for 2 h. Excess solvent was evaporated under reduced pressure and obtained crude was purified by 100-200 mesh silica gel column chromatography using 2% EtOAc/Hexanes as an eluent. Collected pure fractions were evaporated to dryness to afford tert-butyl (1S,3R,5S)-3-{[(3-chloro-6-methoxypyridin-2-yl)oxy]methyl}-2-azabicyclo[3.1.0]hexane-2-carboxylate (560 mg, 48%) as a yellow solid. MS (ESI): m/z 355 [(M+H]+.

Step 10: Synthesis of (1S,3R,5S)-3-{[(3-chloro-6-methoxypyridin-2-yl)oxy]methyl}-2-azabicyclo[3.1.0]hexane hydrochloride

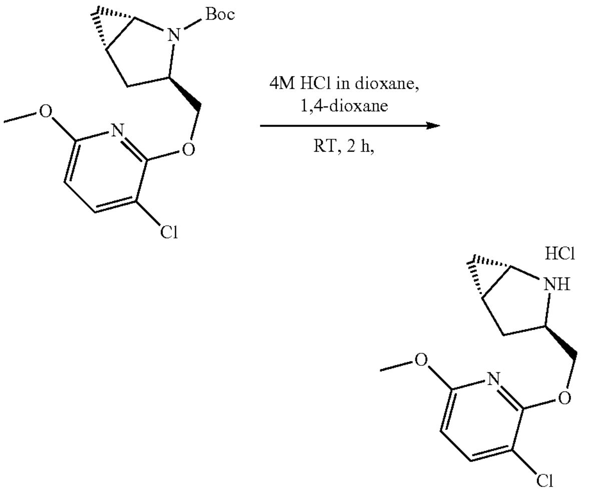

To a stirred solution of tert-butyl (1S,3R,5S)-3-{[(3-chloro-6-methoxypyridin-2-yl)oxy]methyl}-2-azabicyclo[3.1.0]hexane-2-carboxylate (560 mg, 1.57 mmol) in 1,4-dioxane (5 mL) was added 4M hydrochloride in 1,4-dioxane (1.96 mL, 7.84 mmol) and stirred at rt for 2 h. The reaction mixture was evaporated to dryness and obtained solid was washed with diethyl ether, dried under vacuum to afford (1S,3R,5S)-3-{[(3-chloro-6-methoxypyridin-2-yl)oxy]methyl}-2-azabicyclo[3.1.0]hexane hydrochloride (380 mg, 83%) as a pale yellow solid. MS (ESI): m/z 255 [(M−HCl)+H]+.

Step 11: Synthesis of 7-[(1S,3R,5S)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid

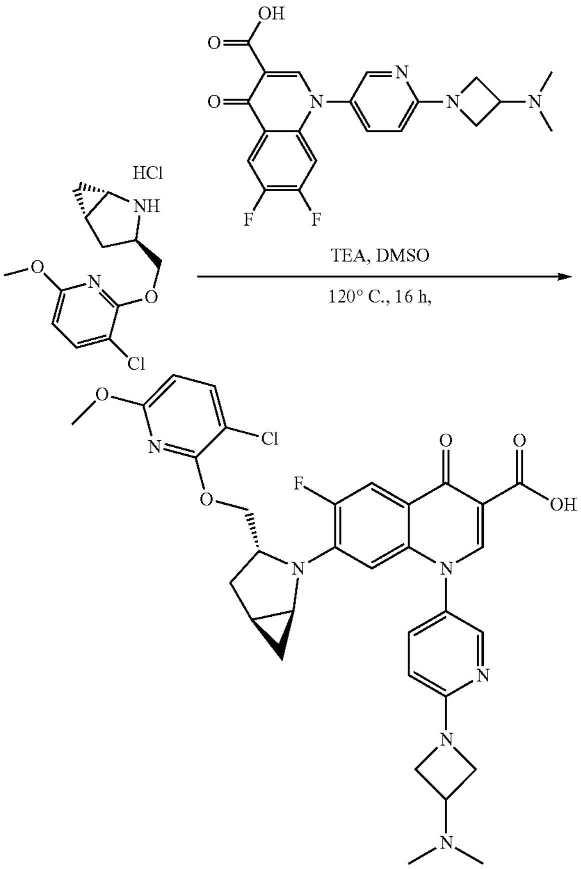

To a stirred solution of 1-{6-[3-(dimethylamino)azetidin-1-yl]pyridin-3-yl}-6,7-difluoro-4-oxo-1,4-dihydroquinoline-3-carboxylic acid (180 mg, 449 μmol) in DMSO (0.5 mL) was added (1S,3R,5S)-3-{[(3-chloro-6-methoxypyridin-2-yl)oxy]methyl}-2-azabicyclo[3.1.0]hexane (114 mg, 449 μmol) followed by triethylamine (311 μL, 2.24 mmol) in a sealed tube and heated to 120° C. for 16 h. The reaction mixture was cooled to rt and diluted with ice cold water then extracted with 10% MeOH/DCM twice. Combined organic layers were washed with cold brine, dried over anhydrous sodium sulphate and evaporated to afford crude. The crude compound was purified by Prep HPLC and collected pure fractions were lyophilized to afford 7-[(1S,3R,5S)-3-{[(3-chloro-6-methoxypyridin-2-yl)oxy]methyl}-2-azabicyclo[3.1.0]hexan-2-yl]-1-{6-[3-(dimethylamino)azetidin-1-yl]pyridin-3-yl}-6-fluoro-4-oxo-1,4-dihydroquinoline-3-carboxylic acid (64.1 mg, 22%) as an off white solid. Prep HPLC conditions: Gemini, C-18 column, 250×21.2×5 μm, A: 0.1% FA buffer, B: ACN, 0/20, 10/40, 20/60, 25/90; diluent: ACN/MeOH. 1H NMR (400 MHz, DMSO-d6) δ 15.36 (s, 1H), 8.52 (s, 1H), 8.34-8.25 (m, 1H), 7.95-7.84 (m, 1H), 7.84-7.72 (m, 2H), 6.58-6.34 (m, 3H), 4.50-4.30 (m, 3H), 4.12-3.98 (m, 2H), 3.90-3.80 (m, 2H), 3.77 (s, 3H), 3.18-3.05 (m, 2H), 2.33-2.18 (m, 6H), 2.12-2.07 (m, 2H), 1.82-1.74 (m, 1H), 0.82-0.74 (m, 1H), 0.38 (d, J=14.0 Hz, 1H); MS (ESI): m/z 635.4 [(M+H]+.

Potency Lin28a-dep Z11 $IC_{50}$ (μM)++++

Example 75: Synthesis of 6-chloro-7-[(2R)-2-{[(3-chloro-4-methoxypyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylic acid

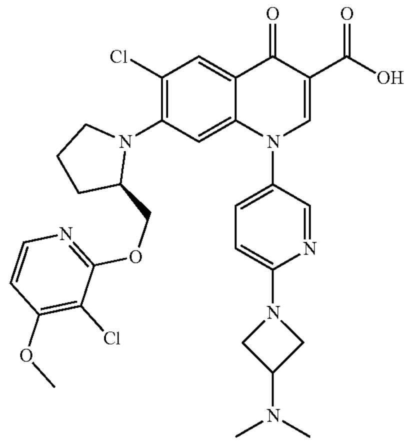 [SMILES: COc1ccnc(OC[C@H]2CCCN2c2cc3c(cc2Cl)c(=O)c(C(=O)O)cn3-c2ccc(N3CC(N(C)C)C3)nc2)c1Cl]

Step 1: Synthesis of 2-chloro-4-methoxy-3-nitropyridine

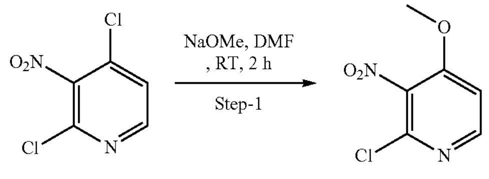

In a 10 mL sealed tube a stirred solution of 2,4-dichloro-3-nitropyridine (500 mg, 2.59 mmol) in MeOH (5 mL) was added sodium methoxide (167 mg, 3.10 mmol) and stirred at Room temperature for 2 h under $N_2$. After completed the starting materials, the reaction mixture was concentrated under reduced pressure, and the crude compound was dissolved in EtOAc (100 mL). The organic layer was washed with water(20 mL) and brine solution (20 mL), dried over anhydrous sodium sulphate, concentrated under reduced pressure to afford the crude compound. The crude compound was purified by silica gel (100-200 mesh) column chromatography using Buffer 10% EtoAC in hexane as eluent to get 2-chloro-4-methoxy-3-nitropyridine (400 mg, 2.12 mmol, 81%) as Pale yellow solid.

$^1$H-NMR (400 MHz, $CDCl_3$): δ 8.37 (d, J=5.6 Hz, 1H), 6.97 (d, J=6.8 Hz, 1H), 4.00 (s, 3H).

Step 2: Synthesis of tert-butyl (2R)-2-{[(4-methoxy-3-nitropyridin-2-yl)oxy]methyl}pyrrolidine-1-carboxylate

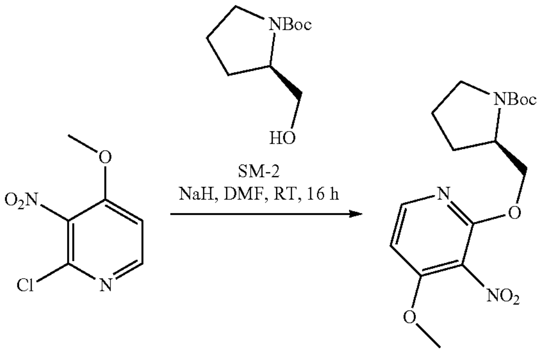 [SMILES: COc1ccnc(Cl)c1[N+](=O)[O-] ; CC(C)(C)OC(=O)N1CCC[C@@H]1CO ; COc1ccnc(OC[C@H]2CCCN2C(=O)OC(C)(C)C)c1[N+](=O)[O-]]

To a stirred solution of 2-chloro-4-methoxy-3-nitropyridine (400 mg, 2.12 mmol) in DMF (5 mL), was added sodium hydride (127 mg, 3.18 mmol) followed by tert-butyl (2R)-2-(hydroxymethyl) pyrrolidine-1-carboxylate (511 mg, 2.54 mmol) at 0° C. The reaction was allowed to room temperature then stirred for 16 h. After completion of reaction, the reaction mixture was quenched with ice-cold water (20 mL) and extracted with EtOAc (2×100 mL). The combined organic layer was washed with brine (20 mL), dried over anhydrous sodium sulphate, concentrated under reduced pressure to afford the crude compound. The crude compound was purified by silica gel (100-200 mesh) column chromatography with 30% EtOAc in hexanes as eluent to afford tert-butyl (2R)-2-{[(4-methoxy-3-nitropyridin-2-yl)oxy]methyl}pyrrolidine-1-carboxylate (285 mg, 806 μmol, 38%) as oil compound. MS (ESI): m/z 354 $[M+H]^+$.

Step 3: Synthesis of tert-butyl (2R)-2-{[(3-amino-4-methoxypyridin-2-yl)oxy]methyl}pyrrolidine-1-carboxylate

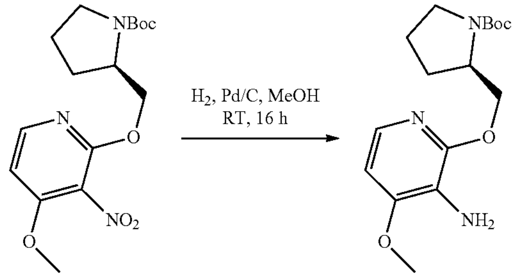 [SMILES: COc1ccnc(OC[C@H]2CCCN2C(=O)OC(C)(C)C)c1[N+](=O)[O-] ; COc1ccnc(OC[C@H]2CCCN2C(=O)OC(C)(C)C)c1N]

To a stirred solution of tert-butyl (2R)-2-{[(4-methoxy-3-nitropyridin-2-yl)oxy]methyl} pyrrolidine-1-carboxylate (300 mg, 806 μmol) in MeOH (5 mL) and was added 10% Pd—C(85.7 mg, 80.6 μmol) at room temperature and stirred for 16 h under hydrogen atmosphere. After completed the reaction (Monitored by TLC), the reaction mixture was filtered through the celite pad and washed with methanol. The filtrate was concentrated under reduced pressure to get crude compound and it was triturated with n-pentane to afford tert-butyl (2R)-2-{[(3-amino-4-methoxypyridin-2-yl)oxy]methyl}pyrrolidine-1-carboxylate (88.7 mg, 274 μmol, 34%) as brown oil compound. MS (ESI): m/z 324.0 $[M+H]^+$ Step 4: Synthesis of tert-butyl (2R)-2-{[(3-chloro-4-methoxypyridin-2-yl)oxy]methyl}pyrrolidine-1-carboxylate

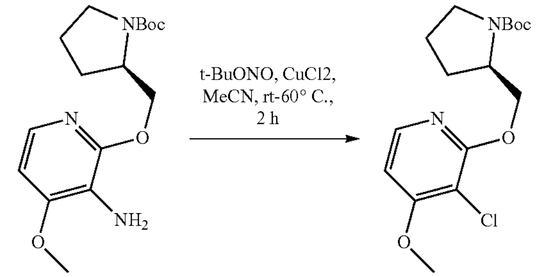 [SMILES: COc1ccnc(OC[C@H]2CCCN2C(=O)OC(C)(C)C)c1N ; COc1ccnc(OC[C@H]2CCCN2C(=O)OC(C)(C)C)c1Cl]

To a stirred solution of tert-butyl (2R)-2-{[(3-amino-4-methoxypyridin-2-yl)oxy]methyl} pyrrolidine-1-carboxylate (500 mg, 1.54 mmol) in ACN (10 mL) and was added tert butyl nitrite (274 μL, 2.31 mmol) and stirred at 0° C. for 10 mins. copper(II) chloride (310 mg, 2.31 mmol) was added into the reaction mixture under N2 and the resulting mixture was stirred for 30 min at 50° C. The resulting solution was extracted with ethyl acetate and water. The organic phase was concentrated and the residue was applied onto a silica gel (100-200 mesh) column eluting with ethyl acetate/Hexane (1:5) to afford tert-butyl (2R)-2-{[(3-chloro-4-methoxypyridin-2-yl)oxy] methyl}pyrrolidine-1-carboxylate (127 mg, 371 μmol, 24%) as oil compound. MS (ESI): m/z 342.9 $[M+H]^+$ Step 5: Synthesis of 3-chloro-4-methoxy-2-{[(2R)-pyrrolidin-2-yl]methoxy} pyridine

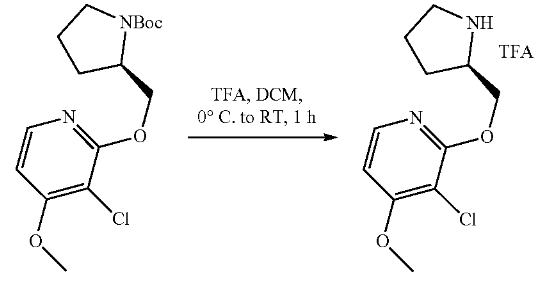 [SMILES: COc1ccnc(OC[C@H]2CCCN2C(=O)OC(C)(C)C)c1Cl ; COc1ccnc(OC[C@H]2CCCN2)c1Cl]

To a stirred solution of tert-butyl (2R)-2-{[(3-chloro-4-methoxypyridin-2-yl)oxy]methyl} pyrrolidine-1-carboxylate (30 mg, 71.7 μmol) in DCM (0.5 mL) was added trifluoroacetic acid (13.6 μL, 179 μmol) at 0° C. under N2 atmosphere. The resulting mixture was stirred at room temperature for 1 hr. The progress of the reaction was (Monitored by TLC). After completed the reaction, the reaction mixture was concentrated under reduced pressure until to remove DCM. Then the residue was triturated with diethyl ether to afforded 3-chloro-4-methoxy-2-{[(2R)-pyrrolidin-2-yl]methoxy}pyridine (14.5 mg, 59.9 μmol, 83%) as brown oil compound. MS (ESI): m/z 242.9 $[M+H]^+$ (for free base).

Step 6: Synthesis of 6-chloro-7-[(2R)-2-{[(3-chloro-4-methoxypyridin-2-yl)oxy]methyl}pyrrolidin-1-yl]-1-{6-[3-(dimethylamino)azetidin-1-yl]pyridin-3-yl}-4-oxo-1,4-dihydro quinoline-3-carboxylic acid

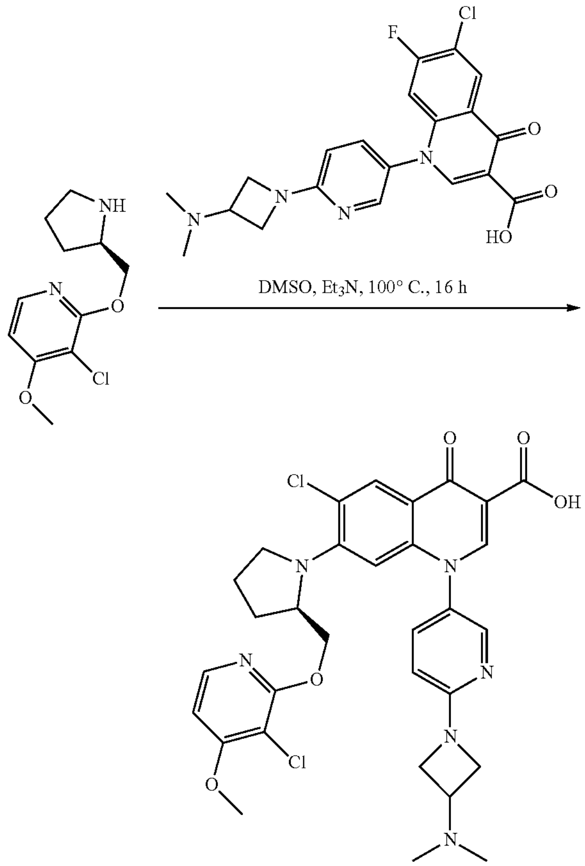

In 10 mL seald tube a solution of 6-chloro-1-{6-[3-(dimethylamino)azetidin-1-yl]pyridin-3-yl}-7-fluoro-4-oxo-1,4-dihydroquinoline-3-carboxylic acid (150 mg, 347 μmol) in DMSO (3 mL) was added triethylamine (241 μL, 1.73 mmol) followed by 3-chloro-4-methoxy-2-{[(2R)-pyrrolidin-2-yl]methoxy}pyridine (100 mg, 416 μmol) at room temperature. The reaction was then heated to 100° C. and stirred for 16 h. After completion of reaction, the reaction mixture was quenched with ice-cold water (10 mL) and extracted with 5% MeOH/DCM (2×100 mL). The combined organic layer was washed with brine solution (10 mL), dried over anhydrous sodium sulfate, concentrated under reduced pressure to afford the crude compound. The crude compound was purified by Prep HPLC purification to afford 6-chloro-7-[(2R)-2-{[(3-chloro-4-methoxypyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylic acid (51.4 mg, 80.4 μmol, 23%) as an off white solid. Prep HPLC condition: Atlantis, C-18 column, 250×21.2×5 μm, A: 0.1% FA buffer, B: ACN, 0/10, 10/40, 20/60; diluent: MeOH/Water/Acetonitrile. $^1$H-NMR (400 MHz, DMSO-$d_6$): δ 15.11 (s, 1H), 8.52 (d, J=11.2 Hz, 1H), 8.24 (dd, J=11.6, 6.0 Hz, 1H), 8.14 (s, 1H), 7.83-7.77 (m, 1H), 7.68-7.64 (m, 1H), 6.85-6.80 (m, 1H), 6.53 (d, J=9.2 Hz, 0.5H), 6.38 (d, J=12.8 Hz, 1H), 6.23 (d, J=8.8 Hz, 0.5H), 4.74 (br s, 0.5H), 4.58 (br s, 0.5H), 4.43-4.31 (m, 1H), 4.20-4.01 (m, 3H), 3.87 (s, 3H), 3.85-3.77 (m, 2H), 3.58-3.47 (m, 1H), 3.28-3.16 (m, 2H), 2.32-2.24 (m, 1H), 2.14 (s, 6H), 2.01-192 (m, 1H), 1.88-1.76 (m, 2H); MS (ESI): m/z 639.3 [M+H]$^+$. Potency Lin28a-dep Z11 $IC_{50}$ (μM)++++

Example 76: Synthesis of (R)-6-chloro-7-(2-(((3-chloropyridin-2-yl)oxy)methyl)pyrrolidin-1-yl)-1-(6,7-dihydro-4H-pyrazolo[5,1-c][1,4]oxazin-2-yl)-4-oxo-1,4-dihydroquinoline-3-carboxylic acid

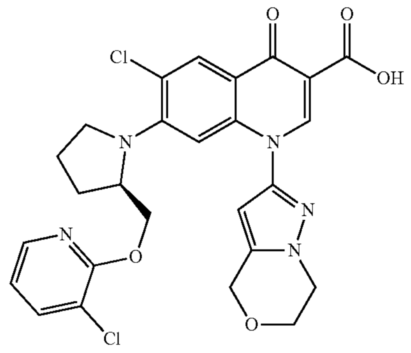 [SMILES: O=C(O)c1cn(-c2cc3n(n2)CCOC3)c2cc(N3CCC[C@@H]3COc3ncccc3Cl)c(Cl)cc2c1=O]

Step 1: Synthesis of (3-nitro-1H-pyrazol-5-yl)methanol

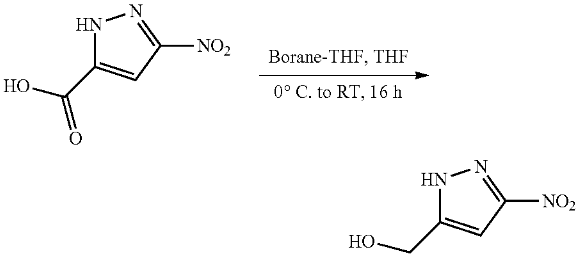

To a stirred solution of 3-nitro-1H-pyrazole-5-carboxylic acid (5 g, 31.8 mmol) in THF (40 mL) was added Borane in 1M THF (8.10 g, 95.4 mmol) at 0° C. reaction was maintained room temperature for 16 hours. After this time the reaction was cooled to 0° C. using an ice/acetone bath, water (1.5 mL) and 4N hydrochloric acid (1.5 mL) was added and the reaction was stirred at reflux for 1 h in order to destroy the borane complex with pyrazole. The reaction was cooled to room temperature and concentrated under reduced pressure to a volume of approximately 5 mL. Ethyl acetate (50 mL) was added and the mixture stirred for 15 min. The aqueous layer was separated and extracted with ethyl acetate (4×20 mL). The combined organic layers were washed with saturated aqueous sodium bicarbonate (2×20 mL), brine (20 mL) and dried over sodium sulfate, the drying agent was removed by filtration, and the filtrate concentrated under reduced pressure to afford (3-nitro-1H-pyrazol-5-yl)methanol (2.30 g, 16.0 mmol) as an off white solid. 1HNMR (400 MHz, DMSO-$d_6$): δ 13.90 (bs, 1H), 6.87 (s, 1H), 4.53 (s, 2H) (—OH proton was not observed).

Step 2: Synthesis of (1-(2-bromoethyl)-3-nitro-1H-pyrazol-5-yl)methanol

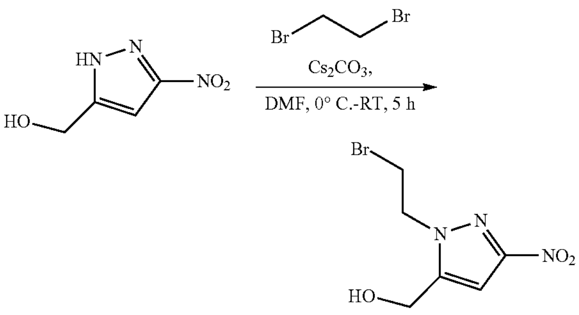

To a stirred solution of (3-nitro-1H-pyrazol-5-yl)methanol (100 mg, 698 μmol) in DMF (1 mL), were added cesium carbonate (272 mg, 837 μmol) and 1,2-dibromoethane (1.30 g, 6.97 mmol) at 0° C. The reaction was stirred at 0° C. for 1 h and room temperature for 4 h. After this time ethyl acetate (20 mL) and water (15 mL) were added. The aqueous layer was separated and extracted with ethyl acetate (2×10 mL). The combined organic layer was washed with water (10 mL), brine (10 mL), dried over sodium sulfate, filtered and concentrated under reduced pressure to afford the crude product, which was purified by silica-gel column chromatography to afford [1-(2-bromoethyl)-3-nitro-1H-pyrazol-5-yl]methanol (80.0 mg, 319 μmol) as a yellow liquid. 1HNMR (400 MHz, CDC13): δ 6.85 (s, 1H), 4.97 (s, 2H), 4.66 (t, J=6.4 Hz, 2H), 3.83 (t, J=6.4 Hz, 2H), 2.15 (bs, 1H).

Step 3: Synthesis of 2-nitro-6,7-dihydro-4H-pyrazolo[5,1-c][1,4]oxazin

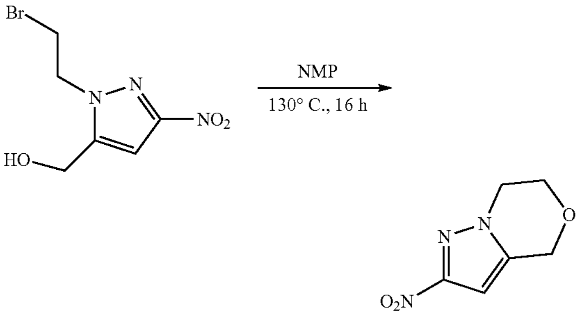

A solution of [1-(2-bromoethyl)-3-nitro-1H-pyrazol-5-yl]methanol (800 mg, 3.19 mmol) in NMP (3.2 mL) was stirred at 130° C. for 6 h. The reaction was cooled to room temperature, then water (60 mL) was added and extracted twice with 60 mL of DCM. The combined organic layer was washed with brine solution, dried over $Na_2SO_4$, filtered and concentrated and the crude compound was purified by silica gel column chromatography to afforded 2-nitro-4H,6H,7H-pyrazolo[3,2-c][1,4]oxazine (380 mg, 2.24 mmol) as an off white solid. 1HNMR (400 MHz, DMSO-d6): δ 6.88 (s, 1H), 4.83 (s, 2H), 4.24 (t, J=6.4 Hz, 2H), 4.13 (t, J=6.4 Hz, 2H), 2.15 (bs, 1H).

Step 4: Synthesis of 6,7-dihydro-4H-pyrazolo[5,1-c][1,4]oxazin-2-amine

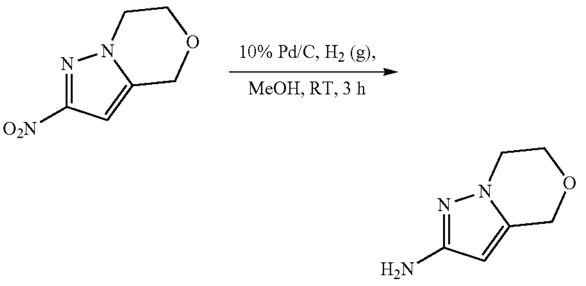

To a stirred solution of 2-nitro-4H,6H,7H-pyrazolo[3,2-c][1,4]oxazine (300 mg, 1.77 mmol) n MeOH (5 mL), was added Pd/C (100 mg, 625 μmol) at room temperature. Reaction was maintained at RT for 3 hours under H2 Balloon. After completion of reaction, reaction mixture was filtered through a celite pad. filterate was concentrated to afforded 4H,6H,7H-pyrazolo[3,2-c][1,4]oxazin-2-amine (220 mg, 1.58 mmol) as a yellow liquid. MS (ESI): m/z 140.4 [M+H]+.

Step 5: Synthesis of ethyl (R)-6-chloro-7-(2-(((3-chloropyridin-2-yl)oxy)methyl)pyrrolidin-1-yl)-1-(6,7-dihydro-4H-pyrazolo[5,1-c][1,4]oxazin-2-yl)-4-oxo-1,4-dihydroquinoline-3-carboxylate

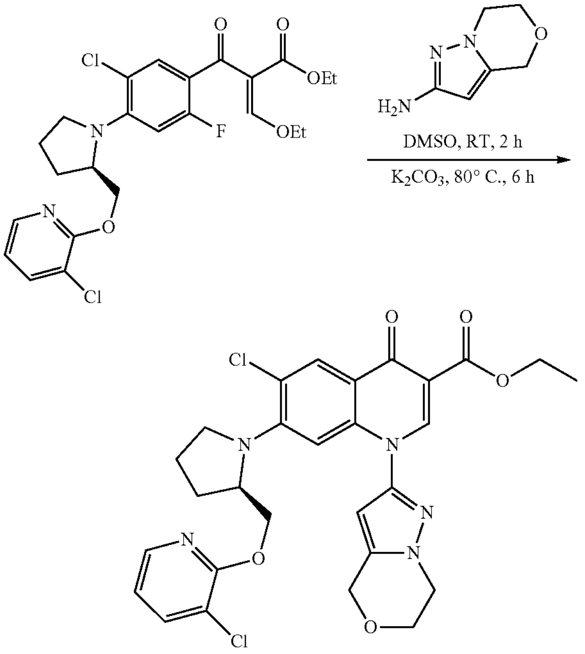

To a stirred solution of ethyl (2Z)-2-[(Z)-5-chloro-4-[(2R)-2-{[(3-chloropyridin-2-yl)oxy]methyl}pyrrolidin-1-yl]-2-fluorobenzoyl]-3-ethoxyprop-2-enoate (50 mg, 97.7 μmol) in DMSO (0.5 mL), was added 4H,6H,7H-pyrazolo[3,2-c][1,4]oxazin-2-amine (16.2 mg, 117 μmol) at room temperature and the mixture was stirred for 2 hours. After completion of starting material, potassium carbonate (20.1 mg, 146 μmol) was added to reaction mixture at same temperature, reaction was maintained at 80° C. for 6 hours. After completion of reaction, the mixture was cooled to room temperature, ice water was added to reaction mixture, solid precipitated was filtered and dried to afforded ethyl 6-chloro-7-[(2R)-2-{[(3-chloropyridin-2-yl)oxy]methyl}pyrrolidin-1-yl]-4-oxo-1-{4H,6H,7H-pyrazolo[3,2-c][1,4]oxazin-2-yl}-1,4-dihydroquinoline-3-carboxylate (20.0 mg, 34.2 μmol) as a brown solid. This solid was treated with charcoal. MS (ESI): m/z 584.2 [M+H]+.

Step 6: Synthesis of (R)-6-chloro-7-(2-(((3-chloropyridin-2-yl)oxy)methyl)pyrrolidin-1-yl)-1-(6,7-dihydro-4H-pyrazolo[5,1-c][1,4]oxazin-2-yl)-4-oxo-1,4-dihydroquinoline-3-carboxylic acid]

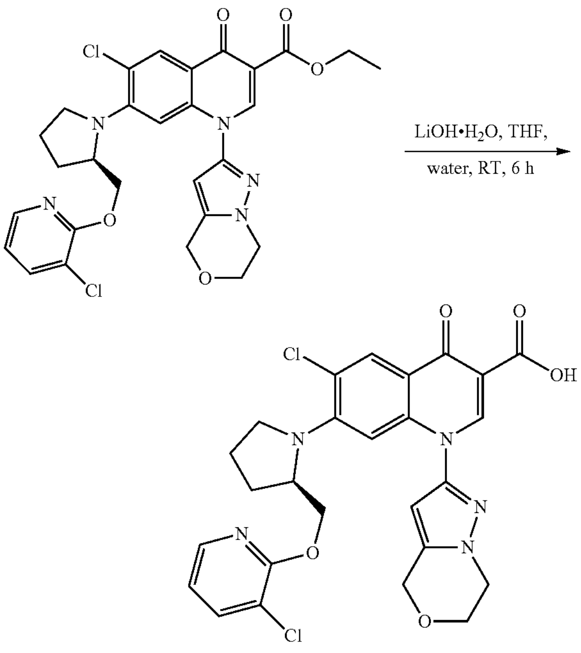

To a stirred solution of ethyl 6-chloro-7-[(2R)-2-{[(3-chloropyridin-2-yl)oxy]methyl}pyrrolidin-1-yl]-4-oxo-1-{4H,6H,7H-pyrazolo[3,2-c][1,4]oxazin-2-yl}-1,4-dihydroquinoline-3-carboxylate (280 mg, 479 μmol) in THF (2 mL) & water (2 mL), was added lithium hydroxide (57.2 mg, 2.39 mmol) at room temperature and the mixture was stirred at same temperature for 6 h. After completion of reaction, solvents were evaporated and acidified with 1N HCl, extracted with ethyl acetate. The combined organic layers were dried over Na2SO4, filtered and concentrated to get crude compound. crude compound was purified by Prep-HPLC and the fraction was lyophilized to afford 6-chloro-7-[(2R)-2-{[(3-chloropyridin-2-yl)oxy]methyl}pyrrolidin-1-yl]-4-oxo-1-{4H,6H,7H-pyrazolo[3,2-c][1,4]oxazin-2-yl}-1,4-dihydroquinoline-3-carboxylic acid (30.0 mg, 53.9 μmol) as an off white solid. Prep-HPLC Condition: Gemini, C-18 column, 250×21.2×5 μm, A: 0.1% formic acid buffer, B: ACN, 0/50, 20/70, 25/95; diluent: THF/ACN+WATER 1H NMR (400 MHz, DMSO-d6): δ 14.98 (s, 1H), 8.60 (s, 1H), 8.13 (s, 1H), 7.87 (dd, J=4.8, 1.6 Hz, 1H), 7.77 (dd, J=7.6, 1.6 Hz, 1H), 6.98 (s, 1H), 6.90 (dd, J=8.0, 5.2 Hz, 1H), 6.51 (s, 1H), 4.85 (d, J=2.4 Hz, 2H), 4.80-4.73 (m, 1H), 4.34 (d, J=4.0 Hz, 2H), 4.22-4.13 (m, 4H), 3.70-3.62 (m, 1H), 3.35-3.24 (m, 1H), 2.34-2.25 (m, 1H), 2.08-1.90 (m, 2H), 1.88-1.70 (m, 1H); MS (ESI): m/z 556.3 [M+H]+.

Potency Lin28a-dep Z11 $IC_{50}$ (μM)++++

Example 77: Synthesis of 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid

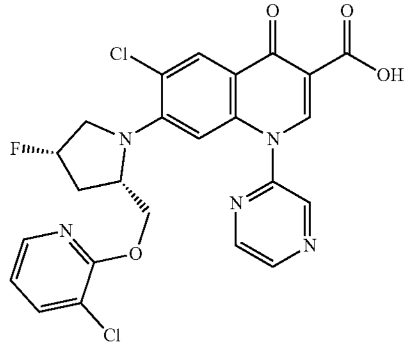 [SMILES: O=C(O)c1cn(-c2cnccn2)c2cc(N3C[C@@H](F)C[C@H]3COc3ncccc3Cl)c(Cl)cc2c1=O]

Step 1: Synthesis of 1-tert-butyl 2-methyl (2S,4S)-4-fluoropyrrolidine-1,2-dicarboxylate

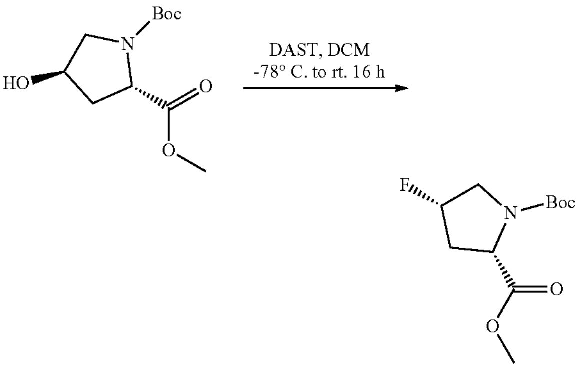

To a stirred solution of 1-tert-butyl 2-methyl (2S,4R)-4-hydroxypyrrolidine-1,2-dicarboxylate (5 g, 20.3 mmol) in dichloromethane (25 mL), was added diethyl amino sulfur trifluoride (3.98 mL, 30.4 mmol) drop wise at −78° C. and stirred for 2 h, then at room temperature for 16 h. After completed the starting material, the reaction mixture was quenched with saturated aqueous NH4Cl solution and extracted with DCM (2×50 mL). The combined organic layer was washed with water (10 mL) and brine solution (10 mL), dried over sodium sulfate and concentrate on vacuum to get crude compound. The crude compound was purified by silica gel column chromatography eluting with ethylacetate in hexane and the compound containing fractions were concentrated to afford 1-tert-butyl 2-methyl (2S,4S)-4-fluoropyrrolidine-1,2-dicarboxylate (3.00 g, 12.1 mmol, 54%) as a pale yellow oil. 1H NMR (400 MHz, DMSO-d6): δ 5.33-5.19 (m, 1H), 4.42-4.36 (m, 1H), 3.67 (s, 3H), 3.62-3.51 (m, 2H), 2.56-2.40 (m, 1H), 2.27-2.17 (m, 1H), 1.42 (s, 9H).

Step 2: Synthesis of tert-butyl (2S,4S)-4-fluoro-2-(hydroxymethyl)pyrrolidine-1-carboxylate

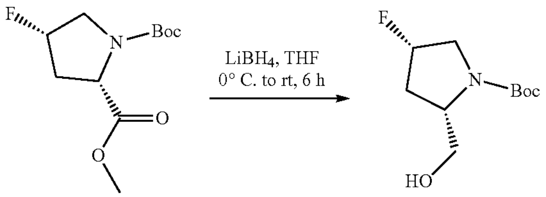 [SMILES: COC(=O)[C@@H]1C[C@H](F)CN1C(=O)OC(C)(C)C ; "LiBH4, THF0° C. to rt, 6 h" ; CC(C)(C)OC(=O)N1C[C@@H](F)C[C@H]1CO]

To a stirred solution of 1-tert-butyl 2-methyl (2S,4S)-4-fluoropyrrolidine-1,2-dicarboxylate (3.0 g, 12.1 mmol) in THF (10 mL) at 0° C., was added lithium borohydride (9.05 mL, 18.1 mmol) slowly for 10 min. The reaction mixture was allowed to rt and stirred for 6 h. The mixture was cooled to 0° C. quenched with diluted acetic acid, then extracted with EtOAc (2×50 mL). The combined organic layer was washed with saturated $NaHCO_3$ and saturated NaCl solution, was dried over sodium sulfate, filtered and concentrated to obtain tert-butyl (2S,4S)-4-fluoro-2-(hydroxymethyl)pyrrolidine-1-carboxylate (2.30 g, 10.4 mmol, 68%) as a pale yellow oil. 1H NMR (400 MHz, DMSO-d6): δ 5.33-5.17 (m, 1H), 4.45 (t, J=5.6 Hz, 1H), 3.86-3.81 (m, 1H), 3.72-3.59 (m, 1H), 3.49-3.40 (m, 1H), 3.30-3.27 (m, 1H), 2.31-2.11 (m, 3H), 1.45 (s, 9H).

Step 3: Synthesis of (2S,4S)-4-fluoropyrrolidin-2-yl]methanol hydrochloride

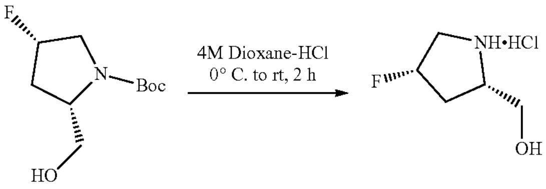

A solution of tert-butyl (2S,4S)-4-fluoro-2-(hydroxymethyl)pyrrolidine-1-carboxylate (1.7 g, 7.75 mmol) in 4N HCl in dioxane (5 mL) was stirred under N2 atmosphere at 0° C. for 15 min, then at room temperature for 2 h. After completion of the starting material, the reaction mixture was concentrated under reduced pressure to get crude compound and it was triturated with diethyl ether and n-pentane to afford [(2S,4S)-4-fluoropyrrolidin-2-yl]methanol hydrochloride (1 g, 6.42 mmol, 83%) as white solid. 1H NMR (400 MHz, DMSO-d6): δ 10.19 (brs, 1H), 9.19 (brs, 1H), 5.47-5.32 (d, J=63.2 Hz, 1H), 3.69-3.47 (m, 5H), 2.42-2.31 (m, 1H), 2.01-1.89 (m, 1H).

Step 4: Synthesis of ethyl 6-chloro-7-[(2S,4S)-4-fluoro-2-(hydroxy methyl) pyrrolidin-1-yl]-4-oxo-1-(pyrazin-2-yl)-1,4-dihydroquinoline-3-carboxylate

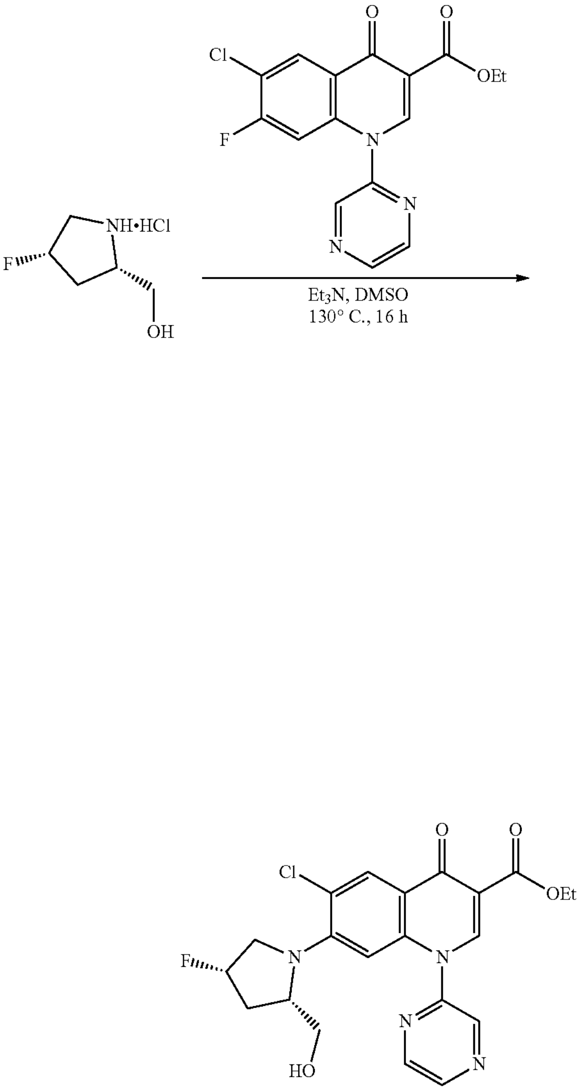

To a stirred solution of ethyl 6-chloro-7-fluoro-4-oxo-1-(pyrazin-2-yl)-1,4-dihydroquinoline-3-carboxylate (500 mg, 1.43 mmol) in dimethyl sulfoxide (10 mL) was added triethylamine (796 μL, 5.72 mmol) followed by [(2R,4R)-4-fluoropyrrolidin-2-yl]methanol (511 mg, 4.29 mmol) at room temperature. The reaction was then heated to 130° C. and stirred for 16 h. After completion of reaction, the reaction mixture was cooled to RT, quenched with ice-cold water (20 mL) and extracted with EtOAc (2×100 mL). The combined organic layer was washed with brine (20 mL), dried over anhydrous sodium sulfate, concentrated under reduced pressure to afford the crude compound. The crude compound was purified by column chromatography with 2% MeOH in DCM as eluent to afford ethyl 6-chloro-7-[(2S,4S)-4-fluoro-2-(hydroxymethyl)pyrrolidin-1-yl]-4-oxo-1-(pyrazin-2-yl)-1,4-dihydroquinoline-3-carboxylate (216 mg, 483 μmol, 34%) yellow oil compound. MS (ESI): m/z 447.1 [M+H]+

Step 5: Synthesis of ethyl 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylate

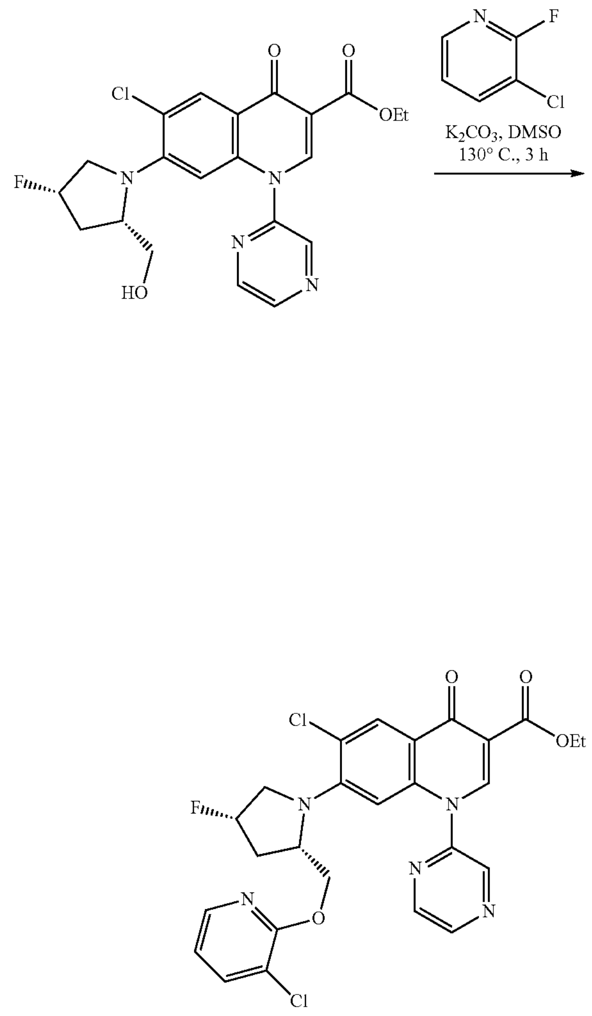

To a stirred solution of ethyl 6-chloro-7-[(2S,4S)-4-fluoro-2-(hydroxymethyl)pyrrolidin-1-yl]-4-oxo-1-(pyrazin-2-yl)-1,4-dihydroquinoline-3-carboxylate (200 mg, 362 μmol) in DMSO (5 mL) was added potassium carbonate (248 mg, 1.80 mmol) followed by 3-chloro-2-fluoropyridine (157 μL, 1.80 mmol) at room temperature. The reaction was then heated to 130° C. and stirred for 3 h. After completion of reaction, the reaction mixture was quenched with ice-cold water (10 mL) and extracted with EtOAc (2×50 mL). The combined organic layer was washed with brine solution (10 mL), dried over anhydrous sodium sulfate, concentrated under reduced pressure to afford the crude compound. The crude compound was purified by silica gel column chromatography using 2% MeOH in DCM as eluent to get ethyl 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylate (36.0 mg, 64.4 μmol, 26%) as yellow solid.

MS (ESI): m/z 558.2 [M+H]+

Step 6: Synthesis of 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid

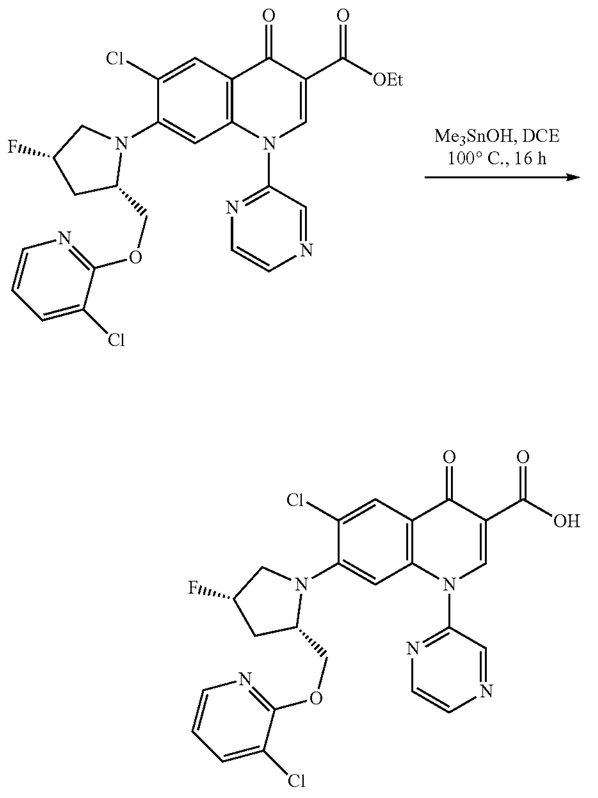

To a stirred solution of ethyl 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylate (100 mg, 109 μmol) in 1,2-dichloroethane (5 mL) and was added trimethyl tin hydroxide (196 mg, 1.08 mmol) at rt, then allowed to heated 100° C. stirred for 16 h. After completion of reaction, the reaction mixture was cooled to RT, quenched with ice-cold water (10 mL) and extracted with 5% MeOH in DCM (2×50 mL). The combined organic layer was washed with brine (10 mL), dried over anhydrous sodium sulfate, concentrated under reduced pressure to afford the crude compound. The crude compound was purified by prep HPLC purification to get 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid (39.6 mg, 74.6 μmol, 68%) as an off white solid.

Prep HPLC condition: Gemini, C-18 column, 250×21.2×5 μm, A: 0.1% formic acid buffer, B: ACN, 0/5, 20/50; diluent: MeOH/CAN. 1H NMR (400 MHz, DMSO-d6): δ 14.77 (brs, 1H), 9.11 (s, 1H), 8.92 (d, J=2.4 Hz, 1H), 8.89 (s, 1H), 8.77 (d, J=1.2 Hz, 1H), 8.20 (s, 1H), 7.89 (dd, J=4.8, 1.6 Hz, 1H), 7.70 (dd, J=7.6, 1.6 Hz, 1H), 6.95-6.92 (m, 1H), 6.65 (s, 1H), 5.46-5.32 (m, 1H), 4.93-4.91 (m, 1H), 4.45-4.41 (m, 1H), 4.31-4.27 (m, 1H), 3.94-3.87 (m, 1H), 3.62-3.52 (m, 1H), 2.55-2.37 (m, 1H), 2.19-2.05 (m, 1H); MS (ESI): m/z 530.2. [M+H]+

Potency Lin28a-dep Z11 $IC_{50}$ (μM)++++

Example 78: Synthesis of 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylic acid

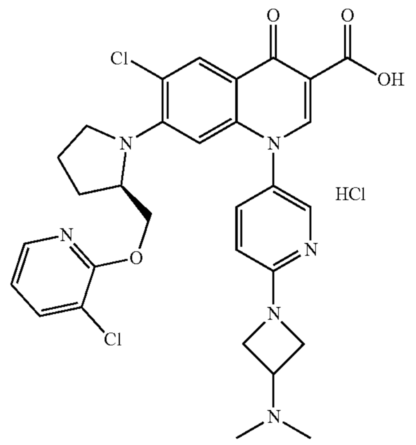 [SMILES: CN(C)C1CN(c2ccc(-n3cc(C(=O)O)c(=O)c4cc(Cl)c(N5CCC[C@@H]5COc5ncccc5Cl)cc43)cn2)C1 ; Cl]

Step 1: Synthesis of ethyl 6-chloro-7-[(2R)-2-{[(3-chloropyridin-2-yl)oxy]methyl}pyrrolidin-1-yl]-1-(6-chloropyridin-3-yl)-4-oxo-1,4-dihydroquinoline-3-carboxylate

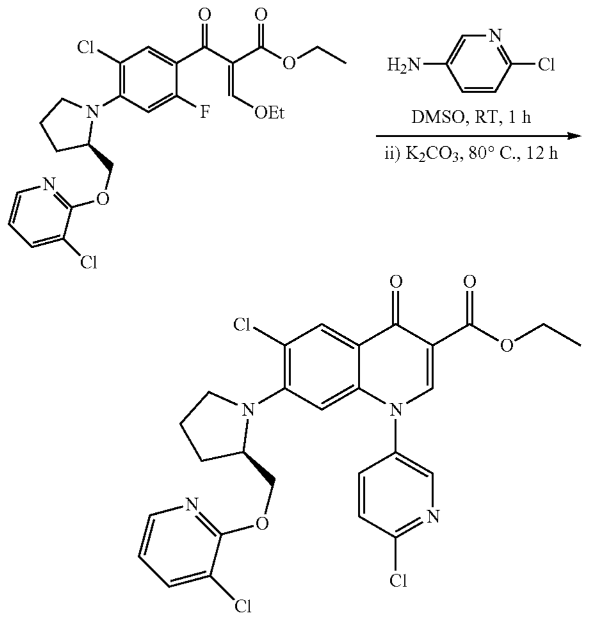

To a stirred solution of ethyl (2Z)-2-[(Z)-5-chloro-4-[(2R)-2-{[(3-chloropyridin-2-yl)oxy]methyl}pyrrolidin-1-yl]-2-fluorobenzoyl]-3-ethoxyprop-2-enoate (21 g, 41.0 mmol) in DMSO (70 mL), was added 6-chloropyridin-3-amine (5.27 g, 41.0 mmol) at room temperature and stirred for 1 h. After 1 h, potassium carbonate (8.49 g, 61.5 mmol) was added and the reaction mixture was heated at 80° C. for 12 h. The reaction mixture was cooled to room temperature and diluted with Ice cold water, resulting solid was filtered and dried under vacuum to afford crude compound. The crude compound was soluble in 10% Methanol-DCM (250 mL) and treated with char-coal (5 g) stirred for 40 min and filtered through celite pad and concentrated under reduced pressure obtained solid was triturated with n-pentane and MTBE (2×40 mL) and solid dried under high vaccum to afford ethyl 6-chloro-7-[(2R)-2-{[(3-chloropyridin-2-yl)oxy]methyl}pyrrolidin-1-yl]-1-(6-chloropyridin-3-yl)-4-oxo-1,4-dihydroquinoline-3-carboxylate (12.2 g, 52%) as yellow solid. MS (ESI): m/z 579.4 [M+H]+

Step 2: Synthesis of ethyl 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylate

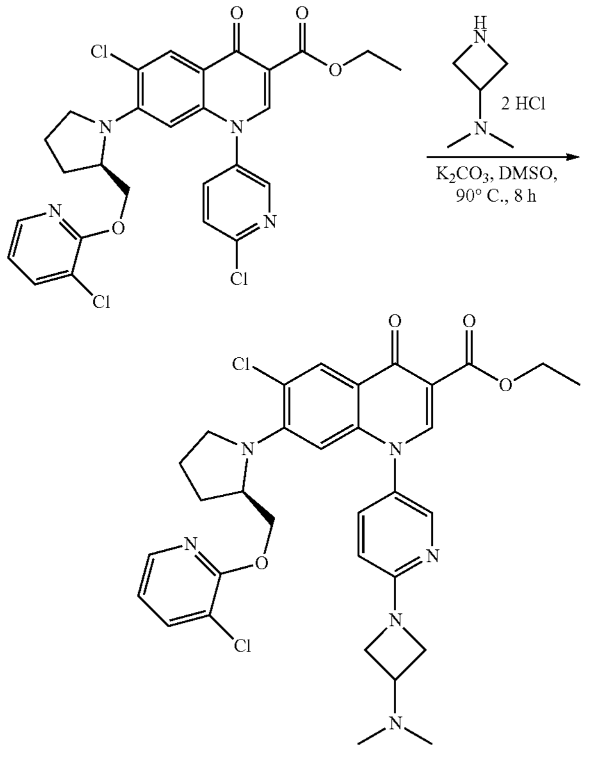

To a stirred solution of N,N-dimethylazetidin-3-amine dihydrochloride (2.87 g, 16.6 mmol) in DMSO (50 mL), was added potassium carbonate (2.87 g, 20.8 mmol) at 0° C. and stirred for 5 min, followed by addition of ethyl 6-chloro-7-[(2R)-2-{[(3-chloropyridin-2-yl)oxy]methyl}pyrrolidin-1-yl]-1-(6-chloropyridin-3-yl)-4-oxo-1,4-dihydroquinoline-3-carboxylate (8 g, 13.9 mmol). The reaction was then heated to 90° C. and stirred for 8 h. The reaction mixture was quenched with ice-cold water and extracted with EtOAc (2×150 mL). The combined organic layer was washed with water (80 mL), brine solution (80 mL), dried over anhydrous sodium sulfate, and concentrated under reduced pressure. The crude compound was washed with 20% acetone in MTBE (3×50 mL) and dried under vacuum to afford ethyl 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylate (6.97 g, 78%) as pale brown solid. MS (ESI): m/z 637.1 [M+H]+

Step 3: Synthesis of 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylic acid hydrochloride

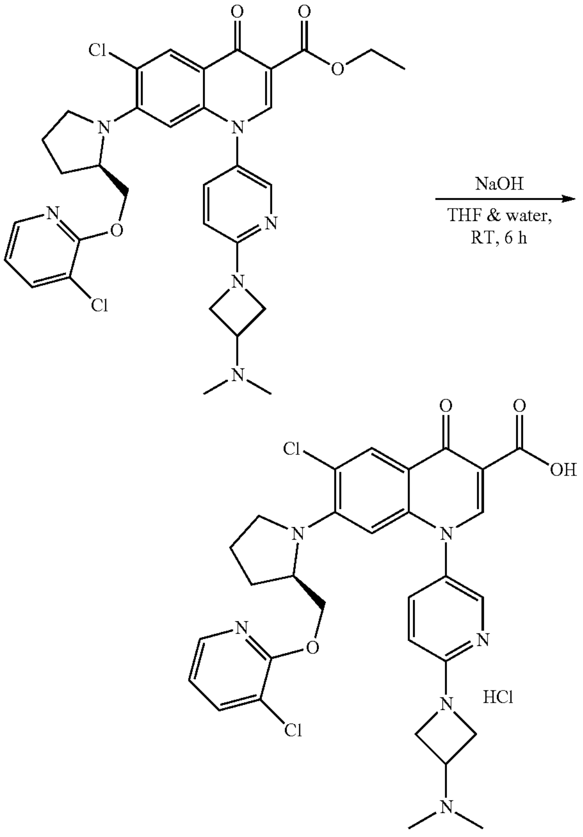

To a stirred solution of ethyl 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylate (17 g, 26.6 mmol) in THF: Water (1:1, 200 mL), was added sodium hydroxide (3.19 g, 79.8 mmol) at 0° C. and the reaction mixture was stirred at room temperature for 6 h. The reaction mixture was concentrated under reduced pressure and reaction mass re-cooled with ice-bath, diluted with water (30 mL), pH was adjusted to 4-5 by using 1N HCl, and extracted with 10% MeOH in DCM (2×250 mL), Organic layer was washed with brine (100 mL) dried over sodium sulphate. and Concentrated under reduced pressure to get crude. crude was washed with 50% acetone in MTBE (3×50 mL) and dried under vacuum and lyophilization to afford 6-chloro-7-[(2R)-2-{[(3-chloropyridin-2-yl)oxy]methyl}pyrrolidin-1-yl]-1-{6-[3-(dimethylamino)azetidin-1-yl]pyridin-3-yl}-4-oxo-1,4-dihydroquinoline-3-carboxylic acid (9.76 g, 60%) as pale brown solid. Compound is in the form of hydrochloride salt. $^1$H NMR (400 MHz, DMSO-$d_6$) δ 15.07 (s, 1H), 11.00 (s, 1H), 8.51 (d, J=8.4 Hz, 1H), 8.31 (s, 1H), 8.15 (s, 1H), 7.90-7.89 (m, 1H), 7.82-7.74 (m, 2H), 6.96-6.92 (m, 1H), 6.66-6.46 (m, 1H), 6.37-6.36 (m, 1H), 4.77-4.68 (m, 1H), 4.35-4.25 (m, 7H), 3.52-3.46 (m, 1H), 3.18-3.16 (m, 1H), 2.75 (bs, 6H), 2.26-2.24 (m, 1H), 1.96-1.90 (m, 2H), 1.82-1.78 (m, 1H); MS (ESI): m/z 609.3 $[M+H]^+$.

Potency Lin28a-dep Z11 $IC_{50}$ (μM)++++

The following compounds were synthesized according to procedures similar to those described in Examples 1-78.

TABLE 1

| Compound | Product | Prep HPLC Method | IUPAC name | Analytical data | Potency Lin28a-dep Z11 $IC_{50}$ (μM) |
|---|---|---|---|---|---|
| 79. | 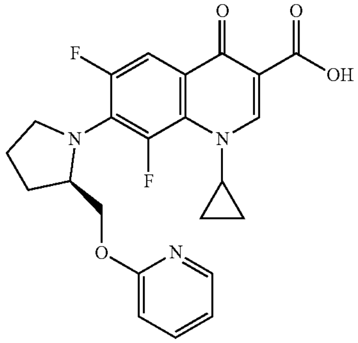 [SMILES: O=C(O)c1cn(C2CC2)c2c(F)c(N3CCC[C@@H]3COc3ccccn3)c(F)cc2c1=O] | Column: XSelect CSH Prep C18 OBD Column, 5 um, 19*150 mm; Mobile Phase A: Water (0.1% FA), Mobile Phase B: acetonitrile; Flow rate: 25 mL/min; Gradient: 52 B to 60 B in 8 min; 254/220 nm. | (R)-1-cyclopropyl-6,8-difluoro-4-oxo-7-(2-((pyridin-2-yloxy)methyl) pyrrolidin-1-yl)-1,4-dihydro-quinoline-3-carboxylic acid | LCMS (ESI): $[M + H]^+$: 442.1 $^1$H NMR (400 MHz, DMSO-$d_6$) δ 14.92 (s, 1H), 8.63 (s, 1H), 7.98-7.92 (m, 1H), 7.75-7.67 (m, 1H), 7.62-7.54 (m, 1H), 6.92-6.85 (m, 1H), 6.52 (d, J = 8.3 Hz, 1H), 4.67-4.58 (m, 1H), 4.43-4.35 (m, 1H), 4.33-4.25 (m, 1H), 4.10-4.02 (m, 1H), 3.90-3.79 (m, 1H), 3.48-3.40 (m, 1H), 2.32-3.23 (m, 1H), 2.09-2.01 (m, 1H), 1.95-1.78 (m, 2H), 1.21-1.03 (m, 4H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 80. | 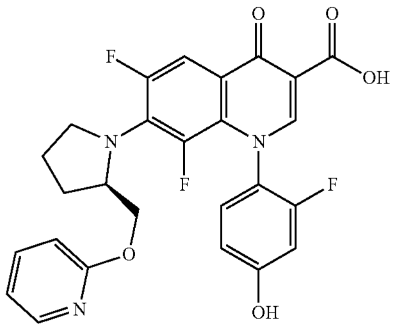 [SMILES: O=C(O)c1cn(-c2ccc(O)cc2F)c2c(F)c(N3CCC[C@@H]3COc3ccccn3)c(F)cc2c1=O] | (Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 50 B to 55 B in 12 min; 254/220 nm; RT1: 10.05; RT2:; Injection Volumn: ml; Number Of Runs:;) | (R)-6,8-difluoro-1-(2-fluoro-4-hydroxy-phenyl)-4-oxo-7-(2-((pyridin-2-yloxy)methyl)pyrrolidin-1-yl)-1,4-dihydro-quinoline-3-carboxylic acid | LCMS (ESI) $[M + H]^+$: 512.2 $^1H$ NMR (300 MHz, DMSO-$d_6$) δ 14.75 (s, 1H), 10.48 (s, 1H), 8.46 (s, 1H), 7.95 (m, 1H), 7.78 (d, J = 13.1 Hz, 1H), 7.55 (m, 2H), 6.94-6.85 (m, 1H), 6.84-6.63 (m, 2H), 6.46 (d, J = 8.3 Hz, 1H), 4.58-4.38 (m, 1H), 4.22 (m, 2H), 3.77-3.57 (m, 1H), 3.30-3.17 (m, 1H), 2.25-2.10 (m, 1H), 1.94 (m, 1H), 1.75 (m, 2H). | +++ |
| a | 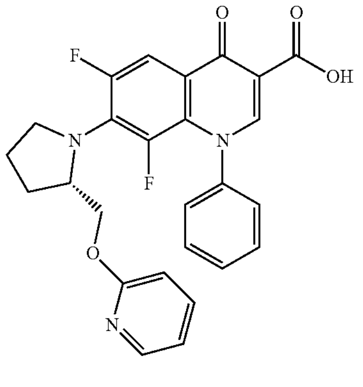 [SMILES: O=C(O)c1cn(-c2ccccc2)c2c(F)c(N3CCC[C@H]3COc3ccccn3)c(F)cc2c1=O] | (Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 15 B to 42 B in 12 min; 254/220 nm; RT1: 10.27; RT2:; Injection Volumn: ml; Number Of Runs:;) | (S)-6,8-difluoro-4-oxo-1-phenyl-7-(2-((pyridin-2-yloxy)methyl)pyrrolidin-1-yl)-1,4-dihydro-quinoline-3-carboxylic acid | LCMS (ESI) $[M + H]^+$: 478.1 $^1H$ NMR (300 MHz, DMSO-$d_6$) δ 14.90 (s, 1H), 8.39 (s, 1H), 8.03-7.93 (m, 1H), 7.88-7.75 (m, 1H), 7.73-7.33 (m, 6H), 6.97-6.88 (m, 1H), 6.50 (d, J = 8.3 Hz, 1H), 4.42 (s, 1H), 4.37-4.24 (m, 1H), 4.24-4.11 (m, 1H), 3.61 (s, 1H), 2.17 (s, 1H), 1.93 (s, 1H), 1.77 (d, J = 16.8 Hz, 2H). | ++ |
| 81. | 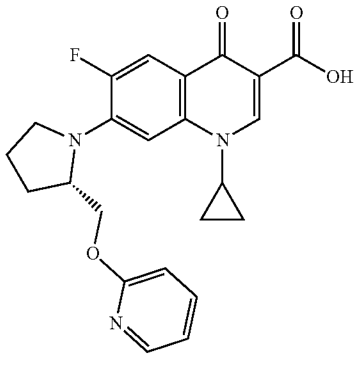 [SMILES: O=C(O)c1cn(C2CC2)c2cc(N3CCC[C@H]3COc3ccccn3)c(F)cc2c1=O] | (Column: SunFire C18 OBD Prep Column, , 100Å, 5 μm, 19 mm X 250 mm; Mobile Phase A: Water (0.05% FA), Mobile Phase B: ACN; Flow rate: 25 mL/min; Gradient: 30 B to 41 B in 12 min; 254/220 nm; RT1: 10.07; RT2:; Injection Volumn: ml; Number Of Runs:;) | (S)-1-cyclopropyl-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 424.1 $^1H$ NMR (300 MHz, DMSO-$d_6$) δ 15.48 (s, 1H), 8.59 (s, 1H), 8.10-8.02 (m, 1H), 7.84 (d, J = 14.6 Hz, 1H), 7.75-7.62 (m, 1H), 7.26 (d, J = 7.6 Hz, 1H), 7.02-6.89 (m, 1H), 6.80-6.72 (m, 1H), 4.66 (s, 1H), 4.55-4.40 (m, 1H), 4.39-4.23 (m, 1H), 3.83-3.62 (m, 2H), 3.54 (d, J = 9.4 Hz, 1H), 2.24-1.81 (m, 4H), 1.42-0.98 (m, 4H). | ++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 82. | 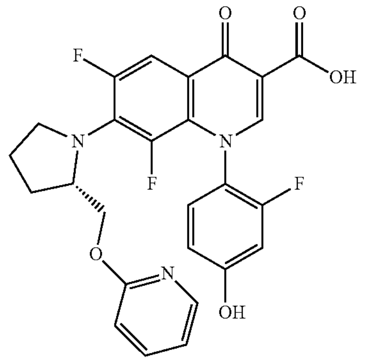 [SMILES: O=C(O)c1cn(-c2ccc(O)cc2F)c2c(F)c(N3CCC[C@H]3COc3ccccn3)c(F)cc2c1=O] | (Column: Xcelect CSH F-pheny OBD Column, 19*250 mm, 5 um; Mobile Phase A: Water (0.05% FA), Mobile Phase B: ACN; Flow rate: 25 mL/min; Gradient: 44 B to 74 B in 8 min; 254/220 nm; RT1: 7.35; RT2:; Injection Volumn: ml; Number Of Runs:;) | (S)-6,8-difluoro-1-(2-fluoro-4-hydroxy-phenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 512.2 $^1H$ NMR (400 MHz, DMSO-$d_6$) δ 14.77 (s, 1H), 10.49 (s, 1H), 8.47 (d, J = 1.4 Hz, 1H), 8.01-7.89 (m, 1H), 7.79 (d, J = 13.1 Hz, 1H), 7.65-7.47 (m, 2H), 6.95-6.86 (m, 1H), 6.84-6.66 (m, 2H), 6.46 (d, J = 8.3 Hz, 1H), 4.47 (s, 1H), 4.31-4.16 (m, 2H), 3.66 (s, 1H), 3.31 (s, 1H), 2.18 (s, 1H), 1.93 (d, J = 12.5 Hz, 1H), 1.75 (s, 2H). | ++ |
| 83. | 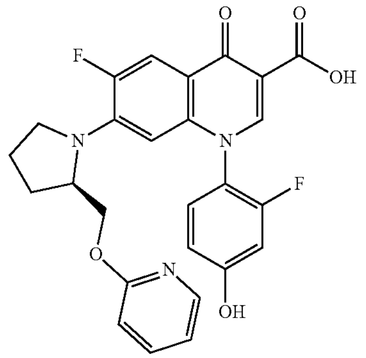 [SMILES: O=C(O)c1cn(-c2ccc(O)cc2F)c2cc(N3CCC[C@@H]3COc3ccccn3)c(F)cc2c1=O] | (Column: Xcelect CSH F-pheny OBD Column, 19*250 mm, 5 um; Mobile Phase A: Water (0.05% FA), Mobile Phase B: ACN; Flow rate: 25 mL/min; Gradient: 44 B to 74 B in 8 min; 254/220 nm; RT1: 7.35; RT2:; Injection Volumn: ml; Number Of Runs:;) | (R)-6-fluoro-1-(2-fluoro-4-hydroxy-phenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 495.2 $^1H$ NMR (300 MHz, DMSO-$d_6$) δ 15.30 (s, 1H), 10.62 (s, 1H), 8.60 (d, J = 1.6 Hz, 1H), 8.13-8.00 (m, 1H), 7.89 (d, J = 14.5 Hz, 1H), 7.73-7.62 (m, 1H), 7.62-7.44 (m, 1H), 7.00-6.82 (m, 2H), 6.74-6.62 (m, 2H), 6.04 (t, J = 7.3 Hz, 1H), 4.40 (s, 1H), 4.21 (d, J = 6.6 Hz, 2H), 3.40 (s, 1H), 3.22 (s, 1H), 2.15-1.83 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 84. | 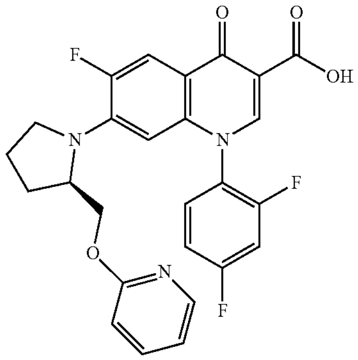 [SMILES: O=C(O)c1cn(-c2ccc(F)cc2F)c2cc(N3CCC[C@@H]3COc3ccccn3)c(F)cc2c1=O] | (Column: Xcelect CSH F-pheny OBD Column, 19*250 mm, 5 um; Mobile Phase A: Water (0.05% FA), Mobile Phase B: ACN; Flow rate: 25 mL/min; Gradient: 44 B to 74 B in 8 min; 254/220 nm; RT1: 7.35; RT2:; Injection Volumn: ml; Number Of Runs:;) | (R)-1-(2,4-difluorophenyl)-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 496.1 $^1H$ NMR (300 MHz, DMSO-$d_6$) δ 15.24 (d, J = 2.0 Hz, 1H), 8.75 (d, J = 3.7 Hz, 1H), 8.17-8.02 (m, 1H), 7.99-7.80 (m, 2H), 7.78-7.61 (m, 2H), 7.48-7.33 (m, 1H), 7.23-7.09 (m, 1H), 7.01-6.91 (m, 1H), 6.73-6.63 (m, 1H), 5.96 (dd, J = 7.3, 4.8 Hz, 1H), 4.37 (s, 1H), 4.29-4.08 (m, 2H), 3.44 (s, 1H), 3.25 (s, 1H), 2.15-1.84 (m, 4H). | ++++ |
| 85. | 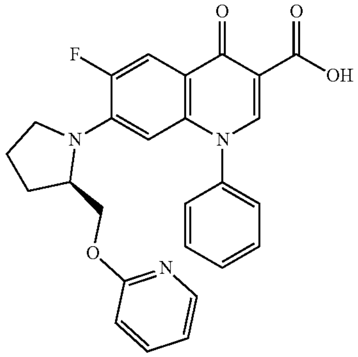 [SMILES: O=C(O)c1cn(-c2ccccc2)c2cc(N3CCC[C@@H]3COc3ccccn3)c(F)cc2c1=O] | (Column: Xcelect CSH F-pheny OBD Column, 19*250 mm, 5 um; Mobile Phase A: Water (0.05% FA), Mobile Phase B: ACN; Flow rate: 25 mL/min; Gradient: 44 B to 74 B in 8 min; 254/220 nm; RT1: 7.35; RT2:; Injection Volumn: ml; Number Of Runs:;) | (R)-6-fluoro-4-oxo-1-phenyl-7-(2-((pyridin-2-yloxy)methyl) pyrrolidin-1-yl)-1,4-dihydro-quinoline-3-carboxylic acid | LCMS (ESI) $[M + H]^+$: 460.2 $^1H$ NMR (300 MHz, DMSO-$d_6$) δ 15.41 (s, 1H), 8.52 (s, 1H), 8.09-7.99 (m, 1H), 7.91 (d, J = 14.5 Hz, 1H), 7.77-7.52 (m, 5H), 7.45 (t, J = 7.7 Hz, 1H), 7.03-6.88 (m, 1H), 6.72-6.62 (m, 1H), 6.05 (d, J = 7.5 Hz, 1H), 4.33 (s, 1H), 4.26-4.04 (m, 2H), 3.18 (d, J = 6.7 Hz, 2H), 2.11-1.86 (m, 4H). | ++++ |
| 86. | 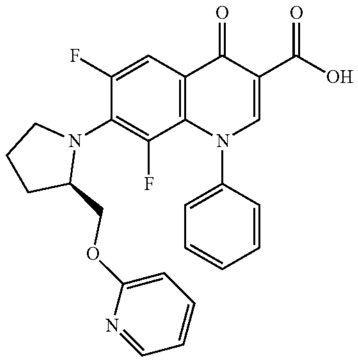 [SMILES: O=C(O)c1cn(-c2ccccc2)c2c(F)c(N3CCC[C@@H]3COc3ccccn3)c(F)cc2c1=O] | (Column: XBridge Shield RP18 OBD Column, 5 um, 19*150 mm; Mobile Phase A: Water (0.05% FA), Mobile Phase B: ACN; Flow rate: 25 mL/min; Gradient: 60% B to 90% B in 8 min; 254/220 nm; Rt: 7.31 min) | (R)-6,8-difluoro-4-oxo-1-phenyl-7-(2-((pyridin-2-yloxy)methyl) pyrrolidin-1-yl)-1,4-dihydro-quinoline-3-carboxylic acid | LCMS (ESI) $[M + H]^+$: 478.3 $^1H$ NMR (300 MHz, DMSO-$d_6$) δ 14.90 (s, 1H), 8.39 (s, 1H), 7.97 (d, J = 4.9 Hz, 1H), 7.80 (d, J = 13.1 Hz, 1H), 7.56 (s, 6H), 6.92 (d, J = 6.0 Hz, 2H), 6.50 (d, J = 8.2 Hz, 1H), 4.42 (s, 1H), 4.35-4.23 (m, 1H), 4.17 (s, 1H), 3.56 (d, J = 30.4 Hz, 1H), 2.17 (s, 1H), 1.93 (s, 1H), 1.74 (s, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 87. | 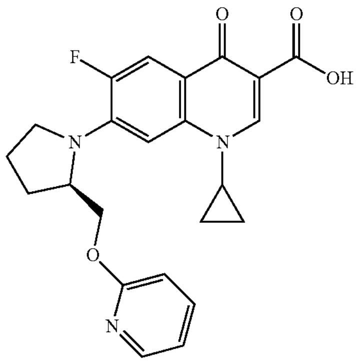 [SMILES: O=C(O)c1cn(C2CC2)c2cc(N3CCC[C@@H]3COc3ccccn3)c(F)cc2c1=O] | (Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min) | (R)-1-cyclopropyl-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 424.3. $^1H$ NMR (300 MHz, DMSO-$d_6$) δ 15.48 (s, 1H), 8.57 (s, 1H), 8.06 (d, J = 5.0, 1.9 Hz, 1H), 7.81 (d, J = 14.6 Hz, 1H), 7.67 (s, 1H), 7.24 (d, J = 7.5 Hz, 1H), 7.04-6.84 (m, 1H), 6.75 (d, J = 8.3 Hz, 1H), 4.65 (s, 1H), 4.45 (d, J = 11.0, 4.0 Hz, 1H), 4.39-4.15 (m, 1H), 3.73 (s, 2H), 3.53 (d, J = 9.3 Hz, 1H), 2.30-1.93 (m, 4H), 1.24 (d, J = 6.7 Hz, 2H), 1.18-0.95 (m, 2H). | +++ |
| 88. | 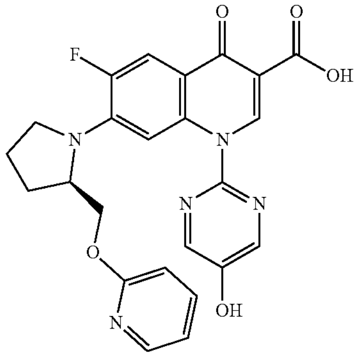 [SMILES: O=C(O)c1cn(-c2ncc(O)cn2)c2cc(N3CCC[C@@H]3COc3ccccn3)c(F)cc2c1=O] | (Column: Kinetex EVO C18 Column, 21.2*150, 5 um; Mobile Phase A: Water (0.05% FA), Mobile Phase B: ACN; Flow rate: 25 mL/min; Gradient: 15 B to 30 B in 8 min; 254 nm; RT1: 6.97; RT2:; Injection Volumn: ml; Number Of Runs:;) | (R)-6-fluoro-1-(5-hydroxy-pyrimidin-2-yl)-4-oxo-7-(2-((pyridin-2-yloxy)methyl) pyrrolidin-1-yl)-1,4-dihydro-quinoline-3-carboxylic acid | LCMS (ESI) $[M + H]^+$: 478.10. $^1H$ NMR (300 MHz, DMSO-$d_6$) δ 8.94 (s, 1H), 8.39-8.28 (m, 2H), 8.07-7.97 (m, 1H), 7.87 (d, J = 14.5 Hz, 1H), 7.71-7.61 (m, 1H), 6.99-6.83 (m, 2H), 6.70 (d, J = 8.3 Hz, 1H), 4.49-4.17 (m, 3H), 3.63-3.49 (m, 2H), 2.10-1.84 (m, 4H). | +++ |
| 89. | 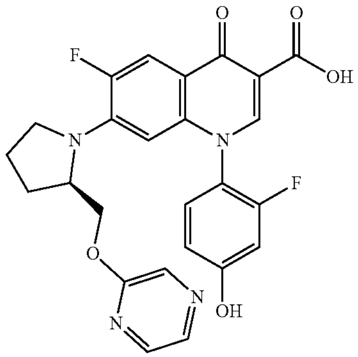 [SMILES: O=C(O)c1cn(-c2ccc(O)cc2F)c2cc(N3CCC[C@@H]3COc3cnccn3)c(F)cc2c1=O] | Column: XBridge Prep C18 OBD Column, 5 um, 19*150 mm; Mobile Phase A: Water (10 MMOL/L $NH_4HCO_3$), Mobile Phase B: acetonitrile; Flow rate: 25 mL/min; Gradient: 21 B to 35 B in 12 min; 254 nm. | (R)-6-fluoro-1-(2-fluoro-4-hydroxy-phenyl)-4-oxo-7-(2-((pyrazin-2-yloxy)methyl) pyrrolidin-1-yl)-1,4-dihydro-quinoline-3-carboxylic acid | LCMS (ESI): $[M + H]^+$: 495.3. $^1H$ NMR (300 MHz, DMSO-$d_6$) δ 14.89 (s, 1H), 10.72 (s, 1H), 8.74-8.49 (m, 1H), 8.15-7.75 (m, 4H), 7.65-7.46 (m, 1H), 6.96-6.79 (m, 2H), 6.68-6.48 (m, 1H), 4.42 (s, 1H), 4.21-4.01 (m, 2H), 3.60-3.48 (m, 1H), 3.30-3.21 (m, 1H), 2.129-1.93 (m, 4H). | ++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 90. | 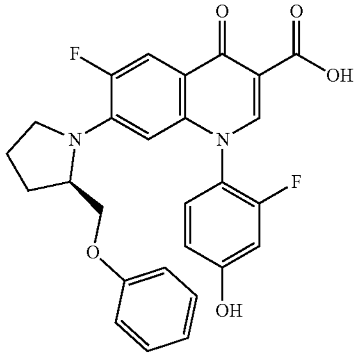 [SMILES: O=C(O)c1cn(-c2ccc(O)cc2F)c2cc(N3CCC[C@@H]3COc3ccccc3)c(F)cc2c1=O] | (Column: XBridge Shield RP18 OBD Column,, 5 um, 19*150 mm; Mobile Phase A: Water (0.05% FA), Mobile Phase B: ACN; Flow rate: 25 mL/min; Gradient: 41 B to 69 B in 10 min; 254 nm; RT1: 8.93; RT2:; Injection Volumn: ml; Number Of Runs:;) | (R)-6-fluoro-1-(2-fluoro-4-hydroxy-phenyl)-4-oxo-7-(2-(phenoxy-methyl) pyrrolidin-1-yl)-1,4-dihydro-quinoline-3-carboxylic acid | LCMS (ESI) $[M + H]^+$: 493.30. $^1H$ NMR (400 MHz, DMSO-$d_6$) δ 15.27 (s, 1H), 10.62 (s, 1H), 8.61 (d, J = 4.1 Hz, 1H), 7.91 (d, J = 14.4 Hz, 1H), 7.56 (q, J = 8.5 Hz, 1H), 7.7-7.23 (m, 2H), 6.95-6.82 (m, 1H), 6.94-6.79 (m, 4H), 6.09 (t, J = 7.9 Hz, 1H), 4.39 (s, 1H), 3.97-3.90 (m, 1H), 3.86 (t, J = 8.4 Hz, 1H), 3.43 (s, 1H), 3.24 (d, J = 8.6 Hz, 1H), 2.21-1.86 (m, 4H). | + |
| 91. | 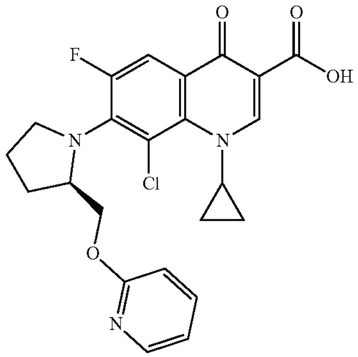 [SMILES: O=C(O)c1cn(C2CC2)c2c(Cl)c(N3CCC[C@@H]3COc3ccccn3)c(F)cc2c1=O] | (Column: XSelect CSH Prep C18 OBD Column,, 5 um, 19*150 mm; Mobile Phase A: Water (0.1% FA), Mobile Phase B: ACN; Flow rate: 25 mL/min; Gradient: 38 B to 53 B in 10 min; 254/220 nm; RT1: 9.42; RT2:; Injection Volumn: ml; Number Of Runs:;) | (R)-8-chloro-1-cyclopropyl-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 458.1. $^1H$ NMR (300 MHz, DMSO-$d_6$) δ 14.73 (s, 1H), 8.81 (s, 1H), 7.97 (d, J = 4.8 Hz, 1H), 7.83 (d, J = 12.7 Hz, 1H), 7.55 (m, 1H), 6.96-6.82 (m, 1H), 6.39 (d, J = 8.4 Hz, 1H), 4.78-4.59 (m, 1H), 4.50-4.23 (m, 2H), 4.20-4.07 (m, 1H), 3.97 (dd, J = 12.1, 4.6 Hz, 1H), 3.26-3.14 (m, 1H), 2.32-2.22 (m, 1H), 2.14-2.03 (m, 1H), 1.99-1.71 (m, 2H), 1.31-1.21 (m, 1H), 1.16-0.92 (m, 2H), 0.87-0.75 (m, 1H). | ++ |
| 92. | 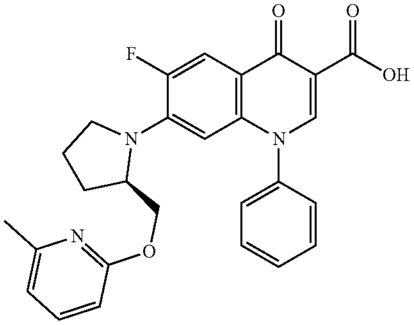 [SMILES: Cc1cccc(OC[C@H]2CCCN2c2cc3c(cc2F)c(=O)c(C(=O)O)cn3-c2ccccc2)n1] | (Column: Gemini-NX C18 AXAI Packed, 21.2*150 mm 5 um; Mobile Phase A: Water (0.05% FA), Mobile Phase B: ACN; Flow rate: 25 mL/min; Gradient: 50 B to 52 B in 12 min; 254 nm; RT1: 11.67; RT2:; Injection Volumn: ml; Number Of Runs:;). | (R)-6-fluoro-7-(2-(((6-methyl-pyridin-2-yl)oxy)methyl) pyrrolidin-1-yl)-4-oxo-1-phenyl-1,4-dihydro-quinoline-3-carboxylic acid | LCMS (ESI) $[M + H]^+$: 474.1. $^1H$ NMR (300 MHz, DMSO-$d_6$) δ 15.43 (s, 1H), 8.52 (s, 1H), 7.90 (d, J = 14.5 Hz, 1H), 7.73-7.65 (m, 1H), 7.65-7.56 (m, 3H), 7.52 (dd, J = 8.2, 7.2 Hz, 1H), 7.49-7.39 (m, 1H), 6.79 (d, J = 7.2 Hz, 1H), 6.43 (d, J = 8.2 Hz, 1H), 5.96 (d, J = 7.5 Hz, 1H), 4.32 (m, 1H), 4.26-4.10 (m, 2H), 3.29-3.21 (m, 1H), 3.20-3.06 (m, 1H), 2.22 (s, 3H), 2.09-1.80 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 93. | 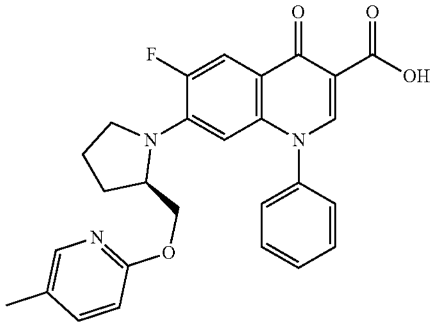 [SMILES: Cc1ccc(OC[C@H]2CCCN2c2cc3c(cc2F)c(=O)c(C(=O)O)cn3-c2ccccc2)nc1] | (Column: XSelect CSH Prep C18 OBD Column, 5 um, 19*150 mm; Mobile Phase A: Water (0.05% FA), Mobile Phase B: ACN; Flow rate: 25 mL/min; Gradient: 50 B to 70 B in 8 min; 254 nm; RT1: 8.13; RT2:; Injection Volumn: ml; Number Of Runs:;) | (R)-6-fluoro-7-(2-(((5-methyl-pyridin-2-yl)oxy)methyl) pyrrolidin-1-yl)-4-oxo-1-phenyl-1,4-dihydro-quinoline-3-carboxylic acid | LCMS (ESI) $[M + H]^+$: 474.1. $^1H$ NMR (300 MHz, DMSO-$d_6$) δ 15.42 (s, 1H), 8.52 (s, 1H), 7.89 (d, J = 14.5 Hz, 1H), 7.86-7.82 (m, 1H), 7.76-7.56 (m, 4H), 7.55-7.37 (m, 2H), 6.57 (d, J = 8.3 Hz, 1H), 6.05 (d, J = 7.5 Hz, 1H), 4.37-4.25 (m, 1H), 4.22-4.04 (m, 2H), 3.32 (s, 1H), 3.24-3.10 (m, 1H), 2.19 (s, 3H), 2.08-1.78 (m, 4H). | ++++ |
| 94. | 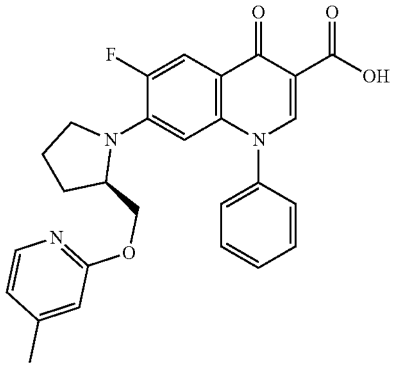 [SMILES: Cc1ccnc(OC[C@H]2CCCN2c2cc3c(cc2F)c(=O)c(C(=O)O)cn3-c2ccccc2)c1] | (Column: Gemini-NX C18 AXAI Packed, 21.2*150 mm 5 um; Mobile Phase A: Water (0.05% FA), Mobile Phase B: ACN; Flow rate: 25 mL/min; Gradient: 35 B to 67 B in 14 min; 254 nm; RT1: 13.63; RT2:; Injection Volumn: ml; Number Of Runs:;) | (R)-6-fluoro-7-(2-(((4-methyl-pyridin-2-yl)oxy)methyl) pyrrolidin-1-yl)-4-oxo-1-phenyl-1,4-dihydro-quinoline-3-carboxylic acid | LCMS (ESI) $[M + H]^+$: 474.20. $^1H$ NMR (400 MHz, DMSO-$d_6$) δ 15.43 (s, 1H), 8.53 (s, 1H), 7.95-7.85 (m, 2H), 7.72-7.56 (m, 4H), 7.47 (t, J = 7.7 Hz, 1H), 6.83-6.77 (m, 1H), 6.47 (s, 1H), 6.03 (d, J = 7.4 Hz, 1H), 4.32 (s, 1H), 4.25-4.17 (m, 1H), 4.15-4.08 (m, 1H), 3.41-3.38 (m, 1H). 3.16 (d, J = 8.5 Hz, 1H), 2.24 (s, 3H), 2.10-1.97 (m, 2H), 1.94-1.82 (m, 2H). | ++++ |
| 95. | 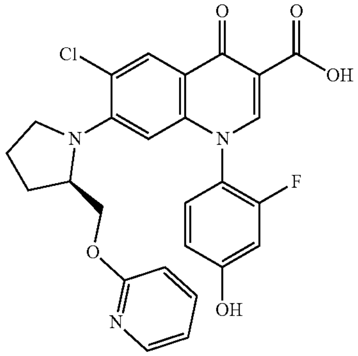 [SMILES: O=C(O)c1cn(-c2ccc(O)cc2F)c2cc(N3CCC[C@@H]3COc3ccccn3)c(Cl)cc2c1=O] | (Column: XSelect CSH Prep C18 OBD Column,, 5 um, 19*150 mm; Mobile Phase A: Water (0.05% FA), Mobile Phase B: ACN; Flow rate: 25 mL/min; Gradient: 50 B to 70 B in 8 min; 254 nm; RT1: 6.07; RT2:; Injection Volumn: ml; Number Of Runs:;) | (R)-6-chloro-1-(2-fluoro-4-hydroxy-phenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 510.1. $^1H$ NMR (300 MHz, DMSO-$d_6$) δ 15.02 (s, 1H), 8.64 (d, J = 3.9 Hz, 1H), 8.18 (d, J = 1.1 Hz, 1H), 8.04-7.96 (m, 1H), 7.70-7.59 (m, 1H), 7.58-7.44 (m, 1H), 6.98-6.82 (m, 2H), 6.67-6.52 (m, 2H), 6.30 (d, J = 11.6 Hz, 1H), 4.54-4.42 (m, 1H), 4.21 (dd, J = 10.7, 4.0 Hz, 1H), 4.15-4.05 (m, 1H), 3.63-3.54 (m, 1H), 3.27-3.17 (m, 1H), 2.29-2.15 (m, 1H), 1.97 (dd, J = 8.8, 3.3 Hz, 1H), 1.90-1.69 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 96. | 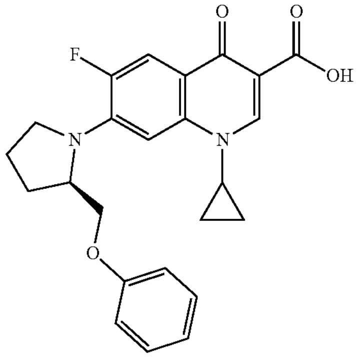 [SMILES: O=C(O)c1cn(C2CC2)c2cc(N3CCC[C@@H]3COc3ccccc3)c(F)cc2c1=O] | (Column: Gemini-NX C18 AXAI Packed, 21.2*150 mm 5 um; Mobile Phase A: Water (0.05% FA), Mobile Phase B: ACN; Flow rate: 25 mL/min; Gradient: 35 B to 74 B in 10 min; 254 nm; RT1: 8; RT2:; Injection Volumn: ml; Number Of Runs:;) | (R)-1-cyclopropyl-6-fluoro-4-oxo-7-(2-(phenoxy-methyl) pyrrolidin-1-yl)-1,4-dihydro-quinoline-3-carboxylic acid | LCMS (ESI) $[M + H]^+$: 423.15. $^1H$ NMR (300 MHz, DMSO-$d_6$) δ 15.48 (s, 1H), 8.58 (s, 1H), 7.84 (d, J = 14.6 Hz, 1H), 7.25 (t, J = 7.7 Hz, 3H), 6.92 (t, J = 7.4 Hz, 3H), 4.72-4.55 (m, 1H), 4.16-4.06 (m, 1H), 4.05-3.94 (m, 1H), 3.85-3.65 (m, 2H), 3.62-3.47 (m, 1H), 2.33-1.87 (m, 4H), 1.29-1.06 (m, 4H). | + |
| 97. | 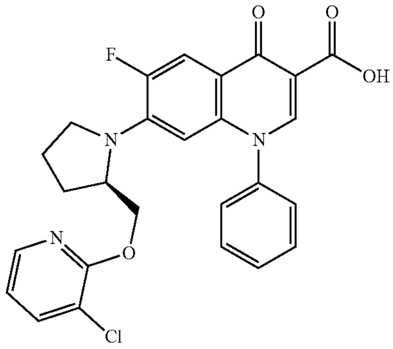 [SMILES: O=C(O)c1cn(-c2ccccc2)c2cc(N3CCC[C@@H]3COc3ncccc3Cl)c(F)cc2c1=O] | Column: Column: SunFire C18 OBD Prep Column, 19 mm X 250 mm; Mobile Phase A: Water (0.05% FA), Mobile Phase B: acetonitrile; Flow rate: 25 mL/min; Gradient: 45 B to 83 B in 12 min; 254 nm. | (R)-7-(2-(((3-chloro-pyridin-2-yl)oxy) methyl) pyrrolidin-1-yl)-6-fluoro-4-oxo-1-phenyl-1,4-dihydro-quinoline-3-carboxylic acid | LCMS (ESI) $[M + H]^+$: 494.05. $^1H$ NMR (400 MHz, DMSO-$d_6$) δ 15.40 (s, 1H), 8.52 (s, 1H), 8.02-7.97 (m, 1H), 7.93-7.83 (m, 2H), 7.73-7.47 (m, 4H), 7.55-7.47 (m, 1H), 7.03-6.98 (m, 1H), 6.02 (d, J = 7.4 Hz, 1H), 4.44 (s, 1H), 4.34-4.27 (m, 2H), 3.32-3.29 (m, 1H), 3.21-3.10 (m, 1H), 2.18-2.01 (m, 2H), 2.00-1.83 (m, 2H). | ++++ |
| 98. | 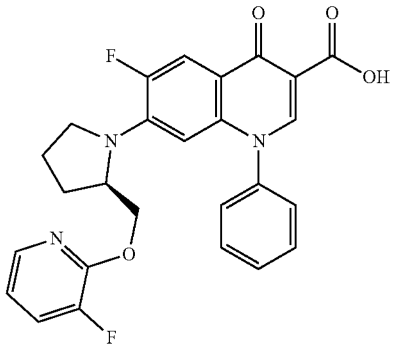 [SMILES: O=C(O)c1cn(-c2ccccc2)c2cc(N3CCC[C@@H]3COc3ncccc3F)c(F)cc2c1=O] | Trituration | (R)-6-fluoro-7-(2-(((3-fluoropyridin-2-yl)oxy) methyl) pyrrolidin-1-yl)-4-oxo-1-phenyl-1,4-dihydro-quinoline-3-carboxylic acid | LCMS (ESI) $[M + H]^+$: 478.10. $^1H$ NMR (300 MHz, DMSO-$d_6$) δ 15.41 (s, 1H), 8.52 (s, 1H), 7.95-7.81 (m, 2H), 7.75-7.54 (m, 5H), 7.45 (t, J = 7.6 Hz, 1H), 7.07-6.96 (m, 1H), 6.01 (d, J = 7.4 Hz, 1H), 4.45-4.36 (m, 1H), 4.36-4.24 (m, 2H), 3.33 (s, 2H), 3.32-3.25 (m, 1 H), 3.20-3.11 (m, 1H), 2.17-1.81 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 99. | 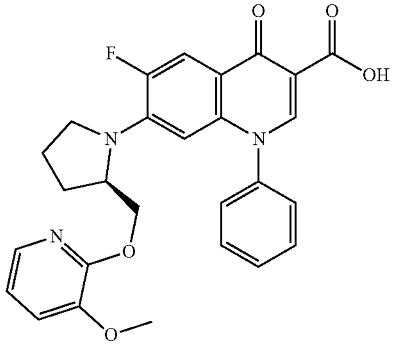 [SMILES: COc1cccnc1OC[C@H]1CCCN1c1cc2c(cc1F)c(=O)c(C(=O)O)cn2-c1ccccc1] | (Column: XBridge Prep OBD C18 Column, 19*250 mm, 5 um; Mobile Phase A: Water (10 MMOL/L $NH_4HCO_3$), Mobile Phase B: ACN; Flow rate: 25 mL/min; Gradient: 40 B to 78 B in 8 min; 254 nm; RT1: 7.83; RT2:; Injection Volumn: ml; Number Of Runs:;) | (R)-6-fluoro-7-(2-(((3-methoxy-pyridin-2-yl)oxy)methyl) pyrrolidin-1-yl)-4-oxo-1-phenyl-1,4-dihydro-quinoline-3-carboxylic acid | LCMS (ESI) $[M + H]^+$: 490.10. $^1H$ NMR (300 MHz, DMSO-$d_6$) δ 15.44 (s, 1H), 8.52 (s, 1H), 7.88 (d, J = 14.5 Hz, 1H), 7.73-7.51 (m, 5H), 7.47-7.36 (m, 1H), 7.28-7.15 (m, 1H), 6.96-6.86 (m, 1H), 6.00 (d, J = 7.4 Hz, 1H), 4.40-4.34 (m, 1H), 4.29-4.19 (m, 1H), 4.19-4.08 (m, 1H), 3.71 (s, 3H), 3.31-3.24 (m, 1 H), 3.21-3.08 (m, 1H), 2.12-1.83 (m, 4H). | ++++ |
| 100. | 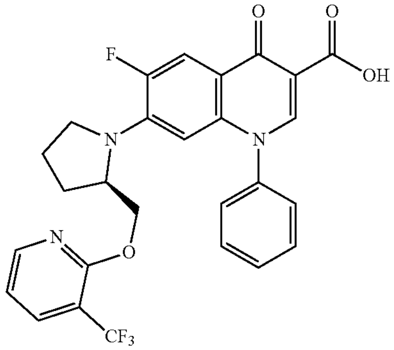 [SMILES: O=C(O)c1cn(-c2ccccc2)c2cc(N3CCC[C@@H]3COc3ncccc3C(F)(F)F)c(F)cc2c1=O] | (Column: XSelect CSH Prep C18 OBD Column,, 5 um, 19*150 mm; Mobile Phase A: Water (0.05% FA), Mobile Phase B: ACN; Flow rate: 25 mL/min; Gradient: 35 B to 70 B in 10 min; 254 nm; RT1: 12.02; RT2:; Injection Volumn: ml; Number Of Runs:;) | (R)-6-fluoro-4-oxo-1-phenyl-7-(2-(((3-(trifluoro-methyl) pyridin-2-yl)oxy) methyl) pyrrolidin-1-yl)-1,4-dihydro-quinoline-3-carboxylic acid | LCMS (ESI) $[M + H]^+$: 528.05. $^1H$ NMR (300 MHz, DMSO-$d_6$) δ 8.52 (s, 1H), 8.31 (d, J = 4.7 Hz, 1H), 8.08 (d, J = 7.5 Hz, 1H), 7.89 (d, J = 14.4 Hz, 1H), 7.67-7.56 (m, 4H), 7.55-7.46 (m, 1H), 7.22-7.12 (m, 1H), 6.03 (d, J = 7.5 Hz, 1H), 4.41-4.25 (m, 3H), 3.30-3.14 (m, 2H), 2.16-1.84 (m, 4H). | ++++ |
| 101. | 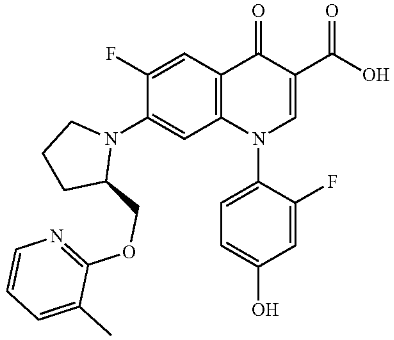 [SMILES: Cc1cccnc1OC[C@H]1CCCN1c1cc2c(cc1F)c(=O)c(C(=O)O)cn2-c1ccc(O)cc1F] | (Column: XSelect CSH Prep C18 OBD Column,, 5 um, 19*150 mm; Mobile Phase A: Water (0.05% FA), Mobile Phase B: ACN; Flow rate :25 mL/min; Gradient: 50 B to 70 B in 8 min; 254 nm; RT1: 6.07; RT2:; Injection Volumn: ml; Number Of Runs:;) | (R)-6-fluoro-1-(2-fluoro-4-hydroxy-phenyl)-7-(2-(((3-methyl-pyridin-2-yl)oxy) methyl) pyrrolidin-1-yl)-4-oxo-1,4-dihydro-quinoline-3-carboxylic acid | LCMS (ESI) $[M + H]^+$: 508.1. $^1H$ NMR (300 MHz, DMSO-$d_6$) δ 15.30 (s, 1H), 10.66 (s, 1H), 8.60 (d, J = 2.6 Hz, 1H), 7.93-7.84 (m, 2H), 7.61-7.45 (m, 2H), 6.94-6.80 (m, 2H), 6.75-6.63 (m, 1H), 6.08-6.00 (m, 1H), 4.56-4.42 (m, 1H), 4.29-4.14 (m, 2H), 3.37-3.36 (m, 1H), 3.28-3.15 (m, 1H), 2.13-1.83 (m, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 102. | 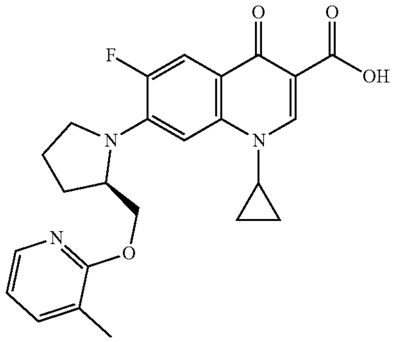 [SMILES: Cc1cccnc1OC[C@H]1CCCN1c1cc2c(cc1F)c(=O)c(C(=O)O)cn2C1CC1] | (Column: Gemini-NX C18 AXAI Packed, 21.2*150 mm 5 um; Mobile Phase A: Water (0.05% FA), Mobile Phase B: ACN; Flow rate: 25 mL/min; Gradient: 35 B to 77 B in 9 min; 254 nm; RT1: 8.65; RT2:; Injection Volumn: ml; Number Of Runs:;) | (R)-1-cyclopropyl-6-fluoro-7-(2-(((3-methyl-pyridin-2-yl)oxy) methyl) pyrrolidin-1-yl)-4-oxo-1,4-dihydro-quinoline-3-carboxylic acid | LCMS (ESI) $[M + H]^+$: 438.15. $^1H$ NMR (300 MHz, DMSO-$d_6$) δ 15.49 (s, 1H), 8.58 (s, 1H), 7.90-7.86 (m, 1H), 7.82 (d, J = 14.6 Hz, 1H), 7.49 (d, J = 6.4 Hz, 1H), 7.25 (d, J = 7.5 Hz, 1H), 6.85 (dd, J = 7.2, 5.0 Hz, 1H), 4.79-4.66 (m, 1H), 4.45 (dd, J = 10.8, 4.3 Hz, 1H), 4.31 (dd, J = 10.9, 5.8 Hz, 1H), 3.83-3.66 (m, 2H), 3.62-3.49 (m, 1H), 2.25-2.13 (m, 2H), 2.05 (s, 5H), 1.25 (d, J = 6.8 Hz, 2H), 1.19-1.05 (m, 2H). | ++++ |
| 103. | 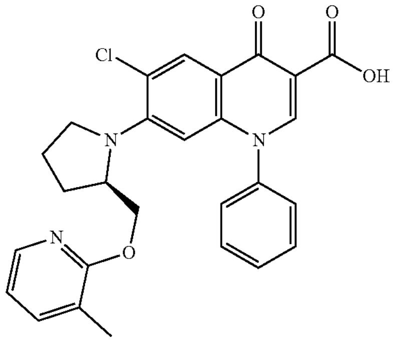 [SMILES: Cc1cccnc1OC[C@H]1CCCN1c1cc2c(cc1Cl)c(=O)c(C(=O)O)cn2-c1ccccc1] | (Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min) | (R)-6-chloro-7-(2-(((3-methyl-pyridin-2-yl)oxy) methyl) pyrrolidin-1-yl)-4-oxo-1-phenyl-1,4-dihydro-quinoline-3-carboxylic acid | LCMS (ESI) $[M + H]^+$: 490.05. $^1H$ NMR (300 MHz, DMSO-$d_6$) δ 15.10 (s, 1H), 8.55 (s, 1H), 8.18 (s, 1H), 7.84-7.75 (m, 1H), 7.72-7.55 (m, 4H), 7.47 (d, J = 7.3 Hz, 2H), 6.82 (s, 1H), 6.29 (s, 1H), 4.60 (d, J = 6.7 Hz, 1H), 4.23 (d, J = 11.3, 3.7 Hz, 1H), 4.12-4.00 (m, 1H), 3.48-3.38 (m, 1H), 3.16 (s, 1H), 2.29-2.13 (m, 1H), 1.89 (s, 6H). | ++++ |
| 104. | 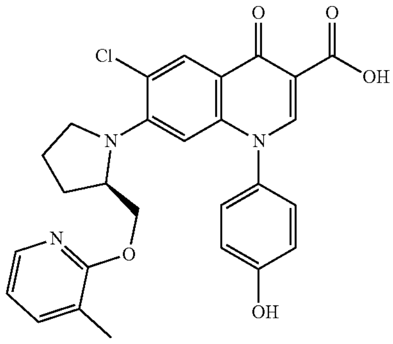 [SMILES: Cc1cccnc1OC[C@H]1CCCN1c1cc2c(cc1Cl)c(=O)c(C(=O)O)cn2-c1ccc(O)cc1] | (Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min) | (R)-6-chloro-1-(4-hydroxy-phenyl)-7-(2-(((3-methyl-pyridin-2-yl)oxy) methyl) pyrrolidin-1-yl)-4-oxo-1,4-dihydro-quinoline-3-carboxylic acid | LCMS (ESI) $[M + H]^+$: 506.10. $^1H$ NMR (300 MHz, DMSO-$d_6$) δ 15.14 (s, 1H), 10.17 (s, 1H), 8.48 (s, 1H), 8.17 (s, 1H), 7.80 (d, J = 5.0, 1.9, 0.8 Hz, 1H), 7.46 (s, 1H), 7.41-7.29 (m, 2H), 7.03-6.94 (m, 1H), 6.86-6.76 (m, 2H), 6.36 (s, 1H), 4.64 (s, 1H), 4.29-4.18 (m, 1H), 4.10 (s, 1H), 3.50-3.39 (m, 1H), 3.17 (d, J = 8.0 Hz, 1H), 2.32-2.18 (m, 1H), 1.91 (s, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 105. | 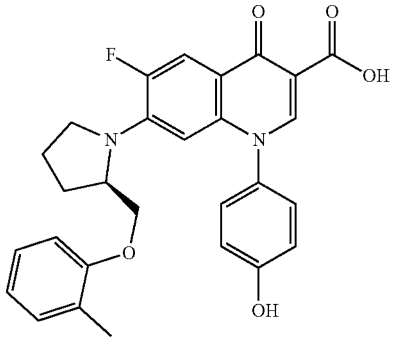 [SMILES: Cc1ccccc1OC[C@H]1CCCN1c1cc2c(cc1F)c(=O)c(C(=O)O)cn2-c1ccc(O)cc1] | (Column: XSelect CSH Prep C18 OBD Column,, 5 um, 19*150 mm; Mobile Phase A: Water (0.1% FA), Mobile Phase B: ACN; Flow rate: 25 mL/min; Gradient: 35 B to 68 B in 11 min; 254 nm; RT1: 11.35; RT2:; Injection Volumn: ml; Number Of Runs:;) | (R)-6-fluoro-1-(4-hydroxy-phenyl)-4-oxo-7-(2-((o-tolyloxy) methyl) pyrrolidin-1-yl)-1,4-dihydro-quinoline-3-carboxylic acid | LCMS (ESI) $[M + H]^+$: 489.17. $^1H$ NMR (300 MHz, DMSO-$d_6$) δ 15.43 (s, 1H), 10.15 (s, 1H), 8.46 (s, 1H), 7.89 (d, J = 14.5 Hz, 1H), 7.49-7.38 (m, 2H), 7.09 (t, J = 7.0 Hz, 2H), 6.99 (dd, J = 8.7, 2.8 Hz, 1H), 6.91-6.76 (m, 3H), 6.16 (d, J = 7.5 Hz, 1H), 4.47 (s, 1H), 3.95 (dd, J = 9.5, 3.6 Hz, 1H), 3.89-3.79 (m, 1H), 3.44-3.37 (m, 1H), 3.20 (d, J = 7.5 Hz, 1H), 2.21-1.81 (m, 7H). | +++ |
| 106. | 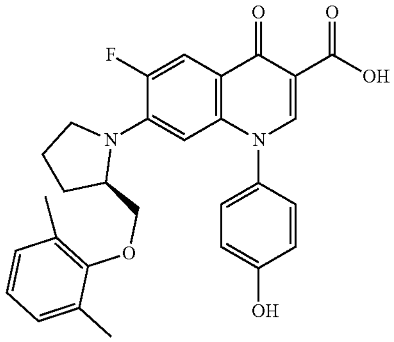 [SMILES: Cc1cccc(C)c1OC[C@H]1CCCN1c1cc2c(cc1F)c(=O)c(C(=O)O)cn2-c1ccc(O)cc1] | (Column: XSelect CSH Prep C18 OBD Column,, 5 um, 19*150 mm; Mobile Phase A: Water (0.1% FA), Mobile Phase B: ACN; Flow rate: 25 mL/min; Gradient: 40 B to 70 B in 12 min; 254 nm; RT1: 11.93; RT2:; Injection Volumn: ml; Number Of Runs:;). | (R)-7-(2-((2,6-dimethyl-phenoxy) methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 503.1. $^1H$ NMR (300 MHz, DMSO-$d_6$) δ 15.43 (s, 1H), 10.15 (s, 1H), 8.45 (s, 1H), 7.90 (d, J = 14.5 Hz, 1H), 7.42 (t, J = 6.4 Hz, 2H), 7.04-6.84 (m, 5H), 6.26 (d, J = 7.4 Hz, 1H), 4.49-4.34 (m, 1H), 3.72-3.55 (m, 2H), 3.44-3.36 (m, 1H), 3.27-3.17 (m, 1H), 2.21-2.05 (m, 3H), 2.04 (s, 6H), 1.98-1.85 (m, 1H). | + |
| 107. | 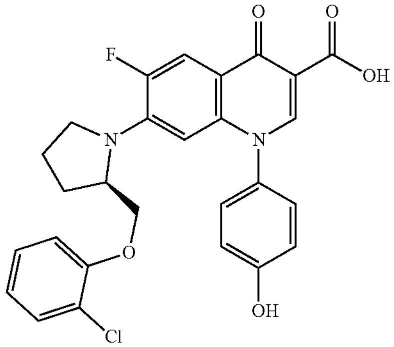 [SMILES: O=C(O)c1cn(-c2ccc(O)cc2)c2cc(N3CCC[C@@H]3COc3ccccc3Cl)c(F)cc2c1=O] | (Column: XSelect CSH Prep C18 OBD Column,, 5 um, 19*150 mm; Mobile Phase A: Water (0.05% FA), Mobile Phase B: ACN; Flow rate: 25 mL/min; Gradient: 50 B to 75 B in 8 min; 254 nm; RT1: 6.86; RT2:; Injection Volumn: ml; Number Of Runs:;). | (R)-7-(2-((2-chlorophenoxy) methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 509.12. $^1H$ NMR (300 MHz, DMSO-$d_6$) δ 15.54-15.28 (m, 1H), 10.32-10.09 (m, 1H), 8.62-8.38 (m, 1H), 7.93-7.83 (m, 1H), 7.48-7.34 (m, 3H), 7.30-7.18 (m, 1H), 7.10-6.85 (m, 4H), 6.20-6.12 (m, 1H), 4.53-4.47 (m, 1H), 4.12-4.03 (m, 1H), 4.01-3.90 (m, 1H), 3.36-3.34 (m, 1H), 3.22-3.10 (m, 1H), 2.11 (d, J = 13.9 Hz, 3H), 1.91 (s, 1H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 108. | 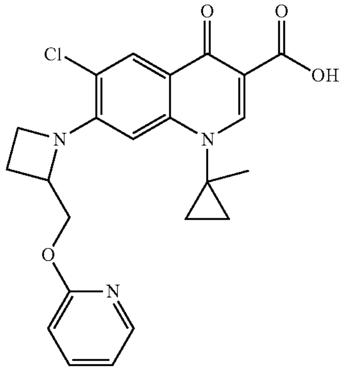 [SMILES: CC1(n2cc(C(=O)O)c(=O)c3cc(Cl)c(N4CCC4COc4ccccn4)cc32)CC1] | (Column: XSelect CSH Prep C18 OBD Column,, 5 um, 19*150 mm; Mobile Phase A: Water (0.1% FA), Mobile Phase B: ACN; Flow rate: 25 mL/min; Gradient: 38 B to 53 B in 10 min; 254/220 nm; RT1: 9.42; RT2:; Injection Volumn: ml; Number Of Runs:;) | 6-chloro-1-(1-methyl-cyclopropyl)-4-oxo-7-(2-((pyridin-2-yloxy)methyl) azetidin-1-yl)-1,4-dihydro-quinoline-3-carboxylic acid | LCMS (ESI) $[M + H]^+$: 440.1. $^1H$ NMR (300 MHz, DMSO-$d_6$) δ 15.21 (s, 1H), 8.75 (d, J = 1.2 Hz, 1H), 8.08 (d, J = 4.5 Hz, 2H), 7.80-7.59 (m, 1H), 7.14 (s, 1H), 6.96 (ddd, J = 7.2, 5.0, 0.9 Hz, 1H), 6.85 (dd, J = 8.4, 5.5 Hz, 1H), 5.03-4.88 (m, 1H), 4.65 (t, J = 4.9 Hz, 2H), 4.54 (q, J = 8.4 Hz, 1H), 4.08 (d, J = 8.1 Hz, 1H), 2.55 (s, 1H), 2.35 (s, 1H), 1.64 (d, J = 26.3 Hz, 3H), 1.44 (dd, J = 10.5, 5.5 Hz, 1H), 1.32-1.10 (m, 3H). | ++ |
| 109. | 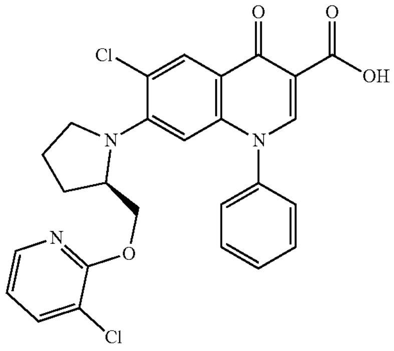 | (Column: XBridge Shield RP18 OBD Column, 5 um, 19*150 mm; Mobile Phase A: Water (0.05% FA), Mobile Phase B: ACN; Flow rate: 25 mL/min; Gradient: 60% B to 90% B in 8 min; 254/220 nm; Rt: 7.31 min) | (R)-6-chloro-7-(2-(((3-chloropyridin-2-yl)oxy)methyl) pyrrolidin-1-yl)-4-oxo-1-phenyl-1,4-dihydro-quinoline-3-carboxylic acid | LCMS (ESI) $[M + H]^+$: 510.10. $^1H$ NMR (300 MHz, DMSO-$d_6$) δ 15.09 (s, 1H), 8.55 (s, 1H), 8.17 (s, 1H), 7.90 (d, J = 4.9, 1.7 Hz, 1H), 7.82 (s, 1H), 7.75-7.56 (m, 4H), 7.54-7.44 (m, 1H), 6.95 (d, J = 7.7, 4.9 Hz, 1H), 6.30 (s, 1H), 4.63 (s, 1H), 4.34-4.16 (m, 2H), 3.43 (s, 1H), 3.20-3.04 (m, 1H), 2.33-2.15 (m, 1H), 2.06-1.84 (m, 2H), 1.84-1.68 (m, 1H). | ++++ |
| 110. | 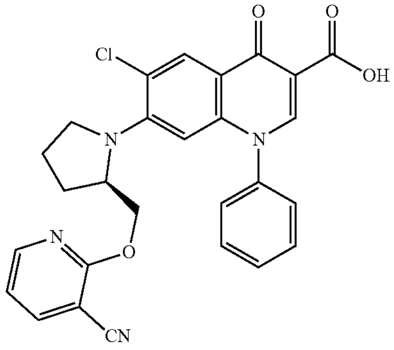 | (Column: XBridge Shield RP18 OBD Column, 5 um, 19*150 mm; Mobile Phase A: Water (0.05% FA), Mobile Phase B: ACN; Flow rate: 25 mL/min; Gradient: 60% B to 90% B in 8 min; 254/220 nm; Rt: 7.31 min) | (R)-6-chloro-7-(2-(((3-cyanopyridin-2-yl)oxy)methyl) pyrrolidin-1-yl)-4-oxo-1-phenyl-1,4-dihydro-quinoline-3-carboxylic acid | LCMS (ESI) $[M + H]^+$: 501.15. $^1H$ NMR (300 MHz, DMSO-$d_6$) δ 15.09 (s, 1H), 8.56 (d, J = 2.1 Hz, 1H), 8.26-8.11 (m, 3H), 7.72-7.51 (m, 5H), 7.12 (d, J = 7.3, 5.0, 2.1 Hz, 1H), 6.31 (d, J = 2.1 Hz, 1H), 4.63 (s, 1H), 4.36 (s, 2H), 3.45 (d, J = 8.8 Hz, 1H), 3.20-3.07 (m, 1H), 2.30-2.15 (m, 1H), 2.02-1.75 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 111. | 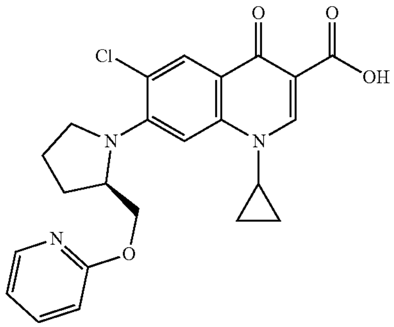 | Column: SunFire Prep C18 OBD Column, 19 × 150 mm 5 um 10 nm; Mobile Phase A: Water (0.1% FA), Mobile Phase B: acetonitrile; Flow rate: 25 mL/min; Gradient: 60 B to 63 B in 8 min; 254/220 nm. | (R)-6-chloro-1-cyclopropyl-4-oxo-7-(2-((pyridin-2-yloxy)methyl) pyrrolidin-1-yl)-1,4-dihydro-quinoline-3-carboxylic acid | LCMS (ESI) $[M + H]^+$: 440.0. $^1H$ NMR (300 MHz, DMSO-$d_6$) δ 15.19 (s, 1H), 8.61 (s, 1H), 8.12 (s, 1H), 8.03-7.94 (m, 1H), 7.68-7.58 (m, 1H), 7.49 (s, 1H), 6.95-6.86 (m, 1H), 6.66 (d, J = 8.3 Hz, 1H), 4.89-4.78 (m, 1H), 4.48-4.38 (m, 1H), 4.29-4.18 (m, 1H), 3.95-3.84 (m, 1H), 3.75-3.65 (m, 1H), 3.50-3.40 (m, 1H), 2.38-2.27 (m, 1H), 2.14-1.81 (m, 3H), 1.31-0.99 (m, 4H). | +++ |
| 112. | 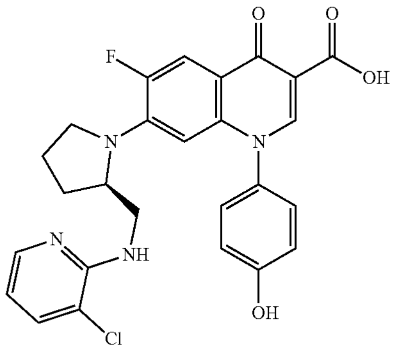 [SMILES: O=C(O)c1cn(-c2ccc(O)cc2)c2cc(N3CCC[C@@H]3CNc3ncccc3Cl)c(F)cc2c1=O] | Column: Column: X Bridge Shield RP18 OBD Column, 5 um, 19*150 mm; Mobile Phase A: Water (0.1% FA), Mobile Phase B: acetonitrile; Flow rate: 25 mL/min; Gradient: 34 B to 68 B in 8 min; 254 nm. | (R)-7-(2-(((3-chloropyridin-2-yl)amino) methyl) pyrrolidin-1-yl)-6-fluoro-1-(4-hydroxy-phenyl)-4-oxo-1,4-dihydro-quinoline-3-carboxylic acid | LCMS (ESI): $[M + H]^+$: 509.0. $^1H$ NMR (300 MHz, DMSO-$d_6$) δ 15.53 (s, 1H), 10.15 (s, 1H), 8.42 (s, 1H), 7.84-7.72 (m, 2H), 7.49-7.35 (m, 3H), 7.01 (d, J = 7.9 Hz, 1H), 6.96-6.86 (m, 1H), 6.53-6.44 (m, 1H), 6.43-6.35 (m, 1H), 6.02 (d, J = 7.4 Hz, 1H), 4.45 (s, 1H), 3.59-3.49 (m, 1H), 3.32-3.29 (m, 1H), 3.28-3.22 (m, 1H), 3.13-3.04 (m, 1H), 2.06-1.79 (m, 4H). | ++++ |
| 113. | 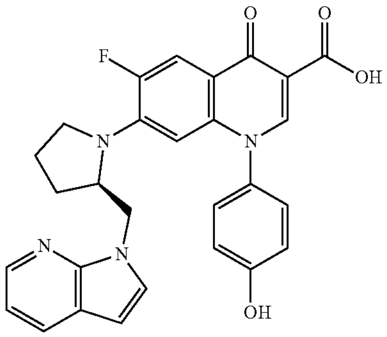 [SMILES: O=C(O)c1cn(-c2ccc(O)cc2)c2cc(N3CCC[C@@H]3Cn3ccc4cccnc43)c(F)cc2c1=O] | (Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min) | (R)-7-(2-((1H-pyrrolo[2,3-b]pyridin-1-yl)methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 499.15. $^1H$ NMR (300 MHz, DMSO-$d_6$) δ 15.45 (s, 1H), 10.22 (s, 1H), 8.46 (s, 1H), 8.16 (d, J = 4.7, 1.6 Hz, 1H), 7.90-7.83 (m, 1H), 7.77 (d, J = 14.4 Hz, 1H), 7.45 (s, 2H), 7.14 (d, J = 3.5 Hz, 1H), 7.08-6.96 (m, 3H), 6.42 (d, J = 3.5 Hz, 1H), 6.10 (d, J = 7.5 Hz, 1H), 4.58-4.46 (m, 1H), 4.32-4.18 (m, 2H), 3.15 (d, J = 8.7 Hz, 2H), 1.79 (d, J = 24.6 Hz, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 114. | 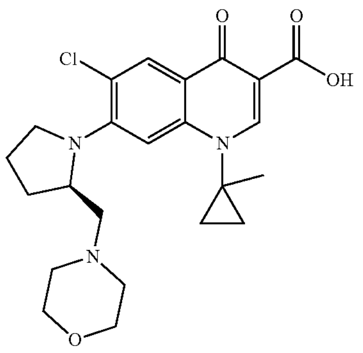 [SMILES: CC1(n2cc(C(=O)O)c(=O)c3cc(Cl)c(N4CCC[C@@H]4CN4CCOCC4)cc32)CC1] | (Column: XSelect CSH Prep C18 OBD Column,, 5 um, 19*150 mm; Mobile Phase A: Water (0.05% FA), Mobile Phase B: ACN; Flow rate: 25 mL/min; Gradient: 50 B to 75 B in 8 min; 254 nm; RT1: 6.86; RT2:; Injection Volumn: ml; Number Of Runs:;). | (R)-6-chloro-1-(1-methylcyclo-propyl)-7-(2-(morpholino-methyl) pyrrolidin-1-yl)-4-oxo-1,4-dihydro-quinoline-3-carboxylic acid | LCMS (ESI) $[M + H]^+$: 446.1. $^1H$ NMR (300 MHz, DMSO-$d_6$) δ 15.20 (s, 1H), 8.77 (s, 1H), 8.24-8.08 (m, 1H), 7.32 (s, 1H), 4.72-4.40 (m, 1H), 3.94-3.73 (m, 1H), 3.50-3.37 (m, 8H), 2.50-2.38 (m, 1H), 2.37-2.33 (m, 2H), 2.21-2.13 (m, 1H), 2.11-2.04 (m, 1H), 1.92-1.78 (m, 2H), 1.69-1.61 (m, 3H), 1.48-1.33 (m, 2H), 1.28-1.11 (m, 2H). | + |
| 115. | 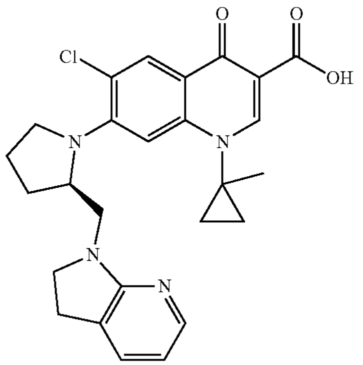 [SMILES: CC1(n2cc(C(=O)O)c(=O)c3cc(Cl)c(N4CCC[C@@H]4CN4CCc5cccnc54)cc32)CC1] | Column: Xselect CSH F-Phenyl OBD column, 19*250, 5 um; Mobile Phase A: Water (0.1% FA), Mobile Phase B: ACN; Flow rate: 25 mL/min; Gradient: 17 B to 37 B in 8 min; 254/220 nm. | (R)-6-chloro-7-(2-((2,3-dihydro-1H-pyrrolo[2,3-b]pyridin-1-yl)methyl) pyrrolidin-1-yl)-1-(1-methylcyclo-propyl)-4-oxo-1,4-dihydro-quinoline-3-carboxylic acid | LCMS (ESI) $[M + H]^+$: 479.2. $^1H$ NMR (300 MHz, Chloroform-d) δ 15.12 (s, 1H), 8.82 (s, 1H), 8.34 (d, J = 7.2 Hz, 1H), 7.69 (s, 1H), 7.37 (d, J = 13.2 Hz, 1H), 7.15 (s, 1H), 6.41 (dd, J = 6.9, 5.6 Hz, 1H), 5.02-4.74 (m, 1H), 4.15-3.93 (m, 1H), 3.93-3.57 (m, 2H), 3.55-3.23 (m, 3H), 3.02-2.77 (m, 2H), 2..51-2.27 (m, 1H), 2.23-2.07 (m, 1H), 2.02-1.89 (m, 2H), 1.75-1.66 (m, 2H), 1.43-1.11 (m, 5H). | +++ |
| 116. | 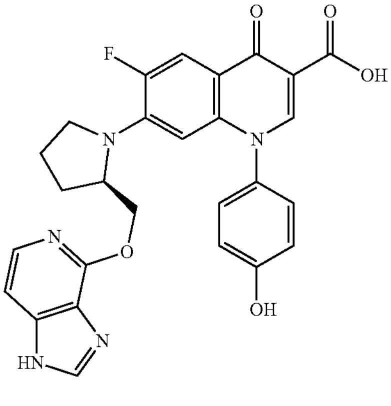 [SMILES: O=C(O)c1cn(-c2ccc(O)cc2)c2cc(N3CCC[C@@H]3COc3nccc4[nH]cnc34)c(F)cc2c1=O] | Column: XSelect CSH Prep C18 OBD Column,, 5 um, 19*150 mm; Mobile Phase A: Water (0.05% FA), Mobile Phase B: ACN; Flow rate: 25 mL/min; Gradient: 15 B to 50 B in 8 min; 254 nm. | (R)-7-(2-(((1H-imidazo[4,5-c] pyridin-4-yl)oxy)methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 516.2. $^1H$ NMR (300 MHz, DMSO-$d_6$) δ 15.47 (s, 1H), 12.76 (s, 1H), 10.12 (s, 1H), 8.44 (s, 1H), 8.16 (s, 1H), 7.84 (d, J = 14.5 Hz, 1H), 7.66 (d, J = 5.7 Hz, 1H), 7.47-7.31 (m, 2H), 7.13 (d, J = 5.4 Hz, 1H), 6.97 (d, J = 8.6 Hz, 1H), 6.82 (d, J = 8.6 Hz, 1H), 6.06 (d, J = 7.7 Hz, 1H), 4.50 (d, J = 21.3 Hz, 3H), 3.32 (s, 1H), 3.13 (s, 1H), 2.10 (s, 3H), 1.90 (s, 1H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 117. | 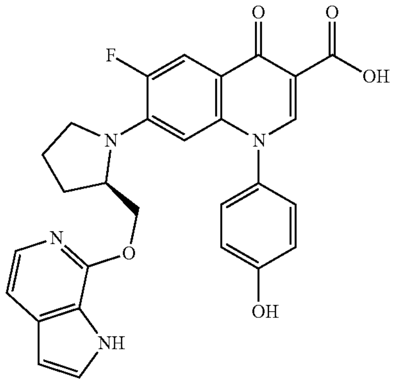 [SMILES: O=C(O)c1cn(-c2ccc(O)cc2)c2cc(N3CCC[C@@H]3COc3nccc4cc[nH]c34)c(F)cc2c1=O] | (Column: XBridge Prep C18 OBD Column, 19 × 150 mm 5 um; Mobile Phase A: Water (0.1% FA), Mobile Phase B: ACN; Flow rate: 25 mL/min; Gradient: 30 B to 50 B in 8 min; 254/220 nm) | (R)-7-(2-(((1H-pyrrolo[2,3-c]pyridin-7-yl)oxy)methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 515.1. $^1H$ NMR (300 MHz, DMSO-$d_6$) δ 15.47 (s, 1H), 11.50 (s, 1H), 10.14 (s, 1H), 8.43 (s, 1H), 7.86 (d, J = 14.5 Hz, 1H), 7.51-7.28 (m, 4H), 7.09 (d, J = 5.6 Hz, 1H), 6.96 (dd, J = 8.6, 2.7 Hz, 1H), 6.86 (dd, J = 8.6, 2.7 Hz, 1H), 6.43 (t, J = 2.3 Hz, 1H), 6.03 (d, J = 7.5 Hz, 1H), 4.65-4.38 (m, 3H), 3.45-3.38 (m, 1H), 3.17-2.99 (m, 1H), 2.20-2.09 (m, 3H), 2.00-1.79 (m, 1H). | ++++ |
| 118. | 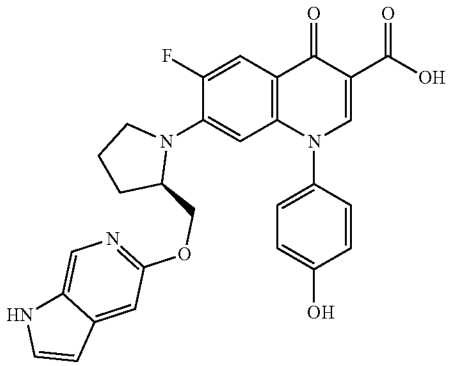 [SMILES: O=C(O)c1cn(-c2ccc(O)cc2)c2cc(N3CCC[C@@H]3COc3cc4cc[nH]c4cn3)c(F)cc2c1=O] | (Column: XBridge Prep C18 OBD Column,, 5 um, 19*150 mm; Mobile Phase A: Water (10 MMOL/L $NH_4HCO_3$), Mobile Phase B: ACN; Flow rate: 25 mL/min; Gradient: 2 B to 26 B in 2 min; 254 nm; RT1: 11.63; RT2:; Injection Volumn: ml; Number Of Runs:;) | (R)-7-(2-(((1H-pyrrolo[2,3-c]pyridin-5-yl)oxy)methyl) pyrrolidin-1-yl)-6-fluoro-1-(4-hydroxy-phenyl)-4-oxo-1,4-dihydro-quinoline-3-carboxylic acid | LCMS (ESI) $[M + H]^+$: 515.25. $^1H$ NMR (300 MHz, DMSO-$d_6$) δ 11.39 (d, J = 68.2 Hz, 1H), 8.41 (d, J = 8.4 Hz, 1H), 8.13 (d, J = 18.4 Hz, 1H), 7.99-7.69 (m, 1H), 7.54 (s, 1H), 7.44-7.17 (m, 1H), 7.04-6.75 (m, 3H), 6.72-6.47 (m, 2H), 6.30 (s, 1H), 6.07-5.87 (m, 1H), 4.44-4.05 (m, 3H), 3.02 (s, 2H), 1.92 (d, J = 53.1 Hz, 4H). | ++++ |
| 119. | 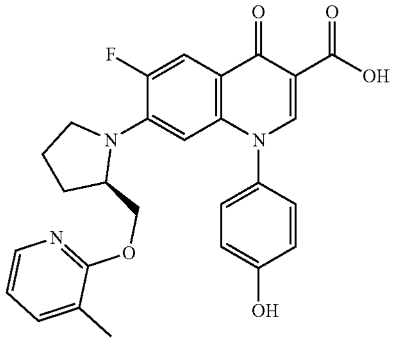 [SMILES: Cc1cccnc1OC[C@H]1CCCN1c1cc2c(cc1F)c(=O)c(C(=O)O)cn2-c1ccc(O)cc1] | (Column: XBridge Shield RP18 OBD Column, 5 um, 19*150 mm; Mobile Phase A: Water (10 MMOL/L $NH_4HCO_3$ + 0.1% $NH_3$•$H_2O$), Mobile Phase B: ACN; Flow rate: 20 mL/min; Gradient: 47% B to 77% B in 8 min; 254 nm; Rt: 7.1 min) | (R)-6-fluoro-1-(4-hydroxy-phenyl)-7-(2-(((3-methylpyridin-2-yl)oxy)methyl) pyrrolidin-1-yl)-4-oxo-1,4-dihydro-quinoline-3-carboxylic acid | LCMS (ESI) $[M + H]^+$: 490.15. $^1H$ NMR (300 MHz, DMSO-$d_6$) δ 15.44 (s, 1H), 10.17 (s, 1H), 8.45 (s, 1H), 7.99-7.81 (m, 2H), 7.49 (d, J = 7.2 Hz, 1H), 7.46-7.35 (m, 2H), 6.99 (d, J = 8.2 Hz, 1H), 6.92-6.78 (m, 2H), 6.12 (d, J = 7.5 Hz, 1H), 4.59-4.37 (m, 1H), 4.22 (m, 2H), 3.32-3.28 (m, 1H), 3.25-3.12 (m, 1H), 2.20-2.00 (m, 2H), 1.99 (s, 3H), 1.97-1.80 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 120. | 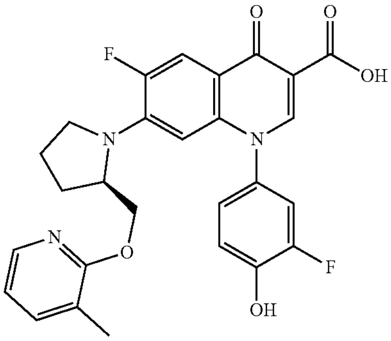 [SMILES: Cc1cccnc1OC[C@H]1CCCN1c1cc2c(cc1F)c(=O)c(C(=O)O)cn2-c1ccc(O)c(F)c1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 49 B to 55 B in 10 min; 254/220 nm; | (R)-6-fluoro-1-(3-fluoro-4-hydroxyphenyl)-7-(2-(((3-methylpyridin-2-yl)oxy)methyl)pyrrolidin-1-yl)-4-oxo-1,4-dihydroquinoline-3-carboxylic acid | LCMS (ESI) $[M + H]^+$: 508.15. $^1H$ NMR (300 MHz, DMSO-$d_6$) δ 15.42 (s, 1H), 10.71 (s, 1H), 8.50 (s, 1H), 7.97-7.82 (m, 2H), 7.60 (d, J = 11.7 Hz, 1H), 7.49 (t, J = 5.5 Hz, 1H), 7.28 (t, J = 8.2 Hz, 1H), 7.13-6.90 (m, 1H), 6.93-6.78 (m, 1H), 6.11 (d, J = 7.3 Hz, 1H), 4.56-4.43 (m, 1H), 4.30-4.09 (m, 2H), 3.33-3.13 (m, 2H), 2.25-1.76 (m, 7H). | ++++ |
| 121. | 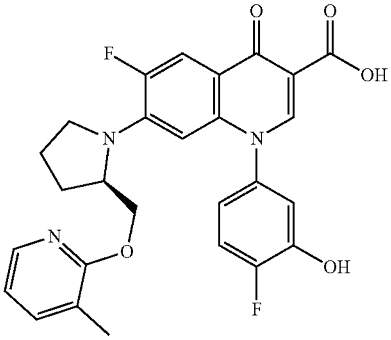 [SMILES: Cc1cccnc1OC[C@H]1CCCN1c1cc2c(cc1F)c(=O)c(C(=O)O)cn2-c1ccc(F)c(O)c1] | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 52 B to 68 B in 10 min; 254 nm | (R)-6-fluoro-1-(4-fluoro-3-hydroxyphenyl)-7-(2-(((3-methylpyridin-2-yl)oxy)methyl)pyrrolidin-1-yl)-4-oxo-1,4-dihydroquinoline-3-carboxylic acid | LCMS (ESI) $[M + H]^+$: 508.1. $^1H$ NMR (300 MHz, DMSO-$d_6$) δ 15.40 (s, 1H), 10.64 (s, 1H), 8.50 (s, 1H), 7.94-7.81 (m, 2H), 7.57-7.16 (m, 3H), 7.11-7.00 (m, 1H), 6.93-6.80 (m, 1H), 6.17-6.06 (m, 1H), 4.61-4.39 (m, 1H), 4.30-4.17 (m, 2H), 3.56-3.44 (m, 1H), 3.22-3.09 (m, 1H), 2.26-2.07 (m, 1H), 2.06-1.88 (m, 6H). | ++++ |
| 122. | 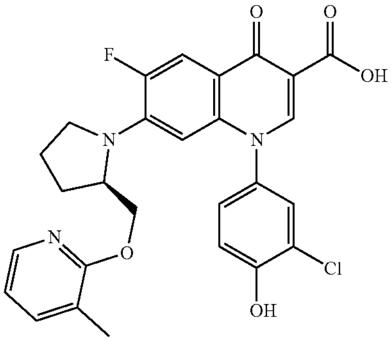 [SMILES: Cc1cccnc1OC[C@H]1CCCN1c1cc2c(cc1F)c(=O)c(C(=O)O)cn2-c1ccc(O)c(Cl)c1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 53 B to 73 B in 15 min; 254 nm | (R)-1-(3-chloro-4-hydroxyphenyl)-6-fluoro-7-(2-(((3-methylpyridin-2-yl)oxy)methyl)pyrrolidin-1-yl)-4-oxo-1,4-dihydroquinoline-3-carboxylic acid | LCMS (ESI) $[M + H]^+$: 524.05. $^1H$ NMR (300 MHz, DMSO-$d_6$) δ 15.40 (s, 1H), 11.05 (s, 1H), 8.50 (s, 1H), 7.96-7.81 (m, 2H), 7.74 (d, J = 2.5 Hz, 1H), 7.48 (d, J = 7.3 Hz, 1H), 7.45-7.36 (m, 1H), 7.12 (dd, J = 36.8, 8.7 Hz, 1H), 6.93-6.80 (m, 1H), 6.09 (t, J = 7.6 Hz, 1H), 4.59-4.42 (m, 1H), 4.33-4.12 (m, 2H), 3.31-3.09 (m, 2H), 2.20-2.01 (m, 2H), 1.99 (s, 3H), 1.90 (dd, J = 15.5, 5.5 Hz, 2H). | ++++ |
| 123. | 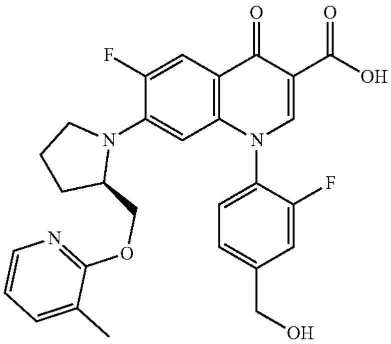 [SMILES: Cc1cccnc1OC[C@H]1CCCN1c1cc2c(cc1F)c(=O)c(C(=O)O)cn2-c1ccc(CO)cc1F] | Column: Gemini-NX C18 AXAI Packed, 21.2*150 mm 5 um; Mobile Phase A: Water (0.1% FA), Mobile Phase B: ACN; Flow rate: 25 mL/min; Gradient: 33 B to 57 B in 12 min; 254 nm; | (R)-6-fluoro-1-(2-fluoro-4-(hydroxymethyl)phenyl)-7-(2-(((3-methylpyridin-2-yl)oxy)methyl)pyrrolidin-1-yl)-4-oxo-1,4-dihydroquinoline-3-carboxylic acid | LCMS (ESI) $[M + H]^+$: 522.1. $^1H$ NMR (300 MHz, DMSO-$d_6$) δ 15.26 (s, 1H), 8.65 (d, J = 3.0 Hz, 1H), 7.96-7.83 (m, 2H), 7.72 (dt, J = 12.7, 8.0 Hz, 1H), 7.55-7.41 (m, 2H), 7.27 (t, J = 8.9 Hz, 1H), 6.86 (dt, J = 7.1, 4.5 Hz, 1H), 6.00 (d, J = 7.3 Hz, 1H), 5.58 (td, J = 5.7, 3.1 Hz, 1H), 4.61 (d, J = 5.5 Hz, 2H), 4.54-4.41 (m, 1H), 4.31-4.11 (m, 2H), 3.42-3.35 (m, 1H), 3.25-3.12 (m, 1H), 2.18-1.82 (m, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 124. | 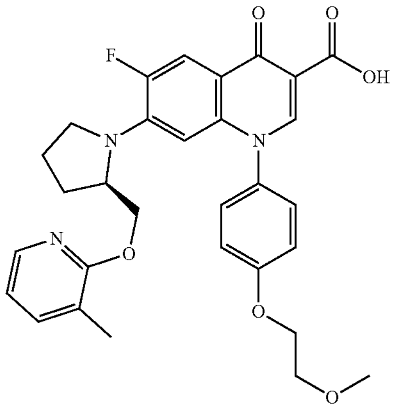 [SMILES: COCCOc1ccc(-n2cc(C(=O)O)c(=O)c3cc(F)c(N4CCC[C@@H]4COc4ncccc4C)cc32)cc1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 54 B to 70 B in 23 min; 254 nm | (R)-6-fluoro-1-(4-(2-methoxyethoxy)phenyl)-7-(2-(((3-methylpyridin-2-yl)oxy)methyl)pyrrolidin-1-yl)-4-oxo-1,4-dihydro-quinoline-3-carboxylic acid | LCMS (ESI) $[M + H]^+$: 548.20. $^1H$ NMR (300 MHz, DMSO-$d_6$) δ 15.45 (s, 1H), 8.47 (s, 1H), 7.99-7.81 (m, 2H), 7.71-7.45 (m, 3H), 7.20 (d, J = 8.4 Hz, 1H), 6.99 (d, J = 8.7 Hz, 1H), 6.87 (dd, J = 7.1, 5.0 Hz, 1H), 6.09 (d, J = 7.4 Hz, 1H), 4.51-4.37 (m, 1H), 4.30-4.07 (m, 4H), 3.71 (t, J = 4.4 Hz, 2H), 3.35 (s, 3H), 3.34-3.29 (m, 1H), 3.27-3.12 (m, 1H), 2.21-1.81 (m, 7H). | ++++ |
| 125. | 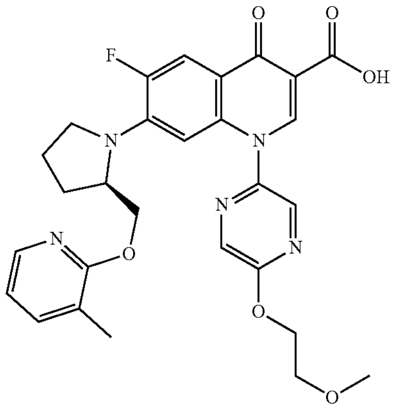 [SMILES: COCCOc1cnc(-n2cc(C(=O)O)c(=O)c3cc(F)c(N4CCC[C@@H]4COc4ncccc4C)cc32)cn1] | Column: XBridge Shield RP18 OBD Column, 5 um, 19*150 mm; Mobile Phase A: Water (10 mmol/L $NH_4HCO_3$ + 0.1% $NH_3$•$H_2O$), Mobile Phase B: ACN; Flow rate: 20 mL/min; Gradient: 47% B to 77% B in 8 min; 254 nm | (R)-6-fluoro-1-(5-(2-methoxyethoxy)pyrazin-2-yl)-7-(2-(((3-methylpyridin-2-yl)oxy)methyl)pyrrolidin-1-yl)-4-oxo-1,4-dihydro-quinoline-3-carboxylic acid | LCMS (ESI) $[M + H]^+$: 550.3. $^1H$ NMR (300 MHz, DMSO-$d_6$) δ 15.25 (s, 1H), 8.81 (s, 1H), 8.65 (s, 1H), 8.31 (s, 1H), 7.98-7.77 (m, 2H), 7.49 (d, J = 7.1 Hz, 1H), 6.86 (dd, J = 7.2, 5.0 Hz, 1H), 6.27 (d, J = 7.3 Hz, 1H), 4.52 (dt, J = 20.1, 3.9 Hz, 3H), 4.35-4.09 (m, 2H), 3.74 (t, J = 4.4 Hz, 2H), 3.56-3.44 (m, 1H), 3.34-3.23 (m, 4H), 2.18-1.82 (m, 7H). | ++++ |
| 126. | 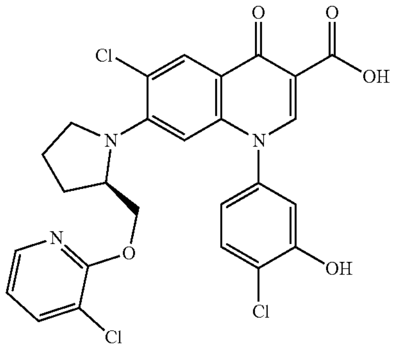 [SMILES: O=C(O)c1cn(-c2ccc(Cl)c(O)c2)c2cc(N3CCC[C@@H]3COc3ncccc3Cl)c(Cl)cc2c1=O] | Column: XSelect CSH Prep C18 OBD Column,, 5 um, 19*150 mm; Mobile Phase A: Water (0.05% FA), Mobile Phase B: ACN; Flow rate: 254 mL/min; Gradient: 50 B to 55 B in 10 min; 254 nm; RT1: 9.45; RT2:; Injection Volumn: ml; Number Of Runs:; | (R)-6-chloro-1-(4-chloro-3-hydroxy-phenyl)-7-(2-(((3-chloropyridin-2-yl)oxy)methyl)pyrrolidin-1-yl)-4-oxo-1,4-dihydro-quinoline-3-carboxylic acid | LCMS (ESI) $[M + H]^+$: 560.05. $^1H$ NMR (300 MHz, DMSO-$d_6$) δ 15.06 (s, 1H), 11.06 (s, 1H), 8.57 (s, 1H), 8.14 (s, 1H), 7.96-7.73 (m, 2H), 7.72-7.29 (m, 1H), 7.15 (d, J = 8.7 Hz, 1H), 7.07-6.83 (m, 2H), 6.41 (d, J = 15.7 Hz, 1H), 4.69 (d, J = 51.8 Hz, 1H), 4.43-4.15 (m, 2H), 3.63-3.48 (m, 1H), 3.22-3.05 (m, 1H), 2.24 (d, J = 9.7 Hz, 1H), 2.08-1.68 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 127. | 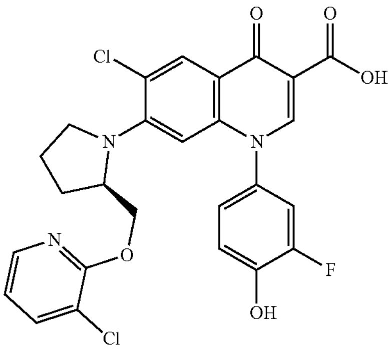 [SMILES: O=C(O)c1cn(-c2ccc(O)c(F)c2)c2cc(N3CCC[C@@H]3COc3ncccc3Cl)c(Cl)cc2c1=O] | Column: XBridge Shield RP18 OBD Column, 5 um, 19*150 mm; Mobile Phase A: Water (10 MMOL/L $NH_4HCO_3$ + 0.1% $NH_3$•$H_2O$), Mobile Phase B: ACN; Flow rate: 20 mL/min; Gradient: 47% B to 77% B in 8 min; 254 nm | (R)-6-chloro-7-(2-(((3-chloropyridin-2-yl)oxy)methyl)pyrrolidin-1-yl)-1-(3-fluoro-4-hydroxy-phenyl)-4-oxo-1,4-dihydro-quinoline-3-carboxylic acid | LCMS (ESI) [M + H]$^+$: 544.15. $^1$H NMR (300 MHz, DMSO-$d_6$) δ 15.09 (s, 1H), 10.65 (s, 1H), 8.54 (d, J = 3.3 Hz, 1H), 8.15 (s, 1H), 7.94-7.85 (m, 1H), 7.85-7.76 (m, 1H), 7.62-7.49 (m, 1H), 7.31-7.12 (m, 1H), 7.10-6.88 (m, 2H), 6.38 (d, J = 4.4 Hz, 1H), 4.75-4.69 (m, 1H), 4.37-4.18 (m, 2H), 3.56-3.41 (m, 1H), 3.21-3.12 (m, 1H), 2.31-2.18 (m, 1H), 1.99-1.93 (m, 2H), 1.91-1.71 (m, 1H). | ++++ |
| 128. | 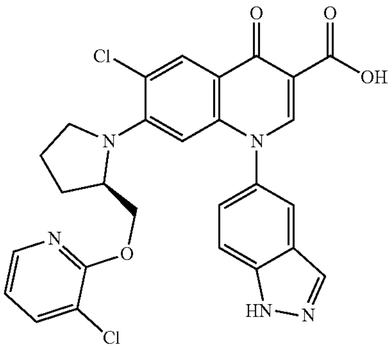 | (Column: XBridge Shield RP18 OBD Column, 5 um, 19*150 mm; Mobile Phase A: water (0.05% FA), Mobile Phase B: ACN; Flow rate: 25 mL/min; Gradient: 60% B to 90% B in 8 min; 254/220 nm; Rt: 7.31 min) | (R)-6-chloro-7-(2-(((3-chloropyridin-2-yl)oxy)methyl)pyrrolidin-1-yl)-1-(1H-indazol-5-yl)-4-oxo-1,4-dihydro-quinoline-3-carboxylic acid | LCMS (ESI) [M + H]$^+$: 550.00. $^1$H NMR (300 MHz, DMSO-$d_6$) δ 15.15 (s, 1H), 13.51 (s, 1H), 8.61 (d, J = 5.3 Hz, 1H), 8.30 (s, 1H), 8.18 (d, J = 2.4 Hz, 1H), 8.12-7.98 (m, 1H), 7.92-7.74 (m, 2H), 7.60 (d, J = 8.7 Hz, 1H), 7.54-7.37 (m, 1H), 7.04-6.87 (m, 1H), 6.33 (d, J = 9.2 Hz, 1H), 4.72-4.52 (m, 1H), 4.33-4.10 (m, 2H), 3.45-3.35 (m, 1H), 3.14-2.97 (m, 1H), 2.27-2.11 (m, 1H), 1.97-1.56 (m, 3H). | ++++ |
| 129. | 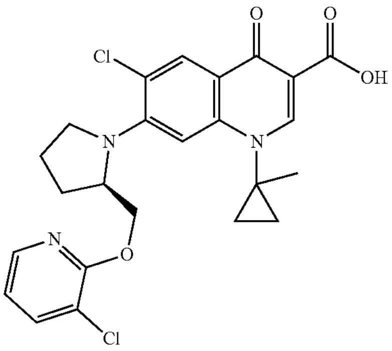 [SMILES: CC1(n2cc(C(=O)O)c(=O)c3cc(Cl)c(N4CCC[C@@H]4COc4ncccc4Cl)cc32)CC1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 56 B to 75 B in 10 min; 254 nm; | (R)-6-chloro-7-(2-(((3-chloropyridin-2-yl)oxy)methyl)pyrrolidin-1-yl)-1-(1-methylcyclo-propyl)-4-oxo-1,4-dihydro-quinoline-3-carboxylic acid | LCMS (ESI) [M + H]$^+$: 488.00. $^1$H NMR (300 MHz, DMSO-$d_6$) δ 15.14 (s, 1H), 8.74 (d, J = 1.8 Hz, 1H), 8.11 (s, 1H), 7.91 (d, J = 4.9 Hz, 1H), 7.86-7.75 (m, 1H), 7.36 (d, J = 8.8 Hz, 1H), 6.97-6.87 (m, 1H), 4.93 (d, J = 6.8 Hz, 1H), 4.47-4.36 (m, 2H), 3.93-3.79 (m, 1H), 3.52-3.42 (m, 2H), 2.40-2.31 (m, 1H), 2.14-2.08 (m, 1H), 2.00-1.88 (m, 1H), 1.58 (s, 3H), 1.47-1.33 (m, 1H), 1.31-1.18 (m, 1H), 1.22-1.08 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 130 | 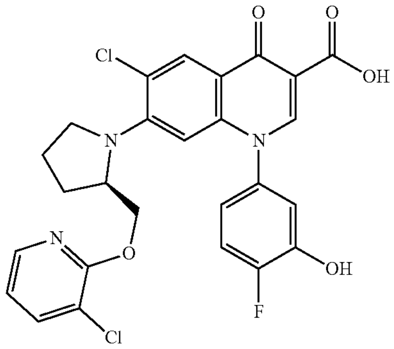 [SMILES: O=C(O)c1cn(-c2ccc(F)c(O)c2)c2cc(N3CCC[C@@H]3COc3ncccc3Cl)c(Cl)cc2c1=O] | Column: XBridge Shield RP18 OBD Column, 5 um, 19*150 mm; Mobile Phase A: Water (10 MMOL/L $NH_4HCO_3$ + 0.1% $NH_3$•$H_2O$), Mobile Phase B: ACN; Flow rate: 20 mL/min; Gradient: 47% B to 77% B in 8 min; 254 n m | (R)-6-chloro-7-(2-(((3-chloropyridin-2-yl)oxy)methyl)pyrrolidin-1-yl)-1-(4-fluoro-3-hydroxy-phenyl)-4-oxo-1,4-dihydro-quinoline-3-carboxylic acid | LCMS (ESI) $[M + H]^+$: 544.10. $^1H$ NMR (300 MHz, DMSO-$d_6$) δ 15.10 (s, 1H), 10.75 (s, 1H), 8.54 (d, J = 4.7 Hz, 1H), 8.15 (s, 1H), 7.94-7.82 (m, 1H), 7.86-7.75 (m, 1H), 7.53-7.11 (m, 2H), 7.03-6.87 (m, 2H), 6.38 (d, J = 12.2 Hz, 1H), 4.83-4.58 (m, 1H), 4.40-4.16 (m, 2H), 3.57-3.41 (m, 1H), 3.15 (q, J = 10.2, 9.6 Hz, 1H), 2.32-2.17 (m, 1H), 2.00-1.94 (m, 2H), 1.90-1.74 (m, 1H). | ++++ |
| 131. | 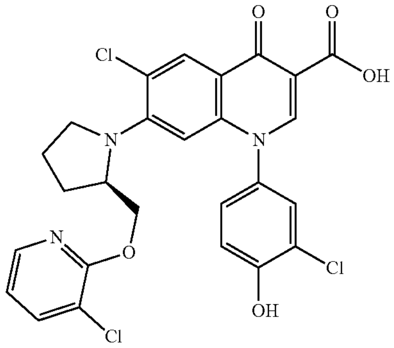 [SMILES: O=C(O)c1cn(-c2ccc(O)c(Cl)c2)c2cc(N3CCC[C@@H]3COc3ncccc3Cl)c(Cl)cc2c1=O] | Column: XSelect CSH Prep C18 OBD Column,, 5 um, 19*150 mm; Mobile Phase A: Water (0.1% FA), Mobile Phase B: MeOH-HPLC; Flow rate: 25 mL/min; Gradient: 57 B to 88 B in 11 min; 254 nm; RT1: 10.73; RT2:; Injection Volumn: ml; Number Of Runs:; | (R)-6-chloro-1-(3-chloro-4-hydroxy-phenyl)-7-(2-(((3-chloropyridin-2-yl)oxy)methyl)pyrrolidin-1-yl)-4-oxo-1,4-dihydro-quinoline-3-carboxylic acid | LCMS (ESI) $[M + H]^+$: 559.95. $^1H$ NMR (300 MHz, DMSO-$d_6$) δ 15.10 (s, 1H), 11.11 (s, 1H) δ 8.54 (s, 1H), 8.16 (s, 1H), 7.89 (d, J = 4.5 Hz, 1H), 7.85-7.75 (m, 1H), 7.70 (d, J = 9.9 Hz, 1H), 7.35 (d, J = 9.9 Hz, 1H), 7.18 (d, J = 8.4 Hz, 1H), 6.99-6.91 (m, 1H), 6.38 (d, J = 6.5 Hz, 1H), 4.72 (s, 1H), 4.32-4.25 (m, 2H), 3.55-3.41 (m, 1H), 3.19-3.13 (m, 1H), 2.34-2.17 (m, 1H), 1.99-1.93 (m, 2H), 1.83-1.74 (m, 1H). | ++++ |
| 132. | 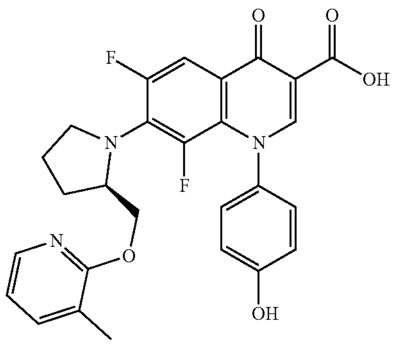 [SMILES: Cc1cccnc1OC[C@H]1CCCN1c1c(F)cc2c(=O)c(C(=O)O)cn(-c3ccc(O)cc3)c2c1F] | Column: Atlantis HILIC OBD Column, 19*150 mm*5 um; Mobile Phase A: Water (0.05% FA), Mobile Phase B: ACN; Flow rate: 25 mL/min; Gradient: 2 B to 2 B in 2 min; 254/220 nm | (R)-6,8-difluoro-1-(4-hydroxy-phenyl)-7-(2-(((3-methylpyridin-2-yl)oxy)methyl)pyrrolidin-1-yl)-4-oxo-1,4-dihydro-quinoline-3-carboxylic acid | LCMS (ESI) $[M + H]^+$: 508.3. $^1H$ NMR (300 MHz, DMSO-$d_6$) δ 14.93 (s, 1H), 10.01 (s, 1H), 8.33 (s, 1H), 7.89-7.70 (m, 2H), 7.53-7.28 (m, 3H), 6.96-6.74 (m, 3H), 4.47 (s, 1H), 4.30-4.17 (m, 2H), 3.67 (s, 1H), 3.33 (s, 1H), 2.19 (s, 1H), 1.96 (s, 1H), 1.76 (s, 5H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 133. | 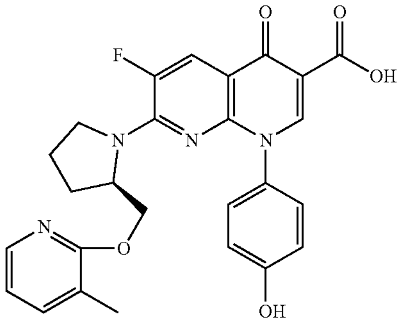 [SMILES: Cc1cccnc1OC[C@H]1CCCN1c1nc2c(cc1F)c(=O)c(C(=O)O)cn2-c1ccc(O)cc1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 26 B to 50 B in 10 min; 254 nm | (R)-6-fluoro-1-(4-hydroxy-phenyl)-7-(2-(((3-methylpyridin-2-yl)oxy)methyl) pyrrolidin-1-yl)-4-oxo-1,4-dihydro-1,8-naphthyridine-3-carboxylic acid | LCMS (ESI) [M + H]+: 491.1. $^1$H NMR (300 MHz, DMSO-$d_6$) δ 15.35 (s, 1H), 9.83 (s, 1H), 8.53 (s, 1H), 8.08 (d, J = 12.8 Hz, 1H), 7.90 (d, J = 5.3, 2.1 Hz, 1H), 7.53-7.50 (m, 1H), 7.31 (d, J = 8.4 Hz, 2H), 6.90-6.85 (m, 1H), 6.73 (s, 2H), 4.61-4.00 (m, 3H), 3.96-3.46 (m, 2H), 2.15-2.05 (m, 4H), 2.04-1.81 (m, 3H). | ++++ |
| 134. | 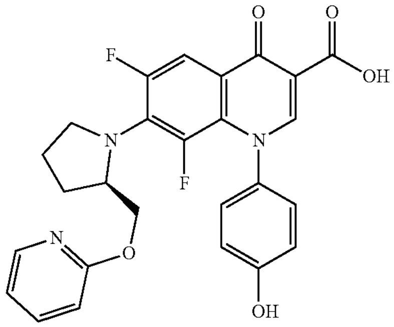 [SMILES: O=C(O)c1cn(-c2ccc(O)cc2)c2c(F)c(N3CCC[C@@H]3COc3ccccn3)c(F)cc2c1=O] | Column: SunFire Prep C18 OBD Column, 19 x 150 mm 5 um 10 nm; Mobile Phase A: Water (0.1% FA), Mobile Phase B: ACN; Flow rate: 25 mL/min; Gradient: 41 B to 64 B in 8 min; 254/220 nm. | (R)-6,8-difluoro-1-(4-hydroxy-phenyl)-4-oxo-7-(2-((pyridin-2-yloxy)methyl) pyrrolidin-1-yl)-1,4-dihydro-quinoline-3-carboxylic acid | LCMS (ESI) [M + H]+: 494.20 $^1$H NMR (300 MHz, DMSO-$d_6$) δ 14.95 (s, 1H), 9.99 (s, 1H), 8.33 (s, 1H), 7.97 (d, J = 5.0, 2.0, 0.8 Hz, 1H), 7.79 (d, J = 13.2, 1.6 Hz, 1H), 7.60 (d, J = 8.4, 7.1, 2.0 Hz, 1H), 7.39 (dd, J = 15.9, 9.2 Hz, 2H), 6.96-6.86 (m, 2H), 6.81 (d, J = 8.6 Hz, 1H), 6.49 (dt, J = 8.4, 0.9 Hz, 1H), 4.43 (s, 1H), 4.29 (dd, J = 11.2, 4.3 Hz, 1H), 4.17 (d, J = 11.2, 5.5 Hz, 1H), 3.64 (s, 1H), 3.28 (s, 1H), 2.18 (s, 1H), 1.94 (s, 1H), 1.77 (d, J = 17.9 Hz, 2H | ++++ |
| 135. | 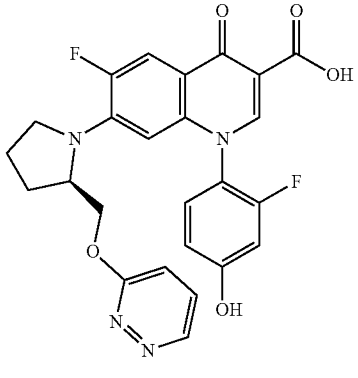 [SMILES: O=C(O)c1cn(-c2ccc(O)cc2F)c2cc(N3CCC[C@@H]3COc3cccnn3)c(F)cc2c1=O] | Column: Gemini-NX C18 AXAI Packed, 21.2*150 mm 5 um; Mobile Phase A: Water (0.05% FA), Mobile Phase B: ACN; Flow rate: 25 mL/min; Gradient: 21 B to 55 B in 12 min; 254 nm | (R)-6-fluoro-1-(2-fluoro-4-hydroxy-phenyl)-4-oxo-7-(2-((pyridazin-3-yloxy)methyl) pyrrolidin-1-yl)-1,4-dihydro-quinoline-3-carboxylic acid | LCMS (ESI) [M + H]+: 495.30 $^1$H NMR (400 MHz, DMSO-$d_6$) δ 15.29 (s, 1H), 10.63 (s, 1H), 8.91-8.84 (m, 1H), 8.64-8.58 (d, J = 1.6 Hz, 1H), 7.90 (d, J = 14.5 Hz, 1H), 7.64-7.48 (m, 2H), 7.11-7.04 (m, 1H), 6.94-6.81 (m, 1H), 6.72-6.61 (m, 1H), 6.09-6.02 (m, 1H), 4.46-4.31 (m, 3H), 3.32-3.29 (m, 1H), 3.26-3.17 (m, 1H), 2.15-1.89 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 136. | 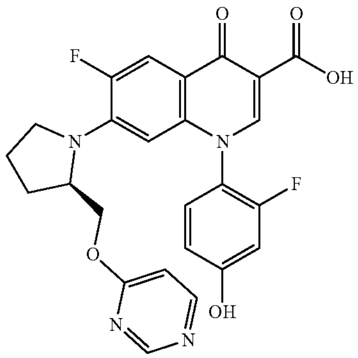 [SMILES: O=C(O)c1cn(-c2ccc(O)cc2F)c2cc(N3CCC[C@@H]3COc3ccncn3)c(F)cc2c1=O] | Column: X Select CSH Prep C18 OBD Column, 5 um, 19*150 mm; Mobile Phase A: Column: XSelect CSH Prep C18 OBD Column,, 5 um, 19*150 mm; Mobile Phase A: Water (0.05% FA), Mobile Phase B: acetonitrile; Flow rate: 25 mL/min; Gradient: 30 B to 53 B in 8 min; 254 nm | (R)-6-fluoro-1-(2-fluoro-4-hydroxy-phenyl)-4-oxo-7-(2-((pyrimidin-4-yloxy)methyl)pyrrolidin-1-yl)-1,4-dihydro-quinoline-3-carboxylic acid | LCMS (ESI) $[M + H]^+$: 495.05. $^1H$ NMR (400 MHz, DMSO-$d_6$) δ 10.71 (s, 1H), 8.68 (s, 1H), 8.61 (m, 1H), 8.50-8.46 (m, 1H), 7.89 (d, J = 14.4 Hz, 1H), 7.59-7.50 (m, 1H), 6.95-6.82 (m, 1H), 6.82-6.78 (m, 1H), 6.76-6.65 (m, 1H), 6.08-5.98 (m, 1H), 4.47-4.36 (m, 1H), 4.36-4.25 (m, 2H), 3.32-3.29 (m, 1H), 3.25-3.17 (m, 1H), 2.13-1.87 (m, 4H). | +++ |
| 137. | 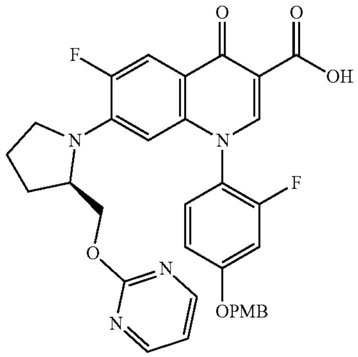 | reverse phase flash chromatography | (R)-6-fluoro-1-(2-fluoro-4-((4-methoxy-benzyl)oxy)phenyl)-4-oxo-7-(2-((pyrimidin-2-yloxy)methyl)pyrrolidin-1-yl)-1,4-dihydro-quinoline-3-carboxylic acid | LCMS (ESI): $[M + H]^+$: 615.15. $^1H$ NMR (400 MHz, DMSO-$d_6$) δ 8.52 (d, J = 4.7 Hz, 2H), 8.38 (s, 1H), 7.82 (d, J = 14.8 Hz, 1H), 7.69-7.57 (m, 1H), 7.44 (d, J = 8.5 Hz, 2H), 7.34-7.26 (m, 0.5H), 7.16-7.03 (m, 2H), 7.03-6.96 (m, 2H), 6.92-6.86 (m, 0.5H), 6.00-5.91 (m, 1H), 5.19-5.04 (m, 2H), 4.37-4.17 (m, 3H), 3.79 (s, 3H), 3.31-3.29 (m, 1H), 3.21-3.13 (m, 1H), 2.14-1.85 (m, 4H). | ++++ |
| 138. | 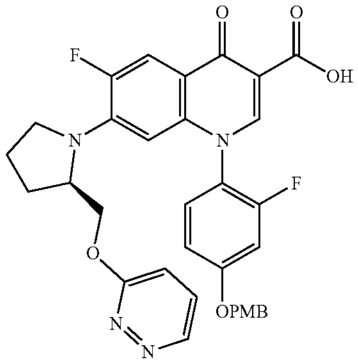 | Column: Mobile Phase A: Water (10 MMOL/L $NH_4HCO_3$), Mobile Phase B: acetonitrile; Flow rate: 30 mL/min; Gradient: 35 B to 60 B in 25 min; 254 nm | (R)-6-fluoro-1-(2-fluoro-4-((4-methoxy-benzyl)oxy)phenyl)-4-oxo-7-(2-((pyridazin-3-yloxy)methyl)pyrrolidin-1-yl)-1,4-dihydro-quinoline-3-carboxylic acid | LCMS (ESI) $[M + H]^+$: 615.15. $^1H$ NMR (300 MHz, DMSO-$d_6$) δ 8.92-8.84 (m, 1H), 8.70-8.62 (m, 1H), 7.91 (d, J = 14.5 Hz, 1H), 7.78-7.62 (m, 1H), 7.60-7.53 (m, 1H), 7.50-7.38 (m, 2H), 7.36-7.28 (m, 0.5H), 7.18-7.04 (m, 2H), 7.03-6.96 (m, 2H), 6.93-6.86 (m, 0.5H), 6.07-5.98 (m, 1H), 5.19-5.03 (m, 2H), 4.47-4.29 (m, 3H), 3.79 (s, 3H), 3.32-3.29 (m, 1H), 3.25-3.17 (m, 1H), 2.16-1.88 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 139. | 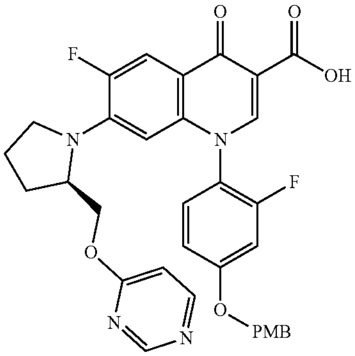 | Column: Mobile Phase A: Water (10 MMOL/L $NH_4HCO_3$), Mobile Phase B: acetonitrile; Flow rate: 30 mL/min; Gradient: 40 B to 70 B in 30 min; 254/220 nm | (R)-6-fluoro-1-(2-fluoro-4-((4-methoxy-benzyl)oxy) phenyl)-4-oxo-7-(2-((pyrimidin-4-yloxy)methyl) pyrrolidin-1-yl)-1,4-dihydro-quinoline-3-carboxylic acid | LCMS (ESI) $[M + H]^+$: 615.10. $^1H$ NMR (400 MHz, DMSO-$d_6$) δ 8.70-8.61 (m, 1H), 8.49-8.42 (m, 1H), 7.94-7.88 (m, 0.5H), 7.75-7.57 (m, 2H), 7.44 (d, J = 8.3 Hz, 2H), 7.37-7.24 (m, 1H), 7.14-7.06 (m, 1H), 7.02-6.96 (m, 2H), 6.95-6.88 (m, 0.5H), 6.84-6.79 (m, 1H), 6.02-5.94 (m, 1H), 5.13-5.04 (m, 2H), 4.45-4.17 (m, 3H), 3.79 (s, 3H), 3.32-3.29 (m, 1H), 3.25-3.10 (m, 1H), 2.13-1.85 (m, 4H). | ++++ |
| 140. | 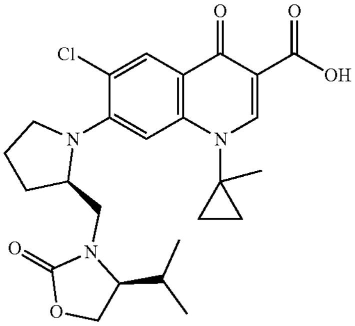 [SMILES: CC(C)[C@H]1COC(=O)N1C[C@H]1CCCN1c1cc2c(cc1Cl)c(=O)c(C(=O)O)cn2C1(C)CC1] | reverse phase flash chromatography | 6-chloro-7-((R)-2-(((S)-4-isopropyl-2-oxooxazolidin-3-yl)methyl) pyrrolidin-1-yl)-1-(1-methylcyclo-propyl)-4-oxo-1,4-dihydro-quinoline-3-carboxylic acid | LCMS (ESI) $[M + H]^+$: 488. $^1H$ NMR (300 MHz, DMSO-d6) δ 15.14 (s, 1H), 8.78 (s, 1H), 8.17 (d, J = 2.0 Hz, 1H), 7.42 (s, 1H), 5.02-4.72 (m, 1H), 4.13-4.02 (m, 1H), 4.02-3.79 (m, 2H), 3.78-3.58 (m, 1H), 3.39 (s, 1H), 3.26 (m, 1H), 3.10 (d, J = 14.0 Hz, 1H), 2.22 (d, J = 7.1 Hz, 1H), 2.08 (d, J = 7.8 Hz, 2H), 1.82 (d, J = 12.5 Hz, 2H), 1.65 (d, J = 11.0 Hz, 3H), 1.54-1.34 (m, 2H), 1.26 (d, J = 15.5 Hz, 1H), 1.19 (d, J = 8.4 Hz, 1H), 0.81 (m, 3H), 0.69 (m, 3H). | + |
| 141. | 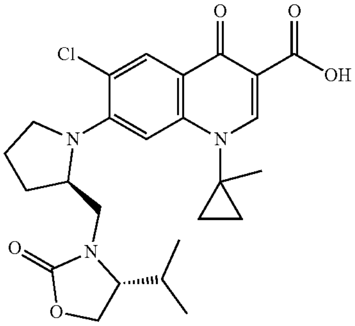 [SMILES: CC(C)[C@@H]1COC(=O)N1C[C@H]1CCCN1c1cc2c(cc1Cl)c(=O)c(C(=O)O)cn2C1(C)CC1] | reverse phase flash chromatography | 6-chloro-7-((R)-2-(((R)-4-isopropyl-2-oxooxazolidin-3-yl)methyl) pyrrolidin-1-yl)-1-(1-methylcyclo-propyl)-4-oxo-1,4-dihydro-quinoline-3-carboxylic acid | LCMS (ESI) $[M + H]^+$: 488. $^1H$ NMR (300 MHz, DMSO-d6) δ 15.14 (s, 1H), 8.79 (d, J = 3.8 Hz, 1H), 8.20 (d, J = 2.4 Hz, 1H), 7.42 (d, J = 24.7 Hz, 1H), 4.63 (d, J = 23.5 Hz, 1H), 4.23-3.83 (m, 3H), 3.83-3.70 (m, 1H), 3.70-3.49 (m, 1H), 3.39 (s, 1H), 3.05 (m, 1H), 2.32-2.12 (m, 1H), 2.06 (d, J = 14.8 Hz, 1H), 1.84 (s, 3H), 1.69 (s, 2H), 1.61 (s, 1H), 1.46 (m, 2H), 1.28-1.08 (m, 2H), 0.70 (m, 3H), 0.60 (m, 3H). | + |
| 142. | 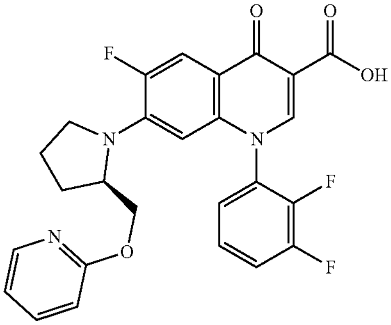 | Charcoal treatment | (R)-1-(2,3-difluorophenyl)-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 496.15. $^1H$ NMR (400 MHz, DMSO-$d_6$) δ 15.23 (s, 1H), 8.80 (d, J = 10.6 Hz, 1H), 8.03 (d, J = 5.7 Hz, 1H), 7.91 (d, J = 14.3 Hz, 1H), 7.80-7.56 (m, 3H), 7.55-7.23 (m, 1H), 6.95 (d, J = 6.6 Hz, 1H), 6.67 (dd, J = 8.3, 5.3 Hz, 1H), 6.01 (t, J = 7.7 Hz, 1H), 4.52-4.31 (m, 1H), 4.20 (t, J = 8.1 Hz, 2H), 3.53-3.41 (m, 1H), 3.26-3.19 (m, 1H), 2.11-1.85 (m, 4H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 143. | 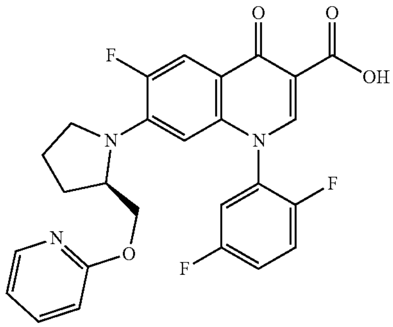 | Charcoal treatment | (R)-1-(2,5-difluorophenyl)-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 496.15 $^1H$ NMR (400 MHz, DMSO-$d_6$) δ 15.20 (s, 1H), 8.72 (s, 1H), 8.04 (t, J = 5.8 Hz, 1H), 7.96-7.79 (m, 2H), 7.75-7.34 (m, 3H), 6.95 (ddd, J = 12.0, 7.0, 5.0 Hz, 1H), 6.67 (t, J = 7.3 Hz, 1H), 6.00 (t, J = 8.1 Hz, 1H), 4.37 (d, J = 19.1 Hz, 1H), 4.18 (qd, J = 10.4, 9.6, 2.9 Hz, 2H), 3.54-3.41 (m, 1H), 3.29-3.15 (m, 1H), 2.19-1.78 (m, 4H). | +++ |
| 144. | 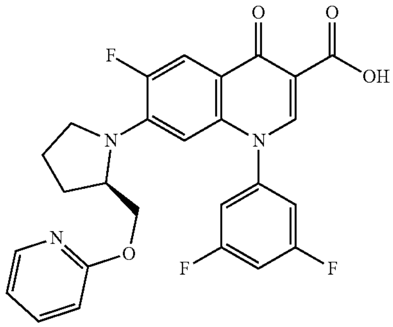 [SMILES: O=C(O)c1cn(-c2cc(F)cc(F)c2)c2cc(N3CCC[C@@H]3COc3ccccn3)c(F)cc2c1=O] | Charcoal treatment | (R)-1-(3,5-difluorophenyl)-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 496.15 $^1H$ NMR (300 MHz, DMSO-$d_6$) δ 15.26 (s, 1H), 8.57 (s, 1H), 8.03 (dd, J = 5.0, 2.0 Hz, 1H), 7.87 (d, J = 14.6 Hz, 1H), 7.67 (td, J = 8.5, 7.8, 2.0 Hz, 1H), 7.57 (dd, J = 11.4, 4.6 Hz, 3H), 6.95 (dd, J = 7.0, 5.1 Hz, 1H), 6.68 (d, J = 8.3 Hz, 1H), 6.09 (d, J = 7.4 Hz, 1H), 4.46-4.30 (m, 1H), 4.27-4.10 (m, 2H), 3.48-3.42 (m, 1H), 3.28-3.18 (m, 1H), 2.15-1.82 (m, 4H). | +++ |
| 145. | 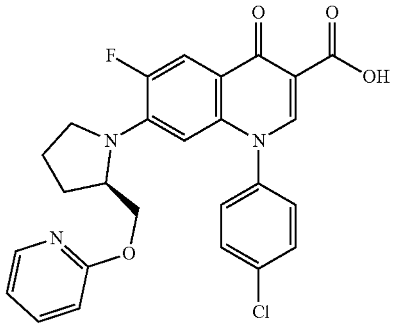 | Column: SunFire Prep C18 OBD Column, 19 × 150 mm 5 um 10 nm; Mobile Phase A: Water (0.05% FA), Mobile Phase B: ACN; Flow rate: 25 mL/min; Gradient: 20 B to 50 B in 8 min; 254/220 nm; RT1: 6.89; RT2:; Injection Volumn: ml; Number Of Runs:; | (R)-1-(4-chlorophenyl)-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 494.00 $^1H$ NMR (400 MHz, DMSO-$d_6$) δ 15.59-15.36 (m, 1H), 8.55 (d, J = 1.8 Hz, 1H), 8.10-8.02 (m, 1H), 7.90 (d, J = 14.5 Hz, 1H), 7.86-7.63 (m, 4H), 7.45 (d, J = 8.3 Hz, 1H), 6.97 (t, J = 6.1 Hz, 1H), 6.67 (d, J = 8.3 Hz, 1H), 6.03 (d, J = 7.2 Hz, 1H), 4.38-4.29 (m, 1H), 4.23 (dd, J = 10.4, 2.5 Hz, 1H), 4.18-4.09 (m, 1H), 3.44-3.39 (m, 1H), 3.28-3.18 (m, 1H), 2.14-1.82 (m, 4H). | ++++ |
| 146. | 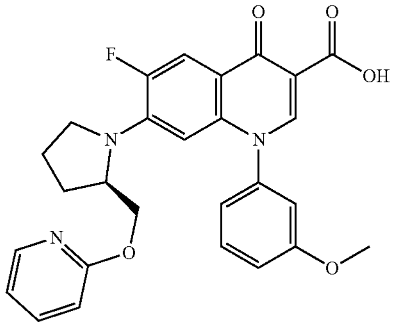 [SMILES: COc1cccc(-n2cc(C(=O)O)c(=O)c3cc(F)c(N4CCC[C@@H]4COc4ccccn4)cc32)c1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 43 B to 70 B in 8 min; 254 nm | (R)-6-fluoro-1-(3-methoxy-phenyl)-4-oxo-7-(2-((pyridin-2-yloxy)methyl)pyrrolidin-1-yl)-1,4-dihydro-quinoline-3-carboxylic acid | LCMS (ESI) $[M + H]^+$: 490.2 $^1H$ NMR (400 MHz, DMSO-$d_6$) δ 15.42 (s, 1H), 8.52 (d, J = 2.3 Hz, 1H), 8.11-7.99 (m, 1H), 7.90 (d, J = 14.5 Hz, 1H), 7.75-7.63 (m, 1H), 7.52-7.25 (m, 2H), 7.17 (s, 2H), 6.96 (s, 1H), 6.68 (s, 1H), 6.17-6.05 (m, 1H), 4.33 (s, 1H), 4.28-4.08 (m, 2H), 3.76 (d, J = 58.3 Hz, 3H), 3.45 (s, 1H), 3.21 (s, 1H), 2.15-1.81 (m, 4H) | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 147. | 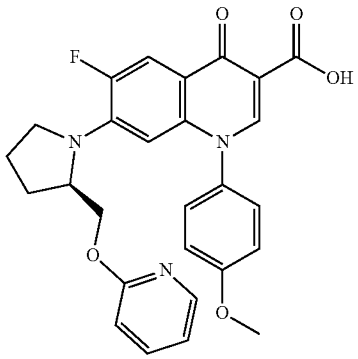 [SMILES: COc1ccc(-n2cc(C(=O)O)c(=O)c3cc(F)c(N4CCC[C@@H]4COc4ccccn4)cc32)cc1] | Charcoal treatment | (R)-6-fluoro-1-(4-methoxy-phenyl)-4-oxo-7-(2-((pyridin-2-yloxy)methyl)pyrrolidin-1-yl)-1,4-dihydro-quinoline-3-carboxylic acid | LCMS (ESI) $[M + H]^+$: 489.3. $^1H$ NMR (300 MHz, DMSO-$d_6$) δ 15.44 (s, 1H), 8.47 (s, 1H), 8.04 (dd, J = 5.2, 2.0 Hz, 1H), 7.89 (d, J = 14.5 Hz, 1H), 7.67 (ddd, J = 8.8, 7.1, 2.0 Hz, 1H), 7.63-7.44 (m, 2H), 7.19 (dd, J = 8.6, 2.9 Hz, 1H), 6.95 (ddt, J = 8.2, 4.9, 1.8 Hz, 2H), 6.67 (d, J = 8.3 Hz, 1H), 6.09 (d, J = 7.5 Hz, 1H), 4.33 (s, 1H), 4.27-4.07 (m, 2H), 3.81 (s, 3H), 3.44-3.36 (m, 1H), 3.20 (dd, J = 15.1, 6.8 Hz, 1H), 2.15-1.79 (m, 4H). | ++++ |
| 148. | 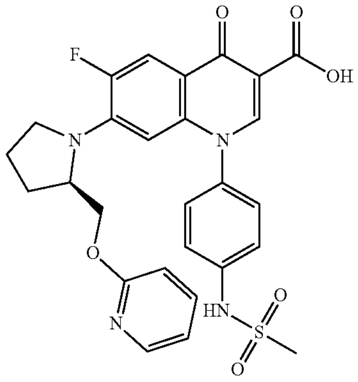 [SMILES: CS(=O)(=O)Nc1ccc(-n2cc(C(=O)O)c(=O)c3cc(F)c(N4CCC[C@@H]4COc4ccccn4)cc32)cc1] | Column: Gemini-NX C18 AXAI Packed, 21.2*150 mm 5 um; Mobile Phase A: Water (0.1% FA), Mobile Phase B: ACN; Flow rate: 30 mL/min; Gradient: 20 B to 75 B in 10 min; 254/220 nm; RT1: 8.77; RT2:; Injection Volumn: ml; Number Of Runs:; | (R)-6-fluoro-1-(4-(methyl-sulfonamido)phenyl)-4-oxo-7-(2-((pyridin-2-yloxy)methyl)pyrrolidin-1-yl)-1,4-dihydro-quinoline-3-carboxylic acid | LCMS (ESI) $[M + H]^+$: 551.1. $^1H$ NMR (300 MHz, DMSO-$d_6$) δ 15.41 (s, 1H), 10.23 (s, 1H), 8.50 (s, 1H), 8.06-8.00 (m, 1H), 7.89 (d, J = 14.5 Hz, 1H), 7.70-7.57 (m, 3H), 7.43 (d, J = 8.7 Hz, 1H), 7.31 (d, J = 8.4 Hz, 1H), 6.99-6.91 (m, 1H), 6.66 (d, J = 8.2 Hz, 1H), 6.13 (d, J = 7.4 Hz, 1H), 4.46-4.37 (m, 1H), 4.27-4.16 (m, 2H), 3.41-3.35 (m, 1H), 3.24-3.15 (m, 1H), 3.09 (s, 3H), 2.11-1.86 (m, 4H). | ++++ |
| 149. | 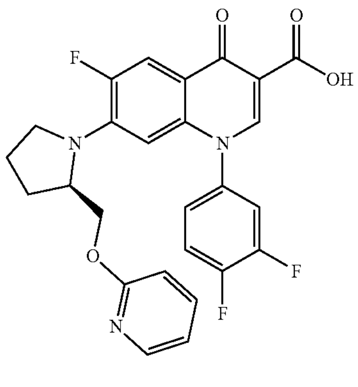 [SMILES: O=C(O)c1cn(-c2ccc(F)c(F)c2)c2cc(N3CCC[C@@H]3COc3ccccn3)c(F)cc2c1=O] | Charcoal treatment | (R)-1-(3,4-difluorophenyl)-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 496.1. $^1H$ NMR (300 MHz, DMSO-$d_6$) δ 15.37 (s, 1H), 8.61 (s, 1H), 8.08-7.93 (m, 2H), 7.90 (d, J = 14.5 Hz, 1H), 7.82-7.39 (m, 3H), 7.01-6.90 (m, 1H), 6.68 (dd, J = 8.2, 4.5 Hz, 1H), 6.05 (d, J = 7.4 Hz, 1H), 4.45-4.32 (m, 1H), 4.26-4.11 (m, 2H), 3.51-3.39 (m, 1H), 3.29-3.19 (m, 1H), 2.14-1.83 (m, 4H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 150. | 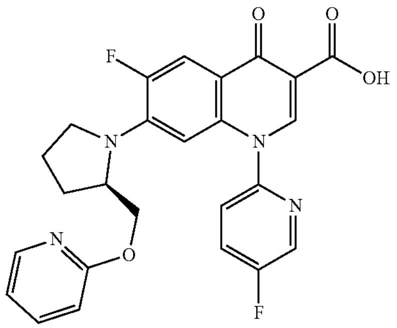 | Column: X Bridge Shield RP18 OBD Column, 5 um, 19*150 mm; Mobile Phase A: Water (10 MMOL/L $NH_4HCO_3$ + 0.1% $NH_3$•$H_2O$), Mobile Phase B: acetonitrile; Flow rate: 20 mL/min; Gradient: 47% B to 77% B in 8 min; 254 nm. | (R)-6-fluoro-1-(5-fluoropyridin-2-yl)-4-oxo-7-(2-((pyridin-2-yloxy)methyl) pyrrolidin-1-yl)-1,4-dihydro-quinoline-3-carboxylic acid | LCMS (ESI) $[M + H]^+$: 479.25. $^1H$ NMR (300 MHz, DMSO-$d_6$) δ 15.27 (s, 1H), 8.77 (s, 1H), 8.66-8.57 (m, 1H), 8.12-8.01 (m, 2H), 8.01-7.93 (m, 1H), 7.92-7.85 (d, J = 14.5 Hz, 1H), 7.73-7.63 ( m, 1H), 7.03-6.93 (m, 1H), 6.68 (d, J = 8.3 Hz, 1H), 6.21 (d, J = 7.4 Hz, 1H), 4.39 (s, 1H), 4.30-4.10 (m, 2H), 3.52-3.42 (m, 1H), 3.31-3.21 (m, 1H), 2.09-1.89 (m, 4H). | +++ |
| 151. | 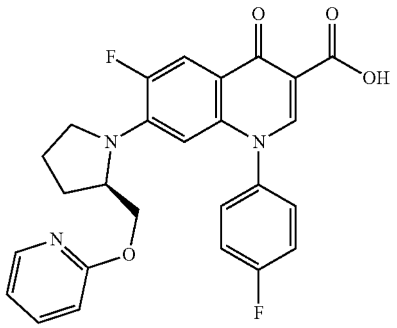 | Column: SunFire Prep C18 OBD Column, 19 x 150 mm 5 um 10 nm; Mobile Phase A: Water (0.05% FA), Mobile Phase B: ACN; Flow rate: 25 mL/min; Gradient: 47 B to 73 B in 8 min; 254/220 nm; RT1: 7.87; RT2:; Injection Volumn: ml; Number Of Runs:; | (R)-6-fluoro-1-(4-fluorophenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 478.00 $^1H$ NMR (300 MHz, DMSO-$d_6$) δ 15.41 (s, 1H), 8.55 (s, 1H), 8.09-8.01 (m, 1H), 7.90 (d, J = 14.5 Hz, 1H), 7.79-7.62 (m, 3H), 7.53 (d, J = 8.6, 3.1 Hz, 1H), 7.24 (d, J = 8.6, 3.0 Hz, 1H), 6.97 (s, 1H), 6.67 (d, J = 8.3 Hz, 1H), 6.01 (d, J = 7.4 Hz, 1H), 4.33 (s, 1H), 4.28-4.17 (m, 1H), 4.14 (s, 1H), 3.22-3.25 (d, J = 8.3 Hz, 2H), 2.03 (s, 2H), 1.93 (s, 2H). | ++++ |
| 152. | 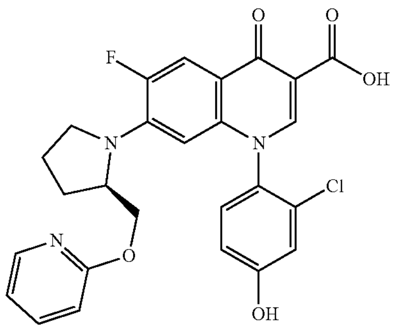 | Charcoal treatment | (R)-1-(2-chloro-4-hydroxy-phenyl)-6-fluoro-4-oxo-7-(2-((pyridin-2-yloxy)methyl) pyrrolidin-1-yl)-1,4-dihydro-quinoline-3-carboxylic acid | LCMS (ESI): $[M + H]^+$: 510.10 $^1H$ NMR (300 MHz, DMSO-$d_6$) δ 15.34 (s, 1H), 10.62 (s, 1H), 8.55 (d, J = 1.0 Hz, 1H), 8.09-7.98 (m, 1H), 7.90 (d, J = 14.5 Hz, 1H), 7.74-7.61 (m, 1H), 7.64-7.50 (m, 1H), 7.13 (d, J = 2.6 Hz, 1H), 7.04-6.92 (m, 1H), 6.92-6.86 (m, 1H), 6.71-6.61 (m, 1H), 6.00-5.80 (m, 1H), 4.35 (s, 1H), 4.26-4.08 (m, 2H), 3.63-3.56 (m, 1H), 3.21 (s, 1H), 2.11-1.86 (m, 4H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 153. | 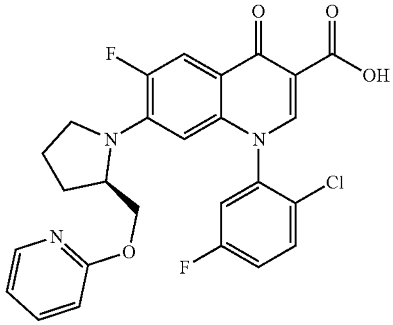 [SMILES: O=C(O)c1cn(-c2cc(F)ccc2Cl)c2cc(N3CCC[C@@H]3COc3ccccn3)c(F)cc2c1=O] | Charcoal treatment | (R)-1-(2-chloro-5-fluorophenyl)-6-fluoro-4-oxo-7-(2-((pyridin-2-yloxy)methyl)pyrrolidin-1-yl)-1,4-dihydro-quinoline-3-carboxylic acid | LCMS (ESI) $[M + H]^+$: 512.19. $^1H$ NMR (300 MHz, DMSO-$d_6$) δ 15.27 (s, 1H), 8.76 (d, J = 1.1 Hz, 1H), 8.05 (ddd, J = 6.7, 4.7, 1.9 Hz, 1H), 7.91 (ddd, J = 11.4, 5.8, 2.8 Hz, 2H), 7.76-7.48 (m, 3H), 7.03-6.90 (m, 1H), 6.69 (t, J = 8.3 Hz, 1H), 5.84 (dd, J = 12.4, 7.4 Hz, 1H), 4.35 (s, 1H), 4.18 (s, 2H), 3.21 (s, 1H), 1.99 (dd, J = 40.6, 9.7 Hz, 5H). | +++ |
| 154. | 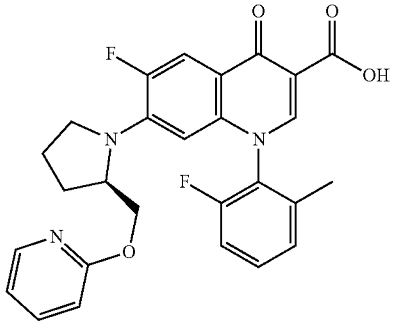 [SMILES: Cc1cccc(F)c1-n1cc(C(=O)O)c(=O)c2cc(F)c(N3CCC[C@@H]3COc3ccccn3)cc21] | Charcoal treatment | (R)-6-fluoro-1-(2-fluoro-6-methylphenyl)-4-oxo-7-(2-((pyridin-2-yloxy)methyl)pyrrolidin-1-yl)-1,4-dihydro-quinoline-3-carboxylic acid | LCMS (ESI) $[M + H]^+$: 492.0 $^1H$ NMR (400 MHz, DMSO-$d_6$) δ 15.26 (s, 1H), 8.74 (d, J = 2.0 Hz, 1H), 8.09-8.02 (m, 1H), 7.92 (s, 1H), 7.75-7.63 (m, 1H), 7.54 (d, J = 7.9, 5.7 Hz, 1H), 7.48-7.36 (m, 1H), 7.20-7.06 (m, 1H), 6.96 (s, 1H), 6.67 (s, 1H), 5.80 (d, J = 11.8, 7.3 Hz, 1H), 4.29 (d, J = 19.9 Hz, 1H), 4.22-4.11 (m, 2H), 3.40 (s, 1H), 3.20 (s, 1H), 2.02 (d, J = 21.2 Hz, 4H), 1.99-1.80 (m, 3H). | +++ |
| 155. | 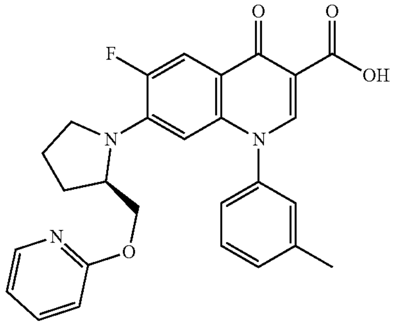 [SMILES: Cc1cccc(-n2cc(C(=O)O)c(=O)c3cc(F)c(N4CCC[C@@H]4COc4ccccn4)cc32)c1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 43 B to 67 B in 10 min; 254 nm; RT1: 9.82; RT2:; Injection Volumn: ml; Number Of Runs:; | (R)-6-fluoro-4-oxo-7-(2-((pyridin-2-yloxy)methyl)pyrrolidin-1-yl)-1-(m-tolyl)-1,4-dihydro-quinoline-3-carboxylic acid | LCMS (ESI): $[M + H]^+$: 474.2. $^1H$ NMR (300 MHz, DMSO-d6) δ 8.50 (s, 1H), 8.07-7.99 (m, 1H), 7.94-7.83 (m, 1H), 7.73-7.62 (m, 1H), 7.58-7.44 (m, 2H), 7.43-7.29 (m, 2H), 7.01-6.91 (m, 1H), 6.72-6.63 (m, 1H), 6.15-6.03 (m, 1H), 4.27 (s, 1H), 4.23-4.11 (m, 2H), 3.49 (s, 1H), 3.38 (s, 1H), 2.43 (s, 2H), 2.22 (s, 1H), 2.05-1.75 (m, 4H). | ++++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 156. | 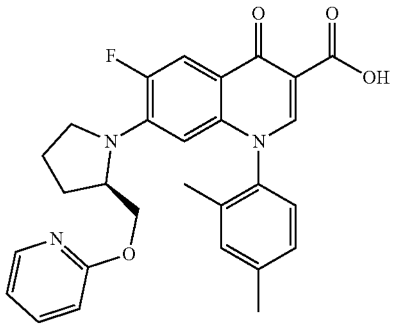 [SMILES: Cc1ccc(-n2cc(C(=O)O)c(=O)c3cc(F)c(N4CCC[C@@H]4COc4ccccn4)cc32)c(C)c1] | Column: SunFire Prep C18 OBD Column, 19 x 150 mm 5 um 10 nm; Mobile Phase A: Water (0.05% FA), Mobile Phase B: ACN; Flow rate: 25 mL/min; Gradient: 20 B to 50 B in 8 min; 254/220 nm; RT1: 6.58; RT2:; Injection Volumn: ml; Number Of Runs:; | (R)-1-(2,4-dimethyl-phenyl)-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 488.25 $^1H$ NMR (400 MHz, DMSO-$d_6$) δ 15.42 (d, J = 2.0 Hz, 1H), 8.46 (d, J = 1.5 Hz, 1H), 8.11-8.02 (m, 1H), 7.95-7.87 (m, 1H), 7.76-7.64 (m, 1H), 7.43-7.25 (m, 2H), 7.04-6.86 (m, 2H), 6.73-6.63 (m, 1H), 5.90-5.78 (m, 1H), 4.27-4.14 (m, 2H), 4.13-4.01 (m, 1H), 3.43 (s, 1H), 3.27-3.16 (m, 1H), 2.32 (s, 3H), 2.10-1.84 (m, 7H). | +++ |
| 157. | 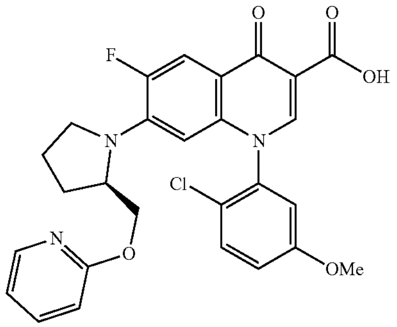 | Column: SunFire Prep C18 OBD Column, 19 x 150 mm 5 um 10 nm; Mobile Phase A: Water (0.05% FA), Mobile Phase B: acetonitrile; Flow rate: 25 mL/min; Gradient: 25 B to 50 B in 8 min; 254/220 nm. | (R)-1-(2-chloro-5-methoxy-phenyl)-6-fluoro-4-oxo-7-(2-((pyridin-2-yloxy)methyl) pyrrolidin-1-yl)-1,4-dihydro-quinoline-3-carboxylic acid | LCMS (ESI): $[M + H]^+$: 524.1 $^1H$ NMR (300 MHz, DMSO-$d_6$) δ 15.31 (s, 1H), 8.63 (d, J = 1.2 Hz, 1H), 8.09-8.00 (m, 1H), 7.91 (dd, J = 14.5, 0.9 Hz, 1H), 7.76-7.62 (m, 1.5H), 7.50 (dd, J = 7.6, 3.0 Hz, 1H), 7.39 (d, J = 9.0 Hz, 0.5H), 7.19 (ddd, J = 9.0, 4.4, 3.0 Hz, 1H), 7.03-6.90 (m, 1H), 6.75-6.63 (m, 1H), 5.88 (dd, J = 14.0, 7.4 Hz, 1H), 4.37-4.23 (m, 1H), 4.15 (d, J = 5.6 Hz, 2H), 3.75 (d, J = 52.9 Hz, 3H), 3.50-3.40 (m, 1H), 3.29-3.13 (m, 1H), 2.14-1.81 (m, 4H). | +++ |
| 158. | 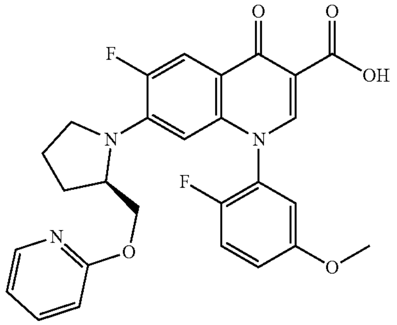 [SMILES: COc1ccc(F)c(-n2cc(C(=O)O)c(=O)c3cc(F)c(N4CCC[C@@H]4COc4ccccn4)cc32)c1] | Column: (Column: Atlantis HILIC OBD Column, 19*150 mm*5 um; Mobile Phase A: Water (0.1% FA), Mobile Phase B: ACN; Flow rate: 30 mL/min; Gradient: 35 B to 75 B in 12 min; 254/220 nm | (R)-6-fluoro-1-(2-fluoro-5-methoxy-phenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 508.2 $^1H$ NMR (400 MHz, DMSO-$d_6$) δ 15.28 (s, 1H), 8.70 (d, J = 2.1 Hz, 1H), 8.05 (d, J = 9.1, 5.1, 2.0, 0.8 Hz, 1H), 7.91 (d, J = 14.5 Hz, 1H), 7.68 (s, 1H), 7.48-7.39 (m, 1H), 7.29-7.14 (m, 1H), 6.96 (s, 1H), 6.68 (d, J = 9.3, 8.4, 1.0 Hz, 1H), 6.12-5.98 (m, 1H), 4.35 (d, J = 19.7 Hz, 1H), 4.19 (s, 2H), 3.74 (d, J = 62.5 Hz, 3H), 3.44 (s, 1H), 3.25 (s, 1H), 2.03 (s, 2H), 1.98-1.85 (m, 2H) | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 159. | 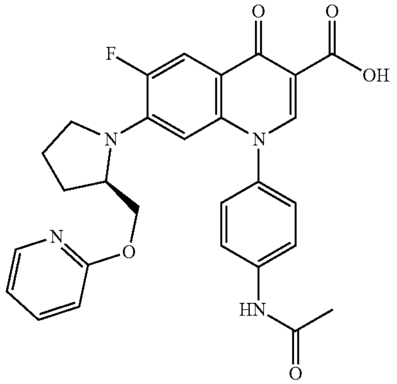 [SMILES: CC(=O)Nc1ccc(-n2cc(C(=O)O)c(=O)c3cc(F)c(N4CCC[C@@H]4COc4ccccn4)cc32)cc1] | Charcoal treatment | (R)-1-(4-acetamido-phenyl)-6-fluoro-4-oxo-7-(2-((pyridin-2-yloxy)methyl) pyrrolidin-1-yl)-1,4-dihydro-quinoline-3-carboxylic acid | LCMS (ESI) $[M + H]^+$: 517.1. $^1H$ NMR (300 MHz, DMSO-$d_6$) δ 15.43 (s, 1H), 10.27 (s, 1H), 8.49 (s, 1H), 8.02 (dd, J = 5.2, 1.9 Hz, 1H), 7.87 (t, J = 11.0 Hz, 2H), 7.77-7.61 (m, 2H), 7.55 (t, J = 7.1 Hz, 2H), 6.94 (dd, J = 7.0, 5.0 Hz, 1H), 6.64 (d, J = 8.3 Hz, 1H), 6.11 (d, J = 7.4 Hz, 1H), 4.50-4.30 (m, 1H), 4.22 (d, J = 11.4 Hz, 2H), 3.32 (m, 1H), 3.25-3.10 (m, 1H), 2.11 (s, 3H), 2.07-1.86 (m, 4H). | ++++ |
| 160. | 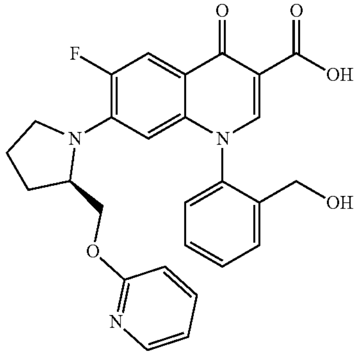 [SMILES: O=C(O)c1cn(-c2ccccc2CO)c2cc(N3CCC[C@@H]3COc3ccccn3)c(F)cc2c1=O] | Column: XSelect CSH Prep C18 OBD Column,, 5 um, 19*150 mm; Mobile Phase A: Water (0.05% FA), Mobile Phase B: ACN; Flow rate: 25 mL/min; Gradient: 20 B to 60 B in 8 min; 254/220 nm; RT1: 6.85; RT2:; Injection Volumn: ml; Number Of Runs | (R)-6-fluoro-1-(2-(hydroxy-methyl)phenyl)-4-oxo-7-(2-((pyridin-2-yloxy)methyl) pyrrolidin-1-yl)-1,4-dihydro-quinoline-3-carboxylic acid | LCMS (ESI) $[M + H]^+$: 490.2. $^1H$ NMR (300 MHz, DMSO-$d_6$) δ 15.47-15.41 (m, 1H), 8.54-8.47 (m, 1H), 8.10-7.99 (m, 1H), 7.95-7.84 (m, 1H), 7.69-7.31 (m, 5H), 7.02-6.92 (m, 1H), 6.72-6.61 (m, 1H), 5.89-5.71 (m, 1H), 5.33-5.18 (m, 1H), 4.34-4.24 (m, 1H), 4.18-4.09 (m, 4H), 3.25-3.03 (m, 2H). 2.04-1.86 (m, 4H). | +++ |
| 161. | 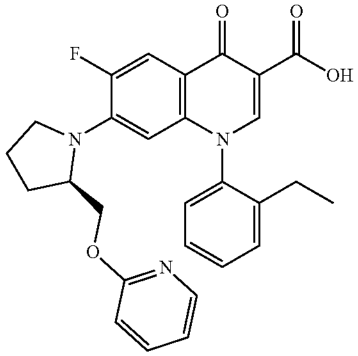 [SMILES: CCc1ccccc1-n1cc(C(=O)O)c(=O)c2cc(F)c(N3CCC[C@@H]3COc3ccccn3)cc21] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 53 B to 70 B in 10 min; 254 nm; RT1: 8.25; RT2:; Injection Volumn: ml; Number Of Runs:; | (R)-1-(2-ethylphenyl)-6-fluoro-4-oxo-7-(2-((pyridin-2-yloxy)methyl) pyrrolidin-1-yl)-1,4-dihydro-quinoline-3-carboxylic acid | LCMS (ESI): $[M + H]^+$: 488.1 $^1H$ NMR (400 MHz, DMSO-$d_6$) δ 15.40 (s, 1H), 8.52 (d, J = 4.3 Hz, 1H), 8.07-8.01 (m, 1H), 7.92 (d, J = 14.5, 3.0 Hz, 1H), 7.69 (d, J = 8.9, 7.0, 2.0 Hz, 1H), 7.62-7.45 (m, 3H), 7.35-7.23 (m, 1H), 6.97 (s, J = 11.9, 7.1, 5.0 Hz, 1H), 6.66 (d, J = 12.7, 8.3 Hz, 1H), 5.79 (d, J = 19.7, 7.4 Hz, 1H), 4.22 (s, 1H), 4.16 (m, J = 4.6 Hz, 1H), 4.11 (s, J = 6.8, 5.8 Hz, 1H), 3.15 (m, J = 8.4 Hz, 2H), 2.29-2.15 (m, 2H), 2.10-1.90 (m, 2H), 1.90 (s, 2H), 0.97 (d, J = 18.1, 7.5 Hz, 3H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 162. | 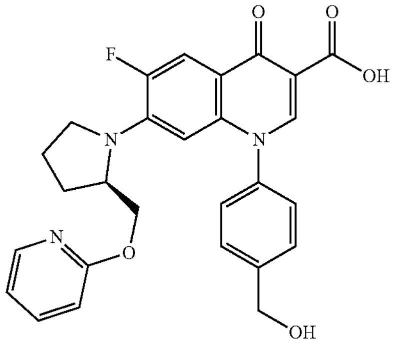 [SMILES: O=C(O)c1cn(-c2ccc(CO)cc2)c2cc(N3CCC[C@@H]3COc3ccccn3)c(F)cc2c1=O] | Column: Gemini-NX C18 AXAI Packed, 21.2*150 mm 5 um; Mobile Phase A: Water (0.1% FA), Mobile Phase B: ACN; Flow rate: 30 mL/min; Gradient: 20 B to 75 B in 10 min; 254/220 nm; RT1: 8.5; RT2:; Injection Volumn: ml; Number Of Runs:; | (R)-6-fluoro-1-(4-(hydroxy-methyl)phenyl)-4-oxo-7-(2-((pyridin-2-yloxy)methyl) pyrrolidin-1-yl)-1,4-dihydro-quinoline-3-carboxylic acid | LCMS (ESI): $[M + H]^+$: 590.05 $^1$H NMR (300 MHz, DMSO-$d_6$) δ 15.42 (s, 1H), 8.48 (s, 1H), 8.08-8.00 (m, 1H), 7.89 (d, J = 14.5 Hz, 1H), 7.73-7.62 (m, 1H), 7.57 (d, J = 16.9 Hz, 3H), 7.35 (d, J = 8.2 Hz, 1H), 7.02-6.91 (m, 1H), 6.72-6.63 (m, 1H), 6.09 (d, J = 7.5 Hz, 1H), 5.49-5.40 (m, 1H), 4.59 (d, J = 5.6 Hz, 2H), 4.34 (s, 1H), 4.24-4.13 (m, 2H), 3.33-3.30 (m, 1H), 3.18 (d, J = 8.3 Hz, 1H), 2.10-1.88 (m, 2H), 1.92 (s, 2H) | ++++ |
| 163. | 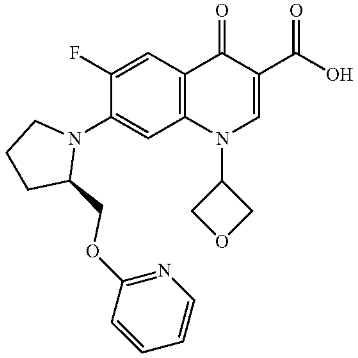 [SMILES: O=C(O)c1cn(C2COC2)c2cc(N3CCC[C@@H]3COc3ccccn3)c(F)cc2c1=O] | Column: Gemini-NX C18 AXAI Packed, 21.2*150 mm 5 um; Mobile Phase A: Water (0.1% FA), Mobile Phase B: ACN; Flow rate: 30 mL/min; Gradient: 20 B to 75 B in 10 min; 254/220 nm; RT1: 8.27; RT2:; Injection Volumn: ml; Number Of Runs:; | (R)-6-fluoro-1-(oxetan-3-yl)-4-oxo-7-(2-((pyridin-2-yloxy)methyl) pyrrolidin-1-yl)-1,4-dihydro-quinoline-3-carboxylic acid | LCMS (ESI) $[M + H]^+$: 478.10. $^1$H NMR (400 MHz, DMSO-$d_6$) δ 15.49 (s, 1H), 8.62 (s, 1H), 8.14-8.08 (m, 1H), 7.87 (d, J = 14.6 Hz, 1H), 7.72-7.64 (m, 1H), 7.00-6.93 (m, 1H), 6.78-6.71 (m, 1H), 6.53 (d, J = 7.3 Hz, 1H), 5.86 (q, J = 7.0 Hz, 1H), 5.12-5.02 (m, 2H), 5.01-4.91 (m, 2H), 4.68 (s, 1H), 4.46-4.37 (m, 1H), 4.30-4.21 (m, 1H), 3.73 (s, 1H), 3.50 (d, J = 9.1 Hz, 1H), 2.17-2.07 (m, 2H), 2.07-1.93 (m, 2H). | +++ |
| 164. | 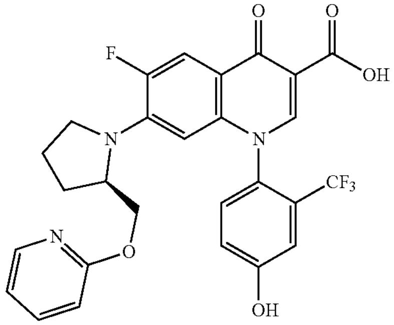 | Column: XSelect CSH Prep C18 OBD Column,, 5 um, 19*150 mm; Mobile Phase A: Water (0.1% FA), Mobile Phase B: ACN; Flow rate: 25 mL/min; Gradient: 43 B to 67 B in 8 min; 254 nm; RT1: 7.25; RT2:; Injection Volumn: ml; Number Of Runs:; | (R)-6-fluoro-1-(4-hydroxy-2-(trifluoro-methyl)phenyl)-4-oxo-7-(2-((pyridin-2-yloxy)methyl) pyrrolidin-1-yl)-1,4-dihydro-quinoline-3-carboxylic acid | LCMS (ESI): $[M + H]^+$: 544.2. $^1$H NMR (300 MHz, DMSO-$d_6$) δ 15.26 (s, 1H), 11.04 (s, 1H), 8.60 (s, 1H), 8.11-7.99 (m, 1H), 7.88 (d, J = 14.5 Hz, 1H), 7.66 (m, 2H), 7.39-7.21 (m, 1H), 7.15-7.01 (m, 1H), 6.96 (dt, J = 7.2, 5.2 Hz, 1H), 6.66 (d, J = 8.3 Hz, 1H), 5.80 (dd, J = 24.5, 7.3 Hz, 1H), 4.41-4.23 (m, 1H), 4.15 (dd, J = 12.6, 4.7 Hz, 2H), 3.31-3.10 (m, 2H), 2.16-1.80 (m, 4H). | ++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 165. | 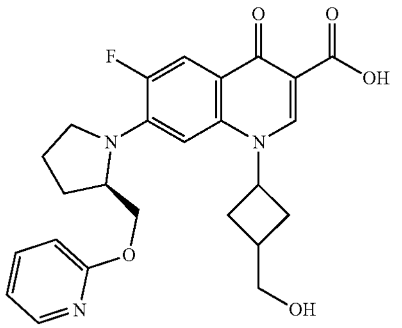 [SMILES: O=C(O)c1cn(C2CC(CO)C2)c2cc(N3CCC[C@@H]3COc3ccccn3)c(F)cc2c1=O] | Column: X Select CSH Prep C18 OBD Column, 5 um, 19*150 mm; Mobile Phase A: Water (0.1% FA), Mobile Phase B: acetonitrile; Flow rate: 25 mL/min; Gradient: 36 B to 52 B in 7 min; 254 nm. | (R)-6-fluoro-1-(3-(hydroxy-methyl)cyclo-butyl)-4-oxo-7-(2-((pyridin-2-yloxy)methyl) pyrrolidin-1-yl)-1,4-dihydro-quinoline-3-carboxylic acid | LCMS (ESI): $[M + H]^+$: 468.30 $^1H$ NMR (300 MHz, DMSO-$d_6$) δ 15.58 (s, 1H), 8.55 (s, 1H), 8.13-8.05 (m, 1H), 7.84 (d, J = 14.6 Hz, 1H), 7.73-7.61 (m, 1H), 7.01-6.91 (m, 1H), 6.84 (s, 1H), 6.73 (d, 1H), 4.95 (s, 1H), 4.71-4.61 (m, 2H), 4.47-4.37 (m, 1H), 4.34-4.26 (m, 1H), 3.75 (s, 1H), 3.52 (s, 1H), 3.43-3.37 (m, 2H), 2.68-2.60 (m, 2H), 2.18-2.12 (m, 7H). | ++ |
| 166. | 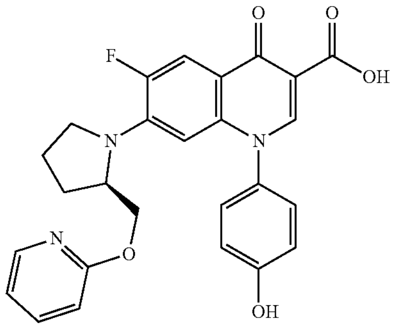 | Column: X Select CSH Prep C18 OBD Column, 5 um, 19*150 mm; Mobile Phase A: Water (0.1% FA), Mobile Phase B: acetonitrile; Flow rate: 25 mL/min; Gradient: 30 B to 67 B in 10 min; 254 nm. | (R)-6-fluoro-1-(4-hydroxy-phenyl)-4-oxo-7-(2-((pyridin-2-yloxy)methyl) pyrrolidin-1-yl)-1,4-dihydro-quinoline-3-carboxylic acid | LCMS (ESI): $[M + H]^+$: 442.1. $^1H$ NMR (300 MHz, DMSO-$d_6$) δ 15.46 (s, 1H), 10.13 (s, 1H), 8.46 (s, 1H), 8.08-8.00 (m, 1H), 7.88 (d, J = 14.5 Hz, 1H), 7.73-7.61 (m, 1H), 7.47-7.36 (m, 2H), 7.04-6.90 (m, 2H), 6.86-6.76 (m, 1H), 6.71-6.62 (m, 1H), 6.12 (d, J = 7.5 Hz, 1H), 4.39 (s, 1H), 4.28-4.14 (m, 2H), 3.35-3.29 (m, 1H), 3.25-3.11 (m, 1H), 2.14-1.97 (m, 2H), 1.97-1.86 (m, 2H). | ++++ |
| 167. | 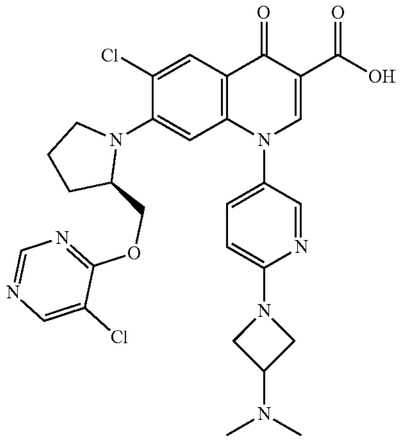 [SMILES: CN(C)C1CN(c2ccc(-n3cc(C(=O)O)c(=O)c4cc(Cl)c(N5CCC[C@@H]5COc5ncncc5Cl)cc43)cn2)C1] | Column: X Select CSH Prep C18 OBD Column, 5 um, 19*150 mm; Mobile Phase A: Water (0.1% FA), Mobile Phase B: acetonitrile; Flow rate: 25 mL/min; Gradient: 55 B to 63 B in 10 min; 254/220 nm. | (R)-6-chloro-7-(2-(((5-chloro-pyrimidin-4-yl)oxy)methyl) pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) $[M + H]^+$: 610.3. $^1H$ NMR (300 MHz, DMSO-$d_6$) δ 8.63 (s, 1H), 8.54 (d, J = 8.0 Hz, 2H), 8.27-8.13 (m, 2H), 7.77-7.64 (m, 1H), 6.61-6.36 (m, 2H), 4.68 (s, 1H), 4.51-4.30 (m, 2H), 4.07 (q, J = 7.9 Hz, 2H), 3.88-3.75 (m, 2H), 3.51 (s, 1H), 3.31-3.14 (m, 2H), 2.28-2.19 (m, 1H), 2.15 (s, 6H), 2.03-1.73 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 168. | 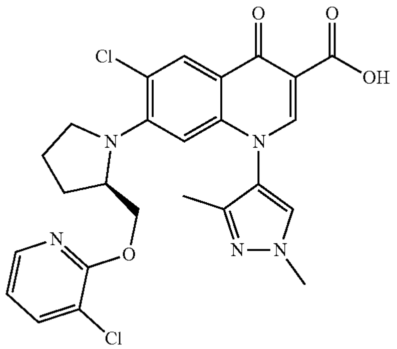 [SMILES: Cc1nn(C)cc1-n1cc(C(=O)O)c(=O)c2cc(Cl)c(N3CCC[C@@H]3COc3ncccc3Cl)cc21] | Column: X Bridge Shield RP18 OBD Column, 5 um, 19*150 mm; Mobile Phase A: Water (0.1% FA), Mobile Phase B: acetonitrile; Flow rate: 25 mL/min; Gradient: 38 B to 68 B in 10 min; 254 nm. | (R)-6-chloro-7-(2-(((3-chloropyridin-2-yl)oxy)methyl)pyrrolidin-1-yl)-1-(1,3-dimethyl-1H-pyrazol-4-yl)-4-oxo-1,4-dihydro-quinoline-3-carboxylic acid | LCMS (ESI) $[M + H]^+$: 528.1. $^1H$ NMR (400 MHz, DMSO-d6) δ 15.02 (s, 1H), 8.51 (s, 1H), 8.14 (d, J = 9.9 Hz, 2H), 7.90 (s, 1H), 7.81 (dd, J = 7.7, 1.7 Hz, 1H), 6.97-6.89 (m, 1H), 6.46 (s, 1H), 4.79 (s, 1H), 4.29 (d, J = 4.1 Hz, 2H), 3.87 (s, 3H), 3.60-3.49 (m, 1H), 3.21 (t, J = 8.3 Hz, 1H), 2.33-2.22 (m, 1H), 2.06-1.77(m, 6H). | ++++ |
| 169. | 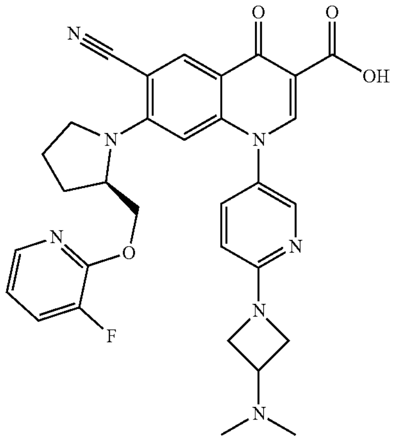 [SMILES: CN(C)C1CN(c2ccc(-n3cc(C(=O)O)c(=O)c4cc(C#N)c(N5CCC[C@@H]5COc5ncccc5F)cc43)cn2)C1] | Column: X Select CSH Prep C18 OBD Column, 5 um, 19*150 mm; Mobile Phase A: Water (0.1% FA), Mobile Phase B: acetonitrile; Flow rate: 25 mL/min; Gradient: 15 B to 30 B in 8 min; 254/220 nm. | (R)-6-cyano-1-(6-(3-(dimethyl-amino)azetidin-1-yl)pyridin-3-yl)-7-(2-(((3-fluoropyridin-2-yl)oxy)methyl)pyrrolidin-1-yl)-4-oxo-1,4-dihydro-quinoline-3-carboxylic acid | LCMS (ESI) $[M + H]^+$: 584.2. $^1H$ NMR (300 MHz, DMSO-d6) δ 14.74 (s, 1H), 8.53 (d, J = 2.9 Hz, 1H), 8.47 (s, 1H), 8.30-8.18 (m, 1H), 7.89-7.79 (m, 1H), 7.79-7.58 (m, 2H), 7.10-6.96 (m, 1H), 6.59-6.14 (m, 2H), 4.68-4.50 (m, 1H), 4.46-4.21 (m, 2H), 4.06-3.93 (m, 2H), 3.86-3.60 (m, 3H), 3.54-3.44 (m, 1H), 3.26-3.20 (m, 1H), 2.16 (s, 8H), 2.04-1.92 (m, 2H). | ++++ |
| 170. | 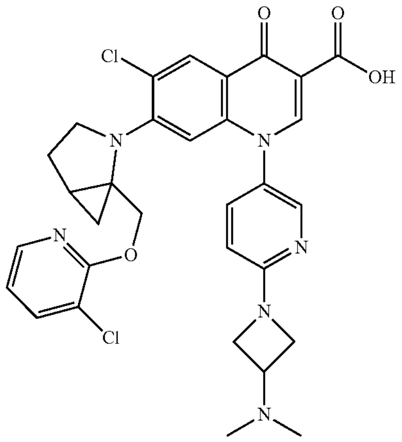 [SMILES: CN(C)C1CN(c2ccc(-n3cc(C(=O)O)c(=O)c4cc(Cl)c(N5CCC6CC65COc5ncccc5Cl)cc43)cn2)C1] | Column: Gemini-NX C18 AXAI Packed, 21.2*150 mm 5 um; Mobile Phase A: Water (0.1% FA), Mobile Phase B: acetonitrile; Flow rate: 25 mL/min; Gradient: 10 B to 10 B in 2 min; 254 nm. | 6-chloro-7-(1-(((3-chloropyridin-2-yl)oxy)methyl)-2-azabicyclo [3.1.0]hexan-2-yl)-1-(6-(3-(dimethyl-amino)azetidin-1-yl)pyridin-3-yl)-4-oxo-1,4-dihydro-quinoline-3-carboxylic acid | LCMS (ESI) $[M + H]^+$: 621.10. $^1H$ NMR (400 MHz, DMSO-d6) δ 15.03 (s, 1H), 8.64 (d, J = 3.4 Hz, 1H), 8.30 (t, J = 3.3 Hz, 1H), 8.21 (s, 1H), 7.93-7.72 (m, 3H), 7.00-6.82 (m, 2H), 6.47 (dd, J = 89.5, 8.8 Hz, 1H), 4.69 (dd, J = 18.5, 12.0 Hz, 1H), 4.26-3.99 (m, 4H), 3.91-3.74 (m, 2H), 2.83 (p, J = 7.7 Hz, 1H), 2.22 (s, 1H), 2.14 (s, 7H), 1.92-1.72 (m, 2H), 1.08-0.90 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 171. | 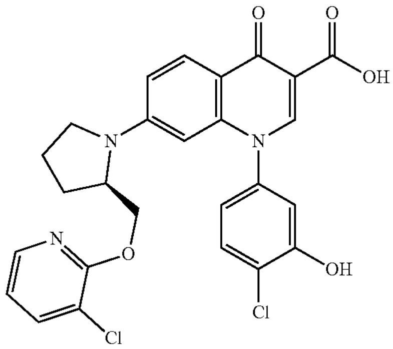 [SMILES: O=C(O)c1cn(-c2ccc(Cl)c(O)c2)c2cc(N3CCC[C@@H]3COc3ncccc3Cl)ccc2c1=O] | Column: Gemini-NX C18 AXAI Packed, 21.2*150 mm 5 um; Mobile Phase A: Water (0.1% FA), Mobile Phase B: acetonitrile; Flow rate: 25 mL/min; Gradient: 45 B to 71 B in 8 min; 254 nm. | (R)-1-(4-chloro-3-hydroxy-phenyl)-7-(2-(((3-chloropyridin-2-yl)oxy)methyl) pyrrolidin-1-yl)-4-oxo-1,4-dihydro-quinoline-3-carboxylic acid | LCMS (ESI) [M + H]$^+$: 526.0. $^1$H NMR (400 MHz, DMSO-d6) δ 15.69 (s, 1H), 10.90 (s, 1H), 8.49 (s, 1H), 8.19 (d, J = 9.1 Hz, 1H), 8.15-8.06 (m, 1H), 7.94-7.86 (m, 1H), 7.63 (s, 0.5H), 7.43 (s, 0.5H), 7.30 (d, J = 11.0 Hz, 1H), 7.20-7.14 (m, 1H), 7.16-7.00 (m, 2H), 6.00 (d, J = 5.2 Hz, 1H), 4.46-4.40 (m, 1H), 4.36-4.14 (m, 2H), 3.32-3.25 (m, 1H), 3.11-3.06 (m, 1H), 2.20-2.16 (m, 1H), 2.03-2.00 (m, 3H). | + |
| 172. | 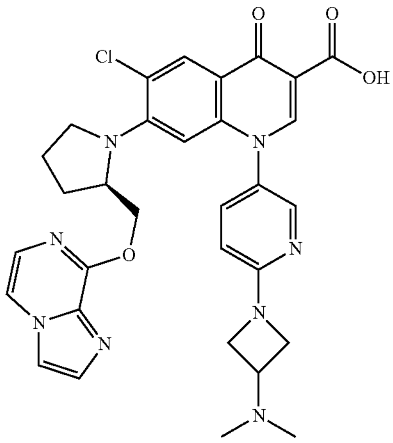 [SMILES: CN(C)C1CN(c2ccc(-n3cc(C(=O)O)c(=O)c4cc(Cl)c(N5CCC[C@@H]5COc5nccn6ccnc56)cc43)cn2)C1] | Column: XSelect CSH Prep C18 OBD Column, 5 um, 19*150 mm; Mobile Phase A: Water (0.1% FA), Mobile Phase B: acetonitrile; Flow rate: 25 mL/min; Gradient: 20 B to 23 B in 8 min; 254/220 nm. | (R)-6-chloro-1-(6-(3-(dimethyl-amino)azetidin-1-yl)pyridin-3-yl)-7-(2-((imidazo [1,2-a]pyrazin-8-yloxy)methyl) pyrrolidin-1-yl)-4-oxo-1,4-dihydro-quinoline-3-carboxylic acid | LCMS (ESI) [M + H]$^+$: 615.3. $^1$H NMR (300 MHz, DMSO-d6) δ 15.09 (s, 1H), 8.50 (d, J = 9.5 Hz, 1H), 8.29-8.20 (m, 1H), 8.17-8.12 (m, 1H), 8.08 (s, 1H), 8.00 (s, 1H), 7.79-7.53 (m, 2H), 7.19 (dd, J = 13.1, 4.5 Hz, 1H), 6.57-6.14 (m, 2H), 4.80-4.44 (m, 2H), 4.40-4.21 (m, 1H), 4.09-3.85 (m, 2H), 3.83-3.62 (m, 2H), 3.60-3.49 (m, 1H), 3.28-3.13 (m, 2H), 2.31-2.25 (m, 1H), 2.14 (s, 6H), 2.03-1.72 (m, 3H). | ++++ |
| 173. | 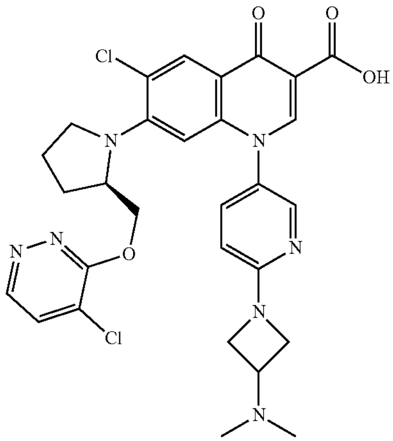 [SMILES: CN(C)C1CN(c2ccc(-n3cc(C(=O)O)c(=O)c4cc(Cl)c(N5CCC[C@@H]5COc5nnccc5Cl)cc43)cn2)C1] | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 14 B to 30 B in 9 min; 254/220 nm. | (R)-6-chloro-7-(2-(((4-chloro-pyridazin-3-yl)oxy)methyl) pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) [M + H]$^+$: 610.30. $^1$H NMR (300 MHz, DMSO-d6) δ 15.03 (s, 1H), 8.95-8.87 (m, 1H), 8.55 (d, J = 8.4 Hz, 1H), 8.26 (d, J = 3.2 Hz, 1H), 8.21-8.15 (m, 1H), 7.71 (dd, J = 18.1, 8.6 Hz, 1H), 7.35-7.29 (m, 1H), 6.59-6.19 (m, 2H), 4.60 (d, J = 21.1 Hz, 1H), 4.23 (s, 1H), 4.09-4.00 (m, 3H), 3.80 (dd, J = 8.7, 5.0 Hz, 2H), 3.66-3.60 (m, 1H), 3.28-3.16 (m, 1H), 2.28 (s, 1H), 2.15 (s, 6H), 2.03-1.97 (m, 1H), 1.89-1.84 (m, 2H). | ++++ |

TABLE 1-continued

| Compound | Product | Prep HPLC Method | IUPAC name | Analytical data | Potency Lin28a-dep Z11 $IC_{50}$ (μM) |
| --- | --- | --- | --- | --- | --- |
| 174. | 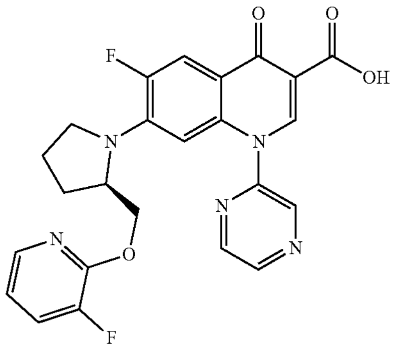 | Column: XSelect CSH Prep C18 OBD Column, 19*150 mm, 5 um; Mobile Phase A: Water (0.1% FA), Mobile Phase B: ACN; Flow rate: 25 mL/min; Gradient: 36% B to 65% B in 8 min, 65% B; Wave Length: 254/220 nm; RT1(min): 7.65; Number Of Runs: 0 | rac-(R)-6-fluoro-7-(2-(((3-fluoropyridin-2-yl)oxy)methyl)pyrrolidin-1-yl)-4-oxo-1-(pyrazin-2-yl)-1,4-dihydro-quinoline-3-carboxylic acid | LCMS (ESI) [M + H]+: 480.14. $^{1}$H NMR (400 MHz, DMSO-d6) δ 15.17 (s, 1H), 9.14 (s, 1H), 8.94-8.88 (m, 2H), 8.76 (d, J = 2.0 Hz, 1H), 7.90 (d, J = 14.5 Hz, 1H), 7.86-7.80 (m, 1H), 7.68-7.59 (m, 1H), 7.04-6.95 (m, 1H), 6.28 (d, J = 7.3 Hz, 1H), 4.53 (s, 1H), 4.33 (d, J = 5.3 Hz, 2H), 3.44 (s, 1H), 3.26 (d, J = 8.5 Hz, 1H), 2.17-2.00 (m, 2H), 2.00-1.82 (m, 2H). | ++++ |
| 175. | 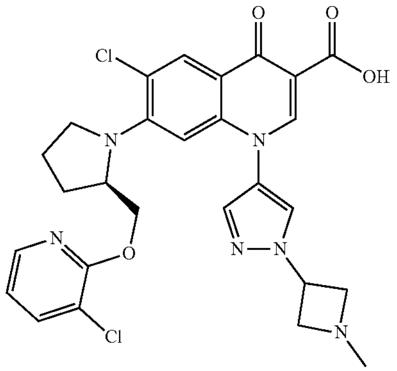 [SMILES: CN1CC(n2cc(-n3cc(C(=O)O)c(=O)c4cc(Cl)c(N5CCC[C@@H]5COc5ncccc5Cl)cc43)cn2)C1] | Column: Xselect CSH F-Phenyl OBD column, 19*250 mm, 5 um; Mobile Phase A: Water (0.1% FA), Mobile Phase B: ACN; Flow rate: 25 mL/min; Gradient: 23% B to 40% B in 8 min, 40% B; Wave Length: 254 nm; RT1(min): 6.3; Number Of Runs: 0 | rac-(R)-6-chloro-7-(2-(((3-chloropyridin-2-yl)oxy)methyl)pyrrolidin-1-yl)-1-(1-(1-methylazetidin-3-yl)-1H-pyrazol-4-yl)-4-oxo-1,4-dihydro-quinoline-3-carboxylic acid | LCMS (ESI) [M + H]+: 569.14. $^{1}$H NMR (300 MHz, DMSO-d6) δ 11.01 (s, 1H), 8.64-8.51 (m, 2H), 8.17-8.05 (m, 2H), 7.91-7.75 (m, 2H), 6.97-6.87 (m, 1H), 6.68 (d, J = 4.2 Hz, 1H), 5.60-5.39 (m, 1H), 4.88-4.60 (m, 3H), 4.48 (s, 1H), 4.32 (d, J = 4.5 Hz, 3H), 3.53 (s, 1H), 3.28 (t, J = 8.1 Hz, 1H), 3.04-2.93 (m, 3H), 2.27 (d, J = 9.2 Hz, 1H), 2.10-1.78 (m, 3H). | ++++ |
| 176. | 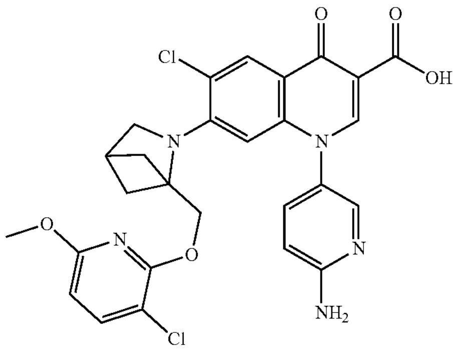 [SMILES: COc1ccc(Cl)c(OCC23CC(CN2c2cc4c(cc2Cl)c(=O)c(C(=O)O)cn4-c2ccc(N)nc2)C3)n1] | Column: XSelect CSH Prep C18 OBD Column, 5 um, 19*150 mm; Mobile Phase A: Water (0.1% FA), Mobile Phase B: ACN; Flow rate: 25 mL/min; Gradient: 42 B to 69 B in 7 min; 254/220 nm. | 1-(6-aminopyridin-3-yl)-6-chloro-7-(1-[[(3-chloro-6-methoxy-pyridin-2-yl)oxy]methyl]-2-azabicyclo[2.1.1]hexan-2-yl)-4-oxoquinoline-3-carboxylic acid | LCMS (ESI) [M + H]$^{+}$: 568.05. $^{1}$H NMR (400 MHz, DMSO-d6) δ 14.88 (s, 1H), 8.67 (s, 1H), 8.31 (s, 1H), 7.99 (d, J = 5.4 Hz, 1H), 7.75 (d, J = 8.4 Hz, 1H), 6.83-6.73 (m, 1H), 6.66 (d, J = 1.9 Hz, 1H), 6.61 (s, 1H), 6.57 (s, 2H), 6.42 (d, J = 8.3 Hz, 1H), 4.52 (d, J = 13.3 Hz, 2H), 3.70 (s, 3H), 3.57 (s, 1H), 3.32 (s, 1H), 2.83-2.95 (m, J = 3.0 Hz, 1H), 1.95 (s, 2H), 1.62 (s, 2H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 177. | 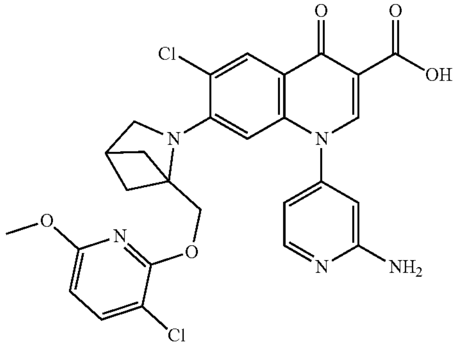 [SMILES: COc1ccc(Cl)c(OCC23CC(CN2c2cc4c(cc2Cl)c(=O)c(C(=O)O)cn4-c2ccnc(N)c2)C3)n1] | Column: XSelect CSH Prep C18 OBD Column, 5 um, 19*150 mm; Mobile Phase A: Water (0.1% FA), Mobile Phase B: ACN; Flow rate: 25 mL/min; Gradient: 42 B to 69 B in 7 min; 254/220 nm. | 1-(2-aminopyridin-4-yl)-6-chloro-7-(1-[[(3-chloro-6-methoxy-pyridin-2-yl)oxy]methyl]-2-azabicyclo[2.1.1]hexan-2-yl)-4-oxoquinoline-3-carboxylic acid | LCMS (ESI) $[M + H]^+$: 568.05 $^1H$ NMR (400 MHz, DMSO-$d_6$) δ 15.00 (s, 1H), 8.63 (s, 1H), 8.31 (s, 1H), 8.14 (d, J = 2.7 Hz, 1H), 7.77-7.56 (m, 2H), 6.61-6.37 (m, 5H), 4.47-4.66 (m, J = 12.2 Hz, 2H), 3.74 (s, 3H), 3.44 (d, J = 16.8 Hz, 2H), 2.82-2.90 (m, J = 3.1 Hz, 1H), 1.98-1.87 (m, 2H), 1.61-2.70 (m, J = 5.1 Hz, 2H). | +++ |
| 178. | 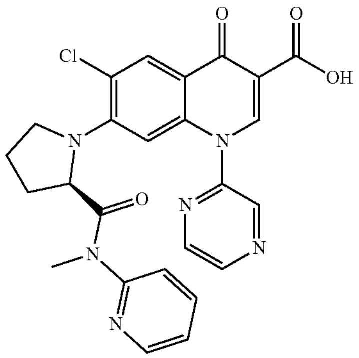 [SMILES: CN(C(=O)[C@H]1CCCN1c1cc2c(cc1Cl)c(=O)c(C(=O)O)cn2-c1cnccn1)c1ccccn1] | reverse phase flash chromatography | rac-(R)-6-chloro-7-(2-(methyl(pyridin-2-yl)carbamoyl)pyrrolidin-1-yl)-4-oxo-1-(pyrazin-2-yl)-1,4-dihydro-quinoline-3-carboxylic acid | LCMS (ESI) [M + H]+: 504.90 $^1H$ NMR (400 MHz, DMSO-d6) δ 14.90 (s, 1H), 9.11 (s, 1H), 8.90 (s, 1H), 8.77 (s, 2H), 8.31-8.27 (m, 1H), 8.16 (s, 1H), 7.91-7.87 (m, 1H), 7.42-7.28 (m, 2H), 6.50 (s, 1H), 5.10 (s, 1H), 3.67-3.62 (m, 2H), 3.60-3.56 (m, 3H), 1.88-1.83 (m, 4H). | + |
| 179. | 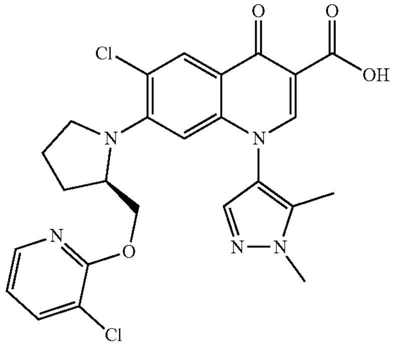 [SMILES: Cc1c(-n2cc(C(=O)O)c(=O)c3cc(Cl)c(N4CCC[C@@H]4COc4ncccc4Cl)cc32)cnn1C] | reverse phase flash chromatography | rac-(R)-6-chloro-7-(2-(((3-chloropyridin-2-yl)oxy)methyl)pyrrolidin-1-yl)-1-(1,5-dimethyl-1H-pyrazol-4-yl)-4-oxo-1,4-dihydro-quinoline-3-carboxylic acid | LCMS (ESI) [M + H]+: 528.1 $^1H$ NMR (300 MHz, DMSO-d6) δ 15.03 (s, 1H), 8.48 (s, 1H), 8.15 (s, 1H), 7.95-7.86 (m, 1H), 7.81 (s, 1H), 7.73 (s, 1H), 6.99-6.89 (m, 1H), 6.59-6.37 (m, 1H), 4.85-4.67 (m, 1H), 4.33-4.27 (m, 2H), 3.89-3.72 (m, 3H), 3.58-3.52 (m, 1H), 3.28-3.17 (m, 1H), 2.34-2.20 (m, 1H), 2.12-1.69 (m, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 180. | 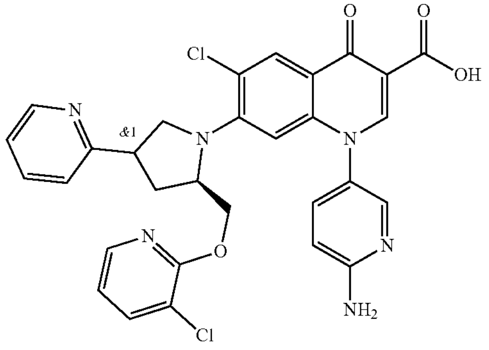 [SMILES: Nc1ccc(-n2cc(C(=O)O)c(=O)c3cc(Cl)c(N4CC(c5ccccn5)C[C@@H]4COc4ncccc4Cl)cc32)cn1] | Column: XSelect CSH Prep C18 OBD Column, 19*250 mm, 5 um; Mobile Phase A: Water (0.05% FA), Mobile Phase B: ACN; Flow rate: 25 mL/min; Gradient: 20% B to 48% B in 7 min, 48% B; Wave Length: 254/220 nm; RT1(min): 7.07; Number Of Runs: 0 | rac-1-(6-aminopyridin-3-yl)-6-chloro-7-((2R)-2-(((3-chloropyridin-2-yl)oxy)methyl)-4-(pyridin-2-yl)pyrrolidin-1-yl)-4-oxo-1,4-dihydroquinoline-3-carboxylic acid | LCMS (ESI) [M + H]+: 603.05 $^1$H NMR (300 MHz, DMSO-d6) δ 15.09 (s, 1H), 8.59-8.48 (m, 2H), 8.18 (s, 1H), 8.10 (d, J = 2.6 Hz, 1H), 7.90 (d, J = 4.9 Hz, 1H), 7.84-7.70 (m, 2H), 7.59-7.49 (m, 1H), 7.36 (d, J = 7.8 Hz, 1H), 7.32-7.23 (m, 1H), 6.97-6.89 (m, 1H), 6.65-6.34 (m, 4H), 4.89-4.74 (m, 1H), 4.46-4.32 (m, 2H), 3.86-3.76 (m, 1H), 3.60-3.54 (m, 2H), 2.63-2.57 (m, 1H), 2.35-2.29 (m, 1H). | ++++ |
| 181. | 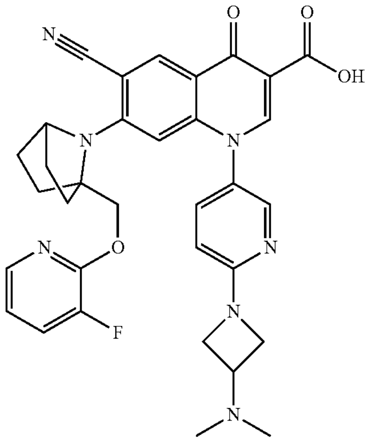 [SMILES: CN(C)C1CN(c2ccc(-n3cc(C(=O)O)c(=O)c4cc(C#N)c(N5C6CCC5(COc5ncccc5F)CC6)cc43)cn2)C1] | Column: YMC-Actus Triart C18, 20 *250 mm, 5 um, 12 nm; Mobile Phase A: Water (0.1% FA), Mobile Phase B: ACN; Flow rate: 25 mL/min; Gradient: 26% B to 36% B in 9 min, 36% B; Wave Length: 254 nm; RT1(min): 5.4; Number Of Runs: 0 | 6-cyano-1-(6-(3-(dimethyl-amino) azetidin-1-yl)pyridin-3-yl)-7-(1-(((3-fluoropyridin-2-yl)oxy) methyl)-7-azabicyclo [2.2.1]heptan-7-yl)-4-oxo-1,4-dihydro-quinoline-3-carboxylic acid | LCMS (ESI) [M + H]+: 610.35 $^1$H NMR (300 MHz, DMSO-d6) δ 8.59 (d, J = 14.4 Hz, 2H), 8.27-8.19 (m, 1H), 7.93-7.85 (m, 1H), 7.75-7.65 (m, 1H), 7.68-7.55 (m, 1H), 7.09-6.97 (m, 1H), 6.74 (s, 1H), 6.42 (d, J = 8.8 Hz, 1H), 4.62 (s, 2H), 4.34-4.28 (m, 1H), 4.04-3.93 (m, 2H), 3.80-3.67 (m, 2H), 3.38-3.13 (m, 1H), 2.12 (s, 6H), 1.82-1.63 (m, 6H), 1.59-1.49 (m, 2H). | ++++ |
| 182. | 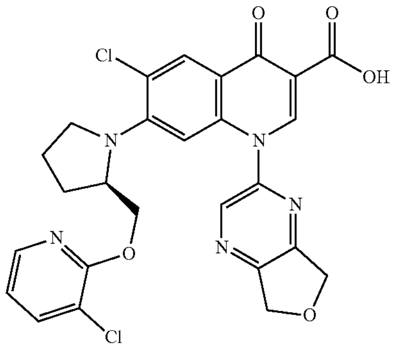 | Column: YMC-Actus Triart C18, 20 *250 mm, 5 um, 12 nm; Mobile Phase A: Water (0.1% FA), Mobile Phase B: ACN; Flow rate: 25 mL/min; Gradient: 55% B to 90% B in 8 min, 90% B; Wave Length: 254 nm; RT1(min): 8.92; Number Of Runs: 0 | rac-(R)-6-chloro-7-(2-(((3-chloropyridin-2-yl)oxy)methyl) pyrrolidin-1-yl)-1-(5,7-dihydrofuro [3,4-b] pyrazin-2-yl)-4-oxo-1,4-dihydro-quinoline-3-carboxylic acid | LCMS (ESI): $[M + H + 2]^+$: 555.75 $^1$H NMR (300 MHz, DMSO-d6) δ 14.86 (s, 1H), 8.95 (s, 1H), 8.88 (s, 1H), 8.17 (s, 1H), 7.92-7.84 (m, 1H), 7.84-7.75 (m, 1H), 6.98-6.88 (m, 1H), 6.66 (s, 1H), 5.21 (s, 2H), 5.16-5.04 (m, 2H), 4.78-4.72 (m, 1H), 4.40-4.22 (m, 2H), 3.67-3.59 (m, 1H), 3.28-3.21 (s, 1H), 2.25-2.19 (m, 1H), 2.00-1.94 (m, 2H), 1.86-1.74 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 183. | 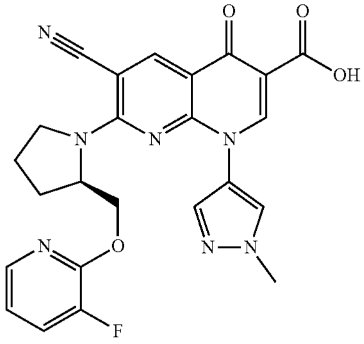 [SMILES: Cn1cc(-n2cc(C(=O)O)c(=O)c3cc(C#N)c(N4CCC[C@@H]4COc4ncccc4F)nc32)cn1] | reverse phase flash chromatography | rac-(R)-6-cyano-7-(2-(((3-fluoropyridin-2-yl)oxy)methyl)pyrrolidin-1-yl)-1-(1-methyl-1H-pyrazol-4-yl)-4-oxo-1,4-dihydro-1,8-naphthyridine-3-carboxylic acid | LCMS (ESI): $[M + H]^+$: 490.1 $^1$H NMR (300 MHz, DMSO-d6) δ 14.54 (s, 1H), 8.78 (s, 1H), 8.65 (s, 1H), 8.16 (s, 1H), 7.87 (d, J = 4.8 Hz, 1H), 7.76 (s, 1H), 7.73-7.61 (m, 1H), 7.07-6.96 (m, 1H), 4.69-4.51 (m, 1H), 4.34-4.28 (m, 2H), 3.94-3.88 (m, 2H), 3.75 (s, 3H), 2.05-1.99 (m, 4H). | +++ |
| 184. | 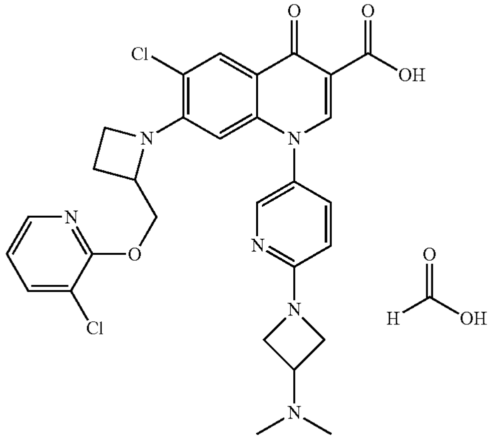 [SMILES: CN(C)C1CN(c2ccc(-n3cc(C(=O)O)c(=O)c4cc(Cl)c(N5CCC5COc5ncccc5Cl)cc43)cn2)C1 ; O=CO] | Column: XSelect CSH Prep C18 OBD Column, 19*150 mm, 5 um; Mobile Phase A: Water (0.1% FA), Mobile Phase B: ACN; Flow rate: 25 mL/min; Gradient: 17% B to 38% B in 8 min, 38% B; Wave Length: 254/220 nm; RT1(min): 7.13; Number Of Runs: 0 | 6-chloro-7-(2-(((3-chloropyridin-2-yl)oxy)methyl)azetidin-1-yl)-1-(6-(3-(dimethylamino)azetidin-1-yl)pyridin-3-yl)-4-oxo-1,4-dihydroquinoline-3-carboxylic acid formic acid | LCMS (ESI): $[M + H]^+$: 595.25 $^1$H NMR (300 MHz, DMSO-d6) δ 15.44-14.81 (m, 1H), 8.51 (d, J = 3.6 Hz, 1H), 8.32-8.25 (m, 1H), 8.20 (s, 0H), 8.11 (s, 1H), 7.97-7.91 (m, 1H), 7.91-7.83 (m, 1H), 7.79-7.70 (m, 1H), 7.01-6.95 (m, 1H), 6.59-6.35 (m, 1H), 6.14-6.07 (m, 1H), 4.82-4.76 (m, 1H), 4.68-4.57 (m, 1H), 4.47-4.41 (m, 1H), 4.32-4.26 (m, 1H), 4.11-3.96 (m, 2H), 3.93-3.73 (m, 3H), 3.26-3.16 (m, 1H), 2.62-2.54 (m, 2H), 2.26-2.20 (m, 1H), 2.14 (s, 6H). | ++++ |
| 185. | 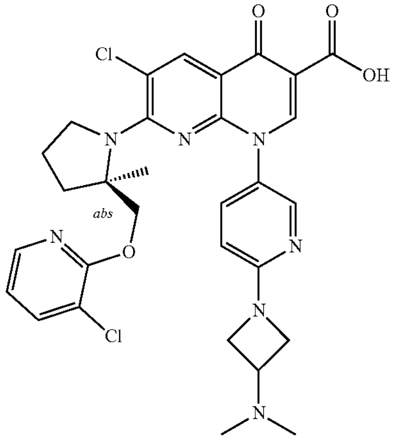 [SMILES: CN(C)C1CN(c2ccc(-n3cc(C(=O)O)c(=O)c4cc(Cl)c(N5CCC[C@]5(C)COc5ncccc5Cl)nc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 5% B to 5% B in 2 min, 5% B to 17% B in 2.5 min, 17% B to 38% B in 10.5 min, 38% B; Wave Length: 254 nm; RT1(min): 10.33; Number Of Runs: 0 | 6-chloro-7-(2-(((3-chloropyridin-2-yl)oxy)methyl)azetidin-1-yl)-1-(6-(3-(dimethylamino)azetidin-1-yl)pyridin-3-yl)-4-oxo-1,4-dihydroquinoline-3-carboxylic acid compound with formic acid (1:1) | LCMS (ESI): $[M + H]^+$: 624.25 $^1$H NMR (300 MHz, DMSO-d6) δ 15.04 (s, 1H), 8.57 (s, 1H), 8.28-8.17 (m, 2H), 8.03-7.97 (m, 1H), 7.90-7.81 (m, 1H), 7.70-7.64 (m, 1H), 7.01-6.95 (m, 1H), 6.49-6.04 (m, 1H), 4.55-4.49 (m, 1H), 4.23-3.80 (m, 5H), 3.77-3.59 (m, 2H), 3.21-3.15 (m, 1H), 2.21-2.05 (m, 7H), 2.02-1.82 (m, 2H), 1.81-1.67 (m, 1H), 1.15 (s, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 186. | 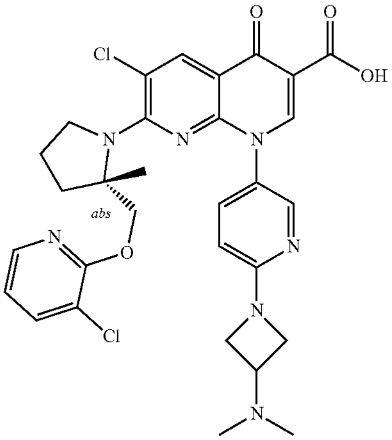 [SMILES: CN(C)C1CN(c2ccc(-n3cc(C(=O)O)c(=O)c4cc(Cl)c(N5CCC[C@@]5(C)COc5ncccc5Cl)nc43)cn2)C1] | reverse phase flash chromatography | rac-(R)-6-chloro-7-(2-(((3-chloropyridin-2-yl)oxy)methyl)-2-methyl-pyrrolidin-1-yl)-1-(6-(3-(dimethyl-amino)azetidin-1-yl)pyridin-3-yl)-4-oxo-1,4-dihydro-1,8-naphthyridine-3-carboxylic acid | LCMS (ESI): $[M + H]^+$: 624.20 $^1H$ NMR (300 MHz, DMSO-d6) δ 15.04 (s, 1H), 8.57 (s, 1H), 8.28-8.17 (m, 2H), 8.03-7.97 (m, 1H), 7.90-7.81 (m, 1H), 7.70-7.64 (m, 1H), 7.01-6.95 (m, 1H), 6.50-6.04 (m, OH), 4.55-4.49 (m, 1H), 4.17-3.81 (m, 5H), 3.75-3.62 (m, 2H), 3.22-3.16 (m, 1H), 2.17-2.11 (m, 7H), 2.02-1.82 (m, 2H), 1.81-1.67 (m, 1H), 1.15 (s, 3H). | ++++ |
| 187. | 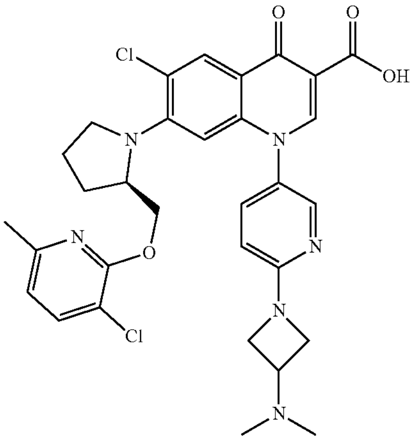 [SMILES: Cc1ccc(Cl)c(OC[C@H]2CCCN2c2cc3c(cc2Cl)c(=O)c(C(=O)O)cn3-c2ccc(N3CC(N(C)C)C3)nc2)n1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 18% B to 35% B in 9 min, 35% B; Wave Length: 254 nm; RT1(min): 9.47; Number Of Runs: 0 | rac-(R)-6-chloro-7-(2-(((3-chloro-6-methylpyridin-2-yl)oxy)methyl)pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) [M + H]+: 623.54 $^1H$ NMR (400 MHz, DMSO-d6) δ 15.10 (s, 1H), 8.52 (d, J = 10.1 Hz, 1H), 8.34-8.07 (m, 2H), 7.65 (d, J = 7.7 Hz, 2H), 6.75 (d, J = 8.1 Hz, 0.5H), 6.32 (t, J = 8.6 Hz, 1.5H), 4.66 (d, J = 41.1 Hz, 1H),4.32 (dd, J = 11.0, 4.0 Hz,2H), 4.07 (t, J = 8.0 Hz, 2H), 3.82 (dd, J = 8.8, 5.3 Hz, 2H), 3.51 (t, J = 8.6 Hz, 1H), 3.19 (s, 2H), 2.15 (d, J = 9.4 Hz, 10H), 1.96 (d, J = 20.2 Hz, 2H), 1.87-1.72 (m, 1H). | ++++ |
| 188. | 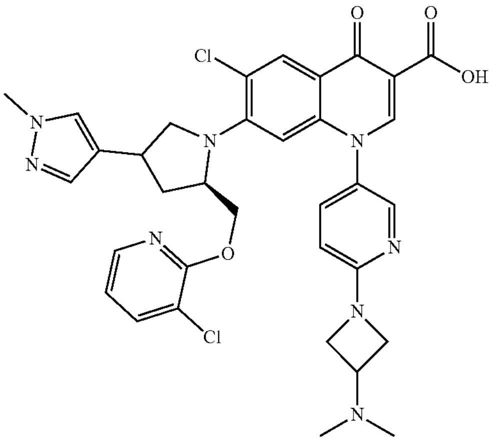 [SMILES: CN(C)C1CN(c2ccc(-n3cc(C(=O)O)c(=O)c4cc(Cl)c(N5CC(c6cnn(C)c6)C[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 5% B to 5% B in 2 min, 5% B to 16% B in 2.5 min, 16% B to 40% B in 10.5 min, 40% B; Wave Length: 254 nm; RT1(min): 9.3; Number Of Runs: 0 | rac-6-chloro-7-((2R)-2-(((3-chloropyridin-2-yl)oxy)methyl)-4-(1-methyl-1H-pyrazol-4-yl)pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) [M + H]+: 689.20 $^1H$ NMR (400 MHz, DMSO-d6) δ 15.07 (s, 1H), 8.52 (d, J = 11.8 Hz, 1H), 8.29-8.15 (m, 2H), 7.95-7.78 (m, 2H), 7.68 (dd, J = 8.9, 2.7 Hz, 1H), 7.58 (s, 1H), 7.33 (s, 1H), 6.96 (ddd, J = 12.0, 7.6, 4.8 Hz, 1H), 6.56 (d, J = 9.0 Hz, 0.5H), 6.46 (d, J = 8.4 Hz, 1H), 6.25 (d, J = 8.9 Hz, 0.5H), 4.64 (d, J = 38.6 Hz, 1H), 4.48-4.23 (m, 2H), 4.05 (s, 2H), 3.79 (s, 5H), 3.57-3.42 (m, 2H), 3.28 (d, J = 16.6 Hz, 2H), 2.55 (d, J = 6.4 Hz, 1H), 2.25-1.92 (m, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 189. | 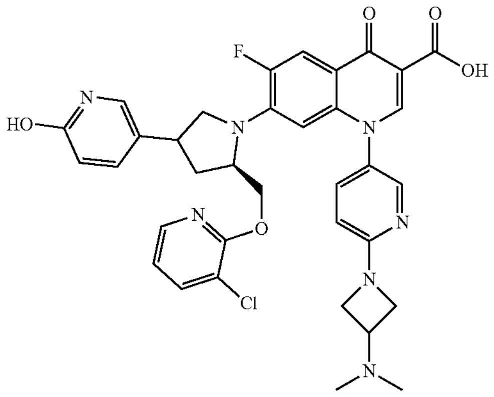 [SMILES: CN(C)C1CN(c2ccc(-n3cc(C(=O)O)c(=O)c4cc(F)c(N5CC(c6ccc(O)nc6)C[C@@H]5COc5ncccc5Cl)cc43)cn2)C1] | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 10% B to 10% B in 2 min, 10% B to 15% B in 2.5 min, 15% B to 36% B in 10.5 min, 36% B; Wave Length: 220 nm; RT1(min): 11.07; Number Of Runs: 0 | rac-7-((2R)-2-(((3-chloropyridin-2-yl)oxy)methyl)-4-(6-hydroxy-pyridin-3-yl)pyrrolidin-1-yl)-1-(6-(3-(dimethyl-amino) azetidin-1-yl)pyridin-3-yl)-6-fluoro-4-oxo-1,4-dihydro-quinoline-3-carboxylic acid | LCMS (ESI) [M + H]+: 686.14 $^{1}H$ NMR (300 MHz, DMSO-d6) δ 15.32 (s, 1H), 11.50 (s, 1H), 8.49 (d, J = 6.2 Hz, 1H), 8.25 (s, 1H), 7.99-7.81 (m, 3H), 7.70 (t, J = 9.4 Hz, 1H), 7.49 (dd, J = 9.6, 2.5 Hz, 1H), 7.26 (s, 1H), 6.99 (q, J = 6.3 Hz, 1H), 6.54 (d, J = 8.9 Hz, 0.4H), 6.32 (dd, J = 15.2, 9.2 Hz, 1.5H), 6.23 (d, J = 7.1 Hz, 1H), 4.63-4.27 (m, 3H), 4.05 (d, J = 10.1 Hz, 2H), 3.78 (d, J = 12.2 Hz, 2H), 3.53 (d, J = 9.9 Hz, 2H), 3.30-3.14 (m, 2H), 2.55 (s,1H), 2.14 (s, 6H), 2.04 (s, 1H). | ++++ |
| 190. | 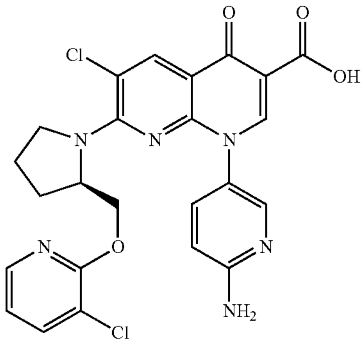 [SMILES: Nc1ccc(-n2cc(C(=O)O)c(=O)c3cc(Cl)c(N4CCC[C@@H]4COc4ncccc4Cl)nc32)cn1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 15% B to 32% B in 8 min, 32% B; Wave Length: 254 nm; RT1(min): 6.70; Number Of Runs: 0 | rac-(R)-1-(6-aminopyridin-3-yl)-6-chloro-7-(2-(((3-chloropyridin-2-yl)oxy)methyl) pyrrolidin-1-yl)-4-oxo-1,4-dihydro-1,8-naphthyridine-3-carboxylic acid | LCMS (ESI): $[M + H]^+$: 527.0 $^{1}H$ NMR (300 MHz, DMSO-d6) δ 8.83 (s, 1H), 8.32 (d, J = 9.5 Hz, 2H), 8.23-7.98 (m, 3H), 7.86 (dd, J = 7.7, 1.6 Hz, 1H), 7.00 (dd, J = 7.7, 4.9 Hz, 1H), 6.91 (d, J = 9.4 Hz, 1H), 4.61-4.55 (m, 1H), 4.42-4.30 (m, 1H), 4.29-4.18 (m, 1H), 3.95-3.79 (m, 2H), 2.12-2.06 (m, 2H), 2.00-1.73 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 191. | 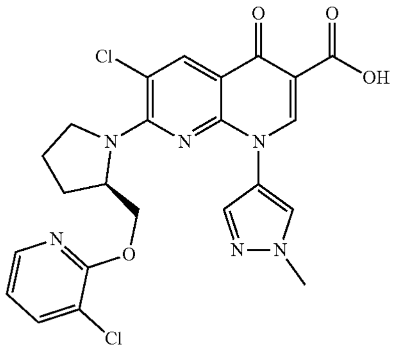 [SMILES: Cn1cc(-n2cc(C(=O)O)c(=O)c3cc(Cl)c(N4CCC[C@@H]4COc4ncccc4Cl)nc32)cn1] | reverse phase flash chromatography | rac-(R)-6-chloro-7-(2-(((3-chloropyridin-2-yl)oxy)methyl)pyrrolidin-1-yl)-1-(1-methyl-1H-pyrazol-4-yl)-4-oxo-1,4-dihydro-1,8-naphthyridine-3-carboxylic acid | LCMS (ESI): $[M + H + 2]^+$: 516.8 $^1H$ NMR (300 MHz, DMSO-d6) δ 14.96 (s, 1H), 8.63 (s, 1H), 8.31 (s, 1H), 8.18 (s, 1H), 8.01-7.93 (m, 1H), 7.90-7.81 (m, 1H), 7.81-7.76 (m, 1H), 7.03-6.93 (m, 1H), 4.72-4.66 (m, 1H), 4.43-4.25 (m, 2H), 4.04-3.76 (m, 5H), 2.21-2.06 (m, 2H), 2.06-1.82 (m, 2H). | ++++ |
| 192. | 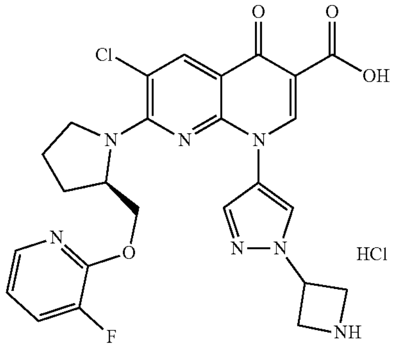 [SMILES: O=C(O)c1cn(-c2cnn(C3CNC3)c2)c2nc(N3CCC[C@@H]3COc3ncccc3F)c(Cl)cc2c1=O ; Cl] HCl | Column: Xselect CSH F-Phenyl OBD column, 19*250 mm, 5 μm; Mobile Phase A: Water (0.1% FA), Mobile Phase B: ACN; Flow rate: 25 mL/min; Gradient: 18% B to 35% B in 8 min, 35% B; Wave Length: 220 nm; RT1(min): 7.38; Number Of Runs: 0 | rac-(R)-1-(1-(azetidin-3-yl)-1H-pyrazol-4-yl)-6-chloro-7-(2-(((3-fluoropyridin-2-yl)oxy)methyl)pyrrolidin-1-yl)-4-oxo-1,4-dihydro-1,8-naphthyridine-3-carboxylic acid hydrochloride | LCMS (ESI): $[M + H]^+$: 540.15 $^1H$ NMR (300 MHz, DMSO-d6) δ 8.65 (s, 1H), 8.36-8.27 (m, 2H), 8.04 (s, 1H), 7.78 (d, J = 4.9 Hz, 1H), 7.65-7.53 (m, 1H), 7.02-6.91 (m, 1H), 5.47-5.36 (m, 1H), 4.67-4.61 (m, 1H), 4.49-4.32 (m, 5H), 4.26-4.15 (m, 1H), 3.90-3.82 (m, 2H), 2.10-2.02 (m, 2H), 1.99-1.73 (m, 2H). | ++++ |
| 193. | 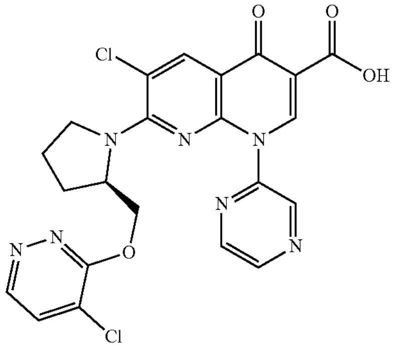 [SMILES: O=C(O)c1cn(-c2cnccn2)c2nc(N3CCC[C@@H]3COc3nnccc3Cl)c(Cl)cc2c1=O] | Column: YMC-Actus Triart C18, 20 *250 mm, 5 μm, 12 nm; Mobile Phase A: Water (0.1% FA), Mobile Phase B: ACN; Flow rate: 25 mL/min; Gradient: 45% B to 78% B in 8 min, 78% B; Wave Length: 220 nm; RT1(min): 6.6; Number Of Runs: 0 | rac-(R)-6-chloro-7-(2-(((4-chloropyridazin-3-yl)oxy)methyl)pyrrolidin-1-yl)-4-oxo-1-(pyrazin-2-yl)-1,4-dihydro-1,8-naphthyridine-3-carboxylic acid | LCMS (ESI): $[M + H + 2]^+$: 515.7 $^1H$ NMR (300 MHz, DMSO-d6) δ 9.89 (s, 1H), 9.02 (d, J = 5.7 Hz, 1H), 8.85-8.29 (m, 3H), 8.15 (s, 1H), 7.21-7.15 (m, 1H), 4.01-3.95 (m, 2H), 3.90-3.75 (m, 3H), 2.14-1.94 (m, 2H), 1.86-1.80 (m, 2H). | +++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 194. | 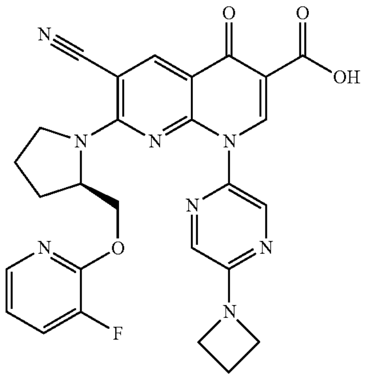 [SMILES: N#Cc1cc2c(=O)c(C(=O)O)cn(-c3cnc(N4CCC4)cn3)c2nc1N1CCC[C@@H]1COc1ncccc1F] | Column: YMC-Actus Triart C18, 20 *250 mm, 5 μm, 12 nm; Mobile Phase A: Water (0.1% FA), Mobile Phase B: ACN; Flow rate: 25 mL/min; Gradient: 10% B to 10% B in 2 min, 10% B to 69% B in 2.5 min, 69% B to 74% B in 9 min, 74% B; Wave Length: 220 nm; RT1(min): 7.3; Number Of Runs: 0 | rac-(R)-1-(5-(azetidin-1-yl)pyrazin-2-yl)-6-cyano-7-(2-(((3-fluoropyridin-2-yl)oxy)methyl) pyrrolidin-1-yl)-4-oxo-1,4-dihydro-1,8-naphthyridine-3-carboxylic acid | LCMS (ESI): $[M + H]^+$: 543.15 $^1H$ NMR (300 MHz, DMSO-d6) δ 14.50 (s, 1H), 8.80 (d, J = 4.3 Hz, 2H), 8.37 (d, J = 1.4 Hz, 1H), 7.89-7.82 (m, 1H), 7.82-7.70 (m, 1H), 7.55 (s, 1H), 7.10-6.99 (m, 1H), 4.43-4.22 (m, 2H), 4.15-3.69 (m, 5H), 2.45-2.29 (m, 2H), 2.14-1.85 (m, 4H). | ++++ |
| 195. | 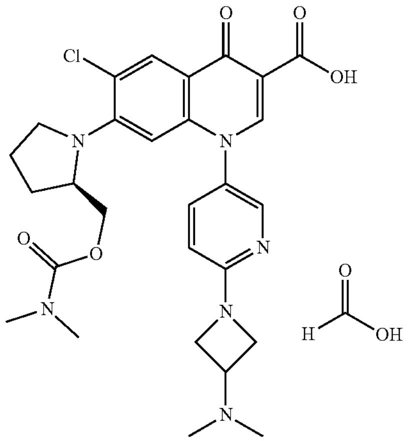 | Column: Gemini-NX C18 AXAI Packed, 21.2*150 mm 5 um; Mobile Phase A: Water (0.1% FA), Mobile Phase B: ACN; Flow rate: 25 mL/min; Gradient: 11% B to 30% B in 9 min, 30% B; Wave Length: 254 nm; RT1(min): 8.4; Number Of Runs: 0 | rac-(R)-6-chloro-1-(6-(3-(dimethyl-amino) azetidin-1-yl)pyridin-3-yl)-7-(2-(((dimethyl carbamoyl) oxy)methyl) pyrrolidin-1-yl)-4-oxo-1,4-dihydro-quinoline-3-carboxylic acid formic acid | LCMS (ESI): $[M + H]^+$: 569.35 $^1H$ NMR (300 MHz, DMSO-d6) δ 15.10 (s, 1H), 8.60-8.48 (m, 1H), 8.30 (d, J = 2.3 Hz, 1H), 8.21 (s, 1H), 8.15 (s, 1H), 7.83-7.73 (m, 1H), 6.62-6.41 (m, 2H), 4.52-4.34 (m, 1H), 4.16-4.04 (m, 2H), 4.04-3.91 (m, 1H), 3.89-3.70 (m, 3H), 3.60-3.44 (m, 1H), 3.29-3.08 (m, 2H), 2.75-2.65 (m, 3H), 2.64-2.52 (m, 3H), 2.18-2.12 (m, 7H), 1.97-1.91 (m, 1H), 1.77-1.71 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 196. | 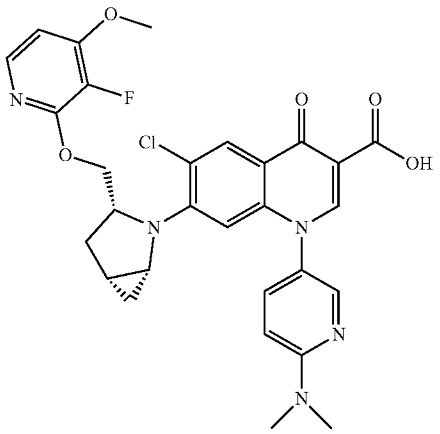 [SMILES: COc1ccnc(OC[C@H]2C[C@H]3C[C@H]3N2c2cc3c(cc2Cl)c(=O)c(C(=O)O)cn3-c2ccc(N(C)C)nc2)c1F] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 45% B to 70% B in 7 min, 70% B; Wave Length: 254/220 nm; RT1(min): 7.93; Number Of Runs: 0 | 6-chloro-1-(6-(dimethyl-amino)pyridin-3-yl)-7-((1R,3R,5R)-3-(((3-fluoro-4-methoxy-pyridin-2-yl)oxy) methyl)-2-azabicyclo [3.1.0]hexan-2-yl)-4-oxo-1,4-dihydro-quinoline-3-carboxylic acid | LCMS (ESI): $[M + H]^+$: 580.3 $^1H$ NMR (300 MHz, DMSO-$d_6$) δ 15.10 (s, 1H), 8.56 (s, 1H), 8.21 (m, 2H), 7.66 (m,2H), 7.02-6.62 (m, 3H), 4.99 (s, 1H), 4.27-3.93 (m, 2H), 3.83 (s, 3H), 3.12 (s, 6H), 3.03 (m, 1H), 2.72-2.62 (m, 1H), 2.05 (m, 1H), 1.62 (m, 1H), 0.73 (m, 2H). | ++++ |
| 197. | 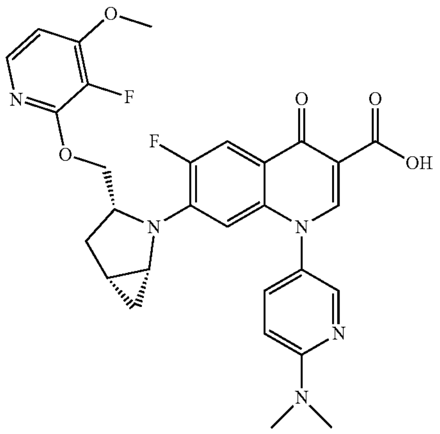 [SMILES: COc1ccnc(OC[C@H]2C[C@H]3C[C@H]3N2c2cc3c(cc2F)c(=O)c(C(=O)O)cn3-c2ccc(N(C)C)nc2)c1F] | Column: XBridge Shield RP18 OBD Column, 19*150 mm, 5 μm; Mobile Phase A: Water (0.05% NH3H2O), Mobile Phase B: ACN; Flow rate: 25 mL/min; Gradient: 19% B to 40% B in 10 min, 40% B; Wave Length: 254/220 nm; RT1(min): 9.07; Number Of Runs: 0 | 1-(6-(dimethyl-amino)pyridin-3-yl)-6-fluoro-7-((1R,3R,5R)-3-(((3-fluoro-4-methoxy-pyridin-2-yl)oxy) methyl)-2-azabicyclo [3.1.0]hexan-2-yl)-4-oxo-1,4-dihydro-quinoline-3-carboxylic acid | LCMS (ESI) $[M + H]^+$: 564.3 $^1H$ NMR (300 MHz, DMSO-$d_6$) δ 14.75 (s, 1H), 10.48 (s, 1H), 8.46 (s, 1H), 7.95 (m, 1H), 7.78 (d, J = 13.1 Hz, 1H), 7.55 (m, 2H), 6.94-6.85 (m, 1H), 6.84-6.63 (m, 2H), 6.46 (d, J = 8.3 Hz, 1H), 4.58-4.38 (m, 1H), 4.22 (m, 2H), 3.77-3.57 (m, 1H), 3.30-3.17 (m, 1H), 2.25-2.10 (m, 1H), 1.94 (m, 1H), 1.75 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 198. | 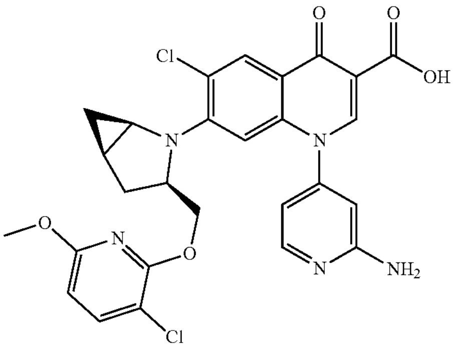 [SMILES: COc1ccc(Cl)c(OC[C@H]2C[C@H]3C[C@H]3N2c2cc3c(cc2Cl)c(=O)c(C(=O)O)cn3-c2ccnc(N)c2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 62% B in 7 min, 62% B; Wave Length: 254/220 nm; RT1(min): 7.22; Number Of Runs: 0 | 1-(2-aminopyridin-4-yl)-6-chloro-7-((1R,3R,5R)-3-(((3-chloro-6-methoxy-pyridin-2-yl)oxy) methyl)-2-azabicyclo [3.1.0]hexan-2-yl)-4-oxo-1,4-dihydro-quinoline-3-carboxylic acid | LCMS (ESI) $[M + H]^+$: 568.2 $^1H$ NMR (300 MHz, DMSO-$d_6$) δ 14.97 (s, 1H), 8.58 (s, 1H), 8.14 (s, 2H), 7.63 (m.4 Hz, 1H), 7.07 (s, 1H), 6.74-6.47 (m, 4H), 6.26 (m, 1H), 5.02 (s, 1H), 4.23 (m, 2H), 3.62 (s, 3H), 3.05 (s, 1H), 2.68 (s, 1H), 2.19-1.98 (m, 1H), 1.67 (m, 1H), 1.05 (s, 1H), 0.68 (s, 1H). | ++++ |
| 199. | 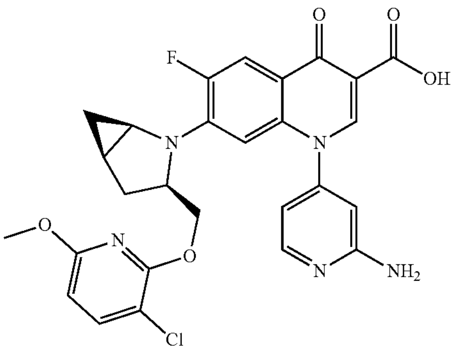 [SMILES: COc1ccc(Cl)c(OC[C@H]2C[C@H]3C[C@H]3N2c2cc3c(cc2F)c(=O)c(C(=O)O)cn3-c2ccnc(N)c2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 61% B in 7 min, 61% B; Wave Length: 254/220 nm; RT1(min): 6.97; Number Of Runs: 0 | 1-(2-aminopyridin-4-yl)-7-((1R,3R,5R)-3-(((3-chloro-6-methoxy-pyridin-2-yl)oxy) methyl)-2-azabicyclo [3.1.0]hexan-2-yl)-6-fluoro-4-oxo-1,4-dihydro-quinoline-3-carboxylic acid | LCMS (ESI) $[M + H]^+$: 552.9 $^1H$ NMR (300 MHz, DMSO-$d_6$) δ 15.23 (s, 1H), 8.54 (s, 1H), 8.27-8.01 (m, 1H), 7.85 (m, 1H), 7.66 (m, 1H), 6.68 (m, 3H), 6.53 (s, 2H), 6.34 (m, 1H), 4.79 (s, 1H), 4.24 (m, 2H), 3.71 (s, 3H), 3.15 (s, 1H), 2.63 (m, 1H), 2.12-1.98 (m, 1H), 1.62 (m, 1H), 0.99 (s, 1H), 0.75 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 200. | 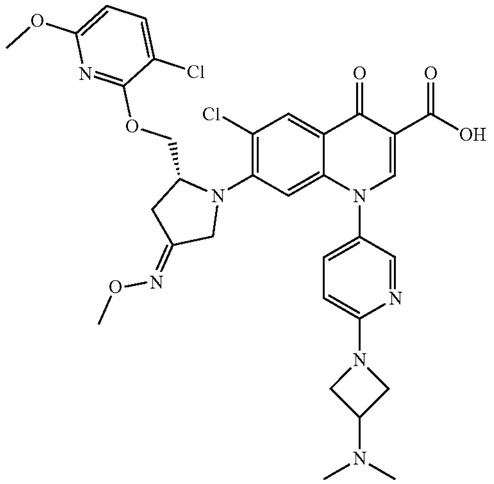 [SMILES: CO/N=C1\C[C@H](COc2nc(OC)ccc2Cl)N(c2cc3c(cc2Cl)c(=O)c(C(=O)O)cn3-c2ccc(N3CC(N(C)C)C3)nc2)C1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 15% B to 40% B in 10 min, 40% B; Wave Length: 254/220 nm; RT1(min): 9.45; Number Of Runs: 0 | (R,E)-6-chloro-7-(2-(((3-chloro-6-methoxy-pyridin-2-yl)oxy) methyl)-4-(methoxyimino) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) $[M + H]^+$: 682.8 $^1$H NMR (300 MHz, DMSO-$d_6$) δ 8.57 (m, 1H), 8.30-8.14 (m, 2H), 7.79-7.54 (m, 2H), 6.50 (m, 2H), 6.37 (m, 1H), 5.16 (m, 1H), 4.45 (m, 1H), 4.37-4.18 (m, 2H), 4.11 (m, 2H), 3.94-3.74 (m, 6H), 3.67 (s, 4H), 3.27-3.20 (m, 1H), 3.06 (s, 1H), 2.68 (s, 1H), 2.16 (s, 6H). | ++++ |
| 201. | 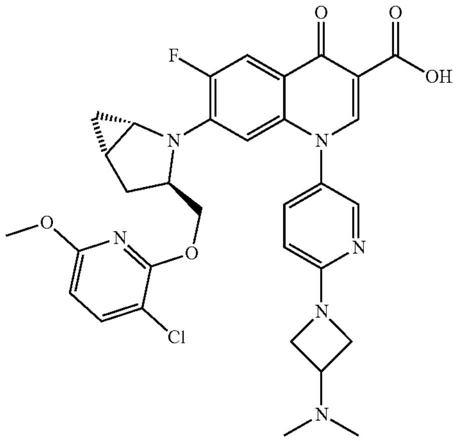 [SMILES: COc1ccc(Cl)c(OC[C@H]2C[C@@H]3C[C@@H]3N2c2cc3c(cc2F)c(=O)c(C(=O)O)cn3-c2ccc(N3CC(N(C)C)C3)nc2)n1] | Column: XSelect CSH Prep C18 OBD Column, 19*150 mm, 5 μm; Mobile Phase A: Water (10 MMOL/L NH4HCO3), Mobile Phase B: ACN; Flow rate: 25 mL/min; Gradient: 31% B to 51% B in 14 min, 51% B; Wave Length: 220 nm; RT1(min): 15.22; Number Of Runs: 0 | 7-((1S,3R,5S)-3-(((3-chloro-6-methoxy-pyridin-2-yl)oxy) methyl)-2-azabicyclo [3.1.0]hexan-2-yl)-1-(6-(3-(dimethyl-amino) azetidin-1-yl)pyridin-3-yl)-6-fluoro-4-oxo-1,4-dihydro-quinoline-3-carboxylic acid | LCMS (ESI) [M + H]+: 635.2 $^1$H NMR (300 MHz, DMSO-d6) δ 8.68-7.92 (m, 2H), 8.56-7.52 (m, 3H), 6.85-6.25 (m, 3H), 4.65-4.23 (m, 3H), 4.15-3.87 (m, 2H), 3.79-3.65 (m, 5H), 3.30-3.11 (m, 2H), 2.31-1.92 (m, 8H), 1.82-1.62 (m, 1H), 0.62-0.95(m, 1H), 0.36-0.28 (m, 1H), | ++++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 202. | 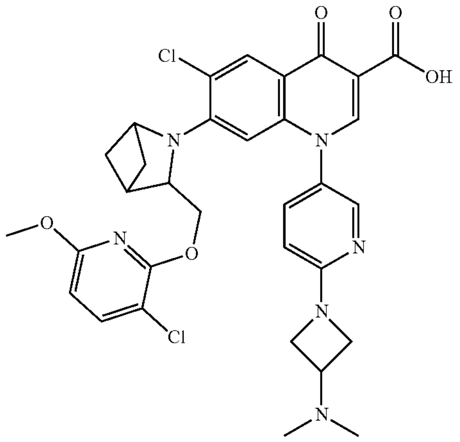 [SMILES: COc1ccc(Cl)c(OCC2C3CC(C3)N2c2cc3c(cc2Cl)c(=O)c(C(=O)O)cn3-c2ccc(N3CC(N(C)C)C3)nc2)n1] | (Column: Xcelect CSH F-pheny OBD Column, 19*250 mm, 5 um; Mobile Phase A: Water (0.05% FA), Mobile Phase B: ACN; Flow rate: 25 mL/min; Gradient: 44 B to 74 B in 8 min; 254/220 nm; RT1: 7.35; RT2 :; Injection Volumn: ml; Number Of Runs:;) | 6-chloro-7-(3-(((3-chloro-6-methoxy-pyridin-2-yl)oxy) methyl)-2-azabicyclo [2.1.1]hexan-2-yl)-1-(6-(3-(dimethyl-amino) azetidin-1-yl)pyridin-3-yl)-4-oxo-1,4-dihydro-quinoline-3-carboxylic acid | LCMS (ESI) [M + H]$^+$: 651.1 $^1$H NMR (300 MHz, Methanol-$d_4$) δ 8.64 (s, 1H), 8.25 (m, 2H), 7.62 (m, 2H), 6.74-6.18 (m, 3H), 4.55 (m, 4H), 4.19 (m, 2H), 4.05 (s, 1H), 3.95 (m, 2H), 3.80 (s, 3H), 3.37 (s, 1H), 2.95 (s, 1H), 2.30 (s, 6H), 1.97 (d, J = 8.9 Hz, 3H), 1.47 (s, 1H). | ++++ |
| 203. | 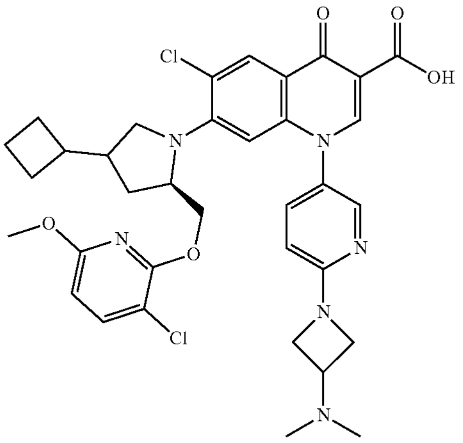 [SMILES: COc1ccc(Cl)c(OC[C@H]2CC(C3CCC3)CN2c2cc3c(cc2Cl)c(=O)c(C(=O)O)cn3-c2ccc(N3CC(N(C)C)C3)nc2)n1] | Column: XSelect CSH Prep C18 OBD Column, 19*250 mm, 5 µm; Mobile Phase A: Water (0.1% FA), Mobile Phase B: ACN; Flow rate: 25 mL/min; Gradient: 25% B to 55% B in 7 min, 55% B; Wave Length: 254/220 nm; RT1(min): 6.83; Number Of Runs: 0 | rac-6-chloro-7-((2R)-2-(((3-chloro-6-methoxy-pyridin-2-yl)oxy) methyl)-4-cyclobutyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]$^+$: 693.2. $^1$H NMR (300 MHz, DMSO-$d_6$) δ 8.53 (m, 1H), 8.23 (m, 1H), 8.14 (m, 1H), 7.65 (m, 2H), 6.68-6.22 (m, 3H), 4.80-4.42 (m, 2H), 4.23 (m, 1H), 4.08 (s, 2H), 3.83 (s, 2H), 3.62 (s, 2H), 2.31 (s, 2H), 3.22 (s, 2H), 2.169 (s, 2H), 2.16 (s, 2H), 2.04-1.87 (m, 3H), 1.81-1.59 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 204. | 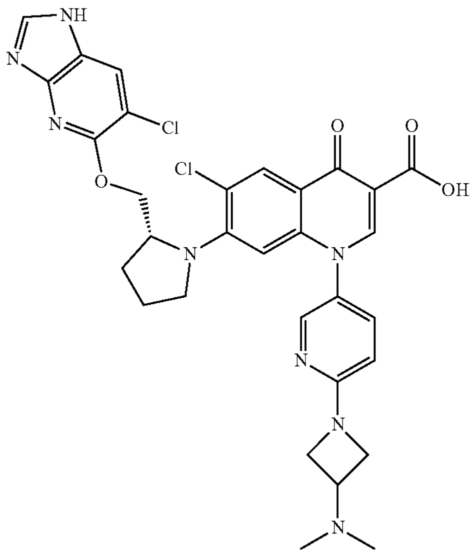 [SMILES: CN(C)C1CN(c2ccc(-n3cc(C(=O)O)c(=O)c4cc(Cl)c(N5CCC[C@@H]5COc5nc6nc[nH]c6cc5Cl)cc43)cn2)C1] | Column: XBridge Prep C18 OBD Column, 5 um, 19*150 mm; Mobile Phase A: Water (10 MMOL/L $NH_4HCO_3$), Mobile Phase B: acetonitrile; Flow rate: 25 mL/min; Gradient: 21 B to 35 B in 12 min; 254 nm. | (R)-6-chloro-7-(2-(((6-chloro-1H-imidazo[4,5-b]pyridin-5-yl)oxy)methyl)pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI): $[M + H]^+$: 649.1. $^1H$ NMR (300 MHz, DMSO-$d_6$) δ 8.56-7.94 (m, 5H), 7.63 (s, 1H), 6.61-6.17 (m, 2H), 4.70 (m, 1H), 4.33 (s, 2H), 4.14-3.94 (m, 2H), 3.90-3.72 (m, 2H), 3.22 (s, 3H), 2.29 (s, 1H), 2.15 (s, 6H), 1.96 (d, J = 21.2 Hz, 2H), 1.78 (d, J = 13.7 Hz, 1H). | ++++ |
| 205. | 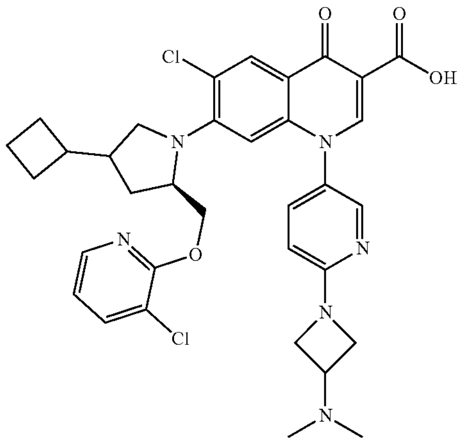 [SMILES: CN(C)C1CN(c2ccc(-n3cc(C(=O)O)c(=O)c4cc(Cl)c(N5CC(C6CCC6)C[C@@H]5COc5ncccc5Cl)cc43)cn2)C1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 25% B to 55% B in 7 min, 55% B; Wave Length: 254/220 nm; RT1(min): 6.05; Number Of Runs: 0 | rac-6-chloro-7-((2R)-2-((3-chloropyridin-2-yl)oxy)methyl)-4-cyclobutyl-pyrrolidin-1-yl)-1-(6-(3-(dimethyl-amino)azetidin-1-yl)pyridin-3-yl)-4-oxo-1,4-dihydro-quinoline-3-carboxylic acido-quinoline-3-carboxylic acid | LCMS (ESI) $[M + H]^+$: 663.3. $^1H$ NMR (300 MHz, DMSO-$d_6$) δ 15.15 (s, 1H), 8.59 (m, 1H), 8.41-8.18 (m, 2H), 8.03-7.85 (m, 2H), 7.80-7.62 (m, 1H), 7.02 (m, 1H), 6.70-6.33 (m, 2H), 4.77 (m, 1H), 4.45-4.22 (m, 2H), 4.13 (m, 2H), 3.88 (m, 2H),3.28 (m, 2H), 2.91 (s, 1H), 2.39 (s, 2H), 2.22 (s, 6H), 2.05-1.77 (m, 4H), 1.68 (m, 2H), 1.35 (s, 1H). 1.31 (s, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 206. | 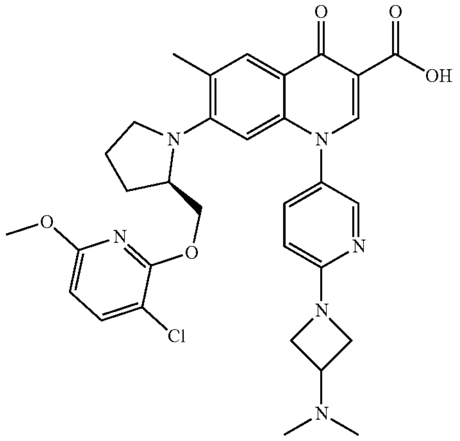 [SMILES: COc1ccc(Cl)c(OC[C@H]2CCCN2c2cc3c(cc2C)c(=O)c(C(=O)O)cn3-c2ccc(N3CC(N(C)C)C3)nc2)n1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 15% B to 43% B in 7 min, 43% B; Wave Length: 254/220 nm; RT1(min): 6.80; Number Of Runs: 0 | (R)-7-(2-(((3-chloro-6-methoxy-pyridin-2-yl)oxy)methyl) pyrrolidin-1-yl)-1-(6-(3-(dimethyl-amino) azetidin-1-yl)pyridin-3-yl)-6-methyl-4-oxo-1,4-dihydro-quinoline-3-carboxylic acid | LCMS (ESI) $[M + H]^+$: 619.2. $^1H$ NMR (300 MHz, DMSO-$d_6$) δ 8.50-8.40 (m, 1H), 8.26-8.16 (m, 1H), 8.01 (s, 1H), 7.66 (m, 2H), 6.59-6.29 (m, 3H), 4.31-4.02 (m, 5H), 3.80 (m, 2H), 3.60-3.48 (m, 4H), 3.23 (s, 2H), 2.32 (s, 4H), 2.15 (s, 7H), 1.95 (s, 2H), 1.77 (m, 1H). | ++++ |
| 207. | 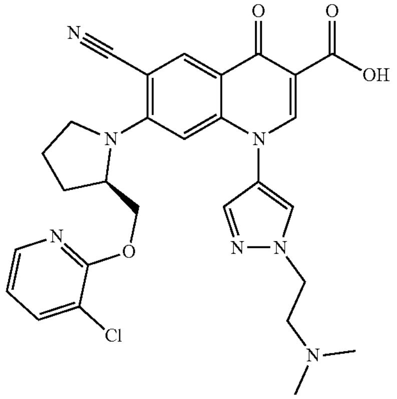 [SMILES: CN(C)CCn1cc(-n2cc(C(=O)O)c(=O)c3cc(C#N)c(N4CCC[C@@H]4COc4ncccc4Cl)cc32)cn1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 14% B to 30% B in 10 min, 30% B; Wave Length: 254/220 nm; RT1(min): 9.70; Number Of Runs: 0 | (R)-7-(2-((3-chloropyridin-2-yl)oxy)methyl) pyrrolidin-1-yl)-6-cyano-1-(1-(2-(dimethyl-amino)ethyl)-1H-pyrazol-4-yl)-4-oxo-1,4-dihydro-quinoline-3-carboxylic acid | LCMS (ESI) $[M + H]^+$: 562.3. $^1H$ NMR (300 MHz, DMSO-$d_6$) δ 8.52 (s, 1H), 8.44 (s, 1H), 8.32 (s, 1H), 7.98 (m, 1H), 7.90-7.76 (m, 2H), 6.99 (m, 1H), 6.41 (s, 1H), 4.82 (s, 1H), 4.54-4.37 (m, 2H), 4.32-4.18 (m, 2H), 3.63 (s, 1H), 3.46 (s, 1H), 2.69 (m, 2H), 2.18 (s, 8H), 2.09-1.84 (m, 2H). | ++++ |
| 208. | 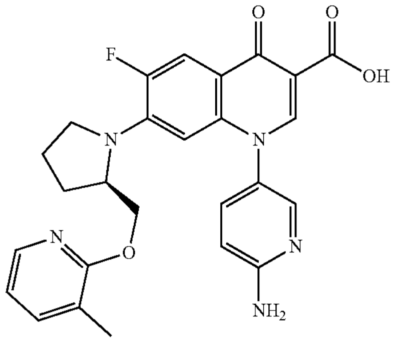 [SMILES: Cc1cccnc1OC[C@H]1CCCN1c1cc2c(cc1F)c(=O)c(C(=O)O)cn2-c1ccc(N)nc1] | (Column: XSelect CSH Prep C18 OBD Column, 5 um, 19*150 mm; Mobile Phase A: Water (0.05% FA), Mobile Phase B: ACN; Flow rate: 25 mL/min; Gradient: 50 B to 70 B in 8 min; 254 nm; RT1: 8.13; RT2:; Injection Volumn: ml; Number Of Runs:;) | (R)-1-(6-aminopyridin-3-yl)-6-fluoro-7-(2-(((3-methylpyridin-2-yl)oxy)methyl) pyrrolidin-1-yl)-4-oxo-1,4-dihydro-quinoline-3-carboxylic acid | LCMS (ESI) $[M + H]^+$: 490.2. $^1H$ NMR (300 MHz, DMSO-$d_6$) δ 8.48 (s, 1H), 8.15-8.04 (m, 1H), 7.93-7.80 (m, 2H), 7.58 (m, 1H), 7.48 (m, 1H), 6.85 (m, 1H), 6.66-6.44 (m, 3H), 6.16 (m, 1H), 4.55 (m, 2H), 4.24 (m, 2H), 3.21 (s, 2H), 1.99 (s, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 209. | 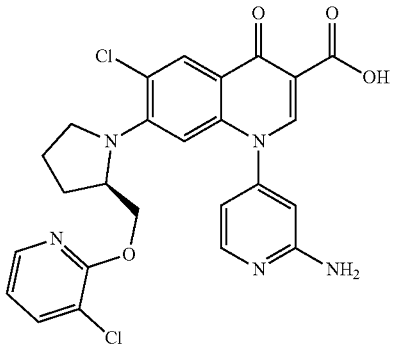 [SMILES: Nc1cc(-n2cc(C(=O)O)c(=O)c3cc(Cl)c(N4CCC[C@@H]4COc4ncccc4Cl)cc32)ccn1] | (Column: Gemini-NX C18 AXAI Packed, 21.2*150 mm 5 um; Mobile Phase A: Water (0.05% FA), Mobile Phase B: ACN; Flow rate: 25 mL/min; Gradient: 35 B to 67 B in 14 min; 254 nm; RT1: 13.63; RT2:; Injection Volumn: ml; Number Of Runs:;) | (R)-1-(2-aminopyridin-4-yl)-6-chloro-7-(2-(((3-chloropyridin-2-yl)oxy)methyl)pyrrolidin-1-yl)-4-oxo-1,4-dihydro-quinoline-3-carboxylic acid | LCMS (ESI) $[M + H]^+$: 526.0. $^1H$ NMR (300 MHz, DMSO-$d_6$) δ 8.55 (s, 1H), 8.14 (s, 1H), 8.01 (m, 1H),7.86 (m, 1H), 7.79 (m, 1H), 6.92 (m, 1H), 6.65 (m, 1H), 6.59 (s, 1H), 6.55 (s, 2H), 4.74 (s, 1H), 4.33 (m, 2H),3.25 (m, 1H), 3.20 (m, 1H), 2.36-2.17 (m, 1H), 2.10-1.70 (m, 3H). | ++++ |
| 210. | 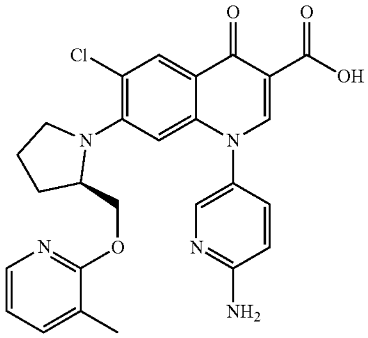 [SMILES: Cc1cccnc1OC[C@H]1CCCN1c1cc2c(cc1Cl)c(=O)c(C(=O)O)cn2-c1ccc(N)nc1] | (Column: XSelect CSH Prep C18 OBD Column,, 5 um, 19*150 mm; Mobile Phase A: Water (0.05% FA), Mobile Phase B: ACN; Flow rate: 25 mL/min; Gradient: 50 B to 70 B in 8 min; 254 nm; RT1: 6.07; RT2:; Injection Volumn: ml; Number Of Runs:;) | (R)-1-(6-aminopyridin-3-yl)-6-chloro-7-(2-(((3-methylpyridin-2-yl)oxy)methyl)pyrrolidin-1-yl)-4-oxo-1,4-dihydro-quinoline-3-carboxylic acid | LCMS (ESI) $[M + H]^+$: 505.9. $^1H$ NMR (300 MHz, DMSO-$d_6$) δ 8.52 (m, 1H), 8.16 (s, 1H), 8.08 (m, 1H), 7.79 (m, 1H), 7.52 (m, 1H), 7.44 (m, 1H), 6.80 (m, 1H), 6.60 (m, 2H), 6.50-6.24 (m, 2H), 4.75 (m, 1H), 4.33-4.06 (m, 2H), 3.51 (s, 1H), 3.20 (m, 1H), 2.24 (s, 1H), 1.97 (s, 1H), 1.97-1.62 (m, 5H). | ++++ |

TABLE 1-continued

| Compound | Product | Prep HPLC Method | IUPAC name | Analytical data | Potency Lin28a-dep Z11 $IC_{50}$ (μM) |
| --- | --- | --- | --- | --- | --- |
| 211. | 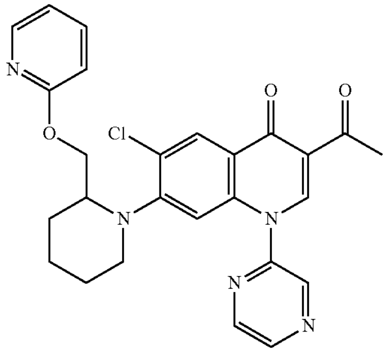 [SMILES: CC(=O)c1cn(-c2cnccn2)c2cc(N3CCCCC3COc3ccccn3)c(Cl)cc2c1=O] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 41% B to 78% B in 12 min, 78% B; Wave Length: 254 nm; RT1(min): 12.22; Number Of Runs: 0 | 6-Chloro-4-oxo-1-(pyrazin-2-yl)-7-{2-[(pyridin-2-yloxy)methyl]piperidin-1-yl}quinoline-3-carboxylic acid | LCMS (ESI) $[M + H]^+$: 492.0 $^1H$ NMR (400 MHz, DMSO-$d_6$) δ 9.95 (s, 1H), 8.92-8.71 (m, 3H), 8.08-7.96 (m, 1H), 7.85 (s, 1H), 7.55 (d, J = 8.7, 7.1, 2.0 Hz, 1H), 6.99-6.82 (m, 1H), 6.31 (d, J = 8.3 Hz, 1H), 5.84 (s, 1H), 4.51 (d, J = 10.9, 8.1 Hz, 1H), 4.36 (s, 1H), 4.26 (s, 1H), 3.05 (s, 1H), 2.80 (d, J = 12.0 Hz, 1H), 1.78 (s, 1H), 1.73-1.61 (m, 2H), 1.60-1.40 (m, 3H) | +++ |
| 212. | 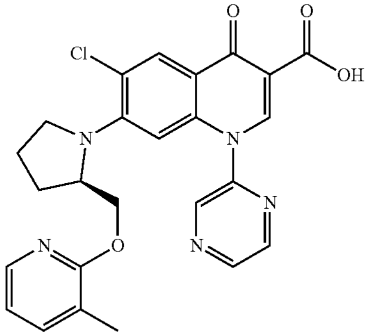 [SMILES: Cc1cccnc1OC[C@H]1CCCN1c1cc2c(cc1Cl)c(=O)c(C(=O)O)cn2-c1cnccn1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 46% B to 77% B in 9 min, 77% B; Wave Length: 254 nm; RT1(min): 7.3; Number Of Runs: 0 | 6-Chloro-7-[(2R)-2-{[(3-methylpyridin-2-yl)oxy]methyl}pyrrolidin-1-yl]-4-oxo-1-(pyrazin-2-yl)quinoline-3-carboxylic acid | LCMS (ESI) $[M + H]^+$: 492.0. $^1H$ NMR (400 MHz, DMSO-d6) δ 14.88 (s, 1H), 9.13 (d, J = 1.4 Hz, 1H), 8.95 (d, J = 2.9 Hz, 2H), 8.82-8.68 (m, 1H), 8.19 (s, 1H), 7.78 (s, 1H), 7.44 (d, J = 7.1 Hz, 1H), 6.81 (s, 1H), 6.56 (s, 1H), 4.74 (d, J = 6.9 Hz, 1H), 4.28-4.09 (m, 2H), 3.55 (d, J = 9.6, 6.5 Hz, 1H), 3.25 (s, 1H), 2.39-2.30 (m, 1H), 2.28-2.15 (m, 1H), 2.06-1.93 (m, 1H), 1.89 (s, 4H), 1.86-1.70 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 213. | 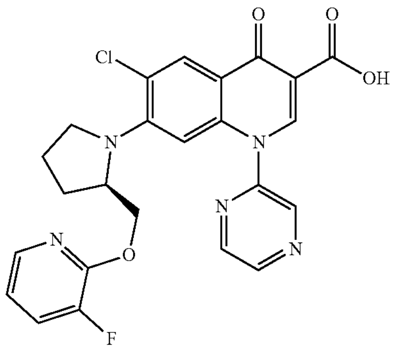 | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 50% B to 75% B in 8 min, 75% B; Wave Length: 254 nm; RT1(min): 6.80; Number Of Runs: 0 | 6-Chloro-7-[(2R)-2-{[(3-fluoropyridin-2-yl)oxy]methyl}pyrrolidin-1-yl]-4-oxo-1-(pyrazin-2-yl)quinoline-3-carboxylic acid | LCMS (ESI) $[M + H]^+$: 496.0 $^1H$ NMR (400 MHz, DMSO-$d_6$) δ 14.87 (s, 1H), 9.12 (d, J = 1.4 Hz, 1H), 9.02-8.90 (m, 2H), 8.81-8.72 (m, 1H), 8.18 (s, 1H), 7.74 (s, 1H), 7.58 (d, J = 10.9, 7.9, 1.5 Hz, 1H), 6.94 (d, J = 8.1, 4.9, 3.3 Hz, 1H), 6.57 (s, 1H), 4.67 (s, 1H), 4.29 (d, J = 4.8 Hz, 2H), 3.63-3.49 (m, 1H), 3.31 (s, 1H), 2.23 (s, 1H), 2.03-1.93 (m, 1H), 1.92-1.82 (m, 1H), 1.82-1.67 (m, 1H). | ++++ |
| 214. | 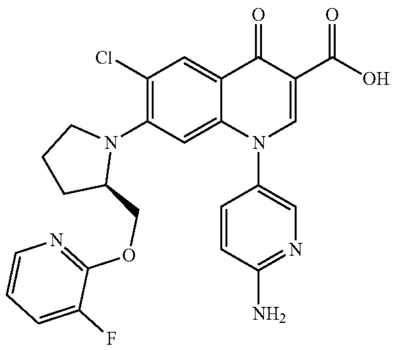 [SMILES: Nc1ccc(-n2cc(C(=O)O)c(=O)c3cc(Cl)c(N4CCC[C@@H]4COc4ncccc4F)cc32)cn1] | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 55% B to 80% B in 8 min, 75% B; Wave Length: 254 nm; RT1(min): 6.80; Number Of Runs: 0 | 1-(6-Aminopyridin-3-yl)-6-chloro-7-[(2R)-2-{[(3-fluoropyridin-2-yl)oxy]methyl}pyrrolidin-1-yl]-4-oxoquinoline-3-carboxylic acid | LCMS (ESI) $[M + H]^+$: 510.0. $^1H$ NMR (300 MHz, DMSO-d6) δ 15.12 (s, 1H), 8.52 (d, J = 2.9 Hz, 1H), 8.15 (s, 1H), 8.08 (s, 1H), 7.86-7.67 (m, 1H), 7.55 (s, 2H), 7.01-6.85 (m, 1H), 6.73-6.26 (m, 4H), 4.70 (d, J = 23.4 Hz, 1H), 4.28 (s, 2H), 3.61-3.41 (m, 1H), 3.25-3.05 (m, 1H), 2.26 (d, J = 10.2 Hz, 1H), 2.09-1.64 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 215. | 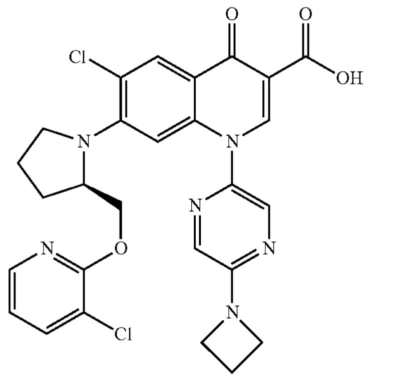 [SMILES: O=C(O)c1cn(-c2cnc(N3CCC3)cn2)c2cc(N3CCC[C@@H]3COc3ncccc3Cl)c(Cl)cc2c1=O] | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 52% B to 85% B in 8 min, 85% B; Wave Length: 25 nm; RT1(min): 7.88; Number Of Runs: 0 | 1-(6-Aminopyridin-3-yl)-6-chloro-7-[(2R)-2-{[(3-fluoropyridin-2-yl)oxy]methyl}pyrrolidin-1-yl]-4-oxoquinoline-3-carboxylic acid | LCMS (ESI) $[M+H]^+$: 510.0. $^1H$ NMR (300 MHz, DMSO-d6) δ 15.12 (s, 1H), 8.52 (d, J = 2.9 Hz, 1H), 8.15 (s, 1H), 8.08 (s, 1H), 7.86-7.67 (m, 1H), 7.55 (s, 2H), 7.01-6.85 (m, 1H), 6.73-6.26 (m, 4H), 4.70 (d, J = 23.4 Hz, 1H), 4.28 (s, 2H), 3.61-3.41 (m, 1H), 3.25-3.05 (m, 1H), 2.26 (d, J = 10.2 Hz, 1H), 2.09-1.64 (m, 3H). | ++++ |
| 216. | 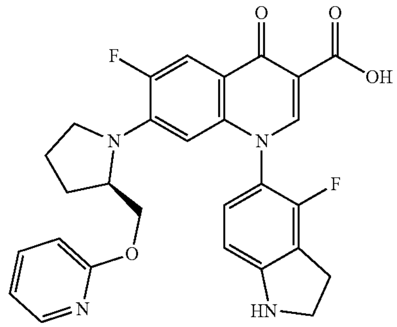 [SMILES: O=C(O)c1cn(-c2ccc3c(c2F)CCN3)c2cc(N3CCC[C@@H]3COc3ccccn3)c(F)cc2c1=O] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 40% B to 90% B in 8 min, 90% B; Wave Length: 220 nm; RT1(min): 9.35; Number Of Runs: 0 | 6-Fluoro-1-(4-fluoro-2,3-dihydro-1H-indol-5-yl)-4-oxo-7-[(2R)-2-[(pyridin-2-yloxy)methyl]pyrrolidin-1-yl]quinoline-3-carboxylic acid | LCMS (ESI) $[M+H]^+$: 519.05. $^1H$ NMR (300 MHz, DMSO-$d_6$) δ 15.33 (s, 1H), 8.52 (d, J = 1.3 Hz, 1H), 8.10-7.99 (m, 1H), 7.91 (d, J = 2.7 Hz, 1H), 7.86 (d, J = 2.7 Hz, 1H), 7.68 (s, 1H), 7.01-6.88 (m, 1H), 6.76-6.64 (m, 1H), 6.45 (d, J = 8.3 Hz, 1H), 6.35 (s, 1H), 6.27 (d, J = 8.3 Hz, 1H), 6.18 (d, J = 7.4 Hz, 1H), 4.38 (d, J = 26.7 Hz, 1H), 4.19 (s, 2H), 3.73-3.60 (m, 1H), 3.59-3.37 (m, 2H), 3.26-2.59 (m, 3H), 2.18-1.82 (m, 4H). | ++++ |
| 217. | 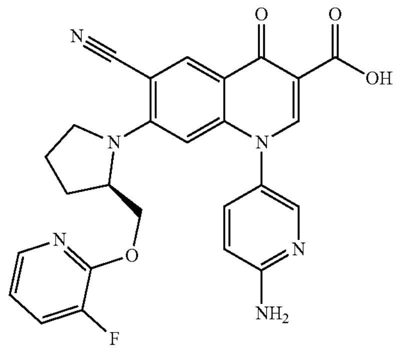 [SMILES: N#Cc1cc2c(=O)c(C(=O)O)cn(-c3ccc(N)nc3)c2cc1N1CCC[C@@H]1COc1ncccc1F] | reverse phase flash chromatography | 6-ethynyl-7-[(2R)-2-[[(3-fluoropyridin-2-yl)oxy]methyl]pyrrolidin-1-yl]-4-oxo-1-(pyrazin-2-yl)quinoline-3-carboxylic acid | LCMS (ESI) $[M+H]^+$: 501.1 $^1H$ NMR (300 MHz, DMSO-$d_6$) δ 14.83 (s, 1H), 8.59 (s, 1H), 8.52 (s, 1H), 8.24-8.09 (m, 1H), 7.90 (d, J = 4.9 Hz, 1H), 7.76-7.51 (m, 2H), 7.13-6.99 (m, 1H), 6.64 (d, J = 24.7 Hz, 3H), 6.27 (d, J = 3.1 Hz, 1H), 4.79 (d, J = 27.2 Hz, 1H), 4.47 (d, J = 4.8 Hz, 2H), 3.66 (d, J = 16.6 Hz, 1H), 3.57-3.44 (m, 1H), 2.31-2.10 (m, 2H), 2.12-1.90 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 218. | 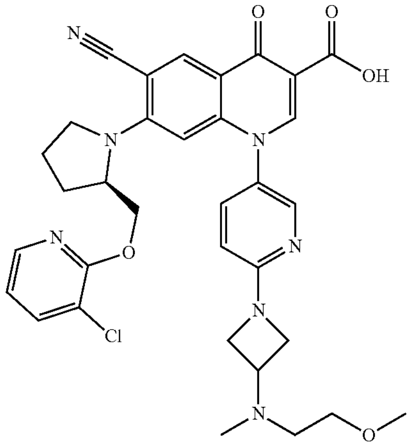 [SMILES: COCCN(C)C1CN(c2ccc(-n3cc(C(=O)O)c(=O)c4cc(C#N)c(N5CCC[C@@H]5COc5ncccc5Cl)cc43)cn2)C1] | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 13% B to 34% B in 10 min, 34% B; Wave Length: 254/220 nm; RT1(min): 9.72; Number Of Runs: 0 | 7-[(2R)-2-[[(3-chloropyridin-2-yl)oxy]methyl]pyrrolidin-1-yl]-6-cyano-1-(6-[3-[(2-methoxyethyl)(methyl)amino]azetidin-1-yl]pyridin-3-yl)-4-oxoquinoline-3-carboxylic acid | LCMS (ESI) $[M + H]^+$: 644.2 $^1H$ NMR (300 MHz, DMSO-$d_6$) δ 14.45 (s, 1H), 8.52 (d, J = 3.7 Hz, 1H), 8.47 (s, 1H), 8.26 (d, J = 11.3 Hz, 1H), 8.07-7.95 (m, 1H), 7.87 (d, J = 7.0 Hz, 1H), 7.71 (s, 1H), 7.11-6.91 (m, 1H), 6.54 (d, J = 8.9 Hz, 1H), 6.21 (d, J = 21.3 Hz, 1H), 4.63 (d, J = 26.6 Hz, 1H), 4.36 (d, J = 6.4 Hz, 2H), 4.11-3.92 (m, 2H), 3.77 (s, 3H), 3.44 (s, 4H), 3.36 (s, 2H),3.25(s, 3H), 2.20 (s, 5H), 1.98 (s, 2H).. | ++++ |
| 219. | 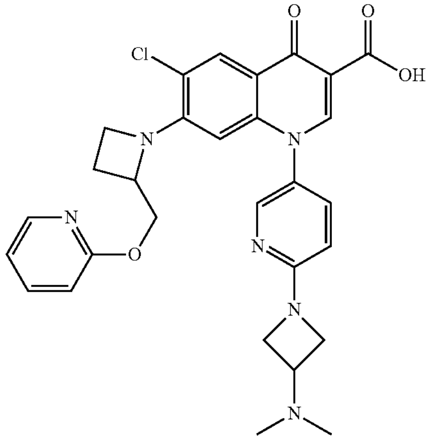 [SMILES: CN(C)C1CN(c2ccc(-n3cc(C(=O)O)c(=O)c4cc(Cl)c(N5CCC5COc5ccccn5)cc43)cn2)C1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 26% B to 29% B in 8 min, 29% B; Wave Length: 254/220 nm; RT1(min): 5.02; Number Of Runs: 0 | 6-chloro-1-[6-[3-(dimethyl-amino)azetidin-1-yl]pyridin-3-yl]-4-oxo-7-[2-[(pyridin-2-yloxy)methyl]azetidin-1-yl]quinoline-3-carboxylic acid | LCMS (ESI) $[M + H]^+$: 561.1 $^1H$ NMR (300 MHz, DMSO-$d_6$) δ 8.57 (d, J = 16.7 Hz, 1H), 8.40 (s, 1H), 8.21 (s, 1H), 8.11 (d, J = 4.9 Hz, 1H), 7.88 (s, 1H), 7.81-7.70 (m, 1H), 7.04 (d, J = 6.0 Hz, 1H), 6.74 (d, J = 8.2 Hz, 2H), 6.70-6.59 (m, 1H), 6.47 (d, J = 7.4 Hz, 2H), 6.36 (s, 1H), 4.65 (s, 1H), 4.46 (s, 3H), 4.15-3.97 (m, 3H), 3.88-3.77 (m, 2H), 3.25 (t, J = 6.1 Hz, 1H), 2.35 (s, 1H), 2.22 (s, 1H). | +++ |
| 220. | 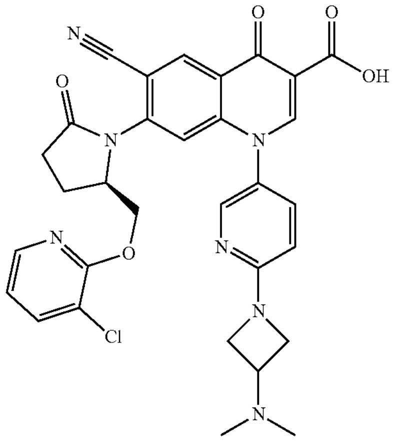 [SMILES: CN(C)C1CN(c2ccc(-n3cc(C(=O)O)c(=O)c4cc(C#N)c(N5C(=O)CC[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 13% B to 35% B in 8 min, 35% B; Wave Length: 254 nm; RT1(min): 5.0; Number Of Runs: 0 | 7-[(2R)-2-[[(3-chloropyridin-2-yl)oxy]methyl]-5-oxopyrrolidin-1-yl]-6-cyano-1-[6-[3-(dimethyl-amino)azetidin-1-yl]pyridin-3-yl]-4-oxoquinoline-3-carboxylic acid | LCMS (ESI) $[M + H]^+$: 614.0. $^1H$ NMR (300 MHz, DMSO-$d_6$) δ 9.99 (s, 1H), 8.27 (d, J = 7.1 Hz, 1H), 8.08-7.97 (m, 1H), 7.88-7.76 (m, 1H), 7.67 (d, J = 2.4 Hz, 2H), 7.30-6.92 (m, 2H), 6.62-6.15 (m, 2H), 4.46 (d, J = 4.0 Hz, 1H), 4.39-3.93 (m, 7H), 2.73 (s, 6H), 2.54 (s, 1H), 2.45-2.41 (m, 1H), 2.41-2.25 (m, 2H), 1.97 (s, 1H). | ++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 221. | 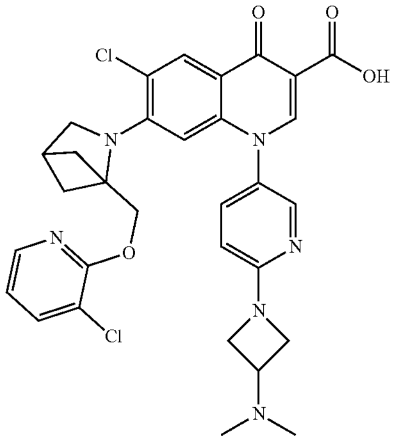 [SMILES: CN(C)C1CN(c2ccc(-n3cc(C(=O)O)c(=O)c4cc(Cl)c(N5CC6CC5(COc5ncccc5Cl)C6)cc43)cn2)C1] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 23% B to 52% B in 8 min, 52% B; Wave Length: 254 nm; RT1(min): 7.32; Number Of Runs: 0 | 6-chloro-7-(1-[[(3-chloropyridin-2-yl)oxy] methyl]-2-azabicyclo [2.1.1]hexan-2-yl)-1-[6-[3-(dimethyl-amino) azetidin-1-yl]pyridin-3-yl]-4-oxoquinoline-3-carboxylic acid | LCMS (ESI) $[M + H]^+$: 621.0. $^1H$ NMR (300 MHz, DMSO-$d_6$) δ 8.62 (s, 1H), 8.39-8.21 (m, 2H), 8.06-7.84 (m, 2H), 7.82-7.66 (m, 1H), 7.13-6.96 (m, 1H), 6.55 (s, 1H), 6.30 (d, J = 8.9 Hz, 1H), 4.58-4.38 (m, 2H), 4.00-3.87 (m, 2H), 3.78-3.62 (m, 2H), 3.60-3.48 (m, 1H), 3.24-3.12 (m, 1H), 2.83 (s, 1H), 2.76-2.69 (m, 1H), 2.13 (s, 6H), 2.01-1.83 (m, 2H), 1.69-1.46 (m, 2H). | +++ |
| 222. | 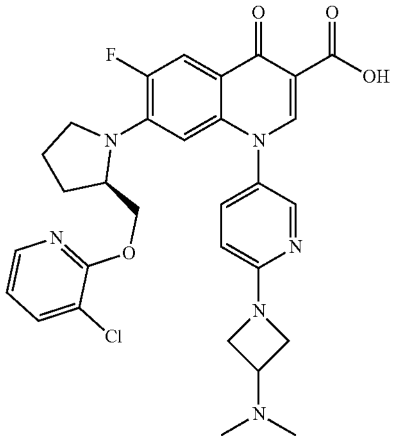 [SMILES: CN(C)C1CN(c2ccc(-n3cc(C(=O)O)c(=O)c4cc(F)c(N5CCC[C@@H]5COc5ncccc5Cl)cc43)cn2)C1] | reverse phase flash chromatography | 7-[(2R)-2-[[(3-chloropyridin-2-yl)oxy]methyl] pyrrolidin-1-yl]-1-[6-[3-(dimethyl-amino) azetidin-1-yl]pyridin-3-yl]-6-fluoro-4-oxoquinoline-3-carboxylic acid | LCMS (ESI): $[M + H]^+$: 593.2. $^1H$ NMR (300 MHz, DMSO-$d_6$) δ 15.39 (s, 1H), 8.48 (d, J = 2.0 Hz, 1H), 8.31 (d, J = 2.6 Hz, 1H), 8.03-7.96 (m, 1H), 7.93-7.83 (m, 2H), 7.83-7.74 (m, 1H), 7.09-6.94 (m, 1H), 6.68-6.36 (m, 1H), 6.11 (d, J = 7.4 Hz, 1H), 4.53 (s, 1H), 4.43-4.26 (m, 2H), 4.18 (s, 2H), 4.02 (s, 2H), 3.41 (s, 1H), 3.21 (s, 2H), 2.70-2.31 (m, 8H), 2.25-1.78 (m, 2H). | ++++ |
| 223. | 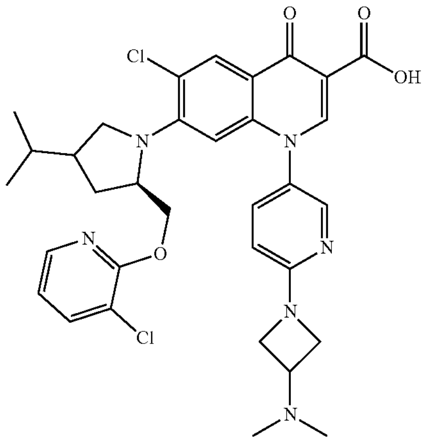 [SMILES: CC(C)C1C[C@H](COc2ncccc2Cl)N(c2cc3c(cc2Cl)c(=O)c(C(=O)O)cn3-c2ccc(N3CC(N(C)C)C3)nc2)C1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 20% B to 45% B in 9 min, 45% B; Wave Length: 254/220 nm; RT1(min): 8.82; Number Of Runs: 0 | Rac-6-chloro-7-((2R)-2-(((3-chloropyridin-2-yl)oxy) methyl)-4-isopropyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) $[M + H]^+$: 651.2. $^1H$ NMR (300 MHz, DMSO-$d_6$) δ 15.08 (s, 1H), 8.54 (d, J = 6.6 Hz, 1H), 8.29-8.08 (m, 2H), 7.97-7.77 (m, 2H), 7.75-7.60 (m, 1H), 7.05-6.87 (m, 1H), 6.62-6.16 (m, 2H), 4.86-4.41 (m, 1H), 4.39-4.14 (m, 2H), 4.12-3.95 (m, 2H), 3.91-3.67 (m, 2H), 3.26 (d, J = 7.0 Hz, 3H), 2.43-2.28 (m, 1H), 2.15 (s, 6H), 1.95-1.74 (m, 1H), 1.73-1.38 (m, 2H), 0.99-0.70 (m, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 224. | 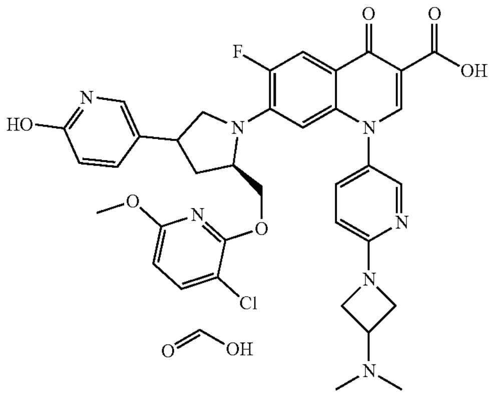 | Column: XSelect CSH Prep C18 OBD Column, 19*250 mm, 5 μm; Mobile Phase A: Water (0.05% FA), Mobile Phase B: ACN; Flow rate: 25 mL/min; Gradient: 10% B to 37% B in 7 min, 37% B; Wave Length: 254/220 nm; RT1(min): 6.72; Number Of Runs: 0 | Formic acid compound with rac-7-((2R)-2-(((3-chloro-6-methoxy-pyridin-2-yl)oxy) methyl)-4-(6-hydroxy-pyridin-3-yl)pyrrolidin-1-yl)-1-(6-(3-(dimethyl-amino) azetidin-1-yl)pyridin-3-yl)-6-fluoro-4-oxo-1,4-dihydro-quinoline-3-carboxylic acid (1:1) | LCMS (ESI) [M + H]$^+$: 716.3. $^1$H NMR (400 MHz, DMSO-$d_6$) δ 15.31 (s, 1H), 11.51 (s, 1H), 8.50 (d, J = 8.7 Hz, 1H), 8.23 (d, J = 2.5 Hz, 1H), 7.90 (d, J = 13.5 Hz, 1H), 7.75-7.62 (m, 2H), 7.52-7.44 (m, 1H), 7.26 (s, 1H), 6.54 (d, J = 8.7 Hz, 1H), 6.40-6.29 (m, 3H), 6.20-6.12 (m, 1H), 4.63-4.54 (m, 2H), 4.52 (s, 1H), 4.11-3.98 (m, 2H), 3.79 (s, 2H), 3.64 (d, J = 4.8 Hz, 3H), 3.56-3.49 (m, 1H), 3.19 (m, 3H), 2.63 (s, 1H), 2.13 (s, 7H), 2.11-1.98 (m, 1H). | ++++ |
| 225. | 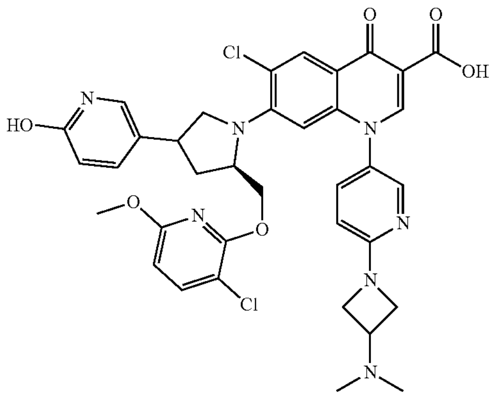 [SMILES: COc1ccc(Cl)c(OC[C@H]2CC(c3ccc(O)nc3)CN2c2cc3c(cc2Cl)c(=O)c(C(=O)O)cn3-c2ccc(N3CC(N(C)C)C3)nc2)n1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 10% B to 35% B in 10 min, 35% B; Wave Length: 254/220 nm; RT1(min): 9.12; Number Of Runs: 0 | Rac-6-chloro-7-((2R)-2-(((3-chloro-6-methoxy-pyridin-2-yl)oxy) methyl)-4-(6-hydroxy-pyridin-3-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]$^+$: 732.2. $^1$H NMR (300 MHz, DMSO-$d_6$) δ 8.54 (d, J = 8.5 Hz, 1H), 8.32-8.21 (m, 1H), 8.25-8.13 (m, 1H), 7.84-7.62 (m, 1H), 7.58-7.42 (m, 1H), 7.38 (s, 1H), 7.32-7.22 (m, 1H), 6.51-6.26 (m, 4H), 4.71-4.46 (m, 3H), 4.51-4.35 (m, 1H), 4.34-4.21 (m, 1H), 4.05 (s, 3H), 3.89-3.75 (m, 3H), 3.58 (d, J = 2.8 Hz, 2H), 2.48-2.38 (m, 1H), 2.14 (s, 7H), 2.09 (s, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 226. | 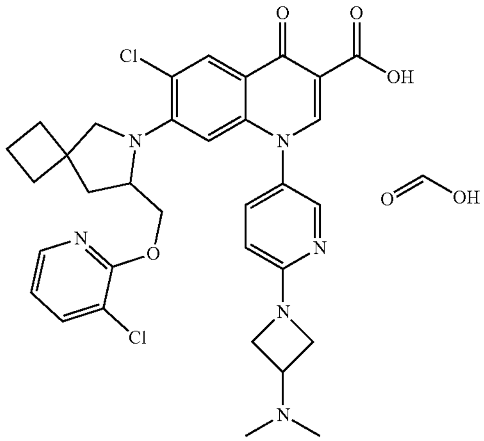 [SMILES: CN(C)C1CN(c2ccc(-n3cc(C(=O)O)c(=O)c4cc(Cl)c(N5CC6(CCC6)CC5COc5ncccc5Cl)cc43)cn2)C1 ; O=CO] | Column: Gemini-NX C18 AXAI Packed, 21.2*150 mm 5 um; Mobile Phase A: Water (10 MMOL/L NH4HCO3), Mobile Phase B: ACN; Flow rate: 25 mL/min; Gradient: 10% B to 10% B in 2 min, 10% B to 48% B in 2.5 min, 48% B to 88% B in 12 min, 88% B; Wave Length: 254 nm; RT1(min): 10.98; Number Of Runs: 0 | 6-Chloro-7-(7-(((3-chloropyridin-2-yl)oxy) methyl)-6-azaspiro [3.4]octan-6-yl)-1-(6-(3-(dimethyl-amino) azetidin-1-yl)pyridin-3-yl)-4-oxo-1,4-dihydro-quinoline-3-carboxylic acid compound with formic acid (1:1) | LCMS (ESI) $[M + H]^+$: 649.15. $^1H$ NMR (400 MHz, DMSO-$d_6$) δ 15.08 (s, 1H), 8.51 (d, J = 9.5 Hz, 1H), 8.25 (d, J = 2.6 Hz, 1H), 8.20 (s, 1H), 8.17 (s, 2H), 7.92-7.79 (m, 2H), 7.73-7.64 (m, 1H), 7.00-6.89 (m, 1H), 6.57 (d, J = 8.9 Hz, 2H), 6.42 (d, J = 13.5 Hz, 2H), 4.56 (s, 1H), 4.45 (s, 2H), 4.37-4.22 (m, 2H), 4.14-4.01 (m, 2H), 3.88-3.77 (m, 2H), 3.52 (d, J = 9.2 Hz, 1H), 3.25 (d, J = 8.3 Hz, 2H), 2.15 (s, 13H). | ++++ |
| 227. | 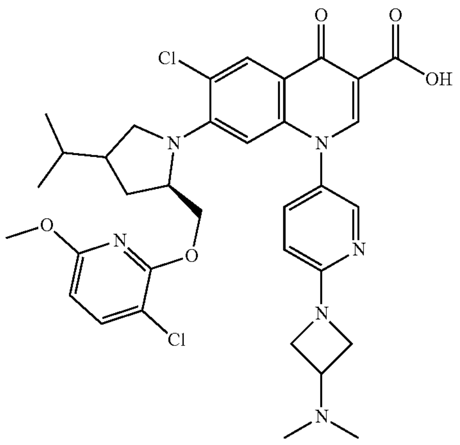 [SMILES: COc1ccc(Cl)c(OC[C@H]2CC(C(C)C)CN2c2cc3c(cc2Cl)c(=O)c(C(=O)O)cn3-c2ccc(N3CC(N(C)C)C3)nc2)n1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 20% B to 54% B in 7 min, 54% B; Wave Length: 254/220 nm; RT1(min): 6.22; Number Of Runs: 0 | Rac-6-chloro-7-((2R)-2-(((3-chloro-6-(11-oxidaneyl) pyridin-2-yl)oxy) methyl)-4-isopropyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) $[M + H]^+$: 681.2. $^1H$ NMR (300 MHz, DMSO-$d_6$) δ 8.57-8.48 (m, 1H), 8.29-8.20 (m, 1H), 8.17-8.10 (m, 1H), 7.77-7.60 (m, 2H), 6.45-6.24 (m, 2H), 4.74 (s, 0H), 4.62-4.42 (m, 1H), 4.42-4.17 (m, 1H), 4.11 (q, J = 8.1 Hz, 2H), 3.84 (d, J = 27.2 Hz, 1H), 3.66 (s, 1H), 3.55 (d, J = 3.4 Hz, 2H), 3.30-3.15 (m, 1H), 2.29 (s, 5H), 2.09-1.61 (m, 1H), 1.61-1.42 (m, 1H), 1.03-0.76 (m, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 228. | 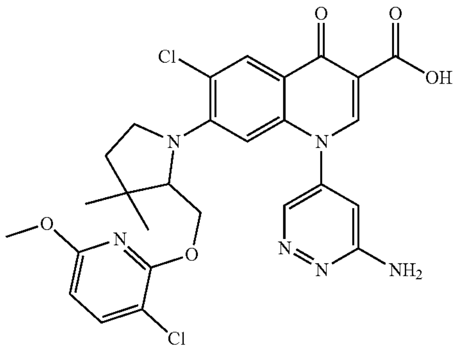 [SMILES: COc1ccc(Cl)c(OCC2N(c3cc4c(cc3Cl)c(=O)c(C(=O)O)cn4-c3cnnc(N)c3)CCC2(C)C)n1] | Column: Atlantis HILIC OBD Column, 19*150 mm*5 um; Mobile Phase A: Water (0.1% FA), Mobile Phase B: ACN; Flow rate: 25 mL/min; Gradient: 2% B to 42% B in 2 min, 42% B to 73% B in 10 min, 73% B; Wave Length: 254 nm; RT1(min): 10.07; Number Of Runs: 0 | 1-(6-Amino-pyridazin-4-yl)-6-chloro-7-(2-(((3-chloro-6-methoxy-pyridin-2-yl)oxy)methyl)-3,3-dimethyl-pyrrolidin-1-yl)-4-oxo-1,4-dihydro-quinoline-3-carboxylic acid | LCMS (ESI) $[M + H]^+$: 585.10. $^1H$ NMR (300 MHz, DMSO-$d_6$) δ 14.97 (s, 1H), 8.75 (s, 1H), 8.67 (d, J = 2.4 Hz, 1H), 8.13 (s, 1H), 7.60 (d, J = 8.4 Hz, 1H), 7.10 (s, 2H), 6.88 (d, J = 2.4 Hz, 1H), 6.49 (s, 1H), 6.32 (d, J = 8.4 Hz, 1H), 4.53-4.41 (m, 2H), 4.36 (d, J = 6.6 Hz, 1H), 3.68 (s, 4H), 3.28-3.16 (m, 1H), 2.01-1.84 (m, 1H), 1.82-1.67 (m, 1H), 1.17 (d, J = 13.7 Hz, 6H). | ++++ |
| 229. | 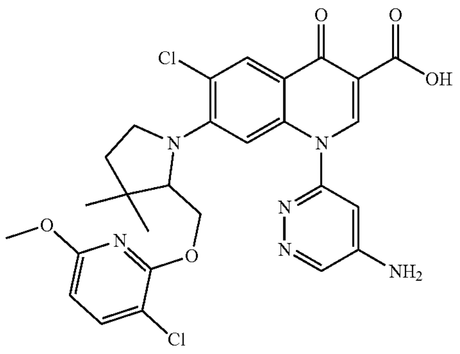 [SMILES: COc1ccc(Cl)c(OCC2N(c3cc4c(cc3Cl)c(=O)c(C(=O)O)cn4-c3cc(N)cnn3)CCC2(C)C)n1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 47% B to 73% B in 7 min, 73% B; Wave Length: 254/220 nm; RT1(min): 6.62; Number Of Runs: 0 | 1-(5-Amino-pyridazin-3-yl)-6-chloro-7-(2-(((3-chloro-6-methoxy-pyridin-2-yl)oxy)methyl)-3,3-dimethyl-pyrrolidin-1-yl)-4-oxo-1,4-dihydro-quinoline-3-carboxylic acid | LCMS (ESI) $[M + H]^+$: 585.15. $^1H$ NMR (300 MHz, DMSO-$d_6$) δ 14.95 (s, 1H), 8.74-8.61 (m, 2H), 8.12 (s, 1H), 7.60 (d, J = 8.4 Hz, 1H), 7.04 (s, 2H), 6.33 (d, J = 8.4 Hz, 2H), 4.61 (s, 1H), 4.46 (d, J = 4.5 Hz, 2H), 3.69 (s, 4H), 3.22 (d, J = 7.5 Hz, 1H), 1.97 (s, 1H), 1.82-1.67 (m, 1H), 1.18 (d, J = 12.4 Hz, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 230. | 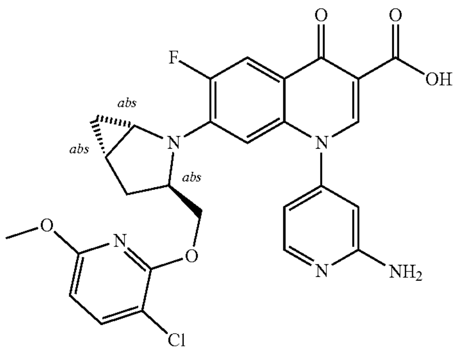 [SMILES: COc1ccc(Cl)c(OC[C@H]2C[C@@H]3C[C@@H]3N2c2cc3c(cc2F)c(=O)c(C(=O)O)cn3-c2ccnc(N)c2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 61% B in 7 min, 61% B; Wave Length: 254/220 nm; RT1(min): 6.97; Number Of Runs: 0 | Rac-1-(2-aminopyridin-4-yl)-7-((1R,3S,5R)-3-(((3-chloro-6-methoxy-pyridin-2-yl)oxy) methyl)-2-azabicyclo [3.1.0]hexan-2-yl)-6-fluoro-4-oxo-1,4-dihydro-quinoline-3-carboxylic acid | LCMS (ESI) $[M + H]^+$: 552.15. $^1H$ NMR (300 MHz, DMSO-$d_6$) δ 15.28 (s, 1H), 8.55 (s, 1H), 8.09 (s, 1H), 7.89 (d, J = 14.2 Hz, 1H), 7.74 (d, J = 8.4 Hz, 1H), 6.73 (d, J = 7.8 Hz, 2H), 6.64 (s, 1H), 6.52 (s, 2H), 6.42 (d, J = 8.4 Hz, 1H), 4.46 (d, J = 12.4 Hz, 3H), 3.77 (s, 3H), 3.09 (s, 1H), 2.33-2.20 (m, 1H), 2.05 (s, 1H), 1.79 (s, 1H), 0.90-0.81 (m, 1H), 0.39 (s, 1H). | ++++ |
| 231. | 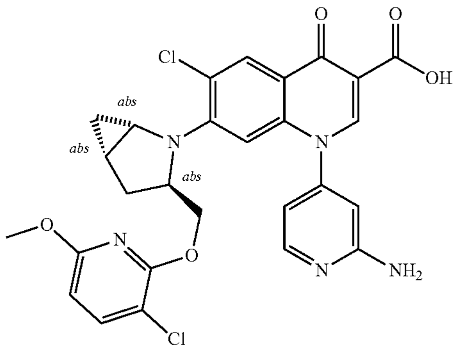 [SMILES: COc1ccc(Cl)c(OC[C@H]2C[C@@H]3C[C@@H]3N2c2cc3c(cc2Cl)c(=O)c(C(=O)O)cn3-c2ccnc(N)c2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 62% B in 7 min, 62% B; Wave Length: 254/220 nm; RT1(min): 7.22; Number Of Runs: 0 | Rac-1-(2-aminopyridin-4-yl)-6-chloro-7-((1R,3S,5R)-3-(((3-chloro-6-methoxy-pyridin-2-yl)oxy) methyl)-2-azabicyclo [3.1.0]hexan-2-yl)-4-oxo-1,4-dihydro-quinoline-3-carboxylic acid | LCMS (ESI) $[M + H]^+$: 568.1. $^1H$ NMR (300 MHz, DMSO-$d_6$) δ 14.93 (s, 1H), 8.61 (s, 1H), 8.21 (s, 1H), 8.08 (s, 1H), 7.91 (s, 1H), 7.71 (d, J = 8.4 Hz, 1H), 6.94 (s, 1H), 6.65 (s, 2H), 6.54 (s, 2H), 6.40 (d, J = 8.4 Hz, 1H), 4.54 (s, 1H), 4.44-4.33 (m, 1H), 4.16 (s, 1H), 3.64 (s, 4H), 3.31 (s, 1H), 2.29-2.17 (m, 1H), 2.12 (s, 1H), 0.55 (s, 2H) | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 232. | 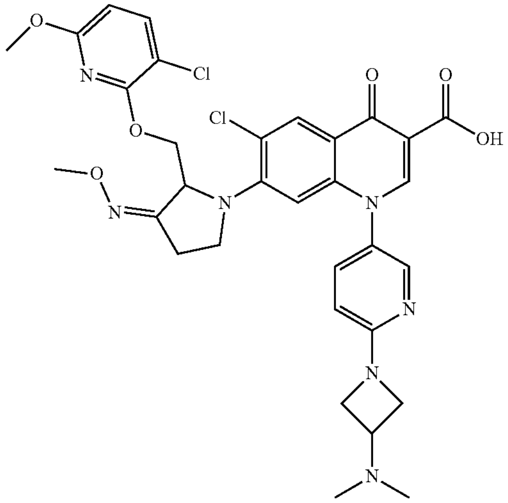 | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 36% B to 50% B in 12 min, 50% B; Wave Length: 220 nm; RT1(min): 11.37; Number Of Runs: 0 | (Z)-6-chloro-7-(2-(((3-chloro-6-methoxy-pyridin-2-yl)oxy) methyl)-3-(methoxyimino) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) $[M + H]^+$: 685.3. $^1H$ NMR (300 MHz, DMSO-$d_6$) δ 8.57 (d, J = 5.4 Hz, 1H), 8.32-8.05 (m, 2H), 7.56 (d, J = 12.7 Hz, 2H), 6.56 (d, J = 8.9 Hz, 1H), 6.46 (s, 1H), 6.32 (d, J = 8.3 Hz, 1H), 5.79 (s, 1H), 4.97-4.69 (m, 1H), 4.40 (s, 1H), 4.11 (d, J = 8.2 Hz, 2H), 3.83 (s, 5H), 3.65 (d, J = 4.0 Hz, 4H), 3.27 (d, J = 6.0 Hz, 3H), 2.73 (p, J = 1.9 Hz, 2H), 2.16 (s, 6H) | ++++ |
| 233. | 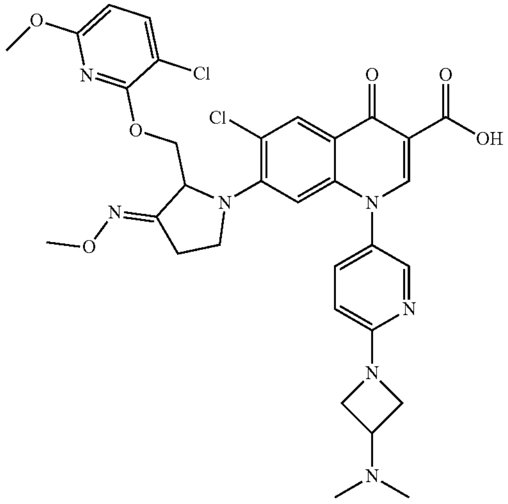 | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 36% B to 50% B in 12 min, 50% B; Wave Length: 220 nm; RT1(min): 11.37; Number Of Runs: 0 | (E)-6-chloro-7-(2-(((3-chloro-6-methoxy-pyridin-2-yl)oxy) methyl)-3-(methoxyimino) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) $[M + H]^+$: 685.3. $^1H$ NMR (300 MHz, DMSO-$d_6$) δ 8.49 (s, 1H), 8.24-7.96 (m, 2H), 7.58 (d, J = 65.1 Hz, 2H), 6.53 (d, J = 8.9 Hz, 1H), 6.42 (s, 1H), 6.24 (d, J = 14.0 Hz, 1H), 5.45 (s, 1H), 4.55 (s, 1H), 4.30 (d, J = 34.2 Hz, 1H), 4.09 (d, J = 8.0 Hz, 2H), 3.83 (s, 5H), 3.59 (d, J = 10.4 Hz, 4H), 3.25 (t, J = 6.2 Hz, 3H), 2.83 (d, J = 16.8 Hz, 1H), 2.72-2.58 (m, 1H), 2.16 (s, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 234. | 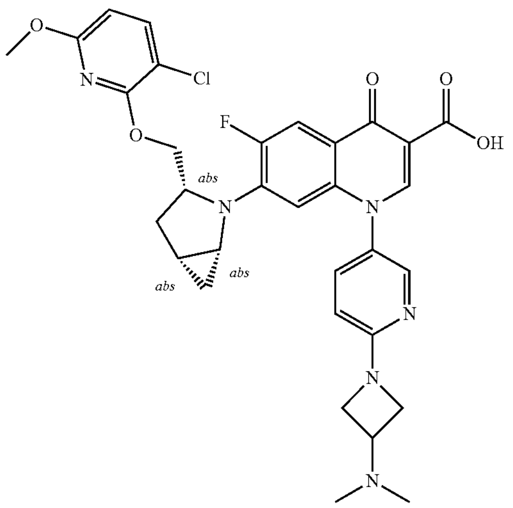 [SMILES: COc1ccc(Cl)c(OC[C@H]2C[C@H]3C[C@H]3N2c2cc3c(cc2F)c(=O)c(C(=O)O)cn3-c2ccc(N3CC(N(C)C)C3)nc2)n1] | reverse phase flash chromatography | Rac-7-((1R,3R,5R)-3-(((3-chloro-6-methoxy-pyridin-2-yl)oxy)methyl)-2-azabicyclo[3.1.0]hexan-2-yl)-1-(6-(3-(dimethyl-amino)azetidin-1-yl)pyridin-3-yl)-6-fluoro-4-oxo-1,4-dihydro-quinoline-3-carboxylic acid | LCMS (ESI) $[M + H]^+$: 635.20. $^1H$ NMR (300 MHz, DMSO-$d_6$) δ 8.46 (d, J = 8.5 Hz, 1H), 8.27 (s, 1H), 7.71 (d, J = 13.8 Hz, 3H), 6.57 (d, J = 8.6 Hz, 3H), , 4.69 (s, 1H), 4.22 (s, 4H), 3.85-3.75 (m, 2H), 3.73 (s, 3H), 3.28-3.18 (m, 1H), 3.08 (s, 1H), 2.14 (s, 6H), 2.02 (d, J = 13.2 Hz, 1H), 1.58 (s, 1H), 0.89 (s, 1H), 0.69 (s, 1H). | ++++ |
| 235. | 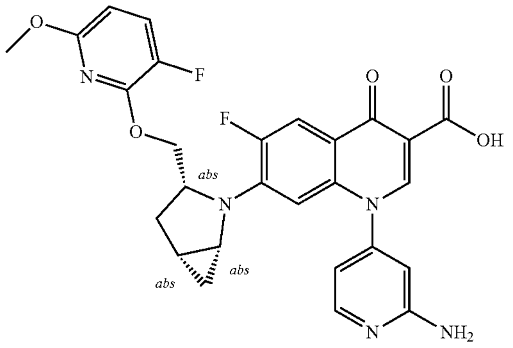 [SMILES: COc1ccc(F)c(OC[C@H]2C[C@H]3C[C@H]3N2c2cc3c(cc2F)c(=O)c(C(=O)O)cn3-c2ccnc(N)c2)n1] | Column: Gemini-NX C18 AXAI Packed, 21.2*150 mm 5 μm; Mobile Phase A: Water (0.1% FA), Mobile Phase B: ACN; Flow rate: 25 mL/min; Gradient: 34% B to 58% B in 8 min, 58% B; Wave Length: 254/220 nm; RT1(min): 7.82; Number Of Runs: 0 | Rac-1-(2-aminopyridin-4-yl)-6-fluoro-7-((1R,3R,5R)-3-(((3-fluoro-6-methoxy-pyridin-2-yl)oxy)methyl)-2-azabicyclo[3.1.0]hexan-2-yl)-4-oxo-1,4-dihydro-quinoline-3-carboxylic acid | LCMS (ESI) $[M + H]^+$: 537.2. $^1H$ NMR (300 MHz, DMSO-$d_6$) δ 15.24 (s, 1H), 8.54 (s, 1H), 8.11 (d, J = 29.3 Hz, 1H), 7.86 (d, J = 13.4 Hz, 1H), 7.54 (s, 1H), 6.71 (s, 2H), 6.63 (s, 1H), 6.52 (s, 2H), 6.26 (s, 1H), 4.78 (s, 1H), 4.32-4.15 (m, 2H), 3.67 (s, 3H), 3.15 (s, 1H), 2.77-2.57 (m, 1H), 2.11-1.98 (m, 1H), 1.63 (d, J = 7.2 Hz, 1H), 0.88 (s, 1H), 0.73 (d, J = 8.3 Hz, 1H). | ++++ |
| 236. | 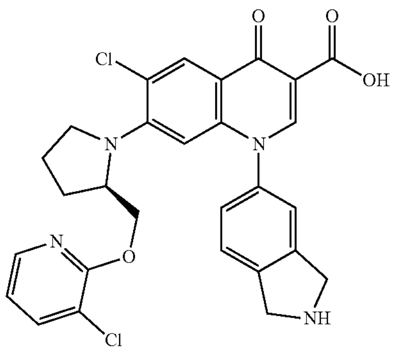 | Column: XSelect CSH Prep C18 OBD Column,, 5 um, 19*150 mm; Mobile Phase A: Water (0.1% FA), Mobile Phase B: ACN; Flow rate: 25 mL/min; Gradient: 53 B to 80 B in 9 min; 254 nm; RT1: 7.18; RT2:; Injection Volumn: ml; Number Of Runs:; | 6-chloro-7-[(2R)-2-[[(3-chloropyridin-2-yl)oxy]methyl]pyrrolidin-1-yl]-1-(2,3-dihydro-1H-isoindol-5-yl)-4-oxoquinoline-3-carboxylic acid | LCMS (ESI) [M + H]+: 535.15. 1H NMR (300 MHz, DMSO-d6) δ 10.83 (s, 1H), 8.53 (s, 1H), 8.17 (s, 1H), 7.89 (d, J = 4.5 Hz, 1H), 7.91-7.78 (m, 1H), 7.70-7.42 (m, 3H), 7.00-6.89 (m, 1H), 6.35 (d, J = 6.4 Hz, 1H), 4.73 (d, J = 23.9 Hz, 1H), 4.47 (d, J = 25.5 Hz, 4H), 4.29 (s, 2H), 3.55 (s, 1H), 3.16 (d, J = 8.5 Hz, 1H), 2.25 (d, J = 10.1 Hz, 1H), 1.97-1.76 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 237. | 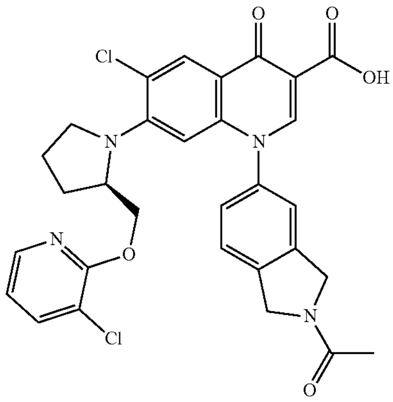 [SMILES: CC(=O)N1Cc2ccc(-n3cc(C(=O)O)c(=O)c4cc(Cl)c(N5CCC[C@@H]5COc5ncccc5Cl)cc43)cc2C1] | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 45 B to 67 B in 8 min; 254/220 nm; RT1: 7.68; RT2:; Injection Volumn: ml; Number Of Runs:; | 1-(2-acetyl-1,3-dihydro-isoindol-5-yl)-6-chloro-7-[(2R)-2-[[(3-chloropyridin-2-yl)oxy] methyl] pyrrolidin-1-yl]-4-oxoquinoline-3-carboxylic acid | LCMS (ESI) [M + H]+: 593.13. 1H NMR (300 MHz, DMSO-d6) δ 15.09 (s, 1H), 8.55 (t, J = 1.6 Hz, 1H), 8.21-8.14 (m, 1H), 7.96-7.75 (m, 2H), 7.69-7.36 (m, 3H), 7.01-6.89 (m, 1H), 6.35 (t, J = 3.4 Hz, 1H), 5.10-4.32 (m, 5H), 4.25 (d, J = 11.1 Hz, 2H), 3.53 (d, J = 7.7 Hz, 1H), 3.15 (s, 1H), 2.31-2.16 (m, 1H), 2.11 (d, J = 5.4 Hz, 2H), 1.99 (d, J = 26.0 Hz, 4H). | ++++ |
| 238. | 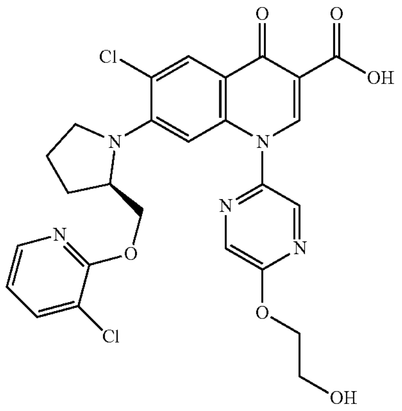 [SMILES: O=C(O)c1cn(-c2cnc(OCCO)cn2)c2cc(N3CCC[C@@H]3COc3ncccc3Cl)c(Cl)cc2c1=O] | reverse phase flash chromatography | 6-chloro-7-[(2R)-2-[[(3-chloropyridin-2-yl)oxy] methyl] pyrrolidin-1-yl]-1-[5-(2-hydroxy-ethoxy) pyrazin-2-yl]-4-oxoquinoline-3-carboxylic acid | 1H NMR (300 MHz, DMSO-d6) δ 8.59 (d, J = 15.8 Hz, 2H), 8.33 (s, 1H), 8.12 (s, 1H), 7.92-7.84 (m, 1H), 7.83-7.74 (m, 1H), 6.97-6.87 (m, 1H), 6.54 (s, 1H), 5.02 (t, J = 5.5 Hz, 1H), 4.63 (s, 1H), 4.42 (t, J = 5.0 Hz, 2H), 4.26 (t, J = 3.9 Hz, 2H), 3.86-3.75 (m, 2H), 3.59 (d, J = 8.4 Hz, 1H), 3.17 (d, J = 5.6 Hz, 1H), 2.30-2.19 (m, 1H), 1.98-1.74 (m, 3H). | ++++ |
| 239. | 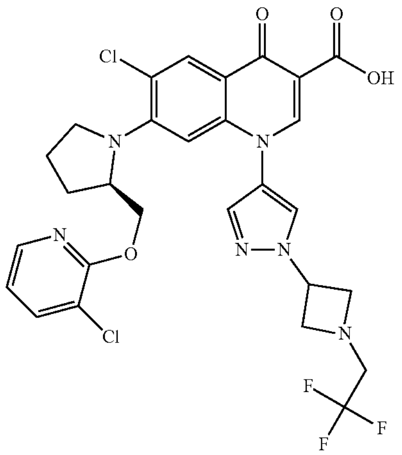 [SMILES: O=C(O)c1cn(-c2cnn(C3CN(CC(F)(F)F)C3)c2)c2cc(N3CCC[C@@H]3COc3ncccc3Cl)c(Cl)cc2c1=O] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 75% B to 88% B in 10 min, 88% B; Wave Length: 254 nm; RT1(min): 8.98; Number Of Runs: 0 | 6-chloro-7-[(2R)-2-[[(3-chloropyridin-2-yl)oxy] methyl] pyrrolidin-1-yl]-4-oxo-1-[1-[1-(2,2,2-trifluoro-ethyl)azetidin-3-yl]pyrazol-4-yl]quinoline-3-carboxylic acid | LCMS (ESI) [M + H]+: 637.13. 1H NMR (300 MHz, DMSO-d6) δ 14.95 (s, 1H), 8.60 (s, 1H), 8.55 (s, 1H), 8.14 (s, 1H), 7.95 (s, 1H), 7.90-7.82 (m, 1H), 7.82-7.74 (m, 1H), 6.96-6.86 (m, 1H), 6.68 (s, 1H), 5.25-5.10 (m, 1H), 4.79 (s, 1H), 4.32 (d, J = 4.1 Hz, 2H), 3.93 (t, J = 7.5 Hz, 2H), 3.79-3.67 (m, 2H), 3.59-3.48 (m, 1H), 3.37 (d, J = 10.1 Hz, 2H), 3.17-3.28 (m, 1H), 2.34-2.20 (m, 1H), 1.99 (s, 2H), 1.89-1.77 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 240. | 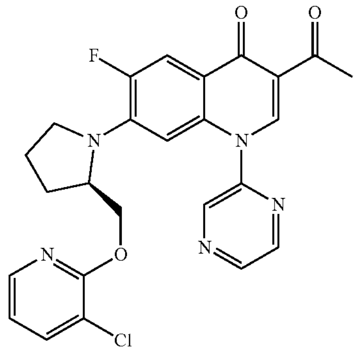 | Column: Gemini-NX C18 AXAI Packed, 21.2*150 mm 5 um; Mobile Phase A: Water (0.1% FA), Mobile Phase B: ACN; Flow rate: 25 mL/min; Gradient: 35 B to 60 B in 12 min; 254 nm; RT1: 12.18; RT2:; Injection Volumn: ml; Number Of Runs:; | 7-[(2R)-2-[[(3-chloropyridin-2-yl)oxy]methyl]pyrrolidin-1-yl]-6-fluoro-4-oxo-1-(pyrazin-2-yl)quinoline-3-carboxylic acid | LCMS (ESI) [M + H]+: 456.11. 1H NMR (400 MHz, DMSO-d6) δ 15.18 (s, 1H), 9.14 (s, 1H), 8.96-8.89 (m, 2H), 8.77 (s, 1H), 8.05-7.95 (m, 1H), 7.90 (d, J = 14.5 Hz, 1H), 7.88-7.81 (m, 1H), 7.03-6.95 (m, 1H), 6.28 (d, J = 7.3 Hz, 1H), 4.56 (s, 1H), 4.33 (t, J = 3.9 Hz, 2H), 3.45 (s, 1H), 3.26 (s, 1H), 2.18-2.02 (m, 2H), 2.02-1.88 (m, 2H). | ++++ |
| 241. | 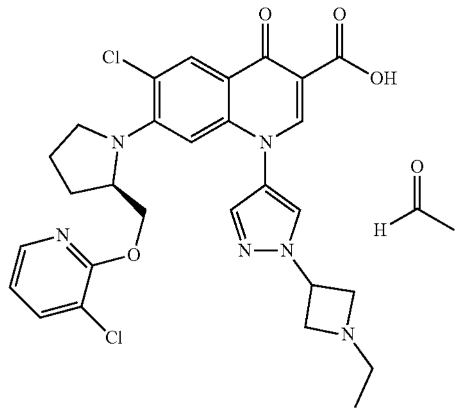 | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 25 B to 30 B in 10 min; 254 nm; RT1: 10.42; RT2:; Injection Volumn: ml; Number Of Runs:; | 6-chloro-7-[(2R)-2-[(3-chloropyridin-2-yl)oxy]methyl]pyrrolidin-1-yl]-1-[1-(1-ethylazetidin-3-yl)pyrazol-4-yl]-4-oxoquinoline-3-carboxylic acid | LCMS (ESI) [M + H]+: 583.15. 1H NMR (300 MHz, DMSO-d6) δ 8.56 (d, J = 18.6 Hz, 2H), 8.15 (s, 1H), 7.93 (s, 1H), 7.90-7.76 (m, 2H), 6.96-6.86 (m, 1H), 6.67 (s, 1H), 5.12-4.99 (m, 1H), 4.77 (s, 1H), 4.31 (d, J = 4.1 Hz, 2H), 3.69 (t, J = 7.4 Hz, 2H), 3.61-3.36 (m, 6H), 2.26 (s, 1H), 2.03 (d, J = 20.3 Hz, 2H), 1.86 (d, J = 34.2 Hz, 1H), 0.92 (t, J = 7.1 Hz, 3H). | ++++ |
| 242. | 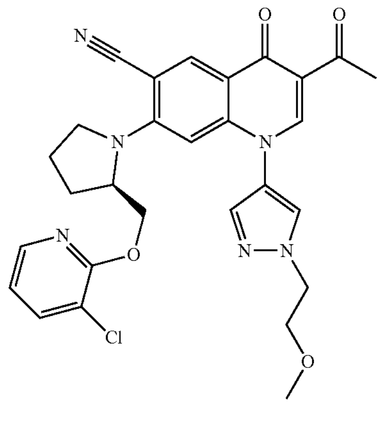 [SMILES: COCCn1cc(-n2cc(C(C)=O)c(=O)c3cc(C#N)c(N4CCC[C@@H]4COc4ncccc4Cl)cc32)cn1] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 36 B to 61 B in 8 min; 254/220 nm; RT1: 7.80; RT2:; Injection Volumn: ml; Number Of Runs:; | 7-[(2R)-2-[[(3-chloropyridin-2-yl)oxy]methyl]pyrrolidin-1-yl]-6-cyano-1-[1-(2-methoxyethyl)pyrazol-4-yl]-4-oxoquinoline-3-carboxylic acid | LCMS (ESI) [M + H]+: 549.16. 1H NMR (300 MHz, DMSO-d6) δ 14.71 (s, 1H), 8.59 (s, 1H), 8.51 (s, 1H), 8.37 (s, 1H), 8.08-7.99 (m, 1H), 7.94 (s, 1H), 7.92-7.86 (m, 1H), 7.10-7.01 (m, 1H), 6.47 (s, 1H), 4.87 (s, 1H), 4.57-4.45 (m, 2H), 4.45-4.32 (m, 2H), 3.80 (t, J = 5.2 Hz, 2H), 3.72 (d, J = 15.6 Hz, 0H), 3.61-3.47 (m, 1H), 3.33 (s, 3H), 2.33-2.17 (m, 2H), 2.16-1.95 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 243. | 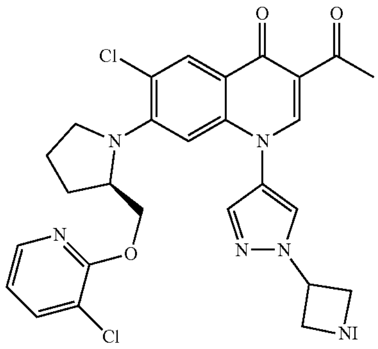 | Column: XSelect CSH Prep C18 OBD Column,, 5 um, 19*150 mm; Mobile Phase A: Water (0.1% FA), Mobile Phase B: ACN; Flow rate: 25 mL/min; Gradient: 15 B to 37 B in 10 min; 254 nm; RT1: 10.63; RT2:; Injection Volumn: ml; Number Of Runs:; | 1-[1-(azetidin-3-yl)pyrazol-4-yl]-6-chloro-7-[(2R)-2-[[(3-chloropyridin-2-yl)oxy]methyl]pyrrolidin-1-yl]-4-oxoquinoline-3-carboxylic acid | LCMS (ESI) [M + H]+: 555.12. 1H NMR (300 MHz, DMSO-d6) δ 8.53 (d, J = 23.1 Hz, 2H), 8.13 (s, 1H), 7.96 (s, 1H), 7.89-7.81 (m, 1H), 7.81-7.72 (m, 1H), 6.95-6.85 (m, 1H), 6.65 (s, 1H), 5.32 (s, 1H), 4.80 (d, J = 7.9 Hz, 1H), 4.31 (d, J = 3.9 Hz, 2H), 3.99 (s, 4H), 3.55 (s, 1H), 3.26 (d, J = 8.8 Hz, 1H), 2.25 (s, 1H), 2.01-1.76 (m, 3H). | ++++ |
| 244. | 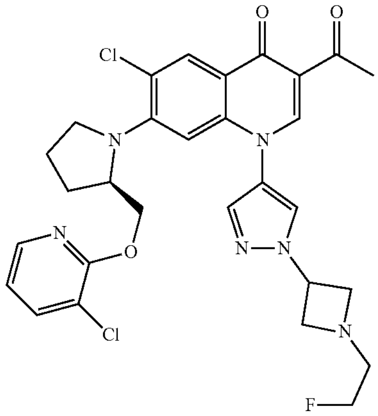 [SMILES: CC(=O)c1cn(-c2cnn(C3CN(CCF)C3)c2)c2cc(N3CCC[C@@H]3COc3ncccc3Cl)c(Cl)cc2c1=O] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 21 B to 39 B in 8 min; 254/220 nm; RT1: 7.08; RT2:; Injection Volumn: ml; Number Of Runs:; | 6-chloro-7-[(2R)-2-[[(3-chloropyridin-2-yl)oxy]methyl]pyrrolidin-1-yl]-1-[1-[1-(2-fluoroethyl)azetidin-3-yl]pyrazol-4-yl]-4-oxoquinoline-3-carboxylic acid | LCMS (ESI) [M + H]+: 601.15. 1H NMR (300 MHz, DMSO-d6) δ 15.00 (s, 1H), 8.59 (s, 1H), 8.54 (s, 1H), 8.14 (s, 1H), 7.94 (s, 1H), 7.90-7.82 (m, 1H), 7.82-7.74 (m, 1H), 6.96-6.86 (m, 1H), 6.68 (s, 1H), 5.17-5.02 (m, 1H), 4.78 (s, 1H), 4.59-4.50 (m, 1H), 4.42-4.28 (m, 3H), 3.86-3.75 (m, 2H), 3.61-3.48 (m, 3H), 3.26 (d, J = 8.1 Hz, 1H), 2.91-2.82 (m, 1H), 2.81-2.72 (m, 1H), 2.26 (t, J = 8.9 Hz, 1H), 2.11-1.77 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 245. | 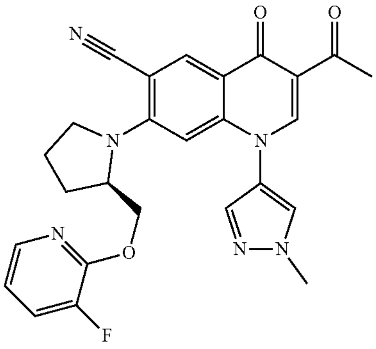 [SMILES: CC(=O)c1cn(-c2cnn(C)c2)c2cc(N3CCC[C@@H]3COc3ncccc3F)c(C#N)cc2c1=O] | Column: XSelect CSH Prep C18 OBD Column, 19*150 mm, 5 μm; Mobile Phase A: Water (0.1% FA), Mobile Phase B: ACN; Flow rate: 25 mL/min: Gradient: 37% B to 44% B in 10 min, 44% B; Wave Length: 254/220 nm; RT1(min): 10.80; Number Of Runs: 0 | rac-(R)-6-cyano-7-(2-(((3-fluoropyridin-2-yl)oxy) methyl) pyrrolidin-1-yl)-1-(1-methyl-1H-pyrazol-4-yl)-4-oxo-1,4-dihydro-quinoline-3-carboxylic acid | LCMS (ESI) $[M + H]^+$: 489.16. 1H NMR (300 MHz, DMSO-d6) δ 14.61 (s, 1H), 8.48 (d, J = 22.2 Hz, 2H), 8.26 (s, 1H), 7.92-7.75 (m, 2H), 7.71-7.58 (m, 1H), 7.07-6.95 (m, 1H), 6.46 (s, 1H), 4.74 (s, 1H), 4.54-4.26 (m, 2H), 3.87 (s, 3H), 3.78-3.59 (m, 1H), 3.50 (d, J = 7.9 Hz, 1H), 2.11 (d, J = 16.2 Hz, 2H), 2.06-1.87 (m, 2H). | ++++ |
| 246. | 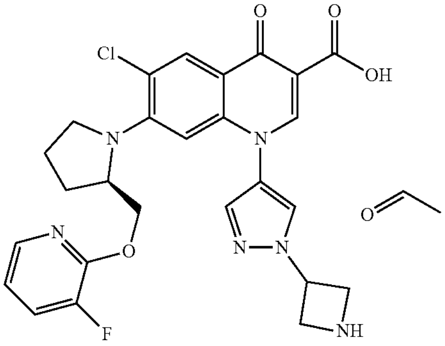 | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 17 B to 35 B in 8 min; 254 nm; RT1: 7.32; RT2:; Injection Volumn: ml; Number Of Runs:; | 1-[1-(azetidin-3-yl)pyrazol-4-yl]-6-chloro-7-[(2R)-2-[[(3-fluoropyridin-2-yl)oxy]methyl] pyrrolidin-1-yl]-4-oxoquinoline-3-carboxylic acid | LCMS (ESI) [M + H]+: 539.15. 1H NMR (300 MHz, DMSO-d6) δ 8.54 (d, J = 21.7 Hz, 2H), 8.13 (s, 1H), 7.95 (s, 1H), 7.78-7.70 (m, 1H), 7.63-7.50 (m, 1H), 6.98-6.87 (m, 1H), 6.66 (s, 1H), 5.30 (s, 1H), 4.72 (s, 1H), 4.40-4.21 (m, 2H), 4.00 (d, J = 7.2 Hz, 2H), 3.94 (d, J = 8.3 Hz, 2H), 3.53 (d, J = 9.0 Hz, 1H), 3.26 (s, 1H), 2.28-2.19 (m, 1H), 1.97 (s, 1H), 1.93-1.76 (m, 2H). | ++++ |
| 247. | 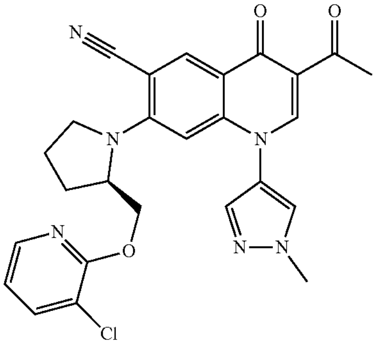 | Column: XSelect CSH Prep C18 OBD Column, 19*150 mm, 5 μm; Mobile Phase A: Water (0.1% FA), Mobile Phase B: ACN; Flow rate: 25 mL/min; Gradient: 38% B to 57% B in 8 min, 57% B; Wave Length: 254/220 nm; RT1(min): 7.35; Number Of Runs: 0 | rac-(R)-7-(2-(((3-chloropyridin-2-yl)oxy) methyl) pyrrolidin-1-yl)-6-cyano-1-(1-methyl-1H-pyrazol-4-yl)-4-oxo-1,4-dihydro-quinoline-3-carboxylic acid | 1H NMR (300 MHz, DMSO-d6) δ 14.73 (s, 1H), 8.59 (s, 1H), 8.52 (s, 1H), 8.33 (s, 1H), 8.09-8.01 (m, 1H), 7.97-7.84 (m, 2H), 7.14-7.04 (m, 1H), 6.52 (s, 1H), 4.85 (s, 1H), 4.49 (d, J = 4.9 Hz, 2H), 3.96 (s, 3H), 3.85-3.69 (m, 1H), 3.59 (d, J = 11.3 Hz, 1H), 2.21 (d, J = 15.1 Hz, 2H), 2.16-1.94 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 248. | 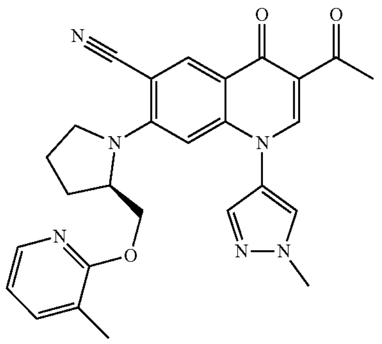 [SMILES: CC(=O)c1cn(-c2cnn(C)c2)c2cc(N3CCC[C@@H]3COc3ncccc3C)c(C#N)cc2c1=O] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 35 B to 53 B in 10 min; 254/220 nm; RT1: 9.07; RT2:; Injection Volumn: ml; Number Of Runs:; | 6-cyano-1-(1-methylpyrazol-4-yl)-7-[(2R)-2-[[(3-methylpyridin-2-yl)oxy]methyl]pyrrolidin-1-yl]-4-oxoquinoline-3-carboxylic acid | LCMS (ESI) [M + H]+: 485.19. 1H NMR (300 MHz, DMSO-d6) δ 14.65 (s, 1H), 8.50 (s, 1H), 8.45 (s, 1H), 8.24 (s, 1H), 7.91-7.78 (m, 2H), 7.52-7.44 (m, 1H), 6.89-6.82 (m, 1H), 6.46 (s, 1H), 4.75 (s, 1H), 4.37-4.24 (m, 2H), 3.86 (s, 3H), 3.70 (d, J = 6.7 Hz, 1H), 3.51 (s, 1H), 2.12 (d, J = 13.6 Hz, 2H), 2.05-1.80 (m, 5H). | ++++ |
| 249. | 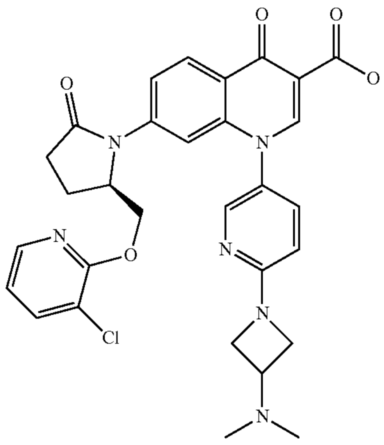 [SMILES: CN(C)C1CN(c2ccc(-n3cc(C(=O)O)c(=O)c4ccc(N5C(=O)CC[C@@H]5COc5ncccc5Cl)cc43)cn2)C1] | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 12 B to 34 B in 8 min; 254 nm; RT1: 5.73; RT2:; Injection Volumn: ml; Number Of Runs:; | (R)-7-(2-(((3-chloropyridin-2-yl)oxy)methyl)-5-oxopyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) [M + H]+: 589.19. 1H NMR (300 MHz, DMSO-d6) δ 8.71 (d, J = 2.3 Hz, 1H), 8.46 (d, J = 8.9 Hz, 1H), 8.37-8.25 (m, 1H), 8.08 (d, J = 4.8 Hz, 1H), 7.97-7.69 (m, 4H), 7.13-7.04 (m, 1H), 6.59 (t, J = 7.7 Hz, 1H), 5.00 (s, 1H), 4.51 (d, J = 3.7 Hz, 2H), 4.17 (t, J = 7.8 Hz, 2H), 3.97-3.85 (m, 2H), 3.35-3.26 (m, 1H), 2.96-2.78 (m, 1H), 2.54-2.33 (m, 2H), 2.23 (s, 6H), 2.13 (t, J = 10.5 Hz, 1H). | +++ |
| 250. | 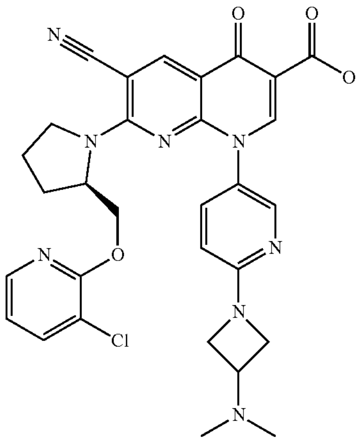 [SMILES: CN(C)C1CN(c2ccc(-n3cc(C(=O)O)c(=O)c4cc(C#N)c(N5CCC[C@@H]5COc5ncccc5Cl)nc43)cn2)C1] | Column: SunFire Prep C18 OBD Column, 19 × 150 mm 5 um 10 nm; Mobile Phase A: Water (0.1% FA), Mobile Phase B: ACN; Flow rate: 25 mL/min; Gradient: 20 B to 30 B in 15 min; 254 nm; RT1: 12.77; RT2:; Injection Volumn: ml; Number Of Runs:; | 7-[(2R)-2-[[(3-chloropyridin-2-yl)oxy]methyl]pyrrolidin-1-yl]-6-cyano-1-[6-[3-(dimethyl-amino)azetidin-1-yl]pyridin-3-yl]-4-oxo-1,8-naphthyridine-3-carboxylic acid | LCMS (ESI) [M + H]+: 601.20. 1H NMR (300 MHz, DMSO-d6) δ 8.75 (s, 1H), 8.58 (s, 1H), 8.23 (d, J = 2.5 Hz, 1H), 8.02-7.96 (m, 1H), 7.94-7.85 (m, 1H), 7.81-7.72 (m, 1H), 7.08-6.97 (m, 1H), 6.37 (s, 1H), 4.35-4.01 (m, 8H), 4.00-3.81 (s, 1H), 2.82 (s, 6H), 2.23-1.84 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 251. | 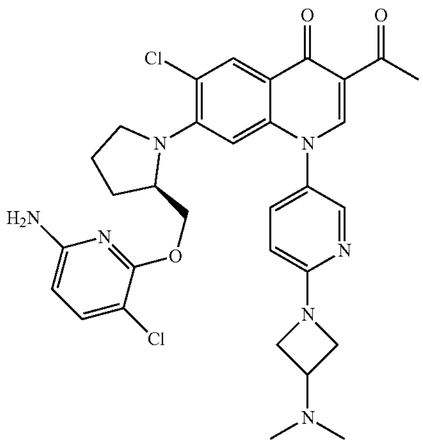 [SMILES: CC(=O)c1cn(-c2ccc(N3CC(N(C)C)C3)nc2)c2cc(N3CCC[C@@H]3COc3nc(N)ccc3Cl)c(Cl)cc2c1=O] | reverse phase flash chromatography | rac-(R)-7-(2-(((6-amino-3-chloropyridin-2-yl)oxy) methyl) pyrrolidin-1-yl)-6-chloro-1-(6-(3-(dimethyl-amino) azetidin-1-yl)pyridin-3-yl)-4-oxo-1,4-dihydro-quinoline-3-carboxylic acid | 1H NMR (300 MHz, DMSO-d6) δ 8.70-8.41 (m, 1H), 8.36-8.01 (m, 2H), 7.88-7.46 (m, 1H), 7.38-7.15 (m, 1H), 6.65-6.12 (m, 2H), 6.09-5.78 (m, 2H), 4.78-4.18 (m, 2H), 4.15-3.95 (m, 3H), 3.79 (d, J = 12.1 Hz, 2H), 3.61 (s, 1H), 3.28-2.98 (m, 2H), 2.26 (d, J = 8.8 Hz, 1H), 2.15 (s, 6H), 1.89 (d, J = 40.3 Hz, 3H). | ++++ |
| 252. | 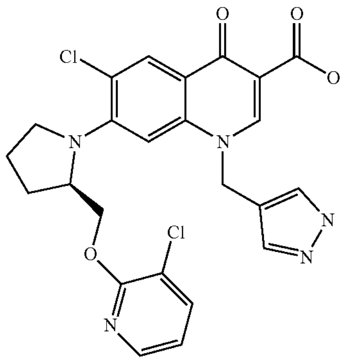 [SMILES: O=C(O)c1cn(Cc2cn[nH]c2)c2cc(N3CCC[C@@H]3COc3ncccc3Cl)c(Cl)cc2c1=O] | Column: YMC-Actus Triart C18, 20*250 MM, 5 um, 12 nm; Mobile Phase A: Water (0.1% FA), Mobile Phase B: ACN; Flow rate: 25 mL/min; Gradient: 40 B to 85 B in 8 min; 254 nm; RT1: 7.32; RT2:; Injection Volumn: ml; Number Of Runs:; | 6-chloro-7-[(2R)-2-[[(3-chloropyridin-2-yl)oxy]methyl] pyrrolidin-1-yl]-1-[(1-methyl-pyrazol-4-yl)methyl]-4-oxoquinoline-3-carboxylic acid | LCMS (ESI) [M + H]+: 528.11. 1H NMR (300 MHz, DMSO-d6) δ 15.31 (s, 1H), 9.12 (s, 1H), 8.17 (s, 1H), 8.04-7.92 (m, 1H), 7.91-7.73 (m, 2H), 7.56 (s, 1H), 7.28 (s, 1H), 7.07-6.92 (m, 1H), 5.63 (s, 2H), 4.98 (s, 1H), 4.36 (d, J = 4.5 Hz, 2H), 4.05-3.85 (m, 1H), 3.78 (s, 3H), 3.39 (s, 1H), 2.37 (d, J = 10.9 Hz, 1H), 2.26-1.82 (m, 3H). | ++++ |
| 253. | 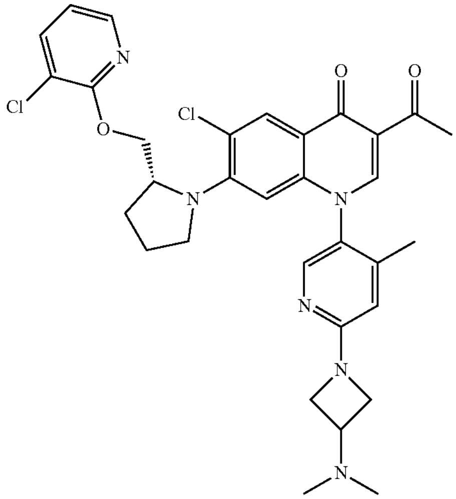 [SMILES: CC(=O)c1cn(-c2cnc(N3CC(N(C)C)C3)cc2C)c2cc(N3CCC[C@@H]3COc3ncccc3Cl)c(Cl)cc2c1=O] | Column: Gemini-NX C18 AXAI Packed, 21.2*150 mm 5 um; Mobile Phase A: Water (0.1% FA), Mobile Phase B: ACN; Flow rate: 25 mL/min; Gradient: 10 B to 10 B in 2 min; 254 nm; RT1: 8.07; RT2:; Injection Volumn: ml; Number Of Runs:; | 6-chloro-1-[4-chloro-6-[3-(dimethyl-amino) azetidin-1-yl]pyridin-3-yl]-7-[(2R)-2-[[(3-chloropyridin-2-yl)oxy] methyl] pyrrolidin-1-yl]-4-oxoquinoline-3-carboxylic acid | LCMS (ESI) [M + H]+: 643.13. 1H NMR (300 MHz, DMSO-d6) δ 8.62 (d, J = 2.1 Hz, 1H), 8.25 (d, J = 6.0 Hz, 1H), 8.18 (d, J = 9.2 Hz, 1H), 8.06-7.94 (m, 1H), 7.94-7.86 (m, 1H), 7.08-6.97 (m, 1H), 6.52-6.25 (m, 2H), 4.76 (d, J = 69.1 Hz, 1H), 4.42-4.21 (m, 2H), 4.20-4.05 (m, 2H), 3.94-3.80 (m, 2H), 3.69-3.49 (m, 1H), 3.33-3.18 (m, 2H), 2.40-2.27 (m, 1H), 2.22 (s, 6H), 2.10-1.75 (m, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 254. | 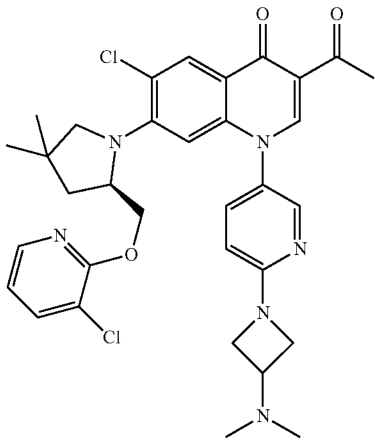 [SMILES: CC(=O)c1cn(-c2ccc(N3CC(N(C)C)C3)nc2)c2cc(N3CC(C)(C)C[C@@H]3COc3ncccc3Cl)c(Cl)cc2c1=O] | Column: SunFire Prep C18 OBD Column, 19 x 150 mm 5 um 10 nm; Mobile Phase A: Water (0.1% FA), Mobile Phase B: ACN; Flow rate: 25 mL/min; Gradient: 25 B to 45 B in 8 min; 254 nm; RT1: 6.68; RT2:; Injection Volumn: ml; Number Of Runs:; | 6-chloro-7-[(2R)-2-[[(3-chloropyridin-2-yl)oxy]methyl]-4,4-dimethyl-pyrrolidin-1-yl]-1-[6-[3-(dimethyl-amino)azetidin-1-yl]pyridin-3-yl]-4-oxoquinoline-3-carboxylic acid | LCMS (ESI) [M + H]+: 637.20. 1H NMR (300 MHz, DMSO-d6) δ 15.07 (s, 1H), 8.51 (d, J = 6.8 Hz, 1H), 8.25 (d, J = 2.6 Hz, 1H), 8.17 (s, 1H), 7.91-7.80 (m, 2H), 7.69 (t, J = 9.0 Hz, 1H), 7.00 -6.89 (m, 1H), 6.58 (d, J = 8.5 Hz, 0.5H), 6.41 (d, J = 5.8 Hz, 1H), 6.34 (d, J = 9.1 Hz, 0.5H), 4.67 (d, J = 23.1 Hz, 1H), 4.30 (s, 2H), 4.07 (t, J = 8.2 Hz, 2H), 3.91-3.74 (m, 2H), 3.43 (d, J = 11.0 Hz, 1H), 3.25 (t, J = 6.2 Hz, 1H), 2.92 (d, J = 9.3 Hz, 1H), 2.15 (s, 6H), 2.03 (d, J = 15.7 Hz, 1H), 1.82 (s, 1H), 1.13 (s, 3H), 1.01 (s, 3H). | ++++ |
| 255. | 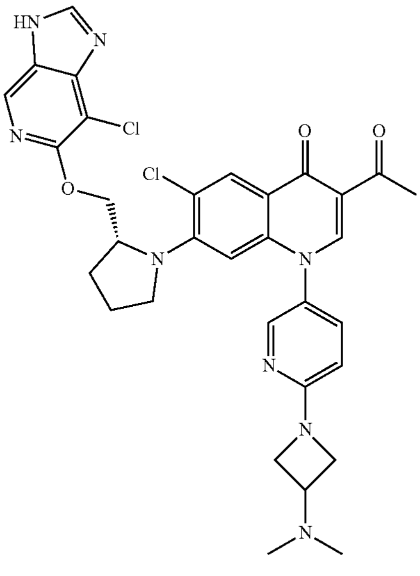 [SMILES: CC(=O)c1cn(-c2ccc(N3CC(N(C)C)C3)nc2)c2cc(N3CCC[C@@H]3COc3ncc4[nH]cnc4c3Cl)c(Cl)cc2c1=O] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 57% B in 7 min, 57% B; Wave Length: 254/220 nm; RT1(min): 6.03; Number Of Runs: 0 | 6-chloro-7-[(2R)-2-[({7-chloro-1H-imidazo[4,5-c]pyridin-6-yl}oxy)methyl]pyrrolidin-1-yl]-1-{6-[3-(dimethyl-amino)azetidin-1-yl]pyridin-3-yl}-4-oxoquinoline-3-carboxylic acid | LCMS (ESI) [M + H]+: 649.18. 1H NMR (300 MHz, DMSO-d6) δ 15.09 (s, 1H), δ 13.05 (s, 1H), 8.46 (d, J = 9.9 Hz, 1H), 8.33 (s, 1H), 8.30-8.18 (m, 2H), 8.14 (d, J = 3.7 Hz, 1H), 7.71-7.52 (m, 1H), 6.55 (d, J = 8.8 Hz, 0.5H), 6.41-6.32 (m, 1H), 6.24 (d, J = 8.8 Hz, 0.5H), 4.70 (d, J = 33.2 Hz, 1H), 4.34 (d, J = 57.3 Hz, 2H), 4.16-3.96 (m, 2H), 3.85 (s, 2H), 3.53 (d, J = 9.8 Hz, 1H), 3.24-3.11 (m, 2H), 2.26 (s, 7H), 2.03 (d, J = 21.7 Hz, 2H), 1.88-1.67 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 256. | 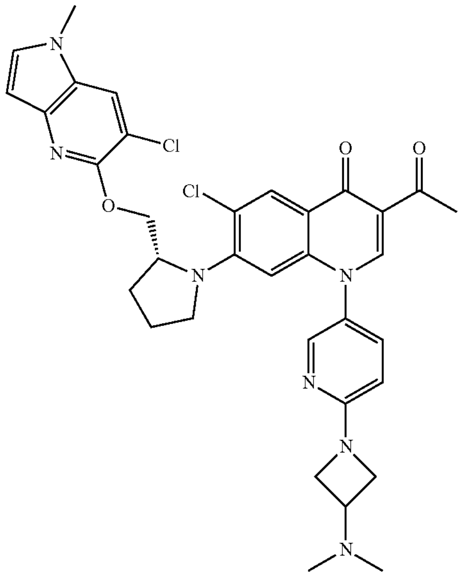 [SMILES: CC(=O)c1cn(-c2ccc(N3CC(N(C)C)C3)nc2)c2cc(N3CCC[C@@H]3COc3nc4ccn(C)c4cc3Cl)c(Cl)cc2c1=O] | Column: XSelect CSH Prep C18 OBD Column,, 5 um, 19*150 mm; Mobile Phase A: Water (0.1% FA), Mobile Phase B: ACN; Flow rate: 25 mL/min; Gradient: 17 B to 50 B in 8 min, 50 B to B in min, B to Bin min, B to B in min, B to B in min; 254 nm; RT1: 6.36; RT2:; Injection Volumn: ml; Number Of Runs:; | 6-chloro-7-[(2R)-2-[([6-chloro-1-methyl-pyrrolo[3,2-b]pyridin-5-yl]oxy)methyl]pyrrolidin-1-yl]-1-[6-[3-(dimethyl-amino)azetidin-1-yl]pyridin-3-yl]-4-oxoquinoline-3-carboxylic acid | LCMS (ESI) [M + H]+: 662.21. 1H NMR (300 MHz, Methanol-d4) δ 8.52 (s, 1H), 8.25-8.03 (m, 2H), 7.82 (s, 1H), 7.69-7.46 (m, 1H), 7.24 (s, 1H), 6.79-6.42 (m, 1H), 6.37 (d, J = 6.8 Hz, 1H), 6.17 (d, J = 3.0 Hz, 1H), 4.82-4.48 (m, 2H), 4.42-4.17 (m, 3H), 4.15-4.01 (m, 2H), 3.74 (d, J = 5.2 Hz, 4H), 3.68-3.44 (m, 1H), 3.23-3.01 (m, 1H), 2.58 (s, 6H), 2.45-2.26 (m, 1H), 2.23-2.03 (m, 2H), 2.01-1.76 (m, 1H). | ++++ |
| 257. | 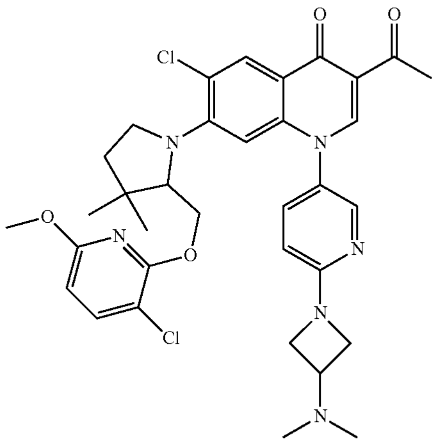 [SMILES: COc1ccc(Cl)c(OCC2N(c3cc4c(cc3Cl)c(=O)c(C(C)=O)cn4-c3ccc(N4CC(N(C)C)C4)nc3)CCC2(C)C)n1] | Column: XSelect CSH Prep C18 OBD Column,, 19*250 mm, 5 um; Mobile Phase A: Water (10 MMOL/L NH4HCO3), Mobile Phase B: ACN; Flow rate: 25 mL/min; Gradient: 47 B to 77 B in 7 min, 77 B to B in min, B to B in min, B to B in min, B to B in min; 254/220 nm; RT1: 6.43; RT2:; Injection Volumn: ml; Number Of Runs:; | 6-chloro-7-(2-{[(3-chloro-6-methoxy-pyridin-2-yl)oxy]methyl}-3,3-dimethyl-pyrrolidin-1-yl)-1-{6-[3-(dimethyl-amino)azetidin-1 yl]pyridin-3-yl}-4-oxoquinoline-3-carboxylic acid | LCMS (ESI) [M + H]$^+$: 667.21. 1H NMR (300 MHz, DMSO-d6) δ 15.12 (s, 1H), 8.52 (d, J = 7.4 Hz, 1H), 8.30-8.11 (m, 2H), 7.74-7.56 (m, 2H), 6.53 (d, J = 8.8 Hz, 0.5 H), 6.38 (dd, J = 12.5, 8.4 Hz, 1H), 6.29 (d, J = 4.7 Hz, 1H), 6.07 (d, J = 8.8 Hz, 0.5 H), 4.53-4.20 (m, 3H), 4.02 (t, J = 8.1 Hz, 2H), 3.86-3.57 (m, 6H), 3.23 (s, 2H), 2.15 (s, 6H), 1.90 (d, J = 16.1 Hz, 1H), 1.80-1.66 (m, 1H), 1.21 (d, J = 7.4 Hz, 3H), 1.13 (s, 3H). | ++++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 258. | 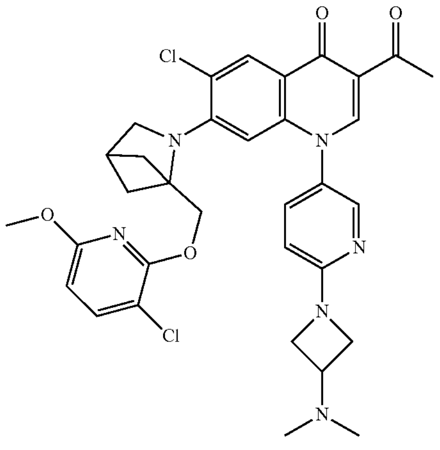 [SMILES: COc1ccc(Cl)c(OCC23CC(CN2c2cc4c(cc2Cl)c(=O)c(C(C)=O)cn4-c2ccc(N4CC(N(C)C)C4)nc2)C3)n1] | reverse phase flash chromatography | 6-chloro-7-(1-(((3-chloro-6-methoxy-pyridin-2-yl)oxy) methyl)-2-azabicyclo [2.1.1]hexan-2-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 651.18. 1H NMR (300 MHz, DMSO-d6) δ 8.64 (d, J = 7.2 Hz, 1H), 8.31 (d, J = 10.4 Hz, 2H), 7.78 (d, J = 8.4 Hz, 2H), 6.50-6.43 (m, 2H), 6.33 (t, J = 8.4 Hz, 1H), 4.53-4.34 (m, 2H), 3.94 (t, J = 7.5 Hz, 2H), 3.74 (d, J = 4.3 Hz, 5H), 3.45 (s, 2H), 3.19 (s, 1H), 2.84 (s, 1H), 2.13 (s, 6H), 1.97 (s, 2H), 1.60 (s, 2H), 1.11 (s, 1H). | +++ |
| 259. | 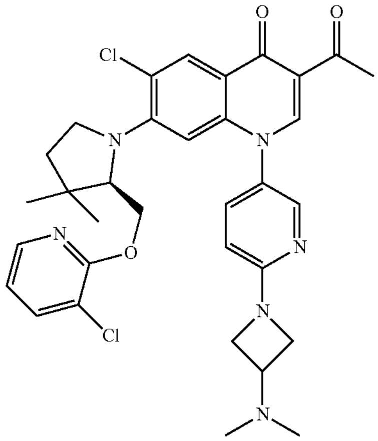 [SMILES: CC(=O)c1cn(-c2ccc(N3CC(N(C)C)C3)nc2)c2cc(N3CCC(C)(C)[C@@H]3COc3ncccc3Cl)c(Cl)cc2c1=O] | Column: XBridge Prep C18 OBD Column, 19*150 mm, 5 µm; Mobile Phase A: Water (10 MMOL/L NH4HCO3), Mobile Phase B: ACN; Flow rate: 25 mL/min; Gradient: 10% B to 10% B in 2 min, 10% B to 36% B in 2.5 min, 36% B to 65% B in 10.5 min, 65% B; Wave Length: 220 nm; RT1(min): 11.2; Number Of Runs: 0 | 6-chloro-7-(2-(((3-chloropyridin-2-yl)oxy) methyl)-3,3-dimethyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 637.20. 1H NMR (300 MHz, DMSO-d6) δ 8.46 (s, 1H), 8.32-7.70 (m, 4H), 7.68-7.15 (m, 1H), 6.99 (s, 1H), 6.66-5.83 (m, 2H), 4.40 (d, J = 10.5 Hz, 1H), 4.28-3.90 (m, 3H), 3.77 (s, 3H), 3.29-2.97 (m, 3H), 2.14 (s, 6H), 1.76 (d, J = 36.7 Hz, 2H), 1.25-1.15 (m, 3H), 1.10 (s, 3H), 0.95 (s, 1H), 0.90-0.72 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 260. | 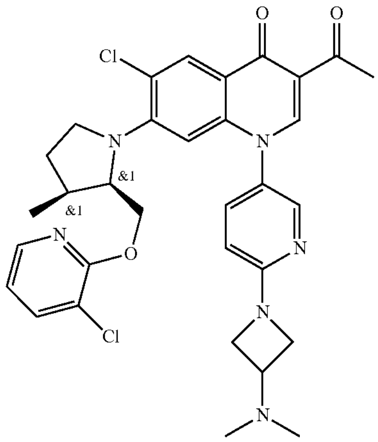 [SMILES: CC(=O)c1cn(-c2ccc(N3CC(N(C)C)C3)nc2)c2cc(N3CC[C@H](C)[C@@H]3COc3ncccc3Cl)c(Cl)cc2c1=O] | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 48% B to 62% B in 8 min, 62% B; Wave Length: 254 nm; RT1(min): 7.83; Number Of Runs: 0 | rac-6-chloro-7-((2R,3S)-2-(((3-chloropyridin-2-yl)oxy) methyl)-3-methyl-pyrrolidin-1-yl)-1-(6-(3-(dimethyl-amino) azetidin-1-yl)pyridin-3-yl)-4-oxo-1,4-dihydro-quinoline-3-carboxylic acic | LCMS (ESI) [M + H]+: 623.2. $^{1}$H NMR (300 MHz, DMSO-d6) δ 8.43 (s, 2H), 8.11 (s, 1H), 8.06-7.91 (m, 4H), 7.79 (s, 2H), 7.55 (s, 2H), 6.98 (s, 2H), 6.52 (s, 1H), 6.31 (d, J = 9.0 Hz, 2H), 6.15 (s, 1H), 4.67 (s, 1H), 4.54 (s, 1H), 4.37 (s, 2H), 4.17 (s, 3H), 4.07-3.96 (m, 4H), 3.78 (s, 5H), 3.23 (s, 1H), 3.08 (s, 2H), 2.15 (s, 12H), 2.04 (s, 2H), 1.73 (s, 2H), 1.24 (s, 0H), 1.07 (d, J = 6.6 Hz, 6H). | ++++ |
| 261. | 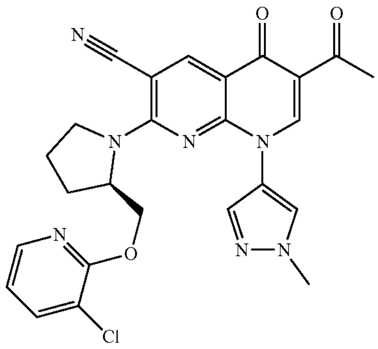 [SMILES: CC(=O)c1cn(-c2cnn(C)c2)c2nc(N3CCC[C@@H]3COc3ncccc3Cl)c(C#N)cc2c1=O] | Column: Gemini-NX C18 AXAI Packed, 21.2*150 mm 5 um; Mobile Phase A: Water (0.1% FA), Mobile Phase B: ACN; Flow rate: 25 mL/min; Gradient: 41% B to 67% B in 8 min, 67% B; Wave Length: 254 nm; RT1(min): 6.7; Number Of Runs: 0 | rac-(R)-7-(2-(((3-chloropyridin-2-yl)oxy) methyl) pyrrolidin-1-yl)-6-cyano-1-(1-methyl-1H-pyrazol-4-yl)-4-oxo-1,4-dihydro-1,8-naphthyridine-3-carboxylic acid | LCMS (ESI) [M + H]+: 505.9. $^{1}$H NMR (300 MHz, DMSO-d6) δ 14.54 (s, 1H), 8.77 (s, 1H), 8.65 (s, 1H), 8.16 (s, 1H), 8.03 (dd, J = 4.9, 1.7 Hz, 1H), 7.88 (dd, J = 7.7, 1.6 Hz, 1H), 7.77 (s, 1H), 7.01 (dd, J = 7.7, 4.9 Hz, 1H), 4.59 (s, 1H), 4.32 (s, 2H), 3.92 (s, 3H), 3.80 (s, 3H), 2.20 (dd, J = 15.5, 8.2 Hz, 1H), 2.04 (s, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 262. | 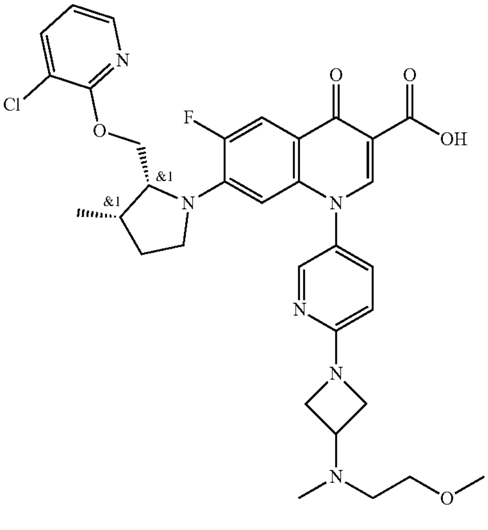 [SMILES: COCCN(C)C1CN(c2ccc(-n3cc(C(=O)O)c(=O)c4cc(F)c(N5CC[C@H](C)[C@@H]5COc5ncccc5Cl)cc43)cn2)C1] | Column: Gemini-NX C18 AXAI Packed, 21.2*150 mm 5 um; Mobile Phase A: Water (10 MMOL/L NH4HCO3), Mobile Phase B: ACN; Flow rate: 25 mL/min; Gradient: 10% B to 10% B in 2 min, 10% B to 41% B in 2.5 min, 41% B to 68% B in 14 min, 68% B; Wave Length: 254 nm; RT1(min): 13.47; Number Of Runs: 0 | rac-7-((2R,3S)-2-(((3-chloropyridin-2-yl)oxy) methyl)-3-methyl-pyrrolidin-1-yl)-6-fluoro-1-(6-(3-((2-methoxy-ethyl)(methyl) amino) azetidin-1-yl)pyridin-3-yl)-4-oxo-1,4-dihydro-quinoline-3-carboxylic acid | LCMS (ESI) [M + H]+: 651.1. $^1$H NMR (300 MHz, DMSO-d6) δ 8.39 (s, 1H), 8.03 (s, 0H), 7.86 (s, 2H), 7.74 (d, J = 7.7 Hz, 1H), 6.93 (s, 1H), 6.52 (s, 1H), 6.27 (s, 1H), 5.91 (s, 1H), 4.33 (s, 2H), 4.01 (s, 4H), 3.77 (s, 2H), 3.42 (t, J = 5.7 Hz, 2H), 3.22 (s, 3H), 3.08 (s, 7H), 2.15 (s, 3H), 1.99 (s, 1H), 1.79 (s, 1H), 1.03 (d, J = 6.6 Hz, 3H). | ++++ |
| 263. | 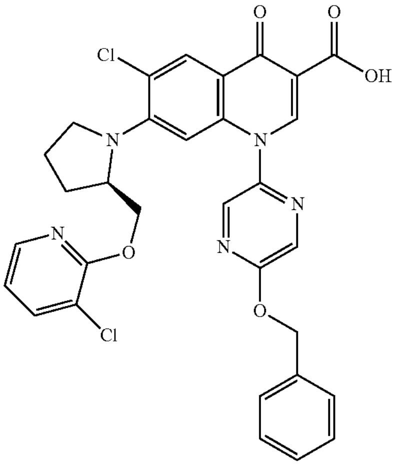 [SMILES: O=C(O)c1cn(-c2cnc(OCc3ccccc3)cn2)c2cc(N3CCC[C@@H]3COc3ncccc3Cl)c(Cl)cc2c1=O] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 60% B to 75% B in 8 min, 75% B; Wave Length: 254 nm; RT1(min): 9.77; Number Of Runs: 0 | rac-(R)-1-(5-(benzyloxy) pyrazin-2-yl)-6-chloro-7-(2-(((3-chloropyridin-2-yl)oxy) methyl) pyrrolidin-1-yl)-4-oxo-1,4-dihydro-quinoline-3-carboxylic acid | LCMS (ESI) [M + H]+: 618.0. $^1$H NMR (300 MHz, DMSO-d6) δ 14.93 (s, 1H), 8.87 (s, 1H), 8.67 (d, J = 1.3 Hz, 1H), 8.40 (d, J = 1.3 Hz, 1H), 8.17 (s, 1H), 7.93-7.85 (m, 1H), 7.83-7.74 (m, 1H), 7.58-7.50 (m, 2H), 7.50-7.37 (m, 3H), 6.98-6.88 (m, 1H), 6.54 (s, 1H), 5.51 (s, 2H), 4.72 (s, 1H), 4.29 (d, J = 4.2 Hz, 2H), 3.64-3.55 (m, 1H), 3.25-3.19 (m, 1H), 2.26-2.20 (m, 1H), 2.00-1.94 (m, 2H), 1.84-1.78 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 264. | 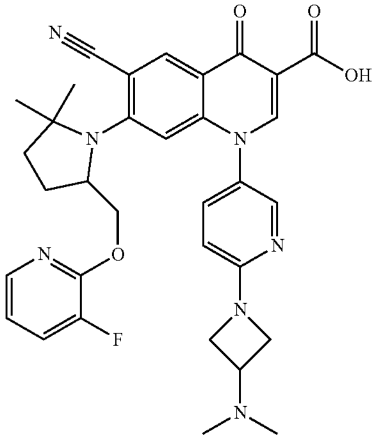 [SMILES: CN(C)C1CN(c2ccc(-n3cc(C(=O)O)c(=O)c4cc(C#N)c(N5C(COc6ncccc6F)CCC5(C)C)cc43)cn2)C1] | Coulmn: Gemini-NX C18 AXAI Packed, 21.2*150 mm 5 um; Mobile Phase A: Water (0.1% FA), Mobile Phase B: ACN, Flow rate: 25 mL/min; Gradient: 5% B to 5% B in 2 min, 5% B to 19% B in 2.5 min, 19% B to 40% B in 10.5 min, 40% B; Wave Length: 254 nm; RT1(min): 7.92; Number Of Runs: 0 | 6-cyano-1-(6-(3-(dimethyl-amino) azetidin-1-yl)pyridin-3-yl)-7-(5-(((3-fluoropyridin-2-yl)oxy) methyl)-2,2-dimethyl-pyrrolidin-1-yl)-4-oxo-1,4-dihydro-quinoline-3-carboxylic acid | LCMS (ESI) [M + H]+: 612.20. $^1$H NMR (300 MHz, Methanol-d4) δ 8.67 (s, 1H), 8.56 (s, 1H), 8.26-8.07 (m, 1H), 7.72-7.55 (m, 2H), 7.39-7.33 (m, 1H), 6.92-6.78 (m, 1H), 6.70-6.54 (m, 2H), 5.18-5.12 (m, 1H), 4.72-4.66 (m, 1H), 4.40-4.30 (m, 1H), 4.30-4.20 (m, 3H), 4.05-3.94 (m, 2H), 3.46-3.36 (m, 1H), 2.32 (s, 6H), 2.27-2.20 (m, 1H), 2.18-2.04 (m, 1H), 2.02-1.90 (m, 2H), 1.25 (s, 3H), 1.21 (d, J = 6.3 Hz, 3H). | +++ |
| 265. | 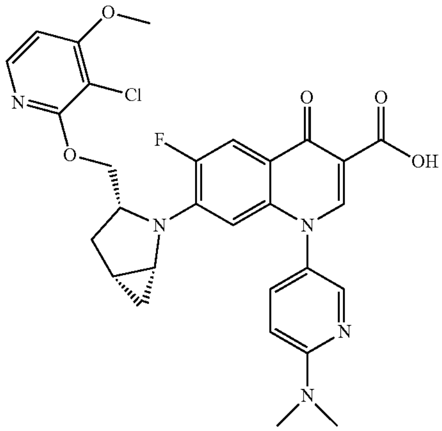 | Column: XSelect CSH Prep C18 OBD Column, 19*150 mm, 5 μm; Mobile Phase A: Water (0.1% FA), Mobile Phase B: ACN; Flow rate: 25 mL/min; Gradient: 45% B to 73% B in 7 min, 73% B; Wave Length: 254/220 nm; RT1 (min): 6.83; Number Of Runs: 0 | 7-((1R,3R,5R)-3-(((3-chloro-4-methoxy-pyridin-2-yl)oxy) methyl)-2-azabicyclo [3.1.0]hexan-2-yl)-1-(6-(dimethyl-amino)pyridin-3-yl)-6-fluoro-4-oxo-1,4-dihydro-quinoline-3-carboxylic acid | LCMS (ESI): [M + H]$^+$: 659.0 $^1$H NMR (300 MHz, DMSO-d6) δ 15.36 (d, J = 1.8 Hz, 1H), 8.50 (s, 1H), 8.30 (t, J = 2.5 Hz, 1H), 7.93-7.81 (m, 2H), 7.79-7.69 (m, 1H), 6.90-6.48 (m, 3H), 4.77-4.71 (m, 1H), 4.27-4.17 (m, 1H), 4.10-4.04 (m, 1H), 3.89 (s, 3H), 3.22-3.04 (m, 7H), 2.68-2.56 (m, 1H), 2.09-1.99 (m, 1H), 1.64-1.56 (m, 1H), 0.94-0.88 (m, 1H), 0.75-0.67 (m, 1H). | ++++ |
| 266. | 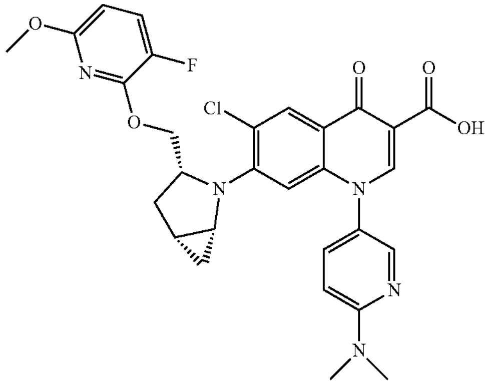 [SMILES: COc1ccc(F)c(OC[C@H]2C[C@H]3C[C@H]3N2c2cc3c(cc2Cl)c(=O)c(C(=O)O)cn3-c2ccc(N(C)C)nc2)n1] | reverse phase flash chromatography | 6-chloro-1-(6-(dimethyl-amino)pyridin-3-yl)-7-((1R,3R,5R)-3-(((3-fluoro-6-methoxy-pyridin-2-yl)oxy) methyl)-2-azabicyclo [3.1.0]hexan-2-yl)-4-oxo-1,4-dihydro-quinoline-3-carboxylic acid | LCMS (ESI): [M + H]$^+$: 580.25 $^1$H NMR (400 MHz, DMSO-d6) δ 15.10 (s, 1H), 8.54 (d, J = 3.3 Hz, 1H), 8.29-8.19 (m, 1H), 8.13 (s, 1H), 7.76-7.61 (m, 1H), 7.56-7.42 (m, 1H), 6.90-6.62 (m, 2H), 6.22-6.09 (m, 1H), 5.01-4.91 (m, 1H), 4.30-4.21 (m, 1H), 4.18-4.07 (m, 1H), 3.61 (d, J = 5.7 Hz, 3H), 3.12 (s, 6H), 3.07-2.96 (m, 1H), 2.73-2.60 (m, 1H), 2.09-1.98 (m, 1H), 1.67-1.57 (m, 1H), 0.93-0.83 (m, 1H), 0.69-0.56 (m, 1H). | ++++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 267. | 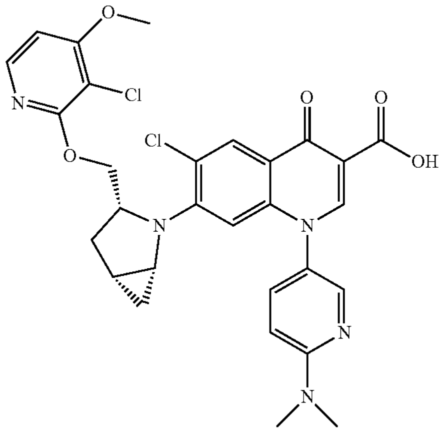 [SMILES: COc1ccnc(OC[C@H]2C[C@H]3C[C@H]3N2c2cc3c(cc2Cl)c(=O)c(C(=O)O)cn3-c2ccc(N(C)C)nc2)c1Cl] | Column: XSelect CSH Prep C18 OBD Column, 19*150 mm, 5 µm; Mobile Phase A: Water (0.1% FA), Mobile Phase B: ACN; Flow rate: 25 mL/min; Gradient: 48% B to 78% B in 7 min, 78% B; Wave Length: 254/220 nm; RT1(min): 6.88; Number Of Runs: 0 | 6-chloro-7-((1R,3R,5R)-3-(((3-chloro-4-methoxy-pyridin-2-yl)oxy) methyl)-2-azabicyclo [3.1.0]hexan-2-yl)-1-(6-(dimethyl-amino)pyridin-3-yl)-4-oxo-1,4-dihydro-quinoline-3-carboxylic acid | LCMS (ESI): $[M + H]^+$: 596.25 $^1H$ NMR (300 MHz, DMSO-d6) δ 15.10 (s, 1H), 8.55 (d, J = 3.4 Hz, 1H), 8.29 (d, J = 2.7 Hz, 1H), 8.15 (d, J = 0.9 Hz, 1H), 7.83-7.66 (m, 2H), 6.98-6.64 (m, 3H), 5.02-4.96 (m, 1H), 4.27-4.12 (m, 1H), 4.03-3.97 (m, 1H), 3.86 (s, 3H), 3.11 (s, 6H), 3.05-2.97 (m, 1H), 2.67-2.61 (m, 1H), 2.08-1.96 (m, 1H), 1.65-1.59 (m, 1H), 1.02-0.92 (m, 1H), 0.67-0.58 (m, 1H). | ++++ |
| 268. | 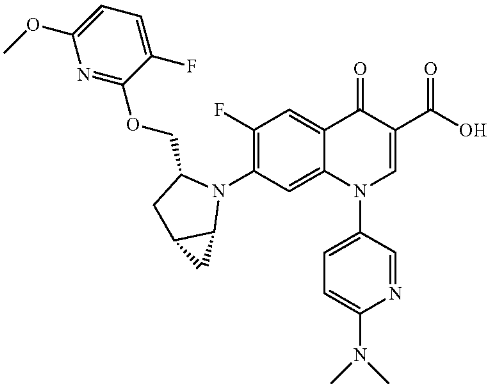 | Column: XSelect CSH Prep C18 OBD Column, 19*150 mm, 5 µm; Mobile Phase A: Water (0.1% FA), Mobile Phase B: ACN; Flow rate: 25 mL/min; Gradient: 45% B to 74% B in 7 min, 74% B; Wave Length: 254/220 nm; RT1(min): 7.23; Number Of Runs: 0 | 1-(6-(dimethyl-amino)pyridin-3-yl)-6-fluoro-7-((1R,3R,5R)-3-(((3-fluoro-6-methoxy-pyridin-2-yl)oxy) methyl)-2-azabicyclo [3.1.0]hexan-2-yl)-4-oxo-1,4-dihydro-quinoline-3-carboxylic acid | LCMS (ESI): $[M + H]^+$: 564.30 $^1H$ NMR (400 MHz, DMSO-d6) δ 15.35 (s, 1H), 8.50 (d, J = 3.9 Hz, 1H), 8.28 (d, J = 2.7 Hz, 1H), 7.86 (d, J = 13.4 Hz, 1H), 7.79-7.68 (m, 1H), 7.59-7.50 (m, 1H), 6.89-6.63 (m, 1H), 6.57-6.47 (m, 1H), 6.31-6.23 (m, 1H), 4.76-4.72 (m, 1H), 4.28-4.13 (m, 2H), 3.69 (d, J = 2.4 Hz, 3H), 3.21-3.04 (m, 7H), 2.74-2.57 (m, 1H), 2.07-1.98 (m, 1H), 1.64-1.59 (m, 1H), 0.88-0.82 (m, 1H), 0.76-0.68 (m, 1H). | ++++ |
| 269. | 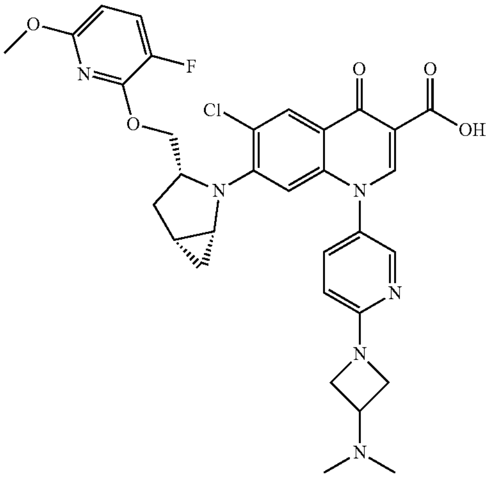 | reverse phase flash chromatography | 6-chloro-7-((1R,3R,5R)-3-(((3-chloro-6-methoxy-pyridin-2-yl)oxy) methyl)-2-azabicyclo [3.1.0]hexan-2-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 651.20 $^1H$ NMR (400 MHz, DMSO-d6) δ 15.04 (s, 1H), 8.56 (d, J = 6.6 Hz, 1H), 8.29-8.21 (m, 1H), 8.14 (s, 1H), 7.79-7.61 (m, 2H), 6.93-6.78 (m, 1H), 6.60-6.42 (m, 1H), 6.32-6.25 (m, 1H), 5.00-4.96 (m, 1H), 4.28-4.14 (m, 2H), 4.12-4.01 (m, 2H), 3.85-3.79 (m, 2H), 3.65 (d, J = 3.0 Hz, 3H), 3.27-3.19 (m, 1H), 3.05-2.96 (m, 1H), 2.67-2.60 (m, 1H), 2.14 (s, 6H), 2.10-1.99 (m, 1H), 1.69-1.57 (m, 1H), 1.05-1.00 (m, 1H), 0.69-0.59 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 270. | 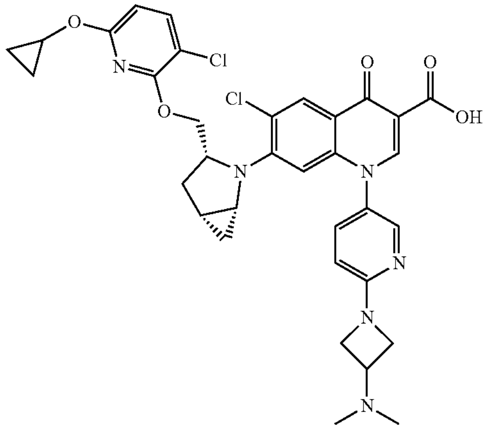 | Column: XSelect CSH Prep C18 OBD Column, 19*150 mm, 5 μm; Mobile Phase A: Water (0.1% FA), Mobile Phase B: ACN; Flow rate: 25 mL/min; Gradient: 1% B to 1% B in 2 min, 1% B to 26% B in 2.5 min, 26% B to 47% B in 10 min, 47% B; Wave Length: 254/220 nm; RT1(min): 9.02; Number Of Runs: 0 | 6-chloro-7-((1R,3R,5R)-3-(((3-chloro-6-cycloprop-oxypyridin-2-yl)oxy) methyl)-2-azabicyclo [3.1.0]hexan-2-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 677.10 $^1H$ NMR (400 MHz, DMSO-d6) δ 15.05 (s, 1H), 8.56 (d, J = 5.9 Hz, 1H), 8.30-8.22 (m, 1H), 8.15 (s, 1H), 7.78-7.65 (m, 2H), 6.87 (d, J = 16.4 Hz, 1H), 6.61-6.39 (m, 2H), 5.00-4.95 (m, 1H), 4.21-4.03 (m, 4H), 3.91-3.77 (m, 3H), 3.25-3.21 (m, 1H), 3.04-2.98 (m, 1H), 2.67-2.59 (m, 1H), 2.14 (s, 6H), 2.07-2.02 (m, 1H), 1.67-1.59 (m, 1H), 1.02-0.96 (m, 2H), 0.71-0.67 (m, 2H), 0.65-0.53 (m, 2H). | ++++ |
| 271. | 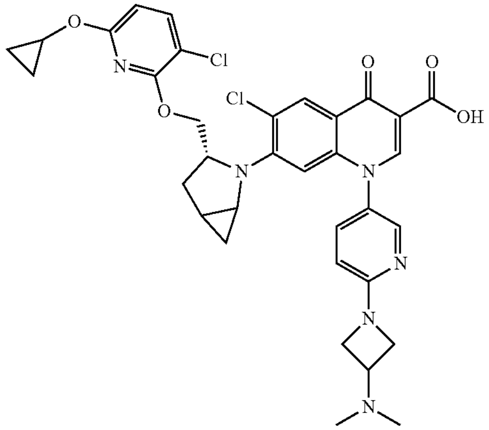 [SMILES: CN(C)C1CN(c2ccc(-n3cc(C(=O)O)c(=O)c4cc(Cl)c(N5C6CC6C[C@@H]5COc5nc(OC6CC6)ccc5Cl)cc43)cn2)C1] | Column: XBridge Shield RP18 OBD Column, 19*150 mm, 5 μm; Mobile Phase A: Water (10 MMOL/L NH4HCO3), Mobile Phase B: ACN; Flow rate: 25 mL/min; Gradient: 40% B to 78% B in 8 min, 78% B; Wave Length: 254/220 nm; RT1(min): 6.62; Number Of Runs: 0 | 6-chloro-7-((3R)-3-(((3-chloro-6-cycloprop-oxypyridin-2-yl)oxy) methyl)-2-azabicyclo [3.1.0]hexan-2-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 677.15 $^1H$ NMR (300 MHz, DMSO-d6) δ 15.04 (s, 1H), 8.61-8.46 (m, 1H), 8.36-8.08 (m, 2H), 7.93-7.41 (m, 2H), 6.93-6.12 (m, 3H), 4.38-4.32 (m, 2H), 4.16-4.02 (m, 4H), 3.89-3.73 (m, 2H), 3.67-3.51 (m, 1H), 3.25-3.12 (m, 1H), 2.19-2.11 (m, 7H), 1.74-1.68 (m, 1H), 1.09-0.73 (m, 1H), 0.71-0.46 (m, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 272. | 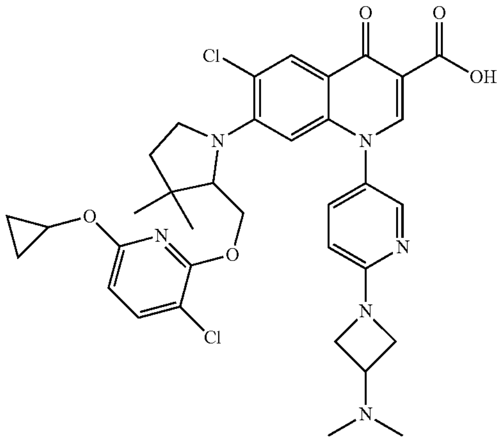 [SMILES: CN(C)C1CN(c2ccc(-n3cc(C(=O)O)c(=O)c4cc(Cl)c(N5CCC(C)(C)C5COc5nc(OC6CC6)ccc5Cl)cc43)cn2)C1] | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 60% B to 90% B in 7 min, 90% B; Wave Length: 254/220 nm; RT1(min): 6.92; Number Of Runs: 0 | 6-chloro-7-(2-(((3-chloro-6-cycloprop-oxypyridin-2-yl)oxy)methyl)-3,3-dimethyl-pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI): $[M + H]^+$: 693.20 $^1H$ NMR (300 MHz, DMSO-d6) δ 15.13 (s, 1H), 8.55-8.47 (m, 1H), 8.26-8.16 (m, 1H), 8.16-8.10 (m, 1H), 7.73-7.57 (m, 2H), 6.58-6.06 (m, 3H), 4.53-4.17 (m, 3H), 4.11-3.89 (m, 3H), 3.85-3.75 (m, 2H), 3.75-3.61 (m, 1H), 3.29-3.13 (m, 2H), 2.16 (s, 6H), 1.88 (s, 1H), 1.80-1.65 (m, 1H), 1.27-1.05 (m, 6H), 0.75-0.58 (m, 3H), 0.57-0.48 (m, 1H). | ++++ |
| 273. | 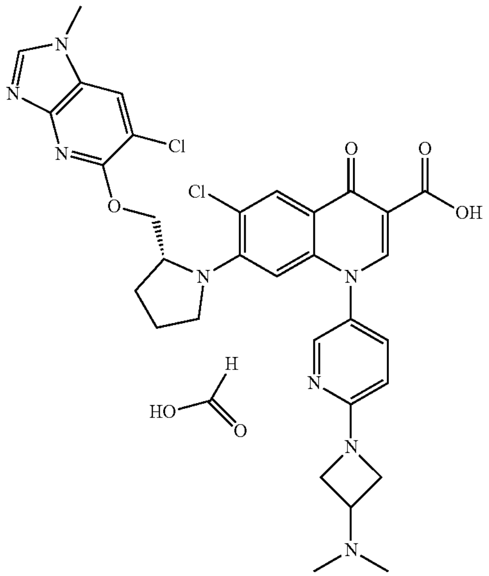 | reverse phase flash chromatography | (R)-6-chloro-7-(2-(((6-chloro-1-methyl-1H-imidazo[4,5-b]pyridin-5-yl)oxy)methyl)pyrrolidin-1-yl)-1-(6-(3-(dimethyl-amino)azetidin-1-yl)pyridin-3-yl)-4-oxo-1,4-dihydro-quinoline-3-carboxylic acid formic acid | LCMS (ESI): $[M + H]^+$: 663.20 $^1H$ NMR (300 MHz, DMSO-d6) δ 15.09 (s, 1H), 8.53-8.43 (m, 1H), 8.29-8.14 (m, 3H), 8.11-8.04 (m, 1H), 7.76-7.63 (m, 1H), 6.60-6.25 (m, 2H), 4.85-4.66 (m, 1H), 4.46-4.32 (m, 1H), 4.30-4.19 (m, 1H), 4.17-4.02 (m, 2H), 3.90-3.83 (m, 2H), 3.78 (d, J = 2.3 Hz, 3H), 3.63-3.50 (m, 2H), 3.25-3.13 (m, 1H), 2.34-2.23 (m, 1H), 2.21 (s, 6H), 2.04-1.76 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 274. | 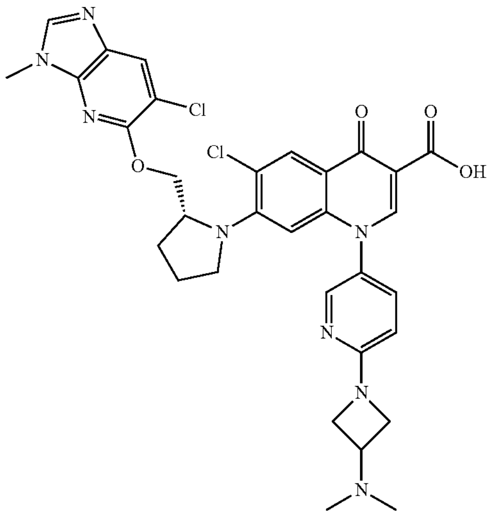 [SMILES: CN(C)C1CN(c2ccc(-n3cc(C(=O)O)c(=O)c4cc(Cl)c(N5CCC[C@@H]5COc5nc6c(cc5Cl)ncn6C)cc43)cn2)C1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 15% B to 43% B in 7 min, 43% B; Wave Length: 254/220 nm; RT1(min): 6.37; Number Of Runs: 0 | rac-(R)-6-chloro-7-(2-(((6-chloro-3-methyl-3H-imidazo [4,5-b] pyridin-5-yl)oxy) methyl) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 663.20 1H NMR (300 MHz, DMSO-d6) δ 15.03 (s, 1H), 8.50-8.40 (m, 1H), 8.20-8.08 (m, 4H), 7.70-7.52 (m, 1H), 6.64-6.16 (m, 2H), 4.77-4.61 (m, 2H), 4.37-4.24 (m, 1H), 4.13-3.98 (m, 2H), 3.87-3.71 (m, 2H), 3.57 (s, 3H), 3.35-3.04 (m, 3H), 2.32-2.26 (m, 1H), 2.17 (s, 6H), 2.08-2.02 (m, 2H), 1.83-1.77 (m, 1H). | ++++ |
| 275. | 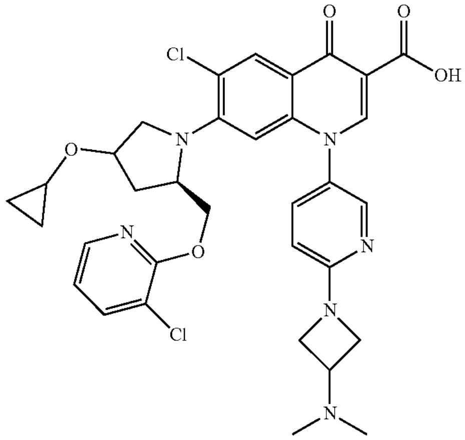 [SMILES: CN(C)C1CN(c2ccc(-n3cc(C(=O)O)c(=O)c4cc(Cl)c(N5CC(OC6CC6)C[C@@H]5COc5ncccc5Cl)cc43)cn2)C1] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 15% B to 43% B in 7 min, 43% B; Wave Length: 254/220 nm; RT1(min): 6.97; Number Of Runs: 0 | 6-chloro-7-((2R)-2-(((3-chloropyridin-2-yl)oxy) methyl)-4-cycloprop-oxypyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 665.15 $^1$H NMR (300 MHz, DMSO-d6) δ 15.04 (s, 1H), 8.64-8.47 (m, 1H), 8.33-8.21 (m, 1H), 8.16 (s, 1H), 7.97-7.88 (m, 1H), 7.85-7.77 (m, 1H), 7.73-7.62 (m, 1H), 7.02-6.92 (m, 1H), 6.63-6.26 (m, 2H), 4.85-4.62 (m, 1H), 4.48-4.34 (m, 1H), 4.31-4.17 (m, 2H), 4.12-3.99 (m, 2H), 3.89-3.79 (m, 2H), 3.55-3.43 (m, 2H), 3.33-3.16 (m, 2H), 2.57-2.52 (m, 1H), 2.15 (s, 6H), 2.00-1.87 (m, 1H), 0.58-0.40 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 276. | 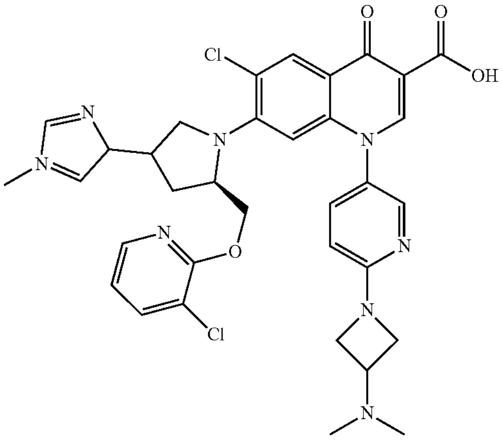 | Column: Gemini-NX C18 AXAI Packed, 21.2*150 mm 5 um; Mobile Phase A: Water (10 MMOL/L NH4HCO3), Mobile Phase B: ACN; Flow rate: 25 mL/min; Gradient: 10% B to 10% B in 2 min, 10% B to 23% B in 2.5 min, 23% B to 42% B in 10.5 min, 42% B; Wave Length: 220 nm; RT1(min): 8.78; Number Of Runs: 0 | 6-chloro-7-((2R)-2-(((3-chloropyridin-2-yl)oxy) methyl)-4-(1-methyl-1H-imidazol-4-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 689.15 $^1$H NMR (300 MHz, DMSO-d6) δ 8.61-8.37 (m, 1H), 8.32-8.00 (m, 2H), 7.96-7.55 (m, 3H), 7.49 (s, 1H), 7.08-6.84 (m, 2H), 6.65-6.16 (m, 2H), 4.80-4.54 (m, 1H), 4.49-4.20 (m, 2H), 4.14-3.97 (m, 2H), 3.92-3.74 (m, 2H), 3.68-3.52 (m, 4H), 3.47-3.39 (m, 1H), 3.28-3.13 (m, 2H), 2.59-2.54 (m, 1H), 2.48-2.38 (m, 1H), 2.14 (s, 6H). | ++++ |
| 277. | 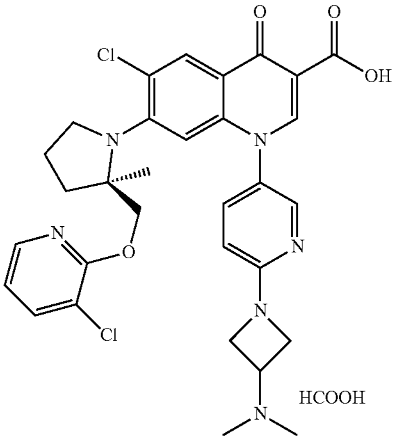 [SMILES: CN(C)C1CN(c2ccc(-n3cc(C(=O)O)c(=O)c4cc(Cl)c(N5CCC[C@]5(C)COc5ncccc5Cl)cc43)cn2)C1 ; "HCOOH"] HCOOH | Column: Gemini-NX C18 AXAI Packed, 21.2*150 mm 5 um; Mobile Phase A: Water (0.1% FA), Mobile Phase B: ACN; Flow rate: 25 mL/min; Gradient: 10% B to 10% B in 2 min, 10% B to 26% B in 2.5 min, 26% B to 48% B in 10.5 min, 48% B; Wave Length: 254 nm; RT1(min): 8.28; Number Of Runs: 0 | (R)-6-chloro-7-(2-(((3-chloropyridin-2-yl)oxy) methyl)-2-methyl-pyrrolidin-1-yl)-1-(6-(3-(dimethyl-amino) azetidin-1-yl)pyridin-3-yl)-4-oxo-1,4-dihydro-quinoline-3-carboxylic acid formic acid | LCMS (ESI): $[M + H]^+$: 623.20 $^1$H NMR (300 MHz, DMSO-d6) δ 14.94 (s, 1H), 8.60 (s, 1H), 8.34-8.18 (m, 2H), 8.08-8.00 (m, 1H), 7.93-7.82 (m, 1H), 7.79-7.65 (m, 1H), 7.11-7.00 (m, 1H), 6.94 (d, J = 15.4 Hz, 1H), 6.45-6.31 (m, 1H), 4.31 (d, J = 11.3 Hz, 1H), 4.18-4.06 (m, 1H), 4.04-3.91 (m, 2H), 3.81-3.54 (m, 4H), 3.24-3.16 (m, 1H), 2.15 (s, 7H), 2.02-1.78 (m, 3H), 1.16 (s, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 278. | 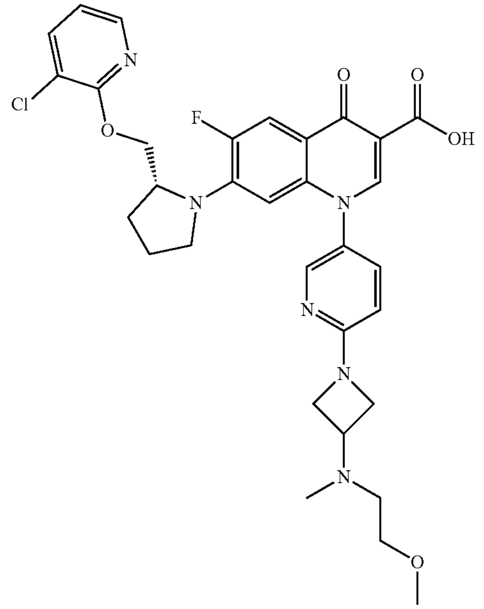 [SMILES: COCCN(C)C1CN(c2ccc(-n3cc(C(=O)O)c(=O)c4cc(F)c(N5CCC[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 5% B to 5% B in 2 min, 5% B to 16% B in 2.5 min, 16% B to 26% B in 10.5 min, 26% B; Wave Length: 254 nm; RT1(min): 10.2; Number Of Runs: 0 | (R)-7-(2-(((3-chloropyridin-2-yl)oxy) methyl) pyrrolidin-1-yl)-6-fluoro-1-(6-(3-((2-methoxyethyl) (methyl) amino) azetidin-1-yl)pyridin-3-yl)-4-oxo-1,4-dihydro-quinoline-3-carboxylic acid | LCMS (ESI): $[M + H]^+$: 637.20 $^1H$ NMR (300 MHz, DMSO-d6) δ 15.38 (s, 1H), 8.53-8.42 (m, 1H), 8.30-8.20 (m, 1H), 8.03-7.95 (m, 1H), 7.93-7.80 (m, 2H), 7.78-7.68 (m, 1H), 7.11-6.94 (m, 1H), 6.62-6.29 (m, 1H), 6.18-6.02 (m, 1H), 4.61-4.44 (m, 1H), 4.43-4.19 (m, 2H), 4.15-3.97 (m, 2H), 3.88-3.72 (m, 2H), 3.54-3.38 (m, 4H), 3.26 (s, 4H), 2.58-2.53 (m, 1H), 2.48-2.42 (m, 1H), 2.20 (s, 4H), 2.14-2.04 (m, 2H), 2.02-1.80 (m, 2H). | ++++ |
| 279. | 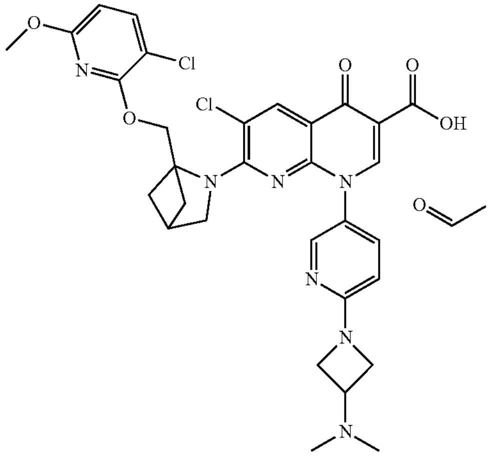 | reverse phase flash chromatography | 6-chloro-7-(1-(((3-chloro-6-methoxy-pyridin-2-yl)oxy) methyl)-2-azabicyclo [2.1.1 ]hexan-2-yl)-1-(6-(3-(dimethyl-amino) azetidin-1-yl)pyridin-3-yl)-4-oxo-1,4-dihydro-1,8-naphthyridine-3-carboxylic acid formic acid | LCMS (ESI): $[M + H]^+$: 652.25 $^1H$ NMR (300 MHz, DMSO-d6) δ 14.88 (s, 1H), 8.70 (s, 1H), 8.51 (s, 1H), 8.21 (d, J = 2.5 Hz, 1H), 7.79-7.65 (m, 2H), 6.41 (d, J = 8.3 Hz, 1H), 6.29 (d, J = 8.8 Hz, 1H), 4.25 (s, 2H), 3.75-3.64 (m, 7H), 3.62-3.52 (m, 2H), 3.06-3.00 (m, 1H), 2.88-2.81 (m, 1H), 2.11 (s, 6H), 1.98-1.91 (m, 2H), 1.58-1.47 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 280. | 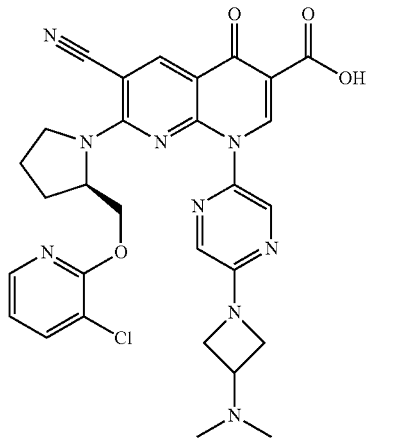 [SMILES: CN(C)C1CN(c2cnc(-n3cc(C(=O)O)c(=O)c4cc(C#N)c(N5CCC[C@@H]5COc5ncccc5Cl)nc43)cn2)C1] | Column: YMC-Actus Triart C18, 20*250 mm, 5 μm, 12 nm; Mobile Phase A: Water (10 MMOL/L NH4HCO3), Mobile Phase B: ACN; Flow rate: 25 mL/min; Gradient: 28% B to 47% B in 8 min, 47% B; Wave Length: 254 nm; RT1(min): 7.07; Number Of Runs: 0 | (R)-7-(2-(((3-chloropyridin-2-yl)oxy) methyl) pyrrolidin-1-yl)-6-cyano-1-(5-(3-(dimethyl-amino) azetidin-1-yl)pyrazin-2-yl)-4-oxo-1,4-dihydro-1,8-naphthyridine-3-carboxylic acid | LCMS (ESI): $[M + H]^+$: 602.25 $^1H$ NMR (300 MHz, DMSO-d6) δ 8.90-8.31 (m, 3H), 8.07-7.83 (m, 2H), 7.63 (s, 1H), 7.11-6.95 (m, 1H), 4.65-4.39 (m, 1H), 4.37-4.23 (m, 1H), 4.13-3.68 (m, 7H), 3.26-3.17 (m, 1H), 2.27-1.86 (m, 10H). | ++++ |
| 281. | 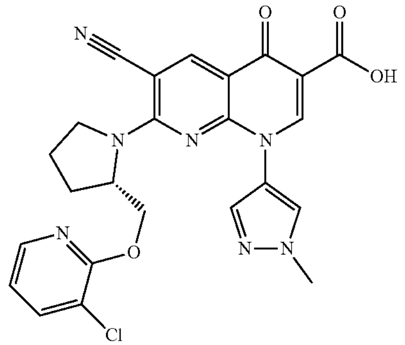 [SMILES: Cn1cc(-n2cc(C(=O)O)c(=O)c3cc(C#N)c(N4CCC[C@H]4COc4ncccc4Cl)nc32)cn1] | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 30% B to 45% B in 8 min, 45% B; Wave Length: 254 nm; RT1 (min): 7.18; Number Of Runs: 0 | (S)-7-(2-(((3-chloropyridin-2-yl)oxy) methyl) pyrrolidin-1-yl)-6-cyano-1-(1-methyl-1H-pyrazol-4-yl)-4-oxo-1,4-dihydro-1,8-naphthyridine-3-carboxylic acid | LCMS (ESI): $[M + H]^+$: 506.25 $^1H$ NMR (300 MHz, DMSO-d6) δ 14.54 (s, 1H), 8.85-8.45 (m, 2H), 8.19-8.13 (m, 1H), 8.05-7.99 (m, 1H), 7.92-7.83 (m, 1H), 7.80-7.72 (m, 1H), 7.04-6.96 (m, 1H), 4.66-4.60 (m, 1H), 4.37-4.31 (m, 2H), 4.07-3.68 (m, 5H), 2.19-1.88 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 282. | 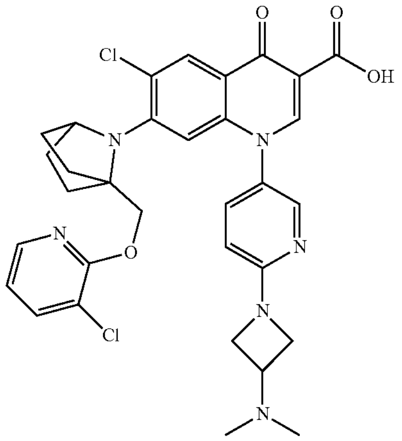 [SMILES: CN(C)C1CN(c2ccc(-n3cc(C(=O)O)c(=O)c4cc(Cl)c(N5C6CCC5(COc5ncccc5Cl)CC6)cc43)cn2)C1] | Column: SunFire Prep C18 OBD Column, 19*150 mm 5 μm 10 nm; Mobile Phase A: Water (0.1% FA), Mobile Phase B: ACN; Flow rate: 25 mL/min; Gradient: 10% B to 53% B in 8 min, 53% B; Wave Length: 254/220 nm; RT1: (min): 6.88; Number Of Runs: 0 | 6-chloro-7-(1-(((3-chloropyridin-2-yl)oxy) methyl)-7-azabicyclo [2.2.1]heptan-7-yl)-1-(6-(3-(dimethyl-amino) azetidin-1-yl)pyridin-3-yl)-4-oxo-1,4-dihydro-quinoline-3-carboxylic acid | LCMS (ESI): $[M + H]^+$: 635.20 $^1$H NMR (300 MHz, DMSO-d6) δ 14.96 (s, 1H), 8.66 (s, 1H), 8.30 (d, J = 2.5 Hz, 1H), 8.26 (s, 1H), 8.04-7.99 (m, 1H), 7.89-7.83 (m, 1H), 7.80-7.72 (m, 1H), 7.06-6.98 (m, 1H), 6.77 (s, 1H), 6.44 (d, J = 8.9 Hz, 1H), 4.59 (s, 2H), 4.19-4.11 (m, 1H), 4.06-3.94 (m, 2H), 3.82-3.70 (m, 2H), 3.26-3.16 (m, 1H), 2.14 (s, 6H), 1.88-1.66 (m, 6H), 1.61-1.46 (m, 2H). | ++++ |
| 283. | 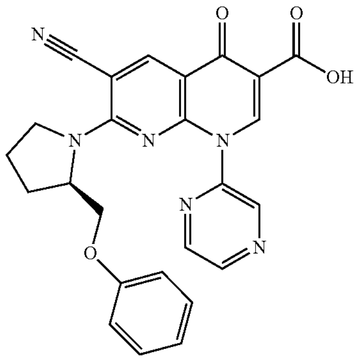 [SMILES: N#Cc1cc2c(=O)c(C(=O)O)cn(-c3cnccn3)c2nc1N1CCC[C@@H]1COc1ccccc1] | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 47% B to 61% B in 8 min, 61% B; Wave Length: 254 nm; RT1(min): 7.85; Number Of Runs: 0 | (R)-6-cyano-4-oxo-7-(2-(phenoxy-methyl) pyrrolidin-1-yl)-1-(pyrazin-2-yl)-1,4-dihydro-1,8-naphthyridine-3-carboxylic acid | LCMS (ESI): $[M + H]^+$: 469.10 $^1$H NMR (300 MHz, DMSO-d6) δ 14.32 (s, 1H), 9.12 (d, J = 1.4 Hz, 1H), 9.03 (s, 1H), 8.83 (s, 1H), 8.62 (s, 1H), 8.49 (s, 1H), 7.32-7.20 (m, 2H), 6.99-6.88 (m, 1H), 6.76 (d, J = 8.0 Hz, 2H), 4.73-3.58 (m, 5H), 2.12-1.91 (m, 4H). | ++ |
| 284. | 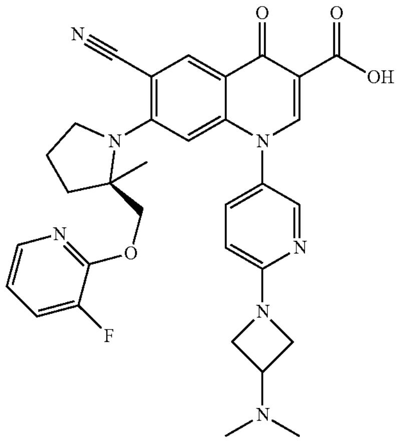 [SMILES: CN(C)C1CN(c2ccc(-n3cc(C(=O)O)c(=O)c4cc(C#N)c(N5CCC[C@]5(C)COc5ncccc5F)cc43)cn2)C1] | reverse phase flash chromatography | (R)-6-cyano-1-(6-(3-(dimethyl-amino) azetidin-1-yl)pyridin-3-yl)-7-(2-(((3-fluoropyridin-2-yl)oxy) methyl)-2-methyl-pyrrolidin-1-yl)-4-oxo-1,4-dihydro-quinoline-3-carboxylic acid | LCMS (ESI): $[M + H]^+$: 598.3 $^1$H NMR (300 MHz, DMSO-d6) δ 14.71 (s, 1H), 8.58 (d, J = 2.6 Hz, 1H), 8.39 (d, J = 1.9 Hz, 1H), 8.34-8.25 (m, 1H), 7.93-7.58 (m, 3H), 7.08-6.93 (m, 1H), 6.65-6.30 (m, 2H), 4.48-4.21 (m, 2H), 4.10-3.86 (m, 4H), 3.85-3.65 (m, 2H), 2.36-2.12 (m, 7H), 2.09-1.84 (m, 3H), 1.33-1.08 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 285. | 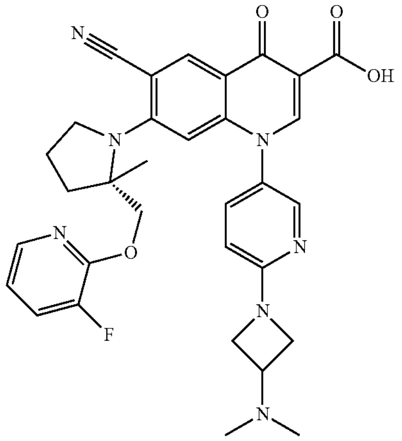 [SMILES: CN(C)C1CN(c2ccc(-n3cc(C(=O)O)c(=O)c4cc(C#N)c(N5CCC[C@@]5(C)COc5ncccc5F)cc43)cn2)C1] | Column: YMC-Actus Triart C18, 20*250 mm, 5 μm, 12 nm; Mobile Phase A: Water (10 MMOL/L NH4HCO3), Mobile Phase B: ACN; Flow rate: 25 mL/min; Gradient: 29% B to 52% B in 10 min, 52% B; Wave Length: 220 nm; RT1(min): 9.83; Number Of Runs: 0 | (S)-6-cyano-1-(6-(3-(dimethyl-amino) azetidin-1-yl)pyridin-3-yl)-7-(2-(((3-fluoropyridin-2-yl)oxy) methyl)-2-methyl-pyrrolidin-1-yl)-4-oxo-1,4-dihydro-quinoline-3-carboxylic acid | LCMS (ESI): $[M + H]^+$: 598.25 $^1H$ NMR (300 MHz, DMSO-d6) δ 14.69 (s, 1H), 8.69-8.08 (m, 3H), 7.94-7.51 (m, 3H), 7.07-6.91 (m, 1H), 6.61-6.27 (m, 2H), 4.46-4.22 (m, 2H), 4.06-3.87 (m, 3H), 3.80-3.61 (m, 2H), 3.26-3.12 (m, 1H), 2.35-2.22 (m, 1H), 2.13 (d, J = 1.5 Hz, 6H), 2.08-1.80 (m, 3H), 1.29-1.15 (m, 3H). | ++++ |
| 286. | 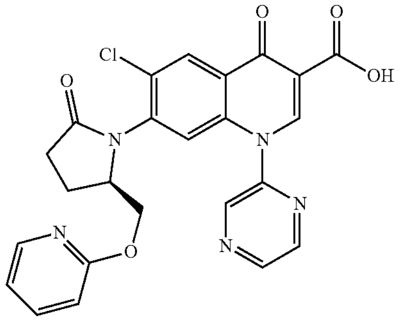 [SMILES: O=C(O)c1cn(-c2cnccn2)c2cc(N3C(=O)CC[C@@H]3COc3ccccn3)c(Cl)cc2c1=O] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 31% B to 55% B in 8 min, 55% B; Wave Length: 254 nm; RT1(min): 6.93; Number Of Runs: 0 | (R)-6-chloro-4-oxo-7-(2-oxo-5-((pyridin-2-yloxy) methyl) pyrrolidin-1-yl)-1-(pyrazin-2-yl)-1,4-dihydro-quinoline-3-carboxylic acid | LCMS (ESI): $[M + H]^+$: 492.15 $^1H$ NMR (300 MHz, DMSO-d6) δ 10.02 (s, 1H), 8.85-8.72 (m, 2H), 8.66 (s, 1H), 8.16 (s, 1H), 8.12-8.03 (m, 1H), 7.71-7.59 (m, 1H), 7.04-6.89 (m, 1H), 6.61 (s, 1H), 6.43 (d, J = 8.3 Hz, 1H), 4.45-4.36 (m, 1H), 4.27-4.17 (m, 1H), 4.15-4.05 (m, 1H), 2.64-2.55 (m, 1H), 2.46-2.38 (m, 1H), 2.38-2.24 (m, 1H), 2.04-1.83 (m, 1H). | + |
| 287. | 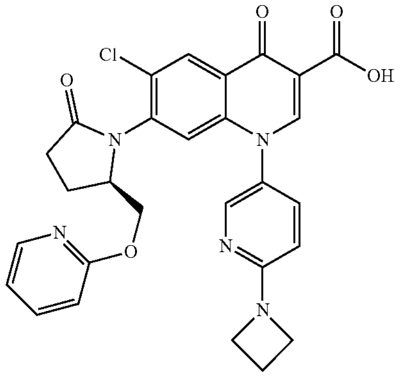 [SMILES: O=C(O)c1cn(-c2ccc(N3CCC3)nc2)c2cc(N3C(=O)CC[C@@H]3COc3ccccn3)c(Cl)cc2c1=O] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 25% B to 45% B in 8 min, 45% B; Wave Length: 254/220 nm; RT1(min): 6.13; Number Of Runs: 0 | (R)-1-(6-(azetidin-1-yl)pyridin-3-yl)-6-chloro-4-oxo-7-(2-oxo-5-((pyridin-2-yloxy)methyl) pyrrolidin-1-yl)-1,4-dihydro-quinoline-3-carboxylic acid | LCMS (ESI): $[M + H]^+$: 546.35 $^1H$ NMR (300 MHz, DMSO-d6) δ 14.63 (s, 1H), 8.66 (s, 1H), 8.44 (d, J = 7.9 Hz, 1H), 8.30-8.01 (m, 2H), 7.74-7.36 (m, 2H), 7.25 (d, J = 25.4 Hz, 1H), 7.06-6.88 (m, 1H), 6.60-6.07 (m, 2H), 4.60-4.44 (m, 1H), 4.36-4.15 (m, 2H), 4.12-3.99 (m, 4H), 2.69-2.55 (m, 1H), 2.45-2.21 (m, 4H), 2.13-1.95 (m, 1H). | ++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 288. | 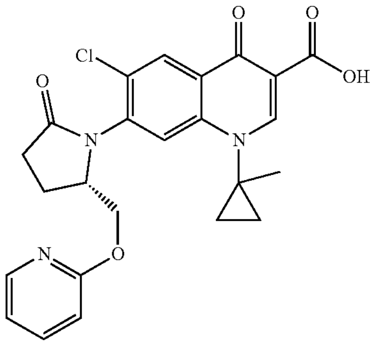 [SMILES: CC1(n2cc(C(=O)O)c(=O)c3cc(Cl)c(N4C(=O)CC[C@H]4COc4ccccn4)cc32)CC1] | Column: XBridge Shield RP18 OBD Column, 19*150 mm, 5 µm; Mobile Phase A: Water (0.1% FA), Mobile Phase B: ACN; Flow rate: 254 mL/min; Gradient: 35% B to 50% B in 8 min, 50% B; Wave Length: 254 nm; RT1(min): 6.35; Number Of Runs: 0 | (S)-6-chloro-1-(1-methylcyclo-propyl)-4-oxo-7-(2-oxo-5-((pyridin-2-yloxy)methyl) pyrrolidin-1-yl)-1,4-dihydro-quinoline-3-carboxylic acid | LCMS (ESI): $[M + H]^+$: 468.15 $^1H$ NMR (300 MHz, DMSO-d6) δ 14.672 (s, 1H), 8.86 (d, J = 1.7 Hz, 1H), 8.40 (d, J = 2.4 Hz, 1H), 8.17-7.98 (m, 2H), 7.66-7.44 (m, 1H), 7.00-6.84 (m, 1H), 6.65-6.32 (m, 1H), 4.79-4.63 (m, 1H), 4.44-4.19 (m, 2H), 2.79-2.65 (m, 1H), 2.64-2.55 (m, 1H), 2.46-2.40 (m, 1H), 2.19-2.02 (m, 1H), 1.52-1.46 (m, 1H), 1.44-1.23 (m, 3H), 1.20-0.96 (m, 3H) | + |
| 289. | 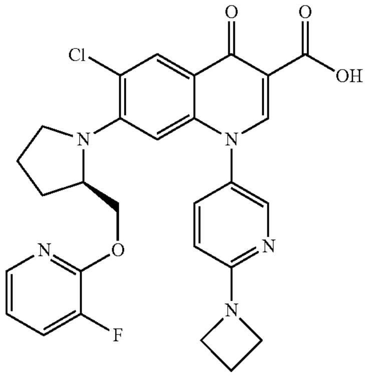 [SMILES: O=C(O)c1cn(-c2ccc(N3CCC3)nc2)c2cc(N3CCC[C@@H]3COc3ncccc3F)c(Cl)cc2c1=O] | Column: XSelect CSH Prep C18 OBD Column, 19*150 mm, 5 µm; Mobile Phase A: Water (0.1% FA), Mobile Phase B: ACN; Flow rate: 25 mL/min; Gradient: 45% B to 70% B in 8 min, 70% B; Wave Length: 254/220 nm; RT1(min): 6.97; Number Of Runs: 0 | (R)-1-(6-(azetidin-1-yl)pyridin-3-yl)-6-chloro-7-(2-(((3-fluoropyridin-2-yl)oxy)methyl) pyrrolidin-1-yl)-4-oxo-1,4-dihydro-quinoline-3-carboxylic acid | LCMS (ESI) [M + H]+: 550.05. 1H NMR (300 MHz, DMSO-d6) δ 15.10 (s, 1H), 8.57-8.43 (m, 1H), 8.29-8.10 (m, 2H), 7.83-7.51 (m, 3H), 7.04-6.91 (m, 1H), 6.62-6.05 (m, 2H), 4.71-4.46 (m, 1H), 4.39-4.31 (m, 1H), 4.23-4.14 (m, 1H), 4.06-3.95 (m, 4H), 3.72-3.41 (m, 1H), 3.28-3.18 (m, 1H), 2.43-2.29 (m, 2H), 2.31-2.18 (m, 1H), 2.01-1.61 (m, 3H). | ++++ |

TABLE 1-continued

| Compound | Product | Prep HPLC Method | IUPAC name | Analytical data | Potency Lin28a-dep Z11 $IC_{50}$ (µM) |
|---|---|---|---|---|---|
| 290. | 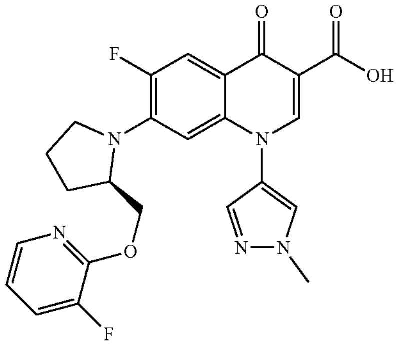 [SMILES: Cn1cc(-n2cc(C(=O)O)c(=O)c3cc(F)c(N4CCC[C@@H]4COc4ncccc4F)cc32)cn1] | Column: XSelect CSH Prep C18 OBD Column, 19*150 mm, 5 µm; Mobile Phase A: Water (0.1% FA), Mobile Phase B: ACN; Flow rate: 25 mL/min; Gradient: 36% B to 65% B in 8 min, 65% B; Wave Length: 254 nm; RT1(min): 6.72; Number Of Runs: 0 | rac-(R)-6-fluoro-7-(2-(((3-fluoropyridin-2-yl)oxy)methyl)pyrrolidin-1-yl)-1-(1-methyl-1H-pyrazol-4-yl)-4-oxo-1,4-dihydro-quinoline-3-carboxylic acid | LCMS (ESI) [M + H]+: 482.00. 1H NMR (300 MHz, DMSO-d6) δ 15.30 (s, 1H), 8.48 (s, 1H), 8.29 (s, 1H), 7.95-7.75 (m, 3H), 7.68-7.45 (m, 1H), 7.07-6.94 (m, 1H), 6.41 (d, J = 7.5 Hz, 1H), 4.65-4.53 (m, 1H), 4.41-4.24 (m, 2H), 3.91 (s, 3H), 3.44 (s, 1H), 3.34 (s, 1H), 2.20-1.89 (m, 4H). | ++++ |
| 291. | 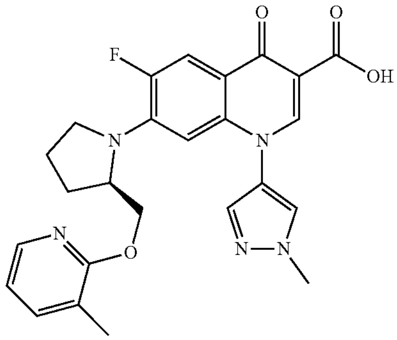 [SMILES: Cc1cccnc1OC[C@H]1CCCN1c1cc2c(cc1F)c(=O)c(C(=O)O)cn2-c1cnn(C)c1] | Column: XBridge Shield RP18 OBD Column, 19*150 mm, 5 µm; Mobile Phase A: Water (0.1% FA), Mobile Phase B: ACN; Flow rate: 25 mL/min; Gradient: 28% B to 65% B in 10 min, 65% B; Wave Length: 254 nm; RT1(min): 10.12; Number Of Runs: 0 | (R)-6-fluoro-1-(1-methyl-1H-pyrazol-4-yl)-7-(2-(((3-methylpyridin-2-yl)oxy)methyl)pyrrolidin-1-yl)-4-oxo-1,4-dihydro-quinoline-3-carboxylic acid | LCMS (ESI) [M + H]+: 478.00. 1H NMR (400 MHz, DMSO-d6) δ 15.32 (s, 1H), 8.48 (s, 1H), 8.28 (s, 1H), 7.94-7.72 (m, 3H), 7.53-7.40 (m, 1H), 6.92-6.79 (m, 1H), 6.47-6.32 (m, 1H), 4.58 (s, 1H), 4.35-4.13 (m, 2H), 3.90 (s, 3H), 3.48-3.44 (m, 1H), 3.30-3.25 (m, 1H), 2.17-1.88 (m, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 292. | 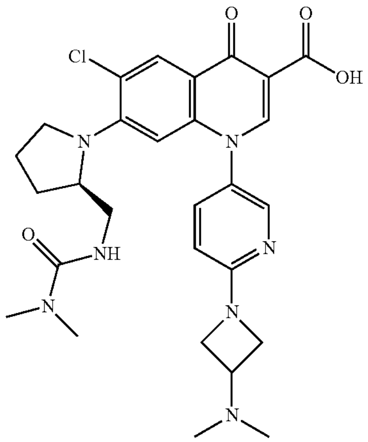 [SMILES: CN(C)C(=O)NC[C@H]1CCCN1c1cc2c(cc1Cl)c(=O)c(C(=O)O)cn2-c1ccc(N2CC(N(C)C)C2)nc1] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 5% B to 5% B in 2 min, 5% B to 18% B in 2.5 min, 18% B to 30% B in 12 min, 30% B; Wave Length: 220 nm; RT1(min): 10.2; Number Of Runs: 0 | (R)-6-chloro-1-(6-(3-(dimethyl-amino) azetidin-1-yl)pyridin-3-yl)-7-(2-((3,3-dimethyl-ureido)methyl) pyrrolidin-1-yl)-4-oxo-1,4-dihydro-quinoline-3-carboxylic acid | LCMS (ESI) [M + H]+: 568.15. 1H NMR (400 MHz, DMSO-d6) δ 15.18 (s, 1H), 8.57-8.42 (m, 1H), 8.31-8.26 (m, 1H), 8.19-8.11 (m, 1H), 7.84-7.73 (m, 1H), 6.65-6.45 (m, 2H), 6.20-6.02 (m, 1H), 4.29 (d, J = 39.6 Hz, 1H), 4.13-3.99 (m, 2H), 3.85-3.78 (m, 2H), 3.62-3.48 (m, 1H), 3.21-3.11 (m, 3H), 2.77-2.66 (m, 1H), 2.65-2.54 (m, 6H), 2.14 (s, 6H), 2.04-1.99 (m, 1H), 1.93-1.87 (m, 1H), 1.75-1.64 (m, 2H). | ++++ |
| 293. | 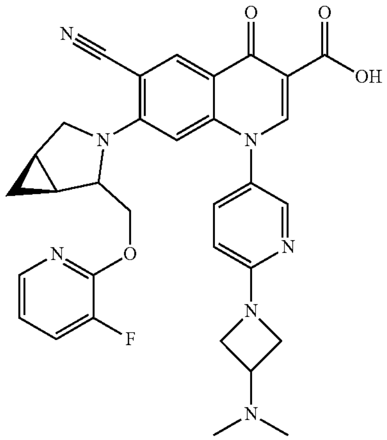 [SMILES: CN(C)C1CN(c2ccc(-n3cc(C(=O)O)c(=O)c4cc(C#N)c(N5C[C@@H]6C[C@@H]6C5COc5ncccc5F)cc43)cn2)C1] | Column: SunFire Prep C18 OBD Column, 19*150 mm, 5 μm 10 nm; Mobile Phase A: Water (0.1% FA), Mobile Phase B: ACN; Flow rate: 25 mL/min; Gradient: 5% B to 19% B in 2 min, 19% B to 29% B in 16 min, 29% B; Wave Length: 254/220 nm; RT1(min): 13.5; Number Of Runs: 0 | 6-cyano-1-(6-(3-(dimethyl-amino) azetidin-1-yl)pyridin-3-yl)-7-((1S,5R)-2-(((3-fluoropyridin-2-yl)oxy) methyl)-3-azabicyclo [3.1.0]hexan-3-yl)-4-oxo-1,4-dihydro-quinoline-3-carboxylic acid | LCMS (ESI) [M + H]+: 596.20. 1H NMR (300 MHz, DMSO-d6) δ 8.66-8.44 (m, 2H), 8.31 (s, 1H), 7.94-7.48 (m, 3H), 7.28-6.91 (m, 1H), 6.48 (d, J = 26.4 Hz, 1H), 5.75 (d, J = 8.8 Hz, 1H), 4.48-4.17 (m, 3H), 4.09-3.75 (m, 3H), 3.75-3.56 (m, 2H), 3.56-3.38 (m, 2H), 2.15 (s, 6H), 1.97-1.91 (m, 1H), 1.91-1.77 (m, 1H), 0.88-0.55 (m, 2H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 294. | 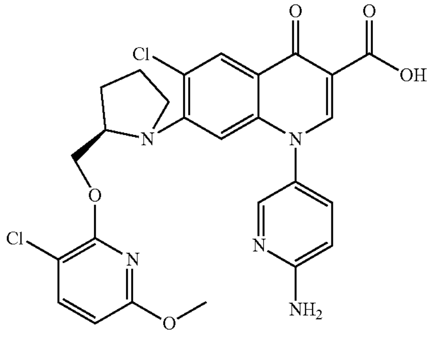 [SMILES: COc1ccc(Cl)c(OC[C@H]2CCCN2c2cc3c(cc2Cl)c(=O)c(C(=O)O)cn3-c2ccc(N)nc2)n1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 33% B to 73% B in 9 min, 73% B; Wave Length: 254 nm; RT1(min): 8.63; Number Of Runs: 0 | (R)-1-(6-aminopyridin-3-yl)-6-chloro-7-(2-(((3-chloro-6-methoxy-pyridin-2-yl)oxy)methyl)pyrrolidin-1-yl)-4-oxo-1,4-dihydro-quinoline-3-carboxylic acid | LCMS (ESI) [M + H]+: 555.95. 1H NMR (300 MHz, DMSO-d6) δ 15.18 (s, 1H), 8.59 (d, J = 5.2 Hz, 1H), 8.27-8.04 (m, 2H), 7.83-7.49 (m, 2H), 6.72-6.50 (m, 3H), 6.45 (s, 1H), 6.34 (d, J = 8.4 Hz, 1H), 4.80 (d, J = 21.2 Hz, 1H), 4.57 (dd, J = 11.6, 3.6 Hz, 1H), 4.34 (dd, J = 11.6, 3.3 Hz, 1H), 3.68 (s, 3H), 3.57-3.48 (m, 1H), 3.30-3.16 (m, 1H), 2.40-2.25 (m, 1H), 2.06 (s, 2H), 1.91-1.75 (m, 1H). | ++++ |
| 295. | 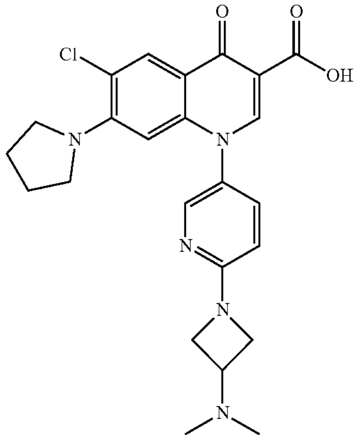 [SMILES: CN(C)C1CN(c2ccc(-n3cc(C(=O)O)c(=O)c4cc(Cl)c(N5CCCC5)cc43)cn2)C1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 15% B to 38% B in 8 min, 38% B; Wave Length: 254 nm; RT1(min): 7.53; Number Of Runs: 0 | C6-chloro-1-(6-(3-(dimethyl-amino)azetidin-1-yl)pyridin-3-yl)-4-oxo-7-(pyrrolidin-1-yl)-1,4-dihydro-quinoline-3-carboxylic acid | LCMS (ESI) [M + H]+: 468.0. 1H NMR (300 MHz, DMSO-d6) δ 15.23 (s, 1H), 8.52 (s, 1H), 8.30 (d, J = 2.5 Hz, 1H), 8.16 (s, 1H), 7.80 (dd, J = 8.8, 2.6 Hz, 1H), 6.57 (d, J = 8.8 Hz, 1H), 6.18 (s, 1H), 4.10 (q, J = 7.1 Hz, 2H), 3.84 (q, J = 7.3, 6.5 Hz, 2H), 3.55-3.39 (m, 3H), 3.31-3.12 (m, 2H), 2.15 (s, 6H), 1.87 (s, 4H). | +++ |
| 296. | 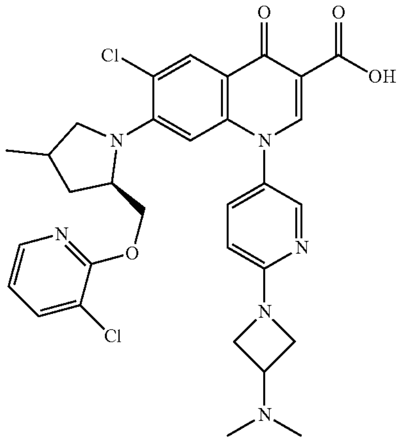 [SMILES: CC1C[C@H](COc2ncccc2Cl)N(c2cc3c(cc2Cl)c(=O)c(C(=O)O)cn3-c2ccc(N3CC(N(C)C)C3)nc2)C1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 26% B to 35% B in 9 min, 35% B; Wave Length: 254 nm; RT1(min): 6.4; Number Of Runs: 0 | 6-chloro-7-((2R)-2-(((3-chloropyridin-2-yl)oxy)methyl)-4-methyl-pyrrolidin-1-yl)-1-(6-(3-(dimethyl-amino)azetidin-1-yl)pyridin-3-yl)-4-oxo-1,4-dihydro-quinoline-3-carboxylic acid | LCMS (ESI) [M + H]+: 623.1. 1H NMR (300 MHz, DMSO-d6) δ 15.09 (s, 1H), 8.57-8.45 (m, 1H), 8.31-8.22 (m, 1H), 8.23-8.13 (m, 1H), 7.99-7.77 (m, 2H), 7.69 (s, 1H), 7.01-6.88 (m, 1H), 6.62-6.22 (m, 2H), 4.66-4.46 (m, 1H), 4.36-4.20 (m, 2H), 4.16-4.05 (m, 2H), 3.89-3.80 (m, 2H), 3.25-3.16 (m, 3H), 2.42-2.13 (m, 8H), 1.71-1.51 (m, 1H), 1.11-0.93 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 297. | 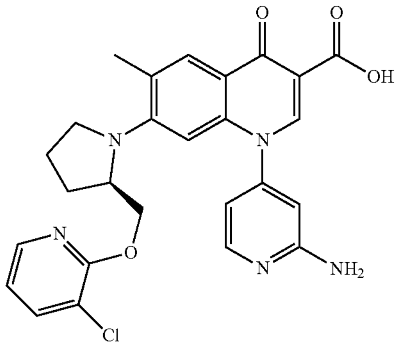 [SMILES: Cc1cc2c(=O)c(C(=O)O)cn(-c3ccnc(N)c3)c2cc1N1CCC[C@@H]1COc1ncccc1Cl] | Column: Gemini-NX C18 AXAI Packed, 21.2*150 mm 5 um; Mobile Phase A: Water (0.1% FA), Mobile Phase B: ACN; Flow rate: 25 mL/min; Gradient: 21% B to 51% B in 10 min, 51% B; Wave Length: 254 nm; RT1(min): 9.18; Number Of Runs: 0 | (R)-1-(2-aminopyridin-4-yl)-7-(2-(((3-chloropyridin-2-yl)oxy)methyl) pyrrolidin-1-yl)-6-methyl-4-oxo-1,4-dihydro-quinoline-3-carboxylic acid | LCMS (ESI) [M + H]+: 506.0. 1H NMR (300 MHz, DMSO-d6) δ 15.50 (s, 1H), 8.50 (s, 1H), 8.13-7.71 (m, 4H), 7.16-6.90 (m, 1H), 6.70-6.47 (m, 5H), 4.42-4.10 (m, 3H), 3.57-3.38 (m, 1H), 3.22-2.82 (m, 1H), 2.38 (s, 3H), 2.29-2.18 (m, 1H), 2.03-1.73 (m, 3H). | ++++ |
| 298. | 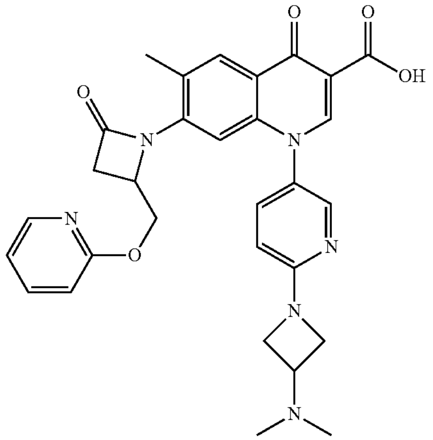 [SMILES: Cc1cc2c(=O)c(C(=O)O)cn(-c3ccc(N4CC(N(C)C)C4)nc3)c2cc1N1C(=O)CC1COc1ccccn1] | Column: Welch XB-C18, 21.2*250 mm, 5 μm; Mobile Phase A: Water (0.1% FA), Mobile Phase B: ACN; Flow rate: 25 mL/min; Gradient: 5% B to 5% B in 2 min, 5% B to 15% B in 2.5 min, 15% B to 40% B in 10.5 min, 40% B; Wave Length: 254 nm; RT1(min): 8.2; Number Of Runs: 0 | 1-(6-(3-(dimethyl-amino) azetidin-1-yl)pyridin-3-yl)-6-methyl-4-oxo-7-(2-oxo-4-((pyridin-2-yloxy)methyl) azetidin-1-yl)-1,4-dihydro-quinoline-3-carboxylic acid | LCMS (ESI) [M + H]+: 555.0. 1H NMR (300 MHz, DMSO-d6) δ 15.08 (s, 1H), 8.62 (s, 1H), 8.36-8.15 (m, 2H), 8.04-7.90 (m, 1H), 7.73-7.59 (m, 2H), 7.14 (s, 1H), 7.03-6.86 (m, 1H), 6.63-6.44 (m, 2H), 4.72-4.65 (m, 1H), 4.54-4.41 (m, 2H), 4.19-4.05 (m, 2H), 3.89-3.77 (m, 2H), 3.24-3.17 (m, 2H), 3.08-2.94 (m, 1H), 2.47 (s, 3H), 2.16 (s, 6H). | ++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 299. | 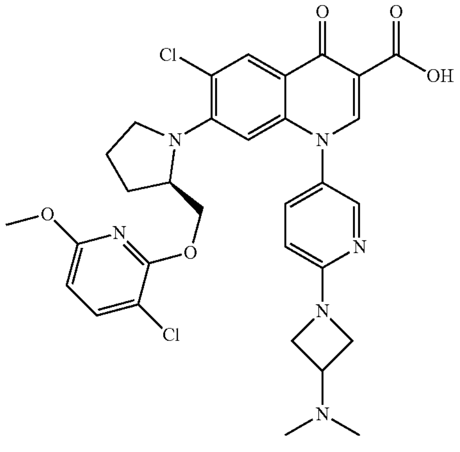 [SMILES: COc1ccc(Cl)c(OC[C@H]2CCCN2c2cc3c(cc2Cl)c(=O)c(C(=O)O)cn3-c2ccc(N3CC(N(C)C)C3)nc2)n1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 15% B to 35% B in 10 min, 35% B; Wave Length: 254 nm; RT1(min): 9.3; Number Of Runs: 0 | (R)-6-chloro-7-(2-(((3-chloro-6-methoxy-pyridin-2-yl)oxy) methyl) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 639.15. 1H NMR (400 MHz, DMSO-d6) δ 15.09 (s, 1H), 8.53 (s, 1H), 8.30-8.01 (m, 2H), 7.77-7.58 (m, 2H), 6.71-6.16 (m, 3H), 4.73-4.58 (m, 1H), 4.49-4.23 (m, 2H), 4.13-4.05 (m, 2H), 3.90-3.82 (m, 2H), 3.62 (s, 3H), 3.54-3.37 (m, 2H), 3.18 (d, J = 8.3 Hz, 1H), 2.24 (s, 7H), 2.07-1.89 (m, 2H), 1.83-1.73 (m, 1H). | ++++ |
| 300. | 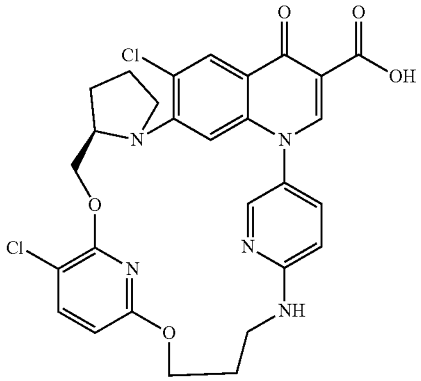 [SMILES: O=C(O)c1cn2c3cc(c(Cl)cc3c1=O)N1CCC[C@@H]1COc1nc(ccc1Cl)OCCCNc1ccc-2cn1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 23% B to 31% B in 8 min, 31% B; Wave Length: 254 nm; RT1(min): 9.23; Number Of Runs: 0 | (R)-26,63-dichloro-24-oxo-21,24-dihydro-5,7-dioxa-11-aza-2(1,7)-quinolina-1(5,2),6(2,6)-dipyridina-3(1,2)-pyrrolidina cyclo-undecaphane-23-carboxylic acid | LCMS (ESI) [M + H]+: 581.95. 1H NMR (300 MHz, Methanol-d4) δ 9.99 (s, 1H), 8.03 (s, 1H), 7.64-7.35 (m, 1H), 7.27-6.93 (m, 2H), 6.63 (d, J = 8.6 Hz, 1H), 6.50-6.37 (m, 1H), 6.06-5.87 (m, 1H), 4.71-4.58 (m, 1H), 4.38-4.04 (m, 4H), 3.99-3.78 (m, 1H), 3.68-3.49 (m, 1H), 3.47-3.41 (m, 1H), 3.20-3.06 (m, 1H), 2.17-1.97 (m, 3H), 1.89-1.76 (m, 3H), 1.31 (s, 2H). | ++++ |
| 301. | 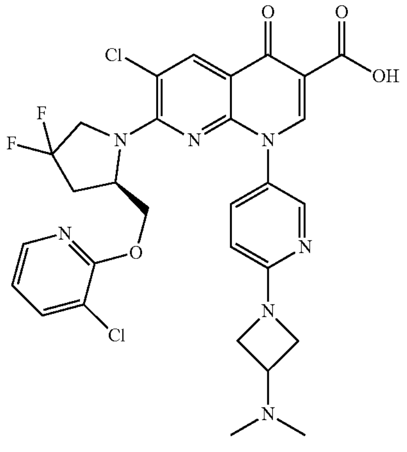 [SMILES: CN(C)C1CN(c2ccc(-n3cc(C(=O)O)c(=O)c4cc(Cl)c(N5CC(F)(F)C[C@@H]5COc5ncccc5Cl)nc43)cn2)C1] | reverse phase flash chromatography | (R)-6-chloro-7-(2-(((3-chloropyridin-2-yl)oxy) methyl)-4,4-difluoro-pyrrolidin-1-yl)-1-(6-(3-(dimethyl-amino) azetidin-1-yl)pyridin-3-yl)-4-oxo-1,4-dihydro-1,8-naphthyridine-3-carboxylic acid | LCMS (ESI) [M + H]+: 646.20. 1H NMR (300 MHz, DMSO-d6) δ 14.62 (s, 1H), 8.68 (s, 1H), 8.43 (s, 1H), 8.20 (s, 1H), 8.03-7.89 (m, 2H), 7.78-7.65 (m, 1H), 7.02 (s, 1H), 6.30-6.06 (m, 1H), 4.75 (s, 1H), 4.41-4.12 (m, 4H), 4.03-3.76 (m, 2H), 3.76-3.59 (m, 2H), 3.22-3.09 (m, 1H), 2.78-2.68 (m, 1H), 2.61-2.57 (m, 1H), 2.13 (s, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 302. | 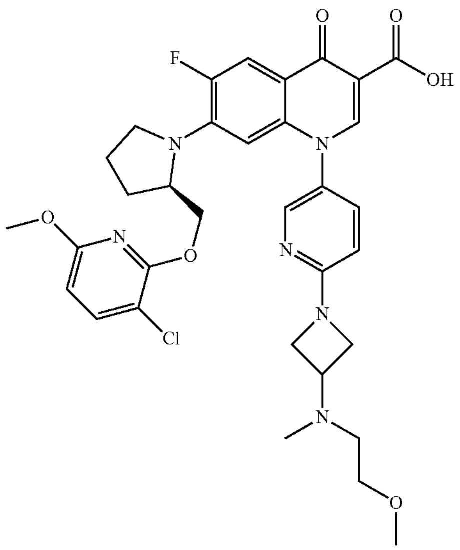 [SMILES: COCCN(C)C1CN(c2ccc(-n3cc(C(=O)O)c(=O)c4cc(F)c(N5CCC[C@@H]5COc5nc(OC)ccc5Cl)cc43)cn2)C1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 20% B to 45% B in 7 min, 45% B; Wave Length: 254/220 nm; RT1(min): 6.98; Number Of Runs: 0 | (R)-7-(2-(((3-chloro-6-methoxy-pyridin-2-yl)oxy)methyl) pyrrolidin-1-yl)-6-fluoro-1-(6-(3-((2-methoxyethyl) (methyl) amino) azetidin-1-yl)pyridin-3-yl)-4-oxo-1,4-dihydro-quinoline-3-carboxylic acid | LCMS (ESI) [M + H]+: 667.30. 1H NMR (400 MHz, Methanol-d4) δ 8.48 (s, 1H), 8.06 (d, J = 7.9 Hz, 1H), 7.80 (d, J = 14.4 Hz, 1H), 7.60-7.35 (m, 2H), 6.44 (d, J = 59.5 Hz, 1H), 6.21-6.13 (m, 1H), 6.04 (s, 1H), 4.50-4.36 (m, 2H), 4.30-4.22 (m, 1H), 4.14-4.04 (m, 2H), 3.93-3.81 (m, 2H), 3.63 (s, 3H), 3.54-3.43 (m, 3H), 3.40-3.34 (m, 1H), 3.28 (s, 3H), 3.21-3.16 (m, 1H), 2.58 (s, 2H), 2.29-2.04 (m, 6H), 0.96-0.63 (m, 1H). | ++++ |
| 303. | 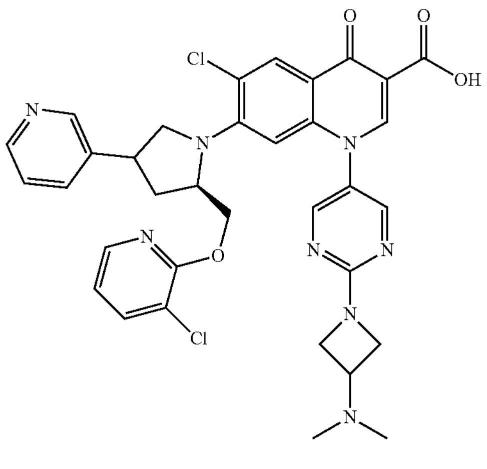 [SMILES: CN(C)C1CN(c2ncc(-n3cc(C(=O)O)c(=O)c4cc(Cl)c(N5CC(c6cccnc6)C[C@@H]5COc5ncccc5Cl)cc43)cn2)C1] | Column: Gemini-NX C18 AXAI Packed, 21.2*150 mm 5 um; Mobile Phase A: Water (10 MMOL/L NH4HCO3), Mobile Phase B: ACN; Flow rate: 25 mL/min; Gradient: 10% B to 10% B in 2 min, 10% B to 26% B in 2.5 min, 26% B to 48% B in 9.5 min, 48% B; Wave Length: 254 nm; RT1(min): 7.75; Number Of Runs: 0 | 6-chloro-7-((2R)-2-(((3-chloropyridin-2-yl)oxy) methyl)-4-(pyridin-3-yl)pyrrolidin-1-yl)-1-(2-(3-(dimethyl-amino) azetidin-1-yl)pyrimidin-5-yl)-4-oxo-1,4-dihydro-quinoline-3-carboxylic acid | LCMS (ESI) [M + H]+: 687.20. 1H NMR (400 MHz, DMSO-d6) δ 15.00 (s, 1H), 8.77-8.34 (m, 5H), 8.20 (s, 1H), 7.94-7.74 (m, 3H), 7.44-7.27 (m, 1H), 7.14-6.91 (m, 1H), 6.58 (s, 1H), 4.87-4.78 (m, 1H), 4.45-4.30 (m, 2H), 4.19-4.05 (m, 2H), 3.93-3.84 (m, 2H), 3.76-3.62 (m, 2H), 3.52-3.42 (m, 1H), 3.25-3.14 (m, 1H), 2.70-2.58 (m, 1H), 2.27-2.18 (m, 1H), 2.13 (s, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 304. | 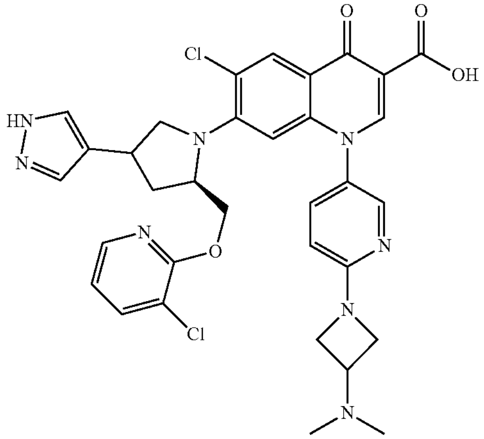 [SMILES: CN(C)C1CN(c2ccc(-n3cc(C(=O)O)c(=O)c4cc(Cl)c(N5CC(c6cn[nH]c6)C[C@@H]5COc5ncccc5Cl)cc43)cn2)C1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 15% B to 43% B in 7 min, 43% B; Wave Length: 254/220 nm; RT1(min): 5.95; Number Of Runs: 0 | 6-chloro-7-((2R)-2-(((3-chloropyridin-2-yl)oxy) methyl)-4-(1H-pyrazol-4-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 675.15. '1H NMR (400 MHz, DMSO-d6) δ 15.09 (s, 1H), 8.62-8.43 (m, 1H), 8.34-8.06 (m, 2H), 7.98-7.82 (m, 2H), 7.72-7.40 (m, 3H), 7.08-6.86 (m, 1H), 6.63-6.17 (m, 2H), 4.66 (d, J = 38.6 Hz, 1H), 4.44-4.20 (m, 2H), 4.15-3.96 (m, 2H), 3.87-3.70 (m, 2H), 3.55-3.45 (m, 2H), 3.24-3.08 (m, 2H), 2.68-2.54 (m, 1H), 2.30-1.91 (m, 7H). | ++++ |
| 305. | 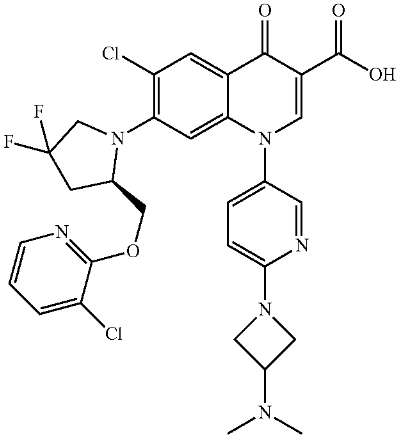 [SMILES: CN(C)C1CN(c2ccc(-n3cc(C(=O)O)c(=O)c4cc(Cl)c(N5CC(F)(F)C[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 21% B to 40% B in 8 min, 40% B; Wave Length: 254 nm; RT1(min): 7.58; Number Of Runs: 0 | rac-(R)-6-chloro-7-(2-(((3-chloropyridin-2-yl)oxy) methyl)-4,4-difluoro-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 645.10. 1H NMR (400 MHz, DMSO-d6) δ 14.82 (s, 1H), 8.62-8.45 (m, 1H), 8.38-8.12 (m, 2H), 7.94-7.53 (m, 3H), 6.98 (t, J = 6.4 Hz, 1H), 6.70-6.35 (m, 2H), 4.96 (s, 1H), 4.48-4.20 (m, 2H), 4.18-4.08 (m, 3H), 3.92-3.67 (m, 2H), 3.72-3.52 (m, 1H), 3.27-3.12 (m, 2H), 2.94-2.77 (m, 1H), 2.24-2.04 (m, 6H). | ++++ |
| 306. | 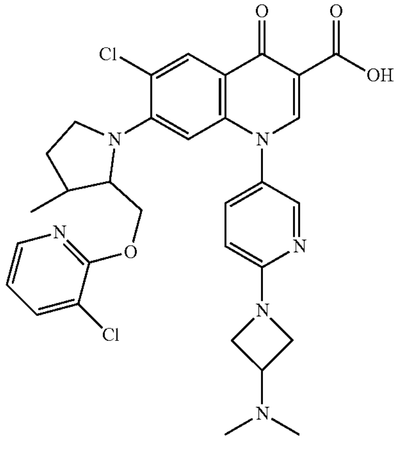 [SMILES: CC1CCN(c2cc3c(cc2Cl)c(=O)c(C(=O)O)cn3-c2ccc(N3CC(N(C)C)C3)nc2)C1COc1ncccc1Cl] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 15% B to 44% B in 7 min, 44% B; Wave Length: 254/220 nm; RT1(min): 6.93; Number Of Runs: 0 | 6-chloro-7-(2-(((3-chloropyridin-2-yl)oxy) methyl)-3-methyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 623.20. 1H NMR (300 MHz, DMSO-d6) δ 15.10 (s, 1H), 8.56-8.41 (m, 1H), 8.29-8.12 (m, 2H), 8.02-7.51 (m, 3H), 7.08-6.90 (m, 1H), 6.61-6.06 (m, 2H), 4.46-4.19 (m, 2H), 4.17-3.96 (m, 2H), 3.86-3.77 (m, 3H), 3.29-3.12 (m, 3H), 2.40-2.29 (m, 1H), 2.18 (s, 7H), 1.86-1.38 (m, 1H), 1.39-0.98 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 307. | 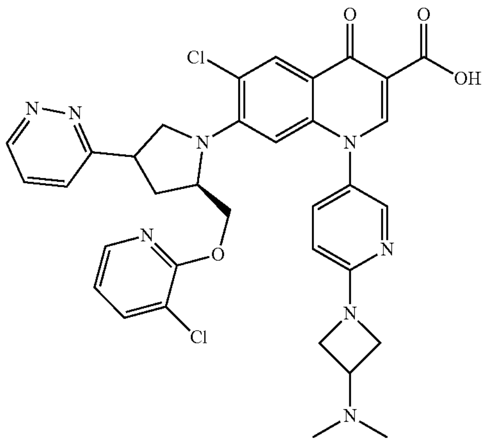 [SMILES: CN(C)C1CN(c2ccc(-n3cc(C(=O)O)c(=O)c4cc(Cl)c(N5CC(c6cccnn6)C[C@@H]5COc5ncccc5Cl)cc43)cn2)C1] | reverse phase flash chromatography | rac-6-chloro-7-((2R)-2-(((3-chloropyridin-2-yl)oxy) methyl)-4-(pyridazin-3-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 687.35. 1H NMR (300 MHz, DMSO-d6) δ 15.03 (s, 1H), 9.34-9.01 (m, 1H), 8.56-8.45 (m, 1H), 8.39-8.32 (m, 1H), 8.27-8.09 (m, 1H), 8.01-7.88 (m, 1H), 7.87-7.75 (m, 2H), 7.77-7.60 (m, 2H), 7.07-6.90 (m, 1H), 6.71-6.33 (m, 2H), 5.00-4.87 (m, 1H), 4.43-4.18 (m, 7H), 4.10-3.93 (m, 2H), 3.51 (s, 2H), 2.85 (s, 6H), 2.66-2.56 (m, 1H). | ++++ |
| 308. | 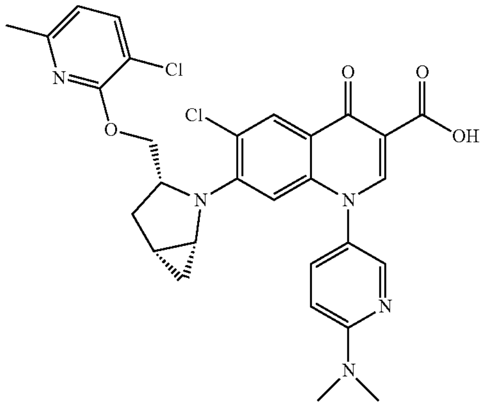 [SMILES: Cc1ccc(Cl)c(OC[C@H]2C[C@H]3C[C@H]3N2c2cc3c(cc2Cl)c(=O)c(C(=O)O)cn3-c2ccc(N(C)C)nc2)n1] | (Column: XSelect CSH Prep C18 OBD Column, 19*150 mm, 5 μm; Mobile Phase A: Water (0.1% FA), Mobile Phase B: ACN; Flow rate: 25 mL/min; Gradient: 55% B to 85% B in 7 min, 85% B; Wave Length: 254/220 nm; RT1(min): 7.53; Number Of Runs: 0 | 6-chloro-7-[(1R,3R,5R)-3-{[(3-chloro-6-methylpyridin-2-yl)oxy] methyl}-2-azabicyclo [3.1.0]hexan-2-yl]-1-[6-(dimethyl-amino)pyridin-3-yl]-4-oxoquinoline-3-carboxylic acid | LCMS (ESI) [M + H]+: 580.25. $^{1}$H NMR (400 MHz, DMSO-$d_6$) δ 15.10 (s, 1H), 8.55 (d, J = 6.0 Hz, 1H), 8.26 (dd, J = 13.8, 2.7 Hz, 1H), 8.16 (d, J = 1.8 Hz, 1H), 7.80-7.59 (m, 2H), 6.94-6.64 (m, 3H), 4.98 (d, J = 4.7 Hz, 1H), 4.34-3.95 (m, 2H), 3.11 (s, 6H), 2.99 (dd, J = 19.6, 12.9 Hz, 1H), 2.71-2.59 (m, 1H), 2.15 (s, 3H), 2.10-1.97 (m, 1H), 1.69-1.55 (m, 1H), 1.03 (d, J = 10.2 Hz, 1H), 0.64 (d, J = 10.7 Hz, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 309. | 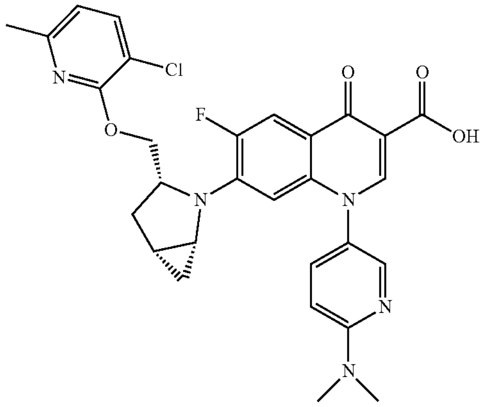 | Column: XSelect CSH Prep C18 OBD Column, 19*150 mm, 5 μm; Mobile Phase A: Water (0.1% FA), Mobile Phase B: ACN; Flow rate: 25 mL/min; Gradient: 50% B to 80% B in 7 min, 80% B; Wave Length: 254/220 nm; RT1(min): 7.53; Number Of Runs: 0 | 6-chloro-7-[(1R,3R,5R)-3-{[(3-chloro-6-methylpyridin-2-yl)oxy] methyl}-2-azabicyclo [3.1.0]hexan-2-yl]-1-[6-(dimethyl-amino)pyridin-3-yl]-4-oxoquinoline-3-carboxylic acid | LCMS (ESI) [M + H]+: 564.25. $^1$H NMR (400 MHz, DMSO-$d_6$) δ 15.37 (s, 1H), 8.50 (d, J = 3.4 Hz, 1H), 8.28 (dd, J = 7.2, 2.7 Hz, 1H), 7.89 (dd, J = 13.3, 2.3 Hz, 1H), 7.80-7.60 (m, 2H), 6.89-6.41 (m, 3H), 4.75 (s, 1H), 4.37-3.98 (m, 2H), 3.15 (s, 1H), 3.10 (d, J = 1.9 Hz, 6H), 2.61 (s, 1H), 2.21 (s, 3H), 2.10-1.98 (m, 1H), 1.61 (s, 1H), 0.95 (d, J = 5.6 Hz, 1H), 0.71 (dd, J = 8.8, 5.6 Hz, 1H). | ++++ |
| 310. | 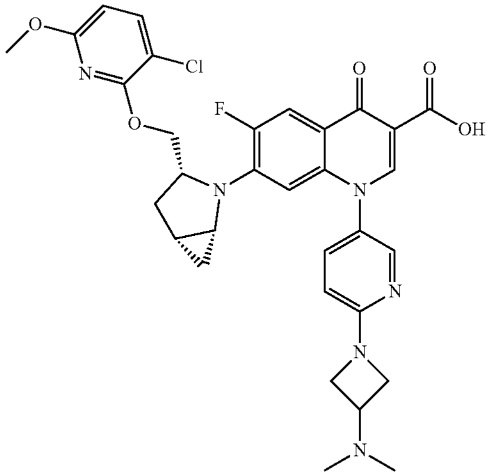 | Column: XSelect CSH Prep C18 OBD Column, 19*150 mm, 5 μm; Mobile Phase A: Water (0.1% FA), Mobile Phase B: ACN; Flow rate: 25 mL/min; Gradient: 40% B to 67% B in 7 min, 67% B; Wave Length: 254/220 nm; RT1(min): 6.65; Number Of Runs: 0 | rac-7-[(1R,3R,5R)-3-{[(3-chloro-6-methoxy-pyridin-2-yl)oxy] methyl}-2-azabicyclo [3.1.0]hexan-2-yl]-1-{6-[3-(dimethyl-amino) azetidin-1-yl]pyridin-3-yl}-6-fluoro-4-oxoquinoline-3-carboxylic acid | LCMS (ESI) [M + H]+: 635.15. $^1$H NMR (400 MHz, DMSO-$d_6$) δ 15.33 (s, 1H), 8.56-8.40 (m, 1H), 8.32-8.14 (m, 1H), 7.94-7.51 (m, 3H), 6.63-6.19 (m, 3H), 4.84-4.57 (m, 1H), 4.32-3.98 (m, 4H), 3.88-3.76 (m, 2H), 3.72 (d, J = 3.1 Hz, 2H), 3.64 (s, 1H), 3.28-2.99 (m, 2H), 2.70-2.59 (m, 1H), 2.23-1.92 (m, 7H), 1.71-1.48 (m, 1H), 1.06-0.82 (m, 1H), 0.78-0.59 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 311. | 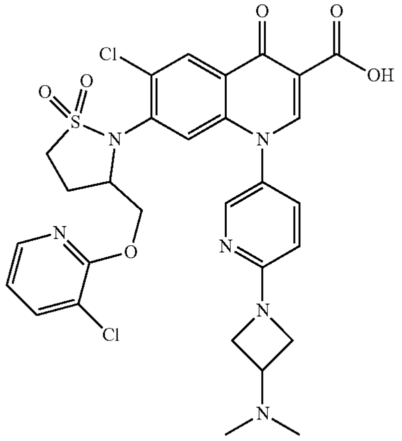 [SMILES: CN(C)C1CN(c2ccc(-n3cc(C(=O)O)c(=O)c4cc(Cl)c(N5C(COc6ncccc6Cl)CCS5(=O)=O)cc43)cn2)C1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 15% B to 32% B in 8 min, 32% B; Wave Length: 254 nm; RT1(min): 6.70; Number Of Runs: 0 | 6-chloro-7-(3-(((3-chloropyridin-2-yl)oxy) methyl)-1,1-dioxidoiso-thiazolidin-2-yl)-1-(6-(3-(dimethyl-amino) azetidin-1-yl)pyridin-3-yl)-4-oxo-1,4-dihydro-quinoline-3-carboxylic acid | LCMS (ESI): [M + H]$^+$: 659.0 $^1$H NMR (300 MHz, DMSO-d6) δ 14.54 (s, 1H), 8.66 (s, 1H), 8.41 (s, 1H), 8.25-8.07 (m, 1H), 8.05-7.94 (m, 1H), 7.83-7.72 (m, 1H), 7.61-7.40 (m, 1H), 7.33 (d, J = 6.1 Hz, 1H), 7.04-6.96 (m, 1H), 6.58-6.37 (m, 1H), 4.65-4.59 (m, 1H), 4.46-4.25 (m, 2H), 4.11 (t, J = 8.0 Hz, 2H), 3.91-3.81 (m, 2H), 3.68-3.45 (m, 2H), 3.29-3.23 (m, 1 H), 2.82-2.63 (m, 0H), 2.34-2.25 (m, 1H), 2.19 (s, 6H). | ++++ |
| 312. | 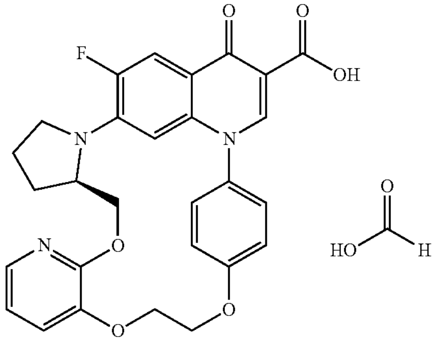 [SMILES: O=C(O)c1cn2c3cc(c(F)cc3c1=O)N1CCC[C@@H]1COc1ncccc1OCCOc1ccc-2cc1 ; O=CO] | Column: YMC-Actus Triart C18, 20*250 mm, 5 μm, 12 nm; Mobile Phase A: Water (0.1% FA), Mobile Phase B: ACN; Flow rate: 25 mL/min; Gradient: 55% B to 78% B in 9 min, 78% B; Wave Length: 254 nm; RT1(min): 9.2; Number Of Runs: 0 | rac-(R)-26-fluoro-24-oxo-21,24-dihydro-5,7,10-trioxa-2(1,7)-quinolina-6(2,3)-pyridina-3(1,2)-pyrrolidina-1(1,4)-benzenacyclo-decaphane-23-carboxylic acid formic acid | LCMS (ESI): [M + H]+: 518.2 1H NMR (300 MHz, DMSO-d6) δ 15.503 (s, 1 H), 8.64-8.49 (m, 1H), 8.32 (s, 1H), 7.97-7.85 (m, 1H), 7.70-7.62 (m, 1H), 7.60-7.41 (m, 2H), 7.39-7.21 (m, 2H), 7.04-6.94 (m, 1H), 6.80-6.71 (m, 1H), 6.07-5.99 (m, 1H), 4.93-4.80 (m, 1H), 4.66-4.46 (m, 2H), 4.42-4.32 (m, 2H), 4.05-3.90 (m, 1H), 3.60-3.50 (m, 3H), 2.02-1.91 (m, 4H). | + |
| 313. | 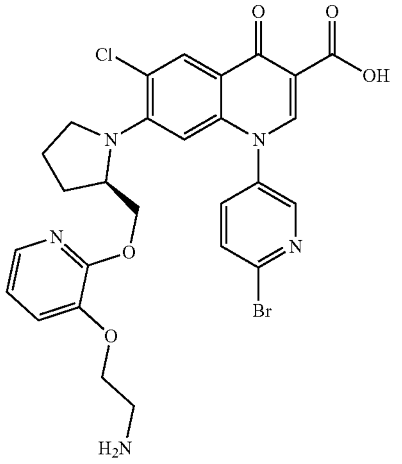 [SMILES: NCCOc1cccnc1OC[C@H]1CCCN1c1cc2c(cc1Cl)c(=O)c(C(=O)O)cn2-c1ccc(Br)nc1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 22% B to 28% B in 8 min, 28% B; Wave Length: 254/220 nm; RT1(min): 6.83; Number Of Runs: 0 | rac-(R)-7-(2-(((3-(2-aminoethoxy) pyridin-2-yl)oxy) methyl) pyrrolidin-1-yl)-1-(6-bromopyridin-3-yl)-6-chloro-4-oxo-1,4-dihydro-quinoline-3-carboxylic acid | LCMS (ESI): [M + H + 2]$^+$: 616.15 1H NMR (300 MHz, DMSO-d6) δ 8.93-8.65 (m, 2H), 8.26 (s, 1H), 8.21-7.97 (m, 2H), 7.84-7.52 (m, 1H), 7.45-7.29 (m, 1H), 6.97 (s, 1H), 6.31 (s, 1H), 4.89-4.61 (m, 1H), 4.49-4.32 (m, 1H), 4.23-3.99 (m, 3H), 3.74-3.53 (m, 2H), 3.26-3.01 (m, 2H), 2.34-2.18 (m, 1H), 2.15-1.75 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 314. | 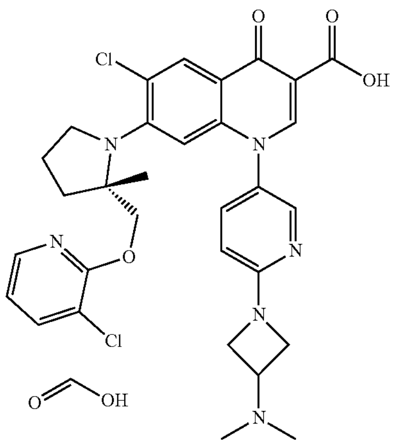 | Column: XBridge Prep C18 OBD Column, 19*150 mm, 5 μm; Mobile Phase A: Water (0.1% FA), Mobile Phase B: ACN; Flow rate: 25 mL/min; Gradient: 10% B to 10% B in 2 min, 10% B to 33% B in 2.5 min, 33% B to 77% B in 11 min, 77% B; Wave Length: 220 nm; RT1(min): 7.58; Number Of Runs: 0 | rac-(R)-6-chloro-7-(2-(((3-chloropyridin-2-yl)oxy) methyl)-2-methyl-pyrrolidin-1-yl)-1-(6-(3-(dimethyl-amino) azetidin-1-yl)pyridin-3-yl)-4-oxo-1,4-dihydro-quinoline-3-carboxylic acid formic acid | LCMS (ESI): $[M + H + 2]^+$: 624.75 1H NMR (300 MHz, DMSO-d6) δ 8.59 (s, 1H), 8.30-8.17 (m, 2H), 8.09-7.96 (m, 1H), 7.94-7.84 (m, 1H), 7.77-7.64 (m, 1H), 7.11-6.90 (m, 2H), 6.42-6.28 (m, 1H), 4.37-4.26 (m, 1H), 4.18-4.06 (m, 1H), 4.02-3.94 (m, 2H), 3.79-3.71 (m, 2H), 3.65-3.55 (m, 2H), 3.24-3.16 (m, 1H), 2.22-2.09 (m, 7H), 2.01-1.77 (m, 3H), 1.29-1.09 (m, 3H). | ++++ |
| 315. | 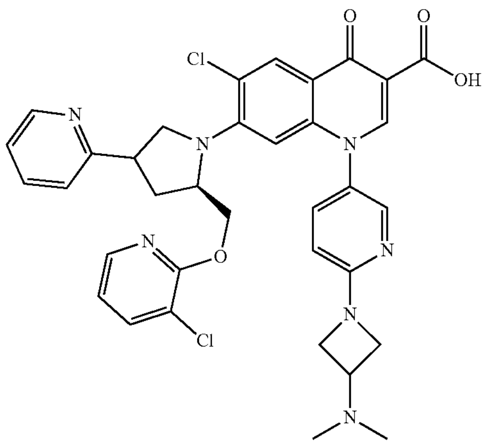 [SMILES: CN(C)C1CN(c2ccc(-n3cc(C(=O)O)c(=O)c4cc(Cl)c(N5CC(c6ccccn6)C[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 10% B to 10% B in 2 min, 10% B to 21% B in 2.5 min, 21% B to 27% B in 9 min, 27% B; Wave Length: 254 nm; RT1(min): 8.33; Number Of Runs: 0 | rac-6-chloro-7-((2R)-2-(((3-chloropyridin-2-yl)oxy) methyl)-4-(pyridin-2-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI): [M + H]+: 686.20 1H NMR (400 MHz, DMSO-d6) δ 15.01 (s, 1H), 8.50-8.33 (m, 2H), 8.22-8.02 (m, 2H), 7.92-7.54 (m, 4H), 7.36-6.86 (m, 3H), 6.55-6.21 (m, 2H), 4.87-4.69 (m, 1H), 4.39-4.21 (m, 2H), 4.06-3.94 (m, 3H), 3.82-3.68 (m, 3H), 3.17-3.09 (m, 2H), 2.57-2.47 (m, 1H), 2.34-2.20 (m, 1H), 2.07 (s, 6H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 316. | 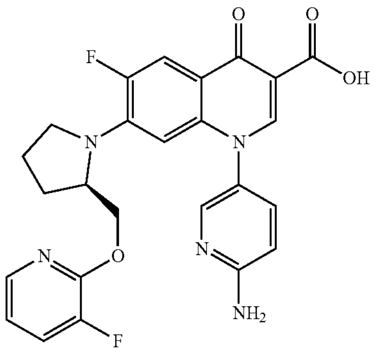 [SMILES: Nc1ccc(-n2cc(C(=O)O)c(=O)c3cc(F)c(N4CCC[C@@H]4COc4ncccc4F)cc32)cn1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 25 B to 53 B in 9 min; 254 nm; RT1: 9.1; RT2:; Injection Volumn: ml; Number Of Runs:; | 1-(6-Aminopyridin-3-yl)-6-fluoro-7-[(2R)-2-[[(3-fluoropyridin-2-yl)oxy]methyl]pyrrolidin-1-yl]-4-oxoquinoline-3-carboxylic acid | LCMS (ESI) [M + H]+: 494.00. $^{1}H$ NMR (300 MHz, DMSO-d6) δ 15.42 (s, 1H), 8.49 (s, 1H), 8.10 (d, J = 2.7 Hz, 1H), 7.96-7.79 (m, 2H), 7.72-7.49 (m, 2H), 7.07-6.91 (m, 1H), 6.71-6.38 (m, 3H), 6.14 (d, J = 7.4 Hz, 1H), 4.56 (d, J = 13.3 Hz, 1H), 4.35 (d, J = 4.7 Hz, 2H), 3.20 (s, 2H), 2.17-1.78 (m, 4H). | ++++ |
| 317. | 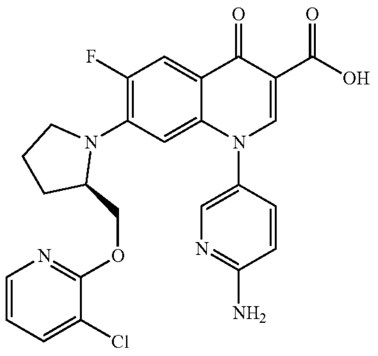 [SMILES: Nc1ccc(-n2cc(C(=O)O)c(=O)c3cc(F)c(N4CCC[C@@H]4COc4ncccc4Cl)cc32)cn1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 23 B to 56 B in 9 min; 254 nm; RT1: 9.97; RT2:; Injection Volumn: ml; Number Of Runs:; | 1-(6-Aminopyridin-3-yl)-7-[(2R)-2-[[(3-chloropyridin-2-yl)oxy]methyl]pyrrolidin-1-yl]-6-fluoro-4-oxoquinoline-3-carboxylic acid | LCMS (ESI) [M + H]+: 509.95. $^{1}H$ NMR (300 MHz, DMSO-d6) δ 15.41 (s, 1H), 8.49 (s, 1H), 8.11 (s, 1H), 8.03-7.95 (m, 1H), 7.92-7.78 (m, 2H), 7.58 (s, 1H), 6.98 (d, J = 7.7, 4.9 Hz, 1H), 6.66-6.44 (m, 3H), 6.15 (d, J = 7.5 Hz, 1H), 4.58 (s, 1H), 4.36 (d, J = 4.6 Hz, 2H), 3.35 (s, 1H), 3.21 (d, J = 9.1 Hz, 1H), 2.22-1.85 (m, 4H). | ++++ |
| 318. | 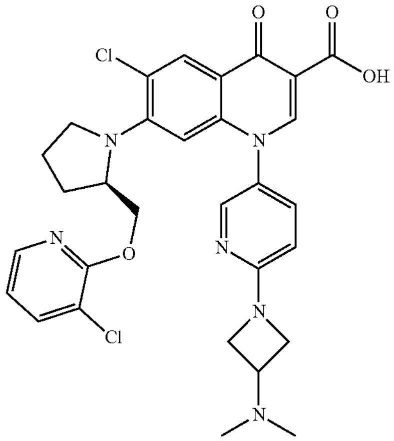 [SMILES: CN(C)C1CN(c2ccc(-n3cc(C(=O)O)c(=O)c4cc(Cl)c(N5CCC[C@@H]5COc5ncccc5Cl)cc43)cn2)C1] | reverse phase flash chromatography | 6-Chloro-7-[(2R)-2-[[(3-chloropyridin-2-yl)oxy]methyl]pyrrolidin-1-yl]-1-[6-[3-(dimethylamino)azetidin-1-yl]pyridin-3-yl]-4-oxoquinoline-3-carboxylic acid | LCMS (ESI) [M + H]+: 609.15. $^{1}H$ NMR (300 MHz, DMSO-d6) δ 15.09 (s, 1H), 8.52 (d, J = 7.2 Hz, 1H), 8.24 (d, J = 2.6 Hz, 1H), 8.16 (s, 1H), 7.90 (td, J = 4.7, 1.7 Hz, 1H), 7.86-7.77 (m, 1H), 7.68 (d, J = 8.0, 7.3, 2.7 Hz, 1H), 6.95 (s, 1H), 6.63-6.21 (m, 2H), 4.68 (d, J = 28.4 Hz, 1H), 4.45-4.15 (m, 2H), 4.13-4.00 (m, 2H), 3.82 (s, 2H), 3.64-3.41 (m, 1H), 3.30-3.10 (m, 2H), 2.25 (d, J = 9.0 Hz, 1H), 2.16 (s, 6H), 2.02-1.71 (m, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 319. | 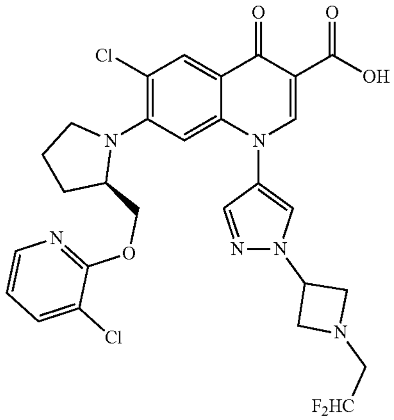 [SMILES: O=C(O)c1cn(-c2cnn(C3CN(CC(F)F)C3)c2)c2cc(N3CCC[C@@H]3COc3ncccc3Cl)c(Cl)cc2c1=O] | Column: SunFire Prep C18 OBD Column, 19Á 150 mm 5 um 10 nm; Mobile Phase A: Water (0.1% FA), Mobile Phase B: ACN; Flow rate: 25 mL/min; Gradient: 35 B to 62 B in 8 min; 254 nm; RT1: 8.37; RT2:; Injection Volumn: ml; Number Of Runs:; | 6-Chloro-7-[(2R)-2-[[(3-chloropyridin-2-yl)oxy] methyl] pyrrolidin-1-yl]-1-[1-[1-(2,2-difluoroethyl) azetidin-3-yl]pyrazol-4-yl]-4-oxoquinoline-3-carboxylic acid | LCMS (ESI) [M + H]+: 619.05. $^1$H NMR (400 MHz, DMSO-d6) δ 14.99 (s, 1H), 8.59 (s, 1H), 8.54 (s, 1H), 8.14 (s, 1H), 7.94 (d, J = 0.7 Hz, 1H), 7.88-7.83 (m, 1H), 7.78 (s, 1H), 7.01-6.82 (m, 1H), 6.67 (s, 1H), 6.01 (d, J = 55.7, 4.1 Hz, 1H), 5.22-5.09 (m, 1H), 4.78 (s, 1H), 4.31 (d, J = 4.2 Hz, 2H), 3.85 (s, 2H), 3.62 (s, 2H), 3.58-3.47 (m, 1H), 3.28 (d, J = 9.9 Hz, 1H), 3.04-2.88 (m, 2H), 2.29 (d, J = 18.8, 10.2 Hz, 1H), 2.08-1.89 (m, 2H), 1.81 (s, 1H). | ++++ |
| 320. | 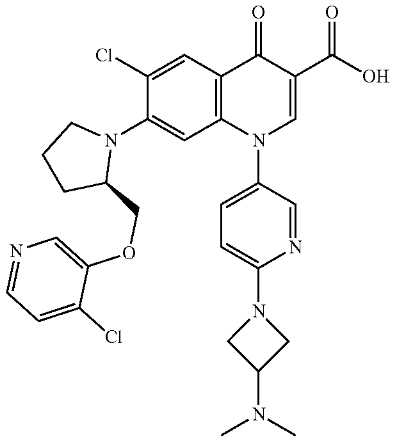 [SMILES: CN(C)C1CN(c2ccc(-n3cc(C(=O)O)c(=O)c4cc(Cl)c(N5CCC[C@@H]5COc5cnccc5Cl)cc43)cn2)C1] | Column: XSelect CSH Prep C18 OBD Column,, 5 um, 19*150 mm; Mobile Phase A: Water (0.1% FA), Mobile Phase B: MeOH-Preparative; Flow rate: 25 mL/min; Gradient: 45 B to 50 B in 8 min; 220 nm; RT1: 5.18; RT2:; Injection Volumn: ml; Number Of Runs:; | 6-Chloro-7-[(2R)-2-[[(4 chloropyridin-3-yl)oxy] methyl] pyrrolidin-1-yl]-1-[6-[3-(dimethyl-amino) azetidin-1-yl]pyridin-3-yl]-4-oxoquinoline-3-carboxylic acid | LCMS (ESI) [M + H]+: 609.25. $^1$H NMR (400 MHz, DMSO-d6) δ 15.07 (s, 1H), 8.54 (d, J = 11.0 Hz, 1H), 8.36-8.23 (m, 2H), 8.17 (d, J = 4.6 Hz, 1H), 8.14-8.08 (m, 1H), 7.80-7.66 (m, 1H), 7.47 (s, 1H), 6.72-6.44 (m, 2H), 6.27 (d, J = 8.8 Hz, 1H), 4.60 (d, J = 44.8 Hz, 1H), 4.29-4.17 (m, 1H), 4.04 (s, 3H), 3.79 (s, 2H), 3.71-3.54 (m, 1H), 3.28-3.06 (m, 2H), 2.35-2.20 (m, 1H), 2.14 (s, 6H), 1.94 (d, J = 17.6, 8.9 Hz, 2H), 1.86-1.74 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 321. | 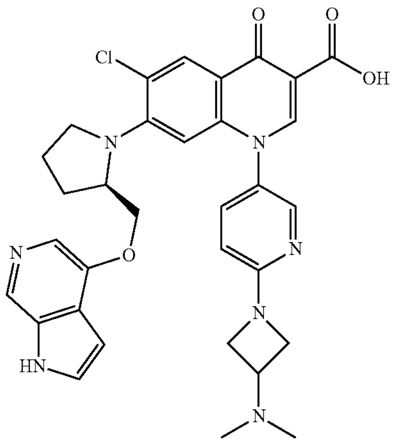 [SMILES: CN(C)C1CN(c2ccc(-n3cc(C(=O)O)c(=O)c4cc(Cl)c(N5CCC[C@@H]5COc5cncc6[nH]ccc56)cc43)cn2)C1] | Column: SunFire Prep C18 OBD Column, 19¡A 150 mm 5 um 10 nm; Mobile Phase A: Water (0.1% FA), Mobile Phase B: ACN; Flow rate: 25 mL/min; Gradient: 12 B to 30 B in 8 min, 30 B to B in min, B to B in min, B to B in min, B to B in min; 254 nm; RT1: 7.03; RT2:; Injection Volumn: ml; Number Of Runs:; | 6-Chloro-1-[6-[3-(dimethyl-amino) azetidin-1-yl]pyridin-3-yl]-4-oxo-7-[(2R)-2-([1H-pyrrolo[3,2-c]pyridin-4-yloxy]methyl) pyrrolidin-1-yl]quinoline-3-carboxylic acid | LCMS (ESI) [M + H]+: 614.1. $^{1}$H NMR (300 MHz, DMSO-d6) δ 15.13 (s, 1H), 11.44 (d, J = 14.3 Hz, 1H), 8.48 (d, J = 9.8 Hz, 1H), 8.35-8.03 (m, 2H), 7.70-7.40 (m, 2H), 7.25 (s, 1H), 6.96 (s, 1H), 6.55-5.84 (m, 3H), 4.56 (s, 1H), 4.46-4.19 (m, 1H), 4.14-3.88 (m, 2H), 3.84-3.50 (m, 4H), 3.19 (s, 2H), 2.41-2.19 (m, 1H), 2.13 (d, J = 5.9 Hz, 6H), 2.04-1.69 (m, 3H). | ++++ |
| 322. | 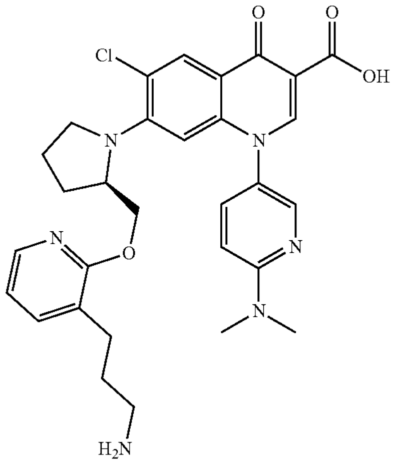 [SMILES: CN(C)c1ccc(-n2cc(C(=O)O)c(=O)c3cc(Cl)c(N4CCC[C@@H]4COc4ncccc4CCCN)cc32)cn1] | Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min | 7-[(2R)-2-([[3-(2-Aminoethoxy) pyridin-2-yl]oxy] methyl) pyrrolidin-1-yl]-6-chloro-1-[6-(dimethyl-amino) pyridin-3-yl]-4-oxoquinoline-3-carboxylic acid | LCMS (ESI) [M + H]+: 579.25. $^{1}$H NMR (300 MHz, DMSO-d6) δ 8.59 (d, J = 6.1 Hz, 1H), 8.34 (d, J = 9.1 Hz, 1H), 8.24 (s, 1H), 7.75 (d, J = 9.9 Hz, 1H), 7.64 (d, J = 5.3 Hz, 1H), 7.37 (d, J = 7.2 Hz, 1H), 7.04-6.85 (m, 1H), 6.60 (d, J = 9.0 Hz, 1H), 6.46 (d, J = 5.2 Hz, 1H), 4.76 (d, J = 27.5 Hz, 1H), 4.45 (s, 1H), 4.21-4.03 (m, 3H), 3.74-3.53 (m, 1H), 3.17 (d, J = 3.8 Hz, 7H), 2.38-2.23 (m, 1H), 2.12-1.75 (m, 3H). | ++++ |
| 323. | 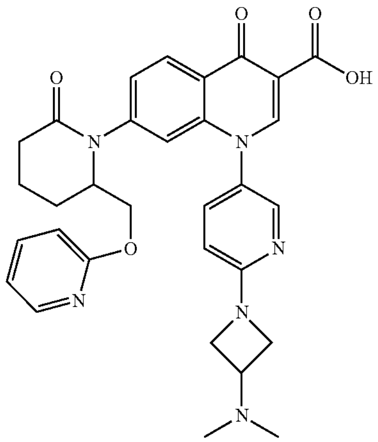 [SMILES: CN(C)C1CN(c2ccc(-n3cc(C(=O)O)c(=O)c4ccc(N5C(=O)CCCC5COc5ccccn5)cc43)cn2)C1] | Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min | 1-[6-[3-(Dimethyl-amino)azetidin-1-yl]pyridin-3-yl]-4-oxo-7-[2-oxo-6-[(pyridin-2-yloxy)methyl] piperidin-1-yl]quinoline-3-carboxylic acid | LCMS (ESI) [M + H]+: 569.30. $^{1}$H NMR (300 MHz, DMSO-d6) δ 8.63 (d, J = 2.1 Hz, 1H), 8.39 (d, J = 7.9 Hz, 1H), 8.30-8.11 (m, 1H), 8.02 (s, 1H), 7.77-7.41 (m, 3H), 7.12 (d, J = 21.4 Hz, 1H), 7.02-6.85 (m, 1H), 6.61-6.26 (m, 2H), 4.33 (s, 1H), 4.23-3.97 (m, 4H), 3.92-3.76 (m, 2H), 3.25 (d, J = 6.1 Hz, 1H), 2.42 (d, J = 16.9 Hz, 2H), 2.15 (s, 7H), 1.96 (s, 2H), 1.81 (s, 1H). | + |

TABLE 1-continued

| Compound | Product | Prep HPLC Method | IUPAC name | Analytical data | Potency Lin28a-dep Z11 $IC_{50}$ (μM) |
| --- | --- | --- | --- | --- | --- |
| 324. | 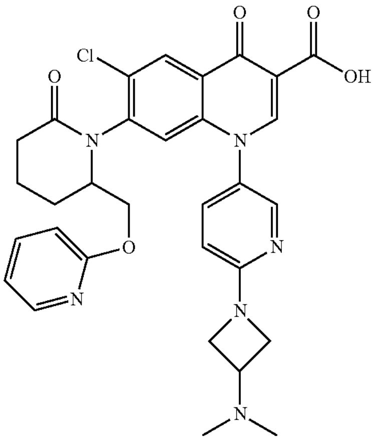 [SMILES: CN(C)C1CN(c2ccc(-n3cc(C(=O)O)c(=O)c4cc(Cl)c(N5C(=O)CCCC5COc5ccccn5)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 17 B to 23 B in 10 min, 23 B to B in min, B to B in min, B to B in min, B to B in min; 254 nm; RT1: 7.02; RT2:; Injection Volumn: ml; Number Of Runs:; | 6-Chloro-1-[6-[3-(dimethyl-amino)azetidin-1-yl]pyridin-3-yl]-4-oxo-7-[2-oxo-6-[(pyridin-2-yloxy)methyl]piperidin-1-yl]quinoline-3-carboxylic acid | LCMS (ESI) [M + H]+: 603.3. $^1$H NMR (300 MHz, DMSO-d6) δ 8.59 (d, J = 13.7 Hz, 1H), 8.52-7.99 (m, 3H), 7.77-7.51 (m, 2H), 7.45 (d, J = 8.1 Hz, 1H), 7.31-7.14 (m, 1H), 6.95 (s, 1H), 6.64-6.48 (m, 1H), 6.45 (s, 1H), 4.84 (d, J = 6.0 Hz, 1H), 4.26-4.03 (m, 4H), 3.96-3.80 (m, 2H), 3.44-3.25 (m, 1H), 2.45 (d, J = 6.3 Hz, 2H), 2.20 (d, J = 1.6 Hz, 7H), 2.14-2.07 (m, 1H), 1.99 (s, 1H), 1.83 (s, 1H). | ++ |
| 325. | 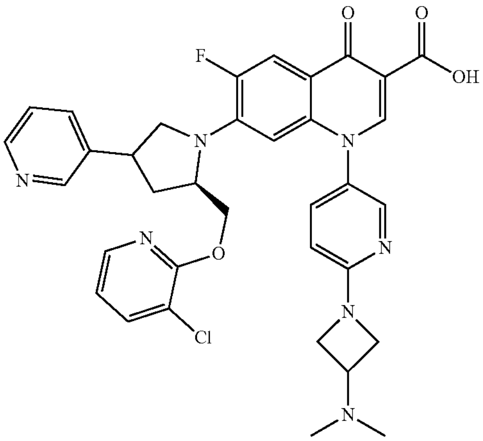 [SMILES: CN(C)C1CN(c2ccc(-n3cc(C(=O)O)c(=O)c4cc(F)c(N5CC(c6cccnc6)C[C@@H]5COc5ncccc5Cl)cc43)cn2)C1] | Column: Gemini-NX C18 AXAI Packed, 21.2*150 mm 5 um; Mobile Phase A: Water (0.1% FA), Mobile Phase B: ACN; Flow rate: 25 mL/min; Gradient: 5 B to 5 B in 2 min, 5 B to 11 B in 2.5 min, 11 B to 32 B in 11 min, 32 B to B in min, B to B in min; 254 nm; RT1: 9.8; RT2:; Injection Volumn: ml; Number Of Runs:; | 7-[(2R)-2-[[(3-Chloropyridin-2-yl)oxy]methyl]-4-(pyridin-3-yl)pyrrolidin-1-yl]-1-[6-[3-(dimethyl-amino)azetidin-1-yl]pyridin-3-yl]-6-fluoro-4-oxoquinoline-3-carboxylic acid | LCMS (ESI) [M + H]+: 670.1. $^1$H NMR (400 MHz, DMSO-d6) δ 15.34 (d, J = 14.8 Hz, 1H), 8.56 (d, J = 2.5 Hz, 1H), 8.53-8.41 (m, 2H), 8.29-8.20 (m, 1H), 7.98-7.84 (m, 3H), 7.83-7.62 (m, 2H), 7.39 (s, 1H), 7.00 (d, J = 8.4, 4.2 Hz, 1H), 6.58-6.48 (m, 1H), 6.27 (s, 2H), 4.46 (d, J = 9.7 Hz, 3H), 4.03 (d, J = 20.0, 9.7 Hz, 2H), 3.84-3.68 (m, 3H), 3.61-3.42 (m, 2H), 3.21 (s, 1H), 2.76-2.63 (m, 1H), 2.12 (s, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 326. | 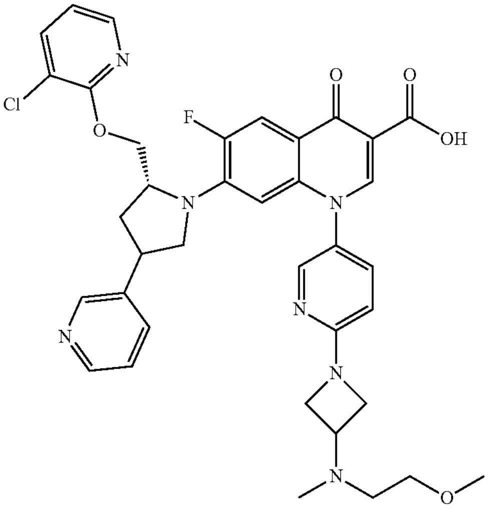 [SMILES: COCCN(C)C1CN(c2ccc(-n3cc(C(=O)O)c(=O)c4cc(F)c(N5CC(c6cccnc6)C[C@@H]5COc5ncccc5Cl)cc43)cn2)C1] | Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min | 7-[(2R)-2-[[(3-Chloropyridin-2-yl)oxy]methyl]-4-(pyridin-3-yl)pyrrolidin-1-yl]-6-fluoro-1-(6-[3-[(2-methoxyethyl)(methyl)amino]azetidin-1-yl]pyridin-3-yl)-4-oxoquinoline-3-carboxylic acid | LCMS (ESI) [M + H]+: 714.30. $^1$H NMR (400 MHz, DMSO-d6) δ 15.29 (s, 1H), 8.56 (d, J = 2.6 Hz, 1H), 8.47 (d, J = 5.3 Hz, 2H), 8.29-8.21 (m, 1H), 7.98-7.84 (m, 3H), 7.81-7.74 (m, 1H), 7.73-7.65 (m, 1H), 7.38 (s, 1H), 7.00 (s, 1H), 6.54 (d, J = 8.8 Hz, 1H), 6.36-6.24 (m, 2H), 4.70-4.32 (m, 3H), 4.12-3.91 (m, 2H), 3.85-3.66 (m, 3H), 3.60-3.39 (m, 5H), 3.25 (d, J = 1.4 Hz, 3H), 2.73-2.61 (m, 1H), 2.47 (s, 2H), 2.17 (d, J = 2.8 Hz, 4H). | ++++ |
| 327. | 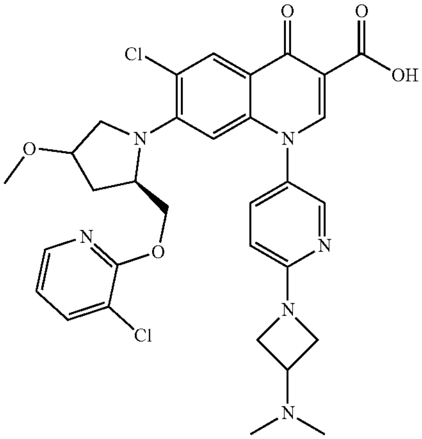 [SMILES: COC1C[C@H](COc2ncccc2Cl)N(c2cc3c(cc2Cl)c(=O)c(C(=O)O)cn3-c2ccc(N3CC(N(C)C)C3)nc2)C1] | Column: XSelect CSH Prep C18 OBD Column,, 19*250 mm, 5 um; Mobile Phase A: Water (0.1% FA), Mobile Phase B: ACN; Flow rate: 25 mL/min; Gradient: 10 B to 40 B in 7 min, 40 B to B in min, B to B in min, B to B in min, B to B in min; 254/220 nm; RT1: 6.87; RT2:; Injection Volumn: ml; Number Of Runs:; | 6-Chloro-7-[(2R)-2-[[(3-chloropyridin-2-yl)oxy]methyl]-4-methoxy-pyrrolidin-1-yl]-1-[6-[3-(dimethyl-amino)azetidin-1-yl]pyridin-3-yl]-4-oxoquinoline-3-carboxylic acid | LCMS (ESI) [M + H]+: 639.20. $^1$H NMR (400 MHz, DMSO-d6) δ 15.06 (s, 1H), 8.52 (d, J = 8.8 Hz, 1H), 8.25 (s, 1H), 8.15 (s, 1H), 7.90 (d, J = 4.5 Hz, 1H), 7.85-7.62 (m, 2H), 6.95 (q, J = 6.3 Hz, 1H), 6.50 (d, J = 88.8 Hz, 2H), 4.89-4.60 (m, 1H), 4.48-4.32 (m, 1H), 4.30-4.10 (m, 3H), 3.99 (s, 3H), 3.26 (d, J = 8.6 Hz, 6H), 2.56 (s, 1H), 2.39 (s, 7H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 328. | 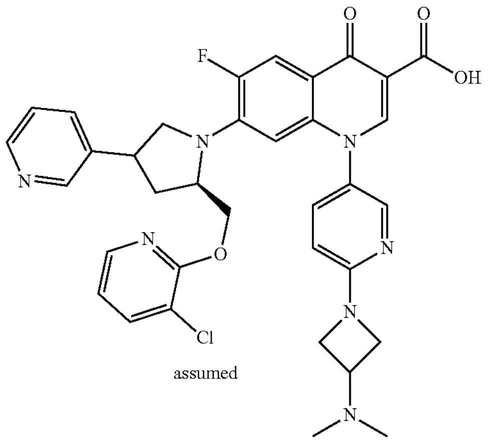 [SMILES: CN(C)C1CN(c2ccc(-n3cc(C(=O)O)c(=O)c4cc(F)c(N5CC(c6cccnc6)C[C@@H]5COc5ncccc5Cl)cc43)cn2)C1] assumed | Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min. | 7-[(2R)-2-[[(3-Chloropyridin-2-yl)oxy]methyl]-4-(pyridin-3-yl)pyrrolidin-1-yl]-1-[6-[3-(dimethyl-amino)azetidin-1-yl]pyridin-3-yl]-6-fluoro-4-oxoquinoline-3-carboxylic acid | LCMS (ESI) [M + H]+: 670.25. $^1$H NMR (400 MHz, DMSO-d6) δ 15.32 (s, 1H), 8.56 (d, J = 2.5 Hz, 1H), 8.53-8.44 (m, 2H), 8.30-8.19 (m, 1H), 7.99-7.86 (m, 3H), 7.85-7.65 (m, 2H), 7.45-7.35 (m, 1H), 6.99 (d, J = 4.9 Hz, 1H), 6.65-6.50 (m, 1H), 6.36-6.20 (m, 2H), 4.46 (d, J = 9.7 Hz, 3H), 4.18-3.94 (m, 2H), 3.88-3.67 (m, 3H), 3.58-3.44 (m, 2H), 3.21 (s, 1H), 2.67 (m, J = 11.4, 6.7 Hz, 1H), 2.12 (s, 7H). | ++++ |
| 329. | 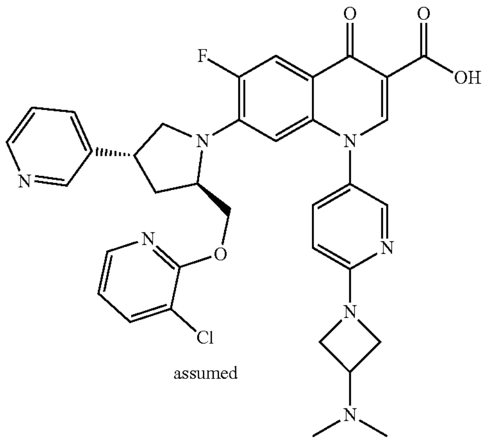 [SMILES: CN(C)C1CN(c2ccc(-n3cc(C(=O)O)c(=O)c4cc(F)c(N5C[C@@H](c6cccnc6)C[C@@H]5COc5ncccc5Cl)cc43)cn2)C1] assumed | Column: XBridge Shield RP18 OBD Column, 5 um, 19*150 mm; Mobile Phase A: Water (0.1% FA), Mobile Phase B: ACN; Flow rate: 25 mL/min; Gradient: 60% B to 90% B in 8 min; 254/220 nm; Rt: 7.31 min | 7-[(2R,4R)-2-[[(3-chloropyridin-2-yl)oxy]methyl]-4-(pyridin-3-yl)pyrrolidin-1-yl]-1-[6-[3-(dimethyl-amino)azetidin-1-yl]pyridin-3-yl]-6-fluoro-4-oxoquinoline-3-carboxylic acid | LCMS (ESI) [M + H]+: 670.20. $^1$H NMR (300 MHz, DMSO-d6) δ 15.30 (s, 1H), 8.57 (s, 1H), 8.54-8.45 (m, 2H), 8.25 (d, J = 2.8 Hz, 1H), 8.01-7.86 (m, 3H), 7.85-7.64 (m, 2H), 7.39 (d, J = 7.9, 4.7 Hz, 1H), 7.07-6.92 (m, 1H), 6.59-6.19 (m, 2H), 4.47 (s, 3H), 4.02 (d, J = 6.6 Hz, 2H), 3.88-3.66 (m, 3H), 3.49 (s, 2H), 3.22 (d, J = 5.6 Hz, 1H), 2.79-2.62 (m, 1H), 2.23 (s, 1H), 2.12 (s, 6H). | ++++ |
| 330. | 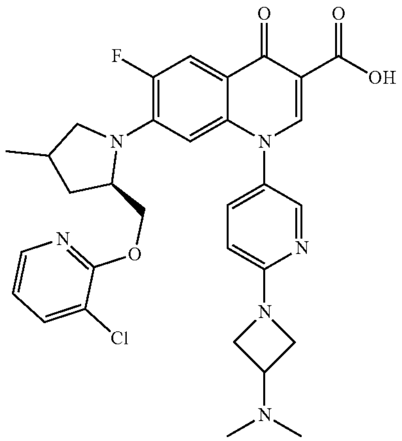 [SMILES: CC1C[C@H](COc2ncccc2Cl)N(c2cc3c(cc2F)c(=O)c(C(=O)O)cn3-c2ccc(N3CC(N(C)C)C3)nc2)C1] | Column: XSelect CSH Prep C18 OBD Column,, 19*250 mm, 5 um; Mobile Phase A: Water (0.05% FA), Mobile Phase B: ACN; Flow rate: 25 mL/min; Gradient: 5 B to 95 B in 7 min, 95 B to B in min, B to B in min, B to B in min, B to B in min; 254/220 nm; RT1: 4.63; RT2:; Injection Volumn: ml; Number Of Runs:; | 7-[(2R)-2-[[(3-Chloropyridin-2-yl)oxy]methyl]-4-methyl-pyrrolidin-1-yl]-1-[6-[3-(dimethyl-amino)azetidin-1-yl]pyridin-3-yl]-6-fluoro-4-oxoquinoline-3-carboxylic acic | LCMS (ESI) [M + H]+: 607.15. $^1$H NMR (300 MHz, DMSO-d6) δ 15.36 (d, J = 11.0 Hz, 1H), 8.47 (d, J = 5.6 Hz, 1H), 8.27 (s, 1H), 7.93-7.80 (m, 3H), 7.79-7.65 (m, 1H), 6.97 (d, J = 7.7, 5.2 Hz, 1H), 6.63-6.26 (m, 1H), 6.15 (d, J = 7.5 Hz, 1H), 4.56-4.28 (m, 3H), 4.20-4.01 (m, 2H), 3.88 (d, J = 7.3 Hz, 2H), 3.35 (s, 2H), 3.13-2.95 (m, 1H), 2.47-2.15 (m, 8H), 1.59 (s, 1H), 1.06 (d, J = 6.2 Hz, 3H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 331. | 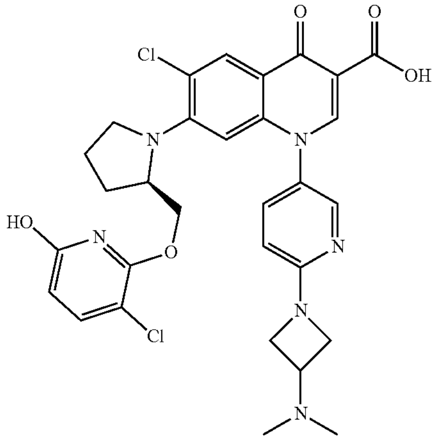 [SMILES: CN(C)C1CN(c2ccc(-n3cc(C(=O)O)c(=O)c4cc(Cl)c(N5CCC[C@@H]5COc5nc(O)ccc5Cl)cc43)cn2)C1] | Column: XSelect CSH Prep C18 OBD Column,, 19*250 mm, 5 um; Mobile Phase A: Water (0.05% FA), Mobile Phase B: ACN; Flow rate: 25 mL/min; Gradient: 10 B to 35 B in 10 min, 35 B to B in min, B to B in min, B to B in min, B to B in min; 254/220 nm; RT1: 9.35; RT2:; Injection Volumn: ml; Number Of Runs:; | 6-Chloro-7-[(2R)-2-[[(3-chloro-6-hydroxy-pyridin-2-yl)oxy] methyl] pyrrolidin-1-yl]-1-[6-[3-(dimethyl-amino) azetidin-1-yl]pyridin-3-yl]-4-oxoquinoline-3-carboxylic acid | LCMS (ESI) [M + H]+: 625.25. $^{1}$H NMR (300 MHz, DMSO-d6) δ 15.12 (s, 1H), 10.71 (s, 1H), 8.53 (d, J = 9.9 Hz, 1H), 8.25 (d, J = 2.6 Hz, 1H), 8.20-8.11 (m, 1H), 7.74-7.62 (m, 1H), 7.60-7.50 (m, 1H), 6.66-6.23 (m, 2H), 6.13 (s, 1H), 4.64 (d, J = 52.0 Hz, 1H), 4.39-3.98 (m, 4H), 3.81 (d, J = 9.0 Hz, 2H), 3.67-3.47 (m, 1H), 3.22 (d, J = 12.2 Hz, 2H), 2.16 (s, 7H), 2.04-1.69 (m, 3H). | ++++ |
| 332. | 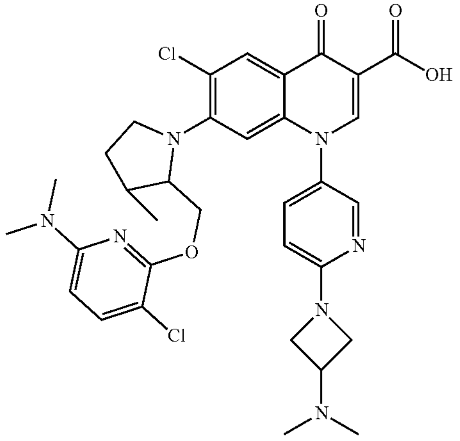 [SMILES: CC1CCN(c2cc3c(cc2Cl)c(=O)c(C(=O)O)cn3-c2ccc(N3CC(N(C)C)C3)nc2)C1COc1nc(N(C)C)ccc1Cl] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 24% B to 50% B in 7 min, 50% B; Wave Length: 254/220 nm; RT1(min): 6.43; Number Of Runs: 0 | 6-Chloro-7-[2-({[3-chloro-6-(dimethyl-amino) pyridin-2-yl]oxy} methyl)-3-methyl-pyrrolidin-1-yl]-1-{6-[3-(dimethyl-amino) azetidin-1-yl]pyridin-3-yl}-4-oxoquinoline-3-carboxylic acid | LCMS (ESI) [M + H]+: 666.25. $^{1}$H NMR (300 MHz, DMSO-d6) δ 15.14 (d, J = 2.3 Hz, 1H), 8.50 (s, 1H), 8.34-8.22 (m, 1H), 8.13 (d, J = 8.9 Hz, 1H), 7.68 (d, J = 9.1 Hz, 1H), 7.46-7.33 (m, 1H), 6.69-6.36 (m, 1H), 6.29 (s, 1H), 6.11-5.81 (m, 1H), 5.02-4.65 (m, 1H), 4.58-4.23 (m, 1H), 4.04 (d, J = 62.7 Hz, 5H), 3.79-3.43 (m, 2H), 3.23-3.06 (m, 1H), 2.83 (s, 6H), 2.31 (d, J = 17.4 Hz, 5H), 2.18-2.01 (m, 1H), 1.95-1.06 (m, 4H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 333. | 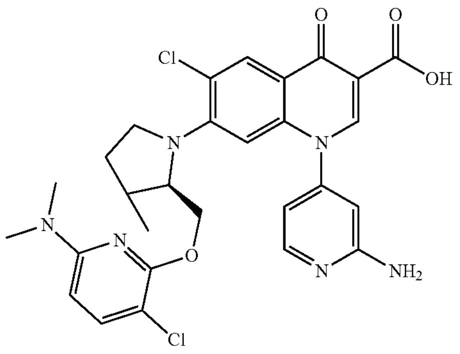 [SMILES: CC1CCN(c2cc3c(cc2Cl)c(=O)c(C(=O)O)cn3-c2ccnc(N)c2)[C@H]1COc1nc(N(C)C)ccc1Cl] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 40% B to 95% B in 7 min, 95% B; Wave Length: 254/220 nm; RT1(min): 6.45; Number Of Runs: 0 | 1-(2-Aminopyridin-4-yl)-6-chloro-7-fluoro-4-oxoquinoline-3-carboxylic acid | LCMS (ESI) [M + H]$^+$: 583.15. $^1$H NMR (300 MHz, DMSO-d6) δ 15.05 (s, 1H), 8.55 (d, J = 7.9 Hz, 1H), 8.29-7.93 (m, 2H), 7.42 (s, 1H), 6.78-6.46 (m, 4H), 6.36 (d, J = 12.2 Hz, 1H), 6.14-5.71 (m, 1H), 5.01-4.77 (m, 1H), 4.72-3.91 (m, 2H), 3.47 (d, J = 29.4 Hz, 1H), 3.27-3.02 (m, 1H), 2.78 (d, J = 25.1 Hz, 6H), 2.60 (s, 1H), 2.19-2.02 (m, 1H), 1.52 (s, 1H), 1.27-1.08 (m, 3H). | ++++ |
| 334. | 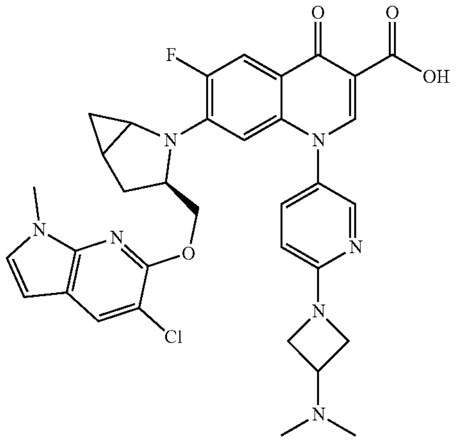 [SMILES: CN(C)C1CN(c2ccc(-n3cc(C(=O)O)c(=O)c4cc(F)c(N5C6CC6C[C@@H]5COc5nc6c(ccn6C)cc5Cl)cc43)cn2)C1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 20% B to 44% B in 10 min, 44% B; Wave Length: 254/220 nm; RT1(min): 9.27; Number Of Runs: 0 | 7-[(3R)-3-[({5-chloro-1-methylpyrrolo[2,3-b]pyridin-6-yl}oxy)methyl]-2-azabicyclo[3.1.0]hexan-2-yl]-1-{6-[3-(dimethylamino)azetidin-1-yl]pyridin-3-yl}-6-fluoro-4-oxoquinoline-3-carboxylic acid | LCMS (ESI) [M + H]+: 658.15. $^1$H NMR (300 MHz, DMSO-d6) δ 15.46 (s, 1H), 8.59 (d, J = 1.6 Hz, 1H), 8.36 (d, J = 2.6 Hz, 1H), 8.11 (d, J = 6.1 Hz, 1H), 8.04-7.92 (m, 1H), 7.87-7.77 (m, 1H), 7.40 (d, J = 3.3 Hz, 1H), 6.67-6.52 (m, 2H), 6.43 (s, 1H), 4.53 (d, J = 24.0 Hz, 3H), 4.10 (d, J = 8.3 Hz, 2H), 3.93 (s, 2H), 3.74 (d, J = 3.2 Hz, 3H), 3.24 (s, 1H), 3.14 (s, 1H), 2.48-2.26 (m, 6H), 2.18 (d, J = 16.3 Hz, 1H), 1.86 (s, 1H), 0.91 (d, J = 8.2 Hz, 2H), 0.46 (d, J = 13.4 Hz, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 335. | 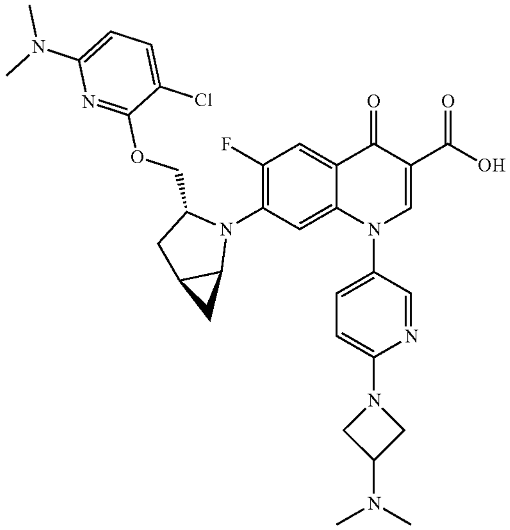 [SMILES: CN(C)c1ccc(Cl)c(OC[C@H]2C[C@@H]3C[C@@H]3N2c2cc3c(cc2F)c(=O)c(C(=O)O)cn3-c2ccc(N3CC(N(C)C)C3)nc2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 20% B to 42% B in 7 min, 42% B; Wave Length: 254/220 nm; RT1(min): 9.55; Number Of Runs: 0 | 7-[(1S,3R,5S)-3-({[3-Chloro-6-(dimethyl-amino)pyridin-2-yl]oxy}methyl)-2-azabicyclo[3.1.0]hexan-2-yl]-1-{6-[3-(dimethyl-amino)azetidin-1-yl]pyridin-3-yl}-6-fluoro-4-oxoquinoline-3-carboxylic acid | LCMS (ESI) [M + H]+: 648.20. $^1$H NMR (300 MHz, DMSO-d6) δ 15.45 (s, 1H), 8.59 (d, J = 2.0 Hz, 1H), 8.44-8.17 (m, 1H), 8.05-7.74 (m, 2H), 7.64-7.46 (m, 1H), 6.74-6.36 (m, 2H), 6.23 (s, 1H), 4.41 (d, J = 20.3 Hz, 3H), 4.12 (s, 2H), 3.91 (s, 2H), 3.20 (d, J = 24.0 Hz, 2H), 3.01 (d, J = 2.0 Hz, 6H), 2.90-2.78 (m, 1H), 2.27 (s, 7H), 2.14 (d, J = 22.1 Hz, 1H), 1.82 (s, 1H), 0.88 (s, 1H), 0.44 (d, J = 12.9 Hz, 1H). | ++++ |
| 336. | 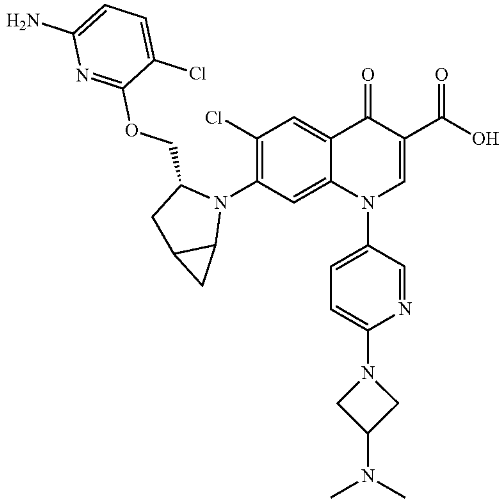 [SMILES: CN(C)C1CN(c2ccc(-n3cc(C(=O)O)c(=O)c4cc(Cl)c(N5C6CC6C[C@@H]5COc5nc(N)ccc5Cl)cc43)cn2)C1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 20% B to 42% B in 7 min, 42% B; Wave Length: 254/220 nm; RT1(min): 9.55; Number Of Runs: 0 | 7-[(3R)-3-{[(6-Amino-3-chloropyridin-2-yl)oxy]methyl}-2-azabicyclo[3.1.0]hexan-2-yl]-6-chloro-1-{6-[3-(dimethyl-amino)azetidin-1-yl]pyridin-3-yl}-4-oxoquinoline-3-carboxylic acid | LCMS (ESI) [M + H]+: 636.15. $^1$H NMR (400 MHz, DMSO-d6) δ 8.54 (s, 1H), 8.20 (d, J = 33.2 Hz, 2H), 7.63 (d, J = 94.1 Hz, 1H), 7.44-7.19 (m, 1H), 6.81-6.46 (m, 1H), 6.28-5.79 (m, 4H), 3.97 (s, 4H), 3.77 (s, 4H), 3.51 (s, 1H), 3.20 (d, J = 6.5 Hz, 1H), 2.23 (s, 1H), 2.13 (s, 8H), 1.64 (s, 1H), 1.24 (s, 5H), 1.09-0.93 (m, 1H), 0.84 (d, J = 7.7 Hz, 2H), 0.59 (s, 1H), 0.33 (s, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 337. | 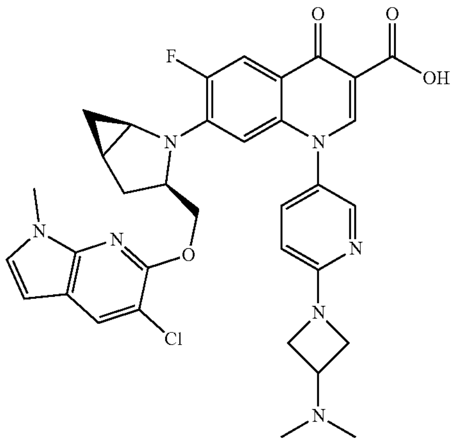 [SMILES: CN(C)C1CN(c2ccc(-n3cc(C(=O)O)c(=O)c4cc(F)c(N5[C@@H](COc6nc7c(ccn7C)cc6Cl)C[C@H]6C[C@H]65)cc43)cn2)C1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 17% B to 47% B in 7 min, 47% B; Wave Length: 254/220 nm; RT1(min): 6.63; Number Of Runs: 0 | 7-[(1R,3R,5R)-3-[{{5-Chloro-1-methyl-pyrrolo[2,3-b]pyridin-6-yl}oxy) methyl]-2-azabicyclo [3.1.0]hexan-2-yl]-1-{6-[3-(dimethyl-amino) azetidin-1-yl]pyridin-3-yl}-6-fluoro-4-oxoquinoline-3-carboxylic acid | LCMS (ESI) [M + H]+: 658.20. $^1H$ NMR (300 MHz, DMSO-d6) δ 15.34 (s, 1H), 8.47 (d, J = 5.3 Hz, 1H), 8.26 (s, 1H), 8.10 (s, 1H), 7.96 (d, J = 6.7 Hz, 1H), 7.88 (d, J = 13.3 Hz, 1H), 7.76-7.41 (m, 1H), 7.30 (d, J = 3.4 Hz, 1H), 6.56 (d, J = 9.0 Hz, 1H), 6.52-6.41 (m, 1H), 6.31 (s, 2H), 4.81 (s, 1H), 4.30 (d, J = 15.8 Hz, 2H), 4.19-3.97 (m, 2H), 3.80 (d, J = 6.7 Hz, 2H), 3.64 (s, 3H), 3.28-3.02 (m, 2H), 2.78-2.59 (m, 1H), 2.14 (s, 7H), 1.63 (s, 1H), 1.08 (d, J = 15.8 Hz, 1H), 0.73 (s, 1H). | ++++ |
| 338. | 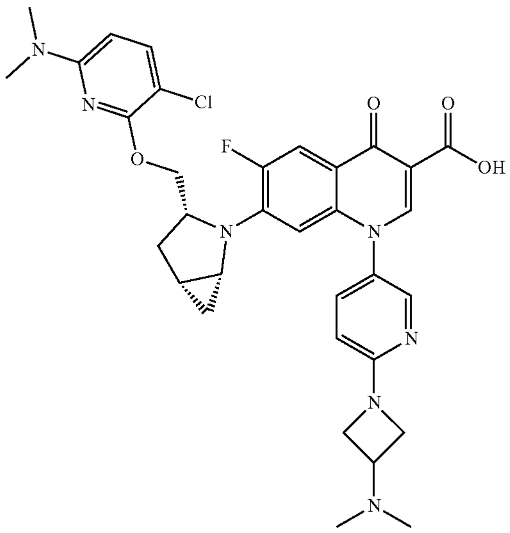 [SMILES: CN(C)c1ccc(Cl)c(OC[C@H]2C[C@H]3C[C@H]3N2c2cc3c(cc2F)c(=O)c(C(=O)O)cn3-c2ccc(N3CC(N(C)C)C3)nc2)n1] | Column: XBridge Prep Phenyl OBD Column, 19*150 mm, 5 μm 13 nm; Mobile Phase A: Water (10 MMOL/L NH4HCO3), Mobile Phase B: ACN; Flow rate: 25 mL/min; Gradient: 10% B to 10% B in 2 min, 10% B to 41% B in 2.5 min, 41% B to 73% B in 12 min, 73% B; Wave Length: 220 nm; RT1(min): 10.32; Number Of Runs: 0 | 7-[(1R,3R,5R)-3-({[3-chloro-6-(dimethyl-amino) pyridin-2-yl]oxy} methyl)-2-azabicyclo [3.1.0]hexan-2-yl]-1-{6-[3-(dimethyl-amino) azetidin-1-yl]pyridin-3-yl}-6-fluoro-4-oxoquinoline-3-carboxylic acid | LCMS (ESI) [M + H]+: 648.25. $^1H$ NMR (400 MHz, DMSO-d6) δ 8.48 (d, J = 28.2 Hz, 1H), 8.31-8.12 (m, 1H), 7.93-7.58 (m, 2H), 7.52-7.31 (m, 1H), 6.65-6.31 (m, 2H), 6.17-5.94 (m, 1H), 4.64 (s, 1H), 4.37-4.01 (m, 4H), 3.91-3.74 (m, 2H), 3.28-3.17 (m, 1H), 3.12-2.96 (m, 1H), 2.91-2.79 (m, 6H), 2.72-2.64 (m, 1H), 2.14 (s, 6H), 2.00 (d, J = 28.4 Hz, 1H), 1.55 (s, 1H), 1.08-0.81 (m, 1H), 0.67 (s, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 339. | 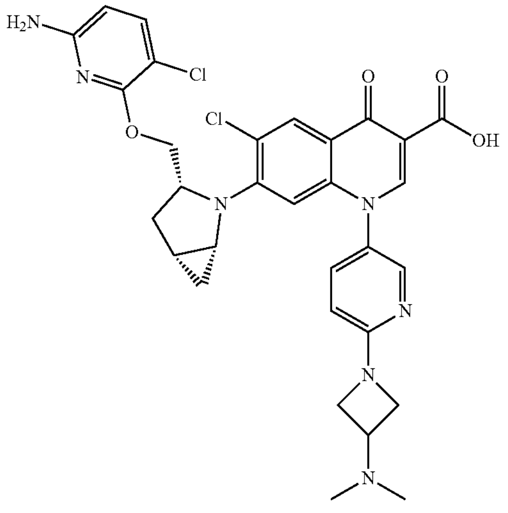 | Column: XSelect CSH Prep C18 OBD Column, 19*250 mm, 5 μm; Mobile Phase A: Water (0.1% FA), Mobile Phase B: ACN; Flow rate: 25 mL/min; Gradient: 15% B to 41% B in 7 min, 41% B; Wave Length: 254/220 nm; RT1(min): 6.63; Number Of Runs: 0 | 7-[(3R)-3-{[(6 Amino-3-chloropyridin-2-yl)oxy] methyl}-2-azabicyclo [3.1.0]hexan-2-yl]-6-chloro-1-{6-[3-(dimethyl-amino) azetidin-1-yl]pyridin-3-yl}-4-oxoquinoline-3-carboxylic acid | LCMS (ESI) [M + H]+: 636.20. $^1$H NMR (400 MHz, DMSO-d6) δ 15.12 (s, 1H), 8.56 (d, J = 8.4 Hz, 1H), 8.35-8.06 (m, 2H), 7.81-7.59 (m, 1H), 7.34-7.22 (m, 1H), 6.88 (d, J = 45.0 Hz, 1H), 6.62-6.33 (m, 1H), 6.01-5.85 (m, 3H), 5.10-4.81 (m, 1H), 4.18-3.97 (m, 3H), 3.96-3.68 (m, 3H), 3.28-3.17 (m, 1H), 3.08-2.93 (m, 1H), 2.71-2.59 (m, 1H), 2.14 (s, 6H), 2.03 (m, J = 13.9, 4.0 Hz, 1H), 1.61 (d, J = 10.2 Hz, 1H), 1.15-0.98 (m, 1H), 0.72-0.51 (m, 1H). | ++++ |
| 340. | 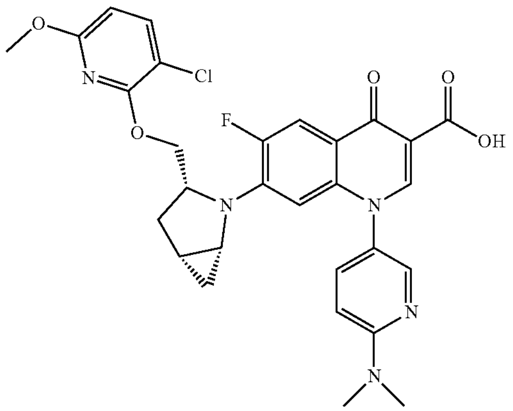 [SMILES: COc1ccc(Cl)c(OC[C@H]2C[C@H]3C[C@H]3N2c2cc3c(cc2F)c(=O)c(C(=O)O)cn3-c2ccc(N(C)C)nc2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 57% B to 87% B in 7 min, 87% B; Wave Length: 254/220 nm; RT1(min): 6.83; Number Of Runs: 0 | 7-[(1R,3R,5R)-3-{[(3-Chloro-6-methoxy-pyridin-2-yl)oxy] methyl}-2-azabicyclo [3.1.0]hexan-2-yl]-1-[6-(dimethyl-amino)pyridin-3-yl]-6-fluoro-4-oxoquinoline-3-carboxylic acid | LCMS (ESI) [M + H]+: 580.20. $^1$H NMR (300 MHz, DMSO-d6) δ 15.35 (s, 1H), 8.50 (d, J = 3.3 Hz, 1H), 8.28 (d, J = 2.4 Hz, 1H), 7.88 (d, J = 13.4 Hz, 1H), 7.80-7.59 (m, 2H), 6.91-6.62 (m, 1H), 6.54 (s, 1H), 6.36 (s, 1H), 4.74 (s, 1H), 4.32-4.04 (m, 2H), 3.73 (d, J = 3.1 Hz, 3H), 3.22-3.15 (m, 1H), 3.11 (s, 6H), 2.70-2.56 (m, 1H), 2.04 (d, J = 13.1 Hz, 1H), 1.62 (s, 1H), 0.96 (s, 1H), 0.74 (d, J = 9.0, 5.2 Hz, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 341. | 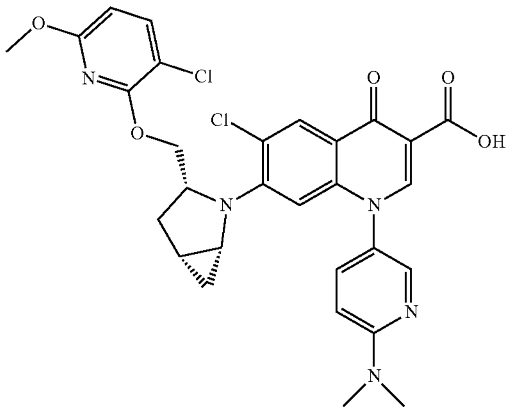 [SMILES: COc1ccc(Cl)c(OC[C@H]2C[C@H]3C[C@H]3N2c2cc3c(cc2Cl)c(=O)c(C(=O)O)cn3-c2ccc(N(C)C)nc2)n1] | Column: XSelect CSH Prep C18 OBD Column, 19*250 mm, 5 μm; Mobile Phase A: Water (0.1% FA), Mobile Phase B: ACN; Flow rate: 25 mL/min; Gradient: 55% B to 85% B in 7 min, 85% B; Wave Length: 254/220 nm; RT1(min): 6.45; Number Of Runs: 0 | 6-Chloro-7-[(1R,3R,5R)-3-{[(3-chloro-6-methoxy-pyridin-2 yl)oxy] methyl}-2-azabicyclo [3.1.0]hexan-2-yl]-1-[6-(dimethyl-amino)pyridin-3-yl]-4-oxoquinoline-3-carboxylic acid | LCMS (ESI) [M + H]+: 596.25. $^1$H NMR (300 MHz, DMSO-d6) δ 15.09 (s, 1H), 8.56 (d, J = 4.4 Hz, 1H), 8.42-8.23 (m, 1H), 8.16 (s, 1H), 7.86-7.54 (m, 2H), 6.96-6.65 (m, 2H), 6.30 (d, J = 8.4 Hz, 1H), 4.97 (s, 1H), 4.19 (d, J = 4.7 Hz, 2H), 3.65 (d, J = 3.1 Hz, 3H), 3.12 (s, 6H), 3.03 (d, J = 6.1 Hz, 1H), 2.80-2.59 (m, 1H), 2.03 (d, J = 8.9 Hz, 1H), 1.62 (d, J = 9.2 Hz, 1H), 1.02 (s, 1H), 0.65 (s, 1H). | ++++ |
| 342. | 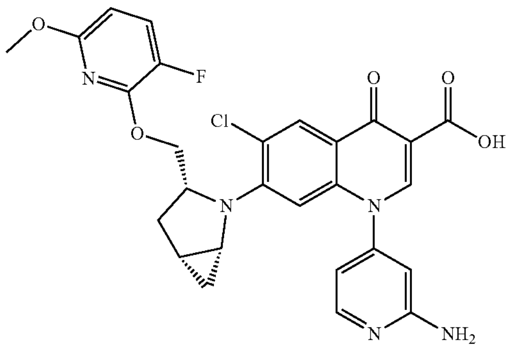 [SMILES: COc1ccc(F)c(OC[C@H]2C[C@H]3C[C@H]3N2c2cc3c(cc2Cl)c(=O)c(C(=O)O)cn3-c2ccnc(N)c2)n1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 32% B to 59% B in 7 min, 59% B; Wave Length: 254/220 nm; RT1(min): 7.10; Number Of Runs: 0 | 1-(2-Aminopyridin-4-yl)-6-chloro-7-[(1R,3R,5R)-3-{[(3-fluoro-6-methoxy-pyridin-2-yl)oxy] methyl}-2-azabicyclo [3.1.0]hexan-2-yl]-4-oxoquinoline-3-carboxylic acid | LCMS (ESI) [M + H]+: 552.25. $^1$H NMR (300 MHz, DMSO-d6) δ 14.97 (s, 1H), 8.58 (s, 1H), 8.13 (s, 2H), 7.51 (d, J = 10.0, 8.5 Hz, 1H), 7.04 (s, 1H), 6.64 (d, J = 20.0 Hz, 1H), 6.53 (s, 3H), 6.22-6.06 (m, 1H), 5.01 (s, 1H), 4.42-4.27 (m, 1H), 4.12 (d, J = 11.9, 4.2 Hz, 1H), 3.59 (s, 3H), 3.04 (s, 1H), 2.83-2.57 (m, 1H), 2.13-2.05 (m, 1H), 1.65 (s, 1H), 0.92 (s, 1H), 0.65 (s, 1H) | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 343. | 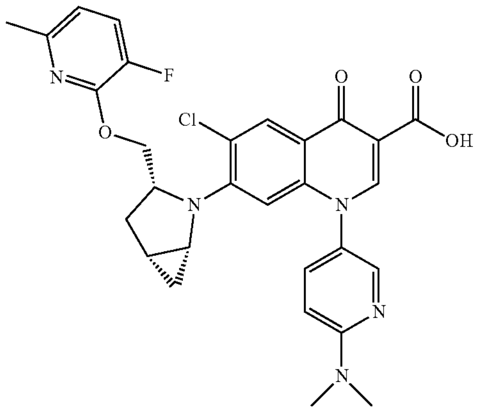 [SMILES: Cc1ccc(F)c(OC[C@H]2C[C@H]3C[C@H]3N2c2cc3c(cc2Cl)c(=O)c(C(=O)O)cn3-c2ccc(N(C)C)nc2)n1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 50% B to 80% B in 7 min, 80% B; Wave Length: 254/220 nm; RT1(min): 7.13; Number Of Runs: 0 | 6-Chloro-1-[6-(dimethyl-amino)pyridin-3-yl]-7-[(1R,3R,5R)-3-{[(3-fluoro-6-methylpyridin-2-yl)oxy] methyl}-2-azabicyclo [3.1.0]hexan-2-yl]-4-oxoquinoline-3-carboxylic acid | LCMS (ESI) [M + H]+: 564.25. $^1H$ NMR (300 MHz, DMSO-d6) δ 15.10 (s, 1H), 8.55 (s, 1H), 8.31-8.23 (m, 1H), 8.16 (s, 1H), 7.79-7.58 (m, 1H), 7.53-7.35 (m, 1H), 6.93-6.63 (m, 3H), 4.96 (d, J = 11.8 Hz, 1H), 4.25 (s, 1H), 4.13-3.96 (m, 1H), 3.12 (s, 6H), 3.01 (s, 1H), 2.79-2.58 (m, 1H), 2.13 (d, J = 1.1 Hz, 4H), 1.63 (s, 1H), 0.90 (d, J = 9.5 Hz, 1H), 0.61 (s, 1H). | ++++ |
| 344. | 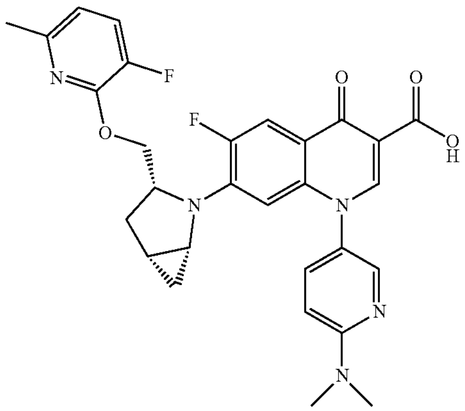 [SMILES: Cc1ccc(F)c(OC[C@H]2C[C@H]3C[C@H]3N2c2cc3c(cc2F)c(=O)c(C(=O)O)cn3-c2ccc(N(C)C)nc2)n1] | Column: XSelect CSH Prep C18 OBD Column, 19*150 mm, 5 μm; Mobile Phase A: Water (0.1% FA), Mobile Phase B: ACN; Flow rate: 25 mL/min; Gradient: 45% B to 75% B in 7 min, 75% B; Wave Length: 254/220 nm; RT1(min): 7.18; Number Of Runs: 0 | 1-[6-(Dimethyl-amino)pyridin-3-yl]-6-fluoro-7-[(1R,3R,5R)-3-{[(3-fluoro-6-methylpyridin-2-yl)oxy] methyl}-2-azabicyclo [3.1.0]hexan-2-yl]-4-oxoquinoline-3-carboxylic acid | LCMS (ESI) [M + H]+: 548.30. $^1H$ NMR (300 MHz, DMSO-d6) δ 15.37 (s, 1H), 8.50 (s, 1H), 8.27 (s, 1H), 7.88 (d, J = 13.4 Hz, 1H), 7.77-7.64 (m, 1H), 7.45 (d, J = 10.7, 8.0 Hz, 1H), 6.90-6.58 (m, 2H), 6.57-6.42 (m, 1H), 4.74 (d, J = 10.4 Hz, 1H), 4.32-4.06 (m, 2H), 3.11 (s, 7H), 2.83-2.58 (m, 1H), 2.19 (s, 3H), 2.04 (d, J = 13.4 Hz, 1H), 1.61 (s, 1H), 0.87 (s, 1H), 0.69 (d, J = 8.5 Hz, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 345. | 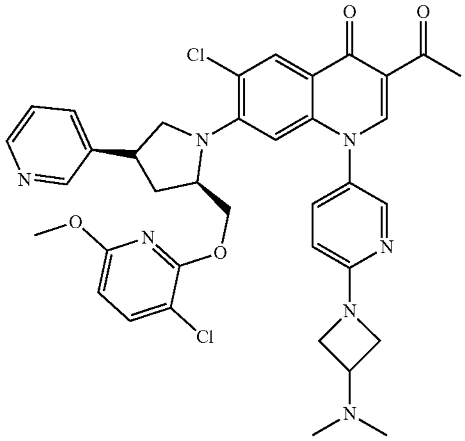 | Column: Sunfire Prep C18 OBD Column, 50*250 mm, 5 μm 10 nm; Mobile Phase A: Water (0.1% FA), Mobile Phase B: ACN; Flow rate: 25 mL/min; Gradient: 17% B to 30% B in 13 min, 30% B; Wave Length: 220 nm; RT1(min): 11.63; Number Of Runs: 0 | 6-chloro-7-((2R,4S)-2-(((3-chloro-6-methoxy-pyridin-2-yl)oxy) methyl)-4-(pyridin-3-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 716.20. $^1$H NMR (300 MHz, DMSO-d6) δ 15.04 (s, 1H), 8.58-8.48 (m, 2H), 8.45-8.40 (m, 1H), 8.24-8.20 (m, 1H), 8.18 (s, 1H), 7.74-7.59 (m, 3H), 7.38-7.27 (m, 1H), 6.60-6.36 (m, 2H), 6.30 (d, J = 8.4 Hz, 1H), 4.94 (s, 1H), 4.51-4.30 (m, 2H), 4.13-3.92 (m, 3H), 3.87-3.78 (m, 2H), 3.75-3.68 (m, 1H), 3.65 (s, 3H), 3.26-3.14 (m, 2H), 2.44-2.31 (m, 2H), 2.14 (s, 6H). | ++++ |
| 346. | 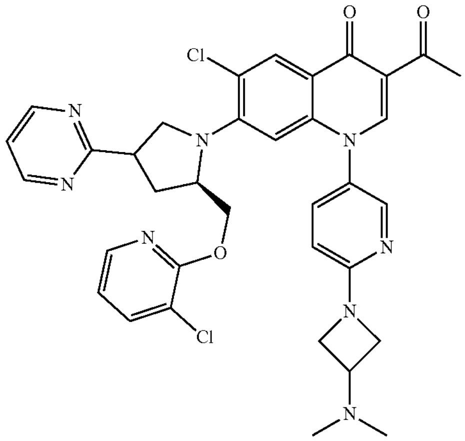 [SMILES: CC(=O)c1cn(-c2ccc(N3CC(N(C)C)C3)nc2)c2cc(N3CC(c4ncccn4)C[C@@H]3COc3ncccc3Cl)c(Cl)cc2c1=O] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 10% B to 40% B in 7 min, 40% B; Wave Length: 254/220 nm; RT1(min): 6.95; Number Of Runs: 0 | 6-chloro-7-((2R)-2-(((3-chloropyridin-2-yl)oxy) methyl)-4-(pyrimidin-2-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 687.25. $^1$H NMR (300 MHz, DMSO-d6) δ 15.06 (s, 1H), 8.82-8.68 (m, 2H), 8.59-8.48 (m, 1H), 8.29-8.19 (m, 1H), 8.17-8.12 (m, 1H), 7.99-7.91 (m, 1H), 7.88-7.77 (m, 1H), 7.75-7.62 (m, 1H), 7.43-7.32 (m, 1H), 7.03-6.92 (m, 1H), 6.62-6.29 (m, 2H), 4.89-4.62 (m, 1H), 4.49-4.25 (m, 2H), 4.14-4.02 (m, 3H), 3.92-3.78 (m, 3H), 3.68-3.56 (m, 1H), 3.27-3.16 (m, 1H), 2.85-2.70 (m, 1H), 2.44-2.31 (m, 1H), 2.15 (s, 6H). | ++++ |
| 347. | 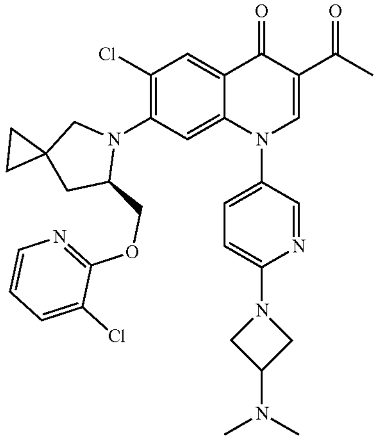 [SMILES: CC(=O)c1cn(-c2ccc(N3CC(N(C)C)C3)nc2)c2cc(N3CC4(CC4)C[C@@H]3COc3ncccc3Cl)c(Cl)cc2c1=O] | reverse phase flash chromatography | (R)-6-chloro-7-(6-(((3-chloropyridin-2-yl)oxy) methyl)-5-azaspiro[2.4] heptan-5-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 635.10. $^1$H NMR (300 MHz, DMSO-d6) δ 15.09 (s, 1H), 8.59-8.48 (m, 1H), 8.46-8.09 (m, 2H), 8.04-7.48 (m, 3H), 7.07-6.88 (m, 1H), 6.66-6.11 (m, 2H), 4.93-4.57 (m, 1H), 4.51-4.21 (m, 2H), 4.15-3.98 (m, 2H), 3.94-3.70 (m, 3H), 3.24-3.16 (m, 1H), 2.94-2.81 (m, 1H), 2.23-2.04 (m, 7H), 2.04-1.83 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 348. | 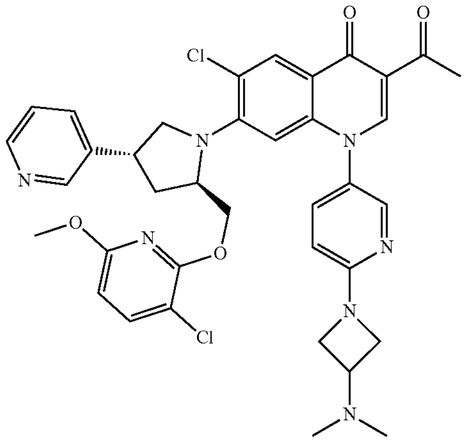 [SMILES: COc1ccc(Cl)c(OC[C@H]2C[C@H](c3cccnc3)CN2c2cc3c(cc2Cl)c(=O)c(C(C)=O)cn3-c2ccc(N3CC(N(C)C)C3)nc2)n1] | reverse phase flash chromatography | 6-chloro-7-((2R,4R)-2-(((3-chloro-6-methoxy-pyridin-2-yl)oxy) methyl)-4-(pyridin-3-yl)pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 716.20. $^1$H NMR (300 MHz, DMSO-d6) δ 15.05 (s, 1H), 8.63-8.41 (m, 3H), 8.29-8.14 (m, 2H), 7.82-7.59 (m, 3H), 7.45-7.32 (m, 1H), 6.62-6.26 (m, 3H), 4.77-4.50 (m, 2H), 4.40-4.23 (m, 1H), 4.10-3.95 (m, 2H), 3.86-3.70 (m, 2H), 3.67-3.42 (m, 6H), 3.26-3.16 (m, 1H), 2.69-2.60 (m, 1H), 2.32-2.20 (m, 1H), 2.13 (s, 6H). | ++++ |
| 349. | 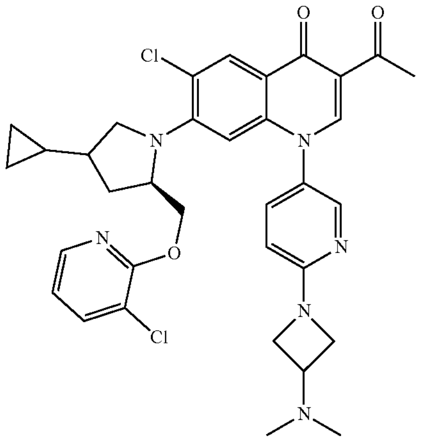 [SMILES: CC(=O)c1cn(-c2ccc(N3CC(N(C)C)C3)nc2)c2cc(N3CC(C4CC4)C[C@@H]3COc3ncccc3Cl)c(Cl)cc2c1=O] | Column: XSelect CSH Prep C18 OBD Column, 19*250 mm, 5 μm; Mobile Phase A: Water (0.05% FA), Mobile Phase B: ACN; Flow rate: 25 mL/min; Gradient: 20% B to 48% B in 7 min, 48% B; Wave Length: 254/220 nm; RT1(min): 6.75; Number Of Runs: 0 | 6-chloro-7-((2R)-2-(((3-chloropyridin-2-yl)oxy) methyl)-4-cyclopropyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 649.20. $^1$H NMR (300 MHz, DMSO-d6) δ 15.16 (s, 1H), 8.59 (d, J = 5.9 Hz, 1H), 8.36-8.19 (m, 2H), 8.04-7.85 (m, 2H), 7.83-7.71 (m, 1H), 7.09-6.96 (m, 1H), 6.70-6.29 (m, 2H), 5.00-4.71 (m, 1H), 4.46-4.25 (m, 2H), 4.21-4.02 (m, 2H), 3.96-3.73 (m, 3H), 3.33-3.23 (m, 1H), 3.15-3.01 (m, 1H), 2.22 (s, 6H), 2.18-2.07 (m, 2H), 1.86-1.71 (m, 1H), 0.96-0.64 (m, 1H), 0.59-0.38 (m, 2H), 0.32-0.14 (m, 2H). | ++++ |

TABLE 1-continued

| Com-pound | Product | Prep HPLC Method | IUPAC name | Analytical data | Potency Lin28a-dep Z11 $IC_{50}$ (μM) |
|---|---|---|---|---|---|
| 350. | 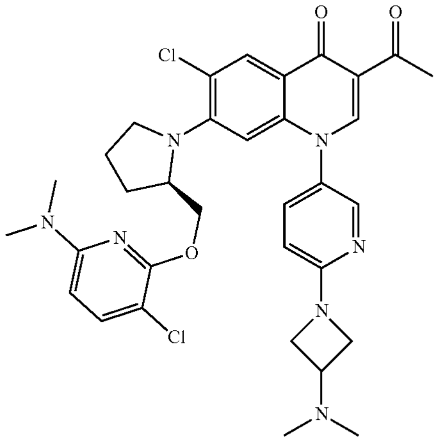 [SMILES: CC(=O)c1cn(-c2ccc(N3CC(N(C)C)C3)nc2)c2cc(N3CCC[C@@H]3COc3nc(N(C)C)ccc3Cl)c(Cl)cc2c1=O] | Column: Gemini-NX C18 AXAI Packed, 21.2*150 mm 5 um; Mobile Phase A: Water (10 MMOL/L NH4HCO3), Mobile Phase B: ACN; Flow rate: 25 mL/min; Gradient: 10% B to 10% B in 2 min, 10% B to 43% B in 2.5 min, 43% B to 85% B in 10.5 min, 85% B; Wave Length: 220 nm; RT1(min): 10.65; Number Of Runs: 0 | (R)-6-chloro-7-(2-(((3-chloro-6-(dimethyl-amino) pyridin-2-yl)oxy) methyl) pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 652.20. $^{1}H$ NMR (300 MHz, DMSO-d6) δ 15.15 (s, 1H), 8.51 (d, J = 7.4 Hz, 1H), 8.28-8.17 (m, 1H), 8.13 (s, 1H), 7.65 (d, J = 8.8 Hz, 1H), 7.42-7.30 (m, 1H), 6.63-6.34 (m, 1H), 6.26 (s, 1H), 5.93 (t, J = 8.4 Hz, 1H), 4.78-4.51 (m, 2H), 4.22-4.01 (m, 3H), 3.88-3.76 (m, 2H), 3.58-3.39 (m, 1H), 3.29-3.20 (m, 1H), 3.17-3.07 (m, 1H), 2.80 (d, J = 4.5 Hz, 6H), 2.32-2.22 (m, 1H), 2.15 (s, 6H), 2.07-1.92 (m, 2H), 1.88-1.70 (m, 1H) | ++++ |
| 351. | 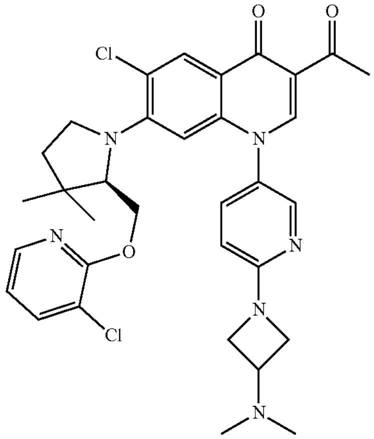 [SMILES: CC(=O)c1cn(-c2ccc(N3CC(N(C)C)C3)nc2)c2cc(N3CCC(C)(C)[C@@H]3COc3ncccc3Cl)c(Cl)cc2c1=O] | Column: XBridge Prep C18 OBD Column, 19*150 mm, 5 μm; Mobile Phase A: Water (10 MMOL/L NH4HCO3), Mobile Phase B: ACN; Flow rate: 25 mL/min; Gradient: 10% B to 10% B in 2 min, 10% B to 36% B in 2.5 min, 36% B to 65% B in 10.5 min, 65% B; Wave Length: 220 nm; RT1(min): 11.2; Number Of Runs: 0 | (R)-6-chloro-7-(2-(((3-chloropyridin-2-yl)oxy) methyl)-3,3-dimethyl-pyrrolidin-1-yl)-1-(6-(3-(dimethyl-amino) azetidin-1-yl)pyridin-3-yl)-4-oxo-1,4-dihydro-quinoline-3-carboxylic acid | LCMS (ESI) [M + H]+: 637.15 $^{1}H$ NMR (300 MHz, DMSO-d6) δ 8.58-8.34 (m, 1H), 8.30-7.70 (m, 4H), 7.65-7.16 (m, 1H), 7.11-6.81 (m, 1H), 6.63-5.79 (m, 2H), 4.54-4.30 (m, 1H), 4.26-3.94 (m, 3H), 3.87-3.57 (m, 3H), 3.30-2.89 (m, 3H), 2.14 (s, 6H), 1.89-1.57 (m, 2H), 1.30-1.15 (m, 3H), 1.13-1.01 (m, 3H), 0.97-0.52 (m, 1H). | ++++ |

TABLE 1-continued

| Compound | Product | Prep HPLC Method | IUPAC name | Analytical data | Potency Lin28a-dep Z11 $IC_{50}$ (μM) |
|---|---|---|---|---|---|
| 352. | 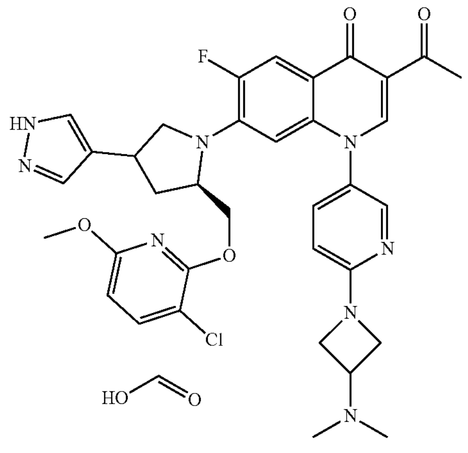 | Column: XSelect CSH Prep C18 OBD Column, 19*250 mm, 5 μm; Mobile Phase A: Water (0.05% FA), Mobile Phase B: ACN; Flow rate: 25 mL/min; Gradient 15% B to 40% B in 7 min, 40% B; Wave Length: 254/220 nm; RT1(min): 6.18; Number Of Runs: 0 | 7-((2R)-2-(((3-chloro-6-methoxy-pyridin-2-yl)oxy) methyl)-4-(1H-pyrazol-4-yl)pyrrolidin-1-yl)-1-(6-(3-(dimethyl-amino) azetidin-1-yl)pyridin-3-yl)-6-fluoro-4-oxo-1,4-dihydro-quinoline-3-carboxylic acid compound with formic acid (1:1) | LCMS (ESI) [M + H]+: 689.25 $^1$H NMR (300 MHz, DMSO-d6) δ 12.53 (s, 1H) 8.58-8.35 (m, 1H), 8.34-8.07 (m, 1H), 7.76-7.29 (m, 5H), 6.67-6.28 (m, 2H), 6.17-5.99 (m, 1H), 4.66-4.26 (m, 3H), 4.08-3.94 (m, 2H), 3.90-3.75 (m, 2H), 3.66-3.47 (m, 5H), 3.28-3.10 (m, 2H), 2.72-2.54 (m, 1H), 2.13 (s, 7H). | ++++ |

| EX # | Structure | IUPAC name | Analytical data | Potency Lin28a-dep Z11 $IC_{50}$ (μM) |
|---|---|---|---|---|
| 353. | 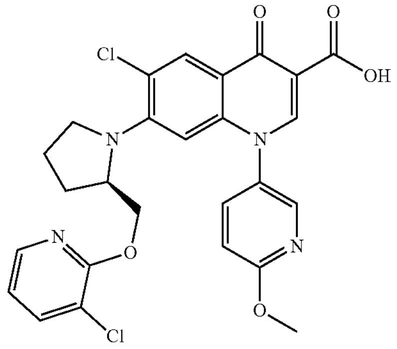 [SMILES: COc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-methoxypyridin-3-yl)-4-oxo-1,4-dihydroquinoline-3-carboxylic acid | $^1$H NMR (400 MHz, DMSO-$d_6$) δ 15.05 (s, 1H), 8.62 (d, J = 10.0 Hz, 1H), 8.43 (d, J = 2.4 Hz, 1H), 8.17 (s, 1H), 8.00-7.89 (m, 2H), 7.83-7.80 (m, 1H), 7.09 (d, J = 8.8 Hz, 0.5H), 6.94 (t, J = 7.2 Hz, 1H), 6.87 (d, J = 8.8 Hz, 0.5H), 6.32 (d, J = 5.6 Hz, 1H), 4.72-4.62 (m, 1H), 4.34-4.20 (m, 2H), 3.97 (s, 2H), 3.92 (s, 1H), 3.60-3.50 (m, 1H), 3.18 (s, J = 8.0 Hz, 1H), 2.30-2.20 (m, 1H), 2.02-1.87 (m, 2H), δ 1.84-1.74 (m, 1H), MS (ESI) m/z: 541.3 $[M + H]^+$. | ++++ |
| 354. | 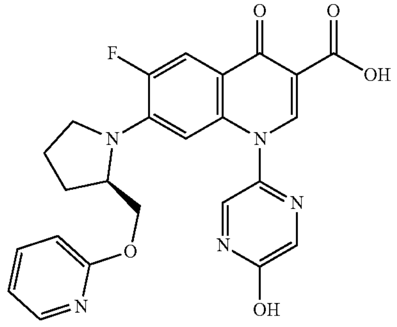 [SMILES: O=C(O)c1cn(-c2cnc(O)cn2)c2cc(N3CCC[C@@H]3COc3ccccn3)c(F)cc2c1=O] | (R)-6-fluoro-1-(5-hydroxypyrazin-2-yl)-4-oxo-7-(2-((pyridin-2-yloxy) methyl)pyrrolidin-1-yl)-1,4-dihydroquinoline-3-carboxylic acid | $^1$H NMR (400 MHz, DMSO-$d_6$): δ 15.29 (s, 1H), 12.78 (brs, 1H), 8.79 (s, 1H), 8.20-8.06 (m, 2H), 7.86 (d, J = 14.4 Hz, 2H), 7.69-7.64 (m, 1H0, 6.97-6.93 (m, 1H), 6.69 (d, J = 8.4 Hz, 1H), 6.39 (d, J = 7.2 Hz, 1H), 4.54 (brs, 1H), 4.29-4.20 (m, 2H), 3.56 (brs, 1H), 3.26 (brs, 1H), 2.11-1.90 (m, 4H), MS (ESI) m/z: 478.3 $[M + H]^+$. | +++ |

-continued

| EX # | Structure | IUPAC name | Analytical data | Potency Lin28a-dep Z11 $IC_{50}$ (μM) |
|---|---|---|---|---|
| 355. | 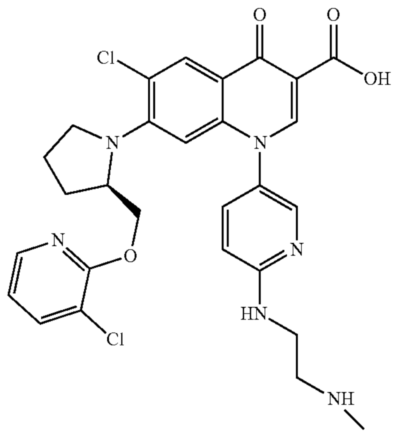 [SMILES: CNCCNc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-((2-(methylamino) ethyl)amino) pyridin-3-yl)-4-oxo-1,4-dihydro-quinoline-3-carboxylic acid | $^1$H-NMR (400 MHz, DMSO-$d_6$): δ 8.91 (bs, 2H), 8.50 (d, J = 10.4 Hz, 1H), 8.24-8.22 (m, 1H), 8.15 (s, 1H), 7.90 (d, J = 4.8 Hz, 1H), 7.82-7.78 (m, 1H), 7.69-7.60 (m, 2H), 6.94 (dd, J = 7.8, 4.8 Hz, 1H), 6.77 (d, J = 8.4 Hz, 0.5H), 6.66 (d, J = 8.8 Hz, 0.5H), 6.45 (s, 1H), 4.77 (brs, 1H), 4.32-4.27 (m, 2H), 3.70-3.68 (m, 1H), 3.39 (s, 2H), 3.22-3.11 (m, 3H), 2.63-2.59 (m, 3H), 2.26-2.24 (m, 1H), 1.99-1.91 (m, 2H), 1.81-1.79 (m, 1H), MS (ESI) m/z: 583.3 [M + H] | ++++ |
| 356. | 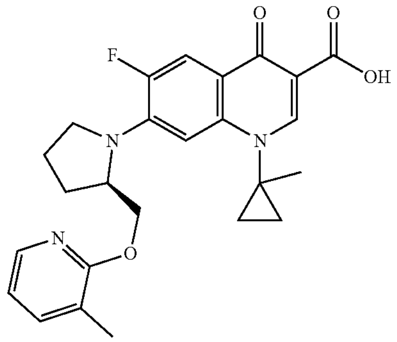 [SMILES: Cc1cccnc1OC[C@H]1CCCN1c1cc2c(cc1F)c(=O)c(C(=O)O)cn2C1(C)CC1] | (R)-6-fluoro-1-(1-methylcyclo-propyl)-7-(2-(((3-methylpyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.44 (s, 1H), 8.71 (s, 1H), 7.88-7.85 (m, 1H), 7.81 (d, J = 1.6 Hz, 1H), 7.50-7.48 (m, 1H), 7.13-7.10 (dd, J = 7.6, 2.8 Hz, 1H), 6.86-6.83 (m, 1H), 4.72-4.64 (m, 1H), 4.46-4.38 (m, 2H), 3.78-3.68 (m, 1H), 3.58-3.50 (m, 1H), 2.22-2.18 (m, 2H), 2.12-2.04 (m, 5H), 1.60 (d, J = 12.4 Hz, 3H), 1.45-1.43 (m, 1H), 1.36-1.15 (m, 3H), MS (ESI) m/z: 452.4 $[M + H]^+$. | ++++ |
| 357. | 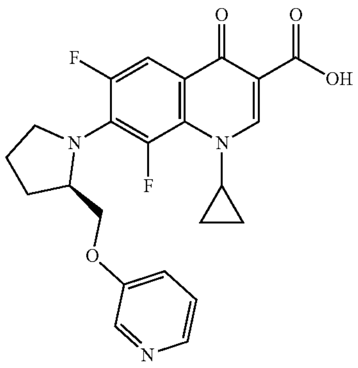 [SMILES: O=C(O)c1cn(C2CC2)c2c(F)c(N3CCC[C@@H]3COc3cccnc3)c(F)cc2c1=O] | (R)-1-cyclopropyl-6,8-difluoro-4-oxo-7-(2-((pyridin-3-yloxy)methyl) pyrrolidin-1-yl)-1,4-dihydro-quinoline-3-carboxylic acid | $^1$H-NMR (400 MHz, DMSO-$d_6$): δ 14.90 (bs, 1H), 8.63 (s, 1H), 8.09 (t, J = 3.2 Hz, 1H), 8.05 (t, J = 1.6 Hz, 1H), 7.76 (d, J = 12.8 Hz, 1H), 7.22-7.21 (m, 2H), 4.68-4.58 (m, 1H), 4.12-4.08 (m, 3H), 3.90-3.83 (m, 1H), 3.45-3.37 (m, 1H), 2.32-2.24 (m, 1H), 2.10-2.00 (m, 1H), 1.91-1.80 (m, 2H), 1.20-1351.04 (m, 4H), MS (ESI) m/z: 442.2 $[M + H]^+$. | +++ |

-continued

| EX # | Structure | IUPAC name | Analytical data | Potency Lin28a-dep Z11 $IC_{50}$ (μM) |
|---|---|---|---|---|
| 358. | 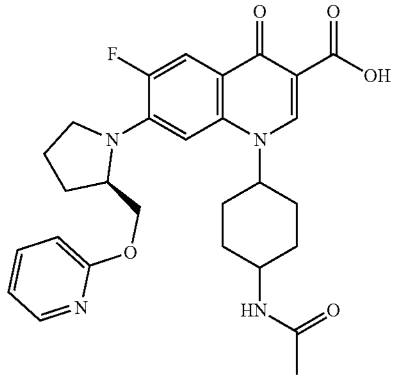 [SMILES: CC(=O)NC1CCC(n2cc(C(=O)O)c(=O)c3cc(F)c(N4CCC[C@@H]4COc4ccccn4)cc32)CC1] | 1-(4-acetamidocyclohexyl)-6-fluoro-4-oxo-7-[(2R)-2-[(pyridin-2-yloxy)methyl]pyrrolo-1-yl]-1,4-dihydroquinoline-3-carboxylic acid | $^1$H NMR (400 MHz, DMSO-$d_6$) δ 15.70 (s, 1H), 8.78 (s, 1H), 8.08-8.04 (m, 2H), 7.87 (d, J = 14.4 Hz, 1H), 7.68-7.63 (m, 1H), 6.94-6.91 (m, 2H), 6.70 (d, J = 8.0 Hz, 1H), 4.81-4.72 (m, 2H), 4.39-4.36 (m, 1H), 4.31-4.27 (m, 1H), 4.10-4.04 (m, 1H), 3.79-3.76 (m, 1H), 3.56-3.50 (m, 1H), 2.20-2.11 (m, 3H), 2.07-1.97 (m, 3H), 1.88-1.81 (m, 6H), 1.78-1.72 (m, 2H), 1.63-1.59 (m, 1H), MS (ESI) m/z: 523.4 [M + H]$^+$. | +++ |
| 359. | 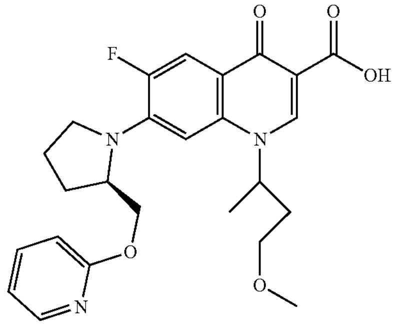 [SMILES: COCCC(C)n1cc(C(=O)O)c(=O)c2cc(F)c(N3CCC[C@@H]3COc3ccccn3)cc21] | (R)-6-fluoro-1-(3-methoxycyclobutyl)-4-oxo-7-(2-((pyridin-2-yloxy)methyl)pyrrolidin-1-yl)-1,4-dihydroquinoline-3-carboxylic acid | $^1$H NMR (400 MHz, DMSO-$d_6$): δ 15.52 (s, 1H), 8.53 (s, 1H), 8.07 (dd, J = 4.8, 1.2 Hz, 1H), 7.86 (d, J = 14.8 Hz, 1H), 7.68-7.64 (m, 1H), 6.96-6.92 (m, 1H), 6.78 (d, J = 7.2 Hz, 1H), 6.72 (d, J = 8.4 Hz, 1H), 4.75-4.60 (m, 2H), 4.41-4.37 (m, 1H), 4.30-4.26 (m, 1H), 3.81-3.74 (m, 2H), 3.52-3.50 (m, 1H), 3.17 (s, 3H), 3.06-3.02 (m, 2H), 2.26-2.15 (m, 4H), 2.10-2.02 (m, 2H), MS (ESI) m/z: 468.3 [M + H]$^+$. | +++ |
| 360. | 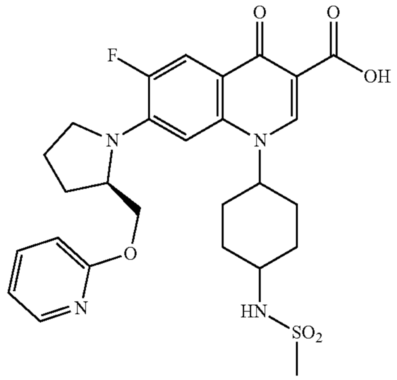 [SMILES: CS(=O)(=O)NC1CCC(n2cc(C(=O)O)c(=O)c3cc(F)c(N4CCC[C@@H]4COc4ccccn4)cc32)CC1] | (R)-6-fluoro-1-(4-(methylsulfonamido)cyclohexyl)-4-oxo-7-(2-((pyridin-2-yloxy)methyl)pyrrolidin-1-yl)-1,4-dihydroquinoline-3-carboxylic acid | $^1$H NMR (400 MHz, DMSO-$d_6$): δ 15.62 (s, 1H), 8.84 (s, 1H), 8.05 (d, J = 3.6 Hz, 1H), 7.85 (d, J = 14.4 Hz, 1H), 7.67-7.63 (m, 1H), 7.55-7.53 (m, 1H), 6.94-6.91 (m, 2H), 6.70 (d, J = 8.0 Hz, 1H), 4.81-4.72 (m, 2H), 4.39-4.36 (m, 1H), 4.32-4.28 (m, 1H), 3.81-3.73 (m, 1H), 3.68-3.63 (m, 1H), 3.57-3.51 (m, 1H), 2.96 (s, 3H), 2.16-2.10 (m, 3H), 2.07-2.04 (m, 3H), 1.88-1.76 (m, 6H), MS (ESI) m/z: 559.3 [M + H]$^+$. | +++ |
| 361. | 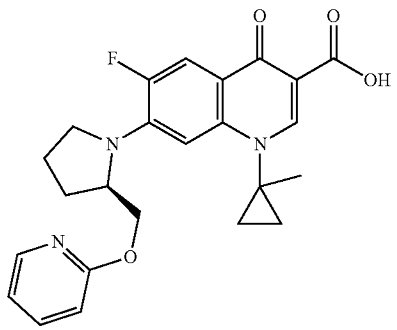 [SMILES: CC1(n2cc(C(=O)O)c(=O)c3cc(F)c(N4CCC[C@@H]4COc4ccccn4)cc32)CC1] | (R)-6-fluoro-1-(1-methylcyclopropyl)-4-oxo-7-(2-((pyridin-2-yloxy)methyl)pyrrolidin-1-yl)-1,4-dihydroquinoline-3-carboxylic acid | $^1$H NMR (400 MHz, DMSO-$d_6$) δ: 15.40 (s, 1H), 8.70 (s, 1H), 8.04 (dd, J = 4.8, 1.2 Hz, 1H), 7.83 (d, J = 14.4 Hz, 1H), 7.68-7.64 (m, 1H), 7.11-7.09 (m, 1H), 6.95-6.91 (m, 1H), 6.74 (d, J = 8.4 Hz, 1H), 4.61 (brs, 1H), 4.43-4.39 (m, 1H), 4.35-4.29 (m, 1H), 3.71 (brs, 1H), 3.53 (brs, 1H), 2.18-2.12 (m, 2H), 2.08-2.03 (m, 2H), 1.61 (s, 1.5H), 1.56 (s, 1.5H), 1.45-1.41 (m, 1H), 1.32-1.22 (m, 3H), MS (ESI) m/z: 438.3 [M + H]$^+$ | ++++ |

-continued

| EX # | Structure | IUPAC name | Analytical data | Potency Lin28a-dep Z11 $IC_{50}$ (μM) |
| --- | --- | --- | --- | --- |
| 362. | 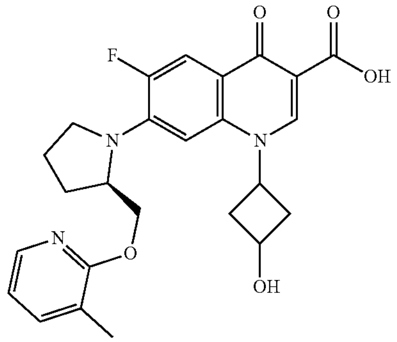 [SMILES: Cc1cccnc1OC[C@H]1CCCN1c1cc2c(cc1F)c(=O)c(C(=O)O)cn2C1CC(O)C1] | (R)-6-fluoro-1-(3-hydroxycyclo-butyl)-7-(2-(((3-methylpyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.55 (s, 1H), 8.57 (s, 1H), 7.90 (t, J = 5.6 Hz, 1H), 7.84 (dd, J = 14.8, 3.6 Hz, 1H), 7.48 (d, J = 7.2 Hz, 1H), 6.86-6.69 (m, 2H), 5.42-5.27 (m, 1H), 4.74 (brs, 1H), 4.41-4.36 (m, 1H), 4.33-4.29 (m, 1H), 3.81-3.79 (m, 1H), 3.56-3.51 (m, 1H), 3.02-3.00 (m, 1H), 2.67-2.61 (m, 1H), 2.37-2.31 (m, 2H), 2.28-2.15 (m, 3H), 2.06-2.02 (m, 6H), MS (ESI) m/z: 468.4 [M + H]$^+$. | ++++ |
| 363. | 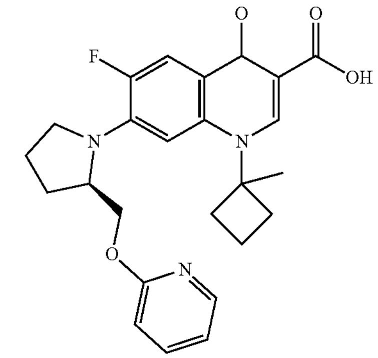 [SMILES: CC1(N2C=C(C(=O)O)C(O)c3cc(F)c(N4CCC[C@@H]4COc4ccccn4)cc32)CCC1] | (R)-6-fluoro-1-(1-methylcyclo-butyl)-4-oxo-7-(2-((pyridin-2-yloxy)methyl) pyrrolidin-1-yl)-1,4-dihydro-quinoline-3-carboxylic acid | $^1$H-NMR (400 MHz, DMSO-$d_6$): δ 15.55 (s, 1H), 8.43 (s, 1H), 8.10-8.00 (m, 1H), 7.85 (d, J = 14.8 Hz, 1H), 7.70-7.60 (m, 1H), 6.98-6.90 (m, 1H), 6.73 (d, J = 8.4 Hz, 1H), 6.58 (d, J = 6.8 Hz, 1H), 4.64-4.56 (m, 1H), 4.30-4.37 (m, 2H), 3.67 (brs, 1H), 3.46 (brs, 1H), 2.80-2.68 (m, 2H), 2.62-2.52 (m, 2H), 2.20-1.90 (m, 5H), 1.88-1.70 (m, 4H), MS (ESI) m/z: 452.3 [M + H]$^+$. | +++ |
| 364. | 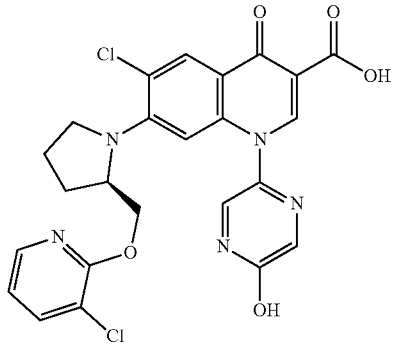 [SMILES: O=C(O)c1cn(-c2cnc(O)cn2)c2cc(N3CCC[C@@H]3COc3ncccc3Cl)c(Cl)cc2c1=O] | 6-Chloro-7-[(2R)-2-{[(3-chloropyridin-2-yl)oxy]methyl} pyrrolidin-1-yl]-1-(5-hydroxy-pyrazin-2-yl)-4-oxo-1,4-dihydroquinoline-3-carboxylic acid | $^1$H NMR (400 MHz, DMSO-$d_6$) δ 14.98 (brs, 1H), 12.80 (brs, 1H), 8.82 (s, 1H), 8.14 (s, 1H), 8.12-8.08 (m, 1H), 7.89 (dd, J = 4.8, 1.6 Hz, 2H), 7.78 (dd, J = 8.0, 2.0 Hz, 1H), 6.92 (dd, J = 7.6, 4.8 Hz, 1H), 6.64 (s, 1H), 4.79 (brs, 1H), 4.36-4.27 (m, 2H), 3.68-3.63 (m, 1H), 3.28-3.23 (m, 1H), 2.26-2.23 (m, 1H), 2.02-1.93 (m, 2H), 1.86-1.75 (m, 1H). MS (ESI) m/z: 528.2 [M + H]$^+$ | ++++ |
| 365. | 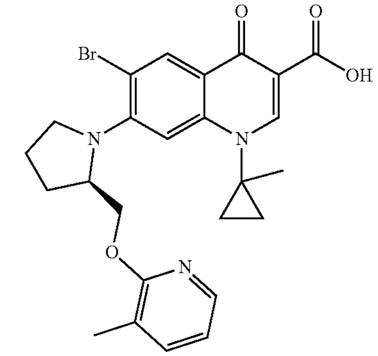 [SMILES: Cc1cccnc1OC[C@H]1CCCN1c1cc2c(cc1Br)c(=O)c(C(=O)O)cn2C1(C)CC1] | 6-Bromo-1-(1-methylcyclo-propyl)-7-[(2R)-2-{[(3-methyl-pyridin-2-yl)oxy] methyl} pyrrolidin-1-yl]-4-oxo-1,4-dihydroquinoline-3-carboxylic acid | $^1$H NMR (400 MHz, DMSO-$d_6$) δ 15.11 (s, 1H), 8.74 (d, J = 3.2 Hz, 1H), 8.33 (d, J = 4.8 Hz, 1H), 7.79 (brs, 1H), 7.43 (d, J = 7.2 Hz, 1H), 7.37 (d, J = 10.4 Hz, 1H), 6.78 (dd, J = 7.2, 5.2 Hz, 1H), 4.96 (brs, 1H), 4.45-4.35 (m, 1H), 4.28-4.25 (m, 1H), 3.90-3.83 (m, 1H), 3.43-3.37 (m, 1H), 2.35-2.32 (m, 1H), 2.15-1.85 (m, 6H), 1.55 (s, 3H), 1.46-1.06 (m, 4H). MS (ESI) m/z: 512.3 [M + H]$^+$ | +++ |

-continued

| EX # | Structure | IUPAC name | Analytical data | Potency Lin28a-dep Z11 $IC_{50}$ (μM) |
|---|---|---|---|---|
| 366. | 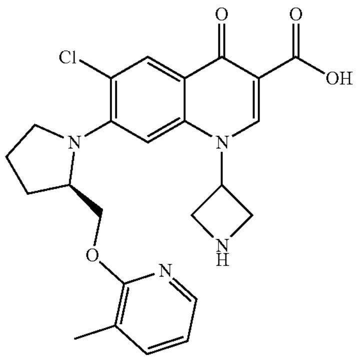 [SMILES: Cc1cccnc1OC[C@H]1CCCN1c1cc2c(cc1Cl)c(=O)c(C(=O)O)cn2C1CNC1] | 1-(Azetidin-3-yl)-6-chloro-7-[(2R)-2-{[(3-methyl-pyridin-2-yl)oxy]methyl}pyrrolidin-1-yl]-4-oxo-1,4-dihydroquinoline-3-carboxylic acid | . $^1H$ NMR (400 MHz, DMSO-$d_6$) δ 8.67 (s, 1H), 8.15 (d, J = 2.8 Hz, 1H), 7.88 (dd, J = 5.2, 1.2 Hz, 1H), 7.44-7.41 (m, 1H), 6.97 (brs, 1H), 6.80 (dd, J = 7.2, 5.2 Hz, 1H), 5.48-5.42 (m, 1H), 4.98-4.91 (m, 1H), 4.38 (dd, J = 11.2, 4.4 Hz, 1H), 4.21 (dd, J = 11.2, 5.2 Hz, 1H), 4.06-3.98 (m, 2H), 3.92-3.82 (m, 4H), 2.33-2.28 (m, 1H), 2.09-2.00 (m, 2H), 1.96 (s, 3H), 1.90-1.85 (m, 1H) (—COOH, NH protons not observed). MS (ESI) m/z: 469.3 [M + H]$^+$ | +++ |
| 367. | 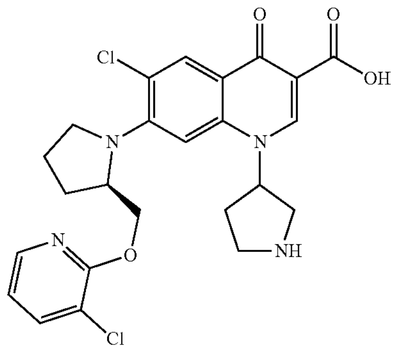 [SMILES: O=C(O)c1cn(C2CCNC2)c2cc(N3CCC[C@@H]3COc3ncccc3Cl)c(Cl)cc2c1=O] | 6-chloro-7-[(2R)-2-{[(3-chloro-pyridin-2-yl)oxy)methyl}pyrrolidin-1-yl]-4-oxo-1-(pyrrolidin-3-yl)-1,4-dihydroquinoline-3-carboxylic acid | $^1H$ NMR (400 MHz, DMSO-$d_6$) δ 8.93 (d, J = 18.0 Hz, 1H), 8.13 (s, 1H), 7.91-7.87 (m, 1H), 7.77 (dd, J = 7.6 Hz, 1.6 Hz, 1H), 7.41 (brs, 1H), 6.92-6.88 (m, 1H), 5.31 (brs, 1H), 4.95 (brs, 1H), 4.45-4.37 (m, 2H), 3.88-3.83 (m, 1H), 3.51-3.22 (m, 4H), 3.10-3.06 (m, 1H), 2.93-2.86 (m, 1H), 2.34-2.30 (m, 1H), 2.08-2.02 (m, 2H), 1.99-1.85 (m, 2H) (—COOH, NH protons not observed). MS (ESI) m/z: 503.3 [M + H]$^+$ | +++ |
| 368. | 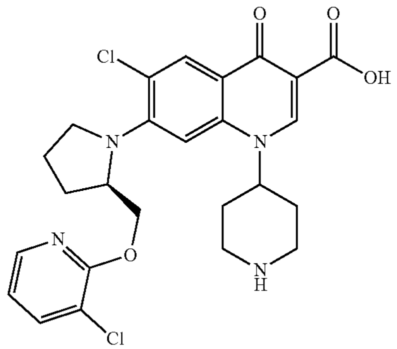 [SMILES: O=C(O)c1cn(C2CCNCC2)c2cc(N3CCC[C@@H]3COc3ncccc3Cl)c(Cl)cc2c1=O] | 6-chloro-7-[(2R)-2-{[(3-chloropyridin-2-yl)oxy]methyl}pyrrolidin-1-yl]-4-oxo-1-(piperidin-4-yl)-1,4-dihydroquinoline-3-carboxylic acid | $^1H$ NMR (400 MHz, DMSO-$d_6$): δ 8.66 (s, 1H), 8.15 (s, 1H), 7.89 (dd, J = 4.8, 3.6 Hz, 1H), 7.77 (dd, J = 7.6, 1.2 Hz, 1H), 7.21 (bs, 1H), 6.89 (dd, J = 7.6, 4.8 Hz, 1H), 6.55 (bs, 1H), 5.04-4.95 (m, 1H), 4.85-4.76 (m, 1H), 4.38 (d, J = 4 Hz, 2H), 3.88-3.84 (m, 1H), 3.21-3.14 (m, 1H), 3.06-3.03 (m, 2H), 2.85-2.70 (m, 2H), 2.40-2.30 (m, 1H), 2.17-2.10 (m, 1H), 2.07-1.92 (m, 3H), ), 1.92-1.80 (m, 3H), MS (ESI) m/z: 517.3 [M + H]$^+$ | +++ |
| 369. | 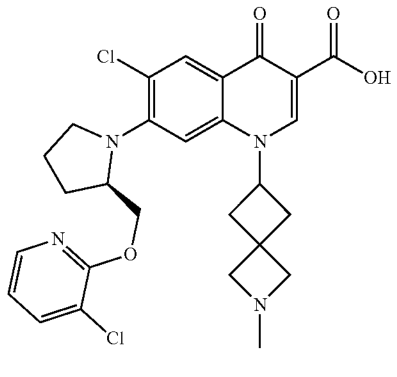 | 1-{2-Azaspiro[3.3]heptan-6-yl}-6-chloro-7-[(2R)-2-{[(3-chloropyridin-2-yl)oxy]methyl}pyrrolidin-1-yl]-4-oxo-1,4-dihydroquinoline-3-carboxylic acid | $^1H$ NMR (400 MHz, DMSO-$d_6$) δ 8.53 (s, 1H), 8.37 (s, 1H), 8.11 (s, 1H), 7.92 (dd, J = 4.8 Hz, 1.6 Hz, 1H), 7.78 (dd, J = 7.6 Hz, 1.6 Hz, 1H), 7.00 (brs, 1H), 6.92 (dd, J = 7.6 Hz, 4.8 Hz, 1H), 4.97-4.88 (m, 2H), 4.43-4.37 (m, 2H), 3.87-3.83 (m, 3H), 3.55-3.50 (m, 2H), 2.98-2.82 (m, 3H), 2.67-2.60 (m, 1H), 2.34-2.31 (m, 1H), 2.12-1.97 (m, 3H), 1.95-1.88 (m, 1H) (—COOH, not observed). MS (ESI) m/z: 529.3 [M + H]$^+$ | +++ |

-continued

| EX # | Structure | IUPAC name | Analytical data | Potency Lin28a-dep Z11 $IC_{50}$ (μM) |
|---|---|---|---|---|
| 370. | 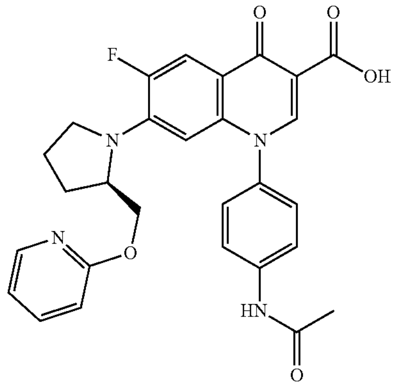 [SMILES: CC(=O)Nc1ccc(-n2cc(C(=O)O)c(=O)c3cc(F)c(N4CCC[C@@H]4COc4ccccn4)cc32)cc1] | (R)-1-(4-acetamidophenyl)-6-fluoro-4-oxo-7-(2-((pyridin-2-yloxy)methyl) pyrrolidin-1-yl)-1,4-dihydro-quinoline-3-carboxylic acid | $^1$H NMR (400 MHz, DMSO-$d_6$): δ 15.41 (s, 1H), 10.25 (s, 1H), 8.48 (s, 1H), 8.01 (dd, J = 4.8, 1.2 Hz, 1H), 7.90-7.83 (m, 2H), 7.72-7.52 (m, 4H), 6.94 (dd, J = 6.4, 5.2 Hz, 1H), 6.63 (d, J = 8.4 Hz, 1H), 6.11 (d, J = 7.6 Hz, 1H), 4.42-4.35 (m, 1H), 4.23-4.18 (m, 2H), 3.41-3.16 (m, 2H), 2.11 (s, 3H), 2.09-1.92 (m, 4H), MS (ESI) m/z 517.3 $[M + H]^+$ | ++++ |
| 371. | 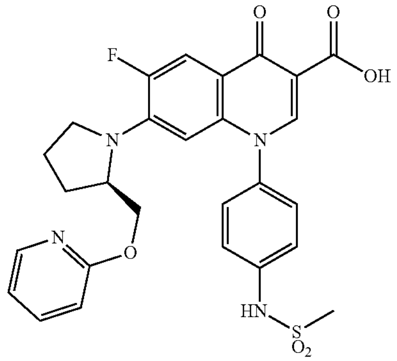 [SMILES: CS(=O)(=O)Nc1ccc(-n2cc(C(=O)O)c(=O)c3cc(F)c(N4CCC[C@@H]4COc4ccccn4)cc32)cc1] | (R)-6-fluoro-1-(4-(methyl-sulfonamido) phenyl)-4-oxo-7-(2-((pyridin-2-yloxy)methyl) pyrrolidin-1-yl)-1,4-dihydro-quinoline-3-carboxylic acid | $^1$HNMR (400 MHz, DMSO-$d_6$): δ 10.22 (s, 1H), 8.50 (s, 1H), 8.04-8.01 (m, 1H), 7.89 (d, J = 14.4 Hz, 1H), 7.68-7.58 (m, 3H), 7.43 (d, J = 7.2 Hz, 1H), 7.31 (d, J = 8.4 Hz, 1H), 6.96-6.93 (m, 1H), 6.65 (d, J = 8.4 Hz, 1H), 6.13 (d, J = 7.6 Hz, 1H), 4.45-4.35 (m, 1H), 4.21 (d, J = 4.8 Hz, 2H), 3.48-3.33 (m, 1H), 3.22-3.11 (m, 1H), 3.09 (s, 3H), 2.09-1.92 (m, 4H) (—COOH, proton not observed), MS (ESI): m/z 553.3 $[M + H]^+$ | ++++ |
| 372. | 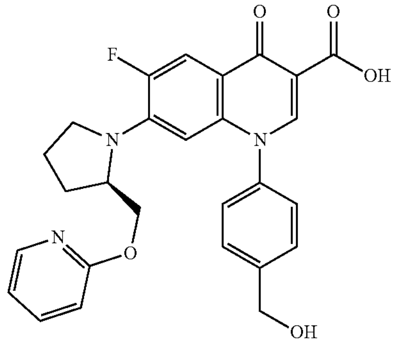 [SMILES: O=C(O)c1cn(-c2ccc(CO)cc2)c2cc(N3CCC[C@@H]3COc3ccccn3)c(F)cc2c1=O] | (R)-6-fluoro-1-(4-(hydroxymethyl) phenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.41 (s, 1H), 8.48 (s, 1H), 8.03 (d, J = 3.6 Hz, 1H), 7.90 (d, J = 14.8 Hz, 1H), 7.69-7.67 (m, 1H), 7.65-7.54 (m, 3H), 7.35 (d, J = 7.2 Hz, 1H), 6.96 (t, J = 6.4 Hz, 1H), 6.66 (d, J = 8.4 Hz, 1H), 6.09 (d, J = 7.2 Hz, 1H), 5.42 (t, J = 5.6 Hz, 1H), 4.59 (d, J = 5.6 Hz, 2H), 4.34 (s, 1H), 4.24-4.13 (m, 2H), 3.35 (s, 1H), 3.18-3.16 (m, 1H), 2.04-1.91 (m, 4H), MS (ESI): m/z 490.3 $[M + H]^+$ | ++++ |
| 373. | 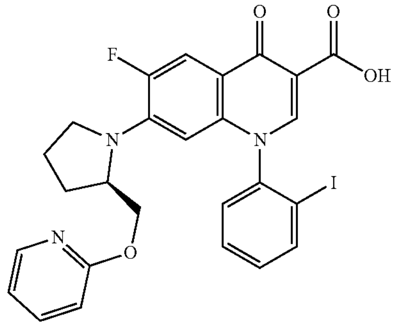 [SMILES: O=C(O)c1cn(-c2ccccc2I)c2cc(N3CCC[C@@H]3COc3ccccn3)c(F)cc2c1=O] | (R)-6-fluoro-1-(2-fluorophenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.25 (s, 1H), 8.70 (d, J = 3.6 Hz, 1H), 8.04 (d, J = 2.8 Hz, 1H), 7.89 (d, J = 14.4 Hz, 1H), 7.81-7.76 (m, 1H), 7.69-7.51 (m, 3H), 7.36-7.27 (m, 1H), 6.98-6.95 (m, 1H), 6.66 (d, J = 8.0 Hz, 1H), 5.95 (t, J = 8.0 Hz, 1H), 4.34 (brs, 1H), 4.22-4.16 (m, 2H), 3.37 (brs, 1H), 3.20 (brs, 1H), 2.07-1.87 (m, 4H). MS (ESI) m/z: 478.3 $[M + H]^+$ | +++ |

-continued

| EX # | Structure | IUPAC name | Analytical data | Potency Lin28a-dep Z11 $IC_{50}$ (μM) |
|---|---|---|---|---|
| 374. | 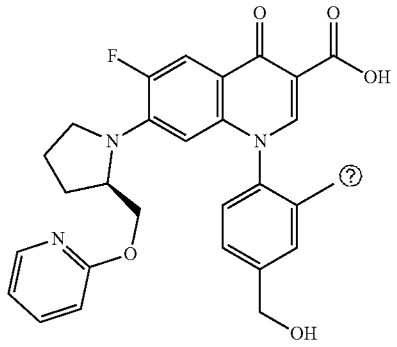 | (R)-6-fluoro-1-(2-fluoro-4-(hydroxymethyl) phenyl)-4-oxo-7-(2-((pyridin-2-yloxy)methyl) pyrrolidin-1-yl)-1,4-dihydroquinoline-3-carboxylic acid | $^{1}$HNMR (400 MHz, DMSO-$d_6$): δ 15.26 (s, 1H), 8.67-8.64 (m, 1H), 8.03 (d, J = 3.6 Hz, 1H), 7.90 (d, J = 14.4, 1H), 7.75-7.64 (m, 2H), 7.47 (dd, J = 28.8, 10.8 Hz, 1H), 7.21 (t, J = 10.8 Hz, 1H), 6.98-6.92 (m, 1H), 6.67 (dd, J = 8.0, 2.4 Hz, 1H), 5.99 (t, J = 7.2 Hz, 1H), 5.57-5.54 (m, 1H), 4.59 (d, J = 4.0 Hz, 2H), 4.35 (brs, 1H), 4.24-4.12 (m, 2H), 3.41-3.20 (m, 2H), 2.09-1.95 (m, 4H), MS (ESI) m/z: 508.3 $[M + H]^+$ | ++++ |
| 375. | 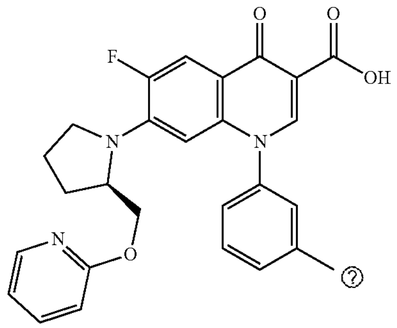 | (R)-6-fluoro-1-(3-fluorophenyl)-4-oxo-7-(2-((pyridin-2-yloxy)methyl) pyrrolidin-1-yl)-1,4-dihydroquinoline-3-carboxylic acid | $^{1}$HNMR (400 MHz, DMSO-$d_6$): δ 8.46 (bs, 1H), 8.02 (bs, 1H), 7.85-7.81 (m, 1H), 7.66-7.60 (m, 3H), 7.43 (s, 2H), 6.95 (s, 1H), 6.70-6.60 (m, J = 8.00 Hz, 1H), 6.06 (d, J = 6.80 Hz, 1H), 4.30 (bs, 1H), 4.20-4.14 (m, 2H), 3.18 (s, 2H), 2.04-1.90 (m, 4H), MS (ESI): m/z 478.3 $[M + H]^+$ | +++ |
| 376. | 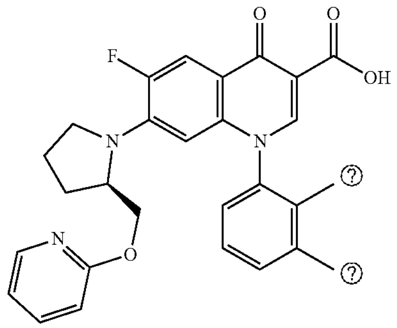 | (R)-1-(2,3-difluorophenyl)-6-fluoro-4-oxo-7-(2-((pyridin-2-yloxy)methyl) pyrrolidin-1-yl)-1,4-dihydroquinoline-3-carboxylic acid | $^{1}$HNMR (400 MHz, DMSO-$d_6$): δ 15.21 (s, 1H), 8.81 (d, J = 10.0 Hz, 1H), 8.03 (t, J = 5.2 Hz, 1H), 7.90 (dd, J = 14.6, 2.80 Hz, 1H), 7.69-7.60 (m, 3H), 7.55-7.50 (m, 0.5H), 7.31-7.26 (m, 0.5H), 6.97-6.93 (m, 1H), 6.66 (dd, J = 8.2, 5.2 Hz, 1H), 6.01 (t, J = 7.2 Hz, 1H), 4.39 (bs, 1H), 4.23-4.15 (m, 2H), 3.47-3.38 (m, 1H), 3.27-3.21 (m, 1H), 2.08-1.92 (m, 4H), MS (ESI) m/z: 496.3 $[M + H]^+$ | +++ |
| 377. | 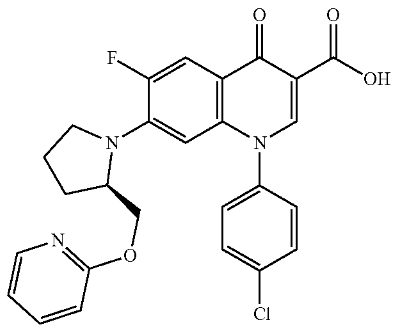 [SMILES: O=C(O)c1cn(-c2ccc(Cl)cc2)c2cc(N3CCC[C@@H]3COc3ccccn3)c(F)cc2c1=O] | (R)-1-(4-chlorophenyl)-6-fluoro-4-oxo-7-(2-((pyridin-2-yloxy)methyl) pyrrolidin-1-yl)-1,4-dihydroquinoline-3-carboxylic acid | $^{1}$HNMR (400 MHz, DMSO-$d_6$): δ 15.36 (s, 1H), 8.46 (s, 1H), 8.04 (d, J = 3.60 Hz, 1H), 7.84 (d, J = 14.4 Hz, 1H), 7.70-7.54 (m, 4H), 7.43 (s, 1H), 6.97 (t, J = 5.6 Hz, 1H), 6.67 (d, J = 8.4 Hz, 1H), 6.03 (d, J = 7.2 Hz, 1H), 4.28-4.23 (m, 2H), 4.13-4.11 (m, 1H), 3.32 (s, 1H), 3.21 (s, 1H), 2.06-1.90 (m, 4H), MS (ESI) m/z: 494.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 378. | 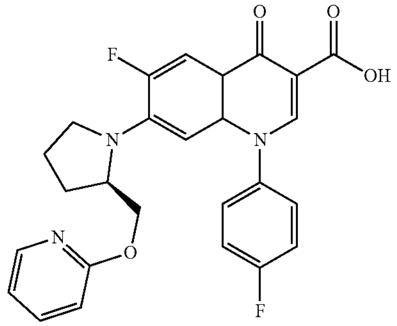 [SMILES: O=C(O)C1=CN(c2ccc(F)cc2)C2C=C(N3CCC[C@@H]3COc3ccccn3)C(F)=CC2C1=O] | (R)-6-fluoro-1-(4-fluorophenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.37 (bs, 1H), 8.53 (bs, 1H), 8.04 (d, J = 3.6 Hz, 1H), 7.88 (d, J = 14.4 Hz, 1H), 7.69-7.66 (m, 3H), 7.52 (bs, 1H), 7.23 (bs, 1H), 6.96 (t, J = 5.6 Hz, 1H), 6.66 (d, J = 8.4 Hz, 1H), 6.00 (d, J = 7.2 Hz, 1H), 4.32 (bs, 1H), 4.33-4.12 (m, 2H), 3.38 (brs, 1H), 3.21 (brs, 1H), 2.06-1.91 (m, 4H), MS (ESI) m/z: 478.3 $[M + H]^+$ | ++++ |
| 379. | 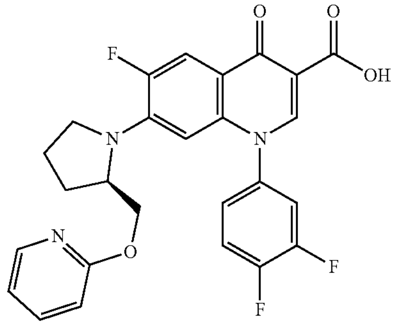 [SMILES: O=C(O)c1cn(-c2ccc(F)c(F)c2)c2cc(N3CCC[C@@H]3COc3ccccn3)c(F)cc2c1=O] | (R)-1-(3,4-difluorophenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.33 (s, 1H), 8.60 (s, 1H), 8.03 (t, J = 5.6 Hz, 1H), 7.98-7.87 (m, 2H), 7.77-7.47 (m, 3H), 6.98-6.93 (m, 1H), 6.67 (t, J = 6.0 Hz, 1H), 6.05 (d, J = 7.6 Hz, 1H), 4.38 (brs, 1H), 4.22-4.17 (m, 2H), 3.44 (brs, 1H), 3.25 (brs, 1H), 2.07-1.91 (m, 4H). MS (ESI) m/z: 496.3 $[M + H]^+$ | +++ |
| 380. | 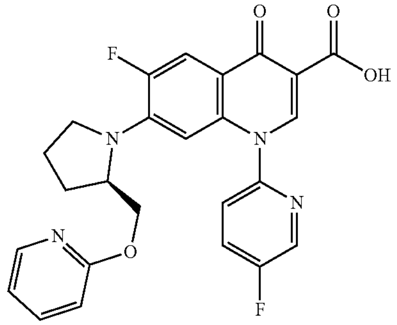 [SMILES: O=C(O)c1cn(-c2ccc(F)cn2)c2cc(N3CCC[C@@H]3COc3ccccn3)c(F)cc2c1=O] | (R)-6-fluoro-1-(5-fluoropyridin-2-yl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.25 (s, 1H), 8.77 (s, 1H), 8.61 (d, J = 2.8 Hz, 1H), 8.07-8.02 (m, 2H), 7.97-7.94 (m, 1H), 7.90 (d, J = 14.4 Hz, 1H), 7.70-7.65 (m, 1H), 6.97-6.94 (m, 1H), 6.67 (d, J = 8.4 Hz, 1H), 6.21 (d, J = 7.2 Hz, 1H), 4.39 (brs, 1H), 4.26-4.22 (m, 1H), 4.18-4.13 (m, 1H), 3.51-3.48 (m, 2H), 2.09-1.93 (m, 4H), MS (ESI) m/z: 479.3 $[M + H]^+$ | +++ |
| 381. | 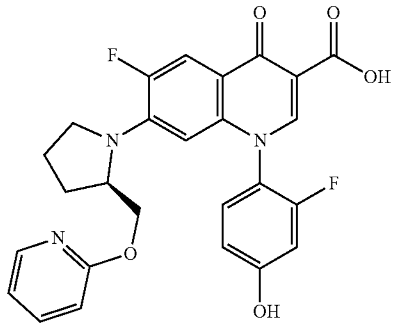 [SMILES: O=C(O)c1cn(-c2ccc(O)cc2F)c2cc(N3CCC[C@@H]3COc3ccccn3)c(F)cc2c1=O] | (R)-6-fluoro-1-(2-fluoro-4-hydroxyphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.30 (s, 1H), 10.61 (s, 1H), 8.59 (d, J = 2.0 Hz, 1H), 8.03 (d, J = 3.6 Hz, 1H), 7.88 (d, J = 14.4 Hz, 1H), 7.69-7.64 (m, 1H), 7.57-7.49 (m, 1H), 6.97-6.91 (m, 1H), 6.89-6.83 (m, 1H), 6.69-6.65 (m, 2H), 6.04 (t, J = 8.4 Hz, 1H), 4.40-4.38 (brs, 1H), 4.24-4.19 (m, 2H), 3.23-3.21 (m, 2H), 2.09-1.92 (m, 4H), MS (ESI) m/z: 494.3 $[M + H]^+$ | +++ |

-continued

| EX # | Structure | IUPAC name | Analytical data | Potency Lin28a-dep Z11 $IC_{50}$ (μM) |
|---|---|---|---|---|
| 382. | 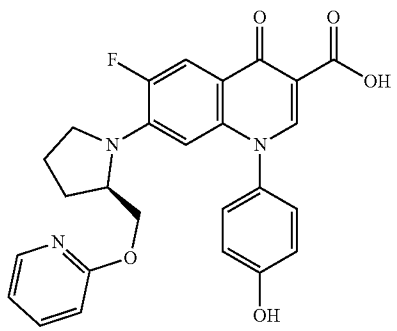 | (R)-6-fluoro-1-(4-hydroxyphenyl)-4-oxo-7-(2-((pyridin-2-yloxy) methyl) pyrrolidin-1-yl)-1,4-dihydroquinoline 3-carboxylic acid | $^1$HNMR (400 MHz, DMSO-$d_6$): δ 15.44 (s, 1H), 10.11 (s, 1H), 8.45 (s, 1H), 8.03 (dd, J = 5.2, 1.6 Hz, 1H), 7.87 (d, J = 14.4 Hz, 1H), 7.68-7.63 (m, 1H), 7.40 (t, J = 6.4 Hz, 2H), 7.00-6.93 (m, 2H), 6.81 (d, J = 8.1 Hz, 1H), 6.65 (d, J = 8.4 Hz, 1H), 6.11 (d, J = 7.2 Hz, 1H), 4.38 (bs, 1H), 4.24-4.18 (m, 2H), 3.32 (bs, 1H), 3.27-3.16 (m, 1H), 2.08-1.87 (m, 4H). MS (ESI) m/z: 476.3 $[M + H]^+$. | ++++ |
| 383. | 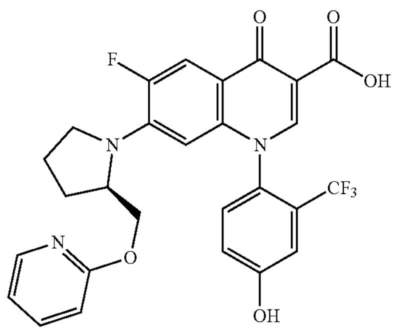 [SMILES: O=C(O)c1cn(-c2ccc(O)cc2C(F)(F)F)c2cc(N3CCC[C@@H]3COc3ccccn3)c(F)cc2c1=O] | (R)-6-fluoro-1-(4-hydroxy-2-(trifluoromethyl) phenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.32 (s, 1H), 10.85 (s, 1H), 8.60 (s, 1H), 8.06-8.02 (m, 1H), 7.88 (d, J = 14.4 Hz, 1H), 7.69-7.60 (m, 2H), 7.32-7.26 (m, 1H), 7.11-7.06 (m, 1H), 6.98-6.93 (m, 1H), 6.65 (d, J = 8.4 Hz, 1H), 5.79 (dd, J = 32.8, 7.6 Hz, 1H), 4.32-4.30 (m, 1H), 4.18-4.12 (m, 2H), 3.34-3.16 (m, 2H), 2.09-1.87 (m, 4H), MS (ESI) m/z: 544.3 $[M + H]^+$ | ++ |
| 384. | 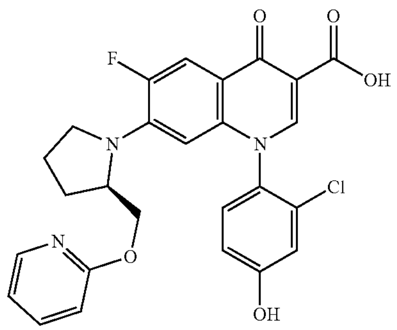 [SMILES: O=C(O)c1cn(-c2ccc(O)cc2Cl)c2cc(N3CCC[C@@H]3COc3ccccn3)c(F)cc2c1=O] | (R)-1-(2-chloro-4-hydroxyphenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.32 (s, 1H), 10.79 (s, 1H), 8.54 (d, J = 1.2 Hz, 1H), 8.04 (d, J = 4.8 Hz, 1H), 7.88 (d, J = 14.4 Hz, 1H), 7.69-7.64 (m, 1H), 7.56 (t, J = 9.6 Hz, 1H), 7.19 (d, J = 2.8 Hz, 0.5H), 7.05-7.01 (m, 0.5H), 7.02-6.81 (m, 2H), 6.68-6.54 (m, 1H), 5.89 (dd, J = 7.6, 8.4 Hz, 1H), 4.35 (s, 1H), 4.19 (d, J = 7.6 Hz, 2H), 3.33 (s, 1H), 3.19 (t, J = 7.2 Hz, 1H), 2.07-1.91 (m, 4H). MS (ESI) m/z: 510.2 $[M + H]^+$ | +++ |
| 385. | 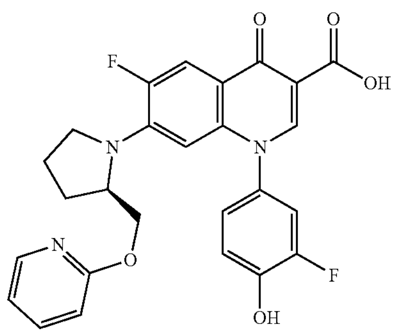 [SMILES: O=C(O)c1cn(-c2ccc(O)c(F)c2)c2cc(N3CCC[C@@H]3COc3ccccn3)c(F)cc2c1=O] | (R)-6-fluoro-1-(3-fluoro-4-hydroxyphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.3 (s, 1H), 10.80 (brs, 1H), 8.49 (s, 1H), 8.02 (s, 1H), 7.87 (d, J = 14.4 Hz, 1H), 7.70-7.56 (m, 2H), 7.30-7.12 (m, 1.5H), 7.05-6.90 (m, 1.5H), 6.70-6.64 (m, 1H), 6.11 (d, J = 5.2 Hz, 1H), 4.40 (brs, 1H), 4.21 (d, J = 4.4 Hz, 2H), 3.30-3.19 (m, 2H), 2.08-1.91, (m, 4H). MS (ESI) m/z: 494.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 386. | 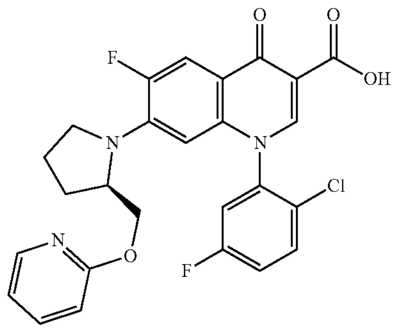 | (R)-1-(2-chloro-5-fluorophenyl)-6-fluoro-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$): δ 15.24 (s, 1H), 8.74 (s, 1H), 8.06-8.03 (m, 1H), 7.93-7.87 (m, 2H), 7.71-7.64 (m, 1H), 7.61-7.52 (m, 2H), 6.99-6.92 (m, 1H), 6.69 (t, J = 8.4 Hz, 1H), 5.84 (dd, J = 7.6, 7.2 Hz, 1H), 4.40-4.30 (m, 1H), 4.24-4.14 (m, 2H), 3.50-3.35 (m, 1H), 3.23-3.19 (m, 1H), 2.06-1.91 (m, 4H). MS (ESI) m/z: 512.3 $[M + H]^+$ | +++ |
| 387. | 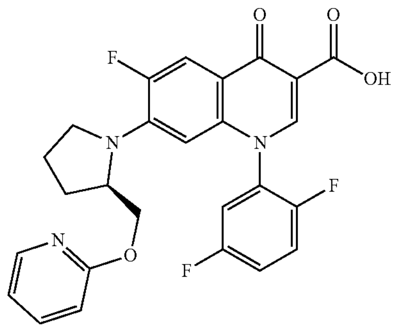 [SMILES: O=C(O)c1cn(-c2cc(F)ccc2F)c2cc(N3CCC[C@@H]3COc3ccccn3)c(F)cc2c1=O] | (R)-1-(2,5-difluorophenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.21 (s, 1H), 8.78 (d, J = 2.4 Hz, 1H), 8.06-8.02 (m, 1H), 7.92-7.88 (m, 1H), 7.84-7.82 (m, 1H), 7.71-7.64 (m, 1.5H), 7.55-7.53 (m, 1H), 7.45-7.40 (m, 0.5H), 6.98-6.92 (m, 1H), 6.69-6.65 (m, 1H), 6.01 (t, J = 8.00 Hz, 1H), 4.44-4.36 (m, 1H), 4.24-4.16 (m, 2H), 3.50-3.38 (m, 2H), 2.09-1.89 (m, 4H). MS (ESI) m/z: 496.3 $[M + H]^+$ | +++ |
| 388. | 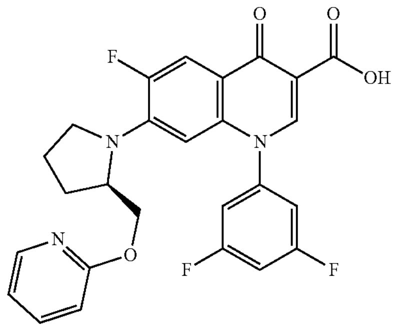 [SMILES: O=C(O)c1cn(-c2cc(F)cc(F)c2)c2cc(N3CCC[C@@H]3COc3ccccn3)c(F)cc2c1=O] | (R)-1-(3,5-difluorophenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.32 (s, 1H), 8.64 (s, 1H), 8.03 (dd, J = 4.80, 1.20 Hz, 1H), 7.90 (d, J = 14.40 Hz, 1H), 7.69-7.53 (m, 4H), 6.97-6.93 (m, 1H), 6.68 (d, J = 8.40 Hz, 1H), 6.10 (d, J = 7.60 Hz, 1H), 4.41-4.39 (m, 1H), 4.20 (d, J = 5.6 Hz, 2H), 3.50-3.44 (m, 1H), 3.27-3.23 (m, 1H), 2.07-1.92 (m, 4H). MS m/z: 496.3 $[M + H]^+$ | +++ |
| 389. | 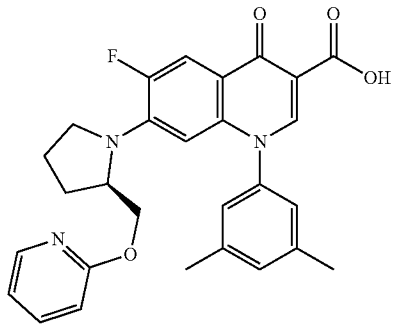 [SMILES: Cc1cc(C)cc(-n2cc(C(=O)O)c(=O)c3cc(F)c(N4CCC[C@@H]4COc4ccccn4)cc32)c1] | (R)-1-(3,5-dimethylphenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.40 (s, 1H), 8.48 (s, 1H), 8.02 (dd, J = 4.8, 1.2 Hz, 1H), 7.88 (d, J = 14.8 Hz, 1H), 7.69-7.65 (m, 1H), 7.26-7.22 (m, 3H), 6.97-6.94 (m, 1H), 6.67 (d, J = 8.4 Hz, 1H), 6.14 (d, J = 7.6 Hz, 1H), 4.29 (brs, 1H), 4.17 (d, J = 7.6 Hz, 2H), 3.40-3.37 (m, 1H), 3.27-3.22 (m, 1H), 2.39 (s, 3H), 2.18 (s, 3H), 2.09-2.00 (m, 2H), 1.99-1.91 (m, 2H). MS (ESI) m/z: 488.3 $[M + H]^+$ | +++ |

-continued

| EX # | Structure | IUPAC name | Analytical data | Potency Lin28a-dep Z11 $IC_{50}$ (μM) |
|---|---|---|---|---|
| 390. | 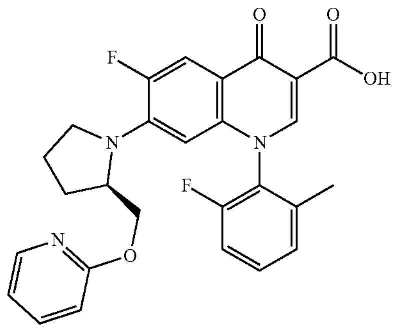 [SMILES: Cc1cccc(F)c1-n1cc(C(=O)O)c(=O)c2cc(F)c(N3CCC[C@@H]3COc3ccccn3)cc21] | (R)-6-fluoro-1-(2-fluoro-6-methylphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.24 (s, 1H), 8.72 (d, J = 1.6 Hz, 1H), 8.05-8.03 (m, 1H), 7.91 (dd, J = 14.4, 2.4 Hz, 1H), 7.71-7.65 (m, 1H), 7.55-7.50 (m, 1H), 7.45-7.38 (m, 1H), 7.17-7.07 (m, 1H), 6.97-6.93 (m, 1H), 6.66 (t, J = 8.4 Hz, 1H), 5.80 (q, J = 7.6 Hz, 1H), 4.31-4.20 (m, 1H), 4.18-4.11 (m, 2H), 3.39-3.32 (m, 1H), 3.24-3.17 (m, 1H), 2.08-1.87 (m, 7H). MS (ESI) m/z: 492.3 $[M + H]^+$. | +++ |
| 391. | 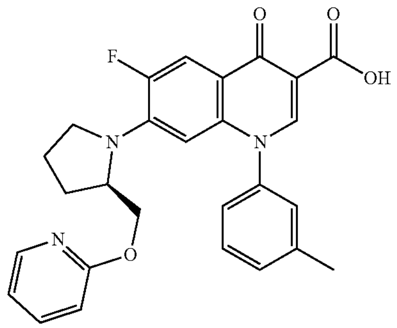 [SMILES: Cc1cccc(-n2cc(C(=O)O)c(=O)c3cc(F)c(N4CCC[C@@H]4COc4ccccn4)cc32)c1] | (R)-6-fluoro-4-oxo-7-(2-((pyridin-2-yloxy)methyl) pyrrolidin-1-yl)-1-(m-tolyl)-1,4-dihydroquinoline-3-carboxylic acid | $^1$HNMR (400 MHz, DMSO-$d_6$-VT): δ 8.45 (s, 1H), 8.00-7.98 (m, 1H), 7.81 (d, J = 14.8 Hz, 1H), 7.63-7.59 (m, 1H), 7.44-7.40 (m, 1H), 7.35-7.26 (m, 3H), 6.91-6.88 (m, 1H), 6.60 (d, J = 8.4 Hz, 1H), 6.14 (d, J = 7.6 Hz, 1H), 4.24-4.18 (m, 3H), 3.39-3.37 (m, 1H), 3.19-3.17 (m, 1H), 2.34 (s, 3H), 2.07-1.89 (m, 4H), (—COOH proton was not observed in $H^1$NMR). MS (ESI) m/z: 474.3 $[M + H]^+$ | ++++ |
| 392. | 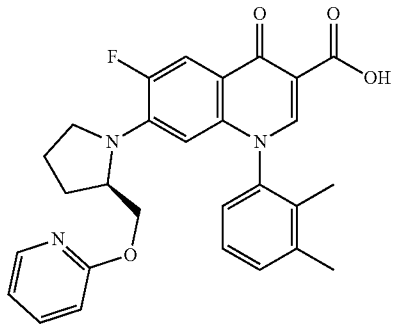 [SMILES: Cc1cccc(-n2cc(C(=O)O)c(=O)c3cc(F)c(N4CCC[C@@H]4COc4ccccn4)cc32)c1C] | (R)-1-(2,3-dimethylphenyl)-6-fluoro-4-oxo-7-(2-((pyridin-2-yloxy) methyl)pyrrolidin-1-yl)-1,4-dihydroquinoline-3-carboxylic acid | $^1$H NMR (400 MHz, DMSO-$d_6$-VT): δ 15.40 (s, 1H), 8.44 (d, J = 12.0 Hz, 1H), 8.03 (d, J = 0.8 Hz, 1H), 7.90 (d, J = 14.8 Hz, 1H), 7.70-7.65 (m, 1H), 7.42-7.29 (m, 2.5H), 7.16-7.12 (m, 0.5H), 6.98-6.93 (m, 1H), 6.67 (t, J = 8.0 Hz, 1H), 5.84-5.79 (m, 1H), 4.32-4.10 (m, 3H), 3.42-3.37 (m, 1H), 3.29-3.21 (m, 1H), 2.36 (s, 1H), 2.11 (s, 2H), 2.10-1.84 (m, 4H) 1.84-1.81 (m, 3H). MS (ESI) m/z: 488.3 $[M + H]^+$ | ++++ |
| 393. | 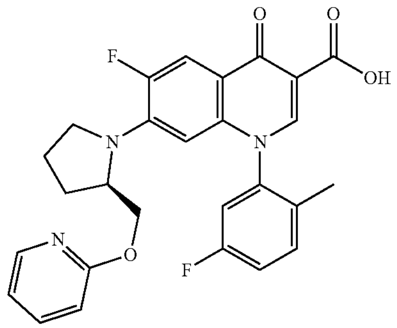 | (R)-6-fluoro-1-(5-fluoro-2-methylphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.24 (s, 1H), 8.58 (d, J = 2.4 Hz, 1H), 8.05-8.01 (m, 1H), 7.91 (dd, J = 14.4, 2.4 Hz, 1H), 7.69-7.66 (m, 1H), 7.59-7.54 (m, 1H), 7.38-7.27 (m, 2H), 6.99-6.93 (m, 1H), 6.69-6.66 (m, 1H), 5.84-5.77 (m, 1H), 4.29 (bs, 1H), 4.15 (t, J = 7.6 Hz, 2H), 3.39 (brs, 1H), 3.21-3.19 (m, 1H), 2.08-1.90 (m, 7H). MS (ESI) m/z: 492.3 $[M + H]^+$. | +++ |

-continued

| EX # | Structure | IUPAC name | Analytical data | Potency Lin28a-dep Z11 $IC_{50}$ (μM) |
|---|---|---|---|---|
| 394. | 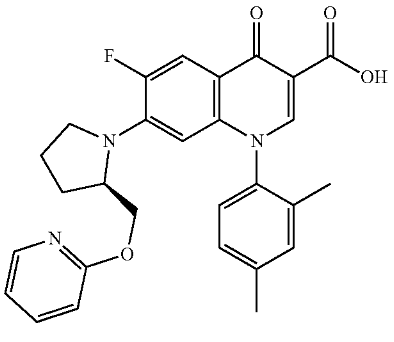 [SMILES: Cc1ccc(-n2cc(C(=O)O)c(=O)c3cc(F)c(N4CCC[C@@H]4COc4ccccn4)cc32)c(C)c1] | (R)-1-(2,4-dimethylphenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.40 (s, 1H), 8.46 (s, 1H), 8.08-8.04 (m, 1H), 7.91 (dd, J = 14.4, 1.2 Hz, 1H), 7.74-7.66 (m, 1H), 7.42-7.26 (m, 2H), 7.01-6.91 (m, 2H), 6.67 (dd, J = 12.0, 8.40 Hz, 1H), 5.84 (dd, J = 19.2, 7.6 Hz, 1H), 4.30-4.00 (m, 3H), 3.50-3.37 (m, 1H), 3.28-3.18 (m, 2H), 2.32 (s, 3H), 2.06-1.98 (m, 2H), 1.95-1.84 (m, 4H), MS m/z: 488.3 $[M + H]^+$ | +++ |
| 395. | 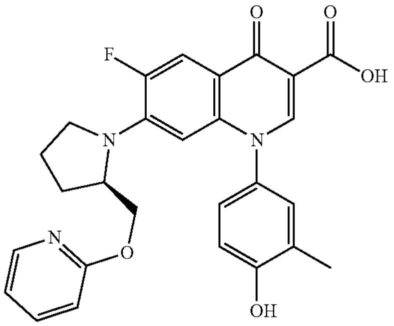 [SMILES: Cc1cc(-n2cc(C(=O)O)c(=O)c3cc(F)c(N4CCC[C@@H]4COc4ccccn4)cc32)ccc1O] | (R)-6-fluoro-1-(4-hydroxy-3-methylphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.44 (s, 1H), 10.02 (s, 1H), 8.44 (d, J = 1.6 Hz, 1H), 8.02 (t, J = 3.2 Hz, 1H), 7.87 (d, J = 14.4 Hz, 1H), 7.68-7.64 (m, 1H), 7.31 (d, J = 2.4 Hz, 1H), 7.26-7.21 (m, 1H), 6.99-6.84 (m, 2H), 6.68-6.64 (m, 1H), 6.17 (dd, J = 18.0, 7.6 Hz, 1H), 4.45-4.28 (m, 1H), 4.23 (d, J = 5.6 Hz, 1H), 4.18 (d, J = 5.6 Hz, 1H), 3.48-3.40 (m, 1H), 3.24-3.17 (m, 1H), 2.20 (s, 1H), 2.09-1.88 (m, 6H). MS (ESI) m/z: 490.2 | +++ |
| 396. | 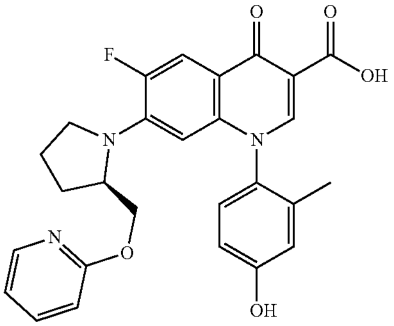 [SMILES: Cc1cc(O)ccc1-n1cc(C(=O)O)c(=O)c2cc(F)c(N3CCC[C@@H]3COc3ccccn3)cc21] | (R)-6-fluoro-1-(4-hydroxy-2-methylphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.43 (s, 1H), 9.99 (s, 1H), 8.44 (d, J = 2.00 Hz, 1H), 8.04-8.02 (m, 1H), 7.89 (dd, J = 14.6, 2.8 Hz, 1H), 7.69-7.63 (m, 1H), 7.28 (dd, J = 8.4, 5.6 Hz, 1H), 6.97-6.92 (m, 1H), 6.86-6.81 (m, 1H), 6.68-6.64 (m, 2H), 5.90 (dd, J = 19.4, 7.2 Hz, 1H), 4.36-4.31 (m, 1H), 4.21-4.17 (m, 2H), 3.20-3.13 (m, 2H), 2.09-1.91 (m, 4H), 1.85 (d, J = 6.8 Hz, 3H), MS (ESI) m/z: 490.3 $[M + H]^+$ | +++ |
| 397. | 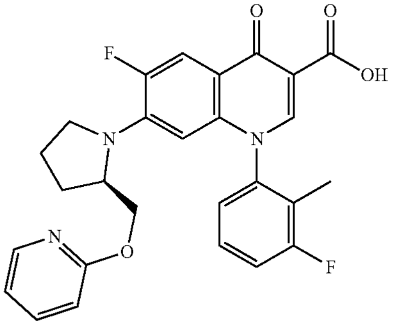 [SMILES: Cc1c(F)cccc1-n1cc(C(=O)O)c(=O)c2cc(F)c(N3CCC[C@@H]3COc3ccccn3)cc21] | (R)-6-fluoro-1-(3-fluoro-2-methylphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.36 (s, 1H), 8.59 (s, 1H), 8.05-8.01 (m, 1H), 7.91 (d, J = 14.4 Hz, 1H), 7.67 (s, 1H), 7.46-7.44 (m, 0.5H), 7.44-7.41 (m, 1H), 7.38-7.30 (m, 0.5H), 6.97-6.92 (m, 1H), 6.66 (d, J = 8.4 Hz, 1H), 5.81 (dd, J = 16.2, 7.2 Hz, 2H), 4.30 (s, 1H), 4.17-4.13 (m, 2H), 3.52-3.35 (m, 1H), 3.29-3.20 (m, 1H), 2.09-1.95 (m, 4H), 1.92-1.86 (m, 3H), MS (ESI) m/z: 492.3 $[M + H]^+$ | +++ |

-continued

| EX # | Structure | IUPAC name | Analytical data | Potency Lin28a-dep Z11 $IC_{50}$ (μM) |
|---|---|---|---|---|
| 398. | 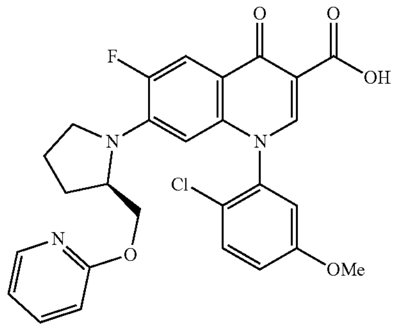 [SMILES: COc1ccc(Cl)c(-n2cc(C(=O)O)c(=O)c3cc(F)c(N4CCC[C@@H]4COc4ccccn4)cc32)c1] | (R)-1-(2-chloro-5-methoxyphenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.30 (s, 1H), 8.62 (bs, 1H), 8.03-8.06 (m, 1H), 7.90 (d, J = 13.6 Hz, 1H), 7.73-7.64 (m, 1.5H), 7.48-7.47 (m, 1H), 7.39 (d, J = 8.8 Hz, 0.5H), 7.21-7.17 (m, 1H), 6.99-6.93 (m, 1H), 6.68 (dd, J = 13.2, 8.4 Hz, 1H), 5.88 (dd, J = 18.4, 8.0 Hz, 1H), 4.30-4.27 (m, 1H), 4.20-4.14 (m, 2H), 3.84 (s, 1.5H), 3.66 (s, 1.5H), 3.51 (s, 1H), 3.20 (s, 1H), 2.07-1.88 (m, 4H), MS (ESI) m/z: 524.3 $[M + H]^+$ | +++ |
| 399. | 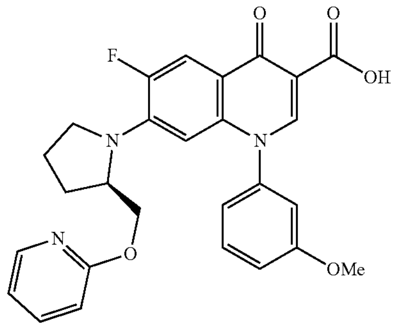 [SMILES: COc1cccc(-n2cc(C(=O)O)c(=O)c3cc(F)c(N4CCC[C@@H]4COc4ccccn4)cc32)c1] | (R)-6-fluoro-1-(3-methoxyphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.30 (s, 1H), 8.50 (s, 1H), 8.02 (dd, J = 5.2, 6.8 Hz, 1H), 7.68 (d, J = 14.8 Hz, 1H), 7.65 (t, J = 6.8 Hz, 0.5H), 7.35-7.28 (m, 1.5H), 7.21-7.10 (m, 2H), 6.94 (dd, J = 11.2, 5.6 Hz, 1H), 6.66 (t, J = 8.4 Hz, 1H), 6.13 (d, J = 7.2 Hz, 1H), 4.33 (brs, 1H), 4.25-4.10 (m, 2H), 3.83 (s, 1.5H), 3.70 (s, 1.5H), 3.44-3.34 (m, 1H), 3.24-3.14 (m, 1H), 2.10-1.86 (m, 4H), MS (ESI) m/z: 490.3. $[M + H]^+$ | ++++ |
| 400. | 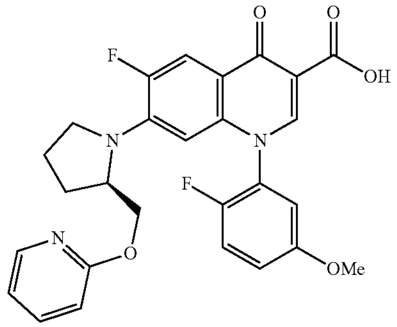 [SMILES: COc1ccc(F)c(-n2cc(C(=O)O)c(=O)c3cc(F)c(N4CCC[C@@H]4COc4ccccn4)cc32)c1] | (R)-6-fluoro-1-(2-fluoro-5-methoxyphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 8.54-8.45 (m, 1H), 8.05-8.02 (m, 1H), 7.84 (d, J = 13.2 Hz, 1H), 7.70-7.64 (m, 1H), 7.52 (t, J = 9.6 Hz, 0.5H), 7.37 (bs, 1H), 7.25-7.14 (m, 1.5H), 6.98-6.92 (m, 1H), 6.68 (t, J = 8.4 Hz, 1H), 6.05-6.00 (m, 1H), 4.33-4.28 (m, 1H), 4.23-4.15 (m, 2H), 3.82 (s, 1.5H), 3.67 (s, 1.5H), 3.42 (s, 1H), 3.20-3.14 (m, 1H), 2.09-1.98 (m, 4H), MS (ESI) m/z: 508.3 $[M + H]^+$ | +++ |
| 401. | 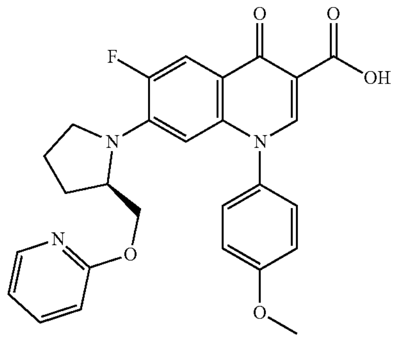 [SMILES: COc1ccc(-n2cc(C(=O)O)c(=O)c3cc(F)c(N4CCC[C@@H]4COc4ccccn4)cc32)cc1] | (R)-6-fluoro-1-(4-methoxyphenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.43 (s, 1H), 8.47 (s, 1H), 8.03 (dd, J = 5.2, 1.2 Hz, 1H), 7.89 (d, J = 14.4 Hz, 1H), 7.69-7.64 (m, 1H), 7.57-7.52 (m, 2H), 7.18 (dd, J = 8.4, 2.4 Hz, 1H), 6.97-6.93 (m, 2H), 6.66 (d, J = 8.4 Hz, 1H), 6.09 (d, J = 7.6 Hz, 1H), 4.39-4.31 (m, 1H), 4.26-4.21 (m, 1H), 4.17-4.12 (m, 1H), 3.81 (s, 3H), 3.38-3.31 (m, 1H), 3.25-3.19 (m, 1H), 2.06-1.87 (m, 4H), MS (ESI) m/z: 490.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 402. | 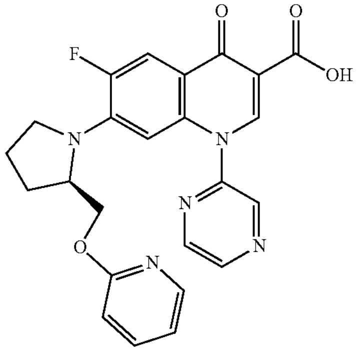 [SMILES: O=C(O)c1cn(-c2cnccn2)c2cc(N3CCC[C@@H]3COc3ccccn3)c(F)cc2c1=O] | (R)-6-fluoro-4-oxo-1-(pyrazin-2-yl)-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.18 (s, 1H), 9.14 (d, J = 1.6 Hz, 1H), 8.91 (d, J = 2.0 Hz, 2H), 8.73 (dd, J = 2.4, 1.2 Hz, 1H), 8.03-8.00 (m, 1H), 7.90 (d, J = 14.4 Hz, 1H), 7.66 (td, J = 7.2, 2.0 Hz, 1H), 6.95 (td, J = 4.8, 0.8 Hz, 1H), 6.67 (d, J = 8.4 Hz, 1H), 6.29 (d, J = 7.6 Hz, 1H), 4.46-4.44 (m, 1H), 4.26-4.16 (m, 2H), 3.48-3.46 (m, 1H), 3.33-3.26 (m, 1H), 2.09-1.92 (m, 4H). MS (ESI) m/z: 462.3 [M + H]$^+$ | +++ |
| 403. | 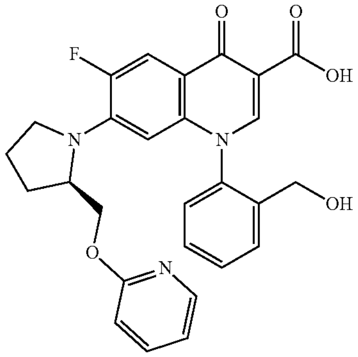 [SMILES: O=C(O)c1cn(-c2ccccc2CO)c2cc(N3CCC[C@@H]3COc3ccccn3)c(F)cc2c1=O] | (R)-6-fluoro-1-(2-(hydroxymethyl) phenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.40 (s, 1H), 8.50 (brs, 1H), 8.04 (dt, J = 8.4, 1.2 Hz, 1H), 7.89 (d, J = 14.4 Hz, 1H), 7.71-7.69 (m, 1.5H), 7.67-7.50 (m, 3H), 7.30 (t, J = 8.0, 0.5H), 6.97 (t, J = 6.0 Hz, 1H), 6.67 (t, J = 8.0 Hz, 1H), 5.79 (dd, J = 29.2, 7.6 Hz, 1H), 5.23 (dt, J = 24.4, 5.2 Hz, 1H), 4.31-4.07 (m, 5H), 3.23 (brs, 1H), 3.12 (brs, 1H), 2.08-1.89 (m, 4H), MS (ESI) m/z: 490.3 [M + H]$^+$ | +++ |
| 404. | 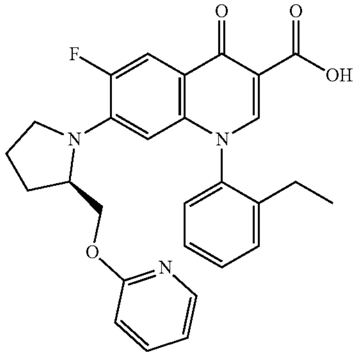 [SMILES: CCc1ccccc1-n1cc(C(=O)O)c(=O)c2cc(F)c(N3CCC[C@@H]3COc3ccccn3)cc21] | (R)-1-(2-ethylphenyl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.45 (brs, 1H), 8.45 (brs, 1H), 8.03 (t, J = 2.0 Hz, 1H), 7.87-7.83 (m, 1H), 7.70-7.64 (m, 1H), 7.58-7.42 (m, 3H), 7.31-7.24 (m, 1H), 6.98-6.92 (m, 1H), 6.64 (dd, J = 14.0, 8.4 Hz, 1H), 5.77 (dd, J = 18.8, 7.2 Hz, 1H), 4.25-4.10 (m, 3H), 3.31-3.21 (m, 1H), 3.15-3.09 (m, 1H), 2.24-2.18 (m, 2H), 2.04-1.84 (m, 4H), 0.98-0.93 (m, 3H). MS (ESI) m/z: 488.3 [M + H]$^+$. | +++ |
| 405. | 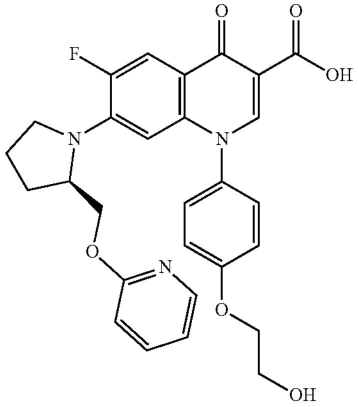 [SMILES: O=C(O)c1cn(-c2ccc(OCCO)cc2)c2cc(N3CCC[C@@H]3COc3ccccn3)c(F)cc2c1=O] | (R)-6-fluoro-1-(4-(2-hydroxyethoxy) phenyl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.43 (s, 1H), 8.46 (s, 1H), 8.04-8.02 (m, 1H), 7.88 (d, J = 14.4 Hz, 1H), 7.69-7.64 (m, 1H), 7.53 (t, J = 9.2 Hz, 2H), 7.20-7.17 (m, 1H), 6.97-6.94 (m, 2H), 6.66 (d, J = 8.4 Hz, 1H), 6.09 (d, J = 7.6 Hz, 1H), 4.94 (t, J = 5.6 Hz, 1H), 4.34 (s, 1H), 4.24-4.13 (m, 2H), 4.06-3.99 (m, 2H), 3.78-3.74 (m, 2H), 3.37 (s, 1H), 3.27-3.18 (m, 1H), 2.08-1.87 (m, 4H), MS (ESI) m/z: 520.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 406. | 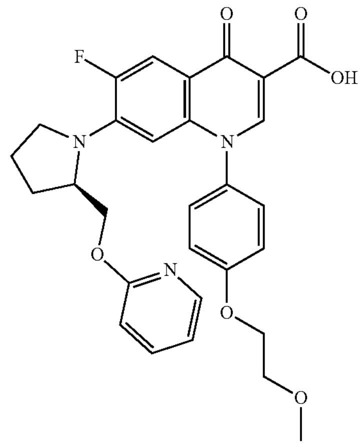 [SMILES: COCCOc1ccc(-n2cc(C(=O)O)c(=O)c3cc(F)c(N4CCC[C@@H]4COc4ccccn4)cc32)cc1] | (R)-6-fluoro-1-(4-(2-methoxyethoxy)phenyl)-4-oxo-7-(2-((pyridin-2-yloxy)methyl)pyrrolidin-1-yl)-1,4-dihydroquinoline-3-carboxylic acid | $^1$HNMR (400 MHz, DMSO-$d_6$): δ 15.42 (s, 1H), 8.47 (s, 1H), 8.03 (d, J = 4.0 Hz, 1H), 7.88 (d, J = 14.8 Hz, 1H), 7.66 (t, J = 6.8 Hz, 1H), 7.54 (t, J = 9.2 Hz, 2H), 7.19 (d, J = 6.4 Hz, 1H), 6.95 (t, J = 6.0 Hz, 2H), 6.65 (d, J = 8.4 Hz, 1H), 6.08 (d, J = 7.6 Hz, 1H), 4.21-4.20 (m, 1H), 4.17-4.11 (m, 4H), 3.71-3.69 (m, 2H), 3.34-3.20 (m, 5H), 2.04-1.91 (m, 4H), MS (ESI) m/z: 534.3 $[M + H]^+$. | ++++ |
| 407. | 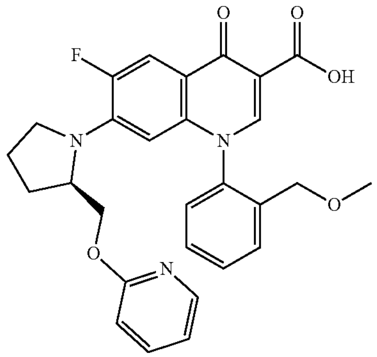 [SMILES: COCc1ccccc1-n1cc(C(=O)O)c(=O)c2cc(F)c(N3CCC[C@@H]3COc3ccccn3)cc21] | (R)-6-fluoro-1-(2-(methoxymethyl)phenyl)-4-oxo-7-(2-((pyridin-2-yloxy)methyl)pyrrolidin-1-yl)-1,4-dihydroquinoline-3-carboxylic acid | $^1$HNMR (400 MHz, DMSO-$d_6$): δ 8.37 (d, J = 2.0 Hz, 1H), 8.10-8.00 (m, 1H), 7.82 (dd, J = 15.2, 2.0 Hz, 1H), 7.69-7.65 (m, 2H) 7.62-7.54 (m, 2H) 7.50-7.36 (m, 2H), 6.97-6.93 (m, 1H) 6.64 (dd, J = 4.8, 8.4 Hz, 1H), 5.75 (dd, J = 26.4, 7.6 Hz, 1H), 4.30-3.99 (m, 5H), 3.27 (brs, 1H), 3.15-3.05 (m, 1H), 3.03 (s, 3H), 2.07-1.88 (m, 5H). MS (ESI) m/z: 504.3 $[M + H]^+$ | +++ |
| 408. | 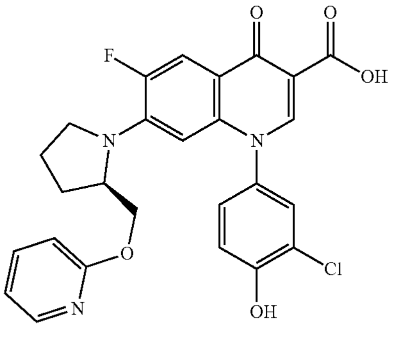 [SMILES: O=C(O)c1cn(-c2ccc(O)c(Cl)c2)c2cc(N3CCC[C@@H]3COc3ccccn3)c(F)cc2c1=O] | (R)-1-(3-chloro-4-hydroxyphenyl)-6-fluoro-4-oxo-7-(2-((pyridin-2-yloxy)methyl)pyrrolidin-1-yl)-1,4-dihydroquinoline-3-carboxylic acid | $^1$HNMR (400 MHz, DMSO-$d_6$): δ 15.39 (s, 1H), 8.50 (s, 1H), 8.01 (dd, J = 4.8, 1.2 Hz, 1H), 7.87 (d, J = 14.4 Hz, 1H), 7.74-7.71 (m, 1H), 7.67-7.63 (m, 1H), 7.42-7.37 (m, 1H), 7.16-6.99 (m, 1H), 6.96-6.91 (m, 1H), 6.65 (d, J = 8.4 Hz, 1H), 6.11 (dd, J = 20.0, 7.2 Hz, 1H), 4.41 (brs, 1H), 4.22 (t, J = 6.0 Hz, 2H), 3.39-3.17 (m, 2H), 2.09-1.91 (m, 5H), MS (ESI) m/z: 510.2 $[M + H]^+$. | ++++ |
| 409. | 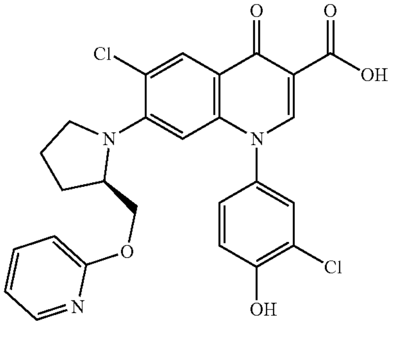 [SMILES: O=C(O)c1cn(-c2ccc(O)c(Cl)c2)c2cc(N3CCC[C@@H]3COc3ccccn3)c(Cl)cc2c1=O] | (R)-6-chloro-1-(3-chloro-4-hydroxyphenyl)-4-oxo-7-(2-((pyridin-2-yloxy)methyl)pyrrolidin-1-yl)-1,4-dihydroquinoline-3-carboxylic acid | $^1$HNMR (400 MHz, DMSO-$d_6$): δ 15.11 (s, 1H), 10.95 (s, 1H), 8.54 (d, J = 2.4 Hz, 1H), 8.17 (s, 1H), 7.96 (brs, 1H), 7.72 (dd, J = 8.0, 2.4 Hz, 1H), 7.65-7.59 (m, 1H), 7.47 (td, J = 8.4, 2.4 Hz, 1H), 7.19-6.88 (m, 2H), 6.56 (d, J = 8.4 Hz, 1H), 6.37 (d, J = 20.4 Hz, 1H), 4.58-4.49 (m, 1H), 4.21-4.10 (m, 2H), 3.57-3.50 (m, 1H), 3.21-3.15 (m, 1H), 2.24-2.20 (m, 1H), 1.97-1.93 (m, 1H), 1.86-1.73 (m, 2H), MS (ESI) m/z: 526.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 410. | 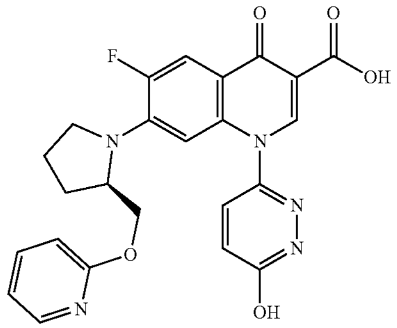 [SMILES: O=C(O)c1cn(-c2ccc(O)nn2)c2cc(N3CCC[C@@H]3COc3ccccn3)c(F)cc2c1=O] | (R)-6-fluoro-1-(6-hydroxypyridazin-3-yl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.16 (s, 1H), 13.42 (s, 1H), 8.85 (s, 1H), 8.04 (dd, J = 1.2, 4.8 Hz, 1H), 7.87 (d, J = 14.4 Hz, 1H), 7.74 (d, J = 10.0 Hz, 1H), 7.68-7.64 (m, 1H), 7.01 (d, J = 10.0 Hz, 1H), 6.96-6.93 (m, 1H), 6.68 (d, J = 8.4 Hz, 1H), 6.33 (d, J = 7.2 Hz, 1H), 4.58-4.52 (m, 1H), 4.31-4.23 (m, 2H), 3.62-3.52 (m, 1H), 3.38-3.34 (m, 1H), 2.09-1.94 (m, 4H). MS (ESI) m/z: 478.2 $[M + H]^+$. | +++ |
| 411. | 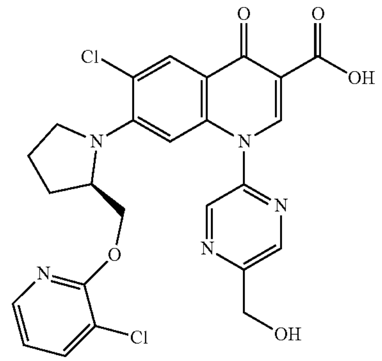 [SMILES: O=C(O)c1cn(-c2cnc(CO)cn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(5-(hydroxy-methyl)pyrazin-2-yl)-4-oxo-1,4-dihydroquinoline-3-carboxylic acid | $^1$HNMR (400 MHz, DMSO-$d_6$): δ 14.86 (s, 1H), 9.01 (s, 1H), 8.91 (s, 1H), 8.77 (s, 1H), 8.17 (s, 1H), 7.87 (d, J = 4.80 Hz, 1H), 7.77 (d, J = 7.20 Hz, 1H), 6.93-6.90 (m, 1H), 6.60 (s, 1H), 5.87 (t, J = 5.6 Hz, 1H), 4.80 (d, J = 5.6 Hz, 2H), 4.75 (s, 1H), 4.29 (bs, 2H), 3.56-3.54 (m, 1H), 3.24-3.20 (m, 1H), 2.24-2.22 (m, 1H), 1.97-1.89 (m, 2H), 1.81-1.80 (m, 1H). MS (ESI) m/z: 542.2 $[M + H]^+$. | ++++ |
| 412. | 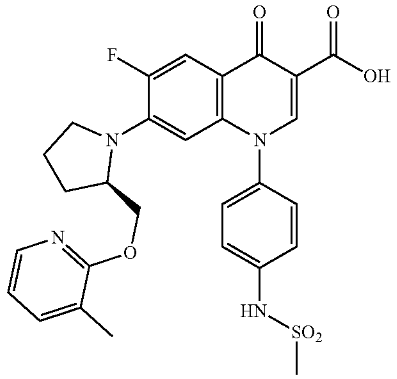 [SMILES: Cc1cccnc1OC[C@H]1CCCN1c1cc2c(cc1F)c(=O)c(C(=O)O)cn2-c1ccc(NS(C)(=O)=O)cc1] | (R)-6-fluoro-7-(2-(((3-methylpyridin-2-yl)oxy)methyl) pyrrolidin-1-yl)-1-(4-(methyl-sulfonamido) phenyl)-4-oxo-1,4-dihydroquinoline-3-carboxylic acid | $^1$HNMR (400 MHz, DMSO-$d_6$): δ 15.38 (brs, 1H), 10.30 (brs, 1H), 8.50 (s, 1H), 7.90-7.85 (m, 2H), 7.60-7.57 (m, 2H), 7.48-7.41 (m, 2H), 7.32 (d, J = 8.4 Hz, 1H), 6.86-6.83 (m, 1H), 6.12 (d, J = 7.2 Hz, 1H), 4.51 (brs, 1H), 4.27-4.18 (m, 2H), 3.38-3.32 (m, 1H), 3.22-3.18 (m, 1H), 3.08 (s, 3H), 2.13-2.08 (m, 2H), 2.01 (s, 3H), 1.93-1.88 (m, 2H), MS (ESI) m/z: 567.3 $[M + H]^+$ | ++++ |
| 413. | 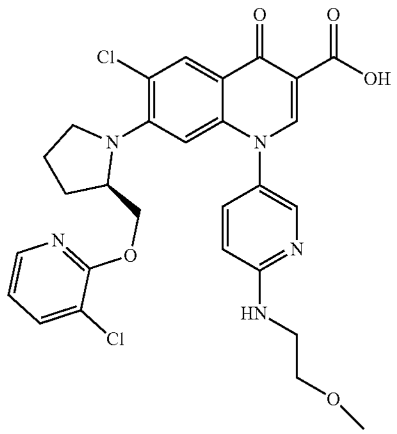 [SMILES: COCCNc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-((2-methoxyethyl) amino)pyridin-3-yl)-4-oxo-1,4-dihydroquinoline-3-carboxylic acid | $^1$HNMR (400 MHz, DMSO-$d_6$): δ 15.09 (s, 1H), 8.51 (d, J = 8.4 Hz, 1H), 8.15-8.12 (m, 2H), 7.89-7.87 (m, 1H), 7.80-7.76 (m, 1H), 7.57-7.47 (m, 1H), 7.22 (bs, 1H), 6.94-6.90 (m, 1H), 6.71-6.56 (m, 1H), 6.44 (d, J = 4.0 Hz, 1H), 4.75 (bs, 1H), 4.35-4.30 (m, 1H), 4.27-4.23 (m, 1H), 3.52-3.44 (m, 5H), 3.32-3.26 (m, 3H), 3.19-3.16 (m, 1H), 2.26-2.22 (m, 1H), 2.08-1.88 (m, 2H), 1.82-1.78 (m, 1H). MS (ESI) m/z: 584.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 414. | 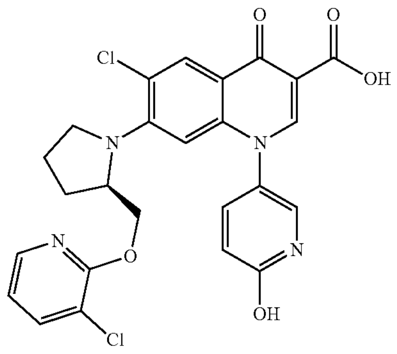 [SMILES: O=C(O)c1cn(-c2ccc(O)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-hydroxy-pyridin-3-yl)-4-oxo-1,4-dihydroquinoline-3-carboxylic acid | $^1$HNMR (400 MHz, DMSO-$d_6$): δ 15.06 (s, 1H), 12.10 (s, 1H), 8.65 (d, J = 9.6 Hz, 1H), 8.15 (s, 1H), 7.94-7.89 (m, 2H), 7.83-7.78 (m, 1H), 7.60-7.51 (m, 1H), 6.95-6.92 (m, 1H), 6.50-6.31 (m, 2H), 4.85-4.77 (m, 1H), 4.36-4.26 (m, 2H), 3.67-3.54 (m, 1H), 3.26-3.17 (m, 1H), 2.33-2.26 (m, 1H), 2.09-1.90 (m, 2H), 1.87-1.82 (m, 1H). MS (ESI) m/z: 527.2 $[M + H]^+$. | ++++ |
| 415. | 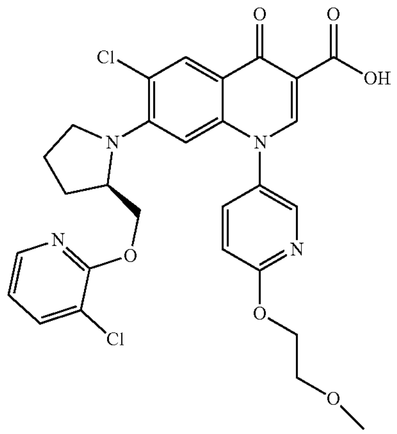 [SMILES: COCCOc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-(2-methoxy-ethoxy)pyridin-3-yl)-4-oxo-1,4-dihydroquinoline-3-carboxylic acid | $^1$HNMR (400 MHz, DMSO-$d_6$): δ 15.04 (s, 1H), 8.62 (bs, 1H), 8.40 (bs, 1H), 8.23 (s, 1H), 7.96-7.90 (m, 2H), 7.81-7.80 (m, 1H), 7.11-6.93 (m, 2H), 6.32 (bs, 1H), 4.69 (bs, 1H), 4.47-4.43 (m, 2H), 4.29-4.23 (m, 2H), 3.72 (bs, 2H), 3.52-3.50 (m, 1H), 3.33 (s, 3H), 3.17-3.10 (m, 1H), 2.33 (bs, 1H), 1.97-1.90 (m, 2H), 1.79-1.77 (m, 1H). MS (ESI) m/z: 585.2 $[M + H]^+$. | ++++ |
| 416. | 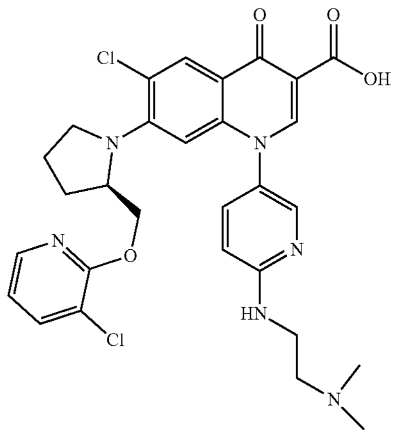 [SMILES: CN(C)CCNc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-((2-(dimethylamino) ethyl)amino) pyridin-3-yl)-4-oxo-1,4-dihydroquinoline-3-carboxylic acid | $^1$HNMR (400 MHz, DMSO-$d_6$): δ 15.10 (s, 1H), 8.51 (d, J = 7.6 Hz, 1H), 8.13 (d, J = 7.6 Hz, 2H), 7.88 (bs, 1H), 7.78 (t, J = 7.2 Hz, 1H), 7.55-7.47 (m, 1H), 7.02 (bs, 1H), 6.92 (dd, J = 7.2, 4.4 Hz, 1H), 6.70-6.55 (m, 1H), 6.45 (d, J = 4.0 Hz, 1H), 4.74 (bs, 1H), 4.74 (bs, 1H), 4.32-4.23 (m, 2H), 3.51-3.47 (m, 1H), 3.19-3.17 (m, 2H), 2.53 (bs, 2H), 2.32-2.20 (m, 8H), 2.02-1.78 (m, 3H), MS (ESI) m/z: 597.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 417. | 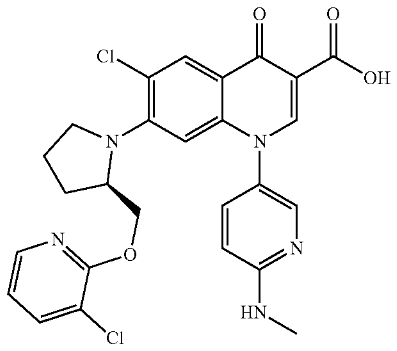 [SMILES: CNc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-(methylamino) pyridin-3-yl)-4-oxo-1,4-dihydroquinoline-3-carboxylic acid | $^1$HNMR (400 MHz, DMSO-$d_6$): δ 15.06 (s, 1H), 8.50 (d, J = 8.4 Hz, 1H), 8.15 (s, 2H), 7.89 (dd, J = 4.8, 1.6 Hz, 1H), 7.79 (d, J = 8.0 Hz, 1H), 7.56-7.49 (m, 1H), 7.14-7.09 (m, 1H), 6.94-6.90 (m, 1H), 6.63-6.45 (m, 2H), 4.75-4.66 (m, 1H), 4.35-4.22 (m, 2H), 3.54-3.50 (m, 1H), 3.19-3.18 (m, 1H), 2.85-2.82 (m, 3H), 2.26-2.22 (m, 1H), 1.99-1.81 (m, 3H). MS (ESI) m/z: 540.3 $[M + H]^+$ | ++++ |
| 418. | 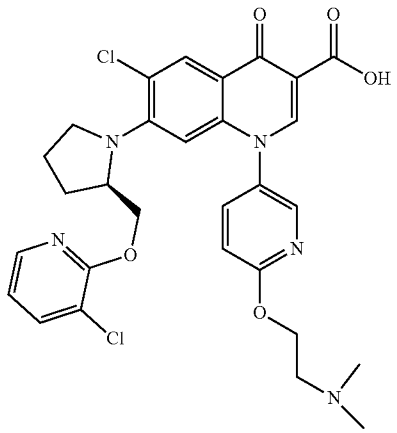 [SMILES: CN(C)CCOc1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-(2-(dimethylamino) ethoxy)pyridin-3-yl)-4-oxo-1,4-dihydroquinoline-3-carboxylic acid | $^1$HNMR (400 MHz, DMSO-$d_6$): δ 15.03 (s, 1H), 8.63 (d, J = 9.2 Hz, 1H), 8.41 (bs, 1H), 8.17 (s, 1H), 7.97-7.93 (m, 1H), 7.90 (dd, J = 5.20, 1.60 Hz, 1H), 7.81 (d, J = 7.6 Hz, 1H), 7.08 (d, J = 9.2 Hz, 0.5H), 6.95 (dd, J = 5.2, 7.4 Hz, 1H), 6.88 (d, J = 8.8 Hz, 0.5H), 6.33-6.31 (m, 1H), 4.69 (bs, 1H), 4.46-4.29 (m, 3H), 4.22 (dd, J = 11.4, 4.8 Hz, 1H), 3.52 (q, J = 9.2 Hz, 1H), 3.18 (t, J = 8.4 Hz, 1H), 2.69-2.65 (m, 2H), 2.23 (d, J = 6.8 Hz, 7H), 1.91-1.97 (m, 2H), 1.77-1.79 (m, 1H), MS (ESI) m/z: 598.3 $[M + H]^+$ | ++++ |
| 419. | 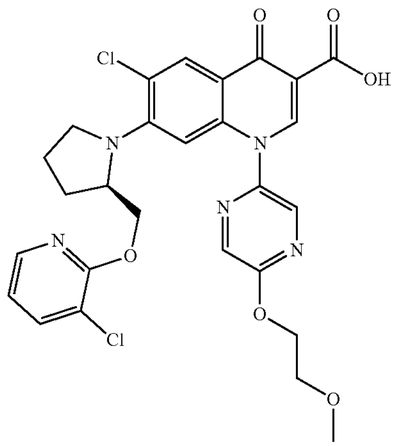 [SMILES: COCCOc1cnc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(5-(2-methoxy-ethoxy)pyrazin-2-yl)-4-oxo-1,4-dihydroquinoline-3-carboxylic acid | $^1$HNMR (400 MHz, DMSO-$d_6$): δ 14.9 (s, 1H), 8.84 (s, 1H), 8.62 (s, 1H), 8.35 (s, 1H), 8.16 (s, 1H), 7.88-7.87 (m, 1H), 7.80-7.77 (m, 1H), 6.94-6.91 (m, 1H), 6.53 (s, 1H), 4.71 (brs, 1H), 4.53-4.50 (m, 2H), 4.32-4.28 (m, 2H), 3.76-3.74 (m, 2H), 3.63-3.56 (m, 1H), 3.35 (s, 3H), 3.23-3.19 (m, 1H), 2.26-2.23 (m, 1H), 1.98-1.78 (m, 3 H), LC-MS (ESI) m/z: 586.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 420. | 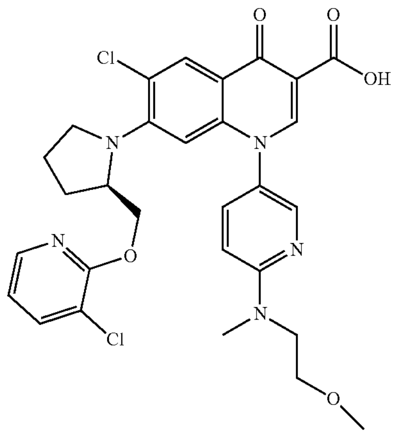 [SMILES: COCCN(C)c1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-((2-methoxy-ethyl)(methyl) amino)pyridin-3-yl)-4-oxo-1,4-dihydroquinoline-3-carboxylic acid | $^1$HNMR (400 MHz, DMSO-$d_6$): δ 15.09 (s, 1H), 8.53 (d, J = 8.4 Hz, 1H), 8.24 (bs, 1H), 8.16 (s, 1H), 7.91-7.88 (m, 1H), 7.81 (d, J = 7.6 Hz, 1H), 7.71-7.63 (m, 1H), 6.96-6.92 (m, 1H), 6.83 (d, J = 9.2 Hz, 0.5H), 6.63 (d, J = 9.2 Hz, 0.5H), 6.44 (s, 1H), 4.70-4.68 (m, 1H), 4.35-4.30 (m, 1H), 4.25-4.20 (m, 1H), 3.80-3.70 (m, 2H), 3.56-3.50 (m, 3H), 3.30-3.26 (m, 3H), 3.22-3.16 (m, 1H), 3.11-3.08 (m, 3H), 2.28-2.24 (m, 1H), 1.98-1.88 (m, 2H), 1.83-1.76 (m, 1H). MS (ESI) m/z: 598.3 $[M + H]^+$ | ++++ |
| 421. | 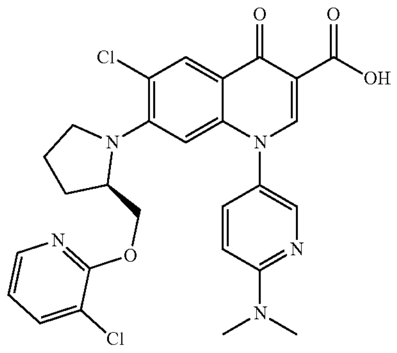 [SMILES: CN(C)c1ccc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(6-(dimethyl-amino)pyridin-3-yl)-4-oxo-1,4-dihydroquinoline-3-carboxylic acid | $^1$HNMR (400 MHz, DMSO-$d_6$): δ 15.08 (s, 1H), 8.51 (d, J = 8.8 Hz, 1H), 8.24 (s, 1H), 8.16 (s, 1H), 7.90 (bs, 1H), 7.81 (dd, J = 7.6, 1.6 Hz, 1H), 7.67 (t, J = 8.0 Hz, 1H), 6.97-6.92 (m, 1H), 6.81 (d, J = 9.6 Hz, 0.5H), 6.59 (d, J = 9.2 Hz, 0.5H), 6.44 (s, 1H), 4.70-4.63 (m, 1H), 4.38-4.34 (m, 1H), 4.30-4.22 (m, 1H), 3.60-3.51 (m, 1H), 3.20 (s, 1H), 3.10 (s, 6H), 2.30-2.22 (m, 1H), 1.20-1.91 (m, 2H), 1.84-1.78 (m, 1H), MS (ESI) m/z: 554.3 $[M + H]^+$ | ++++ |
| 422. | 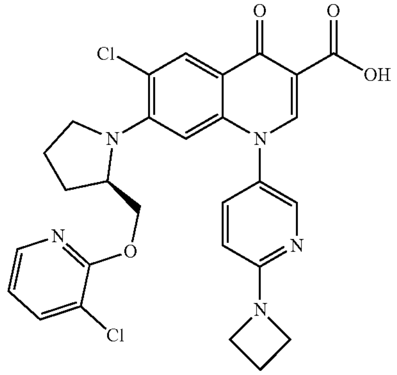 [SMILES: O=C(O)c1cn(-c2ccc(N3CCC3)nc2)c2cc(N3CCC[C@@H]3COc3ncccc3Cl)c(Cl)cc2c1=O] | (R)-1-(6-(azetidin-1-yl)pyridin-3-yl)-6-chloro-7-(2-(((3-chloropyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.09 (s, 1H), 8.50 (d, J = 8.4 Hz, 1H), 8.23 (s, 1H), 8.16 (s, 1H), 7.90 (brs, 1H), 7.82 (d, J = 7.2 Hz, 1H), 7.66 (t, J = 7.2 Hz, 1H), 6.97-6.94 (m, 1H), 6.51-6.26 (m, 2H), 4.70-4.63 (m, 1H), 4.36-4.34 (m, 1H), 4.29-4.18 (m, 1H), 4.02-4.00 (m, 4H), 3.58-3.51 (m, 1H), 3.21-3.19 (m, 1H), 2.42-2.37 (m, 2H), 2.26-2.24 (m, 1H), 1.99-1.81 (m, 2H), 1.78-1.76 (s, 1H). MS (ESI) m/z: 566.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 423. | 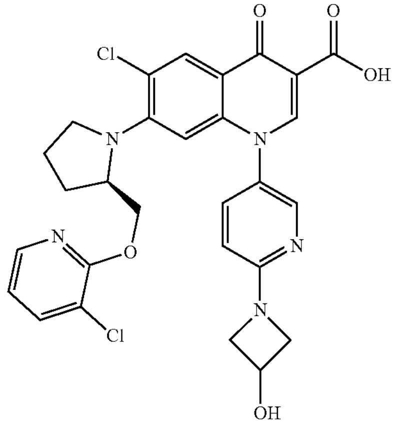 [SMILES: O=C(O)c1cn(-c2ccc(N3CC(O)C3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-(3-hydroxy-azetidin-1-yl) pyridin-3-yl)-4-oxo-1,4-dihydroquinoline-3-carboxylic acid | $^{1}$HNMR (400 MHz, DMSO-$d_6$): δ 15.2 (s, 1H), 8.51 (d, J = 9.6 Hz, 1H), 8.22 (d, J = 2.8 Hz, 1H), 8.15 (s, 1H), 7.90-7.88 (m, 1H), 7.81 (d, J = 8.4 Hz, 1H), 7.69-7.63 (m, 1H), 6.96-6.91 (m, 1H), 6.56-6.30 (m, 2H), 5.77 (d, J = 6.4 Hz, 1H), 4.64-4.63 (m, 2H), 4.25-4.19 (m, 4H), 3.78-3.77 (m, 2H), 3.55-3.50 (m, 1H), 3.48-3.16 (m, 1H), 2.25-2.24 (m, 1H), 2.08-1.78 (m, 3H). MS (ESI) m/z: 582.2 $[M + H]^+$ | ++++ |
| 424. | 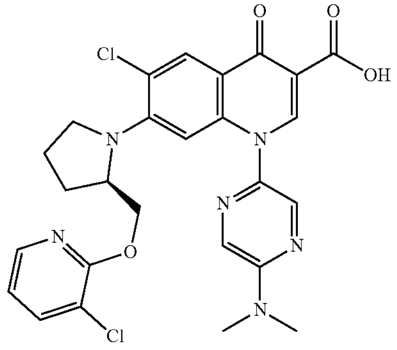 [SMILES: CN(C)c1cnc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(5-(dimethylamino) pyrazin-2-yl)-4-oxo-1,4-dihydroquinoline-3-carboxylic acid | $^{1}$HNMR (400 MHz, DMSO-$d_6$): δ 8.71 (s, 1H), 8.39 (d, J = 1.6 Hz, 1H), 8.16 (s, 1H), 8.08 (d, J = 1.2 Hz, 1H), 7.89-7.87 (m, 1H), 7.80-7.78 (m, 1H), 6.94-6.91 (m, 1H), 6.57 (s, 1H), 4.68 (s, 1H), 4.34-4.30 (m, 1H), 4.26-4.22 (m, 1H), 3.62-3.50 (m, 1H), 3.32-3.23 (m, 1H), 3.16 (s, 6H), 2.32-2.19 (m, 1H), 2.08-2.04 (m, 1H), 1.99-1.98 (m, 1H), 1.88-1.76 (m, 1H), (—COOH proton was not observed in $H^1$NMR). MS (ESI) m/z 555.3 $[M + H]^+$ | ++++ |
| 425. | 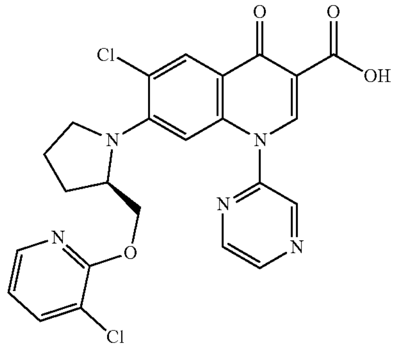 [SMILES: O=C(O)c1cn(-c2cnccn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyrazin-2-yl)-1,4-dihydroquinoline-3-carboxylic acid | $^{1}$HNMR (400 MHz, DMSO-$d_6$): δ 14.85 (s, 1H), 9.12 (d, J = 1.2 Hz, 1H), 8.95 (t, J = 2.4 Hz, 1H), 8.78 (dd, J = 1.2, 2.4 Hz, 2H), 8.17 (s, 1H), 7.87 (dd, J = 2.0, 6.0 Hz, 1H), 7.77 (dd, J = 2.0, 7.6 Hz, 1H), 6.91 (dd, J = 4.8, 7.6 Hz, 1H), 6.56 (s, 1H), 4.73 (s, 1H), 4.29 (dd, J = 4.0, 8.4 Hz, 2H), 3.62-3.56 (m, 1H), 3.24-3.16 (m, 1H), 2.26-2.20 (m, 1H), 2.09-1.87 (m, 2H), 1.81-1.75 (m, 1H). MS m/z: 512.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 426. | 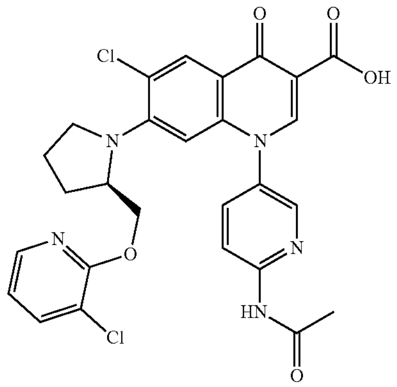 [SMILES: CC(=O)Nc1ccc(-n2cc(C(=O)O)c(=O)c3cc(Cl)c(N4CCC[C@@H]4COc4ncccc4Cl)cc32)cn1] | (R)-1-(6-acetamidopyridin-3-yl)-6-chloro-7-(2-(((3-chloro-pyridin-2-yl)oxy)methyl)pyrrolidin-1-yl)-4-oxo-1,4-dihydroquinoline-3-carboxylic acid | $^1$HNMR (400 MHz, DMSO-$d_6$) δ: 15.03 (s, 1H), 10.89 (d, J = 12.4 Hz, 1H), 8.67 (s, 1H), 8.54 (s, 1H), 8.35-8.15 (m, 2H), 8.02 (dd, J = 9.2, 2.0 Hz, 1H), 7.88 (d, J = 4.4 Hz, 1H), 7.80-7.76 (m, 1H), 6.93 (dd, J = 7.2, 4.8 Hz, 1H), 6.34 (d, J = 8.4 Hz, 1H), 4.73-4.67 (m, 1H), 4.31-4.27 (m, 2H), 3.50-3.48 (m, 1H), 3.20-3.16 (m, 1H), 2.24-2.16 (m, 1H), 2.14 (s, 3H), 1.98-1.80 (m, 2H), 1.60-1.40 (m, 1H). MS (ESI) m/z: 568.4 $[M + H]^+$ | ++++ |
| 427. | 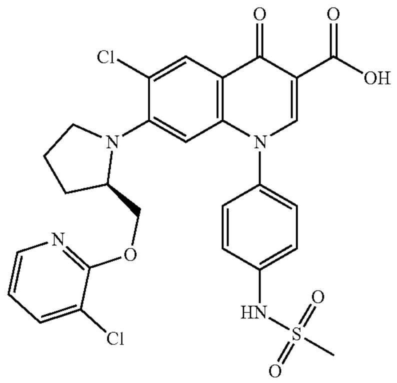 [SMILES: CS(=O)(=O)Nc1ccc(-n2cc(C(=O)O)c(=O)c3cc(Cl)c(N4CCC[C@@H]4COc4ncccc4Cl)cc32)cc1] | (R)-6-chloro-7-(2-(((3-chloropyridin-2-yl)oxy)methyl)pyrrolidin-1-yl)-1-(4-(methyl-sulfonamido)phenyl)-4-oxo-1,4-dihydroquinoline-3-carboxylic acid | $^1$HNMR (400 MHz, DMSO-$d_6$) δ: 15.07 (s, 1H), 10.20 (brs, 1H), 8.53 (s, 1H), 8.16 (s, 1H), 7.88 (dd, J = 5.6, 1.6 Hz, 1H), 7.79 (dd, J = 7.2, 1.6 Hz, 1H), 7.88 (d, J = 4.4 Hz, 1H), 7.60-7.52 (m, 1H), 7.50-7.44 (m, 1H), 7.32 (d, J = 4.8 Hz, 1H), 6.92 (dd, J = 8.0, 4.8 Hz, 1H), 4.67-4.60 (m, 1H), 4.31-4.27 (m, 2H), 3.50-3.40 (m, 1H), 3.20-3.12 (m, 1H), 3.10 (s, 3H), 2.28-2.20 (m, 1H), 2.00-1.74 (m, 3H), MS (ESI) m/z: 603.2 $[M + H]^+$ | ++++ |
| 428. | 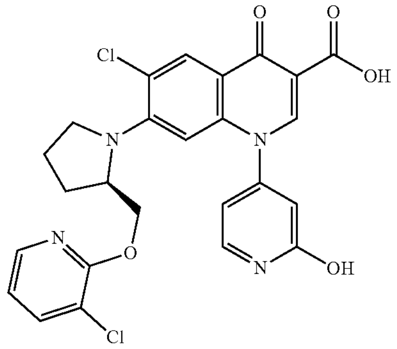 [SMILES: O=C(O)c1cn(-c2ccnc(O)c2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-1-(2-hydroxypyridin-4-yl)-4-oxo-1,4-dihydroquinoline-3-carboxylic acid | 1HNMR (400 MHz, DMSO-$d_6$): δ 14.95 (s, 1H), 12.13 (bs, 1H), 8.61 (bs, 1H), 8.13 (s, 1H), 7.89 (dd, J = 4.8, 1.6 Hz, 1H), 7.77 (d, J = 7.2 Hz, 1H), 7.52 (bs, 1H), 6.93-6.90 (m, 1H), 6.73 (d, J = 1.6 Hz, 1H), 6.64 (s, 1H), 6.39 (bs, 1H), 4.79 (bs, 1H), 4.33 (d, J = 4.0 Hz, 2H), 3.62 (bs, 1H), 3.27-3.23 (m, 1H), 2.33-2.23 (m, 1H), 2.08-1.80 (m, 3H), MS (ESI) m/z: 527.2 $[M + H]^+$ | ++++ |
| 429. | 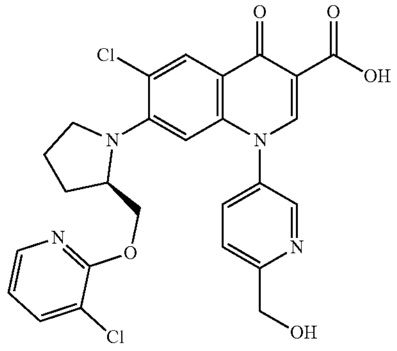 [SMILES: O=C(O)c1cn(-c2ccc(CO)nc2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-1-(6-(hydroxymethyl)pyridin-3-yl)-4-oxo-1,4-dihydroquinoline-3-carboxylic acid | $^1$HNMR (400 MHz, DMSO-$d_6$): δ 15.02 (s, 1H), 8.72 (d, J = 2.0 Hz, 1H), 8.65 (s, 1H), 8.17 (s, 1H), 8.07 (s, 1H), 7.90-7.86 (m, 1H), 7.79-7.59 (m, 2H), 6.95-6.92 (m, 2H), 6.29 (s, 1H), 5.67 (s, 1H), 4.69 (d, J = 5.2 Hz, 3H), 4.28-4.21 (m, 2H), 3.45-3.22 (m, 1H), 3.16 (d, J = 5.6 Hz, 1H), 2.23 (d, J = 8.0 Hz, 1H), 1.96-1.89 (m, 2H), 1.80-1.76 (m, 1H). MS (ESI) m/z: 541.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 430. | 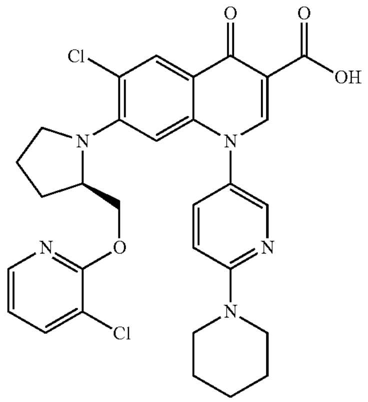 [SMILES: O=C(O)c1cn(-c2ccc(N3CCCCC3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(6-(piperidin-1-yl) pyridin-3-yl)-1,4-dihydroquinoline-3-carboxylic acid | $^1$HNMR (400 MHz, DMSO-$d_6$): δ 15.01 (brs, 1H), 8.43 (s, 1H), 8.18 (s, 1H), 8.12 (s, 1H), 7.90 (s, 1H), 7.80 (d, J = 7.6 Hz, 1H), 7.63 (brs, 1H), 6.93-6.77 (m, 2H), 6.43 (s, 1H), 4.59 (s, 1H), 4.33 (s, 1H), 4.18 (s, 1H), 3.69-3.50 (m, 5H), 3.14 (s, 1H), 2.33-2.24 (m, 1H), 1.97-1.77 (m, 3H), 1.70-1.50 (m, 6H). MS (ESI) m/z: 594.3 $[M + H]^+$ | ++++ |
| 431. | 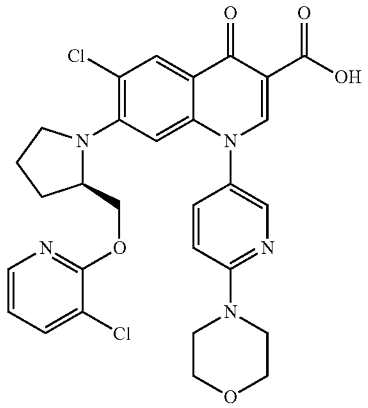 [SMILES: O=C(O)c1cn(-c2ccc(N3CCOCC3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-morpholino-pyridin-3-yl)-4-oxo-1,4-dihydroquinoline-3-carboxylic acid | $^1$HNMR (400 MHz, DMSO-$d_6$): δ 15.02 (s, 1H), 8.52 (d, J = 9.2 Hz, 1H), 8.30 (d, J = 2.4 Hz, 1H), 8.16 (s, 1H), 7.91 (d, J = 4.8 Hz, 1H), 7.81 (dd, J = 1.6, 8.0 Hz, 1H), 7.75 (t, J = 9.2 Hz, 1H), 7.04 (d, J = 8.8 Hz, 1H), 6.95 (dd, J = 4.4, 7.6 Hz, 1H), 6.81 (d, J = 9.2 Hz, 1H), 6.43 (d, J = 2.8 Hz, 1H) 4.65 (brs, 1H), 4.40-4.32 (m, 1H), 4.23-4.16 (m, 1H), 3.76-3.72 (m, 4H), 3.60-3.50 (m, 5H) 3.22-3.16 (m, 1H) 2.28-2.22 (m, 1H) 2.02-1.76 (m, 3H). MS (ESI) m/z: 596.2 $[M + H]^+$ | ++++ |
| 432. | 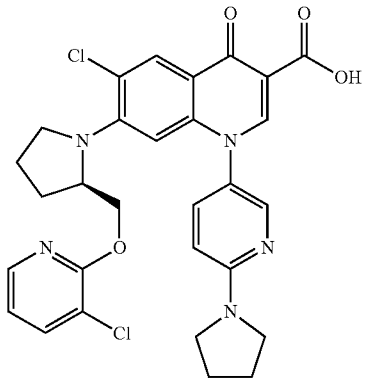 [SMILES: O=C(O)c1cn(-c2ccc(N3CCCC3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(6-(pyrrolidin-1-yl) pyridin-3-yl)-1,4-dihydroquinoline-3-carboxylic acid | $^1$HNMR (400 MHz, DMSO-$d_6$): δ 15.10 (brs, 1H), 8.49 (d, J = 9.2 Hz, 1H), 8.24-8.20 (m, 1H), 8.16 (s, 1H), 7.90 (t, J = 4.0 Hz, 1H), 7.81 (d, J = 7.6 Hz, 1H), 7.68-7.62 (m, 1H), 6.97-6.92 (m, 1H), 6.62 (d, J = 9.2 Hz, 0.5H), 6.46 (d, J = 5.2 Hz, 1H), 6.38 (d, J = 9.2 Hz, 0.5H), 4.72-4.59 (m, 1H), 4.40-4.28 (m, 1H), 4.25-4.15 (m, 1H), 3.65-3.50 (m, 1H), 3.49-3.40 (m, 4H), 3.26-3.16 (m, 1H), 2.04-1.95 (m, 5H), 1.94-1.77 (m, 2H). MS (ESI) m/z: 580.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 433. | 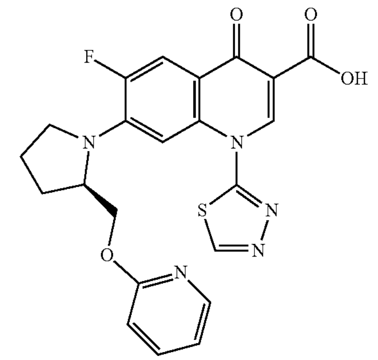 [SMILES: O=C(O)c1cn(-c2nncs2)c2cc(N3CCC[C@@H]3COc3ccccn3)c(F)cc2c1=O] | (R)-6-fluoro-4-oxo-7-(2-((pyridin-2-yloxy)methyl) pyrrolidin-1-yl)-1-(1,3,4-thiadiazol-2-yl)-1,4-dihydroquinoline-3-carboxylic acid | $^1$HNMR (400 MHz, DMSO-$d_6$): δ 9.78 (s, 1H), 9.70 (s, 1H), 8.06 (bs, 1H), 7.67-7.59 (m, 2H), 6.94 (s, 1H), 6.72 (d, J = 8.4 Hz, 1H), 6.08 (d, J = 6.0 Hz, 1H), 4.28 (bs, 1H), 4.19 (s, 1H), 4.15-4.11 (m, 1H), 3.33 (bs, 1H), 3.15 (bs, 1H), 2.05-1.89 (m, 4H), MS m/z: 468.3 $[M + H]^+$ | +++ |
| 434. | 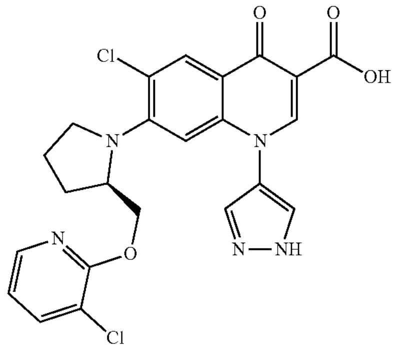 [SMILES: O=C(O)c1cn(-c2cn[nH]c2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(1H-pyrazol-4-yl)-1,4-dihydroquinoline-3-carboxylic acid | $^1$HNMR (400 MHz, DMSO-$d_6$): δ 15.03 (s, 1H), 13.48 (s, 1H), 8.53 (s, 1H), 8.34 (s, 1H), 8.13 (s, 1H), 7.89-7.85 (m, 2H), 7.78-7.75 (m, 1H), 6.92-6.88 (m, 1H), 6.65 (s, 1H), 4.80 (d, J = 6.4 Hz, 1H), 4.32-4.30 (m, 2H), 3.52-3.48 (m, 1H), 3.22 (t, J = 7.6 Hz, 1H), 2.26 (d, J = 8.0 Hz, 1H), 2.01-1.90 (m, 3H). MS (ESI) m/z: 500.2 $[M + H]^+$ | +++ |
| 435. | 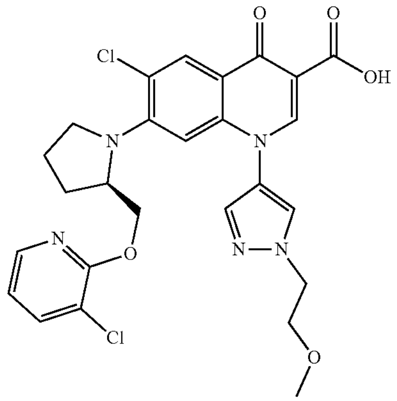 [SMILES: COCCn1cc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(1-(2-methoxy-ethyl)-1H-pyrazol-4-yl)-4-oxo-1,4-dihydroquinoline-3-carboxylic acid | $^1$HNMR (400 MHz, DMSO-$d_6$): δ 15.01 (s, 1H), 8.51 (s, 1H), 8.30 (s, 1H), 8.12 (s, 1H), 7.86-7.84 (m, 2H), 7.77-7.75 (m, 1H), 6.91-6.88 (m, 1H), 6.63 (s, 1H), 4.83 (s, 1H), 4.37-4.31 (m, 4H), 3.74 (t, J = 5.2 Hz, 2H), 3.52-3.48 (m, 1H), 3.27 (s, 3H), 3.20-3.25 (m, 1H), 2.25-2.28 (m, 1H), 2.02-1.74 (m, 3H), MS (ESI) m/z: 558.3 $[M + H]^+$. | ++++ |
| 436. | 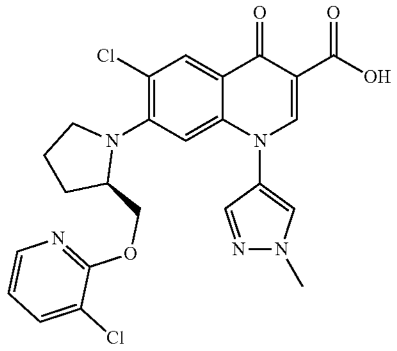 [SMILES: Cn1cc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(1-methyl-1H-pyrazol-4-yl)-4-oxo-1,4-dihydroquinoline-3-carboxylic acid | $^1$HNMR (400 MHz, DMSO-$d_6$): δ 15.01 (s, 1H), 8.52 (s, 1H), 8.26 (s, 1H), 8.13 (s, 1H), 7.87 (dd, J = 1.6, 4.8 Hz, 1H), 7.83 (d, J = 1.6 Hz, 1H), 7.79 (dd, J = 1.6, 7.6 Hz, 1H), 6.91 (dd, J = 5.2, 7.8 Hz, 1H), 6.67 (s, 1H), 4.79 (brs, 1H), 4.35-4.27 (m, 2H), 3.93 (s, 3H), 3.58-3.48 (m, 1H), 3.26-3.22 (m, 1H), 2.33-2.24 (m, 1H), 2.02-1.90 (m, 2H), 1.85-1.78 (m, 1H), MS (ESI) m/z: 514.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 437. | 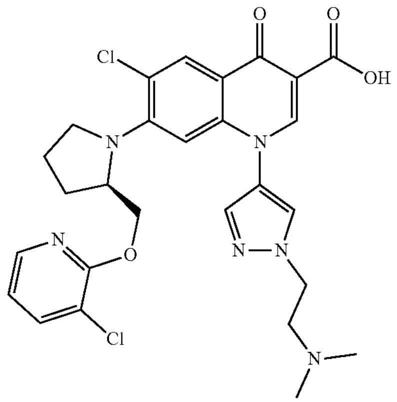 [SMILES: CN(C)CCn1cc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(1-(2-(dimethylamino) ethyl)-1H-pyrazol-4-yl)-4-oxo-1,4-dihydroquinoline-3-carboxylic acid | $^1$HNMR (400 MHz, DMSO-$d_6$): δ 15.01 (s, 1H), 8.52 (s, 1H), 8.33 (s, 1H), 8.13 (s, 1H), 7.86-7.85 (m, 2H), 7.76 (dd, J = 7.6, 9.2 Hz, 1H), 6.91-6.88 (m, 1H), δ 6.64 (s, 1H), 4.82 (s, 1H), 4.32 (d, J = 4.0 Hz, 4H), 3.55-3.48 (m, 1H), 3.23 (t, J = 8.0 Hz 1H), 2.81 (s, 1H), 2.27 (s, 1H), 2.02-1.98 (m, 3H), MS (ESI) m/z: 571.3 $[M + H]^+$ | ++++ |
| 438. | 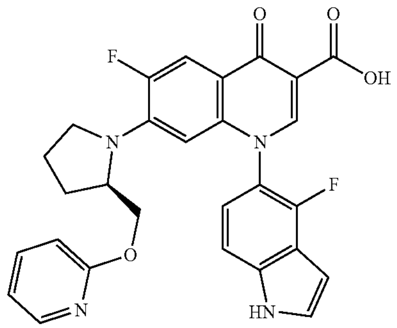 [SMILES: O=C(O)c1cn(-c2ccc3[nH]ccc3c2F)c2cc(N3CCC[C@@H]3COc3ccccn3)c(F)cc2c1=O] | (R)-6-fluoro-1-(4-fluoro-1H-indol-5-yl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 11.84 (s, 1H), 8.51 (bs, 1H), 7.97 (s, 1H), 7.90-7.81 (m, 1H), 7.70-7.58 (m, 1.5H), 7.52-7.47 (m, 1H), 7.30-7.19 (m, 1.5H), 6.98-6.88 (m, 1H), 6.68 (s, 0.5H), 6.56-6.54 (m, 1H), 6.47 (s, 0.5H), 6.02 (s, 1H), 4.32-4.10 (m, 3H), 3.50-3.40 (m, 1H), 3.14-3.03 (m, 1H), 2.10-1.80 (m, 4H) (—COOH proton was not observed). MS (ESI) m/z: 517.3 $[M + H]^+$ | ++++ |
| 439. | 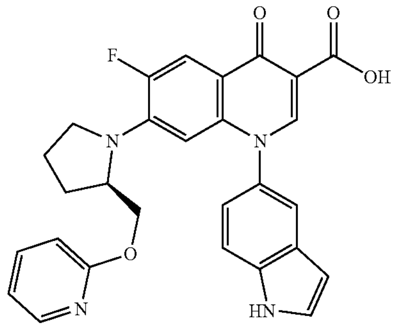 [SMILES: O=C(O)c1cn(-c2ccc3[nH]ccc3c2)c2cc(N3CCC[C@@H]3COc3ccccn3)c(F)cc2c1=O] | (R)-6-fluoro-1-(1H-indol-5-yl)-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.49 (bs, 1H), 11.52 (bs, 1H), 8.53 (s, 1H), 8.00-7.96 (m, 1H), 7.90 (d, J = 14.4 Hz, 1H), 7.81 (s, 1H), 7.68-7.61 (m, 1H), 7.54 (dt, J = 2.4, 24.6 Hz, 1H), 7.41 (d, J = 8.8 Hz, 1H), 7.23 (td, J = 2.0, 8.4 Hz, 1H), 7.00-6.91 (m, 1H), 6.60-6.55 (m, 1.5H), 6.43 (s, 0.5H), 6.16 (dd, J = 7.6, 15.4 Hz, 1H), 4.33-4.31 (m, 1H), 4.22-4.13 (m, 2H), 3.28-3.24 (m, 1H), 3.12-3.06 (m, 1H), 2.04-1.84 (m, 4H), MS (ESI) m/z: 499.3 $[M + H]^+$ | ++++ |
| 440. | 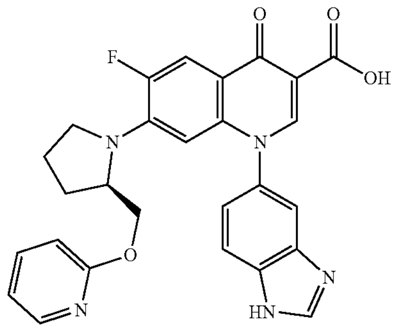 [SMILES: O=C(O)c1cn(-c2ccc3[nH]cnc3c2)c2cc(N3CCC[C@@H]3COc3ccccn3)c(F)cc2c1=O] | (R)-1-(1H-benzo[d]imidazol-5-yl)-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.47 (brs, 1H), 12.83 (brs, 1H), 8.55 (brs, 1H), 8.44-8.38 (m, 1H), 7.99-7.88 (m, 3H), 7.68-7.60 (m, 2H), 7.39-7.37 (m, 1H), 6.97-6.89 (m, 1H), 6.60-6.53 (m, 1H), 6.11-6.09 (m, 1H), 4.36-4.28 (m, 1H), 4.25-4.10 (m, 2H), 3.12-3.06 (m, 2H), 2.01-1.81 (m, 4H). MS (ESI) m/z 500.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 441. | 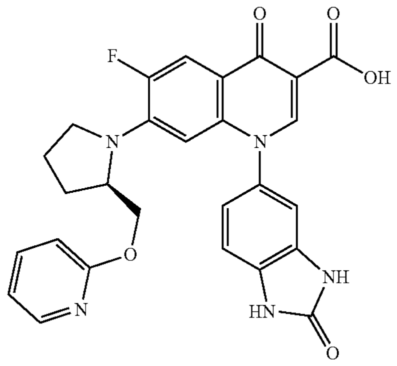 [SMILES: O=C(O)c1cn(-c2ccc3[nH]c(=O)[nH]c3c2)c2cc(N3CCC[C@@H]3COc3ccccn3)c(F)cc2c1=O] | (R)-6-fluoro-4-oxo-1-(2-oxo-2,3-dihydro-1H-benzo[d]imidazol-5-yl)-7-(2-((pyridin-2-yloxy)methyl)pyrrolidin-1-yl)-1,4-dihydroquinoline-3-carboxylic acid | $^1$HNMR (400 MHz, DMSO-$d_6$): δ 15.46 (s, 1H), 11.05-10.92 (m, 2H), 8.49 (s, 1H), 8.02-7.97 (m, 1H), 7.88 (d, J = 14.8 Hz, 1H), 7.69-7.61 (m, 1H), 7.21 (s, 1H), 7.16-6.88 (m, 3H), 6.63-6.57 (m, 1H), 6.14-6.08 (m, 1H), 4.40-4.29 (m, 1H), 4.25-4.12 (m, 2H), 3.20-3.10 (m, 2H), 2.09-1.89 (m, 4H). MS (ESI) m/z: 516.3 $[M + H]^+$ | ++++ |
| 442. | 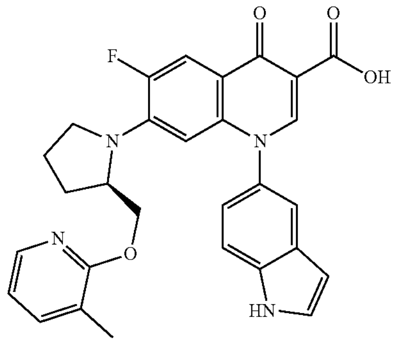 [SMILES: Cc1cccnc1OC[C@H]1CCCN1c1cc2c(cc1F)c(=O)c(C(=O)O)cn2-c1ccc2[nH]ccc2c1] | (R)-6-fluoro-1-(1H-indol-5-yl)-7-(2-(((3-methyl-pyridin-2-yl)oxy)methyl)pyrrolidin-1-yl)-4-oxo-1,4-dihydroquinoline-3-carboxylic acid | $^1$HNMR (400 MHz, DMSO-$d_6$): δ 15.40 (s, 1H), 8.52 (s, 1H), 7.89 (J = 14.0 Hz, 1H), 7.83-7.79 (m, 2H), 7.63-7.40 (m, 3H), 7.25-7.19 (m, 1H), 6.87-6.82 (m, 1H), 6.59 (s, 0.5H), 6.44 (s, 0.5H), 6.15 (t, J = 7.2, 1H), 4.40 (d, J = 18.4, Hz, 1H), 4.22-4.12 (m, 2H), 3.25 (dd, J = 6.0, 19.6, Hz, 1H), 3.12-3.05 (m, 1H), 2.10-2.00 (m, 1H) 1.92-1.81 (m, 6H). MS (ESI) m/z: 513.3 $[M + H]^+$ | ++++ |
| 443. | 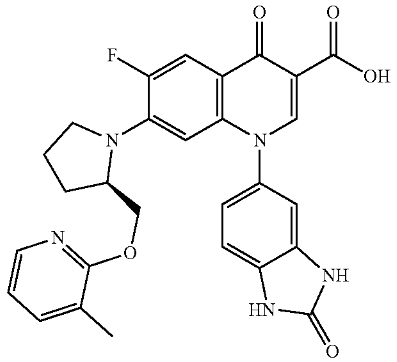 [SMILES: Cc1cccnc1OC[C@H]1CCCN1c1cc2c(cc1F)c(=O)c(C(=O)O)cn2-c1ccc2[nH]c(=O)[nH]c2c1] | (R)-6-fluoro-7-(2-(((3-methylpyridin-2-yl)oxy)methyl)pyrrolidin-1-yl)-4-oxo-1-(2-oxo-2,3-dihydro-1H-benzo[d]imidazol-5-yl)-1,4-dihydroquinoline-3-carboxylic acid | $^1$HNMR (400 MHz, DMSO-$d_6$): δ 15.45 (s, 1H), 11.10-10.09 (m, 2H), 8.48 (s, 1H), 7.89-7.81 (m, 2H), 7.50-7.40 (m, 1H), 7.20 (s, 1H), 7.13-7.08 (m, 1.5H), 6.90-6.80 (m, 1.5H), 5.65-5.51 (m, 1H), 4.50-4.32 (m, 1H), 4.23-4.14 (m, 2H), 3.40-3.36 (m, 1H), 3.21-3.10 (m, 1H), 2.08-1.80 (m, 7H). MS (ESI) m/z: 530.3 $[M + H]^+$ | ++++ |
| 444. | 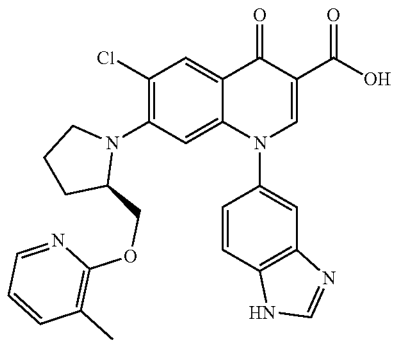 [SMILES: Cc1cccnc1OC[C@H]1CCCN1c1cc2c(cc1Cl)c(=O)c(C(=O)O)cn2-c1ccc2[nH]cnc2c1] | (R)-1-(1H-benzo[d]imidazol-5-yl)-6-chloro-7-(2-(((3-methylpyridin-2-yl)oxy)methyl)pyrrolidin-1-yl)-4-oxo-1,4-dihydroquinoline-3-carboxylic acid | $^1$HNMR (400 MHz, DMSO-$d_6$): δ 15.20 (brs, 1H), 8.64-8.50 (m, 2H), 8.19 (s, 1H), 7.94 (d, J = 7.6 Hz, 1H), 7.90-7.70 (m, 1.5H), 7.62-7.43 (m, 1.5H), 7.40-7.32 (m, 1H), 6.88-6.79 (m, 1H), 6.33 (d, J = 8.0 Hz, 1H), 4.70-4.50 (m, 1H), 4.21-4.04 (m, 3H), 3.20-3.10 (m, 2H), 2.18 (brs, 1H), 1.84-1.71 (m, 7H). MS (ESI) m/z: 530.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 445. | 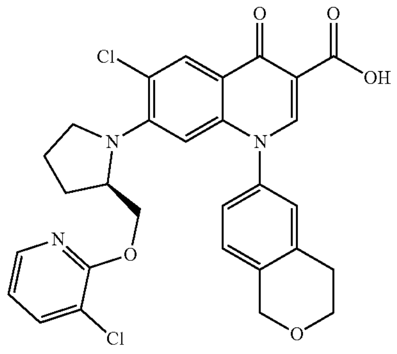 [SMILES: O=C(O)c1cn(-c2ccc3c(c2)CCOC3)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(isochroman-6-yl)-4-oxo-1,4-dihydroquinoline-3-224 carboxylic acid | $^1$HNMR (400 MHz, DMSO-$d_6$): δ 15.07 (bs, 1H), 8.52 (s, 1H), 8.17 (s, 1H), 7.89 (t, J = 4.8 Hz, 1H), 7.82 (dd, J = 7.6, 1.6 Hz, 1H), 7.41-7.33 (m, 2.5H), 7.09 (d, J = 8.0 Hz, 0.5H), 6.94 (dd, J = 7.6, 5.2 Hz, 1H), 6.41 (d, J = 13.6 Hz, 1H), 4.77 (d, J = 12.4 Hz, 2H), 4.64-4.59 (m, 1H), 4.28-4.23 (m, 2H), 3.98-3.74 (m, 2H), 3.54-3.46 (m, 1H), 3.22-3.13 (m, 1H), 2.91-2.80 (m, 1H), 2.74-2.67 (m, 1H), 2.40-2.29 (m, 1H), 1.99-1.74 (m, 3H). MS (ESI): m/z 566.3 $[M + H]^+$ | ++++ |
| 446. | 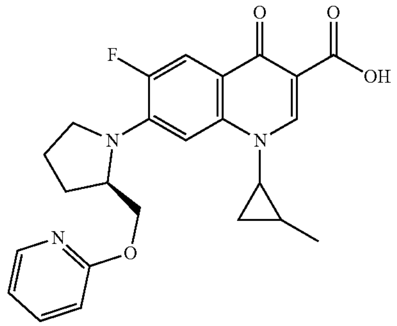 [SMILES: CC1CC1n1cc(C(=O)O)c(=O)c2cc(F)c(N3CCC[C@@H]3COc3ccccn3)cc21] | 6-fluoro-1-(2-methylcyclo-propyl)-4-oxo-7-((R)-2-((pyridin-2-yloxy)methyl) pyrrolidin-1-yl)-1,4-dihydro-quinoline-3-carboxylic acid | $^1$HNMR (400 MHz, DMSO-$d_6$): δ 15.47 (s, 1H), 8.54 (s, 1H), 8.06 (brs, 1H), 7.82 (d, J = 14.4 Hz, 1H), 7.66 (t, J = 8.0 Hz, 1H), 7.05 (d, J = 6.8 Hz, 1H), 6.94 (t, J = 6.0 Hz, 1H), 6.74-6.70 (m, 1H), 4.66 (brs, 1H), 4.44-4.29 (m, 2H), 3.80-3.70 (m, 1H), 3.60-3.50 (m, 1H), 3.43 (brs, 1H), 2.25-1.98 (m, 4H), 1.42-0.95 (m, 6H). MS (ESI): m/z: 438.4 [M + H]+ | +++ |
| 447. | 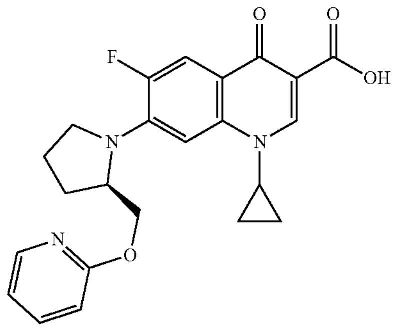 [SMILES: O=C(O)c1cn(C2CC2)c2cc(N3CCC[C@@H]3COc3ccccn3)c(F)cc2c1=O] | (R)-1-cyclopropyl-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.47 (s, 1H), 8.59 (d, J = 8.8 Hz, 1H), 8.06-8.04 (m, 1H), 7.82 (d, J = 14.8 Hz, 1H), 7.68-7.64 (m, 1H), 7.24 (d, J = 7.6 Hz, 1H), 6.96-6.92 (m, 1H), 6.74 (d, J = 8.0 Hz, 1H), 4.65-4.64 (bs, 1H), 4.46-4.42 (m, 1H), 4.32-4.27 (m, 1H), 3.73-3.69 (m, 2H), 3.54-3.52 (bs, 1H), 2.16-2.0 (m, 4H), 1.25-1.08 (m, 4H). MS (ESI) m/z: 424.3 $[M + H]^+$ | +++ |
| 448. | 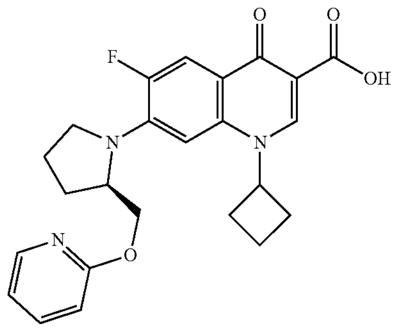 [SMILES: O=C(O)c1cn(C2CCC2)c2cc(N3CCC[C@@H]3COc3ccccn3)c(F)cc2c1=O] | (R)-1-cyclobutyl-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.56 (s, 1H), 8.53 (s, 1H), 8.08 (dd, J = 3.6, 1.6 Hz, 1H), 7.83 (d, J = 14.4 Hz, 1H), 7.67 (dt, J = 1.6, 7.2 Hz, 1H), 6.95 (t, J = 6.0 Hz, 1H), 6.80 (d, J = 7.6 Hz, 1H), 6.72 (d, J = 8.4 Hz, 1H), 5.04-5.10 (m, 1H), 4.68 (brs, 1H), 4.46-4.40 (m, 1H), 4.32-4.25 (m, 1H), 3.80-3.70 (m, 1H), 3.55-3.45 (m, 1H), 2.64-2.59 (m, 2H), 2.49-2.38 (m, 2H), 2.20-1.94 (m, 4H), 1.90-1.78 (m, 2H), MS (ESI) m/z: 438.4 $[M + H]^+$ | +++ |

-continued

| EX # | Structure | IUPAC name | Analytical data | Potency Lin28a-dep Z11 $IC_{50}$ (μM) |
|---|---|---|---|---|
| 449. | 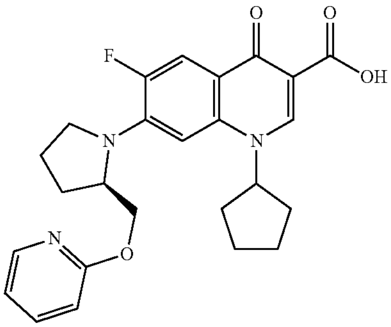 [SMILES: O=C(O)c1cn(C2CCCC2)c2cc(N3CCC[C@@H]3COc3ccccn3)c(F)cc2c1=O] | (R)-1-cyclopentyl-6-fluoro-4-oxo-7-(2-((pyridin-2-yloxy)methyl) pyrrolidin-1-yl)-1,4-dihydroquinoline-3-carboxylic acid | $^1$HNMR (400 MHz, DMSO-$d_6$): δ 15.55 (s, 1H), 8.61 (s, 1H), 8.06 (dd, J = 1.6, 5.2 Hz, 1H), 7.86 (d, J = 14.4 Hz, 1H), 7.68-7.64 (m, 1H), 7.01 (d, J = 7.2 Hz, 1H), 6.96-6.93 (m, 1H), 6.72 (d, J = 8.4 Hz, 1H), 5.20-5.18 (m, 1H), 4.71 (brs, 1H), 4.45-4.41 (m, 1H), 4.30-4.25 (m, 1H), 3.76 (brs, 1H), 3.56-3.49 (m, 1H), 2.33-2.26 (m, 2H), 2.15-2.13 (m, 2H), 2.04-1.93 (m, 4H), 1.80-1.78 (m, 4H). MS (ESI): m/z: 452.3 [M + H]+. | +++ |
| 450. | 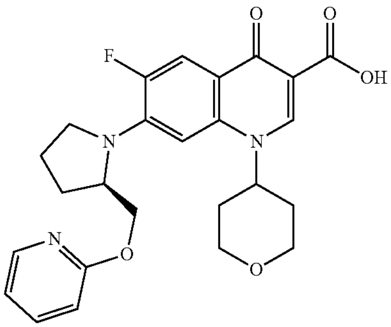 [SMILES: O=C(O)c1cn(C2CCOCC2)c2cc(N3CCC[C@@H]3COc3ccccn3)c(F)cc2c1=O] | (R)-6-fluoro-4-oxo-7-(2-((pyridin-2-yloxy)methyl) pyrrolidin-1-yl)-1-(tetrahydro-2H-pyran-4-yl)-1,4-dihydroquinoline-3-carboxylic acid | $^1$H NMR (400 MHz, DMSO-$d_6$): δ 8.74 (s, 1H), 8.06 (d, J = 3.6 Hz, 1H), 7.81 (d, J = 15.2 Hz, 1H), 7.66 (t, J = 6.8 Hz, 1H), 6.93 (t, J = 6.0 Hz, 1H), 6.87 (d, J = 6.4 Hz, 1H), 6.71 (d, J = 8.4 Hz, 1H), 4.90-4.80 (m, 1H), 4.68-4.59 (m, 1H), 4.38 (d, J = 7.2 Hz, 1H), 4.23 (t, J = 6.8 Hz, 1H), 4.02 (d, J = 10.4, 1H), 3.87 (d, J = 8.4 Hz, 1H), 3.74 (brs, 1H), 3.62 (t, J = 9.6 Hz, 1H), 3.55-3.49 (m, 2H), 2.15-1.84 (m, 8H) (—$CO_2$H proton was not observed). MS (ESI): m/z: 468.3 [M + H]+. | +++ |
| 451. | 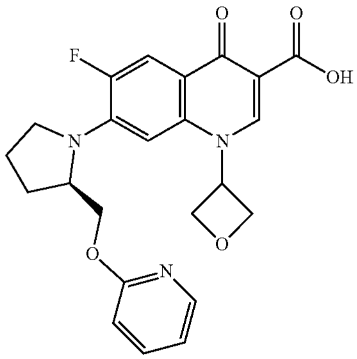 [SMILES: O=C(O)c1cn(C2COC2)c2cc(N3CCC[C@@H]3COc3ccccn3)c(F)cc2c1=O] | (R)-6-fluoro-1-(oxetan-3-yl)-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$): δ 15.47 (s, 1H), 8.62 (s, 1H), 8.10 (dd, J = 1.6, 4.8 Hz, 1H), 7.85 (d, J = 14.8 Hz, 1H), 7.70-7.65 (m, 1H), 6.97-6.94 (m, 1H), 6.73 (d, J = 8.4 Hz, 1H), 6.51 (d, J = 6.4 Hz, 1H), 5.86 (brs, 1H), 5.10-5.04 (m, 2H), 4.95 (d, J = 6.0 Hz, 2H), 4.66 (brs, 1H), 4.43-4.39 (m, 1H), 4.27-4.23 (m, 1H), 3.72 (brs, 1H), 3.52 (brs, 1H), 2.14-1.99 (m, 4H). MS (ESI) m/z: 440.3 [M + H]+. | +++ |
| 452. | 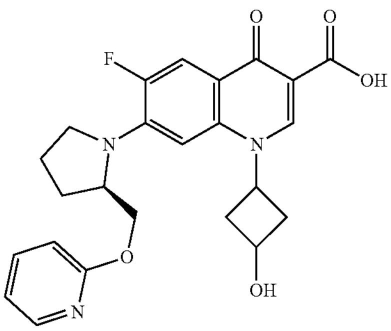 [SMILES: O=C(O)c1cn(C2CC(O)C2)c2cc(N3CCC[C@@H]3COc3ccccn3)c(F)cc2c1=O] | (R)-6-fluoro-1-(3-hydroxycyclo-butyl)-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$): δ 8.75 (s, 1H), 8.10-8.07 (m, 1H), 7.79 (d, J = 14.8 Hz, 1H), 7.68-7.64 (m, 1H), 6.94 (dd, J = 6.4, 5.2 Hz, 1H), 6.73-6.70 (m, 2H), 5.53 (s, 1H), 4.62-4.58 (m, 1H), 4.45-4.38 (m, 2H), 4.25-4.20 (m, 1H), 4.02-3.98 (m, 1H), 3.74-3.68 (m, 1H), 3.50-3.40 (m, 1H), 2.98-2.97 (m, 2H), 2.22-2.12 (m, 4H), 2.08-2.01 (m, 2H) (—COOH proton was not observed). MS (ESI) m/z: 454.3 $[M + H]^+$ | +++ |

-continued

| EX # | Structure | IUPAC name | Analytical data | Potency Lin28a-dep Z11 $IC_{50}$ (μM) |
| --- | --- | --- | --- | --- |
| 453. | 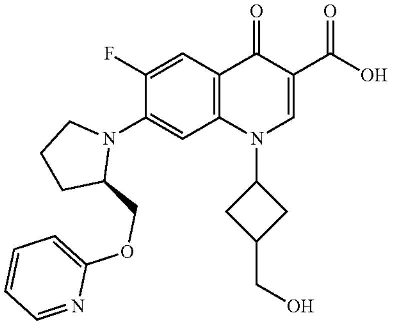 [SMILES: O=C(O)c1cn(C2CC(CO)C2)c2cc(N3CCC[C@@H]3COc3ccccn3)c(F)cc2c1=O] | (R)-6-fluoro-1-(3-(hydroxymethyl) cyclobutyl)-4-oxo-7-(2-((pyridin-2-yloxy)methyl) pyrrolidin-1-yl)-1,4-dihydroquinoline-3-carboxylic acid | $^{1}H$ NMR (400 MHz, DMSO-$d_6$): δ 15.55 (s, 1H), 8.43 (s, 1H), 8.04 (s, 1H), 7.85 (d, J = 14.8 Hz, 1H), 7.66 (t, J = 6.4 Hz, 1H), 6.94 (t, J = 5.6 Hz, 1H), 6.73 (d, J = 8.0 Hz, 1H), 6.57 (d, J = 5.6 Hz, 1H), 4.57 (brs, 1H), 4.42-4.28 (m, 2H), 3.67 (brs, 1H), 3.52-3.45 (m, 2H), 3.29-3.20 (m, 1H), 2.80-2.64 (m, 2H), 2.20-1.90 (m, 5H), 1.84-1.70 (m, 4H). MS (ESI) m/z: 468.4 [M + H]+. | ++ |
| 454. | 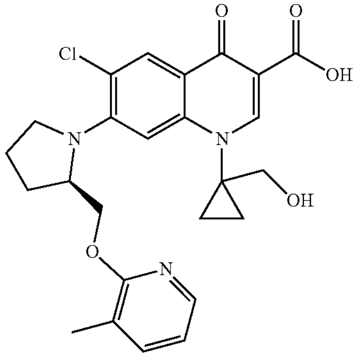 [SMILES: Cc1cccnc1OC[C@H]1CCCN1c1cc2c(cc1Cl)c(=O)c(C(=O)O)cn2C1(CO)CC1] | (R)-6-chloro-1-(1-(hydroxymethyl) cyclopropyl)-7-(2-(((3-methyl-pyridin-2-yl)oxy) methyl) pyrrolidin-1-yl)-4-oxo-1,4-dihydroquinoline-3-carboxylic acid | $^{1}$HNMR (400 MHz, DMSO-$d_6$): δ 15.14 (s, 1H), 8.64 (d, J = 6.8 Hz, 1H), 8.13 (d, J = 4.0 Hz, 1H), 7.84-7.79 (m, 1H), 7.47-7.44 (m, 1H), 7.32 (d, J = 8.8 Hz, 1H), 6.83-6.77 (m, 1H), 5.30-5.24 (m, 1H), 4.94-4.84 (m, 1H), 4.37-4.36 (m, 1H), 4.26-4.24 (m, 1H), 4.04-3.92 (m, 1H), 3.39-3.72 (m, 1H), 3.46 (t, J = 8.2 Hz, 1H), 3.28-3.19 (m, 1H), 2.33-2.31 (m, 1H), 2.12-2.03 (m, 2H), 2.01 (s, 3H), 1.93-1.83 (m, 1H), 1.39-1.30 (m, 2H), 1.29-1.17 (m, 2H), MS (ESI): m/z 484.3 $[M + H]^+$ | +++ |
| 455. | 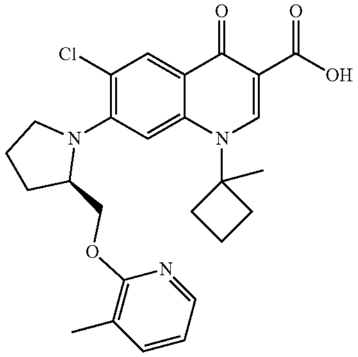 [SMILES: Cc1cccnc1OC[C@H]1CCCN1c1cc2c(cc1Cl)c(=O)c(C(=O)O)cn2C1(C)CCC1] | (R)-6-chloro-1-(1-methylcyclobutyl)-7-(2-(((3-methylpyridin-2-yl)oxy)methyl) pyrrolidin-1-yl)-4-oxo-1,4-dihydroquinoline-3-carboxylic acid | $^{1}$HNMR (400 MHz, DMSO-$d_6$): δ 15.25 (s, 1H), 8.45 (s, 1H), 8.16 (s, 1H), 7.80 (d, J = 4.4 Hz, 1H), 7.44 (d, J = 7.4 Hz, 1H), 6.83-6.77 (m, 2H), 4.89-4.82 (m, 1H), 4.33 (dd, J = 11.2, 5.2 Hz, 1H), 4.24 (dd, J = 11.2, 5.2 Hz, 1H), 3.79-3.74 (m, 1H), 3.41-3.36 (m, 1H), 2.72-2.64 (m, 1H), 2.33-2.30 (m, 1H), 2.08-1.78 (m, 8H), 1.98 (s, 3H), 1.73 (s, 3H), MS (ESI): m/z 482.3 $[M + H]^+$ | +++ |
| 456. | 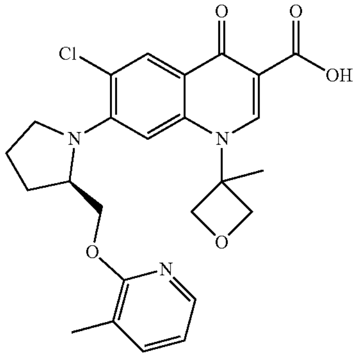 [SMILES: Cc1cccnc1OC[C@H]1CCCN1c1cc2c(cc1Cl)c(=O)c(C(=O)O)cn2C1(C)COC1] | (R)-6-chloro-1-(3-methyloxetan-3-yl)-7-(2-(((3-methylpyridin-2-yl)oxy)methyl) pyrrolidin-1-yl)-4-oxo-1,4-dihydroquinoline-3-carboxylic acid | $^{1}$HNMR (400 MHz, DMSO-$d_6$): δ 15.16 (s, 1H), 8.38 (s, 1H), 8.16 (s, 1H), 7.81 (d, J = 3.6 Hz, 1H), 7.44 (d, J = 6.8 Hz, 1H), 6.79 (dd, J = 6.4, 5.6 Hz, 1H), 6.14 (s, 1H), 5.15-5.00 (m, 2H), 4.95-4.86 (m, 1H), 4.85-4.75 (m, 2H), 4.33 (dd, J = 11.2, 4.0 Hz, 1H), 4.24 (dd, J = 11.6, 5.2 Hz, 1H), 3.80-3.73 (m, 1H), 3.45-3.35 (m, 1H), 2.32-2.29 (m, 1H), 2.08-2.04 (m, 2H), 1.99 (s, 3H), 1.97 (s, 3H), 1.92-1.84 (m, 1H). MS (ESI): m/z 484.3 $[M + H]^+$ | +++ |

-continued

| EX # | Structure | IUPAC name | Analytical data | Potency Lin28a-dep Z11 $IC_{50}$ (μM) |
|---|---|---|---|---|
| 457. | 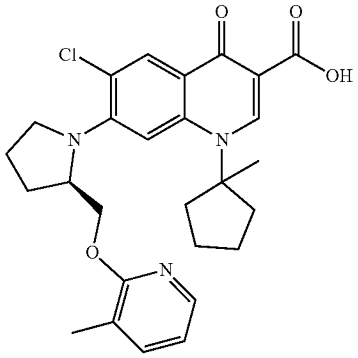 [SMILES: Cc1cccnc1OC[C@H]1CCCN1c1cc2c(cc1Cl)c(=O)c(C(=O)O)cn2C1(C)CCCC1] | (R)-6-chloro-1-(1-methylcyclo-pentyl)-7-(2-(((3-methylpyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.18 (s, 1H), 8.81 (s, 1H), 8.18 (s, 1H), 7.78 (dd, J = 4.8, 1.2 Hz, 1H), 7.42 (dd, J = 7.2, 0.8 Hz, 1H), 7.26 (s, 1H), 6.77 (dd, J = 7.2 Hz, 5.2 Hz, 1H), 4.88-4.85 (m, 1H), 4.37-4.32 (m, 1H), 4.26-4.22 (m, 1H), 3.85-3.79 (m, 1H), 3.45-3.40 (m, 1H), 2.49-2.19 (m, 5H), 2.10-1.90 (m, 6H), 1.73-1.68 (m, 7H), MS (ESI): m/z 496.3 $[M + H]^+$ | ++++ |
| 458. | 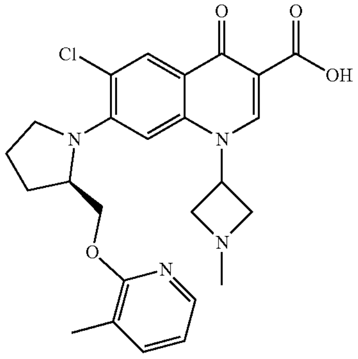 [SMILES: Cc1cccnc1OC[C@H]1CCCN1c1cc2c(cc1Cl)c(=O)c(C(=O)O)cn2C1CN(C)C1] | (R)-6-chloro-1-(1-methylazetidin-3-yl)-7-(2-(((3-methylpyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.21 (s, 1H), 8.68 (s, 1H), 8.15 (s, 1H), 7.88 (dd, J = 5.2, 1.6 Hz, 1H), 7.46-7.43 (m, 1H), 6.95 (brs, 1H), 6.82 (dd, J = 6.8, 4.8 Hz, 1H), 5.27-5.19 (m, 1H), 4.97-4.90 (m, 1H), 4.39 (dd, J = 11.2, 4.4 Hz, 1H), 4.21 (dd, J = 11.2, 5.2 Hz, 1H), 3.94-3.82 (m, 3H), 3.42-3.32 (m, 3H), 3.29-3.20 (m, 1H), 2.33-2.28 (m, 4H), 2.08-2.01 (m, 2H), 1.96 (s, 3H), 1.92-1.87 (m, 1H), MS (ESI): m/z 483.4 $[M + H]^+$ | +++ |
| 459. | 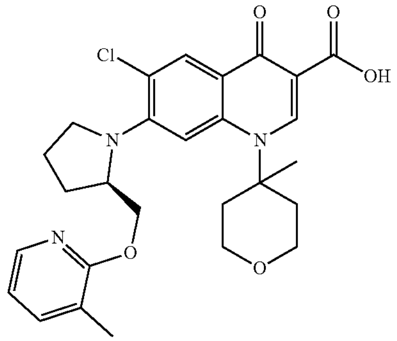 [SMILES: Cc1cccnc1OC[C@H]1CCCN1c1cc2c(cc1Cl)c(=O)c(C(=O)O)cn2C1(C)CCOCC1] | (R)-6-chloro-7-(2-(((3-methylpyridin-2-yl)oxy)methyl) pyrrolidin-1-yl)-1-(4-methyltetra-hydro-2H-pyran-4-yl)-4-oxo-1,4-dihydroquinoline-3-carboxylic acid | $^1$HNMR (400 MHz, DMSO-$d_6$): δ 15.13 (s, 1H), 8.86 (s, 1H), 8.21 (s, 1H), 7.77 (d, J = 3.6 Hz, 1H), 7.42 (d, J = 7.2 Hz, 1H), 7.35 (s, 1H), 6.79-6.76 (m, 1H), 4.95-4.88 (m, 1H), 4.35-4.31 (m, 1H), 4.28-4.24 (m, 1H), 3.82-3.58 (m, 5H), 3.45-3.41 (m, 1H), 2.33-2.21 (m, 5H), 2.12-1.98 (m, 3H), 1.97 (s, 3H), 1.94 (s, 3H). MS (ESI): m/z 512.3 [M + H]+. | +++ |
| 460. | 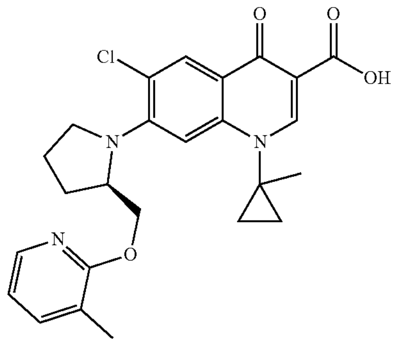 [SMILES: Cc1cccnc1OC[C@H]1CCCN1c1cc2c(cc1Cl)c(=O)c(C(=O)O)cn2C1(C)CC1] | (R)-6-chloro-1-(1-methylcyclo-propyl)-7-(2-(((3-methylpyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.14 (s, 1H), 8.74 (s, 1H), 8.13 (s, 1H), 7.80 (s, 1H), 7.48-7.34 (m, 2H), 6.79 (t, J = 6.4 Hz, 1H), 4.93 (brs, 1H), 4.45-4.23 (m, 2H), 3.90-3.78 (m, 1H), 3.54-3.46 (m, 1H), 2.35-2.33 (m, 1H), 2.16-1.90 (m, 6H), 1.57 (s, 3H), 1.41-1.15 (m, 4H). MS (ESI): m/z 468.4 [M + H]+. | ++++ |

-continued

| EX # | Structure | IUPAC name | Analytical data | Potency Lin28a-dep Z11 $IC_{50}$ (µM) |
|---|---|---|---|---|
| 461. | 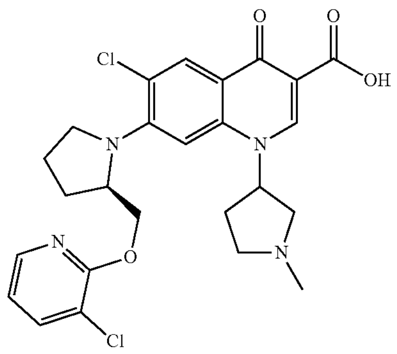 [SMILES: CN1CCC(n2cc(C(=O)O)c(=O)c3cc(Cl)c(N4CCC[C@@H]4COc4ncccc4Cl)cc32)C1] | 6-chloro-7-((R)-2-(((3-chloropyridin-2-yl)oxy)methyl) pyrrolidin-1-yl)-1-(1-methyl-pyrrolidin-3-yl)-4-oxo-1,4-dihydroquinoline-3-carboxylic acid | $^{1}$HNMR (400 MHz, DMSO-$d_6$, VT 90° C.): δ 15.21 (brs, 1H), 8.85 (brs, 1H), 8.15 (s, 1H), 7.92-7.89 (m, 1H), 7.71-7.68 (m, 1H), 7.25 (brs, 1H), 6.90-6.86 (m, 1H), 5.69-5.62 (m, 1H), 5.09-5.01 (m, 1H), 4.45-4.40 (m, 2H), 3.98-3.88 (m, 1H), 3.72-3.36 (m, 4H), 3.39-3.18 (m, 1H), 2.85 (brs, 3H), 2.70-2.65 (m, 1H), 2.33-2.30 (m, 1H), 2.15-2.01 (m, 2H), 1.96-1.90 (m, 2H), MS (ESI): m/z 517.3 $[M + H]^+$ | +++ |
| 462. | 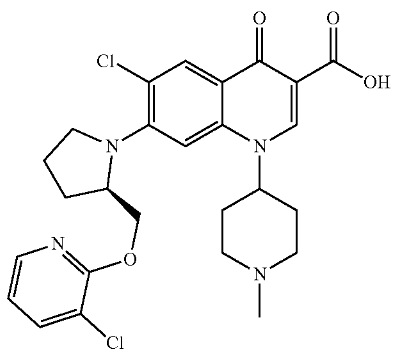 [SMILES: CN1CCC(n2cc(C(=O)O)c(=O)c3cc(Cl)c(N4CCC[C@@H]4COc4ncccc4Cl)cc32)CC1] | (R)-6-chloro-7-(2-(((3-chloropyridin-2-yl)oxy)methyl) pyrrolidin-1-yl)-1-(1-methyl-piperidin-4-yl)-4-oxo-1,4-dihydro-quinoline-3-carboxylic acid | 1HNMR (400 MHz, DMSO-$d_6$): δ 15.19 (s, 1H), 8.64 (s, 1H), 8.16 (s, 1H), 7.90 (dd, J = 4.8, 1.6 Hz, 1H), 7.78 (dd, J = 7.6, 1.6 Hz, 1H), 7.15 (s, 1H), 6.90 (dd, J = 8.0, 5.2 Hz, 1H), 4.97-4.93 (m, 1H), 4.64-4.56 (m, 1H), 4.38 (d, J = 4.0 Hz, 2H), 3.90-3.82 (m, 1H), 3.50-3.40 (m, 1H), 2.96-2.91 (m, 1H), 2.80-2.74 (m, 1H), 2.39-2.32 (m, 1H), 2.22 (s, 3H), 2.19-1.97 (m, 9H), MS (ESI): m/z 531.3 $[M + H]^+$ | +++ |
| 463. | 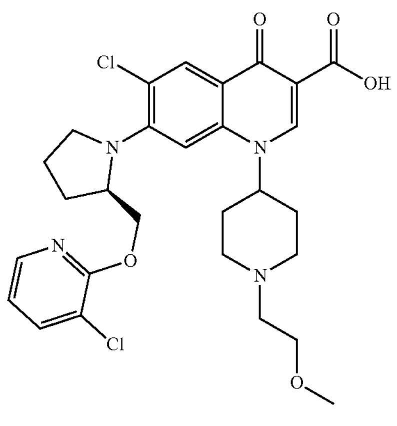 [SMILES: COCCN1CCC(n2cc(C(=O)O)c(=O)c3cc(Cl)c(N4CCC[C@@H]4COc4ncccc4Cl)cc32)CC1] | (R)-6-chloro-7-(2-(((3-chloropyridin-2-yl)oxy)methyl) pyrrolidin-1-yl)-1-(1-(2-methoxy-ethyl)piperidin-4-yl)-4-oxo-1,4-dihydroquinoline-3-carboxylic acid | 1HNMR (400 MHz, DMSO-$d_6$): δ 15.19 (s, 1H), 8.64 (s, 1H), 8.16 (s, 1H), 7.90 (dd, J = 4.8, 1.6 Hz, 1H), 7.78 (dd, J = 7.6, 1.6 Hz, 1H), 7.15 (s, 1H), 6.90 (dd, J = 8.0, 5.2 Hz, 1H), 4.97-4.93 (m, 1H), 4.64-4.58 (m, 1H), 4.42-4.34 (m, 2H), 3.90-3.82 (m, 1H), 3.43 (t, J = 5.6 Hz, 2H), 3.23 (s, 3H), 3.10-3.04 (m, 1H), 2.92-2.86 (m, 1H), 2.60-2.51 (m, 2H), 2.39-2.20 (m, 3H), 2.16-1.85 (s, 7H). MS (ESI): m/z 575.3 $[M + H]^+$ | +++ |

-continued

| EX # | Structure | IUPAC name | Analytical data | Potency Lin28a-dep Z11 $IC_{50}$ (µM) |
| --- | --- | --- | --- | --- |
| 464. | 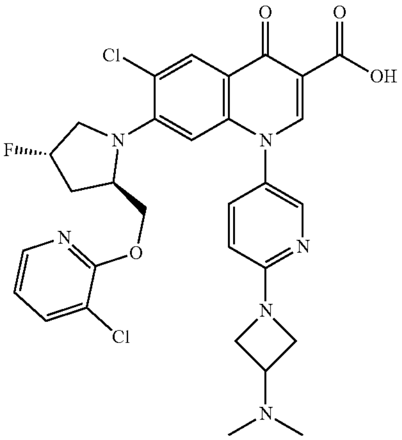 [SMILES: CN(C)C1CN(c2ccc(-n3cc(C(=O)O)c(=O)c4cc(Cl)c(N5C[C@@H](F)C[C@@H]5COc5ncccc5Cl)cc43)cn2)C1] | 6-chloro-7-((2R,4S)-2-(((3-chloropyridin-2-yl)oxy)methyl)-4-fluoropyrrolidin-1-yl)-1-(6-(3-(dimethylamino)azetidin-1-yl)pyridin-3-yl)-4-oxo-1,4-dihydroquinoline-3-carboxylic acid | $^1$H-NMR (400 MHz, DMSO-$d_6$): δ 15.02 (bs, 1H), 8.54 (d, J = 11.60 Hz, 1H), 8.26-8.23 (m, 1H), 8.20 (s, 1H), 7.90-7.88 (m, 1H), 7.82 (d, J = 7.60 Hz, 1H), 7.73-7.65 (m, 1H), 6.97-6.94 (m, 1H), 6.55 (d, J = 9.20 Hz, 0.5H), 6.47-6.43 (m, 1H), 6.36 (d, J = 8.80 Hz, 0.5H), 5.32 (bs, 0.5H), 5.49 (bs, 0.5H), 4.79-4.77 (m, 1H), 4.38-4.26 (m, 2H), 4.07-4.11 (m, 2H), 3.88-3.80 (m, 3H), 3.45-3.37 (m, 1H), 3.25-3.22 (m, 1H), 2.50-2.49 (m, 1H), 2.34-2.28 (m, 1H), 2.15 (s, 6H). MS (ESI) m/z: 627.2 $[M + H]^+$ | ++++ |
| 465. | 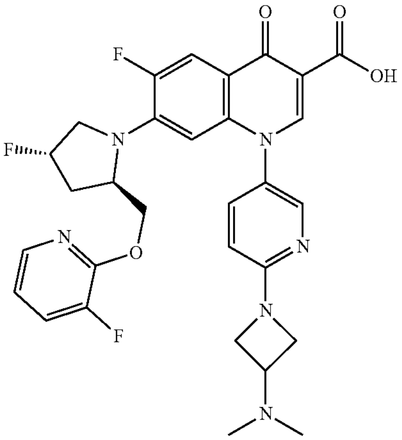 | 1-(6-(3-(dimethylamino)azetidin-1-yl)pyridin-3-yl)-6-fluoro-7-((2R,4S)-4-fluoro-2-(((3-fluoropyridin-2-yl)oxy)methyl)pyrrolidin-1-yl)-4-oxo-1,4-dihydroquinoline-3-carboxylic acid | $^1$H-NMR (400 MHz, DMSO-$d_6$): δ 15.28 (bs, 1H), 8.51 (d, J = 7.2 Hz, 1H), 8.26 (s, 1H), 7.92 (d, J = 13.6 Hz, 1H), 7.78-7.70 (m, 2H), 7.62 (td, J = 9.4, 1.2 Hz, 1H), 7.01-6.97 (m, 1H), 6.56 (d, J = 8.8 Hz, 1H), 6.35 (d, J = 8.8 Hz, 1H), 6.22 (t, J = 7.6 Hz, 1H), 5.48 (bs, 0.5H), 5.35 (bs, 0.5H), 4.58-4.59 (m, 1H), 4.40-4.36 (m, 2H), 4.10-4.03 (m, 2H), 3.84-3.78 (m, 2H), 3.74-3.65 (m, 1H), 3.56-3.37 (m, 1H), 3.27-3.21 (m, 1H), 2.54-2.51 (m, 1H), 2.15 (s, 6H). MS (ESI) m/z: 595.2 $[M + H]^+$ | ++++ |
| 466. | 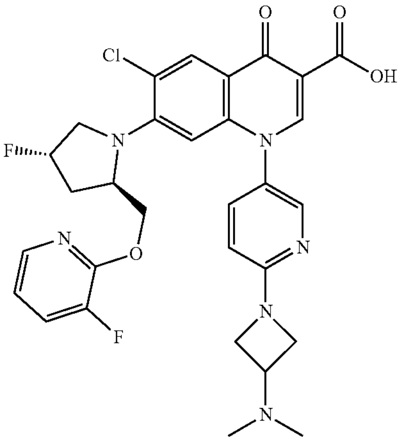 | 6-chloro-1-(6-(3-(dimethylamino)azetidin-1-yl)pyridin-3-yl)-7-((2R,4S)-4-fluoro-2-(((3-fluoropyridin-2-yl)oxy)methyl)pyrrolidin-1-yl)-4-oxo-1,4-dihydroquinoline-3-carboxylic acid | $^1$H-NMR (400 MHz, DMSO-$d_6$): δ 15.28 (bs, 1H), 8.55 (d, J = 9.6 Hz, 1H), 8.26-8.24 (m, 1H), 8.20-8.19 (m, 1H), 7.76-7.74 (m, 1H), 7.70 (d, J = 8.8 Hz, 1H), 7.61 (t, J = 8.0 Hz, 1H), 6.99-6.95 (m, 1H), 6.57 (d, J = 8.8 Hz, 0.5H), 6.49-6.43 (m, 1H), 6.30 (d, J = 8.8 Hz, 0.5H), 5.46 (bs, 0.5H), 5.33 (bs, 0.5H), 4.71-4.66 (m, 1H), 4.39-4.27 (m, 2H), 4.08-4.03 (m, 2H), 3.83-3.78 (m, 3H), 3.45-3.37 (m, 1H), 3.26-3.21 (m, 1H), 2.50-2.49 (m, 1H), 2.32-2.27 (m, 1H), 2.15 (s, 6H). MS (ESI) m/z: 611.4 $[M + H]^+$ | ++++ |

-continued

| EX # | Structure | IUPAC name | Analytical data | Potency Lin28a-dep Z11 $IC_{50}$ (μM) |
|---|---|---|---|---|
| 467. | 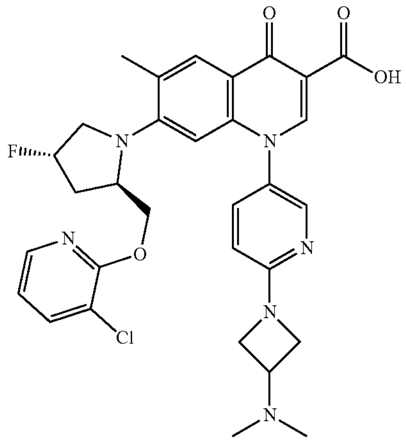 [SMILES: Cc1cc2c(=O)c(C(=O)O)cn(-c3ccc(N4CC(N(C)C)C4)nc3)c2cc1N1C[C@@H](F)C[C@@H]1COc1ncccc1Cl] | 7-((2R,4S)-2-(((3-chloropyridin-2-yl)oxy)methyl)-4-fluoropyrrolidin-1-yl)-1-(6-(3-(dimethylamino)azetidin-1-yl)pyridin-3-yl)-6-methyl-4-oxo-1,4-dihydroquinoline-3-carboxylic acid | $^1$H NMR (400 MHz, DMSO-$d_6$): δ 15.50 (bs, 1H), 8.46 (d, J = 10.4 Hz, 1H), 8.34-8.32 (m, 1H), 8.08 (s, 1H), 7.91 (s, 1H), 7.85-7.76 (m, 2H), 6.99-6.96 (m, 1H), 6.67 (d, J = 8.8 Hz, 0.5H), 6.46 (d, J = 8.8 Hz, 0.5H), 6.37 (d, J = 15.60 Hz, 1H), 5.45 (s, 0.5H), 5.32 (s, 0.5H), 4.37-4.15 (m, 8H), 3.87-3.74 (m, 1H), 3.40-3.34 (m, 1H), 2.86 (s, 6H), 2.40-2.37 (m, 1H), 2.33 (s, 3H), 2.22-2.15 (m, 1H). MS (ESI) m/z: 607.4 $[M + H]^+$ | ++++ |
| 468. | 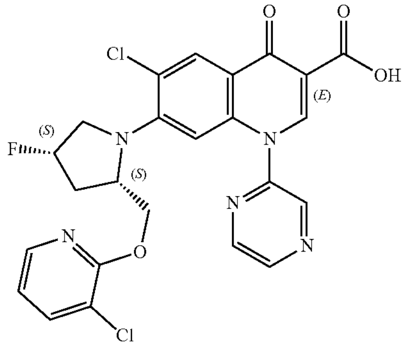 | 6-chloro-7-[(2S,4S)-2-{[(3-chloropyridin-2-yl)oxy]methyl}-4-fluoropyrrolidin-1-yl]-4-oxo-1-(pyrazin-2-yl)-1,4-dihydroquinoline-3-carboxylic acid | $^1$H NMR (400 MHz, DMSO-$d_6$): δ 14.77 (brs, 1H), 9.11 (s, 1H), 8.92 (d, J = 2.4 Hz, 1H), 8.89 (s, 1H), 8.77 (d, J = 1.2 Hz, 1H), 8.20 (s, 1H), 7.89 (dd, J = 4.8, 1.6 Hz, 1H), 7.70 (dd, J = 7.6, 1.6 Hz, 1H), 6.95-6.92 (m, 1H), 6.65 (s, 1H), 5.46-5.32 (m, 1H), 4.93-4.91 (m, 1H), 4.45-4.41 (m, 1H), 4.31-4.27 (m, 1H), 3.94-3.87 (m, 1H), 3.62-3.52 (m, 1H), 2.55-2.37 (m, 1H), 2.19-2.05 (m, 1H). MS (ESI) m/z: 530.2. $[M + H]^+$ | ++ |
| 469. | 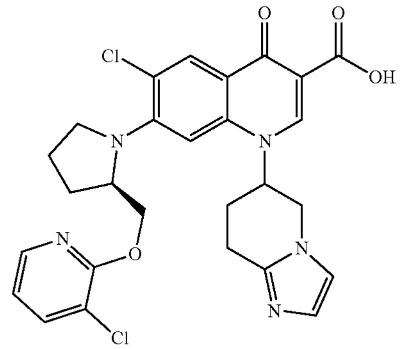 [SMILES: O=C(O)c1cn(C2CCc3nccn3C2)c2cc(N3CCC[C@@H]3COc3ncccc3Cl)c(Cl)cc2c1=O] | 6-chloro-7-((R)-2-(((3-chloropyridin-2-yl)oxy)methyl)pyrrolidin-1-yl)-4-oxo-1-(5,6,7,8-tetrahydroimidazo[1,2-a]pyridin-6-yl)-1,4-dihydroquinoline-3-carboxylic acid | $^1$H NMR (400 MHz, DMSO-$d_6$): δ 15.10 (s, 1H), 8.66 (s, 1H), 8.16 (s, 1H), 7.87-7.89 (m, 1H), 7.76-7.82 (m, 1H), 7.34 (d, J = 7.2, 1H), 7.06 (s, 1H), 6.87-6.94 (m, 2H), 5.53 (brs, 1H), 5.02 (brs, 1H), 4.36-4.48 (m, 4H), 3.82-3.88 (m, 1H), 3.38 (s, 1H), 2.82-2.96 (m, 2H), 2.67 (s, 1H), 2.28-2.33 (m, 2H), 2.04-2.08 (m, 2H), 1.99 (m, 1H); MS (ESI): m/z 554.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 470. | 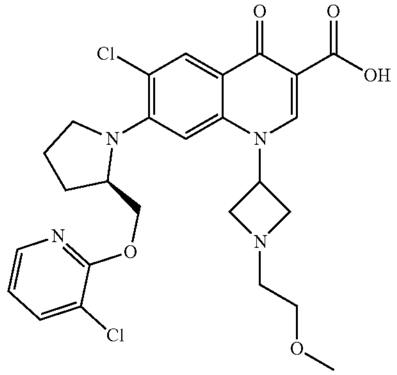 [SMILES: COCCN1CC(n2cc(C(=O)O)c(=O)c3cc(Cl)c(N4CCC[C@@H]4COc4ncccc4Cl)cc32)C1] | (R)-6-chloro-7-(2-(((3-chloropyridin-2-yl)oxy)methyl) pyrrolidin-1-yl)-1-(1-(2-methoxy-ethyl)azetidin-3-yl)-1-(1-(2-methoxyethyl) azetidin-3-yl)-4-oxo-1,4-dihydroquinoline-3-carboxylic acid | $^1$H NMR (400 MHz, DMSO-$d_6$, VT): δ 8.72 (brs, 1H), 8.15 (s, 1H), 7.93 (dd, J = 5.2, 1.6 Hz, 1H), 7.72 (dd, J = 7.6, 1.6 Hz, 1H), 6.89 (dd, J = 7.6, 4.8 Hz, 1H), 6.79 (brs, 1H), 5.46-5.42 (m, 1H), 4.99-4.95 (m, 1H), 4.50-4.35 (m, 4H), 4.30-4.10 (m, 2H), 3.88-3.84 (m, 1H), 3.52-3.49 (m, 2H), 3.43-3.30 (m, 2H), 3.28 (s, 3H), 3.24-2.14 (m, 3H), 2.36-2.28 (m, 1H), 2.17-1.85 (m, 3H) (COOH proton not observed). MS (ESI): m/z 547.3 [M + H]$^+$ | +++ |
| 471. | 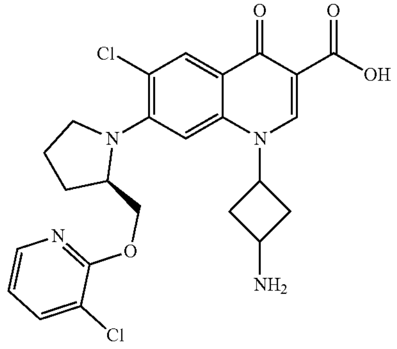 [SMILES: NC1CC(n2cc(C(=O)O)c(=O)c3cc(Cl)c(N4CCC[C@@H]4COc4ncccc4Cl)cc32)C1] | (R)-1-(3-aminocyclobutyl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$) δ 8.61 (s, 1H), 8.34 (bs, 1H), 7.92 (dd, J = 5.2, 1.2 Hz, 1H), 7.79-7.75 (m, 1H), 7.00-6.88 (m, 2H), 5.38-5.26 (m, 1H), 5.00-4.92 (m, 1H), 4.46-4.34 (m, 2H), 3.90-3.80 (m, 2H), 3.60-3.50 (m, 2H), 3.00-2.82 (m, 1H), 2.68-2.58 (m, 1H), 2.45-2.36 (m, 1H), 2.20-1.98 (m, 3H), 1.95-1.86 (m, 1H) (exchangeable protons were not observed). MS (ESI): m/z 503.3 [M + H]$^+$ | +++ |
| 472. | 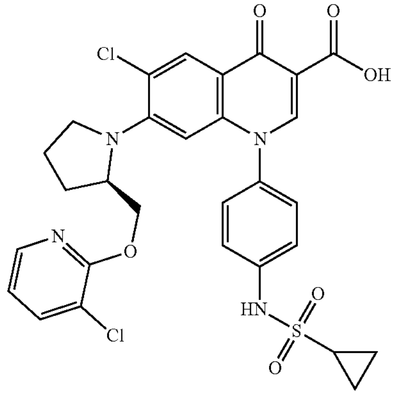 [SMILES: O=C(O)c1cn(-c2ccc(NS(=O)(=O)C3CC3)cc2)c2cc(N3CCC[C@@H]3COc3ncccc3Cl)c(Cl)cc2c1=O] | 6-chloro-7-[(2R)-2-{[(3-chloropyridin-2-yl)oxy)methyl} pyrrolidin-1-yl]-1-(4-cyclopropane-sulfonamido-phenyl)-4-oxo-1,4-dihydroquinoline-3-carboxylic acid | $^1$H-NMR (400 MHz, DMSO-$d_6$): δ 15.07 (s, 1H), 10.20 (bs, 1H), 8.54 (s, 1H), 8.16 (s, 1H), 7.90-7.87 (d, J = 4.4 Hz, 1H), 7.80 (d, J = 7.2 Hz, 1H), 7.60-7.46 (m, 3H), 7.38 (d, J = 8.0 Hz, 1H), 6.94-6.90 (m, 1H), 6.35 (s, 1H), 4.75 (bs, 1H), 4.29 (bs, 2H), 3.50-3.40 (m, 1H), 3.20-3.10 (m, 1H), 2.80-2.71 (m, 1H), 2.30-2.20 (m, 1H), 2.00-1.87 (m, 2H), 1.84-1.75 (m, 1H), 1.03-0.96 (m, 4H). MS (ESI): m/z 629.2 [M + H]$^+$ | ++++ |
| 473. | 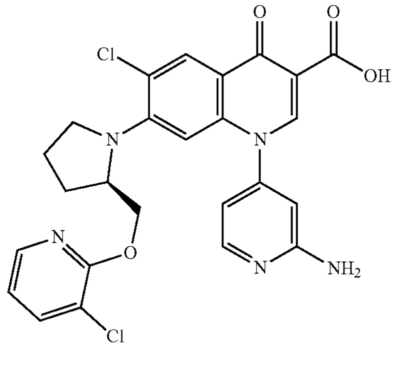 [SMILES: Nc1cc(-n2cc(C(=O)O)c(=O)c3cc(Cl)c(N4CCC[C@@H]4COc4ncccc4Cl)cc32)ccn1] | (R)-1-(2-aminopyridin-4-yl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$): δ 14.90 (s, 1H), 8.54 (s, 1H), 8.14 (s, 1H), 7.99 (t, J = 4.0 Hz, 1H), 7.86 (dd, J = 4.8, 1.6 Hz, 1H), 7.79 (dd, J = 7.6, 1.2 Hz, 1H), 6.91 (dd, J = 7.6, 4.8 Hz, 1H), 6.65 (d, J = 4.8 Hz, 1H), 6.59 (bs, 1H), 6.54 (bs, 3H), 4.81-4.70 (m, 1H), 4.33 (d, J = 4.0 Hz, 2H), 3.51 (bs, 1H), 3.20 (d, J = 8.4 Hz, 1H), 2.26 (d, J = 8.4 Hz, 1H), 2.00-1.91 (m, 2H), 1.82 (t, J = 8.8 Hz, 1H); MS (ESI): m/z 526.3 [M + H]$^+$ | ++++ |

-continued

| EX # | Structure | IUPAC name | Analytical data | Potency Lin28a-dep Z11 $IC_{50}$ (μM) |
|---|---|---|---|---|
| 474. | 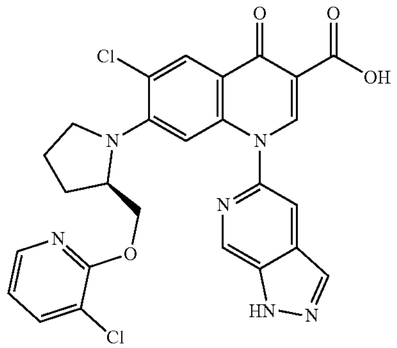 [SMILES: O=C(O)c1cn(-c2cc3cn[nH]c3cn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(1H-pyrazolo[3,4-c]pyridin-5-yl)-1,4-dihydroquinoline-3-carboxylic acid | $^1$H NMR (400 MHz, DMSO-$d_6$): δ 9.04 (s, 1H), 8.79 (s, 1H), 8.39 (s, 1H), 8.20 (s, 1H), 8.16 (s, 1H), 7.84 (dd, J = 4.8, 1.6 Hz, 1H), 7.79 (dd, J = 7.6, 1.2 Hz, 1H), 6.92 (dd, J = 7.6, 4.8 Hz, 1H), 6.47 (s, 1H), 4.62-4.58 (m, 1H), 4.24 (d, J = 4.0 Hz, 2H), 3.50-3.43 (m, 1H), 1.94-1.82 (m, 2H), 1.80-1.70 (m, 1H) (—COOH poton was not observed); MS (ESI): m/z 551.2 [M + H]$^+$ | ++++ |
| 475. | 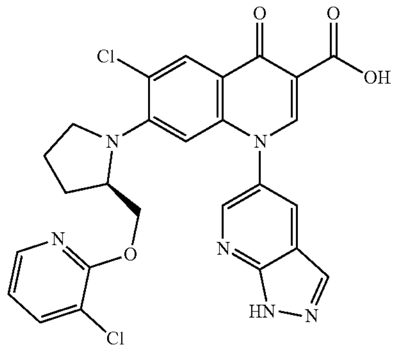 [SMILES: O=C(O)c1cn(-c2cnc3[nH]ncc3c2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(1H-pyrazolo[3,4-b] pyridin-5-yl)-1,4-dihydroquinoline-3-carboxylic acid | $^1$H NMR (400 MHz, DMSO-$d_6$): δ 15.09 (s, 1H), 14.10 (s, 1H), 8.75 (d, J = 2.4 Hz, 1H), 8.69 (dd, J = 8.8, 2.4 Hz, 1H), 8.57 (dd, J = 14.4, 2.4 Hz, 1H), 8.38 (s, 0.5H), 8.20 (d, J = 4.8 Hz, 1H), 8.17 (s, 0.5H), 7.87 (ddd, J = 8.8, 4.8, 1.6 Hz, 1H), 7.83-7.78 (m, 1H), 6.98-6.92 (m, 1H), 6.28 (d, J = 7.6 Hz, 1H), 4.74-4.58 (m, 1H), 4.30-4.18 (m, 2H), 3.46-3.38 (m, 1H), 3.14-3.07 (m, 1H), 2.22-2.15 (m, 1H), 1.94-1.80 (m, 2H), 1.78-1.68 (m, 1H); MS (ESI): m/z 551.2 [M + H]$^+$ | ++++ |
| 476. | 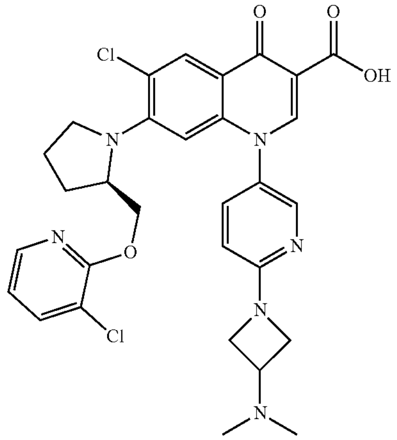 | (R)-6-chloro-7-(2-(((3-chloropyridin-2-yl)oxy)methyl) pyrrolidin-1-yl)-1-(6-(3-(dimethyl-amino)azetidin-1-yl)pyridin-3-yl)-4-oxo-1,4-dihydroquinoline-3-carboxylic acid | 1H NMR (400 MHz, DMSO-d6) δ 15.10 (s, 1H), 8.52 (d, J = 10.0 Hz, 1H), 8.24 (d, J = 2.4 Hz, 1H), 8.24 (s, 1H), 7.91-7.88 (m, 1H), 7.83-7.80 (m, 1H), 7.70-7.65 (m, 1H), 6.97-6.92 (m, 1H), 6.56-6.29 (m, 2H), 4.63-4.52 (m, 1H), 4.38-4.34 (m, 1H), 4.32-4.17 (m, 1H), 4.10-4.03 (m, 2H), 3.83-3.78 (m, 2H), 3.56-3.49 (m, 1H), 3.23-3.17 (m, 2H), 2.26-2.24 (m, 1H), 2.14 (s, 6H), 1.97-1.96 (m, 1H), 1.92-1.89 (m, 1H), 1.80-1.77 (m, 1H); MS (ESI): m/z 609.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 477. | 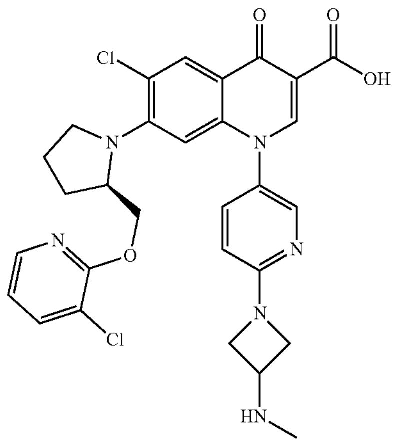 [SMILES: CNC1CN(c2ccc(-n3cc(C(=O)O)c(=O)c4cc(Cl)c(N5CCC[C@@H]5COc5ncccc5Cl)cc43)cn2)C1] | (R)-6-chloro-7-(2-(((3-chloropyridin-2-yl)oxy)methyl) pyrrolidin-1-yl)-1-(6-(3-(methyl-amino)azetidin-1-yl)pyridin-3-yl)-4-oxo-1,4-dihydroquinoline-3-carboxylic acid | $^{1}$HNMR (400 MHz, DMSO-$d_6$): δ 8.48 (d, J = 9.2 Hz, 1H), 8.24 (d, J = 2.4 Hz, 1H), 8.15 (s, 1H), 7.93-7.88 (m, 1H), 7.80 (dd, J = 7.6, 1.6 Hz, 1H), 7.72-7.66 (m, 1H), 6.96-6.90 (m, 1H), 6.57 (d, J = 8.8 Hz, 0.5H), 6.40 (d, J = 4.0 Hz, 1H), 6.36 (d, J = 8.8 Hz, 0.5H), 4.80-4.64 (m, 1H), 4.40-4.15 (m, 4H), 3.88-3.76 (m, 3H), 3.60-3.48 (m, 2H), 3.20-3.14 (m, 1H), 2.37 (s, 3H), 2.30-2.20 (m, 1H), 2.05-1.88 (m, 2H), 1.86-1.76 (m, 1H) (—COOH proton was not observed); MS (ESI): m/z 595.2 $[M + H]^{+}$ | ++++ |
| 478. | 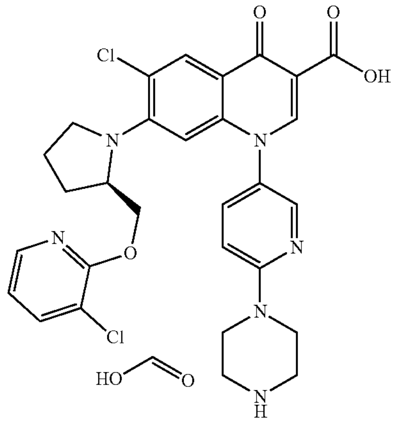 | (R)-6-chloro-7-(2-(((3-chloropyridin-2-yl)oxy)methyl) pyrrolidin-1-yl)-4-oxo-1-(6-(piperazin-1-yl) pyridin-3-yl)-1,4-dihydroquinoline-3-carboxylic acid | $^{1}$H NMR (400 MHz, DMSO-$d_6$): δ 15.02 (s, 1H), 8.81 (s, 2H), 8.50 (d, J = 8.4 Hz, 1H), 8.35 (s, 1H), 8.17 (s, 1H), 7.91 (d, J = 4.8 Hz, 1H), 7.90-7.78 (m, 2H), 7.20-6.93 (m, 3H), 6.42 (s, 1H), 4.72 (bs, 1H), 4.35-4.32 (m, 1H), 4.26-4.20 (m, 1H), 3.86-3.78 (m, 4H), 3.60-3.48 (m, 1H), 3.30-3.18 (m, 5H), 2.30-2.20 (m, 1H), 2.04-1.85 (m, 2H), 1.82-1.77 (m, 1H) (formate salt): MS (ESI): m/z 595.3 $[M + H]^{+}$ | ++++ |
| 479. | 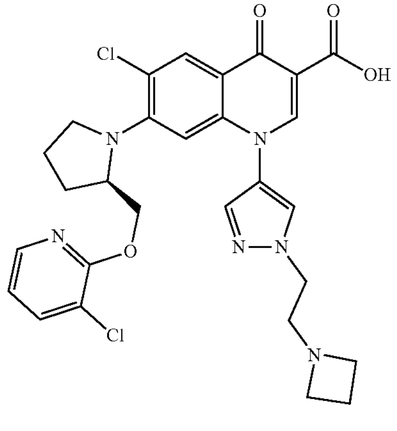 [SMILES: O=C(O)c1cn(-c2cnn(CCN3CCC3)c2)c2cc(N3CCC[C@@H]3COc3ncccc3Cl)c(Cl)cc2c1=O] | (R)-1-(1-(2-(azetidin-1-yl)ethyl)-1H-pyrazol-4-yl)-6-chloro-7-(2-(((3-chloropyridin-2-yl)oxy)methyl) pyrrolidin-1-yl)-4-oxo-1,4-dihydroquinoline-3-carboxylic acid | $^{1}$HNMR (400 MHz, DMSO-$d_6$): δ 15.02 (bs, 1H), 8.50 (s, 1H), 8.31 (bs, 1H), 8.13 (s, 1H), 7.86 (dd, J = 4.8, 1.6 Hz, 1H), 7.84 (s, 1H), 7.78 (dd, J = 7.2, 1.6 Hz, 1H), 6.90 (dd, J = 8.0, 5.2 Hz, 1H), 6.64 (s, 1H), 4.84-4.78 (m, 1H), 4.35-4.28 (m, 2H), 4.16 (t, J = 5.6 Hz, 2H), 3.58-3.48 (m, 1H), 3.26-3.20 (m, 1H), 3.16 (t, J = 6.8 Hz, 4H), 2.86 (t, J = 5.6 Hz, 2H), 2.30-2.20 (m, 1H), 2.05-1.90 (m, 4H), 1.88-1.78 (m, 1H); MS (ESI): m/z 583.2 $[M + H]^{+}$ | ++++ |

-continued

| EX # | Structure | IUPAC name | Analytical data | Potency Lin28a-dep Z11 $IC_{50}$ (μM) |
|---|---|---|---|---|
| 480. | 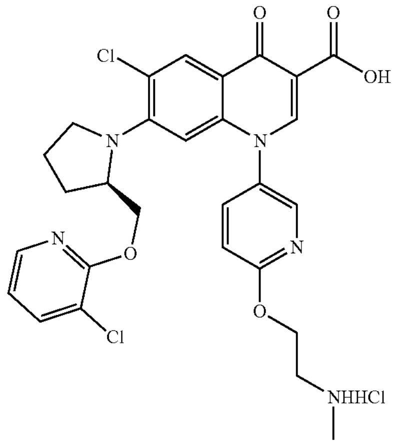 | (R)-6-chloro-7-(2-(((3-chloropyridin-2-yl)oxy)methyl) pyrrolidin-1-yl)-1-(6-(2-(methyl-amino)ethoxy) pyridin-3-yl)-4-oxo-1,4-dihydroquinoline-3-carboxylic acid hydrochloride | $^1$HNMR (400 MHz, DMSO-$d_6$): δ 15.03 (bs, 1H), 9.03 (bs, 2H), 8.61 (d, J = 9.2 Hz, 1H), 8.47 (bs, 1H), 8.17 (s, 1H), 8.07-7.98 (m, 1H), 7.90 (dd, J = 5.2, 1.6 Hz, 1H), 7.82 (d, J = 7.6 Hz, 1H), 7.13 (d, J = 9.2 Hz, 0.5H), 6.98-6.93 (m, 1.5H), 6.33 (s, 1H), 4.80-4.50 (m, 3H), 4.34-4.20 (m, 2H), 3.54-3.46 (m, 1H), 3.38 (bs, 2H), 3.18 (t, J = 8.4 Hz, 1H), 2.65 (s, 3H), 2.30-2.20 (m, 1H), 2.02-1.86 (m, 2H), 1.84-1.76 (m, 1H), MS (ESI) m/z: 584.3 $[M + H]^+$ | ++++ |
| 481. | 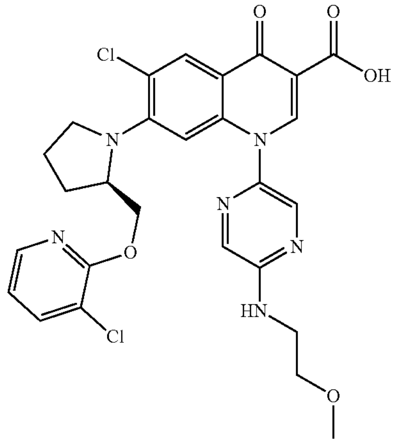 [SMILES: COCCNc1cnc(-n2cc(C(=O)O)c(=O)c3cc(Cl)c(N4CCC[C@@H]4COc4ncccc4Cl)cc32)cn1] | 6-chloro-7-[(2R)-2-{[(3-chloropyridin-2-yl)oxy]methyl} pyrrolidin-1-yl]-1-{5-[(2-methoxyethyl) amino]pyrazin-2-yl}-4-oxo-1,4-dihydroquinoline-3-carboxylic acid | $^1$H NMR (400 MHz, DMSO-$d_6$): δ 14.99 (s, 1H), 8.71 (s, 1H), 8.29 (s, 1H), 8.15 (s, 1H), 7.94 (s, 1H), 7.87 (dd, J = 1.6, 4.8 Hz, 1H), 7.81 (bs, 1H), 7.77 (dd, J = 1.6, 8.0 Hz, 1H), 6.92-6.89 (m, 1H), 6.57 (s, 1H), 4.74 (bs, 1H), 4.33-4.25 (m, 2H), 3.61-3.53 (m, 6H), 3.37-3.31 (m, 2H), 3.23-3.19 (m, 1H), 2.33-2.23 (m, 1H), 2.08-1.91 (m, 2H), 1.89-1.79 (m, 1H), MS (ESI): m/z 585.3 $[M + H]^+$ | ++++ |
| 482. | 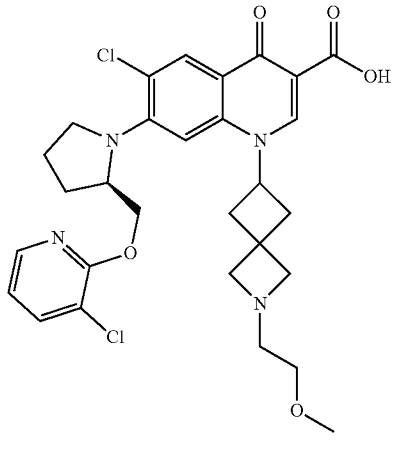 [SMILES: COCCN1CC2(CC(n3cc(C(=O)O)c(=O)c4cc(Cl)c(N5CCC[C@@H]5COc5ncccc5Cl)cc43)C2)C1] | (R)-6-chloro-7-(2-(((3-chloropyridin-2-yl)oxy)methyl) pyrrolidin-1-yl)-1-(2-(2-methoxy-ethyl)-2-azaspiro[3.3] heptan-6-yl)-4-oxo-1,4-dihydroquinoline-3-carboxylic acid | $^1$H NMR (400 MHz, DMSO-$d_6$): δ 15.23 (s, 1H), 8.53 (s, 1H), 8.11 (s, 1H), 7.91 (d, J = 3.6 Hz, 1H), 7.77 (d, J = 6.4 Hz, 1H), 6.99 (brs, 1H), 6.93-6.89 (m, 1H), 4.97 (brs, 2H), 4.39 (s, 2H), 3.88-3.82 (m, 2H), 3.42-3.30 (m, 4H), 3.26 (s, 3H), 2.88-2.78 (m, 3H), 2.74-2.52 (m, 4H), 2.37-2.31 (m, 1H), 2.14-1.87 (m, 4H); MS (ESI): m/z 587.3 $[M + H]^+$. | +++ |

-continued

| EX # | Structure | IUPAC name | Analytical data | Potency Lin28a-dep Z11 $IC_{50}$ (μM) |
|---|---|---|---|---|
| 483. | 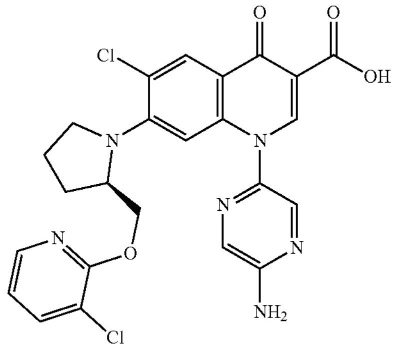 [SMILES: Nc1cnc(-n2cc(C(=O)O)c(=O)c3cc(Cl)c(N4CCC[C@@H]4COc4ncccc4Cl)cc32)cn1] | 1-(5-aminopyrazin-2-yl)-6-chloro-7-[(2R)-2-{[(3-chloropyridin-2-yl)oxy]methyl}pyrrolidin-1-yl]-4-oxo-1,4-dihydroquinoline-3-carboxylic acid | $^1$H NMR (400 MHz, DMSO-$d_6$): δ 8.72 (s, 1H), 8.25 (s, 1H), 8.14 (s, 1H), 7.86 (d, J = 4.8 Hz, 1H), 7.84 (s, 1H), 7.76 (d, J = 7.6 Hz, 1H), 7.12 (bs, 2H), 6.92-6.88 (m, 1H), 6.56 (s, 1H), 4.77 (bs, 1H), 4.35-4.28 (m, 2H), 3.60-3.50 (m, 1H), 3.23-3.18 (m, 1H), 2.30-2.20 (m, 1H), 2.04-1.85 (m, 2H), 1.82-1.77 (m, 1H) (—COOH proton was not observed); MS (ESI): m/z 527.2 $[M + H]^+$ | ++++ |
| 484. | 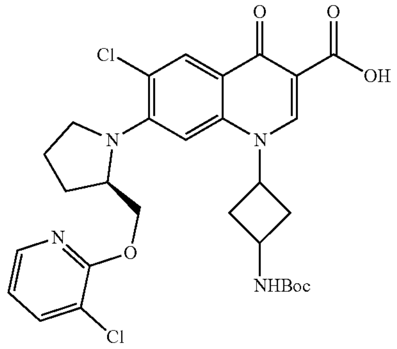 [SMILES: CC(C)(C)OC(=O)NC1CC(n2cc(C(=O)O)c(=O)c3cc(Cl)c(N4CCC[C@@H]4COc4ncccc4Cl)cc32)C1] | (R)-1-(3-((tert-butoxycarbonyl)amino)cyclobutyl)-6-chloro-7-(2-(((3-chloropyridin-2-yl)oxy)methyl)pyrrolidin-1-yl)-4-oxo-1,4-dihydroquinoline-3-carboxylic acid | $^1$H NMR (400 MHz, DMSO-$d_6$): δ 15.24 (s, 1H), 8.62 (s, 0.5H), 8.58 (s, 0.5H), 8.11 (d, J = 2.4 Hz, 1H), 7.92-7.88 (m, 1H), 7.78-7.73 (m, 1H), 7.60 (d, J = 6.8 Hz, 0.5H), 7.15 (d, J = 6.8 Hz, 0.5H), 7.06 (s, 0.5H), 6.95 (s, 0.5H), 6.92-6.86 (m, 1H), 5.26-5.18 (m, 0.5H), 5.04-4.96 (m, 1H), 4.82-4.73 (m, 0.5H), 4.46-4.36 (m, 2H), 4.04-3.93 (m, 1H), 3.90-3.80 (m, 1H), 3.44-3.38 (m, 1H), 3.00-2.90 (m, 1H), 2.80-2.68 (m, 1H), 2.60-2.56 (m, 1H), 2.38-2.26 (m, 2H), 2.14-2.00 (m, 2H), 1.95-1.86 (m, 1H), 1.43 (s, 4.5H), 1.39 (s, 4.5H); MS (ESI): m/z 603.3 $[M + H]^+$ | ++++ |
| 485. | 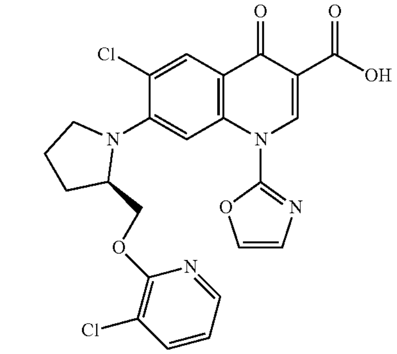 [SMILES: O=C(O)c1cn(-c2ncco2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-1-(oxazol-2-yl)-4-oxo-1,4-dihydroquinoline-3-carboxylic acid | $^1$H NMR (400 MHz, DMSO-$d_6$): δ 9.47 (s, 1H), 8.29 (s, 1H), 7.89 (bs, 1H), 7.86-7.72 (m, 2H), 7.46 (s, 1H), 6.96-6.88 (m, 1H), 5.73 (s, 1H), 4.64 (bs, 1H), 4.24 (s, 2H), 3.52-3.42 (m, 1H), 3.12-3.04 (m, 1H), 2.26-2.18 (m, 1H), 2.00-1.85 (m, 2H), 1.84-1.73 (m, 1H) (—COOH proton was not observed); MS (ESI): m/z 501.2 $[M + H]^+$ | ++++ |
| 486. | 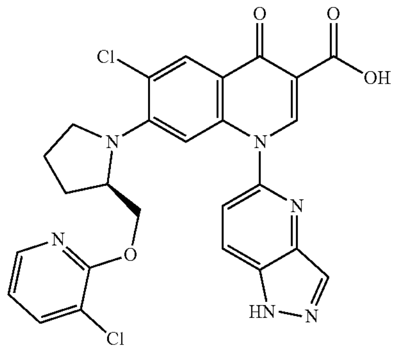 [SMILES: O=C(O)c1cn(-c2ccc3[nH]ncc3n2)c2cc(N3CCC[C@@H]3COc3ncccc3Cl)c(Cl)cc2c1=O] | 6-chloro-7-[(2R)-2-{[(3-chloropyridin-2-yl)oxy]methyl}pyrrolidin-1-yl]-4-oxo-1-{1H-pyrazolo[4,3-b]pyridin-5-yl}-1,4-dihydroquinoline-3-carboxylic acid | $^1$H-NMR (400 MHz, DMSO-$d_6$): δ 15.0 (bs, 1H), 13.8 (bs, 1H), 8.84 (s, 1H), 8.41 (bs, 1H), 8.30 (d, J = 8.4 Hz, 1H), 8.18 (s, 1H), 7.84 (dd, J = 4.8, 1.6 Hz, 1H), 7.78-7.71 (m, 2H), 6.93-6.90 (m, 1H), 6.54 (s, 1H), 4.61 (bs, 1H), 4.30-4.23 (m, 2H), 3.50-3.37 (m, 1H), 3.16 (t, J = 7.6 Hz, 1H), 2.20-2.15 (m, 1H), 1.90-1.83 (m, 2H), 1.79-1.71 (m, 1H); MS (ESI): m/z 551.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 487. | 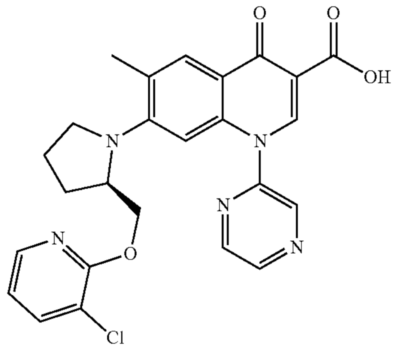 [SMILES: Cc1cc2c(=O)c(C(=O)O)cn(-c3cnccn3)c2cc1N1CCC[C@@H]1COc1ncccc1Cl] | (R)-7-(2-(((3-chloropyridin-2-yl)oxy)methyl) pyrrolidin-1-yl)-6-methyl-4-oxo-1-(pyrazin-2-yl)-1,4-dihydroquinoline-3-carboxylic acid | $^1$H NMR (400 MHz, DMSO-$d_6$): δ 15.36 (s, 1H), 9.10 (d, J = 1.2 Hz, 1H), 8.93 (d, J = 2.8 Hz, 1H), 8.88 (s, 1H), 8.76 (dd, J = 2.3, 1.2 Hz, 1H), 8.03 (s, 1H), 7.87 (dd, J = 4.8, 1.6 Hz, 1H), 7.78 (dd, J = 7.6, 1.6 Hz, 1H), 6.92 (dd, J = 8.0, 1.2 Hz, 1H), 6.44 (s, 1H), 4.38-4.30 (m, 1H), 4.26 (dd, J = 11.2, 3.6 Hz, 1H), 4.14 (dd, J = 11.2, 4.8 Hz, 1H), 3.56-3.48 (m, 1H), 3.15 (d, J = 8.0 Hz, 1H), 2.38 (s, 3H), 2.24-2.18 (m, 1H), 2.00-1.85 (m, 2H), 1.82-1.74 (m, 1H); MS (ESI): m/z 492.3 $[M + H]^+$ | ++++ |
| 488. | 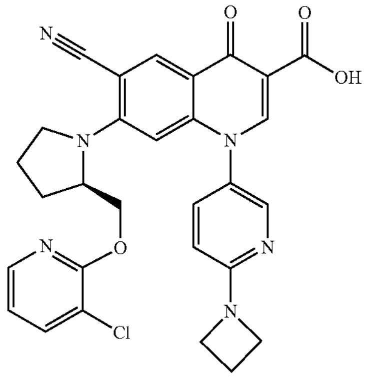 [SMILES: N#Cc1cc2c(=O)c(C(=O)O)cn(-c3ccc(N4CCC4)nc3)c2cc1N1CCC[C@@H]1COc1ncccc1Cl] | 1-[6-(azetidin-1-yl)pyridin-3-yl]-7-[(2R)-2-{[(3-chloro pyridin-2-yl)oxy)methyl} pyrrolidin-1-yl]-6-cyano-4-oxo-1,4-dihydroquinoline-3-carboxylic acid | 1H NMR (400 MHz, DMSO-d6): δ 14.75 (s, 1H), 8.51 (d, J = 3.2 Hz, 1H), 8.47 (s, 1H), 8.24 (dd, J = 18.9, 2.0 Hz, 1H), 7.99 (t, J = 4.8 Hz, 1H), 7.89 (t, J = 6.4 Hz, 1H), 7.67 (dd, J = 8.8, 2.0 Hz, 1H), 7.05-7.00 (m, 1H), 6.51-6.17 (m, 2H), 4.65-4.57 (m, 1H), 4.40-4.27 (m, 2H), 4.04-3.94 (m, 4H), 3.73-3.68 (m, 1H), 3.52-3.47 (m, 1H), 2.39-2.33 (m, 2H), 2.19-2.14 (m, 2H), 2.00-1.95 (m, 2H); MS (ESI): m/z 557.3 $[M + H]^+$ | ++++ |
| 489. | 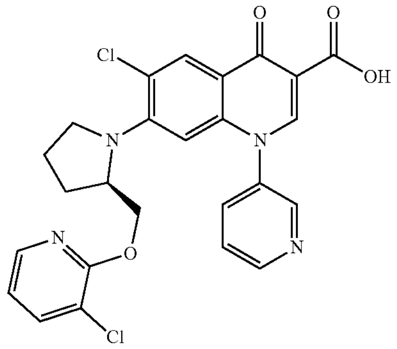 [SMILES: O=C(O)c1cn(-c2cccnc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyridin-3-yl)-1,4-dihydroquinoline-3-carboxylic acid | $^1$H NMR (400 MHz, DMSO-$d_6$): δ 8.80-8.76 (m, 2H), 8.47 (s, 1H), 8.12 (s, 1H), 8.04 (brs, 1H), 7.87-7.84 (m, 1H), 7.79 (dd, J = 1.6, 7.6 Hz, 1H), 7.71-7.54 (m, 1H), 6.92 (dd, J = 4.8, 7.6 Hz, 1H), 6.25 (s, 1H), 4.61 (brs, 1H), 4.30-4.20 (m, 2H), 3.45-3.32 (m, 1H), 3.08 (t, J = 8.0 Hz, 1H), 2.21 (d, J = 8.8 Hz, 1H), 1.95-1.85 (m, 2H), 1.79-1.73 (m, 1H), COOH proton was not observed; MS (ESI): m/z 511.2 $[M + H]^+$ | ++++ |
| 490. | 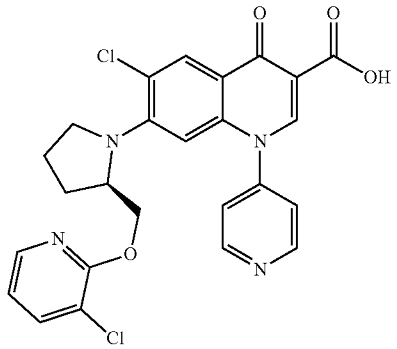 [SMILES: O=C(O)c1cn(-c2ccncc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyridin-4-yl)-1,4-dihydroquinoline-3-carboxylic acid | $^1$H NMR (400 MHz, DMSO-$d_6$): δ 14.95 (s, 1H), 8.84 (brs, 2H), 8.65 (s, 1H), 8.17 (s, 1H), 7.88 (dd, J = 4.8, 1.6 Hz, 1H), 7.81 (dd, J = 6.0, 1.6 Hz, 1H), 7.73 (dd, J = 4.4, 1.6 Hz, 2H), 6.94 (dd, J = 7.6, 4.8 Hz, 1H), 6.36 (s, 1H), 4.73-4.68 (m, 1H), 4.33-4.24 (m, 2H), 3.52-3.44 (m, 1H), 3.20-3.16 (m, 1H), 2.25-2.22 (m, 1H), 1.98-1.92 (m, 2H), 1.85-1.72 (m, 1H); MS (ESI): m/z 511.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 491. | 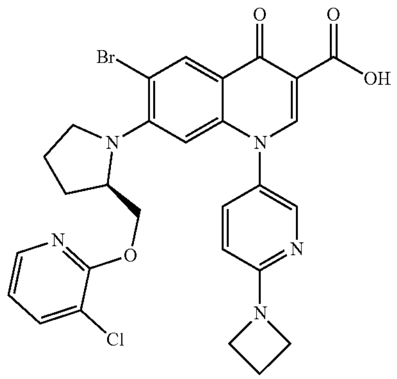 [SMILES: O=C(O)c1cn(-c2ccc(N3CCC3)nc2)c2cc(N3CCC[C@@H]3COc3ncccc3Cl)c(Br)cc2c1=O] | (R)-1-(6-(azetidin-1-yl)pyridin-3-yl)-6-bromo-7-(2-(((3-chloropyridin-2-yl)oxy)methyl) pyrrolidin-1-yl)-4-oxo-1,4-dihydroquinoline-3-carboxylic acid | 1H NMR (400 MHz, DMSO-d6) δ 15.04 (s, 1H), 8.52 (d, J = 9.6 Hz, 1H), 8.35 (s, 1H), 8.22 (s, 1H), 7.90 (t, J = 3.6 Hz, 1H), 7.81 (dd, J = 7.6, 1.2 Hz, 1H), 7.68-7.63 (m, 1H), 6.96-6.91 (m, 1H), 6.52-6.25 (m, 2H), 4.72-4.61 (m, 1H), 4.36-4.26 (m, 1H), 4.22-4.18 (m, 1H), 4.05-4.00 (m, 4H), 3.62-3.57 (m, 1H), 3.18-3.14 (m, 1H), 2.42-2.34 (m, 2H), 2.27-2.25 (m, 1H), 1.98-1.77 (m, 3H); MS (ESI): m/z 610.2 $[M + H]^+$. | ++++ |
| 492. | 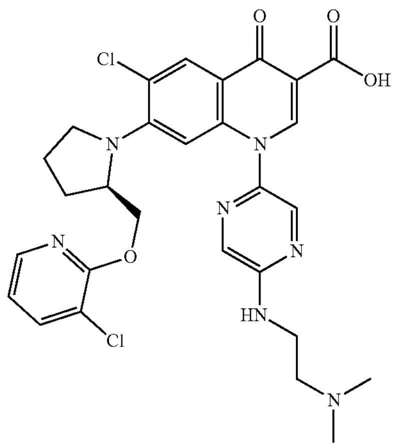 [SMILES: CN(C)CCNc1cnc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(5-((2-(dimethylamino) ethyl)amino) pyrazin-2-yl)-4-oxo-1,4-dihydroquinoline-3-carboxylic acid | $^1H$ NMR (400 MHz, DMSO-$d_6$): δ 14.99 (s, 1H), 8.70 (s, 1H), 8.30 (s, 1H), 8.15 (s, 1H), 7.95 (s, 1H), 7.87 (d, J = 3.2 Hz, 1H), 7.77 (d, J = 7.6 Hz, 1H), 7.69 (bs, 1H), 6.92-6.89 (m, 1H), 6.58 (s, 1H), 4.75 (bs, 1H), 4.33-4.29 (m, 2H), 3.61-3.53 (m, 1H), 3.52-3.44 (m, 2H), 3.26-3.18 (m, 1H), 2.66-2.58 (m, 2H), 2.32 (s, 6H), 2.30-2.20 (m, 1H), 2.04-1.90 (m, 2H), 1.89-1.79 (m, 1H), MS (ESI): m/z 598.3 $[M + H]^+$ | ++++ |
| 493. | 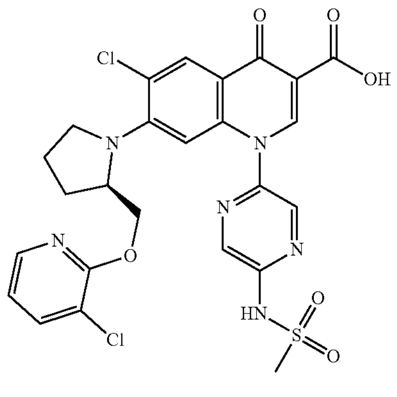 [SMILES: CS(=O)(=O)Nc1cnc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-(5-(methyl-sulfonamido) pyrazin-2-yl)-4-oxo-1,4-dihydroquinoline-3-carboxylic acid | $^1H$-NMR (400 MHz, DMSO-$d_6$): δ 8.65 (s, 1H), 8.19 (s, 1H), 8.14 (s, 1H), 7.87 (dd, J = 5.2, 1.6 Hz, 1H), 7.76 (dd, J = 7.6, 1.6 Hz, 2H), 7.63 (s, 1H), 6.90 (dd, J = 7.6, 4.8 Hz, 1H), 6.64 (s, 1H), 4.77 (bs, 1H), 4.35-4.28 (m, 2H), 3.59-3.50 (m, 1H), 3.19 (t, J = 8.0 Hz, 1H), 2.86 (s, 3H), 2.30-2.20 (m, 1H), 2.04-1.89 (m, 2H), 1.86-1.75 (m, 1H) (—COOH proton was not observed); MS (ESI): m/z 605.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 494. | 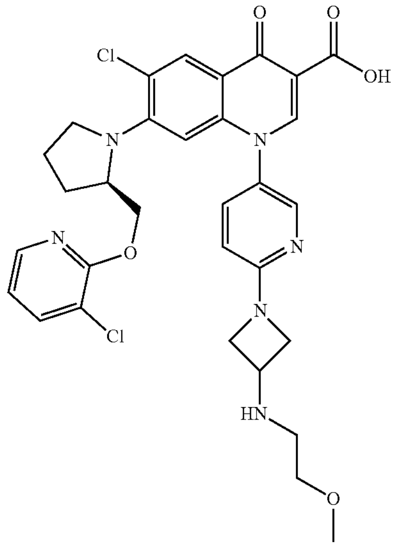 [SMILES: COCCNC1CN(c2ccc(-n3cc(C(=O)O)c(=O)c4cc(Cl)c(N5CCC[C@@H]5COc5ncccc5Cl)cc43)cn2)C1] | (R)-6-chloro-7-(2-(((3-chloropyridin-2-yl)oxy)methyl) pyrrolidin-1-yl)-1-(6-(3-((2-methoxyethyl) amino)azetidin-1-yl)pyridin-3-yl)-4-oxo-1,4-dihydroquinoline-3-carboxylic acid | $^{1}$H NMR (400 MHz, DMSO-$d_6$) δ 15.05 (bs, 1H), 8.49 (d, J = 9.6 Hz, 1H), 8.23 (d, J = 2.4 Hz, 1H), 8.15 (s, 1H), 7.91-7.89 (m, 1H), 7.81 (dd, J = 7.6, 1.6 Hz, 1H), 7.69-7.63 (m, 1H), 6.96-6.92 (m, 1H), 6.55-6.22 (m, 2H), 4.65-4.53 (m, 1H), 4.34-4.29 (m, 1H), 4.26-4.17 (m, 3H), 3.79-3.75 (m, 3H), 3.55-3.53 (m, 1H), 3.50-3.48 (m, 2H), 3.33 (s, 3H), 3.09-3.07 (m, 2H), 2.75-2.73 (m, 2H), 2.26-2.24 (m, 1H), 2.01-1.92 (m, 2H), 1.83-1.78 (m, 1H); MS (ESI): m/z 639.3 $[M + H]^+$. | ++++ |
| 495. | 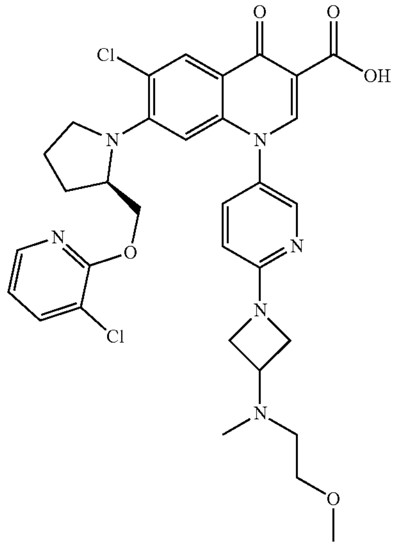 [SMILES: COCCN(C)C1CN(c2ccc(-n3cc(C(=O)O)c(=O)c4cc(Cl)c(N5CCC[C@@H]5COc5ncccc5Cl)cc43)cn2)C1] | (R)-6-chloro-7-(2-(((3-chloropyridin-2-yl)oxy)methyl) pyrrolidin-1-yl)-1-(6-(3-((2-methoxyethyl) (methyl)amino) azetidin-1-yl) pyridin-3-yl)-4-oxo-1,4-dihydroquinoline-3-carboxylic acid | $^{1}$H-NMR (400 MHz, DMSO-$d_6$): δ 15.08 (s, 1H), 8.50 (d, J = 9.6 Hz, 1H), 8.23 (d, J = 1.6 Hz, 1H), 8.14 (s, 1H), 7.90 (t, J = 4.8 Hz, 1H), 7.81 (d, J = 7.6 Hz, 1H), 7.70-7.65 (m, 1H), 6.97-6.92 (m, 1H), 6.55 (d, J = 8.8 Hz, 0.5H), 6.40 (d, J = 6.0 Hz, 1H), 6.30 (d, J = 8.8 Hz, 0.5H), 4.76-4.60 (m, 1H), 4.40-4.30 (m, 1H), 4.29-4.18 (m, 1H), 4.10-4.04 (m, 2H), 3.84-3.75 (m, 2H), 3.57-3.48 (m, 2H), 3.49-3.42 (m, 2H), 3.26 (s, 3H), 3.24-3.18 (m, 1H), 2.54-2.49 (m, 2H), 2.25-2.20 (m, 4H), 1.98-1.78 (m, 3H); LC-MS (ESI): m/z 653.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 496. | 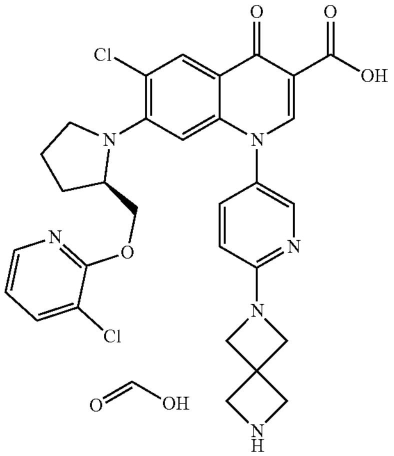 | (R)-1-(6-(2,6-diazaspiro[3.3]heptan-2-yl)pyridin-3-yl)-6-chloro-7-(2-(((3-chloropyridin-2-yl)oxy)methyl)pyrrolidin-1-yl)-4-oxo-1,4-dihydroquinoline-3-carboxylic acid | $^1$H NMR (400 MHz, DMSO-$d_6$) δ 8.49 (d, J = 9.6 Hz, 1H), 8.38 (bs, 1H), 8.23 (bs, 1H), 8.15 (s, 1H), 7.91-7.89 (m, 1H), 7.81 (t, J = 7.6 Hz, 1H), 7.70-7.63 (m, 1H), 6.99-6.92 (m, 1H), 6.66-6.52 (m, 1.5H), 6.40-6.28 (m, 1.5H), 4.75-4.58 (m, 2H), 4.40-4.29 (m, 2H), 4.26-4.07 (m, 4H), 3.82-3.75 (m, 2H), 3.55-3.53 (m, 2H), 3.30-3.20 (m, 1H), 2.30-2.20 (m, 1H), 2.02-1.75 (m, 3H); MS (ESI): m/z 607.3 $[M + H]^+$. | ++++ |
| 497. | 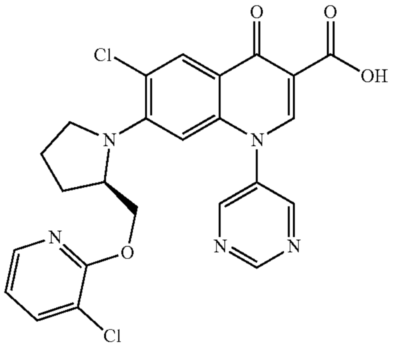 [SMILES: O=C(O)c1cn(-c2cncnc2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-4-oxo-1,4-dihydroquinoline-3-carboxylic acid | $^1$H NMR (400 MHz, DMSO-$d_6$): δ 14.95 (s, 1H), 9.43 (s, 1H), 9.15 (s, 2H), 8.86 (s, 1H), 8.18 (s, 1H), 7.90 (dd, J = 1.6, 4.8 Hz, 1H), 7.80 (dd, J = 1.6, 7.6 Hz, 1H), 6.94 (dd, J = 5.2, 8.0 Hz, 1H), 6.27 (s, 1H), 4.75 (brs, 1H), 4.30-4.22 (m, 2H), 3.51 (q, J = 9.2 Hz, 1H), 3.20 (t, J = 8.0 Hz, 1H), 2.26-2.18 (m, 1H), 1.98-1.88 (m, 2H), 1.82-1.72 (m, 1H); MS (ESI): m/z 512.2 $[M + H]^+$ | ++++ |
| 498. | 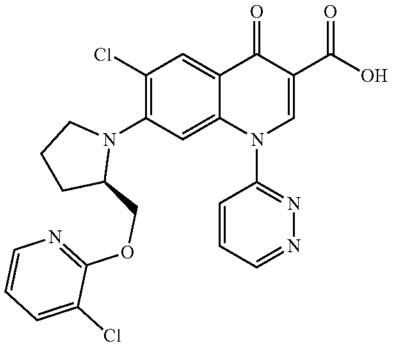 [SMILES: O=C(O)c1cn(-c2cccnn2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-4-oxo-1-(pyridazin-3-yl)-1,4-dihydroquinoline-3-carboxylic acid | $^1$H NMR (400 MHz, DMSO-$d_6$): δ 14.84 (s, 1H), 9.51 (dd, J = 4.8, 1.2 Hz, 1H), 8.94 (s, 1H), 8.21 (dd, J = 8.4, 1.2 Hz, 1H), 8.18 (s, 1H), 8.07 (dd, J = 8.4, 4.8 Hz, 1H), 7.86 (dd, J = 4.8, 1.6 Hz, 1H), 7.76 (dd, J = 7.6, 1.6 Hz, 1H), 6.91 (dd, J = 7.6, 4.8 Hz, 1H), 6.44 (s, 1H), 4.80-4.70 (m, 1H), 4.27 (t, J = 4.0 Hz, 2H), 3.56-3.48 (m, 1H), 3.25-3.16 (m, 1H), 2.28-2.18 (m, 1H), 2.00-1.86 (m, 2H), 1.84-1.72 (m, 1H); MS (ESI): m/z 512.3 $[M + H]^+$ | ++++ |
| 499. | 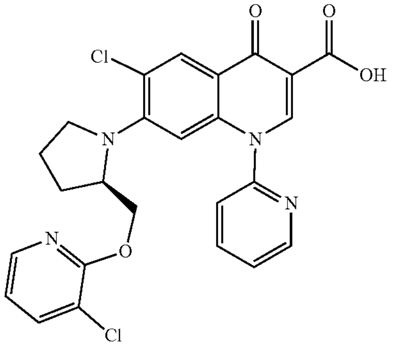 [SMILES: O=C(O)c1cn(-c2ccccn2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-4-oxo-1-(pyridin-2-yl)-1,4-dihydroquinoline-3-carboxylic acid | $^1$H NMR (400 MHz, DMSO-$d_6$): δ 14.94 (bs, 1H), 8.79 (s, 1H), 8.68 (d, J = 3.6 Hz, 1H), 8.17 (s, 1H), 8.13 (dd, J = 7.6, 1.6 Hz, 1H), 7.86 (dd, J = 4.8, 1.6 Hz, 1H), 7.82 (d, J = 8.0 Hz, 1H), 7.77 (dd, J = 7.6, 1.6 Hz, 1H), 7.69 (dd, J = 7.2, 4.8 Hz, 1H), 6.91 (dd, J = 7.6, 4.8 Hz, 1H), 6.54 (s, 1H), 4.67-4.65 (m, 1H), 4.28 (d, J = 4.0 Hz, 2H), 3.52-3.47 (m, 1H), 3.22-3.18 (m, 1H), 2.27-2.20 (m, 1H), 2.06-1.75 (m, 3H); MS (ESI): m/z 511.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 500. | 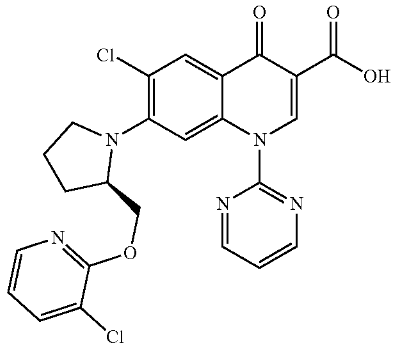 [SMILES: O=C(O)c1cn(-c2ncccn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyrimidin-2-yl)-1,4-dihydroquinoline-3-carboxylic acid | $^1$H-NMR (400 MHz, DMSO-$d_6$) δ 14.70 (bs, 1H), 9.20 (s, 1H), 9.05 (d, J = 4.8 Hz, 2H), 8.15 (s, 1H), 7.83 (dd, J = 5.2, 4.0 Hz, 1H), 7.78 (t, J = 5.2 Hz, 1H), 7.72 (dd, J = 7.6, 2.4 Hz, 1H), 7.49 (s, 1H), 6.89-6.84 (m, 1H), 4.76-4.70 (m, 1H), 4.45-4.40 (m, 1H), 4.34-4.29 (m, 1H), 3.77-3.67 (m, 1H), 3.46-3.42 (m, 1H), 2.40-2.20 (m, 1H), 2.10-1.90 (m, 2H), 1.88-1.79 (m, 1H); MS (ESI): m/z 512.2 $[M + H]^+$ | ++++ |
| 501. | 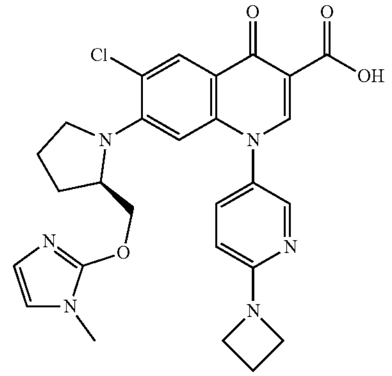 [SMILES: Cn1ccnc1OC[C@H]1CCCN1c1cc2c(cc1Cl)c(=O)c(C(=O)O)cn2-c1ccc(N2CCC2)nc1] | (R)-1-(6-(azetidin-1-yl)pyridin-3-yl)-6-chloro-7-(2-(((1-methyl-1H-imidazol-2-yl)oxy)methyl) pyrrolidin-1-yl)-4-oxo-1,4-dihydroquinoline-3-carboxylic acid | 1H NMR (400 MHz, DMSO-d6) δ 15.08 (bs, 1H), 8.52 (d, J = 9.6 Hz, 1H), 8.26 (bs, 1H), 8.19 (s, 1H), 7.71 (t, J = 8.8 Hz, 1H), 6.63 (d, J = 15.6 Hz, 1H), 6.53 (d, J = 8.8 Hz, 0.5H), 6.41 (d, J = 9.6 Hz, 1H), 6.34-7.28 (m, 1.5H), 4.78-4.52 (m, 1H), 4.30-4.18 (m, 1H), 4.10-4.00 (m, 5H), 3.60-3.40 (m, 2H), 3.23-3.16 (m, 1H), 3.12-3.08 (m, 3H), 2.42-2.34 (m, 2H), 2.27-2.25 (m, 1H), 2.00-1.91 (m, 1H), 1.90-1.84 (m, 2H); MS (ESI): m/z 535.3 $[M + H]^+$. | ++++ |
| 502. | 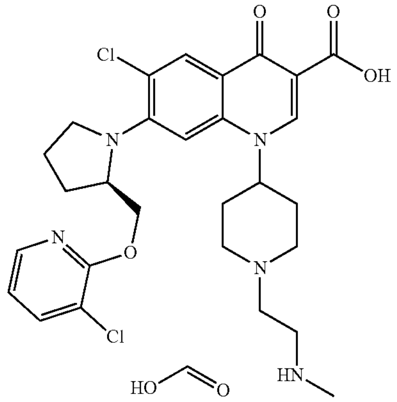 [SMILES: CNCCN1CCC(n2cc(C(=O)O)c(=O)c3cc(Cl)c(N4CCC[C@@H]4COc4ncccc4Cl)cc32)CC1 ; O=CO] | (R)-6-chloro-7-(2-(((3-chloropyridin-2-yl)oxy)methyl) pyrrolidin-1-yl)-1-(1-(2-(methyl-amino)ethyl) piperidin-4-yl)-4-oxo-1,4-dihydroquinoline-3-carboxylic acid | $^1$H NMR (400 MHz, DMSO-$d_6$) δ 8.65 (s, 1H), 8.36 (s, 1H), 8.15 (s, 1H), 7.91 (dd, J = 5.2, 2.0 Hz, 1H), 7.78 (dd, J = 7.6, 1.6 Hz, 1H), 7.18 (s, 1H), 6.93-6.88 (m, 1H), 5.00 (brs, 1H), 4.74-4.64 (m, 1H), 4.38 (d, J = 4.4 Hz, 2H), 3.92-3.82 (m, 1H), 3.44 (t, J = 8.0 Hz, 1H), 3.04 (d, J = 7.2 Hz, 1H), 2.94-2.84 (m, 3H), 2.58-2.53 (m, 1H), 2.47 (s, 3H), 2.40-2.20 (m, 3H), 2.14-1.85 (m, 8H) (—COOH proton was not observed). MS (ESI) m/z: 574.3 $[M + H]^+$. | +++ |
| 503. | 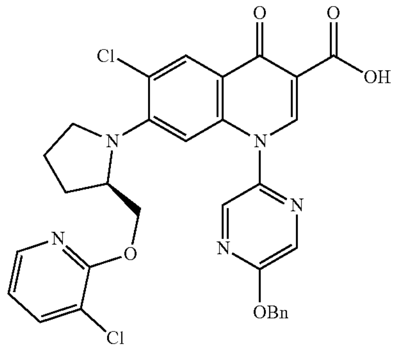 [SMILES: O=C(O)c1cn(-c2cnc(OCc3ccccc3)cn2)c2cc(N3CCC[C@@H]3COc3ncccc3Cl)c(Cl)cc2c1=O] | (R)-1-(5-(benzyloxy) pyrazin-2-yl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$) δ 14.91 (s, 1H), 8.86 (d, J = 1.2 Hz, 1H), 8.82 (d, J = 1.2 Hz, 1H), 8.39 (d, J = 1.2 Hz, 1H), 8.16 (s, 1H), 7.89 (dd, J = 4.8, 1.6 Hz, 1H), 7.78 (dd, J = 8.0, 2.0 Hz, 1H), 7.53 (d, J = 6.8 Hz, 2H), 7.46-7.38-7 (m, 3H), 6.93-6.90 (m, 1H), 6.54 (d, J = 6.8 Hz, 1H), 5.50 (s, 2H), 4.71 (m, 1H), 4.28 (d, J = 4.4 Hz, 1H), 3.60-3.50 (m, 1H), 3.24-3.19 (m, 2H), 2.24-2.18-1.75 (m, 1H), 1.99-1.82 (m, 3H); MS (ESI) m/z: 618.2 $[M + H]^+$. | +++ |

-continued

| EX # | Structure | IUPAC name | Analytical data | Potency Lin28a-dep Z11 $IC_{50}$ (μM) |
|---|---|---|---|---|
| 504. | 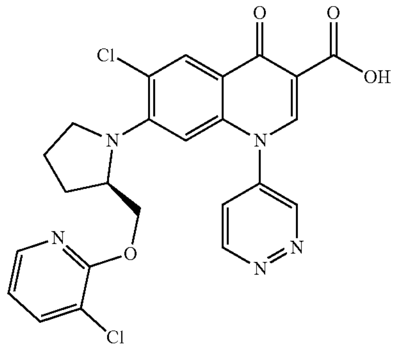 [SMILES: O=C(O)c1cn(-c2ccnnc2)c2cc(N3CCC[C@@H]3COc3ncccc3Cl)c(Cl)cc2c1=O] | 6-chloro-7-[(2R)-2-{[(3-chloropyridin-2-yl)oxy]methyl}pyrrolidin-1-yl]-4-oxo-1-(pyridazin-4-yl)-1,4-dihydroquinoline-3-carboxylic acid | 1H NMR (400 MHz, DMSO-d6) δ 9.90 (s, 1H), 9.46 (brs, 1H), 9.29 (s, 1H), 7.93 (dd J = 4.6, 1.6 Hz, 1H), 7.89 (s, 1H), 7.86-7.83 (m, 2H), 6.97 (dd, J = 7.6, 5.2 Hz, 1H), 5.76 (s, 1H), 4.67 (brs, 1H), 4.25-4.21 (m, 2H), 3.42-3.08 (m, 2H), 2.22-2.13 (m, 1H), 1.95-1.83 (m, 2H), 1.77-1.70 (m, 1H) (COOH proton not observed); MS (ESI) m/z: 512.3 $[M + H]^+$. | ++++ |
| 505. | 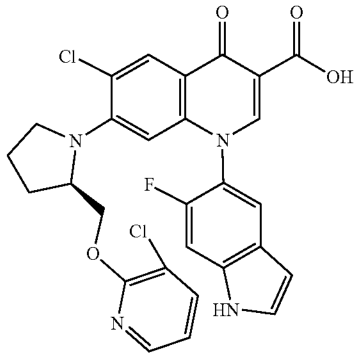 [SMILES: O=C(O)c1cn(-c2cc3cc[nH]c3cc2F)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-1-(6-fluoro-1H-indol-5-yl)-4-oxo-1,4-dihydroquinoline-3-carboxylic acid | 1H NMR (400 MHz, DMSO-d6): δ 14.96 (bs, 1H), 11.61 (s, 1H), 8.58 (bs, 1H), 8.15 (s, 1H), 7.91-7.78 (m, 3H), 7.60-7.50 (m, 1.5H), 7.35 (d, J = 10.8 Hz, 0.5H), 6.98-6.91 (m, 1H), 6.63 (s, 0.5H), 6.43 (s, 0.5H), 6.31 (d, J = 24.8 Hz, 1H), 4.64-4.52 (m, 1H), 4.30-4.14 (m, 2H), 3.46-3.38 (m, 1H), 3.10-3.00 (m, 1H), 2.24-2.16 (m, 1H), 1.96-1.80 (m, 2H), 1.79-1.68 (m, 1H); MS (ESI) m/z: 567.3 $[M + H]^+$ . . . | ++++ |
| 506. | 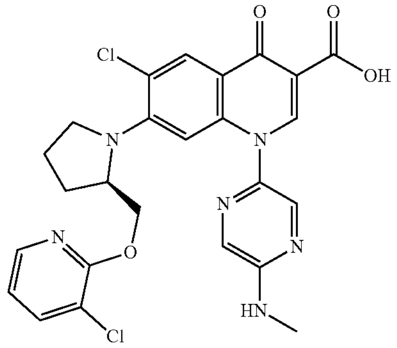 [SMILES: CNc1cnc(-n2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl)pyrrolidin-1-yl)-1-(5-(methylamino)pyrazin-2-yl)-4-oxo-1,4-dihydroquinoline-3-carboxylic acid | 1H NMR (400 MHz, DMSO-d6): δ 8.71 (s, 1H), 8.31 (s, 1H), 8.15 (s, 1H), 7.87 (dd, J = 5.2, 1.6 Hz, 1H), 7.77 (dd, J = 7.6, 1.6 Hz, 1H), 7.69 (d, J = 4.0 Hz, 1H), 6.94-6.89 (m, 1H), 6.56 (s, 1H), 4.72 (bs, 1H), 4.35-4.28 (m, 2H), 3.50-3.40 (m, 2H), 2.89 (d, J = 4.0 Hz, 3H), 2.30-2.20 (m, 1H), 2.04-1.85 (m, 2H), 1.82-1.77 (m, 1H) (—COOH, —NH protons were not observed); MS (ESI) m/z: 541.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 507. | 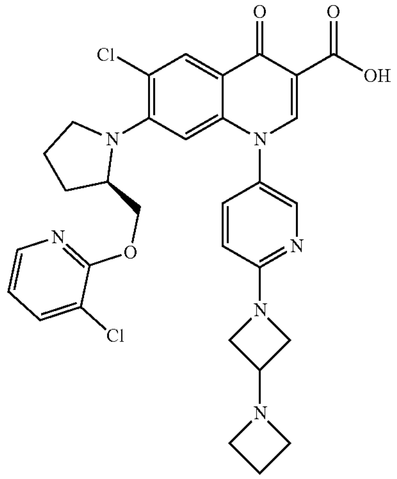 [SMILES: O=C(O)c1cn(-c2ccc(N3CC(N4CCC4)C3)nc2)c2cc(N3CCC[C@@H]3COc3ncccc3Cl)c(Cl)cc2c1=O] | (R)-1-(6-([1,3'-biazetidin]-1'-yl)pyridin-3-yl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.18 (s, 1H), 8.51 (d, J = 9.2 Hz, 1H), 8.22 (d, J = 2.0 Hz, 1H), 8.15 (s, 1H), 7.90 (d, J = 4.8 Hz, 1H), 7.81 (d, J = 7.6 Hz, 1H), 7.66 (t, J = 8.8 Hz, 1H), 6.97-6.92 (m, 1H), 6.54-6.27 (m, 2H), 4.68 (brs, 1H), 4.37-4.34 (m, 1H), 4.29-4.17 (m, 1H), 4.04-4.01 (m, 2H), 3.78-3.75 (m, 2H), 3.54-3.47 (m, 2H), 3.20 (t, J = 6.8 Hz, 4H), 2.58 (s, 1H), 2.25 (d, J = 6.4 Hz, 1H), 2.04-2.01 (m, 3H), 1.99-1.94 (m, 1H), 1.92-1.85 (m, 1H); MS (ESI): m/z 621.3: $[M + H]^+$ | ++++ |
| 508. | 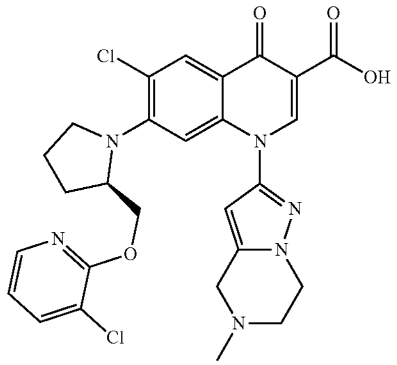 [SMILES: CN1CCn2nc(-n3cc(C(=O)O)c(=O)c4cc(Cl)c(N5CCC[C@@H]5COc5ncccc5Cl)cc43)cc2C1] | (R)-6-chloro-7-(2-(((3-chloropyridin-2-yl)oxy)methyl) pyrrolidin-1-yl)-1-(5-methyl-4,5,6,7-tetrahydropyrazolo [1,5-a]pyrazin-2-yl)-4-oxo-1,4-dihydroquinoline-3-carboxylic acid | $^1$H NMR (400 MHz, DMSO-$d_6$): δ 14.87 (s, 1H), 8.60 (s, 1H), 8.13 (s, 1H), 7.87 (dd, J = 4.8, 1.6 Hz, 1H), 7.77 (dd, J = 7.6, 1.6 Hz, 1H), 6.98 (s, 1H), 6.90 (dd, J = 8.0, 5.2 Hz, 1H), 6.45 (s, 1H), 4.75-4.69 (m, 1H), 4.38-4.28 (m, 2H), 4.20-4.13 (m, 2H), 3.70-3.60 (m, 3H), 3.35-3.26 (m, 1H), 2.96-2.88 (m, 2H), 2.43 (s, 3H), 2.34-2.25 (m, 1H), 2.10-1.90 (m, 2H), 1.88-1.70 (m, 1H); MS (ESI): m/z 569.3: $[M + H]^+$ | ++++ |
| 509. | 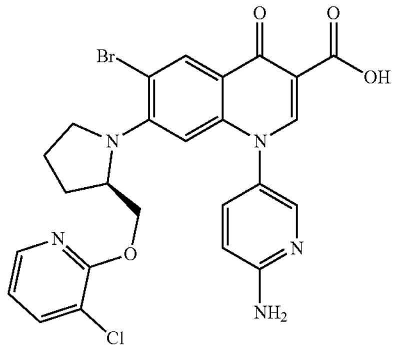 [SMILES: Nc1ccc(-n2cc(C(=O)O)c(=O)c3cc(Br)c(N4CCC[C@@H]4COc4ncccc4Cl)cc32)cn1] | 1-(6-aminopyridin-3-yl)-6-bromo-7-[(2R)-2-{[(3-chloropyridin-2-yl)oxy]methyl} pyrrolidin-1-yl]-4-oxo-1,4-dihydroquinoline-3-carboxylic acid | 1H NMR (400 MHz, DMSO-d6) δ 15.11 (s, 1H), 8.52 (d, J = 7.2 Hz, 1H), 8.33 (s, 1H), 8.07 (dd, J = 8.8, 2.4 Hz, 1H), 7.86 (d, J = 4.8 Hz, 1H), 7.75 (t, J = 6.8 Hz, 1H), 7.56-7.46 (m, 1H), 6.91 (dd, J = 7.6, 4.8 Hz, 1H), 6.62-6.48 (m, 4H), 4.87-4.76 (m, 1H), 4.34-4.24 (m, 2H), 3.58-3.47 (m, 1H), 3.17-3.10 (m, 1H), 2.33-2.24 (m, 1H), 1.99-1.78 (m, 3H); MS (ESI): m/z 570.2: $[M + H]^+$. | ++++ |

-continued

| EX # | Structure | IUPAC name | Analytical data | Potency Lin28a-dep Z11 $IC_{50}$ (μM) |
|---|---|---|---|---|
| 510. | 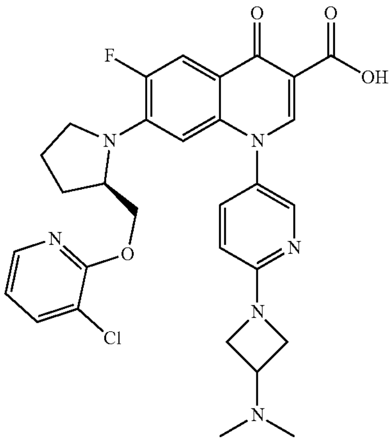 [SMILES: CN(C)C1CN(c2ccc(-n3cc(C(=O)O)c(=O)c4cc(F)c(N5CCC[C@@H]5COc5ncccc5Cl)cc43)cn2)C1] | (R)-7-(2-(((3-chloropyridin-2-yl)oxy)methyl) pyrrolidin-1-yl)-1-(6-(3-(dimethylamino) azetidin-1-yl) pyridin-3-yl)-6-fluoro-4-oxo-1,4-dihydroquinoline-3-carboxylic acid | $^{1}H$ NMR (400 MHz, DMSO-$d_6$) δ 15.37 (s, 1H), 8.48 (d, J = 2.4 Hz, 1H), 8.31 (s, 1H), 7.99-7.97 (m, 1H), 7.89-7.84 (m, 2H), 7.79 (dd, J = 8.8, 2.0 Hz, 1H), 7.01-6.98 (m, 1H), 6.63-6.44 (m, 1H), 6.09 (d, J = 7.6 Hz, 1H), 4.55-4.51 (m, 1H), 4.37-4.30 (m, 3H), 4.19-4.09 (m, 4H), 3.37-3.33 (m, 1H), 3.24-3.19 (m, 1H), 2.67-2.54 (m, 6H), 2.15-2.08 (m, 2H), 1.98-1.91 (m, 2H); MS (ESI): m/z 593.3: $[M + H]^+$ . . . | ++++ |
| 511. | 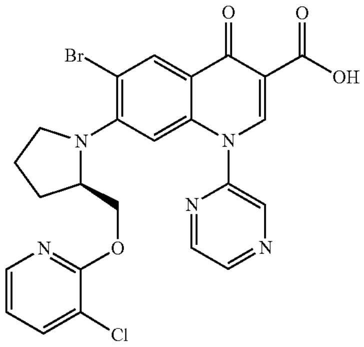 [SMILES: O=C(O)c1cn(-c2cnccn2)c2cc(N3CCC[C@@H]3COc3ncccc3Cl)c(Br)cc2c1=O] | (R)-6-bromo-7-(2-(((3-chloropyridin-2-yl)oxy)methyl) pyrrolidin-1-yl)-4-oxo-1-(pyrazin-2-yl)-1,4-dihydroquinoline-3-carboxylic acid | $^{1}H$ NMR (400 MHz, DMSO-$d_6$): δ 14.85 (s, 1H), 9.10 (s, 1H), 8.95-8.88 (m, 2H), 8.78 (dd, J = 2.4, 1.2 Hz, 2H), 8.35 (s, 1H), 7.85 (dd, J = 6.0, 2.0 Hz, 1H), 7.77 (dd, J = 7.6, 2.0 Hz, 1H), 6.90 (dd, J = 7.6, 4.8 Hz, 1H), 6.62 (s, 1H), 4.75 (bs, 1H), 4.32-4.22 (m, 2H), 3.52-3.56 (m, 1H), 3.24-3.16 (m, 1H), 2.26-2.20 (m, 1H), 2.01-1.84 (m, 2H), 1.81-1.72 (m, 1H); MS m/z: 556.1 $[M + H]^+$ | ++++ |
| 512. | 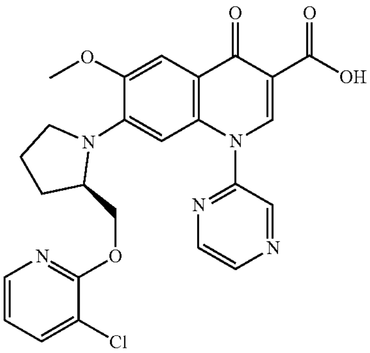 [SMILES: COc1cc2c(=O)c(C(=O)O)cn(-c3cnccn3)c2cc1N1CCC[C@@H]1COc1ncccc1Cl] | (R)-7-(2-(((3-chloropyridin-2-yl)oxy)methyl) pyrrolidin-1-yl)-6-methoxy-4-oxo-1-(pyrazin-2-yl)-1,4-dihydroquinoline-3-carboxylic acid | $^{1}H$ NMR (400 MHz, DMSO-$d_6$): δ 15.6 (s, 1H), 9.12 (s, 1H), 8.94 (d, J = 2.4 Hz, 1H), 8.84 (s, 1H), 8.80-8.79 (m, 1H), 7.94 (dd, J = 4.8, 1.6 Hz, 1H), 7.80 (dd, J = 8.0, 1.6 Hz, 1H), 7.57 (s, 1H), 6.95 (dd, J = 7.6, 4.8 Hz, 1H), 6.18 (s, 1H), 4.84 (m, 1H), 4.32-4.21 (m, 2H), 3.87 (s, 3H), 3.36-3.34 (m, 1H), 3.32-3.12 (m, 1H), 2.18-1.79 (m, 4H); MS m/z: 508.4 $[M + H]^+$. | + |
| 513. | 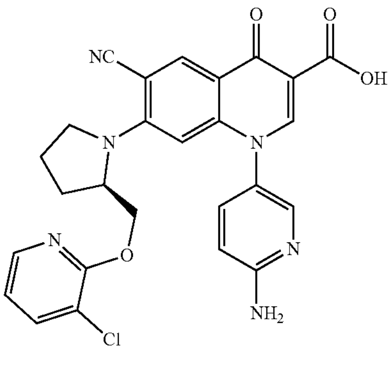 | (R)-1-(6-aminopyridin-3-yl)-7-(2-(((3-chloropyridin-2-yl)oxy)methyl) pyrrolidin-1-yl)-6-cyano-4-oxo-1,4-dihydroquinoline-3-carboxylic acid | $^{1}H$ NMR (400 MHz, DMSO-$d_6$): δ 8.48 (s, 1H), 8.42 (s, 1H), 8.09 (d, J = 2.0 Hz, 1H), 7.96 (dd, J = 4.8, 1.6 Hz, 1H), 7.82 (d, J = 7.2 Hz, 1H), 7.60-7.54 (m, 1H), 6.98-6.97 (m, 1H), 6.43-6.06 (m, 3H), 6.18 (s, 1H), 4.79-4.71 (m, 1H), 4.53-4.23 (m, 2H), 3.60-3.57 (m, 2H), 2.19-1.97 (m, 4H) (—COOH proton not observed); MS (ESI): m/z 593.3: $[M + H]^+$. | ++++ |

-continued

| EX # | Structure | IUPAC name | Analytical data | Potency Lin28a-dep Z11 $IC_{50}$ (μM) |
|---|---|---|---|---|
| 514. | 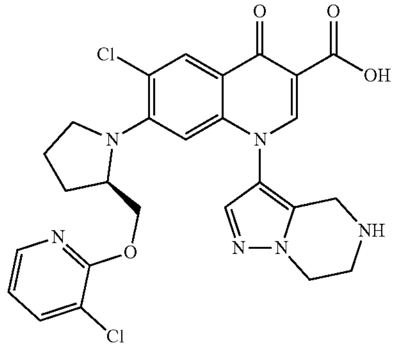 [SMILES: O=C(O)c1cn(-c2cnn3c2CNCC3)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(4,5,6,7-tetrahydropyrazolo [1,5-a]pyrazin-3-yl)-1,4-dihydroquinoline-3-carboxylic acid | $^1$H NMR (400 MHz, DMSO-$d_6$): δ 8.50 (s, 1H), 8.13 (s, 1H), 7.88 (s, 1H), 7.80 (s, 1H), 7.79 (dd, J = 4.8, 1.6 Hz, 1H), 6.92 (dd, J = 7.6, 1.6 Hz, 1H), 6.51 (s, 1H), 4.84-4.77 (m, 1H), 4.30 (d, J = 4.0 Hz, 2H), 4.10-4.03 (m, 2H), 3.80-3.62 (m, 2H), 3.60-3.50 (m, 1H), 3.30-3.20 (m, 1H), 3.19-3.06 (m, 2H), 2.30-2.20 (m, 1H), 2.08-1.90 (m, 2H), 1.88-1.70 (m, 1H) (—COOH and —NH protons were not observed); MS (ESI): m/z 555.3 [M + H]$^+$. | ++++ |
| 515. | 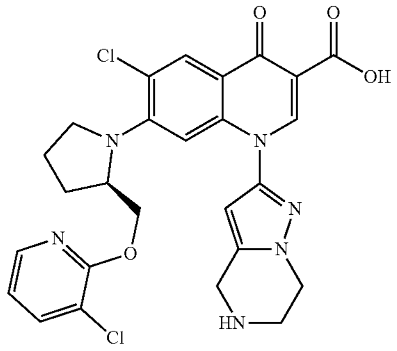 [SMILES: O=C(O)c1cn(-c2cc3n(n2)CCNC3)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(4,5,6,7-tetrahydropyrazolo [1,5-a]pyrazin-2-yl)-1,4-dihydroquinoline-3-carboxylic acid | $^1$H NMR (400 MHz, DMSO-$d_6$): δ 8.58 (s, 1H), 8.13 (s, 1H), 7.87 (dd, J = 4.8, 1.6 Hz, 1H), 7.77 (dd, J = 7.6, 1.6 Hz, 1H), 7.02 (s, 1H), 6.90 (dd, J = 8.0, 5.2 Hz, 1H), 6.41 (s, 1H), 4.80-4.70 (m, 1H), 4.38-4.28 (m, 2H), 4.08-4.01 (m, 2H), 3.93 (s, 2H), 3.70-3.60 (m, 1H), 3.35-3.26 (m, 1H), 3.17 (t, J = 5.2 Hz, 2H), 2.34-2.25 (m, 1H), 2.08-1.90 (m, 2H), 1.88-1.70 (m, 1H) (—COOH and —NH protons were not observed); MS (ESI): m/z 555.3 [M + H]$^+$. | ++++ |
| 516. | 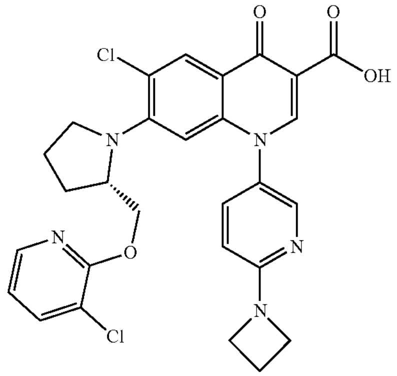 [SMILES: O=C(O)c1cn(-c2ccc(N3CCC3)nc2)c2cc(N3CCC[C@H]3COc3ncccc3Cl)c(Cl)cc2c1=O] | (S)-1-(6-(azetidin-1-yl)pyridin-3-yl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.10 (bs, 1H), 8.51 (s, 0.5H), 8.49 (s, 0.5H), 8.22 (s, 1H), 8.15 (s, 1H), 7.90 (t, J = 4.0 Hz, 1H), 7.82 (dd, J = 7.6, 1.6 Hz, 1H), 7.66 (t, J = 7.6 Hz, 1H), 6.97-6.92 (m, 1H), 6.51 (d, J = 8.8 Hz, 0.5H), 6.40 (d, J = 4.0 Hz, 1H), 6.27 (d, J = 8.8 Hz, 0.5H), 4.76-4.60 (m, 1H), 4.40-4.28 (m, 1H), 4.25-4.18 (m, 1H), 4.08-4.00 (m, 4H), 3.60-3.48 (m, 1H), 3.24-3.16 (m, 1H), 2.44-2.38 (m, 2H), 2.30-2.20 (m, 1H), 2.04-1.88 (m, 2H), 1.84-1.66 (m, 1H); MS (ESI): m/z 566.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 517. | 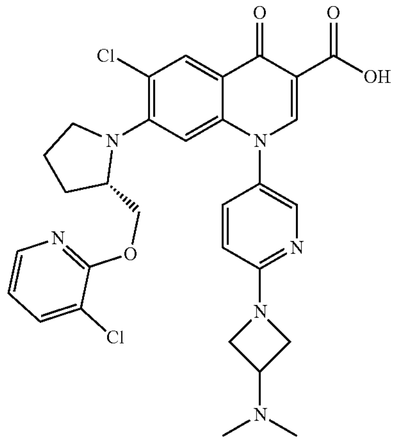 [SMILES: CN(C)C1CN(c2ccc(-n3cc(C(=O)O)c(=O)c4cc(Cl)c(N5CCC[C@H]5COc5ncccc5Cl)cc43)cn2)C1] | (S)-6-chloro-7-(2-(((3-chloropyridin-2-yl)oxy)methyl) pyrrolidin-1-yl)-1-(6-(3-(dimethylamino) azetidin-1-yl) pyridin-3-yl)-4-oxo-1,4-dihydroquinoline-3-carboxylic acid | 1H NMR (400 MHz, DMSO-d6) δ 15.12 (br s, 1H), 8.51 (d, J = 10.0 Hz, 1H), 8.23 (d, J = 2.4 Hz, 1H), 8.16 (s, 1H), 8.15 (s, 1H), 7.90 (t, J = 4.8 Hz, 1H), 7.83-7.80 (m, 1H), 7.70-7.65 (m, 1H), 6.97-6.92 (m, 1H), 6.56-6.29 (m, 2H), 4.78-4.61 (m, 1H), 4.30-4.20 (m, 2H), 4.07-4.03 (m, 2H), 3.82-3.78 (m, 2H), 3.55-3.50 (m, 1H), 3.40-3.35 (m, 1H), 3.24-3.17 (m, 2H), 2.34-2.26 (m, 1H), 2.14 (s, 6H), 1.98-1.77 (m, 3H); MS (ESI): m/z 609.3 $[M + H]^+$ . . . | ++++ |
| 518. | 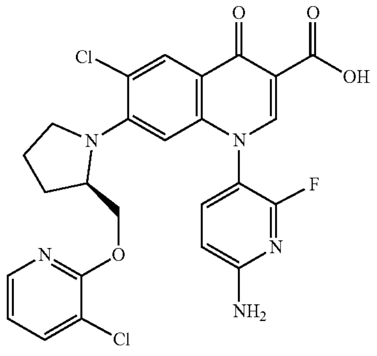 [SMILES: Nc1ccc(-n2cc(C(=O)O)c(=O)c3cc(Cl)c(N4CCC[C@@H]4COc4ncccc4Cl)cc32)c(F)n1] | (R)-1-(6-amino-2-fluoropyridin-3-yl)-6-chloro-7-(2-(((3-chloropyridin-2-yl)oxy)methyl) pyrrolidin-1-yl)-4-oxo-1,4-dihydroquinoline-3-carboxylic acid | 1H NMR (400 MHz, DMSO-d6): δ 14.96 (s, 1H), 8.69 (d, J = 12.0 Hz, 1H), 8.14 (s, 1H), 7.89 (ddd, J = 10.8, 5.2, 1.6 Hz, 1H), 7.77 (ddd, J = 14.4, 9.6, 1.6 Hz, 1H), 7.74-7.67 (m, 1H), 6.99 (bs, 2H), 6.91 (dd, J = 7.2, 2.0 Hz, 1H), 6.49 (d, J = 8.4 Hz, 0.5H), 6.43 (s, 0.5H), 6.38 (s, 0.5H), 6.36 (d, J = 8.4 Hz, 0.5H), 4.88-4.74 (m, 1H), 4.35-4.26 (m, 2H), 3.60-3.48 (m, 1H), 3.26-3.16 (m, 1H), 2.30-2.20 (m, 1H), 2.04-1.88 (m, 2H), 1.84-1.78 (m, 1H); MS (ESI): m/z 544.2 $[M + H]^+$. | ++++ |
| 519. | 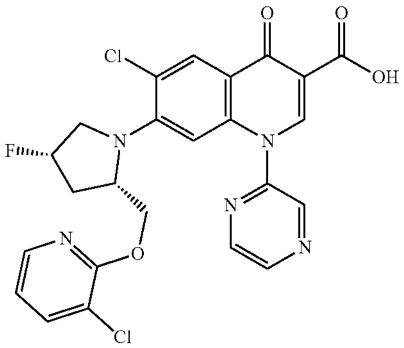 [SMILES: O=C(O)c1cn(-c2cnccn2)c2cc(N3C[C@@H](F)C[C@H]3COc3ncccc3Cl)c(Cl)cc2c1=O] | 6-chloro-7-((2S,4S)-2-(((3-chloropyridin-2-yl)oxy)methyl)-4-fluoropyrrolidin-1-yl)-4-oxo-1-(pyrazin-2-yl)-1,4-dihydroquinoline-3-carboxylic acid | $^1$H NMR (400 MHz, DMSO-$d_6$): δ 14.8 (bs, 1H), 9.13 (s, 1H), 8.95 (d, J = 3.2 Hz, 2H), 8.79 (d, J = 1.2 Hz, 2H), 8.21 (s, 1H), 7.86-7.85 (dd, J = 4.8, 1.6 Hz, 1H), 7.80-7.77 (dd, J = 4.0, 1.4 Hz, 1H), 6.94-6.91 (q, J = 5.2 Hz, 1H), 6.67 (s, 1H), 5.46-5.33 (d, J = 53.2 Hz, 1H), 4.85-4.83 (m, 1H), 4.43-4.39 (dd, J = 12.0, 3.8 Hz, 1H), 4.29-4.26 (dd, J = 11.8, 3.4 Hz, 1H), 3.91-3.75 (m, 1H), 2.42-2.40 (m, 1H), 2.24-2.20 (m, 1H); MS (ESI): m/z 530.3 $[M + H]^+$ . . . | ++++ |

-continued

| EX # | Structure | IUPAC name | Analytical data | Potency Lin28a-dep Z11 $IC_{50}$ (μM) |
|---|---|---|---|---|
| 520. | 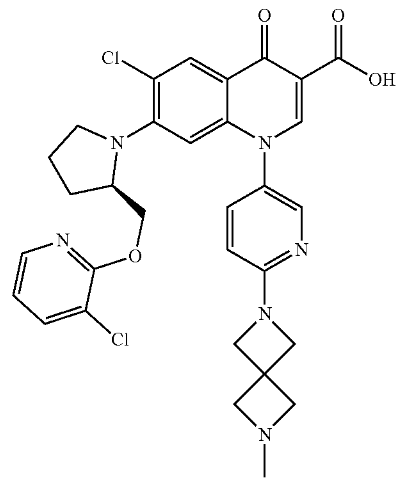 [SMILES: CN1CC2(C1)CN(c1ccc(-n3cc(C(=O)O)c(=O)c4cc(Cl)c(N5CCC[C@@H]5COc5ncccc5Cl)cc43)cn1)C2] | (R)-6-chloro-7-(2-(((3-chloropyridin-2-yl)oxy)methyl) pyrrolidin-1-yl)-1-(6-(6-methyl-2,6-diazaspiro[3.3] heptan-2-yl) pyridin-3-yl)-4-oxo-1,4-dihydroquinoline-3-carboxylic acid | $^{1}H$ NMR (400 MHz, DMSO-$d_6$) δ 8.48 (s, 1H), 8.14 (s, 2H), 7.86 (s, 1H), 7.78 (d, J = 6.4 Hz, 1H), 7.70-7.58 (m, 1H), 6.96-6.90 (m, 1H), 6.60-6.54 (m, 0.5H), 6.40-6.30 (m, 1.5H), 4.76-4.62 (m, 1H), 4.36-4.20 (m, 2H), 4.17-4.07 (m, 4H), 3.59 (bs, 3H), 3.53-3.49 (m, 1H), 3.45-3.42 (m, 1H), 3.23-3.12 (m, 1H), 2.37 (s, 3H), 2.32-2.24 (m, 1H), 2.02-1.88 (m, 2H), 1.84-1.76 (m, 1H) (—COOH ptoton was not observed); MS (ESI): m/z 621.3 $[M + H]^+$. | ++++ |
| 521. | 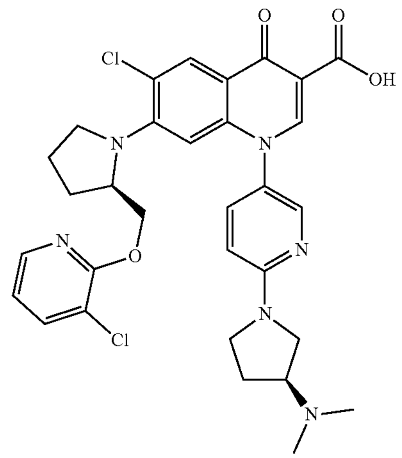 [SMILES: CN(C)[C@H]1CCN(c2ccc(-n3cc(C(=O)O)c(=O)c4cc(Cl)c(N5CCC[C@@H]5COc5ncccc5Cl)cc43)cn2)C1] | 6-chloro-7-((R)-2-(((3-chloropyridin-2-yl)oxy)methyl) pyrrolidin-1-yl)-1-(6-((S)-3-(dimethylamino) pyrrolidin-1-yl) pyridin-3-yl)-4-oxo-1,4-dihydroquinoline-3-carboxylic acid | $^{1}H$ NMR (400 MHz, DMSO-$d_6$): δ 15.21 (brs, 1H), 8.50 (d, J = 10.0 Hz, 1H), 8.24 (brs, 1H), 8.16 (d, J = 5.2 Hz, 1H), 7.90 (t, J = 5.2 Hz, 1H), 7.80 (d, J = 7.2 Hz, 1H), 7.68-7.65 (m, 1H), 6.97-6.91 (m, 1H), 6.66-6.39 (m, 2H), 4.70-4.61 (m, 1H), 4.38-4.17 (m, 2H), 3.73-3.16 (m, 6H), 2.83-2.97 (m, 1H), 2.35 (s, 6H), 2.19-1.78 (m, 6H); MS (ESI): m/z 623.3 $[M + H]^+$ . . . | ++++ |
| 522. | 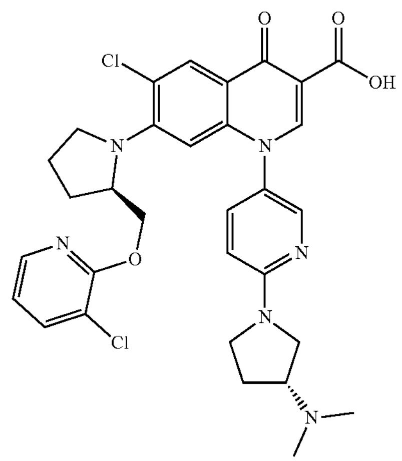 [SMILES: CN(C)[C@@H]1CCN(c2ccc(-n3cc(C(=O)O)c(=O)c4cc(Cl)c(N5CCC[C@@H]5COc5ncccc5Cl)cc43)cn2)C1] | 6-chloro-7-((R)-2-(((3-chloropyridin-2-yl)oxy)methyl) pyrrolidin-1-yl)-1-(6-((R)-3-(dimethylamino) pyrrolidin-1-yl) pyridin-3-yl)-4-oxo-1,4-dihydroquinoline-3-carboxylic acid | $^{1}H$ NMR (400 MHz, DMSO-$d_6$): δ 15.14 (brs, 1H), 8.50 (d, J = 10.0 Hz, 1H), 8.25 (dd, J = 8.8, 2.4 Hz, 1H), 8.16 (s, 1H), 7.90 (t, J = 5.2 Hz, 1H), 7.81 (d, J = 7.2 Hz, 1H), 7.68 (t, J = 6.0 Hz, 1H), 6.97-6.91 (m, 1H), 6.66 (t, J = 8.8 Hz, 0.5H), 6.46-6.41 (m, 1.5H), 4.70-4.61 (m, 1H), 4.38-4.27 (m, 1H), 4.24-4.17 (m, 1H), 3.76-3.50 (m, 3H), 3.44-3.36 (m, 2H), 3.26-3.18 (m, 2H), 2.40-2.20 (m, 8H), 2.03-1.85 (m, 3H), 1.84-1.74 (m, 1H); MS (ESI): m/z 623.4 $[M + H]^+$. | ++++ |

-continued

| EX # | Structure | IUPAC name | Analytical data | Potency Lin28a-dep Z11 $IC_{50}$ (μM) |
|---|---|---|---|---|
| 523. | 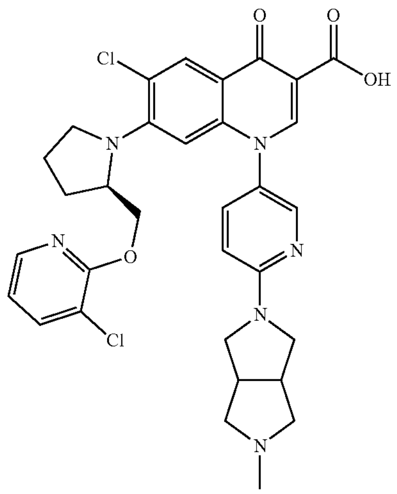 [SMILES: CN1CC2CN(c3ccc(-n4cc(C(=O)O)c(=O)c5cc(Cl)c(N6CCC[C@@H]6COc6ncccc6Cl)cc54)cn3)CC2C1] | 6-chloro-7-((R)-2-(((3-chloropyridin-2-yl)oxy)methyl) pyrrolidin-1-yl)-1-(6-(5-methylhexahydro-pyrrolo[3,4-c] pyrrol-2(1H)-yl) pyridin-3-yl)-4-oxo-1,4-dihydroquinoline-3-carboxylic acid | $^1$H NMR (400 MHz, DMSO-$d_6$): δ 8.52-8.47 (m, 1H), 8.27-8.22 (m, 1H), 8.16 (s, 1H), 7.93-7.88 (m, 1H), 7.81 (d, J = 7.6 Hz, 1H), 7.70-7.66 (m, 1H), 6.99-6.92 (m, 1H), 6.66 (d, J = 8.8 Hz, 0.5H), 6.45 (d, J = 4.0 Hz, 1H), 6.41 (d, J = 9.2 Hz, 0.5H), 4.72-4.60 (m, 1H), 4.41-4.30 (m, 1H), 4.23-4.16 (m, 1H), 3.70-3.62 (m, 2H), 3.57-3.45 (m, 1H), 3.45-3.35 (m, 1H), 3.35-3.25 (m, 3H), 3.25-3.15 (m, 1H), 3.07-2.90 (m, 2H), 2.60-2.50 (m, 2H), 2.31-2.20 (m, 4H), 2.04-1.91 (m, 1H), 1.91-1.82 (m, 1H), 1.82-1.77 (m, 1H) (—COOH proton was not observed). MS (ESI): m/z 635.3 [M + H]$^+$. | ++++ |
| 524. | 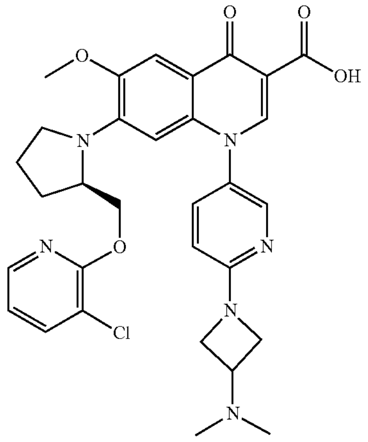 [SMILES: COc1cc2c(=O)c(C(=O)O)cn(-c3ccc(N4CC(N(C)C)C4)nc3)c2cc1N1CCC[C@@H]1COc1ncccc1Cl] | (R)-7-(2-(((3-chloropyridin-2-yl)oxy)methyl) pyrrolidin-1-yl)-1-(6-(3-(dimethylamino) azetidin-1-yl) pyridin-3-yl)-6-methoxy-4-oxo-1,4-dihydroquinoline-3-carboxylic acid | $^1$H NMR (400 MHz, DMSO-$d_6$): δ 15.86 (s, 1H), 8.42 (d, J = 5.6 Hz, 1H), 8.23 (bs, 1H), 7.96 (d, J = 4.8 Hz, 1H), 7.82 (dd, J = 7.6, 1.6 Hz, 1H), 7.75-7.66 (m, 1H), 7.56 (s, 1H), 7.00-6.94 (m, 1H), 6.54 (d, J = 8.8 Hz, 0.5H), 6.38 (d, J = 8.8 Hz, 0.5H), 6.09 (s, 1H), 4.90-4.70 (m, 1H), 4.40-4.30 (m, 1H), 4.21-4.06 (m, 3H), 3.87 (s, 3H), 3.86-3.78 (m, 2H), 3.40-3.32 (m, 1H), 3.28-3.20 (m, 1H), 3.16-3.08 (m, 1H), 2.14 (s, 7H), 2.06-1.80 (m, 3H); MS (ESI): m/z 605.4 [M + H]$^+$. | +++ |
| 525. | 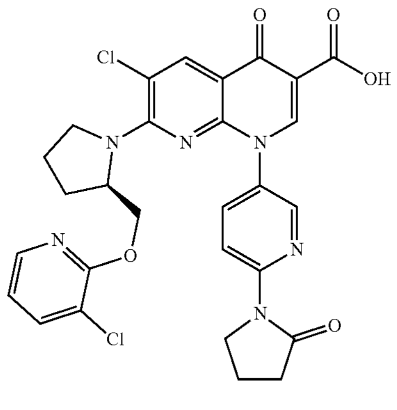 [SMILES: O=C(O)c1cn(-c2ccc(N3CCCC3=O)nc2)c2nc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(6-(2-oxopyrrolidin-1-yl)pyridin-3-yl)-1,4-dihydro-1,8-naphthyridine-3-carboxylic acid | $^1$H NMR (400 MHz, DMSO-$d_6$) δ 14.91 (s, 1H), 8.72 (s, 1H), 8.54 (d, J = 2.4 Hz, 1H), 8.36 (s, 1H), 8.25 (d, J = 9.2 Hz, 1H), 8.02 (dd, J = 9.2, 2.8 Hz, 1H), 7.95 (dd, J = 4.8, 1.6 Hz, 1H), 7.88 (dd, J = 8.0, 1.6 Hz, 1H), 7.02-6.97 (m, 1H), 4.37 (bs, 1H), 4.18-4.14 (m 1H), 4.00-3.76 (m, 5H), 2.59 (t, J = 8.0 Hz, 2H), 2.10-2.00 (m, 4H), 1.92-1.80 (m, 2H); MS (ESI): m/z 595.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 526. | 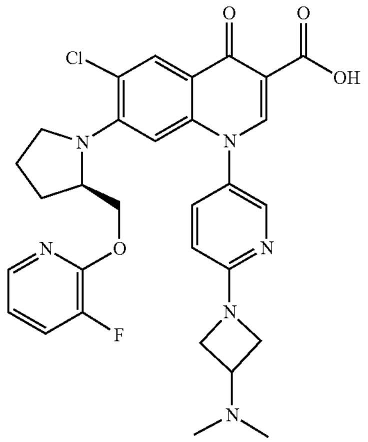 | (R)-6-chloro-1-(6-(3-(dimethylamino) azetidin-1-yl) pyridin-3-yl)-7-(2-(((3-fluoropyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.08 (bs, 1H), 8.54-8.51 (m, 1H), 8.26-2.0 (m, 1H), 8.16 (s, 1H), 7.80 (t, J = 5.2 Hz, 1H), 7.68 (td, J = 9.2, 2.4 Hz, 1H), 7.63-7.56 (m, 1H), 7.00-6.92 (m, 1H), 6.56 (d, J = 8.8 Hz, 0.5H), 6.39 (d, J = 11.6 Hz, 1H), 6.24 (d, J = 8.8 Hz, 0.5H), 4.70-4.50 (m, 1H), 4.40-4.30 (m, 1H), 4.25-4016 (m, 1H), 4.10-4.02 (m, 2H), 3.85-3.74 (m, 2H), 3.60-3.48 (m, 1H), 3.26-3.17 (m, 2H), 2.30-2.20 (m, 1H), 2.15 (s, 6H), 2.05-1.94 (m, 1H), 1.92-1.74 (m, 2H); MS (ESI): m/z 635.3 $[M + H]^+$. | ++++ |
| 527. | 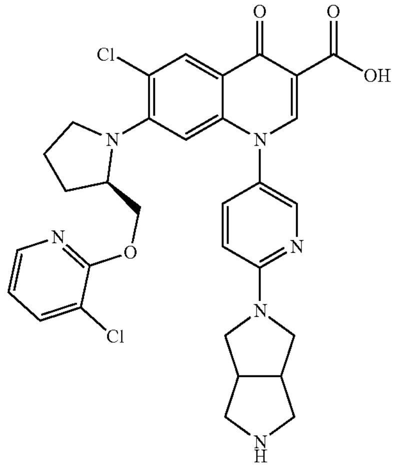 [SMILES: O=C(O)c1cn(-c2ccc(N3CC4CNCC4C3)nc2)c2cc(N3CCC[C@@H]3COc3ncccc3Cl)c(Cl)cc2c1=O] | 6-chloro-7-((R)-2-(((3-chloropyridin-2-yl)oxy)methyl) pyrrolidin-1-yl)-1-(6-(hexahydro-pyrrolo[3,4-c] pyrrol-2(1H)-yl) pyridin-3-yl)-4-oxo-1,4-dihydroquinoline-3-carboxylic acid acid | $^1$H NMR (400 MHz, DMSO-$d_6$): δ 8.49 (d, J = 9.2 Hz, 1H), 8.27-8.25 (m, 2H), 8.16 (s, 1H), 7.91-7.89 (m, 1H), 7.81 (d, J = 7.2 Hz, 1H), 7.71-7.66 (m, 1H), 6.97-6.90 (m, 1H), 6.66 (d, J = 9.2 Hz, 0.5H), 6.45-6.42 (m, 1.5H), 4.76-4.62 (m, 1H), 4.40-4.25 (m, 1H), 4.24-4.17 (m, 1H), 3.71-3.60 (m, 2H), 3.56-3.51 (m, 1H), 3.42-3.31 (m, 2H), 3.25-3.18 (m, 3H), 3.02-2.95 (m, 2H), 2.89-2.86 (m, 2H), 2.30-2.20 (m, 1H), 2.05-1.86 (m, 2H), 1.82-1.75 (m, 1H) (—COOH proton was not observed); MS (ESI): m/z 621.3 $[M + H]^+$ . . . | ++++ |
| 528. | 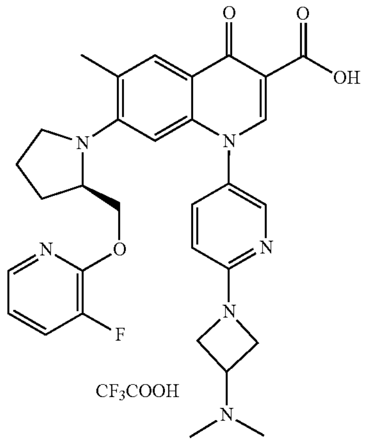 [SMILES: Cc1cc2c(=O)c(C(=O)O)cn(-c3ccc(N4CC(N(C)C)C4)nc3)c2cc1N1CCC[C@@H]1COc1ncccc1F ; "CF3COOH"] $CF_3COOH$ | (R)-1-(6-(3-(dimethylamino) azetidin-1-yl) pyridin-3-yl)-7-(2-(((3-fluoropyridin-2-yl)oxy)methyl) pyrrolidin-1-yl)-6-methyl-4-oxo-1,4-dihydroquinoline-3-carboxylic acid | $^1$H NMR (400 MHz, DMSO-$d_6$): δ 15.86 (s, 1H), 11.28 (bs, 1H), 8.47 (d, J = 5.6 Hz, 1H), 8.31 (dd, J = 18.8, 2.4 Hz, 1H), 8.02 (s, 1H), 7.82-7.74 (m, 2H), 7.63-7.58 (m, 1H), 7.00-6.94 (m, 1H), 6.54 (d, J = 8.8 Hz, 0.5H), 6.38 (d, J = 8.8 Hz, 0.5H), 6.28 (d, J = 14.4 Hz, 1H), 4.40-4.20 (m, 7H), 4.12-4.06 (m, 1H), 3.50-3.40 (m, 1H), 3.16-3.08 (m, 1H), 2.82 (s, 3H), 2.81 (s, 3H), 2.31 (s, 3H), 2.20-2.10 (m, 1H), 2.00-1.70 (m, 3H); MS (ESI): m/z 573.4 $[M + H]^+$. | ++++ |

-continued

| EX # | Structure | IUPAC name | Analytical data | Potency Lin28a-dep Z11 $IC_{50}$ (μM) |
| --- | --- | --- | --- | --- |
| 529. | 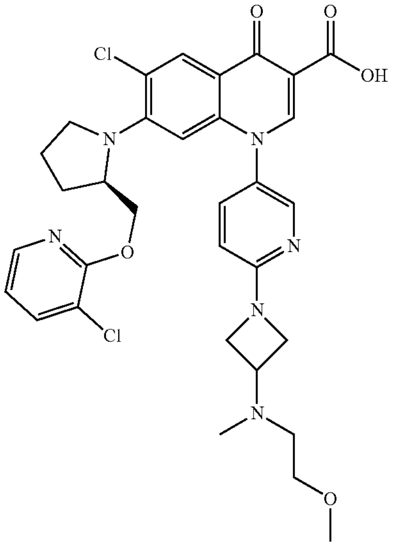 [SMILES: COCCN(C)C1CN(c2ccc(-n3cc(C(=O)O)c(=O)c4cc(Cl)c(N5CCC[C@@H]5COc5ncccc5Cl)cc43)cn2)C1] | (R)-6-chloro-7-(2-(((3-chloropyridin-2-yl)oxy)methyl) pyrrolidin-1-yl)-1-(6-(3-((2-methoxyethyl) (methyl)amino) azetidin-1-yl) pyridin-3-yl)-4-oxo-1,4-dihydroquinoline-3-carboxylic acid | $^1$H-NMR (400 MHz, DMSO-$d_6$): δ 15.08 (s, 1H), 8.50 (d, J = 9.6 Hz, 1H), 8.23 (d, J = 1.6 Hz, 1H), 8.14 (s, 1H), 7.90 (t, J = 4.8 Hz, 1H), 7.81 (d, J = 7.6 Hz, 1H), 7.70-7.65 (m, 1H), 6.97-6.92 (m, 1H), 6.55 (d, J = 8.8 Hz, 0.5H), 6.40 (d, J = 6.0 Hz, 1H), 6.30 (d, J = 8.8 Hz, 0.5H), 4.76-4.60 (m, 1H), 4.40-4.30 (m, 1H), 4.29-4.18 (m, 1H), 4.10-4.04 (m, 2H), 3.84-3.75 (m, 2H), 3.57-3.48 (m, 2H), 3.49-3.42 (m, 2H), 3.26 (s, 3H), 3.24-3.18 (m, 1H), 2.54-2.49 (m, 2H), 2.25-2.20 (m, 4H), 1.98-1.78 (m, 3H); MS (ESI): m/z 653.3 $[M + H]^+$ | ++++ |
| 530. | 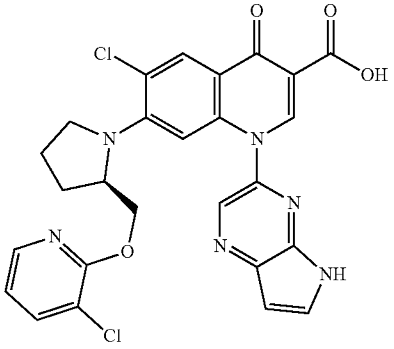 [SMILES: O=C(O)c1cn(-c2cnc3cc[nH]c3n2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(5H-pyrrolo[2,3-b] pyrazin-3-yl)-1,4-dihydroquinoline-3-carboxylic acid | $^1$H NMR (400 MHz, DMSO-$d_6$) δ 14.95 (s, 1H), 12.50 (s, 1H), 8.91 (s, 1H), 8.76 (s, 1H), 8.18 (s, 1H), 8.16 (d, J = 3.6 Hz, 1H), 7.81 (dd, J = 4.8, 1.2 Hz, 1H), 7.75 (dd, J = 7.6, 1.2 Hz, 1H), 6.91-6.87 (m, 1H), 6.85 (d, J = 3.6 Hz, 1H), 6.60 (s, 1H), 4.75-4.66 (m, 1H), 4.35-4.20 (m, 2H), 3.52-3.40 (m, 1H), 3.20-3.11 (m, 1H), 2.22-2.15 (m, 1H), 1.96-1.80 (m, 2H), 1.80-1.69 (m, 1H); MS (ESI): m/z 551.3 $[M + H]^+$ | ++++ |
| 531. | 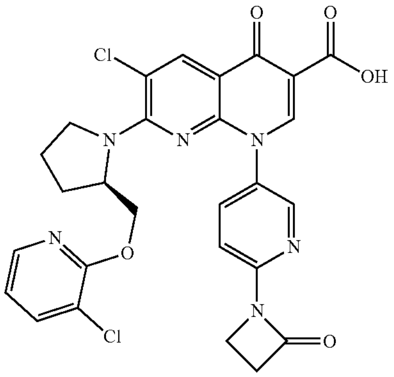 [SMILES: O=C(O)c1cn(-c2ccc(N3CCC3=O)nc2)c2nc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(6-(2-oxoazetidin-1-yl)pyridin-3-yl)-1,4-dihydro-1,8-naphthyridine-3-carboxylic acid | 1H NMR (400 MHz, DMSO-$d_6$): δ 14.97 (s, 1H), 8.71 (s, 1H), 8.49 (d, J = 2.0 Hz, 1H), 8.35 (s, 1H), 8.02 (dd, J = 8.8, 2.0 Hz, 1H), 7.96 (dd, J = 4.8, 1.2 Hz, 1H), 7.88 (dd, J = 8.0, 1.2 Hz, 1H), 7.47 (d, J = 7.6 Hz, 1H), 7.03-6.97 (m, 1H), 4.43-4.34 (m, 1H), 4.17 (dd, J = 10.4, 3.2 Hz, 1H), 4.00-3.91 (m, 2H), 3.90-3.84 (m, 1H), 3.68-3.61 (m, 1H), 3.54-3.48 (m, 1H), 3.11 (t, J = 4.8 Hz, 2H), 2.10-2.00 (m, 2H), 1.94-1.80 (m, 2H); MS (ESI): m/z 581.2 $[M + H]^+$ | ++++ |

-continued

| EX # | Structure | IUPAC name | Analytical data | Potency Lin28a-dep Z11 $IC_{50}$ (μM) |
|---|---|---|---|---|
| 532. | 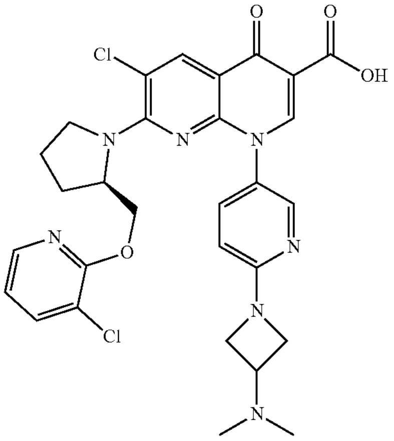 [SMILES: CN(C)C1CN(c2ccc(-n3cc(C(=O)O)c(=O)c4cc(Cl)c(N5CCC[C@@H]5COc5ncccc5Cl)nc43)cn2)C1] | (R)-6-chloro-7-(2-(((3-chloropyridin-2-yl)oxy)methyl) pyrrolidin-1-yl)-1-(6-(3-(dimethylamino) azetidin-1-yl) pyridin-3-yl)-4-oxo-1,4-dihydro-1,8-naphthyridine-3-carboxylic acid | $^1$H NMR (400 MHz, DMSO-$d_6$) δ 11.11 (brs, 1H), 8.61 (s, 1H), 8.33 (s, 1H), 8.27 (d, J = 2.0 Hz, 1H), 7.97-7.93 (m, 1H), 7.91-7.87 (m, 1H), 7.79 (dd, J = 8.8, 2.4 Hz, 1H), 7.02-6.97 (m, 1H), 6.40 (d, J = 8.4 Hz, 1H), 4.41 (brs, 1H), 4.30-4.12 (m, 7H), 3.92-3.78 (m, 2H), 2.80 (s, 6H), 2.10-1.82 (m, 3H), 1.80-1.68 (m, 1H); MS (ESI): m/z 610.2 $[M + H]^+$ | ++++ |
| 533. | 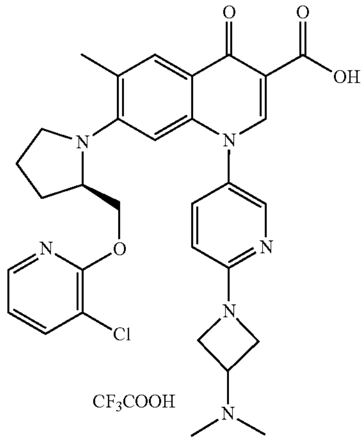 [SMILES: Cc1cc2c(=O)c(C(=O)O)cn(-c3ccc(N4CC(N(C)C)C4)nc3)c2cc1N1CCC[C@@H]1COc1ncccc1Cl ; "CF3COOH"] CF$_3$COOH | (R)-7-(2-(((3-chloropyridin-2-yl)oxy)methyl) pyrrolidin-1-yl)-1-(6-(3-(dimethylamino) azetidin-1-yl) pyridin-3-yl)-6-methyl-4-oxo-1,4-dihydroquinoline-3-carboxylic acid | $^1$H NMR (400 MHz, DMSO-$d_6$): δ 15.60 (s, 1H), 10.38 (bs, 1H), 8.45 (d, J = 8.0 Hz, 1H), 8.26 (s, 1H), 8.02 (s, 1H), 7.94-7.89 (m, 1H), 7.84-7.79 (m, 1H), 7.71 (d, J = 8.4 Hz, 1H), 7.00-6.93 (m, 1H), 6.60 (d, J = 8.8 Hz, 0.5H), 6.31 (d, J = 14.4 Hz, 1.5H), 4.40-4.21 (m, 2H), 4.20-4.12 (m, 2H), 4.10-3.96 (m, 3H), 3.55-3.48 (m, 1H), 3.32 (s, 6H), 3.16-3.08 (m, 1H), 2.39 (s, 3H), 2.30-2.20 (m, 1H), 2.00-1.70 (m, 3H); MS (ESI): m/z 589.3 $[M + H]^+$. | ++++ |
| 534. | 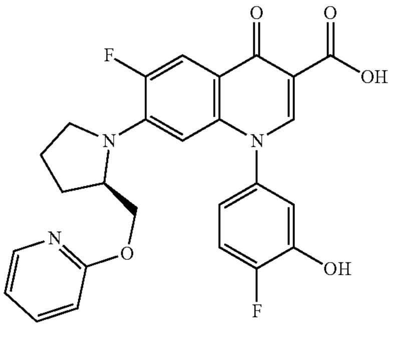 [SMILES: O=C(O)c1cn(-c2ccc(F)c(O)c2)c2cc(N3CCC[C@@H]3COc3ccccn3)c(F)cc2c1=O] | (R)-6-fluoro-1-(4-fluoro-3-hydroxyphenyl)-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$): δ 15.39 (s, 1H), 10.60 (d, J = 26.4 Hz, 1H), 8.50 (s, 1H), 8.00 (dd, J = 16.8, 3.6 Hz, 1H), 7.85 (d, J = 14.8 Hz, 1H), 7.69-7.62 (m, 1H), 7.47-7.10 (m, 2H), 7.06-6.92 (m, 2H), 6.66 (t, J = 8.8 Hz, 1H), 6.11 (t, J = 8.0 Hz, 1H), 4.45-4.31 (m, 1H), 4.24-4.13 (m, 2H), 3.43-3.15 (m, 2H), 2.10-1.88 (m, 4H); MS (ESI): m/z 494.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 535. | 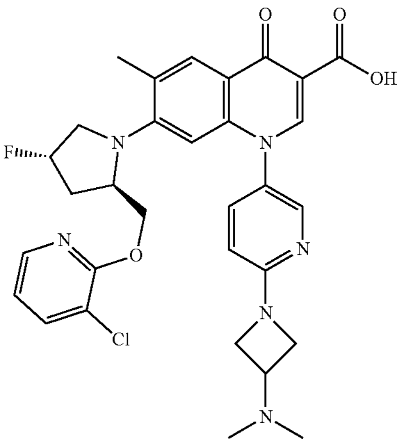 [SMILES: Cc1cc2c(=O)c(C(=O)O)cn(-c3ccc(N4CC(N(C)C)C4)nc3)c2cc1N1C[C@@H](F)C[C@@H]1COc1ncccc1Cl] | 7-((2R,4S)-2-(((3-chloropyridin-2-yl)oxy)methyl)-4-fluoropyrrolidin-1-yl)-1-(6-(3-(dimethylamino) azetidin-1-yl) pyridin-3-yl)-6-methyl-4-oxo-1,4-dihydroquinoline-3-carboxylic acid | $^1$H NMR (400 MHz, DMSO-$d_6$) δ 15.50 (s, 1H), 8.45 (d, J = 12.0 Hz, 1H), 8.32 (d, J = 5.2 Hz, 1H), 8.07 (s, 1H), 7.91-7.76 (m, 3H), 6.99-6.96 (m, 1H), 6.67-6.34 (m, 2H), 5.45 (brs, 0.5H), 5.31 (brs, 0.5H), 4.36-4.15 (m, 8H), 3.86-3.73 (m, 1H), 3.34 (brs, 1H), 2.86 (s, 6H), 2.36 (brs, 1H), 2.32 (s, 3H), 2.21 (brs, 1H); MS (ESI): m/z 607.2 $[M + H]^+$. | ++++ |
| 536. | 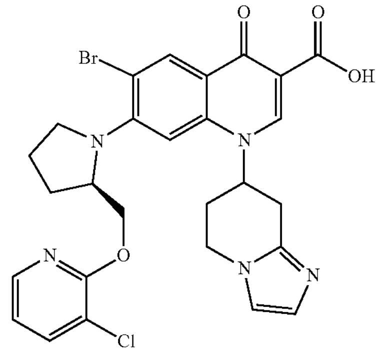 [SMILES: O=C(O)c1cn(C2CCn3ccnc3C2)c2cc(N3CCC[C@@H]3COc3ncccc3Cl)c(Br)cc2c1=O] | 6-bromo-7-((R)-2-(((3-chloropyridin-2-yl)oxy)methyl) pyrrolidin-1-yl)-4-oxo-1-(5,6,7,8-tetrahydroimidazo [1,2-a]pyridin-7-yl)-1,4-dihydroquinoline-3-carboxylic acid | $^1$H NMR (400 MHz, DMSO-$d_6$) δ 15.15 (s, 1H), 8.77 (d, J = 3.2 Hz, 1H), 8.35 (s, 1H), 7.87 (brs, 1H), 7.75 (t, J = 8.0 Hz, 1H), 7.40 (brs, 1H), 7.13 (brs, 1H), 6.92-6.86 (m, 2H), 5.49 (brs, 1H), 5.04 (brs, 1H), 4.35 (t, J = 12.0 Hz, 3H), 4.18 (brs, 2H), 3.89 (brs, 1H), 3.32 (brs, 2H), 2.39-2.32 (m, 3H), 2.08-1.84 (m, 3H); MS (ESI): m/z 598.2 $[M + H]^+$. | ++++ |
| 537. | 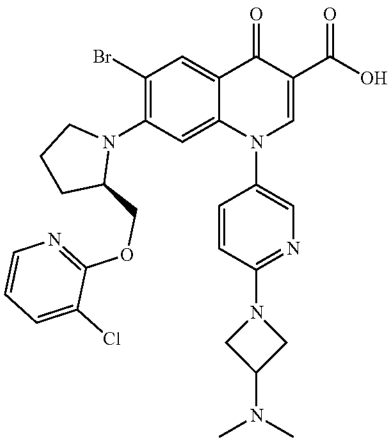 | (R)-6-bromo-7-(2-(((3-chloropyridin-2-yl)oxy)methyl) pyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.04 (bs, 1H), 8.53 (d, J = 10.4 Hz, 1H), 8.35 (s, 1H), 8.23 (d, J = 2.4 Hz, 1H), 7.92-7.88 (m, 1H), 7.81 (d, J = 7.6 Hz, 1H), 7.69-7.65 (m, 1H), 6.96-6.91 (m, 1H), 6.55 (d, J = 8.8 Hz, 0.5H), 6.43 (d, J = 8.0 Hz, 1H), 6.30 (d, J = 8.8 Hz, 0.5H), 4.80-4.62 (m, 1H), 4.40-4.25 (m, 1H), 4.25-4.15 (m, 1H), 4.10-4.03 (m, 2H), 3.85-3.79 (m, 2H), 3.62-3.54 (m, 1H), 3.25-3.22 (m, 1H), 3.16-3.12 (m, 1H), 2.30-2.20 (m, 1H), 2.15 (bs, 6H), 2.05-1.74 (m, 3H); MS (ESI): m/z 653.2 $[M + H]^+$. | ++++ |

-continued

| EX # | Structure | IUPAC name | Analytical data | Potency Lin28a-dep Z11 $IC_{50}$ (μM) |
|---|---|---|---|---|
| 538. | 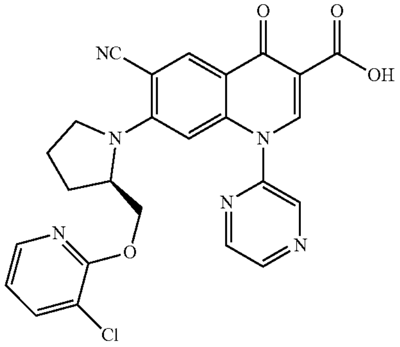 [SMILES: N#Cc1cc2c(=O)c(C(=O)O)cn(-c3cnccn3)c2cc1N1CCC[C@@H]1COc1ncccc1Cl] | (R)-7-(2-(((3-chloropyridin-2-yl)oxy)methyl) pyrrolidin-1-yl)-6-cyano-4-oxo-1-(pyrazin-2-yl)-1,4-dihydroquinoline-3-carboxylic acid | $^1$H NMR (400 MHz, DMSO-$d_6$) δ 14.53 (s, 1H), 9.13 (s, 1H), 8.94 (s, 1H), 8.90 (d, J = 2.4 Hz, 1H), 8.73-7.72 (m, 1H), 8.49 (s, 1H), 7.96 (dd, J = 4.8, 1.6 Hz, 1H), 7.85 (dd, J = 7.8, 1.6 Hz, 1H), 7.01-6.98 (m, 1H), 6.37 (s, 1H), 4.75-4.68 (m, 1H), 4.41-4.39 (m, 1H), 4.35-4.30 (m, 1H), 3.75-3.68 (m, 1H), 3.55-3.45 (m, 1H), 2.16-2.09 (m, 2H), 2.05-1.85 (m, 2H); MS (ESI): m/z 503.2 [M + H]$^+$. | ++++ |
| 539. | 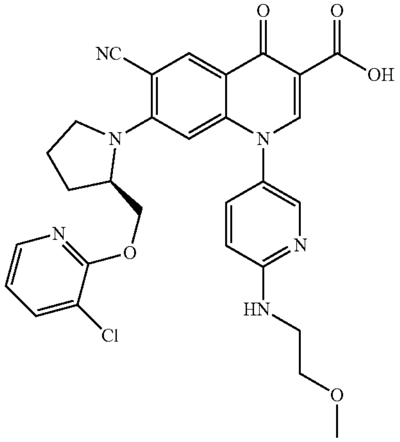 [SMILES: COCCNc1ccc(-n2cc(C(=O)O)c(=O)c3cc(C#N)c(N4CCC[C@@H]4COc4ncccc4Cl)cc32)cn1] | (R)-7-(2-(((3-chloropyridin-2-yl)oxy)methyl) pyrrolidin-1-yl)-6-cyano-1-(6-((2-methoxyethyl) amino)pyridin-3-yl)-4-oxo-1,4-dihydroquinoline-3-carboxylic acid | $^1$H NMR (400 MHz, DMSO-$d_6$): δ 14.79 (s, 1H), 8.53 (s, 1H), 8.45 (s, 1H), 8.18 (d, J = 9.6 Hz, 1H), 7.96 (s, 1H), 7.83 (d, J = 6.0 Hz, 1H), 7.59 (bs, 1H), 7.34 (bs, 0.5H), 7.26 (bs, 0.5H), 7.13 (s, 0.5H), 7.00 (bs, 1.5H), 6.73 (bs, 0.5H), 6.56 (bs, 0.5H), 6.21 (bs, 1H), 4.73 (bs, 1H), 4.46-4.36 (m, 2H), 3.70-3.60 (m, 1H), 3.58-3.48 (m, 5H), 3.30-3.20 (m, 3H), 2.23-2.08 (m, 2H), 2.06-1.88 (m, 2H); MS (ESI): m/z 575.3 [M + H]$^+$ | ++++ |
| 540. | 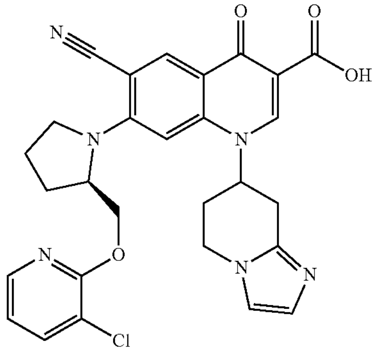 [SMILES: N#Cc1cc2c(=O)c(C(=O)O)cn(C3CCn4ccnc4C3)c2cc1N1CCC[C@@H]1COc1ncccc1Cl] | 7-((R)-2-(((3-chloropyridin-2-yl)oxy)methyl) pyrrolidin-1-yl)-6-cyano-4-oxo-1-(5,6,7,8-tetrahydroimidazo [1,2-a]pyridin-7-yl)-1,4-dihydroquinoline-3-carboxylic acid | $^1$H NMR (400 MHz, DMSO-$d_6$) δ 14.8 (s, 1H), 8.87-8.79 (m, 1H), 8.44 (d, J = 2.8 Hz, 1H), 7.96-7.93 (m, 1H), 7.84-7.80 (m, 1H), 7.43 (brs, 1H), 7.31 (brs, 1H), 7.06 (d, J = 5.6 Hz, 1H), 6.98-6.93 (m, 1H), 5.51 (brs, 1H), 5.16 (brs, 1H), 4.63-8.4.45 (m, 2H), 4.35 (t, J = 12.0 Hz, 1H), 4.18 (t, J = 12.0 Hz, 1H), 3.89 (d, J = 7.2 Hz, 1H), 3.65 (brs, 1H), 3.32 (s, 2H), 2.77-2.67 (m, 1H), 2.49 (s, 1H), 2.32-2.36 (m, 2H), 2.27 (brs, 1H), 2.10 (brs, 1H); MS (ESI): m/z 545.2 [M + H]$^+$. | ++++ |
| 541. | 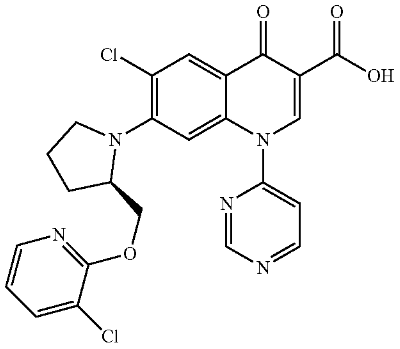 [SMILES: O=C(O)c1cn(-c2ccncn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyrimidin-4-yl)-1,4-dihydroquinoline-3-carboxylic acid | $^1$H NMR (400 MHz, DMSO-$d_6$) δ 14.72 (brs, 1H), 9.35 (s, 1H), 9.14 (d, J = 5.6 Hz, 1H), 8.91 (s, 1H), 8.16 (s, 1H), 8.05 (dd, J = 5.2, 0.8 Hz, 1H), 7.86 (dd, J = 4.8, 1.6 Hz, 1H), 7.76 (dd, J = 7.6, 1.6 Hz, 1H), 6.92-6.89 (m, 1H), 6.86 (s, 1H), 4.78-4.72 (m, 1H), 4.37-4.28 (m, 2H), 3.65-3.59 (m, 1H), 3.32-3.24 (m, 1H), 2.32-2.21 (m, 1H), 2.05-1.88 (m, 2H), 1.85-1.76 (m, 1H); MS (ESI): m/z 512.2 [M + H]$^+$. | ++++ |

-continued

| EX # | Structure | IUPAC name | Analytical data | Potency Lin28a-dep Z11 $IC_{50}$ (μM) |
|---|---|---|---|---|
| 542. | 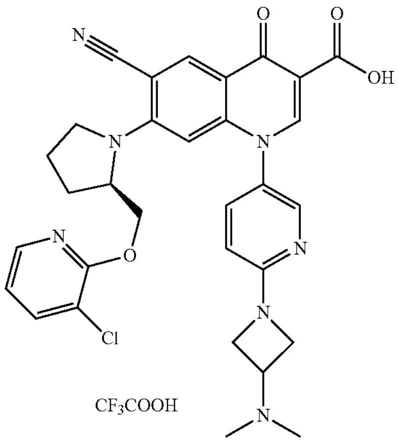 [SMILES: CN(C)C1CN(c2ccc(-n3cc(C(=O)O)c(=O)c4cc(C#N)c(N5CCC[C@@H]5COc5ncccc5Cl)cc43)cn2)C1 ; "CF3COOH"] $CF_3COOH$ | (R)-7-(2-(((3-chloropyridin-2-yl)oxy)methyl) pyrrolidin-1-yl)-6-cyano-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 14.8 (bs, 1H), 10.40 (bs, 1H), 8.53-8.47 (m, 2H), 8.35 (d, J = 10.4 Hz, 1H), 8.01-7.97 (m, 1H), 7.88-7.79 (m, 2H), 7.05-6.97 (m, 1H), 6.65 (d, J = 8.8 Hz, 0.5H), 6.42 (d, J = 8.8 Hz, 0.5 H), 6.12 (bs, 1H), 4.76-4.67 (m, 1H), 4.40-4.36 (m, 2H), 4.34-4.17 (m, 5H), 3.78-3.60 (m, 2H), 2.85 (s, 6H), 2.20-2.05 (m, 2H), 2.05-1.85 (m, 2H); MS (ESI): m/z 600.3 $[M + H]^+$. | ++++ |
| 543. | 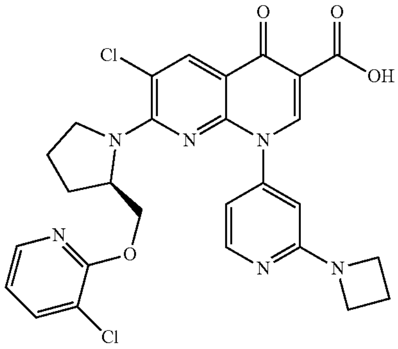 [SMILES: O=C(O)c1cn(-c2ccnc(N3CCC3)c2)c2nc(N3CCC[C@@H]3COc3ncccc3Cl)c(Cl)cc2c1=O] | (R)-1-(2-(azetidin-1-yl)pyridin-4-yl)-6-chloro-7-(2-(((3-chloropyridin-2-yl)oxy)methyl) pyrrolidin-1-yl)-4-oxo-1,4-dihydro-1,8-naphthyridine-3-carboxylic acid | $^1$H NMR (400 MHz, DMSO-$d_6$) δ 14.95 (s, 1H), 8.60 (s, 1H), 8.33 (s, 1H), 8.04 (d, J = 4.8 Hz, 1H), 7.97 (d, J = 4.0 Hz, 1H), 7.88 (d, J = 7.6 Hz, 1H), 7.03-6.99 (m, 1H), 6.80 (d, J = 4.8 Hz, 1H), 6.59 (s, 1H), 4.40 (bs, 1H), 4.25-4.21 (m, 2H), 4.00-3.84 (m, 6H), 2.40-2.20 (m, 2H), 2.10-2.00 (m, 2H), 1.95-1.80 (m, 2H); MS (ESI): m/z 567.3 $[M + H]^+$. | ++++ |
| 544. | 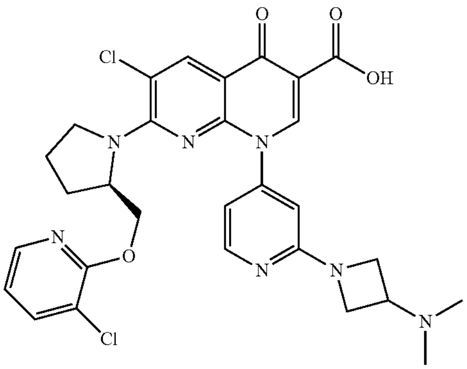 [SMILES: CN(C)C1CN(c2cc(-n3cc(C(=O)O)c(=O)c4cc(Cl)c(N5CCC[C@@H]5COc5ncccc5Cl)nc43)ccn2)C1] | (R)-6-chloro-7-(2-(((3-chloropyridin-2-yl)oxy)methyl) pyrrolidin-1-yl)-1-(2-(3-(dimethylamino) azetidin-1-yl) pyridin-4-yl)-4-oxo-1,4-dihydro-1,8-naphthyridine-3-carboxylic acid | $^1$H NMR (400 MHz, DMSO-$d_6$) δ 14.95 (s, 1H), 8.64 (s, 1H), 8.33 (s, 1H), 8.04 (d, J = 5.2 Hz, 1H), 7.98 (dd, J = 4.8, 1.6 Hz, 1H), 7.86 (dd, J = 7.6, 1.6 Hz, 1H), 7.02-6.98 (m, 1H), 6.82 (d, J = 5.6 Hz, 1H), 6.52 (s, 1H), 4.50-4.42 (m, 1H), 4.32-4.28 (m, 1H), 4.22-4.17 (m, 1H), 3.98-3.90 (m, 3H), 3.88-3.80 (m, 1H), 3.78-3.68 (m, 2H), 3.20-3.10 (m, 1H), 2.11 (s, 6H), 2.10-2.02 (m, 2H), 2.00-1.90 (m, 1H), 1.86-1.78 (m, 1H); MS (ESI): m/z 610.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 545. | 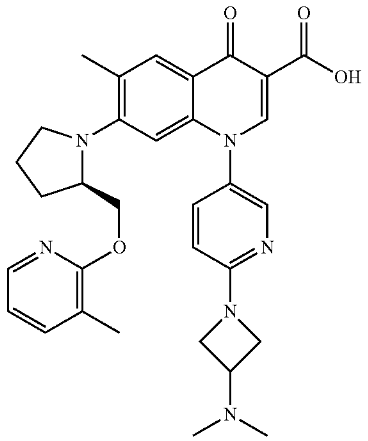 [SMILES: Cc1cc2c(=O)c(C(=O)O)cn(-c3ccc(N4CC(N(C)C)C4)nc3)c2cc1N1CCC[C@@H]1COc1ncccc1C] | (R)-1-(6-(3-(dimethylamino) azetidin-1-yl) pyridin-3-yl)-6-methyl-7-(2-(((3-methylpyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.61 (bs, 1H), 8.47 (s, 0.5H), 8.45 (s, 0.5H), 8.22 (s, 1H), 8.03 (s, 1H), 7.81 (dd, J = 10.8, 6.0 Hz, 1H), 7.65 (dd, J = 18.0, 8.4 Hz, 1H), 7.47 (dd, J = 13.6, 8.4 Hz, 1H), 6.87-6.80 (m, 1H), 6.55 (d, J = 8.0 Hz, 0.5H), 6.32 (d, J = 16.0 Hz, 1H), 6.20 (d, J = 8.0 Hz, 0.5H), 4.34-4.25 (m, 1H), 4.24-4.18 (m, 1H), 4.10-4.02 (m, 2H), 4.00-3.90 (m, 1H), 3.84-3.72 (m, 2H), 3.57-3.44 (m, 1H), 3.24-3.10 (m, 2H), 2.41 (s, 3H), 2.30-2.20 (m, 1H), 2.14 (s, 6H), 2.00-1.94 (m, 1H), 1.93 (s, 3H), 1.90-1.76 (m, 2H); MS (ESI): m/z 569.5 $[M + H]^+$. | ++++ |
| 546. | 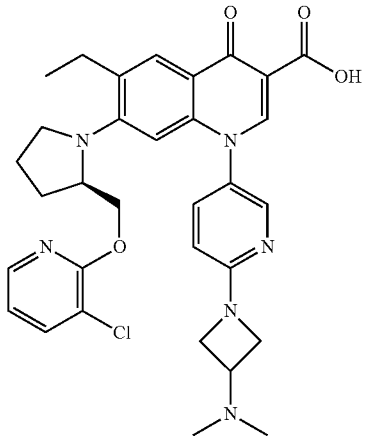 [SMILES: CCc1cc2c(=O)c(C(=O)O)cn(-c3ccc(N4CC(N(C)C)C4)nc3)c2cc1N1CCC[C@@H]1COc1ncccc1Cl] | (R)-7-(2-(((3-chloropyridin-2-yl)oxy)methyl) pyrrolidin-1-yl)-1-(6-(3-(dimethylamino) azetidin-1-yl) pyridin-3-yl)-6-ethyl-4-oxo-1,4-dihydroquinoline-3-carboxylic acid | $^1$H NMR (400 MHz, DMSO-$d_6$): δ 15.58 (bs, 1H), 8.47 (d, J = 8.8 Hz, 1H), 8.23-8.17 (m, 1H), 8.06 (s, 1H), 7.94-7.91 (m, 1H), 7.84-7.80 (m, 1H), 7.69-7.65 (m, 1H), 6.98-6.91 (m, 1H), 6.56-6.22 (m, 2H), 4.40-4.28 (m, 1H), 4.27-4.10 (m, 1H), 4.10-4.01 (m, 2H), 3.85-3.78 (m, 2H), 3.59-3.49 (m, 1H), 3.28-3.20 (m, 2H), 3.15-3.05 (m, 1H), 2.76 (q, J = 7.4 Hz, 2H), 2.30-2.20 (m, 1H), 2.15 (s, 6H), 1.99-1.85 (m, 2H), 1.82-1.75 (m, 1H), 1.19 (t, J = 7.6 Hz, 3H); MS (ESI): m/z 603.4 $[M + H]^+$ . . . | ++++ |
| 547. | 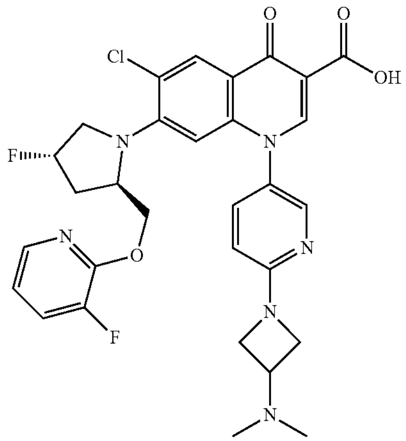 [SMILES: CN(C)C1CN(c2ccc(-n3cc(C(=O)O)c(=O)c4cc(Cl)c(N5C[C@@H](F)C[C@@H]5COc5ncccc5F)cc43)cn2)C1] | 6-chloro-1-(6-(3-(dimethylamino) azetidin-1-yl) pyridin-3-yl)-7-((2R,4S)-4-fluoro-2-(((3-fluoropyridin-2-yl)oxy)methyl) pyrrolidin-1-yl)-4-oxo-1,4-dihydroquinoline-3-carboxylic acid | $^1$H NMR (400 MHz, DMSO-$d_6$) δ 15.0 (brs, 1H), 8.54 (d, J = 9.6 Hz, 1H), 8.26-8.18 (m, 2H), 7.75-7.58 (m, 3H), 6.99-6.95 (m, 1H), 6.58-6.29 (m, 2H), 5.45 (brs, 0.5H), 5.32 (brs, 0.5H), 4.66 (brs, 1H), 4.39-4.27 (m, 2H), 4.10-4.02 (m, 2H), 3.94-3.78 (m, 3H), 3.47-3.35 (m, 1H), 3.22 (t, J = 5.2 Hz, 1H), 2.45-2.40 (m, 1H), 2.40-2.32 (s, 1H), 2.32 (s, 6H); MS (ESI): m/z 611.4 $[M + H]^+$. | ++++ |

-continued

| EX # | Structure | IUPAC name | Analytical data | Potency Lin28a-dep Z11 $IC_{50}$ (μM) |
|---|---|---|---|---|
| 548. | 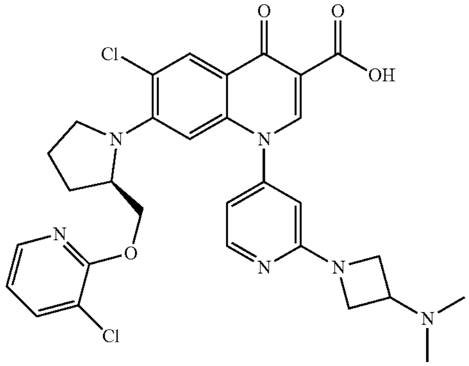 [SMILES: CN(C)C1CN(c2cc(-n3cc(C(=O)O)c(=O)c4cc(Cl)c(N5CCC[C@@H]5COc5ncccc5Cl)cc43)ccn2)C1] | (R)-6-chloro-7-(2-(((3-chloropyridin-2-yl)oxy)methyl) pyrrolidin-1-yl)-1-(2-(3-(dimethylamino) azetidin-1-yl) pyridin-4-yl)-4-oxo-1,4-dihydroquinoline-3-carboxylic acid | $^1$H NMR (400 MHz, DMSO-$d_6$): δ 15.02 (bs, 1H), 8.58 (s, 1H), 8.22 (d, J = 5.2 Hz, 1H), 8.16 (s, 1H), 7.89 (dd, J = 4.8, 1.2 Hz, 1H), 7.81 (dd, J = 7.6, 1.6 Hz, 1H), 6.94 (dd, J = 8.0, 5.6 Hz, 1H), 6.81 (dd, J = 5.6, 1.6 Hz, 1H), 6.70 (s, 1H), 6.57 (s, 1H), 4.73-4.68 (m, 1H), 4.36-4.24 (m, 2H), 4.10-3.98 (m, 2H), 3.80-3.70 (m, 2H), 3.60-3.50 (m, 1H), 3.24-3.18 (m, 2H), 2.30-2.20 (m, 1H), 2.11 (bs, 6H), 2.02-1.98 (m, 2H), 1.84-1.76 (m, 1H); MS (ESI): m/z 609.3 [M + H]$^+$. | ++++ |
| 549. | 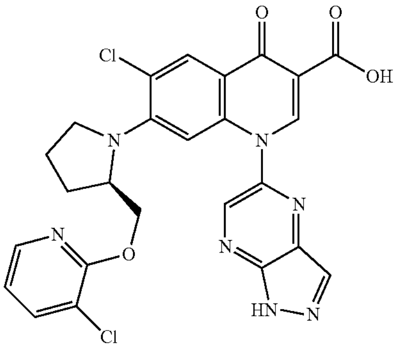 [SMILES: O=C(O)c1cn(-c2cnc3[nH]ncc3n2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(1H-pyrazolo[3,4-b] pyrazin-5-yl)-1,4-dihydroquinoline-3-carboxylic acid | $^1$H NMR (400 MHz, DMSO-$d_6$) δ 14.91 (s, 1H), 14.54 (s, 1H), 8.97 (s, 1H), 8.55 (s, 1H), 8.19 (s, 1H), 7.86 (dd, J = 4.8, 1.6 Hz, 1H), 7.78 (dd, J = 8.0, 2.4 Hz, 1H), 6.95-6.90 (m, 1H), 6.60 (s, 1H), 4.71-4.66 (m, 1H), 4.32-4.22 (m, 2H), 3.56-3.50 (m, 1H), 3.22-3.16 (m, 1H), 2.22-2.15 (m, 1H), 1.96-1.81 (m, 2H), 1.80-1.69 (m, 1H); MS (ESI): m/z 522.2 [M + H]$^+$ | ++++ |
| 550. | 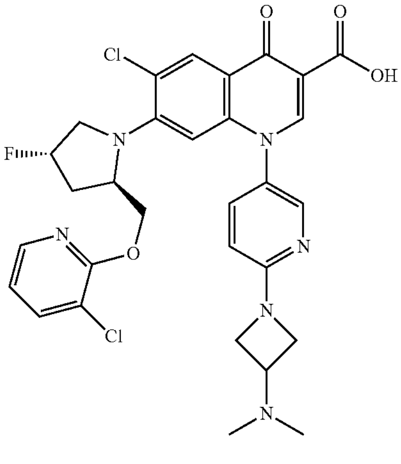 [SMILES: CN(C)C1CN(c2ccc(-n3cc(C(=O)O)c(=O)c4cc(Cl)c(N5C[C@@H](F)C[C@@H]5COc5ncccc5Cl)cc43)cn2)C1] | 6-chloro-7-((2R,4S)-2-(((3-chloropyridin-2-yl)oxy)methyl)-4-fluoropyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.02 (bs, 1H), 8.54 (d, J = 11.60 Hz, 1H), 8.26-8.23 (m, 1H), 8.20 (s, 1H), 7.90-7.88 (m, 1H), 7.82 (d, J = 7.60 Hz, 1H), 7.73-7.65 (m, 1H), 6.97-6.94 (m, 1H), 6.55 (d, J = 9.20 Hz, 0.5H), 6.47-6.43 (m, 1H), 6.36 (d, J = 8.80 Hz, 0.5H), 5.32 (bs, 0.5H), 5.49 (bs, 0.5H), 4.79-4.77 (m, 1H), 4.38-4.26 (m, 2H), 4.07-4.11 (m, 2H), 3.88-3.80 (m, 3H), 3.45-3.37 (m, 1H), 3.25-3.22 (m, 1H), 2.50-2.49 (m, 1H), 2.34-2.28 (m, 1H), 2.15 (s, 6H); MS (ESI) m/z: 627.2 [M + H]$^+$ | ++++ |
| 551. | 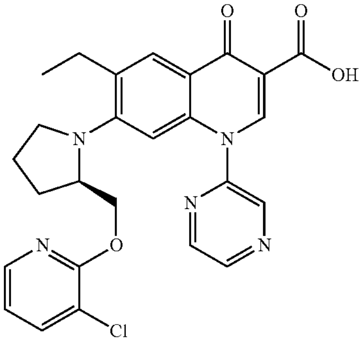 [SMILES: CCc1cc2c(=O)c(C(=O)O)cn(-c3cnccn3)c2cc1N1CCC[C@@H]1COc1ncccc1Cl] | (R)-7-(2-(((3-chloropyridin-2-yl)oxy)methyl) pyrrolidin-1-yl)-6-ethyl-4-oxo-1-(pyrazin-2-yl)-1,4-dihydroquinoline-3-carboxylic acid | $^1$H NMR (400 MHz, DMSO-$d_6$): δ 9.08 (s, 1H), 8.92-8.91 (m, 1H), 8.83 (s, 1H), 8.76 (s, 1H), 8.42 (s, 1H), 8.06 (s, 1H), 7.89-7.87 (m, 1H), 7.77 (dd, J = 1.2, 7.6 Hz, 1H), 6.94-6.90 (m, 1H), 6.56 (s, 1H), 4.30-4.10 (m, 3H), 3.60-3.50 (m, 1H), 3.12 (t, J = 14.8 Hz, 1H), 2.73 (q, J = 7.2 Hz, 2H), 2.37-2.21 (m, 1H), 2.00-1.94 (m, 2H), 1.90-1.80 (m, 1H), 1.19 (t, J = 7.6 Hz, 3H) (—COOH proton was not observed); MS (ESI) m/z: 506.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 552. | 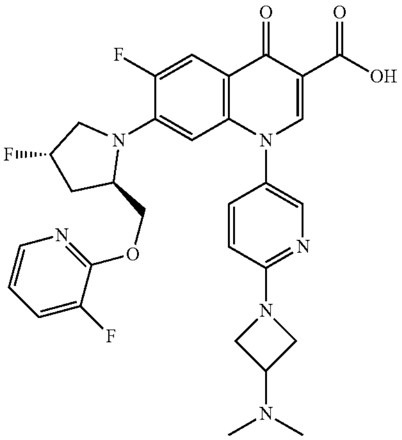 | 1-(6-(3-(dimethylamino) azetidin-1-yl) pyridin-3-yl)-6-fluoro-7-((2R,4S)-4-fluoro-2-(((3-fluoropyridin-2-yl) oxy)methyl) pyrrolidin-1-yl)-4-oxo-1,4-dihydroquinoline-3-carboxylic acid | $^1$H-NMR (400 MHz, DMSO-$d_6$): δ 15.28 (bs, 1H), 8.51 (d, J = 7.2 Hz, 1H), 8.26 (s, 1H), 7.92 (d, J = 13.6 Hz, 1H), 7.78-7.70 (m, 2H), 7.62 (td, J = 9.4, 1.2 Hz, 1H), 7.01-6.97 (m, 1H), 6.56 (d, J = 8.8 Hz, 1H), 6.35 (d, J = 8.8 Hz, 1H), 6.22 (t, J = 7.6 Hz, 1H), 5.48 (bs, 0.5H), 5.35 (bs, 0.5H), 4.58-4.59 (m, 1H), 4.40-4.36 (m, 2H), 4.10-4.03 (m, 2H), 3.84-3.78 (m, 2H), 3.74-3.65 (m, 1H), 3.56-3.37 (m, 1H), 3.27-3.21 (m, 1H), 2.54-2.51 (m, 1H), 2.15 (s, 6H). MS (ESI) m/z: 595.2 $[M + H]^+$ | ++++ |
| 553. | 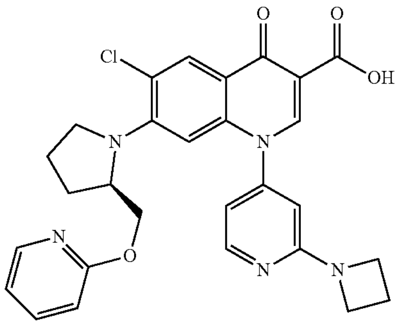 [SMILES: O=C(O)c1cn(-c2ccnc(N3CCC3)c2)c2cc(N3CCC[C@@H]3COc3ccccn3)c(Cl)cc2c1=O] | (R)-1-(2-(azetidin-1-yl)pyridin-4-yl)-6-chloro-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$): δ 15.00 (brs, 1H), 8.55 (s, 1H), 8.33 (brs, 0.4H), 8.18 (s, 1H), 7.98 (d, J = 3.6 Hz, 1H), 7.93 (brs, 0.4H), 7.65 (t, J = 8.8 Hz, 1H), 6.94-6.91 (m, 1H), 6.78 (brs, 1H), 6.67 (brs, 1H), 6.60 (d, J = 8.4 Hz, 1H), 6.54 (brs, 1H), 4.46 (brs, 1H), 4.23 (brs, 1H), 4.13-4.09 (m, 1H), 4.09-3.80 (m, 4H), 3.64 (brs, 1H), 3.26 (m, 1H), 2.32 (m, 2H), 2.22 (m, 1H), 1.97 (m, 1H), 1.90-1.76 (m, 2H); MS (ESI) m/z: 532.4 $[M + H]^+$ | ++++ |
| 554. | 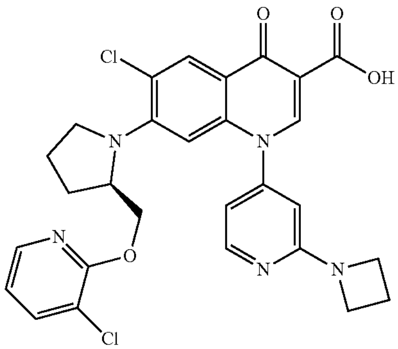 [SMILES: O=C(O)c1cn(-c2ccnc(N3CCC3)c2)c2cc(N3CCC[C@@H]3COc3ncccc3Cl)c(Cl)cc2c1=O] | (R)-1-(2-(azetidin-1-yl)pyridin-4-yl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$) δ 14.82 (bs, 1H), 8.50 (s, 1H), 8.21 (d, J = 5.2 Hz, 1H), 8.16 (s, 1H), 7.88 (dd, J = 5.2, 2.0 Hz, 1H), 7.88 (dd, J = 7.6, 1.6 Hz, 1H), 6.92-6.89 (m, 1H), 6.72 (dd, J = 5.2, 2.0 Hz, 1H), 6.59-6.57 (m, 2H), 4.66-4.65 (m, 1H), 4.32-4.30 (m, 2H), 4.00-3.99 (m, 4H), 3.64-3.61 (m, 1H), 3.24-3.22 (m, 1H), 2.37-2.31 (m, 2H), 2.24-2.22 (m, 1H), 2.00-1.92 (m, 2H), 1.85-1.80 (m, 1H); MS (ESI) m/z: 566.3 $[M + H]^+$ | ++++ |
| 555. | 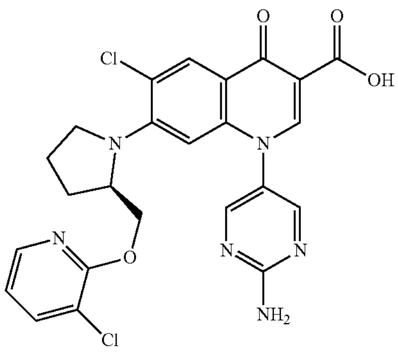 [SMILES: Nc1ncc(-n2cc(C(=O)O)c(=O)c3cc(Cl)c(N4CCC[C@@H]4COc4ncccc4Cl)cc32)cn1] | (R)-1-(2-aminopyrimidin-5-yl)-6-chloro-7-(2-(((3-chloropyridin-2-yl)oxy)methyl) pyrrolidin-1-yl)-4-oxo-1,4-dihydroquinoline-3-carboxylic acid | 1H NMR (400 MHz, DMSO-$d_6$): δ 15.05 (bs, 1H), 8.64 (s, 1H), 8.45 (s, 1H), 8.41 (s, 1H), 8.15 (s, 1H), 7.89 (dd, J = 4.8, 1.6 Hz, 1H), 7.77 (dd, J = 7.6, 2.4 Hz, 1H), 7.29 (bs, 2H), 6.94-6.89 (m, 1H), 6.45 (s, 1H), 4.82 (bs, 1H), 4.35-4.26 (m, 2H), 3.58-3.50 (m, 1H), 3.21 (t, J = 7.6 Hz, 1H), 2.30-2.20 (m, 1H), 2.04-1.85 (m, 2H), 1.82-1.77 (m, 1H); MS (ESI) m/z: 527.0 $[M + H]^+$ . . . | ++++ |

-continued

| EX # | Structure | IUPAC name | Analytical data | Potency Lin28a-dep Z11 $IC_{50}$ (μM) |
|---|---|---|---|---|
| 556. | 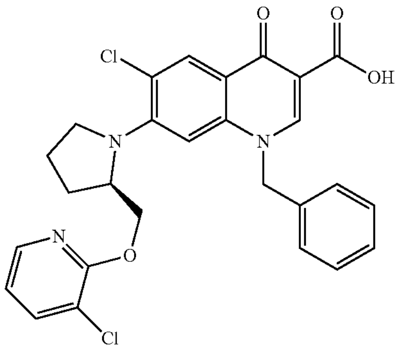 [SMILES: O=C(O)c1cn(Cc2ccccc2)c2cc(N3CCC[C@@H]3COc3ncccc3Cl)c(Cl)cc2c1=O] | (R)-1-benzyl-6-chloro-7-(2-(((3-chloropyridin-2-yl)oxy)methyl) pyrrolidin-1-yl)-4-oxo-1,4-dihydroquinoline-3-carboxylic acid | 1HNMR (400 MHz, DMSO-$d_6$): δ 15.22 (s, 1H), 9.15 (s, 1H), 8.10 (s, 1H), 7.89-7.88 (m, 1H), 7.80-7.78 (dd, J = 7.6, 1.6 Hz, 1H), 7.26-7.21 (m, 4H), 7.11-7.08 (m, 1H), 6.96-6.91 (m, 2H), 5.79-5.69 (m, 2H), 4.75 (t, J = 5.2 Hz, 1H), 4.10-4.05 (m, 1H), 4.00-3.97 (m, 1H), 3.76-3.69 (m, 1H), 3.19 (t, J = 8.0 Hz, 1H), 2.26-2.23 (m, 1H), 2.03-1.98 (m, 1H), 1.94-1.82 (m, 2H); MS (ESI) m/z: 524.3 $[M + H]^+$. | +++ |
| 557. | 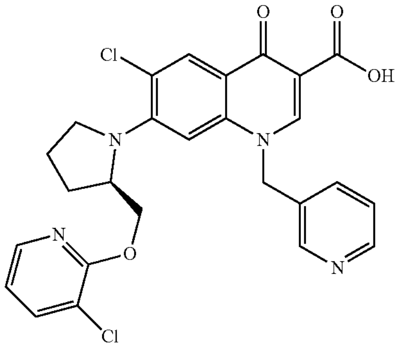 [SMILES: O=C(O)c1cn(Cc2cccnc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyridin-3-ylmethyl)-1,4-dihydroquinoline-3-carboxylic acid | $^1H$ NMR (400 MHz, DMSO-$d_6$): δ 15.20 (s, 1H), 9.18 (s, 1H), 8.59 (s, 1H), 8.35 (d, J = 3.6 Hz, 1H), 8.10 (s, 1H), 7.87 (dd, J = 4.8, 1.6 Hz, 1H), 7.76 (dd, J = 8.0, 1.6 Hz, 1H), 7.62 (d, J = 8.0 Hz, 1H), 7.23 (dd, J = 8.0, 4.8 Hz, 1H), 6.94-6.90 (m, 2H), 5.81 (s, 2H), 4.85-4.75 (m, 1H), 4.11-4.00 (m, 2H), 3.75-3.69 (m, 1H), 3.19 (t, J = 8.0 Hz, 1H), 2.30-2.22 (m, 1H), 2.07-2.00 (m, 1H), 1.97-1.90 (m, 1H), 1.84-1.74 (m, 1H); MS (ESI): m/z 525.2 $[M + H]^+$ | ++++ |
| 558. | 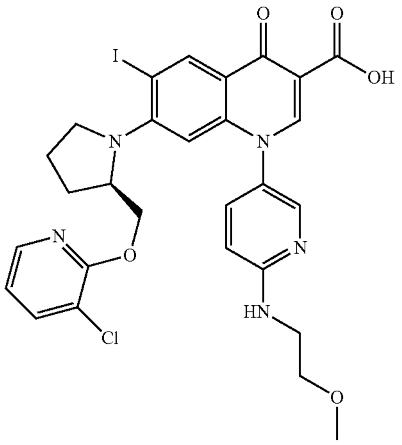 [SMILES: COCCNc1ccc(-n2cc(C(=O)O)c(=O)c3cc(I)c(N4CCC[C@@H]4COc4ncccc4Cl)cc32)cn1] | (R)-7-(2-(((3-chloropyridin-2-yl)oxy)methyl) pyrrolidin-1-yl)-6-iodo-1-(6-((2-methoxyethyl) amino)pyridin-3-yl)-4-oxo-1,4-dihydroquinoline-3-carboxylic acid | $^1H$ NMR (400 MHz, DMSO-$d_6$) δ 15.07 (bs, 1H), 8.64 (d, J = 3.6 Hz, 1H), 8.52 (d, J = 8.4 Hz, 1H), 8.12 (s, 1H), 7.91-7.89 (m, 1H), 7.77 (t, J = 6.4 Hz, 1H), 7.54-7.46 (m, 1H), 7.24-7.19 (m, 1H), 6.94-6.90 (m, 1H), 6.69 (d, J = 8.8 Hz, 0.5H), 6.57 (d, J = 8.8 Hz, 0.5H), 6.48 (d, J = 7.6 Hz, 1H), 4.84-4.76 (m, 1H), 4.34-4.29 (m, 1H), 4.22-4.15 (m, 1H), 3.70-3.60 (m, 1H), 3.58-3.48 (m, 4H), 3.29 (s, 3H), 3.09-3.00 (m, 1H), 2.30-2.20 (m, 1H), 2.01-1.84 (m, 2H), 1.83-1.75 (m, 1H); MS (ESI): m/z 676.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 559. | 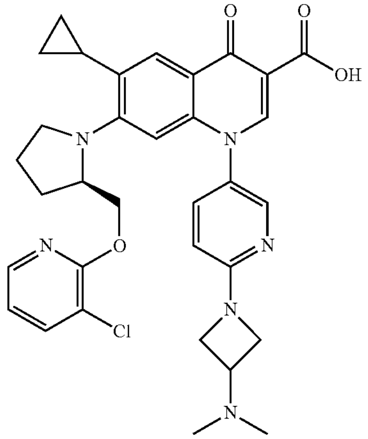 [SMILES: CN(C)C1CN(c2ccc(-n3cc(C(=O)O)c(=O)c4cc(C5CC5)c(N5CCC[C@@H]5COc5ncccc5Cl)cc43)cn2)C1] | (R)-7-(2-(((3-chloropyridin-2-yl)oxy)methyl) pyrrolidin-1-yl)-6-cyclopropyl-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.56 (bs, 1H), 8.45 (d, J = 8.8 Hz, 1H), 8.24-8.19 (m, 1H), 7.95-7.92 (m, 1H), 7.89 (s, 1H), 7.85-7.80 (m, 1H), 7.66 (dd, J = 6.0, 2.4 Hz, 1H), 7.00 (m, 1H), 6.54 (d, J = 8.4 Hz, 0.5 H), 6.31 (d, J = 13.6 Hz, 1H), 6.24 (d, J = 9.6 Hz, 0.5 H), 4.58-4.32 (m, 2H), 4.16-4.03 (m, 3H), 3.86-3.77 (m, 2H), 3.72-3.61 (m, 1H), 3.32-3.21 (m, 2H), 2.29-2.18 (m, 1H), 2.16 (s, 6H), 2.12-1.85 (m, 3H), 1.85-1.75 (m, 1H), 1.19-1.10 (m, 1H), 0.94-0.88 (m, 1H), 0.75-0.61 (m, 2H); MS (ESI): m/z 615.4 $[M + H]^+$ . . . | ++++ |
| 560. | 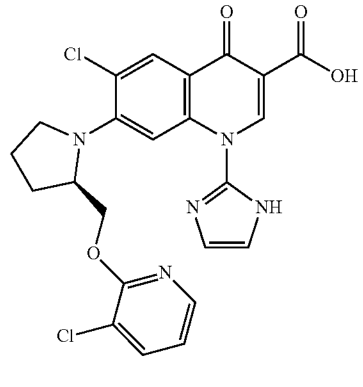 [SMILES: O=C(O)c1cn(-c2ncc[nH]2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(1H-imidazol-2-yl)-4-oxo-1,4-dihydroquinoline-3-carboxylic acid | $^1$H-NMR (400 MHz, DMSO-$d_6$): δ 14.8 (s, 1H), 13.1 (bs, 1H), 8.77 (s, 1H), 8.14 (s, 1H), 7.88 (dd, J = 4.8, 1.6 Hz, 1H), 7.76 (dd, J = 7.6, 1.6 Hz, 1H), 7.23 (bs, 2H), 6.92-6.89 (m, 1H), 6.79 (s, 1H), 4.74 (bs, 1H), 4.35-4.27 (m, 2H), 3.63-3.55 (m, 1H), 3.32-3.23 (m, 1H), 2.30-2.24 (m, 1H), 2.03-1.90 (m, 2H), 1.89-1.78 (m, 1H); MS (ESI): m/z 500.3 $[M + H]^+$. | ++++ |
| 561. | 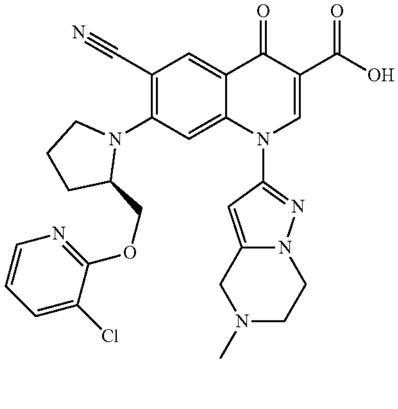 [SMILES: CN1CCn2nc(-n3cc(C(=O)O)c(=O)c4cc(C#N)c(N5CCC[C@@H]5COc5ncccc5Cl)cc43)cc2C1] | (R)-7-(2-(((3-chloropyridin-2-yl)oxy)methyl) pyrrolidin-1-yl)-6-cyano-1-(5-methyl-4,5,6,7-tetrahydropyrazolo [1,5-a]pyrazin-2-yl)-4-oxo-1,4-dihydroquinoline-3-carboxylic acid | $^1$H NMR (400 MHz, DMSO-$d_6$): δ 14.43 (s, 1H), 8.59 (s, 1H), 8.44 (s, 1H), 7.99 (dd, J = 4.8, 1.6 Hz, 1H), 7.85 (dd, J = 7.6, 1.6 Hz, 1H), 7.00 (dd, J = 8.0, 5.2 Hz, 1H), 6.71 (s, 1H), 6.47 (s, 1H), 4.70-4.64 (m, 1H), 4.44-4.38 (m, 2H), 4.18-4.07 (m, 2H), 3.83-3.78 (m, 1H), 3.61-3.48 (m, 3H), 2.88-2.83 (m, 2H), 2.38 (s, 3H), 2.22-2.10 (m, 2H), 2.09-1.92 (m, 2H); MS (ESI): m/z 560.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 562. | 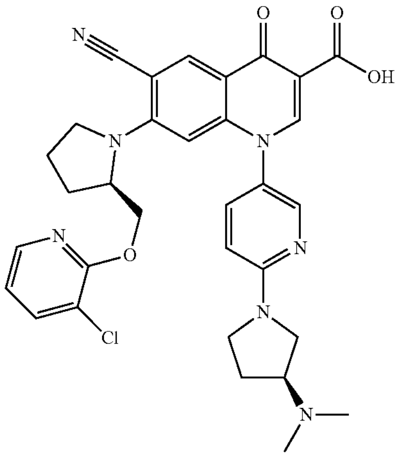 [SMILES: CN(C)[C@H]1CCN(c2ccc(-n3cc(C(=O)O)c(=O)c4cc(C#N)c(N5CCC[C@@H]5COc5ncccc5Cl)cc43)cn2)C1] | 7-((R)-2-(((3-chloropyridin-2-yl)oxy)methyl) pyrrolidin-1-yl)-6-cyano-1-(6-((S)-3-(dimethylamino) pyrrolidin-1-yl)pyridin-3-yl)-4-oxo-1,4-dihydroquinoline-3-carboxylic acid | $^1H$ NMR (400 MHz, DMSO-$d_6$): δ 14.75 (bs, 1H), 8.50 (d, J = 5.2 Hz, 1H), 8.47 (s, 1H), 8.30-8.25 (m, 1H), 7.98-7.95 (m, 1H), 7.87-7.83 (m, 1H), 7.76-7.68 (m, 1H), 7.04-6.98 (m, 1H), 6.66 (d, J = 8.8 Hz, 0.5H), 6.36 (d, J = 8.4 Hz, 0.5H), 6.21 (d, J = 3.2 Hz, 1H), 4.70-4.55 (m, 1H), 4.40-4.27 (m, 2H), 3.80-3.55 (m, 3H), 3.54-3.35 (m, 2H), 3.30-3.15 (m, 2H), 2.45-2.30 (m, 6H), 2.30-2.05 (m, 3H), 2.04-1.94 (m, 3H); MS (ESI): m/z 614.3 $[M + H]^+$. | ++++ |
| 563. | 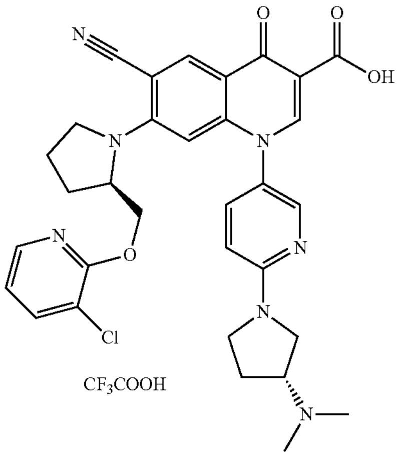 [SMILES: CN(C)[C@@H]1CCN(c2ccc(-n3cc(C(=O)O)c(=O)c4cc(C#N)c(N5CCC[C@@H]5COc5ncccc5Cl)cc43)cn2)C1 ; "CF3COOH"] $CF_3COOH$ | 7-((R)-2-(((3-chloropyridin-2-yl)oxy)methyl) pyrrolidin-1-yl)-6-cyano-1-(6-((R)-3-(dimethylamino) pyrrolidin-1-yl)pyridin-3-yl)-4-oxo-1,4-dihydroquinoline-3-carboxylic acid | $^1H$ NMR (400 MHz, DMSO-$d_6$): δ 14.7 (bs, 1H), 10.13 (bs, 1H), 8.60-8.41 (m, 2H), 8.40-8.24 (m, 1H), 8.05-7.72 (m, 3H), 7.10-6.95 (m, 1H), 6.8-6.4 (m, 1H), 6.25-6.1 (m, 1H), 4.72-4.60 (m, 1H), 4.42-4.25 (m, 2H), 4.10-3.35 (m, 7H), 2.90 (s, 6H), 2.40-1.85 (m, 6H); MS (ESI): m/z 614.4 $[M + H]^+$. | ++++ |
| 564. | 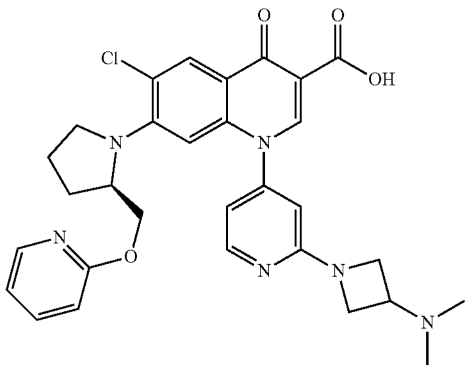 [SMILES: CN(C)C1CN(c2cc(-n3cc(C(=O)O)c(=O)c4cc(Cl)c(N5CCC[C@@H]5COc5ccccn5)cc43)ccn2)C1] | (R)-6-chloro-1-(2-(3-(dimethylamino) azetidin-1-yl) pyridin-4-yl)-4-oxo-7-(2-((pyridin-2-yloxy)methyl) pyrrolidin-1-yl)-1,4-dihydroquinoline-3-carboxylic acid | $^1H$ NMR (400 MHz, DMSO-$d_6$): δ 15.03 (bs, 1H), 8.58 (s, 1H), 8.28 (bs, 0.5H), 8.18 (s, 1H), 7.97 (bs, 1.5H), 7.64 (t, J = 8.4 Hz, 1H), 6.92 (t, J = 6.4 Hz, 1H), 6.80 (bs, 1H), 6.71 (s, 1H), 6.62-6.50 (m, 2H), 4.53-4.46 (m, 1H), 4.30-4.20 (m, 1H), 4.19-4.10 (m, 2H), 4.09-3.98 (m, 1H), 3.90-3.70 (m, 2H), 3.69-3.60 (m, 1H), 3.30-3.20 (m, 1H), 3.14-3.04 (m, 1H), 2.38-2.30 (m, 1H), 2.10 (bs, 6H), 2.02-1.92 (m, 1H), 1.90-1.70 (m, 2H); MS (ESI): m/z 575.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 565. | 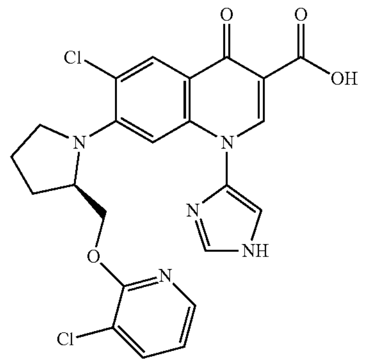 [SMILES: O=C(O)c1cn(-c2c[nH]cn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(1H-imidazol-4-yl)-4-oxo-1,4-dihydroquinoline-3-carboxylic acid | $^{1}$H-NMR (400 MHz, DMSO-$d_6$): δ 14.94 (s, 1H), 12.78 (bs, 1H), 8.60 (s, 1H), 8.13 (s, 1H), 7.85 (dd, J = 4.8, 1.6 Hz, 1H), 7.75 (dd, J = 7.6, 1.6 Hz, 1H), 7.68 (s, 1H), 6.94 (s, 1H), 6.92-6.89 (m, 1H), 4.74 (bs, 1H), 4.35-4.27 (m, 2H), 3.63-3.55 (m, 1H), 3.30-3.20 (m, 1H), 2.32-2.22 (m, 1H), 2.05-1.90 (m, 2H), 1.89-1.78 (m, 1H); MS (ESI): m/z 500.3 $[M + H]^+$. | ++++ |
| 566. | 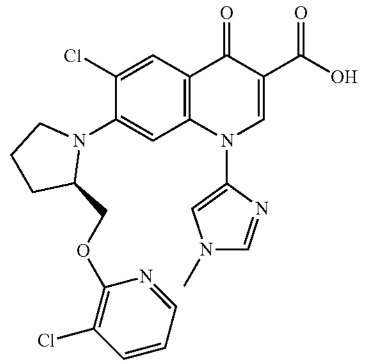 [SMILES: Cn1cnc(-n2cc(C(=O)O)c(=O)c3cc(Cl)c(N4CCC[C@@H]4COc4ncccc4Cl)cc32)c1] | (R)-6-chloro-7-(2-(((3-chloropyridin-2-yl)oxy)methyl) pyrrolidin-1-yl)-1-(1-methyl-1H-imidazol-4-yl)-4-oxo-1,4-dihydroquinoline-3-carboxylic acid | $^{1}$H NMR (400 MHz, DMSO-$d_6$): δ 14.96 (s, 1H), 8.75 (s, 1H), 8.12 (s, 1H), 7.85 (dd, J = 4.8, 1.6 Hz, 1H), 7.79 (d, J = 1.2 Hz, 1H), 7.76 (dd, J = 7.6, 1.6 Hz, 1H), 7.66 (d, J = 1.2 Hz, 1H), 6.97 (s, 1H), 6.92-6.89 (m, 1H), 4.80-4.70 (m, 1H), 4.32 (d, J = 4.4 Hz, 2H), 3.76 (s, 3H), 3.63-3.55 (m, 1H), 3.30-3.20 (m, 1H), 2.31-2.22 (m, 1H), 2.05-1.90 (m, 2H), 1.89-1.78 (m, 1H); MS (ESI): m/z 514.2 $[M + H]^+$. | ++++ |
| 567. | 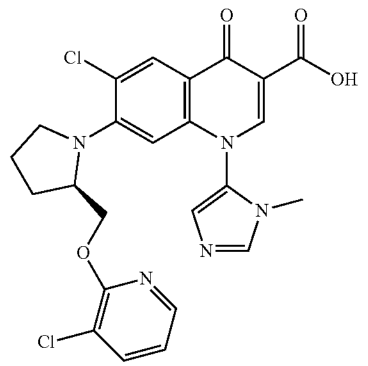 [SMILES: Cn1cncc1-n1cc(C(=O)O)c(=O)c2cc(Cl)c(N3CCC[C@@H]3COc3ncccc3Cl)cc21] | (R)-6-chloro-7-(2-(((3-chloropyridin-2-yl)oxy)methyl) pyrrolidin-1-yl)-1-(1-methyl-1H-imidazol-5-yl)-4-oxo-1,4-dihydroquinoline-3-carboxylic acid | VT-$^{1}$H-NMR (400 MHz, DMSO-$d_6$): δ 14.50 (bs, 1H), 8.58 (s, 1H), 8.14 (s, 1H), 7.90 (bs, 1H), 7.79 (bs, 1H), 7.74 (d, J = 7.6 Hz, 1H), 7.25 (s, 1H), 6.93-6.88 (m, 1H), 6.19 (bs, 1H), 4.73 (bs, 1H), 4.31 (d, J = 4.0 Hz, 2H), 3.57-3.53 (m, 1H), 3.32 (s, 3H), 3.21 (t, J = 7.6 Hz, 1H), 2.33-2.28 (m, 1H), 2.07-1.91 (m, 2H), 1.87-1.78 (m, 1H); MS (ESI): m/z 514.2 $[M + H]^+$. | ++++ |
| 568. | 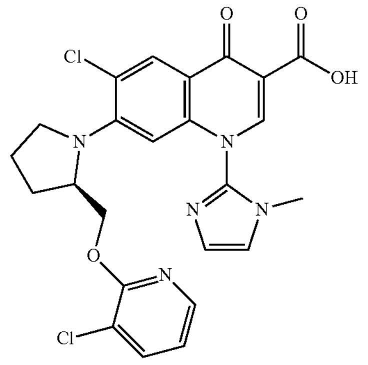 [SMILES: Cn1ccnc1-n1cc(C(=O)O)c(=O)c2cc(Cl)c(N3CCC[C@@H]3COc3ncccc3Cl)cc21] | (R)-6-chloro-7-(2-(((3-chloropyridin-2-yl)oxy)methyl) pyrrolidin-1-yl)-1-(1-methyl-1H-imidazol-2-yl)-4-oxo-1,4-dihydroquinoline-3-carboxylic acid | $^{1}$H-NMR (400 MHz, DMSO-$d_6$): δ 14.8 (bs, 1H), 8.81 (s, 1H), 8.14 (s, 1H), 7.91 (dd, J = 4.8, 1.6 Hz, 1H), 7.80 (dd, J = 7.6, 4.8 Hz, 1H), 7.40 (s, 1H), 7.08 (s, 1H), 6.95-6.91 (m, 1H), 6.00 (s, 1H), 4.73 (bs, 1H), 4.29-4.26 (m, 2H), 3.54-3.48 (m, 1H), 3.38 (s, 3H), 3.21 (t, J = 7.6 Hz, 1H), 2.33-2.28 (m, 1H), 2.07-1.99 (m, 2H), 1.97-1.78 (m, 1H); MS (ESI): m/z 514.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 569. | 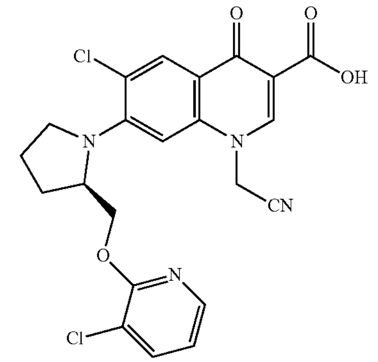 [SMILES: N#CCn1cc(C(=O)O)c(=O)c2cc(Cl)c(N3CCC[C@@H]3COc3ncccc3Cl)cc21] | (R)-6-chloro-7-(2-(((3-chloropyridin-2-yl)oxy)methyl) pyrrolidin-1-yl)-1-(cyanomethyl)-4-oxo-1,4-dihydroquinoline-3-carboxylic acid | $^1$H NMR (400 MHz, DMSO-$d_6$) δ 14.92 (s, 1H), 9.00 (s, 1H), 8.13 (s, 1H), 7.91 (dd, J = 4.8, 1.6 Hz, 1H), 7.78 (dd, J = 7.6, 1.6 Hz, 1H), 7.11 (s, 1H), 6.92 (dd, J = 7.6, 4.8 Hz, 1H), 5.77 (s, 2H), 5.08-4.98 (m, 1H), 4.45-4.41 (m, 2H), 3.90-3.86 (m, 1H), 3.48-3.44 (m, 1H), 2.36-2.29 (m, 1H), 2.13-2.02 (m, 2H), 1.92-1.88 (m, 1H); MS (ESI): m/z 473.2 $[M + H]^+$ . . . | ++++ |
| 570. | 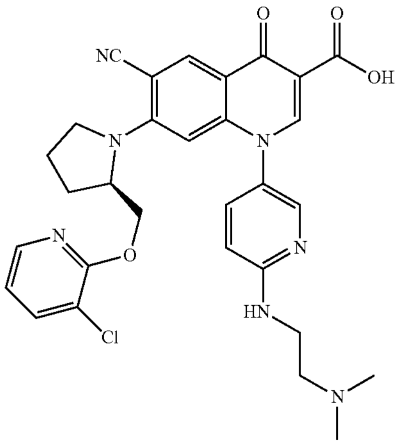 [SMILES: CN(C)CCNc1ccc(-n2cc(C(=O)O)c(=O)c3cc(C#N)c(N4CCC[C@@H]4COc4ncccc4Cl)cc32)cn1] | (R)-7-(2-(((3-chloropyridin-2-yl)oxy)methyl) pyrrolidin-1-yl)-6-cyano-1-(6-((2-(dimethylamino) ethyl)amino) pyridin-3-yl)-4-oxo-1,4-dihydroquinoline-3-carboxylic acid | $^1$H NMR (400 MHz, DMSO-$d_6$) δ 14.87 (s, 1H), 8.51 (d, J = 2.8 Hz, 1H), 8.45 (s, 1H), 8.16 (dd, J = 9.6, 1.6 Hz, 1H), 7.97 (dd, J = 4.8, 1.6 Hz, 1H), 7.83 (d, J = 7.6 Hz, 1H), 7.58-7.52 (m, 1H), 7.04-6.94 (m, 2H), 6.68 (d, J = 8.8 Hz, 0.5H), 6.51 (d, J = 8.8 Hz, 0.5H), 6.21 (d, J = 4.8 Hz, 1H), 4.84-4.76 (m, 1H), 4.43-4.35 (m, 2H), 3.70-3.60 (m, 1H), 3.42-3.32 (m, 3H), 2.48-2.40 (m, 2H), 2.21 (s, 3H), 2.20 (s, 3H), 2.19-2.09 (m, 2H), 2.04-1.88 (m, 2H); MS (ESI): m/z 588.3 $[M + H]^+$. | ++++ |
| 571. | 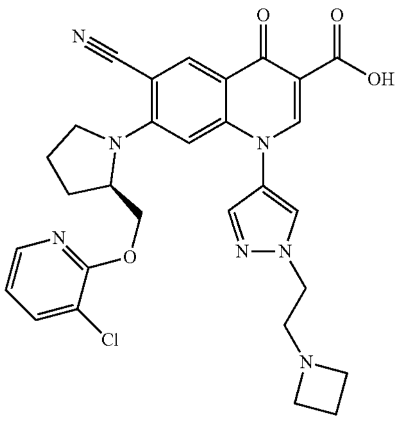 [SMILES: N#Cc1cc2c(=O)c(C(=O)O)cn(-c3cnn(CCN4CCC4)c3)c2cc1N1CCC[C@@H]1COc1ncccc1Cl] | (R)-1-(1-(2-(azetidin-1-yl)ethyl)-1H-pyrazol-4-yl)-7-(2-(((3-chloropyridin-2-yl)oxy)methyl) pyrrolidin-1-yl)-6-cyano-4-oxo-1,4-dihydroquinoline-3-carboxylic acid | $^1$H NMR (400 MHz, DMSO-$d_6$) δ 14.57 (bs, 1H), 8.51 (s, 1H), 8.44 (s, 1H), 8.31 (s, 1H), 7.98 (dd, J = 4.8, 1.6 Hz, 1H), 7.85 (s, 1H), 7.83 (dd, J = 7.6, 1.6 Hz, 1H), 7.04-6.96 (m, 1H), 6.41 (s, 1H), 4.84-4.76 (m, 1H), 4.43-4.35 (m, 2H), 4.20-4.10 (m, 2H), 3.70-3.60 (m, 1H), 3.50-3.40 (m, 1H), 3.24-3.14 (m, 4H), 2.90-2.80 (m, 2H), 2.22-2.11 (m, 2H), 2.09-1.90 (m, 2H); MS (ESI): m/z 574.4 $[M + H]^+$. | ++++ |

-continued

| EX # | Structure | IUPAC name | Analytical data | Potency Lin28a-dep Z11 $IC_{50}$ (μM) |
|---|---|---|---|---|
| 572. | 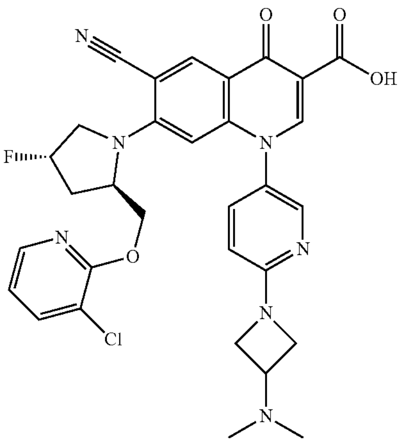 [SMILES: CN(C)C1CN(c2ccc(-n3cc(C(=O)O)c(=O)c4cc(C#N)c(N5C[C@@H](F)C[C@@H]5COc5ncccc5Cl)cc43)cn2)C1] | 7-((2R,4S)-2-(((3-chloropyridin-2-yl)oxy)methyl)-4-fluoropyrrolidin-1-yl)-6-cyano-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 8.55-8.49 (m, 2H), 8.36 (s, 1H), 7.92 (bs, 1H), 7.84 (d, J = 7.6 Hz, 2H), 6.99-6.98 (m, 1H), 6.69 (d, J = 8.4 Hz, 0.5H), 6.50 (d, J = 8.4 Hz, 0.5H), 6.27 (d, J = 9.6 Hz, 1H), 5.46 (d, J = 53.2 Hz, 1H), 4.80-4.70 (m, 1H), 4.54-4.49 (m, 1H), 4.40-4.22 (m, 6H), 4.00-3.84 (m, 3H), 2.85 (s, 6H), 2.51-2.50 (m, 1H), 2.43-2.38 (m, 1H) (—COOH proton was not observed); MS (ESI): m/z 618.3 [M + H]$^+$. . . | ++++ |
| 573. | 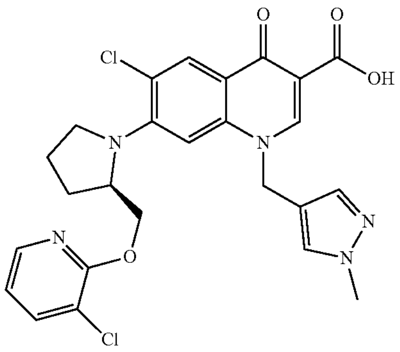 [SMILES: Cn1cc(Cn2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-((1-methyl-1H-pyrazol-4-yl) methyl)-4-oxo-1,4-dihydroquinoline-3-carboxylic acid | $^1$H NMR (400 MHz, DMSO-$d_6$): δ 15.30 (s, 1H), 9.10-8.80 (m, 1H), 8.08 (s, 1H), 7.89 (dd, J = 4.8, 1.6 Hz, 1H), 7.79 (dd, J = 8.0, 1.6 Hz, 1H), 7.69 (bs, 1H), 7.42 (bs, 1H), 7.17 (bs, 1H), 6.94-6.90 (m, 1H), 5.60-5.30 (m, 2H), 4.90-4.76 (m, 1H), 4.36-4.20 (m, 2H), 3.90-3.80 (m, 1H), 3.71 (s, 3H), 3.30-3.20 (m, 1H), 2.35-2.24 (m, 1H), 2.10-1.93 (m, 2H), 1.90-1.80 (m, 1H); MS (ESI): m/z 528.3 [M + H]$^+$ | ++++ |
| 574. | 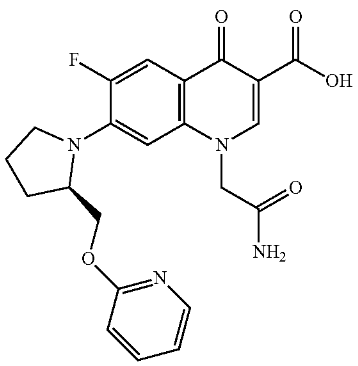 [SMILES: NC(=O)Cn1cc(C(=O)O)c(=O)c2cc(F)c(N3CCC[C@@H]3COc3ccccn3)cc21] | (R)-1-(2-amino-2-oxoethyl)-6-fluoro-4-oxo-7-(2-((pyridin-2-yloxy)methyl) pyrrolidin-1-yl)-1,4-dihydroquinoline-3-carboxylic acid | $^1$H NMR (400 MHz, DMSO-$d_6$) δ 15.50 (s, 1H), 8.85 (s, 1H), 8.07 (dd, J = 4.8, 1.2 Hz, 1H), 7.95 (s, 1H), 7.84 (d, J = 14.4 Hz, 1H), 7.68-7.63 (m, 1H), 7.53 (s, 1H), 6.94 (dd, J = 6.8, 5.6 Hz, 1H), 6.71 (d, J = 8.0 Hz, 1H), 6.58 (d, J = 7.6 Hz, 1H), 5.13 (s, 2H), 4.68-4.62 (m, 1H), 4.36-4.28 (m, 2H), 3.64-3.58 (m, 1H), 3.46-3.34 (m, 1H), 2.18-2.08 (m, 2H), 2.06-1.96 (m, 2H); MS (ESI): m/z 441.3 [M + H]$^+$. | +++ |

-continued

| EX # | Structure | IUPAC name | Analytical data | Potency Lin28a-dep Z11 $IC_{50}$ (μM) |
|---|---|---|---|---|
| 575. | 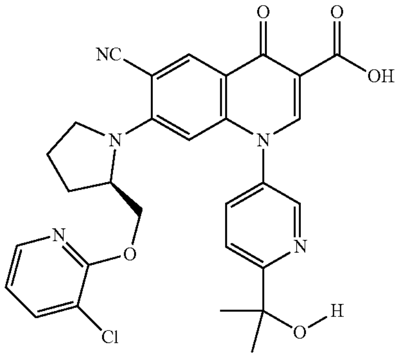 [SMILES: CC(C)(O)c1ccc(-n2cc(C(=O)O)c(=O)c3cc(C#N)c(N4CCC[C@@H]4COc4ncccc4Cl)cc32)cn1] | (R)-7-(2-(((3-chloropyridin-2-yl)oxy)methyl) pyrrolidin-1-yl)-6-cyano-1-(6-(2-hydroxypropan-2-yl)pyridin-3-yl)-4-oxo-1,4-dihydroquinoline-3-carboxylic acid | $^1$H NMR (400 MHz, DMSO-$d_6$): δ 14.67 (s, 1H), 8.75 (s, 1H), 8.68 (s, 1H), 8.48 (s, 1H), 8.08 (d, J = 7.6 Hz, 1H), 7.97 (dd, J = 4.8, 1.6 Hz, 1H), 7.90 (bs, 0.5H), 7.82 (dd, J = 8.0, 1.6 Hz, 1H), 7.76 (bs, 0.5H), 7.05-6.97 (m, 1H), 6.03 (s, 1H), 5.41 (s, 1H), 4.70-4.60 (m, 1H), 4.34 (s, 2H), 3.64-3.58 (m, 1H), 3.48-3.38 (m, 1H), 2.20-2.05 (m, 2H), 2.04-1.87 (m, 2H), 1.49 (s, 3H), 1.40 (bs, 3H); MS (ESI): m/z 560.3 [M + H]$^+$. | ++++ |
| 576. | 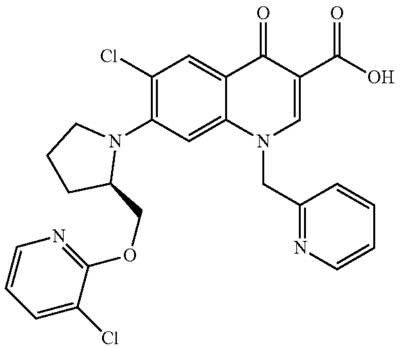 | (R)-6-chloro-7-(2-(((3-chloropyridin-2-yl)oxy)methyl) pyrrolidin-1-yl)-4-oxo-1-(pyridin-2-ylmethyl)-1,4-dihydroquinoline-3-carboxylic acid | $^1$H NMR (400 MHz, DMSO-$d_6$): δ 8.90 (s, 1H), 8.40 (dd, J = 4.8, 0.8 Hz, 1H), 8.07 (s, 1H), 7.91 (dd, J = 4.8, 1.6 Hz, 1H), 7.79 (dd, J = 7.6, 1.6 Hz, 1H), 7.64 (t, J = 7.2 Hz, 1H), 7.36 (bs, 1H), 7.10 (t, J = 5.6 Hz, 1H), 6.96-6.90 (m, 2H), 5.64 (s, 2H), 4.70-4.60 (m, 1H), 4.11-4.00 (m, 2H), 3.75-3.69 (m, 1H), 3.09 (bs, 1H), 2.30-2.20 (m, 1H), 2.05-1.97 (m, 1H), 1.96-1.87 (m, 1H), 1.83-1.74 (m, 1H) (—COOH proton was not observed); MS (ESI): m/z 525.0 [M + H]$^+$ | ++++ |
| 577. | 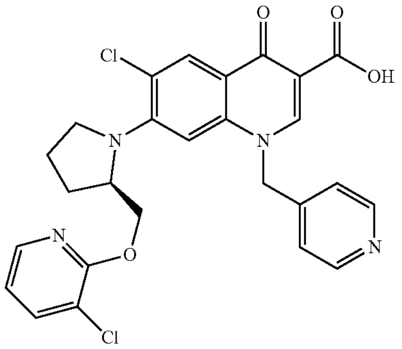 [SMILES: O=C(O)c1cn(Cc2ccncc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(pyridin-4-ylmethyl)-1,4-dihydroquinoline-3-carboxylic acid | $^1$H-NMR (400 MHz, DMSO-$d_6$) δ 15.18 (s, 1H), 9.15 (s, 1H), 8.41 (d, J = 6.0 Hz, 2H), 8.11 (s, 1H), 7.87 (dd, J = 4.8, 1.6 Hz, 1H), 7.77 (dd, J = 8.0, 1.6 Hz, 1H), 7.21 (d, J = 6.0 Hz, 2H), 6.93-6.90 (m, 1H), 6.80 (s, 1H), 5.82 (s, 2H), 4.75 (br s, 1H), 4.12-4.08 (m, 1H), 4.00-3.96 (m, 1H), 3.71-3.65 (m, 1H), 3.16 (t, J = 8.4 Hz, 1H), 2.33-2.22 (m, 1H), 2.00-1.87 (m, 2H), 1.81-1.72 (m, 1H); MS (ESI): m/z 525.2 [M + H]$^+$ | +++ |
| 578. | 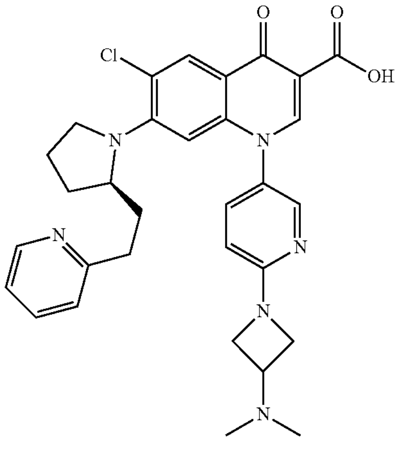 [SMILES: CN(C)C1CN(c2ccc(-n3cc(C(=O)O)c(=O)c4cc(Cl)c(N5CCC[C@@H]5CCc5ccccn5)cc43)cn2)C1] | (R)-6-chloro-1-(6-(3-(dimethylamino) azetidin-1-yl) pyridin-3-yl)-4-oxo-7-(2-(2-(pyridin-2-yl) ethyl)pyrrolidin-1-yl)-1,4-dihydroquinoline-3-carboxylic acid | $^1$H NMR (400 MHz, DMSO-$d_6$) δ 15.26 (bs, 1H), 8.56 (s, 1H), 8.42 (dd, J = 14.0, 4.4 Hz, 1H), 8.31 (dd, J = 15.6, 2.4 Hz, 1H), 8.18 (s, 1H), 7.85-7.74 (m, 1H), 7.70-7.64 (m, 1H), 7.21-7.15 (m, 2H), 6.66 (d, J = 8.8 Hz, 0.5H), 6.38 (d, J = 8.8 Hz, 0.5H), 6.27 (s, 1H), 4.06-3.98 (m, 2H), 3.80-3.71 (m, 4H), 3.27-3.16 (m, 3H), 2.61-2.52 (m, 1H), 2.33 (bs, 1H), 2.14 (s, 3H), 2.11 (s, 3H), 2.00-1.80 (m, 2H), 1.78-1.45 (m, 3H); MS (ESI): m/z 573.4 [M + H]$^+$ | +++ |

-continued

| EX # | Structure | IUPAC name | Analytical data | Potency Lin28a-dep Z11 $IC_{50}$ (μM) |
|---|---|---|---|---|
| 579. | 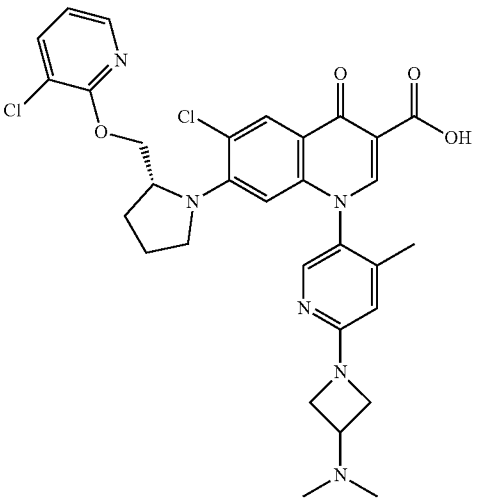 [SMILES: Cc1cc(N2CC(N(C)C)C2)ncc1-n1cc(C(=O)O)c(=O)c2cc(Cl)c(N3CCC[C@@H]3COc3ncccc3Cl)cc21] | (R)-6-chloro-7-(2-(((3-chloropyridin-2-yl)oxy)methyl) pyrrolidin-1-yl)-1-(5-(3-(dimethylamino) azetidin-1-yl)-4-methylpyridin-3-yl)-4-oxo-1,4-dihydroquinoline-3-carboxylic acid | $^1$H NMR (400 MHz, DMSO-$d_6$) δ 15.09 (bs, 1H), 8.54 (s, 1H), 8.18 (d, J = 3.2 Hz, 1H), 8.15 (s, 1H), 7.95-7.86 (m, 1H), 7.82 (dd, J = 7.6, 1.6 Hz, 1H), 7.00-6.93 (m, 1H), 6.50 (s, 0.5H), 6.37 (s, 0.5H), 6.24 (s, 0.5H), 6.19 (s, 0.5H), 4.83 (bs, 0.5H), 4.59 (bs, 0.5H), 4.30-4.10 (m, 7H), 3.60-3.40 (m, 1H), 3.24-3.10 (m, 1H), 2.64 (bs, 6H), 2.30-2.20 (m, 1H) 2.03-1.86 (m, 4H), 1.84-1.63 (m, 2H); MS (ESI): m/z 623.1 $[M + H]^+$ | ++++ |
| 580. | 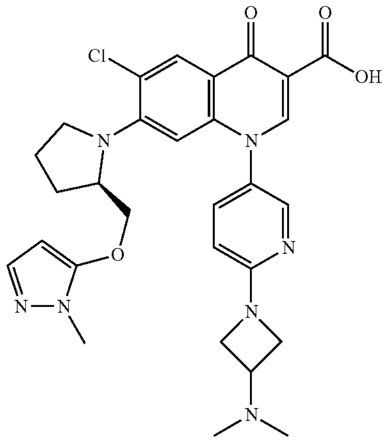 [SMILES: CN(C)C1CN(c2ccc(-n3cc(C(=O)O)c(=O)c4cc(Cl)c(N5CCC[C@@H]5COc5ccnn5C)cc43)cn2)C1] | (R)-6-chloro-1-(6-(3-(dimethylamino) azetidin-1-yl) pyridin-3-yl)-7-(2-(((1-methyl-1H-pyrazol-5-yl)oxy) methyl)pyrrolidin-1-yl)-4-oxo-1,4-dihydroquinoline-3-carboxylic acid | VT-$^1$H-NMR (400 MHz, DMSO-$d_6$): δ 14.78 (bs, 1H), 8.48 (s, 1H), 8.22 (d, J = 2.8 Hz, 1H), 8.20 (s, 1H), 7.65 (dd, J = 8.8, 2.4 Hz, 1H), 7.07 (d, J = 2.0 Hz, 1H), 6.46 (s, 1H), 6.43 (bs, 1H), 5.40 (d, J = 2.0 Hz, 1H), 4.53 (bs, 1H), 4.10-4.04 (m, 2H), 4.00-3.94 (m, 1H), 3.90-3.80 (m, 3H), 3.67-3.60 (m, 1H), 3.32 (s, 3H), 3.30-3.20 (m, 2H), 2.28-2.20 (m, 1H), 2.16 (s, 6H), 2.02-1.92 (m, 1H), 1.90-1.78 (m, 2H); MS (ESI): m/z 578.4 $[M + H]^+$. | ++++ |
| 581. | 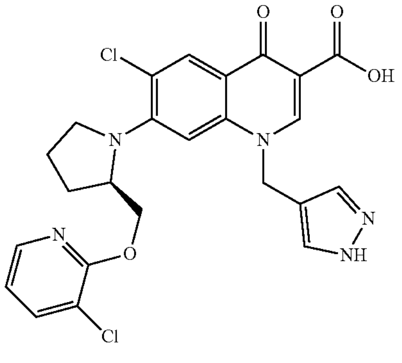 [SMILES: O=C(O)c1cn(Cc2cn[nH]c2)c2cc(N3CCC[C@@H]3COc3ncccc3Cl)c(Cl)cc2c1=O] | (R)-1-((1H-pyrazol-4-yl)methyl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.26 (s, 1H), 12.94 (s, 1H), 9.00 (s, 1H), 8.09 (s, 1H), 7.87 (dd, J = 4.8, 1.6 Hz, 1H), 7.85 (s, 1H), 7.77 (dd, J = 8.0, 1.6 Hz, 1H), 7.56 (bs, 1H), 6.92-6.88 (m, 1H), 5.56 (s, 2H), 4.96-4.90 (m, 1H), 4.40-4.30 (m, 2H), 3.90-3.80 (m, 1H), 3.30-3.20 (m, 1H), 2.35-2.24 (m, 1H), 2.10-1.93 (m, 2H), 1.90-1.80 (m, 1H); MS (ESI): 514.3 $[M + H]^+$ | +++ |

-continued

| EX # | Structure | IUPAC name | Analytical data | Potency Lin28a-dep Z11 $IC_{50}$ (μM) |
|---|---|---|---|---|
| 582. | 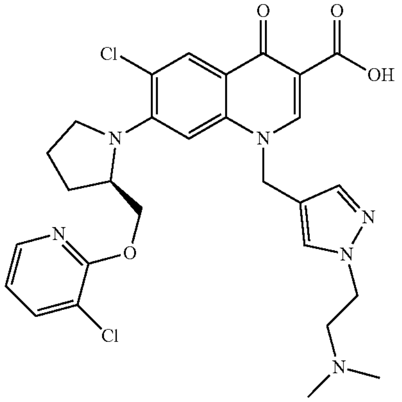 [SMILES: CN(C)CCn1cc(Cn2cc(C(=O)O)c(=O)c3cc(Cl)c(N4CCC[C@@H]4COc4ncccc4Cl)cc32)cn1] | (R)-6-chloro-7-(2-(((3-chloropyridin-2-yl)oxy)methyl) pyrrolidin-1-yl)-1-((1-(2-(dimethylamino) ethyl)-1H-pyrazol-4-yl)methyl)-4-oxo-1,4-dihydroquinoline-3-carboxylic acid | $^1$H NMR (400 MHz, DMSO-$d_6$) δ 15.26 (s, 1H), 9.05 (s, 1H), 8.09 (s, 1H), 7.88 (dd, J = 4.8, 1.6 Hz, 1H), 7.80 (s, 1H), 7.77 (dd, J = 7.6, 1.6 Hz, 1H), 7.49 (s, 1H), 7.20 (s, 1H), 6.93-6.90 (m, 1H), 5.56 (s, 2H), 4.94-4.88 (m, 1H), 4.31 (d, J = 8.0 Hz, 2H), 4.06 (t, J = 4.0 Hz, 2H), 3.88-3.80 (m, 1H), 3.30-3.20 (m, 1H), 2.67-2.55 (m, 2H), 2.33-2.28 (m, 1H), 2.07 (s, 7H), 2.08-1.87 (m, 2H); MS (ESI): m/z 585.3 [M + H]$^+$ | +++ |
| 583. | 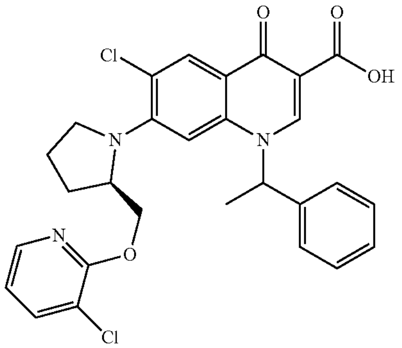 [SMILES: CC(c1ccccc1)n1cc(C(=O)O)c(=O)c2cc(Cl)c(N3CCC[C@@H]3COc3ncccc3Cl)cc21] | 6-chloro-7-((R)-2-(((3-chloropyridin-2-yl)oxy)methyl) pyrrolidin-1-yl)-4-oxo-1-(1-phentylethyl)-1,4-dihydroquinoline-3-carboxylic acid | $^1$H-NMR (400 MHz, DMSO-$d_6$): δ 15.20 (s, 1H), 8.81 (bs, 1H), 8.12 (bs, 1H), 7.88 (d, J = 4.4 Hz, 1H), 7.81-7.76 (m, 1H), 7.38-7.24 (m, 4H), 7.14 (t, J = 8.0 Hz, 1H), 6.94-6.91 (m, 1H), 6.30-6.22 (m, 1H), 4.79 (t, J = 6.0 Hz, 1H), 4.27-4.19 (m, 1H), 4.11-4.00 (m, 1H), 3.81-3.74 (m, 0.5 H), 3.67-3.60 (m, 0.5 H), 3.20-3.12 (m, 2H), 2.28-2.21 (m, 1H), 2.07-2.00 (m, 2H), 1.99 (t, J = 9.0 Hz, 3H), 1.83-1.76 (m, 1H); MS (ESI): m/z 537.9 [M + H]$^+$ | +++ |
| 584. | 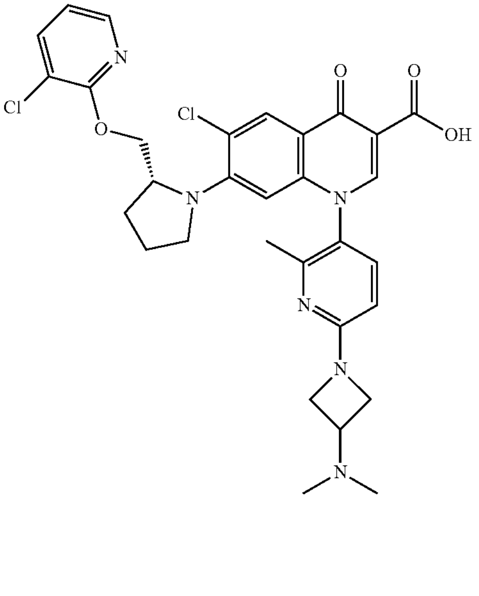 [SMILES: Cc1nc(N2CC(N(C)C)C2)ccc1-n1cc(C(=O)O)c(=O)c2cc(Cl)c(N3CCC[C@@H]3COc3ncccc3Cl)cc21] | (R)-6-chloro-7-(2-(((3-chloropyridin-2-yl)oxy)methyl) pyrrolidin-1-yl)-1-(6-(3-(dimethylamino) azetidin-1-yl)-2-methylpyridin-3-yl)-4-oxo-1,4-dihydroquinoline-3-carboxylic acid | $^1$H NMR (400 MHz, DMSO-$d_6$) δ 8.52 (d, J = 5.6 Hz, 1H), 8.18 (d, J = 8.0 Hz, 1H), 7.97-7.87 (m, 1H), 7.82 (td, J = 7.6, 1.6 Hz, 1H), 7.66-7.58 (m, 1H), 7.00-6.93 (m, 1H), 6.48 (d, J = 8.4 Hz, 0.5H), 6.28 (bs, 0.5H), 6.23 (s, 0.5H), 6.19 (s, 0.5H), 4.71 (bs, 1H), 4.30-4.10 (m, 7H), 3.60-3.40 (m, 1H), 3.21-3.14 (m, 1H), 2.58 (bs, 6H), 2.30-2.20 (m, 1H) 2.03-1.86 (m, 5H), 1.84-1.63 (m, 1H) (—COOH proton was not observed); MS (ESI): m/z 623.0 [M + H]$^+$ | ++++ |

-continued

| EX # | Structure | IUPAC name | Analytical data | Potency Lin28a-dep Z11 $IC_{50}$ (μM) |
|---|---|---|---|---|
| 585. | 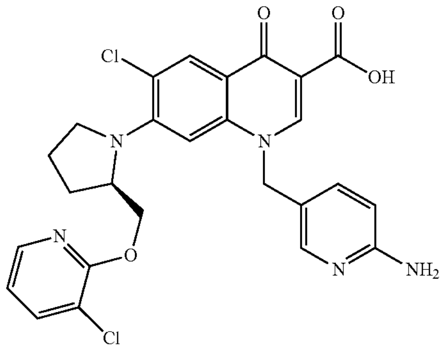 [SMILES: Nc1ccc(Cn2cc(C(=O)O)c(=O)c3cc(Cl)c(N4CCC[C@@H]4COc4ncccc4Cl)cc32)cn1] | (R)-1-((6-aminopyridin-3-yl)methyl)-6-chloro-7-(2-(((3-chloropyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.23 (s, 1H), 9.03 (s, 1H), 8.08 (s, 1H), 8.00 (d, J = 4.0 Hz, 1H), 7.88 (dd, J = 1.6, 4.4 Hz, 1H), 7.76 (dd, J = 1.6, 7.6 Hz, 1H), 7.31 (dd, J = 1.6, 8.8 Hz, 1H), 7.11 (s, 1H), 6.91-6.87 (m, 1H), 6.38 (d, J = 8.0 Hz, 1H), 6.07 (bs, 2H), 5.50 (s, 2H), 4.93-4.88 (m, 1H), 4.29 (d, J = 4.0 Hz, 2H), 3.82-3.75 (m, 1H), 3.31-3.24 (m, 1H), 2.33-2.28 (m, 1H), 1.99-1.95 (m, 2H), 1.87-1.85 (m, 1H); MS (ESI): m/z 540.3 $[M + H]^+$ | +++ |
| 586. | 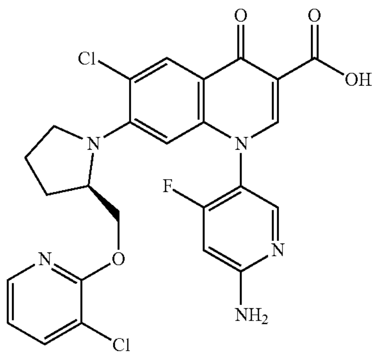 [SMILES: Nc1cc(F)c(-n2cc(C(=O)O)c(=O)c3cc(Cl)c(N4CCC[C@@H]4COc4ncccc4Cl)cc32)cn1] | (R)-1-(6-amino-4-fluoropyridin-3-yl)-6-chloro-7-(2-(((3-chloropyridin-2-yl)oxy)methyl) pyrrolidin-1-yl)-4-oxo-1,4-dihydroquinoline-3-carboxylic acid | 1H NMR (400 MHz, DMSO-$d_6$): 14.93 (s, 1H), 8.61 (d, J = 12.0 Hz, 1H), 8.22-8.14 (m, 2H), 7.88 (ddd, J = 10.8, 5.2, 1.6 Hz, 1H), 7.80-7.75 (m, 1H), 6.97-6.86 (m, 3H), 6.44-6.26 (m, 2H), 4.80-4.60 (m, 1H), 4.35-4.26 (m, 2H), 3.60-3.48 (m, 1H), 3.26-3.16 (m, 1H), 2.30-2.20 (m, 1H), 2.04-1.88 (m, 2H), 1.84-1.78 (m, 1H); MS (ESI): m/z 543.9 $[M + H]^+$. | ++++ |
| 587. | 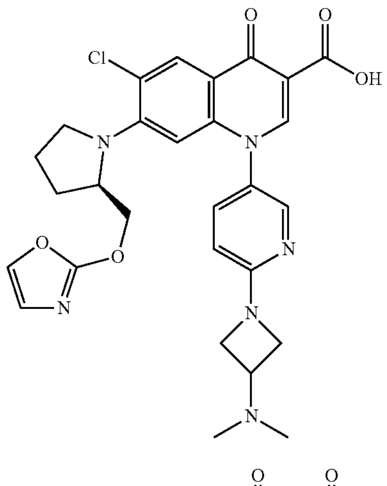 | (R)-6-chloro-1-(6-(3-(dimethylamino) azetidin-1-yl) pyridin-3-yl)-7-(2-((oxazol-2-yloxy) methyl) pyrrolidin-1-yl)-4-oxo-1,4-dihydroquinoline-3-carboxylic acid | VT $^1$H-NMR (400 MHz, DMSO-$d_6$): δ 8.49 (s, 1H), 8.20 (d, J = 16.8 Hz, 2H), 7.66 (bs, 1H), 7.44 (s, 1H), 6.75 (s, 1H), 6.48 (s, 2H), 4.50 (bs, 1H), 4.31-4.21 (m, 2H), 4.10-4.04 (m, 2H), 3.61-3.58 (m, 2H), 3.32-3.26 (m, 1H), 3.18 (bs, 3H), 2.24-2.21 (m, 1H), 2.17 (s, 6H), 1.97-1.88 (m, 1H), 1.87-1.75 (m, 2H) (—COOH proton was not observed); MS (ESI): m/z 565.0 $[M + H]^+$. | ++++ |
| 588. | 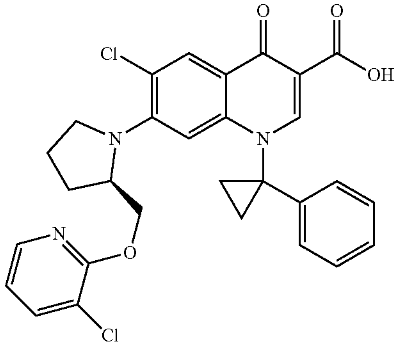 [SMILES: O=C(O)c1cn(C2(c3ccccc3)CC2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-4-oxo-1-(1-phenylcyclo-propyl)-1,4-dihydroquinoline-3-carboxylic acid | VT $^1$H NMR (400 MHz, DMSO-$d_6$) δ 14.82 (bs, 1H), 8.83 (s, 1H), 8.13 (s, 1H), 7.88 (d, J = 4.4 Hz, 1H), 7.73 (d, J = 8.0 Hz, 1H), 7.24-7.18 (m, 2H), 7.11 (s, 2H), 6.99 (d, J = 7.6 Hz, 2H), 6.92-6.89 (m, 1H), 4.70-4.62 (m, 1H), 4.40-4.00 (m, 2H), 3.82-3.60 (m, 1H), 3.30-3.08 (m, 1H), 2.38-2.18 (m, 1H), 2.08-1.9 (m, 4H), 1.90-1.76 (m, 2H), 1.7-1.5 (m, 1H); MS (ESI): m/z 550.3 $[M + H]^+$. | +++ |

-continued

| EX # | Structure | IUPAC name | Analytical data | Potency Lin28a-dep Z11 $IC_{50}$ (µM) |
|---|---|---|---|---|
| 589. | 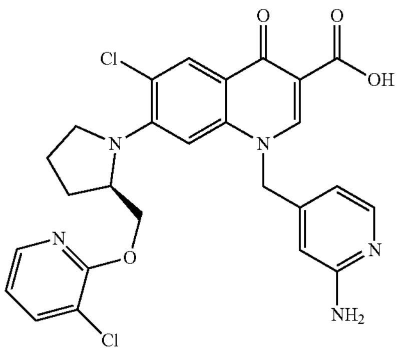 [SMILES: Nc1cc(Cn2cc(C(=O)O)c(=O)c3cc(Cl)c(N4CCC[C@@H]4COc4ncccc4Cl)cc32)ccn1] | (R)-1-((2-aminopyridin-4-yl)methyl)-6-chloro-7-(2-(((3-chloropyridin-2-yl)oxy)methyl) pyrrolidin-1-yl)-4-oxo-1,4-dihydroquinoline-3-carboxylic acid | $^{1}$H NMR (400 MHz, DMSO-$d_6$): δ 15.15 (bs, 1H), 9.12 (s, 1H), 8.13 (s, 1H), 7.89-7.85 (m, 2H), 7.82 (bs, 2H), 7.75 (dd, J = 7.8, 1.8 Hz, 1H), 6.93-6.89 (m, 1H), 6.79-6.76 (m, 2H), 6.47 (s, 1H), 5.85 (s, 2H), 4.85-4.75 (m, 1H), 4.18 (dd, J = 11.6, 4.4 Hz, 1H), 4.07 (dd, J = 11.6, 4.4 Hz, 1H), 3.78-3.71 (m, 1H), 3.34-3.30 (m, 1H), 2.27-2.20 (m, 1H), 2.08-1.98 (m, 2H), 1.85-1.76 (m, 1H); MS (ESI): m/z 540.2 [M + H]$^+$. | +++ |
| 590. | 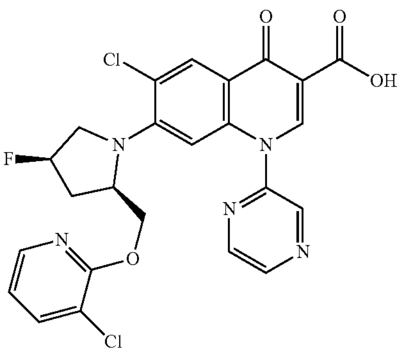 [SMILES: O=C(O)c1cn(-c2cnccn2)c2cc(N3C[C@H](F)C[C@@H]3COc3ncccc3Cl)c(Cl)cc2c1=O] | 6-chloro-7-((2R,4R)-2-(((3-chloropyridin-2-yl)oxy)methyl)-4-fluoropyrrolidin-1-yl)-4-oxo-1-(pyrazin-2-yl)-1,4-dihydroquinoline-3-carboxylic acid | $^{1}$H NMR (400 MHz, DMSO-$d_6$) δ 14.77 (s, 1H), 9.11 (s, 1H), 8.97-8.93 (m, 2H), 8.79-8.76 (m, 1H), 8.19 (s, 1H), 7.93 (dd, J = 4.8, 1.6 Hz, 1H), 7.75 (dd, J = 7.6, 1.6 Hz, 1H), 6.96-6.93 (m, 1H), 6.72 (s, 1H), 5.46-5.30 (m, 1H), 4.94-4.89 (m, 1H), 4.45-4.38 (m 1H), 4.34-4.26 (m, 1H), 4.00-3.88 (m, 1H), 3.65-3.53 (m, 1H), 2.60-2.50 (m, 1H), 2.20-2.10 (m, 1H); MS (ESI): m/z 530.2 [M + H]$^+$. | ++++ |
| 591. | 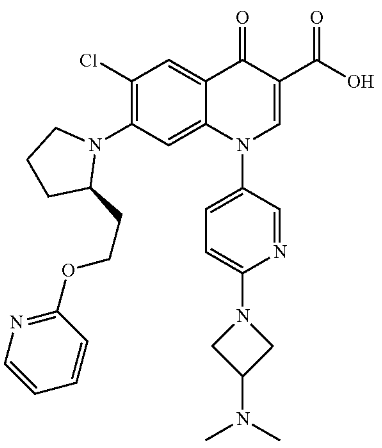 [SMILES: CN(C)C1CN(c2ccc(-n3cc(C(=O)O)c(=O)c4cc(Cl)c(N5CCC[C@@H]5CCOc5ccccn5)cc43)cn2)C1] | (R)-6-chloro-1-(6-(3-(dimethylamino) azetidin-1-yl) pyridin-3-yl)-4-oxo-7-(2-(2-(pyridin-2-yloxy) ethyl)pyrrolidin-1-yl)-1,4-dihydroquinoline-3-carboxylic acid | $^{1}$H NMR (400 MHz, DMSO-$d_6$) δ 15.26 (bs, 1H), 8.56 (d, J = 8.8 Hz, 1H), 8.30 (dd, J = 14.0, 4.4 Hz, 1H), 8.19 (s, 1H), 8.16-8.12 (m, 1H), 7.83-7.77 (m, 1H), 7.74-7.67 (m, 1H), 7.00-6.94 (m, 1H), 6.73-6.67 (m, 1H), 6.71 (d, J = 8.8 Hz, 0.5H), 6.57 (d, J = 8.8 Hz, 0.5H), 6.32 (d, J = 6.4 Hz, 1H), 4.20-4.10 (m, 2H), 4.07-4.00 (m, 1H), 3.98-3.88 (m, 2H), 3.80-3.70 (m, 3H), 3.27-3.20 (m, 1H), 3.19-3.10 (m, 1H), 2.24-2.18 (m, 1H), 2.10 (s, 6H), 2.09-1.88 (m, 2H), 1.78-1.55 (m, 3H); MS (ESI): m/z 589.4 [M + H]$^+$ | ++++ |

-continued

| EX # | Structure | IUPAC name | Analytical data | Potency Lin28a-dep Z11 $IC_{50}$ (μM) |
|---|---|---|---|---|
| 592. | 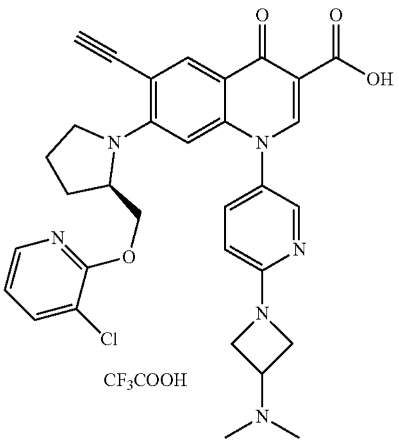 [SMILES: C#Cc1cc2c(=O)c(C(=O)O)cn(-c3ccc(N4CC(N(C)C)C4)nc3)c2cc1N1CCC[C@@H]1COc1ncccc1Cl ; "CF3COOH"] $CF_3COOH$ | (R)-7-(2-(((3-chloropyridin-2-yl)oxy)methyl) pyrrolidin-1-yl)-1-(6-(3-(dimethylamino) azetidin-1-yl) pyridin-3-yl)-6-ethynyl-4-oxo-1,4-dihydroquinoline-3-carboxylic acid | $^1$H NMR (400 MHz, DMSO-$d_6$): δ 15.18 (bs, 1H), 10.44 (bs, 1H), 8.44 (d, J = 4.8 Hz, 1H), 8.35 (s, 1H), 8.23 (s, 1H), 7.96 (d, J = 4.0 Hz, 1H), 7.86-7.80 (m, 2H), 7.05-6.97 (m, 1H), 6.66 (d, J = 8.8 Hz, 0.5 H), 6.47 (d, J = 8.8 Hz, 0.5H), 6.07 (s, 1H), 5.20-5.00 (m, 1H), 4.52 (s, 1H), 4.36-4.16 (m, 7H), 3.34-3.24 (m, 2H), 2.85 (s, 6H), 2.20-2.10 (m, 1H), 2.09-1.95 (m, 2H), 1.92-1.80 (m, 1H); MS (ESI): m/z 599.3 [M + H]$^+$. | ++++ |
| 593. | 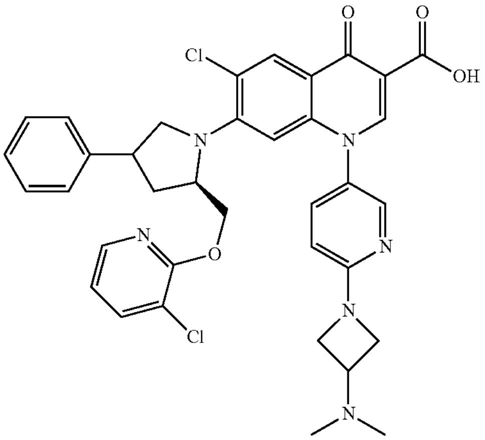 [SMILES: CN(C)C1CN(c2ccc(-n3cc(C(=O)O)c(=O)c4cc(Cl)c(N5CC(c6ccccc6)C[C@@H]5COc5ncccc5Cl)cc43)cn2)C1] | 6-chloro-7-((2R)-2-(((3-chloropyridin-2-yl)oxy)methyl)-4-phenyl-pyrrolidin-1-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.05 (s, 1H), 8.53 (d, J = 7.6 Hz, 1H), 8.24 (s, 1H), 8.19 (s, 1H), 7.94-7.82 (m, 2H), 7.68 (d, J = 8.8 Hz, 1H), 7.35-7.32 (m, 4H), 7.30-7.23 (m, 1H), 7.02-6.94 (m, 1H), 6.57-6.49 (m, 1.5H), 6.26 (d, J = 8.8 Hz, 0.5H), 4.80-4.60 (m, 1H), 4.46-4.34 (m, 2H), 4.10-4.00 (m, 2H), 3.82-3.75 (m, 2H), 3.72-3.52 (m, 2H), 3.48-3.36 (m, 1H), 3.28-3.19 (m, 1H), 2.65-2.57 (m, 1H), 2.24-2.15 (m, 1H), 2.14 (s, 6H); MS (ESI) m/z: 685.3 [M + H]$^+$ | ++++ |
| 594. | 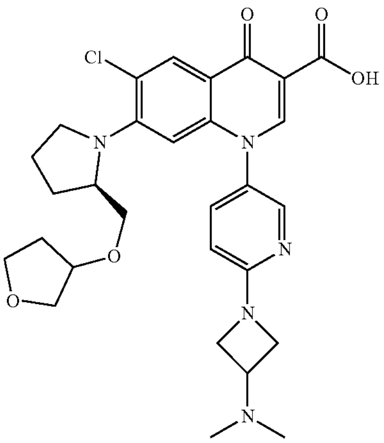 [SMILES: CN(C)C1CN(c2ccc(-n3cc(C(=O)O)c(=O)c4cc(Cl)c(N5CCC[C@@H]5COC5CCOC5)cc43)cn2)C1] | 6-chloro-1-(6-(3-(dimethylamino) azetidin-1-yl) pyridin-3-yl)-4-oxo-7-((2R)-2-(((tetrahydro-furan-3-yl)oxy) methyl) pyrrolidin-1-yl)-1,4-dihydroquinoline-3-carboxylic acid | $^1$H NMR (400 MHz, DMSO-$d_6$): δ 15.11 (bs, 1H), 8.55 (d, J = 6.0 Hz, 1H), 8.33 (s, 1H), 8.20 (s, 1H), 7.86-7.80 (m, 1H), 6.64-6.58 (m, 1H), 6.41-6.37 (m, 1H), 4.29-4.12 (m, 3H), 4.09-3.95 (m, 2H), 3.85-3.75 (m, 1H), 3.62-3.42 (m, 5H), 3.30-3.21 (m, 2H), 3.20-3.11 (m, 2H), 2.41 (s, 6H), 2.16-2.12 (m, 1H), 1.91-1.85 (m, 1H), 1.81-1.65 (m, 3H), 1.64-1.45 (m, 1H); MS (ESI): m/z 568.4 [M + H]$^+$ | +++ |

-continued

| EX # | Structure | IUPAC name | Analytical data | Potency Lin28a-dep Z11 $IC_{50}$ (μM) |
|---|---|---|---|---|
| 595. | 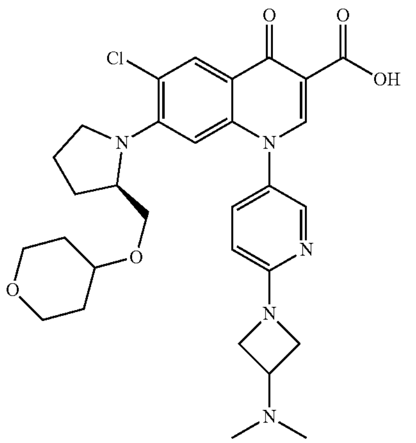 [SMILES: CN(C)C1CN(c2ccc(-n3cc(C(=O)O)c(=O)c4cc(Cl)c(N5CCC[C@@H]5COC5CCOCC5)cc43)cn2)C1] | (R)-6-chloro-1-(6-(3-(dimethylamino)azetidin-1-yl)pyridin-3-yl)-4-oxo-7-(2-(((tetrahydro-2H-pyran-4-yl)oxy)methyl)pyrrolidin-1-yl)-1,4-dihydroquinoline-3-carboxylic acid | $^1$H-NMR (400 MHz, DMSO-$d_6$): δ 15.16 (s, 1H), 8.54 (d, J = 6.0 Hz, 1H), 8.28 (s, 1H), 8.19 (s, 1H), 7.81-7.74 (m, 1H), 6.59-6.51 (m, 1H), 6.40 (d, J = 6.0 Hz, 1H), 4.19 (bs, 1H), 4.12-4.08 (m, 2H), 3.85-3.80 (m, 2H), 3.65-3.55 (m, 3H), 3.36-3.29 (m, 1H), 3.28-3.16 (m, 6H), 2.13 (s, 7H), 1.92-1.85 (m, 1H), 1.78-1.63 (m, 2H), 1.61-1.52 (m, 2H), 1.23-1.16 (m, 2H); MS (ESI): m/z 582.4 $[M + H]^+$ | +++ |
| 596. | 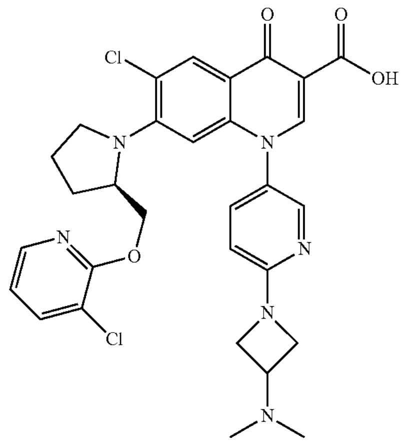 | (R)-6-chloro-7-(2-(((3-chloropyridin-2-yl)thio)methyl)pyrrolidin-1-yl)-1-(6-(3-(dimethylamino)azetidin-1-yl)pyridin-3-yl)-4-oxo-1,4-dihydroquinoline-3-carboxylic acid | 1H NMR (400 MHz, DMSO-d6) δ 15.10 (brs, 1H), 8.54 (d, J = 8.0 Hz, 1H), 8.32-8.24 (m, 1H), 8.26-8.22 (m, 1H), 8.20-8.05 (m, 2H), 7.92-7.61 (m, 2H), 7.15-7.05 (m, 1H), 6.34 (d, J = 12.4 Hz, 1H), 4.44-4.25 (m, 1H), 4.01-3.90 (m, 2H), 3.95-3.65 (m, 3H), 3.53-3.22 (m, 4H), 2.14 (s, 7H), 2.00-1.95 (m, 1H), 1.83-1.68 (m, 2H) MS (ESI): m/z 625.3 $[M + H]^+$ | ++++ |
| 597. | 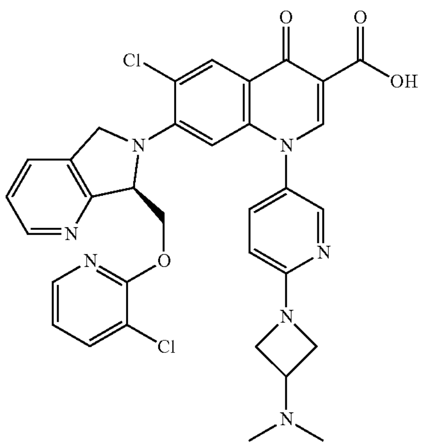 [SMILES: CN(C)C1CN(c2ccc(-n3cc(C(=O)O)c(=O)c4cc(Cl)c(N5Cc6cccnc6[C@@H]5COc5ncccc5Cl)cc43)cn2)C1] | (R)-6-chloro-7-(7-(((3-chloropyridin-2-yl)oxy)methyl)-5,7-dihydro-6H-pyrrolo[3,4-b]pyridin-6-yl)-1-(6-(3-(dimethylamino)azetidin-1-yl)pyridin-3-yl)-4-oxo-1,4-dihydroquinoline-3-carboxylic acid | 1H NMR (400 MHz, DMSO-$d_6$) δ 15.00 (brs, 1H), 8.54 (d, J = 8.0 Hz, 1H), 8.50 (d, J = 4.4 Hz, 1H), 8.32-8.19 (m, 2H), 7.92-7.60 (m, 3.5H), 7.61 (d, J = 6.8 Hz, 0.5H), 7.36-7.32 (m, 1H), 6.92-6.88 (m, 1H), 6.68 (d, J = 4.0 Hz, 1H), 6.60-6.53 (m, 1H), 6.06 (d, J = 15.6 Hz, 1H), 4.94 (t, J = 14.4 Hz, 1H), 4.70-4.60 (m, 2H), 4.54-4.46 (m, 1H), 4.15-4.08 (m, 2H), 3.90-3.80 (m, 2H), 3.28-3.22 (m, 1H), 2.15 (s, 6H); MS (ESI): m/z 658.2 $[M + H]^+$ | ++++ |

-continued

| EX # | Structure | IUPAC name | Analytical data | Potency Lin28a-dep Z11 $IC_{50}$ (μM) |
| --- | --- | --- | --- | --- |
| 598. | 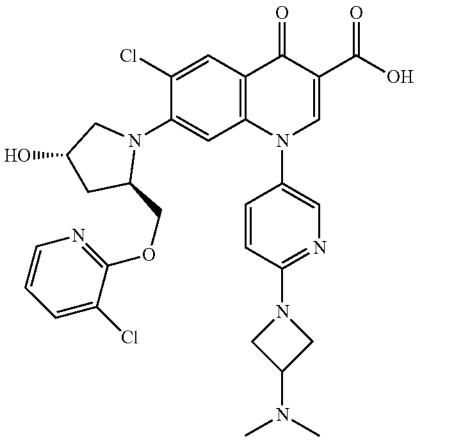 [SMILES: CN(C)C1CN(c2ccc(-n3cc(C(=O)O)c(=O)c4cc(Cl)c(N5C[C@@H](O)C[C@@H]5COc5ncccc5Cl)cc43)cn2)C1] | 6-chloro-7-((2R,4S)-2-(((3-chloropyridin-2-yl)oxy)methyl)-4-hydroxypyrrolidin-1-yl)-1-(6-(3-(dimethylamino)azetidin-1-yl)pyridin-3-yl)-4-oxo-1,4-dihydroquinoline-3-carboxylic acid | $^1$H-NMR (400 MHz, DMSO-$d_6$): δ 15.02 (bs, 1H), 8.53 (d, J = 11.60 Hz, 1H), 8.28-8.22 (m, 1H), 8.18 (s, 1H), 7.94-7.82 (m, 2H), 7.74-7.65 (m, 1H), 7.02-6.94 (m, 1H), 6.55 (d, J = 9.20 Hz, 0.5H), 6.40 (d, J = 7.6 Hz, 1H), 6.21 (d, J = 8.80 Hz, 0.5H), 4.93 (s, 1H), 4.60-4.46 (m, 1H), 4.40-4.24 (m, 3H), 4.10-4.00 (m, 2H), 3.86-3.78 (m, 3H), 3.25-3.19 (m, 1H), 3.15-3.06 (m, 1H), 2.15 (s, 7H), 2.10-2.00 (m, 1H); MS (ESI) m/z: 625.2 $[M + H]^+$ | ++++ |
| 599. | 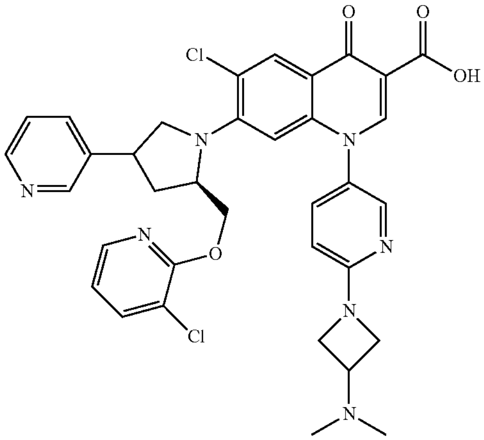 | 6-chloro-7-((2R)-2-(((3-chloropyridin-2-yl)oxy)methyl)-4-(pyridin-3-yl)pyrrolidin-1-yl)-1-(6-(3-(dimethylamino)azetidin-1-yl)pyridin-3-yl)-4-oxo-1,4-dihydroquinoline-3-carboxylic acid | $^1$H-NMR (400 MHz, DMSO-$d_6$): δ 15.02 (bs, 1H), 8.58-8.54 (m, 2H), 8.48 (dd, J = 4.8, 1.6 Hz, 1H), 8.20 (s, 1H), 7.94-7.82 (m, 2H), 7.85 (d, J = 8.0 Hz, 1H), 7.67 (dd, J = 8.8, 2.8 Hz, 1H), 7.42-7.36 (m, 1H), 7.02-6.94 (m, 1H), 6.57-6.51 (m, 1.5H), 6.24 (d, J = 8.8 Hz, 0.5H), 4.80-4.60 (m, 1H), 4.48-4.30 (m, 2H), 4.10-4.00 (m, 2H), 3.82-3.75 (m, 2H), 3.72-3.60 (m, 2H), 3.50-3.40 (m, 1H), 3.25-3.19 (m, 1H), 3.15-3.06 (m, 1H), 2.70-2.60 (m, 1H), 2.24-2.14 (m, 1H), 2.13 (s, 6H); MS (ESI) m/z: 686.2 $[M + H]^+$ | ++++ |
| 600. | 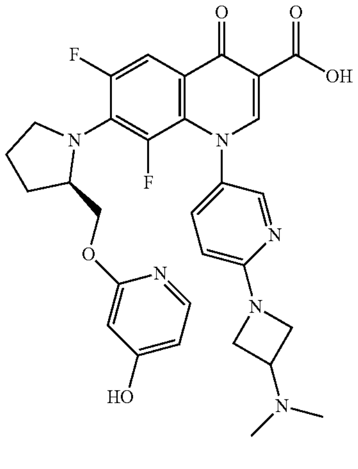 [SMILES: CN(C)C1CN(c2ccc(-n3cc(C(=O)O)c(=O)c4cc(F)c(N5CCC[C@@H]5COc5cc(O)ccn5)c(F)c43)cn2)C1] | (R)-1-(6-(3-(dimethylamino)azetidin-1-yl)pyridin-3-yl)-6,8-difluoro-7-(2-(((4-hydroxypyridin-2-yl)oxy)methyl)pyrrolidin-1-yl)-4-oxo-1,4-dihydroquinoline-3-carboxylic acid | $^1$H-NMR (400 MHz, DMSO-$d_6$): δ 14.96 (bs, 1H), 10.54 (bs, 1H), 8.38 (d, J = 5.6 Hz, 1H), 8.26 (d, J = 15.6 Hz, 1H), 7.80-7.64 (m, 3H), 6.49-6.34 (m, 2H), 5.71 (d, J = 6.4 Hz, 1H), 4.46-4.38 (m, 1H), 4.24-4.00 (m, 4H), 3.84-3.77 (m, 2H), 3.72-3.60 (m, 1H), 3.30-3.18 (m, 2H), 2.13 (s, 7H), 2.00-1.90 (m, 1H), 1.80-1.60 (m, 2H); MS (ESI) m/z: 593.4 $[M + H]^+$ | ++++ |

-continued

| EX # | Structure | IUPAC name | Analytical data | Potency Lin28a-dep Z11 $IC_{50}$ (μM) |
|---|---|---|---|---|
| 601. | 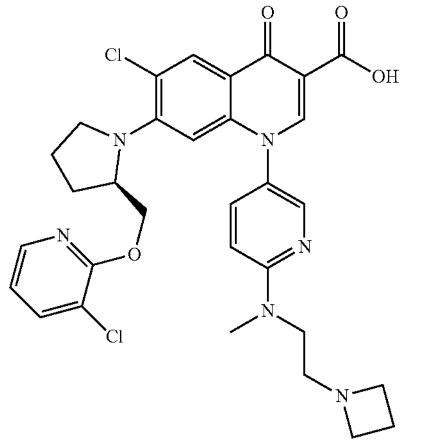 [SMILES: CN(CCN1CCC1)c1ccc(-n2cc(C(=O)O)c(=O)c3cc(Cl)c(N4CCC[C@@H]4COc4ncccc4Cl)cc32)cn1] | (R)-1-(6-((2-(azetidin-1-yl)ethyl)(methyl)amino)pyridin-3-yl)-6-chloro-7-(2-(((3-chloropyridin-2-yl)oxy)methyl)pyrrolidin-1-yl)-4-oxo-1,4-dihydroquinoline-3-carboxylic acid | 1H NMR (400 MHz, DMSO-$d_6$): δ 15.12 (bs, 1H), 8.52 (d, J = 7.6 Hz, 1H), 8.23 (brs, 1H), 8.16 (s, 1H), 7.93-7.88 (m, 1H), 7.80 (d, J = 7.6 Hz, 1H), 7.72-7.62 (m, 1H), 6.98-6.92 (m, 1H), 6.80 (d, J = 8.8 Hz, 0.5H), 6.21 (d, J = 8.8 Hz, 0.5H), 6.43 (s, 1H), 4.76-4.68 (m, 1H), 4.40-4.20 (m, 2H), 3.68-3.48 (m, 4H), 3.30-3.18 (m, 5H), 3.06 (d, J = 6.4 Hz, 3H), 2.74-2.68 (m, 1H), 2.30-2.20 (m, 1H), 2.10-1.90 (m, 4H), 1.84-1.74 (m, 1H); MS (ESI) m/z: 623.3 $[M + H]^+$. | ++++ |
| 602. | 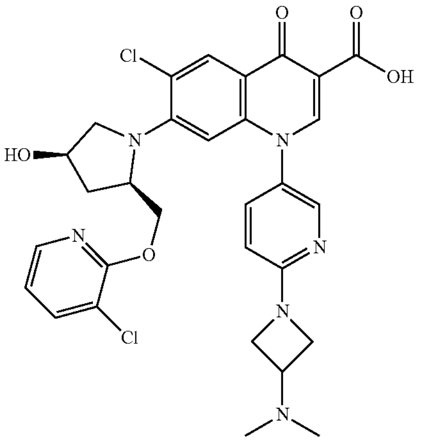 [SMILES: CN(C)C1CN(c2ccc(-n3cc(C(=O)O)c(=O)c4cc(Cl)c(N5C[C@H](O)C[C@@H]5COc5ncccc5Cl)cc43)cn2)C1] | 6-chloro-7-((2R,4R)-2-(((3-chloroypyridin-2-yl)oxy)methyl)-4-hydroxypyrrolidin-1-yl)-1-(6-(3-(dimethylamino)azetidin-1-yl)pyridin-3-yl)-4-oxo-1,4-dihydroquinoline-3-carboxylic acid | $^1H$ NMR (400 MHz, DMSO-$d_6$) δ 15.06 (s, 1H), 8.52 (d, J = 8.4 Hz, 1H), 8.24 (s, 1H), 8.14 (s, 1H), 7.92-7.88 (m, 1H), 7.83-7.75 (m, 1H), 7.67 (d, J = 8.0 Hz, 1H), 6.97-6.88 (m, 1H), 6.37 (s, 1H), 6.31 (d, J = 8.8 Hz, 1H), 5.3-5.26 (m, 1H), 4.74-4.64 (m, 1H), 4.45-4.38 (m, 1H), 4.30-4.22 (m, 2H), 4.12-4.02 (m, 2H), 3.85-3.78 (m, 2H), 3.45-3.18 (m, 2H), 2.4-2.32 (m, 1H), 2.14 (s, 6H), 1.82-1.78 (m, 2H); MS (ESI) m/z: 625.3 $[M + H]^+$. | ++++ |
| 603. | 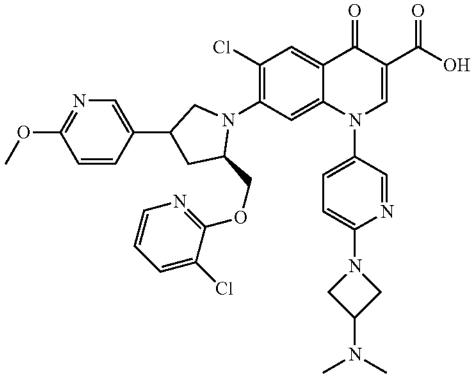 [SMILES: COc1ccc(C2C[C@H](COc3ncccc3Cl)N(c3cc4c(cc3Cl)c(=O)c(C(=O)O)cn4-c3ccc(N4CC(N(C)C)C4)nc3)C2)cn1] | 6-chloro-7-((2R)-2-(((3-chloropyridin-2-yl)oxy)methyl)-4-(6-methoxypyridin-3-yl)pyrrolidin-1-yl)-1-(6-(3-(dimethylamino)azetidin-1-yl)pyridin-3-yl)-4-oxo-1,4-dihydroquinoline-3-carboxylic acid | $^1H$-NMR (400 MHz, DMSO-$d_6$): δ 15.02 (bs, 1H), 8.53 (d, J = 11.6 Hz, 1H), 8.24 (s, 1H), 8.20 (s, 1H), 8.10 (s, 1H), 7.94-7.82 (m, 2H), 7.72-7.66 (m, 2H), 7.00-6.92 (m, 1H), 6.82 (d, J = 8.4 Hz, 1H), 6.55 (d, J = 8.8 Hz, 0.5H), 6.50 (d, J = 9.2 Hz, 1H), 6.25 (d, J = 8.8 Hz, 0.5H), 4.80-4.60 (m, 1H), 4.48-4.30 (m, 2H), 4.10-4.00 (m, 2H), 3.83 (s, 3H), 3.82-3.73 (m, 2H), 3.66-3.52 (m, 2H), 3.44-3.34 (m, 1H), 3.25-3.19 (m, 1H), 2.64-2.56 (m, 1H), 2.08 (s, 7H); MS (ESI) m/z: 716.3 $[M + H]^+$ | ++++ |

-continued

| EX # | Structure | IUPAC name | Analytical data | Potency Lin28a-dep Z11 $IC_{50}$ (μM) |
|---|---|---|---|---|
| 604. | 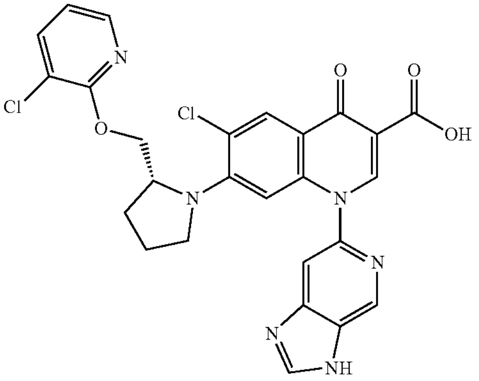 [SMILES: O=C(O)c1cn(-c2cc3nc[nH]c3cn2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(3H-imidazo[4,5-c] pyridin-6-yl)-4-oxo-1,4-dihydroquinoline-3-carboxylic acid | $^1$H NMR (400 MHz, DMSO-$d_6$) δ 15.06 (s, 1H), 14.38 (s, 1H), 8.91 (s, 1H), 8.78 (s, 1H), 8.63 (s, 1H), 8.18 (s, 1H), 8.06 (s, 1H), 7.83 (dd, J = 4.8, 1.6 Hz, 1H), 7.77 (dd, J = 8.0, 2.4 Hz, 1H), 6.95-6.90 (m, 1H), 6.51 (s, 1H), 4.64-4.57 (m, 1H), 4.24 (d, J = 4.0 Hz, 2H), 3.50-3.40 (m, 1H), 3.16-3.10 (m, 1H), 2.22-2.15 (m, 1H), 1.96-1.81 (m, 2H), 1.80-1.69 (m, 1H); MS (ESI): m/z 551.3 $[M + H]^+$ | ++++ |
| 605. | 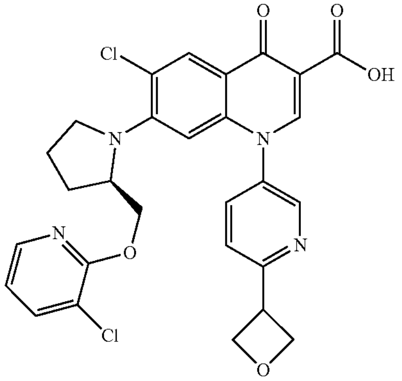 [SMILES: O=C(O)c1cn(-c2ccc(C3COC3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-(oxetan-3-yl) pyridin-3-yl)-4-oxo-1,4-dihydroquinoline-3-carboxylic acid | $^1$HNMR (400 MHz, DMSO-$d_6$): δ 15.00 (s, 1H), 8.85 (d, J = 2.4 Hz, 1H), 8.67 (s, 1H), 8.18 (s, 1H), 8.06 (d, J = 7.2 Hz, 1H), 7.90 (d, J = 4.4 Hz, 1H), 7.81 (d, J = 7.2 Hz, 1H), 7.67 (bs, 0.5H), 7.42 (d, J = 8.8 Hz, 0.5H), 6.95 (bs, 1H), 6.31 (s, 1H), 5.00-4.92 (m, 2H), 4.90-4.78 (m, 2H), 4.70-4.50 (m, 2H), 4.34-4.15 (m, 2H), 3.55-3.46 (m, 1H), 3.18 (t, J = 8.0 Hz, 1H), 2.28-2.20 (m, 1H), 2.00-1.86 (m, 2H), 1.82-1.74 (m, 1H); MS (ESI): m/z 567.2 $[M + H]^+$ | ++++ |
| 606. | 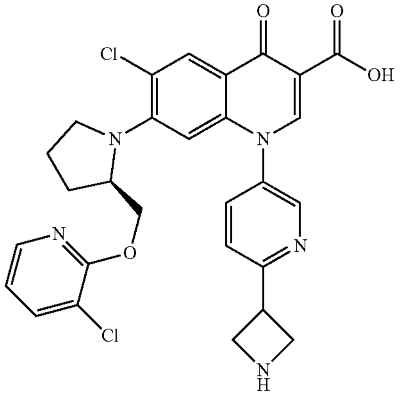 [SMILES: O=C(O)c1cn(-c2ccc(C3CNC3)nc2)c2cc(N3CCC[C@@H]3COc3ncccc3Cl)c(Cl)cc2c1=O] | (R)-1-(6-(azetidin-3-yl)pyridin-3-yl)-6-chloro-7-(2-(((3-chloropyridin-2-yl)oxy)methyl) pyrrolidin-1-yl)-4-oxo-1,4-dihydroquinoline-3-carboxylic acid | $^1$HNMR (400 MHz, DMSO-$d_6$): δ 8.80 (d, J = 2.0 Hz, 1H), 8.65 (s, 1H), 8.18 (s, 1H), 8.03 (d, J = 7.2 Hz, 1H), 7.89 (s, 1H), 7.81 (d, J = 7.2 Hz, 1H), 7.67 (bs, 0.5H), 7.42 (d, J = 8.8 Hz, 0.5H), 6.95 (bs, 1H), 6.31 (s, 1H), 4.72-4.62 (m, 1H), 4.34-4.14 (m, 3H), 4.00-3.85 (m, 4H), 3.54-3.46 (m, 1H), 3.18 (t, J = 7.6 Hz, 1H), 2.28-2.18 (m, 1H), 2.00-1.86 (m, 2H), 1.82-1.74 (m, 1H) (—COOH and —NH protons were not observed); MS (ESI): m/z 565.9 $[M + H]^+$ | ++++ |

-continued

| EX # | Structure | IUPAC name | Analytical data | Potency Lin28a-dep Z11 $IC_{50}$ (μM) |
|---|---|---|---|---|
| 607. | 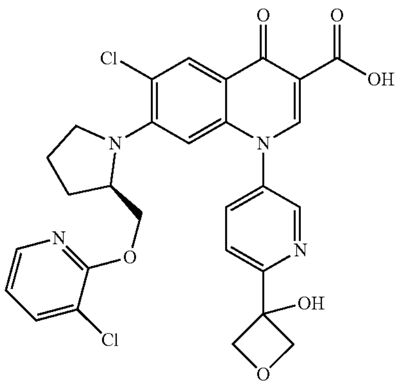 [SMILES: O=C(O)c1cn(-c2ccc(C3(O)COC3)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-(3-hydroxy-oxetan-3-yl) pyridin-3-yl)-4-oxo-1,4-dihydroquinoline-3-carboxylic acid | $^1$HNMR (400 MHz, DMSO-$d_6$): δ 15.00 (s, 1H), 8.89 (bs, 1H), 8.69 (bs, 1H), 8.18 (s, 1H), 8.17-8.08 (m, 1H), 7.90-7.84 (m, 1.5H), 7.79 (dd, J = 7.6, 1.6 Hz, 1H), 7.73-7.68 (bs, 0.5H), 6.96-6.92 (m, 1H), 6.84 (bs, 1H), 6.32 (s, 1H), 5.04-4.90 (m, 2H), 4.80-4.70 (m, 3H), 4.44-4.20 (m, 2H), 3.50-3.40 (m, 1H), 3.18 (t, J = 8.0 Hz, 1H), 2.28-2.20 (m, 1H), 2.00-1.86 (m, 2H), 1.82-1.74 (m, 1H); MS (ESI): m/z 583.2 $[M + H]^+$ | ++++ |
| 608. | 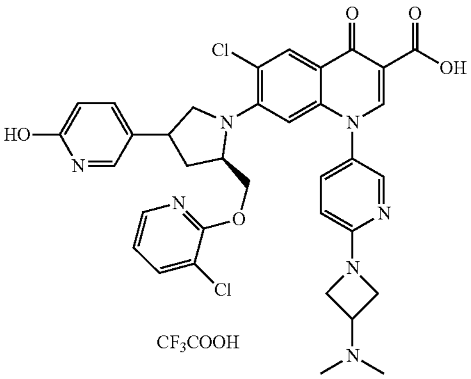 [SMILES: CN(C)C1CN(c2ccc(-n3cc(C(=O)O)c(=O)c4cc(Cl)c(N5CC(c6ccc(O)nc6)C[C@@H]5COc5ncccc5Cl)cc43)cn2)C1 ; "CF3COOH"] CF$_3$COOH | 6-chloro-7-((2R)-2-(((3-chloropyridin-2-yl)oxy)methyl)-4-(6-hydroxypyrrolidin-3-yl)pyrrolidin-1-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.02 (bs, 1H), 11.68 (bs, 1H), 10.35 (bs, 1H), 8.46 (d, J = 10.0 Hz, 1H), 8.32 (d, J = 2.4 Hz, 1H), 8.20 (s, 1H), 7.92-7.88 (m, 1H), 7.85 (dd, J = 7.6, 1.6 Hz, 1H), 7.81-7.75 (m, 1H), 7.45 (d, J = 9.6 Hz, 1H), 7.27 (s, 1H), 7.00-6.92 (m, 1H), 6.66 (d, J = 9.2 Hz, 0.5H), 6.44 (d, J = 3.6 Hz, 1.5H), 6.35 (d, J = 9.6 Hz, 1H), 4.82-4.606 (m, 1H), 4.40-4.15 (m, 7H), 3.44-3.38 (m, 2H), 3.25-3.19 (m, 1H), 2.84 (s, 6H), 2.45-2.40 (m, 1H), 2.12-2.00 (m, 1H); MS (ESI) m/z: 702.1 $[M + H]^+$ | ++++ |
| 609. | 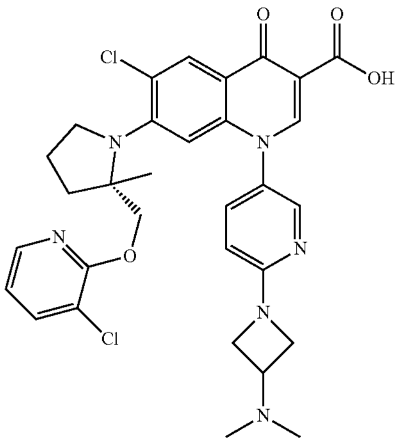 [SMILES: CN(C)C1CN(c2ccc(-n3cc(C(=O)O)c(=O)c4cc(Cl)c(N5CCC[C@@]5(C)COc5ncccc5Cl)cc43)cn2)C1] | (S)-6-chloro-7-(2-(((3-chloropyridin-2-yl)oxy)methyl)-2-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 8.37 (d, J = 1.2 Hz, 1H), 8.24-8.21 (m, 1H), 8.17-8.16 (m, 1H), 7.86 (dd, J = 7.6, 2.0 Hz, 1H), 7.73-7.70 (m, 1H), 7.62-7.56 (m, 1H), 7.48-7.45 (m, 1H), 6.53 (d, J = 9.2 Hz, 1H), 6.35 (t, J = 6.8 Hz, 1H), 4.78-4.75 (m, 1H), 4.04 (t, J = 8.0 Hz, 2H), 3.86-3.78 (m, 3H), 3.53-3.49 (m, 2H), 3.22-3.18 (m, 1H), 2.11 (s, 6H), 2.10-2.07 (m, 1H), 1.77-1.74 (m, 2H), 1.65-1.59 (m, 1H), 1.38 (s, 3H); MS (ESI) m/z: 623.0 $[M + H]^+$ | ++++ |

-continued

| EX # | Structure | IUPAC name | Analytical data | Potency Lin28a-dep Z11 $IC_{50}$ (μM) |
|---|---|---|---|---|
| 610. | 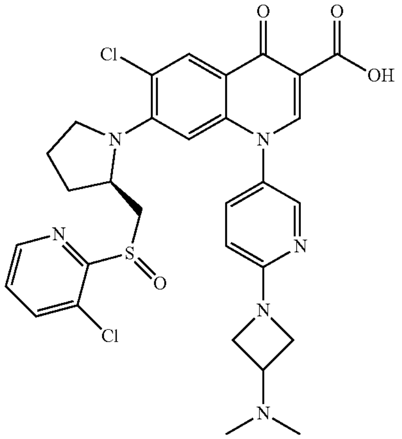 [SMILES: CN(C)C1CN(c2ccc(-n3cc(C(=O)O)c(=O)c4cc(Cl)c(N5CCC[C@@H]5CS(=O)c5ncccc5Cl)cc43)cn2)C1] | 6-chloro-7-((2R)-2-(((3-chloropyridin-2-yl)sulfinyl)methyl)pyrrolidin-1-yl)-1-(6-(3-(dimethylamino)azetidin-1-yl)pyridin-3-yl)-4-oxo-1,4-dihydroquinoline-3-carboxylic acid | $^1$H NMR (400 MHz, DMSO-$d_6$): δ 15.10 (bs, 1H), 8.69-8.49 (m, 2H), 8.31-8.29 (m, 1H), 8.20-8.01 (m, 2H), 7.81-7.76 (m, 1H), 7.64-7.48 (m, 1H), 6.60-6.37 (m, 2H), 4.56-4.20 (m, 1H), 4.12-4.06 (m, 2H), 3.85-3.70 (m, 2H), 3.69-3.62 (m, 1H), 3.29-3.12 (m, 3H), 3.10-2.90 (m, 1H), 2.24-2.15 (m, 1H), 2.12 (s, 6H), 2.03-1.90 (m, 1H), 1.88-1.70 (m, 2H); MS (ESI) m/z: 641.2 $[M + H]^+$. | +++ |
| 611. | 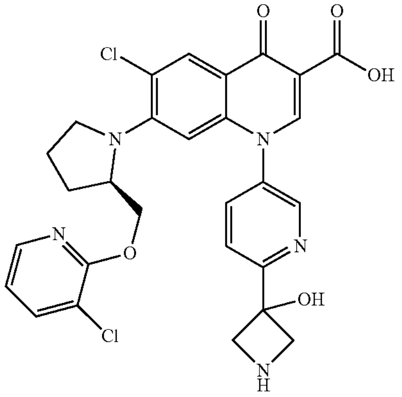 [SMILES: O=C(O)c1cn(-c2ccc(C3(O)CNC3)nc2)c2cc(N3CCC[C@@H]3COc3ncccc3Cl)c(Cl)cc2c1=O] | (R)-6-chloro-7-(2-(((3-chloropyridin-2-yl)oxy)methyl)pyrrolidin-1-yl)-1-(6-(3-hydroxyazetidin-3-yl)pyridin-3-yl)-4-oxo-1,4-dihydroquinoline-3-carboxylic acid | $^1$HNMR (400 MHz, DMSO-$d_6$): δ 14.99 (bs, 1H), 9.26 (bs, 1H), 9.08 (bs, 1H), 8.94 (bs, 1H), 8.66 (d, J = 6.0 Hz, 1H), 8.23-8.18 (m, 2H), 7.90 (bs, 1.5H), 7.81-7.75 (m, 1.5H), 7.29 (bs, 1H), 7.00-6.90 (m, 1H), 6.32 (s, 1H), 4.80-4.70 (m, 1H), 4.54-4.10 (m, 6H), 3.20-3.10 (m, 1H), 2.28-2.18 (m, 1H), 2.00-1.86 (m, 2H), 1.82-1.74 (m, 1H); MS (ESI): m/z 582.2 $[M + H]^+$ | ++++ |
| 612. | 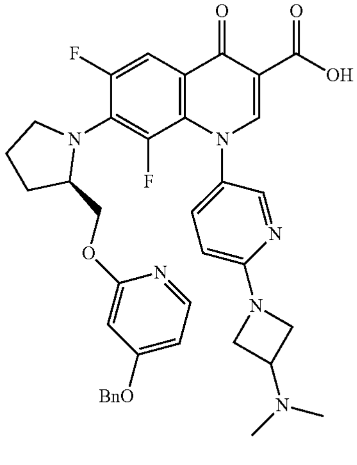 [SMILES: CN(C)C1CN(c2ccc(-n3cc(C(=O)O)c(=O)c4cc(F)c(N5CCC[C@@H]5COc5cc(OCc6ccccc6)ccn5)c(F)c43)cn2)C1] | (R)-7-(2-(((4-(benzyloxy)pyridin-2-yl)oxy)methyl)pyrrolidin-1-yl)-1-(6-(3-(dimethylamino)azetidin-1-yl)pyridin-3-yl)-6,8 difluoro-4-oxo-1,4-dihydroquinoline-3-carboxylic acid | VT $^1$H NMR (400 MHz, DMSO-$d_6$): δ 8.35 (s, 1H), 8.18 (br s, 1H), 7.75 (d, J = 5.6 Hz, 2H), 7.60 (br s, 1H), 7.42-7.38 (m, 5H), 6.56 (d, J = 4.0 Hz, 1H), 6.38 (d, J = 8.8 Hz, 1H), 6.01 (d, J = 1.6 Hz, 1H), 5.01 (s, 2H), 4.43-4.32 (m, 1H), 4.30-4.14 (m, 2H), 4.03 (t, J = 8.0 Hz, 2H), 3.82-3.78 (m, 2H), 3.62 (brs, 1H), 3.30-3.19 (m, 2H), 2.11-2.09 (m, 7H), 1.92 (brs, 1H), 1.80-1.70 (m, 2H) (—COOH proton was not observed); MS (ESI): m/z 683.4 $[M + H]^+$ | ++++ |

-continued

| EX # | Structure | IUPAC name | Analytical data | Potency Lin28a-dep Z11 $IC_{50}$ (μM) |
|---|---|---|---|---|
| 613. | 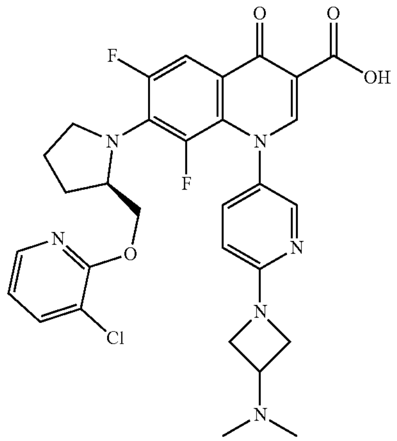 [SMILES: CN(C)C1CN(c2ccc(-n3cc(C(=O)O)c(=O)c4cc(F)c(N5CCC[C@@H]5COc5ncccc5Cl)c(F)c43)cn2)C1] | (R)-7-(2-(((3-chloropyridin-2-yl)oxy)methyl) pyrrolidin-1-yl)-6-fluoro-1-(6-(3-((2-methoxyethyl) (methyl)amino) azetidin-1-yl) pyridin-3-yl)-4-oxo-1,4-dihydroquinoline-3-carboxylic acid | $^1$H NMR (400 MHz, DMSO-$d_6$): δ 14.85 (bs, 1H), 8.38 (d, J = 6.0 Hz, 1H), 8.25 (dd, J = 16.0, 2.4 Hz, 1H), 7.91 (dd, J = 4.8, 1.6 Hz, 1H), 7.80-7.66 (m, 3H), 6.97-6.92 (m, 1H), 6.41 (dd, J = 23.6, 8.8 Hz, 1H), 4.52 4.46 (m, 1H), 4.44-4.38 (m, 1H), 4.30-4.25 (m, 1H), 4.06 (t, J = 8.0 Hz, 2H), 3.82-3.77 (m, 2H), 3.72-3.62 (m, 1H), 3.26-3.19 (m, 2H), 2.21-2.16 (m, 1H), 2.13 (s, 6H), 2.00-1.90 (m, 1H), 1.82-1.70 (m, 2H); MS (ESI): m/z 611.0 [M + H]$^+$ | ++++ |
| 614. | 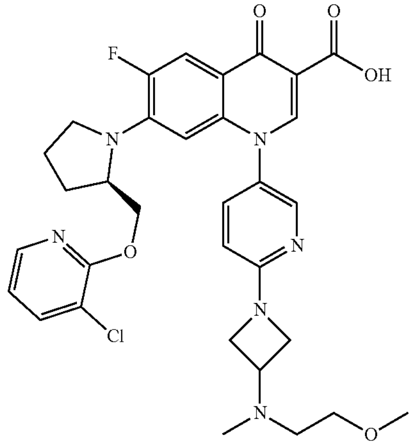 [SMILES: COCCN(C)C1CN(c2ccc(-n3cc(C(=O)O)c(=O)c4cc(F)c(N5CCC[C@@H]5COc5ncccc5Cl)cc43)cn2)C1] | (R)-7-(2-(((3-chloropyridin-2-yl)oxy)methyl) pyrrolidin-1-yl)-6-fluoro-1-(6-(3-((2-methoxyethyl) (methyl)amino) azetidin-1-yl) pyridin-3-yl)-4-oxo-1,4-dihydroquinoline-3-carboxylic acid | $^1$H NMR (400 MHz, DMSO-$d_6$) δ 15.38 (s, 1H), 8.48 (d, J = 3.2 Hz, 1H), 8.25 (t, J = 2.8 Hz, 1H), 7.98 (d, J = 3.2 Hz, 1H), 7.90-7.84 (m, 2H), 7.74-7.70 (m, 1H), 7.02-6.98 (m, 1H), 6.54 (d, J = 8.0 Hz, 0.5H), 6.34 (d, J = 8.0 Hz, 0.5H), 6.13 (d, J = 7.2 Hz, 1H), 4.56-4.46 (m, 1H), 4.40-4.28 (m, 2H), 4.10-4.00 (m, 2H), 3.86-3.76 (m, 2H), 3.50-3.40 (m, 6H), 3.27 (s, 3H), 3.26-3.18 (m, 1H), 2.20 (s, 3H), 3.16-3.04 (m, 2H), 2.02-1.88 (m, 2H); MS (ESI): m/z 637.2 [M + H]$^+$ | ++++ |
| 615. | 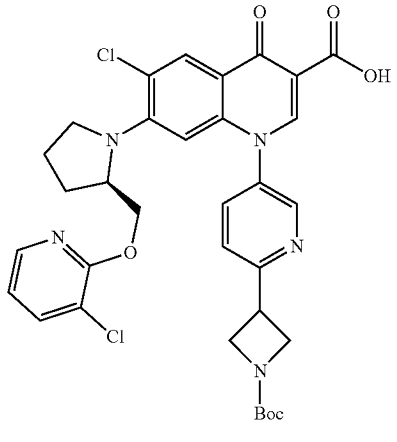 [SMILES: CC(C)(C)OC(=O)N1CC(c2ccc(-n3cc(C(=O)O)c(=O)c4cc(Cl)c(N5CCC[C@@H]5COc5ncccc5Cl)cc43)cn2)C1] | (R)-1-(6-(1-(tert-butoxycarbonyl) azetidin-3-yl) pyridin-3-yl)-6-chloro-7-(2-(((3-chloropyridin-2-yl)oxy)methyl) pyrrolidin-1-yl)-4-oxo-1,4-dihydroquinoline-3-carboxylic acid | $^1$HNMR (400 MHz, DMSO-$d_6$): δ 15.00 (s, 1H), 8.83 (d, J = 2.0 Hz, 1H), 8.67 (bs, 1H), 8.18 (s, 1H), 8.05 (d, J = 8.0 Hz, 1H), 7.89 (s, 1H), 7.81 (d, J = 7.6 Hz, 1H), 7.66 (d, J = 6.8 Hz, 0.5H), 7.42 (d, J = 6.8 Hz, 0.5H), 6.95 (bs, 1H), 6.30 (s, 1H), 4.72-4.62 (m, 1H), 4.34-4.16 (m, 4H), 4.14-3.98 (m, 3H), 3.54-3.46 (m, 1H), 3.18 (t, J = 7.6 Hz, 1H), 2.30-2.20 (m, 1H), 2.00-1.86 (m, 2H), 1.82-1.74 (m, 1H), 1.42 (s, 9H); MS (ESI): m/z 666.1 [M + H]$^+$ | ++++ |

-continued

| EX # | Structure | IUPAC name | Analytical data | Potency Lin28a-dep Z11 $IC_{50}$ (μM) |
|---|---|---|---|---|
| 616. | 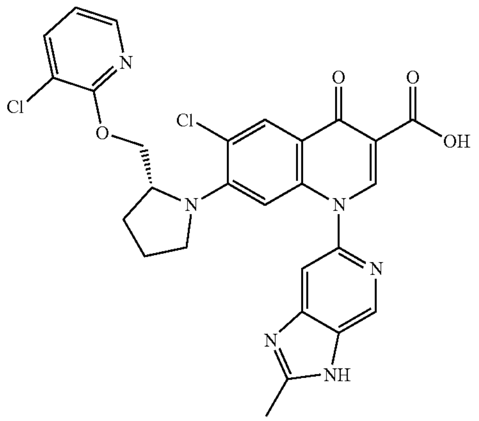 [SMILES: Cc1nc2cc(-n3cc(C(=O)O)c(=O)c4cc(Cl)c(N5CCC[C@@H]5COc5ncccc5Cl)cc43)ncc2[nH]1] | (R)-6-chloro-7-(2-(((3-chloropyridin-2-yl)oxy)methyl) pyrrolidin-1-yl)-1-(2-methyl-3H-imidazo[4,5-c] pyridin-6-yl)-4-oxo-1,4-dihydroquinoline-3-carboxylic acid | $^1$H NMR (400 MHz, DMSO-$d_6$) δ 8.74 (s, 2H), 8.17 (s, 1H), 7.94 (s, 1H), 7.84 (dd, J = 4.8, 1.6 Hz, 1H), 7.77 (dd, J = 8.0, 2.4 Hz, 1H), 6.95-6.90 (m, 1H), 6.50 (s, 1H), 4.62-4.56 (m, 1H), 4.24 (d, J = 2.8 Hz, 2H), 3.50-3.40 (m, 1H), 3.16-3.10 (m, 1H), 2.66 (s, 3H), 2.22-2.15 (m, 1H), 1.96-1.81 (m, 2H), 1.80-1.69 (m, 1H) (—COOH & —NH protons were not observed); MS (ESI): m/z 565.0 [M + H]$^+$ | ++++ |
| 617. | 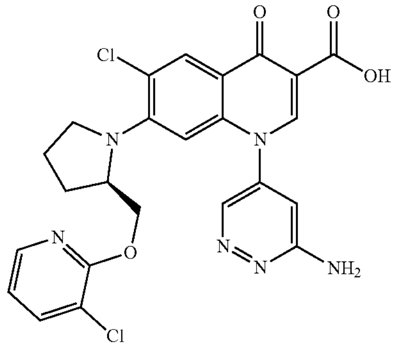 [SMILES: Nc1cc(-n2cc(C(=O)O)c(=O)c3cc(Cl)c(N4CCC[C@@H]4COc4ncccc4Cl)cc32)cnn1] | (R)-1-(6-aminopyridazin-4-yl)-6-chloro-7-(2-(((3-chloropyridin-2-yl)oxy)methyl) pyrrolidin-1-yl)-4-oxo-1,4-dihydroquinoline-3-carboxylic acid | $^1$H-NMR (400 MHz, DMSO-$d_6$): δ 14.85 (s, 1H), 8.74 (s, 1H), 8.67 (d, J = 2.0 Hz, 1H), 8.15 (s, 1H), 7.88 (dd, J = 4.8, 1.6 Hz, 1H), 7.78 (dd, J = 8.0, 1.6 Hz, 1H), 7.61 (bs, 2H), 7.29 (bs, 1H), 6.95-6.91 (m, 1H), 6.49 (s, 1H), 4.84 (bs, 1H), 4.30 (t, J = 3.6 Hz, 2H), 3.60-3.54 (m, 1H), 3.23 (t, J = 8.0 Hz, 1H), 2.30-2.21 (m, 1H), 2.08-1.88 (m, 2H), 1.87-1.75 (m, 1H); MS (ESI): m/z 527.0 [M + H]$^+$. | ++++ |
| 618. | 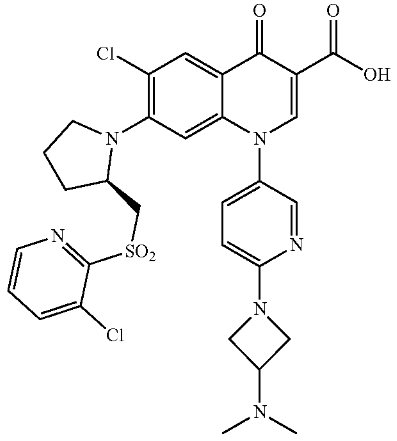 [SMILES: CN(C)C1CN(c2ccc(-n3cc(C(=O)O)c(=O)c4cc(Cl)c(N5CCC[C@@H]5CS(=O)(=O)c5ncccc5Cl)cc43)cn2)C1] | (R)-6-chloro-7-(2-(((3-chloropyridin-2-yl)sulfonyl) methyl)pyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 14.28 (bs, 1H), 8.82 (d, J = 2.0 Hz, 1H), 8.40 (d, J = 6.8 Hz, 1H), 8.32 (d, J = 2.4 Hz, 1H), 7.85 (dd, J = 15.2, 3.6 Hz, 1H), 7.81-7.76 (m, 2H), 7.45 (dd, J = 7.6, 1.6 Hz, 1H), 6.75-6.70 (m, 1H), 6.64-6.58 (m, 1H), 4.46-4.38 (m, 1H), 4.18-4.04 (m, 3H), 4.00-3.85 (m, 3H), 3.69-3.58 (m, 1H), 3.29-3.22 (m, 2H), 2.16 (s, 6H), 2.06-1.83 (m, 3H), 1.72-1.64 (m, 1H); MS (ESI) m/z: 657.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 619. | 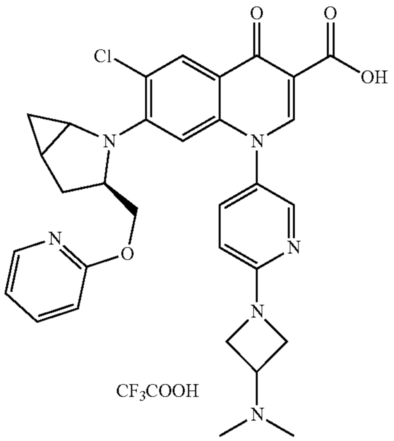 [SMILES: CN(C)C1CN(c2ccc(-n3cc(C(=O)O)c(=O)c4cc(Cl)c(N5C6CC6C[C@@H]5COc5ccccn5)cc43)cn2)C1 ; "CF3COOH"] $CF_3COOH$ | 6-chloro-1-(6-(3-(dimethylamino) azetidin-1-yl) pyridin-3-yl)-4-oxo-7-((3R)-3-((pyridin-2-yloxy) methyl)-2-azabicyclo[3.1.0] hexan-2-yl)-1,4-dihydroquinoline-3-carboxylic acid | $^1$H NMR (400 MHz, DMSO-$d_6$) δ 15.09 (bs, 1H), 10.35 (bs, 1H), 8.54 (s, 1H), 8.38-8.36 (m, 1H), 8.19 (s, 1H), 7.95-7.92 (m, 1H), 7.88-7.84 (m, 1H), 7.64 (t, J = 7.6 Hz, 1H), 6.92-6.80 (m, 2H), 6.73 (d, J = 9.2 Hz, 0.5H), 6.61 (d, J = 8.4 Hz, 1H), 6.50 (d, J = 9.2 Hz, 0.5H), 5.04-4.91 (m, 1H), 4.30-4.25 (m, 2H), 4.23-4.15 (m, 3H), 4.05-3.98 (m, 1H), 3.95-3.90 (m, 1H), 3.08-2.98 (m, 1H), 2.85 (s, 6H), 2.67-2.60 (m, 1H), 2.08-2.01 (m, 1H), 1.67-1.63 (m, 1H), 0.73-0.72 (m, 1H), 0.67-0.60 (m, 1H); v MS (ESI) m/z: 587.4 [M + H]$^+$. | ++++ |
| 620. | 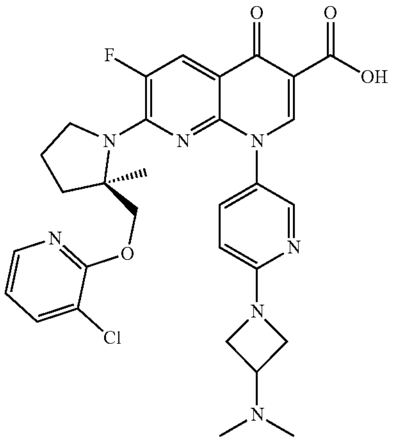 [SMILES: CN(C)C1CN(c2ccc(-n3cc(C(=O)O)c(=O)c4cc(F)c(N5CCC[C@]5(C)COc5ncccc5Cl)nc43)cn2)C1] | (R)-7-(2-(((3-chloropyridin-2-yl)oxy)methyl)-2-methylpyrrolidin-1-yl)-1-(6-(3-(dimethylamino) azetidin-1-yl) pyridin-3-yl)-6-fluoro-4-oxo-1,4-dihydro-1,8-naphthyridine-3-carboxylic acid | $^1$H NMR (400 MHz, DMSO-$d_6$) δ 15.26 (bs, 1H), 8.55 (s, 1H), 8.18 (s, 1H), 8.01 (d, J = 5.2 Hz, 2H), 7.85 (d, J = 7.6 Hz, 1H), 7.63 (bs, 1H), 7.02-6.96 (m, 1H), 6.55 (s, 1H), 4.50-4.42 (m, 1H), 4.16-4.10 (m, 1H), 3.98-3.90 (m, 2H), 3.89-3.80 (m, 2H), 3.70-3.62 (m, 2H), 3.20-3.10 (m, 1H), 2.11 (s, 10H), 2.04-1.95 (m, 1H), 1.92-1.86 (m, 1H), 1.80-1.70 (m, 1H); MS (ESI): m/z 608.1 [M + H]$^+$ | ++++ |
| 621. | 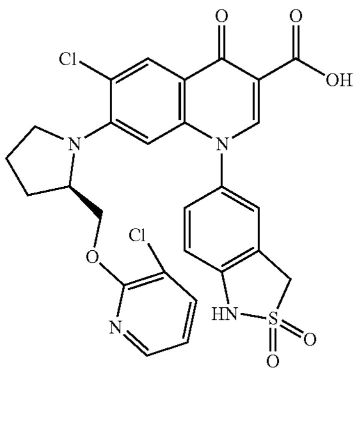 [SMILES: O=C(O)c1cn(-c2ccc3c(c2)CS(=O)(=O)N3)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(2,2-dioxido-1,3-dihydrobenzo[c] isothiazol-5-yl)-4-oxo-1,4-dihydroquinoline-3-carboxylic acid | $^1$H NMR (400 MHz, DMSO-$d_6$) δ 15.08 (s, 1H), 11.07 (s, 1H), 8.53 (s, 1H), 8.15 (s, 1H), 7.88-7.85 (m, 1H), 7.83-7.78 (m, 1H), 7.55-7.42 (m, 2H), 7.03 (d, J = 8.4 Hz, 0.5H), 6.95-6.87 (m, 1.5H), 6.36 (d, J = 7.6 Hz, 1H), 4.80-4.58 (m, 3H), 4.24 (d, J = 2.8 Hz, 2H), 3.50-3.40 (m, 1H), 3.20-3.10 (m, 1H), 2.20-2.10 (m, 1H), 2.02-1.87 (m, 2H), 1.84-1.74 (m, 1H); MS (ESI): m/z 601.1 [M + H]$^+$ | ++++ |

-continued

| EX # | Structure | IUPAC name | Analytical data | Potency Lin28a-dep Z11 $IC_{50}$ (μM) |
|---|---|---|---|---|
| 622. | 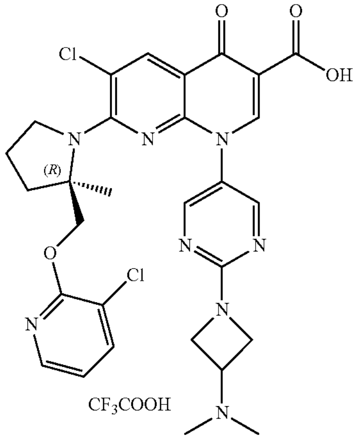 $CF_3COOH$ | (R)-6-chloro-7-(2-(((3-chloropyridin-2-yl)oxy)methyl)-2-methylpyrrolidin-1-yl)-1-(2-(3-(dimethylamino)azetidin-1-yl)pyrimidin-5-yl)-4-oxo-1,4-dihydro-1,8-naphthyridine-3-carboxylic acid | $^1H$ NMR (400 MHz, DMSO-$d_6$) δ 15.02 (bs, 1H), 10.60 (bs, 1H), 8.69 (s, 1H), 8.62 (s, 2H), 8.24 (s, 1H), 7.93 (dd, J = 4.8, 1.6 Hz, 1H), 7.84 (dd, J = 7.6, 1.6 Hz, 1H), 7.00-6.92 (m, 1H), 4.72-4.66 (m, 1H), 4.30-4.18 (m, 5H), 4.10-4.00 (m, 3H), 2.84 (s, 6H), 2.23-2.15 (m, 1H), 2.04-1.95 (m, 1H), 1.92-1.80 (m, 1H), 1.78-1.70 (m, 1H), 1.09 (s, 3H); MS (ESI): m/z 625.4 $[M + H]^+$ | +++ |
| 623. | 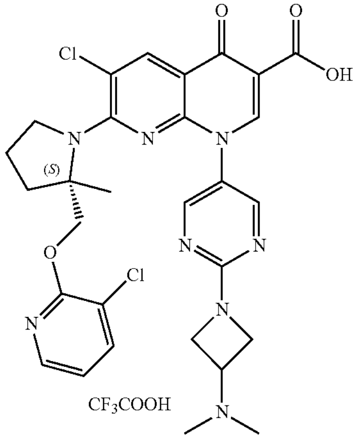 $CF_3COOH$ | (S)-6-chloro-7-(2-(((3-chloropyridin-2-yl)oxy)methyl)-2-methylpyrrolidin-1-yl)-1-(2-(3-(dimethylamino)azetidin-1-yl)pyrimidin-5-yl)-4-oxo-1,4-dihydro-1,8-naphthyridine-3-carboxylic acid | $^1H$ NMR (400 MHz, DMSO-$d_6$) δ 14.98 (bs, 1H), 10.42 (bs, 1H), 8.69 (s, 1H), 8.62 (s, 2H), 8.24 (s, 1H), 7.93 (dd, J = 4.8, 1.6 Hz, 1H), 7.84 (dd, J = 7.6, 1.6 Hz, 1H), 7.00-6.92 (m, 1H), 4.72-4.66 (m, 1H), 4.30-4.18 (m, 5H), 4.10-4.00 (m, 3H), 2.84 (s, 6H), 2.23-2.15 (m, 1H), 2.04-1.95 (m, 1H), 1.92-1.80 (m, 1H), 1.78-1.70 (m, 1H), 1.17 (s, 3H); MS (ESI): m/z 625.4 $[M + H]^+$ | ++++ |
| 624. | 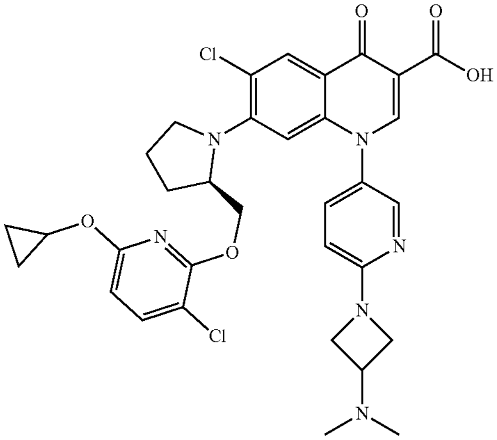 [SMILES: CN(C)C1CN(c2ccc(-n3cc(C(=O)O)c(=O)c4cc(Cl)c(N5CCC[C@@H]5COc5nc(OC6CC6)ccc5Cl)cc43)cn2)C1] | (R)-6-chloro-7-(2-(((3-chloro-6-cyclopropoxypyridin-2-yl)oxy)methyl)pyrrolidin-1-yl)-1-(6-(3-(dimethylamino)azetidin-1-yl)pyridin-3-yl)-4-oxo-1,4-dihydroquinoline-3-carboxylic acid | $^1H$-NMR (400 MHz, DMSO-$d_6$): δ 15.22 (br s, 1H), 8.49 (d, J = 8.0 Hz, 1H), 8.31 (s, 1H), 8.15 (s, 1H), 7.81-7.74 (m, 1H), 7.68 (t, J = 8.0 Hz, 1H), 6.66 (d, J = 8.8 Hz, 0.5H), 6.52 (d, J = 8.8 Hz, 0.5H), 6.41 (d, J = 8.4 Hz, 1H), 6.32 (d, J = 6.0 Hz, 1H), 4.75-4.69 (m, 1H), 4.39-4.17 (m, 7H), 3.87 (d, J = 3.2 Hz, 1H), 3.51-3.49 (m, 1H), 3.19-3.10 (m, 1H), 2.85 (s, 6H), 2.32 (t, J = 1.6 Hz, 1H), 2.01-1.82 (m, 2H), 1.80-1.77 (m, 1H), 0.68 (d, J = 4.8 Hz, 2H), 0.55 (d, J = 8.4 Hz, 2H); MS (ESI): m/z 665.4 $[M + H]^+$ | ++++ |

-continued

| EX # | Structure | IUPAC name | Analytical data | Potency Lin28a-dep Z11 $IC_{50}$ (μM) |
|---|---|---|---|---|
| 625. | 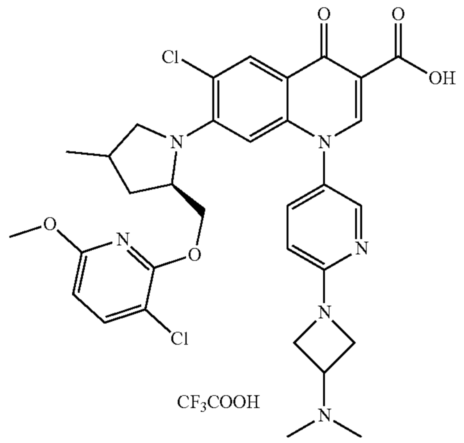 [SMILES: COc1ccc(Cl)c(OC[C@H]2CC(C)CN2c2cc3c(cc2Cl)c(=O)c(C(=O)O)cn3-c2ccc(N3CC(N(C)C)C3)nc2)n1 ; "CF3COOH"] $CF_3COOH$ | 6-chloro-7-((2R)-2-(((3-chloro-6-methoxypyridin-2-yl)oxy)methyl)-4-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 15.09 (br s, 1H), 10.35 (br s, 1H), 8.50-8.46 (m, 1H), 8.36-8.30 (m, 1H), 8.16 (s, 1H), 7.81-7.74 (m, 1H), 7.69-7.63 (m, 1H), 6.69 (d, J = 8.8 Hz, 0.5H), 6.50 (d, J = 8.8 Hz, 0.5H), 6.32-6.27 (m, 2H), 4.70-4.40 (m, 2H), 4.38-4.17 (m, 6H), 3.62-3.58 (m, 1H), 3.57 (s, 3H), 3.30-3.20 (m, 1H), 3.16-3.07 (m, 1H), 2.86 (s, 6H), 2.28-2.14 (m, 1H), 1.70-1.60 (m, 1H), 1.06-0.96 (m, 3H); MS (ESI): m/z 653.4 $[M + H]^+$. | ++++ |
| 626. | 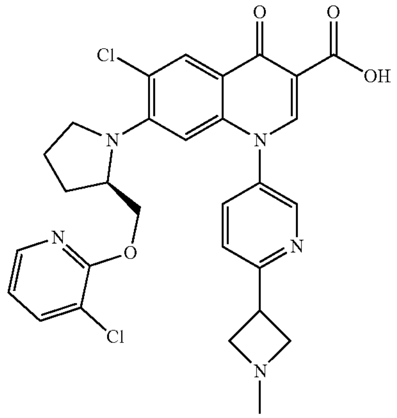 [SMILES: CN1CC(c2ccc(-n3cc(C(=O)O)c(=O)c4cc(Cl)c(N5CCC[C@@H]5COc5ncccc5Cl)cc43)cn2)C1] | (R)-6-chloro-7-(2-(((3-chloropyridin-2-yl)oxy)methyl) pyrrolidin-1-yl)-1-(6-(1-methyl-azetidin-3-yl) pyridin-3-yl)-4-oxo-1,4-dihydroquinoline-3-carboxylic acid | $^1$HNMR (400 MHz, DMSO-$d_6$): δ 15.00 (s, 1H), 8.87 (d, J = 2.0 Hz, 1H), 8.63 (d, J = 9.6 Hz, 1H), 8.18 (s, 1H), 8.09 (t, J = 8.0 Hz, 1H), 7.90 (bs, 1H), 7.82 (dd, J = 7.6, 1.6 Hz, 1H), 7.71 (d, J = 7.6 Hz, 0.5H), 7.50 (d, J = 8.0 Hz, 0.5H), 6.95 (bs, 1H), 6.30 (s, 1H), 4.74-4.68 (m, 1H), 4.34-4.16 (m, 5H), 4.02-3.88 (m, 2H), 3.54-3.46 (m, 1H), 3.18 (t, J = 7.6 Hz, 1H), 2.74-2.68 (m, 3H), 2.30-2.20 (m, 1H), 2.00-1.86 (m, 2H), 1.82-1.74 (m, 1H); MS (ESI): m/z 580.3 $[M + H]^+$ | ++++ |
| 627. | 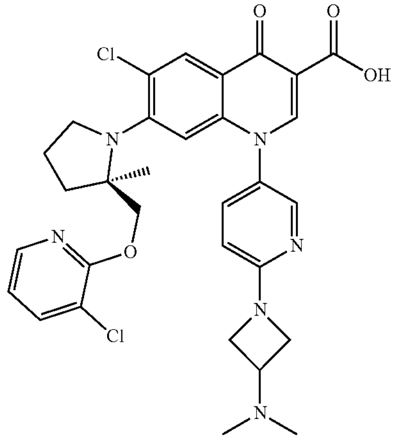 [SMILES: CN(C)C1CN(c2ccc(-n3cc(C(=O)O)c(=O)c4cc(Cl)c(N5CCC[C@]5(C)COc5ncccc5Cl)cc43)cn2)C1] | (R)-6-chloro-7-(2-(((3-chloropyridin-2-yl)oxy)methyl)-2-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 8.37 (d, J = 0.8 Hz, 1H), 8.23-8.22 (m, 1H), 8.15 (d, J = 3.2 Hz, 1H), 7.86-7.84 (m, 1H), 7.70 (brs, 1H), 7.56 (brs, 1H), 7.47-7.45 (m, 1H), 6.52 (d, J = 8.8 Hz, 1H), 6.35 (t, J = 7.2 Hz, 1H), 4.75 (brs, 1H), 4.06-4.02 (m, 2H), 3.85-3.78 (m, 3H), 3.54-3.50 (m, 2H), 3.36-3.35 (m, 1H), 2.11 (s, 6H), 2.12-2.08 (m, 1H), 1.76-1.74 (m, 2H), 1.63-1.60 (m, 1H), 1.39 (d, J = 1.2 Hz, 3H), COOH proton was not observed; MS (ESI): m/z 623.0 $[M + H]^+$ | ++++ |

-continued

| EX # | Structure | IUPAC name | Analytical data | Potency Lin28a-dep Z11 $IC_{50}$ (μM) |
|---|---|---|---|---|
| 628. | 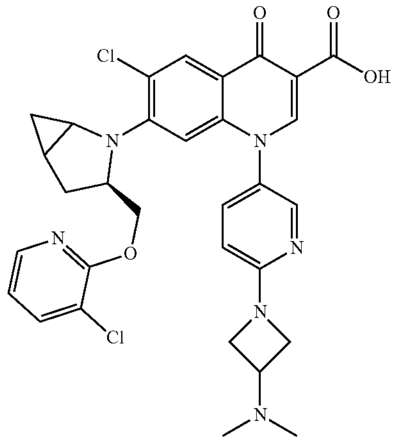 [SMILES: CN(C)C1CN(c2ccc(-n3cc(C(=O)O)c(=O)c4cc(Cl)c(N5C6CC6C[C@@H]5COc5ncccc5Cl)cc43)cn2)C1] | 6-chloro-7-((3R)-3-(((3-chloropyridin-2-yl)oxy)methyl)-2-azabicyclo[3.1.0]hexan-2-yl)-1-(6-(3-(dimethylamino)azetidin-1-yl)pyridin-3-yl)-4-oxo-1,4-dihydroquinoline-3-carboxylic acid | $^1$H NMR (400 MHz, DMSO-$d_6$) δ 15.09 (br s, 1H), 8.57 (d, J = 5.6 Hz, 1H), 8.28 (d, J = 8.0 Hz, 1H), 8.16 (s, 1H), 7.90 (d, J = 4.4 Hz, 1H), 7.82 (d, J = 7.6 Hz, 1H), 7.75-7.72 (m, 1H), 6.95-6.88 (m, 2H), 6.59 (d, J = 8.8 Hz, 0.5H), 6.45 (d, J = 8.8 Hz, 0.5H), 5.11-5.01 (m, 1H), 4.19-4.16 (m, 1H), 4.13-4.07 (m, 3H), 3.87-3.81 (m, 2H), 3.24-3.21 (m, 1H), 3.09-3.02 (m, 1H), 2.65-2.61 (m, 1H), 2.14 (s, 6H), 2.09-2.03 (m, 1H), 1.69-1.62 (m, 1H), 1.02-0.97 (m, 1H), 0.65-0.62 (m, 1H); MS (ESI): m/z 621.3 [M + H]$^+$. | ++++ |
| 629. | 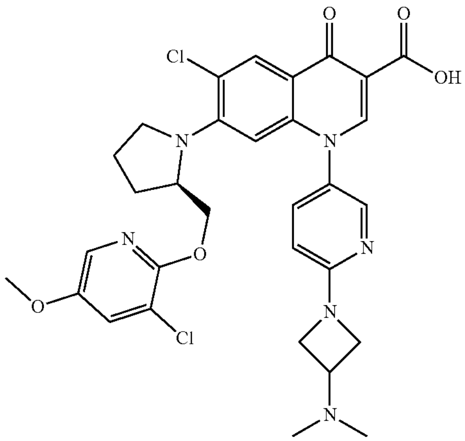 [SMILES: COc1cnc(OC[C@H]2CCCN2c2cc3c(cc2Cl)c(=O)c(C(=O)O)cn3-c2ccc(N3CC(N(C)C)C3)nc2)c(Cl)c1] | (R)-6-chloro-7-(2-(((3-chloro-5-methoxypyridin-2-yl)oxy)methyl)pyrrolidin-1-yl)-1-(6-(3-(dimethylamino)aztidin-1-yl)pyridin-3-yl)-4-oxo-1,4-dihydroquinoline-3-carboxylic acid | $^1$H NMR (400 MHz, DMSO-$d_6$): δ 15.10 (brs, 1H), 8.52 (d, J = 10.8 Hz, 1H), 8.26-8.22 (m, 1H), 8.15 (d, J = 4.0 Hz, 1H), 7.82-7.78 (m, 1H), 7.68-7.64 (m, 1H), 6.85-6.80 (m, 1H), 6.53 (d, J = 8.8 Hz, 0.5H), 6.38 (d, J = 12.8 Hz, 1H), 6.23 (d, J = 8.8 Hz, 0.5H), 4.25-4.10 (m, 1H), 4.40-4.39 (m, 1H), 4.13-4.01 (m, 3H), 3.87 (d, J = 3.2 Hz, 3H), 3.82-3.77 (m, 2H), 3.59-3.42 (m, 1H), 3.25-3.16 (m, 2H), 2.33-2.23 (m, 1H), 2.14 (s, 6H), 1.99-1.97 (brs, 1H), 1.89-1.76 (m, 2H); MS (ESI): m/z 639.3 [M + H]$^+$. | ++++ |
| 630. | 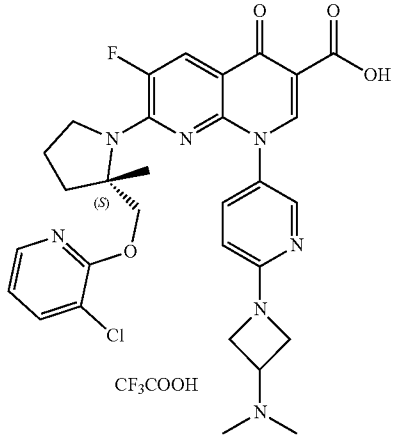 CF$_3$COOH | (S)-7-(2-(((3-chloropyridin-2-yl)oxy)methyl)-2-methylpyrrolidin-1-yl)-1-(6-(3-(dimethylamino)azetidin-1-yl)pyridin-3-yl)-6-fluoro-4-oxo-1,4-dihydro-1,8-naphthyridine-3-carboxylic acid | $^1$H NMR (400 MHz, DMSO-$d_6$) δ 15.25 (bs, 1H), 10.42 (bs, 1H), 8.51 (s, 1H), 8.27 (s, 1H), 8.01 (d, J = 13.2 Hz, 2H), 7.85 (d, J = 7.6 Hz, 1H), 7.76 (d, J = 9.2 Hz, 1H), 7.00-6.96 (m, 1H), 6.60-6.40 (m, 1H), 4.58 (d, J = 10.4 Hz, 1H), 4.28-4.01 (m, 6H), 4.00-3.78 (m, 2H), 2.82 (s, 6H), 2.20-2.10 (m, 1H), 2.09-1.99 (m, 1H), 1.94-1.82 (m, 1H), 1.80-1.70 (m, 1H), 1.14 (s, 3H); MS (ESI): m/z 608.3 [M + H]$^+$ | ++++ |

-continued

| EX # | Structure | IUPAC name | Analytical data | Potency Lin28a-dep Z11 $IC_{50}$ (μM) |
| --- | --- | --- | --- | --- |
| 631. | 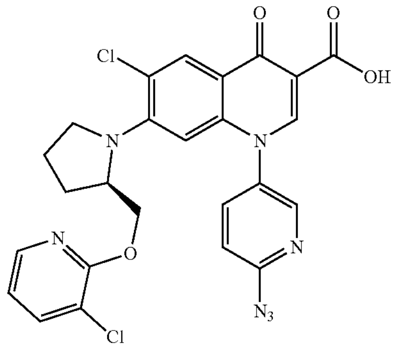 [SMILES: [N-]=[N+]=Nc1ccc(-n2cc(C(=O)O)c(=O)c3cc(Cl)c(N4CCC[C@@H]4COc4ncccc4Cl)cc32)cn1] | (R)-1-(6-azidopyridin-3-yl)-6-chloro-7-(2-(((3-chloropyridin-2-yl)oxy)methyl) pyrrolidin-1-yl)-4-oxo-1,4-dihydroquinoline-3-carboxylic acid | VT $^1$H NMR (400 MHz, DMSO-$d_6$) δ 14.65 (brs, 1H), 9.87 (s, 1H), 8.84 (s, 1H), 8.34-8.22 (m, 1H), 8.19 (s, 1H), 8.03-7.98 (m, 1H), 7.89 (d, J = 4.0 Hz, 1H), 7.76-7.72 (m, 1H), 6.94-6.90 (m, 1H), 6.52 (s, 1H), 4.68-4.74 (m, 1H), 4.29-4.27 (m, 2H), 3.65-3.58 (m, 1H), 3.23-3.19 (m, 1H), 2.20-2.14 (m, 1H), 1.98-1.87 (m, 2H), 1.80-1.75 (m, 1H); MS (ESI): m/z 580.1 [M + H]$^+$. | ++++ |
| 632. | 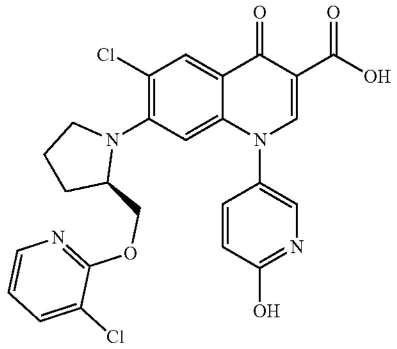 [SMILES: O=C(O)c1cn(-c2ccc(O)nc2)c2cc(N3CCC[C@@H]3COc3ncccc3Cl)c(Cl)cc2c1=O] | (R)-6-chloro-7-(2-(((3-chloropyridin-2-yl)oxy)methyl) pyrrolidin-1-yl)-1-(6-hydroxypyridin-3-yl)-4-oxo-1,4-dihydroquinoline-3-carboxylic acid | $^1$H NMR (400 MHz, DMSO-$d_6$) δ 15.26 (br s, 1H), 12.26 (s, 1H), 8.65 (d, J = 8.0 Hz, 1H), 8.14 (s, 1H), 7.94-7.89 (m, 2H), 7.82-7.22 (m, 1H), δ 7.61-7.50 (m, 1H), 6.95-6.92 (m, 1H), 6.50 (d, J = 3.2 Hz, 1H), 6.31 (d, J = 9.6 Hz, 1H), 4.85 (brs, 1H), 4.36-4.26 (m, 2H), 3.67-3.56 (m, 1H), 3.24 (t, J = 7.6 Hz, 1H), 2.26 (brs, 1H), 2.00-1.78 (m, 3H); MS (ESI): m/z 527.2 [M + H]$^+$. | ++++ |
| 633. | 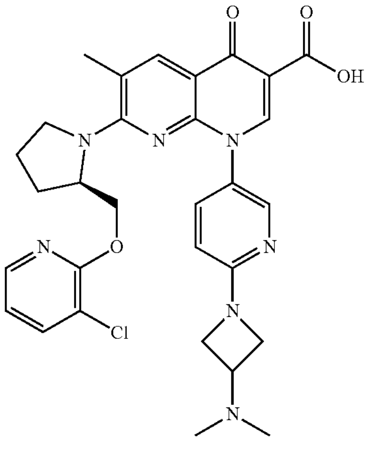 [SMILES: Cc1cc2c(=O)c(C(=O)O)cn(-c3ccc(N4CC(N(C)C)C4)nc3)c2nc1N1CCC[C@@H]1COc1ncccc1Cl] | (R)-7-(2-(((3-chloropyridin-2-yl)oxy)methyl) pyrrolidin-1-yl)-1-(6-(3-(dimethylamino) azetidin-1-yl) pyridin-3-yl)-6-methyl-4-oxo-1,4-dihydro-1,8-naphthyridine-3-carboxylic acid | $^1$H NMR (400 MHz, DMSO-$d_6$) δ 15.65 (bs, 1H), 8.52 (s, 1H), 8.26 (d, J = 2.4 Hz, 1H), 8.13 (d, J = 0.8 Hz, 1H), 7.97 (dd, J = 4.8, 1.6 Hz, 1H), 7.90 (dd, J = 7.6, 1.6 Hz, 1H), 7.78 (dd, J = 8.8, 2.8 Hz, 1H), 7.00 (dd, J = 7.6, 4.8 Hz, 1H), 6.32 (d, J = 8.4 Hz, 1H), 4.35-4.33 (m, 1H), 4.23-4.19 (m, 3H), 4.14-4.07 (m, 4H), 3.84-3.80 (m, 1H), 3.77-3.74 (m, 1H), 2.83 (s, 6H), 2.45 (s, 3H), 2.07-2.00 (m, 2H), 1.93-1.87 (m, 1H), 1.82-1.78 (m, 1H); MS (ESI): m/z 590.4 [M + H]$^+$. | ++++ |

-continued

| EX # | Structure | IUPAC name | Analytical data | Potency Lin28a-dep Z11 $IC_{50}$ (μM) |
|---|---|---|---|---|
| 634. | 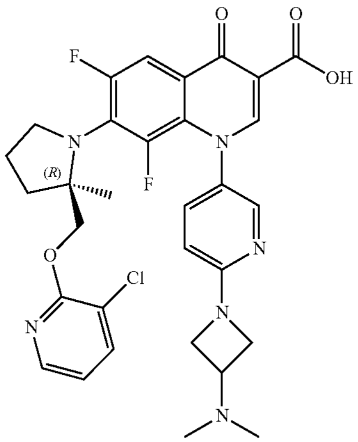 | (R)-7-(2-(((3-chloropyridin-2-yl)oxy)methyl)-2-methylpyrrolidin-1-yl)-1-(6-(3-(dimethylamino) azetidin-1-yl) pyridin-3-yl)-6,8-difluoro-4-oxo-1,4-dihydroquinoline-3-carboxylic acid | $^1$H NMR (400 MHz, DMSO-$d_6$) δ 8.46 (s, 1H), 8.30-8.24 (m, 1H), 8.10-8.02 (m, 2H), 7.90-7.75 (m, 2.5H), 7.50-7.40 (m, 0.5H), 7.03-6.96 (m, 1H), 6.46 (d, J = 8.8 Hz, 0.5H), 6.31 (d, J = 8.8 Hz, 0.5H), 4.20-4.00 (m, 4H), 3.85-3.70 (m, 2H), 3.56-3.46 (m, 1H), 3.24-3.18 (m, 1H), 2.14 (s, 6H), 2.13-1.90 (m, 3H), 1.83-1.76 (m, 1H), 1.17 (s, 3H) (—COOH proton was not observed); MS (ESI): m/z 625.4 [M + H]$^+$. | ++++ |
| 635. | 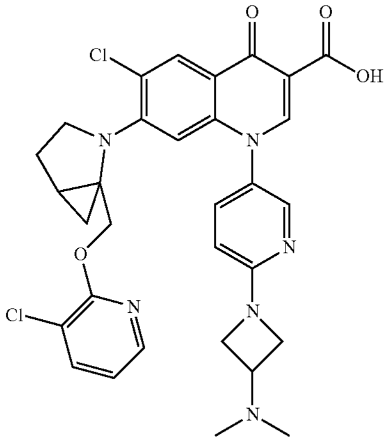 [SMILES: CN(C)C1CN(c2ccc(-n3cc(C(=O)O)c(=O)c4cc(Cl)c(N5CCC6CC65COc5ncccc5Cl)cc43)cn2)C1] | 6-chloro-7-(1-(((3-chloropyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.04 (s, 1H), 8.64 (d, J = 3.6 Hz, 1H), 8.31 (d, J = 3.2 Hz, 1H), 8.21 (s, 1H), 7.90-7.74 (m, 3H), 6.98-6.92 (m, 1H), 6.91 (s, 0.5H), 6.85 (s, 0.5H), 6.58 (d, J = 8.8 Hz, 0.5H), 6.36 (d, J = 8.8 Hz, 0.5H), 4.73-4.65 (m, 1H), 4.24-4.04 (m, 4H), 3.80 (bs, 2H), 3.32 (bs, 1H), 2.84-2.80 (m, 1H), 2.33-2.07 (m, 7H), 1.88-1.86 (m, 1H), 1.79-1.77 (m, 1H), 1.01-0.93 (m, 2H); MS (ESI): m/z 621.0 [M + H]$^+$. | ++++ |
| 636. | 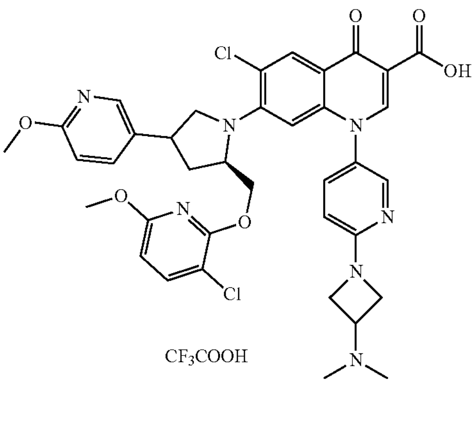 [SMILES: COc1ccc(C2C[C@H](COc3nc(OC)ccc3Cl)N(c3cc4c(cc3Cl)c(=O)c(C(=O)O)cn4-c3ccc(N4CC(N(C)C)C4)nc3)C2)cn1 ; "CF3COOH"] $CF_3COOH$ | 6-chloro-7-((2R)-2-(((3-chloro-6-methoxypyridin-2-yl)oxy)methyl)-4-(6-methoxypyridin-3-yl)pyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.10 (bs, 1H), 10.34 (bs, 1H), 8.48 (d, J = 10.8 Hz, 1H), 8.33 (d, J = 16.0 Hz, 1H), 8.19 (s, 1H), 8.11 (s, 1H), 7.78 (dd, J = 9.2, 2.8 Hz, 1H), 7.69 (d, J = 8.4 Hz, 2H), 6.84 (d, J = 8.4 Hz, 1H), 6.67 (d, J = 8.8 Hz, 0.5H), 6.48 (d, J = 8.8 Hz, 0.5H), 6.40 (s, 1H), 6.33-6.29 (m, 1H), 4.80-4.60 (m, 2H), 4.34-4.16 (m, 6H), 3.85 (s, 3H), 3.58 (s, 3H), 3.54-3.48 (m, 2H), 2.83 (s, 6H), 2.64-2.54 (m, 2H), 1.80-1.70 (m, 1H); MS (ESI): m/z 746.4 [M + H]$^+$. | ++++ |

-continued

| EX # | Structure | IUPAC name | Analytical data | Potency Lin28a-dep Z11 $IC_{50}$ (μM) |
|---|---|---|---|---|
| 637. | 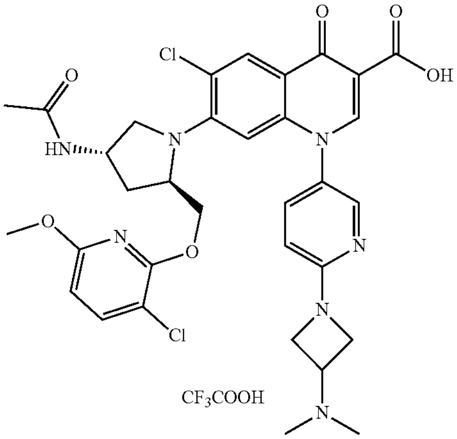 [SMILES: COc1ccc(Cl)c(OC[C@H]2C[C@H](NC(C)=O)CN2c2cc3c(cc2Cl)c(=O)c(C(=O)O)cn3-c2ccc(N3CC(N(C)C)C3)nc2)n1 ; "CF3COOH"] $CF_3COOH$ | 6-chloro-7-[(2R)-2-{[(3-chloro-6-methoxypyridin-2-yl)oxy]methyl}-4-acetamido-pyrrolidin-1-yl]-1-{6-[3-(dimethylamino) azetidin-1-yl] pyridin-3-yl}-4-oxo-1,4-dihydroquinoline-3-carboxylic acid | $^1$H NMR (400 MHz, DMSO-$d_6$) δ 15.04 (br s, 1H), 10.40 (br s, 1H), 8.50 (d, J = 6.8 Hz, 1H), 8.32 (br s, 1H), 8.26-8.22 (m, 1H), 8.18 (s, 1H), 7.81-7.73 (m, 1H), 7.66 (d, J = 11.2 Hz, 1H), 6.68 (d, J = 9.2 Hz, 0.5H), 6.52 (d, J = 9.2 Hz, 0.5H), 6.31-6.20 (m, 2H), 5.00-4.80 (m, 1H), 4.50-4.40 (m, 1H), 4.36-4.18 (m, 7H), 3.62-3.56 (m, 1H), 3.64 (s, 3H), 3.10-3.00 (m, 1H), 2.86 (s, 6H), 2.30-2.16 (m, 2H), 1.77 (s, 3H); MS (ESI): m/z 696.1 [M + H]$^+$. | ++++ |
| 638. | 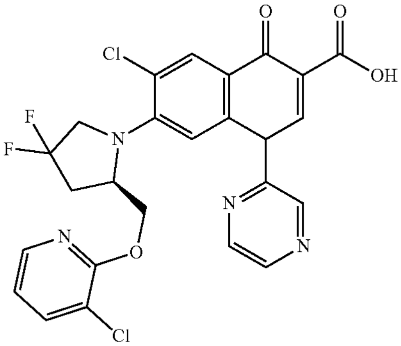 [SMILES: O=C(O)C1=CC(c2cnccn2)c2cc(N3CC(F)(F)C[C@@H]3COc3ncccc3Cl)c(Cl)cc2C1=O] | (R)-6-chloro-7-(2-(((3-chloropyridin-2-yl)oxy)methyl)-4,4-difluoropyrrolidin-1-yl)-4-oxo-1-(pyrazin-2-yl)-1,4-dihydroquinoline-3-carboxylic acid | $^1$H NMR (400 MHz, DMSO-$d_6$) δ 14.68 (s, 1H), 9.12 (d, J = 1.2 Hz, 1H), 8.98-8.97 (m, 2H), 8.81-8.79 (m, 1H), 8.23 (s, 1H), 7.90 (dd, J = 1.6, 4.8 Hz, 1H), 7.79 (dd, J = 1.6, 7.6 Hz, 1H), 6.96-6.93 (m, 1H), 6.79 (s, 1H), 5.09-5.02 (m, 1H), 4.41-4.33 (m, 2H), 4.14-4.04 (m, 1H), 3.67 (t, J = 12.4 Hz, 1H), 2.85-2.72 (m, 1H), 2.68-2.67 (m, 1H); MS (ESI): m/z 547.9 [M + H]$^+$. | ++++ |
| 639. | 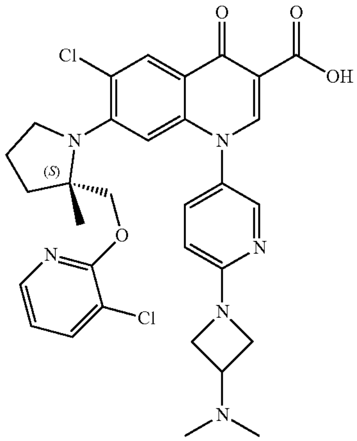 | (S)-6-chloro-7-(2-(((3-chloropyridin-2-yl)oxy)methyl)-2-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 14.95 (br s, 1H), 8.62-8.58 (m, 1H), 8.25-8.21 (m, 1H), 8.02-8.00 (m, 1H), 7.87-7.84 (m, 1H), 7.72-7.61 (m, 1H), 7.03-7.00 (m, 1H), 6.95-6.90 (m, 1H), 6.63-6.61 (m, 1H), 6.39-6.33 (m, 1H), 4.31-4.28 (m, 1H), 4.13-4.09 (m, 1H), 4.05-4.02 (m, 1H), 3.67-3.58 (m, 2H), 3.22-3.15 (m, 2H), 2.23-2.15 (m, 6H), 2.12-2.02 (m, 1H), 1.98-1.92 (m, 2H), 1.89-1.81 (m, 2H), 1.67-1.51 (m, 1H), 1.23 (s, 3H); MS (ESI): m/z 623.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 640. | 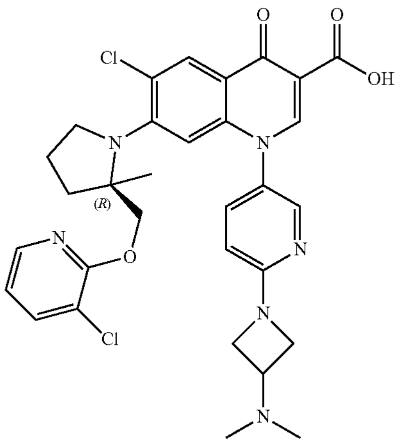 | (R)-6-chloro-7-(2-(((3-chloropyridin-2-yl)oxy)methyl)-2-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 14.95 (bs, 1H), 8.60 (s, 1H), 8.25-8.21 (m, 2H), 8.02 (dd, J = 4.8, 1.6 Hz, 1H), 7.87-7.83 (m, 1H), 7.73-7.68 (m, 1H), 7.03-7.00 (m, 1H), 6.95-6.90 (m, 1H), 6.34 (dd, J = 8.8, 3.2 Hz, 1H), 4.30 (d, J = 11.2 Hz, 1H), 4.11 (dd, J = 11.6, 5.6 Hz, 1H), 3.97 (t, J = 7.2 Hz, 2H), 3.76-3.58 (m, 4H), 3.22-3.15 (m, 1H), 2.4 (s, 7H), 2.00-1.80 (m, 3H), 1.16 (s, 3H); MS (ESI): m/z 623.4 [M + H]$^+$. | ++++ |
| 641. | 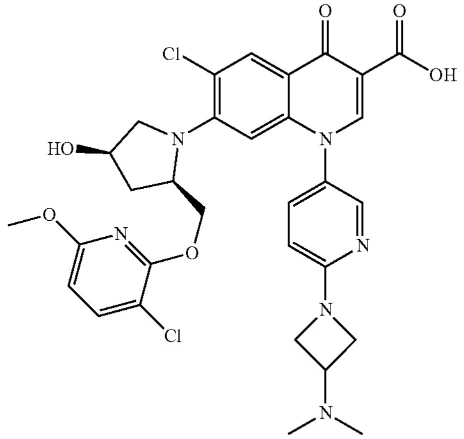 [SMILES: COc1ccc(Cl)c(OC[C@H]2C[C@@H](O)CN2c2cc3c(cc2Cl)c(=O)c(C(=O)O)cn3-c2ccc(N3CC(N(C)C)C3)nc2)n1] | 6-chloro-7-((2R,4R)-2-(((3-chloro-6-methoxypyridin-2-yl)oxy)methyl)-4-hydroxypyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.10 (brs, 1H), 8.52 (d, J = 10.0 Hz, 1H), 8.23-8.20 (m, 1H), 8.12 (d, J = 1.6 Hz, 1H), 7.69-7.66 (m, 1H), 7.63-7.60 (m, 1H), 6.57 (d, J = 8.8 Hz, 0.5H), 6.35 (d, J = 8.8 Hz, 0.5H), 6.31-6.27 (m, 2H), 5.29 (brs, 1H), 4.79-4.60 (m, 1H), 4.41-4.38 (m, 2H), 4.26 (t, J = 6.6 Hz, 1H), 4.10-4.04 (m, 2H), 3.84-3.79 (m, 2H), 3.68 (s, 3H), 3.25-3.21 (m, 3H), 2.48-2.38 (m, 1H), 2.14 (s, 6H), 1.84-1.81 (m, 1H); MS (ESI): m/z 655.1 [M + H]$^+$. | ++++ |
| 642. | 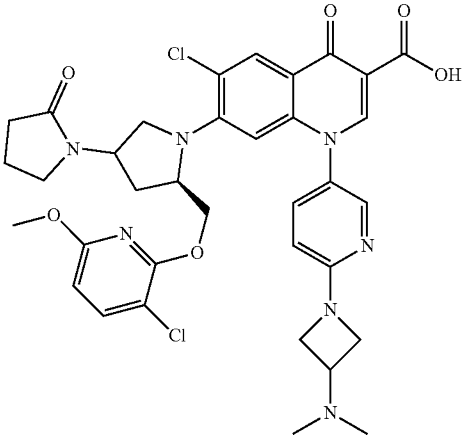 [SMILES: COc1ccc(Cl)c(OC[C@H]2CC(N3CCCC3=O)CN2c2cc3c(cc2Cl)c(=O)c(C(=O)O)cn3-c2ccc(N3CC(N(C)C)C3)nc2)n1] | 6-chloro-7-((5'R)-5'-(((3-chloro-6-methoxypyridin-2-yl)oxy)methyl)-2-oxo-[1,3'-bipyrrolidin]-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.04 (s, 1H), 8.57-8.51 (m, 1H), 8.28-8.17 (m, 1H), 8.16 (s, 1H), 7.75-7.56 (m, 2H), 6.58-6.47 (m, 1H), 6.35-6.27 (m, 2H), 5.12-5.08 (m, 1H), 4.76-4.68 (m, 1H), 4.60-4.48 (m, 1H), 4.33 (br s, 1H), 4.15-4.03 (m, 2H), 3.90-3.78 (m, 2H), 3.72-3.65 (m, 1H), 3.65 (s, 3H), 3.50-3.40 (m, 2H), 3.30-3.20 (m, 1H), 3.12-3.08 (m, 1H), 2.30-2.10 (m, 9H), 2.00-1.80 (m, 3H); MS (ESI): m/z 722.2 [M + H]$^+$. | ++++ |

-continued

| EX # | Structure | IUPAC name | Analytical data | Potency Lin28a-dep Z11 $IC_{50}$ (μM) |
|---|---|---|---|---|
| 643. | 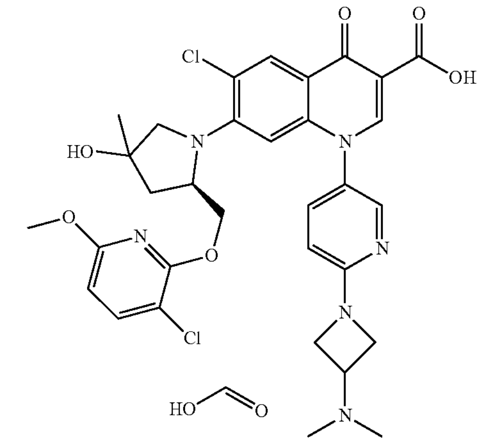 | 6-chloro-7-((2R)-2-(((3-chloro-6-methoxypyridin-2-yl)oxy)methyl)-4-hydroxy-4-methylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 15.26 (s, 1H), 8.52 (d, J = 9.2 Hz, 1H), 8.24-8.20 (m, 1H), 8.15 (s, 1H), 8.13 (s, 1H), 7.69-7.62 (m, 2H), 6.57 (d, J = 8.8 Hz, 0.5H), 6.37 (d, J = 8.8 Hz, 0.5H), 6.32-6.26 (m, 2H), 5.19 (bs, 1H), 4.70-4.59 (m, 1H), 4.48-4.32 (m, 2H), 4.12-4.03 (m, 2H), 3.84-3.79 (m, 2H), 3.63 (s, 3H), 3.57-3.46 (m, 1H), 3.30-3.20 (m, 1H), 2.96 (t, J = 7.6 Hz, 1H), 2.15 (s, 6H), 2.14-2.00 (m, 2H), 1.26 (s, 3H); MS (ESI): m/z 669.4 [M + H]$^+$. | ++++ |
| 644. | 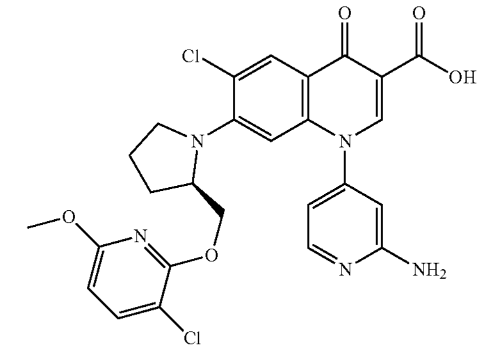 [SMILES: COc1ccc(Cl)c(OC[C@H]2CCCN2c2cc3c(cc2Cl)c(=O)c(C(=O)O)cn3-c2ccnc(N)c2)n1] | (R)-1-(2-aminopyridin-4-yl)-6-chloro-7-(2-(((3-chloro-6-methoxypyridin-2-yl)oxy)methyl) pyrrolidin-1-yl)-4-oxo-1,4-dihydroquinoline-3-carboxylic acid | $^1$H NMR (400 MHz, DMSO-$d_6$) δ 14.98 (bs, 1H), 8.54 (s, 1H), 8.12 (s, 1H), 8.06-8.04 (m, 1H), 7.62 (d, J = 8.0 Hz, 1H), 6.63-6.62 (m, 1H), 6.56-6.48 (m, 4H), 6.24 (d, J = 8.4 Hz, 1H), 4.68-4.65 (m, 1H), 4.57-4.53 (m, 1H), 4.27-4.23 (m, 1H), 3.57 (s, 3H), 3.45-3.40 (m, 1H), 3.19-3.15 (m, 1H), 2.33-2.25 (m, 1H), 2.02-1.96 (m, 2H), 1.811-1.80 (m, 1H); MS (ESI): m/z 556.3 [M + H]$^+$. | ++++ |
| 645. | 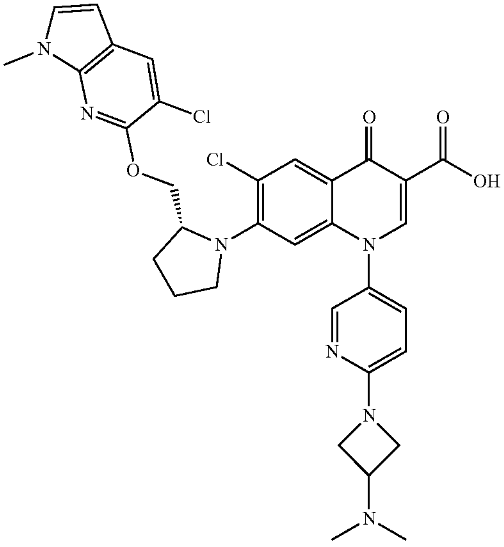 [SMILES: CN(C)C1CN(c2ccc(-n3cc(C(=O)O)c(=O)c4cc(Cl)c(N5CCC[C@@H]5COc5nc6c(ccn6C)cc5Cl)cc43)cn2)C1] | (R)-6-chloro-7-(2-(((5-chloro-1-methyl-1H-pyrrolo[2,3-b]pyridin-6-yl)oxy)methyl) pyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.03 (br s, 1H), 8.43-8.36 (m, 1H), 8.14 (s, 1H), 8.10 (s, 1H), 7.95 (d, J = 4.0 Hz, 1H), 7.60 (dd, J = 8.4, 2.4 Hz, 0.5H), 7.51 (dd, J = 8.4, 2.8 Hz, 0.5H), 7.16 (t, J = 1.6 Hz, 1H), 6.57 (d, J = 8.8 Hz, 0.5H), 6.27-6.16 (m, 2.5H), 4.80-4.60 (m, 2H), 4.30-4.20 (m, 1H), 4.10-4.00 (m, 2H), 3.85-3.75 (m, 2H), 3.56-3.52 (m, 3H), 3.50-3.40 (m, 1H), 3.28-3.20 (m, 1H), 3.18-3.08 (m, 1H), 2.31-2.28 (m, 1H), 2.14 (s, 6H), 2.12-1.97 (m, 2H), 1.82-1.74 (m, 1H); MS (ESI): m/z 662.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 646. | 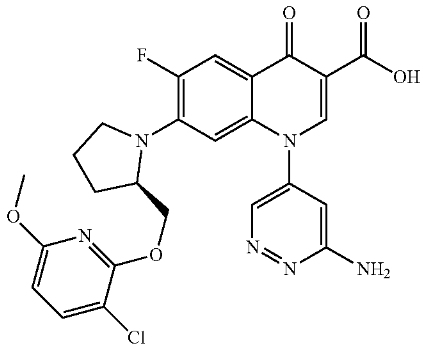 [SMILES: COc1ccc(Cl)c(OC[C@H]2CCCN2c2cc3c(cc2F)c(=O)c(C(=O)O)cn3-c2cnnc(N)c2)n1] | (R)-1-(6-aminopyridazin-4-yl)-7-(2-(((3-chloro-6-methoxypyridin-2-yl)oxy)methyl) pyrrolidin-1-yl)-6-fluoro-4-oxo-1,4-dihydroquinoline-3-carboxylic acid | $^1$H-NMR (400 MHz, DMSO-$d_6$): δ 15.22 (s, 1H), 8.66 (s, 2H), 7.88 (d, J = 14.4 Hz, 1H), 7.68 (d, J = 8.4 Hz, 1H), 7.03 (d, J = 1.6 Hz, 1H), 6.94 (bs, 2H), 6.36 (d, J = 8.4 Hz, 1H), 6.12 (d, J = 7.2, Hz, 1H), 4.60 (bs, 1H), 4.48-4.37 (m, 2H), 3.70 (s, 3H), 3.18-3.15 (m, 2H), 2.18-2.08 (m, 2H), 2.07-1.88 (m, 2H); MS (ESI): m/z 541.0 $[M + H]^+$. | ++++ |
| 647. | 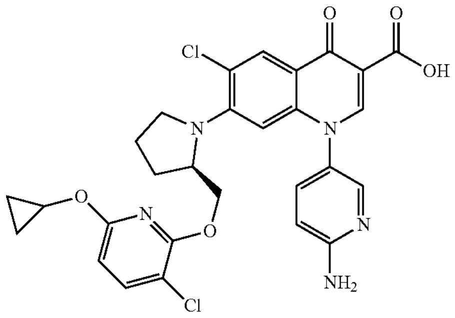 [SMILES: Nc1ccc(-n2cc(C(=O)O)c(=O)c3cc(Cl)c(N4CCC[C@@H]4COc4nc(OC5CC5)ccc4Cl)cc32)cn1] | (R)-1-(6-aminopyridin-3-yl)-6-chloro-7-(2-(((3-chloro-6-cyclopropoxy-pyridin-2-yl)oxy)methyl) pyrrolidin-1-yl)-4-oxo-1,4-dihydroquinoline-3-carboxylic acid | $^1$H NMR (400 MHz, DMSO-$d_6$): δ 15.13 (s, 1H), 8.52 (d, J = 6.8 Hz, 1H), 8.13 (s, 1H), 8.07-8.05 (m, 1H), 7.67-7.62 (m, 1H), 7.55-7.45 (m, 1H), 6.61-6.49 (m, 3H), 6.39 (s, 1H), 6.38 (d, J = 3.6 Hz, 1H), 4.79 (bs, 0.5H), 4.73 (bs, 0.5H), 4.46-4.34 (m, 1H), 4.30-4.27 (m, 1H), 3.85 (bs, 1H), 3.49-3.40 (m, 1H), 3.16 (t, J = 8.4 Hz, 1H), 2.28-2.22 (m, 1H), 2.09-1.90 (m, 2H), 1.85-1.74 (m, 1H), 0.68-0.65 (m, 2H), 0.57-0.49 (m, 2H); MS (ESI): m/z 582.3 $[M + H]^+$. | ++++ |
| 648. | 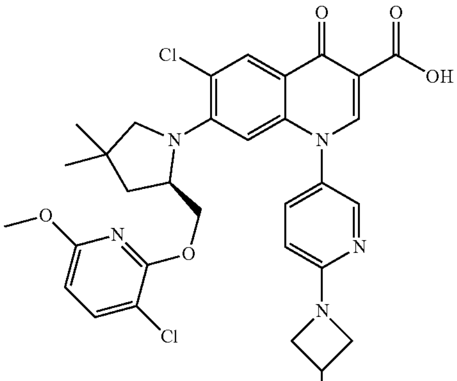 $CF_3COOH$ | (R)-6-chloro-7-(2-(((3-chloro-6-methoxypyridin-2-yl)oxy)methyl)-4,4-dimethylpyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.02 (bs, 1H), 10.46 (bs, 1H), 8.46 (d, J = 9.6 Hz, 1H), 8.33 (dd, J = 12.4, 2.4 Hz, 1H), 8.16 (s, 1H), 7.81-7.77 (m, 1H), 7.67-7.64 (m, 1H), 6.69 (d, J = 8.8 Hz, 0.5H), 6.53 (d, J = 8.8 Hz, 0.5H), 6.31-6.26 (m, 2H), 4.72-4.55 (m, 2H), 4.33-4.15 (m, 6H), 3.56 (s, 3H), 3.31 (t, J = 9.6 Hz, 1H), 2.86 (s, 7H), 1.99-1.88 (m, 2H), 1.12 (s, 3H), 1.01 (s, 3H); MS (ESI): m/z 667.4 $[M + H]^+$. | ++++ |
| 649. | 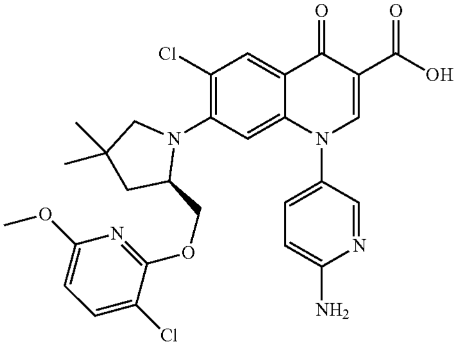 [SMILES: COc1ccc(Cl)c(OC[C@H]2CC(C)(C)CN2c2cc3c(cc2Cl)c(=O)c(C(=O)O)cn3-c2ccc(N)nc2)n1] | (R)-1-(6-aminopyridin-3-yl)-6-chloro-7-(2-(((3-chloro-6-methoxypyridin-2-yl)oxy)methyl)-4,4-dimethylpyrrolidin-1-yl)-4-oxo-1,4-dihydroquinoline-3-carboxylic acid | $^1$H NMR (400 MHz, DMSO-$d_6$) δ 15.12 (brs, 1H), 8.51 (d, J = 6.4 Hz, 1H), 8.14 (s, 1H), 8.08-8.06 (m, 1H), 7.65 (dd, J = 20.0, 8.4 Hz, 1H), 7.54-7.48 (m, 1H), 6.64-6.52 (m, 3H), 6.35 (s, 1H), 6.25 (d, J = 8.0 Hz, 1H), 4.73-4.63 (m, 2H), 4.17 (d, J = 11.6 Hz, 1H), 3.55 (s, 3H), 3.35-3.28 (m, 1H), 2.86 (t, J = 11.6 Hz, 1H), 2.09-1.97 (m, 1H), 1.93-1.88 (m, 1H), 1.13 (s, 3H), 1.02 (d, J = 3.6 Hz, 3H); MS (ESI): m/z 584.3 $[M + H]^+$. | ++++ |

-continued

| EX # | Structure | IUPAC name | Analytical data | Potency Lin28a-dep Z11 $IC_{50}$ (μM) |
| --- | --- | --- | --- | --- |
| 650. | 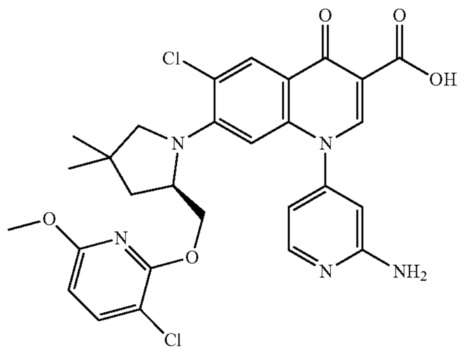 [SMILES: COc1ccc(Cl)c(OC[C@H]2CC(C)(C)CN2c2cc3c(cc2Cl)c(=O)c(C(=O)O)cn3-c2ccnc(N)c2)n1] | (R)-1-(2-aminopyridin-4-yl)-6-chloro-7-(2-(((3-chloro-6-methoxypyridin-2-yl)oxy)methyl)-4,4-dimethylpyrrolidin-1-yl)-4-oxo-1,4-dihydroquinoline-3-carboxylic acid | $^{1}$H NMR (400 MHz, DMSO-$d_6$) δ 14.96 (bs, 1H), 8.54 (s, 1H), 8.13 (s, 1H), 8.06 (bs, 1H), 7.65 (d, J = 8.4 Hz, 1H), 6.63 (dd, J = 5.2, 1.6 Hz, 1H), 6.60-6.50 (m, 3H), 6.47-6.41 (m, 1H), 6.23 (d, J = 8.4 Hz, 1H), 4.73-4.66 (m, 2H), 4.16-4.10 (m, 1H), 3.50 (s, 3H), 3.37-3.31 (m, 1H), 2.86 (d, J = 8.0 Hz, 1H), 2.00-1.90 (m, 2H), 1.13 (s, 3H), 1.02 (s, 3H); MS (ESI): m/z 584.3 [M + H]$^+$. | ++++ |
| 651. | 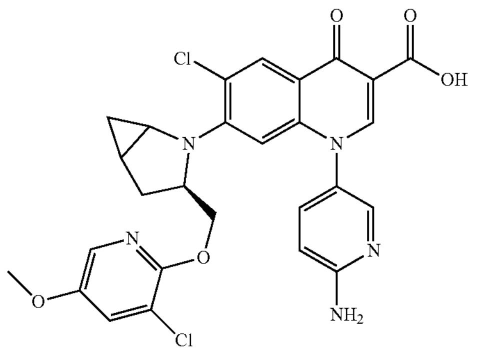 [SMILES: COc1cnc(OC[C@H]2CC3CC3N2c2cc3c(cc2Cl)c(=O)c(C(=O)O)cn3-c2ccc(N)nc2)c(Cl)c1] | 1-(6-aminopyridin-3-yl)-6-chloro-7-((3R)-3-(((3-chloro-5-methoxypyridin-2-yl)oxy)methyl)-2-azabicyclo[3.1.0]hexan-2-yl)-4-oxo-1,4-dihydroquinoline-3-carboxylic acid | $^{1}$H NMR (400 MHz, DMSO-$d_6$) δ 15.09 (bs, 1H), 8.55 (s, 1H), 8.16-8.09 (m, 2H), 7.61-7.55 (m, 3H), 6.97 (d, J = 11.2 Hz, 1H), 6.64-6.53 (m, 3H), 5.09-5.02 (m, 1H), 4.08-4.00 (m, 2H), 3.69 (s, 3H), 3.01-2.98 (m, 1H), 2.69-2.62 (m, 1H), 2.08-2.02 (m, 1H), 1.64-1.59 (m, 1H), 1.08-1.01 (m, 1H), 0.61-0.57 (m, 1H); MS (ESI): m/z 568.3 [M + H]$^+$. | ++++ |
| 652. | 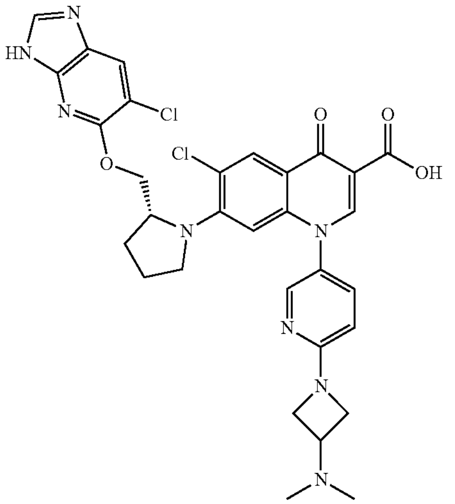 [SMILES: CN(C)C1CN(c2ccc(-n3cc(C(=O)O)c(=O)c4cc(Cl)c(N5CCC[C@@H]5COc5nc6[nH]cnc6cc5Cl)cc43)cn2)C1] | (R)-6-chloro-7-(2-(((6-chloro-3H-imidazo[4,5-b]pyridin-5-yl)oxy)methyl)pyrrolidin-1-yl)-1-(6-(3-(dimethylamino)azetidin-1-yl)pyridin-3-yl)-4-oxo-1,4-dihydroquinoline-3-carboxylic acid | $^{1}$H NMR (400 MHz, DMSO-$d_6$): δ 15.13 (bs, 1H), 12.84 (bs, 1H), 8.47 (d, J = 13.2 Hz, 1H), 8.24-8.04 (m, 4H), 7.65 (d, J = 8.8 Hz, 0.5H), 6.56-6.53 (m, 1H), 6.37 (bs, 1H), 6.25 (d, J = 8.8 Hz, 0.5H), 4.80-4.60 (m, 1H), 4.44-4.26 (m, 2H), 4.10-4.00 (m, 2H), 3.85-3.75 (m, 2H), 3.60-3.48 (m, 1H), 3.28-3.16 (m, 2H), 2.32-2.26 (m, 1H), 2.14 (s, 6H), 2.09-1.90 (m, 2H), 1.88-1.74 (m, 1H); MS (ESI): m/z 649.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 653. | 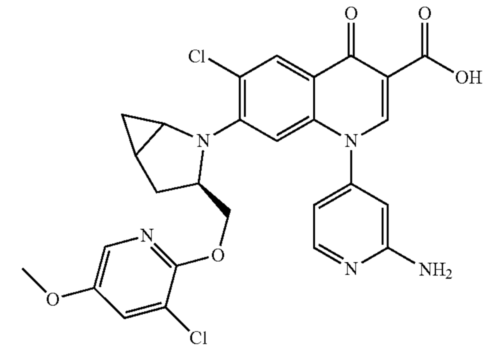 [SMILES: COc1cnc(OC[C@H]2CC3CC3N2c2cc3c(cc2Cl)c(=O)c(C(=O)O)cn3-c2ccnc(N)c2)c(Cl)c1] | 1-(2-aminopyridin-4-yl)-6-chloro-7-((3R)-3-(((3-chloro-5-methoxypyridin-2-yl)oxy)methyl)-2-azabicyclo[3.1.0]hexan-2-yl)-4-oxo-1,4-dihydroquinoline-3-carboxylic acid | $^1$H NMR (400 MHz, DMSO-$d_6$) δ 14.97 (bs, 1H), 8.59 (s, 1H), 8.19-8.08 (m, 2H), 7.56 (s, 2H), 7.15 (bs, 1H), 6.72 (bs, 1H), 6.64 (s, 1H), 6.54 (bs, 2H), 5.09-5.02 (m, 1H), 4.06-4.05 (m, 2H), 3.68 (s, 3H), 3.05-3.01 (m, 1H), 2.63-2.60 (m, 1H), 2.08-2.05 (m, 1H), 1.68-1.62 (m, 1H), 1.05-1.01 (m, 1H), 0.65-0.63 (m, 1H); MS (ESI): m/z 568.3 $[M + H]^+$. | ++++ |
| 654. | 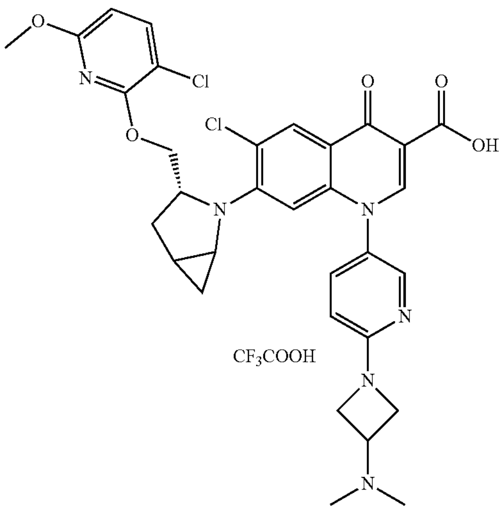 [SMILES: COc1ccc(Cl)c(OC[C@H]2CC3CC3N2c2cc3c(cc2Cl)c(=O)c(C(=O)O)cn3-c2ccc(N3CC(N(C)C)C3)nc2)n1 ; "CF3COOH"] $CF_3COOH$ | 6-chloro-7-((3R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-4-oxo-1,4-dihydroquinoline-3-carboxylic acid | $^1$H NMR (400 MHz, DMSO-$d_6$) δ 15.10 (bs, 1H), 10.34 (bs, 1H), 8.53 (d, J = 6.8 Hz, 1H), 8.38-8.32 (m, 1H), 8.16 (s, 1H), 7.87 (d, J = 6.4 Hz, 0.5H), 7.78 (d, J = 6.4 Hz, 0.5H), 7.64 (dd, J = 8.8, 3.6 Hz, 1H), 6.86 (d, J = 13.2 Hz, 1H), 6.70 (d, J = 9.2 Hz, 0.5H), 6.58 (d, J = 9.2 Hz, 0.5H), 6.29 (d, J = 8.4 Hz, 1H), 5.00 (bs, 1H), 4.39-4.10 (m, 6H), 3.66 (d, J = 3.6 Hz, 3H), 3.28-3.20 (m, 1H), 3.05-2.98 (m, 1H), 2.85 (s, 6H), 2.10-2.00 (m, 2H), 1.70-1.60 (m, 1H), 1.10-1.00 (m, 1H), 0.64-0.59 (m, 1H); MS (ESI): m/z 651.4 $[M + H]^+$. | ++++ |
| 655. | 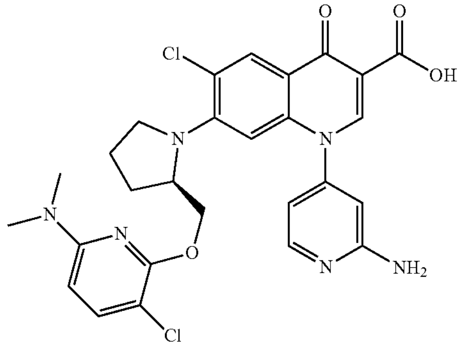 [SMILES: CN(C)c1ccc(Cl)c(OC[C@H]2CCCN2c2cc3c(cc2Cl)c(=O)c(C(=O)O)cn3-c2ccnc(N)c2)n1] | (R)-1-(2-aminopyridin-4-yl)-6-chloro-7-(2-(((3-chloro-6-(dimethylamino)pyridin-2-yl)oxy)methyl)pyrrolidin-1-yl)-4-oxo-1,4-dihydroquinoline-3-carboxylic acid | $^1$H-NMR (400 MHz, DMSO-$d_6$): δ 15.04 (bs, 1H), 8.53 (s, 1H), 8.13 (s, 1H), 8.10-8.00 (m, 2H), 7.35 (d, J = 8.4 Hz, 1H), 6.61 (d, J = 4.4 Hz, 1H), 6.56 (s, 1H), 6.34 (bs, 1H), 5.83 (d, J = 8.8 Hz, 1H), 4.80-4.60 (m, 3H), 4.03 (d, J = 10.4 Hz, 1H), 3.40-3.30 (m, 1H), 3.12 (t, J = 8.4 Hz, 1H), 2.74 (s, 6H), 2.30-2.20 (m, 1H), 2.12-1.96 (m, 2H), 1.82-1.74 (m, 1H); MS (ESI): m/z 569.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 656. | 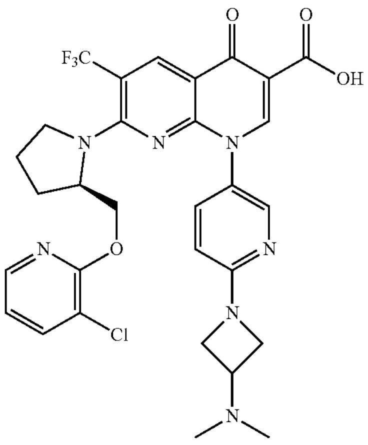 | (R)-7-(2-(((3-chloropyridin-2-yl)oxy)methyl) pyrrolidin-1-yl)-1-(6-(3-(dimethylamino) azetidin-1-yl) pyridin-3-yl)-4-oxo-6-(trifluoromethyl)-1,4-dihydroquinoline-3-carboxylic acid | $^1$H NMR (400 MHz, DMSO-$d_6$): δ 8.55-8.51 (m, 2H), 8.31-8.18 (m, 1H), 7.94 (t, J = 4.4 Hz, 1H), 7.81 (t, J = 8.0 Hz, 1H), 7.73-7.68 (m, 0.5H), 7.62-7.58 (m, 0.5H), 7.01-6.94 (m, 1H), 6.62-6.53 (m, 1.5H), 6.23 (d, J = 9.2 Hz, 0.5H), 4.36-4.19 (m, 2H), 4.14 (bs, 1H), 4.10-4.02 (m, 2H), 3.84-3.75 (m, 2H), 3.51 (d, J = 8.0 Hz, 1H), 3.22 (t, J = 6.0 Hz, 2H), 2.21 (bs, 1H), 2.14 (s, 6H), 1.97 (bs, 1H), 1.88-1.76 (m, 2H (—COOH proton was not observed); MS (ESI): m/z 569.3 $[M + H]^+$. | +++ |
| 657. | 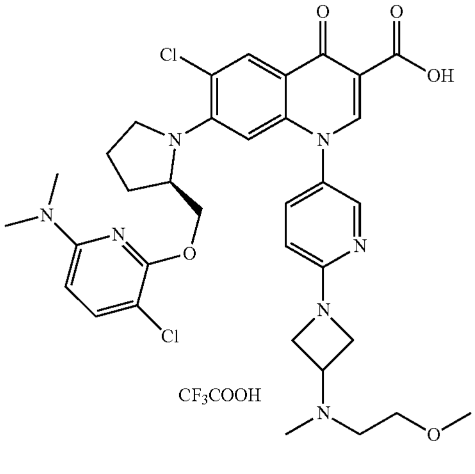 CF$_3$COOH | (R)-6-chloro-7-(2-(((3-chloro-6-(dimethylamino) pyridin-2-yl)oxy)methyl) pyrrolidin-1-yl)-1-(6-(3-((2-methoxyethyl) (methyl)amino) azetidin-1-yl) pyridin-3-yl)-4-oxo-1,4-dihydroquinoline-3-carboxylic acid | $^1$H-NMR (400 MHz, DMSO-$d_6$): δ 15.2 (bs, 1H), 10.23 (bs, 1H), 8.53-8.45 (m, 1H), 8.32-8.28 (m, 1H), 8.13 (s, 1H), 7.77-7.73 (m, 1H), 7.38-7.33 (m, 1H), 6.69 (d, J = 8.8 Hz, 0.5H), 6.53 (d, J = 8.8 Hz, 0.5H), 6.23 (s, 1H), 5.93-5.89 (m, 1H), 4.74-4.59 (m, 2H), 4.40-4.04 (m, 6H), 3.68 (brs, 2H), 3.35 (s, 6H), 3.15-3.08 (m, 1H), 2.85 (s, 3H), 2.79 (s, 6H), 2.30-2.20 (m, 1H), 2.08-1.96 (m, 2H), 1.81-1.75 (m, 1H); MS (ESI): m/z 696.3 $[M + H]^+$. | ++++ |
| 658. | 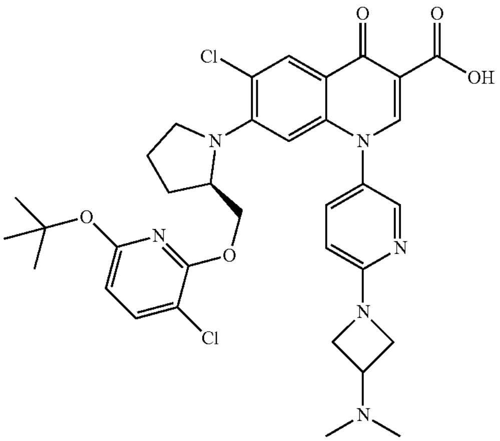 [SMILES: CN(C)C1CN(c2ccc(-n3cc(C(=O)O)c(=O)c4cc(Cl)c(N5CCC[C@@H]5COc5nc(OC(C)(C)C)ccc5Cl)cc43)cn2)C1] | (R)-7-(2-(((6-(tert-butoxy)-3-chloropyridin-2-yl)oxy)methyl) pyrrolidin-1-yl)-6-chloro-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.04 (s, 1H), 8.51 (d, J = 6.8 Hz, 1H), 8.21 (d, J = 7.2 Hz, 1H), 8.15 (s, 1H), 7.74-7.57 (m, 2H), 6.54 (d, J = 8.8 Hz, 0.5H), 6.43-6.37 (m, 1.5H), 6.21 (dd, J = 8.4, 3.2 Hz, 1H), 4.80-4.60 (m, 1H), 4.28-4.06 (m, 5H), 3.84-3.75 (m, 2H), 3.60-3.51 (m, 1H), 3.28-3.16 (m, 1H), 2.30-2.20 (m, 1H), 2.14 (s, 6H), 2.04-1.87 (m, 2H), 1.84-1.76 (m, 1H), 1.45 (s, 9H); MS (ESI): m/z 681.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 659. | 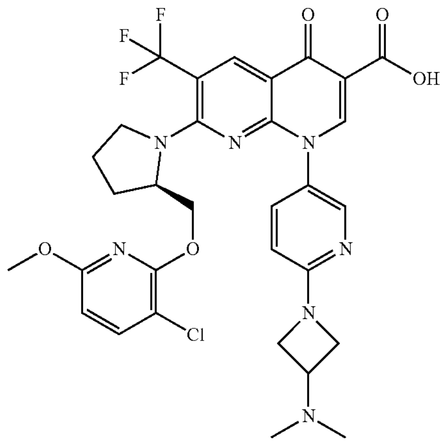 [SMILES: COc1ccc(Cl)c(OC[C@H]2CCCN2c2nc3c(cc2C(F)(F)F)c(=O)c(C(=O)O)cn3-c2ccc(N3CC(N(C)C)C3)nc2)n1] | (R)-7-(2-(((3-chloro-6-methoxypyridin-2-yl)oxy)methyl) pyrrolidin-1-yl)-1-(6-(3-(dimethylamino) azetidin-1-yl) pyridin-3-yl)-4-oxo-6-(trifluoromethyl)-1,4-dihydroquinoline-3-carboxylic acid | $^1H$ NMR (400 MHz, DMSO-$d_6$): δ 14.84 (s, 1H), 8.59 (d, J = 6.8 Hz, 1H), 8.49 (s, 1H), 8.28 (d, J = 2.4 Hz, 0.5H), 8.19 (s, 0.5H), 7.74-7.63 (m, 2H), 6.57-6.50 (m, 1.5H), 6.37-6.28 (m, 1.5H), 4.50-4.40 (m, 1H), 4.30-4.20 (m, 1H), 4.20-4.10 (m, 2H), 4.10-4.00 (m, 2H), 3.61 (s, 3H), 3.64-3.54 (m, 1H), 3.28-3.18 (m, 2H), 2.30-2.20 (m, 1H), 2.16 (s, 6H), 2.04-1.87 (m, 3H), 1.84-1.76 (m, 1H); MS (ESI): m/z 673.3 [M + H]$^+$. | ++++ |
| 660. | 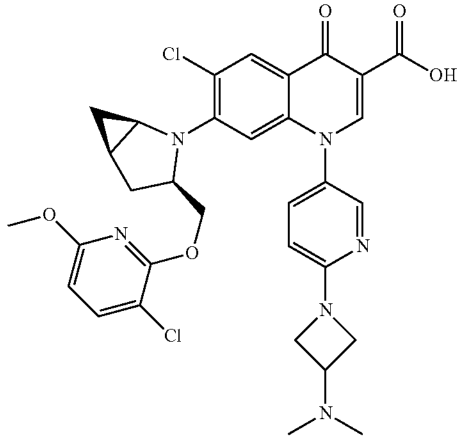 [SMILES: COc1ccc(Cl)c(OC[C@H]2C[C@H]3C[C@H]3N2c2cc3c(cc2Cl)c(=O)c(C(=O)O)cn3-c2ccc(N3CC(N(C)C)C3)nc2)n1] | 6-chloro-7-((1R,3R,5R)-3-(((3-chloro-6-methoxypyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1H$ NMR (400 MHz, DMSO-$d_6$) δ 15.10 (bs, 1H), 8.55 (d, J = 6.8 Hz, 1H), 8.26-8.23 (m, 1H), 8.14 (s, 1H), 7.76-7.67 (m, 1H), 7.66-7.62 (m, 1H), 6.84 (d, J = 18.0 Hz, 1H), 6.59-6.43 (m, 1H), 6.28 (d, J = 8.4 Hz, 1H), 5.02-4.96 (m, 1H), 4.24-4.14 (m, 2H), 4.08-4.05 (m, 2H), 3.83-3.80 (m, 2H), 3.64 (d, J = 2.8 Hz, 3H), 3.22-3.20 (m, 1H), 3.05-3.02 (m, 1H), 2.69-2.66 (m, 1H), 2.13 (s, 6H), 2.07-2.01 (m, 1H), 1.66-1.59 (m, 1H), 1.03-1.00 (m, 1H), 0.66-0.63 (m, 1H); MS (ESI): m/z 651.4 [M + H]$^+$. | ++++ |
| 661. | 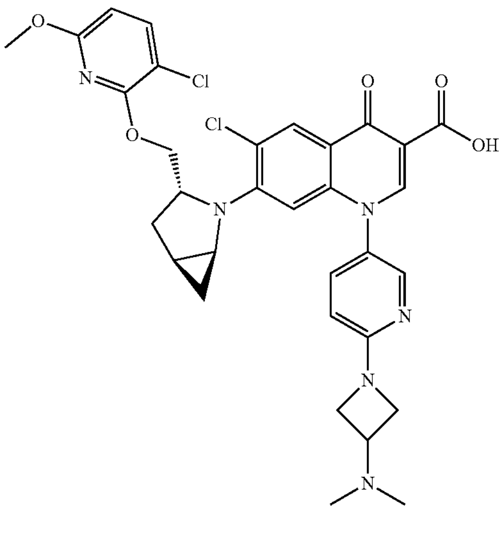 [SMILES: COc1ccc(Cl)c(OC[C@H]2C[C@@H]3C[C@@H]3N2c2cc3c(cc2Cl)c(=O)c(C(=O)O)cn3-c2ccc(N3CC(N(C)C)C3)nc2)n1] | 6-chloro-7-((1S,3R,5S)-3-(((3-chloro-6-methoxypyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1H$ NMR (400 MHz, DMSO-$d_6$) δ 15.10 (bs, 1H), 8.55 (d, J = 6.8 Hz, 1H), 8.32-8.18 (m, 2H), 7.81-7.59 (m, 2H), 6.70 (d, J = 10.8 Hz, 1H), 6.54 (d, J = 8.4 Hz, 0.5H), 6.45-6.37 (m, 1H), 6.15 (d, J = 8.8 Hz, 0.5H), 4.39-4.32 (m, 2H), 4.09-3.97 (m, 3H), 3.83-3.73 (m, 2H), 3.66 (d, J = 3.6 Hz, 3H), 3.55 (bs, 1H), 3.21-3.15 (m, 1H), 2.21-2.17 (m, 2H), 2.13 (s, 6H), 1.72-1.65 (m, 1H), 0.56-0.49 (m, 2H); MS (ESI): m/z 651.3 [M + H]$^+$. | ++++ |

-continued

| EX # | Structure | IUPAC name | Analytical data | Potency Lin28a-dep Z11 $IC_{50}$ (μM) |
|---|---|---|---|---|
| 662. | 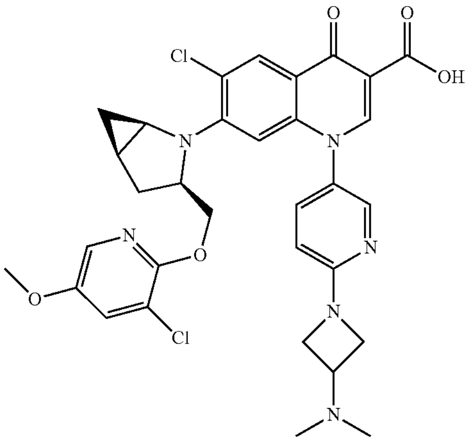 [SMILES: COc1cnc(OC[C@H]2C[C@H]3C[C@H]3N2c2cc3c(cc2Cl)c(=O)c(C(=O)O)cn3-c2ccc(N3CC(N(C)C)C3)nc2)c(Cl)c1] | 6-chloro-7-((1R,3R,5R)-3-(((3-chloro-5-methoxypyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$): δ 15.05 (brs, 1H), 8.56 (d, J = 6.4 Hz, 1H), 8.27 (brs, 1H), 8.14 (s, 1H), 7.74 (t, J = 9.6 Hz, 1H), 7.60 (d, J = 2.8 Hz, 1H), 7.57 (d, J = 2.4 Hz, 1H), 6.91 (d, J = 19.2 Hz, 1H), ), 6.58 (d, J = 8.8 Hz, 0.5H), 6.46 (d, J = 8.8 Hz, 0.5H), 4.99 (brs, 1H), 4.09-4.05 (m, 3H), 4.00-3.97 (m, 1H), 3.83-3.79 (m, 2H), 3.70 (s, 3H), 3.23 (brs, 1H), 3.00-2.99 (m, 1H), 2.68-2.63 (m, 1H), 2.13 (s, 6H), 2.08-2.02 (m, 1H), 1.64-1.61 (m, 1H), 0.97 (brs, 1H), 0.61 (brs, 1H); MS (ESI): m/z 651.0 [M + H]$^+$. | ++++ |
| 663. | 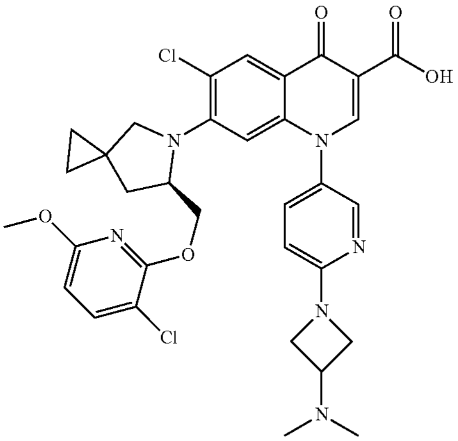 [SMILES: COc1ccc(Cl)c(OC[C@H]2CC3(CC3)CN2c2cc3c(cc2Cl)c(=O)c(C(=O)O)cn3-c2ccc(N3CC(N(C)C)C3)nc2)n1] | (R)-6-chloro-7-(6-(((3-chloro-6-methoxypyridin-2-yl)oxy)methyl)-5-azaspiro[2.4] heptan-5-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.08 (s, 1H), 8.52 (d, J = 11.2 Hz, 1H), 8.25-8.20 (m, 1H), 8.16 (s, 1H), 7.68-7.64 (m, 2H), 6.56 (d, J = 8.8 Hz, 1H), 6.34-6.28 (m, 2H), 4.77 (br s, 1H), 4.66 (br s, 1H), 4.46-4.34 (m, 2H), 4.10-4.04 (m, 2H), 3.88-3.79 (m, 4H), 3.63 (s, 3H), 3.25-3.19 (m, 1H), 2.88-2.81 (m, 1H), 2.25-2.18 (m, 1H), 2.15 (s, 6H), 1.99-1.90 (m, 1H), 0.66-0.53 (m, 2H); MS (ESI): m/z 665.3 [M + H]$^+$. | ++++ |
| 664. | 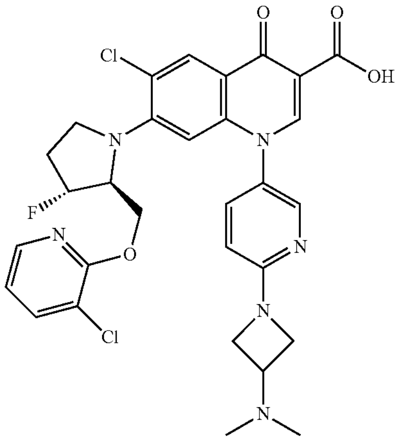 [SMILES: CN(C)C1CN(c2ccc(-n3cc(C(=O)O)c(=O)c4cc(Cl)c(N5CC[C@@H](F)[C@@H]5COc5ncccc5Cl)cc43)cn2)C1] | 6-chloro-7-((2S,3R)-2-(((3-chloropyridin-2-yl)oxy)methyl)-3-fluoropyrrolidin-1-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.04 (bs, 1H), 8.53 (d, J = 7.6 Hz, 1H), 8.23 (dd, J = 19.2, 2.4 Hz, 1H), 8.18 (d, J = 2.8 Hz, 1H), 7.95 (d, J = 4.8 Hz, 1H), 7.82 (t, J = 7.6 Hz, 1H), 7.74 (dd, J = 9.2, 2.8 Hz, 0.5H), 7.64 (dd, J = 9.2, 1.6 Hz, 0.5H), 7.01-6.96 (m, 1H), 6.53 (d, J = 8.8 Hz, 0.5H), 6.45 (d, J = 8.8 Hz, 0.5H), 6.39 (s, 1H), 5.49-5.35 (m, 1H), 5.16-5.02 (m, 1H), 4.46-4.40 (m, 1H), 4.32-4.26 (m, 1H), 4.12-4.03 (m, 2H), 3.88-3.78 (m, 2H), 3.55-3.48 (m, 1H), 3.28-3.20 (m, 2H), 2.26-2.10 (m, 8H),; MS (ESI): m/z 627.2 [M + H]$^+$. | ++++ |

-continued

| EX # | Structure | IUPAC name | Analytical data | Potency Lin28a-dep Z11 $IC_{50}$ (μM) |
|---|---|---|---|---|
| 665. | 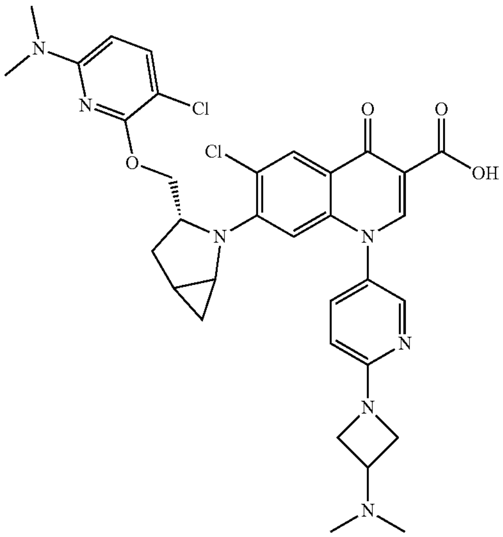 [SMILES: CN(C)c1ccc(Cl)c(OC[C@H]2CC3CC3N2c2cc3c(cc2Cl)c(=O)c(C(=O)O)cn3-c2ccc(N3CC(N(C)C)C3)nc2)n1] | 6-chloro-7-((3R)-3-(((3-chloro-6-(dimethylamino) pyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.13 (s, 1H), 8.55 (d, J = 5.6 Hz, 1H), 8.22 (d, J = 10.4 Hz, 1H), 8.14 (s, 1H), 7.74 (d, J = 6.8 Hz, 0.5H), 7.60 (dd, J = 8.4, 2.0 Hz, 0.5H), 7.37 (d, J = 8.4 Hz, 1H), 6.58 (d, J = 8.8 Hz, 0.5H), 6.46 (d, J = 8.8 Hz, 0.5H), 5.93 (t, J = 8.0 Hz, 1H), 5.02-4.98 (m, 1H), 4.44-4.30 (m, 1H), 4.16-4.06 (m, 2H), 4.04-3.92 (m, 1H), 3.90-3.80 (m, 2H), 3.40-3.30 (m, 1H), 3.04-2.92 (m, 1H), 2.87-2.80 (m, 7H), 2.70-2.60 (m, 1H), 2.24 (bs, 6H), 2.12-2.04 (m, 1H), 1.66-1.58 (m, 1H), 1.20-1.10 (m, 1H). 0.63-0.52 (m, 1H); MS (ESI): m/z 664.3 $[M + H]^+$. | ++++ |
| 666. | 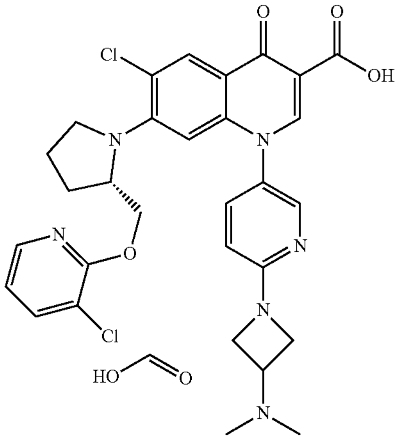 | (S)-6-chloro-7-(2-(((3-chloropyridin-2-yl)oxy)methyl) pyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 15.12 (br s, 1H), 8.51 (d, J = 10.0 Hz, 1H), 8.23 (d, J = 2.4 Hz, 1H), 8.16 (s, 1H), 8.15 (s, 1H), 7.90 (t, J = 4.8 Hz, 1H), 7.83-7.80 (m, 1H), 7.70-7.65 (m, 1H), 6.97-6.92 (m, 1H), 6.56-6.29 (m, 2H), 4.78-4.61 (m, 1H), 4.30-4.20 (m, 2H), 4.07-4.03 (m, 2H), 3.82-3.78 (m, 2H), 3.55-3.50 (m, 1H), 3.40-3.35 (m, 1H), 3.24-3.17 (m, 2H), 2.34-2.26 (m, 1H), 2.14 (s, 6H), 1.98-1.77 (m, 3H); MS (ESI): m/z 609.3 $[M + H]^+$. | ++++ |
| 667. | 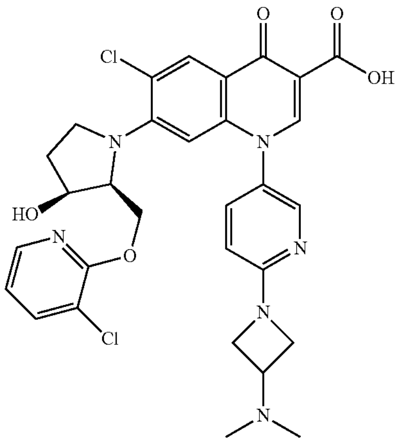 [SMILES: CN(C)C1CN(c2ccc(-n3cc(C(=O)O)c(=O)c4cc(Cl)c(N5CC[C@H](O)[C@@H]5COc5ncccc5Cl)cc43)cn2)C1] | 6-chloro-7-((2S,3S)-2-(((3-chloropyridin-2-yl)oxy)methyl)-3-hydroxypyrrolidin-1-yl)-1-(6-(3-(dimethylamino) azetidin-1-yl) pyridin-3-yl)-4-oxo-1,4-dihydroquinoline-3-carboxylic acid | VT $^1$H NMR (400 MHz, DMSO-$d_6$) δ 8.46 (s, 1H), 8.33-8.28 (m, 1H), 8.18-8.12 (m, 2H), 7.97 (d, J = 4.0 Hz, 1H), 7.75 (d, J = 7.6 Hz, 1H), 7.54-7.48 (m, 1H), 6.95 (dd, J = 7.6, 5.2 Hz, 1H), 6.46 (s, 1H), 6.26 (brs, 1H), 4.52-4.48 (m, 1H), 4.40-4.36 (m, 2H), 4.05-4.00 (m, 2H), 3.98-3.90 (m, 1H), 3.83-3.78 (m, 2H), 3.30-3.25 (m, 2H), 2.17 (s, 6H), 2.05-2.01 (m, 2H), 1.93-1.91 (m, 1H) (—COOH proton was not observed); MS (ESI): m/z 625.3 $[M + H]^+$. | ++++ |

-continued

| EX # | Structure | IUPAC name | Analytical data | Potency Lin28a-dep Z11 $IC_{50}$ (μM) |
|---|---|---|---|---|
| 668. | 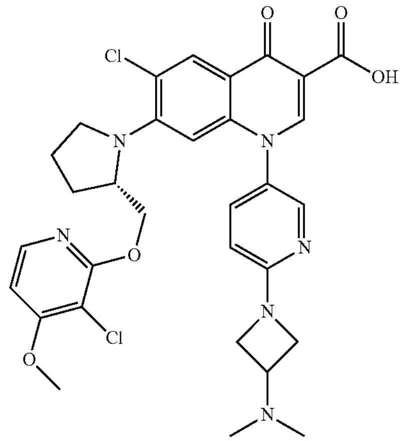 [SMILES: COc1ccnc(OC[C@@H]2CCCN2c2cc3c(cc2Cl)c(=O)c(C(=O)O)cn3-c2ccc(N3CC(N(C)C)C3)nc2)c1Cl] | (S)-6-chloro-7-(2-(((3-chloro-4-methoxypyridin-2-yl)oxy)methyl) pyrrolidin-1-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.11 (s, 1H), 8.52 (d, J = 11.2 Hz, 1H), 8.24 (dd, J = 11.6, 6.0 Hz, 1H), 8.14 (s, 1H), 7.83-7.77 (m, 1H), 7.68-7.64 (m, 1H), 6.85-6.80 (m, 1H), 6.53 (d, J = 9.2 Hz, 0.5H), 6.38 (d, J = 12.8 Hz, 1H), 6.23 (d, J = 8.8 Hz, 0.5H), 4.74 (br s, 0.5H), 4.58 (bs, 0.5H), 4.43-4.31 (m, 1H), 4.20-4.01 (m, 3H), 3.87 (s, 3H), 3.85-3.77 (m, 2H), 3.58-3.47 (m, 1H), 3.28-3.16 (m, 2H), 2.32-2.24 (m, 1H), 2.14 (s, 6H), 2.01-1.92 (m, 1H), 1.88-1.76 (m, 2H); MS (ESI): m/z 639.2 [M + H]$^+$. | ++++ |
| 669. | 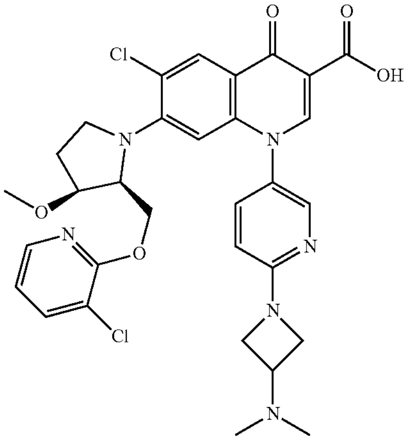 [SMILES: CO[C@H]1CCN(c2cc3c(cc2Cl)c(=O)c(C(=O)O)cn3-c2ccc(N3CC(N(C)C)C3)nc2)[C@H]1COc1ncccc1Cl] | 6-chloro-7-((2S,3S)-2-(((3-chloropyridin-2-yl)oxy)methyl)-3-methoxypyrrolidin-1-yl)-1-(6-(3-(dimethylamino) azetidin-1-yl) pyridin-3-yl)-4-oxo-1,4-dihydroquinoline-3-carboxylic acid | VT $^1$H NMR (400 MHz, DMSO-$d_6$) δ 14.70 (brs, 1H), 8.47 (s, 1H), 8.20-8.17 (m, 2H), 7.97 (dd, J = 4.8, 1.2 Hz, 1H), 7.76 (d, J = 7.6 Hz, 1H), 7.59 (d, J = 6.8 Hz, 1H), 6.98-6.95 (m, 1H), 6.49 (s, 1H), 6.24 (brs, 1H), 4.65-4.58 (brs, 1H), 4.40 (dd, J = 10.8, 4.8 Hz, 1H), 4.34-4.29 (m, 1H), 4.17-4.16 (m, 1H), 4.05-3.98 (m, 2H), 3.83-3.77 (m, 3H), 3.33 (s, 3H), 3.30-3.26 (m, 1H), 3.21-3.19 (m, 1H), 2.17 (s, 6H), 2.07-2.02 (m, 2H); MS (ESI): m/z 639.2 [M + H]$^+$ . . . | ++++ |
| 670. | 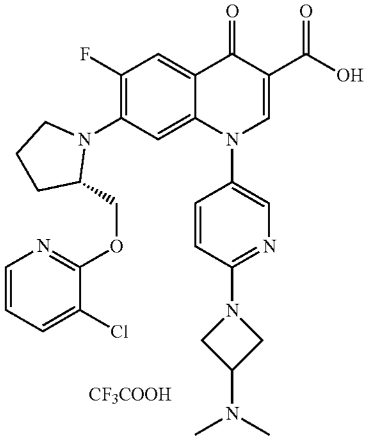 [SMILES: CN(C)C1CN(c2ccc(-n3cc(C(=O)O)c(=O)c4cc(F)c(N5CCC[C@H]5COc5ncccc5Cl)cc43)cn2)C1 ; "CF3COOH"] $CF_3COOH$ | (S)-7-(2-(((3-chloropyridin-2-yl)oxy)methyl) pyrrolidin-1-yl)-1-(6-(3-(dimethylamino) azetidin-1-yl) pyridin-3-yl)-6-fluoro-4-oxo-1,4-dihydroquinoline-3-carboxylic acid | $^1$H NMR (400 MHz, DMSO-$d_6$) δ 15.37 (bs, 1H), 10.70 (s, 1H), 8.45 (d, J = 2.4 Hz, 1H), 8.35 (d, J = 2.4 Hz, 1H), 7.99 (d, J = 4.4 Hz, 1H), 7.90-7.82 (m, 3H), 7.02-6.97 (m, 1H), 6.66 (d, J = 8.8 Hz, 0.5H), 6.51 (d, J = 8.8 Hz, 0.5H), 6.09 (d, J = 6.4 Hz, 1H), 4.60-4.50 (m, 1H), 4.40-4.15 (m, 7H), 3.40-3.30 (m, 1H), 3.24-3.16 (m, 1H), 2.84 (s, 6H), 2.20-2.04 (m, 2H), 2.03-1.88 (m, 2H); MS (ESI): m/z 593.3 [M + H]$^+$. | +++ |

-continued

| EX # | Structure | IUPAC name | Analytical data | Potency Lin28a-dep Z11 $IC_{50}$ (μM) |
|---|---|---|---|---|
| 671. | 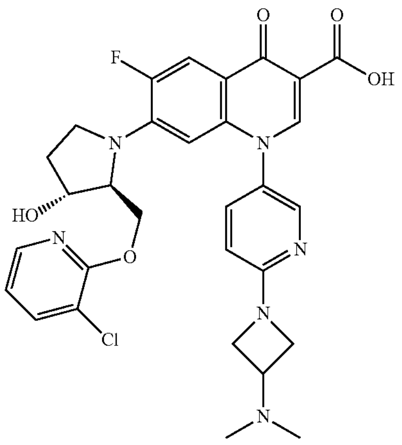 [SMILES: CN(C)C1CN(c2ccc(-n3cc(C(=O)O)c(=O)c4cc(F)c(N5CC[C@@H](O)[C@@H]5COc5ncccc5Cl)cc43)cn2)C1] | 7-((2S,3R)-2-(((3-chloropyridin-2-yl)oxy)methyl)-3-fluoropyrrolidin-1-yl)-1-(6-(3-(dimethylamino) azetidin-1-yl) pyridin-3-yl)-6-fluoro-4-oxo-1,4-dihydroquinoline-3-carboxylic acid | $^1$H-NMR (400 MHz, DMS0) δ 15.50 (bs, 1H), 8.53-8.50 (m, 1H), 8.27 (s, 1H), 8.00 (m, 1H), 7.96-7.87 (m, 2H), 7.78-7.72 (m, 1H), 7.04-7.01 (m, 1H), 6.55 (d, J = 8.8 Hz, 0.5H), 6.42 (d, J = 8.8 Hz, 0.5H), 6.15 (d, J = 7.6 Hz, 1H), 5.49-5.35 (m, 1H), 4.72-4.62 (m, 1H), 4.50-4.35 (m, 2H), 4.12-4.00 (m, 2H), 3.88-3.78 (m, 2H), 3.55-3.45 (m, 1H), 3.40-3.30 (m, 2H), 2.60-2.52 (m, 1H), 2.30-2.20 (m, 1H), 2.14 (s, 6H); MS (ESI): m/z 611.3 [M + H]$^+$. | ++++ |
| 672. | 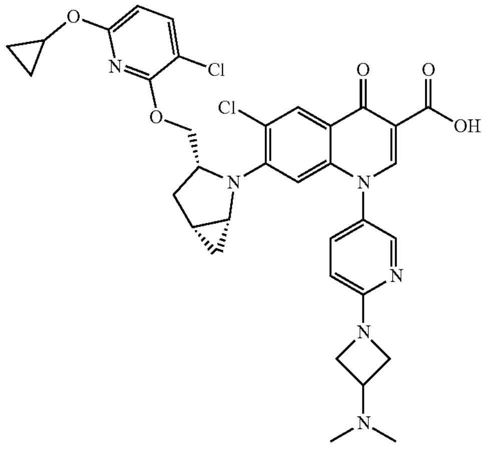 [SMILES: CN(C)C1CN(c2ccc(-n3cc(C(=O)O)c(=O)c4cc(Cl)c(N5[C@@H](COc6nc(OC7CC7)ccc6Cl)C[C@H]6C[C@H]65)cc43)cn2)C1] | 6-chloro-7-((1R,3R,5R)-3-(((3-chloro-6-cyclopropoxy-pyridin-2-yl)oxy)methyl)-2-azabicyclo[3.1.0] hexan-2-yl)-1-(6-(3-(dimethylamino) azetidin-1-yl) pyridin-3-yl)-4-oxo-1,4-dihydroquinoline-3-carboxylic acid | $^1$H-NMR (400 MHz, DMSO-$d_6$): δ 15.13 (s, 1H), 8.56 (d, J = 5.6 Hz, 1H), 8.25 (d, J = 10.4 Hz, 1H), 8.15 (s, 1H), 7.76-7.67 (m, 2H), 7.87 (d, J = 8.4 Hz, 1H), 6.57 (d, J = 8.8 Hz, 0.5H), 6.45 (d, J = 8.8 Hz, 0.5H), 6.20 (d, J = 8.0 Hz, 1H), 5.02-4.98 (m, 1H), 4.20-4.06 (m, 4H), 3.90-3.80 (m, 3H), 3.30-3.20 (m, 1H), 3.04-2.96 (m, 1H), 2.70-2.60 (m, 1H), 2.14 (s, 6H), 2.09-1.98 (m, 1H), 1.68-1.58 (m, 1H), 1.03-0.96 (m, 1H). 0.73-0.55 (m, 5H); MS (ESI): m/z 677.3 [M + H]$^+$. | ++++ |
| 673. | 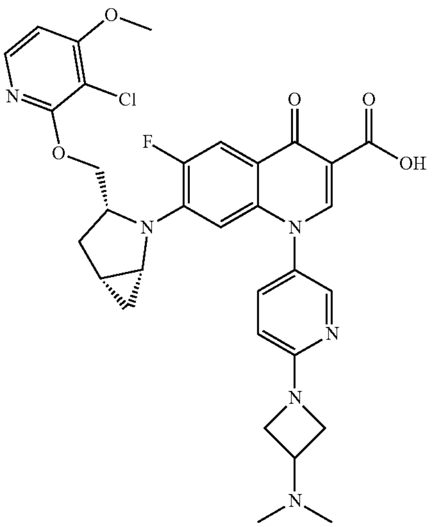 [SMILES: COc1ccnc(OC[C@H]2C[C@H]3C[C@H]3N2c2cc3c(cc2F)c(=O)c(C(=O)O)cn3-c2ccc(N3CC(N(C)C)C3)nc2)c1Cl] | 7-((1R,3R,5R)-3-(((3-chloro-4-methoxypyridin-2-yl)oxy)methyl)-2-azabicyclo[3.1.0] hexan-2-yl)-1-(6-(3-(dimethylamino) azetidin-1-yl) pyridin-3-yl)-6-fluoro-4-oxo-1,4-dihydroquinoline-3-carboxylic acid | $^1$H-NMR (400 MHz, DMSO-$d_6$): δ 15.30 (s, 1H), 8.50 (s, 1H), 8.27 (d, J = 2.4 Hz, 1H), 7.89 (s, 1H), 7.84 (t, J = 6.4 Hz, 1H), 7.73 (d, J = 8.8 Hz, 1H), 6.88-6.82 (m, 1H), 6.56 (t, J = 4.4 Hz, 1H), 6.48-6.30 (m, 1H), 4.73 (br s, 1H), 4.26-4.19 (m, 1H), 4.08-3.98 (m, 3H), 3.88 (d, J = 3.2 Hz, 3H), 3.83-3.76 (m, 2H), 3.25-3.10 (m, 2H), 2.62-2.51 (m, 1H), 2.13 (s, 6H), 2.09-1.98 (m, 1H), 1.61 (br s, 1H), 0.93-0.88 (m, 1H). 0.73-0.65 (m, 1H); MS (ESI): m/z 635.3 | ++++ |

-continued

| EX # | Structure | IUPAC name | Analytical data | Potency Lin28a-dep Z11 $IC_{50}$ (μM) |
|---|---|---|---|---|
| 674. | 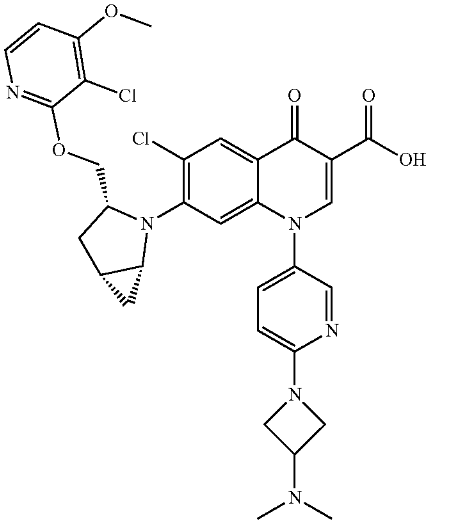 [SMILES: COc1ccnc(OC[C@H]2C[C@H]3C[C@H]3N2c2cc3c(cc2Cl)c(=O)c(C(=O)O)cn3-c2ccc(N3CC(N(C)C)C3)nc2)c1Cl] | 6-chloro-7-((1R,3R,5R)-3-(((3-chloro-4-methoxypyridin-2-yl)oxy)methyl)-2-azabicyclo[3.1.0]hexan-2-yl)-1-(6-(3-(dimethylamino)azetidin-1-yl)pyridin-3-yl)-4-oxo-1,4-dihydroquinoline-3-carboxylic acid | $^1$H-NMR (400 MHz, DMSO-$d_6$) δ 15.07 (s, 1H), 8.55 (d, J = 5.6 Hz, 1H), 8.29 (s, 1H), 8.14 (s, 1H), 7.79-7.72 (m, 2H), 6.88 (d, J = 27.6 Hz, 1H), 6.80 (t, J = 4.8 Hz, 1H), 6.61-6.42 (m, 1H), 5.00 (br s, 1H), 4.20-4.08 (m, 3H), 4.02-3.97 (m, 1H), 3.96-3.85 (m, 5H), 3.43 (s, 1H), 2.99 (t, J = 7.2 Hz, 1H), 2.69-2.60 (m, 1H), 2.35 (br s, 6H), 2.09-1.99 (m, 1H), 1.68-1.59 (m, 1H) ), 1.05-0.95 (m, 1H) ), 0.61 (s, 1H); MS (ESI): m/z 651.3 [M + H]$^+$. | ++++ |
| 675. | 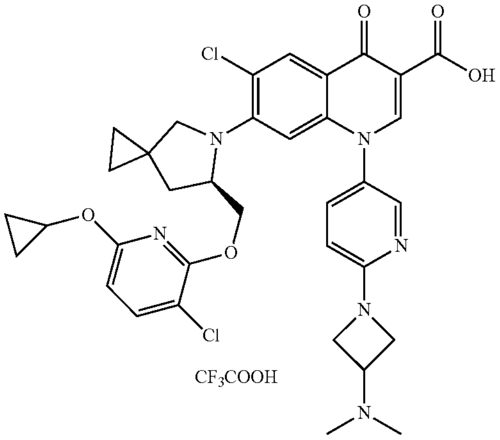 [SMILES: CN(C)C1CN(c2ccc(-n3cc(C(=O)O)c(=O)c4cc(Cl)c(N5CC6(CC6)C[C@@H]5COc5nc(OC6CC6)ccc5Cl)cc43)cn2)C1 ; "CF3COOH"] $CF_3COOH$ | (R)-6-chloro-7-(6-(((3-chloro-6-cyclopropoxy-pyridin-2-yl)oxy)methyl)-5-azaspiro[2.4]heptan-5-yl)-1-(6-(3-(dimethylamino)azetidin-1-yl)pyridin-3-yl)-4-oxo-1,4-dihydroquinoline-3-carboxylic acid | $^1$H-NMR (400 MHz, DMSO-$d_6$): δ 15.08 (s, 1H), 10.42 (bs, 1H), 8.48 (d, J = 11.2 Hz, 1H), 8.31 (dd, J = 4.8, 1.2 Hz, 1H), 8.16 (s, 1H), 7.77 (dd, J = 8.8, 2.4 Hz, 1H), 7.69 (dd, J = 8.4, 2.0 Hz, 1H), 6.67 (d, J = 8.8 Hz, 0.5H), 6.50-6.42 (m, 1.5H), 6.33 (d, J = 6.4 Hz, 1H), 4.84-4.70 (m, 1H), 4.50-4.20 (m, 9H), 3.94-3.76 (m, 3H), 2.81 (s, 7H), 2.25-2.16 (m, 1H), 2.00-1.90 (m, 1H), 1.99-1.80 (m, 1H), 0.70-0.50 (m, 4H); MS (ESI): m/z 691.0 [M + H]$^+$. | ++++ |
| 676. | 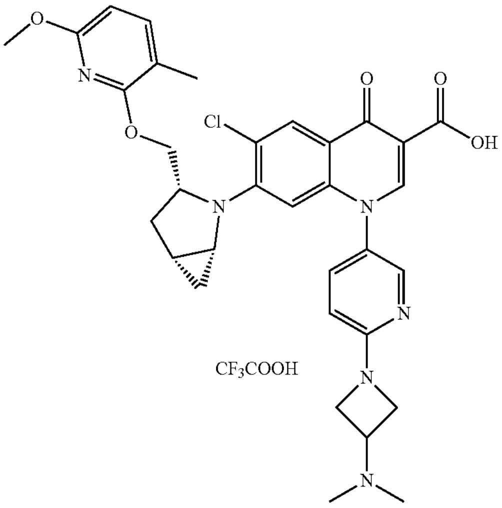 $CF_3COOH$ | 6-chloro-1-(6-(3-(dimethylamino)azetidin-1-yl)pyridin-3-yl)-7-((1R,3R,5R)-3-(((6-methoxy-3-methylpyridin-2-yl)oxy)methyl)-2-azabicyclo[3.1.0]hexan-2-yl)-4-oxo-1,4-dihydroquinoline-3-carboxylic acid | $^1$H NMR (400 MHz, DMSO-$d_6$) δ 15.16 (brs, 1H), 10.42 (bs, 1H), 8.56 (s, 1H), 8.29 (d, J = 2.4 Hz, 1H), 8.11 (d, J = 12.4 Hz, 1H), 7.84 (dd, J = 8.8, 2.4 Hz, 1H), 7.75 (d, J = 8.4 Hz, 1H), 6.41 (d, J = 8.4 Hz, 2H), 4.61 (brs, 1H), 4.25-3.92 (m, 8H), 3.84 (brs, 1H), 3.79 (brs, 1H), 3.74 (s, 3H), 2.83 (s, 6H), 2.02 (dd, J = 12.8, 1.6 Hz, 1H), 1.74-1.70 (m, 1H), 1.13 (bs, 1H), 0.96 (bs, 1H); MS (ESI): m/z 636.0 [M + H]$^+$. | ++++ |

-continued

| EX # | Structure | IUPAC name | Analytical data | Potency Lin28a-dep Z11 $IC_{50}$ (μM) |
|---|---|---|---|---|
| 677. | 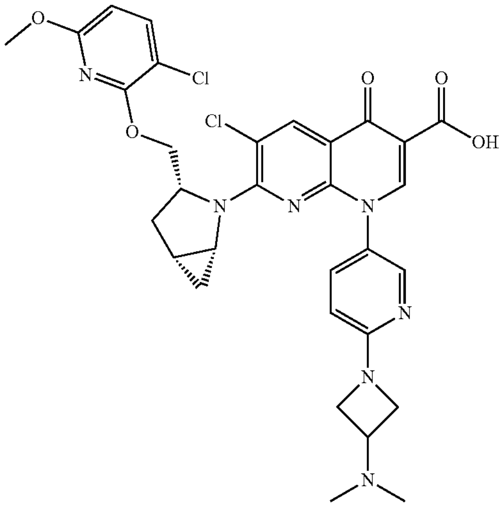 [SMILES: COc1ccc(Cl)c(OC[C@H]2C[C@H]3C[C@H]3N2c2nc3c(cc2Cl)c(=O)c(C(=O)O)cn3-c2ccc(N3CC(N(C)C)C3)nc2)n1] | 6-chloro-7-((1R,3R,5R)-3-(((3-chloro-6-methoxypyridin-2-yl)oxy)methyl)-2-azabicyclo[3.1.0]hexan-2-yl)-1-(6-(3-(dimethylamino)azetidin-1-yl)pyridin-3-yl)-4-oxo-1,4-dihydro-1,8-naphthyridine-3-carboxylic aci | $^1$H NMR (400 MHz, DMSO-$d_6$) δ 15.05 (bs, 1H), 8.63 (s, 1H), 8.35 (s, 1H), 8.21-8.19 (m, 1H), 7.75-7.71 (m, 2H), 6.38 (d, J = 8.4 Hz, 1H), 6.32 (d, J = 8.8 Hz, 1H), 4.68-4.62 (m, 1H), 4.24-4.21 (m, 1H), 4.01-3.92 (m, 3H), 3.76-3.69 (m, 3H), 3.67 (s, 3H), 3.19-3.27 (m, 1H), 2.49-2.46 (m, 1H), 2.11 (s, 6H), 1.99-1.94 (m, 1H), 1.78-1.72 (m, 1H), 1.11-1.04 (m, 2H); MS (ESI): m/z 652.1 $[M + H]^+$. | ++++ |
| 678. | 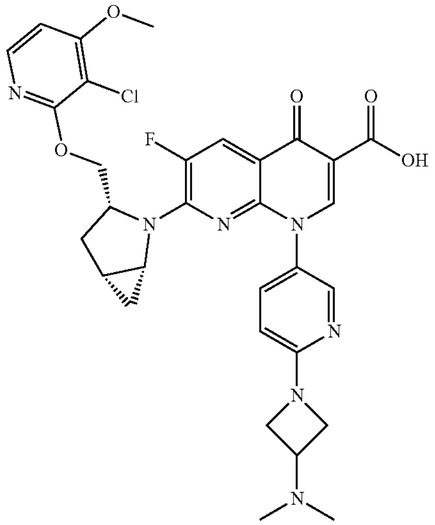 [SMILES: COc1ccnc(OC[C@H]2C[C@H]3C[C@H]3N2c2nc3c(cc2F)c(=O)c(C(=O)O)cn3-c2ccc(N3CC(N(C)C)C3)nc2)c1Cl] | 7-((1R,3R,5R)-3-(((3-chloro-4-methoxypyridin-2-yl)oxy)methyl)-2-azabicyclo[3.1.0]hexan-2-yl)-1-(6-(3-(dimethylamino)azetidin-1-yl)pyridin-3-yl)-6-fluoro-4-oxo-1,4-dihydro-1,8-naphthyridine-3-carboxylic acid | $^1$H-NMR (400 MHz, DMSO-$d_6$) δ 15.28 (s, 1H), 8.57 (s, 1H), 8.16-8.07 (m, 2H), 7.91 (d, J = 5.6 Hz, 1H), 7.63 (d, J = 8.8 Hz, 1H), 6.89 (d, J = 5.6 Hz, 1H), 6.12 (bs, 1H), 4.59 (bs, 1H), 4.19-4.14 (m, 1H), 4.01-3.89 (m, 5H), 3.84-3.78 (m, 2H), 3.70-3.67 (m, 2H), 3.14 (t, J = 6.8 Hz, 1H), 2.49-2.43 (m, 1H), 2.11 (s, 6H), 1.99-1.94 (m, 1H), 1.73-1.69 (m, 1H), 1.05-0.88 (m, 2H); MS (ESI): m/z 636.4 $[M + H]^+$. | ++++ |

-continued

| EX # | Structure | IUPAC name | Analytical data | Potency Lin28a-dep Z11 $IC_{50}$ (μM) |
|---|---|---|---|---|
| 679. | 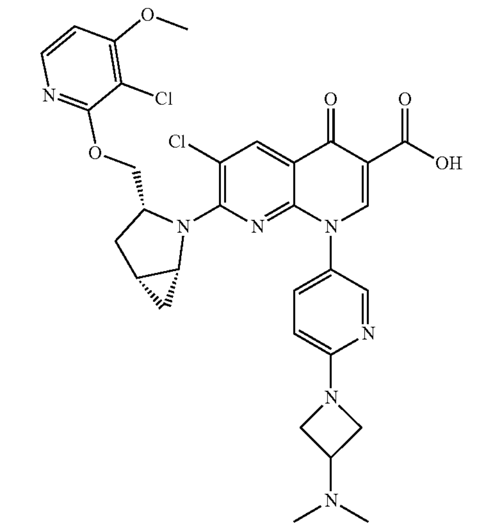 | 6-chloro-7-((1R,3R,5R)-3-(((3-chloro-4-methoxypyridin-2-yl)oxy)methyl)-2-azabicyclo[3.1.0]hexan-2-yl)-1-(6-(3-(dimethylamino)azetidin-1-yl)pyridin-3-yl)-4-oxo-1,4-dihydro-1,8-naphthyridine-3-carboxylic acid | $^1$H-NMR (400 MHz, DMSO-$d_6$) δ 15.05 (s, 1H), 8.62 (s, 1H), 8.35 (s, 1H), 8.18 (d, J = 2.4 Hz, 1H), 7.86 (d, J = 5.6 Hz, 1H), 7.66 (dd, J = 8.8, 2.4 Hz, 1H), 6.87 (d, J = 6.0 Hz, 1H), 6.20 (d, J = 8.4 Hz, 1H), 4.67 (br s, 1H), 4.12-4.07 (m, 2H), 3.99-3.93 (m, 1H), 3.91-3.87 (m, 4H), 3.75-3.69 (m, 3H), 3.16 (t, J = 5.6 Hz, 1H), 2.49-2.43 (m, 1H), 2.11 (s, 6H), 1.94-1.90 (m, 1H), 1.79-1.72 (m, 1H), 1.05-0.96 (m, 2H); MS (ESI): m/z 636.4 [M + H]$^+$. | ++++ |
| 680. | 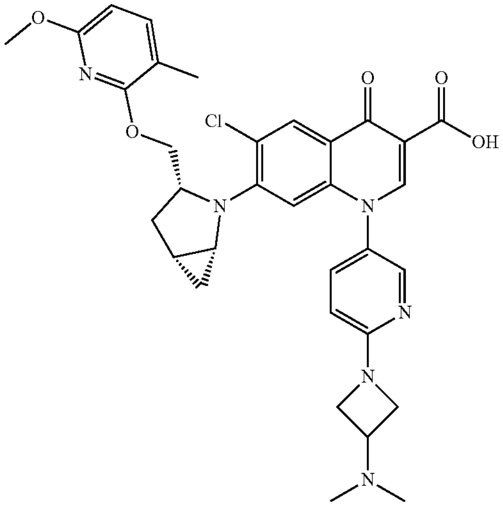 | 6-chloro-1-(6-(3-(dimethylamino)azetidin-1-yl)pyridin-3-yl)-7-((1R,3R,5R)-3-(((6-methoxy-3-methylpyridin-2-yl)oxy)methyl)-2-azabicyclo[3.1.0]hexan-2-yl)-4-oxo-1,4-dihydroquinoline-3-carboxylic acid | $^1$H NMR (400 MHz, DMSO-$d_6$) δ 15.08 (s, 1H), 8.56 (d, J = 4.4 Hz, 1H), 8.26 (d, J = 8.0 Hz, 1H), 8.16 (s, 1H), 7.73 (t, J = 8.0 Hz, 1H), 7.34 (d, J = 8.0 Hz, 1H), 6.85 (s, 0.5H), 6.79 (s, 0.5H), 6.59 (d, J = 9.2 Hz, 0.5H), 6.42 (d, J = 9.2 Hz, 0.5H), 6.18 (dd, J = 8.0, 2.8 Hz, 1H), 5.04-4.80 (m, 1H), 4.18-4.00 (m, 4H), 3.90-3.80 (m, 2H), 3.83 (s, 3H), 3.10-3.00 (m, 1H), 2.50-2.40 (m, 2H), 2.22-2.10 (m, 6H), 2.09-2.00 (m, 1H), 1.92-1.87 (m, 3H), 1.70-1.60 (m, 1H), 0.81 (bs, 1H), 0.72-0.60 (m, 1H); MS (ESI): m/z 636.4 [M + H]$^+$. | ++++ |

-continued

| EX # | Structure | IUPAC name | Analytical data | Potency Lin28a-dep Z11 $IC_{50}$ (μM) |
| --- | --- | --- | --- | --- |
| 681. | 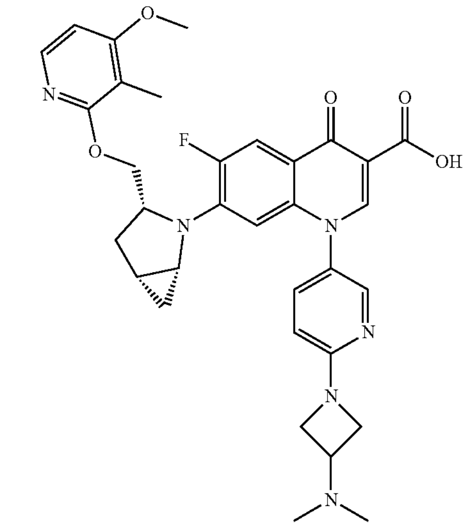 [SMILES: COc1ccnc(OC[C@H]2C[C@H]3C[C@H]3N2c2cc3c(cc2F)c(=O)c(C(=O)O)cn3-c2ccc(N3CC(N(C)C)C3)nc2)c1C] | 1-(6-(3-(dimethylamino) azetidin-1-yl) pyridin-3-yl)-6-fluoro-7-((1R,3R,5R)-3-(((4-methoxy-3-methylpyridin-2-yl)oxy)methyl)-2-azabicyclo[3.1.0] hexan-2-yl)-4-oxo-1,4-dihydroquinoline-3-carboxylic acid | $^{1}$H-NMR (400 MHz, DMS0) δ 15.35 (s, 1H), 8.50 (s, 1H), 8.29 (brs, 1H), 7.90 (d, J = 13.6 Hz, 1H), 7.78-7.70 (m, 2H), 6.71-6.66 (m, 1H), 6.58 (d, J = 8.8 Hz, 1H), 6.46 (d, J = 8.8 Hz, 0.5H), 6.28 (d, J = 8.8 Hz, 0.5H), 4.60-4.45 (m, 1H), 4.30-4.06 (m, 3H), 3.95-3.78 (m, 6H), 3.26-3.15 (m, 1H), 2.60-2.52 (m, 2H), 2.19 (bs, 6H), 2.09-2.02 (m, 1H), 1.84 (s, 3H), 1.65-1.58 (m, 1H), 0.80-0.70 (m, 2H); MS (ESI): m/z 615.1 $[M + H]^{+}$. | ++++ |
| 682. | 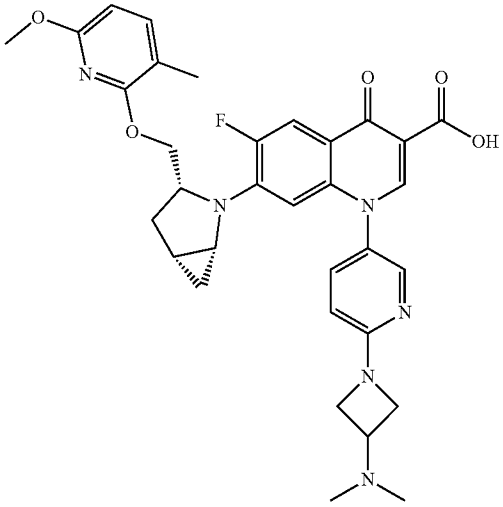 [SMILES: COc1ccc(C)c(OC[C@H]2C[C@H]3C[C@H]3N2c2cc3c(cc2F)c(=O)c(C(=O)O)cn3-c2ccc(N3CC(N(C)C)C3)nc2)n1] | 1-(6-(3-(dimethylamino) azetidin-1-yl) pyridin-3-yl)-6-fluoro-7-((1R,3R, 5R)-3-(((6-methoxy-3-methylpyridin-2-yl)oxy)methyl)-2-azabicyclo[3.1.0] hexan-2-yl)-4-oxo-1,4-dihydroquinoline-3-carboxylic acid | $^{1}$H NMR (400 MHz, DMSO-$d_6$) δ 15.28 (s, 1H), 8.51 (d, J = 2.8 Hz, 1H), 8.27 (d, J = 2.4 Hz, 1H), 7.88 (d, J = 10.8 Hz, 1H), 7.77-7.72 (m, 1H), 7.38 (t, J = 8.0 Hz, 1H), 6.60-6.53 (m, 1H), 6.47 (d, J = 6.8 Hz, 0.5H), 6.34 (d, J = 8.8 Hz, 0.5H), 6.23 (t, J = 8.0 Hz, 1H), 4.80-4.68 (m, 1H), 4.20-4.12 (m, 1H), 4.10-4.00 (m, 3H), 3.85-3.75 (m, 2H), 3.69 (s, 3H), 3.25-3.18 (m, 2H), 2.65-2.55 (m, 1H), 2.14 (s, 6H), 2.09-2.00 (m, 1H), 1.92 (s, 3H), 1.60-1.50 (m, 1H), 0.80-0.70 (m, 2H); MS (ESI): m/z 615.5 $[M + H]^{+}$. | ++++ |

-continued

| EX # | Structure | IUPAC name | Analytical data | Potency Lin28a-dep Z11 $IC_{50}$ (μM) |
|---|---|---|---|---|
| 683. | 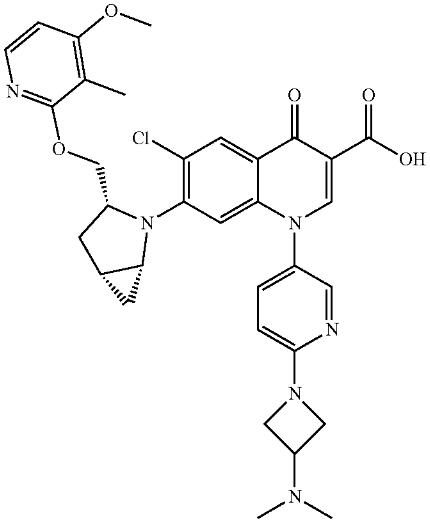 [SMILES: COc1ccnc(OC[C@H]2C[C@H]3C[C@H]3N2c2cc3c(cc2Cl)c(=O)c(C(=O)O)cn3-c2ccc(N3CC(N(C)C)C3)nc2)c1C] | 6-chloro-1-(6-(3-(dimethylamino) azetidin-1-yl) pyridin-3-yl)-7-((1R,3R,5R)-3-(((4-methoxy-3-methylpyridin-2-yl)oxy)methyl)-2-azabicyclo[3.1.0] hexan-2-yl)-4-oxo-1,4-dihydroquinoline-3-carboxylic acid | $^1$H-NMR (400 MHz, DMS0) δ 15.03 (brs, 1H), 8.56 (d, J = 2.8 Hz, 1H), 8.30-8.27 (m, 1H), 8.16 (s, 1H), 7.78-7.70 (m, 2H), 6.65-6.53 (m, 2.5H), 6.35 (d, J = 8.8 Hz, 0.5H), 5.02-4.90 (m, 1H), 4.25-4.02 (m, 3H), 3.95-3.75 (m, 6H), 3.24-3.20 (m, 1H), 3.10-2.98 (m, 1H), 2.65-2.58 (m, 1H), 2.14 (s, 6H), 2.08-1.98 (m, 1H), 1.81 (d, J = 6.4 Hz, 3H), 1.65-1.58 (m, 1H), 0.76-0.50 (m, 2H); MS (ESI): m/z 631.0 [M + H]$^+$. | ++++ |
| 684. | 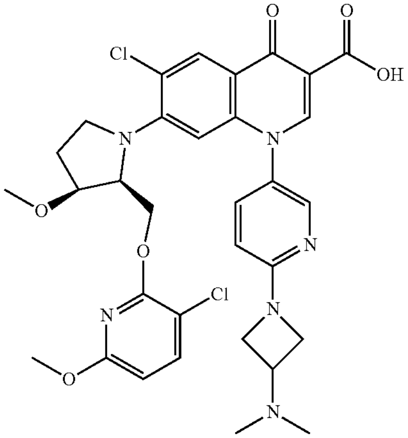 | 6-chloro-7-((2S,3S)-2-(((3-chloro-6-methoxypyridin-2-yl)oxy)methyl)-3-methoxypyrrolidin-1-yl)-1-(6-(3-(dimethylamino) azetidin-1-yl) pyridin-3-yl)-4-oxo-1,4-dihydroquinoline-3-carboxylic acid | $^1$H NMR (400 MHz, DMSO-$d_6$) δ 15.07 (s, 1H), 8.54 (d, J = 10.4 Hz, 1H), 8.27 (d, J = 2.4 Hz, 0.6H), 8.17 (d, J = 7.6 Hz, 1.4H), 7.74-7.59 (m, 2H), 6.53 (d, 0.4H), 6.45-6.37 (m, 2H), 5.91 (d, 0.6H), 4.62-4.68 (m, 0.4H), 4.43-4.40 (m, 0.6H), 4.39-4.37 (m, 1H), 4.36-4.25 (m, 1H), 4.18-4.16 (m, 1H), 4.01-3.94 (m, 2H), 3.85-3.70 (m, 6H), 3.32 (d, J = 4.0 Hz, 3H) 3.28-3.20 (m, 2H), 2.14 (s, 6H), 2.06-1.94 (m, 2H); MS (ESI): m/z 631.0 [M + H]$^+$. | ++++ |
| 685. | 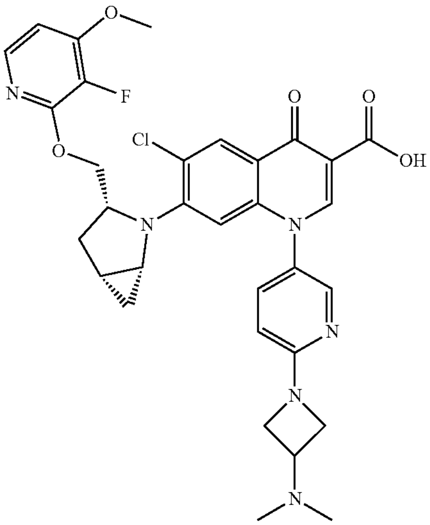 [SMILES: COc1ccnc(OC[C@H]2C[C@H]3C[C@H]3N2c2cc3c(cc2Cl)c(=O)c(C(=O)O)cn3-c2ccc(N3CC(N(C)C)C3)nc2)c1F] | 6-chloro-1-(6-(3-(dimethylamino) azetidin-1-yl) pyridin-3-yl)-7-((1R,3R,5R)-3-(((3-fluoro-4-methoxypyridin-2-yl)oxy)methyl)-2-azabicyclo[3.1.0] hexan-2-yl)-4-oxo-1,4-dihydroquinoline-3-carboxylic acid | $^1$H-NMR (400 MHz, DMSO-$d_6$) δ 15.08 (s, 1H), 8.55 (d, J = 5.6 Hz, 1H), 8.29 (s, 1H), 8.14 (s, 1H), 7.79-7.72 (m, 1H), 7.61 (d, J = 5.6 Hz, 1H), 6.90 (s, 1H), 6.82 (s, 1H), 6.63-6.43 (m, 1H), 5.00 (br s, 1H), 4.20-4.08 (m, 3H), 4.02-3.99 (m, 4H), 3.98-3.84 (m, 1H), 3.83 (s, 3H), 3.00 (t, J = 6.4 Hz, 1H), 2.33-2.08 (m, 5H), 2.07-2.01 (m, 2H), 1.68-1.59 (m, 1H), 0.88-0.81 (m, 1H), 0.61 (s, 1H); MS (ESI): m/z 635.5 [M + H]$^+$. | ++++ |

-continued

| EX # | Structure | IUPAC name | Analytical data | Potency Lin28a-dep Z11 $IC_{50}$ (μM) |
|---|---|---|---|---|
| 686. | 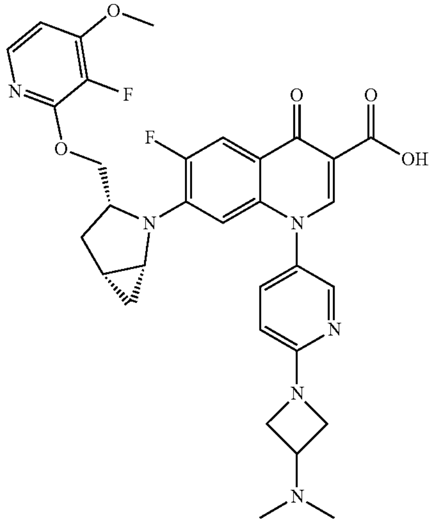 | 1-(6-(3-(dimethylamino)azetidin-1-yl)pyridin-3-yl)-6-fluoro-7-((1R,3R,5R)-3-(((3-fluoro-4-methoxypyridin-2-yl)oxy)methyl)-2-azabicyclo[3.1.0]hexan-2-yl)-4-oxo-1,4-dihydroquinoline-3-carboxylic acid | $^1$H-NMR (400 MHz, DMSO-$d_6$) δ 15.36 (s, 1H), 8.50 (s, 1H), 8.31 (s, 1H), 7.87 (d, J = 13.2 Hz, 1H), 7.78 (d, J = 8.8 Hz, 1H), 7.68 (t, J = 4.8 Hz, 1H), 6.90-6.84 (m, 1H), 6.63-6.36 (m, 2H), 4.80-4.70 (m, 1H), 4.25-4.05 (m, 4H), 4.00-3.90 (m, 2H), 3.85 (s, 3H), 3.20-3.08 (m, 1H), 3.64-2.54 (m, 1H), 2.40 (bs, 7H), 22.07-2.00 (m, 1H), 1.65-1.59 (m, 1H), 0.88-0.79 (m, 1H), 0.72-0.68 (m, 1H); MS (ESI): m/z 691.5 $[M + H]^+$. | ++++ |
| 687. | 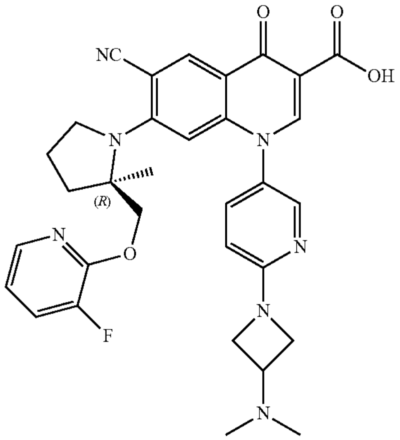 | (R)-6-cyano-1-(6-(3-(dimethylamino)azetidin-1-yl)pyridin-3-yl)-7-(2-(((3-fluoropyridin-2-yl)oxy)methyl)-2-methylpyrrolidin-1-yl)-4-oxo-1,4-dihydroquinoline-3-carboxylic acid Column: X Select CSH Prep C18 OBD Column, 5 um, 19*150 mm; Mobile Phase A; Water (0.1% FA), Mobile Phase B: acetonitrile; Flow rate: 25 mL/min; Gradient: 30 B to 67 B in 10 min; 254 nm. | LCMS (ESI) $[M + H]^+$: 598.20. $^1$H NMR (300 MHz, DMSO-d6) δ 14.66 (s, 1H), 8.58 (d, J = 2.6 Hz, 1H), 8.39 (d, J = 1.8 Hz, 1H), 8.35-8.22 (m, 1H), 7.94-7.57 (m, 3H), 7.00 (m, 1H), 6.61-6.29 (m, 2H), 4.40 (dd, J = 11.4, 4.4 Hz, 1H), 4.32-4.17 (m, 1H), 4.08-3.87 (m, 4H), 3.81-3.62 (m, 2H), 3.24-3.12 (m, 1H), 2.32-2.22 (m, 1H), 2.13 (d, J = 1.0 Hz, 6H), 1.96 (m, 3H), 1.22 (d, J = 11.5 Hz, 3H). | ++++ |

Example 4-1. TUTase Assay

The purpose of the Zcchc11 assay is to determine compound potency against Zcchc11 enzyme through the measurement of $IC_{50}$. Compound inhibition is measured as a function of polyuridine tails added to RNA substrates in the presence of active TUTase, UTP, and inhibitor. The Zcchc11 assay was done in a black, non-binding, 384 well plate (Corning #3575). All steps were performed at room temperature. For a typical assay, a 29 ul aliquot of assay buffer (50 mM HEPES pH 7.3, 150 mM KCl, 5 mM MgCl2, 10 mM DTT, 0.01% Triton X-100, 40 U/ml RNAsin (Promega)) containing LIN28A protein (final concentration: 10 nM) is added to each well. Next, 1 ul of compound in 100% DMSO is transferred from a compound dilution plate in which the compound is serially diluted. Next, 10 ul of a 5× mix of Zcchc11 and RNA substrate (5'-fluorescein labeled pre-let-7 miRNA (Dharmacon)) is added (final concentrations: 0.2 nM and 2 nM, respectively). The plate is placed on a plate shaker for 30 seconds to produce mixing, then incubated for 30 minutes. Next, 10 ul of a 5× mix of UTP and the quenching probe (3'-rhodamine labeled $A_{20}$, poly-adenosine nucleotide, (IDT)) is added (final concentrations: 5 uM and 4 nM, respectively). The plate is immediately placed in a Biotek Cytation 5 plate reader, and the time-dependent decrease in fluorescein fluorescence resulting from annealing of the $A_{20}$ probe to polyuridine tails is recorded, using the kinetics mode of the reader. Reaction rates are obtained using linear fits to the early portion of progress curves. $IC_{50}$ values are calculated using a four parameter fit with 100% enzyme activity determined from the DMSO control and 0% activity from control samples lacking UTP.

The LIN28A protein was expressed in and purified from *E. coli*, strain Rosetta II (Novagen). The entire coding sequence of the human, wild-type protein was cloned into expression vector pMAL (NEB), down-stream from a maltose-binding protein tag. The linker sequence contained a TEV protease cleavage site. The protein was purified from bacterial extracts using an MBP-Trap column (GE Healthcare Life Sciences), followed by tag cleavage and removal of the tag by ion-exchange chromatography. When necessary, contaminating bacterial RNA was removed using the procedure describe by Faehnle C R. et al. (2017) Multi-domain utilization by TUT4 and TUT7 in control of let-7 biogenesis. Nat Struct Mol Biol, 24:658-665.

The Zcchc11 protein was expressed in and purified from HEK293 cells. A truncated protein comprising residues 212-1420 of the human sequence was cloned into expression vector pTT5 (Viva Biotech) down-stream from a maltose-binding protein tag. The linker sequence contained a TEV protease cleavage site, and a FLAG tag was added to the carboxyl terminus of the protein. The protein was purified from cell extracts using an MBP-Trap column (GE Healthcare Life Sciences), followed by tag cleavage and further enrichment of the full length construct using anti-FLAG affinity media (Sigma Aldrich).

The potency of the compounds described herein against Zcchc11 enzyme is shown in Table 1 above. "+" represents an $IC_{50}$ value that is greater than 50 μM; "++" represents an $IC_{50}$ value that is greater than 10 μM and equal to or less than 50 μM; "+++" represents an $IC_{50}$ value that is greater than 1 μM and equal to or less than 10 μM; and "++++" represents an $IC_{50}$ value that is equal to or less than 1 μM.

What is claimed is:

1. A compound represented by Formula (I):

(I)

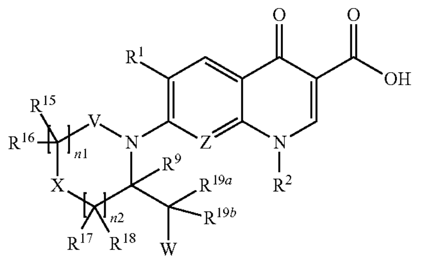

or a pharmaceutically acceptable salt thereof, wherein:

W is $—CH_2Y—R^3$, $—S(O)_2R^3$, $—SCH_2R^3$, $Y—R^3$, $—OC(═O)NR^{11}R^{12}$ or $—N(C═O)NR^{11}R^{12}$;

V is —C(═O)—, $—S(═O)_2—$ or $CR^{13}R^{14}$;

X is $CR^4R^5$, $NR^6$ or O;

Y is O;

Z is $CR^8$ or N;

$R^1$ is halo, —CN, $—OR^{1a}$, —C≡CH, a $C_{3-6}$ carbocyclyl, or a $C_{1-6}$ alkyl, wherein the $C_{1-6}$ alkyl is optionally substituted with one or more $R^{10}$;

$R^{1a}$ is H or $C_{1-6}$ alkyl optionally substituted with one or more $R^{10}$;

$R^{10}$, for each occurrence, is independently selected from halo, —CN and $—OR^{10a}$;

$R^{10a}$, for each occurrence, is independently selected from H and $C_{1-6}$ alkyl;

$R^2$ is —CN, $—CHR^zCN$, $—C(O)NH_2$, $—CHR^zC(O)NH_2$, 3- to 12-membered carbocyclyl, $—(CHR^z)—$(3- to 12-membered carbocyclyl), 3- to 12-membered heterocyclyl, or $—(CHR^z)$-(3 to 12-membered heterocyclyl), wherein the 3 to 12-membered carbocyclyl and the 3 to 12-membered heterocyclyl represented by $R^2$ or in the group represented by $R^2$ are optionally substituted with one or more $R^{20}$, and $R^z$ is H or methyl;

$R^{20}$, for each occurrence, is independently selected from H, halo, CN, oxo, $—C(O)R^{20a}$, $—C(O)_2R^{20a}$, $—C(O)NR^{20a}$, $—N(R^{20a})_2$, $—N(R^{20a})C(O)R^{20a}$, $—N(R^{20a})C(O)_2R^{20a}$, $—N(R^{20a})C(O)N(R^{20a})_2$, $—N(R^{20a})S(O)_2R^{20a}$, $—OR^{20a}$, $—OC(O)R^{20a}$, $—OC(O)N(R^{20a})_2$, $—SR^{20a}$, $—S(O)_2R^{20a}$, $—S(O)N(R^{20a})_2$, $—S(O)_2N(R^{20a})_2$, $C_{1-6}$ alkyl, $C_{3-8}$ cycloalkyl, and 4- to 7-membered monocyclic heterocyclyl, wherein the $C_{1-6}$ alkyl, $C_{3-8}$ cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$ alkyl, $C_{3-8}$ cycloalkyl and 4- to 7-membered monocyclic heterocyclyl, wherein the $C_{1-6}$ alkyl, $C_{3-8}$ cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —C═O, $—C(O)O(C_1-C_6$ alkyl), 4- to 6-membered heterocyclyl optionally substituted with OH, $—N(R^{25a})_2$, or $—OR^{25a}$, or phenyl optionally substituted with $C_{1-6}$ alkyl, halo, $—N(R^{25a})_2$ or $—OR^{25a}$;

$R^{25a}$ is H, $C_{1-6}$alkyl; or two $R^{25a}$ together with the nitrogen atom from which they are attached form a 4- to 7-membered heterocyclyl, wherein the $C_{1-6}$alkyl is optionally substituted with $—OCH_3$;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, $—C(O)R^{30a}$, $—C(O)_2R^{30a}$, $—C(O)NR^{30a}$, $—N(R^{30a})_2$, $—N(R^{30a})C(O)R^{30a}$, $—N(R^{30a})C(O)_2R^{30a}$, $—N(R^{30a})C(O)N(R^{30a})_2$, $—N(R^{30a})S(O)_2R^{30a}$, $—OR^{30a}$, $—OC(O)R^{30a}$, $—OC(O)N(R^{30a})_2$, $—SR^{30a}$, $—S(O)_2R^{30a}$, $—S(O)N(R^{30a})_2$, $—S(O)_2N(R^{30a})_2$, $C_{1-6}$ alkyl, $C_{3-8}$ cycloalkyl, and 4- to 7-membered monocyclic heterocyclyl, wherein the $C_{1-6}$ alkyl, $C_{3-8}$ cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$ cycloalkyl and 4- to 7-membered monocyclic heterocyclyl, wherein the $C_{1-6}$ alkyl, $C_{3-8}$ cycloalkyl and 4- to 7-membered monocyclic heterocyclyl represented by $R^{30a}$ are each optionally substituted with one or more $R^{35}$;

$R^{35}$, for each occurrence, is independently H, $—NH_2$, $C_{1-6}$alkyl, halo or $—OR^{35a}$; and $R^{35a}$ is H or $C_{1-6}$ alkyl;

$R^4$, $R^5$, $R^{15}$, $R^{16}$, $R^{17}$ and $R^{18}$ are each independently selected from H, $C_{1-6}$ alkyl, halo, —CN, $—OR^{4a}$, $—NHC(O)CH_3$, 4- to 6-membered carbocyclyl, or 4- to 6-membered heterocyclyl, wherein the $C_{1-6}$ alkyl is optionally substituted with one or more substituents independently selected from halo, and wherein the heterocyclyl and carbocyclyl are optionally substituted with halo, —CN, —$OR^{4a}$, $C_1$-$C_6$ alkyl or ═O (when the carbocyclyl or heterocyclyl are non-aromatic), or wherein $R^{15}$ and $R^{16}$ taken together or $R^{17}$ and $R^{18}$ taken together are ═NOH or ═$NHOCH_3$;

$R^{4a}$ is H or $C_{1-6}$ alkyl, optionally substituted with one or more halo;

$R^6$ is H or $C_{1-6}$alkyl optionally substituted with one or more substituents independently selected from halo, —CN and —$OR^{6a}$;

$R^{6a}$ is H or $C_{1-6}$ alkyl optionally substituted with one or more halo;

$R^8$ is H, halo, —CN, —$OR^{8a}$ or $C_{1-6}$ alkyl optionally substituted with one or more halo;

$R^{8a}$ is H or $C_{1-6}$ alkyl optionally substituted with one or more halo;

$R^9$, $R^{13}$ and $R^{14}$ are each independently selected from H, $C_{1-6}$alkyl, and $C_{3-6}$ cycloalkyl, wherein the $C_{1-6}$ alkyl and the $C_{3-6}$ cycloalkyl are each optionally substituted with one or more substituents independently selected from halo, —CN, —$OR^{9a}$ and $C_{1-6}$ alkyl optionally substituted with one or more halo;

$R^{9a}$ is H or $C_{1-6}$ alkyl optionally substituted with one or more halo;

$R^{11}$ and $R^{12}$ are each independently H or $C_{1-6}$ alkyl, or $R^{11}$ and $R^{12}$ together with the nitrogen atom from which they are attached form a 4- to 7-membered monocyclic heterocyclyl optionally substituted with one or more substituents independently selected from $C_{1-6}$ alkyl, halo, —OH, and $C_{1-6}$ alkoxy;

or any two of $R^4$, $R^5$, $R^9$, $R^{13}$, $R^{14}$, $R^{15}$, $R^{16}$, $R^{17}$ and $R^{18}$ together form a —$C_{1-5}$ alkylene-, optionally substituted with one or more substituents independently selected from halo, —$OR^a$, —$N(R^a)_2$ and $C_{1-6}$ alkyl, provided that $R^4$ and $R^5$, $R^{13}$ and $R^{14}$, $R^{15}$ and $R^{16}$ and $R^{17}$ and $R^{18}$ taken together form a —$C_{3-5}$ alkylene-, optionally substituted with one or more substituents independently selected from halo, —$OR^a$, —$N(R^a)_2$ and $C_{1-6}$ alkyl;

or $R^4$ and $R^{15}$ taken together with their intervening carbon atoms form phenyl or a 6 membered heteroaryl; and $R^a$, for each occurrence, is independently H or $C_{1-6}$ alkyl optionally substituted with one or more halo;

$R^{19a}$ and $R^{19b}$ are each independently H or $C_{1-6}$ alkyl optionally substituted with one or more halo, or $R^{19a}$ and $R^{19b}$ together with the carbon atom from which they are attached form —C(═O); or one $R^{20}$ group and one $R^{30}$ group taken together form —O—$CH_2CH_2$—O— or —O—$CH_2CH_2$—NH—; and n1 is 0, 1 or 2; and n2 is 0, 1 or 2, provided when X is $NR^6$ or O, n1 and n2 cannot be 0.

2. The compound of claim 1, represented by Formula (I'):

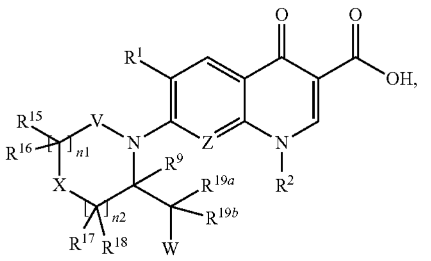

(I')

or a pharmaceutically acceptable salt thereof, wherein:

W is Y—$R^3$, —OC(═O)$NR^{11}R^{12}$ or —N(C═O)$NR^{11}R^{12}$;

V is —C(═O)—, —$S(═O)_2$— or $CR^{13}R^{14}$;

X is $CR^4R^5$, $NR^6$ or O;

Y is O;

Z is $CR^8$ or N;

$R^1$ is halo, CN, —$OR^{1a}$, —C≡CH, or a $C_{1-6}$ alkyl, wherein the $C_{1-6}$ alkyl is optionally substituted with one or more $R^{10}$;

$R^{1a}$ is H or $C_{1-6}$ alkyl optionally substituted with one or more $R^{10}$;

$R^{10}$, for each occurrence, is independently selected from halo, CN and $OR^{10a}$;

$R^{10a}$, for each occurrence, is independently selected from H and $C_{1-6}$ alkyl;

$R^2$ is a 3 to 12-membered carbocyclyl or a 3 to 12-membered heterocyclyl, wherein the 3 to 12-membered carbocyclyl and the 3 to 12-membered heterocyclyl represented by $R^2$ are optionally substituted with one or more $R^{20}$;

$R^{20}$, for each occurrence, is independently selected from H, halo, CN, oxo, —$C(O)R^{20a}$, —$C(O)_2R^{20a}$, —$C(O)NR^{20a}$, —$N(R^{20a})_2$, —$N(R^{20a})C(O)R^{20a}$, —$N(R^{20a})C(O)_2R^{20a}$, —$N(R^{20a})C(O)N(R^{20a})_2$, —$N(R^{20a})S(O)_2R^{20a}$, —$OR^{20a}$, —$OC(O)R^{20a}$, —$OC(O)N(R^{20a})_2$, —$SR^{20a}$, $S(O)_2R^{20a}$, —$S(O)N(R^{20a})_2$, —$S(O)_2N(R^{20a})_2$, $C_{1-6}$ alkyl, $C_{3-8}$ cycloalkyl, and 4- to 7-membered monocyclic heterocyclyl, wherein the $C_{1-6}$ alkyl, $C_{3-8}$ cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$ alkyl, $C_{3-8}$ cycloalkyl and 4- to 7-membered monocyclic heterocyclyl, wherein the $C_{1-6}$ alkyl, $C_{3-8}$ cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —$N(R^{25a})_2$, —$OR^{25a}$, phenyl optionally substituted with $C_{1-6}$ alkyl, halo, —$N(R^{25a})_2$ or —$OR^{25a}$; and $R^{25a}$ is H or $C_{1-6}$alkyl;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, —$C(O)R^{30a}$, —$C(O)_2R^{30a}$, —$C(O)NR^{30a}$, —$N(R^{30a})_2$, —$N(R^{30a})C(O)R^{30a}$, —$N(R^{30a})C(O)_2R^{30a}$, —$N(R^{30a})C(O)N(R^{30a})_2$, —$N(R^{30a})S(O)_2R^{30a}$, —$OR^{30a}$, —$OC(O)R^{30a}$, —$OC(O)N(R^{30a})_2$, —$SR^{30a}$, —$S(O)_2R^{30a}$, —$S(O)N(R^{30a})_2$, —$S(O)_2N(R^{30a})_2$, $C_{1-6}$ alkyl, $C_{3-8}$ cycloalkyl, and 4- to 7-membered monocyclic heterocyclyl, wherein the $C_{1-6}$ alkyl, $C_{3-8}$ cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$ cycloalkyl and 4- to 7-membered monocyclic heterocyclyl, wherein the $C_{1-6}$ alkyl, $C_{3-8}$ cycloalkyl and 4- to 7-membered monocyclic heterocyclyl represented by $R^{30a}$ are each optionally substituted with one or more $R^{35}$;

$R^{35}$, for each occurrence, is independently H, $C_{1-6}$alkyl, halo or —$OR^{35a}$; and $R^{35a}$ is H or $C_{1-6}$alkyl;

$R^4$, $R^5$, $R^{15}$, $R^{16}$, $R^{17}$ and $R^{18}$ are each independently selected from H, $C_{1-6}$ alkyl, halo, —CN and —$OR^{4a}$, wherein the $C_{1-6}$ alkyl is optionally substituted with one or more substituents independently selected from halo, CN and —$OR^{4a}$;

$R^{4a}$ is H or $C_{1-6}$ alkyl optionally substituted with one or more halo;

$R^6$ is H or $C_{1-6}$alkyl wherein the $C_{1-6}$ alkyl is optionally substituted with one or more substituents independently selected from halo, CN and —$OR^{4a}$;

$R^{6a}$ is H or $C_{1-6}$ alkyl optionally substituted with one or more halo;

$R^8$ is H, halo, CN, —$OR^{8a}$ or $C_{1-6}$ alkyl optionally substituted with one or more halo;

$R^{8a}$ is H or $C_{1-6}$ alkyl optionally substituted with one or more halo;

$R^9$, $R^{13}$ and $R^{14}$ are each independently selected from H, $C_{1-6}$alkyl and $C_{3-6}$ cycloalkyl, wherein the $C_{1-6}$ alkyl and the $C_{3-6}$ cycloalkyl are each optionally substituted with one or more substituents independently selected from halo, CN, —$OR^{9a}$ and $C_{1-6}$ alkyl optionally substituted with one or more halo;

$R^{9a}$ is H or $C_{1-6}$ alkyl optionally substituted with one or more halo;

$R^{11}$ and $R^{12}$ are each independently H or $C_{1-6}$ alkyl, or $R^{11}$ and $R^{12}$ together with the nitrogen atom from which they are attached form a 4- to 7-membered monocyclic heterocyclyl optionally substituted with one or more substituents independently selected from $C_{1-6}$ alkyl, halo, OH, and $C_{1-6}$ alkoxy;

or any two of $R^4$, $R^5$, $R^9$, $R^{13}$, $R^{14}$, $R^{15}$, $R^{16}$, $R^{17}$ and $R^{18}$ together form a —$C_{3-5}$ alkylene-, [—$C_{1-5}$ alkylene-]optionally substituted with one or more substituents independently selected from halo, —$OR^a$, —$N(R^a)_2$ and $C_{1-6}$ alkyl, provided that $R^4$ and $R^5$, $R^{13}$ and $R^{14}$, $R^{15}$ and $R^{16}$ and $R^{17}$ and $R^{18}$ taken together form a —$C_{3-5}$ alkylene-, optionally substituted with one or more substituents independently selected from halo, —$OR^a$, —$N(R^a)_2$ and $C_{1-6}$ alkyl;

$R^a$, for each occurrence, is independently H or $C_{1-6}$ alkyl optionally substituted with one or more halo;

$R^{19a}$ and $R^{19b}$ are each independently H or $C_{1-6}$ alkyl optionally substituted with one or more halo or $R^{19a}$ and $R^{19b}$ together with the carbon atom from which they are attached form —C(═O)—;

n1 is 0, 1 or 2; and n2 is 0, 1 or 2, provided when X is $NR^6$ or O, n1 and n2 cannot be 0.

3. The compound of claim 2, or a pharmaceutically acceptable salt thereof, wherein the compound is represented by Formula (Ia) or (Ib):

(Ia)

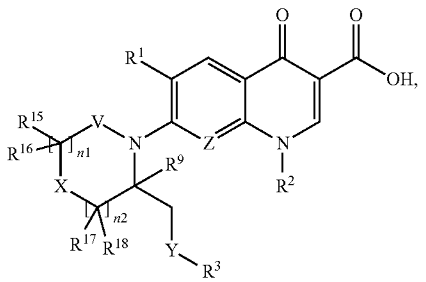

or (Ib)

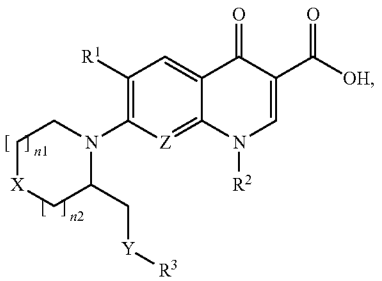

, or a pharmaceutically acceptable salt thereof, wherein:

X is $CR^4R^5$, $NR^6$ or O;

Y is O;

Z is $CR^8$ or N;

$R^1$ is halo, CN, —$OR^{1a}$, —C≡CH, or $C_{1-6}$ alkyl, wherein the $C_{1-6}$alkyl is optionally substituted with one or more $R^{10}$;

$R^{1a}$ is H or $C_{1-6}$alkyl optionally substituted with one or more $R^{10}$;

$R^{10}$, for each occurrence, is independently selected from halo, CN and $OR^{10a}$;

$R^{10a}$, for each occurrence, is independently selected from H and $C_{1-6}$ alkyl;

$R^2$ is a 3 to 12-membered carbocyclyl or a 3 to 12-membered heterocyclyl, wherein the 3 to 12-membered carbocyclyl and the 3 to 12-membered heterocyclyl represented by $R^2$ are optionally substituted with one or more $R^{20}$;

$R^{20}$, for each occurrence, is independently selected from H, halo, CN, oxo, —$C(O)R^{20a}$, —$C(O)_2R^{20a}$, —$C(O)NR^{20a}$, —$N(R^{20a})_2$, —$N(R^{20a})C(O)R^{20a}$, —$N(R^{20a})C(O)_2R^{20a}$, —$N(R^{20a})C(O)N(R^{20a})_2$, —$N(R^{20a})S(O)_2R^{20a}$, —$OR^{20a}$, —$OC(O)R^{20a}$, —$OC(O)N(R^{20a})_2$, —$SR^{20a}$, —$S(O)_2R^{20a}$, —$S(O)N(R^{20a})_2$, —$S(O)_2N(R^{20a})_2$, $C_{1-6}$ alkyl, $C_{3-8}$ cycloalkyl, and 4- to 7-membered monocyclic heterocyclyl, wherein the $C_{1-6}$alkyl, $C_{3-8}$cycloalkyl, and 4- to 7-membered monocyclic heterocyclyl represented by $R^{20}$ are each optionally substituted with one or more $R^{25}$;

$R^{20a}$, for each occurrence, is independently selected from H, $C_{1-6}$ alkyl, $C_{3-8}$ cycloalkyl and 4- to 7-membered monocyclic heterocyclyl, wherein the $C_{1-6}$alkyl, $C_{3-8}$-cycloalkyl and 4- to 7-membered monocyclic heterocyclyl represented by $R^{20a}$ are each optionally substituted with one or more $R^{25}$, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —$N(R^{25a})_2$, —$OR^{25a}$, phenyl optionally substituted with $C_{1-6}$alkyl, halo, —$N(R^{25a})_2$ or —$OR^{25a}$; and $R^{25a}$ is H or $C_{1-6}$ alkyl;

$R^3$ is a 3 to 12-membered carbocyclyl or a 3 to 12-membered heterocyclyl, wherein the 3 to 12-membered carbocyclyl and the 3 to 12-membered heterocyclyl represented by $R^3$ are optionally substituted with one or more $R^{30}$;

$R^{30}$, for each occurrence, is independently selected from H, halo, oxo, —CN, —$C(O)R^{30a}$, —$C(O)_2R^{30a}$, —$C(O)NR^{30a}$, —$N(R^{30a})_2$, —$N(R^{30a})C(O)R^{30a}$, —$N(R^{30a})C(O)_2R^{30a}$, —$N(R^{30a})C(O)N(R^{30a})_2$, —$N(R^{30a})S(O)_2R^{30a}$, —$OR^{30a}$, —$OC(O)R^{30a}$, —$OC(O)N(R^{30a})_2$, —$SR^{30a}$, —$S(O)_2R^{30a}$, —$S(O)N(R^{30a})_2$, —$S(O)_2N(R^{30a})_2$, $C_{1-6}$ alkyl, $C_{3-8}$ cycloalkyl, and 4- to 7-membered monocyclic heterocyclyl, wherein the $C_{1-6}$alkyl, $C_{3-8}$cycloalkyl, and 4- to 7-membered monocyclic heterocyclyl represented by $R^{30}$ are each optionally substituted with one or more $R^{35}$;

$R^{30a}$, for each occurrence, is independently selected from H, $C_{1-6}$ alkyl, $C_{3-8}$ cycloalkyl and 4- to 7-membered monocyclic heterocyclyl, wherein the $C_{1-6}$ alkyl, $C_{3-8}$ cycloalkyl and 4- to 7-membered monocyclic heterocyclyl represented by $R^{30a}$ are each optionally substituted with one or more $R^{35}$;

$R^{35}$, for each occurrence, is independently H, $C_{1-6}$ alkyl, halo or —$OR^{35a}$; and $R^{35a}$ is H or $C_{1-6}$ alkyl;

$R^4$ and $R^5$ are each independently selected from H, $C_{1-6}$ alkyl, halo, —CN and —$OR^{4a}$, wherein the $C_{1-6}$ alkyl is optionally substituted with one or more substituents independently selected from halo, CN and —$OR^{4a}$;

$R^{4a}$ is H or $C_{1-6}$ alkyl optionally substituted with one or more halo;

$R^6$ is H or $C_{1-6}$ alkyl optionally substituted with one or more substituents independently selected from halo, CN and —$OR^{6a}$;

$R^{6a}$ is H or $C_{1-6}$alkyl optionally substituted with one or more halo;

$R^8$ is H, halo, CN, —$OR^{8a}$ or $C_{1-6}$ alkyl optionally substituted with one or more halo;

$R^{8a}$ is H or $C_{1-6}$alkyl optionally substituted with one or more halo;

n1 is 0, 1 or 2; and n2 is 0, 1 or 2, or, for formula (Ia), any two of $R^4$, $R^5$, $R^9$, $R^{13}$, $R^{14}$, $R^{15}$, $R^{16}$, $R^{17}$ and $R^{18}$ together form a —$C_{1-5}$ alkylene- optionally substituted with one or more substituents independently selected from halo, —$OR^a$, —$N(R^a)_2$ and $C_{1-6}$ alkyl, provided that $R^4$ and $R^5$, $R^{13}$ and $R^{14}$, $R^{15}$ and $R^{16}$ and $R^{17}$ and $R^{18}$ taken together form a —$C_{3-5}$ alkylene-, optionally substituted with one or more substituents independently selected from halo, —$OR^a$, —$N(R^a)_2$ and $C_{1-6}$ alkyl; wherein $R^a$, for each occurrence, is independently H or $C_{1-6}$ alkyl optionally substituted with one or more halo.

4. The compound of 3, or a pharmaceutically acceptable salt thereof, wherein the compound is represented by Formula (IIIa), (IIIb), (III-1a) or (III-1b):

(IIIa)

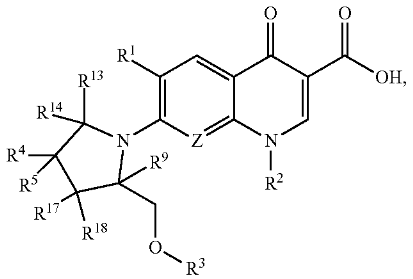

(IIIb)

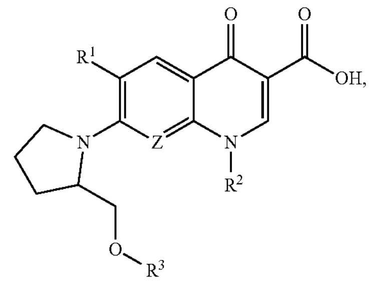

(III-1a)

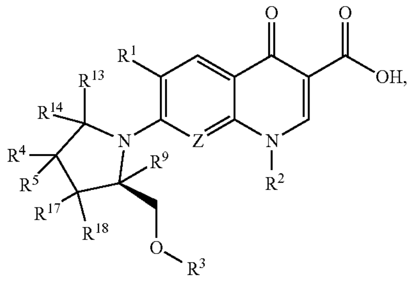

or (III-1b)

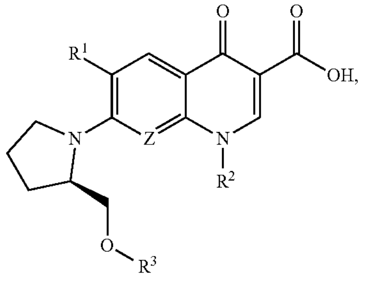

or a pharmaceutically acceptable salt thereof.

5. The compound of claim 4, or a pharmaceutically acceptable salt thereof, wherein:

$R^1$ is Cl, Br, CN, —$OR^9$ or $C_{1-6}$ alkyl;

$R^2$ is $C_{3-8}$ cycloalkyl, phenyl, a 4 to 6-membered saturated monocyclic heterocyclyl, a 7 to 10-membered saturated or partially saturated bicyclic heterocyclyl, a 5 or 6-membered monocyclic heteroaryl or a 9 to 10-membered bicyclic heteroaryl, each of which is optionally substituted with one to three $R^{20}$;

$R^{20}$, for each occurrence, is independently selected from H, halo, —CN, oxo, —$C(O)R^{20a}$, —$C(O)NR^{20a}$, —$N(R^{20a})_2$, —$N(R^{20a})C(O)R^{20a}$, —$N(R^{20a})$ $S(O)_2R^{20a}$, $—OR^{20a}$, $C_{1-6}$ alkyl, $C_{3-8}$ cycloalkyl, and 4- to 7-membered saturated monocyclic heterocyclyl, wherein the $C_{1-6}$ alkyl, $C_{3-8}$ cycloalkyl, and 4- to 7-membered saturated monocyclic heterocyclyl represented by $R^{20}$ are each optionally substituted with one or two $R^{25}$;

$R^{20a}$, for each occurrence, is independently selected from H and $C_{1-6}$ alkyl, wherein the $C_{1-6}$alkyl represented by $R^{20a}$ is optionally substituted with one or more $R^{25}$;

$R^{25}$, for each occurrence, is independently H, $C_{1-6}$alkyl, halo, $—N(R^{25a})_2$, $—OR^{25a}$, phenyl optionally substituted with $C_{1-6}$ alkyl, halo, $—N(R^{25a})_2$ or $—OR^{25a}$; and $R^{25a}$ is H or $C_{1-6}$ alkyl;

$R^3$ is phenyl, a 5 or 6-membered monocyclic heteroaryl or a 9 or 10-membered bicyclic heteroaryl, wherein the phenyl, 5 or 6-membered monocyclic heteroaryl and 9 or 10-membered bicyclic heteroaryl represented by $R^3$ are each optionally substituted with one to three $R^{30}$, $R^{30}$, for each occurrence, is H, halo, CN, $—C(O)NR^{30a}$, $—N(R^{30a})_2$, $—N(R^{30a})C(O)R^{30a}$, $—N(R^{30a})S(O)_2R^{30a}$, $—OR^{30a}$, or $C_{1-6}$ alkyl, wherein the $C_{1-6}$ alkyl is optionally substituted with one to three $R^{35}$;

$R^{30a}$, for each occurrence, is independently H or $C_{1-6}$ alkyl optionally substituted with one to three $R^{35}$;

$R^{35}$, for each occurrence, is independently H, halo and $—OR^{35a}$; and $R^{35a}$ is H or $C_{1-3}$ alkyl; and $R^8$ is H, halo, or $OR^{8a}$.

6. The compound of claim 5, a pharmaceutically acceptable salt thereof, wherein the compound is represented by Formula (Va), or (Vb):

(Va)

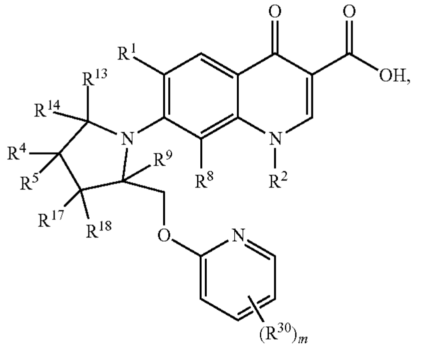

or (Vb)

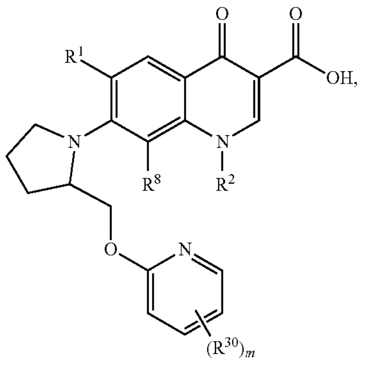

or a pharmaceutically acceptable salt thereof, wherein m is 0, 1 or 2.

7. The compound of claim 6, or a pharmaceutically acceptable salt thereof, wherein the compound is represented by Formula (V-1a) or (V-1b):

(V-1a)

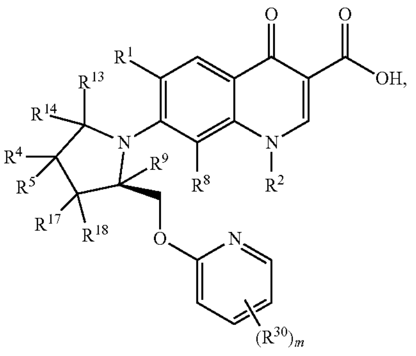

or (V-1b)

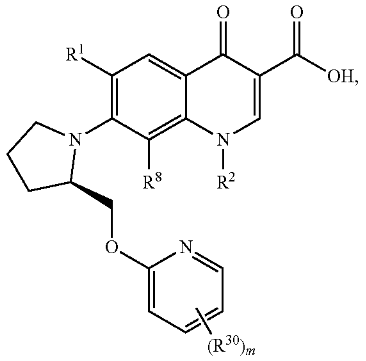

or a pharmaceutically acceptable salt thereof.

8. The compound of claim 6, or a pharmaceutically acceptable salt thereof, wherein the compound is represented by Formula (VAa), (VBa), (VCa), or (VDa):

(VAa)

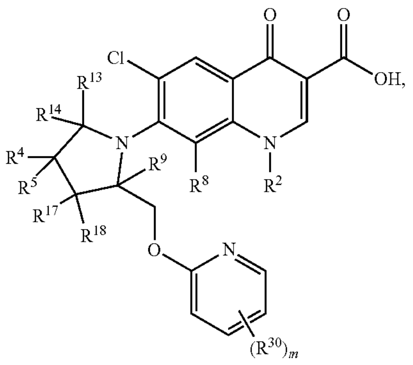

-continued (VBa)

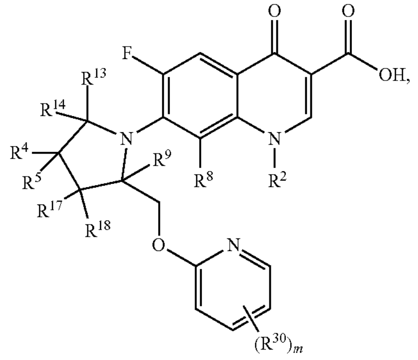

(VCa)

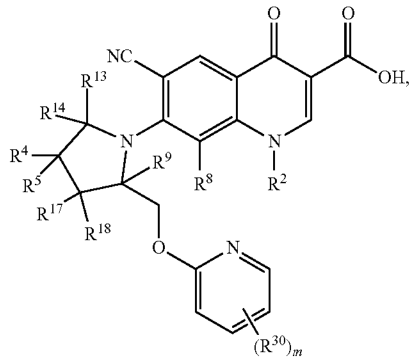

or (VDa)

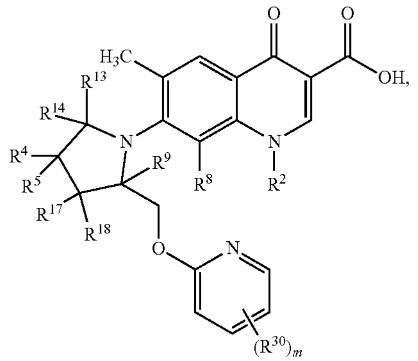

or a pharmaceutically acceptable salt thereof.

9. The compound of claim 5, or a pharmaceutically acceptable salt thereof, wherein the compound is represented by Formula (VAb), (VBb), (VCb) or (VDb):

(VAb)

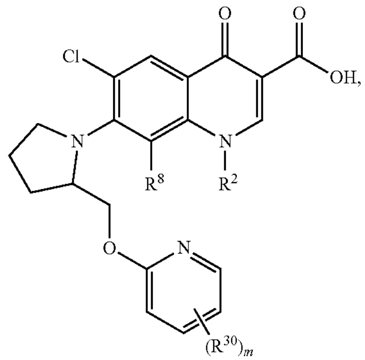

-continued (VBb)

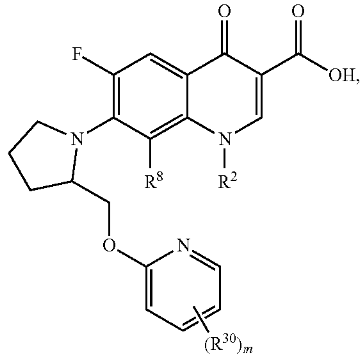

(VCb)

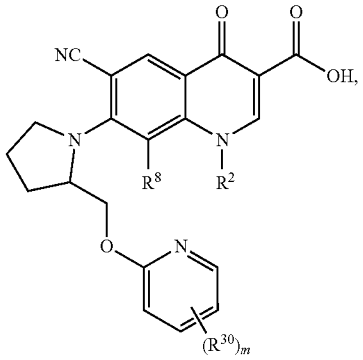

or (VDb)

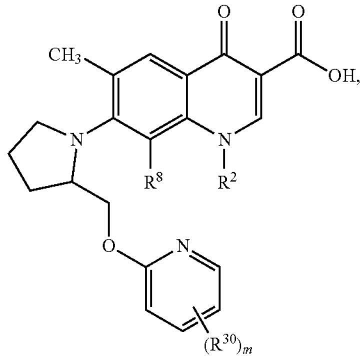

or a pharmaceutically acceptable salt thereof.

10. The compound of claim 5, or a pharmaceutically acceptable salt thereof, wherein $R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{20}$.

11. The compound of claim 1, or a pharmaceutically acceptable salt thereof, wherein the compound is represented by Formula (VIIA-1a), (VIIB-1a), (VIIC-1a), or (VIID-1a):

(VIIA-1a)

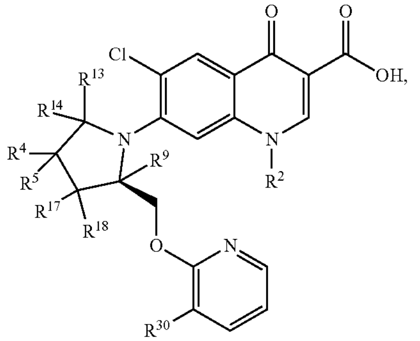

(VIIB-1a)

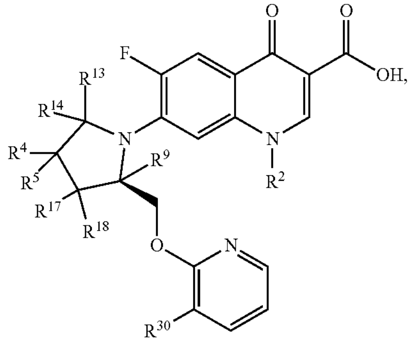

(VIIC-1a)

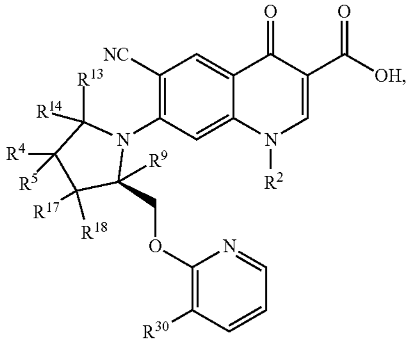

or (VIID-1a)

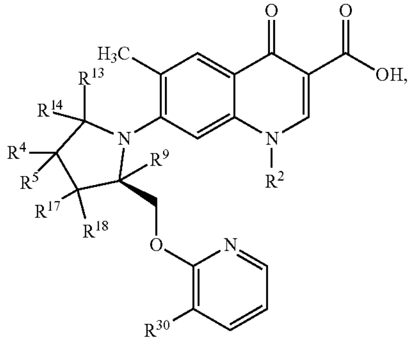

or a pharmaceutically acceptable salt thereof, wherein:

$R^{30}$ is H, halo, CN, —$OR^{30a}$, or $C_{1-6}$ alkyl optionally substituted with one to three halo; and $R^{30a}$ is H or $C_{1-6}$ alkyl optionally substituted with one to three halo; and $R^2$ is phenyl or a 6-membered monocyclic heteroaryl containing 1 to 3 nitrogen atoms, wherein the phenyl and the 6-membered monocyclic heteroaryl are each optionally substituted with one to three $R^{20}$;

$R^{20}$, for each occurrence, is independently selected from halo, and —$N(R^{20a})_2$; and $R^{20a}$, for each occurrence, is independently selected from H and $C_{1-3}$ alkyl, or two $R^{20a}$ together with the nitrogen atom from which they are attached form a 4- to 7-membered heterocyclyl optionally substituted with one or more $R^{25}$;

$R^{25}$, for each occurrence, is independently H, $C_{1-6}$ alkyl, halo, —$N(R^{25a})_2$, or —$OR^{25a}$; and $R^{25a}$ is H or $C_{1-6}$ alkyl.

12. The compound of claim 1, or a pharmaceutically acceptable salt thereof, wherein the compound is represented by Formula (VIIA-1b), (VIIB-1b), (VIIC-1b) or (VIID-1b):

(VIIA-b)

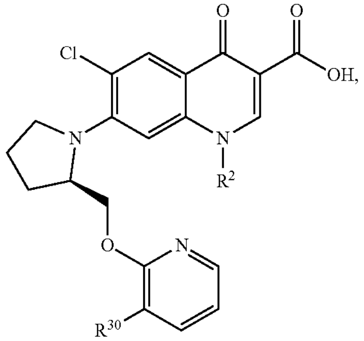

(VIIB-1b)

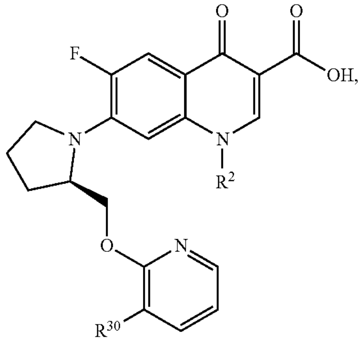

(VIIC-1b)

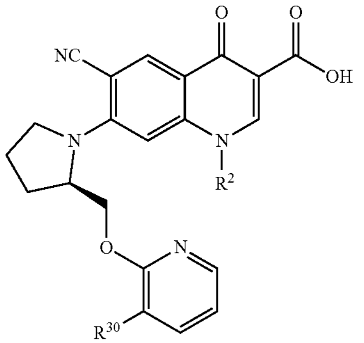

or

-continued (VIID-1b)

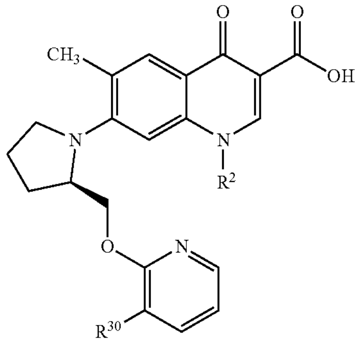

or a pharmaceutically acceptable salt thereof.

13. The compound of claim 12, or a pharmaceutically acceptable salt thereof, wherein:

$R^{30}$ is halo or $C_{1-3}$ alkyl;

$R^2$ is phenyl, pyridinyl or pyrazinyl, each of which is optionally substituted with —$N(R^{20a})_2$; and $R^{20a}$, for each occurrence, is H or methyl, or two $R^{20a}$ together with the nitrogen atom from which they are attached form a 4- to 6-membered heterocyclyl optionally substituted with one $R^{25}$;

$R^{25}$ is —$N(R^{25a})_2$; and $R^{25a}$ is H or Me.

14. The compound of claim 6 or a pharmaceutically acceptable salt thereof, wherein, for formula (Va), (i) $R^4$, $R^5$, $R^{13}$, $R^{14}$, $R^{17}$ and $R^{18}$ are all H, and $R^9$ is $C_{1-6}$alkyl or $C_{3-6}$ cycloalkyl, wherein the $C_{1-6}$ alkyl and the $C_{3-6}$ cycloalkyl are each optionally substituted with one or more substituents independently selected from halo, CN, —$OR^{9a}$ and $C_{1-6}$ alkyl optionally substituted with one or more halo; wherein $R^{9a}$ is H or $C_{1-6}$ alkyl optionally substituted with one or more halo; (ii) $R^5$, $R^9$, $R^{13}$, $R^{14}$, $R^{17}$ and $R^{18}$ are all H, and $R^4$ is $C_{1-6}$ alkyl, halo, —CN or —$OR^{4a}$, wherein the $C_{1-6}$ alkyl is optionally substituted with one or more substituents independently selected from halo, CN and —$OR^{4a}$; and $R^{4a}$ is H or $C_{1-6}$ alkyl optionally substituted with one or more halo; or (iii) $R^4$, $R^5$, $R^{14}$, $R^{17}$ and $R^{18}$ are all H, and $R^{13}$ and $R^9$ together form a —$C_{1-3}$ alkylene optionally substituted with one or more substituents independently selected from halo, —$OR^a$, —$N(R^a)_2$ and $C_{1-6}$ alkyl; wherein $R^a$, for each occurrence, is independently H or $C_{1-6}$ alkyl optionally substituted with one or more halo.

15. A compound represented by Formula (IV-1a):

(IV-1a)

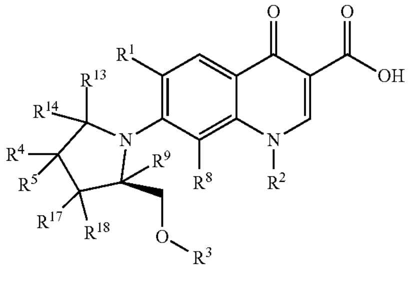

or a pharmaceutically acceptable salt thereof, wherein:

$R^1$ is F, Cl, CN or $CH_3$;

$R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyrimidinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{20}$;

$R^{20}$, for each occurrence, is independently selected from H, halo, —CN, oxo, —$C(O)R^{20a}$, —$C(O)NR^{20a}$, —$N(R^{20a})_2$, —$N(R^{20a})C(O)R^{20a}$, —$N(R^{20a})S(O)_2R^{20a}$, —$OR^{20a}$, $C_{1-6}$ alkyl, $C_{3-8}$ cycloalkyl, and 4- to 7-membered saturated monocyclic heterocyclyl, wherein the $C_{1-6}$ alkyl, $C_{3-8}$ cycloalkyl, and 4- to 7-membered saturated monocyclic heterocyclyl represented by $R^{20}$ are each optionally substituted with one or two $R^{25}$;

$R^{20a}$, for each occurrence, is independently selected from H and $C_{1-6}$ alkyl, wherein the $C_{1-6}$alkyl represented by $R^{20a}$ is optionally substituted with one or more $R^{25}$;

$R^{25}$, for each occurrence, is independently H, $C_{1-6}$alkyl, halo, —$N(R^{25a})_2$, —$OR^{25a}$, phenyl optionally substituted with $C_{1-6}$alkyl, halo, —$N(R^{25a})_2$ or —$OR^{25a}$; and $R^{25a}$ is H, $C_{1-6}$ alkyl, or $C_{1-6}$ alkyl substituted with —$OCH_3$;

$R^3$ is phenyl, pyridinyl, pyrimidinyl, pyrazinyl, pyridazinyl, 1H-pyrrolo[2,3-c]pyridinyl, 1H-imidazo[4,5-c]pyridinyl, 1H-pyrrolo[2,3-b]pyridinyl, 1H-imidazo[4,5-b]pyridinyl, 1H-pyrrolo[3,2-b]pyridinyl, 3H-imidazo[4,5-b]pyridinyl,or 1H-imidazo[4,5-c]pyridinyl, each of which is optionally substituted with one to three $R^{30}$;

$R^{30}$, for each occurrence, is H, halo, CN, —$C(O)NR^{30a}$, —$N(R^{30a})_2$, —$N(R^{30a})C(O)R^{30a}$, —$N(R^{30a})S(O)_2R^{30a}$, —$OR^{30a}$, or $C_{1-6}$ alkyl, wherein the $C_{1-6}$ alkyl is optionally substituted with one to three $R^{35}$;

$R^{30a}$, for each occurrence, is independently H, $C_{1-6}$ alkyl optionally substituted with one to three $R^{35}$ or $C_{3-6}$ cycloalkyl;

$R^{35}$, for each occurrence, is independently H, halo or —$OR^{35a}$; and $R^{35a}$ is H or $C_{1-3}$ alkyl;

$R^4$ is H, halo, —CN, —$OR^{4a}$, $C_{1-6}$ alkyl, pyridinyl, or pyrazolyl, wherein the $C_{1-6}$alkyl is optionally substituted with one or more substituents independently selected from halo, CN and —$OR^{4a}$; wherein the pyridinyl, or pyrazolyl is optionally substituted with —OH, —$C_1$-$C_6$ alkyl or —O—$C_1$-$C_6$ alkyl; and $R^{4a}$ is H, $C_{1-6}$ alkyl optionally substituted with one or more halo, or $C_3$-$C_6$ cycloalkyl;

$R^5$ is H or halo, or $R^4$ and $R^5$ taken together are =NOH, or =$NHOCH_3$, or $R^4$ and $R^5$ taken together with the carbon to which they are connected form a $C_3$-$C_6$ cycloalkyl, or $R^5$ and $R^{13}$ taken together with their intervening atoms form a cyclopropyl; and;

$R^8$, $R^{13}$ and $R^{14}$ are each H;

$R^9$ is H, $C_1$-$C_6$ alkoxy or $C_1$-$C_6$ alkyl, or $R^9$ and $R^{13}$ together form a —$C_{1-3}$ alkylene- optionally substituted with one or more substituents independently selected from halo, —$OR^a$, —$N(R^a)_2$ and $C_{1-6}$ alkyl; wherein $R^a$, for each occurrence, is independently H or $C_{1-6}$ alkyl optionally substituted with one or more halo;

$R^{17}$ is H, halo or $C_{1-6}$alkyl; and $R^{18}$ is H, —OH, —O($C_1$-$C_6$ alkyl) or $C_{1-6}$ alkyl, or $R^{17}$ and $R^{18}$ taken together are =NOH or =$NHOCH_3$.

16. The compound of claim 15, or a pharmaceutically acceptable salt thereof, wherein the compound is represented by Formula (IV-1a):

(IV-1a)

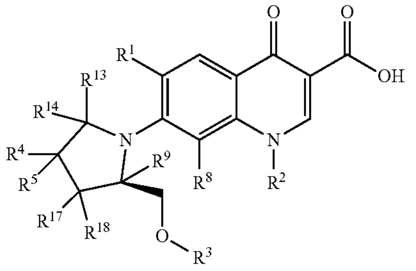

wherein:

$R^1$ is F, Cl, CN or $CH_3$, $R^2$ is selected from cyclopropyl, cyclobutyl, cyclopentyl, cyclohexyl, phenyl, azetidinyl, pyrrolidinyl, piperidinyl, 2-azaspiro[3.3]heptanyl, 1H-indolyl, 2,3-dihydro-1H-benzo[d]imidazolyl, 1H-benzo[d]imidazolyl, 1,3,4-thiadiazoly, indolinyl, tetrahydro-2H-pyranyl, pyridinyl, pyrimidinyl, pyridazinyl, pyrazinyl, oxetanyl, tetrahydro-2H-pyranyl, 1H-benzo[d]imidazolyl, 1H-indazolyl, isochromanyl, and 1,3-dihydroisobenzofuranyl, each of which is optionally substituted with one or two $R^{20}$;

$R^{20}$, for each occurrence, is independently selected from —F, —OH, —Cl, —$CH_3$, —$CH_2CH_3$, —$CH_2OH$, —$CH_2OCH_3$, —$CH_2CH_2OCH_3$, —$CH_2CH_2OH$, —$CH_2CH_2N(CH_3)_2$, —$OCH_3$, —$OCH_2CH_2OCH_3$, —$OCH_2CH_2OH$, —$OCH_2CH_2N(CH_3)_2$, (4-methoxybenzyl)oxy, oxo, —C(O)$CH_3$, —$NH_2$, —$NHCH_3$, —$N(CH_3)_2$, —$N(CH_3)(CH_2CH_2OCH_3)$, —$NHCH_2CH_2OMe$, —$NHCH_2CH_2N(CH_3)_2$, —$NHSO_2CH_3$, —$NHSO_2CH_2CH_3$, —NHC(O)$CH_3$, azetidin-yl, 3-aminoazeitidin-1-yl, piperidin-1-yl, morpholinyl, pyrrolidin-1-yl; and 3-(dimethylamino)azetidin-1-yl or

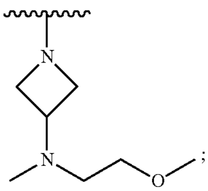

;

$R^3$ is phenyl, pyridinyl, pyrimidinyl, pyrazinyl, pyridazinyl, 1H-pyrrolo[2,3-c]pyridinyl, 1H-imidazo[4,5-c]pyridinyl, 1H-imidazo[4,5-c]pyridinyl, 1H-pyrrolo[2,3-b]pyridinyl, 1H-imidazo[4,5-b]pyridinyl; 1H-pyrrolo[3,2-b]pyridinyl, or 3H-imidazo[4,5-b]pyridinyl each of which is optionally substituted with one to three $R^{30}$;

$R^{30}$, for each occurrence, is H, F, Cl, Br, CN, —$OCH_3$, —O(cyclopropyl), —$NH_2$, —$NH(CH_3)_2$, —$CH_3$, —$CH_2CH_3$ or —$CF_3$;

$R^4$ is H, halo, —CN, $OR^{4a}$, $C_{1-6}$ alkyl, pyridinyl, or pyrazolyl, wherein the $C_{1-6}$ alkyl is optionally substituted with one or more substituents independently selected from halo, CN and —$OR^{4a}$; wherein the pyridinyl, or pyrazolyl is optionally substituted with —OH, —$CH_3$ or —$OCH_3$; and $R^{4a}$ is H, —$CH_3$, or —$CH_2CH_3$ optionally substituted with one or more halo, or cyclopropyl;

$R^5$ is H or F, or $R^4$ and $R^5$ taken together are =$NHOCH_3$, or $R^4$ and $R^5$ taken together with the carbon to which they are connected form cyclopropyl, or $R^5$ and $R^{13}$ taken together with their intervening atoms form a cyclopropyl; and $R^8$, $R^{13}$ and $R^{14}$ are all H;

$R^9$ is H or —$CH_3$, or $R^9$ and $R^{13}$ together form a —$C_2$ alkylene-;

$R^{17}$ is H, F or —$CH_3$; and $R^{18}$ is H, —OH, —$OCH_3$ or —$CH_3$, or $R^{17}$ and $R^{18}$ taken together are =$NHOCH_3$.

17. A compound represented by Formula (IV-1a):

(IV-1a)

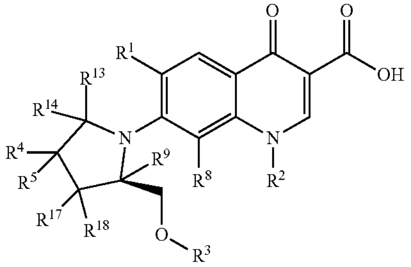

or a pharmaceutically acceptable salt thereof wherein:

$R^1$ is F or Cl;

$R^2$ is selected from pyridinyl, pyriminidinyl and pyridazinyl, each of which is substituted with $R^{20}$;

$R^{20}$, for each occurrence, is independently selected from —$NH_2$, —$NHCH_3$, $N(CH_3)_2$, and 4- to 7-membered saturated monocyclic heterocyclyl, wherein the 4- to 7-membered saturated monocyclic heterocyclyl represented by $R^{20}$ substituted with —$N(R^{25a})_2$;

each $R^{25a}$ is independently H, $C_{1-6}$ alkyl, or $C_{1-6}$ alkyl substituted with —$OCH_3$;

$R^3$ is pyridinyl, 1H-imidazo[4,5-c]pyridinyl, 1H-pyrrolo[2,3-b]pyridinyl, 1H-pyrrolo[3,2-b]pyridinyl or 3H-imidazo[4,5-b]pyridinyl, each of which is optionally substituted with one to three $R^{30}$;

$R^{30}$, for each occurrence, is H, halo, $C_1$-$C_6$alkyl, —$N(R^{30a})_2$ and —$OR^{30a}$;

$R^{30a}$, for each occurrence, is independently H, $C_{1-6}$ alkyl or $C_{3-6}$ cycloalkyl;

$R^4$ is H, halo, —$OR^{4a}$, $C_{1-6}$ alkyl, pyridinyl, or pyrazolyl, wherein the pyridinyl, or pyrazolyl is optionally substituted with —OH, —$C_1$-$C_6$alkyl or —O—($C_1$-$C_6$alkyl);

$R^{4a}$ is H, $C_{1-6}$ alkyl or $C_3$-$C_6$ cycloalkyl;

$R^5$ is H or halo, or $R^4$ and $R^5$ taken together are =NOH or =$NHOCH_3$, or $R^4$ and $R^5$ taken together with the carbon to which they are connected form a $C_3$-$C_6$ cycloalkyl, or $R^5$ and $R^{13}$ taken together with their intervening atoms form a cyclopropyl; and;

$R^8$, $R^{13}$ and $R^{14}$ are each H;

$R^9$ is H or $C_1$-$C_6$alkyl;

$R^{17}$ is H, halo, $C_1$-$C_6$ alkoxy or $C_{1-6}$ alkyl;

$R^{18}$ is H, or $C_{1-6}$ alkyl.

18. The compound of claim 17, or a pharmaceutically acceptable salt thereof, wherein the compound is represented by Formula (IV-1a):

(IV-1a)

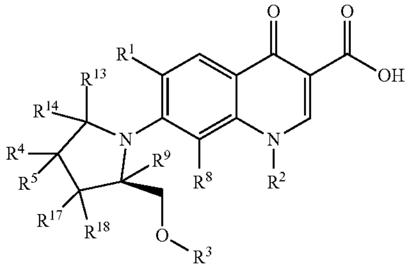

wherein:

$R^1$ is F or Cl;

$R^2$ is selected from pyridinyl, pyrimidinyl and pyridazinyl, each of which is substituted with $R^{20}$;

$R^{20}$ is —$NH_2$, —$NHCH_3$, $N(CH_3)_2$, 3-(dimethylamino)azetidin-1-yl or

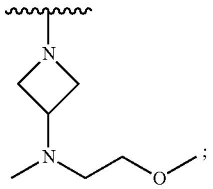

;

$R^3$ is pyridinyl, 1H-imidazo[4,5-c]pyridinyl, 1H-pyrrolo[2,3-b]pyridinyl, 1H-pyrrolo[3,2-b]pyridinyl, or 3H-imidazo[4,5-b]pyridinyl each of which is optionally substituted with one to three $R^{30}$;

$R^{30}$, for each occurrence, is H, Cl, $CH_3$, —$OCH_3$, —O(cyclopropyl), —$NH_2$, —$NHCH_3$ or —$N(CH_3)_2$;

$R^4$ is H, F, OH, —$OCH_3$, —O-(cyclopropyl), —$C_1$-$C_3$ alkyl, pyridinyl, or pyrazolyl, wherein the pyridinyl or pyrazolyl is optionally substituted with —OH, —$CH_3$ or —$OCH_3$;

$R^5$ is H or F, or $R^4$ and $R^5$ taken together are =$NHOCH_3$, or $R^4$ and $R^5$ taken together with the carbon to which they are connected form cyclopropyl, or $R^5$ and $R^{13}$ taken together with their intervening atoms form a cyclopropyl; and $R^8$, $R^{13}$ and $R^{14}$ are each H;

$R^9$ is H or —$CH_3$;

$R^{17}$ is H, F, —$OCH_3$ or —$CH_3$; and $R^{18}$ is H or —$CH_3$.

19. A pharmaceutical composition, comprising a compound of claim 1 or a pharmaceutically acceptable salt thereof and a pharmaceutically acceptable carrier.

* * * * *